US012686889B2

(12) United States Patent
Gore et al.

(10) Patent No.: US 12,686,889 B2
(45) Date of Patent: Jul. 21, 2026

(54) COMPOSITIONS AND METHODS FOR CANCER AND NEOPLASIA ASSESSMENT

(71) Applicant: SINGLERA GENOMICS, INC., La Jolla, CA (US)

(72) Inventors: Athurva J. Gore, La Jolla, CA (US); Jeffrey A. Gole, La Jolla, CA (US); Rui Liu, La Jolla, CA (US)

(73) Assignee: SINGLERA GENOMICS, INC., La Jolla, CA (US)

( * ) Notice: Subject to any disclaimer, the term of this patent is extended or adjusted under 35 U.S.C. 154(b) by 861 days.

(21) Appl. No.: 17/066,144

(22) PCT Filed: Apr. 8, 2019

(86) PCT No.: PCT/US2019/026395
§ 371 (c)(1),
(2) Date: Oct. 8, 2020

(87) PCT Pub. No.: WO2019/199696
PCT Pub. Date: Oct. 17, 2019

(65) Prior Publication Data
US 2021/0388445 A1    Dec. 16, 2021

Related U.S. Application Data

(60) Provisional application No. 62/656,820, filed on Apr. 12, 2018.

(51) Int. Cl.
*C12Q 1/6886*          (2018.01)
(52) U.S. Cl.
CPC ..... *C12Q 1/6886* (2013.01); *C12Q 2600/154* (2013.01); *C12Q 2600/16* (2013.01)
(58) Field of Classification Search
CPC ............ C12Q 1/6886; C12Q 2600/154; C12Q 2600/16; C12Q 2531/113
See application file for complete search history.

(56) References Cited

U.S. PATENT DOCUMENTS

| | | | |
|---|---|---|---|
| 7,620,386 B2 | 11/2009 | Wood, III | |
| 9,365,902 B2 | 6/2016 | Huang et al. | |
| 9,719,131 B2 * | 8/2017 | Olek .................... | C12Q 1/6827 |
| 11,965,157 B2 | 4/2024 | Gole et al. | |
| 2006/0134643 A1 | 6/2006 | Berlin et al. | |
| 2009/0108917 A1 | 4/2009 | Chellappa | |
| 2010/0297067 A1 | 11/2010 | Herman et al. | |
| 2011/0223180 A1 | 9/2011 | Aldape et al. | |
| 2015/0152505 A1 | 6/2015 | Lapointe et al. | |
| 2016/0355885 A1 | 12/2016 | Weinhausel et al. | |
| 2017/0283887 A1 | 10/2017 | Wielscher et al. | |
| 2017/0335401 A1 | 11/2017 | Allawi et al. | |
| 2020/0048697 A1 | 2/2020 | Liu | |
| 2020/0123538 A1 | 4/2020 | Gole et al. | |
| 2023/0193395 A1 | 6/2023 | Liu et al. | |

FOREIGN PATENT DOCUMENTS

| | | |
|---|---|---|
| CN | 103014155 A | 4/2013 |
| CN | 105339507 A | 2/2016 |
| CN | 107592885 A | 1/2018 |
| WO | 20090108917 A2 | 9/2009 |
| WO | 20100094040 A1 | 8/2010 |
| WO | 2016/115530 A1 | 7/2016 |
| WO | 2016138105 A2 | 9/2016 |
| WO | 20160138105 A2 | 9/2016 |
| WO | 20170048932 A1 | 3/2017 |

OTHER PUBLICATIONS

International Search Report for international patent application PCT/US2019/026395, dated Sep. 12, 2019, 5 pages.
Written Opinion of the International Searching Authority for international patent application PCT/US2019/026395, dated Sep. 12, 2019, 6 pages.
International Preliminary Report on Patenability for international patent application PCT/US2019/026395, dated Oct. 13, 20120 7 pages.
Office Action for ROC (Taiwan) Pat. Appln. No. 108112820, dated Jun. 8, 2023, 22 pages.
Office Action (Translation) for ROC (Taiwan) Pat. Appln. No. 108112820, dated Jun. 8, 2023, 6 pages.
Search Report (Translation) for ROC (Taiwan) Pat. Appln. No. 108112820, dated Jun. 8, 2023, 1 page.
Notice of reasons for Rejection (Translation) for Japanese patent application JP2020-555453, dated May 1, 2023, 6 pages.
Office Action for Japanese patent applicatio JP2020-555453, May 1, 2023, 3 pages.
Filling Argument for Japanese patent application JP2020-555453, dated May 2, 2023, 13 pages.
Amended Claims for Japanese patent application JP2020-555453, dated Oct. Oct. 2, 2023, 3 pages.
Filing an Argument for Japanese patent application JP2020-555453, dated Oct. 2, 2023, 3 pages.
Claims (clean) for European patent application EP19785565, dated Jun. 24, 2022, 4 pages.
The Extended Search Report for European patent application EP19785565, dated Nov. 29, 2021, 9 pages.
Communication pursuant to Rules 70(2) and 70a(2) EPC for European patent application EP19785565, 1 page.
Additional Test Data for European patent application EP19785565, dated Jun. 24, 2022, 2 pages.

(Continued)

*Primary Examiner* — Nelson B Moseley, II

(57)          ABSTRACT

The present disclosure relates to certain compositions, kits, devices, systems and methods, e.g., certain compositions, kits, devices, systems and methods for assessing cancer or neoplasia in a subject. In particular aspects, provided herein are compositions, kits, devices, systems and methods for assessing cancer or neoplasia in a subject based on assessing methylation status of selected target polynucleotide sequences, e.g., target genomic DNA sequences, from the subject.

18 Claims, 204 Drawing Sheets

Specification includes a Sequence Listing.

(56) References Cited

OTHER PUBLICATIONS

Claims for European patent application EP19785565, dated Jun. 24, 2022, 4 pages.
Response to Office Action for European patent application EP19785565, dated Jun. 24, 2022, 14 pages.
Request for Examination and Amendment for Korean patent application KR10-2020-7032480, dated Mar. 28, 2022, 23 pages.
Asakawa et al., "Human BAC library construction and rapid screening", Gene 191(1997) 69-79.
Chen et al., "Non-invasive early detection of cancer four years before conventional diagnosis using a blood test", Nature Communication (2020) 11:3475 https://doi.org/10.1038/s41467-020-17316-z.
International Search Report for international patent application WO2019199696, dated Oct. 17, 2019, 5 pages.
Written Opinion of the International Searching Authority for international patent application WO2019199696, dated Oct. 17, 2019, 6 pages.
International Preliminary Report on Patenability for international patent application WO2019199696, dated Oct. 22, 2019, 7 pages.
Office Action for Japanese patent application JP2020-555453, dated Mar. 19, 2022, 22 pages.
Office Action (Translation) for Japanese patent application JP2020-555453, dated Mar. 19, 2022, 6 pages.
Search Report (Translation) for Japanese patent application JP2020-555453, dated Mar. 19, 2022, 1 page.
Penultimate Official Action for Japanese patent application JP2020-555453, dated Nov. 2, 2023, 4 pages with extra 7 pages of English language equivalent or summery.
Benjamini et al., "Controlling the False Discovery Rate: a Practical and Powerful Approach to Multiple Testing", Journal of the Royal Statistical Society Series B (Methodological) (1995)57, No. 1, pp. 289-300.
Gansauge et al., "Single-stranded DNA library preparation for the sequencing of ancient or damaged DNA" Nature Protocols, 2013, vol. 8, No. 4, pp. 737-748 doi:10.1038/nprot.2013.038.
Osborn et al., "Stool screening for colorectal cancer: molecular approaches", Gastroenterology 2005;128:192-206 doi:10.1053/j.gastro.2004.10.041.
Smyth, "Linear Models and Empirical Bays Methods for Assessing Differential Expression in Microarray Experiments", 2004, Stat. Appl. Genet. Mol. Biol. vol. 3, Iss. 1, Article 3, 28 pages Doi: 10.2202/1544-6115.1027.
Taiwan App. No. 108112820, Response dated Dec. 12, 2023.
Taiwan App. No. 108112820, Amended claims dated Dec. 12, 2023.
Australia App. No. 2019253569, Examination Report dated Jul. 30, 2024.
Canada App. No. 3,096,668, Examiner's Report dated Mar. 8, 2024.
Canada App. No. 3,096,668, Response to Examiner's Report dated Jul. 4, 2024.
Canada App. No. 3,096,668, Amended claims dated Jul. 4, 2024.
China App. No. 201980039559.6, First Office Action dated Jan. 26, 2024.
China App. No. 201980039559.6, Search Report dated Jan. 26, 2024.
China App. No. 201980039559.6, Response to First Office Action dated Jun. 26, 2024.
Yin Shuhui et al., "Research progress on the relationship between DNA methylation and renal cancer" Journal of Baotou Medical College, Dec. 9, 2014, vol. 30; Issue 6; pp. 162-164.

Yang Lanhui et al., "Research progress on methylation of cancer suppressor genes in lung cancer," International Journal of Respiration, S1, Dec. 3, 2005; vol. 25; pp. 72-75.
Shuichi Asakawa et al., "Human BAC library: construction and rapid screening," Gene, Dec. 5, 2015, vol. 191, Issue 1; pp. 69-79.
Japan App. No. 2020-555453, Final Office Action dated Jul. 23, 2024.
Japan App. No. 2020-555453, Amendment to Final Office Action dated May 2, 2024.
Japan App. No. 2020-555453, Argument to Final Office Action dated May 2, 2024.
Japan App. No. 2020-555453, Amended claims dated May 2, 2024.
Malaysia App. No. PI2020005330, Substantive Examination—Adverse Report dated May 15, 2024.
Malaysia App. No. PI2020005330, Search Report dated May 15, 2024.
Taiwan App. No. 108112820, Decision of Rejection of application dated Apr. 18, 2024.
Taiwan App. No. 108112820, Rejected Claims dated Apr. 18, 2024.
European Patent Application 19 785 565.3, Examination Report dated Sep. 4, 2024.
Xingdong Chen et al: "Non-invasive early detection of cancer four years before conventional diagnosis using a blood test", Nature Communications, vol. 11, No. 1, Jul. 21, 2020 (Jul. 21, 2020), XP055755888, Doi: 10.1038/S41467-020-17316-z.
Singapore Patent Application No. 11202009866X; Supplementary Examination Written Opinion.
Notice for failure to gain acceptance for Australian Patent Application No. 2019253569.
Second Office Action for Chinese National Phase Application No. 201980039559.6.
Response to the second office action filed on Nov. 4, 2024 for Chinese National Phase Application No. 201980039559.6.
Decision of Rejection issued on Dec. 31, 2024 for Chinese National Phase Application No. 201980039559.6.
Request for re-examination filed on Mar. 27, 2025 for Chinese National Phase Application No. 201980039559.6.
Filing Receipt for Reexamination Request issued by the China National Intellectual Property Administration (CNIPA) on Apr. 7, 2025 for Chinese National Phase Application No. 201980039559.6.
Response to the Sep. 4, 2024 Examination Report filed on Feb. 27, 2025 for European Patent Application 19 785 565.3.
Experimental Data submitted with the response to the Examination Report filed on Feb. 27, 2025 for European Patent Application 19 785 565.3.
Amended claims submitted with the response to the Examination Report filed on Feb. 27, 2025 for European Patent Application 19 785 565.3.
Examination Report dated Jul. 24, 2025 for European Patent Application 19 785 565.3.
Office Action dated Nov. 20, 2024 for Korean Patent Application No. 10-2020-7032480.
English translation of the Office Action dated Nov. 20, 2024 for Korean Patent Application No. 10-2020-7032480.
Asakawa et al., Gene, 191(1): 69-79 (May 20, 1997).
A Examiner's Report dated Jan. 23, 2026 for Canadian Patent Application No. 3,096,668.
Reply to examination report filed on Jan. 22, 2026 for European Patent Application 19 785 565.3.
Claim amendments filed with the Reply to examination report filed on Jan. 22, 2026 for European Patent Application 19 785 565.3.

* cited by examiner

Figure 2

Python Code:

```python
from sklearn import svm training_set = ['BC Colon Healthy 1', 'BC Colon Healthy 2', 'BC Colon Healthy 3', 'BC Colon Healthy 4',
                'BC Colon Cancer 1', 'BC Colon Cancer 2', 'BC Colon Cancer 3', 'BC Colon Cancer 4',
                'BC Colon Cancer 5', 'BC Colon Cancer 6', 'BC Colon Cancer 7', 'BC Colon Cancer 8',
                'BC Colon Cancer 9', 'BC Colon Cancer 10', 'BC Colon Cancer 11', 'BC Colon Cancer 12',
                'BC Colon Cancer 13', 'BC Colon Cancer 14', 'BC Colon Cancer 15', 'BC Colon Cancer 16',
                'BC Colon Cancer 17', 'BC Colon Cancer 18', 'BC Colon Cancer 19', 'BC Colon Cancer 20']
test_set = ['BC Colon Healthy 5', 'BC Colon Healthy 6', 'BC Colon Healthy 7', 'BC Colon Healthy 8',
            'BC Colon Cancer 21', 'BC Colon Cancer 22', 'BC Colon Cancer 23', 'BC Colon Cancer 24',
            'BC Colon Cancer 25', 'BC Colon Cancer 26', 'BC Colon Cancer 27', 'BC Colon Cancer 28',
            'BC Colon Cancer 29', 'BC Colon Cancer 30', 'BC Colon Cancer 31', 'BC Colon Cancer 32',
            'BC Colon Cancer 33', 'BC Colon Cancer 34', 'BC Colon Cancer 35', 'BC Colon Cancer 36',
            'BC Colon Cancer 37', 'BC Colon Cancer 38', 'BC Colon Cancer 39', 'BC Colon Cancer 40']
X = data_matrix.loc[training_set].values
y = np.array(['Healthy']*4 + ['Cancer']*20)
clf = svm.SVC(C=10, kernel='linear', gamma='auto')
clf.fit(X, y)
predictions = clf.predict(data_matrix.loc[test_set].values)
results = pd.DataFrame(zip(test_set, predictions))
results.columns = ['Sample', 'Predicition']
results.set_index('Sample')
print "Specificity: %s" % (float(results.loc[test_set[:4]].query('Prediction == "Healthy"').count()) / 4)
print "Sensitivity: %s" % (float(results.loc[test_set[4:]].query('Prediction != "Healthy"').count()) /
20)
```

Code Results:

```
Specificity: 1.0
Sensitivity: 1.0
```

Figure 3a

Python Code:

```
col_colors = [sns.color_palette()[1]] * len(healthy_plasma [0:5]) + \
             [sns.color_palette()[0]] * len(healthy_plasma [5:10]) + \
             [sns.color_palette()[2]] * len(lung_cancer_plasma) + \
             [sns.color_palette()[3]] * len(BC_Lung_Cancer)

to_plot = data_matrix.loc[:, healthy_plasma+lung_cancer_plasma+BC_Lung_Cancer]

z = sns.clustermap(to_plot.fillna(0),
              mask=to_plot.isnull(),
              cmap='viridis', yticklabels=False,
              col_cluster=True, row_cluster=True,
              col_colors=col_colors)
```

Figure 3b

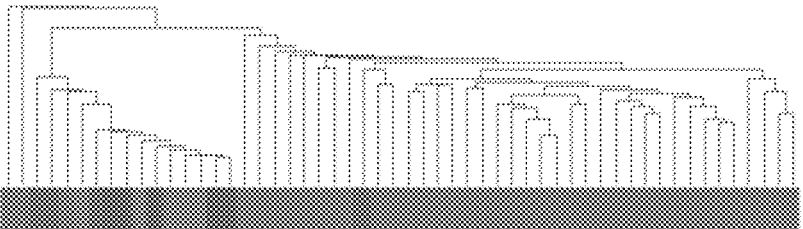

Figure 4

Python Code:

```python
from sklearn import linear_model filter_matrix = data_matrix >= 0.1
methylation_sums = data_matrix[filter_matrix].sum()

clf = linear_model.LogisticRegression(C=5)

# Fit to training set
X = np.array([methylation_sums.loc[healthy_plasma[:10]+cancer_plasma[:6]+cancer_plasma[:6]].values]).T
y = [0]*len(healthy_plasma[:10]) + [1]*len(cancer_plasma[:6]+cancer_plasma[:6])
clf.fit(X, y)

# Predict on test set
print "Sample\tP(Cancer)\tCall"
for i, methylation_sum in enumerate(methylation_sums.loc[healthy_plasma[10:]]):
    probability_cancer = min(1, max(0, model(float(clf.coef_)*methylation_sum + float(clf.intercept_))))
    if probability_cancer > 0.5:
        call = 'Cancer'
    else:
        call = 'Healthy'
    print "Healthy Sample %s\t%s\t%s" % (i+1, probability_cancer, call)

for i, methylation_sum in enumerate(methylation_sums.loc[cancer_plasma[6:]]):
    probability_cancer = min(1, max(0, model(float(clf.coef_)*methylation_sum + float(clf.intercept_))))
    if probability_cancer > 0.5:
        call = 'Cancer'
    else:
        call = 'Healthy'
    print "Cancer Sample %s\t%s\t%s" % (i+1, probability_cancer, call)
```

Code Results:

| Sample | P(Cancer) | Call |
|---|---|---|
| Healthy Sample 1 | 0.48991419229 | Healthy |
| Healthy Sample 2 | 0.402222997727 | Healthy |
| Healthy Sample 3 | 0.362647868404 | Healthy |
| Healthy Sample 4 | 0.291360093105 | Healthy |
| Healthy Sample 5 | 0.666083361246 | Cancer |
| Healthy Sample 6 | 0.444135105722 | Healthy |
| Healthy Sample 7 | 0.404667407834 | Healthy |
| Healthy Sample 8 | 0.674616468424 | Cancer |
| Healthy Sample 9 | 0.248090390611 | Healthy |
| Healthy Sample 10 | 0.270796583956 | Healthy |
| Cancer Sample 1 | 0.860345212988 | Cancer |
| Cancer Sample 2 | 0.613016848532 | Cancer |
| Cancer Sample 3 | 0.682635445446 | Cancer |
| Cancer Sample 4 | 0.59569270394 | Cancer |
| Cancer Sample 5 | 0.562216154423 | Cancer |
| Cancer Sample 6 | 0.475035178964 | Healthy |
| Cancer Sample 7 | 0.966879847323 | Cancer |

| Target Name | Target Region | Example Primers |
|---|---|---|
| Target1 | chr1:1098736-1098773 | TAGGGGGAGGCGGTTTTTTGTAGGGGG (SEQ ID NO:1), AATTTGTCGGGGTAGGTAAGGGCGGGT (SEQ ID NO:2), GCGTAGGGGGAGGCGGTTTTTTGTAGG (SEQ ID NO:3), GGCGTAGGGGGAGGCGGTTTTTTGTAG (SEQ ID NO:4), GGGGAGGCGGTTTTTTGTAGGGGGGTT (SEQ ID NO:5), TTTTTTGGACGTTGGTTAGGTTGGCGA (SEQ ID NO:6), TTTTTTGGACGTTGGTTAGGTTGGCGAT (SEQ ID NO:7), TTTTTTGGACGTTGGTTAGGTTGGCGATAG (SEQ ID NO:8), TTTTTTGGACGTTGGTTAGGTTGGCGATAG (SEQ ID NO:9), AGGATTCGTTTTAGTTTGTGTTTGTAGTGATCGGA (SEQ ID NO:10) |
| Target2 | chr1:1098787-1099554 | AAGGGTTTGGTCGGGTGCGAGGATGAT (SEQ ID NO:11), GGGTTTTGGAGTTTGCGGTGGGAAGGG (SEQ ID NO:12), AGGTCGGTCGAGTTTATGGGCGGTGAG (SEQ ID NO:13), AGAGGTCGGTCGAGTTTATGGGCGGTG (SEQ ID NO:14), GAGGTCGGTCGAGTTTATGGGCGGTGA (SEQ ID NO:15), GCGCGGGGTTTGGGAATCGGTTTTAGT (SEQ ID NO:16), AGCGCGGGGTTTGGGAATCGGTTTTAG (SEQ ID NO:17), AGGACGGCGGTGGTTGTTTTTGGAGAG (SEQ ID NO:18), GGACGGCGGTGGTTGTTTTTGGAGAGA (SEQ ID NO:19), ATAGCGCGGGGTTTGGGAATCGGTTTT (SEQ ID NO:20) |
| Target3 | chr1:1474968-1474978 | TGGTAGTTTTTAAGGGTGGAAGGCGGT (SEQ ID NO:21), TGGTAGTTTTTAAGGGTGGAAGGCGGTT (SEQ ID NO:22), TTGGTAGTTTTTAAGGGTGGAAGGCGGT (SEQ ID NO:23), TGGTAGTTTTTAAGGGTGGAAGGCGGTTC (SEQ ID NO:24), GGTAGTTTTTAAGGGTGGAAGGCGGTTC (SEQ ID NO:25), GGTTTATTCGGGGCGCGGGGGAATTAG (SEQ ID NO:26), TTCGGGGCGCGGGGGAATTAGTTTTAC (SEQ ID NO:27), GGGTTTATTCGGGGCGCGGGGGAATTA (SEQ ID NO:28), CGTGAGCGTATATGTGTGGCGGGGTTT (SEQ ID NO:29), TCGGGGCGCGGGGGAATTAGTTTTACG (SEQ ID NO:30) |
| Target4 | chr1:1474994-1475002 | GCGGTTTGCGTGGGGTTGGTTTTTTCG (SEQ ID NO:31), GCGGTTTGCGTGGGGTTGGTTTTTTC (SEQ ID NO:32), CGGTTTGCGTGGGGTTGGTTTTTTCG (SEQ ID NO:33), TGGTAGTTTTTAAGGGTGGAAGGCGGT (SEQ ID NO:34), GCGGTTTGCGTGGGGTTGGTTTTTT (SEQ ID NO:35), CGTGAGCGTATATGTGTGGCGGGGTTT (SEQ ID NO:36), ATATGTGTGGCGGGGTTTATTCGGGGC (SEQ ID NO:37), TATGTGTGGCGGGGTTTATTCGGGGCG (SEQ ID NO:38), ATATGTGTGGCGGGGTTTATTCGGGGCG (SEQ ID NO:39), TATGTGTGGCGGGGTTTATTCGGGGC (SEQ ID NO:40) |
| Target5 | chr1:1475031-1475165 | GCGGTTTGCGTGGGGTTGGTTTTTTCG (SEQ ID NO:41), CGGTTTTCGTTTCGTAGGTGCGGGAGG (SEQ ID NO:42), GGTTTTCGTTTCGTAGGTGCGGGAGGA (SEQ ID NO:43), CGTAGGTGCGGGAGGATGTAGTTGTGG (SEQ ID NO:44), CGGTTTTCGTTTCGTAGGTGCGGGAGGA (SEQ ID NO:45), TGTGGTCGGTGAGTTTATAATCGGCGT (SEQ ID NO:46), CGTTTCGTTTCGTTCGTTTTTTGGCGT (SEQ ID NO:47), TCGTTTCGTTTCGTTCGTTTTTTGGCGT (SEQ ID NO:48), TCGTTTCGTTTCGTTCGTTTTTTGGCGG (SEQ ID NO:49), TGTGGTCGGTGAGTTTATAATCGGCGTC (SEQ ID NO:50) |
| Target6 | chr1:2375223-2375249 | GTAGGGGGTGTGGTGCGGGCGGTAC (SEQ ID NO:51), GGTAGGGGGTGTGGTGCGGGCGGTAC (SEQ ID NO:52), TAGGGGGTGTGGTGCGGGCGGTAC (SEQ ID NO:53), GTAGGGGGTGTGGTGCGGGCGGTA (SEQ ID NO:54), GGGTAGGGGGTGTGGTGCGGGCGGTAC (SEQ ID NO:55), CGGGGTTCGGGGTTGGGGTTTCGGTTTTC (SEQ ID NO:56), CGGTATCGTTTCGTTAGTTCGGGCGGT (SEQ ID NO:57), CGGGGTTCGGGGTTGGGGTTTCGGTTTT (SEQ ID NO:58), CGGTATCGTTTCGTTAGTTCGGGCGGTT (SEQ ID NO:59), CGGGGTTCGGGGTTGGGGTTTCGGTTT (SEQ ID NO:60) |
| Target7 | chr1:2375267-2375277 | TCGTTCGAGTTGGCGGGGCGATGTC (SEQ ID NO:61), CGTTCGAGTTGGCGGGGCGATGTC (SEQ ID NO:62), TCGTTCGAGTTGGCGGGGCGATGT (SEQ ID NO:63), CGTTCGAGTTGGCGGGGCGATGT (SEQ ID NO:64), TCGTTCGAGTTGGCGGGGCGATG (SEQ ID NO:65), CGGGTTCGGGGTTGGGGTTTCGGTTTTC (SEQ ID NO:66), CGGGTTCGGGGTTGGGGTTTCGGTTTT (SEQ ID NO:67), CGGGGTTCGGGGTTGGGGTTTCGGTTT (SEQ ID NO:68), GGGTTCGGGGTTGGGGTTTCGGTTTTC (SEQ ID NO:69), CGGGTTCGGGGTTGGGGTTTCGGTT (SEQ ID NO:70) |
| Target8 | chr1:2705891-2705920 | TCGGATTGCGGTTCGGTCGATGGAAGT (SEQ ID NO:71), TTCGGATTGCGGTTCGGTCGATGGAAG (SEQ ID NO:72), TTTCGGATTGCGGTTCGGTCGATGGAA (SEQ ID NO:73), TTTTCGGATTGCGGTTCGGTCGATGGA (SEQ ID NO:74), TTCGGATTGCGGTTCGGTCGATGGAAGT (SEQ ID NO:75), TGGGGTCGTTGTTTTTTGCGGGTTTTT (SEQ ID NO:76), AGGAATGAACGGAGGTAGTGGTTGGTG (SEQ ID NO:77), GGAATGAACGGAGGTAGTGGTTGGTGA (SEQ ID NO:78), AGGAATGAACGGAGGTAGTGGTTGGTGA (SEQ ID NO:79), TGGGGTCGTTGTTTTTTGCGGGTTTTT (SEQ ID NO:80) |
| Target9 | chr1:2706004-2706027 | TCGGATTGCGGTTCGGTCGATGGAAGT (SEQ ID NO:81), TTCGGATTGCGGTTCGGTCGATGGAAG (SEQ ID NO:82), TTTCGGATTGCGGTTCGGTCGATGGAA (SEQ ID NO:83), TTTTCGGATTGCGGTTCGGTCGATGGA (SEQ ID NO:84), TTCGGATTGCGGTTCGGTCGATGGAAGT (SEQ ID NO:85), CGTAGGAGGGGTGAGGATTCGTTCGGG (SEQ ID NO:86), GAGCGTAGGGTCGGAGGGAGGTCGTAG (SEQ ID NO:87), ACGTAGGAGGGGTGAGGATTCGTTCGG (SEQ ID NO:88), CGTTGGGGTCGTTGTTTTTTGCGGGTT (SEQ ID NO:89), AGGAGGGGTGAGGATTCGTTCGGGTAC (SEQ ID NO:90) |

FIGURE 5

| | | |
|---|---|---|
| Target10 | chr1:2706076-2706092 | TTTTTTGCGTGGTGGGGTCGTTCG (SEQ ID NO:91), TTTTTGCGTGGTGGGGTCGTTCG (SEQ ID NO:92), TTTTGCGTGGTGGGGTCGTTCG (SEQ ID NO:93), TTTGCGTGGTGGGGTCGTTCG (SEQ ID NO:94), GCGGGAGGAGGTTCGTGGGATGTTGTA (SEQ ID NO:95), GTTGTTGTTGGTGGTGTTGCGGGAGGA (SEQ ID NO:96), GGTTGTTGTTGGTGGTGTTGCGGGAGG (SEQ ID NO:97), GGGTTGTTGTTGGTGGTGTTGCGGGAG (SEQ ID NO:98), TTGTTGGTGGTGTTGCGGGAGGAGGTT (SEQ ID NO:99) |
| Target11 | chr1:2706118-2706138 | TGGTGGGGTCGTTCGTTTTTGCGGTTT (SEQ ID NO:100), GTGGTGGGGTCGTTCGTTTTTGCGGTT (SEQ ID NO:101), TTGCGTGGTGGGGTCGTTCGTTTTTGC (SEQ ID NO:102), GGTGGGGTCGTTCGTTTTTGCGGTTTT (SEQ ID NO:103), TGGTGGGGTCGTTCGTTTTTGCGGTTTT (SEQ ID NO:104), GCGGGAGGAGGTTCGTGGGATGTTGTA (SEQ ID NO:105), GTTTGTAGGTTGCGGTTCGAGGAGGCG (SEQ ID NO:106), CGTTTGTAGGTTGCGGTTCGAGGAGGC (SEQ ID NO:107), TAGGTTGCGGTTCGAGGAGGCGTTGTT (SEQ ID NO:108), TTGTAGGTTGCGGTTCGAGGAGGCGTT (SEQ ID NO:109) |
| Target12 | chr1:2706146-2706174 | TGGTGGGGTCGTTCGTTTTTGCGGTTT (SEQ ID NO:110), GTGGTGGGGTCGTTCGTTTTTGCGGTT (SEQ ID NO:111), GGTTCGGCGCGTGGAGATCGTTGTAGT (SEQ ID NO:112), TTGCGTGGTGGGGTCGTTCGTTTTTGC (SEQ ID NO:113), GGTGGGGTCGTTCGTTTTTGCGGTTTT (SEQ ID NO:114), GCGGGAGGAGGTTCGTGGGATGTTGTA (SEQ ID NO:115), GTTTGTAGGTTGCGGTTCGAGGAGGCG (SEQ ID NO:116), CGTTTGTAGGTTGCGGTTCGAGGAGGC (SEQ ID NO:117), TAGGTTGCGGTTCGAGGAGGCGTTGTT (SEQ ID NO:118), TTGTAGGTTGCGGTTCGAGGAGGCGTT (SEQ ID NO:119) |
| Target13 | chr1:2706213-2706262 | GGTTCGGCGCGTGGAGATCGTTGTAGT (SEQ ID NO:120), GGTTCGGCGCGTGGAGATCGTTGTAGTA (SEQ ID NO:121), GTTCGGCGCGTGGAGATCGTTGTAGTA (SEQ ID NO:122), CGGTTCGGCGCGTGGAGATCGTTGTAG (SEQ ID NO:123), GGTTCGGCGCGTGGAGATCGTTGTAG (SEQ ID NO:124), ACGGTAGTGGAGTAGGGGGCGTCGTAT (SEQ ID NO:125), TAGACGGTAGTGGAGTAGGGGGCGTCG (SEQ ID NO:126), GTTTGTAGGTTGCGGTTCGAGGAGGCG (SEQ ID NO:127), CGTTTGTAGGTTGCGGTTCGAGGAGGC (SEQ ID NO:128), TAGGTTGCGGTTCGAGGAGGCGTTGTT (SEQ ID NO:129) |
| Target14 | chr1:2706277-2706336 | TTCGGGTCGTAGTTTGTAGGCGGTGAT (SEQ ID NO:130), TCGGGTCGTAGTTTGTAGGCGGTGATA (SEQ ID NO:131), TCGGGTCGTAGTTTGTAGGCGGTGAT (SEQ ID NO:132), CGGGTCGTAGTTTGTAGGCGGTGATAT (SEQ ID NO:133), TCGGGTCGTAGTTTGTAGGCGGTGATAT (SEQ ID NO:134), ACGGTAGTGGAGTAGGGGGCGTCGTAT (SEQ ID NO:135), TAGACGGTAGTGGAGTAGGGGGCGTCG (SEQ ID NO:136), GACGGTAGTGGAGTAGGGGGCGTCGTA (SEQ ID NO:137), CGGTAGTGGAGTAGGGGGCGTCGTATT (SEQ ID NO:138), ACGGTAGTGGAGTAGGGGGCGTCGTA (SEQ ID NO:139) |
| Target15 | chr1:2706355-2706422 | TTTCGGGTCGTAGTTTGTAGGCGGTGA (SEQ ID NO:140), GCGTATATAGTTTTTCGGGTGCGGCGT (SEQ ID NO:141), TTCGGGTCGTAGTTTGTAGGCGGTGAT (SEQ ID NO:142), AGTTTTTCGGGTGCGGCGTTTTTTGTT (SEQ ID NO:143), TTTTCGGGTCGTAGTTTGTAGGCGGTG (SEQ ID NO:144), GGATTTTGCGGGGGATCGTGTAGGGGA (SEQ ID NO:145), AGGATTTTGCGGGGGATCGTGTAGGGG (SEQ ID NO:146), GGATTTTGCGGGGGATCGTGTAGGGGAT (SEQ ID NO:147), TGAGGATTTTGCGGGGGATCGTGTAGGG (SEQ ID NO:148), GAGGATTTTGCGGGGGATCGTGTAGGG (SEQ ID NO:149) |
| Target16 | chr1:2706423-2706476 | GCGTAGAGTTAGGAGAGGTGCGCGGTT (SEQ ID NO:150), GGAGAGGTGCGCGGTTTTTTGTACGGT (SEQ ID NO:151), AGGAGAGGTGCGCGGTTTTTTGTACGG (SEQ ID NO:152), GCGTAGAGTTAGGAGAGGTGCGCGGT (SEQ ID NO:153), GCGTAGAGTTAGGAGAGGTGCGCGGTTT (SEQ ID NO:154), GGATTTTGCGGGGGATCGTGTAGGGGA (SEQ ID NO:155), AGGATTTTGCGGGGGATCGTGTAGGGG (SEQ ID NO:156), GTGTTTGTTGTTGGTAGGGGACGCGGC (SEQ ID NO:157), AGTGTTTGTTGTTGGTAGGGGACGCGC (SEQ ID NO:158), GGATTTTGCGGGGGATCGTGTAGGGGAT (SEQ ID NO:159) |
| Target17 | chr1:2706491-2706525 | CGTGCGGGTCGTAGTAGGCGTTCGTAT (SEQ ID NO:160), GCGTAGAGTTAGGAGAGGTGCGCGGTT (SEQ ID NO:161), GGAGAGGTGCGCGGTTTTTTGTACGGT (SEQ ID NO:162), TTCGTAGGGTTTTTAGGGCGTGCGGGT (SEQ ID NO:163), TAGGGTTTTTAGGGCGTGCGGGTCGTA (SEQ ID NO:164), GTGTTTGTTGTTGGTAGGGGACGCGGC (SEQ ID NO:165), AGTGTTTGTTGTTGGTAGGGGACGCGG (SEQ ID NO:166), TGTTTGTTGTTGGTAGGGGACGCGGC (SEQ ID NO:167), TTCGGGTTATGTGCGAGCGTTTGTTGC (SEQ ID NO:168), CGAGTGTTTGTTGTTGGTAGGGGACGCG (SEQ ID NO:169) |
| Target18 | chr1:2706532-2706583 | CGTGCGGGTCGTAGTAGGCGTTCGTAT (SEQ ID NO:170), GCGTAGAGTTAGGAGAGGTGCGCGGTT (SEQ ID NO:171), GGTATTCGGCGAGGCGGGTTTTTAGCG (SEQ ID NO:172), GGCGTTCGTATATGGTTCGGGCGTTCG (SEQ ID NO:173), GGAGAGGTGCGCGGTTTTTTGTACGGT (SEQ ID NO:174), GTGTTTGTTGTTGGTAGGGGACGCGGT (SEQ ID NO:175), AGTGTTTGTTGTTGGTAGGGGACGCGG (SEQ ID NO:176), CGAGTGTTTGTTGTTGGTAGGGGACGCG (SEQ ID NO:177), AGTGTTTGTTGTTGGTAGGGGACGCGGT (SEQ ID NO:178), GAGTGTTTGTTGTTGGTAGGGGACGCGG (SEQ ID NO:179) |
| Target19 | chr1:2706587-2706602 | CGTGCGGGTCGTAGTAGGCGTTCGTAT (SEQ ID NO:180), GGTATTCGGCGAGGCGGGTTTTTAGCG (SEQ ID NO:181), GGCGTTCGTATATGGTTCGGGCGTTCG (SEQ ID NO:182), TAGGGTTTTTAGGGCGTGCGGGTCGTA (SEQ ID NO:183), TTTTAGGGCGTGCGGGTCGTAGTAGGC (SEQ ID NO:184), CGAGTTGTTGGTTTCGGTAATTCGCGCG (SEQ ID NO:185), |

FIGURE 5 CONTINUED

|  |  |  |
|---|---|---|
|  |  | AGTTGTTGGTTTCGGTAATTCGCGCGT (SEQ ID NO:186), CGAGTTGTTGGTTTCGGTAATTCGCGCGT (SEQ ID NO:187), GAGTTGTTGGTTTCGGTAATTCGCGCGT (SEQ ID NO:188), GAGTTGTTGGTTTCGGTAATTCGCGCG (SEQ ID NO:189) |
| Target20 | chr1:2706608-2706621 | CGTGCGGGTCGTAGTAGGCGTTCGTAT (SEQ ID NO:190), GGTATTCGGCGAGGCGGGTTTTTAGCG (SEQ ID NO:191), GGCGTTCGTATATGGTTCGGGCGTTCG (SEQ ID NO:192), GCGTTCGTATATGGTTCGGGCGTTCGT (SEQ ID NO:193), AGGTATTCGGCGAGGCGGGTTTTTAGC (SEQ ID NO:194), CGAGTTGTTGGTTTCGGTAATTCGCGCG (SEQ ID NO:195), AGTTGTTGGTTTCGGTAATTCGCGCGT (SEQ ID NO:196), CGAGTTGTTGGTTTCGGTAATTCGCGCGT (SEQ ID NO:197), GAGTTGTTGGTTTCGGTAATTCGCGCGT (SEQ ID NO:198), GAGTTGTTGGTTTCGGTAATTCGCGCG (SEQ ID NO:199) |
| Target21 | chr1:2706629-2706667 | GGTATTCGGCGAGGCGGGTTTTTAGCG (SEQ ID NO:200), GGCGTTCGTATATGGTTCGGGCGTTCG (SEQ ID NO:201), GCGTTCGTATATGGTTCGGGCGTTCGT (SEQ ID NO:202), AGGTATTCGGCGAGGCGGGTTTTTAGC (SEQ ID NO:203), AGGCGTTCGTATATGGTTCGGGCGTTC (SEQ ID NO:204), GCGTTCGGGTTTAGGCGTAGGAGGTCG (SEQ ID NO:205), GCGTTCGGGTTTAGGCGTAGGAGGTC (SEQ ID NO:206), CGTTCGGGTTTAGGCGTAGGAGGTCG (SEQ ID NO:207), TCGTTCGTTTTTAGGAAGTCGTGCGGA (SEQ ID NO:208), GCGTTCGGGTTTAGGCGTAGGAGGT (SEQ ID NO:209) |
| Target22 | chr1:2706668-2706691 | GGTATTCGGCGAGGCGGGTTTTTAGCG (SEQ ID NO:210), AGGTATTCGGCGAGGCGGGTTTTTAGC (SEQ ID NO:211), AGTAGTAGGTATTCGGCGAGGCGGGTT (SEQ ID NO:212), TCGCGGAGTTTAGGGTGGTTTCGTACG (SEQ ID NO:213), AGTAGGTATTCGGCGAGGCGGGTTTTT (SEQ ID NO:214), TTGGGGCGCGGAGGTAGTTTTAGGTCG (SEQ ID NO:215), GCGTTCGGGTTTAGGCGTAGGAGGTCG (SEQ ID NO:216), GGGGCGCGGAGGTAGTTTTAGGTCGTG (SEQ ID NO:217), TTTGGGGCGCGGAGGTAGTTTTAGGTC (SEQ ID NO:218), TGGGGCGCGGAGGTAGTTTTAGGTCG (SEQ ID NO:219) |
| Target23 | chr1:2706721-2706734 | CGCGGAGTTTAGGGTGGTTTCGTACGG (SEQ ID NO:220), TCGCGGAGTTTAGGGTGGTTTCGTACGG (SEQ ID NO:221), GCGGAGTTTAGGGTGGTTTCGTACGGT (SEQ ID NO:222), CGCGGAGTTTAGGGTGGTTTCGTACGGT (SEQ ID NO:223), TCGCGGAGTTTAGGGTGGTTTCGTACG (SEQ ID NO:224), CGTTCGGGTTTAGGCGTAGGAGGTCGT (SEQ ID NO:225), GGGCGCGGAGGTAGTTTTAGGTCGTGT (SEQ ID NO:226), TTGGGGCGCGGAGGTAGTTTTAGGTCG (SEQ ID NO:227), GCGTTCGGGTTTAGGCGTAGGAGGTCG (SEQ ID NO:228), GGGGCGCGGAGGTAGTTTTAGGTCGTG (SEQ ID NO:229) |
| Target24 | chr1:6125159-6125201 | GGCGTTGTAGTTAGGGTGGATTTTGCGGG (SEQ ID NO:230), AGGGTGGATTTTGCGGGTTGGATGTTT (SEQ ID NO:231), GGGTGGATTTTGCGGGTTGGATGTTTG (SEQ ID NO:232), GCGTTGTAGTTAGGGTGGATTTTGCGGG (SEQ ID NO:233), GGCGTTGTAGTTAGGGTGGATTTTGCGG (SEQ ID NO:234) |
| Target25 | chr1:6125229-6125498 | GGTGTCGTTGGGTATGCGTTAGGGAGGT (SEQ ID NO:235), GGTGTCGTTGGGTATGCGTTAGGGAGG (SEQ ID NO:236), AGGTGTCGTTGGGTATGCGTTAGGGAGG (SEQ ID NO:237), GTGTCGTTGGGTATGCGTTAGGGAGGT (SEQ ID NO:238), AGGTGTCGTTGGGTATGCGTTAGGGAG (SEQ ID NO:239), AGGGTGGATTTTGCGGGTTGGATGTTT (SEQ ID NO:240), GGATTGGTTTGAGGTTTGGGTAGGCGT (SEQ ID NO:241), GGGTGGATTTTGCGGGTTGGATGTTTG (SEQ ID NO:242), AGGATTGGTTTGAGGTTTGGGTAGGCGT (SEQ ID NO:243), TTGGTTTGAGGTTTGGGTAGGCGTTGT (SEQ ID NO:244) |
| Target26 | chr1:7728694-7728716 | CGTTTGGTTGCGTTGAATTGGTGGTGACG (SEQ ID NO:245), TTTGGTTGCGTTGAATTGGTGGTGACG (SEQ ID NO:246), CGTTTGGTTGCGTTGAATTGGTGGTGA (SEQ ID NO:247), TCGTTTGGTTGCGTTGAATTGGTGGTG (SEQ ID NO:248), TCGTTTGGTTGCGTTGAATTGGTGGTGA (SEQ ID NO:249) |
| Target27 | chr1:7728839-7729031 | TGGATGTTGAGTTGTTTTGCGGCGGTT (SEQ ID NO:250), ATGGATGTTGAGTTGTTTTGCGGCGGT (SEQ ID NO:251), GGATGGATGTTGAGTTGTTTTGCGGCGG (SEQ ID NO:252), TGGATGGATGTTGAGTTGTTTTGCGGCGG (SEQ ID NO:253), GATGGATGTTGAGTTGTTTTGCGGCGGT (SEQ ID NO:254), GGGTATTGGGGGGGAGTGGGTGTTTGGT (SEQ ID NO:255), GTTTCGTGGAAGTGGCGGGGTATTGGG (SEQ ID NO:256), TGGGGGGAGTGGGTGTTTGGTTGAGAA (SEQ ID NO:257), TTGGGGGGAGTGGGTGTTTGGTTGAGA (SEQ ID NO:258), GGGGTATTGGGGGGGAGTGGGTGTTTGG (SEQ ID NO:259) |
| Target28 | chr1:8137417-8137568 | CGTGGTTGGGTTGTAGGGTCGTAGGGT (SEQ ID NO:260), ACGTGGTTGGGTTGTAGGGTCGTAGGG (SEQ ID NO:261), TGGGTTGTAGGGTCGTAGGGTTGTGGT (SEQ ID NO:262), GACGTGGTTGGGTTGTAGGGTCGTAGGG (SEQ ID NO:263), CGTGGTTGGGTTGTAGGGTCGTAGGGTT (SEQ ID NO:264) |
| Target29 | chr1:9377821-9377886 | GGGATTATAGGCGTGAGTTATCGTGTTTGGT (SEQ ID NO:265), TGGGATTATAGGCGTGAGTTATCGTGTTTGG (SEQ ID NO:266), GTGTTGGGATTATAGGCGTGAGTTATCGTGT (SEQ ID NO:267), TGGGATTATAGGCGTGAGTTATCGTGTTTGGT (SEQ ID NO:268), AGTGTTGGGATTATAGGCGTGAGTTATCGTG (SEQ ID NO:269), CGGAGCGAATGGTGTGTTAAGGAAGTAAGA (SEQ ID NO:270), CGGAGCGAATGGTGTGTTAAGGAAGTAAGAA (SEQ ID NO:271), CGGAGCGAATGGTGTGTTAAGGAAGTAAGAAA (SEQ ID NO:272), |

FIGURE 5 CONTINUED

CGGAGCGAATGGTGTGTTAAGGAAGTAAGAAAT (SEQ ID NO:273),
CGGAGCGAATGGTGTGTTAAGGAAGTAAGAAATT (SEQ ID NO:274)

| | | |
|---|---|---|
| Target30 | chr1:9377977-9378177 | AGATTGGCGGGTCGTTTTGGTGGGAGT (SEQ ID NO:275), GATTGGCGGGTCGTTTTGGTGGGAGTT (SEQ ID NO:276), TGGCGGGTCGTTTTGGTGGGAGTTTTT (SEQ ID NO:277), TTGGCGGGTCGTTTTGGTGGGAGTTTT (SEQ ID NO:278), ATTGGCGGGTCGTTTTGGTGGGAGTTT (SEQ ID NO:279), TGTATTCGTGGTGGAGGATTTGGGGGT (SEQ ID NO:280), CGGTTGTATTCGTGGTGGAGGATTTGGGG (SEQ ID NO:281), GGTTGTATTCGTGGTGGAGGATTTGGGGG (SEQ ID NO:282), GGTTGTATTCGTGGTGGAGGATTTGGGGGT (SEQ ID NO:283), TTGTATTCGTGGTGGAGGATTTGGGGGT (SEQ ID NO:284) |
| Target31 | chr1:9378325-9378377 | GGGAAGGTGGGTGTGGGTATTCGGAGG (SEQ ID NO:285), GGGGAAGGTGGGTGTGGGTATTCGGAG (SEQ ID NO:286), GTGGGGGAAGGTGGGTGTGGGTATTCG (SEQ ID NO:287), AGTGGGGGAAGGTGGGTGTGGGTATTC (SEQ ID NO:288), GGAAGGTGGGTGTGGGTATTCGGAGGT (SEQ ID NO:289), AGTAAGGGAGGCGTGGGTGGGTAGAGA (SEQ ID NO:290), AAGGGAGGCGTGGGTGGGTAGAGATTT (SEQ ID NO:291), GCGTGGGTGGGTAGAGATTTAAGCGGG (SEQ ID NO:292), GGCGTGGGTGGGTAGAGATTTAAGCGG (SEQ ID NO:293), GTAAGGGAGGCGTGGGTGGGTAGAGAT (SEQ ID NO:294) |
| Target32 | chr1:9378451-9378489 | TGCGGATAGATAGGGAATGGGGATAGCGT (SEQ ID NO:295), GCGGATAGATAGGGAATGGGGATAGCGT (SEQ ID NO:296), TGCGGATAGATAGGGAATGGGGATAGCG (SEQ ID NO:297), GCGGATAGATAGGGAATGGGGATAGCG (SEQ ID NO:298), GCGGATAGATAGGGAATGGGGATAGCGTT (SEQ ID NO:299), TGGGAGTGGAGGAAGGAGGGTGGTTTT (SEQ ID NO:300), TTGGGAGTGGAGGAAGGAGGGTGGTTT (SEQ ID NO:301), TTTGGGAGTGGAGGAAGGAGGGTGGTT (SEQ ID NO:302), ATTTGGGAGTGGAGGAAGGAGGGTGGT (SEQ ID NO:303), GGAATATGGTAGGGGGGTTTCGTGGGC (SEQ ID NO:304) |
| Target33 | chr1:15672463-15672644 | TGATTTAGATGTGTGAAAATAGGGGCGTTCGT (SEQ ID NO:305), ATGATTTAGATGTGTGAAAATAGGGGCGTTCGT (SEQ ID NO:306), TGATTTAGATGTGTGAAAATAGGGGCGTTCGTA (SEQ ID NO:307), GATGATTTAGATGTGTGAAAATAGGGGCGTTCG (SEQ ID NO:308), GATGATTTAGATGTGTGAAAATAGGGGCGTTCGT (SEQ ID NO:309), ATAAGGGCGTTTGGGTTCGGGGAGGAG (SEQ ID NO:310), TATTTTGTGGGAGCGTAGGGGAGGGCG (SEQ ID NO:311), AGCGTAGGGGAGGGCGGAGGATTGATA (SEQ ID NO:312), GGCGTTTGGGTTCGGGGAGGAGTAGAT (SEQ ID NO:313), AATAAGGGCGTTTGGGTTCGGGGAGGA (SEQ ID NO:314) |
| Target34 | chr1:29586062-29586108 | GCGTCGTTTTAGTGTATGGTCGCGGGT (SEQ ID NO:315), GCGTCGTTTTAGTGTATGGTCGCGGGTA (SEQ ID NO:316), CGGGAGCGGTGATTTTGGTTGGGGGG (SEQ ID NO:317), GGGAGCGGTGATTTTGGTTGGGGGC (SEQ ID NO:318), GGAGCGGTGATTTTGGTTGGGGGCG (SEQ ID NO:319), GCGTAGAGTAGAGTTAGGGGAGGGTCGGG (SEQ ID NO:320), AGAGTAGAGTTAGGGGAGGGTCGGGAC (SEQ ID NO:321), GCGTAGAGTAGAGTTAGGGGAGGGTCGG (SEQ ID NO:322), AGCGTAGAGTAGAGTTAGGGGAGGGTCGG (SEQ ID NO:323), CGTAGAGTAGAGTTAGGGGAGGGTCGG (SEQ ID NO:324) |
| Target35 | chr1:29586281-29586300 | TTATGTTCGCGCGGTGTAGTAGGGACG (SEQ ID NO:325), TTTATGTTCGCGCGGTGTAGTAGGGACG (SEQ ID NO:326), TATGTTCGCGCGGTGTAGTAGGGACG (SEQ ID NO:327), TTTATGTTCGCGCGGTGTAGTAGGGAC (SEQ ID NO:328), ATGTTCGCGCGGTGTAGTAGGGACG (SEQ ID NO:329), GAGAGTGAGGGGGTTAGGGGCGTTTCG (SEQ ID NO:330), AGGGAAGAGAGTGAGGGGGTTAGGGGC (SEQ ID NO:331), AGAGAGTGAGGGGGTTAGGGGCGTTTC (SEQ ID NO:332), GAAGAGAGTGAGGGGGTTAGGGGCGTT (SEQ ID NO:333), GGAAGAGAGTGAGGGGGTTAGGGGCGT (SEQ ID NO:334) |
| Target36 | chr1:29586324-29586346 | GTTCGCGCGGTGTAGTAGGGACGGTTA (SEQ ID NO:335), TATGTTCGCGCGGTGTAGTAGGGACGG (SEQ ID NO:336), TCGCGCGGTGTAGTAGGGACGGTTAAA (SEQ ID NO:337), TTCGCGCGGTGTAGTAGGGACGGTTAA (SEQ ID NO:338), TTATGTTCGCGCGGTGTAGTAGGGACGG (SEQ ID NO:339), GAGAGTGAGGGGGTTAGGGGCGTTTCG (SEQ ID NO:340), AGCGTCGGTGGTTGATGTGTCGTACGT (SEQ ID NO:341), AGGAAGCGTCGGTGGTTGATGTGTCGT (SEQ ID NO:342), AGGGAAGAGAGTGAGGGGGTTAGGGGC (SEQ ID NO:343), AGCGGGAAAGTGGTTAGGAAGCGTCGG (SEQ ID NO:344) |
| Target37 | chr1:29586382-29586522 | GTTCGCGCGGTGTAGTAGGGACGGTTA (SEQ ID NO:345), TATGTTCGCGCGGTGTAGTAGGGACGG (SEQ ID NO:346), CGTTGTGTGTTTTAGGTTTCGCGCGGC (SEQ ID NO:347), TCGCGCGGTGTAGTAGGGACGGTTAAA (SEQ ID NO:348), TTCGCGCGGTGTAGTAGGGACGGTTAA (SEQ ID NO:349), GCGGTATAGGTTTTGTTCGGCGCGGTT (SEQ ID NO:350), AGCGTCGGTGGTTGATGTGTCGTACGT (SEQ ID NO:351), AGGAAGCGTCGGTGGTTGATGTGTCGT (SEQ ID NO:352), AGCGGGAAAGTGGTTAGGAAGCGTCGG (SEQ ID NO:353), GCGTCGGTGGTTGATGTGTCGTACGTT (SEQ ID NO:354) |
| Target38 | chr1:29586539-29586574 | CGTTGTGTGTTTTAGGTTTCGCGCGGC (SEQ ID NO:355), TCGTTGTGTGTTTTAGGTTTCGCGCGG (SEQ ID NO:356), TCGTTGTGTGTTTTAGGTTTCGCGCGGC (SEQ ID NO:357), ATCGTTGTGTGTTTTAGGTTTCGCGCGG (SEQ ID NO:358), ATCGTTGTGTGTTTTAGGTTTCGCGCGGC (SEQ ID NO:359), CGAGGGTGAGGTTTCGGCGTTTTTC (SEQ ID NO:360), CGAGGGTGAGGTTTCGGCGTTTTT (SEQ ID NO:361), CGAGGGTGAGGTTTCGGCGTTTT (SEQ ID |

FIGURE 5 CONTINUED

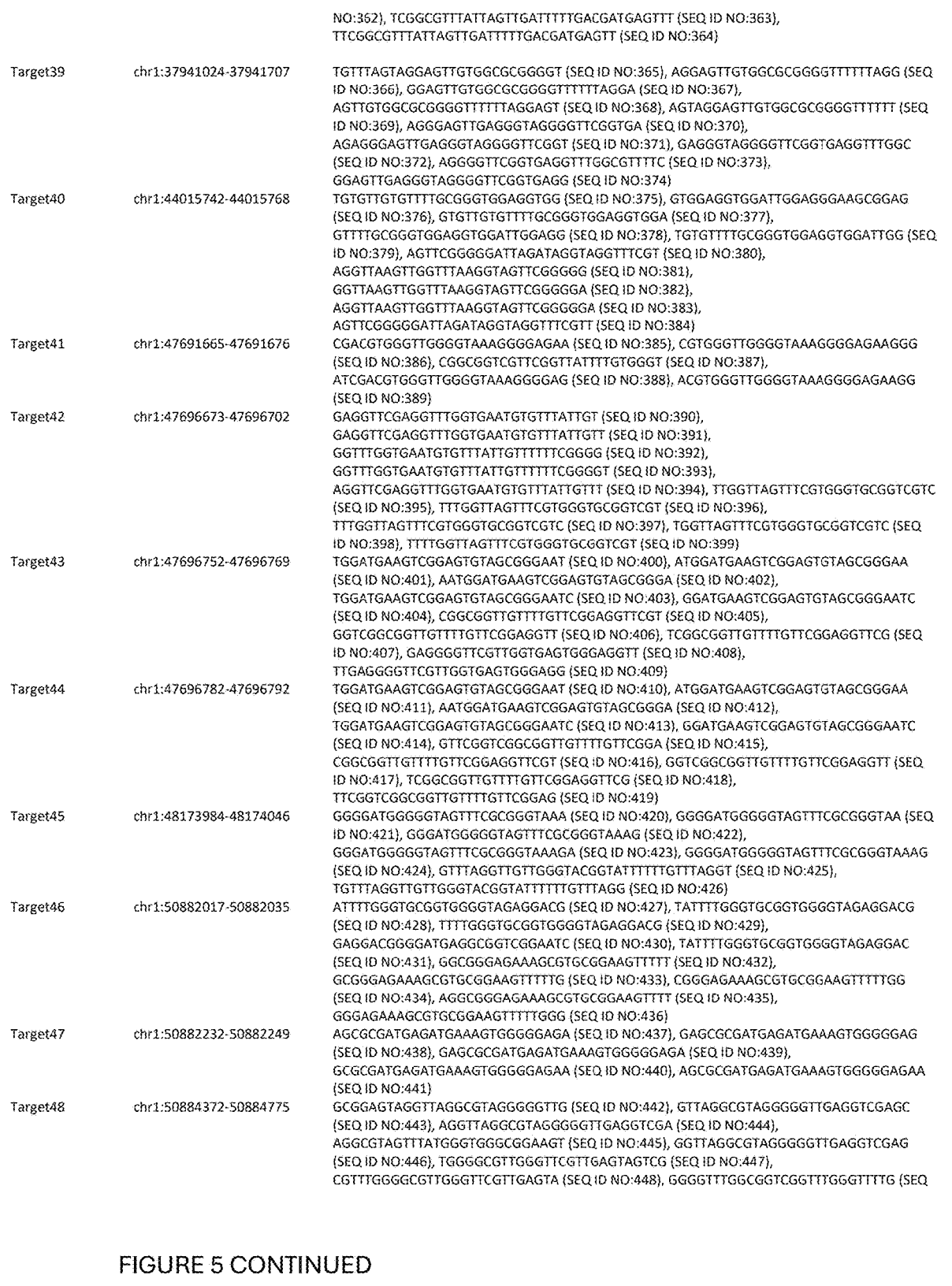

NO:362), TCGGCGTTTATTAGTTGATTTTTGACGATGAGTTT (SEQ ID NO:363),
TTCGGCGTTTATTAGTTGATTTTTGACGATGAGTT (SEQ ID NO:364)

| Target39 | chr1:37941024-37941707 | TGTTTAGTAGGAGTTGTGGCGCGGGGT (SEQ ID NO:365), AGGAGTTGTGGCGCGGGGGTTTTTTAGG (SEQ ID NO:366), GGAGTTGTGGCGCGGGGGTTTTTTAGGA (SEQ ID NO:367), AGTTGTGGCGCGGGGGTTTTTTAGGAGT (SEQ ID NO:368), AGTAGGAGTTGTGGCGCGGGGGTTTTTT (SEQ ID NO:369), AGGGGAGTTGAGGGTAGGGGTTCGGTGA (SEQ ID NO:370), AGAGGGAGTTGAGGGTAGGGGTTCGGT (SEQ ID NO:371), GAGGGTAGGGGTTCGGTGAGGTTTGGC (SEQ ID NO:372), AGGGGTTCGGTGAGGTTTGGCGTTTC (SEQ ID NO:373), GGAGTTGAGGGTAGGGGTTCGGTGAGG (SEQ ID NO:374) |
| Target40 | chr1:44015742-44015768 | TGTGTTGTGTTTTGCGGGTGGAGGTGG (SEQ ID NO:375), GTGGAGGTGGATTGGAGGGAAGCGGAG (SEQ ID NO:376), GTGTTGTGTTTTGCGGGTGGAGGTGGA (SEQ ID NO:377), GTTTTGCGGGTGGAGGTGGATTGGAGG (SEQ ID NO:378), TGTGTTTTGCGGGTGGAGGTGGATTGG (SEQ ID NO:379), AGTTCGGGGGGATTAGATAGGTAGGTTTCGT (SEQ ID NO:380), AGGTTAAGTTGGTTTAAGGTAGTTCGGGGG (SEQ ID NO:381), GGTTAAGTTGGTTTAAGGTAGTTCGGGGGA (SEQ ID NO:382), AGGTTAAGTTGGTTTAAGGTAGTTCGGGGGA (SEQ ID NO:383), AGTTCGGGGGGATTAGATAGGTAGGTTTCGTT (SEQ ID NO:384) |
| Target41 | chr1:47691665-47691676 | CGACGTGGGTTGGGGTAAAGGGGAGAA (SEQ ID NO:385), CGTGGGTTGGGGTAAAGGGGAGAAGGG (SEQ ID NO:386), CGGCGGTCGTTCGGTTATTTTGTGGGT (SEQ ID NO:387), ATCGACGTGGGTTGGGGTAAAGGGGAG (SEQ ID NO:388), ACGTGGGTTGGGGTAAAGGGGAGAAGG (SEQ ID NO:389) |
| Target42 | chr1:47696673-47696702 | GAGGTTCGAGGTTTGGTGAATGTGTTTATTGT (SEQ ID NO:390), GAGGTTCGAGGTTTGGTGAATGTGTTTATTGTT (SEQ ID NO:391), GGTTTGGTGAATGTGTTTATTGTTTTTTCGGGG (SEQ ID NO:392), GGTTTGGTGAATGTGTTTATTGTTTTTTCGGGGT (SEQ ID NO:393), AGGTTCGAGGTTTGGTGAATGTGTTTATTGTTT (SEQ ID NO:394), TTGGTTAGTTTCGTGGGTGCGGTCGTC (SEQ ID NO:395), TTTGGTTAGTTTCGTGGGTGCGGTCGT (SEQ ID NO:396), TTTGGTTAGTTTCGTGGGTGCGGTCGTC (SEQ ID NO:397), TGGTTAGTTTCGTGGGTGCGGTCGTC (SEQ ID NO:398), TTTTGGTTAGTTTCGTGGGTGCGGTCGT (SEQ ID NO:399) |
| Target43 | chr1:47696752-47696769 | TGGATGAAGTCGGAGTGTAGCGGGAAT (SEQ ID NO:400), ATGGATGAAGTCGGAGTGTAGCGGGAA (SEQ ID NO:401), AATGGATGAAGTCGGAGTGTAGCGGGA (SEQ ID NO:402), TGGATGAAGTCGGAGTGTAGCGGGAATC (SEQ ID NO:403), GGATGAAGTCGGAGTGTAGCGGGAATC (SEQ ID NO:404), CGGCGGTTGTTTTGTTCGGAGGTTCGT (SEQ ID NO:405), GGTCGGCGGTTGTTTTGTTCGGAGGTT (SEQ ID NO:406), TCGGCGGTTGTTTTGTTCGGAGGTTCG (SEQ ID NO:407), GAGGGGTTCGTTGGTGAGTGGGAGGTT (SEQ ID NO:408), TTGAGGGGTTCGTTGGTGAGTGGGAGG (SEQ ID NO:409) |
| Target44 | chr1:47696782-47696792 | TGGATGAAGTCGGAGTGTAGCGGGAAT (SEQ ID NO:410), ATGGATGAAGTCGGAGTGTAGCGGGAA (SEQ ID NO:411), AATGGATGAAGTCGGAGTGTAGCGGGA (SEQ ID NO:412), TGGATGAAGTCGGAGTGTAGCGGGAATC (SEQ ID NO:413), GTTCGGTCGGCGGTTGTTTTGTTCGGA (SEQ ID NO:414), CGGCGGTTGTTTTGTTCGGAGGTTCGT (SEQ ID NO:415), GGTCGGCGGTTGTTTTGTTCGGAGGTT (SEQ ID NO:416), TCGGCGGTTGTTTTGTTCGGAGGTTCG (SEQ ID NO:417), TCGGCGGTTGTTTTGTTCGGAGGTTCG (SEQ ID NO:418), TTCGGTCGGCGGTTGTTTTGTTCGGAG (SEQ ID NO:419) |
| Target45 | chr1:48173984-48174046 | GGGGATGGGGGTAGTTTCGCGGGTAAA (SEQ ID NO:420), GGGGATGGGGGTAGTTTCGCGGGTAA (SEQ ID NO:421), GGGGATGGGGGTAGTTTCGCGGGTAAAG (SEQ ID NO:422), GGGGATGGGGGTAGTTTCGCGGGTAAAGA (SEQ ID NO:423), GGGGATGGGGGTAGTTTCGCGGGTAAAG (SEQ ID NO:424), GTTTAGGTTGTTGGGTACGGTATTTTTTGTTTAGGT (SEQ ID NO:425), TGTTTAGGTTGTTGGGTACGGTATTTTTTGTTAGG (SEQ ID NO:426) |
| Target46 | chr1:50882017-50882035 | ATTTTGGGTGCGGTGGGGTAGAGGACG (SEQ ID NO:427), TATTTTGGGTGCGGTGGGGTAGAGGACG (SEQ ID NO:428), TTTTGGGTGCGGTGGGGTAGAGGACG (SEQ ID NO:429), GAGGACGCGGGGATGAGGCGGTCGGAATC (SEQ ID NO:430), TATTTTGGGTGCGGTGGGGTAGAGGAC (SEQ ID NO:431), GGCGGGAGAAAGCGTGCGGAAGTTTTT (SEQ ID NO:432), GCGGGAGAAAGCGTGCGGAAGTTTTTG (SEQ ID NO:433), CGGGAGAAAGCGTGCGGAAGTTTTTGG (SEQ ID NO:434), AGGCGGGAGAAAGCGTGCGGAAGTTTT (SEQ ID NO:435), GGGAGAAAGCGTGCGGAAGTTTTTGGG (SEQ ID NO:436) |
| Target47 | chr1:50882232-50882249 | AGCGCGATGAGATGAAAGTGGGGGAG (SEQ ID NO:437), GAGCGCGATGAGATGAAAGTGGGGGAG (SEQ ID NO:438), GAGCGCGATGAGATGAAAGTGGGGGAGA (SEQ ID NO:439), GCGCGATGAGATGAAAGTGGGGGAGAA (SEQ ID NO:440), AGCGCGATGAGATGAAAGTGGGGGAGAA (SEQ ID NO:441) |
| Target48 | chr1:50884372-50884775 | GCGGAGTAGGTTAGGCGTAGGGGGTTG (SEQ ID NO:442), GTTAGGCGTAGGGGGTTGAGGTCGAGC (SEQ ID NO:443), AGGTTAGGCGTAGGGGGTTGAGGTCGA (SEQ ID NO:444), AGGCGTAGTTTATGGGTGGGCGGAAGT (SEQ ID NO:445), GGTTAGGCGTAGGGGGTTGAGGTCGAG (SEQ ID NO:446), TGGGGCGTTGGGTTCGTTGAGTAGTCG (SEQ ID NO:447), CGTTTGGGGCGTTGGGTTCGTTGAGTA (SEQ ID NO:448), GGGGTTTGGCGGTCGGTTTGGGTTTTG (SEQ |

FIGURE 5 CONTINUED

ID NO:449), GGGCGTTGGGTTCGTTGAGTAGTCGTT (SEQ ID NO:450),
CGTTTGGGGCGTTGGGTTCGTTGAGT (SEQ ID NO:451)

Target49     chr1:50884780-50884810     CGGGTTTCGTTTGTAGCGGCGTAGGTA (SEQ ID NO:452), GCGTCGGTTAGTAAGGGTTTGTGGTGCG
(SEQ ID NO:453), TAGTAAGGGTTTGTGGTGCGGAGGTGC (SEQ ID NO:454),
GGCGTCGGTTAGTAAGGGTTTGTGGTGC (SEQ ID NO:455), GGCGTTATGGCGTCGGTTAGTAAGGGT
(SEQ ID NO:456), TATTATCGTGGGGGTTTGGCGGTCGGT (SEQ ID NO:457),
GGTCGGTTTGGGTTTTGCGGCGTTTTT (SEQ ID NO:458), ATTATCGTGGGGGTTTGGCGGTCGGTT (SEQ
ID NO:459), TTATCGTGGGGGTTTGGCGGTCGGTTT (SEQ ID NO:460),
GGGGTTTGGCGGTCGGTTTGGGTTTTG (SEQ ID NO:461)

Target50     chr1:50884820-50884826     CGGGTTTCGTTTGTAGCGGCGTAGGTA (SEQ ID NO:462), GCGTCGGTTAGTAAGGGTTTGTGGTGCG
(SEQ ID NO:463), TAGTAAGGGTTTGTGGTGCGGAGGTGC (SEQ ID NO:464),
GGCGTCGGTTAGTAAGGGTTTGTGGTGC (SEQ ID NO:465), CGTCGGTTAGTAAGGGTTTGTGGTGCGG
(SEQ ID NO:466), TATTATCGTGGGGGTTTGGCGGTCGGT (SEQ ID NO:467),
GGTCGGTTTGGGTTTTGCGGCGTTTTT (SEQ ID NO:468), ATTATCGTGGGGGTTTGGCGGTCGGTT (SEQ
ID NO:469), TTATCGTGGGGGTTTGGCGGTCGGTTT (SEQ ID NO:470),
GGGGTTTGGCGGTCGGTTTGGGTTTTG (SEQ ID NO:471)

Target51     chr1:50884849-50884886     GCGGTTTTATTTGGGGGCGTCGTAGGG (SEQ ID NO:472), TTTGGGGGCGTCGTAGGGTTTAGGTCG (SEQ
ID NO:473), CGGTTTTATTTGGGGGCGTCGTAGGGT (SEQ ID NO:474),
TTGGGGGCGTCGTAGGGTTTAGGTCG (SEQ ID NO:475), ATTTGGGGGCGTCGTAGGGTTTAGGTCG (SEQ
ID NO:476), GGCGAGGCGTTTTGGAGTTGGTGTTGT (SEQ ID NO:477),
TATTATCGTGGGGGTTTGGCGGTCGGT (SEQ ID NO:478), GGTCGGTTTGGGTTTTGCGGCGTTTTT (SEQ
ID NO:479), ATTATCGTGGGGGTTTGGCGGTCGGTT (SEQ ID NO:480),
TTGGAGTTGGTGTTGTAGGGTTGCGGC (SEQ ID NO:481)

Target52     chr1:50884939-50884946     GGCGTCGTAGGGTTTAGGTCGGTCGTT (SEQ ID NO:482), GCGGTTTTATTTGGGGGCGTCGTAGGG (SEQ
ID NO:483), GGCGGTTTTATTTGGGGGCGTCGTAGG (SEQ ID NO:484),
TTTGGGGGCGTCGTAGGGTTTAGGTCG (SEQ ID NO:485), CGGTTTTATTTGGGGGCGTCGTAGGGT (SEQ
ID NO:486), TAGGGTTGGGCGGAGGTTCGGGTTTAC (SEQ ID NO:487),
TTGGGCGGAGGTTCGGGTTTACGGTAG (SEQ ID NO:488), GGCGAGGCGTTTTGGAGTTGGTGTTGT (SEQ
ID NO:489), GTTGGGCGGAGGTTCGGGTTTACGGTA (SEQ ID NO:490),
TTGGAGTTGGTGTTGTAGGGTTGCGGC (SEQ ID NO:491)

Target53     chr1:50885018-50885048     CGTCGGTGGTTTGGGAATACGCGTGTT (SEQ ID NO:492), TCGTCGGTGGTTTGGGAATACGCGTGT (SEQ
ID NO:493), TTCGTCGGTGGTTTGGGAATACGCGTG (SEQ ID NO:494),
TTTCGTCGGTGGTTTGGGAATACGCGT (SEQ ID NO:495), CGTTTCGTCGGTGGTTTGGGAATACGCG (SEQ
ID NO:496), TAGGGTTGGGCGGAGGTTCGGGTTTAC (SEQ ID NO:497),
TAAAGAAGAGGGTGAGGTCGCGTCGGC (SEQ ID NO:498), GTTGGGCGGAGGTTCGGGTTTACGGTA
(SEQ ID NO:499), GGAGGTTCGGGTTTACGGTAGCGGACG (SEQ ID NO:500),
CGGAGGTTCGGGTTTACGGTAGCGGAC (SEQ ID NO:501)

Target54     chr1:50885060-50885069     CGTCGGTGGTTTGGGAATACGCGTGTT (SEQ ID NO:502), TCGTCGGTGGTTTGGGAATACGCGTGT (SEQ
ID NO:503), TTCGTCGGTGGTTTGGGAATACGCGTG (SEQ ID NO:504),
TTTCGTCGGTGGTTTGGGAATACGCGT (SEQ ID NO:505), CGTTTCGTCGGTGGTTTGGGAATACGCG (SEQ
ID NO:506), TTTAGGTAGCGTTGGTTTTGGCGGCGG (SEQ ID NO:507),
TAAAGAAGAGGGTGAGGTCGCGTCGGT (SEQ ID NO:508), GTTTAGGTAGCGTTGGTTTTGGCGGCG (SEQ
ID NO:509), TGTTTAGGTAGCGTTGGTTTTGGCGGCG (SEQ ID NO:510),
TTAGGTAGCGTTGGTTTTGGCGGCGG (SEQ ID NO:511)

Target55     chr1:50885146-50885156     TCGGATTTAGAGTTTAGAGGGTTAGCGGAGT (SEQ ID NO:512),
CGGATTTAGAGTTTAGAGGGTTAGCGGAGTT (SEQ ID NO:513),
TCGGATTTAGAGTTTAGAGGGTTAGCGGAGTT (SEQ ID NO:514),
ATCGGATTTAGAGTTTAGAGGGTTAGCGGAGT (SEQ ID NO:515),
CGGATTTAGAGTTTAGAGGGTTAGCGGAGTTC (SEQ ID NO:516),
TTTAGGTAGCGTTGGTTTTGGCGGCGG (SEQ ID NO:517), AGGTGCGGTTCGGTTTAGGTTCGGAGA (SEQ
ID NO:518), AGAGGTGCGGTTCGGTTTAGGTTCGGA (SEQ ID NO:519),
GAGGTGCGGTTCGGTTTAGGTTCGGAG (SEQ ID NO:520), GTTTAGGTAGCGTTGGTTTTGGCGGCG (SEQ
ID NO:521)

Target56     chr1:50885205-50885295     TGAGTCGGGTCGTATTTTTGGGGACGA (SEQ ID NO:522), TTGAGTCGGGTCGTATTTTTGGGGACGA (SEQ
ID NO:523), TTGAGTCGGGTCGTATTTTTGGGGACGA (SEQ ID NO:524),
TTTTTTGGAGGTTCGAGTTAGGGGCGA (SEQ ID NO:525), TTTGAGTCGGGTCGTATTTTTGGGGACG (SEQ
ID NO:526), AGGTGCGGTTCGGTTTAGGTTCGGAGA (SEQ ID NO:527),
AGAGGTGCGGTTCGGTTTAGGTTCGGA (SEQ ID NO:528), GAGGTGCGGTTCGGTTTAGGTTCGGAG (SEQ
ID NO:529), AGAGGTGCGGTTCGGTTTAGGTTCGGAG (SEQ ID NO:530),
GAGGTGCGGTTCGGTTTAGGTTCGGAGA (SEQ ID NO:531)

Target57     chr1:50885302-50885309     TGAGTCGGGTCGTATTTTTGGGGACGA (SEQ ID NO:532), TTGAGTCGGGTCGTATTTTTGGGGACG (SEQ
ID NO:533), TTGAGTCGGGTCGTATTTTTGGGGACGA (SEQ ID NO:534),
TTTTTTGGAGGTTCGAGTTAGGGGCGA (SEQ ID NO:535), TTTGAGTCGGGTCGTATTTTTGGGGACG (SEQ
ID NO:536), ACGTTGTTGTAGGTAGGTCGTTCGGGT (SEQ ID NO:537),
AGGTAGGTCGTTCGGGTAGTTCGTTGT (SEQ ID NO:538), GACGTTGTTGTAGGTAGGTCGTTCGGGT (SEQ

FIGURE 5 CONTINUED

ID NO:539}, GACGTTGTTGTAGGTAGGTCGTTCGGG {SEQ ID NO:540},
GGTAGGTCGTTCGGGTAGTTCGTTGTC {SEQ ID NO:541}

| | | |
|---|---|---|
| Target58 | chr1:50885327-50885349 | TGAGTCGGGTCGTATTTTTGGGGACGA {SEQ ID NO:542}, TTGAGTCGGGTCGTATTTTTGGGGACG {SEQ ID NO:543}, TTGAGTCGGGTCGTATTTTTGGGGACGA {SEQ ID NO:544}, TTTGAGTCGGGTCGTATTTTTGGGGACG {SEQ ID NO:545}, TTTGAGTCGGGTCGTATTTTTGGGGACGA {SEQ ID NO:546}, ACGTTGTTGTAGGTAGGTCGTTCGGG {SEQ ID NO:547}, AGGTAGGTCGTTCGGGTAGTTCGTTGT {SEQ ID NO:548}, GACGTTGTTGTAGGTAGGTCGTTCGGGT {SEQ ID NO:549}, GACGTTGTTGTAGGTAGGTCGTTCGGG {SEQ ID NO:550}, GGTAGGTCGTTCGGGTAGTTCGTTGTC {SEQ ID NO:551} |
| Target59 | chr1:50885369-50885429 | TAGCGGGTTGTTCGGGCGGTTTGTTTG {SEQ ID NO:552}, GTAGCGGGTTGTTCGGGCGGTTTGTTT {SEQ ID NO:553}, GCGGGTTGTTCGGGCGGTTTGTTTGTA {SEQ ID NO:554}, GTAGCGGGTTGTTCGGGCGGTTTGTT {SEQ ID NO:555}, CGGGTTGTTCGGGCGGTTTGTTTGTAG {SEQ ID NO:556}, AGGGTTGTGGGGTTGAGGGAGAGGAAA {SEQ ID NO:557}, AAGGGTTGTGGGGTTGAGGGAGAGGAA {SEQ ID NO:558}, TAAGGGTTGTGGGGTTGAGGGAGAGGA {SEQ ID NO:559}, AAGGGTTGTGGGGTTGAGGGAGAGGAAA {SEQ ID NO:560}, GGGTTGTGGGGTTGAGGGAGAGGAAAT {SEQ ID NO:561} |
| Target60 | chr1:63785937-63785947 | GGGTCGTGGTAGAGGGAGGGTAGGAGG {SEQ ID NO:562}, GGTCGTGGTAGAGGGAGGGTAGGAGGT {SEQ ID NO:563}, TGGGTCGTGGTAGAGGGAGGGTAGGAG {SEQ ID NO:564}, AGGTTGGGTCGTGGTAGAGGGAGGGTA {SEQ ID NO:565}, TAGGTTGGGTCGTGGTAGAGGGAGGGT {SEQ ID NO:566}, GGTTTTGGTGGTTGGGTTCGCGTGGAT {SEQ ID NO:567}, TGCGCGTCGGAGGATGGTGGTTATAGG {SEQ ID NO:568}, AGTATGTGTGGATGCGCGTCGGAGGAT {SEQ ID NO:569}, TTGTCGCGGTTTTGGTGGTTGGGTTCG {SEQ ID NO:570}, CGCGTCGGAGGATGGTGGTTATAGGGT {SEQ ID NO:571} |
| Target61 | chr1:63786016-63786079 | CGGGTTTAGTTATTAAGGTCGCGGTAGGG {SEQ ID NO:572}, CGGGTTTAGTTATTAAGGTCGCGGTAGGGT {SEQ ID NO:573}, GGGTTTAGTTATTAAGGTCGCGGTAGGGT {SEQ ID NO:574}, CGGGTTTAGTTATTAAGGTCGCGCGGTAGGGTT {SEQ ID NO:575}, GGGTTTAGTTATTAAGGTCGCGGTAGGGTT {SEQ ID NO:576}, GGTTTTGGTGGTTGGGTTCGCGTGGAT {SEQ ID NO:577}, TTGTCGCGGTTTTGGTGGTTGGGTTCG {SEQ ID NO:578}, GGTTTTGTCGCGGTTTTGGTGGTTGGG {SEQ ID NO:579}, CGTTGGTTTTGTCGCGGTTTTGGTGGT {SEQ ID NO:580}, GGTTTTGGTGGTTGGGTTCGCGTGGA {SEQ ID NO:581} |
| Target62 | chr1:63795446-63795472 | TAGTTCGGCGATGAGTGGTTTTGCGGG {SEQ ID NO:582}, TTCGGCGATGAGTGGTTTTGCGGGGAT {SEQ ID NO:583}, TCGGCGATGAGTGGTTTTGCGGGGATC {SEQ ID NO:584}, AGTTCGGCGATGAGTGGTTTTGCGGG {SEQ ID NO:585}, ACGCGTCGGGCTCGGTGGAATTTAGTTT {SEQ ID NO:586}, CGAGGTAAGAAGGAAATGGGGTCGTCGG {SEQ ID NO:587}, CGAGGTAAGAAGGAAATGGGGTCGTCGGT {SEQ ID NO:588}, AGGTAAGAAGGAAATGGGGTCGTCGGT {SEQ ID NO:589}, GGGGAGTTTCGGGTTTGTAGTTGTCGT {SEQ ID NO:590}, CGAGGTAAGAAGGAAATGGGGTCGTCG {SEQ ID NO:591} |
| Target63 | chr1:68025026-68025081 | TAGGGACGGTTAGAGGGGCGTGTGAGA {SEQ ID NO:592}, TAGGTAGGGACGGTTAGAGGGGCGTGT {SEQ ID NO:593}, GGGACGGTTAGAGGGGCGTGTGAGATT {SEQ ID NO:594}, GTAGGGACGGTTAGAGGGGCGTGTGAG {SEQ ID NO:595}, AGGGACGGTTAGAGGGGCGTGTGAGAT {SEQ ID NO:596} |
| Target64 | chr1:68025115-68025305 | TTTGGTCGTTTTTGTTTGGGATATCGAGTTGAA {SEQ ID NO:597}, TTTTGGTCGTTTTTGTTTGGGATATCGAGTTGA {SEQ ID NO:598}, TTTTGGTCGTTTTTGTTTGGGATATCGAGTTGAA {SEQ ID NO:599}, TGGTCGTTTTTGTTTGGGATATCGAGTTGAATTT {SEQ ID NO:600}, TTGGTCGTTTTTGTTTGGGATATCGAGTTGAATT {SEQ ID NO:601}, TAGGGACGGTTAGAGGGGCGTGTGAGA {SEQ ID NO:602}, TAGGTAGGGACGGTTAGAGGGGCGTGT {SEQ ID NO:603}, GGGACGGTTAGAGGGGCGTGTGAGATT {SEQ ID NO:604}, GTAGGGACGGTTAGAGGGGCGTGTGAG {SEQ ID NO:605}, AGGGACGGTTAGAGGGGCGTGTGAGAT {SEQ ID NO:606} |
| Target65 | chr1:91183133-91183416 | GCGGTTGCGGTAATTCGAGGAGGAGGA {SEQ ID NO:607}, AGGAGGAGGAGGAAGAGGAGGACGACG {SEQ ID NO:608}, CGAGGAGGAGGAGGAAGAGGAGGACGA {SEQ ID NO:609}, TCGAGGAGGAGGAGGAAGAGGAGGACG {SEQ ID NO:610}, AGGCGGCGGGAAGTTACGTTAAAGTCG {SEQ ID NO:611}, GTTGTGGGTAGATTTCGGTAGCGGCGG {SEQ ID NO:612}, GGTTGTGGGTAGATTTCGGTAGCGGCG {SEQ ID NO:613}, AGGTTGTGGGTAGATTTCGGTAGCGGCG {SEQ ID NO:614}, AGGTTGTGGGTAGATTTCGGTAGCGGC {SEQ ID NO:615}, CGTTGTCGTTCGGTGTTAGGTTGTGGGT {SEQ ID NO:616} |
| Target66 | chr1:91183444-91183454 | GCGGTTGCGGTAATTCGAGGAGGAGGA {SEQ ID NO:617}, GGAGGAGGAGGAAGAGGAGGACGACGA {SEQ ID NO:618}, AGGAGGAGGAAGAGGAGGACGACGAGA {SEQ ID NO:619}, CGGTTGCGGTAATTCGAGGAGGAGGAGG {SEQ ID NO:620}, GGAGGAGGAGGAAGAGGAGGACGACGAG {SEQ ID NO:621}, GAGCGGCGGTAGTGGTCGTGACGTTAC {SEQ ID NO:622}, GAGCGGCGGTAGTGGTCGTGACGTTA {SEQ ID NO:623}, AGCGGCGGTAGTGGTCGTGACGTTAC {SEQ ID NO:624}, GGAGCGGCGGTAGTGGTCGTGACGTTA {SEQ ID NO:625}, AGCGGCGGTAGTGGTCGTGACGTTA {SEQ ID NO:626} |

FIGURE 5 CONTINUED

| | | |
|---|---|---|
| Target67 | chr1:91183455-91183523 | GCGGTTGCGGTAATTCGAGGAGGAGGA (SEQ ID NO:627), CGGTTGCGGTAATTCGAGGAGGAGGAGG (SEQ ID NO:628), CGGTTGCGGTAATTCGAGGAGGAGGAG (SEQ ID NO:629), GCGGTTGCGGTAATTCGAGGAGGAGGAG (SEQ ID NO:630), GGTTGCGGTAATTCGAGGAGGAGGAGG (SEQ ID NO:631), GAGCGGCGGTAGTGGTCGTGACGTTAC (SEQ ID NO:632), GAGCGGCGGTAGTGGTCGTGACGTTA (SEQ ID NO:633), AGCGGCGGTAGTGGTCGTGACGTTAC (SEQ ID NO:634), GGAGCGGCGGTAGTGGTCGTGACGTTA (SEQ ID NO:635), AGCGGCGGTAGTGGTCGTGACGTTA (SEQ ID NO:636) |
| Target68 | chr1:91183553-91183587 | CGCGTTCGTTTGTAATTCGGTTGTTGGCG (SEQ ID NO:637), GCGTTCGTTTGTAATTCGGTTGTTGGCGG (SEQ ID NO:638), CGTTCGTTTGTAATTCGGTTGTTGGCGGG (SEQ ID NO:639), GCGTTCGTTTGTAATTCGGTTGTTGGCG (SEQ ID NO:640), CGCGTTCGTTTGTAATTCGGTTGTTGGC (SEQ ID NO:641), GCGGTTAATAGGGGCGCGGGGTC (SEQ ID NO:642), TGCGTTTATTGGTTTTTTGGTACGTCGGC (SEQ ID NO:643), GCGTTTATTGGTTTTTTGGTACGTCGGC (SEQ ID NO:644), CGAGCGTTGCGTTTATTGGTTTTTTGGT (SEQ ID NO:645), GCGGTTAATAGGGGCGCGGGGT (SEQ ID NO:646) |
| Target69 | chr1:91183598-91183770 | CGTTTGTAATTCGGTTGTTGGCGGGCGG (SEQ ID NO:647), GTTTGTAATTCGGTTGTTGGCGGGCGG (SEQ ID NO:648), TCGTTTGTAATTCGGTTGTTGGCGGGCG (SEQ ID NO:649), TCGTTTGTAATTCGGTTGTTGGCGGGC (SEQ ID NO:650), CGTTTGTAATTCGGTTGTTGGCGGGCGG (SEQ ID NO:651), GTTGCGGGTTTAGGGATGTGCGGGGTTT (SEQ ID NO:652), TAGGGGTTGCGGGTTTAGGGATGTGCGG (SEQ ID NO:653), TGCGGGGTTTAGGGATGTGCGGGGTTTTT (SEQ ID NO:654), TTGCGGGTTTAGGGATGTGCGGGGTTTT (SEQ ID NO:655), TTAGGGGTTGCGGGTTTAGGGATGTGCG (SEQ ID NO:656) |
| Target70 | chr1:110334826-110334876 | TGGGATTTAGGTGGGTTGGGGGGGTTGG (SEQ ID NO:657), GGGTTGGGGGGGTTGGGGGAATGTAGAT (SEQ ID NO:658), GTGGGTTGGGGGGGTTGGGGGAATGTAG (SEQ ID NO:659), GATTTAGGTGGGTTGGGGGGGTTGGGGG (SEQ ID NO:660), GGATTTAGGTGGGTTGGGGGGGTTGGGG (SEQ ID NO:661), GTGGGGTTTGAGTGTTGTAGAGTAGGAAGT (SEQ ID NO:662), AGTGGGGTTTGAGTGTTGTAGAGTAGGAAGT (SEQ ID NO:663), GTGGGGTTTGAGTGTTGTAGAGTAGGAAGTT (SEQ ID NO:664), AGTGGGGTTTGAGTGTTGTAGAGTAGGAAGTT (SEQ ID NO:665), TAGTGGGGTTTGAGTGTTGTAGAGTAGGAAGT (SEQ ID NO:666) |
| Target71 | chr1:110612365-110612398 | GCGCGGGGAAGTTAAGATTGTTAGAAGGGC (SEQ ID NO:667), CGCGGGGAAGTTAAGATTGTTAGAAGGGCG (SEQ ID NO:668), GCGGGGAAGTTAAGATTGTTAGAAGGGCGG (SEQ ID NO:669), GCGGGGAAGTTAAGATTGTTAGAAGGGCGGT (SEQ ID NO:670), AGCGCGGGGAAGTTAAGATTGTTAGAAGGGC (SEQ ID NO:671), GGTCGGTTGGGGATTGCGGTTTGGTTT (SEQ ID NO:672), CGGTTGGGGATTGCGGTTTGGTTTTGG (SEQ ID NO:673), GGTCGGTTGGGGATTGCGGTTTGGTT (SEQ ID NO:674), TCGGTTGGGGATTGCGGTTTGGTTTTGG (SEQ ID NO:675), GGTCGGTTGGGGATTGCGGTTTGGTTTT (SEQ ID NO:676) |
| Target72 | chr1:110612544-110612555 | AGGTTAGGTTCGGGGAGGAGAGACGGG (SEQ ID NO:677), GGTTAGGTTCGGGGAGGAGAGACGGGT (SEQ ID NO:678), GTTAGGTTCGGGGAGGAGAGACGGGTT (SEQ ID NO:679), AGGTTCGGGGAGGAGAGACGGGTTAAG (SEQ ID NO:680), AAGGTTAGGTTCGGGGAGGAGAGACGG (SEQ ID NO:681), GTTTAGATTCGGTCGAGGGTTGTGGAGT (SEQ ID NO:682), AGTTTAGATTCGGTCGAGGGTTGTGGAGT (SEQ ID NO:683), AGTTTAGATTCGGTCGAGGGTTGTGGAG (SEQ ID NO:684), TTTAGATTCGGTCGAGGGTTGTGGAGTT (SEQ ID NO:685), AAGTTTAGATTCGGTCGAGGGTTGTGGA (SEQ ID NO:686) |
| Target73 | chr1:110612670-110612689 | CGGTCGGGTTTGGGTTTTAGGGTAGGT (SEQ ID NO:687), TCGGTCGGGTTTGGGTTTTAGGGTAGGT (SEQ ID NO:688), TCGGTCGGGTTTGGGTTTTAGGGTAGG (SEQ ID NO:689), CGGTCGGGTTTGGGTTTTAGGGTAGGTG (SEQ ID NO:690), GGTCGGGTTTGGGTTTTAGGGTAGGTGGT (SEQ ID NO:691), AGTGTGGGGCGGGAGGGTGAATTATCG (SEQ ID NO:692), TGTGGGGCGGGAGGGTGAATTATCGTT (SEQ ID NO:693), GGTTAGTGTGGGGCGGGAGGGTGAATT (SEQ ID NO:694), GGTAAAGGTTAGTGTGGGGCGGGAGGG (SEQ ID NO:695), GAATGGAAGGCGGGAGGTCGAGGGAAG (SEQ ID NO:696) |
| Target74 | chr1:110612735-110612742 | AGTGTGGGGCGGGAGGGTGAATTATCG (SEQ ID NO:697), TGTGGGGCGGGAGGGTGAATTATCGTT (SEQ ID NO:698), GGTTAGTGTGGGGCGGGAGGGTGAATT (SEQ ID NO:699), GGTAAAGGTTAGTGTGGGGCGGGAGGG (SEQ ID NO:700), GTGTGGGGCGGGAGGGTGAATTATCGT (SEQ ID NO:701) |
| Target75 | chr1:110612790-110612823 | TGGTTTTTGTTTGGTTCGGGTTAGCGT (SEQ ID NO:702), TGGTTTTTGTTTGGTTCGGGTTAGCGTT (SEQ ID NO:703), TTGGTTTTTGTTTGGTTCGGGTTAGCGT (SEQ ID NO:704), TGTTTGGTTCGGGTTAGCGTTAATTCGG (SEQ ID NO:705), TTGGTTTTTGTTTGGTTCGGGTTAGCGTT (SEQ ID NO:706), GGAAGTCGGGTTGGCGTTGGTTT (SEQ ID NO:707), GGAAGTCGGGTTGGCGTTGGTT (SEQ ID NO:708) |
| Target76 | chr1:110612834-110612867 | TGGTTTTTGTTTGGTTCGGGTTAGCGT (SEQ ID NO:709), TGGTTTTTGTTTGGTTCGGGTTAGCGTT (SEQ ID NO:710), TTGGTTTTTGTTTGGTTCGGGTTAGCGT (SEQ ID NO:711), TGTTTGGTTCGGGTTAGCGTTAATTCGG (SEQ ID NO:712), CGGTTTTCGTGGAAGTCGTGGCGA (SEQ ID NO:713) |

FIGURE 5 CONTINUED

Target77    chr1:110626175-110626311    TGGGTTTTCGTTTGGGGAGGGATTTGGT (SEQ ID NO:714), GGGTTTTCGTTTGGGGAGGGATTTGGTTGG (SEQ ID NO:715), GGGTTTTCGTTTGGGGAGGGATTTGGTTGGT (SEQ ID NO:716), TGGGTTTTCGTTTGGGGAGGGATTTGGTTGG (SEQ ID NO:717), TGGGTTTTCGTTTGGGGAGGGATTTGGTT (SEQ ID NO:718), TACGGTTTTGGCGGAGGGGGAATCGAA (SEQ ID NO:719), ATACGGTTTTGGCGGAGGGGGAATCGA (SEQ ID NO:720), GCGGAGGGGGAATCGAAGTTGGGGAAT (SEQ ID NO:721), TTTGGCGGAGGGGGAATCGAAGTTGGG (SEQ ID NO:722), GGTTTTGGCGGAGGGGGAATCGAAGTT (SEQ ID NO:723)

Target78    chr1:110626375-110626397    TGGTTGGAGATAGAGATAAGGAGAGTTAGAAAGCG (SEQ ID NO:724), GGTTGGAGATAGAGATAAGGAGAGTTAGAAAGCGA (SEQ ID NO:725), TGGTTGGAGATAGAGATAAGGAGAGTTAGAAAGCGA (SEQ ID NO:726), ATGGTTGGAGATAGAGATAAGGAGAGTTAGAAAGCG (SEQ ID NO:727), GGTTGGAGATAGAGATAAGGAGAGTTAGAAAGCGAT (SEQ ID NO:728), TTATACGGTTTTGGCGGAGGGGGAATT (SEQ ID NO:729), ATTATACGGTTTTGGCGGAGGGGGAAT (SEQ ID NO:730), ATTATACGGTTTTGGCGGAGGGGGAATT (SEQ ID NO:731), TCGGGGTAGGAGGTAAGTTTTTAGGGGT (SEQ ID NO:732), TATACGGTTTTGGCGGAGGGGGAATT (SEQ ID NO:733)

Target79    chr1:110626480-110626703    GCGGTAGTGGCGGCGGTTTTTAGTTTT (SEQ ID NO:734), CGGGGATTGCGGAGGGAGGGTTTAGG (SEQ ID NO:735), GGGGATTGCGGAGGGAGGGTTTAGGC (SEQ ID NO:736), GGGGATTGCGGAGGGAGGGTTTAGGCG (SEQ ID NO:737), GCGGGGATTGCGGAGGGAGGGTTTAG (SEQ ID NO:738), TTAGGGCGTTCGGAGGTATAGGGTGCG (SEQ ID NO:739), CGGGGAGATTAGGGCGTTCGGAGGTAT (SEQ ID NO:740), GCGGGGAGATTAGGGCGTTCGGAGGTA (SEQ ID NO:741), ATTAGGGCGTTCGGAGGTATAGGGTGCG (SEQ ID NO:742), TAGGGCGTTCGGAGGTATAGGGTGCG (SEQ ID NO:743)

Target80    chr1:111813478-111813500    TGACGTCGTTTTTGGTTGTTTGGTCGT (SEQ ID NO:744), TGACGTCGTTTTTGGTTGTTTGGTCGTT (SEQ ID NO:745), ATGACGTCGTTTTTGGTTGTTTGGTCGT (SEQ ID NO:746), TGACGTCGTTTTTGGTTGTTTGGTCGTT (SEQ ID NO:747), ATGACGTCGTTTTTGGTTGTTTGGTCGTT (SEQ ID NO:748), TCGTAGGTTGTGTGGGTGTGAGGTGGT (SEQ ID NO:749), GTGGGTGTGAGGTGGTTTTCGGTTCGT (SEQ ID NO:750), TGTGGGTGTGAGGTGGTTTTCGGTTCG (SEQ ID NO:751), GGTTGTGTGGGTGTGAGGTGGTTTTCGG (SEQ ID NO:752), TGGGTGTGAGGTGGTTTTCGGTTCGTT (SEQ ID NO:753)

Target81    chr1:111813562-111813604    ATAAGGTGAGGGTAGTTCGCGCGGGG (SEQ ID NO:754), TCGGGTGGTTTAGGGTAAGGCGGATCG (SEQ ID NO:755), GGGTGGTTTAGGGTAAGGCGGATCGGG (SEQ ID NO:756), GGTGGTTTAGGGTAAGGCGGATCGGGA (SEQ ID NO:757), CGGGTGGTTTAGGGTAAGGCGGATCGG (SEQ ID NO:758), GGATATTTTTTGGCGAGGGGGTCGGAGCG (SEQ ID NO:759), CGGATATTTTTTGGCGAGGGGGTCGGAGC (SEQ ID NO:760), ATATTTTTTGGCGAGGGGGTCGGAGCGA (SEQ ID NO:761), TCGGATATTTTTTGGCGAGGGGGTCGGA (SEQ ID NO:762), GATATTTTTTGGCGAGGGGGTCGGAGCG (SEQ ID NO:763)

Target82    chr1:111813667-111813827    ATAAGGTGAGGGTAGTTCGCGCGGGG (SEQ ID NO:764), CGATAAGGTGAGGGTAGTTTCGCGCGGG (SEQ ID NO:765), GATAAGGTGAGGGTAGTTTCGCGCGGG (SEQ ID NO:766), TATTGAGTTGATGTGACGGCGCGGAGG (SEQ ID NO:767), TCGATAAGGTGAGGGTAGTTTCGCGCGG (SEQ ID NO:768), GGATATTTTTTGGCGAGGGGGTCGGAGCG (SEQ ID NO:769), CGGATATTTTTTGGCGAGGGGGTCGGAGC (SEQ ID NO:770), ATATTTTTTGGCGAGGGGGTCGGAGCGA (SEQ ID NO:771), TCGGATATTTTTTGGCGAGGGGGTCGGA (SEQ ID NO:772), GATATTTTTTGGCGAGGGGGTCGGAGCG (SEQ ID NO:773)

Target83    chr1:119522444-119522487    GGGTTTCGGGTTTTTAGGGTTTCGGGT (SEQ ID NO:774), GGGTTTCGGGTTTTTAGGGTTTCGGGTT (SEQ ID NO:775), AGGGTTTCGGGTTTTTAAGGTTTCGCG (SEQ ID NO:776), GGTTTCGGGTTTTTAGGGTTTCGGGTT (SEQ ID NO:777), GGGTTTCGGGTTTTTAGGGTTTCGGGTTT (SEQ ID NO:778), TTTTCGGTTCGGTTTTGGAGGCGTCGC (SEQ ID NO:779), CGGTTTTTCGGTTCGGTTTTGGAGGCG (SEQ ID NO:780), TCGGTTTTTCGGTTCGGTTTTGGAGGCG (SEQ ID NO:781), CGGTTTTTCGGTTCGGTTTTGGAGGCGT (SEQ ID NO:782), TTTCGGTTCGGTTTTGGAGGCGTCGC (SEQ ID NO:783)

Target84    chr1:119522500-119522638    GGTGGGGTTAGCGCGGAGTTTTAGGC (SEQ ID NO:784), GGGTTTCGGGTTTTTAGGGTTTCGGGT (SEQ ID NO:785), GCGGAGTTTTAGGCGCGAGAATAGGAA (SEQ ID NO:786), GGGTTTCGGGTTTTTAGGGTTTCGGGTT (SEQ ID NO:787), AGGGTTTCGGGTTTTTAAGGTTTCGCG (SEQ ID NO:788), TTTTCGGTTCGGTTTTGGAGGCGTCGC (SEQ ID NO:789), CGGTTTTTCGGTTCGGTTTTGGAGGC (SEQ ID NO:790), TCGGTTTTTCGGTTCGGTTTTGGAGGCG (SEQ ID NO:791), CGGTTTTTCGGTTCGGTTTTGGAGGCGT (SEQ ID NO:792), TTTCGGTTCGGTTTTGGAGGCGTCGC (SEQ ID NO:793)

Target85    chr1:119526848-119526885    TAGTTGAGTTGACGGGTGCGTGCGAGA (SEQ ID NO:794), AGTAGTTGAGTTGACGGGTGCGTGCGA (SEQ ID NO:795), GTTGAGTTGACGGGTGCGTGCGAGAAT (SEQ ID NO:796), TTGAGTTGACGGGTGCGTGCGAGAATG (SEQ ID NO:797), GTAGTTGAGTTGACGGGTGCGTGCGAG (SEQ ID NO:798), TTTAGAGGTTTGGGGATGTGGTGGCGC (SEQ ID NO:799), TTAGAGGTTTGGGGATGTGGTGGCGCG (SEQ ID NO:800), TTTTAGAGGTTTGGGGATGTGGTGGCGC (SEQ ID NO:801), GCGCGCGGGTGGGTATTTAGATAGGTA (SEQ ID NO:802), TAGAGGTTTGGGGATGTGGTGGCGCG (SEQ ID NO:803)

FIGURE 5 CONTINUED

| | | |
|---|---|---|
| Target86 | chr1:119526915-119527309 | AGGGGTTGAGGTTCGAGCGTAGATGGC (SEQ ID NO:804), GGGTGGAGTAGGGGTTGAGGTTCGAGC (SEQ ID NO:805), GGTGGAGTAGGGGTTGAGGTTCGAGCG (SEQ ID NO:806), TCGGGTGGAGTAGGGGTTGAGGTTCGA (SEQ ID NO:807), GTTTTGGGAGAGGGCGGGGGAGAGTAG (SEQ ID NO:808), TCGGCGGCGTTATTTGCGTTCGGATT (SEQ ID NO:809), TTCGGCGGCGTTATTTGCGTTCGGATT (SEQ ID NO:810), GTTCGGCGGCGTTATTTGCGTTCGGAT (SEQ ID NO:811), CGGCGGCGTTATTTGCGTTCGGATTTT (SEQ ID NO:812), TCGGCGGCGTTATTTGCGTTCGGATT (SEQ ID NO:813) |
| Target87 | chr1:119527311-119527546 | GGCGGGTTTTGGGGTTTTTCGGGGTTA (SEQ ID NO:814), GTTTTGGGAGAGGGCGGGGGAGAGTAG (SEQ ID NO:815), TGTTTTAAGTTGCGGGTGTTCGGGCGT (SEQ ID NO:816), TTTGTTGTTTTGGGAGAGGGCGGGGGA (SEQ ID NO:817), TTTTGTTGTTTTGGGAGAGGGCGGGGG (SEQ ID NO:818), GGGGGATTAGTTCGGTTTGCGCGTTGT (SEQ ID NO:819), CGGGGGATTAGTTCGGTTTGCGCGTTG (SEQ ID NO:820), TAACGGGGGATTAGTTCGGTTTGCGCG (SEQ ID NO:821), ACGGGGGATTAGTTCGGTTTGCGCGTT (SEQ ID NO:822), AACGGGGGATTAGTTCGGTTTGCGCGT (SEQ ID NO:823) |
| Target88 | chr1:119532785-119533029 | ATTTGGGGAGTTCGGATGGAGAGGCGT (SEQ ID NO:824), GGGGAGTTCGGATGGAGAGGCGTAGGA (SEQ ID NO:825), TTGGGGAGTTCGGATGGAGAGGCGTAG (SEQ ID NO:826), TGGGGAGTTCGGATGGAGAGGCGTAGG (SEQ ID NO:827), TTTGGGGAGTTCGGATGGAGAGGCGTA (SEQ ID NO:828), AGTCGTTGGGGAAGGAAATTGCGGGTT (SEQ ID NO:829), TAGTCGTTGGGGAAGGAAATTGCGGGT (SEQ ID NO:830), GTCGTTGGGGAAGGAAATTGCGGGTTT (SEQ ID NO:831), AGTCGTTGGGGAAGGAAATTGCGGGTTT (SEQ ID NO:832), AGTCGTTGGGGAAGGAAATTGCGGGT (SEQ ID NO:833) |
| Target89 | chr1:119535725-119535751 | GGGGTAAGAGGAGAGCGAAAAGGGGGG (SEQ ID NO:834), TGGGGTAAGAGGAGAGCGAAAAGGGGG (SEQ ID NO:835), GTCGTCGCGGTGTGGTCGGTAGAGTC (SEQ ID NO:836), TTGGGGTAAGAGGAGAGCGAAAAGGGGG (SEQ ID NO:837), TGGGGTAAGAGGAGAGCGAAAAGGGGG (SEQ ID NO:838), TGGGGAAAGAGAAGTTGGGTTTGGGGG (SEQ ID NO:839), TGGGGAAAGAGAAGTTGGGTTTGGGGGA (SEQ ID NO:840), GGGGAAAGAGAAGTTGGGTTTGGGGGA (SEQ ID NO:841), GTGGGGAAAGAGAAGTTGGGTTTGGGGG (SEQ ID NO:842), GTGGGGAAAGAGAAGTTGGGTTTGGGGGA (SEQ ID NO:843) |
| Target90 | chr1:119535812-119535824 | TTTTGTGTGGTTAGGTCGGAGCGGTCG (SEQ ID NO:844), GTTTTGTGTGGTTAGGTCGGAGCGGTCG (SEQ ID NO:845), GTCGTCGCGGTGTGGTCGGTAGAGTC (SEQ ID NO:846), AGTTTTGTGTGGTTAGGTCGGAGCGGT (SEQ ID NO:847), GGAGTTTTGTGTGGTTAGGTCGGAGCGG (SEQ ID NO:848), TGGAACGGCGGGCGTATTTTGTAGTCG (SEQ ID NO:849), CGGCGGGCGTATTTTGTAGTCGAAGGT (SEQ ID NO:850), ACGGCGGGCGTATTTTGTAGTCGAAGG (SEQ ID NO:851), GGAACGGCGGGCGTATTTTGTAGTCGA (SEQ ID NO:852), TGGAACGGCGGGCGTATTTTGTAGTCGA (SEQ ID NO:853) |
| Target91 | chr1:119535884-119535902 | TTTTGTGTGGTTAGGTCGGAGCGGTCG (SEQ ID NO:854), GTTTTGTGTGGTTAGGTCGGAGCGGTCG (SEQ ID NO:855), AGTTTTGTGTGGTTAGGTCGGAGCGGT (SEQ ID NO:856), GGAGTTTTGTGTGGTTAGGTCGGAGCGG (SEQ ID NO:857), GGGAGTTTTGTGTGGTTAGGTCGGAGCG (SEQ ID NO:858), TGGAACGGCGGGCGTATTTTGTAGTC (SEQ ID NO:859), CGGCGGGCGTATTTTGTAGTCGAAGGT (SEQ ID NO:860), ACGGCGGGCGTATTTTGTAGTCGAAGG (SEQ ID NO:861), GGAACGGCGGGCGTATTTTGTAGTCGA (SEQ ID NO:862), GCGAAGGTAGGTAGGATCGGAGTTGGCG (SEQ ID NO:863) |
| Target92 | chr1:119535921-119535963 | TTTGTGTGGTTAGGTCGGAGCGGTCG (SEQ ID NO:864), TTGTGTGGTTAGGTCGGAGCGGTCG (SEQ ID NO:865), TGTGTGGTTAGGTCGGAGCGGTCG (SEQ ID NO:866), GTTCGTCGTTTTAGGCGTTAGTTTCGGT (SEQ ID NO:867), TTTGTGTGGTTAGGTCGGAGCGGTC (SEQ ID NO:868), GCGAAGGTAGGTAGGATCGGAGTTGGCG (SEQ ID NO:869), TGCGAAGGTAGGTAGGATCGGAGTTGGC (SEQ ID NO:870), GCGAAGGTAGGTAGGATCGGAGTTGGC (SEQ ID NO:871), CGAAGGTAGGTAGGATCGGAGTTGGCGT (SEQ ID NO:872), CGAAGGTAGGTAGGATCGGAGTTGGCG (SEQ ID NO:873) |
| Target93 | chr1:119542854-119542943 | CGGAAGGATTGGGGGAGATTTAGATTATTTGGG (SEQ ID NO:874), CGGAAGGATTGGGGGAGATTTAGATTATTTGGGA (SEQ ID NO:875), TCGGAAGGATTGGGGGAGATTTAGATTATTTGGG (SEQ ID NO:876), TCGGAAGGATTGGGGGAGATTTAGATTATTTGGGA (SEQ ID NO:877), TCGGAAGGATTGGGGGAGATTTAGATTATTTGG (SEQ ID NO:878), GGAAAGCGTAGTGGGGATAGAGGTAATTTTTGT (SEQ ID NO:879), AGGAAAGCGTAGTGGGGATAGAGGTAATTTTTG (SEQ ID NO:880), AGGAAAGCGTAGTGGGGATAGAGGTAATTTTTGT (SEQ ID NO:881), AAGGAAAGCGTAGTGGGGATAGAGGTAATTTTT (SEQ ID NO:882), GGAAAGCGTAGTGGGGATAGAGGTAATTTTTGTT (SEQ ID NO:883) |
| Target94 | chr1:119542959-119543008 | GGTTAGCGGGGTATAGAGGTTAGCGGGT (SEQ ID NO:884), GGTTAGCGGGGTATAGAGGTTAGCGGG (SEQ ID NO:885), AGGTTAGCGGGGTATAGAGGTTAGCGGGT (SEQ ID NO:886), AGGTTAGCGGGGTATAGAGGTTAGCGGG (SEQ ID NO:887), AGCGGGGTATAGAGGTTAGCGGGTTTT (SEQ ID NO:888), GGAAAGCGTAGTGGGGATAGAGGTAATTTTTGT (SEQ ID NO:889), AGGAAAGCGTAGTGGGGATAGAGGTAATTTTTG (SEQ ID NO:890), AGGAAAGCGTAGTGGGGATAGAGGTAATTTTTGT (SEQ ID NO:891), |

FIGURE 5 CONTINUED

AAGGAAAGCGTAGTGGGGATAGAGGTAATTTTT (SEQ ID NO:892),
GGAAAGCGTAGTGGGGATAGAGGTAATTTTTGTT (SEQ ID NO:893)

| | | |
|---|---|---|
| Target95 | chr1:119543057-119543271 | GGGTTTGGGGAGTTTTTTGCGGCGGAAG (SEQ ID NO:894), CGTAGGGTTTGGGAGTTTTTTGCGGCG (SEQ ID NO:895), GGGTTTGGGGAGTTTTTTGCGGCGGAAGA (SEQ ID NO:896), AGGGTTTGGGGAGTTTTTTGCGGCGGAAG (SEQ ID NO:897), GTAGGGTTTGGGAGTTTTTTGCGGCGG (SEQ ID NO:898), AAGGTCGTTGGGAGTTCGGTGAGGACG (SEQ ID NO:899), GAGTTCGGTGAGGACGTGGCGGTTTTT (SEQ ID NO:900), GTCGTTGGGAGTTCGGTGAGGACGTGG (SEQ ID NO:901), GGTCGTTGGGAGTTCGGTGAGGACGTG (SEQ ID NO:902), AGTTCGGTGAGGACGTGGCGGTTTTTT (SEQ ID NO:903) |
| Target96 | chr1:145030711-145031192 | CGGGTTTGTTGGTAATAATGTTGTTTTTGTGGTGT (SEQ ID NO:904), TCGGGTTTGTTGGTAATAATGTTGTTTTTGTGGTGT (SEQ ID NO:905), AGGTAAGGTTAGATGTGTAGGTGGGAATAATTGGT (SEQ ID NO:906), CGGGTTTGTTGGTAATAATGTTGTTTTTGTGGTGTT (SEQ ID NO:907), TCGGTTTTTTGGGGAATGTTTTTTGGAAAGTTTTT (SEQ ID NO:908), CGGGGAGTTGGTTGGAGAGTTATTGCG (SEQ ID NO:909), CGGGGAGTTGGTTGGAGAGTTATTGCGA (SEQ ID NO:910), TCGGGGAGTTGGTTGGAGAGTTATTGCG (SEQ ID NO:911), TCGGGGAGTTGGTTGGAGAGTTATTGCGA (SEQ ID NO:912), GGGGGAGTTGGTTGGAGAGTTATTGCGA (SEQ ID NO:913) |
| Target97 | chr1:145075536-145075651 | GTTCGGGGTTTTAGTTTTTCGCGCGGT (SEQ ID NO:914), AGTTCGGGGTTTTAGTTTTTCGCGCGGT (SEQ ID NO:915), AGTTCGGGGTTTTAGTTTTTCGCGCGG (SEQ ID NO:916), AGGCGTCGGGATTTTTAGTTCGGGGTTT (SEQ ID NO:917), TTCGGGGTTTTAGTTTTTCGCGCGGTT (SEQ ID NO:918), GCGTTCGGAGTTAGTCGGGAGTTGGGT (SEQ ID NO:919), CGAGGAGGAAGAAGTAGTTGCGGCGGT (SEQ ID NO:920), TCGAGGAGGAAGAAGTAGTTGCGGCGG (SEQ ID NO:921), AGTCGGGAGTTGGGTAGTAGCGGTCGA (SEQ ID NO:922), GTCGGGAGTTGGGTAGTAGCGGTCGAG (SEQ ID NO:923) |
| Target98 | chr1:145075691-145075709 | TGTTTAGTTTTCGGTTGGTTTCGGGCGT (SEQ ID NO:924), GTTTAGTTTTCGGTTGGTTTCGGGCGT (SEQ ID NO:925), TGTTTAGTTTTCGGTTGGTTTCGGGCG (SEQ ID NO:926), TTTAGTTTTCGGTTGGTTTCGGGCGTC (SEQ ID NO:927), GTTTAGTTTTCGGTTGGTTTCGGGCGTC (SEQ ID NO:928), CGATTTTGGTTGTTGTTGTCGCGCGTT (SEQ ID NO:929), CGATTTTGGTTGTTGTTGTCGCGCGTTT (SEQ ID NO:930), CGATTTTGGTTGTTGTTGTCGCGCGT (SEQ ID NO:931), CGATTTTGGTTGTTGTTGTCGCGCGTTC (SEQ ID NO:932), ATTTTGGTTGTTGTTGTCGCGCGTTTC (SEQ ID NO:933) |
| Target99 | chr1:145075722-145075928 | TCGGCGGCGGTAGTAGGATTCGTTGTT (SEQ ID NO:934), GTTTGTCGTGGGGATTGAGGGGTTCGC (SEQ ID NO:935), CGTATCGGCGGCGGTAGTAGGATTCGT (SEQ ID NO:936), ATCGGCGGCGGTAGTAGGATTCGTTGT (SEQ ID NO:937), TTTTTCGGTTCGGGGTTTGTCGTGGGG (SEQ ID NO:938), AGGTGGTAGAGGTAGTCGCGGAGGAGG (SEQ ID NO:939), GGTGGTAGAGGTAGTCGCGGAGGAGGT (SEQ ID NO:940), GCGGAGTAGGTGGTAGAGGTAGTCGCG (SEQ ID NO:941), GGCGGAGTAGGTGGTAGAGGTAGTCGC (SEQ ID NO:942), CGGAGTAGGTGGTAGAGGTAGTCGCGG (SEQ ID NO:943) |
| Target100 | chr1:145562692-145562810 | TGGGGAAGTTGGAGGAAGAGTTGCGGG (SEQ ID NO:944), GGGGAAGTTGGAGGAAGAGTTGCGGGT (SEQ ID NO:945), TTGGGGAAGTTGGAGGAAGAGTTGCGGG (SEQ ID NO:946), TTGGGGAAGTTGGAGGAAGAGTTGCGG (SEQ ID NO:947), GGGGAAGTTGGAGGAAGAGTTGCGGGTA (SEQ ID NO:948), CGTGTTGTCGTAGGTTGGTTGTTTTTCGGG (SEQ ID NO:949), CGTGTTGTCGTAGGTTGGTTGTTTTTCGGGT (SEQ ID NO:950), TGTTGTCGTAGGTTGGTTGTTTTTCGGGT (SEQ ID NO:951), GTTGTCGTAGGTTGGTTGTTTTTCGGGT (SEQ ID NO:952), TGTTGTCGTAGGTTGGTTGTTTTTCGGG (SEQ ID NO:953) |
| Target101 | chr1:145562817-145562835 | AGTGGTTGAGTTAAGGGTTCGGGAGGT (SEQ ID NO:954), TGAGCGGGAAGAGTTAGGAGATCGGAA (SEQ ID NO:955), ATGAGCGGGAAGAGTTAGGAGATCGGA (SEQ ID NO:956), AAGTGGTTGAGTTAAGGGTTCGGGAGGT (SEQ ID NO:957), AAGTGGTTGAGTTAAGGGTTCGGGAGG (SEQ ID NO:958) |
| Target102 | chr1:145562897-145563019 | TACGGTTTGTCGGGAAGTGGGTCGGTT (SEQ ID NO:959), ATACGGTTTGTCGGGAAGTGGGTCGGT (SEQ ID NO:960), ACGGTTTGTCGGGAAGTGGGTCGGTTG (SEQ ID NO:961), GGTTTGTCGGGAAGTGGGTCGGTTGC (SEQ ID NO:962), CGGTTTGTCGGGAAGTGGGTCGGTTG (SEQ ID NO:963), TGAGCGGTTAGGTTTTCGTTTCGGCGG (SEQ ID NO:964), CGGTTAGGTTTTCGTTTCGGCGGCGTT (SEQ ID NO:965), GAGCGGTTAGGTTTTCGTTTCGGCGGC (SEQ ID NO:966), TTGAGCGGTTAGGTTTTCGTTTCGGCGG (SEQ ID NO:967), GGTTAGGTTTTCGTTTCGGCGGCGTTT (SEQ ID NO:968) |
| Target103 | chr1:155265010-155265083 | CGTCGTTAATGTAGATGCGGTTTTTTATCGGT (SEQ ID NO:969), TCGTCGTTAATGTAGATGCGGTTTTTTATCGG (SEQ ID NO:970), TCGTCGTTAATGTAGATGCGGTTTTTTATCGGT (SEQ ID NO:971), TTCGTCGTTAATGTAGATGCGGTTTTTTATCGG (SEQ ID NO:972), GATGAGTTCGTCGTTAATGTAGATGCGGTTTTT (SEQ ID NO:973), CGGCGTTTGTAGGGTTGGGTTTAGGCG (SEQ ID NO:974), GGCGGCGTTTGTAGGGTTGGGTTTAGG (SEQ ID NO:975), GTCGGAAAGGCGGCGTTTGTAGGGTTG (SEQ ID NO:976), |

FIGURE 5 CONTINUED

GAAAGGCGGCGTTTGTAGGGTTGGGTT (SEQ ID NO:977), GCGGCGTTTGTAGGGTTGGGTTTAGGC (SEQ ID NO:978)

| | | |
|---|---|---|
| Target104 | chr1:155265132-155265147 | AGGAGGGAGTTAGAGGAGATGTGAGTTTTGA (SEQ ID NO:979), AGAGGAGATGTGAGTTTTGAGTTTCGGAGTT (SEQ ID NO:980), GGAGGGAGTTAGAGGAGATGTGAGTTTTGAGT (SEQ ID NO:981), AGGAGGGAGTTAGAGGAGATGTGAGTTTTGAG (SEQ ID NO:982), AGGAGGGAGTTAGAGGAGATGTGAGTTTTGAGT (SEQ ID NO:983), CGGCGTTTGTAGGGTTGGGTTTAGGCG (SEQ ID NO:984), GGGGGTGAGTAGTGGGGTTGGGATTCG (SEQ ID NO:985), GGCGGCGTTTGTAGGGTTGGGTTTAGG (SEQ ID NO:986), TGTAGGGGGTGAGTAGTGGGGTTGGGA (SEQ ID NO:987), GTCGGAAAGGCGGCGTTTGTAGGGTTG (SEQ ID NO:988) |
| Target105 | chr1:155265158-155265276 | GGCGTCGTTTTTTCGGTTTTGGTTTAGC (SEQ ID NO:989), AGGCGTCGTTTTTTCGGTTTTGGTTTAGC (SEQ ID NO:990), GCGGATTTTCGGTTTTTTGGTGTTTAGGGCG (SEQ ID NO:991), GCGGATTTTCGGTTTTTTGGTGTTTAGGGC (SEQ ID NO:992), TGCGGATTTTCGGTTTTTTGGTGTTTAGGGCG (SEQ ID NO:993), GGGGGTGAGTAGTGGGGTTGGGATTCG (SEQ ID NO:994), CGGGAGGCGGTGGAGAGTTTTGTAGGT (SEQ ID NO:995), GGCGGCGTTTGTAGGGTTGGGTTTAGG (SEQ ID NO:996), TGTAGGGGGTGAGTAGTGGGGTTGGGA (SEQ ID NO:997), GTCGGAAAGGCGGCGTTTGTAGGGTTG (SEQ ID NO:998) |
| Target106 | chr1:155265331-155265342 | TGGTTACGGGTCGGTAGTTGAGTGGGG (SEQ ID NO:999), GGTTACGGGTCGGTAGTTGAGTGGGGA (SEQ ID NO:1000), TGGTTACGGGTCGGTAGTTGAGTGGGGA (SEQ ID NO:1001), TGGTGTTTAGGGCGATGGTTACGGGTC (SEQ ID NO:1002), ATGGTTACGGGTCGGTAGTTGAGTGGGG (SEQ ID NO:1003), TCGGGTAGTGGGTGGGGTAGGAGGATG (SEQ ID NO:1004), GTCGGGTAGTGGGTGGGGTAGGAGGAT (SEQ ID NO:1005), CGGGTAGTGGGTGGGGTAGGAGGATGT (SEQ ID NO:1006), GGGTGGGGTAGGAGGATGTTTCGAGGT (SEQ ID NO:1007), TGGGTGGGGTAGGAGGATGTTTCGAGG (SEQ ID NO:1008) |
| Target107 | chr1:155265438-155265468 | GGAGCGAGGGTTTTAGGGGAAGGTGGT (SEQ ID NO:1009), CGGAGCGAGGGTTTTAGGGGAAGGTGG (SEQ ID NO:1010), GGAGCGAGGGTTTTAGGGGAAGGTGGTT (SEQ ID NO:1011), AGTATGGTATTGGGGGAGGGAGCGGAG (SEQ ID NO:1012), GAGCGAGGGTTTTAGGGGAAGGTGGTT (SEQ ID NO:1013), GGAGCGTTTTAAGGAGATGATTAAGGTCGGG (SEQ ID NO:1014), TGGAGCGTTTTAAGGAGATGATTAAGGTCGGG (SEQ ID NO:1015), GGAGCGTTTTAAGGAGATGATTAAGGTCGGGA (SEQ ID NO:1016), TGGAGCGTTTTAAGGAGATGATTAAGGTCGGGA (SEQ ID NO:1017), TGGAGCGTTTTAAGGAGATGATTAAGGTCGG (SEQ ID NO:1018) |
| Target108 | chr1:156092302-156092455 | TTTTTTGGACGGTGGAAAGGGTTGTGTT (SEQ ID NO:1019), TGGACGGTGGAAAGGGTTGTGTTATAGAGT (SEQ ID NO:1020), GGACGGTGGAAAGGGTTGTGTTATAGAGT (SEQ ID NO:1021), TGGACGGTGGAAAGGGTTGTGTTATAGAG (SEQ ID NO:1022), TTGGACGGTGGAAAGGGTTGTGTTATAGA (SEQ ID NO:1023), GTTTAGAAGGGAGAGGTATCGAAAACGAGTTGT (SEQ ID NO:1024) |
| Target109 | chr1:156092497-156092579 | TTGATTCGGGTTGGGGGTTAGGGCGAA (SEQ ID NO:1025), ATTGATTCGGGTTGGGGGTTAGGGCGA (SEQ ID NO:1026), CGGGTTGGGGGTTAGGGCGAAGGTTTA (SEQ ID NO:1027), TGATTCGGGTTGGGGGTTAGGGCGAAG (SEQ ID NO:1028), AGTGTTTGGAATCGGGGGGAGGGGTAC (SEQ ID NO:1029), TGGGTGTTGGAAGGGTAGAAGGTGGGT (SEQ ID NO:1030), ATGGGTGTTGGAAGGGTAGAAGGTGGGT (SEQ ID NO:1031), ATGGGTGTTGGAAGGGTAGAAGGTGGG (SEQ ID NO:1032), TGGGTGTTGGAAGGGTAGAAGGTGGGTA (SEQ ID NO:1033), GGGTGTTGGAAGGGTAGAAGGTGGGTA (SEQ ID NO:1034) |
| Target110 | chr1:156406194-156406230 | CGTAGTGTTTGGGTTCGCGGCGTTAAG (SEQ ID NO:1035), GCGTGTGTTTTCGGTTGCGAGGTTTTG (SEQ ID NO:1036), GCGTGTGTTTTCGGTTGCGAGGTTTTGT (SEQ ID NO:1037), CGTGTGTTTTCGGTTGCGAGGTTTTGT (SEQ ID NO:1038), CGTAGTGTTTGGGTTCGCGGCGTTAA (SEQ ID NO:1039), GTTGGGGTTTCGAACGGTTGGCGGG (SEQ ID NO:1040), TTGGGGTTTCGAACGGTTGGCGGGGAG (SEQ ID NO:1041), GTTGGGGTTTCGAACGGTTGGCGGGGA (SEQ ID NO:1042), TTGGGGTTTCGAACGGTTGGCGGG (SEQ ID NO:1043), GGGTTTCGAACGGTTGGCGGGGAG (SEQ ID NO:1044) |
| Target111 | chr1:156406255-156406284 | CGTAGTGTTTGGGTTCGCGGCGTTAAG (SEQ ID NO:1045), GCGTGTGTTTTCGGTTGCGAGGTTTTG (SEQ ID NO:1046), GCGTGTGTTTTCGGTTGCGAGGTTTTGT (SEQ ID NO:1047), CGTGTGTTTTCGGTTGCGAGGTTTTGT (SEQ ID NO:1048), CGTAGTGTTTGGGTTCGCGGCGTTAA (SEQ ID NO:1049), GTTGGGGTTTCGAACGGTTGGCGGG (SEQ ID NO:1050), TTGGGGTTTCGAACGGTTGGCGGGGAG (SEQ ID NO:1051), GTTGGGGTTTCGAACGGTTGGCGGGGA (SEQ ID NO:1052), TTGGGGTTTCGAACGGTTGGCGGG (SEQ ID NO:1053), GGGTTTCGAACGGTTGGCGGGGAG (SEQ ID NO:1054) |
| Target112 | chr1:156406318-156406350 | CGTAGTGTTTGGGTTCGCGGCGTTAAG (SEQ ID NO:1055), CGTAGTGTTTGGGTTCGCGGCGTTAA (SEQ ID NO:1056), AGTCGTTCGGGATTTTAGTTTGGGGGA (SEQ ID NO:1057), CGTAGTGTTTGGGTTCGCGGCGTTA (SEQ ID NO:1058), GTAGTGTTTGGGTTCGCGGCGTTAAG (SEQ ID NO:1059), AGTTTAGGTTGTCGCGTGGAGTTTGC (SEQ ID NO:1060), |

FIGURE 5 CONTINUED

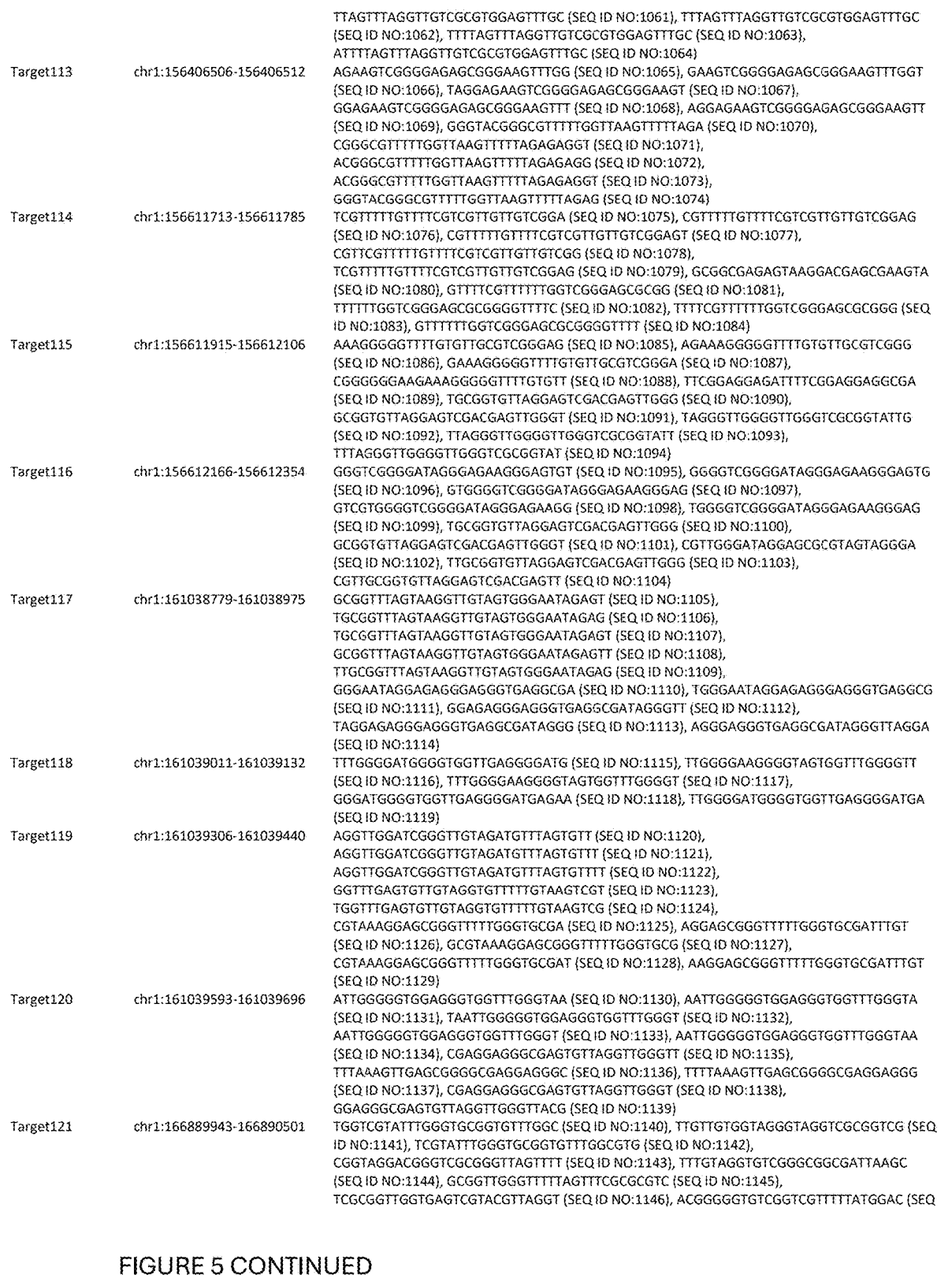

|  |  | TTAGTTTAGGTTGTCGCGTGGAGTTTGC (SEQ ID NO:1061), TTTAGTTTAGGTTGTCGCGTGGAGTTTGC (SEQ ID NO:1062), TTTTAGTTTAGGTTGTCGCGTGGAGTTTGC (SEQ ID NO:1063), ATTTTAGTTTAGGTTGTCGCGTGGAGTTTGC (SEQ ID NO:1064) |
|---|---|---|
| Target113 | chr1:156406506-156406512 | AGAAGTCGGGGAGAGCGGGAAGTTTGG (SEQ ID NO:1065), GAAGTCGGGGAGAGCGGGAAGTTTGGT (SEQ ID NO:1066), TAGGAGAAGTCGGGGAGAGCGGGAAGT (SEQ ID NO:1067), GGAGGAAGTCGGGGAGAGCGGGAAGTTT (SEQ ID NO:1068), AGGAGAAGTCGGGGAGAGCGGGAAGTT (SEQ ID NO:1069), GGGTACGGGCGTTTTTGGTTAAGTTTTTAGA (SEQ ID NO:1070), CGGGGCGTTTTTGGTTAAGTTTTTAGAGAGGT (SEQ ID NO:1071), ACGGGCGTTTTTGGTTAAGTTTTTAGAGAGG (SEQ ID NO:1072), ACGGGCGTTTTTGGTTAAGTTTTTAGAGAGGT (SEQ ID NO:1073), GGGTACGGGCGTTTTTGGTTAAGTTTTTAGAG (SEQ ID NO:1074) |
| Target114 | chr1:156611713-156611785 | TCGTTTTTGTTTTCGTCGTTGTTGTCGGA (SEQ ID NO:1075), CGTTTTTGTTTTCGTCGTTGTTGTCGGAG (SEQ ID NO:1076), CGTTTTTGTTTTCGTCGTTGTTGTCGGAGT (SEQ ID NO:1077), CGTTCGTTTTTGTTTTCGTCGTTGTTGTCGG (SEQ ID NO:1078), TCGTTTTTGTTTTCGTCGTTGTTGTCGGAG (SEQ ID NO:1079), GCGGCGAGAGTAAGGACGAGCGAAGTA (SEQ ID NO:1080), GTTTTCGTTTTTTGGTCGGGAGCGCGG (SEQ ID NO:1081), TTTTTTGGTCGGGAGCGCGGGGTTTTC (SEQ ID NO:1082), TTTTCGTTTTTTGGTCGGGAGCGCGGG (SEQ ID NO:1083), GTTTTTTGGTCGGGAGCGCGGGGTTTT (SEQ ID NO:1084) |
| Target115 | chr1:156611915-156612106 | AAAGGGGGTTTTGTGTTGCGTCGGGAG (SEQ ID NO:1085), AGAAAGGGGGTTTTGTGTTGCGTCGGG (SEQ ID NO:1086), GAAAGGGGGTTTTGTGTTGCGTCGGGA (SEQ ID NO:1087), CGGGGGGGAAGAAAGGGGGTTTTGTGTT (SEQ ID NO:1088), TTCGGAGGAGATTTTCGGAGGAGGCGA (SEQ ID NO:1089), TGCGGTGTTAGGAGTCGACGAGTTGGG (SEQ ID NO:1090), GCGGTGTTAGGAGTCGACGAGTTGGGT (SEQ ID NO:1091), TAGGGTTGGGGTTGGGTCGCGGTATTG (SEQ ID NO:1092), TTAGGGTTGGGGTTGGGTCGCGGTATT (SEQ ID NO:1093), TTTAGGGTTGGGGTTGGGTCGCGGTAT (SEQ ID NO:1094) |
| Target116 | chr1:156612166-156612354 | GGGTCGGGGGATAGGGAGAAGGGAGTGT (SEQ ID NO:1095), GGGGTCGGGGATAGGGAGAAGGGAGTG (SEQ ID NO:1096), GTGGGGTCGGGGATAGGGAGAAGGGAG (SEQ ID NO:1097), GTCGTGGGGTCGGGGATAGGGAGAAGG (SEQ ID NO:1098), TGGGGTCGGGGATAGGGAGAAGGGAG (SEQ ID NO:1099), TGCGGTGTTAGGAGTCGACGAGTTGGG (SEQ ID NO:1100), GCGGTGTTAGGAGTCGACGAGTTGGGT (SEQ ID NO:1101), CGTTGGGATAGGAGCGCGTAGTAGGGA (SEQ ID NO:1102), TTGCGGTGTTAGGAGTCGACGAGTTGGG (SEQ ID NO:1103), CGTTGCGGTGTTAGGAGTCGACGAGTT (SEQ ID NO:1104) |
| Target117 | chr1:161038779-161038975 | GCGGTTTAGTAAGGTTGTAGTGGGAATAGAGT (SEQ ID NO:1105), TGCGGTTTAGTAAGGTTGTAGTGGGAATAGAG (SEQ ID NO:1106), TGCGGTTTAGTAAGGTTGTAGTGGGAATAGAGT (SEQ ID NO:1107), GCGGTTTAGTAAGGTTGTAGTGGGAATAGAGTT (SEQ ID NO:1108), TTGCGGTTTAGTAAGGTTGTAGTGGGAATAGAG (SEQ ID NO:1109), GGGAATAGGAGAGGGAGGGTGAGGCGA (SEQ ID NO:1110), TGGGAATAGGAGAGGGAGGGTGAGGCG (SEQ ID NO:1111), GGAGAGGGAGGGTGAGGCGATAGGGTT (SEQ ID NO:1112), TAGGAGAGGGAGGGTGAGGCGATAGGG (SEQ ID NO:1113), AGGGAGGGTGAGGCGATAGGGTTAGGA (SEQ ID NO:1114) |
| Target118 | chr1:161039011-161039132 | TTTGGGGATGGGGTGGTTGAGGGGATG (SEQ ID NO:1115), TTGGGGAAGGGGTAGTGGTTTGGGGTT (SEQ ID NO:1116), TTTGGGGAAGGGGTAGTGGTTTGGGGT (SEQ ID NO:1117), GGGATGGGGTGGTTGAGGGGATGAGAA (SEQ ID NO:1118), TTGGGGATGGGGTGGTTGAGGGGATGA (SEQ ID NO:1119) |
| Target119 | chr1:161039306-161039440 | AGGTTGGATCGGGTTGTAGATGTTTAGTGTT (SEQ ID NO:1120), AGGTTGGATCGGGTTGTAGATGTTTAGTGTTT (SEQ ID NO:1121), AGGTTGGATCGGGTTGTAGATGTTTAGTGTTTT (SEQ ID NO:1122), GGTTTGAGTGTTGTAGGTGTTTTTGTAAGTCGT (SEQ ID NO:1123), TGGTTTGAGTGTTGTAGGTGTTTTTGTAAGTCG (SEQ ID NO:1124), CGTAAAGGAGCGGGTTTTTGGGTGCGA (SEQ ID NO:1125), AGGAGCGGGTTTTTGGGTGCGATTTGT (SEQ ID NO:1126), GCGTAAAGGAGCGGGTTTTTGGGTGCG (SEQ ID NO:1127), CGTAAAGGAGCGGGTTTTTGGGTGCGAT (SEQ ID NO:1128), AAGGAGCGGGTTTTTGGGTGCGATTTGT (SEQ ID NO:1129) |
| Target120 | chr1:161039593-161039696 | ATTGGGGGTGGAGGGTGGTTTGGGTAA (SEQ ID NO:1130), AATTGGGGGTGGAGGGTGGTTTGGGTA (SEQ ID NO:1131), TAATTGGGGGTGGAGGGTGGTTTGGGT (SEQ ID NO:1132), AATTGGGGGTGGAGGGTGGTTTGGGT (SEQ ID NO:1133), AATTGGGGGTGGAGGGTGGTTTGGGTAA (SEQ ID NO:1134), CGAGGAGGGCGAGTGTTAGGTTGGGTT (SEQ ID NO:1135), TTTAAAGTTGAGCGGGGCGAGGAGGGC (SEQ ID NO:1136), TTTTAAAGTTGAGCGGGGCGAGGAGGG (SEQ ID NO:1137), CGAGGAGGGCGAGTGTTAGGTTGGGT (SEQ ID NO:1138), GGAGGGCGAGTGTTAGGTTGGGTTACG (SEQ ID NO:1139) |
| Target121 | chr1:166889943-166890501 | TGGTCGTATTTGGGTGCGGTGTTTGGC (SEQ ID NO:1140), TTGTTGTGGTAGGGTAGGTCGCGGTCG (SEQ ID NO:1141), TCGTATTTGGGTGCGGTGTTTGGCGTG (SEQ ID NO:1142), CGGTAGGACGGGTCGCGGGTTAGTTTT (SEQ ID NO:1143), TTTGTAGGTGTCGGGCGGCGATTAAGC (SEQ ID NO:1144), GCGGTTGGGTTTTTAGTTTCGCGCGTC (SEQ ID NO:1145), TCGCGGTTGGTGAGTCGTACGTTAGGT (SEQ ID NO:1146), ACGGGGGTGTCGGTCGTTTTTATGGAC (SEQ |

FIGURE 5 CONTINUED

ID NO:1147), TATTCGTATTTGGGTAGCGCGCGGGAG (SEQ ID NO:1148),
AGAATTTCGTTACGGGGGTGTCGGTCG (SEQ ID NO:1149)

| | | |
|---|---|---|
| Target122 | chr1:166890503-166890517 | GCGTTTCGTGATTGTTGTCGTTTGTTCGG (SEQ ID NO:1150), GCGTTTCGTGATTGTTGTCGTTTGTTCG (SEQ ID NO:1151), GGAGTCGTTTTGGTAGAAGTCGTTGTGC (SEQ ID NO:1152), AGGAGTCGTTTTGGTAGAAGTCGTTGTGC (SEQ ID NO:1153), CGTTTCGTGATTGTTGTCGTTTGTTCGG (SEQ ID NO:1154), ACGGGGGTGTCGGTCGTTTTTATGGAC (SEQ ID NO:1155), AGAATTTCGTTACGGGGGTGTCGGTCG (SEQ ID NO:1156), AAGAATTTCGTTACGGGGGTGTCGGTCG (SEQ ID NO:1157), ACGGGGGTGTCGGTCGTTTTTATGGA (SEQ ID NO:1158), GAAGAATTTCGTTACGGGGGTGTCGGTCG (SEQ ID NO:1159) |
| Target123 | chr1:166890584-166890611 | GCGTTTCGTGATTGTTGTCGTTTGTTCGG (SEQ ID NO:1160), GCGTTTCGTGATTGTTGTCGTTTGTTCG (SEQ ID NO:1161), CGTTTCGTGATTGTTGTCGTTTGTTCGG (SEQ ID NO:1162), TGGAGTTTTAGGGAGGGATCGGTCGTT (SEQ ID NO:1163), TTGGAGTTTTAGGGAGGGATCGGTCGT (SEQ ID NO:1164), TGGAGTTTTAGGGAGGGATCGGTCGTTT (SEQ ID NO:1165), TTGGAGTTTTAGGGAGGGATCGGTCGTT (SEQ ID NO:1166), TTTGGAGTTTTAGGGAGGGATCGGTCGT (SEQ ID NO:1167) |
| Target124 | chr1:180904425-180904463 | GGTGGGTATAGGTCGAGGCGGGGTTTT (SEQ ID NO:1168), TTTAGCGGTGGGTATAGGTCGAGGCGG (SEQ ID NO:1169), TTAGCGGTGGGTATAGGTCGAGGCGGG (SEQ ID NO:1170), GTTTAGCGGTGGGTATAGGTCGAGGCGG (SEQ ID NO:1171), GGTGGGTATAGGTCGAGGCGGGGTTTTT (SEQ ID NO:1172), CGTAGGGGGTTTTGGTTCGCGGTTTGT (SEQ ID NO:1173), GTCGGGTTTGGAGCGTAGGGGGTTTTG (SEQ ID NO:1174), TCGGGTTTGGAGCGTAGGGGGTTTTGG (SEQ ID NO:1175), GGTCGGGTTTGGAGCGTAGGGGGGTTTT (SEQ ID NO:1176), CGGGGAGTTTCGTTGATGTAGTCGGCG (SEQ ID NO:1177) |
| Target125 | chr1:180904552-180904566 | TGTAGGTCGCGGATTAGGGTTTTTTGC (SEQ ID NO:1178), TTGTAGGTCGCGGATTAGGGTTTTTTGC (SEQ ID NO:1179), GTTGTAGGTCGCGGATTAGGGTTTTTTGC (SEQ ID NO:1180), TGTTGTAGGTCGCGGATTAGGGTTTTTTGC (SEQ ID NO:1181), GTGTTGTAGGTCGCGGATTAGGGTTTTTTGC (SEQ ID NO:1182), CGGTGTCGGGTGTTTTTTGCGGTTTAGG (SEQ ID NO:1183), CGGTGTCGGGTGTTTTTTGCGGTTTAGGT (SEQ ID NO:1184), CGGTGTCGGGTGTTTTTTGCGGTTTAG (SEQ ID NO:1185), GGTGTCGGGTGTTTTTTGCGGTTTAGGT (SEQ ID NO:1186), GGTGTCGGGTGTTTTTTGCGGTTTAGG (SEQ ID NO:1187) |
| Target126 | chr1:180904606-180904626 | TGTAGGTCGCGGATTAGGGTTTTTTGC (SEQ ID NO:1188), GGTTTGTGGGTAGTTTGGATCGTAGGGG (SEQ ID NO:1189), AGGTTTGTGGGTAGTTTGGATCGTAGGGG (SEQ ID NO:1190), GGTTTGTGGGTAGTTTGGATCGTAGGGA (SEQ ID NO:1191), GGGACGCGGGGTAGGGGATATTTTATAGG (SEQ ID NO:1192), GTTTTTTGGAGGGTTTTGGGGACGGGGG (SEQ ID NO:1193), AGTTTTTTGGAGGGTTTTGGGGACGGGG (SEQ ID NO:1194), TTTTTTGGAGGGTTTTGGGGACGGGGGG (SEQ ID NO:1195), GGTTTTTGGGGACGGGGGGGCGTTTTT (SEQ ID NO:1196), GAGTTTTTTGGAGGGTTTTGGGGACGGGG (SEQ ID NO:1197) |
| Target127 | chr1:180904628-180904642 | GGTTTGTGGGTAGTTTGGATCGTAGGGG (SEQ ID NO:1198), AGGTTTGTGGGTAGTTTGGATCGTAGGGG (SEQ ID NO:1199), GGTTTGTGGGTAGTTTGGATCGTAGGGGA (SEQ ID NO:1200), GGGACGCGGGGTAGGGGATATTTTATAGG (SEQ ID NO:1201), GGGACGCGGGGTAGGGGATATTTTATAGGT (SEQ ID NO:1202), GTTTTTTGGAGGGTTTTGGGGACGGGGG (SEQ ID NO:1203), AGTTTTTTGGAGGGTTTTGGGGACGGGG (SEQ ID NO:1204), TTTTTTGGAGGGTTTTGGGGACGGGGGG (SEQ ID NO:1205), GGTTTTTGGGGACGGGGGGGCGTTTTT (SEQ ID NO:1206), GAGTTTTTTGGAGGGTTTTGGGGACGGGG (SEQ ID NO:1207) |
| Target128 | chr1:180904682-180904704 | AGCGAGAGGAGGTGTTAGGTTTGCGGT (SEQ ID NO:1208), TCGGGTAGCGAGAGGAGGTGTTAGGTT (SEQ ID NO:1209), GCGAGAGGAGGTGTTAGGTTTGCGGTA (SEQ ID NO:1210), ATCGGGTAGCGAGAGGAGGTGTTAGGT (SEQ ID NO:1211), AGCGAGAGGAGGTGTTAGGTTTGCGGTA (SEQ ID NO:1212), GTTTTTTGGAGGGTTTTGGGGACGGGGG (SEQ ID NO:1213), AGTTTTTTGGAGGGTTTTGGGGACGGGG (SEQ ID NO:1214), TTTTTTGGAGGGTTTTGGGGACGGGGGG (SEQ ID NO:1215), GGTTTTTGGGGACGGGGGGGCGTTTTT (SEQ ID NO:1216), GAGTTTTTTGGAGGGTTTTGGGGACGGGG (SEQ ID NO:1217) |
| Target129 | chr1:180904786-180904863 | GTGGGATGGAGAGGGTGTTGGGTGGTT (SEQ ID NO:1218), TTGTGGGATGGAGAGGGTGTTGGGTGG (SEQ ID NO:1219), TGGGATGGAGAGGGTGTTGGGTGGTTT (SEQ ID NO:1220), TGTGGGATGGAGAGGGTGTTGGGTGGT (SEQ ID NO:1221), GGGATGGAGAGGGTGTTGGGTGGTTTG (SEQ ID NO:1222), AGTCGCGGGTTGTTGTTTTGGGTTCGT (SEQ ID NO:1223), GTCGCGGGTTGTTGTTTTGGGTTCGTT (SEQ ID NO:1224), AGTCGCGGGTTGTTGTTTTGGGTTCGTT (SEQ ID NO:1225), TCGCGGGTTGTTGTTTTGGGTTCGTTT (SEQ ID NO:1226), CGTAGTCGCGGGTTGTTGTTTTGGGTT (SEQ ID NO:1227) |
| Target130 | chr1:203598330-203598987 | TTAGGGGTCGATGTTGGTGGGTTCGGG (SEQ ID NO:1228), GCGTATCGGGTCGTTTGAGTTCGGGGT (SEQ ID NO:1229), CGTATCGGGTCGTTTGAGTTCGGGGTC (SEQ ID NO:1230), ATTAGGGGTCGATGTTGGTGGGTTCGG (SEQ ID NO:1231), TAGGGGTCGATGTTGGTGGGTTCGGG (SEQ ID NO:1232), AGGGGAAATTGGAGGTTAGACGGCGGG (SEQ ID NO:1233), CGTGTTGGGCGTTGGGAGTTTTAGGGG (SEQ ID NO:1234), GGGGAAATTGGAGGTTAGACGGCGGGT |

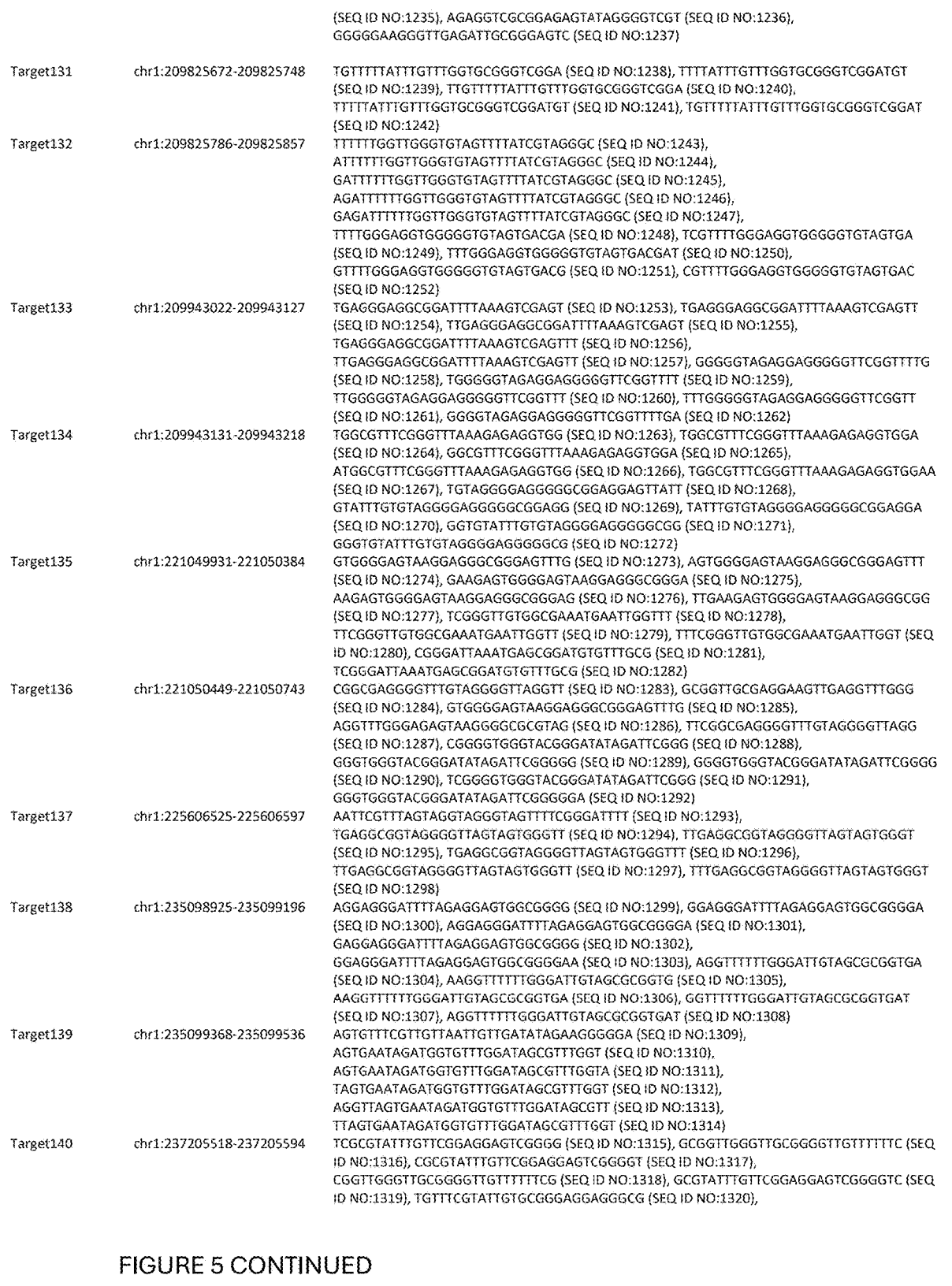

FIGURE 5 CONTINUED (SEQ ID NO:1235), AGAGGTCGCGGAGAGTATAGGGGTCGT (SEQ ID NO:1236),
GGGGGAAGGGTTGAGATTGCGGGAGTC (SEQ ID NO:1237)

Target131    chr1:209825672-209825748    TGTTTTTATTTGTTTGGTGCGGGTCGGA (SEQ ID NO:1238), TTTTATTTGTTTGGTGCGGGTCGGATGT (SEQ ID NO:1239), TTGTTTTTATTTGTTTGGTGCGGGTCGGA (SEQ ID NO:1240), TTTTTATTTGTTTGGTGCGGGTCGGATGT (SEQ ID NO:1241), TGTTTTTATTTGTTTGGTGCGGGTCGGAT (SEQ ID NO:1242)

Target132    chr1:209825786-209825857    TTTTTTGGTTGGGTGTAGTTTTATCGTAGGGC (SEQ ID NO:1243), ATTTTTTTGGTTGGGTGTAGTTTTATCGTAGGGC (SEQ ID NO:1244), GATTTTTTGGTTGGGTGTAGTTTTATCGTAGGGC (SEQ ID NO:1245), AGATTTTTTGGTTGGGTGTAGTTTTATCGTAGGGC (SEQ ID NO:1246), GAGATTTTTTGGTTGGGTGTAGTTTTATCGTAGGGC (SEQ ID NO:1247), TTTTGGGAGGTGGGGGTGTAGTGACGA (SEQ ID NO:1248), TCGTTTTGGGAGGTGGGGGTGTAGTGA (SEQ ID NO:1249), TTTGGGAGGTGGGGGTGTAGTGACGAT (SEQ ID NO:1250), GTTTTGGGAGGTGGGGGTGTAGTGACG (SEQ ID NO:1251), CGTTTTGGGAGGTGGGGGTGTAGTGAC (SEQ ID NO:1252)

Target133    chr1:209943022-209943127    TGAGGGAGGCGGATTTTAAAGTCGAGT (SEQ ID NO:1253), TGAGGGAGGCGGATTTTAAAGTCGAGTT (SEQ ID NO:1254), TTGAGGGAGGCGGATTTTAAAGTCGAGT (SEQ ID NO:1255), TGAGGGAGGCGGATTTTAAAGTCGAGTTT (SEQ ID NO:1256), TTGAGGGAGGCGGATTTTAAAGTCGAGTT (SEQ ID NO:1257), GGGGGTAGAGGAGGGGGTTCGGTTTTG (SEQ ID NO:1258), TGGGGGTAGAGGAGGGGGTTCGGTTTT (SEQ ID NO:1259), TTGGGGGTAGAGGAGGGGGTTCGGTTT (SEQ ID NO:1260), TTTGGGGGTAGAGGAGGGGGTTCGGTT (SEQ ID NO:1261), GGGGTAGAGGAGGGGGGTTCGGTTTTGA (SEQ ID NO:1262)

Target134    chr1:209943131-209943218    TGGCGTTTCGGGTTTAAAGAGAGGTGG (SEQ ID NO:1263), TGGCGTTTCGGGTTTAAAGAGAGGTGGA (SEQ ID NO:1264), GGCGTTTCGGGTTTAAAGAGAGGTGGA (SEQ ID NO:1265), ATGGCGTTTCGGGTTTAAAGAGAGGTGG (SEQ ID NO:1266), TGGCGTTTCGGGTTTAAAGAGAGGTGGAA (SEQ ID NO:1267), TGTAGGGGAGGGGGCGGAGGAGTTATT (SEQ ID NO:1268), GTATTTGTGTAGGGGAGGGGGCGGAGG (SEQ ID NO:1269), TATTTGTGTAGGGGAGGGGGCGGAGGA (SEQ ID NO:1270), GGTGTATTTGTGTAGGGGAGGGGGCGG (SEQ ID NO:1271), GGGTGTATTTGTGTAGGGGAGGGGGCG (SEQ ID NO:1272)

Target135    chr1:221049931-221050384    GTGGGGAGTAAGGAGGGCGGGAGTTTG (SEQ ID NO:1273), AGTGGGGAGTAAGGAGGGCGGGAGTTT (SEQ ID NO:1274), GAAGAGTGGGGAGTAAGGAGGGCGGGA (SEQ ID NO:1275), AAGAGTGGGGAGTAAGGAGGGCGGGAG (SEQ ID NO:1276), TTGAAGAGTGGGGAGTAAGGAGGGCGG (SEQ ID NO:1277), TCGGGTTGTGGCGAAATGAATTGGTTT (SEQ ID NO:1278), TTCGGGTTGTGGCGAAATGAATTGGTT (SEQ ID NO:1279), TTTCGGGTTGTGGCGAAATGAATTGGT (SEQ ID NO:1280), CGGGATTAAATGAGCGGATGTGTTTGCG (SEQ ID NO:1281), TCGGGATTAAATGAGCGGATGTGTTTGCG (SEQ ID NO:1282)

Target136    chr1:221050449-221050743    CGGCGAGGGGTTTGTAGGGGTTAGGTT (SEQ ID NO:1283), GCGGTTGCGAGGAAGTTGAGGTTTGGG (SEQ ID NO:1284), GTGGGGAGTAAGGAGGGCGGGAGTTTG (SEQ ID NO:1285), AGGTTTGGGAGAGTAAGGAGGCGCGTAG (SEQ ID NO:1286), TTCGGCGAGGGGTTTGTAGGGGTTAGG (SEQ ID NO:1287), CGGGGTGGGTACGGGATATAGATTCGGG (SEQ ID NO:1288), GGGTGGGTACGGGATATAGATTCGGGGG (SEQ ID NO:1289), GGGGTGGGTACGGGATATAGATTCGGGG (SEQ ID NO:1290), TCGGGGTGGGTACGGGATATAGATTCGGG (SEQ ID NO:1291), GGGTGGGTACGGGATATAGATTCGGGGGA (SEQ ID NO:1292)

Target137    chr1:225606525-225606597    AATTCGTTTAGTAGGTAGGGTAGTTTTCGGGATTTT (SEQ ID NO:1293), TGAGGCGGTAGGGGTTAGTAGTGGGTT (SEQ ID NO:1294), TTGAGGCGGTAGGGGTTAGTAGTGGGT (SEQ ID NO:1295), TGAGGCGGTAGGGGTTAGTAGTGGGTT (SEQ ID NO:1296), TTGAGGCGGTAGGGGTTAGTAGTGGGTT (SEQ ID NO:1297), TTTGAGGCGGTAGGGGTTAGTAGTGGGT (SEQ ID NO:1298)

Target138    chr1:235098925-235099196    AGGAGGGGATTTTAGAGGAGTGGCGGGG (SEQ ID NO:1299), GGAGGGGATTTTAGAGGAGTGGCGGGGA (SEQ ID NO:1300), AGGAGGGGATTTTAGAGGAGTGGCGGGGA (SEQ ID NO:1301), GAGGAGGGGATTTTAGAGGAGTGGCGGGG (SEQ ID NO:1302), GGAGGGGATTTTAGAGGAGTGGCGGGGAA (SEQ ID NO:1303), AGGTTTTTTGGGATTGTAGCGCGGTGA (SEQ ID NO:1304), AAGGTTTTTTGGGATTGTAGCGCGGTG (SEQ ID NO:1305), AAGGTTTTTTGGGATTGTAGCGCGGTGA (SEQ ID NO:1306), GGTTTTTTGGGATTGTAGCGCGGTGAT (SEQ ID NO:1307), AGGTTTTTTGGGATTGTAGCGCGGTGAT (SEQ ID NO:1308)

Target139    chr1:235099368-235099536    AGTGTTTCGTTGTTAATTGTTGATATAGAAGGGGGA (SEQ ID NO:1309), AGTGAATAGATGGTGTTTGGATAGCGTTTGGGT (SEQ ID NO:1310), AGTGAATAGATGGTGTTTGGATAGCGTTTGGTA (SEQ ID NO:1311), TAGTGAATAGATGGTGTTTGGATAGCGTTTGGT (SEQ ID NO:1312), AGGTTAGTGAATAGATGGTGTTTGGATAGCGTT (SEQ ID NO:1313), TTAGTGAATAGATGGTGTTTGGATAGCGTTTGGT (SEQ ID NO:1314)

Target140    chr1:237205518-237205594    TCGCGTATTTGTTCGGAGGAGTCGGGG (SEQ ID NO:1315), GCGGTTGGGTTGCGGGGTTGTTTTTTC (SEQ ID NO:1316), CGCGTATTTGTTCGGAGGAGTCGGGGT (SEQ ID NO:1317), CGGTTGGGTTGCGGGGTTGTTTTTTCG (SEQ ID NO:1318), GCGTATTTGTTCGGAGGAGTCGGGGTC (SEQ ID NO:1319), TGTTTCGTATTGTGCGGGAGGAGGGCG (SEQ ID NO:1320),

FIGURE 5 CONTINUED

|  |  | TTGTTTCGTATTGTGCGGGAGGAGGGC (SEQ ID NO:1321), GTTTCGTATTGTGCGGGAGGAGGGCGG (SEQ ID NO:1322), GTTTCGTATTGTGCGGGAGGAGGGCG (SEQ ID NO:1323), TTTGTTTCGTATTGTGCGGGAGGAGGGC (SEQ ID NO:1324) |
|---|---|---|
| Target141 | chr1:237205633-237206037 | GTGCGTCGCGTGTGTTGTTAGGGGAAG (SEQ ID NO:1325), GGGGCGAGGGGGTGTGTTTTTTGAGGATGC (SEQ ID NO:1326), CGAGGGGGTGTTTTTTGAGGATGCGGG (SEQ ID NO:1327), GTTGTTAGGGGAAGGGGGCGTTAGGGT (SEQ ID NO:1328), TGTTGTTAGGGGAAGGGGGCGTTAGGG (SEQ ID NO:1329), GTTTGTAGAGCGGAGGAGGAGGCGCG (SEQ ID NO:1330), CGTTTGTAGAGCGGAGGAGGAGGCGC (SEQ ID NO:1331), GTTTGTAGAGCGGAGGAGGAGGCGCGG (SEQ ID NO:1332), TTTGTAGAGCGGAGGAGGAGGCGCG (SEQ ID NO:1333), CGTTTGTAGAGCGGAGGAGGAGGCGCG (SEQ ID NO:1334) |
| Target142 | chr1:237206046-237206177 | GCGCGCGTGTGGAAAGTTAGAGGATGG (SEQ ID NO:1335), TTGTGCGCGCGTGTGGAAAGTTAGAGG (SEQ ID NO:1336), GGGCGAGGGGGTGTTTTTTGAGGATGC (SEQ ID NO:1337), CGAGGGGGTGTTTTTTGAGGATGCGGG (SEQ ID NO:1338), GAGGGAAGGTAAGGGCGCGTGTTTGTG (SEQ ID NO:1339), CGGTCGTTCGGGAGGTTTTAGTCGTGT (SEQ ID NO:1340), TCGGTCGTTCGGGAGGTTTTAGTCGTGT (SEQ ID NO:1341), TCGGTCGTTCGGGAGGTTTTAGTCGTG (SEQ ID NO:1342), TTCGGTCGTTCGGGAGGTTTTAGTCGT (SEQ ID NO:1343), CGGTCGTTCGGGAGGTTTTAGTCGTGTT (SEQ ID NO:1344) |
| Target143 | chr1:240161087-240161285 | GGGATTAGGGTTTCGGAGGGTGTCGG (SEQ ID NO:1345), CGGGATTAGGGTTTCGGAGGGTGTCGG (SEQ ID NO:1346), GGGAACGGGTTGGTGGCGGTTTTAAGC (SEQ ID NO:1347), GGATTAGGGTTTCGGAGGGTGTCGGGC (SEQ ID NO:1348), TCGGGATTAGGGTTTCGGAGGGTGTCG (SEQ ID NO:1349), GCGCGCGGGAGGAATTGTTTGAGTAGG (SEQ ID NO:1350), GGCGCGCGGGAGGAATTGTTTGAGTAG (SEQ ID NO:1351), CGTTTTTTGCGTAGGTGGGTGGGTGGG (SEQ ID NO:1352), CGTAAGGTCGTTAGGGGGGTCGCGTGTC (SEQ ID NO:1353), GTTTTTTGCGTAGGTGGGTGGGTGGGA (SEQ ID NO:1354) |
| Target144 | chr1:240161289-240161383 | GGGATTAGGGTTTCGGAGGGTGTCGG (SEQ ID NO:1355), CGGGATTAGGGTTTCGGAGGGTGTCGG (SEQ ID NO:1356), GGGAACGGGTTGGTGGCGGTTTTAAGC (SEQ ID NO:1357), GGATTAGGGTTTCGGAGGGTGTCGGGC (SEQ ID NO:1358), TCGGGATTAGGGTTTCGGAGGGTGTCG (SEQ ID NO:1359), TCGGAGTAGGGTCGTAATTTCGCGGTT (SEQ ID NO:1360), TTCGGAGTAGGGTCGTAATTTCGCGGT (SEQ ID NO:1361), CGGAGTAGGGTCGTAATTTCGCGGTTT (SEQ ID NO:1362), TCGGAGTAGGGTCGTAATTTCGCGGTTT (SEQ ID NO:1363), TTCGGAGTAGGGTCGTAATTTCGCGGTT (SEQ ID NO:1364) |
| Target145 | chr1:240161390-240161547 | GCGAGGTTGCGGTTTTGTTTCGAATTT (SEQ ID NO:1365), GGGGCGTCGCGGGTGTTAAAGGG (SEQ ID NO:1366), GCGAGGTTGCGGTTTTGTTTCGAATTTC (SEQ ID NO:1367), GGGCGTCGCGGGTGTTAAAGGGC (SEQ ID NO:1368), GAGTTTACGCGGATGTTACGGTCGTC (SEQ ID NO:1369), TTTTGCGGTTCGGGCGGTTGTATTTCG (SEQ ID NO:1370), TTAGTTTTTTGCGGTTCGGGCGGTTGT (SEQ ID NO:1371), AGTTTTTTGCGGTTCGGGCGGTTGTAT (SEQ ID NO:1372), TTTTTGCGGTTCGGGCGGTTGTATTTCG (SEQ ID NO:1373), TCGGAGTAGGGTCGTAATTTCGCGGTT (SEQ ID NO:1374) |
| Target146 | chr1:240161558-240161600 | TTGGGGATTCGCGGGGTGTAGTCGTTC (SEQ ID NO:1375), GGGGTGTAGTCGTTCGGGTCGTAGGAGG (SEQ ID NO:1376), GGGGTGTAGTCGTTCGGGTCGTAGGAG (SEQ ID NO:1377), GTTGGGGATTCGCGGGGTGTAGTCGTT (SEQ ID NO:1378), TTTCGGTTGGGGATTCGCGGGGTGTAG (SEQ ID NO:1379), TTTTGCGGTTCGGGCGGTTGTATTTCGT (SEQ ID NO:1380), TTTTTGCGGTTCGGGCGGTTGTATTTCG (SEQ ID NO:1381), TTTTTGCGGTTCGGGCGGTTGTATTTCGT (SEQ ID NO:1382), TTGCGGTTCGGGCGGTTGTATTTCGT (SEQ ID NO:1383), TTAGTTTTTTGCGGTTCGGGCGGTTGT (SEQ ID NO:1384) |
| Target147 | chr1:248020450-248020544 | TGTGACGGGGGCGGGGAATTATAACGT (SEQ ID NO:1385), TTGTGTAGATCGCGCGAGGGGGAGACGGTG (SEQ ID NO:1386), TTTGTGTAGATCGCGAGGGGGAGACGGTG (SEQ ID NO:1387), GGTCGGGAGCGTAGTTTTTCGGGAGGC (SEQ ID NO:1388), TGTGACGGGGGCGGGGAATTATAACGTT (SEQ ID NO:1389), TCGGGCGGCGTTAGGTTATGATTCGT (SEQ ID NO:1390), CGGGCGGCGTTAGGTTATGATTCGTT (SEQ ID NO:1391), TCGGGCGGCGTTAGGTTATGATTCGTT (SEQ ID NO:1392), TTCGGGCGGCGTTAGGTTATGATTCGT (SEQ ID NO:1393), TTCGGGCGGCGTTAGGTTATGATTCG (SEQ ID NO:1394) |
| Target148 | chr1:248020559-248020742 | TTGTGTAGATCGCGAGGGGGAGACGTG (SEQ ID NO:1395), GGAGCGTAGTTTTTCGGGAGGCGGGTT (SEQ ID NO:1396), TTTTCGGGAGGCGGGTTATGGTTTGGG (SEQ ID NO:1397), TTTGTGTAGATCGCGAGGGGGAGACGGT (SEQ ID NO:1398), GGTCGGGAGCGTAGTTTTTCGGGAGGC (SEQ ID NO:1399), AGGTTCGTTAGTTGTCGGTTGGGGCGA (SEQ ID NO:1400), GGTTCGTTAGTTGTCGGTTGGGGCGAA (SEQ ID NO:1401), AGGTTCGTTAGTTGTCGGTTGGGGCGAA (SEQ ID NO:1402), TAGGTTCGTTAGTTGTCGGTTGGGGCG (SEQ ID NO:1403), TCGTTAGTTGTCGGTTGGGGCGAAAGT (SEQ ID NO:1404) |
| Target149 | chr1:248020748-248020776 | CGGGTTTTCGTTTTAATCGGTAGTTGGCG (SEQ ID NO:1405), TCGGGTTTTCGTTTTAATCGGTAGTTGGCG (SEQ ID NO:1406), TCGGGTTTTCGTTTTAATCGGTAGTTGGC (SEQ ID NO:1407), TTCGGGTTTTCGTTTTAATCGGTAGTTGGCG (SEQ ID NO:1408), TTCGGGTTTTCGTTTTAATCGGTAGTTGGC (SEQ ID NO:1409), AGGTTCGTTAGTTGTCGGTTGGGGCGA (SEQ ID NO:1410), GGTTCGTTAGTTGTCGGTTGGGGCGAA (SEQ ID NO:1411), AGGTTCGTTAGTTGTCGGTTGGGGCGAA (SEQ ID NO:1412), TAGGTTCGTTAGTTGTCGGTTGGGGCG (SEQ ID NO:1413), TCGTTAGTTGTCGGTTGGGGCGAAAGT (SEQ ID NO:1414) |

FIGURE 5 CONTINUED

| | | |
|---|---|---|
| *Target150* | chr1:248020791-248021097 | TCGGTAGTTGGCGGGTTTGGTGGAGAG (SEQ ID NO:1415), ATCGGTAGTTGGCGGGTTTGGTGGAGA (SEQ ID NO:1416), TAGTTGGCGGGTTTGGTGGAGAGCGTG (SEQ ID NO:1417), GTAGTTGGCGGGTTTGGTGGAGAGCGT (SEQ ID NO:1418), AATCGGTAGTTGGCGGGTTTGGTGGAG (SEQ ID NO:1419), GGGGGAGGGGCGGACGGTGTAAAATAA (SEQ ID NO:1420), GGAGCGGTCGTGGGAGTCGTTTAGGAG (SEQ ID NO:1421), GATAGGAGAGTGTTTGGGGGAGGGGCG (SEQ ID NO:1422), CGATAGGAGAGTGTTTGGGGGAGGGGC (SEQ ID NO:1423), TAGCGTTCGTAGTTTTCGTCGGGGGGC (SEQ ID NO:1424) |
| *Target151* | chr2:467943-467958 | ACGTCGGGGGTTTAGGTAGGTAGAGAA (SEQ ID NO:1425), GGTCGAGTTATTTTAGGCGTTCGTGGGT (SEQ ID NO:1426), GGTCGAGTTATTTTAGGCGTTCGTGGG (SEQ ID NO:1427), AGGTCGAGTTATTTTAGGCGTTCGTGGGT (SEQ ID NO:1428), AGGTCGAGTTATTTTAGGCGTTCGTGGG (SEQ ID NO:1429), ACGAGGGTTTTGAATGTATAGCGCGGG (SEQ ID NO:1430), ACGAGGGTTTTGAATGTATAGCGCGGGA (SEQ ID NO:1431), CGAGGGTTTTGAATGTATAGCGCGGGA (SEQ ID NO:1432), AGCGCGGGAGTTTTAGGTTTAGGAGTG (SEQ ID NO:1433), GCGCGGGAGTTTTAGGTTTAGGAGTGA (SEQ ID NO:1434) |
| *Target152* | chr2:467982-468022 | AGGGTTTTCGTGGTTTTTAGAGGCGCG (SEQ ID NO:1435), TAGGGTTTTCGTGGTTTTTAGAGGCGCG (SEQ ID NO:1436), GGGTTTTCGTGGTTTTTAGAGGCGCG (SEQ ID NO:1437), ACGTCGGGGGTTTAGGTAGGTAGAGAA (SEQ ID NO:1438), GGTCGAGTTATTTTAGGCGTTCGTGGGT (SEQ ID NO:1439), CGCGGTTTTTTCGTTTTGGTTTTTGCGT (SEQ ID NO:1440), CGCGGTTTTTTCGTTTTGGTTTTTGCG (SEQ ID NO:1441), CGCGGTTTTTTCGTTTTGGTTTTTGCGTT (SEQ ID NO:1442), CGCGGTTTTTTCGTTTTGGTTTTTGCGTTT (SEQ ID NO:1443), CGCGGTTTTTTCGTTTTGGTTTTTGCGTTTT (SEQ ID NO:1444) |
| *Target153* | chr2:468061-468079 | GTTGGGTAGTTTCGTCGGGTTGTGGCG (SEQ ID NO:1445), TTGGGTAGTTTCGTCGGGTTGTGGCGA (SEQ ID NO:1446), GGTTGGGTAGTTTCGTCGGGTTGTGGC (SEQ ID NO:1447), GGGTTGGGTAGTTTCGTCGGGTTGTGG (SEQ ID NO:1448), TGGGTAGTTTCGTCGGGTTGTGGCGA (SEQ ID NO:1449), AGGTTTCGCGTTTATTTTGGTTCGGTGTC (SEQ ID NO:1450), TAGGTTTCGCGTTTATTTTGGTTCGGTGTC (SEQ ID NO:1451), TTAGGTTTCGCGTTTATTTTGGTTCGGTGTC (SEQ ID NO:1452), TTTAGGTTTCGCGTTTATTTTGGTTCGGTGTC (SEQ ID NO:1453) |
| *Target154* | chr2:468093-468192 | CGCGAGGGGTAGGACGAGGTTGTATGG (SEQ ID NO:1454), GTTGGGTAGTTTCGTCGGGTTGTGGCG (SEQ ID NO:1455), GCGAGGGGTAGGACGAGGTTGTATGGG (SEQ ID NO:1456), TTGGGTAGTTTCGTCGGGTTGTGGCGA (SEQ ID NO:1457), GGTTGGGTAGTTTCGTCGGGTTGTGGC (SEQ ID NO:1458), TTTTCGGTTTTTTGGGCGGGTTTTGCG (SEQ ID NO:1459), TTCGGTTTTTTGGGCGGGTTTTGCGT (SEQ ID NO:1460), CGCGGTTTAGTTCGGTGTAGTTGAGGG (SEQ ID NO:1461), TTTTTCGGTTTTTTGGGCGGGTTTTGCG (SEQ ID NO:1462), CGCGGTTTAGTTCGGTGTAGTTGAGGA (SEQ ID NO:1463) |
| *Target155* | chr2:468212-468304 | CGCGAGGGGTAGGACGAGGTTGTATGG (SEQ ID NO:1464), GCGAGGGGTAGGACGAGGTTGTATGGG (SEQ ID NO:1465), TCGAGTTAGAGTGAGCGCGGGGTTTGG (SEQ ID NO:1466), CGAGGTTGTATGGGTTAGCGAGGGGGT (SEQ ID NO:1467), ACGAGGTTGTATGGGTTAGCGAGGGGG (SEQ ID NO:1468), TCGGAGGCGCGCGTTGTTTTGTAGTTT (SEQ ID NO:1469), TTCGGAGGCGCGCGTTGTTTTGTAGTT (SEQ ID NO:1470), TTTCGGAGGCGCGCGTTGTTTTGTAGT (SEQ ID NO:1471), AGTTTCGGAGGCGCGCGTTGTTTTGTA (SEQ ID NO:1472), GTTTCGGAGGCGCGCGTTGTTTTGTAG (SEQ ID NO:1473) |
| *Target156* | chr2:468313-468383 | GGCGTAGAGTTCGTTTAGGGAGTCGGGA (SEQ ID NO:1474), GCGTAGAGTTCGTTTAGGGAGTCGGGA (SEQ ID NO:1475), GGCGTAGAGTTCGTTTAGGGAGTCGGGAG (SEQ ID NO:1476), GCGTAGAGTTCGTTTAGGGAGTCGGGAG (SEQ ID NO:1477), GCGTAGAGTTCGTTTAGGGAGTCGGGAGA (SEQ ID NO:1478), TTAAGGGGCGCGTAGGAGTTTCGGAGG (SEQ ID NO:1479), TCGGAGGCGCGCGTTGTTTTGTAGTTT (SEQ ID NO:1480), TTCGGAGGCGCGCGTTGTTTTGTAGTT (SEQ ID NO:1481), TTTCGGAGGCGCGCGTTGTTTTGTAGT (SEQ ID NO:1482), AGTTTCGGAGGCGCGCGTTGTTTTGTA (SEQ ID NO:1483) |
| *Target157* | chr2:468413-468458 | AGGGGTGCGTTTTTTAAGTTTCGGGTG (SEQ ID NO:1484), GGGGTGCGTTTTTTAAGTTTCGGGTGA (SEQ ID NO:1485), GGGGTGCGTTTTTTAAGTTTCGGGTGAGG (SEQ ID NO:1486), GGGGTGCGTTTTTTAAGTTTCGGGTGAGGT (SEQ ID NO:1487), AGGGGTGCGTTTTTTAAGTTTCGGGTGA (SEQ ID NO:1488), GGGAGGTAGGAGGTGGGAGTGCGTTTC (SEQ ID NO:1489), TTAAGGGGCGCGTAGGAGTTTCGGAGG (SEQ ID NO:1490), GGAGGTAGGAGGTGGGAGTGCGTTTCG (SEQ ID NO:1491), GAGGTAGGAGGTGGGAGTGCGTTTCGT (SEQ ID NO:1492), GTTTCGGGGAGGTAGGAGGTGGGAGTG (SEQ ID NO:1493) |
| *Target158* | chr2:1036257-1036451 | TTTTGGTTGGAGTTTTTGTCGGTTATTGTCGA (SEQ ID NO:1494), TTTTTGGTTGGAGTTTTTGTCGGTTATTGTCGA (SEQ ID NO:1495), TTTTTTGGTTGGAGTTTTTGTCGGTTATTGTCGA (SEQ ID NO:1496), AACGTTAAGGGTGGTAGGATAGGGAGGA (SEQ ID NO:1497), ACGTTAAGGGTGGTAGGATAGGGAGGAT (SEQ ID NO:1498), AAACGTTAAGGGTGGTAGGATAGGGAGGA (SEQ ID NO:1499), ACGTTAAGGGTGGTAGGATAGGGAGGATT (SEQ ID NO:1500), AACGTTAAGGGTGGTAGGATAGGGAGGAT (SEQ ID NO:1501) |
| *Target159* | chr2:2120400-2120800 | CGTGGAGAGGTTGTGTAGGGAGTGAGGG (SEQ ID NO:1502), AGGTTGTGTAGGGAGTGAGGGAGGTGT (SEQ ID NO:1503), AGAGGTTGTGTAGGGAGTGAGGGAGGT (SEQ ID NO:1504), ACGTGGAGAGGTTGTGTAGGGAGTGAGG (SEQ ID NO:1505), TGGAGAGGTTGTGTAGGGAGTGAGGGA |

FIGURE 5 CONTINUED

|  |  | {SEQ ID NO:1506}, TGGTTTGGTTTTTTCGGGGGCGGATTT {SEQ ID NO:1507}, ATGGTTTGGTTTTTTCGGGGGCGGATT {SEQ ID NO:1508}, TGTGGGTGTTTTGTAGGGGGAGAGGTT {SEQ ID NO:1509}, TTGTGGGTGTTTTGTAGGGGGAGAGGT {SEQ ID NO:1510}, TATGGTTTGGTTTTTTCGGGGGCGGAT {SEQ ID NO:1511} |
| Target160 | chr2:5832899-5832916 | GTGGGAGGGGGAGGGGGATTTTCGTAC {SEQ ID NO:1512}, GGAGGGGGGAGGGGGATTTTCGTACGAG {SEQ ID NO:1513}, GGGAGGGGGAGGGGGATTTTCGTACGA {SEQ ID NO:1514}, GGTGGGAGGGGGAGGGGGATTTTCGTA {SEQ ID NO:1515}, AGGCGGAGAGTTTGGAAGCGGAGAGTA {SEQ ID NO:1516}, CGTTTAGGGTTATCGGGTTGTAAGTTATGAATTCGT {SEQ ID NO:1517}, TCGTTTAGGGTTATCGGGTTGTAAGTTATGAATTCG {SEQ ID NO:1518} |
| Target161 | chr2:5832945-5832965 | AGGCGGAGAGTTTGGAAGCGGAGAGTA {SEQ ID NO:1519}, TAGGCGGAGAGTTTGGAAGCGGAGAGT {SEQ ID NO:1520}, AGTAGGCGGAGAGTTTGGAAGCGGAGA {SEQ ID NO:1521}, GTAGGCGGAGAGTTTGGAAGCGGAGAGT {SEQ ID NO:1522}, GTAGGCGGAGAGTTTGGAAGCGGAGAG {SEQ ID NO:1523} |
| Target162 | chr2:5832990-5833082 | GCGGAGAGTAATTTGTTTCGGGAGGCGT {SEQ ID NO:1524}, GCGGAGAGTAATTTGTTTCGGGAGGCG {SEQ ID NO:1525}, AGCGGAGAGTAATTTGTTTCGGGAGGCG {SEQ ID NO:1526}, AGCGGAGAGTAATTTGTTTCGGGAGGCGT {SEQ ID NO:1527}, GCGGAGAGTAATTTGTTTCGGGAGGCGTT {SEQ ID NO:1528}, TGGAGATTTCGGCGTTGTGTATGTTCGG {SEQ ID NO:1529}, GGAGATTTCGGCGTTGTGTATGTTCGG {SEQ ID NO:1530}, TGGAGATTTCGGCGTTGTGTATGTTCGGA {SEQ ID NO:1531}, GGAGATTTCGGCGTTGTGTATGTTCGGA {SEQ ID NO:1532}, CGGGGTAGTCGGTTATGTGTTTGAGTCGT {SEQ ID NO:1533} |
| Target163 | chr2:5833151-5833215 | AGCGTTGGAAAATGTTGAAGGATAGCGAG {SEQ ID NO:1534}, GCGTTGGAAAATGTTGAAGGATAGCGAGA {SEQ ID NO:1535}, GGTTGGGTAAGCGTTGGAAAATGTTGAAGG {SEQ ID NO:1536}, AGCGTTGGAAAATGTTGAAGGATAGCGAGA {SEQ ID NO:1537}, GGTTGGGTAAGCGTTGGAAAATGTTGAAGGA {SEQ ID NO:1538}, TTTGGTTGGCGTTGGGTTTGGTCGAGG {SEQ ID NO:1539}, TGGGTTTTGGTTGGCGTTGGGTTTGGT {SEQ ID NO:1540}, TGGCGTTGGGTTTGGTCGAGGGGGTTTA {SEQ ID NO:1541}, GGTTTTGGTTGGCGTTGGGTTTGGTCG {SEQ ID NO:1542}, GGGTTTTGGTTGGCGTTGGGTTTGGTC {SEQ ID NO:1543} |
| Target164 | chr2:8314701-8315101 | TGGGGTTGTTTTGAGGAGGAGAGTAGGG {SEQ ID NO:1544}, AGGTGGTATTAGGGGCGGTTTGTTGGAT {SEQ ID NO:1545}, GGGGTTGTTTTGAGGAGGAGAGTAGGG {SEQ ID NO:1546}, TGGGGTTGTTTTGAGGAGGAGAGTAGGGA {SEQ ID NO:1547}, GGGGTTGTTTTGAGGAGGAGAGTAGGGA {SEQ ID NO:1548}, AGTTATGGTGGGGTGGGGGTGGAAGTT {SEQ ID NO:1549}, TAGTTATGGTGGGGTGGGGGTGGAAGT {SEQ ID NO:1550}, GTTATGGTGGGGTGGGGGTGGAAGTTT {SEQ ID NO:1551}, TATGGTGGGGTGGGGGTGGAAGTTTTG {SEQ ID NO:1552}, AGTTATGGTGGGGTGGGGGTGGAAGTTT {SEQ ID NO:1553} |
| Target165 | chr2:10471440-10471578 | CGGGGAGTTCGGAGTTTTGTAGGTACGGG {SEQ ID NO:1554}, GGGGAGTTCGGAGTTTTGTAGGTACGGGG {SEQ ID NO:1555}, TCGGAGTTTTGTAGGTACGGGGTTGGT {SEQ ID NO:1556}, CGGGGAGTTCGGAGTTTTGTAGGTACGG {SEQ ID NO:1557}, GGGAGTTCGGAGTTTTGTAGGTACGGGGT {SEQ ID NO:1558}, TAGGTGGCGAGGTGAGGAAGGAGAGGG {SEQ ID NO:1559}, GATGCGTAGGTGGCGAGGTGAGGAAGG {SEQ ID NO:1560}, CGTAGGTGGCGAGGTGAGGAAGGAGAG {SEQ ID NO:1561}, CGATGCGTAGGTGGCGAGGTGAGGAAG {SEQ ID NO:1562}, GTAGGTGGCGAGGTGAGGAAGGAGAGG {SEQ ID NO:1563} |
| Target166 | chr2:10471621-10471748 | CGTTGGTTGGTGGTGGAGTTGCGTTGA {SEQ ID NO:1564}, TAAGCGTTGGTTGGTGGTGGAGTTGCG {SEQ ID NO:1565}, CGGTTAAGCGTTGGTTGGTGGTGGAGT {SEQ ID NO:1566}, ACGGTTAAGCGTTGGTTGGTGGTGGAG {SEQ ID NO:1567}, GCGTTGGTTGGTGGTGGAGTTGCGTTG {SEQ ID NO:1568}, TGATAGTCGGGCGTGTAGTGGGGGGTA {SEQ ID NO:1569}, TCGGGCGTGTAGTGGGGGGTAGATAGT {SEQ ID NO:1570}, AGTCGGGCGTGTAGTGGGGGGTAGATA {SEQ ID NO:1571}, TAGTCGGGCGTGTAGTGGGGGGTAGAT {SEQ ID NO:1572}, ATAGTCGGGCGTGTAGTGGGGGGTAGA {SEQ ID NO:1573} |
| Target167 | chr2:19550067-19550093 | GCGTGGTTTTGAGCGTGGAGGTTAGGG {SEQ ID NO:1574}, GGGTTGGTTAGTAGGGGGTAGCGTGGT {SEQ ID NO:1575}, AGGGTTGGTTAGTAGGGGGTAGCGTGG {SEQ ID NO:1576}, CGTGGAGGTTAGGGTTGGTTCGCGTCG {SEQ ID NO:1577}, CGTGGTTTTGAGCGTGGAGGTTAGGGT {SEQ ID NO:1578}, TATTGGAGGTTGGTTTTGTCGGCGCGG {SEQ ID NO:1579}, GGAGGTTGGTTTTGTCGGCGCGGATTA {SEQ ID NO:1580}, AGGTTGGTTTTGTCGGCGCGGATTAGT {SEQ ID NO:1581}, GGAGGTTGGTTTTGTCGGCGCGGATTAG {SEQ ID NO:1582}, GTATTGGAGGTTGGTTTTGTCGGCGCG {SEQ ID NO:1583} |
| Target168 | chr2:19550147-19550409 | GGAGGTGGGGATGGGGTGGTGAAAGTT {SEQ ID NO:1584}, GAGGAGGTGGGGATGGGGTGGTGAAAG {SEQ ID NO:1585}, GGGTTGGTTCGCGTCGGTAGGGTTAGT {SEQ ID NO:1586}, AGGGTTGGTTCGCGTCGGTAGGGTTAG {SEQ ID NO:1587}, AGGTTAGGGTTGGTTCGCGTCGGTAGG {SEQ ID NO:1588}, TGTTGGTTGAGAAAGCGGTAGGGGATGT {SEQ ID NO:1589}, GTTGGTTGAGAAAGCGGTAGGGGATGT {SEQ ID NO:1590}, TGTTGGTTGAGAAAGCGGTAGGGGATG {SEQ ID NO:1591}, CGGGTTTTGTTGGTTGAGAAAGCGGTAGGG {SEQ ID NO:1592}, TTTGTTGGTTGAGAAAGCGGTAGGGGA {SEQ ID NO:1593} |

FIGURE 5 CONTINUED

| Target169 | chr2:19556691-19556772 | CGAGTTTGCGTTTGGGGGAGTTTAGTAGT (SEQ ID NO:1594), CGAGTTTGCGTTTGGGGGAGTTTAGTAG (SEQ ID NO:1595), TGAGAACGGGAGCGAATTTTACGAGTTTG (SEQ ID NO:1596), TGGTTTATTCGGGGTTAATTGAGCGTGAGT (SEQ ID NO:1597), AGTGGTTTATTCGGGGTTAATTGAGCGTGA (SEQ ID NO:1598), CGGGGGGTTCGGACGTTTGTTATTATTCGT (SEQ ID NO:1599), CGGGGGGTTCGGACGTTTGTTATTATTCG (SEQ ID NO:1600), CGGGGGGTTCGGACGTTTGTTATTATTCGTT (SEQ ID NO:1601), CGGGGGGTTCGGACGTTTATTATTCGTTGG (SEQ ID NO:1602), CGGGGGGTTCGGACGTTTGTTATTATTCGTTG (SEQ ID NO:1603) |
| Target170 | chr2:19556789-19556914 | CGAGTGGTGATAGGCGTTCGGATTTTCG (SEQ ID NO:1604), CGAGTGGTGATAGGCGTTCGGATTTTCGT (SEQ ID NO:1605), ACGAGTGGTGATAGGCGTTCGGATTTTCG (SEQ ID NO:1606), ACGAGTGGTGATAGGCGTTCGGATTTTCGT (SEQ ID NO:1607), AGGCGTTCGGATTTTCGTGAAGAGGAT (SEQ ID NO:1608), GCGTTGGAGGGGATTAGTAGCGATCGG (SEQ ID NO:1609), AGCGTTGGAGGGGATTAGTAGCGATCGG (SEQ ID NO:1610), AGCGTTGGAGGGGATTAGTAGCGATCG (SEQ ID NO:1611), AAGCGTTGGAGGGGATTAGTAGCGATCGG (SEQ ID NO:1612), AGAAGCGTTGGAGGGGATTAGTAGCGA (SEQ ID NO:1613) |
| Target171 | chr2:19556981-19556988 | GGCGGTTATTCGGTTGTATTTAAATGTTCGTTGCG (SEQ ID NO:1614), GCGGTTATTCGGTTGTATTTAAATGTTCGTTGCG (SEQ ID NO:1615), GGCGGTTATTCGGTTGTATTTAAATGTTCGTTGCGT (SEQ ID NO:1616), GGCGGTTATTCGGTTGTATTTAAATGTTCGTTGC (SEQ ID NO:1617), GCGGTTATTCGGTTGTATTTAAATGTTCGTTGCGT (SEQ ID NO:1618), GCGTTGGAGGGGATTAGTAGCGATCGG (SEQ ID NO:1619), AGCGTTGGAGGGGATTAGTAGCGATCGG (SEQ ID NO:1620), AGCGTTGGAGGGGATTAGTAGCGATCG (SEQ ID NO:1621), AAGCGTTGGAGGGGATTAGTAGCGATCGG (SEQ ID NO:1622), AGAAGCGTTGGAGGGGATTAGTAGCGA (SEQ ID NO:1623) |
| Target172 | chr2:19556991-19557085 | GGCGGTTATTCGGTTGTATTTAAATGTTCGTTGCG (SEQ ID NO:1624), GCGGTTATTCGGTTGTATTTAAATGTTCGTTGCG (SEQ ID NO:1625), GGCGGTTATTCGGTTGTATTTAAATGTTCGTTGCGT (SEQ ID NO:1626), GGCGGTTATTCGGTTGTATTTAAATGTTCGTTGC (SEQ ID NO:1627), GCGGTTATTCGGTTGTATTTAAATGTTCGTTGCGT (SEQ ID NO:1628), TTTAGGGAAGAGAAGCGTTGGAGGGGA (SEQ ID NO:1629), AGGGAAGAGAAGCGTTGGAGGGGATTA (SEQ ID NO:1630), TAGGGAAGAGAAGCGTTGGAGGGGATT (SEQ ID NO:1631), TTAGGGAAGAGAAGCGTTGGAGGGGAT (SEQ ID NO:1632), GGGAAGAGAAGCGTTGGAGGGGATTAGT (SEQ ID NO:1633) |
| Target173 | chr2:30453420-30453497 | GCGGTAGCGTTGGGTTTCGAGTGAGAT (SEQ ID NO:1634), GCGGTAGCGTTGGGTTTCGAGTGAGATT (SEQ ID NO:1635), GCGGTAGCGTTGGGTTTCGAGTGAGA (SEQ ID NO:1636), TGTGGTTTTGGGGGGGTTGCGTAGTTTT (SEQ ID NO:1637), ATGTGGTTTTGGGGGGGTTGCGTAGTTT (SEQ ID NO:1638), GGGCGTTTGTTTAGGTAGTTAAAGTTGCGT (SEQ ID NO:1639), TGGGCGTTTGTTTAGGTAGTTAAAGTTGCG (SEQ ID NO:1640), TGGGCGTTTGTTTAGGTAGTTAAAGTTGCGT (SEQ ID NO:1641), TTGGGCGTTTGTTTAGGTAGTTAAAGTTGCG (SEQ ID NO:1642), TTGGGCGTTTGTTTAGGTAGTTAAAGTTGCGT (SEQ ID NO:1643) |
| Target174 | chr2:30453567-30453656 | TTTGGGTAGTGTGGGAGGCGTTCGGTT (SEQ ID NO:1644), TTTTGGGTAGTGTGGGAGGCGTTCGGT (SEQ ID NO:1645), GAGTTAAGGATGGGGGGCGGCCGTGTAT (SEQ ID NO:1646), AAGACGTGGGAGTTAAGGATGGGGGGC (SEQ ID NO:1647), TAAGGATGGGGGGCGGCCGTGTATATCG (SEQ ID NO:1648), TTTGTAGCGGGGGTAGAAGGTGTGGGC (SEQ ID NO:1649), GCGTTGGTTTGCGAAGGGTTGGTTTGT (SEQ ID NO:1650), TTGTAGCGGGGGTAGAAGGTGTGGGC (SEQ ID NO:1651), GTTTGTAGCGGGGGTAGAAGGTGTGGGC (SEQ ID NO:1652), GGTTTGTAGCGGGGGTAGAAGGTGTGG (SEQ ID NO:1653) |
| Target175 | chr2:30453758-30453913 | GGTTGCGGGCGAGGATTTTAGAGAGAGG (SEQ ID NO:1654), GGTTGCGGGCGAGGATTTTAGAGAGAGGT (SEQ ID NO:1655), TGCGGGCGAGGATTTTAGAGAGAGGTT (SEQ ID NO:1656), TTGCGGGCGAGGATTTTAGAGAGAGGT (SEQ ID NO:1657), AGGTTGCGGGCGAGGATTTTAGAGAGA (SEQ ID NO:1658), ATAGTTCGGCGGTTGTTTTGCGTCGGG (SEQ ID NO:1659), GAGTGTTTACGGGGCGCGTTGGTTTGT (SEQ ID NO:1660), AGAAGCGGTGGGAAGGTGGTAGAGACG (SEQ ID NO:1661), CGAGTGTTTACGGGGCGCGTTGGTTTG (SEQ ID NO:1662), ATCGAGTGTTTACGGGGCGCGTTGGTT (SEQ ID NO:1663) |
| Target176 | chr2:30453966-30454000 | AGAGGGGTTCGAGGTGGGTTGGGGATA (SEQ ID NO:1664), TAGAGGGGTTCGAGGTGGGTTGGGGAT (SEQ ID NO:1665), TTAGAGGGGTTCGAGGTGGGTTGGGGA (SEQ ID NO:1666), AGGGGTTCGAGGTGGGTTGGGGATAGT (SEQ ID NO:1667), GAGGGGTTCGAGGTGGGTTGGGGATAG (SEQ ID NO:1668), ATAGTTCGGCGGTTGTTTTGCGTCGGG (SEQ ID NO:1669), TTTCGAATTTTAGCGCGGCGGAGGTGG (SEQ ID NO:1670), GCGGTTGTTTTGCGTCGGGGTAGGGTA (SEQ ID NO:1671), ATTTCGAATTTTAGCGCGGCGGAGGTGG (SEQ ID NO:1672), CGGTTGTTTTGCGTCGGGGTAGGGTAT (SEQ ID NO:1673) |
| Target177 | chr2:31805327-31805336 | AGGTGAAGGAAGAAAGGGAAGCGGGGCGG (SEQ ID NO:1674), GTGAAGGAAGAAAGGGAAGCGGGGCGG (SEQ ID NO:1675), GGTGAAGGAAGAAAGGGAAGCGGGGCG (SEQ ID NO:1676), GTGAAGGAAGAAAGGGAAGCGGGGCG (SEQ ID NO:1677), GGTGAAGGAAGAAAGGGAAGCGGGGC (SEQ ID NO:1678), AGAGAAAGAGGTTTTGCGGGCGGGAGG (SEQ ID NO:1679), |

FIGURE 5 CONTINUED

GAGAGAAAGAGGTTTTGCGGGCGGGAG (SEQ ID NO:1680), CGAGAGAAAGAGGTTTTGCGGGCGGGA (SEQ ID NO:1681), CGAGAGAAAGAGGTTTTGCGGGCGGG (SEQ ID NO:1682), GAGAAAGAGGTTTTGCGGGCGGGAGG (SEQ ID NO:1683)

Target178     chr2:31805451-31805496     GGAGTGAAGGCGGCGTTTGTGTCGTAG (SEQ ID NO:1684), GTTTTGGGGGAGTGAAGGCGGCGTTTG (SEQ ID NO:1685), AGAGCGGATGAGGTTTTGGGGGAGTGA (SEQ ID NO:1686), TGAGAGCGGATGAGGTTTTGGGGGAGT (SEQ ID NO:1687), AGTGAAGGCGGCGTTTGTGTCGTAGTC (SEQ ID NO:1688), AGGAACGCGGAGGTTAGTTTGTTTGGC (SEQ ID NO:1689), GAGGAACGCGGAGGTTAGTTTGTTTGGC (SEQ ID NO:1690), TGAGGAACGCGGAGGTTAGTTTGTTTGGC (SEQ ID NO:1691), GTGAGGAACGCGGAGGTTAGTTTGTTTGGC (SEQ ID NO:1692), TGTGAGGAACGCGGAGGTTAGTTTGTT (SEQ ID NO:1693)

Target179     chr2:31805530-31805547     GGAGTGAAGGCGGCGTTTGTGTCGTAG (SEQ ID NO:1694), GTTTTGGGGGAGTGAAGGCGGCGTTTG (SEQ ID NO:1695), AGAGCGGATGAGGTTTTGGGGGAGTGA (SEQ ID NO:1696), TGAGAGCGGATGAGGTTTTGGGGGAGT (SEQ ID NO:1697), AGTGAAGGCGGCGTTTGTGTCGTAGTC (SEQ ID NO:1698), AGGAACGCGGAGGTTAGTTTGTTTGGC (SEQ ID NO:1699), GAGGAACGCGGAGGTTAGTTTGTTTGGC (SEQ ID NO:1700), TGAGGAACGCGGAGGTTAGTTTGTTTGGC (SEQ ID NO:1701), GTGAGGAACGCGGAGGTTAGTTTGTTTGGC (SEQ ID NO:1702), TGTGAGGAACGCGGAGGTTAGTTTGTT (SEQ ID NO:1703)

Target180     chr2:31805579-31805627     GGAGTGAAGGCGGCGTTTGTGTCGTAG (SEQ ID NO:1704), GTTTTGGGGGAGTGAAGGCGGCGTTTG (SEQ ID NO:1705), AGTGAAGGCGGCGTTTGTGTCGTAGTC (SEQ ID NO:1706), GAGTGAAGGCGGCGTTTGTGTCGTAGT (SEQ ID NO:1707), GGGAGTGAAGGCGGCGTTTGTGTCGTA (SEQ ID NO:1708), TGCGGGCGTTTAGTGTAGCGTATTGTT (SEQ ID NO:1709), TTGCGGGCGTTTAGTGTAGCGTATTGT (SEQ ID NO:1710), TGCGGGCGTTTAGTGTAGCGTATTGTTT (SEQ ID NO:1711), TTGCGGGCGTTTAGTGTAGCGTATTGTT (SEQ ID NO:1712), GCGGGCGTTTAGTGTAGCGTATTGTTT (SEQ ID NO:1713)

Target181     chr2:31805639-31805672     GGACGTCGGGAGTAGGGTAGTGCGTTG (SEQ ID NO:1714), TTTGGACGTCGGGAGTAGGGTAGTGCG (SEQ ID NO:1715), GACGTCGGGAGTAGGGTAGTGCGTTGT (SEQ ID NO:1716), TGGACGTCGGGAGTAGGGTAGTGCGTT (SEQ ID NO:1717), TTGGACGTCGGGAGTAGGGTAGTGCGT (SEQ ID NO:1718), GGTGTTCGCGGGGATTTTCGTTCGGTA (SEQ ID NO:1719), GGTGTTCGCGGGGATTTTCGTTCGGT (SEQ ID NO:1720), GGTGTTCGCGGGGATTTTCGTTCGGTAG (SEQ ID NO:1721), TGTTCGCGGGGATTTTCGTTCGGTAGT (SEQ ID NO:1722), CGGTGTTCGCGGGGATTTTCGTTCGGT (SEQ ID NO:1723)

Target182     chr2:31805762-31805779     GGAGAGGGGTTGTCGGGCGAGGATTTT (SEQ ID NO:1724), GGGTAGTGCGTTGTATTGGGCGTTCGT (SEQ ID NO:1725), AGGGTAGTGCGTTGTATTGGGCGTTCG (SEQ ID NO:1726), GAGAGGGGTTGTCGGGCGAGGATTTTC (SEQ ID NO:1727), GGAGAGGGGTTGTCGGGCGAGGATTT (SEQ ID NO:1728), GCGGTTATTCGTTTGTTAGTTCGCGTCG (SEQ ID NO:1729), GCGGTTATTCGTTTGTTAGTTCGCGTCGT (SEQ ID NO:1730), TCGTTTGTTAGTTCGCGTCGTTTGGTT (SEQ ID NO:1731), TTCGTTTGTTAGTTCGCGTCGTTTGGT (SEQ ID NO:1732), CGCGTCGTTTGGTTTTTGTAGGAGTTGT (SEQ ID NO:1733)

Target183     chr2:31805785-31805818     GGAGAGGGGTTGTCGGGCGAGGATTTT (SEQ ID NO:1734), GAGAGGGGTTGTCGGGCGAGGATTTTC (SEQ ID NO:1735), GGAGAGGGGTTGTCGGGCGAGGATTT (SEQ ID NO:1736), GGAGAGGGGTTGTCGGGCGAGGATTTTC (SEQ ID NO:1737), GAAGAGGGAGAGGGGTTGTCGGGCGAG (SEQ ID NO:1738), TGGGGTATTGGTTTTGTACGTCGCGAA (SEQ ID NO:1739), TTGGGGTATTGGTTTTGTACGTCGCGA (SEQ ID NO:1740), TGGGGTATTGGTTTTGTACGTCGCGAAGT (SEQ ID NO:1741), GGGGTATTGGTTTTGTACGTCGCGAAGT (SEQ ID NO:1742), TGGGGTATTGGTTTTGTACGTCGCGAAG (SEQ ID NO:1743)

Target184     chr2:31805820-31805872     GGAGAGGGGTTGTCGGGCGAGGATTTT (SEQ ID NO:1744), TAGGAATTAGGCGGCGCGGGTTGGTAG (SEQ ID NO:1745), TTTGTAGGAATTAGGCGGCGCGGGTTG (SEQ ID NO:1746), GTAGGAATTAGGCGGCGCGGGTTGGTA (SEQ ID NO:1747), TTTTGTAGGAATTAGGCGGCGCGGGTT (SEQ ID NO:1748), TGGGGTATTGGTTTTGTACGTCGCGAA (SEQ ID NO:1749), TTGGGGTATTGGTTTTGTACGTCGCGA (SEQ ID NO:1750), CGAGGAATACGGCGCGATGTAGGTTTA (SEQ ID NO:1751), TGGGGTATTGGTTTTGTACGTCGCGAAGT (SEQ ID NO:1752), GGGGTATTGGTTTTGTACGTCGCGAAGT (SEQ ID NO:1753)

Target185     chr2:31805886-31805916     TAGGAATTAGGCGGCGCGGGTTGGTAG (SEQ ID NO:1754), TTTGTAGGAATTAGGCGGCGCGGGTTG (SEQ ID NO:1755), GTAGGAATTAGGCGGCGCGGGTTGGTA (SEQ ID NO:1756), TTTTGTAGGAATTAGGCGGCGCGGGTT (SEQ ID NO:1757), TTTTTGTAGGAATTAGGCGGCGCGGGT (SEQ ID NO:1758), CGAGGAATACGGCGCGATGTAGGTTTA (SEQ ID NO:1759), ACGGCGCGATGTAGGTTTAGTGTTAGT (SEQ ID NO:1760), CGAGGAATACGGCGCGATGTAGGTTTAG (SEQ ID NO:1761), CGAGGAATACGGCGCGATGTAGGTTTAGT (SEQ ID NO:1762), CGAGGAATACGGCGCGATGTAGGTTT (SEQ ID NO:1763)

Target186     chr2:38301518-38301736     GCGGTGGATAGGGTGTTTTGGTTGGCG (SEQ ID NO:1764), CGCGGTGGATAGGGTGTTTTGGTTGGC (SEQ ID NO:1765), GCGCGGTGGATAGGGTGTTTTGGTTGG (SEQ ID NO:1766), AGCGCGGTGGATAGGGTGTTTTGGTTG (SEQ ID NO:1767), CGGTGGATAGGGTGTTTTGGTTGGCGT (SEQ ID NO:1768), GCGCGCGGTTGGATTTGGAGAACGTAT (SEQ ID NO:1769), CGGAAAAGAAGGCGGTCGGGGATTCGT (SEQ ID NO:1770), TTGCGGAAAAGAAGGCGGTCGGGGATT (SEQ ID NO:1771), TTTGCGGAAAAGAAGGCGGTCGGGGAT (SEQ ID NO:1772), TTTTGCGGAAAAGAAGGCGGTCGGGGA (SEQ ID NO:1773)

FIGURE 5 CONTINUED

Target187    chr2:38301748-38301774    TGTTGAAGTTGCGGTTGAGTTGTTCGA (SEQ ID NO:1774), TGTTGAAGTTGCGGTTGAGTTGTTCGAA (SEQ ID NO:1775), TTGTTGAAGTTGCGGTTGAGTTGTTCGA (SEQ ID NO:1776), GTTGTTGAAGTTGCGGTTGAGTTGTTCG (SEQ ID NO:1777), AGTTGTTGAAGTTGCGGTTGAGTTGTTCG (SEQ ID NO:1778), GCGGGTAGTTTGGTGGACGTGATGTTT (SEQ ID NO:1779), GTACGGTGGGCGCGGGTAGTTTGGTG (SEQ ID NO:1780), GTACGGTGGGCGCGGGTAGTTTGGTGG (SEQ ID NO:1781), TACGGTGGGCGCGGGTAGTTTGGTG (SEQ ID NO:1782), GTACGGTGGGCGCGGGTAGTTTGGT (SEQ ID NO:1783)

Target188    chr2:38301867-38301884    CGGTGCGTATCGGGTTGGGGAAGTATT (SEQ ID NO:1784), CGGTGCGTATCGGGTTGGGGAAGTATTG (SEQ ID NO:1785), CGGTGCGTATCGGGTTGGGGAAGTATTGT (SEQ ID NO:1786), GGTGCGTATCGGGTTGGGGAAGTATTGT (SEQ ID NO:1787), GGTGCGTATCGGGTTGGGGAAGTATTG (SEQ ID NO:1788), GCGAGTTGGTGGCGTTGTTGGTGC (SEQ ID NO:1789), GCGAGTTGGTGGCGTTGTTGGTGCG (SEQ ID NO:1790), CGAGTTGGTGGCGTTGTTGGTGCG (SEQ ID NO:1791), CGTTATGAGTGTCGTGTGTTTCGGTTGT (SEQ ID NO:1792), CGTTATGAGTGTCGTGTGTTTCGGTTGTC (SEQ ID NO:1793)

Target189    chr2:38301901-38301923    GGGGTCGTCGTGGTTGTAGCGGTAGTC (SEQ ID NO:1794), GGGGTCGTCGTGGTTGTAGCGGTAGT (SEQ ID NO:1795), CGGGGTCGTCGTGGTTGTAGCGGTAGT (SEQ ID NO:1796), CGGGGTCGTCGTGGTTGTAGCGGTAG (SEQ ID NO:1797), GGGTCGTCGTGGTTGTAGCGGTAGTC (SEQ ID NO:1798), TTCGAGGGTTACGTGTTGAGCGAGGCG (SEQ ID NO:1799), TTTCGAGGGTTACGTGTTGAGCGAGGC (SEQ ID NO:1800), TCGAGGGTTACGTGTTGAGCGAGGCG (SEQ ID NO:1801), TTTCGAGGGTTACGTGTTGAGCGAGGCG (SEQ ID NO:1802), TTTTCGAGGGTTACGTGTTGAGCGAGGC (SEQ ID NO:1803)

Target190    chr2:38301931-38301959    GGGGTCGTCGTGGTTGTAGCGGTAGTC (SEQ ID NO:1804), GGGGTCGTCGTGGTTGTAGCGGTAGT (SEQ ID NO:1805), CGGGGTCGTCGTGGTTGTAGCGGTAGT (SEQ ID NO:1806), CGGGGTCGTCGTGGTTGTAGCGGTAG (SEQ ID NO:1807), GGGTCGTCGTGGTTGTAGCGGTAGTC (SEQ ID NO:1808), TTCGAGGGTTACGTGTTGAGCGAGGC (SEQ ID NO:1809), TTTCGAGGGTTACGTGTTGAGCGAGGC (SEQ ID NO:1810), TCGAGGGTTACGTGTTGAGCGAGGCG (SEQ ID NO:1811), TTTCGAGGGTTACGTGTTGAGCGAGGCG (SEQ ID NO:1812), TTTTCGAGGGTTACGTGTTGAGCGAGGC (SEQ ID NO:1813)

Target191    chr2:38301974-38301983    GGGGTCGTCGTGGTTGTAGCGGTAGTC (SEQ ID NO:1814), GGGGTCGTCGTGGTTGTAGCGGTAGT (SEQ ID NO:1815), CGGGGTCGTCGTGGTTGTAGCGGTAGT (SEQ ID NO:1816), CGGGGTCGTCGTGGTTGTAGCGGTAG (SEQ ID NO:1817), GGGTCGTCGTGGTTGTAGCGGTAGTC (SEQ ID NO:1818), TTCGAGGGTTACGTGTTGAGCGAGGCG (SEQ ID NO:1819), TTTCGAGGGTTACGTGTTGAGCGAGGC (SEQ ID NO:1820), TCGAGGGTTACGTGTTGAGCGAGGCG (SEQ ID NO:1821), TTTCGAGGGTTACGTGTTGAGCGAGGCG (SEQ ID NO:1822), TTTTCGAGGGTTACGTGTTGAGCGAGGC (SEQ ID NO:1823)

Target192    chr2:45029057-45029072    GCGGTCGTTTGGGCGTGATTTTTTGGT (SEQ ID NO:1824), GGTGCGGTCGTTTGGGCGTGATTTTTT (SEQ ID NO:1825), TGCGGTCGTTTGGGCGTGATTTTTTGG (SEQ ID NO:1826), CGGTGCGGTCGTTTGGGCGTGATTTTTT (SEQ ID NO:1827), AGGGGCGTAGAGGGAAGGATTAGCGTT (SEQ ID NO:1828), GGAAAGGGCGGTGGTTGTGGGTAAAGC (SEQ ID NO:1829), GGGCGGTGGTTGTGGGTAAAGCGTTTT (SEQ ID NO:1830), GAAAGGGCGGTGGTTGTGGGTAAAGCG (SEQ ID NO:1831), AGGGCGGTGGTTGTGGGTAAAGCGTTT (SEQ ID NO:1832), AAGGGCGGTGGTTGTGGGTAAAGCGTT (SEQ ID NO:1833)

Target193    chr2:45029106-45029129    AGGGGCGTAGAGGGAAGGATTAGCGTT (SEQ ID NO:1834), TGGTTGGGGGTTGTAGGGGGTTCGTTTT (SEQ ID NO:1835), TTGGTTGGGGGTTGTAGGGGGTTCGTTT (SEQ ID NO:1836), TAGGGGCGTAGAGGGAAGGATTAGCGT (SEQ ID NO:1837), TGTAGGGGGTTCGTTTTTTAGGGGCGT (SEQ ID NO:1838), GGAAAGGGCGGTGGTTGTGGGTAAAGC (SEQ ID NO:1839), GCGCGGGTTTTCGTAGGGAGAAGAGGA (SEQ ID NO:1840), GGGCGGTGGTTGTGGGTAAAGCGTTTT (SEQ ID NO:1841), GAAAGGGCGGTGGTTGTGGGTAAAGCG (SEQ ID NO:1842), AGGGAGAAGAGGAGGAGAGTCGGCGTC (SEQ ID NO:1843)

Target194    chr2:45029176-45029190    AGAGCGAGGTTAAGGTTTGGGGGTAGT (SEQ ID NO:1844), GAGAGCGAGGTTAAGGTTTGGGGGTAGT (SEQ ID NO:1845), GAGAGCGAGGTTAAGGTTTGGGGGTAG (SEQ ID NO:1846), GAGCGAGGTTAAGGTTTGGGGGTAGTT (SEQ ID NO:1847), AGAGCGAGGTTAAGGTTTGGGGGTAGTT (SEQ ID NO:1848), GCGCGGGTTTTCGTAGGGAGAAGAGGA (SEQ ID NO:1849), CGGCGGTGGTTTAGTCGTTGGGTTTCG (SEQ ID NO:1850), AGGGAGAAGAGGAGGAGAGTCGGCGTC (SEQ ID NO:1851), TTTTTTAGGATTGGGTTCGGGCGGCGC (SEQ ID NO:1852), TAGGGAGAAGAGGAGGAGAGTCGGCGT (SEQ ID NO:1853)

Target195    chr2:45227645-45227657    GGGTGTCGGTTTGGGGGTTTTGGATTGG (SEQ ID NO:1854), GGTGTCGGTTTGGGGGTTTTGGATTGG (SEQ ID NO:1855), GGTGTCGGTTTGGGGGTTTTGGATTGG (SEQ ID NO:1856), GGGTGTCGGTTTGGGGGTTTTGGATTG (SEQ ID NO:1857), GTGTCGGTTTGGGGGTTTTGGATTGGT (SEQ ID NO:1858), GGGTTTTGAGGTTAGGGGAGCGTGGGA (SEQ ID NO:1859), TTTCGGTTCGTTGAGTCGGCGGTTTGG (SEQ ID NO:1860), TGGGTTTTGAGGTTAGGGGAGCGTGGG (SEQ ID NO:1861), TTCGGTTCGTTGAGTCGGCGGTTTGGT (SEQ ID NO:1862), TCGGTTCGTTGAGTCGGCGGTTTGGTC (SEQ ID NO:1863)

Target196    chr2:45227701-45227718    GCGTTTTGGGTTTTAGGTTTTTGTTTTACGGT (SEQ ID NO:1864), AGCGTTTTGGGTTTTAGGTTTTTGTTTTACGGT (SEQ ID NO:1865), GCGTTTTGGGTTTTAGGTTTTTGTTTTACGGTT (SEQ ID NO:1866),

FIGURE 5 CONTINUED

|  |  |  |
|---|---|---|
|  |  | TGGGTTTTAGGTTTTTGTTTTACGGTTAGGTCG (SEQ ID NO:1867), AAGCGTTTTGGGTTTTAGGTTTTTGTTTTACGG (SEQ ID NO:1868), GGGTTTTGAGGTTAGGGGAGCGTGGGA (SEQ ID NO:1869), TGGGTTTTGAGGTTAGGGGAGCGTGGG (SEQ ID NO:1870), GGCGGGGGCGGTTTTTTAGGGAGAGTA (SEQ ID NO:1871), GGGTTTTGAGGTTAGGGGAGCGTGGGAT (SEQ ID NO:1872), GCGGGGGCGGTTTTTTAGGGAGAGTAA (SEQ ID NO:1873) |
| Target197 | chr2:45227791-45227834 | GGCGGGGGCGGTTTTTTAGGGAGAGTA (SEQ ID NO:1874), GCGGGGGCGGTTTTTTAGGGAGAGTAA (SEQ ID NO:1875), GGCGGGGGCGGTTTTTTAGGGAGAGTAA (SEQ ID NO:1876), GGCGGGGGCGGTTTTTTAGGGAGAGT (SEQ ID NO:1877), GCGGGGGCGGTTTTTTAGGGAGAGTAAT (SEQ ID NO:1878) |
| Target198 | chr2:45227917-45227934 | TTTTTGGAGTCGGTTTGCGGTGAGGTCG (SEQ ID NO:1879), TTTTTGGAGTCGGTTTGCGGTGAGGTCG (SEQ ID NO:1880), TTTGGAGTCGGTTTGCGGTGAGGTCG (SEQ ID NO:1881), TTCGTCGGGGTAAGTGGGAGTTGTTGT (SEQ ID NO:1882), TTTTTGGAGTCGGTTTGCGGTGAGGTC (SEQ ID NO:1883), TCGGAGAGGTCGGTATAAAGGCGGATA (SEQ ID NO:1884), TCGGAGAGGTCGGTATAAAGGCGGAT (SEQ ID NO:1885), TCGGAGAGGTCGGTATAAAGGCGGATAT (SEQ ID NO:1886), CGGAGAGGTCGGTATAAAGGCGGATATG (SEQ ID NO:1887), CGGAGAGGTCGGTATAAAGGCGGATATGA (SEQ ID NO:1888) |
| Target199 | chr2:45227960-45228019 | GGAGTCGGTTTGCGGTGAGGTCGGTAT (SEQ ID NO:1889), TTTTGGAGTCGGTTTGCGGTGAGGTCG (SEQ ID NO:1890), TTTGGAGTCGGTTTGCGGTGAGGTCGG (SEQ ID NO:1891), GGAGTCGGTTTGCGGTGAGGTCGGTA (SEQ ID NO:1892), TGGAGTCGGTTTGCGGTGAGGTCGGTA (SEQ ID NO:1893), TCGGAGAGGTCGGTATAAAGGCGGATA (SEQ ID NO:1894), TCGGAGAGGTCGGTATAAAGGCGGAT (SEQ ID NO:1895), TCGGAGAGGTCGGTATAAAGGCGGATAT (SEQ ID NO:1896), CGGAGAGGTCGGTATAAAGGCGGATATG (SEQ ID NO:1897), CGGAGAGGTCGGTATAAAGGCGGATATGA (SEQ ID NO:1898) |
| Target200 | chr2:45231539-45231586 | GGGGGCGTTGTAGGTTAATTGATAGTTACGG (SEQ ID NO:1899), AGGGGGCGTTGTAGGTTAATTGATAGTTACGG (SEQ ID NO:1900), GGGGGCGTTGTAGGTTAATTGATAGTTACGGA (SEQ ID NO:1901), AGGGGGCGTTGTAGGTTAATTGATAGTTACGGA (SEQ ID NO:1902), AGGGGGCGTTGTAGGTTAATTGATAGTTACG (SEQ ID NO:1903) |
| Target201 | chr2:45231697-45231725 | GGTCGTCGGTTCGGTCGTTTTGAGTTCG (SEQ ID NO:1904), GTCGTCGGTTCGGTCGTTTTGAGTTCG (SEQ ID NO:1905), GGTCGTCGGTTCGGTCGTTTTGAGTTC (SEQ ID NO:1906), GGTCGTCGGTTCGGTCGTTTTGAGTT (SEQ ID NO:1907), TCGTCGGTTCGGTCGTTTTGAGTTCG (SEQ ID NO:1908), AAATCGGATTTAGGGCGGTCGGGTCGG (SEQ ID NO:1909), AATCGGATTTAGGGCGGTCGGGTCGG (SEQ ID NO:1910), TTTCGGTGTTGCGTGTGGTAGTGGAGT (SEQ ID NO:1911), AGTTTCGGTGTTGCGTGTGGTAGTGGA (SEQ ID NO:1912), GTTTCGGTGTTGCGTGTGGTAGTGGAGT (SEQ ID NO:1913) |
| Target202 | chr2:45231782-45232069 | GGTCGTCGGTTCGGTCGTTTTGAGTTCG (SEQ ID NO:1914), TCGTCGGTTCGGTCGTTTTGAGTTCGA (SEQ ID NO:1915), GTCGTCGGTTCGGTCGTTTTGAGTTCG (SEQ ID NO:1916), GGTCGTCGGTTCGGTCGTTTTGAGTTC (SEQ ID NO:1917), GTCGTCGGTTCGGTCGTTTTGAGTTCGA (SEQ ID NO:1918), TCGTTGTAGAAGCGGGGAGGGGTAGTT (SEQ ID NO:1919), TTCGTTGTAGAAGCGGGGAGGGGTAGT (SEQ ID NO:1920), TTTCGGTGTTGCGTGTGGTAGTGGAGT (SEQ ID NO:1921), AGTTTCGGTGTTGCGTGTGGTAGTGGA (SEQ ID NO:1922), GTTTCGGTGTTGCGTGTGGTAGTGGAGT (SEQ ID NO:1923) |
| Target203 | chr2:45232071-45232426 | GCGTCGTTGGTGTGGGGAGGGTAGTAG (SEQ ID NO:1924), CGTCGTTGGTGTGGGGAGGGTAGTAGG (SEQ ID NO:1925), GTCGTTGGTGTGGGGAGGGTAGTAGGT (SEQ ID NO:1926), GCGTCGTTGGTGTGGGGAGGGTAGTA (SEQ ID NO:1927), CGCGTCGTTGGTGTGGGGAGGGTAGTA (SEQ ID NO:1928), ATTTCGGGTGGGTCGTTTTGGTTGGCG (SEQ ID NO:1929), TTTCGGGTGGGTCGTTTTGGTTGGCGA (SEQ ID NO:1930), GCGGGTCGGGAGTGTAGTTGTGTTTGA (SEQ ID NO:1931), TCGTTGTAGAAGCGGGGAGGGGTAGTT (SEQ ID NO:1932), TTCGTTGTAGAAGCGGGGAGGGGTAGT (SEQ ID NO:1933) |
| Target204 | chr2:45232433-45232535 | CGGTGTGGCGGGGGTTTCGTTAAGAGAG (SEQ ID NO:1934), GCGGTGTGGCGGGGGTTTCGTTAAGAGA (SEQ ID NO:1935), GCGGTGTGGCGGGGGTTTCGTTAAGAG (SEQ ID NO:1936), CGGTGTGGCGGGGGTTTCGTTAAGAGAGA (SEQ ID NO:1937), GGTGTGGCGGGGGTTTCGTTAAGAGAGA (SEQ ID NO:1938), TGTGGGTTAGTGGGAGTTGTAGGTGTTAGT (SEQ ID NO:1939), CGTTTATGTGGGTTAGTGGGAGTTGTAGGT (SEQ ID NO:1940), TCGTTTATGTGGGTTAGTGGGAGTTGTAGG (SEQ ID NO:1941), TCGTTTATGTGGGTTAGTGGGAGTTGTAGGT (SEQ ID NO:1942), TGTGGGTTAGTGGGAGTTGTAGGTGTTAGT (SEQ ID NO:1943) |
| Target205 | chr2:45232541-45232569 | CGAGGCGGCCGTTTAGGGGTTTTTGTGG (SEQ ID NO:1944), CGGTGTGGCGGGGGTTTCGTTAAGAGAG (SEQ ID NO:1945), GAGGCGGCCGTTTAGGGGTTTTTGTGGC (SEQ ID NO:1946), GCGGTGTGGCGGGGGTTTCGTTAAGAGA (SEQ ID NO:1947), GCGGTGTGGCGGGGGTTTCGTTAAGAG (SEQ ID NO:1948), TGTGGGTTAGTGGGAGTTGTAGGTGTTAGT (SEQ ID NO:1949), CGTTTATGTGGGTTAGTGGGAGTTGTAGGT (SEQ ID NO:1950), TCGTTTATGTGGGTTAGTGGGAGTTGTAGG (SEQ ID NO:1951), TCGTTTATGTGGGTTAGTGGGAGTTGTAGGT (SEQ ID NO:1952), TGTGGGTTAGTGGGAGTTGTAGGTGTTAGTT (SEQ ID NO:1953) |

FIGURE 5 CONTINUED

| | | |
|---|---|---|
| Target206 | chr2:47270902-47271041 | AGGATGTGGTCGGGTTGAGAAAATTCGT (SEQ ID NO:1954), TGGTCGGGTTGAGAAAATTCGTTTTGGGT (SEQ ID NO:1955), GGTCGGGTTGAGAAAATTCGTTTTGGGT (SEQ ID NO:1956), TGGTCGGGTTGAGAAAATTCGTTTTGGG (SEQ ID NO:1957), GTGGTCGGGTTGAGAAAATTCGTTTTGGG (SEQ ID NO:1958), TGAGGGTCGGAATGGGTTTAGGGTAGA (SEQ ID NO:1959), TTTTGAGGGTCGGAATGGGTTTAGGGT (SEQ ID NO:1960), TTGAGGGTCGGAATGGGTTTAGGGTAGA (SEQ ID NO:1961), GGGTCGGAATGGGTTTAGGGTAGATTCG (SEQ ID NO:1962), TGAGGGTCGGAATGGGTTTAGGGTAGAT (SEQ ID NO:1963) |
| Target207 | chr2:66666251-66666865 | TTGGGTTTGGGGGAGGGGGAGGAAAAG (SEQ ID NO:1964), TGGATGTGTAGTGGAGGGGACGAGGGT (SEQ ID NO:1965), AGGGGAATGTGCGTGGAGTTGAGGAGG (SEQ ID NO:1966), AGGGAGGGGAATGTGCGTGGAGTTGAG (SEQ ID NO:1967), CGGTTATTTGGGTTTGGGGGAGGGGGA (SEQ ID NO:1968), GTTGGGGAGGGTTGGTTTTTGCGGGTT (SEQ ID NO:1969), GAGTTGGGGAGGGTTGGTTTTTGCGGG (SEQ ID NO:1970), AGGATTCGGTGGAGGAGAAAGGCGTCG (SEQ ID NO:1971), TTCGGGGGGATTTCGGTGGTAGGCGTTT (SEQ ID NO:1972), TAGGTTCGGGGGATTTCGGTGGTAGGC (SEQ ID NO:1973) |
| Target208 | chr2:69026808-69027254 | GTCGCGGTGGGAATTGGGTTGTGGTTT (SEQ ID NO:1974), GATGTCGCGGTGGGAATTGGGTTGTGG (SEQ ID NO:1975), GGATGTCGCGGTGGGAATTGGGTTGTG (SEQ ID NO:1976), CGAGGGGAAGTGTTGGGGGAAGAAGGG (SEQ ID NO:1977), GGTCGGGAGGGTTGGGGTAGGTGTAGA (SEQ ID NO:1978), TGGGGATGTGAGGTATGGTAGGGTCGA (SEQ ID NO:1979), TTGGGGATGTGAGGTATGGTAGGGTCG (SEQ ID NO:1980), TGGGGATGTGAGGTATGGTAGGGTCGAA (SEQ ID NO:1981), TTGGGGATGTGAGGTATGGTAGGGTCGA (SEQ ID NO:1982), GGGGATGTGAGGTATGGTAGGGTCGAA (SEQ ID NO:1983) |
| Target209 | chr2:71115936-71115963 | TATGGGTTTTGGTCGGGAGGAATGAGC (SEQ ID NO:1984), ATGGGTTTTGGTCGGGAGGAATGAGC (SEQ ID NO:1985), TTATGGGTTTTGGTCGGGAGGAATGAGC (SEQ ID NO:1986), TGGGTTTTGGTCGGGAGGAATGAGC (SEQ ID NO:1987), ATTATGGGTTTTGGTCGGGAGGAATGAGC (SEQ ID NO:1988) |
| Target210 | chr2:71115968-71116031 | CGCGTGGAGGGTTCGGTCGGTATTC (SEQ ID NO:1989), TATGGGTTTTGGTCGGGAGGAATGAGC (SEQ ID NO:1990), ATGGGTTTTGGTCGGGAGGAATGAGC (SEQ ID NO:1991), TTATGGGTTTTGGTCGGGAGGAATGAGC (SEQ ID NO:1992), CGCGTGGAGGGTTCGGTCGGTATT (SEQ ID NO:1993) |
| Target211 | chr2:71116036-71116068 | CGCGTGGAGGGTTCGGTCGGTATTC (SEQ ID NO:1994), TATGGGTTTTGGTCGGGAGGAATGAGC (SEQ ID NO:1995), GCGGGGAGGTTGTATCGGGAAGTTTAA (SEQ ID NO:1996), GCGGGGAGGTTGTATCGGGAAGTTTAAGT (SEQ ID NO:1997), ATGGGTTTTGGTCGGGAGGAATGAGC (SEQ ID NO:1998) |
| Target212 | chr2:71116096-71116227 | GCGGTCGTTAGAGGGCGCGGTTTATAT (SEQ ID NO:1999), GCGGTCGTTAGAGGGCGCGGTTTATATT (SEQ ID NO:2000), CGCGTTCGGAATTTGGGTTTTTCGGTGT (SEQ ID NO:2001), CGCGTTCGGAATTTGGGTTTTTCGGTG (SEQ ID NO:2002), GCGGTCGTTAGAGGGCGCGGTTTATA (SEQ ID NO:2003), TCGGATTGGGTTCGGGAAAGGTAGCGG (SEQ ID NO:2004), GGATTGGGTTCGGGAAAGGTAGCGGT (SEQ ID NO:2005), GGGTTCGGGAAAGGTAGCGGGTATTGC (SEQ ID NO:2006), CGGATTGGGTTCGGGAAAGGTAGCGGG (SEQ ID NO:2007), GGGTTTCGGATTGGGTTCGGGAAAGGT (SEQ ID NO:2008) |
| Target213 | chr2:71116233-71116330 | CGGGGATTTTGATTTCGCGCGGATTTC (SEQ ID NO:2009), CGGGGATTTTGATTTCGCGCGGATTT (SEQ ID NO:2010), TGGGTTTTTCGGTGTAGTTTTTTCGCGA (SEQ ID NO:2011), CGGGGATTTTGATTTCGCGCGGATT (SEQ ID NO:2012), TTGGGTTTTTCGGTGTAGTTTTTTCGCGA (SEQ ID NO:2013), GAGGTTCGCGCGAGGTTAAGGTTTTCG (SEQ ID NO:2014), AGGTTCGCGCGAGGTTAAGGTTTTCG (SEQ ID NO:2015), AGGGAGAGTTAAGTAAGGCGACGAGGT (SEQ ID NO:2016), GGGAGAGTTAAGTAAGGCGACGAGGTT (SEQ ID NO:2017), AGGGAGAGTTAAGTAAGGCGACGAGGTT (SEQ ID NO:2018) |
| Target214 | chr2:71116334-71116353 | CGGGGATTTTGATTTCGCGCGGATTTC (SEQ ID NO:2019), CGGGGATTTTGATTTCGCGCGGATTT (SEQ ID NO:2020), CGGGGATTTTGATTTCGCGCGGATT (SEQ ID NO:2021), CGGGGATTTTGATTTCGCGCGGAT (SEQ ID NO:2022), CGGGGATTTTGATTTCGCGCGGA (SEQ ID NO:2023), CGGGAAGTTTTTATTTTGGTTATAGTCGCGCG (SEQ ID NO:2024), CGGGAAGTTTTTATTTTGGTTATAGTCGCGCGA (SEQ ID NO:2025), GCGGAGAGAGGCGGCGGGG (SEQ ID NO:2026), GGGAAGTTTTTATTTTGGTTATAGTCGCGCGA (SEQ ID NO:2027), AGGCGGGAAGTTTTTATTTTGGTTATAGTCGC (SEQ ID NO:2028) |
| Target215 | chr2:71116373-71116394 | GCGGTAATTTTTCGTTTCGGTTTTGGCGC (SEQ ID NO:2029), CGCGGTAATTTTTCGTTTCGGTTTTGGCGC (SEQ ID NO:2030), GCGGTAATTTTTCGTTTCGGTTTTGGCGC (SEQ ID NO:2031), CGGTAATTTTTCGTTTCGGTTTTGGCGC (SEQ ID NO:2032), CGCGGTAATTTTTCGTTTCGGTTTTGGCG (SEQ ID NO:2033), CGGGTTGGGGATAATGCGGGGGTAGTA (SEQ ID NO:2034), CGGGTTGGGGATAATGCGGGGGTAGT (SEQ ID NO:2035), CGGGTTGGGGATAATGCGGGGGTAGTAG (SEQ ID NO:2036), GGGTTGGGGATAATGCGGGGGTAGTAGT (SEQ ID NO:2037), GGGTTGGGGATAATGCGGGGGTAGTAG (SEQ ID NO:2038) |
| Target216 | chr2:71116407-71116485 | TCGCGCGGTTGTGATTAGGATAAGGGT (SEQ ID NO:2039), CGTTCGCGCGGTTGTGATTAGGATAAGGG (SEQ ID NO:2040), CGCGCGGTTGTGATTAGGATAAGGGTT (SEQ ID NO:2041), TCGCGCGGTTGTGATTAGGATAAGGGTT (SEQ ID NO:2042), TTCGCGCGGTTGTGATTAGGATAAGGGT (SEQ ID NO:2043), CGGGTTGGGGATAATGCGGGGGTAGTA (SEQ ID NO:2044), TTTGTTTGGGTTTTGGGGGTGCGAGCG (SEQ ID NO:2045), ACGTTTTGTTTGGGTTTTGGGGGTGCG (SEQ |

FIGURE 5 CONTINUED

ID NO:2046), TTTTGTTTGGGTTTTGGGGGTGCGAGC (SEQ ID NO:2047),
CGGGTTGGGGATAATGCGGGGGTAGT (SEQ ID NO:2048)

| | | |
|---|---|---|
| Target217 | chr2:71116500-71116531 | TCGCGCGGTTGTGATTAGGATAAGGGT (SEQ ID NO:2049), CGTTCGCGCGGTTGTGATTAGGATAAGGG (SEQ ID NO:2050), CGCGCGGTTGTGATTAGGATAAGGGTT (SEQ ID NO:2051), TCGCGCGGTTGTGATTAGGATAAGGGT (SEQ ID NO:2052), TTCGCGCGGTTGTGATTAGGATAAGGGT (SEQ ID NO:2053), TTTGTTTGGGTTTTGGGGGTGCGAGCG (SEQ ID NO:2054), ACGTTTTGTTTGGGTTTTGGGGGTGCG (SEQ ID NO:2055), TTTTGTTTGGGTTTTGGGGGTGCGAGC (SEQ ID NO:2056), ACGTTTTGTTTGGGTTTTGGGGGTGCGA (SEQ ID NO:2057), CGTTTTGTTTGGGTTTTGGGGGTGCGA (SEQ ID NO:2058) |
| Target218 | chr2:73147283-73147306 | GGTTCGGAGGAGAGGGCGGGGTC (SEQ ID NO:2059), GGTTCGGAGGAGAGGGCGGGGT (SEQ ID NO:2060), GGGTTCGGAGGAGAGGGCGGGGTC (SEQ ID NO:2061), CGGAGTCGGTATTTTGGGTCGTATTTTCGG (SEQ ID NO:2062), CGGAGTCGGTATTTTGGGTCGTATTTTCGGT (SEQ ID NO:2063), AGGAAGCGGCGGTAATTTTTAAGAGGGT (SEQ ID NO:2064), GCGGCGGTAATTTTTAAGAGGGTTTTGCG (SEQ ID NO:2065), AGCGGCGGTAATTTTTAAGAGGGTTTTGCG (SEQ ID NO:2066), GCGGCGGTAATTTTTAAGAGGGTTTTGCGA (SEQ ID NO:2067), AGCGGCGGTAATTTTTAAGAGGGTTTTGCGA (SEQ ID NO:2068) |
| Target219 | chr2:73147350-73147383 | AGGGTCGGGGGCGTTTGGAGAGAAATT (SEQ ID NO:2069), GAGGGTCGGGGGCGTTTGGAGAGAAAT (SEQ ID NO:2070), GGGTCGGGGGCGTTTGGAGAGAAATTT (SEQ ID NO:2071), AGGGTCGGGGGCGTTTGGAGAGAAATTT (SEQ ID NO:2072), AGGGTCGGGGGCGTTTGGAGAGAAAT (SEQ ID NO:2073), AGGAAGCGGCGGTAATTTTTAAGAGGGT (SEQ ID NO:2074), GCGGCGGTAATTTTTAAGAGGGTTTTGCG (SEQ ID NO:2075), AGCGGCGGTAATTTTTAAGAGGGTTTTGCG (SEQ ID NO:2076), GCGGCGGTAATTTTTAAGAGGGTTTTGCGA (SEQ ID NO:2077), AGCGGCGGTAATTTTTAAGAGGGTTTTGCGA (SEQ ID NO:2078) |
| Target220 | chr2:73147432-73147445 | GGGTCGGGGGCGTTTGGAGAGAAATTT (SEQ ID NO:2079), TGAGCGTTTTTAGTTAGGCGAGGCGGA (SEQ ID NO:2080), GGGTCGGGGGCGTTTGGAGAGAAATT (SEQ ID NO:2081), TTGAGCGTTTTTAGTTAGGCGAGGCGG (SEQ ID NO:2082), GGGTCGGGGGCGTTTGGAGAGAAATTTA (SEQ ID NO:2083), TCGCGTTTAGATTCGGTTTTTGAGGGAAAA (SEQ ID NO:2084), TTCGCGTTTAGATTCGGTTTTTGAGGGAAA (SEQ ID NO:2085), TTTCGCGTTTAGATTCGGTTTTTGAGGGAA (SEQ ID NO:2086), TTTTCGCGTTTAGATTCGGTTTTTGAGGGA (SEQ ID NO:2087), TTCGCGTTTAGATTCGGTTTTTGAGGGAAAA (SEQ ID NO:2088) |
| Target221 | chr2:73147537-73147621 | TGGACGCGGAGATGGAGTTAAGTGTGGT (SEQ ID NO:2089), GGACGCGGAGATGGAGTTAAGTGTGGT (SEQ ID NO:2090), TGGACGCGGAGATGGAGTTAAGTGTGG (SEQ ID NO:2091), GGACGCGGAGATGGAGTTAAGTGTGGTT (SEQ ID NO:2092), TTGGACGCGGAGATGGAGTTAAGTGTGG (SEQ ID NO:2093), AGGTTTGGTCGGGATTGGAGGGCGTAG (SEQ ID NO:2094), GGTTTGGTCGGGATTGGAGGGCGTAGA (SEQ ID NO:2095), GAGGTTTGGTCGGGATTGGAGGGCGTA (SEQ ID NO:2096), GGCGTAGAGTCGTCGGGGAGCGTATTC (SEQ ID NO:2097), TAGAGGTTTGGTCGGGATTGGAGGGCG (SEQ ID NO:2098) |
| Target222 | chr2:73147668-73147679 | AGGTTTTTGGGTTGGGAGTCGAGTCGT (SEQ ID NO:2099), GGTTTTTGGGTTGGGAGTCGAGTCGTT (SEQ ID NO:2100), AGGTTTTTGGGTTGGGAGTCGAGTCGTT (SEQ ID NO:2101), CGGTTAGGTTTTTGGGTTGGGAGTCGA (SEQ ID NO:2102), TCGGTTAGGTTTTTGGGTTGGGAGTCG (SEQ ID NO:2103), TCGTTCGTGTGGGGTTTCGTTTGTTGT (SEQ ID NO:2104), TTCGTTCGTGTGGGGTTTCGTTTGTTGT (SEQ ID NO:2105), TTCGTTCGTGTGGGGTTTCGTTTGTTG (SEQ ID NO:2106), CGTTCGTGTGGGGTTTCGTTTGTTGTA (SEQ ID NO:2107), TTTCGTTCGTGTGGGGTTTCGTTTGTT (SEQ ID NO:2108) |
| Target223 | chr2:73147687-73147711 | AGGTTTTTGGGTTGGGAGTCGAGTCGT (SEQ ID NO:2109), GGTTTTTGGGTTGGGAGTCGAGTCGTT (SEQ ID NO:2110), AGGTTTTTGGGTTGGGAGTCGAGTCGTT (SEQ ID NO:2111), CGGTTAGGTTTTTGGGTTGGGAGTCGA (SEQ ID NO:2112), TCGGTTAGGTTTTTGGGTTGGGAGTCG (SEQ ID NO:2113), GCGTCGTTTAAGCGTTGCGTAGAGAGC (SEQ ID NO:2114), TCGTTCGTGTGGGGTTTCGTTTGTTGT (SEQ ID NO:2115), TTCGTTCGTGTGGGGTTTCGTTTGTTGT (SEQ ID NO:2116), TTCGTTCGTGTGGGGTTTCGTTTGTTG (SEQ ID NO:2117), CGTTCGTGTGGGGTTTCGTTTGTTGTA (SEQ ID NO:2118) |
| Target224 | chr2:73147720-73147968 | ATCGAGGCGTTGGAAGGGGAAAAGCGA (SEQ ID NO:2119), CGAGGCGTTGGAAGGGGAAAAGCGAAT (SEQ ID NO:2120), AATCGAGGCGTTGGAAGGGGAAAAGCG (SEQ ID NO:2121), TCGAGGCGTTGGAAGGGGAAAAGCGAA (SEQ ID NO:2122), CGAGGCGTTGGAAGGGGAAAAGCGAATG (SEQ ID NO:2123), GCGTCGTTTAAGCGTTGCGTAGAGAGC (SEQ ID NO:2124), TCGTTCGTGTGGGGTTTCGTTTGTTGT (SEQ ID NO:2125), TTCGTTCGTGTGGGGTTTCGTTTGTTGT (SEQ ID NO:2126), TTCGTTCGTGTGGGGTTTCGTTTGTTG (SEQ ID NO:2127), CGTTCGTGTGGGGTTTCGTTTGTTGTA (SEQ ID NO:2128) |
| Target225 | chr2:73148052-73148084 | CGGGTTTAGGAGTAACGTTTGGAGGGGG (SEQ ID NO:2129), CGGGTTTAGGAGTAACGTTTGGAGGGGGT (SEQ ID NO:2130), TCGGGTTTAGGAGTAACGTTTGGAGGGGG (SEQ ID NO:2131), GGGAGGAGTCGACGAAGATTAGGAGTGGG (SEQ ID NO:2132), |

FIGURE 5 CONTINUED

GGGGAGGAGTCGACGAAGATTAGGGAGTGG (SEQ ID NO:2133), GTCGGTTAGGGGGTTTAGGGTCGGACGG (SEQ ID NO:2134), CGTCGTCGGTTAGGGGGTTTAGGGTCGG (SEQ ID NO:2135), AGGGAGAGGGGAGAGGTAGGGATAGGCGGC (SEQ ID NO:2136), GGGGAGAGGTAGGGATAGGCGGCGGAGAT (SEQ ID NO:2137), ACGGTTGGGCGGAGGGTTTTAGGGGTTA (SEQ ID NO:2138)

| Target226 | chr2:74725894-74726747 | TAGAGGGTGTTCGGGGGATTATGCGCG (SEQ ID NO:2139), GCGGTTCGGTTGTTCGTTGCGTTAGGT (SEQ ID NO:2140), GGGGAGGATTAGGGTGGGTGGTTTGGG (SEQ ID NO:2141), GGGGGATTATGCGCGGGGTTAGGATGT (SEQ ID NO:2142), CGGCGTAGAGGGTGTTCGGGGGATTAT (SEQ ID NO:2143), GAGGTTGGGGGTTCGGATTGGGAGTCG (SEQ ID NO:2144), CGAGGTTGGGGGTTCGGATTGGGAGTC (SEQ ID NO:2145), GGTGGGGGCGTAGGAGGAGGGGTATAC (SEQ ID NO:2146), AGGTTGGGGGTTCGGATTGGGAGTCGA (SEQ ID NO:2147), AGGTGGGGGCGTAGGAGGAGGGGTATA (SEQ ID NO:2148) |

| Target227 | chr2:74726766-74726785 | GCGGTTCGGTTGTTCGTTGCGTTAGGT (SEQ ID NO:2149), GGCGGTTCGGTTGTTCGTTGCGTTAGG (SEQ ID NO:2150), GGGCGGTTCGGTTGTTCGTTGCGTTAG (SEQ ID NO:2151), GAGTTTATGGTCGGTCGGGTTGGGGCG (SEQ ID NO:2152), GCGGTTCGGTTGTTCGTTGCGTTAGGTT (SEQ ID NO:2153), GGTGGGGGCGTAGGAGGAGGGGTATAC (SEQ ID NO:2154), AGGTGGGGGCGTAGGAGGAGGGGTATA (SEQ ID NO:2155), GGTGGGGGCGTAGGAGGAGGGGTATA (SEQ ID NO:2156), GAGGTGGGGGCGTAGGAGGAGGGGTAT (SEQ ID NO:2157), GTGGGGGCGTAGGAGGAGGGGTATAC (SEQ ID NO:2158) |

| Target228 | chr2:74726809-74726893 | TCGGGTCGCGGTGGATTTGGAGTTTTT (SEQ ID NO:2159), TTCGGGTCGCGGTGGATTTGGAGTTTT (SEQ ID NO:2160), TTTCGGGTCGCGGTGGATTTGGAGTTT (SEQ ID NO:2161), ATTTCGGGTCGCGGTGGATTTGGAGTT (SEQ ID NO:2162), TATTTCGGGTCGCGGTGGATTTGGAGT (SEQ ID NO:2163), AGCGTTTGGAGGTATGGTTCGGTTTGA (SEQ ID NO:2164), TCGGTTTGATTGTGTACGGTGTAGCGT (SEQ ID NO:2165), CGGTTTGATTGTGTACGGTGTAGCGTT (SEQ ID NO:2166), GGTTCGGTTTGATTGTGTACGGTGTAGCG (SEQ ID NO:2167), GGTTCGGTTTGATTGTGTACGGTGTAGCGT (SEQ ID NO:2168) |

| Target229 | chr2:74726908-74727022 | GGTTGGGGTAGGCGCGGAGAGTAGAAG (SEQ ID NO:2169), TAGGTTGGGGTAGGCGCGGAGAGTAGA (SEQ ID NO:2170), AGGTTGGGGTAGGCGCGGAGAGTAGAA (SEQ ID NO:2171), GTTGGGGTAGGCGCGGAGAGTAGAAGT (SEQ ID NO:2172), GCGTTGCGGGGCGTTGTATCGTGTATA (SEQ ID NO:2173), AGCGTTTGGAGGTATGGTTCGGTTTGA (SEQ ID NO:2174), TCGGTTTGATTGTGTACGGTGTAGCGT (SEQ ID NO:2175), CGGTTTGATTGTGTACGGTGTAGCGTT (SEQ ID NO:2176), GGTTCGGTTTGATTGTGTACGGTGTAGCG (SEQ ID NO:2177), GGTTCGGTTTGATTGTGTACGGTGTAGCGT (SEQ ID NO:2178) |

| Target230 | chr2:85811382-85811589 | GGGGTCGTTGGTATTGCGGTCGTTTCG (SEQ ID NO:2179), CGGGGTCGTTGGTATTGCGGTCGTTTC (SEQ ID NO:2180), AGGTTTTTGGGGTTCGGGAGGGTTCGA (SEQ ID NO:2181), GGGTCGTTGGTATTGCGGTCGTTTCGT (SEQ ID NO:2182), CGGGGTCGTTGGTATTGCGGTCGTTT (SEQ ID NO:2183), TTTTGTTCGTCGTAGGGTTGGTCGGTT (SEQ ID NO:2184), TTTTTGTTCGTCGTAGGGTTGGTCGGT (SEQ ID NO:2185), TTCGGAGGAAGAGTAGGGGCGGGGC (SEQ ID NO:2186), TTCGGAGGAAGAGTAGGGGCGGGG (SEQ ID NO:2187), CGTTTTTTGTTCGTCGTAGGGTTGGTCGG (SEQ ID NO:2188) |

| Target231 | chr2:85811597-85811726 | GGGGTCGTTGGTATTGCGGTCGTTTCG (SEQ ID NO:2189), CGGGGTCGTTGGTATTGCGGTCGTTTC (SEQ ID NO:2190), AGTAGCGATGGTGAGGGTTTAGGCGGG (SEQ ID NO:2191), AGTGGCGAGGGTGGGAGAGAGGAGTTT (SEQ ID NO:2192), GTAGCGATGGTGAGGGTTTAGGCGGGG (SEQ ID NO:2193), GCGTAGGGAGTGGAGGGTTCGTTTCGT (SEQ ID NO:2194), GCGTAGGGAGTGGAGGGTTCGTTTCGTT (SEQ ID NO:2195), CGTAGGGAGTGGAGGGTTCGTTTCGTT (SEQ ID NO:2196), GCGTAGGGAGTGGAGGGTTCGTTTCG (SEQ ID NO:2197), GGGAGTGGAGGGTTCGTTTCGTTTTGT (SEQ ID NO:2198) |

| Target232 | chr2:85811743-85812024 | AGTGGCGAGGGTGGGAGAGAGGAGTTT (SEQ ID NO:2199), CGGGGTCGGTTAGTTTTGCGACGGGTA (SEQ ID NO:2200), AGTTTTGCGACGGGTAGAGGGCGAGTG (SEQ ID NO:2201), TAGTTTTGCGACGGGTAGAGGGCGAGT (SEQ ID NO:2202), GGTTAGTTTTGCGACGGGTAGAGGGCG (SEQ ID NO:2203), GCGTAGGGAGTGGAGGGTTCGTTTCGT (SEQ ID NO:2204), GCGTAGGGAGTGGAGGGTTCGTTTCGTT (SEQ ID NO:2205), GACGCGGAAAAGGAGGTTTAGGGAGGT (SEQ ID NO:2206), CGTAGGGAGTGGAGGGTTCGTTTCGTT (SEQ ID NO:2207), AGACGCGGAAAAGGAGGTTTAGGGAGGT (SEQ ID NO:2208) |

| Target233 | chr2:86163587-86163632 | TTGGGAGAAGGGTGTGGTTGGGGGTTGC (SEQ ID NO:2209), TTTGGGAGAAGGGTGTGGTTGGGGTTG (SEQ ID NO:2210), TTTTGGGAGAAGGGTGTGGTTGGGGTT (SEQ ID NO:2211), TTTTTGGGAGAAGGGTGTGGTTGGGGT (SEQ ID NO:2212), TGGGAGAAGGGTGTGGTTGGGGGTTGC (SEQ ID NO:2213), AGGAGGAATTTTGAGATGGGGTTAGAATAGGGT (SEQ ID NO:2214), GGAGGAATTTTGAGATGGGGTTAGAATAGGGTT (SEQ ID NO:2215), AGGAGGAATTTTGAGATGGGGTTAGAATAGGGTT (SEQ ID NO:2216), TAGGAGGAATTTTGAGATGGGGTTAGAATAGGGT (SEQ ID NO:2217), AGGAGGAATTTTGAGATGGGGTTAGAATAGGGTA (SEQ ID NO:2218) |

| Target234 | chr2:86163860-86163938 | CGGGAAGGGGTAGGAGTGGGAGGTTTT (SEQ ID NO:2219), GCGGGAAGGGGTAGGAGTGGGAGGTTT (SEQ ID NO:2220), CGGGAAGGGGTAGGAGTGGGAGGTTTTT (SEQ ID NO:2221), CGGGAAGGGGTAGGAGTGGGAGGTTT (SEQ ID NO:2222), GCGGGAAGGGGTAGGAGTGGGAGGTT (SEQ ID NO:2223), CGGGAGAATGGGCGTAGTTTTTTGGTT (SEQ ID NO:2224), CGGGAGAATGGGCGTAGTTTTTTGGTTT (SEQ ID NO:2225), CGGGAGAATGGGCGTAGTTTTTTGGTTTT |

FIGURE 5 CONTINUED (SEQ ID NO:2226), CGGGAGAATGGGCGTAGTTTTTTGGTTTTT (SEQ ID NO:2227),
TGGGCGTAGTTTTTTGGTTTTTGTATGGGG (SEQ ID NO:2228)

| | | |
|---|---|---|
| Target235 | chr2:86164076-86164203 | TTAGGTTTGGTCGGGGTTGGTAGCGGG (SEQ ID NO:2229), GGGGTACGGGGAGGTGGGAGTTGATTT (SEQ ID NO:2230), GTTTGGTCGGGGTTGGTAGCGGGGTAC (SEQ ID NO:2231), GTTAGGTTTGGTCGGGGTTGGTAGCGG (SEQ ID NO:2232), AGTTAGGTTTGGTCGGGGTTGGTAGCGG (SEQ ID NO:2233), TGTCGTGGGTTAGGGTTGGGTAAGAGT (SEQ ID NO:2234), TGTCGTGGGTTAGGGTTGGGTAAGAGTT (SEQ ID NO:2235), TTGTCGTGGGTTAGGGTTGGGTAAGAGT (SEQ ID NO:2236), GTCGTGGGTTAGGGTTGGGTAAGAGTT (SEQ ID NO:2237), TTGTCGTGGGTTAGGGTTGGGTAAGAG (SEQ ID NO:2238) |
| Target236 | chr2:89064644-89064868 | AGGGCGGCGTAGTTTGTGGGGTTTTTG (SEQ ID NO:2239), TTTCGGTTCGGGTTGTAGGAGGCGTGT (SEQ ID NO:2240), GTTGGTAAGGGCGGCGTAGTTTGTGGG (SEQ ID NO:2241), TGGGTTTCGGTTCGGGTTGTAGGAGGC (SEQ ID NO:2242), GAGCGTTGGGTATGGGTTTCGGTTCGG (SEQ ID NO:2243), GGGGTTCGTACGGTTGGAGGCGTAGTT (SEQ ID NO:2244), GGTTGGGGTTGGCGGGGTTTATTTGGG (SEQ ID NO:2245), TTTGGTTCGTGTGTTGGTGGCGGTTGT (SEQ ID NO:2246), GGGGTTGGCGGGGTTTATTTGGGATGG (SEQ ID NO:2247), GGTTGGAGGCGTAGTTTTGGTCGGGGA (SEQ ID NO:2248) |
| Target237 | chr2:89064904-89065163 | TTTCGGTTCGGGTTGTAGGAGGCGTGT (SEQ ID NO:2249), GGAGTCGGTGGAAGAGGAGAAGAGCGC (SEQ ID NO:2250), GAGTCGGTGGAAGAGGAGAAGAGCGCG (SEQ ID NO:2251), GGGAGTCGGTGGAAGAGGAGAAGAGCG (SEQ ID NO:2252), TGGGTTTCGGTTCGGGTTGTAGGAGGC (SEQ ID NO:2253), AGGCGGAAGGATTGGATTCGGGGTTGT (SEQ ID NO:2254), CGAGGCGGAAGGATTGGATTCGGGGTT (SEQ ID NO:2255), GAGGCGGAAGGATTGGATTCGGGGTTG (SEQ ID NO:2256), GGCGGAAGGATTGGATTCGGGGTTGTT (SEQ ID NO:2257), AGGCGGAAGGATTGGATTCGGGGTTGTT (SEQ ID NO:2258) |
| Target238 | chr2:95401381-95401629 | GGGGATATGGGGAGTTGGTTGAAGGCGT (SEQ ID NO:2259), GGGGATATGGGGAGTTGGTTGAAGGCG (SEQ ID NO:2260), CGGGGATATGGGGAGTTGGTTGAAGGC (SEQ ID NO:2261), TCGGGGATATGGGGAGTTGGTTGAAGGC (SEQ ID NO:2262), GGGAGTTGGTTGAAGGCGTAAAGGAGCG (SEQ ID NO:2263), GCGTGGTGGCGTTGTGTTTGGTTTGAG (SEQ ID NO:2264), CGGTGGTGGCGGGAAGTTTTAGGTCGT (SEQ ID NO:2265), CGTGGTGGCGTTGTGTTTGGTTTGAGG (SEQ ID NO:2266), GCGGTGGTGGCGGGAAGTTTTAGGTC (SEQ ID NO:2267), CGTGGTGGCGTTGTGTTTGGTTTGAGGT (SEQ ID NO:2268) |
| Target239 | chr2:99438970-99439638 | GTTGGTTCGTTTTAGCGGGCGGGAGAC (SEQ ID NO:2269), GGGGTTCGGGGAGATTTTGGAGGTCGT (SEQ ID NO:2270), GGTTAGGTTTCGCGTGTTGGGGTTCGG (SEQ ID NO:2271), GGGTTAGGTTTCGCGTGTTGGGGTTCG (SEQ ID NO:2272), TGGGGTTCGGGGAGATTTTGGAGGTCG (SEQ ID NO:2273), GGCGGAAAGTAGGATGGGGAGGCGTTT (SEQ ID NO:2274), ACGGATAAGGCGGAGGAGGTGGTTTGT (SEQ ID NO:2275), AGGAGAAGGGGTTTTTAGGGTCGGCGT (SEQ ID NO:2276), GGTTACGGATAAGGCGGAGGAGGTGGT (SEQ ID NO:2277), GCGGAAAGTAGGATGGGGAGGCGTTT (SEQ ID NO:2278) |
| Target240 | chr2:99439662-99439907 | TTTGGTACGGGTTTTTTCGGGTGGCGG (SEQ ID NO:2279), TGGTACGGGTTTTTTCGGGTGGCGGTA (SEQ ID NO:2280), AGGGCGTCGGTGGTTTAGGTTTAGGGT (SEQ ID NO:2281), GGTACGGGTTTTTTCGGGTGGCGGTAA (SEQ ID NO:2282), GCGGTAAGGGCGTCGGTGGTTTAGGTT (SEQ ID NO:2283), GTTTACGGTTAGCGTGGAGGAGGGGGG (SEQ ID NO:2284), GTTAGCGTGGAGGAGGGGGCGTTTTC (SEQ ID NO:2285), TTTACGGTTAGCGTGGAGGAGGGGGG (SEQ ID NO:2286), TTAGCGTGGAGGAGGGGGGCGTTTTC (SEQ ID NO:2287), TTTACGGTTAGCGTGGAGGAGGGGGGC (SEQ ID NO:2288) |
| Target241 | chr2:105459126-105459192 | CGAGGAGGGGGGTTGGGGTAGAATAAT (SEQ ID NO:2289), CGAGGAGGGGGGGTTGGGGTAGAATAATT (SEQ ID NO:2290), CGAGGAGGGGGGGTTGGGGTAGAATAA (SEQ ID NO:2291), TGTTTTGTTTTGTTTTGTTTTGCGCGCGT (SEQ ID NO:2292), GTTTTGTTTTGTTTTGTTTTGCGCGCGT (SEQ ID NO:2293), GAGGGTAGAGCGGCGGGGAATAGTGTG (SEQ ID NO:2294), TCGGTGAGCGCGTTTTAGAGGAGTCGT (SEQ ID NO:2295), GTTGGTTTGGGTCGGGTTGGGTCGTTT (SEQ ID NO:2296), TAGGTTGGTTTGGGTCGGGTTGGGTCG (SEQ ID NO:2297), AGAGGGTAGAGCGGCGGGGAATAGTGT (SEQ ID NO:2298) |
| Target242 | chr2:105459219-105459243 | TGTTTTGTTTTGTTTTGTTTTGCGCGCGT (SEQ ID NO:2299), GTTTTGTTTTGTTTTGTTTTGCGCGCGT (SEQ ID NO:2300), TGTTTTGTTTTGTTTTGTTTTGCGCGCG (SEQ ID NO:2301), TTGTTTTGTTTTGTTTTGTTTTGCGCGCG (SEQ ID NO:2302), TTGTTTTGTTTTGTTTTGTTTTGCGCGCGT (SEQ ID NO:2303), GTTGGTTTGGGTCGGGTTGGGTCGTTT (SEQ ID NO:2304), TAGGTTGGTTTGGGTCGGGTTGGGTCG (SEQ ID NO:2305), TTGGTTTGGGTCGGGTTGGGTCGTTTT (SEQ ID NO:2306), GGTTGGTTTGGGTCGGGTTGGGTCGTT (SEQ ID NO:2307), GTTGGTTTGGGTCGGGTTGGGTCGTTTT (SEQ ID NO:2308) |
| Target243 | chr2:105459288-105459368 | GTTGTTTTTGTGGGGAGGTAGCGCGGT (SEQ ID NO:2309), TCGTTGTTTTTGTGGGGAGGTAGCGCGC (SEQ ID NO:2310), CGTTGTTTTTGTGGGGAGGTAGCGCGCG (SEQ ID NO:2311), TGTTTTTGTGGGGAGGTAGCGCGCGGTT (SEQ ID NO:2312), TTGTTTTTGTGGGGAGGTAGCGCGCGTT (SEQ ID NO:2313), AGCGGGGTGGGTAGTCGGCGTTATTTT (SEQ ID NO:2314), AGAGAGGGTTATAGAGGGAGGCGCGGA (SEQ ID NO:2315), GAGCGGGGTGGGTAGTCGGCGTTATTT (SEQ ID NO:2316), GCGGGGTGGGTAGTCGGCGTTATTTTT (SEQ ID NO:2317), GAGAGGGTTATAGAGGGAGGCGCGGAG (SEQ ID NO:2318) |

FIGURE 5 CONTINUED

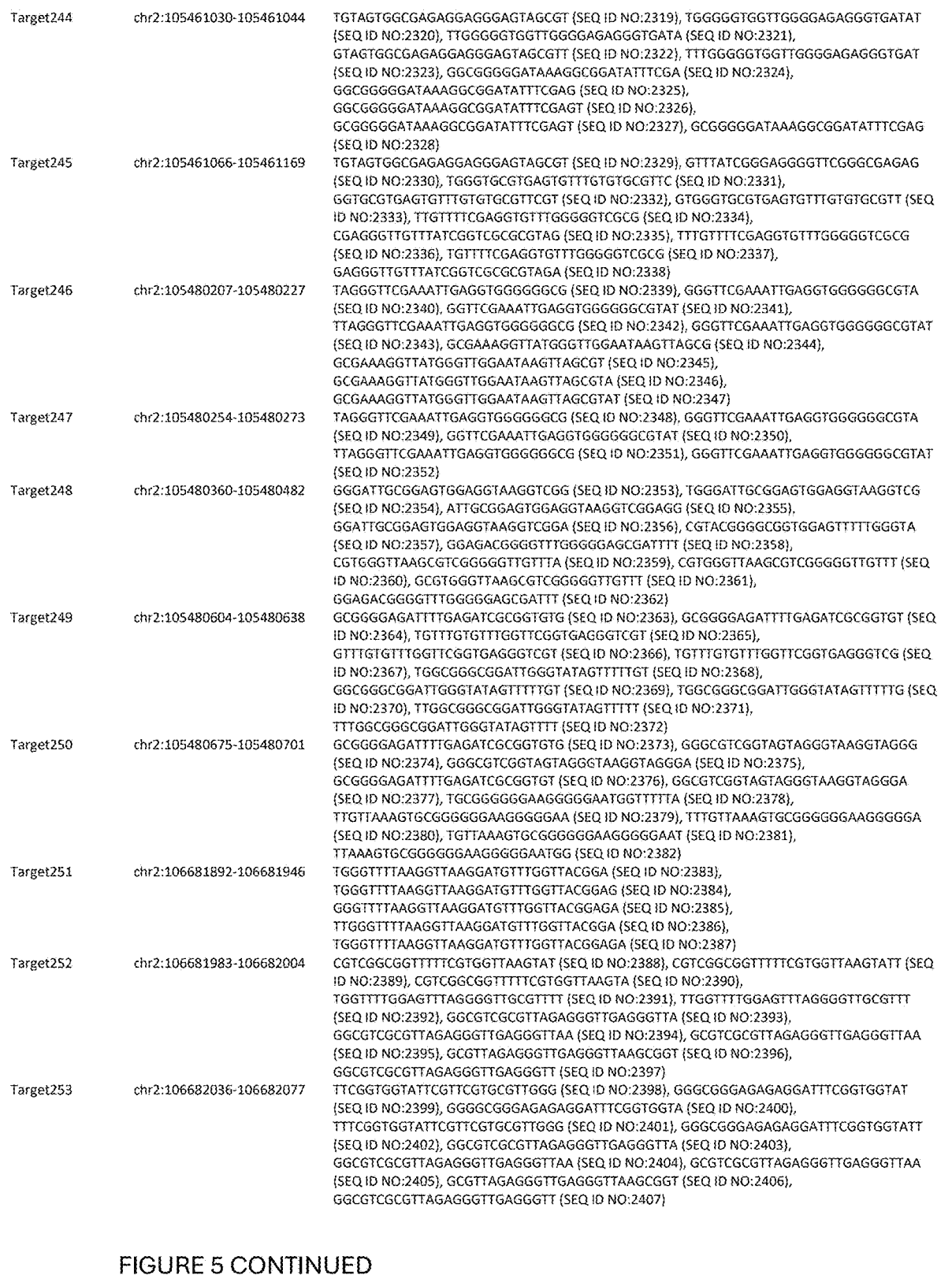

Target244 chr2:105461030-105461044 TGTAGTGGCGAGAGGAGGGAGTAGCGT (SEQ ID NO:2319), TGGGGGTGGTTGGGGAGAGGGTGATAT (SEQ ID NO:2320), TTGGGGGTGGTTGGGGAGAGGGTGATA (SEQ ID NO:2321), GTAGTGGCGAGAGGAGGGAGTAGCGTT (SEQ ID NO:2322), TTTGGGGGTGGTTGGGGAGAGGGTGAT (SEQ ID NO:2323), GGCGGGGGGATAAAGGCGGATATTTCGA (SEQ ID NO:2324), GGCGGGGGATAAAGGCGGATATTTCGAG (SEQ ID NO:2325), GGCGGGGGATAAAGGCGGATATTTCGAGT (SEQ ID NO:2326), GCGGGGGATAAAGGCGGATATTTCGAGT (SEQ ID NO:2327), GCGGGGGATAAAGGCGGATATTTCGAG (SEQ ID NO:2328)

Target245 chr2:105461066-105461169 TGTAGTGGCGAGAGGAGGGAGTAGCGT (SEQ ID NO:2329), GTTTATCGGGAGGGGTTCGGGCGAGAG (SEQ ID NO:2330), TGGGTGCGTGAGTGTTTGTGTGCGTTC (SEQ ID NO:2331), GGTGCGTGAGTGTTTGTGTGCGTTCGT (SEQ ID NO:2332), GTGGGTGCGTGAGTGTTTGTGTGCGTT (SEQ ID NO:2333), TTGTTTTCGAGGTGTTTGGGGGTCGCG (SEQ ID NO:2334), CGAGGGTTGTTTATCGGTCGCGCGTAG (SEQ ID NO:2335), TTTGTTTTCGAGGTGTTTGGGGGTCGCG (SEQ ID NO:2336), TGTTTTCGAGGTGTTTGGGGGTCGCG (SEQ ID NO:2337), GAGGGTTGTTTATCGGTCGCGCGTAGA (SEQ ID NO:2338)

Target246 chr2:105480207-105480227 TAGGGTTCGAAATTGAGGTGGGGGGGCG (SEQ ID NO:2339), GGGTTCGAAATTGAGGTGGGGGGGCGTA (SEQ ID NO:2340), GGTTCGAAATTGAGGTGGGGGGGCGTAT (SEQ ID NO:2341), TTAGGGTTCGAAATTGAGGTGGGGGGGCG (SEQ ID NO:2342), GGGTTCGAAATTGAGGTGGGGGGGCGTAT (SEQ ID NO:2343), GCGAAAGGTTATGGGTTGGAATAAGTTAGCG (SEQ ID NO:2344), GCGAAAGGTTATGGGTTGGAATAAGTTAGCGT (SEQ ID NO:2345), GCGAAAGGTTATGGGTTGGAATAAGTTAGCGTA (SEQ ID NO:2346), GCGAAAGGTTATGGGTTGGAATAAGTTAGCGTAT (SEQ ID NO:2347)

Target247 chr2:105480254-105480273 TAGGGTTCGAAATTGAGGTGGGGGGGCG (SEQ ID NO:2348), GGGTTCGAAATTGAGGTGGGGGGGCGTA (SEQ ID NO:2349), GGTTCGAAATTGAGGTGGGGGGGCGTAT (SEQ ID NO:2350), TTAGGGTTCGAAATTGAGGTGGGGGGGCG (SEQ ID NO:2351), GGGTTCGAAATTGAGGTGGGGGGGCGTAT (SEQ ID NO:2352)

Target248 chr2:105480360-105480482 GGGATTGCGGAGTGGAGGTAAGGTCGG (SEQ ID NO:2353), TGGGATTGCGGAGTGGAGGTAAGGTCG (SEQ ID NO:2354), ATTGCGGAGTGGAGGTAAGGTCGGAGG (SEQ ID NO:2355), GGATTGCGGAGTGGAGGTAAGGTCGGA (SEQ ID NO:2356), CGTACGGGGCGGTGGAGTTTTTGGGTA (SEQ ID NO:2357), GGAGACGGGGTTTGGGGGAGCGATTTT (SEQ ID NO:2358), CGTGGGTTAAGCGTCGGGGGTTGTTTA (SEQ ID NO:2359), CGTGGGTTAAGCGTCGGGGGTTGTTT (SEQ ID NO:2360), GCGTGGGTTAAGCGTCGGGGGTTGTTT (SEQ ID NO:2361), GGAGACGGGGTTTGGGGGAGCGATTT (SEQ ID NO:2362)

Target249 chr2:105480604-105480638 GCGGGGGAGATTTTGAGATCGCGGTGTG (SEQ ID NO:2363), GCGGGGGAGATTTTGAGATCGCGGTGT (SEQ ID NO:2364), TGTTTGTGTTTGGTTCGGTGAGGGTCGT (SEQ ID NO:2365), GTTTGTGTTTGGTTCGGTGAGGGTCGT (SEQ ID NO:2366), TGTTTGTGTTTGGTTCGGTGAGGGTCG (SEQ ID NO:2367), TGGCGGGCGGATTGGGTATAGTTTTTGT (SEQ ID NO:2368), GGCGGGCGGATTGGGTATAGTTTTTGT (SEQ ID NO:2369), TGGCGGGCGGATTGGGTATAGTTTTTG (SEQ ID NO:2370), TTGGCGGGCGGATTGGGTATAGTTTTT (SEQ ID NO:2371), TTTGGCGGGCGGATTGGGTATAGTTTT (SEQ ID NO:2372)

Target250 chr2:105480675-105480701 GCGGGGGAGATTTTGAGATCGCGGTGTG (SEQ ID NO:2373), GGGCGTCGGTAGTAGGGTAAGGTAGGG (SEQ ID NO:2374), GGGCGTCGGTAGTAGGGTAAGGTAGGGA (SEQ ID NO:2375), GCGGGGGAGATTTTGAGATCGCGGTGT (SEQ ID NO:2376), GGCGTCGGTAGTAGGGTAAGGTAGGGA (SEQ ID NO:2377), TGCGGGGGGGAAGGGGGAATGGTTTTTA (SEQ ID NO:2378), TTGTTAAAGTGCGGGGGGGAAGGGGGAA (SEQ ID NO:2379), TTTGTTAAAGTGCGGGGGGGAAGGGGGA (SEQ ID NO:2380), TGTTAAAGTGCGGGGGGGAAGGGGGAAT (SEQ ID NO:2381), TTAAAGTGCGGGGGGGAAGGGGGAATGG (SEQ ID NO:2382)

Target251 chr2:106681892-106681946 TGGGTTTTAAGGTTAAGGATGTTTGGTTACGGA (SEQ ID NO:2383), TGGGTTTTAAGGTTAAGGATGTTTGGTTACGGAG (SEQ ID NO:2384), GGGTTTTAAGGTTAAGGATGTTTGGTTACGGAGA (SEQ ID NO:2385), TTGGGTTTTAAGGTTAAGGATGTTTGGTTACGGA (SEQ ID NO:2386), TGGGTTTTAAGGTTAAGGATGTTTGGTTACGGAGA (SEQ ID NO:2387)

Target252 chr2:106681983-106682004 CGTCGGCGGTTTTTCGTGGTTAAGTAT (SEQ ID NO:2388), CGTCGGCGGTTTTTCGTGGTTAAGTATT (SEQ ID NO:2389), CGTCGGCGGTTTTTCGTGGTTAAGTA (SEQ ID NO:2390), TGGTTTTGGAGTTTAGGGGTTGCGTTTT (SEQ ID NO:2391), TTGGTTTTGGAGTTTAGGGGTTGCGTTT (SEQ ID NO:2392), GGCGTCGCGTTAGAGGGTTGAGGGTTA (SEQ ID NO:2393), GGCGTCGCGTTAGAGGGTTGAGGGTTAA (SEQ ID NO:2394), GCGTCGCGTTAGAGGGTTGAGGGTTAA (SEQ ID NO:2395), GCGTTAGAGGGTTGAGGGTTAAGCGGT (SEQ ID NO:2396), GGCGTCGCGTTAGAGGGTTGAGGGTT (SEQ ID NO:2397)

Target253 chr2:106682036-106682077 TTCGGTGGTATTCGTTCGTGCGTTGGG (SEQ ID NO:2398), GGGCGGGAGAGAGGATTTCGGTGGTAT (SEQ ID NO:2399), GGGGCGGGAGAGAGGATTTCGGTGGTA (SEQ ID NO:2400), TTTCGGTGGTATTCGTTCGTGCGTTGGG (SEQ ID NO:2401), GGGCGGGAGAGAGGATTTCGGTGGTATT (SEQ ID NO:2402), GGCGTCGCGTTAGAGGGTTGAGGGTTA (SEQ ID NO:2403), GGCGTCGCGTTAGAGGGTTGAGGGTTAA (SEQ ID NO:2404), GCGTCGCGTTAGAGGGTTGAGGGTTAA (SEQ ID NO:2405), GCGTTAGAGGGTTGAGGGTTAAGCGGT (SEQ ID NO:2406), GGCGTCGCGTTAGAGGGTTGAGGGTT (SEQ ID NO:2407)

FIGURE 5 CONTINUED

Target254    chr2:106682084-106682218    TTGGCGCGGCGTTTATTCGTTGGGTTT (SEQ ID NO:2408), TTTGGCGCGGCCGTTTATTCGTTGGGTT (SEQ ID NO:2409), TTTTTGGCGCGGCGTTTATTCGTTGGGT (SEQ ID NO:2410), TTCGGTGGTATTCGTTCGTGCGTTGGG (SEQ ID NO:2411), TTTTTGGCGCGGCGTTTATTCGTTGGG (SEQ ID NO:2412), GGTTAGGATAGTAGGTCGCGCGGGGGA (SEQ ID NO:2413), AGGGTTAGGATAGTAGGTCGCGCGGGG (SEQ ID NO:2414), GGTTAGGATAGTAGGTCGCGCGGGGG (SEQ ID NO:2416), GGGTTAGGATAGTAGGTCGCGCGGGG (SEQ ID NO:2416), TAGGGTTAGGATAGTAGGTCGCGCGGG (SEQ ID NO:2417)

Target255    chr2:106682237-106682271    TCGCGCGGTTTGTTGTTTTGGTTTTGA (SEQ ID NO:2418), GCGGTCGCGCGTTTGTTCGTTCGTATTTT (SEQ ID NO:2419), GCGCGGTTTGTTGTTTTGGTTTTGATCGGG (SEQ ID NO:2420), CGCGCGGTTTGTTGTTTTGGTTTTGATCGG (SEQ ID NO:2421), TTCGCGCGGTTTGTTGTTTTGGTTTTG (SEQ ID NO:2422), AGTTCGGTTAGGGTTAGGATAGTAGGTCGT (SEQ ID NO:2423), GCGTTAGTTCGGTTAGGGTTAGGATAGTAGGT (SEQ ID NO:2424), GCGTTAGTTCGGTTAGGGTTAGGATAGTAGGTCG (SEQ ID NO:2425), GCGTTAGTTCGGTTAGGGTTAGGATAGTAGGTCGT (SEQ ID NO:2426), GCGTTAGTTCGGTTAGGGTTAGGATAGTAGGTC (SEQ ID NO:2427)

Target256    chr2:106690422-106690449    GCGTTAGAAGCGGTAGTTGTGGGATCGG (SEQ ID NO:2428), GCGTTAGAAGCGGTAGTTGTGGGATCGGA (SEQ ID NO:2429), GCGTTAGAAGCGGTAGTTGTGGGATCG (SEQ ID NO:2430), CGTTAGAAGCGGTAGTTGTGGGATCGG (SEQ ID NO:2431), CGTTAGAAGCGGTAGTTGTGGGATCGGA (SEQ ID NO:2432), TTTTGTGGAAGTTAGGTTTGTAGTCGGAGGT (SEQ ID NO:2433), TTTTTGTGGAAGTTAGGTTTGTAGTCGGAGGT (SEQ ID NO:2434), TTTTTTGTGGAAGTTAGGTTTGTAGTCGGAGGT (SEQ ID NO:2435), TTTTGTGGAAGTTAGGTTTGTAGTCGGAGGTAA (SEQ ID NO:2436), TTTTTGTGGAAGTTAGGTTTGTAGTCGGAGGTA (SEQ ID NO:2437)

Target257    chr2:106690493-106690515    GCGTTAGAAGCGGTAGTTGTGGGATCGG (SEQ ID NO:2438), GCGTTAGAAGCGGTAGTTGTGGGATCGGA (SEQ ID NO:2439), TGGGTTTTGACGAAGCGGTAGGTGTTGT (SEQ ID NO:2440), GGGTTTTGACGAAGCGGTAGGTGTTGT (SEQ ID NO:2441), TGGGTTTTGACGAAGCGGTAGGTGTTG (SEQ ID NO:2442), TTTTGTGGAAGTTAGGTTTGTAGTCGGAGGT (SEQ ID NO:2443), TTTTTGTGGAAGTTAGGTTTGTAGTCGGAGGT (SEQ ID NO:2444), TTTTTTGTGGAAGTTAGGTTTGTAGTCGGAGGT (SEQ ID NO:2445), TTTTGTGGAAGTTAGGTTTGTAGTCGGAGGTAA (SEQ ID NO:2446), TTTTTGTGGAAGTTAGGTTTGTAGTCGGAGGTA (SEQ ID NO:2447)

Target258    chr2:111876312-111876756    GGGGGCGGCGAGGTTGTAAGGTTGTAT (SEQ ID NO:2448), GGCGCGGGAGAAGGTTGTAAGGGTTTT (SEQ ID NO:2449), CGGCGCGGGAGAAGGTTGTAAGGGTTT (SEQ ID NO:2450), GGGGGCGGCGAGGTTGTAAGGTTGTATA (SEQ ID NO:2451), GGGTTTTTGGTTTTCGACGCGGTTTGGG (SEQ ID NO:2452), TCGGTTAGAGGTGGCGGGTTTATGCGT (SEQ ID NO:2453), AGGAAGTCGGTTAGAGGTGGCGGGTTT (SEQ ID NO:2454), AAGGAAGTCGGTTAGAGGTGGCGGGTT (SEQ ID NO:2455), AAAGGAAGTCGGTTAGAGGTGGCGGGT (SEQ ID NO:2456), AGTCGGGGGAAGTAACGGGTTAAGCGT (SEQ ID NO:2457)

Target259    chr2:111876775-111877077    GCGTTGAGATTTTGGTATGGGGTTGCG (SEQ ID NO:2458), TGCGTTGAGATTTTGGTATGGGGTTGCG (SEQ ID NO:2459), TGCGTTGAGATTTTGGTATGGGGTTGC (SEQ ID NO:2460), GCGTTGAGATTTTGGTATGGGGTTGCG (SEQ ID NO:2461), TGCGTTGAGATTTTGGTATGGGGTTGC (SEQ ID NO:2462), CGTAGTCGGTAGGGAGAAGGAAGGGGT (SEQ ID NO:2463), TGAGCGAGGTGAAGGAGGTTTTGGGTT (SEQ ID NO:2464), TTGAGCGAGGTGAAGGAGGTTTTGGGT (SEQ ID NO:2465), GCGAGGTGAAGGAGGTTTTGGGTTTCGG (SEQ ID NO:2466), CGTAGTCGGTAGGGAGAAGGAAGGGGTT (SEQ ID NO:2467)

Target260    chr2:111877108-111877178    GCGTTGAGATTTTGGTATGGGGTTGCG (SEQ ID NO:2468), TGCGTTGAGATTTTGGTATGGGGTTGCG (SEQ ID NO:2469), TGCGTTGAGATTTTGGTATGGGGTTGCGT (SEQ ID NO:2470), GCGTTGAGATTTTGGTATGGGGTTGCG (SEQ ID NO:2471), TGCGTTGAGATTTTGGTATGGGGTTGC (SEQ ID NO:2472), GGTGTGGGAGGTGGATCGGGAAATGGA (SEQ ID NO:2473), TAATTGTAGCGGGGGTGTGGGAGGTGG (SEQ ID NO:2474), GGGTGTGGGAGGTGGATCGGGAAATGG (SEQ ID NO:2475), GGGGTGTGGGAGGTGGATCGGGAAATG (SEQ ID NO:2476), ATTGTAGCGGGGGTGTGGGAGGTGGAT (SEQ ID NO:2477)

Target261    chr2:113931398-113931767    GGGGAGTAGGAGGGGTGTGTGTTGTGG (SEQ ID NO:2478), CGGGGAGTAGGAGGGGTGTGTGTTGTG (SEQ ID NO:2479), TGTGGTAGGGGTTGGGGTAGGTGGGTA (SEQ ID NO:2480), GGGTATGGGGAAAGGGGTTGTAGGCGT (SEQ ID NO:2481), GTGGGTAGGGGAGAGGCGAGGGTTTTG (SEQ ID NO:2482), GAGGAGGGGTAGGTTGAGGGAGGAGGG (SEQ ID NO:2483), GGTTGAGGGAGGAGGGGGACGGGATAT (SEQ ID NO:2484), TGAGGAGGGGTAGGTTGAGGGAGGAGG (SEQ ID NO:2485), AGGAGGGGTAGGTTGAGGGAGGAGGGG (SEQ ID NO:2486), AGGTTGAGGGAGGAGGGGGACGGGATA (SEQ ID NO:2487)

Target262    chr2:114034275-114034368    AGCGGTAGAGAGTAAGGGTTTAGTTCGGT (SEQ ID NO:2488), TGGGTAGCGGTAGAGAGTAAGGGTTTAGT (SEQ ID NO:2489), GCGGTAGAGAGTAAGGGTTTAGTTCGGTT (SEQ ID NO:2490), AGCGGTAGAGAGTAAGGGTTTAGTTCGGTT (SEQ ID NO:2491), GGGTAGCGGTAGAGAGTAAGGGTTTAGTTCGG (SEQ ID NO:2492), CGGCGGTGGTAGGAGGAGTGAGTGTTT (SEQ ID NO:2493), TTTCGGCGGTGGTAGGAGGAGTGAGTG

FIGURE 5 CONTINUED

|  |  | (SEQ ID NO:2494), TCGGCGGTGGTAGGAGGAGTGAGTGTT (SEQ ID NO:2495), TTCGGCGGTGGTAGGAGGAGTGAGTGT (SEQ ID NO:2496), TTTTCGGCGGTGGTAGGAGGAGTGAGT (SEQ ID NO:2497) |
| Target263 | chr2:114034478-114034535 | CGTCGGAAGGGTTAGGGGAAGGTTAGG (SEQ ID NO:2498), CGTCGGAAGGGTTAGGGGAAGGTTAGGA (SEQ ID NO:2499), TCGTCGGAAGGGTTAGGGGAAGGTTAGG (SEQ ID NO:2500), TCGTCGGAAGGGTTAGGGGAAGGTTAGGA (SEQ ID NO:2501), CGGAAGGGTTAGGGGAAGGTTAGGAGG (SEQ ID NO:2502) |
| Target264 | chr2:131721486-131721513 | GCGGTTATAGAGTTCGAGCGGGGGGTC (SEQ ID NO:2503), GCGGTTATAGAGTTCGAGCGGGGGGT (SEQ ID NO:2504), CGGTTATAGAGTTCGAGCGGGGGGTC (SEQ ID NO:2505), GCGGTTATAGAGTTCGAGCGGGGGG (SEQ ID NO:2506), CGGTTATAGAGTTCGAGCGGGGGGT (SEQ ID NO:2507), TATAGGTTCGGGGAAGGTTGGGTCGGG (SEQ ID NO:2508), ATAGGTTCGGGGAAGGTTGGGTCGGG (SEQ ID NO:2509), ATAGGTTCGGGGAAGGTTGGGTCGGG (SEQ ID NO:2510), TATAGGTTCGGGGAAGGTTGGGTCGGGG (SEQ ID NO:2511), TTATAGGTTCGGGGAAGGTTGGGTCGGG (SEQ ID NO:2512) |
| Target265 | chr2:131721523-131721558 | GCGGTTATAGAGTTCGAGCGGGGGGTC (SEQ ID NO:2513), GCGGTTATAGAGTTCGAGCGGGGGGT (SEQ ID NO:2514), CGGTTATAGAGTTCGAGCGGGGGGTC (SEQ ID NO:2515), GCGGTTATAGAGTTCGAGCGGGGGG (SEQ ID NO:2516), CGGTTATAGAGTTCGAGCGGGGGGT (SEQ ID NO:2517), TATAGGTTCGGGGAAGGTTGGGTCGGG (SEQ ID NO:2518), ATAGGTTCGGGGAAGGTTGGGTCGGGG (SEQ ID NO:2519), ATAGGTTCGGGGAAGGTTGGGTCGGG (SEQ ID NO:2520), TATAGGTTCGGGGAAGGTTGGGTCGGGG (SEQ ID NO:2521), TTATAGGTTCGGGGAAGGTTGGGTCGGG (SEQ ID NO:2522) |
| Target266 | chr2:131721562-131721672 | GCGTGCGGGCGTAGTAATGTTTTAGCG (SEQ ID NO:2523), GCGTGCGGGCGTAGTAATGTTTTAGCGA (SEQ ID NO:2524), GCGTGCGGGCGTAGTAATGTTTTAGCGAG (SEQ ID NO:2525), CGTGCGGGCGTAGTAATGTTTTAGCGA (SEQ ID NO:2526), TCGAGTTTGTGGTTGGAGTTCGGGTTC (SEQ ID NO:2527), TATAGGTTCGGGGAAGGTTGGGTCGGG (SEQ ID NO:2528), ATAGGTTCGGGGAAGGTTGGGTCGGGG (SEQ ID NO:2529), GGAGTTCGGGGATAGTTCGGCGTTGTT (SEQ ID NO:2530), ATAGGTTCGGGGAAGGTTGGGTCGGG (SEQ ID NO:2531), TCGGGGATAGTTCGGCGTTGTTGTTGT (SEQ ID NO:2532) |
| Target267 | chr2:131721692-131721867 | TTCGGATAGTAGCGGCGTGGTGTGTGG (SEQ ID NO:2533), TCGATTCGGATAGTAGCGGCGTGGTGT (SEQ ID NO:2534), CGATTCGGATAGTAGCGGCGTGGTGTG (SEQ ID NO:2535), TCGATTCGGATAGTAGCGGCGTGGTGTG (SEQ ID NO:2536), GCGTGCGGGCGTAGTAATGTTTTAGCG (SEQ ID NO:2537), GAGGGGGGCGGGGGGGTTTTAAGAGTAT (SEQ ID NO:2538), AGGAGAAGGAAAGGTAGGAGGGGGGCG (SEQ ID NO:2539), GAGGAGAAGGAAAGGTAGGAGGGGGGC (SEQ ID NO:2540), TAGGAGGGGGGCGGGGGGGTTTTAAGAG (SEQ ID NO:2541), GGAGGGGGGCGGGGGGTTTTAAGAGTA (SEQ ID NO:2542) |
| Target268 | chr2:131792027-131792037 | AGGTTGTAGGTTGTGTCGAGTGGAGGT (SEQ ID NO:2543), AGGTTGTGTCGAGTGGAGGTAGAGGAA (SEQ ID NO:2544), AAGGTTGTAGGTTGTGTCGAGTGGAGGT (SEQ ID NO:2545), AAGGTTGTAGGTTGTGTCGAGTGGAGG (SEQ ID NO:2546), GGTTGTGTCGAGTGGAGGTAGAGGAAGT (SEQ ID NO:2547), GCGTAGGAATGTAGGGATGGCGGAGGT (SEQ ID NO:2548), GCGTAGGAATGTAGGGATGGCGGAGGTA (SEQ ID NO:2549), AGGAATGTAGGGATGGCGGAGGTAGGA (SEQ ID NO:2550), GCGTAGGAATGTAGGGATGGCGCGAGG (SEQ ID NO:2551), GCGTAGGAATGTAGGGATGGCGGAGGTAG (SEQ ID NO:2552) |
| Target269 | chr2:131792397-131792426 | AGGGTTAGGATTGTTGTGTCGGCGTGG (SEQ ID NO:2553), GGGTTAGGATTGTTGTGTCGGCGTGGA (SEQ ID NO:2554), AGGGTTAGGATTGTTGTGTCGGCGTGGA (SEQ ID NO:2555), GGGTTAGGATTGTTGTGTCGGCGTGGAG (SEQ ID NO:2556), GGGTTAGGATTGTTGTGTCGGCGTGGAGA (SEQ ID NO:2557), AGAGGTTTAGAGGGATCGCGGCGGTTC (SEQ ID NO:2558), GAGAGGTTTAGAGGGATCGCGGCGGTT (SEQ ID NO:2559), TTGGAGAGGTTTAGAGGGATCGCGGCG (SEQ ID NO:2560), GTAATTAAGTCGGTTGTGCGGGCGGGG (SEQ ID NO:2561), GGTAATTAAGTCGGTTGTGCGGGCGGG (SEQ ID NO:2562) |
| Target270 | chr2:131792452-131792468 | AGGGTTAGGATTGTTGTGTCGGCGTGG (SEQ ID NO:2563), GGGTTAGGATTGTTGTGTCGGCGTGGA (SEQ ID NO:2564), AGGGTTAGGATTGTTGTGTCGGCGTGGA (SEQ ID NO:2565), GGGTTAGGATTGTTGTGTCGGCGTGGAG (SEQ ID NO:2566), GGGTTAGGATTGTTGTGTCGGCGTGGAGA (SEQ ID NO:2567), GTAATTAAGTCGGTTGTGCGGGCGGGG (SEQ ID NO:2568), GGTAATTAAGTCGGTTGTGCGGGCGGG (SEQ ID NO:2569), TGGTAATTAAGTCGGTTGTGCGGGCGG (SEQ ID NO:2570), TAATTAAGTCGGTTGTGCGGGCGGGGG (SEQ ID NO:2571), TTGGTAATTAAGTCGGTTGTGCGGGCGG (SEQ ID NO:2572) |
| Target271 | chr2:131792471-131792650 | TTTTCGGGCGTTGCGGGTTATCGGTTC (SEQ ID NO:2573), TGTTAGGGTTTGGGGTTTGGGAGGCGT (SEQ ID NO:2574), TGCGGGTTATCGGTTCGGTTTTGTGCG (SEQ ID NO:2575), GGCGTTGCGGGTTATCGGTTCGGTTTT (SEQ ID NO:2576), TTTTTCGGGCGTTGCGGGTTATCGGTT (SEQ ID NO:2577), GTCGGGGTTGCGGGGTTTTCGTTATGG (SEQ ID NO:2578), TTGCGGGGTTTTCGTTATGGCGTTCGG (SEQ ID NO:2579), GCGGGGTTTTCGTTATGGCGTTCGGTT (SEQ ID NO:2580), CGTCGGGGTTGCGGGGTTTTCGTTATG (SEQ ID NO:2581), GGGTTGCGGGGTTTTCGTTATGGCGTT (SEQ ID NO:2582) |
| Target272 | chr2:135464416-135464530 | TGGGGATGGGAGGAGGTGAGGTTAGT (SEQ ID NO:2583), ATGGGGATGGGAGGAGGTGAGGTTAGT (SEQ ID NO:2584), ATGGGGATGGGAGGAGGTGAGGTTAGTT (SEQ ID NO:2585), TGGGGATGGGAGGAGGTGAGGTTAGT (SEQ ID NO:2586), TGGGGATGGGAGGAGGTGAGGTTAGTTA |

FIGURE 5 CONTINUED

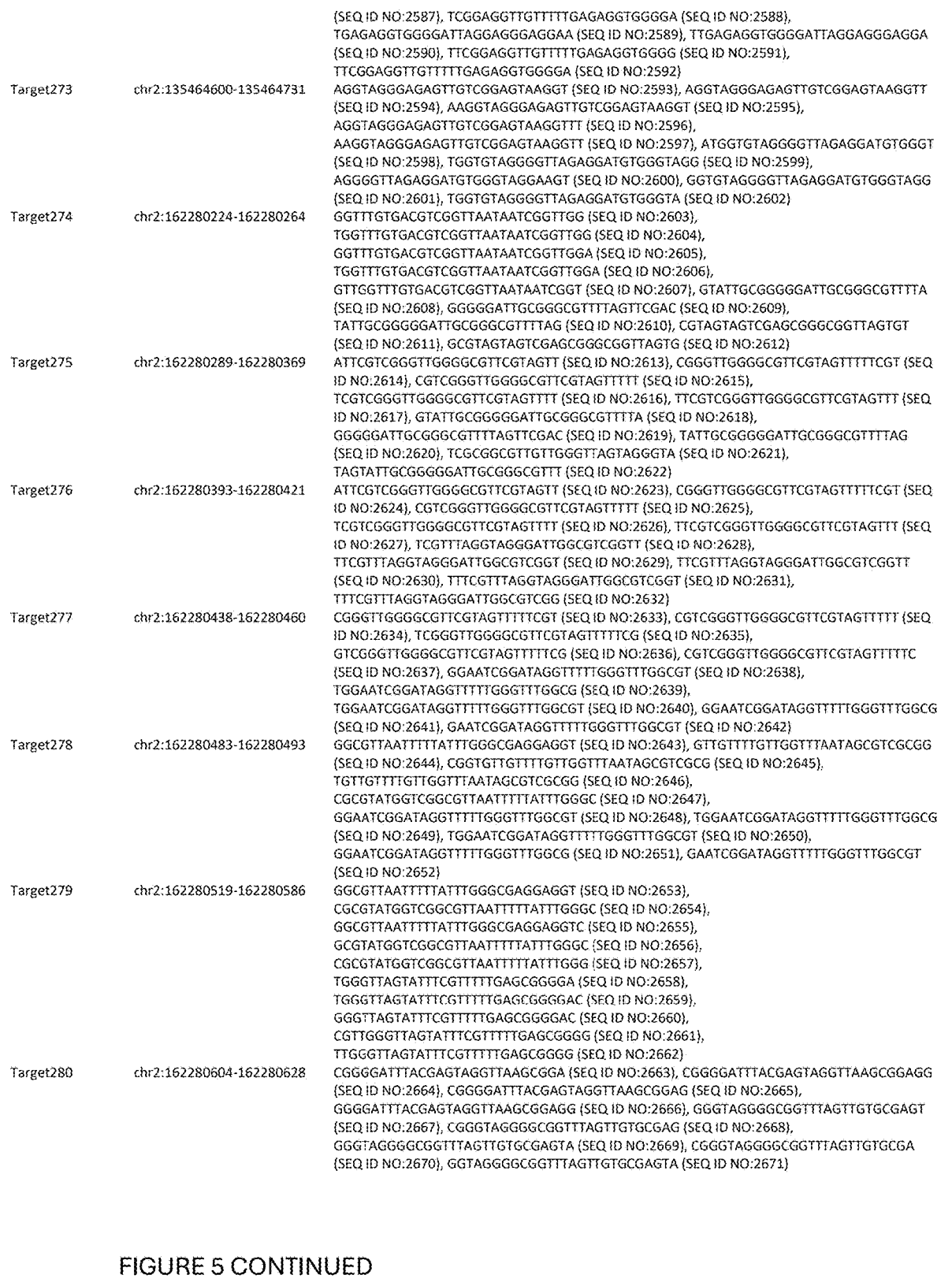

|  |  | {SEQ ID NO:2587}, TCGGAGGTTGTTTTTGAGAGGTGGGGA (SEQ ID NO:2588}, TGAGAGGTGGGGATTAGGAGGGAGGAA {SEQ ID NO:2589}, TTGAGAGGTGGGGATTAGGAGGGAGGA {SEQ ID NO:2590}, TTCGGAGGTTGTTTTTGAGAGGTGGGG (SEQ ID NO:2591}, TTCGGAGGTTGTTTTTGAGAGGTGGGGA {SEQ ID NO:2592} |
|---|---|---|
| Target273 | chr2:135464600-135464731 | AGGTAGGGAGAGTTGTCGGAGTAAGGT {SEQ ID NO:2593}, AGGTAGGGAGAGTTGTCGGAGTAAGGTT {SEQ ID NO:2594}, AAGGTAGGGAGAGTTGTCGGAGTAAGGT {SEQ ID NO:2595}, AGGTAGGGAGAGTTGTCGGAGTAAGGTTT {SEQ ID NO:2596}, AAGGTAGGGAGAGTTGTCGGAGTAAGGTT {SEQ ID NO:2597}, ATGGTGTAGGGGTTAGAGGATGTGGGT {SEQ ID NO:2598}, TGGTGTAGGGGTTAGAGGATGTGGGTAGG {SEQ ID NO:2599}, AGGGGTTAGAGGATGTGGGTAGGAAGT {SEQ ID NO:2600}, GGTGTAGGGGTTAGAGGATGTGGGTAGG {SEQ ID NO:2601}, TGGTGTAGGGGTTAGAGGATGTGGGTA {SEQ ID NO:2602} |
| Target274 | chr2:162280224-162280264 | GGTTTGTGACGTCGGTTAATAATCGGTTGG (SEQ ID NO:2603}, TGGTTTGTGACGTCGGTTAATAATCGGTTGG {SEQ ID NO:2604}, GGTTTGTGACGTCGGTTAATAATCGGTTGGA {SEQ ID NO:2605}, TGGTTTGTGACGTCGGTTAATAATCGGTTGGA {SEQ ID NO:2606}, GTTGGTTTGTGACGTCGGTTAATAATCGGT {SEQ ID NO:2607}, GTATTGCGGGGGATTGCGGGCGTTTTA {SEQ ID NO:2608}, GGGGGATTGCGGGCGTTTTAGTTCGAC {SEQ ID NO:2609}, TATTGCGGGGGATTGCGGGCGTTTTAG (SEQ ID NO:2610}, CGTAGTAGTCGAGCGGGCGGTTAGTGT {SEQ ID NO:2611}, GCGTAGTAGTCGAGCGGGCGGTTAGTG (SEQ ID NO:2612} |
| Target275 | chr2:162280289-162280369 | ATTCGTCGGGTTGGGGCGTTCGTAGTT {SEQ ID NO:2613}, CGGGTTGGGGCGTTCGTAGTTTTTCGT {SEQ ID NO:2614}, CGTCGGGTTGGGGCGTTCGTAGTTTTT {SEQ ID NO:2615}, TCGTCGGGTTGGGGCGTTCGTAGTTTT {SEQ ID NO:2616}, TTCGTCGGGTTGGGGCGTTCGTAGTTT {SEQ ID NO:2617}, GTATTGCGGGGGATTGCGGGCGTTTTA {SEQ ID NO:2618}, GGGGGATTGCGGGCGTTTTAGTTCGAC {SEQ ID NO:2619}, TATTGCGGGGGATTGCGGGCGTTTTAG {SEQ ID NO:2620}, TCGCGGCGTTGTTGGGTTAGTAGGGTA {SEQ ID NO:2621}, TAGTATTGCGGGGGATTGCGGGCGTTT {SEQ ID NO:2622} |
| Target276 | chr2:162280393-162280421 | ATTCGTCGGGTTGGGGCGTTCGTAGTT {SEQ ID NO:2623}, CGGGTTGGGGCGTTCGTAGTTTTTCGT {SEQ ID NO:2624}, CGTCGGGTTGGGGCGTTCGTAGTTTTT {SEQ ID NO:2625}, TCGTCGGGTTGGGGCGTTCGTAGTTTT {SEQ ID NO:2626}, TTCGTCGGGTTGGGGCGTTCGTAGTTT {SEQ ID NO:2627}, TCGTTTAGGTAGGGATTGGCGTCGGTT {SEQ ID NO:2628}, TTCGTTTAGGTAGGGATTGGCGTCGGT {SEQ ID NO:2629}, TTCGTTTAGGTAGGGATTGGCGTCGGTT {SEQ ID NO:2630}, TTTCGTTTAGGTAGGGATTGGCGTCGGT {SEQ ID NO:2631}, TTTCGTTTAGGTAGGGATTGGCGTCGG {SEQ ID NO:2632} |
| Target277 | chr2:162280438-162280460 | CGGGTTGGGGCGTTCGTAGTTTTTCGT {SEQ ID NO:2633}, CGTCGGGTTGGGGCGTTCGTAGTTTTT {SEQ ID NO:2634}, TCGGGTTGGGGCGTTCGTAGTTTTTCG {SEQ ID NO:2635}, GTCGGGTTGGGGCGTTCGTAGTTTTTCG {SEQ ID NO:2636}, CGTCGGGTTGGGGCGTTCGTAGTTTTTC {SEQ ID NO:2637}, GGAATCGGATAGGTTTTTGGGTTTGGCGT {SEQ ID NO:2638}, TGGAATCGGATAGGTTTTTGGGTTTGGCG {SEQ ID NO:2639}, TGGAATCGGATAGGTTTTTGGGTTTGGCGT {SEQ ID NO:2640}, GGAATCGGATAGGTTTTTGGGTTTGGCG {SEQ ID NO:2641}, GAATCGGATAGGTTTTTGGGTTTGGCGT {SEQ ID NO:2642} |
| Target278 | chr2:162280483-162280493 | GGCGTTAATTTTTATTTGGGCGAGGAGGT {SEQ ID NO:2643}, GTTGTTTTGTTGGTTTAATAGCGTCGCGG {SEQ ID NO:2644}, CGGTGTTGTTTTTGTTGGTTTAATAGCGTCGCGG {SEQ ID NO:2645}, TGTTGTTTTGTTGGTTTAATAGCGTCGCGG {SEQ ID NO:2646}, CGCGTATGGTCGGCGTTAATTTTTATTTGGGC {SEQ ID NO:2647}, GGAATCGGATAGGTTTTTGGGTTTGGCGT {SEQ ID NO:2648}, TGGAATCGGATAGGTTTTTGGGTTTGGCG {SEQ ID NO:2649}, TGGAATCGGATAGGTTTTTGGGTTTGGCGT {SEQ ID NO:2650}, GGAATCGGATAGGTTTTTGGGTTTGGCG {SEQ ID NO:2651}, GAATCGGATAGGTTTTTGGGTTTGGCGT {SEQ ID NO:2652} |
| Target279 | chr2:162280519-162280586 | GGCGTTAATTTTTATTTGGGCGAGGAGGT {SEQ ID NO:2653}, CGCGTATGGTCGGCGTTAATTTTTATTTGGGC {SEQ ID NO:2654}, GGCGTTAATTTTTATTTGGGCGAGGAGGTC {SEQ ID NO:2655}, GCGTATGGTCGGCGTTAATTTTTATTTGGGC {SEQ ID NO:2656}, CGCGTATGGTCGGCGTTAATTTTTATTTGGG {SEQ ID NO:2657}, TGGGTTAGTATTTCGTTTTTGAGCGGGGA {SEQ ID NO:2658}, TGGGTTAGTATTTCGTTTTTGAGCGGGGAC {SEQ ID NO:2659}, GGGTTAGTATTTCGTTTTTGAGCGGGGAC {SEQ ID NO:2660}, CGTTGGGTTAGTATTTCGTTTTTGAGCGGGG {SEQ ID NO:2661}, TTGGGTTAGTATTTCGTTTTTGAGCGGGG {SEQ ID NO:2662} |
| Target280 | chr2:162280604-162280628 | CGGGGATTTACGAGTAGGTTAAGCGGA {SEQ ID NO:2663}, CGGGGATTTACGAGTAGGTTAAGCGGAGG {SEQ ID NO:2664}, CGGGGATTTACGAGTAGGTTAAGCGGAG {SEQ ID NO:2665}, GGGGATTTACGAGTAGGTTAAGCGGAGG {SEQ ID NO:2666}, GGGTAGGGGCGGTTTAGTTGTGCGAGT {SEQ ID NO:2667}, CGGGTAGGGGCGGTTTAGTTGTGCGAG {SEQ ID NO:2668}, GGGTAGGGGCGGTTTAGTTGTGCGAGTA {SEQ ID NO:2669}, CGGGTAGGGGCGGTTTAGTTGTGCGA {SEQ ID NO:2670}, GGTAGGGGCGGTTTAGTTGTGCGAGTA {SEQ ID NO:2671} |

FIGURE 5 CONTINUED

| Target281 | chr2:162280761-162280772 | AGCGAGGTGTTGGTTTAGCGGGATTGC (SEQ ID NO:2672), GAGCGAGGTGTTGGTTTAGCGGGATTGC (SEQ ID NO:2673), AGAGCGAGGTGTTGGTTTAGCGGGATT (SEQ ID NO:2674), AAGAGCGAGGTGTTGGTTTAGCGGGAT (SEQ ID NO:2675), GAGCGAGGTGTTGGTTTAGCGGGATTG (SEQ ID NO:2676), AGGCGGAGTTGGGGAAGAGTTGTGAGG (SEQ ID NO:2677), GGAGGCGGAGTTGGGGAAGAGTTGTGA (SEQ ID NO:2678), TAAGGAGGAGTGTGGGGAGGCGGAGTT (SEQ ID NO:2679), CGGAGTTGGGGAAGAGTTGTGAGGGGT (SEQ ID NO:2680), AGAGTTGTGAGGGGTTGGTTGGGGGTT (SEQ ID NO:2681) |
| Target282 | chr2:166650143-166650508 | TATAGGGATTGGCGGGGGGTATCGTGGG (SEQ ID NO:2682), GGGTCGTTTTATAGGGATTGGCGGGGGT (SEQ ID NO:2683), GGGTCGTTTTATAGGGATTGGCGGGGG (SEQ ID NO:2684), GGGGTCGTTTTATAGGGATTGGCGGGG (SEQ ID NO:2685), AGGGGTCGTTTTATAGGGATTGGCGGGG (SEQ ID NO:2686), ATTTTGAGAGGGAGGGTTCGGCGGGAG (SEQ ID NO:2687), GATTTTGAGAGGGAGGGTTCGGCGGGA (SEQ ID NO:2688), TGGGGATTTTGAGAGGGAGGGTTCGGC (SEQ ID NO:2689), GGGAGGGTCGTAGCGTGGGGATTTTGA (SEQ ID NO:2690), TTGGGTTGCGTTAGAGTAGGCGGGAGG (SEQ ID NO:2691) |
| Target283 | chr2:166650529-166651284 | TGGGTTAGGCGTTAGGTGTAGGTGGCG (SEQ ID NO:2692), TTCGGGTTAAGTTTGGTTGTCGCGCGG (SEQ ID NO:2693), TCGGGTTTATTTGGCGGGTGGGTAGGGT (SEQ ID NO:2694), CGGGTTAAGTTTGGTTGTCGCGCGGTT (SEQ ID NO:2695), GGGTTAGGCGTTAGGTGTAGGTGGCGG (SEQ ID NO:2696), CGAGGAGGAAGGGAGGAATCGTGTGGG (SEQ ID NO:2697), TTGGAGCGTTTAGGTAGGGTTGGGGCG (SEQ ID NO:2698), GAGGAGGAAGGGAGGAATCGTGTGGGG (SEQ ID NO:2699), GAGGAAGGGAGGAATCGTGTGGGGGAA (SEQ ID NO:2700), CGGCGGCGGAGGAGGAGTTTTATTGAG (SEQ ID NO:2701) |
| Target284 | chr2:171679526-171679830 | TTGGAGAGGCGGGGGAAGATTAACGGG (SEQ ID NO:2702), TTTTCGGGTAGAGGTTGGAGAGGCGGG (SEQ ID NO:2703), GGTAGAGGTTGGAGAGGCGGGGGAAGA (SEQ ID NO:2704), GTAGAGGTTGGAGAGGCGGGGGAAGAT (SEQ ID NO:2705), CGTTAGTTTTTGCGCGCGGGAGATAGC (SEQ ID NO:2706), CGGCGCGGTTAAGTAGGGAAGGGAGTA (SEQ ID NO:2707), TTTTAGAAATGTAGGGAGGGCGCGGCG (SEQ ID NO:2708), CGGCGCGGTTAAGTAGGGAAGGGAGT (SEQ ID NO:2709), CGGCGCGGTTAAGTAGGGAAGGGAGTAG (SEQ ID NO:2710), GTTTTAGAAATGTAGGGAGGGCGCGGCG (SEQ ID NO:2711) |
| Target285 | chr2:171679840-171679912 | CGTTCGTTCGTTTTAGTTTCGGAGCGTG (SEQ ID NO:2712), CGTTCGTTCGTTTTAGTTTCGGAGCGT (SEQ ID NO:2713), TTCGTTCGTTTTAGTTTCGGAGCGTCG (SEQ ID NO:2714), CGAGGGCGGTGGTAGTTTGTAGTTAGA (SEQ ID NO:2715), GTTCGTTCGTTTTAGTTTCGGAGCGTCG (SEQ ID NO:2716), CGGCGCGGTTAAGTAGGGAAGGGAGTA (SEQ ID NO:2717), TTTTAGAAATGTAGGGAGGGCGCGGCG (SEQ ID NO:2718), GGCGGTAGGGTTGGGTTTTCGGTGGAA (SEQ ID NO:2719), TTCGGCGGTAGGGTTGGGTTTTCGGTG (SEQ ID NO:2720), GTTCGGCGGTAGGGTTGGGTTTTCGGT (SEQ ID NO:2721) |
| Target286 | chr2:171830684-171830708 | TGTGTATAAGTTCGGGGCGTCGGGGTG (SEQ ID NO:2722), TTGTGTATAAGTTCGGGGCGTCGGGGT (SEQ ID NO:2723), GGGCGGTTGGGTTTGGGTTTAGGTGTT (SEQ ID NO:2724), GTGTATAAGTTCGGGGCGTCGGGGTGG (SEQ ID NO:2725), GTTGTGTATAAGTTCGGGGCGTCGGGG (SEQ ID NO:2726) |
| Target287 | chr2:172965364-172965371 | GTGATGGTGGTGGTGGTGATGCGGTTG (SEQ ID NO:2727), TGCGGGGTTTGAGTGGGGTGTAGTAGC (SEQ ID NO:2728), GGTTTGAGTGGGGTGTAGTAGCGGCGT (SEQ ID NO:2729), CGGGGTTTGAGTGGGGTGTAGTAGCGG (SEQ ID NO:2730), CGTCGTCGTGATGGTGGTGGTGGTGAT (SEQ ID NO:2731), CGGCGTCGGTAGTTCGGGTTTTAGTTCG (SEQ ID NO:2732), CGGCGTCGGTAGTTCGGGTTTTAGTTCGA (SEQ ID NO:2733), GGCGTCGGTAGTTCGGGTTTTAGTTCG (SEQ ID NO:2734), CGGCGTCGGTAGTTCGGGTTTTAGTTC (SEQ ID NO:2735), GGCGTCGGTAGTTCGGGTTTTAGTTCGA (SEQ ID NO:2736) |
| Target288 | chr2:172965397-172965521 | GTGATGGTGGTGGTGGTGATGCGGTTG (SEQ ID NO:2737), TGCGGGGTTTGAGTGGGGTGTAGTAGC (SEQ ID NO:2738), GGTTTGAGTGGGGTGTAGTAGCGGCGT (SEQ ID NO:2739), CGGGGTTTGAGTGGGGTGTAGTAGCGG (SEQ ID NO:2740), CGTCGTGGTTTGTAGGTGTGAGGCGGA (SEQ ID NO:2741), CGGCGTCGGTAGTTCGGGTTTTAGTTCG (SEQ ID NO:2742), TGGGATTTTGGTGTGTCGTAGCGGATGG (SEQ ID NO:2743), GGGATTTTGGTGTGTCGTAGCGGATGG (SEQ ID NO:2744), CGGCGTCGGTAGTTCGGGTTTTAGTTCGA (SEQ ID NO:2745), GGCGTCGGTAGTTCGGGTTTTAGTTCG (SEQ ID NO:2746) |
| Target289 | chr2:172965544-172965563 | TTTTAGGAGGTCGGCGTTGAGATTGGC (SEQ ID NO:2747), GTTTTAGGAGGTCGGCGTTGAGATTGGC (SEQ ID NO:2748), AGTTTTAGGAGGTCGGCGTTGAGATTGGC (SEQ ID NO:2749), TTTAGGAGGTCGGCGTTGAGATTGGC (SEQ ID NO:2750), GTTTTAGGAGGTCGGCGTTGAGATTGG (SEQ ID NO:2751), TGGTGAGATTTTTTCGGAGTAGTATTTTGGGGT (SEQ ID NO:2752), GTGGTGAGATTTTTTCGGAGTAGTATTTTGGGGT (SEQ ID NO:2753), AGTGGTGAGATTTTTTCGGAGTAGTATTTTGGGG (SEQ ID NO:2754), AGTGGTGAGATTTTTTCGGAGTAGTATTTTGGGGT (SEQ ID NO:2755), AGATTTTTTCGGAGTAGTATTTTGGGGTTAGCGT (SEQ ID NO:2756) |
| Target290 | chr2:175201775-175201998 | TTCGGGTTGCGGTAAGGTGTACGGGAA (SEQ ID NO:2757), TTTCGGGTTGCGGTAAGGTGTACGGGA (SEQ ID NO:2758), ATTTCGGGTTGCGGTAAGGTGTACGGG (SEQ ID NO:2759), TTTCGGGTTGCGGTAAGGTGTACGGGAA (SEQ ID NO:2760), ATTTCGGGTTGCGGTAAGGTGTACGGGA (SEQ ID NO:2761), GGGGCGTTTTTAGGTTGTTGGCGTTCG (SEQ ID NO:2762), CGGGGCGTTTTTAGGTTGTTGGCGTTC (SEQ ID NO:2763), GGGCGTTTTTAGGTTGTTGGCGTTCGTG |

FIGURE 5 CONTINUED

{SEQ ID NO:2764}, GGGTCGTTCGTTCGTGTGTTAGCGTAGG {SEQ ID NO:2765},
CGGGGCGTTTTTAGGTTGTTGGCGTTCG {SEQ ID NO:2766}

| Target291 | chr2:175202051-175202065 | GTTCGGACGAGTTGTAGCGGTATTTGC {SEQ ID NO:2767}, AGCGTTTCGTTTGTTCGGTGTGTAATAAGC {SEQ ID NO:2768}, GGGGCGTTTTTAGGTTGTTGGCGTTCG {SEQ ID NO:2769}, CGGGGCGTTTTTAGGTTGTTGGCGTTC {SEQ ID NO:2770}, GGGCGTTTTTAGGTTGTTGGCGTTCGT {SEQ ID NO:2771}, GGGGCGTTTTTAGGTTGTTGGCGTTCGT {SEQ ID NO:2772}, TGTAGGATGAGGTCGGGGGATTCGGAA {SEQ ID NO:2773} |
| Target292 | chr2:175202067-175202376 | GGAGGCGGGAGGGTAGGGGTTTTAGTG {SEQ ID NO:2774}, GGCGGGAGGGTAGGGGTTTTAGTGACG {SEQ ID NO:2775}, TGATTTCGGCGTTAGTGTCGTTCGGGC {SEQ ID NO:2776}, GCGGCGGGGGTAAAAAGGGTAGCGATA {SEQ ID NO:2777}, TATAACGGGGGCGGCGGGGGTAAAAAG {SEQ ID NO:2778}, TTTATTCGGGCGCGGAAGGTAGAGGGG {SEQ ID NO:2779}, GCGTTTAGTTCGGGTTTTGGGGGCGTT {SEQ ID NO:2780}, GGGCGCGGAAGGTAGAGGGGAGTTTTT {SEQ ID NO:2781}, GCGCGGAAGGTAGAGGGGAGTTTTTCG {SEQ ID NO:2782}, GGGGCGTTTTTAGGTTGTTGGCGTTCG {SEQ ID NO:2783} |
| Target293 | chr2:175202388-175202400 | GGAGGCGGGAGGGTAGGGGTTTTAGTG {SEQ ID NO:2784}, GGCGGGAGGGTAGGGGTTTTAGTGACG {SEQ ID NO:2785}, GCGGGAGGGTAGGGGTTTTAGTGACGT {SEQ ID NO:2786}, GACGTTTTTAGGGTTCGGGTTGGGCGC {SEQ ID NO:2787}, TGACGTTTTTAGGGTTCGGGTTGGGCG {SEQ ID NO:2788}, TTTATTCGGGCGCGGAAGGTAGAGGGG {SEQ ID NO:2789}, GGGCGCGGAAGGTAGAGGGGAGTTTTT {SEQ ID NO:2790}, GCGCGGAAGGTAGAGGGGAGTTTTTCG {SEQ ID NO:2791}, TTATTCGGGCGCGGAAGGTAGAGGGGA {SEQ ID NO:2792}, GGCGCGGAAGGTAGAGGGGAGTTTTTC {SEQ ID NO:2793} |
| Target294 | chr2:175202430-175202523 | GGAGGCGGGAGGGTAGGGGTTTTAGTG {SEQ ID NO:2794}, GGCGGGAGGGTAGGGGTTTTAGTGACG {SEQ ID NO:2795}, GCGGGAGGGTAGGGGTTTTAGTGACGT {SEQ ID NO:2796}, GGGTTTTCGGGTTGCGGTTCGTTCGTT {SEQ ID NO:2797}, GACGTTTTTAGGGTTCGGGTTGGGCGC {SEQ ID NO:2798}, TTTATTCGGGCGCGGAAGGTAGAGGGG {SEQ ID NO:2799}, GGGCGCGGAAGGTAGAGGGGAGTTTTT {SEQ ID NO:2800}, AGTTTGGGCGAGTGGTATGTGTGTGCG {SEQ ID NO:2801}, GCGCGGAAGGTAGAGGGGAGTTTTTCG {SEQ ID NO:2802}, TTATTCGGGCGCGGAAGGTAGAGGGGA {SEQ ID NO:2803} |
| Target295 | chr2:176945119-176945216 | GTAGGGTGTAGAGTCGTCGTTGGGGGGG {SEQ ID NO:2804}, TAGGGTGTAGAGTCGTCGTTGGGGGGC {SEQ ID NO:2805}, AGTAGGGTGTAGAGTCGTCGTTGGGGG {SEQ ID NO:2806}, AGTAGGGTGTAGAGTCGTCGTTGGGGGG {SEQ ID NO:2807}, GAGTAGGGTGTAGAGTCGTCGTTGGGGG {SEQ ID NO:2808}, TCGGTCGGAGTTGTTGTGTAGTTTTCGT {SEQ ID NO:2809}, CGGTCGGAGTTGTTGTGTAGTTTTCGTT {SEQ ID NO:2810}, TCGGTCGGAGTTGTTGTGTAGTTTTCGTT {SEQ ID NO:2811}, TTCGGTCGGAGTTGTTGTGTAGTTTTCGT {SEQ ID NO:2812}, TTTCGGTCGGAGTTGTTGTGTAGTTTTCG {SEQ ID NO:2813} |
| Target296 | chr2:176945218-176945225 | GTAGGGTGTAGAGTCGTCGTTGGGGGGG {SEQ ID NO:2814}, TAGGGTGTAGAGTCGTCGTTGGGGGGC {SEQ ID NO:2815}, AGTAGGGTGTAGAGTCGTCGTTGGGGG {SEQ ID NO:2816}, AGTAGGGTGTAGAGTCGTCGTTGGGGGG {SEQ ID NO:2817}, GAGTAGGGTGTAGAGTCGTCGTTGGGGG {SEQ ID NO:2818}, TCGGTCGGAGTTGTTGTGTAGTTTTCGT {SEQ ID NO:2819}, CGGTCGGAGTTGTTGTGTAGTTTTCGTT {SEQ ID NO:2820}, TCGGTCGGAGTTGTTGTGTAGTTTTCGTT {SEQ ID NO:2821}, TTCGGTCGGAGTTGTTGTGTAGTTTTCGT {SEQ ID NO:2822}, TTTCGGTCGGAGTTGTTGTGTAGTTTTCG {SEQ ID NO:2823} |
| Target297 | chr2:176945270-176945337 | GCGCGGAAGGTGTTTAGTGGTCGGATG {SEQ ID NO:2824}, AGAGGGCGCGGAAGGTGTTTAGTGGTC {SEQ ID NO:2825}, GAGAGGGCGCGGAAGGTGTTTAGTGGT {SEQ ID NO:2826}, CGCGGAAGGTGTTTAGTGGTCGGATGG {SEQ ID NO:2827}, TTCGGTCGAGAGTAGGGGTGCGAGAGG {SEQ ID NO:2828}, CGGTTGTAGTTTTAGGCGCGGCGGTC {SEQ ID NO:2829}, CGGTTGTAGTTTTAGGCGCGGCGGT {SEQ ID NO:2830}, GCGGTTGTAGTTTTAGGCGCGGCGGTC {SEQ ID NO:2831}, GCGGTTGTAGTTTTAGGCGCGGCGG {SEQ ID NO:2832}, GCGGTTGTAGTTTTAGGCGCGGCGGT {SEQ ID NO:2833} |
| Target298 | chr2:176945339-176945352 | GCGCGGAAGGTGTTTAGTGGTCGGATG {SEQ ID NO:2834}, AGAGGGCGCGGAAGGTGTTTAGTGGTC {SEQ ID NO:2835}, GAGAGGGCGCGGAAGGTGTTTAGTGGT {SEQ ID NO:2836}, CGCGGAAGGTGTTTAGTGGTCGGATGG {SEQ ID NO:2837}, TTCGGTCGAGAGTAGGGGTGCGAGAGG {SEQ ID NO:2838}, CGGTTGTAGTTTTAGGCGCGGCGGTC {SEQ ID NO:2839}, CGGTTGTAGTTTTAGGCGCGGCGGT {SEQ ID NO:2840}, GCGGTTGTAGTTTTAGGCGCGGCGGTC {SEQ ID NO:2841}, GCGGTTGTAGTTTTAGGCGCGGCGG {SEQ ID NO:2842}, GCGGTTGTAGTTTTAGGCGCGGCGGT {SEQ ID NO:2843} |
| Target299 | chr2:176945372-176945459 | AAGGGGTAGGGTAGGTTTTCGGTGGCG {SEQ ID NO:2844}, GCGCGGAAGGTGTTTAGTGGTCGGATG {SEQ ID NO:2845}, AGAGGGCGCGGAAGGTGTTTAGTGGTC {SEQ ID NO:2846}, GAGAGGGCGCGGAAGGTGTTTAGTGGT {SEQ ID NO:2847}, CGGTCGTCGCGTTTGAGGTTGTAGTCG {SEQ ID NO:2848}, TCGTAGGTGTGGTTTTAGAATCGGCGT {SEQ ID NO:2849}, GCGGTAGCGTTTGGTTATGTTTTGGTCG {SEQ ID NO:2850}, GCGGTAGCGTTTGGTTATGTTTTGGTCGT {SEQ ID NO:2851}, TTCGTAGGTGTGGTTTTAGAATCGGCGT {SEQ ID NO:2852}, CGGTAGCGTTTGGTTATGTTTTGGTCGT {SEQ ID NO:2853} |

FIGURE 5 CONTINUED

| | | |
|---|---|---|
| Target300 | chr2:176945462-176945469 | AAGGGGTAGGGTAGGTTTTCGGTGGCG (SEQ ID NO:2854), CGGTCGTCGCGTTTGAGGTTGTAGTCG (SEQ ID NO:2855), GGGTAGGGTAGGTTTTCGGTGGCGGTC (SEQ ID NO:2856), GGTAGGGTAGGTTTTCGGTGGCGGTCG (SEQ ID NO:2857), GTGCGAGTGGAAGGGGTAGGGTAGGTT (SEQ ID NO:2858), TCGTAGGTGTGGTTTTAGAATCGGCGT (SEQ ID NO:2859), GCGGTAGCGTTTGGTTATGTTTTGGTCG (SEQ ID NO:2860), GCGGTAGCGTTTGGTTATGTTTTGGTCGT (SEQ ID NO:2861), TTCGTAGGTGTGGTTTTAGAATCGGCGT (SEQ ID NO:2862), CGGTAGCGTTTGGTTATGTTTTGGTCGT (SEQ ID NO:2863) |
| Target301 | chr2:176945532-176945551 | AAGGGGTAGGGTAGGTTTTCGGTGGCG (SEQ ID NO:2864), GGGGTCGGTTGGGTGCGGTTAGGATAT (SEQ ID NO:2865), GGGTAGGGTAGGTTTTCGGTGGCGGTC (SEQ ID NO:2866), TGTAGAAGTTGGGGTCGGTTGGGTGCG (SEQ ID NO:2867), GGTAGGGTAGGTTTTCGGTGGCGGTCG (SEQ ID NO:2868), TGGGATAGGAGTTGGGAATACGGGGCG (SEQ ID NO:2869), TTGGGATAGGAGTTGGGAATACGGGGCG (SEQ ID NO:2870), AGGTTCGGAAGGGGTAGAGGTTTTGGG (SEQ ID NO:2871), GGTTCGGAAGGGGTAGAGGTTTTGGGA (SEQ ID NO:2872), TTGGGATAGGAGTTGGGAATACGGGGC (SEQ ID NO:2873) |
| Target302 | chr2:176945604-176945648 | GGGGTCGGTTGGGTGCGGTTAGGATAT (SEQ ID NO:2874), TGTAGAAGTTGGGGTCGGTTGGGTGCG (SEQ ID NO:2875), GTGTAGAAGTTGGGGTCGGTTGGGTGC (SEQ ID NO:2876), GAAGTTGGGGTCGGTTGGGTGCGGTTA (SEQ ID NO:2877), AAGTTGGGGTCGGTTGGGTGCGGTTAG (SEQ ID NO:2878), GGGTATTCGGGGTTGGGTTTGGTCGGA (SEQ ID NO:2879), AGGGTATTCGGGGTTGGGTTTGGTCGG (SEQ ID NO:2880), GGTATTCGGGGTTGGGTTTGGTCGGAG (SEQ ID NO:2881), GGTATTCGGGGTTGGGTTTGGTCGGAGA (SEQ ID NO:2882), TAGGGTATTCGGGGTTGGGTTTGGTCGG (SEQ ID NO:2883) |
| Target303 | chr2:176947000-176947053 | GTGGTTTCGGGTAGGTTGAGTGTCGCG (SEQ ID NO:2884), GGTGGTTTCGGGTAGGTTGAGTGTCGC (SEQ ID NO:2885), TGAGTGTCGCGGTTAGTTCGTATCGGC (SEQ ID NO:2886), TGGTGGTTTCGGGTAGGTTGAGTGTCGC (SEQ ID NO:2887), CGGGTAGGTTGAGTGTCGCGGTTAGTT (SEQ ID NO:2888), GGGTGGTTTCGGTTTTGGCGCGGATTA (SEQ ID NO:2889), CGGCGTCGGGTTAGGTTTCGGAAGTT (SEQ ID NO:2890), GGGTGGTTTCGGTTTTGGCGCGGATTAA (SEQ ID NO:2891), GGTGGTTTCGGTTTTGGCGCGGATTAA (SEQ ID NO:2892), CGGCGTCGGGTTAGGTTTCGGAAGTTT (SEQ ID NO:2893) |
| Target304 | chr2:176947061-176947080 | GCGGTTAGTTCGTATCGGCGGGGTC (SEQ ID NO:2894), GCGTTAGAGTCGGAGTTATTTAGCGTCGCG (SEQ ID NO:2895), GCGGTTAGTTCGTATCGGCGGGGT (SEQ ID NO:2896), GCGTTAGAGTCGGAGTTATTTAGCGTCGC (SEQ ID NO:2897), CGTTAGAGTCGGAGTTATTTAGCGTCGCG (SEQ ID NO:2898), CGGCGTCGGGTTAGGTTTCGGAAGTT (SEQ ID NO:2899), CGGCGTCGGGTTAGGTTTCGGAAGTTT (SEQ ID NO:2900), CGGCGTCGGGTTAGGTTTCGGAAGT (SEQ ID NO:2901), CGGCGTCGGGTTAGGTTTCGGAAGTTTG (SEQ ID NO:2902), GGCGTCGGGTTAGGTTTCGGAAGTTT (SEQ ID NO:2903) |
| Target305 | chr2:176947118-176947173 | AGAGTCGGAGTTATTTAGCGTCGCGTT (SEQ ID NO:2904), GCGTTAGAGTCGGAGTTATTTAGCGTCGCG (SEQ ID NO:2905), GCGTTAGAGTCGGAGTTATTTAGCGTCGCGT (SEQ ID NO:2906), AGAGTCGGAGTTATTTAGCGTCGCGTTT (SEQ ID NO:2907), GCGTTAGAGTCGGAGTTATTTAGCGTCGC (SEQ ID NO:2908), TGTTAGGGTACGTAGAGAGCGGTTCGG (SEQ ID NO:2909), TTGTTAGGGTACGTAGAGAGCGGTTCGG (SEQ ID NO:2910), TTGTTAGGGTACGTAGAGAGCGGTTCG (SEQ ID NO:2911), TGCGTTGTTGGTCGTTTGTTTGTTAGGGT (SEQ ID NO:2912), GCGTTGTTGGTCGTTTGTTTGTTAGGGT (SEQ ID NO:2913) |
| Target306 | chr2:176947242-176947252 | AGTGGTTGTAGGATTAATAGTTCGGCGTTGG (SEQ ID NO:2914), GGTAGTCGAGTCGTTTTTTGCGTATTTTGGT (SEQ ID NO:2915), GAGTGGTTGTAGGATTAATAGTTCGGCGTTGG (SEQ ID NO:2916), TGAGTGGTTGTAGGATTAATAGTTCGGCGTT (SEQ ID NO:2917), TGAGTGGTTGTAGGATTAATAGTTCGGCGTTGG (SEQ ID NO:2918) |
| Target307 | chr2:176956535-176956546 | CGGGCGGGAGTGGGTGGTGATTGTAAA (SEQ ID NO:2919), ATTTGGTGTGAGAAACGGGCGGGAGTG (SEQ ID NO:2920), TTTGGTGTGAGAAACGGGCGGGAGTGG (SEQ ID NO:2921), GGGCGGGAGTGGGTGGTGATTGTAAAA (SEQ ID NO:2922), AATTTGGTGTGAGAAACGGGCGGGAGT (SEQ ID NO:2923), CGGCGTCGGGGGAGAAAGTTATTTAGT (SEQ ID NO:2924), CGGCGTCGGGGGAGAAAGTTATTTAGTT (SEQ ID NO:2925), TCGATTTGGGTTTTTTAGTTTTCGCGGGT (SEQ ID NO:2926), TCGATTTGGGTTTTTTAGTTTTCGCGGGTT (SEQ ID NO:2927), TTCGATTTGGGTTTTTTAGTTTTCGCGGGT (SEQ ID NO:2928) |
| Target308 | chr2:176956573-176956707 | CGCGGGAGTTGAGAGGTTTAGGTCGGA (SEQ ID NO:2929), TCGCGGGAGTTGAGAGGTTTAGGTCGG (SEQ ID NO:2930), CGGGCGGGAGTGGGTGGTGATTGTAAA (SEQ ID NO:2931), ATTTGGTGTGAGAAACGGGCGGGAGTG (SEQ ID NO:2932), TTTGGTGTGAGAAACGGGCGGGAGTGG (SEQ ID NO:2933), TGAAGCGTTTTTGGGGTTGGCGGTAGA (SEQ ID NO:2934), AAGCGTTTTTGGGGTTGGCGGTAGAGA (SEQ ID NO:2935), AGCGTTTTTGGGGTTGGCGGTAGAGAT (SEQ ID NO:2936), TGAAGCGTTTTTGGGGTTGGCGGTAGAG (SEQ ID NO:2937), GAAGCGTTTTTGGGGTTGGCGGTAGAG (SEQ ID NO:2938) |
| Target309 | chr2:176964663-176964673 | AGAGCGGGTTATGTGGGTTCGTTTTTG (SEQ ID NO:2939), GAGCGGGTTATGTGGGTTCGTTTTTGA (SEQ ID NO:2940), AGAGCGGGTTATGTGGGTTCGTTTTTGA (SEQ ID NO:2941), GAGCGGGTTATGTGGGTTCGTTTTTGAA (SEQ ID NO:2942), AGAGCGGGTTATGTGGGTTCGTTTTTGAA (SEQ ID NO:2943), GTTGTTGGGGGGTTGTAGGTCGAGAGGT (SEQ ID NO:2944), TGTTGGGGGGTTGTAGGTCGAGAGGTTC (SEQ ID NO:2945), TTGTTGGGGGGTTGTAGGTCGAGAGGTT |

FIGURE 5 CONTINUED

{SEQ ID NO:2946}, GTTGTTGGGGGTTGTAGGTCGAGAGGTT {SEQ ID NO:2947},
GAGAAGTCGTCGAAGGTAGTGGCGTTC {SEQ ID NO:2948}

Target310    chr2:176964709-176964740    GCGCGTTGTTTGGGTCGTTACGTTCG {SEQ ID NO:2949}, GGCGCGTTGTTTGGGTCGTTACGTTC {SEQ ID NO:2950}, CGCGTTGTTTGGGTCGTTACGTTCGT {SEQ ID NO:2951}, GCGCGTTGTTTGGGTCGTTACGTTCGT {SEQ ID NO:2952}, GGCGCGTTGTTTGGGTCGTTACGTTCG {SEQ ID NO:2953}, TTTTGGTTTAGCGGTCGTTTCGGGCGT {SEQ ID NO:2954}, TTTGGTTTAGCGGTCGTTTCGGGCGTA {SEQ ID NO:2955}, TTGGTTTAGCGGTCGTTTCGGGCGTAT {SEQ ID NO:2956}, GAAGGTAGTGGCGTTCGTAGGTTGCGT {SEQ ID NO:2957}, TTTTTGGTTTAGCGGTCGTTTCGGGCG {SEQ ID NO:2958}

Target311    chr2:176964769-176964806    GCGCGTTGTTTGGGTCGTTACGTTCG {SEQ ID NO:2959}, GGCGCGTTGTTTGGGTCGTTACGTTC {SEQ ID NO:2960}, CGCGTTGTTTGGGTCGTTACGTTCGT {SEQ ID NO:2961}, GCGCGTTGTTTGGGTCGTTACGTTCGT {SEQ ID NO:2962}, GGCGCGTTGTTTGGGTCGTTACGTTCG {SEQ ID NO:2963}, TTTTGGTTTAGCGGTCGTTTCGGGCGT {SEQ ID NO:2964}, TTTGGTTTAGCGGTCGTTTCGGGCGTA {SEQ ID NO:2965}, TTGGTTTAGCGGTCGTTTCGGGCGTAT {SEQ ID NO:2966}, TTTTTGGTTTAGCGGTCGTTTCGGGCG {SEQ ID NO:2967}, TTTTTGGTTTAGCGGTCGTTTCGGGCGT {SEQ ID NO:2968}

Target312    chr2:176964811-176964887    GGTCGTTGGGTTAGAGGAGCGCGGTC {SEQ ID NO:2969}, GGTCGTTGGGTTAGAGGAGCGCGGT {SEQ ID NO:2970}, GTCGTTGGGTTAGAGGAGCGCGGTC {SEQ ID NO:2971}, GCGTAGTTTGCGGGCGTTATTGTTTTCG {SEQ ID NO:2972}, GCGTAGTTTGCGGGCGTTATTGTTTTCG {SEQ ID NO:2973}, TTTTGGTTTAGCGGTCGTTTCGGGCGT {SEQ ID NO:2974}, TTTGGTTTAGCGGTCGTTTCGGGCGTA {SEQ ID NO:2975}, TTGGTTTAGCGGTCGTTTCGGGCGTAT {SEQ ID NO:2976}, TTTTTGGTTTAGCGGTCGTTTCGGGCG {SEQ ID NO:2977}, TTTTTGGTTTAGCGGTCGTTTCGGGCGT {SEQ ID NO:2978}

Target313    chr2:176964946-176964970    GGTCGTTGGGTTAGAGGAGCGCGGTC {SEQ ID NO:2979}, GGTCGTTGGGTTAGAGGAGCGCGGT {SEQ ID NO:2980}, GTCGTTGGGTTAGAGGAGCGCGGTC {SEQ ID NO:2981}, GGTCGTTGGGTTAGAGGAGCGCGG {SEQ ID NO:2982}, GTCGTTGGGTTAGAGGAGCGCGGT {SEQ ID NO:2983}, TTTTGGAGTAGGGTCGTGGAGTTCGGC {SEQ ID NO:2984}, TTTTTGGAGTAGGGTCGTGGAGTTCGGC {SEQ ID NO:2985}, GGGGCGTAGGGAGTTTTTTGGAGTAGGGT {SEQ ID NO:2986}, GGGGCGTAGGGAGTTTTTTGGAGTAGGG {SEQ ID NO:2987}, AGGGGCGTAGGGAGTTTTTTGGAGTAGGG {SEQ ID NO:2988}

Target314    chr2:176965003-176965036    GGGGGTTTTTTGCGTTTTTGGTTTTAAGGACG {SEQ ID NO:2989}, AGGGGGTTTTTTGCGTTTTTGGTTTTAAGGACG {SEQ ID NO:2990}, GGGGGTTTTTTGCGTTTTTGGTTTTAAGGACGA {SEQ ID NO:2991}, AGGGGGTTTTTTGCGTTTTTGGTTTTAAGGA {SEQ ID NO:2992}, GGGGTTTTTTGCGTTTTTGGTTTTAAGGACG {SEQ ID NO:2993}, TCGGTTCGGGGAGTATGGGTATCGTTT {SEQ ID NO:2994}, ATCGGTTCGGGGAGTATGGGTATCGTT {SEQ ID NO:2995}, AATCGGTTCGGGGAGTATGGGTATCGT {SEQ ID NO:2996}, TCGTCGGGTAGTGAAGGTCGTAGGTAA {SEQ ID NO:2997}, AGTTGAGCGGGTTTTTGGTGTCGTTTT {SEQ ID NO:2998}

Target315    chr2:176969353-176969393    TGGTTGCGTTTCGAAGGTTTGGTGCGT {SEQ ID NO:2999}, GCGGTTGGTTGCGTTTCGAAGGTTTGG {SEQ ID NO:3000}, GGTTGCGTTTCGAAGGTTTGGTGCGTT {SEQ ID NO:3001}, TTGGTTGCGTTTCGAAGGTTTGGTGCG {SEQ ID NO:3002}, TGGTTGCGTTTCGAAGGTTTGGTGCGTT {SEQ ID NO:3003}

Target316    chr2:176969516-176969530    GGGGGGGTAAGGGTTCGCGTTAAGGAGT {SEQ ID NO:3004}, AAGCGTTTTGGGTTGTGGAGTGGGTCG {SEQ ID NO:3005}, CGGGGGGGTAAGGGTTCGCGTTAAGGAG {SEQ ID NO:3006}, AGCGGGTTGGGATTGGAATGAAAGCGT {SEQ ID NO:3007}, CGGGGGGGTAAGGGGTTCGCGTTAAGGA {SEQ ID NO:3008}, ATAGGGGAAGGGGGCGGTCGGTTTTTT {SEQ ID NO:3009}, TTGTAGTGGCGCGTCGGTGTATAGGGG {SEQ ID NO:3010}, GTATAGGGGAAGGGGGCGGTCGGTTTT {SEQ ID NO:3011}, GTAGTGGCGCGTCGGTGTATAGGGGAA {SEQ ID NO:3012}, TAGTGGCGCGTCGGTGTATAGGGGAAG {SEQ ID NO:3013}

Target317    chr2:176969563-176969569    GGGGGGGTAAGGGTTCGCGTTAAGGAGT {SEQ ID NO:3014}, AAGCGTTTTGGGTTGTGGAGTGGGTCG {SEQ ID NO:3015}, CGGGGGGGTAAGGGTTCGCGTTAAGGAG {SEQ ID NO:3016}, AGCGGGTTGGGATTGGAATGAAAGCGT {SEQ ID NO:3017}, CGGGGGGGTAAGGGGTTCGCGTTAAGGA {SEQ ID NO:3018}, GCGATTTGGCGGGGGAGGGTGAGTTAT {SEQ ID NO:3019}, CGATTTGGCGGGGGAGGGTGAGTTATT {SEQ ID NO:3020}, GCGATTTGGCGGGGGAGGGTGAGTTA {SEQ ID NO:3021}, GCGATTTGGCGGGGGAGGGTGAGTTATT {SEQ ID NO:3022}, TTTGGCGGGGGAGGGTGAGTTATTTGT {SEQ ID NO:3023}

Target318    chr2:176969603-176969616    GGGGGGGTAAGGGTTCGCGTTAAGGAGT {SEQ ID NO:3024}, CGGGGGGGTAAGGGTTCGCGTTAAGGAG {SEQ ID NO:3025}, CGGGGGGGTAAGGGTTCGCGTTAAGGA {SEQ ID NO:3026}, GGGGGGGTAAGGGTTCGCGTTAAGGAGTC {SEQ ID NO:3027}, CGTTTTGGGTTGTGGAGTGGGTCGGG {SEQ ID NO:3028}, GGGTGGGGTGTAGGTAGTTCGGCGTTT {SEQ ID NO:3029}, GTACGGGGTGGGGTGTAGGTAGTTCGG {SEQ ID NO:3030}, GGTACGGGGTGGGGTGTAGGTAGTTCG {SEQ ID NO:3031}, TACGGGGTGGGGTGTAGGTAGTTCGGC {SEQ ID NO:3032}, GGGTGGGGTGTAGGTAGTTCGGCGTT {SEQ ID NO:3033}

FIGURE 5 CONTINUED

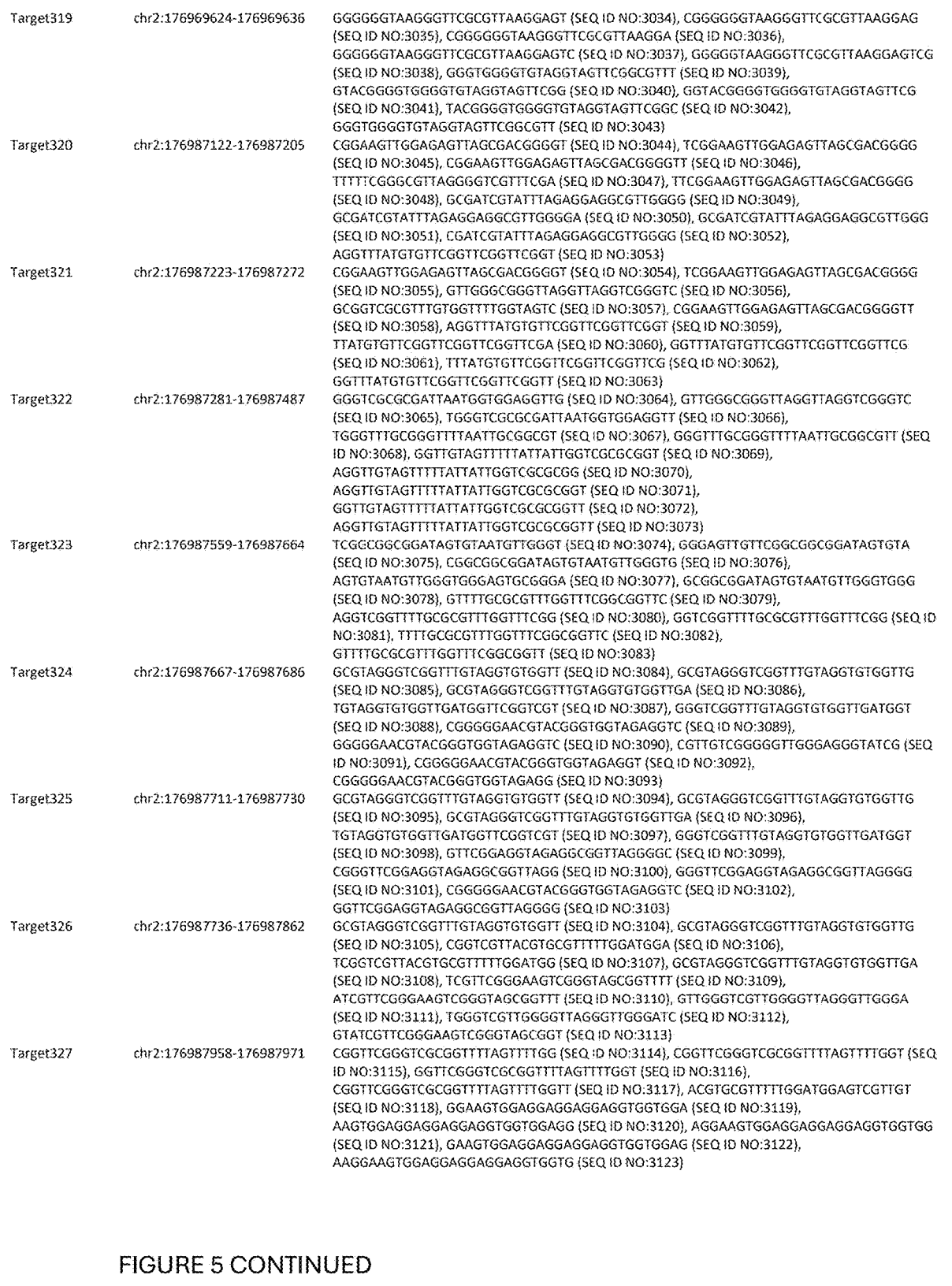

| | | |
|---|---|---|
| Target319 | chr2:176969624-176969636 | GGGGGGTAAGGGTTCGCGTTAAGGAGT (SEQ ID NO:3034), CGGGGGGTAAGGGTTCGCGTTAAGGAG (SEQ ID NO:3035), CGGGGGGTAAGGGTTCGCGTTAAGGA (SEQ ID NO:3036), GGGGGGTAAGGGTTCGCGTTAAGGAGTC (SEQ ID NO:3037), GGGGGTAAGGGTTCGCGTTAAGGAGTCG (SEQ ID NO:3038), GGGTGGGGTGTAGGGTAGTTCGGCGTTT (SEQ ID NO:3039), GTACGGGGTGGGGTGTAGGGTAGTTCGG (SEQ ID NO:3040), GGTACGGGGTGGGGTGTAGGGTAGTTCG (SEQ ID NO:3041), TACGGGGTGGGGTGTAGGGTAGTTCGGC (SEQ ID NO:3042), GGGTGGGGTGTAGGGTAGTTCGGCGTT (SEQ ID NO:3043) |
| Target320 | chr2:176987122-176987205 | CGGAAGTTGGAGAGTTAGCGACGGGGT (SEQ ID NO:3044), TCGGAAGTTGGAGAGTTAGCGACGGGG (SEQ ID NO:3045), CGGAAGTTGGAGAGTTAGCGACGGGGTT (SEQ ID NO:3046), TTTTTCGGGCGTTAGGGGTCGTTTCGA (SEQ ID NO:3047), TTCGGAAGTTGGAGAGTTAGCGACGGGG (SEQ ID NO:3048), GCGATCGTATTTAGAGGAGGCGTTGGGG (SEQ ID NO:3049), GCGATCGTATTTAGAGGAGGCGTTGGGGA (SEQ ID NO:3050), GCGATCGTATTTAGAGGAGGCGTTGGG (SEQ ID NO:3051), CGATCGTATTTAGAGGAGGCGTTGGGG (SEQ ID NO:3052), AGGTTTATGTGTTCGGTTCGGTTCGGT (SEQ ID NO:3053) |
| Target321 | chr2:176987223-176987272 | CGGAAGTTGGAGAGTTAGCGACGGGGT (SEQ ID NO:3054), TCGGAAGTTGGAGAGTTAGCGACGGGG (SEQ ID NO:3055), GTTGGGCGGGTTAGGTTAGGTCGGGTC (SEQ ID NO:3056), GCGGTCGCGTTTGTGGTTTTGGTAGTC (SEQ ID NO:3057), CGGAAGTTGGAGAGTTAGCGACGGGGTT (SEQ ID NO:3058), AGGTTTATGTGTTCGGTTCGGTTCGGT (SEQ ID NO:3059), TTATGTGTTCGGTTCGGTTCGGTTCGA (SEQ ID NO:3060), GGTTTATGTGTTCGGTTCGGTTCGGTTCG (SEQ ID NO:3061), TTTATGTGTTCGGTTCGGTTCGGTTCG (SEQ ID NO:3062), GGTTTATGTGTTCGGTTCGGTTCGGTT (SEQ ID NO:3063) |
| Target322 | chr2:176987281-176987487 | GGGTCGCGCGATTAATGGTGGAGGTTG (SEQ ID NO:3064), GTTGGGCGGGTTAGGTTAGGTCGGGTC (SEQ ID NO:3065), TGGGTCGCGCGATTAATGGTGGAGGTT (SEQ ID NO:3066), TGGGTTTGCGGGTTTTAATTGCGGCGT (SEQ ID NO:3067), GGGTTTGCGGGTTTTAATTGCGGCGTT (SEQ ID NO:3068), GGTTGTAGTTTTTATTATTGGTCGCGCGGT (SEQ ID NO:3069), AGGTTGTAGTTTTTATTATTGGTCGCGCGG (SEQ ID NO:3070), AGGTTGTAGTTTTTATTATTGGTCGCGCGGT (SEQ ID NO:3071), GGTTGTAGTTTTTATTATTGGTCGCGCGGTT (SEQ ID NO:3072), AGGTTGTAGTTTTTATTATTGGTCGCGCGGTT (SEQ ID NO:3073) |
| Target323 | chr2:176987559-176987664 | TCGGCGGCGGATAGTGTAATGTTGGGT (SEQ ID NO:3074), GGGAGTTGTTCGGCGGCGGATAGTGTA (SEQ ID NO:3075), CGGCGGCGGATAGTGTAATGTTGGGTG (SEQ ID NO:3076), AGTGTAATGTTGGGTGGGAGTGCGGGA (SEQ ID NO:3077), GCGGCGGATAGTGTAATGTTGGGTGGG (SEQ ID NO:3078), GTTTTGCGCGTTTGGTTTCGGCGGTTC (SEQ ID NO:3079), AGGTCGGTTTTGCGCGTTTGGTTTCGG (SEQ ID NO:3080), GGTCGGTTTTGCGCGTTTGGTTTCGG (SEQ ID NO:3081), TTTTGCGCGTTTGGTTTCGGCGGTTC (SEQ ID NO:3082), GTTTTGCGCGTTTGGTTTCGGCGGTT (SEQ ID NO:3083) |
| Target324 | chr2:176987667-176987686 | GCGTAGGGTCGGTTTGTAGGTGTGGTT (SEQ ID NO:3084), GCGTAGGGTCGGTTTGTAGGTGTGGTTG (SEQ ID NO:3085), GCGTAGGGTCGGTTTGTAGGTGTGGTTGA (SEQ ID NO:3086), TGTAGGTGTGGTTGATGGTTCGGTCGT (SEQ ID NO:3087), GGGTCGGTTTGTAGGTGTGGTTGATGGT (SEQ ID NO:3088), CGGGGGAACGTACGGGTGGTAGAGGTC (SEQ ID NO:3089), GGGGGGAACGTACGGGTGGTAGAGGTC (SEQ ID NO:3090), CGTTGTCGGGGGTTGGGAGGGTATCG (SEQ ID NO:3091), CGGGGGGAACGTACGGGTGGTAGAGGT (SEQ ID NO:3092), CGGGGGAACGTACGGGTGGTAGAGG (SEQ ID NO:3093) |
| Target325 | chr2:176987711-176987730 | GCGTAGGGTCGGTTTGTAGGTGTGGTT (SEQ ID NO:3094), GCGTAGGGTCGGTTTGTAGGTGTGGTTG (SEQ ID NO:3095), GCGTAGGGTCGGTTTGTAGGTGTGGTTGA (SEQ ID NO:3096), TGTAGGTGTGGTTGATGGTTCGGTCGT (SEQ ID NO:3097), GGGTCGGTTTGTAGGTGTGGTTGATGGT (SEQ ID NO:3098), GTTCGGAGGTAGAGGCGGTTAGGGGC (SEQ ID NO:3099), CGGGTTCGGAGGTAGAGGCGGTTAGG (SEQ ID NO:3100), GGGTTCGGAGGTAGAGGCGGTTAGGGG (SEQ ID NO:3101), CGGGGGAACGTACGGGTGGTAGAGGTC (SEQ ID NO:3102), GGTTCGGAGGTAGAGGCGGTTAGGGG (SEQ ID NO:3103) |
| Target326 | chr2:176987736-176987862 | GCGTAGGGTCGGTTTGTAGGTGTGGTT (SEQ ID NO:3104), GCGTAGGGTCGGTTTGTAGGTGTGGTTG (SEQ ID NO:3105), CGGTCGTTACGTGCGTTTTTGGATGG (SEQ ID NO:3106), TCGGTCGTTACGTGCGTTTTTGGATGG (SEQ ID NO:3107), GCGTAGGGTCGGTTTGTAGGTGTGGTTGA (SEQ ID NO:3108), TCGTTCGGGAAGTCGGGTAGCGGTTTT (SEQ ID NO:3109), ATCGTTCGGGAAGTCGGGTAGCGGTTT (SEQ ID NO:3110), GTTGGGTCGTTGGGGTTAGGGTTGGGA (SEQ ID NO:3111), TGGGTCGTTGGGGTTAGGGTTGGGATC (SEQ ID NO:3112), GTATCGTTCGGGAAGTCGGGTAGCGGT (SEQ ID NO:3113) |
| Target327 | chr2:176987958-176987971 | CGGTTCGGGTCGCGGTTTTAGTTTTGG (SEQ ID NO:3114), CGGTTCGGGTCGCGGTTTTAGTTTTGGT (SEQ ID NO:3115), GGTTCGGGTCGCGGTTTTAGTTTTGGT (SEQ ID NO:3116), CGGTTCGGGTCGCGGTTTTAGTTTTGGTT (SEQ ID NO:3117), ACGTGCGTTTTTGGATGGAGTCGTTGT (SEQ ID NO:3118), GGAAGTGGAGGAGGAGGAGGTGGTGGA (SEQ ID NO:3119), AAGTGGAGGAGGAGGAGGTGGTGGAGG (SEQ ID NO:3120), AGGAAGTGGAGGAGGAGGAGGTGGTGG (SEQ ID NO:3121), GAAGTGGAGGAGGAGGAGGTGGTGGAG (SEQ ID NO:3122), AAGGAAGTGGAGGAGGAGGAGGTGGTG (SEQ ID NO:3123) |

FIGURE 5 CONTINUED

| | | |
|---|---|---|
| Target328 | chr2:176988078-176988129 | GGTTCGGGAGTTTTAGGGGAGTAGCGGT (SEQ ID NO:3124), TGGTTCGGGAGTTTTAGGGGAGTAGCGG (SEQ ID NO:3125), GGTTCGGGAGTTTTAGGGGAGTAGCGG (SEQ ID NO:3126), GTGGTTCGGGAGTTTTAGGGGAGTAGCGG (SEQ ID NO:3127), GTTCGGGAGTTTTAGGGGAGTAGCGGT (SEQ ID NO:3128), TCGGGTGGTCGTTGTAAGTTGAGGGTT (SEQ ID NO:3129), GGGATCGGGTGGTCGTTGTAAGTTGAGGG (SEQ ID NO:3130), ATCGGGTGGTCGTTGTAAGTTGAGGGT (SEQ ID NO:3131), TGGGATCGGGTGGTCGTTGTAAGTTGA (SEQ ID NO:3132), GGATCGGGTGGTCGTTGTAAGTTGAGGG (SEQ ID NO:3133) |
| Target329 | chr2:176988152-176988159 | GGTTCGGGAGTTTTAGGGGAGTAGCGGT (SEQ ID NO:3134), TGGTTCGGGAGTTTTAGGGGAGTAGCGG (SEQ ID NO:3135), GGTTCGGGAGTTTTAGGGGAGTAGCGG (SEQ ID NO:3136), GTGGTTCGGGAGTTTTAGGGGAGTAGCGG (SEQ ID NO:3137), GTTCGGGAGTTTTAGGGGAGTAGCGG (SEQ ID NO:3138), TCGGGTGGTCGTTGTAAGTTGAGGGTT (SEQ ID NO:3139), GGGATCGGGTGGTCGTTGTAAGTTGAGGG (SEQ ID NO:3140), ATCGGGTGGTCGTTGTAAGTTGAGGGT (SEQ ID NO:3141), TGGGATCGGGTGGTCGTTGTAAGTTGA (SEQ ID NO:3142), GGATCGGGTGGTCGTTGTAAGTTGAGGG (SEQ ID NO:3143) |
| Target330 | chr2:176988168-176988204 | GGGGGAATCGGGTTTGGGGTAGGGATC (SEQ ID NO:3144), GAATCGGGTTTGGGGTAGGGATCGGGG (SEQ ID NO:3145), GGAATCGGGTTTGGGGTAGGGATCGGG (SEQ ID NO:3146), GGGAATCGGGTTTGGGGTAGGGATCGG (SEQ ID NO:3147), GGGGAATCGGGTTTGGGGTAGGGATCG (SEQ ID NO:3148), TCGGGTGGTCGTTGTAAGTTGAGGGTT (SEQ ID NO:3149), GGGATCGGGTGGTCGTTGTAAGTTGAGGG (SEQ ID NO:3150), ATCGGGTGGTCGTTGTAAGTTGAGGGT (SEQ ID NO:3151), TGGGATCGGGTGGTCGTTGTAAGTTGA (SEQ ID NO:3152), GGATCGGGTGGTCGTTGTAAGTTGAGGG (SEQ ID NO:3153) |
| Target331 | chr2:176988234-176988258 | GGGGGAATCGGGTTTGGGGTAGGGATC (SEQ ID NO:3154), GAATCGGGTTTGGGGTAGGGATCGGGG (SEQ ID NO:3155), GGAATCGGGTTTGGGGTAGGGATCGGG (SEQ ID NO:3156), GGGAATCGGGTTTGGGGTAGGGATCGG (SEQ ID NO:3157), GGGGAATCGGGTTTGGGGTAGGGATCG (SEQ ID NO:3158), ATTTATTTGGGTTAAGTTGTTGTTGTTGCGGTTG (SEQ ID NO:3159), TGTATTTATTTGGGTTAAGTTGTTGTTGTTGCGGT (SEQ ID NO:3160), TGTATTTATTTGGGTTAAGTTGTTGTTGTTGCGGTT (SEQ ID NO:3161), TTGTATTTATTTGGGTTAAGTTGTTGTTGTTGCGGT (SEQ ID NO:3162), GTATTTATTTGGGTTAAGTTGTTGTTGTTGCGGTTG (SEQ ID NO:3163) |
| Target332 | chr2:176994682-176994729 | GGTGGCGGCGGGTAGAGGGTGTTTTTT (SEQ ID NO:3164), GTGGCGGCGGGTAGAGGGTGTTTTTT (SEQ ID NO:3165), GTAAGAGGTGGCGGCGGGTAGAGGGTG (SEQ ID NO:3166), AGGTGGCGGCGGGTAGAGGGTGTTTTT (SEQ ID NO:3167), GGTGGCGGCGGGTAGAGGGTGTTTTT (SEQ ID NO:3168), CGGGGTTTCGTTTAGTTTTCGCGCGTC (SEQ ID NO:3169), CGGGTCGCGGGGTTTCGTTTAGTTTTCG (SEQ ID NO:3170), GGGTCGCGGGGTTTCGTTTAGTTTTCG (SEQ ID NO:3171), CGGGTCGCGGGGTTTCGTTTAGTTTTC (SEQ ID NO:3172), CGGGGTTTCGTTTAGTTTTCGCGCGT (SEQ ID NO:3173) |
| Target333 | chr2:176994747-176994872 | GTGGAGGTAGCGGGGTAGGTCGTTTGG (SEQ ID NO:3174), GATTATATTGCGGTCGAGTCGGGGCGC (SEQ ID NO:3175), AGTGGAGGTAGCGGGGTAGGTCGTTTG (SEQ ID NO:3176), ATTATATTGCGGTCGAGTCGGGGCGCG (SEQ ID NO:3177), GAGGTAGCGGGGTAGGTCGTTTGGGG (SEQ ID NO:3178), CGGGGTTTCGTTTAGTTTTCGCGCGTC (SEQ ID NO:3179), CGGGTCGCGGGGTTTCGTTTAGTTTTCG (SEQ ID NO:3180), GGGTCGCGGGGTTTCGTTTAGTTTTCG (SEQ ID NO:3181), CGGGTCGCGGGGTTTCGTTTAGTTTTC (SEQ ID NO:3182), CGTTTTTGAGGTTAGGTAGTCGCGGGC (SEQ ID NO:3183) |
| Target334 | chr2:176994931-176994997 | CGGGTATGAGCGTTTAGTAGTTGAGCGT (SEQ ID NO:3184), TCGGGTATGAGCGTTTAGTAGTTGAGCGT (SEQ ID NO:3185), TCGGGTATGAGCGTTTAGTAGTTGAGCG (SEQ ID NO:3186), GTCGGGTATGAGCGTTTAGTAGTTGAGCG (SEQ ID NO:3187), GTCGGGTATGAGCGTTTAGTAGTTGAGCGT (SEQ ID NO:3188), GGTTTGTGGGGCGGTTGTTTTCGTCGT (SEQ ID NO:3189), TTCGGTCGTATTGTCGCGGGGGTTTGT (SEQ ID NO:3190), ATTCGGTCGTATTGTCGCGGGGGTTTG (SEQ ID NO:3191), GGGGTTTGTGGGGCGGTTGTTTTCGTC (SEQ ID NO:3192), GGGTTTGTGGGGCGGTTGTTTTCGTCG (SEQ ID NO:3193) |
| Target335 | chr2:176995021-176995056 | CGGTTTCGGCGGCGAGAGTAGTC (SEQ ID NO:3194), CGGTTTCGGCGGCGAGAGTAGT (SEQ ID NO:3195), GTAGTCGTTTTATAGGTTTTCGCGGTAGTGC (SEQ ID NO:3196), AGTAGTCGTTTTATAGGTTTTCGCGGTAGTGC (SEQ ID NO:3197), GAGTAGTCGTTTTATAGGTTTTCGCGGTAGTGC (SEQ ID NO:3198), GCGGGCGGCGTTAAGTAGTTAGAGAGC (SEQ ID NO:3199), CGGGCGGCGTTAAGTAGTTAGAGAGCG (SEQ ID NO:3200), CGGGCGGCGTTAAGTAGTTAGAGAGCGA (SEQ ID NO:3201), GCGGGCGGCGTTAAGTAGTTAGAGAGCG (SEQ ID NO:3202), GGGCGGCGTTAAGTAGTTAGAGAGCGA (SEQ ID NO:3203) |
| Target336 | chr2:176995079-176995332 | AGGTTCGTTTTTTGGTTGTTTAGCGTCGT (SEQ ID NO:3204), GAGGTTCGTTTTTTGGTTGTTTAGCGTCGT (SEQ ID NO:3205), CGGTTTCGGCGGCGAGAGTAGTC (SEQ ID NO:3206), AGGTTCGTTTTTTGGTTGTTTAGCGTCGTT (SEQ ID NO:3207), GGTTCGTTTTTTGGTTGTTTAGCGTCGTTC (SEQ ID NO:3208), TCGGGTTGTTTTCGTCGGGGTGGAAGT (SEQ ID NO:3209), TATTTAGTTTCGGAGGGCGGCGGGGAC (SEQ ID NO:3210), GTATTTAGTTTCGGAGGGCGGCGGGGA (SEQ ID NO:3211), GTCGGGTTGTTTTCGTCGGGGTGGAAG (SEQ ID NO:3212), CGGTTTGGTAGGTAGCGGTCGGGGTTGT (SEQ ID NO:3213) |

FIGURE 5 CONTINUED

| Target337 | chr2:177016978-177017125 | GTTCGGTTGTGGGCGTAAAAGGGGGTG (SEQ ID NO:3214), GGGGCGTGTGGAGTTTTTATGGGCGTC (SEQ ID NO:3215), GTGGGGGCGTGTGGAGTTTTTATGGGC (SEQ ID NO:3216), ATGTGGTTGGTTGTTCGGTTGTGGGCG (SEQ ID NO:3217), GGCGTGTGGAGTTTTTATGGGCGTCGT (SEQ ID NO:3218) |
|---|---|---|
| Target338 | chr2:177017223-177017375 | GGCGGGAGGGAGGAAGTAAGCGAGTTT (SEQ ID NO:3219), TGTTTGAGGAGGTGGGTGGGAGTGAGC (SEQ ID NO:3220), GGTGTGTTTGAGGAGGTGGGTGGGAGT (SEQ ID NO:3221), TGTGGGTGTGTTTGAGGAGGTGGGTGG (SEQ ID NO:3222), GGGTGTGTTTGAGGAGGTGGGTGGGAG (SEQ ID NO:3223), TTGTTGTCGGGTGTAGGTCGTTCGGGA (SEQ ID NO:3224), TGTTGTCGGGTGTAGGTCGTTCGGGAT (SEQ ID NO:3225), TTTGTTGTCGGGTGTAGGTCGTTCGGG (SEQ ID NO:3226), TGTTGTCGGGTGTAGGTCGTTCGGGATC (SEQ ID NO:3227), GTTGTCGGGTGTAGGTCGTTCGGGATC (SEQ ID NO:3228) |
| Target339 | chr2:177017446-177017464 | GGGTGTGAGCGATTTTAATTCGACGGT (SEQ ID NO:3229), AGGGTGTGAGCGATTTTAATTCGACGGT (SEQ ID NO:3230), TAGGGTGTGAGCGATTTTAATTCGACGGT (SEQ ID NO:3231), ATAGGGTGTGAGCGATTTTAATTCGACGGT (SEQ ID NO:3232), TATAGGGTGTGAGCGATTTTAATTCGACGGT (SEQ ID NO:3233) |
| Target340 | chr2:177017483-177017516 | TGTGTTTGTCGGAGCGTTAGATTAAGATTTGGT (SEQ ID NO:3234), GTGTTTGTCGGAGCGTTAGATTAAGATTTGGTT (SEQ ID NO:3235), TTGTGTTTGTCGGAGCGTTAGATTAAGATTTGG (SEQ ID NO:3236), TGTGTTTGTCGGAGCGTTAGATTAAGATTTGGTT (SEQ ID NO:3237), TTGTGTTTGTCGGAGCGTTAGATTAAGATTTGGT (SEQ ID NO:3238), TGTTGGTTGGGGGCGATTGAGGAGGAG (SEQ ID NO:3239), GTTGGTTGGGGGCGATTGAGGAGGAGT (SEQ ID NO:3240), ATGTTGGTTGGGGGCGATTGAGGAGGA (SEQ ID NO:3241), TGGTTGGGGGCGATTGAGGAGGAGTAA (SEQ ID NO:3242), TTGGTTGGGGGCGATTGAGGAGGAGTA (SEQ ID NO:3243) |
| Target341 | chr2:177024222-177024286 | CGTTTTTGGAGTGGGGATGCGGTGGAT (SEQ ID NO:3244), CGTTTTTGGAGTGGGGATGCGGTGGATT (SEQ ID NO:3245), CGTTTTTGGAGTGGGGATGCGGTGGA (SEQ ID NO:3246), GTTTTTGGAGTGGGGATGCGGTGGATT (SEQ ID NO:3247), CGTTTTTGGAGTGGGGATGCGGTGGATTT (SEQ ID NO:3248), GGTTGGTGGGAATGATTTTGTAATGTGGAA (SEQ ID NO:3249), AGTAGCGGATTTTTTGGTTTGTAATGAGCGT (SEQ ID NO:3250), GGTTGGTGGGAATGATTTTGTAATGTGGGAAA (SEQ ID NO:3251), AGTAGCGGATTTTTTGGTTTGTAATGAGCGTT (SEQ ID NO:3252), GCGTTAGTAGCGGATTTTTTGGTTTGTAATGAGCG (SEQ ID NO:3253) |
| Target342 | chr2:177024294-177024328 | AGTGTGGTTTCGGTTGGGGGAGGGTTT (SEQ ID NO:3254), GTGGTTTCGGTTGGGGGAGGGTTTTGG (SEQ ID NO:3255), GAGTGTGGTTTCGGTTGGGGGAGGGTT (SEQ ID NO:3256), GTGTGGTTTCGGTTGGGGGAGGGTTTT (SEQ ID NO:3257), TGTGGTTTCGGTTGGGGGAGGGTTTTG (SEQ ID NO:3258), TGGTTGGTGGGAATGATTTTGTAATGTGGG (SEQ ID NO:3259), TGGTTGGTGGGAATGATTTTGTAATGTGGGA (SEQ ID NO:3260), GTGGTTGGTGGGAATGATTTTGTAATGTGGG (SEQ ID NO:3261), AGTGGTTGGTGGGAATGATTTTGTAATGTGGG (SEQ ID NO:3262), GTGGTTGGTGGGAATGATTTTGTAATGTGGGA (SEQ ID NO:3263) |
| Target343 | chr2:177024350-177024656 | AGTGTGGTTTCGGTTGGGGGAGGGTTT (SEQ ID NO:3264), GGTTTGGCGGTTGTTGGGTTTGTGGGA (SEQ ID NO:3265), GTGGTTTCGGTTGGGGGAGGGTTTTGG (SEQ ID NO:3266), GCGGTTGTTGGGTTTGTGGGATTTGCG (SEQ ID NO:3267), GAGTGTGGTTTCGGTTGGGGGAGGGTT (SEQ ID NO:3268), AGGAAGGCGAGGAGGATTGCGTAATGA (SEQ ID NO:3269), GGAAGGCGAGGAGGATTGCGTAATGAGT (SEQ ID NO:3270), GGAAGGCGAGGAGGATTGCGTAATGAG (SEQ ID NO:3271), CGAGGTTTGGAGTCGTTTAGGCGTTGA (SEQ ID NO:3272), AGGAAGGCGAGGAGGATTGCGTAATGAGT (SEQ ID NO:3273) |
| Target344 | chr2:177029880-177029993 | AGGGTGTAAGAGCGGGAAAAGTGCGGA (SEQ ID NO:3274), AGAGCGGGAAAAGTGCGGAGTAGGGAA (SEQ ID NO:3275), AAGAGCGGGAAAAGTGCGGAGTAGGGA (SEQ ID NO:3276), GGGTGTAAGAGCGGGAAAAGTGCGGAG (SEQ ID NO:3277), GGTGTAAGAGCGGGAAAAGTGCGGAGT (SEQ ID NO:3278), GCGTTTATAGCGATTAGGGGACGGGGT (SEQ ID NO:3279), GCGTTTATAGCGATTAGGGGACGGGGTT (SEQ ID NO:3280), CGGCGGTAGTAAACGTTTCGGTAAGGA (SEQ ID NO:3281), CGTTTATAGCGATTAGGGGACGGGGTT (SEQ ID NO:3282), GCGTTTATAGCGATTAGGGGACGGGG (SEQ ID NO:3283) |
| Target345 | chr2:177030040-177030172 | ATTAGGGTTCGGTTGTTTTGGAGGCGT (SEQ ID NO:3284), TAGGGTTCGGTTGTTTTGGAGGCGTAG (SEQ ID NO:3285), TTAGGGTTCGGTTGTTTTGGAGGCGTA (SEQ ID NO:3286), AGGGTTCGGTTGTTTTGGAGGCGTAG (SEQ ID NO:3287), TTAGGGTTCGGTTGTTTTGGAGGCGTAG (SEQ ID NO:3288), TGTCGGAAGGAAGGTATTTTTTGAGCGGT (SEQ ID NO:3289), TGTCGGAAGGAAGGTATTTTTTGAGCGGTT (SEQ ID NO:3290), TTGTCGGAAGGAAGGTATTTTTTGAGCGGT (SEQ ID NO:3291), GTCGGAAGGAAGGTATTTTTTGAGCGGTT (SEQ ID NO:3292), TTGTCGGAAGGAAGGTATTTTTTGAGCGG (SEQ ID NO:3293) |
| Target346 | chr2:177030178-177030289 | ATTAGGGTTCGGTTGTTTTGGAGGCGT (SEQ ID NO:3294), TAGGGTTCGGTTGTTTTGGAGGCGTAG (SEQ ID NO:3295), TTAGGGTTCGGTTGTTTTGGAGGCGTA (SEQ ID NO:3296), GGTTTTGTATTTCGGGTTTGCGGTTGGGT (SEQ ID NO:3297), TGGTTTTGTATTTCGGGTTTGCGGTTGGG (SEQ ID NO:3298), GGGTTAAACGGTTTTTTGTCGGAAGGAAGG (SEQ ID NO:3299), |

FIGURE 5 CONTINUED

GGGTTAAACGGTTTTTTGTCGGAAGGAAGGT (SEQ ID NO:3300),
AGGGTTAAACGGTTTTTTGTCGGAAGGAAGG (SEQ ID NO:3301),
AGGGGTTAAACGGTTTTTTGTCGGAAGGAAGGT (SEQ ID NO:3302),
GGTTAAACGGTTTTTTGTCGGAAGGAAGGT (SEQ ID NO:3303)

Target347   chr2:198650923-198650988   TATTTGGCGGGTGGGGAGAAGCGGATT (SEQ ID NO:3304), TTATTTGGCGGGTGGGGAGAAGCGGAT (SEQ ID NO:3305), GATTGCGTCGTTTCGGGTGGTAGGTGG (SEQ ID NO:3306), GGATTGCGTCGTTTCGGGTGGTAGGTG (SEQ ID NO:3307), GCGGCGAGGGTGGTTGTGGTAGTTGTA (SEQ ID NO:3308), CGTTCGTTTCGTTGTGTCGTGCGTTTT (SEQ ID NO:3309), CGTTCGTTTCGTTGTGTCGTGCGTTTTG (SEQ ID NO:3310), CGTTCGTTTCGTTGTGTCGTGCGTTTTGT (SEQ ID NO:3311), TCGTTTCGTTGTGTCGTGCGTTTGTT (SEQ ID NO:3312), TTCGTTTCGTTGTGTCGTGCGTTTTGT (SEQ ID NO:3313)

Target348   chr2:198651002-198651144   GTGGTTTTGGGATTTCGAGTCGGGGCG (SEQ ID NO:3314), TATTTGGCGGGTGGGGAGAAGCGGATT (SEQ ID NO:3315), TTATTTGGCGGGTGGGGAGAAGCGGAT (SEQ ID NO:3316), GGGCGTTTTAGGGGGTAGAGCGTACGGT (SEQ ID NO:3317), TCGGGGCGTTTTAGGGGGTAGAGCGTAC (SEQ ID NO:3318), TGGAGGAGAGGGGAAGGCGTGTATGGA (SEQ ID NO:3319), GTGGAGGAGAGGGGAAGGCGTGTATGG (SEQ ID NO:3320), GGAGGAGAGGGGAAGGCGTGTATGGAG (SEQ ID NO:3321), AGTGGAGGAGAGGGGAAGGCGTGTATG (SEQ ID NO:3322), AGTCGTTTGAGAGAAGGCGAGAGGGGT (SEQ ID NO:3323)

Target349   chr2:200335558-200335593   TGTCGGAGTTTTCGTATCGTGCGTTTT (SEQ ID NO:3324), TTGTCGGAGTTTTCGTATCGTGCGTTTT (SEQ ID NO:3325), TTTGTCGGAGTTTTCGTATCGTGCGTTT (SEQ ID NO:3326), TTTTGTCGGAGTTTTCGTATCGTGCGTT (SEQ ID NO:3327), TTTTTGTCGGAGTTTTCGTATCGTGCGT (SEQ ID NO:3328), CGGGGTCGTTAGTTTTTTTGAAGGGCGT (SEQ ID NO:3329), TTTTGGGGTGAAAGATTCGGGTGCGAA (SEQ ID NO:3330), TTTTTGGGGTGAAAGATTCGGGTGCGA (SEQ ID NO:3331), TTTTTTGGGGTGAAAGATTCGGGTGCG (SEQ ID NO:3332), TTTTTTGGGGTGAAAGATTCGGGTGCGAA (SEQ ID NO:3333)

Target350   chr2:200335807-200335821   CGGCGAGTGTAAAGTAGTTGCGTTTCG (SEQ ID NO:3334), TCGGCGAGTGTAAAGTAGTTGCGTTTCG (SEQ ID NO:3335), ATCGGCGAGTGTAAAGTAGTTGCGTTTCG (SEQ ID NO:3336), AGAATCGGCGAGTGTAAAGTAGTTGCGT (SEQ ID NO:3337), ATCGGCGAGTGTAAAGTAGTTGCGTTTC (SEQ ID NO:3338), TGTTCGGTATTTGCGCGTGTTTTGGGT (SEQ ID NO:3339), TCGGTATTTGCGCGTGTTTTGGGTAGT (SEQ ID NO:3340), TTGTTCGGTATTTGCGCGTGTTTTGGGT (SEQ ID NO:3341), TTGTTCGGTATTTGCGCGTGTTTTGGG (SEQ ID NO:3342), TGTTCGGTATTTGCGCGTGTTTTGGGTA (SEQ ID NO:3343)

Target351   chr2:209271397-209271466   ATATTGCGAATCGGGGGTGGCGGTAGT (SEQ ID NO:3344), ATTGCGAATCGGGGGTGGCGGTAGTAG (SEQ ID NO:3345), GAAATATTGCGAATCGGGGGTGGCGGT (SEQ ID NO:3346), TATTGCGAATCGGGGGTGGCGGTAGTA (SEQ ID NO:3347), AGAAATATTGCGAATCGGGGGTGGCGG (SEQ ID NO:3348), CGGCGCGAGGTTGGTTTTGTTTTTCGG (SEQ ID NO:3349), GCGGCGCGAGGTTGGTTTTGTTTTTCG (SEQ ID NO:3350), GGCGCGAGGTTGGTTTTGTTTTTCGGA (SEQ ID NO:3351), CGGCGCGAGGTTGGTTTTGTTTTTCGGA (SEQ ID NO:3352), GGCGCGAGGTTGGTTTTGTTTTTCGGAG (SEQ ID NO:3353)

Target352   chr2:209271483-209271606   GGGATTTAGTGATTTCGAGGAGGAGCGCG (SEQ ID NO:3354), CGGGATTTAGTGATTTCGAGGAGGAGCGC (SEQ ID NO:3355), GCGGGATTTAGTGATTTCGAGGAGGAGCG (SEQ ID NO:3356), TGCGGGATTTAGTGATTTCGAGGAGGAGCG (SEQ ID NO:3357), GGGATTTAGTGATTTCGAGGAGGAGCGCGA (SEQ ID NO:3358), GGGTTATCGGTCGAGGGTGTTTGGGGT (SEQ ID NO:3359), CGAGGGTGTTTGGGGTTTTGTCGTCGG (SEQ ID NO:3360), CGGTCGAGGGTGTTTGGGGTTTTGTCG (SEQ ID NO:3361), TCGGGTTATCGGTCGAGGGTGTTTGGG (SEQ ID NO:3362), CGGCGCGAGGTTGGTTTTGTTTTTCGG (SEQ ID NO:3363)

Target353   chr2:209271626-209271639   CGGCGATAAGATTTTAAGTATTTTCGGTCGGTGG (SEQ ID NO:3364), TCGGCGATAAGATTTTAAGTATTTTCGGTCGGT (SEQ ID NO:3365), CGGCGATAAGATTTTAAGTATTTTCGGTCGGTGGT (SEQ ID NO:3366), CGGCGATAAGATTTTAAGTATTTTCGGTCGGTG (SEQ ID NO:3367), TCGGCGATAAGATTTTAAGTATTTTCGGTCGGTGG (SEQ ID NO:3368), CGCGTAGTTGGGGTGGTCGGGGTTC (SEQ ID NO:3369), CGCGTAGTTGGGGTGGTCGGGGTT (SEQ ID NO:3370), CGCGTAGTTGGGGTGGTCGGGGT (SEQ ID NO:3371), GCGTAGTTGGGGTGGTCGGGGTTC (SEQ ID NO:3372), GACGCGTAGTTGGGGTGGTCGG (SEQ ID NO:3373)

Target354   chr2:220313171-220313218   TCGTTTAGGTTGGTGCGCGTCGGTTTT (SEQ ID NO:3374), TGGAGTAGTTTAAGTCGGAGCGCGGCG (SEQ ID NO:3375), ATCGTTTAGGTTGGTGCGCGTCGGTTT (SEQ ID NO:3376), GGAGTAGTTTAAGTCGGAGCGCGGCG (SEQ ID NO:3377), CGTTTAGGTTGGTGCGCGTCGGTTTTC (SEQ ID NO:3378), GAGGTTTCGGGGGTGTTTTACGGTGCG (SEQ ID NO:3379), AGGTTTCGGGGGTGTTTTACGGTGCG (SEQ ID NO:3380), GGTCGTTTTTTGTTGGAATAGGCGGCGT (SEQ ID NO:3381), GGTCGTTTTTTGTTGGAATAGGCGGCG (SEQ ID NO:3382), AGGTCGTTTTTTGTTGGAATAGGCGGCG (SEQ ID NO:3383)

Target355   chr2:220313238-220313493   GTTTTACGTCGCGGGAGGAGTTGGTGC (SEQ ID NO:3384), AGTTTAAGTCGGAGCGCGGCGTATCGT (SEQ ID NO:3385), CGGCGTATCGTGGGGTATTTTCGGGGT (SEQ ID NO:3386), TGGAGTAGTTTAAGTCGGAGCGCGGCG (SEQ ID NO:3387), GGAGTAGTTTAAGTCGGAGCGCGGCGT (SEQ ID NO:3388), CGATGTTTTGGGGGTGGAGGGTCGAGA (SEQ ID NO:3389),

FIGURE 5 CONTINUED

|  |  | CGAGGTTTGAGGTCGGGTTGCGTTGAC (SEQ ID NO:3390), TGTTCGTCGGTTCGCGGTTTTTGGGTT (SEQ ID NO:3391), CGGGTTTTCGAGGGGATGGGGTACGTT (SEQ ID NO:3392), TACGGTTCGCGATGTTTTGGGGGTGGA (SEQ ID NO:3393) |
|---|---|---|
| Target356 | chr2:220313516-220313601 | GGGGGACGAGTTTGGGAGGTTTAGGGAGT (SEQ ID NO:3394), GGGGGACGAGTTTGGGAGGTTTAGGGAG (SEQ ID NO:3395), GCGGGAGGAGTTGGTGCGTTCGTAC (SEQ ID NO:3396), GGGGACGAGTTTGGGAGGTTTAGGGAGT (SEQ ID NO:3397), GGGGGACGAGTTTGGGAGGTTTAGGGAGTC (SEQ ID NO:3398), TGTTCGTCGGTTCGCGGTTTTTGGGTT (SEQ ID NO:3399), TTGTTCGTCGGTTCGCGGTTTTTGGGT (SEQ ID NO:3400), GTTCGTCGGTTCGCGGTTTTTGGGTTT (SEQ ID NO:3401), TTTGTTCGTCGGTTCGCGGTTTTTGGG (SEQ ID NO:3402), TGTTCGTCGGTTCGCGGTTTTTGGGTTT (SEQ ID NO:3403) |
| Target357 | chr2:220313607-220313723 | GCGGGTAGGATAGAGTCGGGGGAAGGT (SEQ ID NO:3404), AGTTTGGGAGGTTTAGGGAGTCGCGGGT (SEQ ID NO:3405), GGCGGGTAGGATAGAGTCGGGGGGAAGG (SEQ ID NO:3406), CGGCGGGTAGGATAGAGTCGGGGGAAG (SEQ ID NO:3407), GTTTGGGAGGTTTAGGGAGTCGCGGGTC (SEQ ID NO:3408), TCGTTTTGGTTTTTGGGGGATCGGCGG (SEQ ID NO:3409), GTACGGTTTGCGTCGGGGGTTTCGTT (SEQ ID NO:3410), TTCGGCGTGGTTTAGGGTAGGAAGCGT (SEQ ID NO:3411), TACGGTTTGCGTCGGGGGTTTCGTTT (SEQ ID NO:3412), CGGTTTGCGTCGGGGGTTTCGTTTTC (SEQ ID NO:3413) |
| Target358 | chr2:220313761-220313815 | GGTCGTGCGTTTTTTGTTTTGGGTTACG (SEQ ID NO:3414), AGGTCGTGCGTTTTTTGTTTTGGGTTACG (SEQ ID NO:3415), GGCGTCGGGATTAATTTTCGTTGATTCGG (SEQ ID NO:3416), AGGCGTCGGGATTAATTTTCGTTGATTCGG (SEQ ID NO:3417), GGCGTCGGGATTAATTTTCGTTGATTCGGA (SEQ ID NO:3418), ACGGTTTGCGTCGGGGGTTTTCGTTTT (SEQ ID NO:3419), GTACGGTTTGCGTCGGGGGTTTTCGTT (SEQ ID NO:3420), TTCGGCGTGGTTTAGGGTAGGAAGCGT (SEQ ID NO:3421), TACGGTTTGCGTCGGGGGTTTTCGTTT (SEQ ID NO:3422), CGGTTTGCGTCGGGGGTTTTCGTTTTC (SEQ ID NO:3423) |
| Target359 | chr2:220313830-220313892 | ACGTCGGGTTTGGAGGGCGTTGTTGTA (SEQ ID NO:3424), CGTCGGGTTTGGAGGGCGTTGTTGTAT (SEQ ID NO:3425), TTTTGGGTTACGTCGGGTTTGGAGGGC (SEQ ID NO:3426), GGGCGGGGTTTGAGGTAGAGAAGAGGT (SEQ ID NO:3427), AGGGCGGGGTTTGAGGTAGAGAAGAGG (SEQ ID NO:3428), CGAGTTTAGGGGGAGGTGGGTCGGGTTC (SEQ ID NO:3429), ATCGAGTTTAGGGGGAGGTGGGTCGGGT (SEQ ID NO:3430), TCGAGTTTAGGGGGAGGTGGGTCGGGTT (SEQ ID NO:3431), GCGGGTTTTTCGGCGGTTTTAGGGTTT (SEQ ID NO:3432), TCGGCGATTTTTGTTTTGGTTGCGGGT (SEQ ID NO:3433) |
| Target360 | chr2:223163071-223164036 | TTGGAATTCGGGAAAGGGGAGGACGGG (SEQ ID NO:3434), GAATTCGGGAAAGGGGAGGACGGGGAG (SEQ ID NO:3435), TTACGGCGAGTCGGGGAGTTTGGTGAG (SEQ ID NO:3436), GAGTTACGGCGAGTCGGGGAGTTTGGT (SEQ ID NO:3437), AGTTTGGTGAGGTTGGAGCGCGGTTTG (SEQ ID NO:3438), AGGGAGGGTTTTAGCGCGTCGTTTGGA (SEQ ID NO:3439), AAGGGAGGGTTTTAGCGCGTCGTTTGG (SEQ ID NO:3440), GGGAGGGTTTTAGCGCGTCGTTTGGAT (SEQ ID NO:3441), GGTAAGGGAGGGTTTTAGCGCGTCGTT (SEQ ID NO:3442), AGGGAGGGTTTTAGCGCGTCGTTTGGAT (SEQ ID NO:3443) |
| Target361 | chr2:225266080-225266368 | GCGAATGTTGGAGAGAGTTTAGGACGC (SEQ ID NO:3444), TGGCGAATGTTGGAGAGAGTTTAGGACG (SEQ ID NO:3445), TTGGGTGGGGTAGTATTGTTATGGCGAA (SEQ ID NO:3446), TTTGGGTGGGGTAGTATTGTTATGGCGA (SEQ ID NO:3447), ATGGCGAATGTTGGAGAGAGTTTAGGACG (SEQ ID NO:3448), TGGGGGGTGAGGTAGGTGTATTGTGGT (SEQ ID NO:3449), TGGGGGGTGAGGTAGGTGTATTGTGGTT (SEQ ID NO:3450), TTGGGGGGTGAGGTAGGTGTATTGTGGT (SEQ ID NO:3451), GGGGGGGTGAGGTAGGTGTATTGTGGTT (SEQ ID NO:3452), TTGGGGGGTGAGGTAGGTGTATTGTGG (SEQ ID NO:3453) |
| Target362 | chr2:230933210-230933223 | TTTTCGGGGGTTTTTGGGGGTGTAGCGG (SEQ ID NO:3454), CGGGGGTTTTTGGGGGTGTAGCGGTTA (SEQ ID NO:3455), TTTCGGGGGTTTTTGGGGGTGTAGCGG (SEQ ID NO:3456), GGGGGTTTTTGGGGGTGTAGCGGTTAT (SEQ ID NO:3457), TTTTTCGGGGGTTTTTGGGGGTGTAGCG (SEQ ID NO:3458), GGGTTTCGGGCGGTGAGTATTCGAGGT (SEQ ID NO:3459), GGTTTCGGGCGGTGAGTATTCGAGGTC (SEQ ID NO:3460), GGGTTTCGGGCGGTGAGTATTCGAGGTC (SEQ ID NO:3461), GGGTTTCGGGCGGTGAGTATTCGAGG (SEQ ID NO:3462), CGGGTTTGGGGAATGGAGCGACGTC (SEQ ID NO:3463) |
| Target363 | chr2:230933225-230933272 | TTTTCGGGGGTTTTTGGGGGTGTAGCG (SEQ ID NO:3464), CGGGGGTTTTTGGGGGTGTAGCGGTTA (SEQ ID NO:3465), TTTCGGGGGTTTTTGGGGGTGTAGCGG (SEQ ID NO:3466), GGGGGTTTTTGGGGGTGTAGCGGTTAT (SEQ ID NO:3467), TTTTTCGGGGGTTTTTGGGGGTGTAGCG (SEQ ID NO:3468), GGGTTTCGGGCGGTGAGTATTCGAGGT (SEQ ID NO:3469), GGTTTCGGGCGGTGAGTATTCGAGGTC (SEQ ID NO:3470), GGGTTTCGGGCGGTGAGTATTCGAGGTC (SEQ ID NO:3471), GGGTTTCGGGCGGTGAGTATTCGAGG (SEQ ID NO:3472), GGTTTCGGGCGGTGAGTATTCGAGGT (SEQ ID NO:3473) |
| Target364 | chr2:230933275-230933303 | TTTTCGGGGGTTTTTGGGGGTGTAGCG (SEQ ID NO:3474), CGGGGGTTTTTGGGGGTGTAGCGGTTA (SEQ ID NO:3475), TTTCGGGGGTTTTTGGGGGTGTAGCGG (SEQ ID NO:3476), GGGGGTTTTTGGGGGTGTAGCGGTTAT (SEQ ID NO:3477), TTTTTCGGGGGTTTTTGGGGGTGTAGCG (SEQ ID NO:3478), GCGGAGAGTTGAGTCGTAGGTATTCGCG (SEQ ID NO:3479), GCGGAGAGTTGAGTCGTAGGTATTCGCGT (SEQ ID NO:3480), GCGGAGAGTTGAGTCGTAGGTATTCGC (SEQ ID NO:3481), TCGGGCGTGGAGTCGAGTGAGGTC (SEQ ID NO:3482), CGGAGAGTTGAGTCGTAGGTATTCGCGT (SEQ ID NO:3483) |

FIGURE 5 CONTINUED

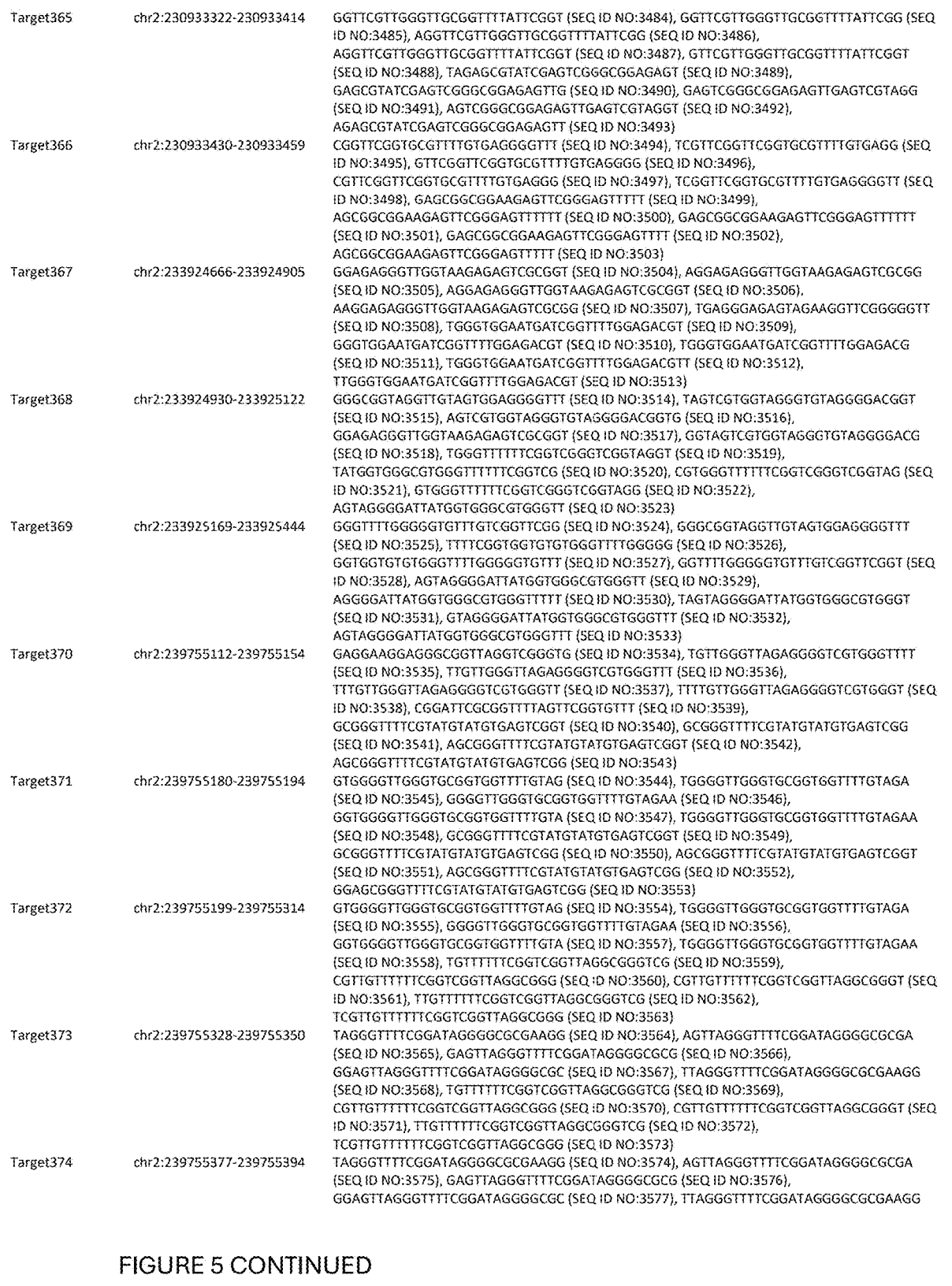

| Target365 | chr2:230933322-230933414 | GGTTCGTTGGGTTGCGGTTTTATTCGGT (SEQ ID NO:3484), GGTTCGTTGGGTTGCGGTTTTATTCGG (SEQ ID NO:3485), AGGTTCGTTGGGTTGCGGTTTTATTCGG (SEQ ID NO:3486), AGGTTCGTTGGGTTGCGGTTTTATTCGGT (SEQ ID NO:3487), GTTCGTTGGGTTGCGGTTTTATTCGGT (SEQ ID NO:3488), TAGAGCGTATCGAGTCGGGCGGAGAGT (SEQ ID NO:3489), GAGCGTATCGAGTCGGGCGGAGAGTTG (SEQ ID NO:3490), GAGTCGGGCGGAGAGTTGAGTCGTAGG (SEQ ID NO:3491), AGTCGGGCGGAGAGTTGAGTCGTAGGT (SEQ ID NO:3492), AGAGCGTATCGAGTCGGGCGGAGAGTT (SEQ ID NO:3493) |
|---|---|---|
| Target366 | chr2:230933430-230933459 | CGGTTCGGTGCGTTTTGTGAGGGGTTT (SEQ ID NO:3494), TCGTTCGGTTCGGTGCGTTTTGTGAGG (SEQ ID NO:3495), GTTCGGTTCGGTGCGTTTTGTGAGGGG (SEQ ID NO:3496), CGTTCGGTTCGGTGCGTTTTGTGAGGG (SEQ ID NO:3497), TCGGTTCGGTGCGTTTTGTGAGGGGTT (SEQ ID NO:3498), GAGCGGCGGAAGAGTTCGGGAGTTTTT (SEQ ID NO:3499), AGCGGCGGAAGAGTTCGGGAGTTTTTT (SEQ ID NO:3500), GAGCGGCGGAAGAGTTCGGGAGTTTTTT (SEQ ID NO:3501), GAGCGGCGGAAGAGTTCGGGAGTTTT (SEQ ID NO:3502), AGCGGCGGAAGAGTTCGGGAGTTTTT (SEQ ID NO:3503) |
| Target367 | chr2:233924666-233924905 | GGAGAGGGTTGGTAAGAGAGTCGCGGT (SEQ ID NO:3504), AGGAGAGGGTTGGTAAGAGAGTCGCGG (SEQ ID NO:3505), AGGAGAGGGTTGGTAAGAGAGTCGCGGT (SEQ ID NO:3506), AAGGAGAGGGTTGGTAAGAGAGTCGCG (SEQ ID NO:3507), TGAGGGAGAGTAGAAGGTTCGGGGGTT (SEQ ID NO:3508), TGGGTGGAATGATCGGTTTTGGAGACGT (SEQ ID NO:3509), GGGTGGAATGATCGGTTTTGGAGACGT (SEQ ID NO:3510), TGGGTGGAATGATCGGTTTTGGAGACG (SEQ ID NO:3511), TGGGTGGAATGATCGGTTTTGGAGACGTT (SEQ ID NO:3512), TTGGGTGGAATGATCGGTTTTGGAGACGT (SEQ ID NO:3513) |
| Target368 | chr2:233924930-233925122 | GGGCGGTAGGTTGTAGTGGAGGGGTTT (SEQ ID NO:3514), TAGTCGTGGTAGGGTGTAGGGGACGGT (SEQ ID NO:3515), AGTCGTGGTAGGGTGTAGGGGACGGTG (SEQ ID NO:3516), GGAGAGGGTTGGTAAGAGAGTCGCGGT (SEQ ID NO:3517), GGTAGTCGTGGTAGGGTGTAGGGGACG (SEQ ID NO:3518), TGGGTTTTTTCGGTCGGGTCGGTAGGT (SEQ ID NO:3519), TATGGTGGGCGTGGGTTTTTTCGGTCG (SEQ ID NO:3520), CGTGGGTTTTTTCGGTCGGGTCGGTAG (SEQ ID NO:3521), GTGGGTTTTTTCGGTCGGGTCGGTAGG (SEQ ID NO:3522), AGTAGGGGATTATGGTGGGCGTGGGTT (SEQ ID NO:3523) |
| Target369 | chr2:233925169-233925444 | GGGTTTTGGGGGTGTTTGTCGGTTCGG (SEQ ID NO:3524), GGGCGGTAGGTTGTAGTGGAGGGGTTT (SEQ ID NO:3525), TTTTCGGTGGTGTGTGGGTTTTGGGGG (SEQ ID NO:3526), GGTGGTGTGTGGGTTTTGGGGGTGTTT (SEQ ID NO:3527), GGTTTTGGGGGTGTTTGTCGGTTCGGT (SEQ ID NO:3528), AGTAGGGGATTATGGTGGGCGTGGGTT (SEQ ID NO:3529), AGGGGATTATGGTGGGCGTGGGTTTTT (SEQ ID NO:3530), TAGTAGGGGATTATGGTGGGCGTGGGT (SEQ ID NO:3531), GTAGGGGATTATGGTGGGCGTGGGTTT (SEQ ID NO:3532), AGTAGGGGATTATGGTGGGCGTGGGTTT (SEQ ID NO:3533) |
| Target370 | chr2:239755112-239755154 | GAGGAAGGAGGGCGGTTAGGTCGGGTG (SEQ ID NO:3534), TGTTGGGTTAGAGGGGTCGTGGGTTTT (SEQ ID NO:3535), TTGTTGGGTTAGAGGGGTCGTGGGTTTT (SEQ ID NO:3536), TTTGTTGGGTTAGAGGGGTCGTGGGTT (SEQ ID NO:3537), TTTTGTTGGGTTAGAGGGGTCGTGGGT (SEQ ID NO:3538), CGGATTCGCGGTTTTAGTTCGGTGTTT (SEQ ID NO:3539), GCGGGTTTTCGTATGTATGTGAGTCGGT (SEQ ID NO:3540), GCGGGTTTTCGTATGTATGTGAGTCGG (SEQ ID NO:3541), AGCGGGTTTTCGTATGTATGTGAGTCGGT (SEQ ID NO:3542), AGCGGGTTTTCGTATGTATGTGAGTCGG (SEQ ID NO:3543) |
| Target371 | chr2:239755180-239755194 | GTGGGGTTGGGTGCGGTGGTTTTGTAG (SEQ ID NO:3544), TGGGGTTGGGTGCGGTGGTTTTGTAGA (SEQ ID NO:3545), GGGGTTGGGTGCGGTGGTTTTGTAGAA (SEQ ID NO:3546), GGTGGGGTTGGGTGCGGTGGTTTTGTA (SEQ ID NO:3547), TGGGGTTGGGTGCGGTGGTTTTGTAGAA (SEQ ID NO:3548), GCGGGTTTTCGTATGTATGTGAGTCGGT (SEQ ID NO:3549), GCGGGTTTTCGTATGTATGTGAGTCGG (SEQ ID NO:3550), AGCGGGTTTTCGTATGTATGTGAGTCGGT (SEQ ID NO:3551), AGCGGGTTTTCGTATGTATGTGAGTCGG (SEQ ID NO:3552), GGAGCGGGTTTTCGTATGTATGTGAGTCGG (SEQ ID NO:3553) |
| Target372 | chr2:239755199-239755314 | GTGGGGTTGGGTGCGGTGGTTTTGTAG (SEQ ID NO:3554), TGGGGTTGGGTGCGGTGGTTTTGTAGA (SEQ ID NO:3555), GGGGTTGGGTGCGGTGGTTTTGTAGAA (SEQ ID NO:3556), GGTGGGGTTGGGTGCGGTGGTTTTGTA (SEQ ID NO:3557), TGGGGTTGGGTGCGGTGGTTTTGTAGAA (SEQ ID NO:3558), TGTTTTTTCGGTCGGTTAGGCGGGTCG (SEQ ID NO:3559), CGTTGTTTTTTCGGTCGGTTAGGCGGG (SEQ ID NO:3560), CGTTGTTTTTTCGGTCGGTTAGGCGGGT (SEQ ID NO:3561), TTGTTTTTTCGGTCGGTTAGGCGGGTCG (SEQ ID NO:3562), TCGTTGTTTTTTCGGTCGGTTAGGCGGG (SEQ ID NO:3563) |
| Target373 | chr2:239755328-239755350 | TAGGGTTTTCGGATAGGGGCGCGAAGG (SEQ ID NO:3564), AGTTAGGGTTTTCGGATAGGGGCGCGA (SEQ ID NO:3565), GAGTTAGGGTTTTCGGATAGGGGCGCG (SEQ ID NO:3566), GGAGTTAGGGTTTTCGGATAGGGGCGC (SEQ ID NO:3567), TTAGGGTTTTCGGATAGGGGCGCGAAGG (SEQ ID NO:3568), TGTTTTTTCGGTCGGTTAGGCGGGTCG (SEQ ID NO:3569), CGTTGTTTTTTCGGTCGGTTAGGCGGG (SEQ ID NO:3570), CGTTGTTTTTTCGGTCGGTTAGGCGGGT (SEQ ID NO:3571), TTGTTTTTTCGGTCGGTTAGGCGGGTCG (SEQ ID NO:3572), TCGTTGTTTTTTCGGTCGGTTAGGCGGG (SEQ ID NO:3573) |
| Target374 | chr2:239755377-239755394 | TAGGGTTTTCGGATAGGGGCGCGAAGG (SEQ ID NO:3574), AGTTAGGGTTTTCGGATAGGGGCGCGA (SEQ ID NO:3575), GAGTTAGGGTTTTCGGATAGGGGCGCG (SEQ ID NO:3576), GGAGTTAGGGTTTTCGGATAGGGGCGC (SEQ ID NO:3577), TTAGGGTTTTCGGATAGGGGCGCGAAGG |

FIGURE 5 CONTINUED

|  |  | (SEQ ID NO:3578), TGTTTTTTCGGTCGGTTAGGCGGGTCG (SEQ ID NO:3579), CGTTGTTTTTTCGGTCGGTTAGGCGGG (SEQ ID NO:3580), CGTTGTTTTTTCGGTCGGTTAGGCGGGT (SEQ ID NO:3581), TTGTTTTTTCGGTCGGTTAGGCGGGTCG (SEQ ID NO:3582), TCGTTGTTTTTTCGGTCGGTTAGGCGGG (SEQ ID NO:3583) |
| Target375 | chr2:239755407-239755456 | TAGGGGTTTTCGGATAGGGGCGCGAAGG (SEQ ID NO:3584), CGGTTCGTTTGGTCGGTCGGAGGAGTA (SEQ ID NO:3585), AGTTAGGGTTTTCGGATAGGGGCGCGA (SEQ ID NO:3586), GAGTTAGGGTTTTCGGATAGGGGCGCGA (SEQ ID NO:3587), GTTCGTTTGGTCGGTCGGAGGAGTAGC (SEQ ID NO:3588), GTTTTTTCGGTCGGTTAGGCGGGTCGT (SEQ ID NO:3589), TGTTTTTTCGGTCGGTTAGGCGGGTCG (SEQ ID NO:3590), CGTTGTTTTTTCGGTCGGTTAGGCGGG (SEQ ID NO:3591), CGTTGTTTTTTCGGTCGGTTAGGCGGGT (SEQ ID NO:3592), TTGTTTTTTCGGTCGGTTAGGCGGGTCG (SEQ ID NO:3593) |
| Target376 | chr2:239755491-239755506 | CGGTTCGTTTGGTCGGTCGGAGGAGTA (SEQ ID NO:3594), GTTCGTTTGGTCGGTCGGAGGAGTAGC (SEQ ID NO:3595), CGGTTCGTTTGGTCGGTCGGAGGAGTAG (SEQ ID NO:3596), CGGTTCGTTTGGTCGGTCGGAGGAGT (SEQ ID NO:3597), GGTTCGTTTGGTCGGTCGGAGGAGTAGC (SEQ ID NO:3598), AGTCGGGTTGTTAGGTAAGTCGCGTGA (SEQ ID NO:3599), TGAGTCGGGTTGTTAGGTAAGTCGCGT (SEQ ID NO:3600), GGTTCGGGTTTGAGTCGGGTTGTTAGGT (SEQ ID NO:3601), GGTTCGGGTTTGAGTCGGGTTGTTAGG (SEQ ID NO:3602), AGGTTCGGGTTTGAGTCGGGTTGTTAGG (SEQ ID NO:3603) |
| Target377 | chr2:241393792-241393817 | AGGAGGTTGTTGGACGTGTCGGAGGAT (SEQ ID NO:3604), GGAGGTTGTTGGACGTGTCGGAGGATGT (SEQ ID NO:3605), GGAGGTTGTTGGACGTGTCGGAGGATG (SEQ ID NO:3606), AGGAGGTTGTTGGACGTGTCGGAGGATG (SEQ ID NO:3607), TAGGAGGTTGTTGGACGTGTCGGAGGA (SEQ ID NO:3608), TTTTCGGATTTTAATTAGTTTCGGTGGTTGTGGT (SEQ ID NO:3609), GTTTTCGGATTTTAATTAGTTTCGGTGGTTGTGGT (SEQ ID NO:3610), TGTTTTCGGATTTTAATTAGTTTCGGTGGTTGTGG (SEQ ID NO:3611), TGTTTTCGGATTTTAATTAGTTTCGGTGGTTGTGGT (SEQ ID NO:3612), TTGTTTTCGGATTTTAATTAGTTTCGGTGGTTGTGG (SEQ ID NO:3613) |
| Target378 | chr2:241393833-241393881 | AGGAGGTTGTTGGACGTGTCGGAGGAT (SEQ ID NO:3614), GGAGGTTGTTGGACGTGTCGGAGGATGT (SEQ ID NO:3615), GGAGGTTGTTGGACGTGTCGGAGGATG (SEQ ID NO:3616), TGGGTTAGGGGTTGGGGTAGGTTTCGA (SEQ ID NO:3617), AGGAGGTTGTTGGACGTGTCGGAGGATG (SEQ ID NO:3618) |
| Target379 | chr2:242824433-242824450 | GCGTGGGTGGTTTTTGGTTGGGGAAGT (SEQ ID NO:3619), AGCGTGGGTGGTTTTTGGTTGGGGAAG (SEQ ID NO:3620), AGGTTGTGGCGTGTTTGGTGGTGTTGT (SEQ ID NO:3621), TGTAGCGTGGGTGGTTTTTGGTTGGGG (SEQ ID NO:3622), GTAGCGTGGGTGGTTTTTGGTTGGGGA (SEQ ID NO:3623), CGTTACGTGTTTGGAGAGGCGGTGTTA (SEQ ID NO:3624), CGTTACGTGTTTGGAGAGGCGGTGTT (SEQ ID NO:3625), CGTTACGTGTTTGGAGAGGCGGTGTTAT (SEQ ID NO:3626), CGTTACGTGTTTGGAGAGGCGGTGT (SEQ ID NO:3627), CGTTACGTGTTTGGAGAGGCGGTGTTATT (SEQ ID NO:3628) |
| Target380 | chr2:242824532-242824595 | TGGTGAGAGGTGGTTGGGAGGAAGTTT (SEQ ID NO:3629), TTGGTGAGAGGTGGTTGGGAGGAAGTT (SEQ ID NO:3630), TTTGGTGAGAGGTGGTTGGGAGGAAGT (SEQ ID NO:3631), TTGGTGAGAGGTGGTTGGGAGGAAGTTT (SEQ ID NO:3632), TTTGGTGAGAGGTGGTTGGGAGGAAGTT (SEQ ID NO:3633), CGTTTGCGGGGGGTAGAGGGAGAGAAGG (SEQ ID NO:3634), TTGCGGGGGGTAGAGGGAGAGAAGGAGA (SEQ ID NO:3635), TGCGGGGGGTAGAGGGAGAGAAGGAGAT (SEQ ID NO:3636), TTTGCGGGGGGTAGAGGGAGAGAAGGAG (SEQ ID NO:3637), TTTGCGGGGGGTAGAGGGAGAGAAGGAGA (SEQ ID NO:3638) |
| Target381 | chr3:9177892-9177965 | CGCGGCGGTTGATTTCGGTTCGGTATT (SEQ ID NO:3639), GGAGAAGGGCGGTAATGGGGAGTTCGT (SEQ ID NO:3640), AGGAGAAGGGCGGTAATGGGGAGTTCG (SEQ ID NO:3641), AGAAGGGCGGTAATGGGGAGTTCGTGT (SEQ ID NO:3642), CGCGGCGGTTGATTTCGGTTCGGTAT (SEQ ID NO:3643) |
| Target382 | chr3:9177983-9178004 | CGCGGCGGTTGATTTCGGTTCGGTATT (SEQ ID NO:3644), CGCGGCGGTTGATTTCGGTTCGGTAT (SEQ ID NO:3645), CGCGGCGGTTGATTTCGGTTCGGTATTT (SEQ ID NO:3646), GCGGCGGTTGATTTCGGTTCGGTATTT (SEQ ID NO:3647), GCGCGGCGGTTGATTTCGGTTCGGTAT (SEQ ID NO:3648) |
| Target383 | chr3:9178006-9178062 | TGGAGGTAGTAGATGTCGGGTCGGGGT (SEQ ID NO:3649), TAGATGTCGGGTCGGGGTTAGTCGTCG (SEQ ID NO:3650), CGGGGTTGGAGGTAGTAGATGTCGGGT (SEQ ID NO:3651), GCGTCGGGGTTGGAGGTAGTAGATGTCG (SEQ ID NO:3652), TGGAGGTAGTAGATGTCGGGTCGGGGTT (SEQ ID NO:3653), CGCGGCGGTTGATTTCGGTTCGGTATT (SEQ ID NO:3654), CGCGGCGGTTGATTTCGGTTCGGTAT (SEQ ID NO:3655), CGCGGCGGTTGATTTCGGTTCGGTATTT (SEQ ID NO:3656), GCGGCGGTTGATTTCGGTTCGGTATTT (SEQ ID NO:3657), GCGCGGCGGTTGATTTCGGTTCGGTAT (SEQ ID NO:3658) |
| Target384 | chr3:9178096-9178250 | AGTAGTCGGGGTGGTTGAAAGCGGGTT (SEQ ID NO:3659), TGGAGGTAGTAGATGTCGGGTCGGGGT (SEQ ID NO:3660), AGTCGGGGTGGTTGAAAGCGGGTTTTT (SEQ ID NO:3661), TAGTAGTCGGGGTGGTTGAAAGCGGGT (SEQ ID NO:3662), GTAGTCGGGGTGGTTGAAAGCGGGTTT (SEQ ID NO:3663), AGTTATTTCGGTTGTTGTACGTGGCGC (SEQ ID NO:3664), AGGGTGTTAGGGAGTTTGTTCGCGTTTG (SEQ ID NO:3665), TGGTCGAATATAGGAAGGGGAGAGGGAG (SEQ ID NO:3666), TAGTTATTTCGGTTGTTGTACGTGGCGC (SEQ ID NO:3667), TGGTCGAATATAGGAAGGGGAGAGGGAGA (SEQ ID NO:3668) |

FIGURE 5 CONTINUED

Target385    chr3:52828402-52828911    GTGAGCGAGGGGTTTTGTTGTGGAGGT (SEQ ID NO:3669), AGTGAGCGAGGGGTTTTGTTGTGGAGGT (SEQ ID NO:3670), AGTGAGCGAGGGGTTTTGTTGTGGAGG (SEQ ID NO:3671), GGGTAGTGAGCGAGGGGTTTTGTTGTGG (SEQ ID NO:3672), AGGGTAGTGAGCGAGGGGTTTTGTTGT (SEQ ID NO:3673), GCGTGGATGATGGAGATGGGGTGTGGA (SEQ ID NO:3674), GGTGGGAGGAGTGGAGGTAGGAAGGGT (SEQ ID NO:3675), TTGGCGTGGATGATGGAGATGGGGTGT (SEQ ID NO:3676), GTGATTTGTAGCGGGGGTGGGAGGAGT (SEQ ID NO:3677), TGATTTGTAGCGGGGGTGGGAGGAGTG (SEQ ID NO:3678)

Target386    chr3:62356123-62356237    GGAAGAGGCGGGCGTTTTAGGGGTAGT (SEQ ID NO:3679), GTAGAATGGTGGGGAGGAAGAGGCGGG (SEQ ID NO:3680), AGGAAGAGGCGGGCGTTTTAGGGGTAG (SEQ ID NO:3681), GAGGAAGAGGCGGGCGTTTTAGGGGTA (SEQ ID NO:3682), GTGGGGAGGAAGAGGCGGGCGTTTTAG (SEQ ID NO:3683), GAGCGCGGCGGGAGGGAAGTTGTATTA (SEQ ID NO:3684), AGCGCGGCGGGAGGGAAGTTGTATTAG (SEQ ID NO:3685), GCGCGGCGGGAGGGAAGTTGTATTAGT (SEQ ID NO:3686), AGCGCGGCGGGAGGGAAGTTGTATTA (SEQ ID NO:3687), CGCGGCGGGAGGGAAGTTGTATTAGTT (SEQ ID NO:3688)

Target387    chr3:62356280-62356286    CGTAAGCGTTAAGTCGGGTGTTTTTTCGA (SEQ ID NO:3689), TGCGTTTTTGTTTTGTTCGTTATAGAGGTTGGT (SEQ ID NO:3690), GCGTTTTTGTTTTGTTCGTTATAGAGGTTGGTG (SEQ ID NO:3691), GCGTTTTTGTTTTGTTCGTTATAGAGGTTGGTGT (SEQ ID NO:3692), TGCGTTTTTGTTTTGTTCGTTATAGAGGTTGGTG (SEQ ID NO:3693), GGGTTACGTAAAAGTTTTTCGGTTCGCGG (SEQ ID NO:3694), TGGGTTACGTAAAAGTTTTTCGGTTCGCGG (SEQ ID NO:3695), GGGTTACGTAAAAGTTTTTCGGTTCGCGGA (SEQ ID NO:3696), TGGGTTACGTAAAAGTTTTTCGGTTCGCGGA (SEQ ID NO:3697), TGGGTTACGTAAAAGTTTTTCGGTTCGCG (SEQ ID NO:3698)

Target388    chr3:62356310-62356329    GCGGGTCGGGAAATTTTTGCGTAGTTT (SEQ ID NO:3699), GCGGGTCGGGAAATTTTTGCGTAGTT (SEQ ID NO:3700), GCGGGTCGGGAAATTTTTGCGTAGTTTA (SEQ ID NO:3701), GCGGGTCGGGAAATTTTTGCGTAGTTTAG (SEQ ID NO:3702), GCGGGTCGGGAAATTTTTGCGTAGTTTAGA (SEQ ID NO:3703), TTGGTAGTTGGGGGGCGAGAAAGAAGT (SEQ ID NO:3704), AGTTGGTAGTTGGGGGGCGAGAAAGAA (SEQ ID NO:3705), GTTGGTAGTTGGGGGGCGAGAAAGAAGT (SEQ ID NO:3706), GTTGGTAGTTGGGGGGCGAGAAAGAAG (SEQ ID NO:3707), AGTTGGTAGTTGGGGGGCGAGAAAGAAGT (SEQ ID NO:3708)

Target389    chr3:62356353-62356372    GCGGGTCGGGAAATTTTTGCGTAGTTT (SEQ ID NO:3709), GCGGGTCGGGAAATTTTTGCGTAGTT (SEQ ID NO:3710), GCGGGTCGGGAAATTTTTGCGTAGTTTA (SEQ ID NO:3711), GCGGGTCGGGAAATTTTTGCGTAGTTTAG (SEQ ID NO:3712), GCGGGTCGGGAAATTTTTGCGTAGTTTAGA (SEQ ID NO:3713), TTGGTAGTTGGGGGGCGAGAAAGAAGT (SEQ ID NO:3714), AGTTGGTAGTTGGGGGGCGAGAAAGAA (SEQ ID NO:3715), GTTGGTAGTTGGGGGGCGAGAAAGAAGT (SEQ ID NO:3716), GTTGGTAGTTGGGGGGCGAGAAAGAAG (SEQ ID NO:3717), AGTTGGTAGTTGGGGGGCGAGAAAGAAGT (SEQ ID NO:3718)

Target390    chr3:62362918-62362940    TTTTCGGCGGCGGTAGGGAAATAGACG (SEQ ID NO:3719), GGTTGGGTTTTAAATTTTCGGCGGCGGT (SEQ ID NO:3720), ATTTTCGGCGGCGGTAGGGAAATAGACG (SEQ ID NO:3721), GGTTGGGTTTTAAATTTTCGGCGGCGG (SEQ ID NO:3722), TTTCGGCGGCGGTAGGGAAATAGACG (SEQ ID NO:3723), GCGTTTTGTTTTTCGGCGTGGGAAGGA (SEQ ID NO:3724), GCGTGGGAAGGATATAGGTCGTCGAGGG (SEQ ID NO:3725), GGCGTGGGAAGGATATAGGTCGTCGAGG (SEQ ID NO:3726), CGTGGGAAGGATATAGGTCGTCGAGGGG (SEQ ID NO:3727), GCGTGGGAAGGATATAGGTCGTCGAGG (SEQ ID NO:3728)

Target391    chr3:62363001-62363017    TTTCGGCGGCGGTAGGGAAATAGACG (SEQ ID NO:3729), TCGGCGGCGGTAGGGAAATAGACGATT (SEQ ID NO:3730), TTCGGCGGCGGTAGGGAAATAGACGAT (SEQ ID NO:3731), TTTTCGGCGGCGGTAGGGAAATAGACG (SEQ ID NO:3732), TTTTCGGCGGCGGTAGGGAAATAGACGA (SEQ ID NO:3733), GTGGTGTGCGGGTTGTTTGGTTAGGGC (SEQ ID NO:3734), AGTGGTGTGCGGGTTGTTTGGTTAGGG (SEQ ID NO:3735), TGGTGTGCGGGTTGTTTGGTTAGGGC (SEQ ID NO:3736), TGGTGTGCGGGTTGTTTGGTTAGGGCG (SEQ ID NO:3737), GGTGTGCGGGTTGTTTGGTTAGGGCG (SEQ ID NO:3738)

Target392    chr3:62363063-62363069    TCGTTGTTTTGCGGGGTTTGATCGGGG (SEQ ID NO:3739), GTTTGATCGGGGCGGCGATTTTTGGGA (SEQ ID NO:3740), TGATCGGGGCGGCGATTTTTGGGATTC (SEQ ID NO:3741), TTGATCGGGGCGGCGATTTTTGGGATT (SEQ ID NO:3742), TTTGATCGGGGCGGCGATTTTTGGGAT (SEQ ID NO:3743), GTGGTGTGCGGGTTGTTTGGTTAGGGC (SEQ ID NO:3744), AGTGGTGTGCGGGTTGTTTGGTTAGGG (SEQ ID NO:3745), TGGTGTGCGGGTTGTTTGGTTAGGGC (SEQ ID NO:3746), TGGTGTGCGGGTTGTTTGGTTAGGGCG (SEQ ID NO:3747), GGTGTGCGGGTTGTTTGGTTAGGGC (SEQ ID NO:3748)

Target393    chr3:62363076-62363082    TCGTTGTTTTGCGGGGTTTGATCGGGG (SEQ ID NO:3749), GTTTGATCGGGGCGGCGATTTTTGGGA (SEQ ID NO:3750), TGATCGGGGCGGCGATTTTTGGGATTC (SEQ ID NO:3751), TTGATCGGGGCGGCGATTTTTGGGATT (SEQ ID NO:3752), TTTGATCGGGGCGGCGATTTTTGGGAT (SEQ ID NO:3753), GTGGTGTGCGGGTTGTTTGGTTAGGGC (SEQ ID NO:3754), AGTGGTGTGCGGGTTGTTTGGTTAGGG (SEQ ID NO:3755), TGGTGTGCGGGTTGTTTGGTTAGGGC (SEQ ID NO:3756), TGGTGTGCGGGTTGTTTGGTTAGGGCG (SEQ ID NO:3757), GGTGTGCGGGTTGTTTGGTTAGGGCG (SEQ ID NO:3758)

FIGURE 5 CONTINUED

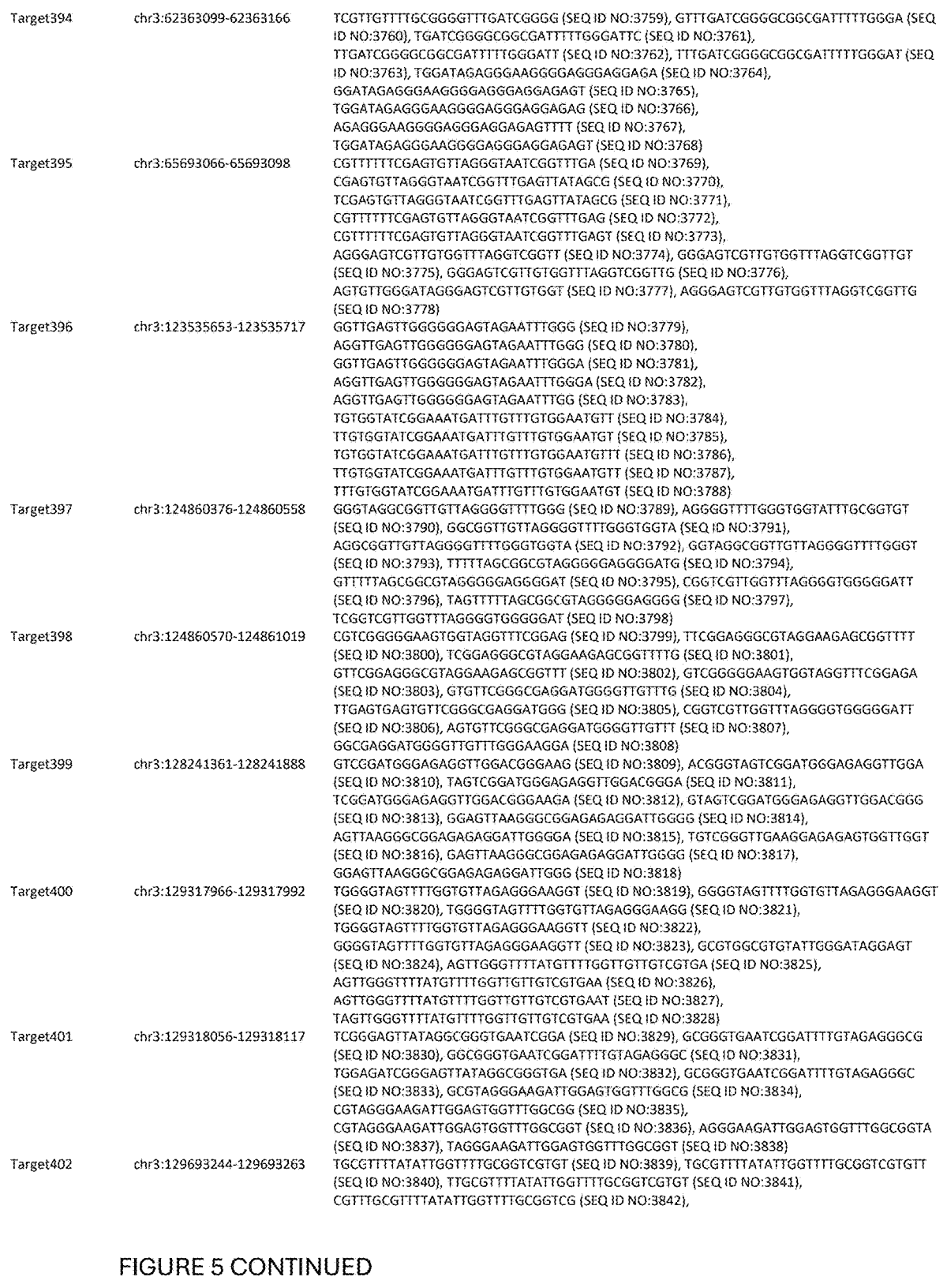

| | | |
|---|---|---|
| Target394 | chr3:62363099-62363166 | TCGTTGTTTTGCGGGGTTTGATCGGGG (SEQ ID NO:3759), GTTTGATCGGGGCGGCGATTTTTGGGA (SEQ ID NO:3760), TGATCGGGGCGGCGATTTTTGGGATTC (SEQ ID NO:3761), TTGATCGGGGCGGCGATTTTTGGGATT (SEQ ID NO:3762), TTTGATCGGGGCGGCGATTTTTGGGAT (SEQ ID NO:3763), TGGATAGAGGGAAGGGGAGGGAGGAGA (SEQ ID NO:3764), GGATAGAGGGAAGGGGAGGGAGGAGAGT (SEQ ID NO:3765), TGGATAGAGGGAAGGGGAGGGAGGAGAG (SEQ ID NO:3766), AGAGGGAAGGGGAGGGAGGAGAGTTTT (SEQ ID NO:3767), TGGATAGAGGGAAGGGGAGGGAGGAGAGT (SEQ ID NO:3768) |
| Target395 | chr3:65693066-65693098 | CGTTTTTTCGAGTGTTAGGGTAATCGGTTTGA (SEQ ID NO:3769), CGAGTGTTAGGGTAATCGGTTTGAGTTATAGCG (SEQ ID NO:3770), TCGAGTGTTAGGGTAATCGGTTTGAGTTATAGCG (SEQ ID NO:3771), CGTTTTTTCGAGTGTTAGGGTAATCGGTTTGAG (SEQ ID NO:3772), CGTTTTTTCGAGTGTTAGGGTAATCGGTTTGAGT (SEQ ID NO:3773), AGGGAGTCGTTGTGGTTAGGTCGGTT (SEQ ID NO:3774), GGGAGTCGTTGTGGTTAGGTCGGTTGT (SEQ ID NO:3775), GGGAGTCGTTGTGGTTAGGTCGGTTG (SEQ ID NO:3776), AGTGTTGGGATAGGGAGTCGTTGTGGT (SEQ ID NO:3777), AGGGAGTCGTTGTGGTTAGGTCGGTTG (SEQ ID NO:3778) |
| Target396 | chr3:123535653-123535717 | GGTTGAGTTGGGGGGAGTAGAATTTGGG (SEQ ID NO:3779), AGGTTGAGTTGGGGGGAGTAGAATTTGGG (SEQ ID NO:3780), GGTTGAGTTGGGGGGAGTAGAATTTGGGA (SEQ ID NO:3781), AGGTTGAGTTGGGGGGAGTAGAATTTGGGA (SEQ ID NO:3782), AGGTTGAGTTGGGGGGAGTAGAATTTGG (SEQ ID NO:3783), TGTGGTATCGGAAATGATTTGTTTGTGGAATGTT (SEQ ID NO:3784), TTGTGGTATCGGAAATGATTTGTTTGTGGAATGT (SEQ ID NO:3785), TGTGGTATCGGAAATGATTTGTTTGTGGAATGTTT (SEQ ID NO:3786), TTGTGGTATCGGAAATGATTTGTTTGTGGAATGTT (SEQ ID NO:3787), TTTGTGGTATCGGAAATGATTTGTTTGTGGAATGT (SEQ ID NO:3788) |
| Target397 | chr3:124860376-124860558 | GGGTAGGCGGTTGTTAGGGGTTTTGGG (SEQ ID NO:3789), AGGGGTTTTGGGTGGTATTTGCGGTGT (SEQ ID NO:3790), GGCGGTTGTTAGGGGTTTTGGGTGGTA (SEQ ID NO:3791), AGGCGGTTGTTAGGGGTTTTGGGTGGTA (SEQ ID NO:3792), GGTAGGCGGTTGTTAGGGGTTTTGGGT (SEQ ID NO:3793), TTTTTAGCGGCGTAGGGGGAGGGGATG (SEQ ID NO:3794), GTTTTTAGCGGCGTAGGGGGAGGGGAT (SEQ ID NO:3795), CGGTCGTTGGTTTAGGGGTGGGGGATT (SEQ ID NO:3796), TAGTTTTTAGCGGCGTAGGGGGAGGGG (SEQ ID NO:3797), TCGGTCGTTGGTTTAGGGGTGGGGGAT (SEQ ID NO:3798) |
| Target398 | chr3:124860570-124861019 | CGTCGGGGGAAGTGGTAGGTTTCGGAG (SEQ ID NO:3799), TTCGGAGGGGCGTAGGAAGAGCGGTTTT (SEQ ID NO:3800), TCGGAGGGGCGTAGGAAGAGCGGTTTTG (SEQ ID NO:3801), GTTCGGAGGGGCGTAGGAAGAGCGGTTT (SEQ ID NO:3802), GTCGGGGGAAGTGGTAGGTTTCGGAGA (SEQ ID NO:3803), GTGTTCGGGCGAGGATGGGGTTGTTG (SEQ ID NO:3804), TTGAGTGAGTGTTCGGGCGAGGATGGG (SEQ ID NO:3805), CGGTCGTTGGTTTAGGGGTGGGGGATT (SEQ ID NO:3806), AGTGTTCGGGCGAGGATGGGGTTGTTT (SEQ ID NO:3807), GGCGAGGATGGGGTTGTTTGGGAAGGA (SEQ ID NO:3808) |
| Target399 | chr3:128241361-128241888 | GTCGGATGGGAGAGGTTGGACGGGAAG (SEQ ID NO:3809), ACGGGTAGTCGGATGGGAGAGGTTGGA (SEQ ID NO:3810), TAGTCGGATGGGAGAGGTTGGACGGGA (SEQ ID NO:3811), TCGGATGGGAGAGGTTGGACGGGAAGA (SEQ ID NO:3812), GTAGTCGGATGGGAGAGGTTGGACGGG (SEQ ID NO:3813), GGAGTTAAGGGCGGAGAGAGGATTGGGG (SEQ ID NO:3814), AGTTAAGGGCGGAGAGAGGATTGGGGA (SEQ ID NO:3815), TGTCGGGTTGAAGGAGAGAGTGGTTGGT (SEQ ID NO:3816), GAGTTAAGGGCGGAGAGAGGATTGGGG (SEQ ID NO:3817), GGAGTTAAGGGCGGAGAGAGGATTGGG (SEQ ID NO:3818) |
| Target400 | chr3:129317966-129317992 | TGGGGTAGTTTTGGTGTTAGAGGGAAGGT (SEQ ID NO:3819), GGGGTAGTTTTGGTGTTAGAGGGAAGGT (SEQ ID NO:3820), TGGGGTAGTTTTGGTGTTAGAGGGAAGG (SEQ ID NO:3821), TGGGGTAGTTTTGGTGTTAGAGGGAAGGTT (SEQ ID NO:3822), GGGGTAGTTTTGGTGTTAGAGGGAAGGTT (SEQ ID NO:3823), GCGTGGCGTGTATTGGGATAGGAGT (SEQ ID NO:3824), AGTTGGGTTTTATGTTTTGGTTGTTGTCGTGA (SEQ ID NO:3825), AGTTGGGTTTTATGTTTTGGTTGTTGTCGTGAA (SEQ ID NO:3826), AGTTGGGTTTTATGTTTTGGTTGTTGTCGTGAAT (SEQ ID NO:3827), TAGTTGGGTTTTATGTTTTGGTTGTTGTCGTGAA (SEQ ID NO:3828) |
| Target401 | chr3:129318056-129318117 | TCGGGAGTTATAGGCGGGTGAATCGGA (SEQ ID NO:3829), GCGGGTGAATCGGATTTTGTAGAGGGCG (SEQ ID NO:3830), GGCGGGTGAATCGGATTTTGTAGAGGGC (SEQ ID NO:3831), TGGAGATCGGGAGTTATAGGCGGGTGA (SEQ ID NO:3832), GCGGGTGAATCGGATTTTGTAGAGGGC (SEQ ID NO:3833), GCGTAGGGAAGATTGGAGTGGTTTGGCG (SEQ ID NO:3834), CGTAGGGAAGATTGGAGTGGTTTGGCGG (SEQ ID NO:3835), CGTAGGGAAGATTGGAGTGGTTTGGCGGT (SEQ ID NO:3836), AGGGAAGATTGGAGTGGTTTGGCGGTA (SEQ ID NO:3837), TAGGGAAGATTGGAGTGGTTTGGCGGT (SEQ ID NO:3838) |
| Target402 | chr3:129693244-129693263 | TGCGTTTTATATTGGTTTTGCGGTCGTGT (SEQ ID NO:3839), TGCGTTTTATATTGGTTTTGCGGTCGTGTT (SEQ ID NO:3840), TTGCGTTTTATATTGGTTTTGCGGTCGTGT (SEQ ID NO:3841), CGTTTGCGTTTTATATTGGTTTTGCGGTCG (SEQ ID NO:3842), |

FIGURE 5 CONTINUED

CGTTTGCGTTTATATTGGTTTTGCGGTCGT (SEQ ID NO:3843), CGGAGGTATTGGTCGTAGGATGGGGCG
(SEQ ID NO:3844), CGCGGAGGTATTGGTCGTAGGATGGGG (SEQ ID NO:3845),
GGTATTGGTCGTAGGATGGGGCGTCGG (SEQ ID NO:3846), GCGGAGGTATTGGTCGTAGGATGGGGC
(SEQ ID NO:3847), AGGTATTGGTCGTAGGATGGGGCGTCG (SEQ ID NO:3848)

| | | |
|---|---|---|
| Target403 | chr3:129693303-129693314 | TTCGTGCGTTTGTGTTTAATCGTGCGT (SEQ ID NO:3849), TTTCGTGCGTTTGTGTTTAATCGTGCGT (SEQ ID NO:3850), TTTCGTGCGTTTGTGTTTAATCGTGCG (SEQ ID NO:3851), TCGTGCGTTTGTGTTTAATCGTGCGT (SEQ ID NO:3852), TTTTCGTGCGTTTGTGTTTAATCGTGCGT (SEQ ID NO:3853), CGGAGGTATTGGTCGTAGGATGGGGCG (SEQ ID NO:3854), CGCGGAGGTATTGGTCGTAGGATGGGG (SEQ ID NO:3855), GGTATTGGTCGTAGGATGGGGCGTCGG (SEQ ID NO:3856), GCGGAGGTATTGGTCGTAGGATGGGGC (SEQ ID NO:3857), AGGTATTGGTCGTAGGATGGGGCGTCG (SEQ ID NO:3858) |
| Target404 | chr3:129693344-129693386 | TCGTGCGTTTGTGTTTAATCGTGCGTT (SEQ ID NO:3859), TTCGTGCGTTTGTGTTTAATCGTGCGT (SEQ ID NO:3860), CGTGCGTTTGTGTTTAATCGTGCGTT (SEQ ID NO:3861), TCGTGCGTTTGTGTTTAATCGTGCGTTT (SEQ ID NO:3862), TTCGTGCGTTTGTGTTTAATCGTGCGTT (SEQ ID NO:3863), CGGAGGTATTGGTCGTAGGATGGGGCG (SEQ ID NO:3864), CGCGGAGGTATTGGTCGTAGGATGGGG (SEQ ID NO:3865), GGTATTGGTCGTAGGATGGGGCGTCGG (SEQ ID NO:3866), GCGGAGGTATTGGTCGTAGGATGGGGC (SEQ ID NO:3867), AGGTATTGGTCGTAGGATGGGGCGTCG (SEQ ID NO:3868) |
| Target405 | chr3:129693390-129693413 | CGTCGGCGTTTTATTTTGCGGTTAGTGT (SEQ ID NO:3869), CGTCGGCGTTTTATTTTGCGGTTAGTGTT (SEQ ID NO:3870), CGTCGGCGTTTTATTTTGCGGTTAGTGTTT (SEQ ID NO:3871), CGGCGTTTTATTTTGCGGTTAGTGTTTCG (SEQ ID NO:3872), CGTCGGCGTTTTATTTTGCGGTTAGTGTTTT (SEQ ID NO:3873), TTAGGCGGCGGTTCGAGTGAGGTTAGC (SEQ ID NO:3874), TTCGAGTGAGGTTAGCGGGGAGGGGTC (SEQ ID NO:3875), GTTAGGCGGCGGTTCGAGTGAGGTTAG (SEQ ID NO:3876), GTTCGAGTGAGGTTAGCGGGGAGGGG (SEQ ID NO:3877), GGTTCGAGTGAGGTTAGCGGGGAGGG (SEQ ID NO:3878) |
| Target406 | chr3:129693449-129693458 | TAGATTTTCGGAGGAGTAGGCGGGCGG (SEQ ID NO:3879), AGATTTTCGGAGGAGTAGGCGGGCGG (SEQ ID NO:3880), TTAGATTTTCGGAGGAGTAGGCGGGCGG (SEQ ID NO:3881), AGATTTTCGGAGGAGTAGGCGGGCGGG (SEQ ID NO:3882), TTAGATTTTCGGAGGAGTAGGCGGGCG (SEQ ID NO:3883), TTAGGCGGCGGTTCGAGTGAGGTTAGC (SEQ ID NO:3884), TTCGAGTGAGGTTAGCGGGGAGGGGTC (SEQ ID NO:3885), GTTAGGCGGCGGTTCGAGTGAGGTTAG (SEQ ID NO:3886), GTTCGAGTGAGGTTAGCGGGGAGGGG (SEQ ID NO:3887), GGTTCGAGTGAGGTTAGCGGGGAGGG (SEQ ID NO:3888) |
| Target407 | chr3:129693540-129693629 | TTGAAGAGGGTTCGGTAGGCGTTCGGG (SEQ ID NO:3889), TAGATTTTCGGAGGAGTAGGCGGGCGG (SEQ ID NO:3890), CGGTAGGCGTTCGGGGTTTTTAGCGTT (SEQ ID NO:3891), TTCGGTAGGCGTTCGGGGTTTTTAGCG (SEQ ID NO:3892), TGAAGAGGGTTCGGTAGGCGTTCGGG (SEQ ID NO:3893), GGAAGGAGAGGGGTTGGGGCGGTTATT (SEQ ID NO:3894), AGGAGAGGGGTTGGGGCGGTTATTTGT (SEQ ID NO:3895), GGTGAGGGCGGGTCGAGAGGGTTTTTT (SEQ ID NO:3896), GGAAGGAGAGGGGTTGGGGCGGTTATTT (SEQ ID NO:3897), GGAGAGGGGTTGGGGCGGTTATTTGTT (SEQ ID NO:3898) |
| Target408 | chr3:129693672-129693706 | TTGAAGAGGGTTCGGTAGGCGTTCGGG (SEQ ID NO:3899), AGGGTTCGGTAGGCGTTCGGGGTTTTT (SEQ ID NO:3900), CGGTAGGCGTTCGGGGTTTTTAGCGTT (SEQ ID NO:3901), GAGGGTTCGGTAGGCGTTCGGGGTTTT (SEQ ID NO:3902), TTCGGTAGGCGTTCGGGGTTTTTAGCG (SEQ ID NO:3903), GGGGAGGGATTCGGGGGTGCGAGTATAG (SEQ ID NO:3904), GGTGAGGGCGGGTCGAGAGGGTTTTTT (SEQ ID NO:3905), CGGGGAGGGATTCGGGGGTGCGAGTATA (SEQ ID NO:3906), AGGTGAGGGCGGGTCGAGAGGGTTTTT (SEQ ID NO:3907), AAGGTGAGGGCGGGTCGAGAGGGTTTT (SEQ ID NO:3908) |
| Target409 | chr3:133578115-133578515 | TTGGGTTGGGGGTGGGTGTTAGGGTTT (SEQ ID NO:3909), TTTGGGTTGGGGGTGGGTGTTAGGGTT (SEQ ID NO:3910), TTTTGGGTTGGGGGTGGGTGTTAGGGT (SEQ ID NO:3911), TGGGTTGGGGGTGGGTGTTAGGGTTA (SEQ ID NO:3912), TTTGGGTTGGGGGTGGGTGTTAGGGTTT (SEQ ID NO:3913), AGGTGGTTTAGGGGGTTGTTAGTTTTGGT (SEQ ID NO:3914), GGTGGTTTAGGGGGTTGTTAGTTTTGGTAGT (SEQ ID NO:3915), AGGTGGTTTAGGGGGTTGTTAGTTTTGGTAG (SEQ ID NO:3916), AGGTGGTTTAGGGGGTTGTTAGTTTTGGTAGT (SEQ ID NO:3917), TTAGGTGGTTTAGGGGGTTGTTAGTTTTGGT (SEQ ID NO:3918) |
| Target410 | chr3:137483751-137484225 | ATGGTATGGTTTCGGGGTTAGCGGCGT (SEQ ID NO:3919), TGGTATGGTTTCGGGGTTAGCGGCGTA (SEQ ID NO:3920), GGCGGTTGGTTTGTTCGTGGGGGTTTT (SEQ ID NO:3921), TTAAGGCGGTTGGTTTGTTCGTGGGGG (SEQ ID NO:3922), TAAGGCGGTTGGTTTGTTCGTGGGGGT (SEQ ID NO:3923), GTAGTTAGGGTTGGTGGGGGACGGGTG (SEQ ID NO:3924), GAGGTCGGCGGTAAGAAGGTTCGGGTT (SEQ ID NO:3925), ACGGGGGGTTGTAGGGTGGAGGTAGAT (SEQ ID NO:3926), AGGTCGGCGGTAAGAAGGTTCGGGTTT (SEQ ID NO:3927), GCGGGGTTTAGTAGGGAGTAGGGCGTC (SEQ ID NO:3928) |
| Target411 | chr3:138171444-138171844 | TGGGAGGAGGTTTAGTTCGTAGTAGGAATGA (SEQ ID NO:3929), TTGGGAGGAGGTTTAGTTCGTAGTAGGAATGA (SEQ ID NO:3930), TGGGAGGAGGTTTAGTTCGTAGTAGGAATGAT (SEQ ID NO:3931), TGTTTTTGGGAGGAGGTTTAGTTCGTAGTAGG (SEQ ID NO:3932), TGTTTTTGGGAGGAGGTTTAGTTCGTAGTAGGA (SEQ ID NO:3933), |

FIGURE 5 CONTINUED

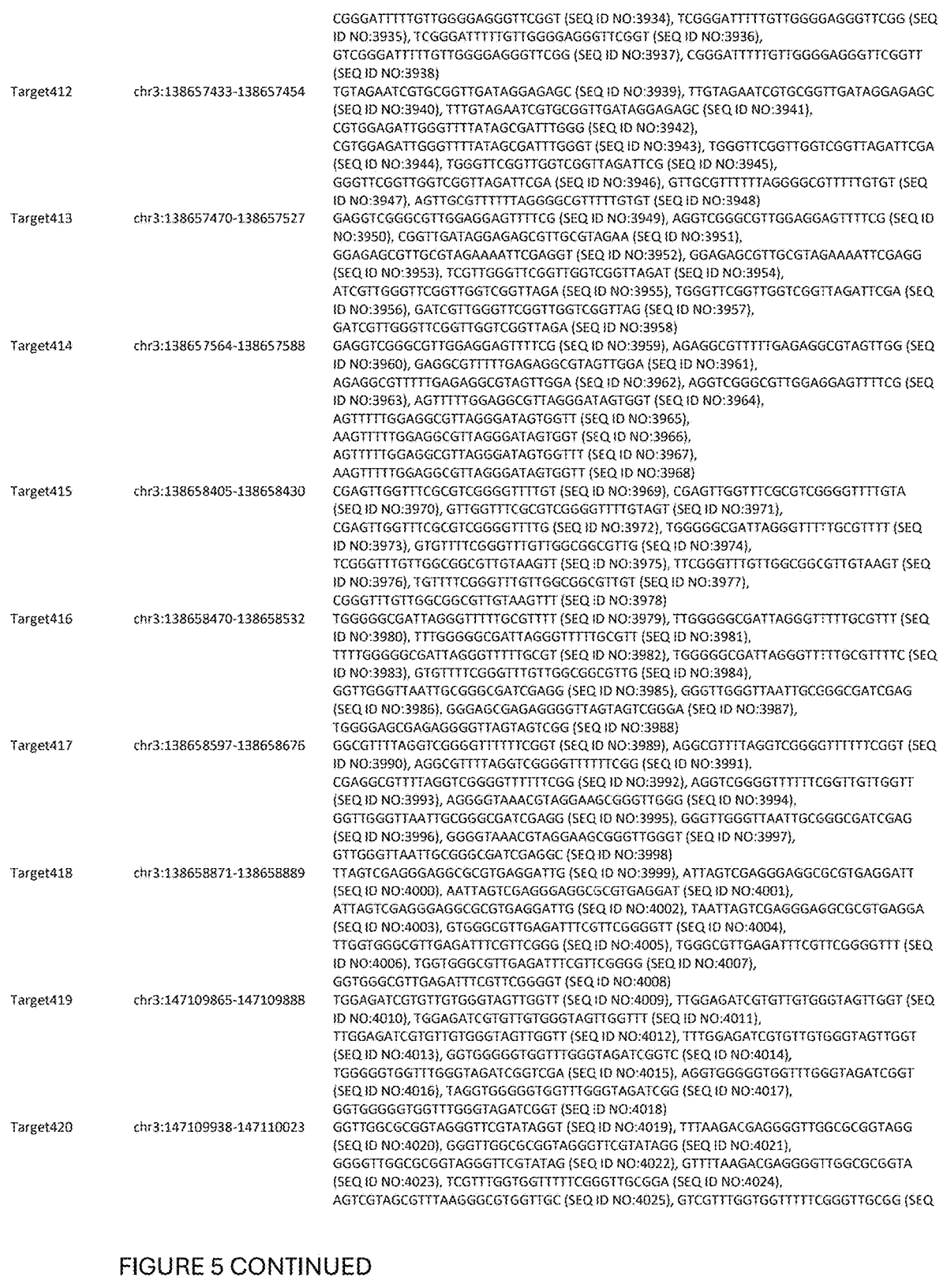

|  |  | CGGGATTTTTGTTGGGGAGGGGTTCGGT (SEQ ID NO:3934), TCGGGATTTTTGTTGGGGAGGGTTCGG (SEQ ID NO:3935), TCGGGATTTTTGTTGGGGAGGGTTCGGT (SEQ ID NO:3936), GTCGGGATTTTTGTTGGGGAGGGTTCGG (SEQ ID NO:3937), CGGGATTTTTGTTGGGGAGGGTTCGGTT (SEQ ID NO:3938) |
| Target412 | chr3:138657433-138657454 | TGTAGAATCGTGCGGTTGATAGGAGAGC (SEQ ID NO:3939), TTGTAGAATCGTGCGGTTGATAGGAGAGC (SEQ ID NO:3940), TTTGTAGAATCGTGCGGTTGATAGGAGAGC (SEQ ID NO:3941), CGTGGAGATTGGGTTTTATAGCGATTTGGG (SEQ ID NO:3942), CGTGGAGATTGGGTTTTATAGCGATTTGGGT (SEQ ID NO:3943), TGGGTTCGGTTGGTCGGTTAGATTCGA (SEQ ID NO:3944), TGGGTTCGGTTGGTCGGTTAGATTCG (SEQ ID NO:3945), GGGTTCGGTTGGTCGGTTAGATTCGA (SEQ ID NO:3946), GTTGCGTTTTTTAGGGGCGTTTTTGTGT (SEQ ID NO:3947), AGTTGCGTTTTTTAGGGGCGTTTTTGTGT (SEQ ID NO:3948) |
| Target413 | chr3:138657470-138657527 | GAGGTCGGGCGTTGGAGGGAGTTTTCG (SEQ ID NO:3949), AGGTCGGGCGTTGGAGGGAGTTTTCG (SEQ ID NO:3950), CGGTTGATAGGAGAGCGTTGCGTAGAA (SEQ ID NO:3951), GGAGAGCGTTGCGTAGAAAAATTCGAGGT (SEQ ID NO:3952), GGAGAGCGTTGCGTAGAAAAATTCGAGG (SEQ ID NO:3953), TCGTTGGGTTCGGTTGGTCGGTTAGAT (SEQ ID NO:3954), ATCGTTGGGTTCGGTTGGTCGGTTAGA (SEQ ID NO:3955), TGGGTTCGGTTGGTCGGTTAGATTCGA (SEQ ID NO:3956), GATCGTTGGGTTCGGTTGGTCGGTTAG (SEQ ID NO:3957), GATCGTTGGGTTCGGTTGGTCGGTTAGA (SEQ ID NO:3958) |
| Target414 | chr3:138657564-138657588 | GAGGTCGGGCGTTGGAGGGAGTTTTCG (SEQ ID NO:3959), AGAGGCGTTTTTGAGAGGCGTAGTTGG (SEQ ID NO:3960), GAGGCGTTTTTGAGAGGCGTAGTTGGA (SEQ ID NO:3961), AGAGGCGTTTTTGAGAGGCGTAGTTGGA (SEQ ID NO:3962), AGGTCGGGCGTTGGAGGGAGTTTTCG (SEQ ID NO:3963), AGTTTTTGGAGGCGTTAGGGATAGTGGT (SEQ ID NO:3964), AGTTTTTGGAGGCGTTAGGGATAGTGGTT (SEQ ID NO:3965), AAGTTTTTGGAGGCGTTAGGGATAGTGGT (SEQ ID NO:3966), AGTTTTTGGAGGCGTTAGGGATAGTGGTTT (SEQ ID NO:3967), AAGTTTTTGGAGGCGTTAGGGATAGTGGTT (SEQ ID NO:3968) |
| Target415 | chr3:138658405-138658430 | CGAGTTGGTTTCGCGTCGGGGTTTTGT (SEQ ID NO:3969), CGAGTTGGTTTCGCGTCGGGGTTTTGTA (SEQ ID NO:3970), GTTGGTTTCGCGTCGGGGTTTTGTAGT (SEQ ID NO:3971), CGAGTTGGTTTCGCGTCGGGGTTTTG (SEQ ID NO:3972), TGGGGGGCGATTAGGGGTTTTTGCGTTTT (SEQ ID NO:3973), GTGTTTTCGGGTTTGTTGGCGGCGTTG (SEQ ID NO:3974), TCGGGTTTGTTGGCGGCGTTGTAAGTT (SEQ ID NO:3975), TTCGGGTTTGTTGGCGGCGTTGTAAGT (SEQ ID NO:3976), TGTTTTCGGGTTTGTTGGCGGCGTTGT (SEQ ID NO:3977), CGGGTTTGTTGGCGGCGTTGTAAGTTT (SEQ ID NO:3978) |
| Target416 | chr3:138658470-138658532 | TGGGGGGCGATTAGGGGTTTTTGCGTTTT (SEQ ID NO:3979), TTGGGGGGCGATTAGGGGTTTTTGCGTTT (SEQ ID NO:3980), TTTGGGGGGCGATTAGGGGTTTTTGCGTT (SEQ ID NO:3981), TTTTGGGGGGCGATTAGGGGTTTTTGCGT (SEQ ID NO:3982), TGGGGGGCGATTAGGGGTTTTTGCGTTTTC (SEQ ID NO:3983), GTGTTTTCGGGTTTGTTGGCGGCGTTG (SEQ ID NO:3984), GGTTGGGTTAATTGCGGGCGATCGAGG (SEQ ID NO:3985), GGGTTGGGTTAATTGCGGGCGATCGAG (SEQ ID NO:3986), GGGAGCGAGAGGGGGTTAGTAGTCGGGA (SEQ ID NO:3987), TGGGAGCGAGAGGGGGTTAGTAGTCGG (SEQ ID NO:3988) |
| Target417 | chr3:138658597-138658676 | GGCGTTTTAGGTCGGGGTTTTTTCGGT (SEQ ID NO:3989), AGGCGTTTTAGGTCGGGGTTTTTTCGGT (SEQ ID NO:3990), AGGCGTTTTAGGTCGGGGTTTTTTCGG (SEQ ID NO:3991), CGAGGCGTTTTAGGTCGGGGTTTTTTCGG (SEQ ID NO:3992), AGGTCGGGGTTTTTTCGGTTGTTGGTT (SEQ ID NO:3993), AGGGGTAAACGTAGGAAGCGGGTTGGG (SEQ ID NO:3994), GGTTGGGTTAATTGCGGGCGATCGAGG (SEQ ID NO:3995), GGGTTGGGTTAATTGCGGGCGATCGAG (SEQ ID NO:3996), GGGGTAAACGTAGGAAGCGGGTTGGGT (SEQ ID NO:3997), GTTGGGTTAATTGCGGGCGATCGAGGC (SEQ ID NO:3998) |
| Target418 | chr3:138658871-138658889 | TTAGTCGAGGGAGGCGCGTGAGGATTG (SEQ ID NO:3999), ATTAGTCGAGGGAGGCGCGTGAGGATT (SEQ ID NO:4000), AATTAGTCGAGGGAGGCGCGTGAGGAT (SEQ ID NO:4001), ATTAGTCGAGGGAGGCGCGTGAGGATTG (SEQ ID NO:4002), TAATTAGTCGAGGGAGGCGCGTGAGGA (SEQ ID NO:4003), GTGGGCGTTGAGATTTCGTTCGGGGTT (SEQ ID NO:4004), TTGGTGGGCGTTGAGATTTCGTTCGGG (SEQ ID NO:4005), TGGGCGTTGAGATTTCGTTCGGGGTTT (SEQ ID NO:4006), TGGTGGGCGTTGAGATTTCGTTCGGGG (SEQ ID NO:4007), GGTGGGCGTTGAGATTTCGTTCGGGGT (SEQ ID NO:4008) |
| Target419 | chr3:147109865-147109888 | TGGAGATCGTGTTGTGGGTAGTTGGTT (SEQ ID NO:4009), TTGGAGATCGTGTTGTGGGTAGTTGGT (SEQ ID NO:4010), TGGAGATCGTGTTGTGGGTAGTTGGTTT (SEQ ID NO:4011), TTGGAGATCGTGTTGTGGGTAGTTGGTT (SEQ ID NO:4012), TTTGGAGATCGTGTTGTGGGTAGTTGGT (SEQ ID NO:4013), GGTGGGGGTGGTTTGGGTAGATCGGTC (SEQ ID NO:4014), TGGGGGTGGTTTGGGTAGATCGGTCGA (SEQ ID NO:4015), AGGTGGGGGTGGTTTGGGTAGATCGGT (SEQ ID NO:4016), TAGGTGGGGGTGGTTTGGGTAGATCGG (SEQ ID NO:4017), GGTGGGGGTGGTTTGGGTAGATCGGT (SEQ ID NO:4018) |
| Target420 | chr3:147109938-147110023 | GGTTGGCGCGGTAGGGGTTCGTATAGGT (SEQ ID NO:4019), TTTAAGACGAGGGGTTGGCGCGGTAGG (SEQ ID NO:4020), GGGTTGGCGCGGTAGGGGTTCGTATAGG (SEQ ID NO:4021), GGGGTTGGCGCGGTAGGGGTTCGTATAG (SEQ ID NO:4022), GTTTTAAGACGAGGGGTTGGCGCGGTA (SEQ ID NO:4023), TCGTTTGGTGGTTTTTCGGGTTGCGGA (SEQ ID NO:4024), AGTCGTAGCGTTTAAGGGCGTGGTTGC (SEQ ID NO:4025), GTCGTTTGGTGGTTTTTCGGGTTGCGG (SEQ |

FIGURE 5 CONTINUED

ID NO:4026), CGTTTGGTGGTTTTTCGGGTTGCGGAG (SEQ ID NO:4027), TCGTTTGGTGGTTTTTCGGGTTGCGGAG (SEQ ID NO:4028)

| Target421 | chr3:147110063-147110086 | GGTTGGCGCGGTAGGGTTCGTATAGGT (SEQ ID NO:4029), GGGTTGGCGCGGTAGGGTTCGTATAGG (SEQ ID NO:4030), GGGGTTGGCGCGGTAGGGTTCGTATAG (SEQ ID NO:4031), AGGGGTTGGCGCGGTAGGGTTCGTATA (SEQ ID NO:4032), GGTTGGCGCGGTAGGGTTCGTATAGGTT (SEQ ID NO:4033), TGTTAGTCGTTTGGTGGTTTTTCGGGTTGT (SEQ ID NO:4034), GTTAGTCGTTTGGTGGTTTTTCGGGTTGT (SEQ ID NO:4035), TGTTAGTCGTTTGGTGGTTTTTCGGGTTG (SEQ ID NO:4036), ATGTTAGTCGTTTGGTGGTTTTTCGGGTTG (SEQ ID NO:4037), ATGTTAGTCGTTTGGTGGTTTTTCGGGTTGT (SEQ ID NO:4038) |
|---|---|---|
| Target422 | chr3:147110125-147110230 | TTGGTATAGGTCGGGGAGGGGGTTGGGA (SEQ ID NO:4039), CGGTTGGTATAGGTCGGGGAGGGGGTTG (SEQ ID NO:4040), TGGTATAGGTCGGGGAGGGGGTTGGGAT (SEQ ID NO:4041), TATAGGTCGGGGAGGGGTTGGGATCGG (SEQ ID NO:4042), GGGTTGGGATCGGTGGTTGCGATGTTT (SEQ ID NO:4043), GGAATTTAGGTTTTCGGGTTTTCGGGGT (SEQ ID NO:4044), AGGAATTTAGGTTTTCGGGTTTTCGGGGT (SEQ ID NO:4045), GGAATTTAGGTTTTCGGGTTTTCGGGGTT (SEQ ID NO:4046), AGGAATTTAGGTTTTCGGGTTTTCGGGGTT (SEQ ID NO:4047), CGGTAGGAATTTAGGTTTTCGGGTTTTCGGGG (SEQ ID NO:4048) |
| Target423 | chr3:147110251-147110296 | TGTTTTGTAGAGTCGAGGGAAGGCGCG (SEQ ID NO:4049), TGTTTTGTAGAGTCGAGGGAAGGCGCGA (SEQ ID NO:4050), GTTTTGTAGAGTCGAGGGAAGGCGCGA (SEQ ID NO:4051), ATGTTTTGTAGAGTCGAGGGAAGGCGCG (SEQ ID NO:4052), ATGTTTTGTAGAGTCGAGGGAAGGCGCGA (SEQ ID NO:4053), GCGTTGGGAGGTAGTTATTTGTTTAAAGCGT (SEQ ID NO:4054), AGCGTTGGGAGGTAGTTATTTGTTTAAAGCG (SEQ ID NO:4055), GTCGGTTTTTTAATTTAGAGCGTTGGGAGGT (SEQ ID NO:4056), AGCGTTGGGAGGTAGTTATTTGTTTAAAGCGT (SEQ ID NO:4057), AGTCGGTTTTTTAATTTAGAGCGTTGGGAGGT (SEQ ID NO:4058) |
| Target424 | chr3:147110349-147110461 | AGTGTTGCGGAAATGGGGGAAGAAGGT (SEQ ID NO:4059), CGGAAATGGGGGAAGAAGGTTTTTGGGCG (SEQ ID NO:4060), GTGTTGCGGAAATGGGGGAAGAAGGTT (SEQ ID NO:4061), TGGGGGAAGAAGGTTTTTGGGCGTTTT (SEQ ID NO:4062), GCGGAAATGGGGGAAGAAGGTTTTTGGGC (SEQ ID NO:4063), TTCGGGTTTAGGAGTCGTTGATTGCGT (SEQ ID NO:4064), GGGTTCGGGAATTGGGGTTTTGTTTGT (SEQ ID NO:4065), AGGGTTCGGGAATTGGGGTTTTGTTTGT (SEQ ID NO:4066), AGGGTTCGGGAATTGGGGTTTTGTTTG (SEQ ID NO:4067), CGGAGATTCGGGTTTAGGAGTCGTTGA (SEQ ID NO:4068) |
| Target425 | chr3:157812170-157812185 | AGAGGAGGTAAGGGCGTCGCGAGTTTT (SEQ ID NO:4069), AAGAGGAGGTAAGGGCGTCGCGAGTTT (SEQ ID NO:4070), GTAAGAGGAGGTAAGGGCGTCGCGAGT (SEQ ID NO:4071), TAAGAGGAGGTAAGGGCGTCGCGAGTT (SEQ ID NO:4072), AGGAGGTAAGGGCGTCGCGAGTTTTTC (SEQ ID NO:4073), AGGTTCGCGGAGGTAGTTAGGTTCGGC (SEQ ID NO:4074), CGGAGAGGTTCGCGGAGGTAGTTAGGT (SEQ ID NO:4075), GAGGTTCGCGGAGGTAGTTAGGTTCGGC (SEQ ID NO:4076), GAGGTTCGCGGAGGTAGTTAGGTTCGG (SEQ ID NO:4077), AGAGGTTCGCGGAGGTAGTTAGGTTCGG (SEQ ID NO:4078) |
| Target426 | chr3:157812206-157812227 | AGAGGAGGTAAGGGCGTCGCGAGTTTT (SEQ ID NO:4079), AAGAGGAGGTAAGGGCGTCGCGAGTTT (SEQ ID NO:4080), GTAAGAGGAGGTAAGGGCGTCGCGAGT (SEQ ID NO:4081), TAAGAGGAGGTAAGGGCGTCGCGAGTT (SEQ ID NO:4082), AGGAGGTAAGGGCGTCGCGAGTTTTTC (SEQ ID NO:4083), AGTTAGGTGGGTTCGGCGCGGAGATTC (SEQ ID NO:4084), CGGAGAGGTTCGCGGAGGTAGTTAGGT (SEQ ID NO:4085), AGTTAGGTGGGTTCGGCGCGGAGATT (SEQ ID NO:4086), GTTAGGTGGGTTCGGCGCGGAGATTCG (SEQ ID NO:4087), GAGTTAGGTGGGTTCGGCGCGGAGAT (SEQ ID NO:4088) |
| Target427 | chr3:157812296-157812438 | TCGTCGGATTTGGTTGTTTTCGCGGGT (SEQ ID NO:4089), TTCGTCGGATTTGGTTGTTTTCGCGGGT (SEQ ID NO:4090), TTCGTCGGATTTGGTTGTTTTCGCGGG (SEQ ID NO:4091), TTTCGTCGGATTTGGTTGTTTTCGCGGG (SEQ ID NO:4092), CGTCGGATTTGGTTGTTTTCGCGGGT (SEQ ID NO:4093), TGCGATAGGAGTTAGGTGGGTTCGGCG (SEQ ID NO:4094), AGTTCGAGGTTAAAGGAGGCGGTGCGT (SEQ ID NO:4095), AGTTAGGTGGGTTCGGCGCGGAGATTC (SEQ ID NO:4096), GAGTTAGGTGGGTTCGGCGCGGAGATT (SEQ ID NO:4097), GATAGGAGTTAGGTGGGTTCGGCGCGG (SEQ ID NO:4098) |
| Target428 | chr3:157812457-157812476 | TGGAGATTTTGGAGTAGGGGAGATGGTGGT (SEQ ID NO:4099), GGAGATTTTGGAGTAGGGGAGATGGTGGT (SEQ ID NO:4100), TGGAGATTTTGGAGTAGGGGAGATGGTGG (SEQ ID NO:4101), GGAGATTTTGGAGTAGGGGAGATGGTGG (SEQ ID NO:4102), GGAGATTTTGGAGTAGGGGAGATGGTGGTT (SEQ ID NO:4103) |
| Target429 | chr3:157812608-157812618 | CGTGTTGGGATTTGGGTTAGGATTAGGGT (SEQ ID NO:4104), TCGTGTTGGGATTTGGGTTAGGATTAGGGT (SEQ ID NO:4105), TCGTGTTGGGATTTGGGTTAGGATTAGGG (SEQ ID NO:4106), CGTGTTGGGATTTGGGTTAGGATTAGGGTT (SEQ ID NO:4107), TTCGTGTTGGGATTTGGGTTAGGATTAGGG (SEQ ID NO:4108), TCGTCGTGGTTTTGTGGTTTTTAGCGA (SEQ ID NO:4109), CGTCGTGGTTTTGTGGTTTTTAGCGAGT (SEQ ID NO:4110), TCGTCGTGGTTTTGTGGTTTTTAGCGAGT (SEQ ID NO:4111), TCGTCGTGGTTTTGTGGTTTTTAGCGAG (SEQ ID NO:4112), TTCGTCGTGGTTTTGTGGTTTTTAGCGA (SEQ ID NO:4113) |

FIGURE 5 CONTINUED

| Target430 | chr3:157812620-157812652 | CGTGTTGGGATTTGGGTTAGGATTAGGGT (SEQ ID NO:4114),<br>TCGTGTTGGGATTTGGGTTAGGATTAGGGT (SEQ ID NO:4115),<br>TCGTGTTGGGATTTGGGTTAGGATTAGGG (SEQ ID NO:4116),<br>CGTGTTGGGATTTGGGTTAGGATTAGGGTT (SEQ ID NO:4117),<br>TTCGTGTTGGGATTTGGGTTAGGATTAGGG (SEQ ID NO:4118), TCGTCGTGGTTTTGTGGTTTTTAGCGA<br>(SEQ ID NO:4119), CGTCGTGGTTTTGTGGTTTTTAGCGAGT (SEQ ID NO:4120),<br>TCGTCGTGGTTTTGTGGTTTTTAGCGAGT (SEQ ID NO:4121), TCGTCGTGGTTTTGTGGTTTTTAGCGAG<br>(SEQ ID NO:4122), TTCGTCGTGGTTTTGTGGTTTTTAGCGA (SEQ ID NO:4123) |
| Target431 | chr3:170137078-170137103 | TCGGGTAAGGATTCGAGTTTGGCGGCG (SEQ ID NO:4124), CGGGTAAGGATTCGAGTTTGGCGGCG (SEQ<br>ID NO:4125), TCGGGTAAGGATTCGAGTTTGGCGGC (SEQ ID NO:4126),<br>AGTTGGGTTTTAAGGGGTTGTGGGTCG (SEQ ID NO:4127), GTTGGGTTTTAAGGGGTTGTGGGTCGA<br>(SEQ ID NO:4128), TGGGAGTCGTCGTTAAGTTCGGGTTTT (SEQ ID NO:4129),<br>TTGGGAGTCGTCGTTAAGTTCGGGTTT (SEQ ID NO:4130), TTTGGGAGTCGTCGTTAAGTTCGGGTT (SEQ<br>ID NO:4131), ATTTGGGAGTCGTCGTTAAGTTCGGGT (SEQ ID NO:4132),<br>GGATTTGGGAGTCGTCGTTAAGTTCGGGT (SEQ ID NO:4133) |
| Target432 | chr3:170137305-170137869 | TTTCGCGTCGTTGGGTTGGATAGGGAC (SEQ ID NO:4134), GTTTCGCGTCGTTGGGTTGGATAGGGA (SEQ<br>ID NO:4135), TTTATTGGGGAGATACGGAGCGCGTCG (SEQ ID NO:4136),<br>GTTTCGCGTCGTTGGGTTGGATAGGGAC (SEQ ID NO:4137), CGTTGGGTTGGATAGGGACGAGCGGG<br>(SEQ ID NO:4138), ATTTCGGGAAGCGGACGGTGGAAGGAT (SEQ ID NO:4139),<br>CGGGGGGTAGCGGAGATGGTTTTGGGTA (SEQ ID NO:4140), TATTTCGGGAAGCGGACGGTGGAAGGA<br>(SEQ ID NO:4141), CGGAGATGGTTTTGGGTACGTGCGGGA (SEQ ID NO:4142),<br>TTTCGGGAAGCGGACGGTGGAAGGATG (SEQ ID NO:4143) |
| Target433 | chr3:171175787-171176317 | TCGTTGCGTAGGGGGGTAGTCGGTTTT (SEQ ID NO:4144), TTCGTTGCGTAGGGGGGTAGTCGGTTTT (SEQ<br>ID NO:4145), TTTCGTTGCGTAGGGGGGTAGTCGGTTT (SEQ ID NO:4146),<br>ATTTCGTTGCGTAGGGGGGTAGTCGGTT (SEQ ID NO:4147), CGTTGCGTAGGGGGGTAGTCGGTTTTTG (SEQ<br>ID NO:4148), CGTAGCGGGGTGGGGTTGGTAATAGGG (SEQ ID NO:4149),<br>GGGGTGGGGTTGGTAATAGGGTGGGTG (SEQ ID NO:4150), ATGGATGGTTTCGATTGGGGGGTGGGGT<br>(SEQ ID NO:4151), CGGGAAGTGGTAAAGGGGGAAGGGGTT (SEQ ID NO:4152),<br>GGGTGGGGTTGGTAATAGGGTGGGTGT (SEQ ID NO:4153) |
| Target434 | chr3:181444205-181444223 | AGGATGAGGGTGGTGGTGGTTTTTGGG (SEQ ID NO:4154), GGATGAGGGTGGTGGTGGTTTTTGGGA<br>(SEQ ID NO:4155), AGGATGAGGGTGGTGGTGGTTTTTGGGA (SEQ ID NO:4156),<br>TGAGGGTGGTGGTGGTTTTTGGGAGAA (SEQ ID NO:4157), GGATGAGGGTGGTGGTGGTTTTTGGGAG<br>(SEQ ID NO:4158) |
| Target435 | chr3:181444455-181444464 | GTTTTGAAAGGTAGGGTTCGCGGCGGT (SEQ ID NO:4159), AGTTTTGAAAGGTAGGGTTCGCGGCGG<br>(SEQ ID NO:4160), AGTTTTGAAAGGTAGGGTTCGCGGCGGT (SEQ ID NO:4161),<br>TTTTGAAAGGTAGGGTTCGCGGCGGT (SEQ ID NO:4162), TAGTTTTGAAAGGTAGGGTTCGCGGCGG<br>(SEQ ID NO:4163) |
| Target436 | chr3:188012659-188012871 | CGTTTAGGAGGTGTCGTTCGAGTTTTGGT (SEQ ID NO:4164), CGTTTAGGAGGTGTCGTTCGAGTTTTGG<br>(SEQ ID NO:4165), AGGAGGTGTCGTTCGAGTTTTGGTTAGT (SEQ ID NO:4166),<br>TCGTTTAGGAGGTGTCGTTCGAGTTTTGG (SEQ ID NO:4167), TCGTTTAGGAGGTGTCGTTCGAGTTTTGGT<br>(SEQ ID NO:4168), AGGTGGGATAATGATTTTGATGGAGGATGGG (SEQ ID NO:4169),<br>GGTGGGATAATGATTTTGATGGAGGATGGGA (SEQ ID NO:4170),<br>AGGTGGGATAATGATTTTGATGGAGGATGGGA (SEQ ID NO:4171),<br>AAGGTGGGATAATGATTTTGATGGAGGATGGG (SEQ ID NO:4172),<br>GGTGGGATAATGATTTTGATGGAGGATGGGAA (SEQ ID NO:4173) |
| Target437 | chr3:188012918-188012956 | GGTGGACGTGTGTAGAGGTTGAAGGAG (SEQ ID NO:4174), GGTGGACGTGTGTAGAGGTTGAAGGAGA<br>(SEQ ID NO:4175), GGTGGACGTGTGTAGAGGTTGAAGGAGAG (SEQ ID NO:4176),<br>GGTGGACGTGTGTAGAGGTTGAAGGAGAGT (SEQ ID NO:4177),<br>TGGACGTGTGTAGAGGTTGAAGGAGAGT (SEQ ID NO:4178) |
| Target438 | chr3:192125830-192125856 | CGGGGGTTTCGAGGTGTTTTGAGGAGG (SEQ ID NO:4179), GGGGGTTTCGAGGTGTTTTGAGGAGGG<br>(SEQ ID NO:4180), ACGGGGGTTTCGAGGTGTTTTGAGGAGG (SEQ ID NO:4181),<br>GGGGGTTTCGAGGTGTTTTGAGGAGGGA (SEQ ID NO:4182), ACGGGGGTTTCGAGGTGTTTTGAGGAG<br>(SEQ ID NO:4183), AAGACGGGCGTTTTTTGTGCGAGAGGT (SEQ ID NO:4184),<br>AGACGGGCGTTTTTTGTGCGAGAGGTA (SEQ ID NO:4185), GACGGGCGTTTTTTGTGCGAGAGGTAC<br>(SEQ ID NO:4186), AGACGGGCGTTTTTTGTGCGAGAGGTAC (SEQ ID NO:4187),<br>AGACGGGCGTTTTTTGTGCGAGAGGT (SEQ ID NO:4188) |
| Target439 | chr3:192125889-192126115 | GTTTTTCGGTTTGCGTTTCGTCGGGGC (SEQ ID NO:4189), GCGTTCGTTTTTGTTGGGGTTGGAGCG (SEQ<br>ID NO:4190), GCGAGGGTAGGATTTGGGCGGTTAGGG (SEQ ID NO:4191),<br>GGCGAGGGTAGGATTTGGGCGGTTAGG (SEQ ID NO:4192), GGGCGAGGGTAGGATTTGGGCGGTTAG<br>(SEQ ID NO:4193), TCGGAGGGCGTAGTAGAGGTTGGGGTT (SEQ ID NO:4194),<br>CGGAGGGCGTAGTAGAGGTTGGGGTTT (SEQ ID NO:4195), AGTCGGAGGGCGTAGTAGAGGTTGGGG<br>(SEQ ID NO:4196), GTCGGAGGGCGTAGTAGAGGTTGGGGT (SEQ ID NO:4197),<br>AAGTCGGAGGGCGTAGTAGAGGTTGGG (SEQ ID NO:4198) |
| Target440 | chr3:192126116-192126199 | GTTTTTCGGTTTGCGTTTCGTCGGGGC (SEQ ID NO:4199), GTTAGGGAAAGGGTAGTCGCGGGGAGG<br>(SEQ ID NO:4200), GGTTAGGGAAAGGGTAGTCGCGGGGAG (SEQ ID NO:4201),<br>GGAAAGGGTAGTCGCGGGGAGGTAGTG (SEQ ID NO:4202), TTAGGGAAAGGGTAGTCGCGGGGAGGT |

FIGURE 5 CONTINUED

|  |  | (SEQ ID NO:4203), TCGTTTTGGGGTGTAAGTTTGGGGTGT (SEQ ID NO:4204), AGAGGGTTTGGGATCGTTTCGTTTCGT (SEQ ID NO:4205), GAGGGTTTGGGATCGTTTCGTTTCGTT (SEQ ID NO:4206), TTCGGTCGTTAGAGGTTGGGGAAGTTT (SEQ ID NO:4207), TTTCGGTCGTTAGAGGTTGGGGAAGTT (SEQ ID NO:4208) |
|---|---|---|
| Target441 | chr3:192126244-192126266 | TTTTAATTTTTGGCGGTCGGGGGGCGG (SEQ ID NO:4209), TTTTTAATTTTTGGCGGTCGGGGGGCG (SEQ ID NO:4210), TTTAATTTTTGGCGGTCGGGGGGCGG (SEQ ID NO:4211), TTTTTAATTTTTGGCGGTCGGGGGGCGG (SEQ ID NO:4212), TTTAATTTTTGGCGGTCGGGGGGCGGG (SEQ ID NO:4213), TCGTTTTGGGGTGTAAGTTTGGGGTGT (SEQ ID NO:4214), AGAGGGTTTGGGATCGTTTCGTTTCGT (SEQ ID NO:4215), CGATCGTTTTGGGGTGTAAGTTTGGGGT (SEQ ID NO:4216), CGATCGTTTTGGGGTGTAAGTTTGGGG (SEQ ID NO:4217), TCGATCGTTTTGGGGTGTAAGTTTGGGGT (SEQ ID NO:4218) |
| Target442 | chr3:192126283-192126367 | TTTTAATTTTTGGCGGTCGGGGGGCGG (SEQ ID NO:4219), TCGGCGTTTAAGGGGGTAGTGGGGAGTT (SEQ ID NO:4220), ATCGGCGTTTAAGGGGGTAGTGGGGAGT (SEQ ID NO:4221), TTTTTAATTTTTGGCGGTCGGGGGGCG (SEQ ID NO:4222), TTTAATTTTTGGCGGTCGGGGGGCGG (SEQ ID NO:4223), TCGTTTTGGGGTGTAAGTTTGGGGTGT (SEQ ID NO:4224), CGATCGTTTTGGGGTGTAAGTTTGGGGT (SEQ ID NO:4225), CGATCGTTTTGGGGTGTAAGTTTGGGG (SEQ ID NO:4226), TCGATCGTTTTGGGGTGTAAGTTTGGGGT (SEQ ID NO:4227), TCGATCGTTTTGGGGTGTAAGTTTGGGG (SEQ ID NO:4228) |
| Target443 | chr3:193894534-193894595 | CGTGGAGTTGTTGTTAGAGGTGCGGGA (SEQ ID NO:4229), TCGTGGAGTTGTTGTTAGAGGTGCGGG (SEQ ID NO:4230), TCGTGGAGTTGTTGTTAGAGGTGCGGGA (SEQ ID NO:4231), GTCGGTGTTTGTAGGCGGTTGTTGAGT (SEQ ID NO:4232), CGTGGAGTTGTTGTTAGAGGTGCGGGAT (SEQ ID NO:4233), CGGGGGTTCGGTCGTTTAGTTGGGTTG (SEQ ID NO:4234), GGGGGTTCGGTCGTTTAGTTGGGTTGG (SEQ ID NO:4235), GGGGTTCGGTCGTTTAGTTGGGTTGGT (SEQ ID NO:4236), GGGGGTTCGGTCGTTTAGTTGGGTTGGT (SEQ ID NO:4237), GGGGTTCGGTCGTTTAGTTGGGTTGGTT (SEQ ID NO:4238) |
| Target444 | chr3:193894619-193894705 | CGTGGAGTTGTTGTTAGAGGTGCGGGA (SEQ ID NO:4239), TCGTGGAGTTGTTGTTAGAGGTGCGGG (SEQ ID NO:4240), TCGTGGAGTTGTTGTTAGAGGTGCGGGA (SEQ ID NO:4241), TGGGCGGTCGGATTTTCGTTTGAGTTGT (SEQ ID NO:4242), GGGCGGTCGGATTTTCGTTTGAGTTGT (SEQ ID NO:4243), AGGGTTGGAAGAGTGTAAATAGGATTGCGT (SEQ ID NO:4244), AGGATTGCGTGAGGTTTCGTGTTTATGTTT (SEQ ID NO:4245), AGGGTTGGAAGAGTGTAAATAGGATTGCGTG (SEQ ID NO:4246), GGGTTGGAAGAGTGTAAATAGGATTGCGTGA (SEQ ID NO:4247), AGTGTAAATAGGATTGCGTGAGGTTTCGTGT (SEQ ID NO:4248) |
| Target445 | chr3:196367455-196367942 | GGAGGAGGTCGGATCGGGGGTTTTAGG (SEQ ID NO:4249), GATTGGAGGAGGTCGGATCGGGGGTTT (SEQ ID NO:4250), TCGGATAGGGTTGGTCGGGGTTGTTGT (SEQ ID NO:4251), ATTGGAGGAGGTCGGATCGGGGGTTTT (SEQ ID NO:4252), CGGATAGGGTTGGTCGGGGTTGTTGTG (SEQ ID NO:4253), CGAGGGTTACGGAAGAGCGTTCGAGTT (SEQ ID NO:4254), CGAGGGTTACGGAAGAGCGTTCGAGTTT (SEQ ID NO:4255), CGAGGGTTACGGAAGAGCGTTCGAGT (SEQ ID NO:4256), GAGGGTTACGGAAGAGCGTTCGAGTTT (SEQ ID NO:4257), CGAGGGTTACGGAAGAGCGTTCGAGTTTT (SEQ ID NO:4258) |
| Target446 | chr3:196387459-196387506 | GTCGTCGAGGGAGTGGTGGTTTAGTTT (SEQ ID NO:4259), GTCGTCGAGGGAGATGGTGGTTTAGTTT (SEQ ID NO:4260), GTCGTCGAGGGAGATGGTGGTTTAGT (SEQ ID NO:4261), TCGTCGAGGGAGATGGTGGTTTAGTTTT (SEQ ID NO:4262), GTCGTCGAGGGAGATGGTGGTTTAGTTTT (SEQ ID NO:4263), TGGTGGAGGTTTAGGTGGGAGAGGGAA (SEQ ID NO:4264), TTGGTGGAGGTTTAGGTGGGAGAGGGA (SEQ ID NO:4265), GGTGGAGGTTTAGGTGGGAGAGGGAAGG (SEQ ID NO:4266), TGGAGGTTTAGGTGGGAGAGGGAAGGT (SEQ ID NO:4267), GTGGAGGTTTAGGTGGGAGAGGGAAGGT (SEQ ID NO:4268) |
| Target447 | chr3:196387611-196387699 | TTAGTTCGGTGAGCGTTTCGGGGGGGTT (SEQ ID NO:4269), TTTAGTTCGGTGAGCGTTTCGGGGGGT (SEQ ID NO:4270), GTGAGCGTTTCGGGGGGTTCGTGTTTT (SEQ ID NO:4271), TAGTTCGGTGAGCGTTTCGGGGGGGTC (SEQ ID NO:4272), TGAGCGTTTCGGGGGGGTTCGTGTTTTC (SEQ ID NO:4273) |
| Target448 | chr3:196387727-196387781 | TGGTTTCGGGGTTGGTTAGTTGTTTGGGT (SEQ ID NO:4274), GGTTTCGGGGTTGGTTAGTTGTTTGGGT (SEQ ID NO:4275), TGGTTTCGGGGTTGGTTAGTTGTTTGGG (SEQ ID NO:4276), TGTCGGAGTTGTATTTGGTTTCGGGGT (SEQ ID NO:4277), GGTTTCGGGGTTGGTTAGTTGTTTGGG (SEQ ID NO:4278), TTGGCGAAGAGGTTAGGGGGGACGTTT (SEQ ID NO:4279), ATTGGCGAAGAGGTTAGGGGGGACGTT (SEQ ID NO:4280), TGGCGAAGAGGTTAGGGGGGACGTTTA (SEQ ID NO:4281), AGGGGGGACGTTTAGGGAGTTGGTTGGA (SEQ ID NO:4282), TATTGGCGAAGAGGTTAGGGGGGACGT (SEQ ID NO:4283) |
| Target449 | chr3:197639602-197639700 | GCGTTACGTGGTTTTGTAGTGTTGGTGA (SEQ ID NO:4284), GCGTTACGTGGTTTTGTAGTGTTGGTGAA (SEQ ID NO:4285), TGCGGGGAAGACGTATTGGTATTTGATTGT (SEQ ID NO:4286), GCGTTACGTGGTTTTGTAGTGTTGGTGAAT (SEQ ID NO:4287), AGTTTTGCGGGGAAGACGTATTGGTATTTG (SEQ ID NO:4288) |
| Target450 | chr3:197639785-197639810 | GTGGCGCGGTATTGTGTGTGGATTGC (SEQ ID NO:4289), AGAGTAGTAGTTCGGTCGGTAGTTGAGGT (SEQ ID NO:4290), GAGAGTAGTAGTTCGGTCGGTAGTTGAGGT (SEQ ID NO:4291), TGAGAGTAGTAGTTCGGTCGGTAGTTGAGG (SEQ ID NO:4292), TGAGAGTAGTAGTTCGGTCGGTAGTTGAGGT (SEQ ID NO:4293), |

FIGURE 5 CONTINUED

|  |  |  |
|---|---|---|
|  |  | TGGAGCGTCGTTTTTGTTTTTTAGTGGGT (SEQ ID NO:4294), TTGGAGCGTCGTTTTTGTTTTTTAGTGGGT (SEQ ID NO:4295), TTTGGAGCGTCGTTTTTGTTTTTTAGTGGGT (SEQ ID NO:4296), TTGGAGCGTCGTTTTTGTTTTTTAGTGGGTA (SEQ ID NO:4297), TTTTGGAGCGTCGTTTTTGTTTTTTAGTGGGT (SEQ ID NO:4298) |
| Target451 | chr3:197639879-197639946 | GCGGTATTGTGTGGATTGCGTGTGTTT (SEQ ID NO:4299), GCGGTATTGTGTGGATTGCGTGTGTTTT (SEQ ID NO:4300), GCGGTATTGTGTGGATTGCGTGTGTT (SEQ ID NO:4301), AGGGGGGATTTCGGAGTGTTAGGAAGAGT (SEQ ID NO:4302), TGTGGGGTTTAAAAAGGGGGATTTCGGA (SEQ ID NO:4303), TGGGTCGTGGAATTTGTGTGTGGGAGG (SEQ ID NO:4304), TGGGTCGTGGAATTTGTGTGTGGGAGGA (SEQ ID NO:4305), GGGTCGTGGAATTTGTGTGTGGGAGGA (SEQ ID NO:4306), TTGGGTCGTGGAATTTGTGTGTGGGAGG (SEQ ID NO:4307), TTGGGTCGTGGAATTTGTGTGTGGGAGGA (SEQ ID NO:4308) |
| Target452 | chr4:2813724-2813793 | AGGTGGTTTTGCGGGGAGGTAGTAGGG (SEQ ID NO:4309), GGTGGTTTTGCGGGGAGGTAGTAGGGA (SEQ ID NO:4310), GGTGGTTTTGCGGGGAGGTAGTAGGGAG (SEQ ID NO:4311), GAGGTGGTTTTGCGGGGAGGTAGTAGGG (SEQ ID NO:4312), TGGTTTTGCGGGGAGGTAGTAGGGAGT (SEQ ID NO:4313), GAGGTTTTGAAAGTTGTTTGGGGGTTAGGGT (SEQ ID NO:4314), TGAGGTTTTGAAAGTTGTTTGGGGGTTAGGG (SEQ ID NO:4315), TGAGGTTTTGAAAGTTGTTTGGGGGTTAGGGT (SEQ ID NO:4316), GGTTTTGAAAGTTGTTTGGGGGTTAGGGTTGT (SEQ ID NO:4317), AGGTTTTGAAAGTTGTTTGGGGGTTTAGGGTTG (SEQ ID NO:4318) |
| Target453 | chr4:2813941-2814002 | GGGAATAGGAAGTTTCGGGTGGGGAGG (SEQ ID NO:4319), AGGGAATAGGAAGTTTCGGGTGGGGAGG (SEQ ID NO:4320), GGGAATAGGAAGTTTCGGGTGGGGAGGA (SEQ ID NO:4321), AGGGAATAGGAAGTTTCGGGTGGGGAGGA (SEQ ID NO:4322), CGGATGGTGGATGAGGGGTAGTTTTGGGT (SEQ ID NO:4323), TGTGAGGTTTGACGCGTTTGGTTGTTT (SEQ ID NO:4324), TGTTTTTGAGGTTTGTGGTCGTCGGTGT (SEQ ID NO:4325), ATGTGAGGTTTGACGCGTTTGGTTGTT (SEQ ID NO:4326), GTTTTTGAGGTTTGTGGTCGTCGGTGT (SEQ ID NO:4327), TGTTTTTGAGGTTTGTGGTCGTCGGTG (SEQ ID NO:4328) |
| Target454 | chr4:2814004-2814242 | AGTTTCGGGTGGGGAGGAAGTATCGGC (SEQ ID NO:4329), GGGTGGGGAGGAAGTATCGGCGGTTAT (SEQ ID NO:4330), GTTTCGGGTGGGGAGGAAGTATCGGCG (SEQ ID NO:4331), TTTCGGGTGGGGAGGAAGTATCGGCG (SEQ ID NO:4332), AAGTTTCGGGTGGGGAGGAAGTATCGGC (SEQ ID NO:4333), CGGGGTCGGTGTTTTGGGGTTTAGGGA (SEQ ID NO:4334), GGGTCGGTGTTTTGGGGTTTAGGGAGG (SEQ ID NO:4335), GGGGTCGGTGTTTTGGGGTTTAGGGAG (SEQ ID NO:4336), GGGTCGGTGTTTTGGGGTTTAGGGAGGT (SEQ ID NO:4337), GGGGTCGGTGTTTTGGGGTTTAGGGAGG (SEQ ID NO:4338) |
| Target455 | chr4:2814283-2814401 | ATTGGGGTTCGGGAGGCGGTATTGGTT (SEQ ID NO:4339), AGGATTGGGGTTCGGGAGGCGGTATTG (SEQ ID NO:4340), TTGGGGTTCGGGAGGCGGTATTGGTTT (SEQ ID NO:4341), TTTTTAGGATTGGGGTTCGGGAGGCGGT (SEQ ID NO:4342), GATTGGGGTTCGGGAGGCGGTATTGGT (SEQ ID NO:4343), TTTTTGTCGGTCGTATGTGATGGGGGG (SEQ ID NO:4344), TTTTTTGTCGGTCGTATGTGATGGGGGG (SEQ ID NO:4345), ACGGTTAGTTTCGAGGAAGGTTGTGGT (SEQ ID NO:4346), TTTTGTCGGTCGTATGTGATGGGGGGG (SEQ ID NO:4347), ACGGTTAGTTTCGAGGAAGGTTGTGTT (SEQ ID NO:4348) |
| Target456 | chr4:3311897-3312297 | GGGCGGGTAGGTTTATGTTGTTTTGGGT (SEQ ID NO:4349), GGGCGGGTAGGTTTATGTTGTTTTGGG (SEQ ID NO:4350), AGGGCGGGTAGGTTTATGTTGTTTTGGGT (SEQ ID NO:4351), AGGGCGGGTAGGTTTATGTTGTTTTGGG (SEQ ID NO:4352), CGTGTTTTGTTGTGTTTAGGGCGGGTAGGT (SEQ ID NO:4353), TGGGGTGTAGCGTGGATTGGAGATAGT (SEQ ID NO:4354), TTTTTGGGGTGTAGCGTGGATTGGAGA (SEQ ID NO:4355), TTTTGGGGTGTAGCGTGGATTGGAGAT (SEQ ID NO:4356), TGGGGTGTAGCGTGGATTGGAGATAGTT (SEQ ID NO:4357), TTGGGGTGTAGCGTGGATTGGAGATAGT (SEQ ID NO:4358) |
| Target457 | chr4:8582287-8582301 | GGTTGGGAGGTTCGGTTGGAGGTGTGA (SEQ ID NO:4359), GGCGTGGCGAGGGTTGTGTTGTTTAGG (SEQ ID NO:4360), AGGCGTGGCGAGGGTTGTGTTGTTTAG (SEQ ID NO:4361), GCGTGGCGAGGGTTGTGTTGTTTAGGA (SEQ ID NO:4362), TAGGGTTGGGAGGTTCGGTTGGAGGTG (SEQ ID NO:4363), GCGTGGTAGGATGGGATTTTGCGCGTT (SEQ ID NO:4364), CGTGGCGTGGTAGGATGGGATTTTGCG (SEQ ID NO:4365), TCGTGGCGTGGTAGGATGGGATTTTGC (SEQ ID NO:4366), GCGTGGTAGGATGGGATTTTGCGCGT (SEQ ID NO:4367), TTTTGAGGTTGAAGCGAGGCGTAGGGG (SEQ ID NO:4368) |
| Target458 | chr4:8859601-8859631 | GAGTTTCGGGTTTTAGTTTTAGGAGTCGCG (SEQ ID NO:4369), GGGGATTCGAGGTTTTTGAGGATTTTAAATTGTCG (SEQ ID NO:4370), GGGGATTCGAGGTTTTTGAGGATTTTAAATTGTCGT (SEQ ID NO:4371), AGGGGATTCGAGGTTTTTGAGGATTTTAAATTGTCG (SEQ ID NO:4372), GGGATTCGAGGTTTTTGAGGATTTTAAATTGTCGT (SEQ ID NO:4373), GCGGTTTTTGGAATTGGGGTTCGGGGT (SEQ ID NO:4374), ACGCGGTTTTTGGAATTGGGGTTCGGG (SEQ ID NO:4375), CGCGGTTTTTGGAATTGGGGTTCGGGG (SEQ ID NO:4376), GACGCGGTTTTTGGAATTGGGGTTCGG (SEQ ID NO:4377), AGACGCGGTTTTTGGAATTGGGGTTCGG (SEQ ID NO:4378) |
| Target459 | chr4:8859638-8859725 | GGAGGGGTGAAGTCGAGGGGTGGTTTT (SEQ ID NO:4379), GAGAGAGTAGGGTTTCGGGCGTTCGGG (SEQ ID NO:4380), TGAGAGAGTAGGGTTTCGGGCGTTCGG (SEQ ID NO:4381), AGGAGGGGTGAAGTCGAGGGGTGGTTT (SEQ ID NO:4382), GAGGAGGGGTGAAGTCGAGGGGTGGTT |

FIGURE 5 CONTINUED (SEQ ID NO:4383), GGTTTGGGGGCGGTCGGTTTGTTGTTT (SEQ ID NO:4384),
GTTTGGGGGCGGTCGGTTTGTTGTTTT (SEQ ID NO:4385), GGTTTGGGGGCGGTCGGTTTGTTGTT (SEQ
ID NO:4386), GGTTTGGGGGCGGTCGGTTTGTTGTTTT (SEQ ID NO:4387),
TTGGGGGCGGTCGGTTTGTTGTTTTTT (SEQ ID NO:4388)

Target460    chr4:8859834-8859850    GGGGGGAGGGGGTAGTAGGTCGATCGTT (SEQ ID NO:4389), GTGGGGGAGGGGGTAGTAGGTCGATCG
(SEQ ID NO:4390), CGTGGGGGAGGGGGTAGTAGGTCGATC (SEQ ID NO:4391),
TGGGGGAGGGGGTAGTAGGTCGATCG (SEQ ID NO:4392), GGGGGAGGGGGTAGTAGGTCGATCGT (SEQ
ID NO:4393), ATGGACGGGGGTTTCGATCGGTTTGGG (SEQ ID NO:4394),
AATGGACGGGGGTTTCGATCGGTTTGG (SEQ ID NO:4395), AAATGGACGGGGGTTTCGATCGGTTTGG
(SEQ ID NO:4396), AATGGACGGGGGTTTCGATCGGTTTGGG (SEQ ID NO:4397),
TGGACGGGGGTTTCGATCGGTTTGGG (SEQ ID NO:4398)

Target461    chr4:8859927-8859996    GGGGGAGGGGGTAGTAGGTCGATCGTT (SEQ ID NO:4399), GAGGTTCGGATGTGTTGACGTTGCGGT
(SEQ ID NO:4400), GTGGGGGAGGGGGTAGTAGGTCGATCG (SEQ ID NO:4401),
CGTGGGGGAGGGGGTAGTAGGTCGATC (SEQ ID NO:4402), AGGTTCGGATGTGTTGACGTTGCGGTT
(SEQ ID NO:4403)

Target462    chr4:8859998-8860005    GAGGTTCGGATGTGTTGACGTTGCGGT (SEQ ID NO:4404), AGGTTCGGATGTGTTGACGTTGCGGTT (SEQ
ID NO:4405), GAGGTTCGGATGTGTTGACGTTGCGGTT (SEQ ID NO:4406),
AGGTTCGGATGTGTTGACGTTGCGGT (SEQ ID NO:4407), GGTTCGGATGTGTTGACGTTGCGGTTA (SEQ
ID NO:4408)

Target463    chr4:8862980-8863016    GGGTTTTAGCGGGGTAGGTAGGGTTCGG (SEQ ID NO:4409), GGTTTTAGCGGGGTAGGTAGGGTTCGG
(SEQ ID NO:4410), GGGTTTTAGCGGGGTAGGTAGGGTTCG (SEQ ID NO:4411),
AGGGTTTTAGCGGGGTAGGTAGGGTTCG (SEQ ID NO:4412), GGTTTTAGCGGGGTAGGTAGGGTTCGGA
(SEQ ID NO:4413), GTCGTTCGGTCGGGTAGTGGGAAGTCG (SEQ ID NO:4414),
GTTCGGTCGGGTAGTGGGAAGTCGGTG (SEQ ID NO:4415), TTCGGTCGGGTAGTGGGAAGTCGGTGT
(SEQ ID NO:4416), TCGGTCGGGTAGTGGGAAGTCGGTGTC (SEQ ID NO:4417),
CGGTCGGGTAGTGGGAAGTCGGTGTC (SEQ ID NO:4418)

Target464    chr4:8863143-8863155    TTTGGGAGGGGCGGGTCGGGATTAGAG (SEQ ID NO:4419), GTTTGGGAGGGGCGGGTCGGGATTAGA
(SEQ ID NO:4420), GTTTGGGAGGGGCGGGTCGGGATTAG (SEQ ID NO:4421),
TTTGGGAGGGGCGGGTCGGGATTAGA (SEQ ID NO:4422), TTTGGGAGGGGCGGGTCGGGATTAG (SEQ
ID NO:4423), GCGCGCGTGTATTTGTTTTGGTTATCG (SEQ ID NO:4424),
GCGCGCGTGTATTTGTTTTGGTTATCGA (SEQ ID NO:4425), GCGCGCGTGTATTTGTTTTGGTTATCGAGG
(SEQ ID NO:4426), GCGCGCGTGTATTTGTTTTGGTTATCGAGGT (SEQ ID NO:4427),
GCGCGCGTGTATTTGTTTTGGTTATCGAG (SEQ ID NO:4428)

Target465    chr4:8863239-8863244    CGACGGGGGGAGTTTCGGTGATTAGGGT (SEQ ID NO:4429), TACGTTCGGGAAAGGGGGGTAGGGAAC
(SEQ ID NO:4430), ACGTTCGGGAAAGGGGGGTAGGGAAC (SEQ ID NO:4431),
TTACGTTCGGGAAAGGGGGGTAGGGAA (SEQ ID NO:4432), ATTACGTTCGGGAAAGGGGGGTAGGGA
(SEQ ID NO:4433), GCGTAGTTTCGGTCGTGTTTTCGGGGT (SEQ ID NO:4434),
GCGTAGTTTCGGTCGTGTTTTCGGGGTT (SEQ ID NO:4435), GTTTCGGTCGTGTTTTCGGGGTTTCGT (SEQ
ID NO:4436), AGTTTCGGTCGTGTTTTCGGGGTTTCGT (SEQ ID NO:4437),
AGTTTCGGTCGTGTTTTCGGGGTTTCG (SEQ ID NO:4438)

Target466    chr4:8863260-8863266    CGACGGGGGGAGTTTCGGTGATTAGGGT (SEQ ID NO:4439), TACGTTCGGGAAAGGGGGGTAGGGAAC
(SEQ ID NO:4440), ACGTTCGGGAAAGGGGGGTAGGGAAC (SEQ ID NO:4441),
TTACGTTCGGGAAAGGGGGGTAGGGAA (SEQ ID NO:4442), ATTACGTTCGGGAAAGGGGGGTAGGGA
(SEQ ID NO:4443), GCGTAGTTTCGGTCGTGTTTTCGGGGT (SEQ ID NO:4444),
GCGTAGTTTCGGTCGTGTTTTCGGGGTT (SEQ ID NO:4445), GTTTCGGTCGTGTTTTCGGGGTTTCGT (SEQ
ID NO:4446), AGTTTCGGTCGTGTTTTCGGGGTTTCGT (SEQ ID NO:4447),
AGTTTCGGTCGTGTTTTCGGGGTTTCG (SEQ ID NO:4448)

Target467    chr4:8863304-8863317    CGACGGGGGGAGTTTCGGTGATTAGGGT (SEQ ID NO:4449), ACGTTCGGGAAAGGGGGGTAGGGAAC
(SEQ ID NO:4450), GTTCGGGAAAGGGGGGTAGGGAACGA (SEQ ID NO:4451),
CGACGGGGGGAGTTTCGGTGATTAGGGTA (SEQ ID NO:4452), CGACGGGGGGAGTTTCGGTGATTAGGG
(SEQ ID NO:4453), GCGTAGTTTCGGTCGTGTTTTCGGGGT (SEQ ID NO:4454),
GCGTAGTTTCGGTCGTGTTTTCGGGGTT (SEQ ID NO:4455), AGTTTCGGTCGTGTTTTCGGGGTTTCG (SEQ
ID NO:4456), CGTAGTTTCGGTCGTGTTTTCGGGGTT (SEQ ID NO:4457),
GCGTAGTTTCGGTCGTGTTTTCGGGGTTT (SEQ ID NO:4458)

Target468    chr4:8863338-8863351    GTAGGCGGAGTTTCGGGGGTACGGTC (SEQ ID NO:4459), GTAGGCGGAGTTTCGGGGGTACGGTCG
(SEQ ID NO:4460), CGTAGGCGGAGTTTCGGGGGTACGGTC (SEQ ID NO:4461),
GTAGGCGGAGTTTCGGGGGTACGGT (SEQ ID NO:4462), TAGGCGGAGTTTCGGGGGTACGGTC (SEQ ID
NO:4463), CGACGGCGTTTTAGGTTAGAGTTGTGGG (SEQ ID NO:4464),
CGACGGCGTTTTAGGTTAGAGTTGTGGGT (SEQ ID NO:4465), ACGGCGTTTTAGGTTAGAGTTGTGGGT
(SEQ ID NO:4466), CGACGGCGTTTTAGGTTAGAGTTGTGG (SEQ ID NO:4467),
GACGGCGTTTTAGGTTAGAGTTGTGGGT (SEQ ID NO:4468)

Target469    chr4:8863569-8863591    TGGGTCGGGCGTTGTAGATTAAGTACGT (SEQ ID NO:4469), GGGTCGGGCGTTGTAGATTAAGTACGT
(SEQ ID NO:4470), TGGGTCGGGCGTTGTAGATTAAGTACG (SEQ ID NO:4471),
GTGGGTCGGGCGTTGTAGATTAAGTACGT (SEQ ID NO:4472), GTGGGTCGGGCGTTGTAGATTAAGTACG
(SEQ ID NO:4473), CGTTGTAGTGTTTGGGAGGTTGCGCGT (SEQ ID NO:4474),
TCGTTGTAGTGTTTGGGAGGTTGCGCG (SEQ ID NO:4475), CGGGTGCGTTGTTTTTGGTTTTCGGGT (SEQ

FIGURE 5 CONTINUED

ID NO:4476), TCGGGTGCGTTGTTTTTGGTTTTCGGGT (SEQ ID NO:4477), TCGGGTGCGTTGTTTTTGGTTTTCGGG (SEQ ID NO:4478)

| Target470 | chr4:8863629-8863637 | TTCGGGATTAAGAGGAGGTCGTTGCGC (SEQ ID NO:4479), ATTCGGGATTAAGAGGAGGTCGTTGCGC (SEQ ID NO:4480), TCGGGATTAAGAGGAGGTCGTTGCGC (SEQ ID NO:4481), ATTCGGGATTAAGAGGAGGTCGTTGCG (SEQ ID NO:4482), TGGGTCGGGCGTTGTAGATTAAGTACGT (SEQ ID NO:4483), CGTTGTAGTGTTTGGGAGGTTGCGCGT (SEQ ID NO:4484), TCGTTGTAGTGTTTGGGAGGTTGCGCG (SEQ ID NO:4485), TTCGTTGTAGTGTTTGGGAGGTTGCGCG (SEQ ID NO:4486), AGGGAGGACGGATAAGGGTTGAAGGGT (SEQ ID NO:4487), TGTAGTGTTTGGGAGGTTGCGCGTAGT (SEQ ID NO:4488) |
| Target471 | chr4:13543525-13543536 | CGGGAGTTGGAGTTGGGTTTTATTTTTAGGTG (SEQ ID NO:4489), CGGGAGTTGGAGTTGGGTTTTATTTTTAGGTGT (SEQ ID NO:4490), CGGGAGTTGGAGTTGGGTTTTATTTTTAGGTGTT (SEQ ID NO:4491), CGGGAGTTGGAGTTGGGTTTTATTTTTAGGTGTTT (SEQ ID NO:4492), GGGAGTTGGAGTTGGGTTTTATTTTTAGGTGTTT (SEQ ID NO:4493), CGGTTTCGGATCGGCGTTGATAGTTGT (SEQ ID NO:4494), TCGTTTGGGTTGAGGTAGCGAGTGATT (SEQ ID NO:4495), TTCGTTTGGGTTGAGGTAGCGAGTGAT (SEQ ID NO:4496), ATTCGTTTGGGTTGAGGTAGCGAGTGA (SEQ ID NO:4497), CGGTTTCGGATCGGCGTTGATAGTTGTA (SEQ ID NO:4498) |
| Target472 | chr4:13543563-13543934 | TTTTTGGCGGGGCGTTTCGTGTAGGTT (SEQ ID NO:4499), TTTTTTGGCGGGGCGTTTCGTGTAGGT (SEQ ID NO:4500), GCGGTAGTTGCGTAGGTGGAGAGCGTT (SEQ ID NO:4501), CGGAGTCGGAGCGCGGGAATTATTCGT (SEQ ID NO:4502), TTTTGGCGGGGCGTTTCGTGTAGGTTA (SEQ ID NO:4503), AAGGTGGTCGTAAAGGTGTTGGTGCGC (SEQ ID NO:4504), GGAGGAGGAGGAGTCGGCGGCGTTTAAGTT (SEQ ID NO:4505), GAGGAGGAGGAGTCGGCGGCGTTTAAG (SEQ ID NO:4506), GAGGAGGAGGAGTCGGCGGCGTTTAA (SEQ ID NO:4507), GAAGGTGGTCGTAAAGGTGTTGGTGCGC (SEQ ID NO:4508) |
| Target473 | chr4:13543948-13544043 | CGTTTTTTGCGTGGTTTGGGCGTCGTC (SEQ ID NO:4509), CGGGTTCGGATAGGTAGCGTTGGTGGT (SEQ ID NO:4510), CGGGTTCGGATAGGTAGCGTTGGTGGTT (SEQ ID NO:4511), CGTTTTTTGCGTGGTTTGGGCGTCGT (SEQ ID NO:4512), GCGTTTTTTGCGTGGTTTGGGCGTCGT (SEQ ID NO:4513), GGAGGAGGAGGAGTCGGCGGCGTTTAAGTT (SEQ ID NO:4514), GAGGAGGAGGAGTCGGCGGCGTTTAAG (SEQ ID NO:4515), GAGGAGGAGGAGTCGGCGGCGTTTAA (SEQ ID NO:4516), AGGAGGAGGAGTCGGCGGCGTTTAAG (SEQ ID NO:4517), AGGAGGAGGAGTCGGCGGCGTTTAAGT (SEQ ID NO:4518) |
| Target474 | chr4:24801646-24801871 | ATCGCGTCGGTTTGGTCGTTTCGTTCG (SEQ ID NO:4519), GGTATCGCGTCGGTTTGGTCGTTTCGT (SEQ ID NO:4520), AGGTATCGCGTCGGTTTGGTCGTTTCG (SEQ ID NO:4521), CGGTTCGCGACGGTAGTTTTTGGAGGT (SEQ ID NO:4522), TCGCGTCGGTTTGGTCGTTTCGTTCG (SEQ ID NO:4523), ACGTTGGTTTGGTTGTCGTCGCGGTTT (SEQ ID NO:4524), GGGTTTCGGGGGTTTTTGGTCGTCGTC (SEQ ID NO:4525), AGAGGGGGGTTTCGGGGGTTTTTGGTC (SEQ ID NO:4526), TAGAGGGGGGTTTCGGGGGTTTTTGGT (SEQ ID NO:4527), TACGTTGGTTTGGTTGTCGTCGCGGTT (SEQ ID NO:4528) |
| Target475 | chr4:24801881-24801888 | CGGGTTCGGGTTTTGGGAGCGTTAGG (SEQ ID NO:4529), GTCGTTTGAGCGCGGTTTTTATTCGGC (SEQ ID NO:4530), TGGTTTGTTGCGTGGTGGGCGTGTG (SEQ ID NO:4531), TGGTTTGTTGCGTGGTGGGCGTGT (SEQ ID NO:4532), GGTTTGTTGCGTGGTGGGCGTGTG (SEQ ID NO:4533), ATTTTTGGGTGGAGAGGGTTGCGGGGA (SEQ ID NO:4534), GGGTTTCGGGGGTTTTTGGTCGTCGTT (SEQ ID NO:4535), AGAGGGGGGTTTCGGGGGTTTTTGGTC (SEQ ID NO:4536), TAGAGGGGGGTTTCGGGGGTTTTTGGT (SEQ ID NO:4537), TTTTTGGGTGGAGAGGGTTGCGGGGAG (SEQ ID NO:4538) |
| Target476 | chr4:24801971-24802055 | GCGGTTTTTATTCGGCGGCGGTTAGGG (SEQ ID NO:4539), GGCGGCGGTTAGGGGATTTTCGAGGTTT (SEQ ID NO:4540), CGGTTTTTATTCGGCGGCGGTTAGGGA (SEQ ID NO:4541), ATTCGGCGGCGGTTAGGGGATTTTCGAG (SEQ ID NO:4542), TTCGGCGGCGGTTAGGGGATTTTCGAGG (SEQ ID NO:4543), GGGGAAGGAGGGTTTGGGTGGAAAGGT (SEQ ID NO:4544), TGGGGAAGGAGGGTTTGGGTGGAAAGG (SEQ ID NO:4545), ATTTTTGGGTGGAGAGGGTTGCGGGGA (SEQ ID NO:4546), ATTGAGTGGGGGGTTTCGAGGGTTGGG (SEQ ID NO:4547), GGGTGGAGAGGGTTGCGGGGAGATTTT (SEQ ID NO:4548) |
| Target477 | chr4:38672865-38673330 | TGTTTGGGGAGGTGGAAGAGTGGTGTGT (SEQ ID NO:4549), GTTTGGGGAGGTGGAAGAGTGGTGTGT (SEQ ID NO:4550), TGTTTGGGGAGGTGGAAGAGTGGTGTG (SEQ ID NO:4551), TTTGGGGAGGTGGAAGAGTGGTGTGT (SEQ ID NO:4552), TTGTTTGGGGAGGTGGAAGAGTGGTGT (SEQ ID NO:4553), TCGGAGAAGATAGAACGTGGGGATAGTTTGT (SEQ ID NO:4554), CGGAGAAGATAGAACGTGGGGATAGTTTGTT (SEQ ID NO:4555), TCGGAGAAGATAGAACGTGGGGATAGTTTGTT (SEQ ID NO:4556), CGGAGAAGATAGAACGTGGGGATAGTTTGTTT (SEQ ID NO:4557), TCGGAGAAGATAGAACGTGGGGATAGTTTGTTT (SEQ ID NO:4558) |
| Target478 | chr4:40858832-40859392 | CGTTTATTGGTTGTTGGGGGAGGCGCGT (SEQ ID NO:4559), GTTGGGGAGGCGCGTGGTTTCGTTTTA (SEQ ID NO:4560), AAGTCGGGCGGGGATGTCGTTTTAGGT (SEQ ID NO:4561), TCGGGCGGGGATGTCGTTTTAGGTGTT (SEQ ID NO:4562), CGGTGTCGTCGTTAAGTAGTCGCGCG (SEQ ID NO:4563), GACGGTTGGAAGGGTTGAAGAGGGGGT (SEQ ID NO:4564), |

FIGURE 5 CONTINUED

|  |  | TGGACGGTTGGAAGGGTTGAAGAGGGG (SEQ ID NO:4565), AGGAAGGGAGTATGTTGGGGTGGGGGA (SEQ ID NO:4566), AGGTGAGGAAGTTGGCGAAGGAACGGT (SEQ ID NO:4567), ACGGTTGGAAGGGTTGAAGAGGGGGTT (SEQ ID NO:4568) |
| Target479 | chr4:44449387-44449403 | GAGCGGGTTGGGTCGAGAAGGTAAGAT (SEQ ID NO:4569), AGCGGGTTGGGTCGAGAAGGTAAGATT (SEQ ID NO:4570), TTTTGGTATTTGGGAGCGGGTTGGGTC (SEQ ID NO:4571), ATTTTGGTATTTGGGAGCGGGTTGGGT (SEQ ID NO:4572), GAGCGGGTTGGGTCGAGAAGGTAAGATT (SEQ ID NO:4573), GGGGTGTTCGGGGTAGGCGTTGGTTAA (SEQ ID NO:4574), TTGAGTTTCGTTGGAGGTTTCGCGGGG (SEQ ID NO:4575), TTTCGTTGGAGGTTTCGCGGGGGTGTT (SEQ ID NO:4576), TGAGTTTCGTTGGAGGTTTCGCGGGGG (SEQ ID NO:4577), GAGTTTCGTTGGAGGTTTCGCGGGGGT (SEQ ID NO:4578) |
| Target480 | chr4:44449486-44449529 | GCGTTTGTTTCGGATATTTTCGCGGGGT (SEQ ID NO:4579), GCGTTTGTTTCGGATATTTTCGCGGGG (SEQ ID NO:4580), GGTTTTTAGCGGGGTTTAAATTGGCGGCG (SEQ ID NO:4581), TTTTTAGCGGGGTTTAAATTGGCGGCG (SEQ ID NO:4582), GGGTTTTTAGCGGGGTTTAAATTGGCGGC (SEQ ID NO:4583), TTGAGTTTCGTTGGAGGTTTCGCGGGG (SEQ ID NO:4584), TTCGTTGGAGGTTTCGCGGGGGTGTTT (SEQ ID NO:4585), TTTCGTTGGAGGTTTCGCGGGGGTGTT (SEQ ID NO:4586), TGAGTTTCGTTGGAGGTTTCGCGGGGG (SEQ ID NO:4587), GAGTTTCGTTGGAGGTTTCGCGGGGGT (SEQ ID NO:4588) |
| Target481 | chr4:44449579-44450217 | GTGTTGGGAAACGTCGGGGTTGCGAAT (SEQ ID NO:4589), GTTTAGTAGGGGGCGAGGGGTGTTGGG (SEQ ID NO:4590), GGTTTAGTAGGGGGCGAGGGGTGTTGG (SEQ ID NO:4591), ACGTCGGAATTTGGCGTCGGTTTGGTT (SEQ ID NO:4592), AGCGGGGTTTAAATTGGCGGCGGTTTA (SEQ ID NO:4593), CGAGTTGTTTAGGGATAGTCGGGCGCG (SEQ ID NO:4594), CGCGTTGGTTAAGGAGGTTTTCGGGGA (SEQ ID NO:4595), TCGCGTTGGTTAAGGAGGTTTTCGGGG (SEQ ID NO:4596), TCGCGTTGGTTAAGGAGGTTTTCGGGGA (SEQ ID NO:4597), CGAGTTGTTTAGGGATAGTCGGGCGCGT (SEQ ID NO:4598) |
| Target482 | chr4:57521419-57521450 | TGTAGCGTGAGTTTTGTAGTTCGGGGG (SEQ ID NO:4599), TGTAGCGTGAGTTTTGTAGTTCGGGGGA (SEQ ID NO:4600), TAGCGTGAGTTTTGTAGTTCGGGGGAC (SEQ ID NO:4601), GTAGCGTGAGTTTTGTAGTTCGGGGGA (SEQ ID NO:4602), GTGTAGCGTGAGTTTTGTAGTTCGGGGG (SEQ ID NO:4603), GGGCGTTGTTAGGATGGTAGGAGCGGT (SEQ ID NO:4604), TTAGGAGGTTGAGGTCGGGAGGGAGGG (SEQ ID NO:4605), AGGGCGTTGTTAGGATGGTAGGAGCGG (SEQ ID NO:4606), GTCGGGAGGGAGGGCGTTGTTAGGATG (SEQ ID NO:4607), GGGAGGGAGGGCGTTGTTAGGATGGTA (SEQ ID NO:4608) |
| Target483 | chr4:57521506-57521734 | TCGGGAAGGCGAGATAGGGATAGGCGA (SEQ ID NO:4609), GTCGGGAAGGCGAGATAGGGATAGGCG (SEQ ID NO:4610), CGGGAAGGCGAGATAGGGATAGGCGAG (SEQ ID NO:4611), ATTAGAGGGGATCGAGTCGGGAAGGCG (SEQ ID NO:4612), GGGGGACGTTGTAGTGTGATGTGGTGG (SEQ ID NO:4613), TTAGGAGGTTGAGGTCGGGAGGGAGGG (SEQ ID NO:4614), TGGCGAATTAGGAGGTTGAGGTCGGGA (SEQ ID NO:4615), GGCGGGAATGTTAGAGTTGGAAGGCGT (SEQ ID NO:4616), TAGGAGGTTGAGGTCGGGAGGGAGGG (SEQ ID NO:4617), ATTAGGAGGTTGAGGTCGGGAGGGAGGG (SEQ ID NO:4618) |
| Target484 | chr4:57521777-57521797 | TCGGGAAGGCGAGATAGGGATAGGCGA (SEQ ID NO:4619), GTCGGGAAGGCGAGATAGGGATAGGCG (SEQ ID NO:4620), AGCGTGTATTTCGGGTTGTCGGGGAGA (SEQ ID NO:4621), CGGGAAGGCGAGATAGGGATAGGCGAG (SEQ ID NO:4622), GCGTGTATTTCGGGTTGTCGGGGAGAG (SEQ ID NO:4623), TCGTTTTTTATGGGCGTTCGGTTTTTTCGT (SEQ ID NO:4624), TCGTTTTTTCGTTTTTATGGGCGTTCGGT (SEQ ID NO:4625), CGTTTTTATGGGCGTTCGGTTTTTTCGTT (SEQ ID NO:4626), CGTTTTTTCGTTTTTATGGGCGTTCGGTT (SEQ ID NO:4627), TCGTTTTTATGGGCGTTCGGTTTTTTCGTT (SEQ ID NO:4628) |
| Target485 | chr4:57521838-57522347 | TTTAGTTTAGGTAGGGGTCGGGGCGCG (SEQ ID NO:4629), TCGGGGAATTACGGTTGGATGGGGGTG (SEQ ID NO:4630), AGCGTGGTGGAATTCGGGTGTTTGTCG (SEQ ID NO:4631), GCGTGGTGGAATTCGGGTGTTTGTCGA (SEQ ID NO:4632), AGCGTGTATTTCGGGTTGTCGGGGAGA (SEQ ID NO:4633), GCGTGTAGTTATCGGGGATTTGCGCGG (SEQ ID NO:4634), GAGGTTCGGGTGGGGGGTAGTCGTAAG (SEQ ID NO:4635), GTTTTTGTAAGGGGTTTCGGGGGGCGC (SEQ ID NO:4636), AGTTTTTGTAAGGGGTTTCGGGGGGCG (SEQ ID NO:4637), GGAGGTTCGGGTGGGGGGTAGTCGTAA (SEQ ID NO:4638) |
| Target486 | chr4:74864044-74864329 | GGGTCGCGCGGTTGGATAGGAGGTTTA (SEQ ID NO:4639), GGGTCGCGCGGTTGGATAGGAGGTTTAT (SEQ ID NO:4640), GGTCGCGCGGTTGGATAGGAGGTTTAT (SEQ ID NO:4641), GGGTCGCGCGGTTGGATAGGAGGTTT (SEQ ID NO:4642), TTGGCGATGGGTTTTGGTTGCGTTAGT (SEQ ID NO:4643), TGTGCGCGTTGTTGGTGTTGTTGTTGT (SEQ ID NO:4644), TGCGCGTTGTTGGTGTTGTTGTTGTTGT (SEQ ID NO:4645), TGTGCGCGTTGTTGGTGTTGTTGTTGTT (SEQ ID NO:4646), TTGTGCGCGTTGTTGGTGTTGTTGTTGT (SEQ ID NO:4647), GCGCGTTGTTGGTGTTGTTGTTGTTGT (SEQ ID NO:4648) |
| Target487 | chr4:74864368-74864404 | CGGTCGCGGGTTTTTGAATTGGGTGGA (SEQ ID NO:4649), GGAGGAGCGGAGATTGGAGGAGCGAAG (SEQ ID NO:4650), GGGTCGCGCGGTTGGATAGGAGGTTTA (SEQ ID NO:4651), GAGGAGCGGAGATTGGAGGAGCGAAGA (SEQ ID NO:4652), TGGAGGAGCGGAGATTGGAGGAGCGAA (SEQ ID NO:4653), TGGGGAGAGATGAGTGTAGATAAAAGGAGTGT (SEQ ID NO:4654), TGAGTTTTTTGTTAGTGGGGGAGAGATGAGTGT (SEQ ID NO:4655), AGTGGGGAGAGATGAGTGTAGATAAAAGGAGT (SEQ ID NO:4656), |

FIGURE 5 CONTINUED

GTGGGGAGAGATGAGTGTAGATAAAAGGAGTGT (SEQ ID NO:4657),
AGTGGGGAGAGATGAGTGTAGATAAAAGGAGTG (SEQ ID NO:4658)

| | | |
|---|---|---|
| Target488 | chr4:74864587-74864615 | GTGGAAAGAAGAGGTTGGGGGAGGGGG (SEQ ID NO:4659), GTGGGGAGGGTGGTTAGGAGGAGTTGC (SEQ ID NO:4660), TGGTGGGGAGGGTGGTTAGGAGGAGTT (SEQ ID NO:4661), TTGGTGGGGAGGGTGGTTAGGAGGAGT (SEQ ID NO:4662), GGGAGGGTGGTTAGGAGGAGTTGCGTG (SEQ ID NO:4663), GAGGGTTGCGTGTTTTAGAAAAGTCGGT (SEQ ID NO:4664), AGAGGGTTGCGTGTTTTAGAAAAGTCGGT (SEQ ID NO:4665), AGAGGGTTGCGTGTTTTAGAAAAGTCGGTA (SEQ ID NO:4666), TAGAGGGTTGCGTGTTTTAGAAAAGTCGGT (SEQ ID NO:4667), TTAGAGGGTTGCGTGTTTTAGAAAAGTCGGT (SEQ ID NO:4668) |
| Target489 | chr4:84035837-84035923 | TCGAGTAGGAAATGTTTTGTGGTTTGGGAGA (SEQ ID NO:4669), CGAGTAGGAAATGTTTTGTGGTTTGGGAGAG (SEQ ID NO:4670), CGAGTAGGAAATGTTTTGTGGTTTGGGAGAGA (SEQ ID NO:4671), TCGAGTAGGAAATGTTTTGTGGTTTGGGAGAG (SEQ ID NO:4672), TTCGAGTAGGAAATGTTTTGTGGTTTGGGAGA (SEQ ID NO:4673) |
| Target490 | chr4:94755670-94755872 | AGCGTGGGGGTGGTTTGTCGTAATGTG (SEQ ID NO:4674), GCGTGGGGGTGGTTTGTCGTAATGTGA (SEQ ID NO:4675), AAGCGTGGGGGTGGTTTGTCGTAATGT (SEQ ID NO:4676), AGCGTGGGGGTGGTTTGTCGTAATGTGA (SEQ ID NO:4677), GGGAGAGGTAGGGGAGGAGAGAAGTCGG (SEQ ID NO:4678), TTGAGGAGGTCGGGGAGGGGGTGATGAT (SEQ ID NO:4679), AGGAGGAGGTCGAGGTTGAGGAGGTCG (SEQ ID NO:4680), TGAGGAGGTCGGGGAGGGGTGATGATG (SEQ ID NO:4681), GGTCGGGGAGGGGTGATGATGGTGTTA (SEQ ID NO:4682), GTTGAGGAGGTCGGGGAGGGGTGATGA (SEQ ID NO:4683) |
| Target491 | chr4:94755903-94755934 | AGGTAGTTTTTCGGGGAGTTGTGCGGT (SEQ ID NO:4684), GGTAGTTTTTCGGGGAGTTGTGCGGTT (SEQ ID NO:4685), AGGTAGTTTTTCGGGGAGTTGTGCGGTT (SEQ ID NO:4686), TAGGTAGTTTTTCGGGGAGTTGTGCGGT (SEQ ID NO:4687), TAGGTAGTTTTTCGGGGAGTTGTGCGG (SEQ ID NO:4688), GCGTAGTTGGGGGAGGAGAGGGGTTTC (SEQ ID NO:4689), TAGTTGGGGGAGGAGAGGGGTTTCGGT (SEQ ID NO:4690), CGGTTTTTCGTTGCGTAGTTGGGGGAGG (SEQ ID NO:4691), CGTAGTTGGGGGAGGAGAGGGGTTTCG (SEQ ID NO:4692), TTCGTTGCGTAGTTGGGGGAGGAGAGG (SEQ ID NO:4693) |
| Target492 | chr4:94755975-94755997 | GCGTAGTTGGGGGAGGAGAGGGGTTTC (SEQ ID NO:4694), TAGTTGGGGGAGGAGAGGGGTTTCGGT (SEQ ID NO:4695), TTGCGTGTTGGGTTGGTTGTTGGGAGG (SEQ ID NO:4696), GTTGGGAGGTGTAGTGGGTAGTGGCGG (SEQ ID NO:4697), CGGTTTTTCGTTGCGTAGTTGGGGGAGG (SEQ ID NO:4698) |
| Target493 | chr4:94756002-94756032 | GCGTAGTTGGGGGAGGAGAGGGGTTTC (SEQ ID NO:4699), TAGTTGGGGGAGGAGAGGGGTTTCGGT (SEQ ID NO:4700), TTGCGTGTTGGGTTGGTTGTTGGGAGG (SEQ ID NO:4701), GTTGGGAGGTGTAGTGGGTAGTGGCGG (SEQ ID NO:4702), CGGTTTTTCGTTGCGTAGTTGGGGGAGG (SEQ ID NO:4703) |
| Target494 | chr4:94756141-94756154 | TAAGGGGAGGGGAAGTTGGAGGCGGTA (SEQ ID NO:4704), GTTAAGGGGAGGGGAAGTTGGAGGCGG (SEQ ID NO:4705), TGTTAAGGGGAGGGGAAGTTGGAGGCG (SEQ ID NO:4706), TTAAGGGGAGGGGAAGTTGGAGGCGGT (SEQ ID NO:4707), AAGGGGAGGGGAAGTTGGAGGCGGTAG (SEQ ID NO:4708) |
| Target495 | chr4:101111813-101111928 | TCGGGTTATTGGGATCGTAATTTCGGGT (SEQ ID NO:4709), CGGGTTATTGGGATCGTAATTTCGGGTGT (SEQ ID NO:4710), TCGGGTTATTGGGATCGTAATTTCGGGTGT (SEQ ID NO:4711), TCGGGTTATTGGGATCGTAATTTCGGGTG (SEQ ID NO:4712), TTCGGGTTATTGGGATCGTAATTTCGGGT (SEQ ID NO:4713), GGACGTTCGGGGAGGGGTCGTATTGAA (SEQ ID NO:4714), CGGACGTTCGGGGAGGGGTCGTATTGA (SEQ ID NO:4715), GGACGTTCGGGGAGGGGTCGTATTGAAT (SEQ ID NO:4716), CGGGAGTAGTTTGAGTGTGAAAGCGCGG (SEQ ID NO:4717), GGACGTTCGGGGAGGGGTCGTATTGA (SEQ ID NO:4718) |
| Target496 | chr4:101111950-101111971 | TGTTTTCGGTAGCGGGAAGTTTTAAGCG (SEQ ID NO:4719), TCGGGTTATTGGGATCGTAATTTCGGGT (SEQ ID NO:4720), CGGGTTATTGGGATCGTAATTTCGGGTGT (SEQ ID NO:4721), TCGGGTTATTGGGATCGTAATTTCGGGTGT (SEQ ID NO:4722), TCGGGTTATTGGGATCGTAATTTCGGGTG (SEQ ID NO:4723) |
| Target497 | chr4:102712099-102712325 | ATTTGGACGTTACGAGGAGGGAGCGCG (SEQ ID NO:4724), TATTTGGACGTTACGAGGAGGGAGCGCG (SEQ ID NO:4725), CGTATTCGGAGGGGTTTGACGTCGAGGT (SEQ ID NO:4726), CGTATTCGGAGGGGTTTGACGTCGAGG (SEQ ID NO:4727), GTTCGGCGGGTAGTAGTGCGTAGGTTT (SEQ ID NO:4728), GGATTTTGATTCGGGTGTTGGGGAAAGT (SEQ ID NO:4729), AGGATTTTGATTCGGGTGTTGGGGAAAGT (SEQ ID NO:4730), TGGGTTGTTGGCGGTAGGATAAAAAGGA (SEQ ID NO:4731), GGATTTTGATTCGGGTGTTGGGGAAAGTT (SEQ ID NO:4732), TGGGTTGTTTGGCGGTAGGATAAAAAGGAG (SEQ ID NO:4733) |
| Target498 | chr4:102712452-102712469 | GGGAGTTTTGGTTAGCGGGTTATTTTTAGTGTT (SEQ ID NO:4734), GGGAGTTTTGGTTAGCGGGTTATTTTTAGTGTT (SEQ ID NO:4735), GGGAGTTTTGGTTAGCGGGTTATTTTTAGTGTTG (SEQ ID NO:4736), GGGAGTTTTGGTTAGCGGGTTATTTTTAGTGTTGT (SEQ ID NO:4737), GGAGTTTTGGTTAGCGGGTTATTTTTAGTGTTGT (SEQ ID NO:4738), |

FIGURE 5 CONTINUED

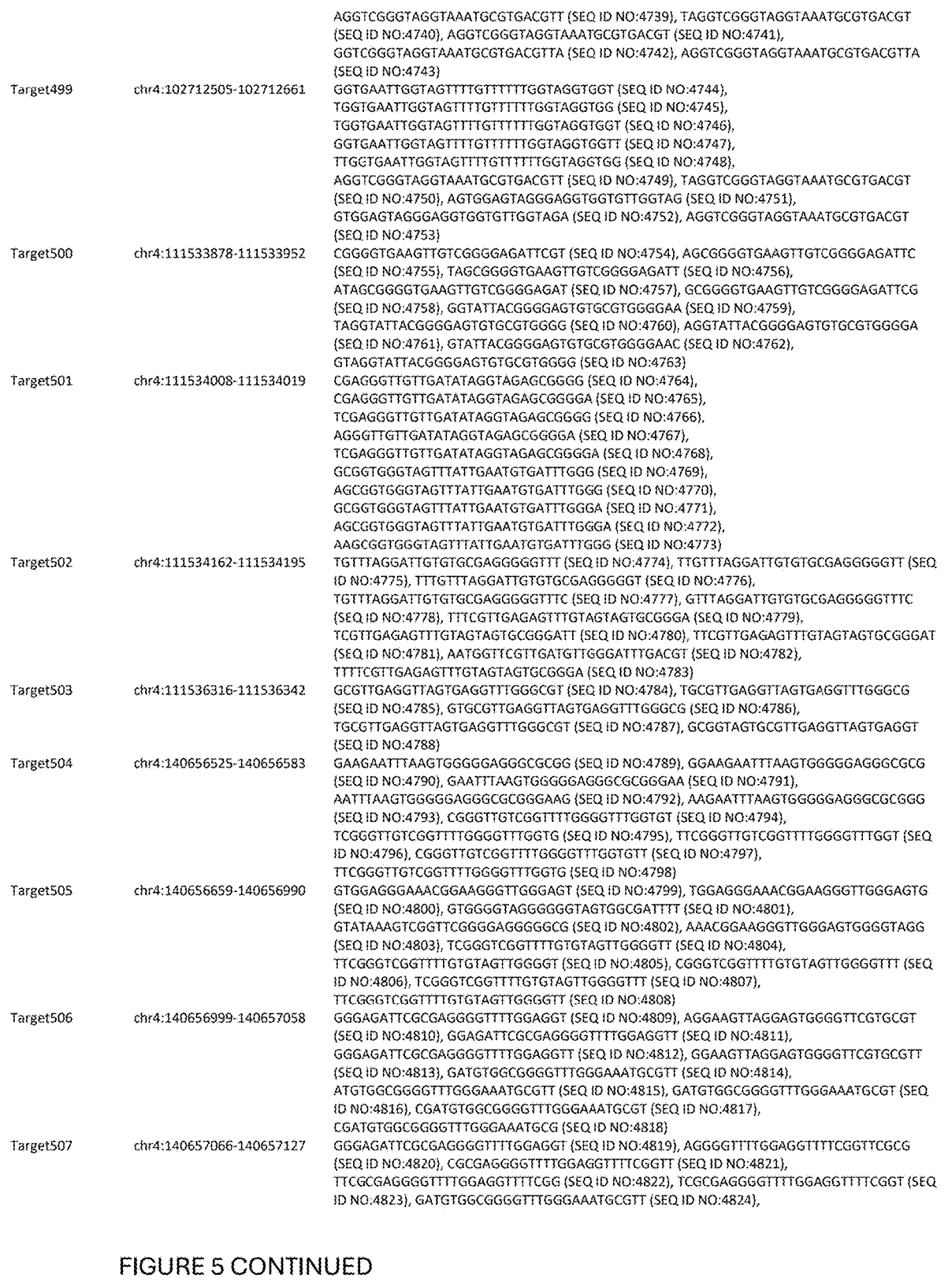

|  |  | AGGTCGGGTAGGTAAATGCGTGACGTT (SEQ ID NO:4739), TAGGTCGGGTAGGTAAATGCGTGACGT (SEQ ID NO:4740), AGGTCGGGTAGGTAAATGCGTGACGT (SEQ ID NO:4741), GGTCGGGTAGGTAAATGCGTGACGTTA (SEQ ID NO:4742), AGGTCGGGTAGGTAAATGCGTGACGTTA (SEQ ID NO:4743) |
|---|---|---|
| Target499 | chr4:102712505-102712661 | GGTGAATTGGTAGTTTTGTTTTTTGGTAGGTGGT (SEQ ID NO:4744), TGGTGAATTGGTAGTTTTGTTTTTTGGTAGGTGG (SEQ ID NO:4745), TGGTGAATTGGTAGTTTTGTTTTTTGGTAGGTGGT (SEQ ID NO:4746), GGTGAATTGGTAGTTTTGTTTTTTGGTAGGTGGTT (SEQ ID NO:4747), TTGGTGAATTGGTAGTTTTGTTTTTTGGTAGGTGG (SEQ ID NO:4748), AGGTCGGGTAGGTAAATGCGTGACGTT (SEQ ID NO:4749), TAGGTCGGGTAGGTAAATGCGTGACGT (SEQ ID NO:4750), AGTGGAGTAGGGAGGTGGTGTTGGTAG (SEQ ID NO:4751), GTGGAGTAGGGAGGTGGTGTTGGTAGA (SEQ ID NO:4752), AGGTCGGGTAGGTAAATGCGTGACGT (SEQ ID NO:4753) |
| Target500 | chr4:111533878-111533952 | CGGGGGTGAAGTTGTCGGGGAGATTCGT (SEQ ID NO:4754), AGCGGGGTGAAGTTGTCGGGGAGATTC (SEQ ID NO:4755), TAGCGGGGTGAAGTTGTCGGGGAGATT (SEQ ID NO:4756), ATAGCGGGGTGAAGTTGTCGGGGAGAT (SEQ ID NO:4757), GCGGGGTGAAGTTGTCGGGGAGATTCG (SEQ ID NO:4758), GGTATTACGGGGAGTGTGCGTGGGGAA (SEQ ID NO:4759), TAGGTATTACGGGGAGTGTGCGTGGGG (SEQ ID NO:4760), AGGTATTACGGGGAGTGTGCGTGGGGA (SEQ ID NO:4761), GTATTACGGGGAGTGTGCGTGGGGAAC (SEQ ID NO:4762), GTAGGTATTACGGGGAGTGTGCGTGGGG (SEQ ID NO:4763) |
| Target501 | chr4:111534008-111534019 | CGAGGGTTGTTGATATAGGTAGAGCGGGG (SEQ ID NO:4764), CGAGGGTTGTTGATATAGGTAGAGCGGGGA (SEQ ID NO:4765), TCGAGGGTTGTTGATATAGGTAGAGCGGGG (SEQ ID NO:4766), AGGGTTGTTGATATAGGTAGAGCGGGGA (SEQ ID NO:4767), TCGAGGGTTGTTGATATAGGTAGAGCGGGGA (SEQ ID NO:4768), GCGGTGGGTAGTTTATTGAATGTGATTTGGG (SEQ ID NO:4769), AGCGGTGGGTAGTTTATTGAATGTGATTTGGG (SEQ ID NO:4770), GCGGTGGGTAGTTTATTGAATGTGATTTGGGA (SEQ ID NO:4771), AGCGGTGGGTAGTTTATTGAATGTGATTTGGGA (SEQ ID NO:4772), AAGCGGTGGGTAGTTTATTGAATGTGATTTGGG (SEQ ID NO:4773) |
| Target502 | chr4:111534162-111534195 | TGTTTAGGATTGTGTGCGAGGGGGTTT (SEQ ID NO:4774), TTGTTTAGGATTGTGTGCGAGGGGGTT (SEQ ID NO:4775), TTTGTTTAGGATTGTGTGCGAGGGGGT (SEQ ID NO:4776), TGTTTAGGATTGTGTGCGAGGGGGTTTC (SEQ ID NO:4777), GTTTAGGATTGTGTGCGAGGGGGTTTC (SEQ ID NO:4778), TTTCGTTGAGAGTTTGTAGTAGTGCGGGA (SEQ ID NO:4779), TCGTTGAGAGTTTGTAGTAGTGCGGGATT (SEQ ID NO:4780), TTCGTTGAGAGTTTGTAGTAGTGCGGGAT (SEQ ID NO:4781), AATGGTTCGTTGATGTTGGGATTTGACGT (SEQ ID NO:4782), TTTTCGTTGAGAGTTTGTAGTAGTGCGGGA (SEQ ID NO:4783) |
| Target503 | chr4:111536316-111536342 | GCGTTGAGGTTAGTGAGGTTTGGGCGT (SEQ ID NO:4784), TGCGTTGAGGTTAGTGAGGTTTGGGCG (SEQ ID NO:4785), GTGCGTTGAGGTTAGTGAGGTTTGGGCG (SEQ ID NO:4786), TGCGTTGAGGTTAGTGAGGTTTGGGCGT (SEQ ID NO:4787), GCGGTAGTGCGTTGAGGTTAGTGAGGT (SEQ ID NO:4788) |
| Target504 | chr4:140656525-140656583 | GAAGAATTTAAGTGGGGGAGGGCGCGG (SEQ ID NO:4789), GGAAGAATTTAAGTGGGGGAGGGCGCG (SEQ ID NO:4790), GAATTTAAGTGGGGGAGGGCGCGGGAA (SEQ ID NO:4791), AATTTAAGTGGGGGAGGGCGCGGGAAG (SEQ ID NO:4792), AAGAATTTAAGTGGGGGAGGGCGCGGG (SEQ ID NO:4793), CGGGTTGTCGGTTTTGGGGTTTGGTGT (SEQ ID NO:4794), TCGGGTTGTCGGTTTTGGGGTTTGGTG (SEQ ID NO:4795), TTCGGGTTGTCGGTTTTGGGGTTTGGT (SEQ ID NO:4796), CGGGTTGTCGGTTTTGGGGTTTGGTGTT (SEQ ID NO:4797), TTCGGGTTGTCGGTTTTGGGGTTTGGTG (SEQ ID NO:4798) |
| Target505 | chr4:140656659-140656990 | GTGGAGGGAAACGGAAGGGTTGGGAGT (SEQ ID NO:4799), TGGAGGGAAACGGAAGGGTTGGGAGTG (SEQ ID NO:4800), GTGGGGTAGGGGGGGTAGTGGCGATTTT (SEQ ID NO:4801), GTATAAAGTCGGTTCGGGGAGGGGGGCG (SEQ ID NO:4802), AAACGGAAGGGTTGGGAGTGGGGTAGG (SEQ ID NO:4803), TCGGGTCGGTTTTGTGTAGTTGGGGT (SEQ ID NO:4804), TTCGGGTCGGTTTTGTGTAGTTGGGGT (SEQ ID NO:4805), CGGGTCGGTTTTGTGTAGTTGGGGTTT (SEQ ID NO:4806), TCGGGTCGGTTTTGTGTAGTTGGGGTTT (SEQ ID NO:4807), TTCGGGTCGGTTTTGTGTAGTTGGGGTT (SEQ ID NO:4808) |
| Target506 | chr4:140656999-140657058 | GGGAGATTCGCGAGGGGTTTTGGAGGT (SEQ ID NO:4809), AGGAAGTTAGGAGTGGGGTTCGTGCGT (SEQ ID NO:4810), GGAGATTCGCGAGGGGTTTTGGAGGTT (SEQ ID NO:4811), GGGAGATTCGCGAGGGGTTTTGGAGGT (SEQ ID NO:4812), GGAAGTTAGGAGTGGGGTTCGTGCGTT (SEQ ID NO:4813), GATGTGGCGGGGTTTGGGAAATGCGTT (SEQ ID NO:4814), ATGTGGCGGGGTTTGGGAAATGCGTT (SEQ ID NO:4815), GATGTGGCGGGGTTTGGGAAATGCGT (SEQ ID NO:4816), CGATGTGGCGGGGTTTGGGAAATGCGT (SEQ ID NO:4817), CGATGTGGCGGGGTTTGGGAAATGCG (SEQ ID NO:4818) |
| Target507 | chr4:140657066-140657127 | GGGAGATTCGCGAGGGGTTTTGGAGGT (SEQ ID NO:4819), AGGGGTTTTGGAGGTTTTCGGTTCGCG (SEQ ID NO:4820), CGCGAGGGGTTTTGGAGGTTTTCGGTT (SEQ ID NO:4821), TTCGCGAGGGGTTTTGGAGGTTTTCGG (SEQ ID NO:4822), TCGCGAGGGGTTTTGGAGGTTTTCGGT (SEQ ID NO:4823), GATGTGGCGGGGTTTGGGAAATGCGTT (SEQ ID NO:4824), |

FIGURE 5 CONTINUED

|  |  | ATGTGGCGGGGTTTGGGAAATGCGTT (SEQ ID NO:4825), GATGTGGCGGGGTTTGGGAAATGCGT (SEQ ID NO:4826), CGATGTGGCGGGGTTTGGGAAATGCGT (SEQ ID NO:4827), CGATGTGGCGGGGTTTGGGAAATGCG (SEQ ID NO:4828) |
|---|---|---|
| Target508 | chr4:147560029-147560039 | GGCGCGGGGAGAGGGGAGTATAATTCG (SEQ ID NO:4829), GCGTTTTTTGGTAAGGGAGGGCGGAGG (SEQ ID NO:4830), GGCGTTTTTTGGTAAGGGAGGGCGGAG (SEQ ID NO:4831), GCGCGGGGAGAGGGGAGTATAATTCGT (SEQ ID NO:4832), AGTCGGCGTTTTTTGGTAAGGGAGGGC (SEQ ID NO:4833), CGCGTTTTTTCGTCGTTTTTGTTGTTAGTTTGA (SEQ ID NO:4834), CGCGTTTTTTCGTCGTTTTTGTTGTTAGTTTGAA (SEQ ID NO:4835), CGCGTTTTTTCGTCGTTTTTGTTGTTAGTTTGAAC (SEQ ID NO:4836) |
| Target509 | chr4:147560073-147560116 | GGCGCGGGGAGAGGGGAGTATAATTCG (SEQ ID NO:4837), GCGCGGGGAGAGGGGAGTATAATTCGT (SEQ ID NO:4838), AGGCGCGGGGAGAGGGGAGTATAATTC (SEQ ID NO:4839), GCGCGGGGAGAGGGGAGTATAATTCGTC (SEQ ID NO:4840), GTAGGCGCGGGGAGAGGGGAGTATAAT (SEQ ID NO:4841), CGGGTTAGTCGGGGTTGGAGTTGGGAA (SEQ ID NO:4842), AGTCGGGGTTGGAGTTGGGAAGGGTTG (SEQ ID NO:4843), TGTCGGGTTAGTCGGGGTTGGAGTTGG (SEQ ID NO:4844), TCGGGGTTGGAGTTGGGAAGGGTTGTG (SEQ ID NO:4845), GTCGGGGTTGGAGTTGGGAAGGGTTGT (SEQ ID NO:4846) |
| Target510 | chr4:147560126-147560184 | GAGGAGCGGGGGTAGTTTCGGGTGTC (SEQ ID NO:4847), AGGAGCGGGGGTAGTTTCGGGTGTC (SEQ ID NO:4848), GAGGAGCGGGGGTAGTTTCGGGTGT (SEQ ID NO:4849), GCGGCGGCGGGTGAGTTTAATTTCG (SEQ ID NO:4850), GATTGATAGTAGAGGCGGCGAAGGAGC (SEQ ID NO:4851), CGGGTTAGTCGGGGTTGGAGTTGGGAA (SEQ ID NO:4852), AGTCGGGGTTGGAGTTGGGAAGGGTTG (SEQ ID NO:4853), TGTCGGGTTAGTCGGGGTTGGAGTTGG (SEQ ID NO:4854), TCGGGGTTGGAGTTGGGAAGGGTTGTG (SEQ ID NO:4855), GTCGGGGTTGGAGTTGGGAAGGGTTGT (SEQ ID NO:4856) |
| Target511 | chr4:147560209-147560239 | GCGGCGGCGGGTGAGTTTAATTTCGTA (SEQ ID NO:4857), GCGGCGGCGGGTGAGTTTAATTTCGTAT (SEQ ID NO:4858), GCGGCGGCGGGTGAGTTTAATTTCGT (SEQ ID NO:4859), CGGCGGCGGGTGAGTTTAATTTCGTAT (SEQ ID NO:4860), CGGTTGGTTCGGTATTTTTCGGAGGGT (SEQ ID NO:4861), GTTCGTCGGGGCGTTGGTTCGTAGA (SEQ ID NO:4862), TTCGTCGGGGCGTTGGTTCGTAGA (SEQ ID NO:4863), GTTCGTCGGGGCGTTGGTTCGTAG (SEQ ID NO:4864), TCGTCGGGGCGTTGGTTCGTAGA (SEQ ID NO:4865), GTTCGTCGGGGCGTTGGTTCGTA (SEQ ID NO:4866) |
| Target512 | chr4:147560266-147560287 | GCGGCGGCGGGTGAGTTTAATTTCGTA (SEQ ID NO:4867), GCGGCGGCGGGTGAGTTTAATTTCGTAT (SEQ ID NO:4868), GCGGCGGCGGGTGAGTTTAATTTCGT (SEQ ID NO:4869), CGGCGGCGGGTGAGTTTAATTTCGTAT (SEQ ID NO:4870), CGGTTGGTTCGGTATTTTTCGGAGGGT (SEQ ID NO:4871), TCGGCGAGGTGTTGTGTAGTGTCGAGT (SEQ ID NO:4872), AGTTCGGCGAGGTGTTGTGTAGTGTCG (SEQ ID NO:4873), GTTCGGCGAGGTGTTGTGTAGTGTCGA (SEQ ID NO:4874), GGAGTTCGGCGAGGTGTTGTGTAGTGT (SEQ ID NO:4875), TTCGGCGAGGTGTTGTGTAGTGTCGAGT (SEQ ID NO:4876) |
| Target513 | chr4:147560324-147560344 | GTTTCGGCGGGCGGGAAGATGATGATG (SEQ ID NO:4877), TTCGGCGGGCGGGAAGATGATGATGAT (SEQ ID NO:4878), TTTCGGCGGGCGGGAAGATGATGATGA (SEQ ID NO:4879), TCGGCGGGCGGGAAGATGATGATGATG (SEQ ID NO:4880), CGGCGGGCGGGAAGATGATGATGATGT (SEQ ID NO:4881), TCGAGTTGTTGGGGGAGTTGGTCGAGG (SEQ ID NO:4882), TCGGCGAGGTGTTGTGTAGTGTCGAGT (SEQ ID NO:4883), CGAGTTGTTGGGGGAGTTGGTCGAGGG (SEQ ID NO:4884), GAGTTGTTGGGGGAGTTGGTCGAGGGC (SEQ ID NO:4885), TGTTCGAGTTGTTGGGGGAGTTGGTCG (SEQ ID NO:4886) |
| Target514 | chr4:147560372-147560403 | GTTTCGGCGGGCGGGAAGATGATGATG (SEQ ID NO:4887), TTCGGCGGGCGGGAAGATGATGATGAT (SEQ ID NO:4888), TTTCGGCGGGCGGGAAGATGATGATGA (SEQ ID NO:4889), TCGGCGGGCGGGAAGATGATGATGATG (SEQ ID NO:4890), CGGCGGGCGGGAAGATGATGATGATGT (SEQ ID NO:4891), TCGAGTTGTTGGGGGAGTTGGTCGAGG (SEQ ID NO:4892), CGAGTTGTTGGGGGAGTTGGTCGAGGG (SEQ ID NO:4893), GAGTTGTTGGGGGAGTTGGTCGAGGGC (SEQ ID NO:4894), TGTTCGAGTTGTTGGGGGAGTTGGTCG (SEQ ID NO:4895), TGTTCGAGTTGTTGGGGGAGTTGGTCGA (SEQ ID NO:4896) |
| Target515 | chr4:147560414-147560442 | CGTCGGGTTTTTCGGTTTTTATCGCGT (SEQ ID NO:4897), TCGTCGGGTTTTTCGGTTTTTATCGCGT (SEQ ID NO:4898), TCGTCGGGTTTTTCGGTTTTTATCGCG (SEQ ID NO:4899), ACGGCGGTAGTTTGTACGTGGAGTTTA (SEQ ID NO:4900), CGTCGGGTTTTTCGGTTTTTATCGCGTT (SEQ ID NO:4901), GAGTTGTTGGGGGAGTTGGTCGAGGGT (SEQ ID NO:4902), TCGAGTTGTTGGGGGAGTTGGTCGAGG (SEQ ID NO:4903), CGAGTTGTTGGGGGAGTTGGTCGAGGG (SEQ ID NO:4904), TGTTCGAGTTGTTGGGGGAGTTGGTCG (SEQ ID NO:4905), TGTTCGAGTTGTTGGGGGAGTTGGTCGA (SEQ ID NO:4906) |
| Target516 | chr4:147560460-147560533 | CGTCGGGTTTTTCGGTTTTTATCGCGT (SEQ ID NO:4907), TCGTCGGGTTTTTCGGTTTTTATCGCGT (SEQ ID NO:4908), TCGTCGGGTTTTTCGGTTTTTATCGCG (SEQ ID NO:4909), GAGTAACGTTGGTGGTGGCGGCGG (SEQ ID NO:4910), ACGGCGGTAGTTTGTACGTGGAGTTTA (SEQ ID NO:4911), CGTATCGGTGGGGTTGGAAGATAGGT (SEQ ID NO:4912), CGGTGGGGTTGGAAGATAGGTTTTTCGT (SEQ ID NO:4913), CGGTGGGGTTGGAAGATAGGTTTTTCG (SEQ ID NO:4914), TCGGTGGGGTTGGAAGATAGGTTTTTCGT (SEQ ID NO:4915), TCGGTGGGGTTGGAAGATAGGTTTTTCG (SEQ ID NO:4916) |

FIGURE 5 CONTINUED

| | | |
|---|---|---|
| Target517 | chr4:154709576-154709641 | CGGTGGTTGGTAGGAGGTGGTCGTTGT (SEQ ID NO:4917), TCGGTGGTTGGTAGGAGGTGGTCGTTG (SEQ ID NO:4918), TTCGGTGGTTGGTAGGAGGTGGTCGTT (SEQ ID NO:4919), TTTCGGTGGTTGGTAGGAGGTGGTCGT (SEQ ID NO:4920), TTCGGTGGTTGGTAGGAGGTGGTCGTTG (SEQ ID NO:4921), TGCGTGTAGGTGAAGGATCGTTGCGTT (SEQ ID NO:4922), TTGCGTGTAGGTGAAGGATCGTTGCGT (SEQ ID NO:4923), TGCGTGTAGGTGAAGGATCGTTGCGTTT (SEQ ID NO:4924), TTGCGTGTAGGTGAAGGATCGTTGCGTT (SEQ ID NO:4925), TTTGCGTGTAGGTGAAGGATCGTTGCGT (SEQ ID NO:4926) |
| Target518 | chr4:154709675-154709698 | AGGTTATCGAGGTAGACGGGGGCGAAG (SEQ ID NO:4927), GGTTATCGAGGTAGACGGGGGCGAAGA (SEQ ID NO:4928), AGGTTATCGAGGTAGACGGGGGCGAAGA (SEQ ID NO:4929), GGTTATCGAGGTAGACGGGGGCGAAGAG (SEQ ID NO:4930), TAGGTTATCGAGGTAGACGGGGGCGAA (SEQ ID NO:4931), GAAGGAGGTGTTGGAGTAGGTCGGCGT (SEQ ID NO:4932), TGAAGGAGGTGTTGGAGTAGGTCGGCG (SEQ ID NO:4933), AGGTGTTGGAGTAGGTCGGCGTTTGGA (SEQ ID NO:4934), AGGAGGTGTTGGAGTAGGTCGGCGTTT (SEQ ID NO:4935), AAGGAGGTGTTGGAGTAGGTCGGCGTT (SEQ ID NO:4936) |
| Target519 | chr4:154709745-154709760 | AGGTTATCGAGGTAGACGGGGGCGAAG (SEQ ID NO:4937), GGTTATCGAGGTAGACGGGGGCGAAGA (SEQ ID NO:4938), AGGTTATCGAGGTAGACGGGGGCGAAGA (SEQ ID NO:4939), GGTTATCGAGGTAGACGGGGGCGAAGAG (SEQ ID NO:4940), TAGGTTATCGAGGTAGACGGGGGCGAA (SEQ ID NO:4942), GAAGGAGGTGTTGGAGTAGGTCGGCGT (SEQ ID NO:4942), TGAAGGAGGTGTTGGAGTAGGTCGGCG (SEQ ID NO:4943), AGGTGTTGGAGTAGGTCGGCGTTTGGA (SEQ ID NO:4944), AGGAGGTGTTGGAGTAGGTCGGCGTTT (SEQ ID NO:4945), AAGGAGGTGTTGGAGTAGGTCGGCGTT (SEQ ID NO:4946) |
| Target520 | chr4:154709812-154709968 | AGGTAGTAGTGCGAGGCGAGGAAGAGT (SEQ ID NO:4947), TGCGTTTGTAGGAGAAGTCGGGTTGGT (SEQ ID NO:4948), TGCGAGGCGAGGAAGAGTAGTAGTAGC (SEQ ID NO:4949), GCGAGGCGAGGAAGAGTAGTAGTAGCG (SEQ ID NO:4950), GGGTTGGTTAAAGAGGAAGAGTTCGCGCG (SEQ ID NO:4951), TCGTATTGTTGTTTGGGTTCGGCGCGC (SEQ ID NO:4952), TTCGTATTGTTGTTTGGGTTCGGCGCG (SEQ ID NO:4953), GTATTGTTGTTTGGGTTCGGCGCGCG (SEQ ID NO:4954), CGTATTGTTGTTTGGGTTCGGCGCGC (SEQ ID NO:4955), GTATTGTTGTTTGGGTTCGGCGCGCGG (SEQ ID NO:4956) |
| Target521 | chr4:155663750-155663883 | CGGTGGGGATATCGCGTGTTAAGTTTGGC (SEQ ID NO:4957), GGTGGGGATATCGCGTGTTAAGTTTGGC (SEQ ID NO:4958), CGGTGGGGATATCGCGTGTTAAGTTTGG (SEQ ID NO:4959), TCGGTGGGGATATCGCGTGTTAAGTTTGG (SEQ ID NO:4960), AGCGTCGATTGGGTAGTTTTGTGGAGT (SEQ ID NO:4961), TAGGGAGTTGTCGGGTGAGGGAGTCGT (SEQ ID NO:4962), GGGAGTTGTCGGGTGAGGGAGTCGTTG (SEQ ID NO:4963), GGAGTTGTCGGGTGAGGGAGTCGTTGA (SEQ ID NO:4964), TCGGGTGAGGGAGTCGTTGAAGCGTTG (SEQ ID NO:4965), TTGTCGGGTGAGGGAGTCGTTGAAGCG (SEQ ID NO:4966) |
| Target522 | chr4:155663971-155663991 | GGAGGTATTGGAGTCGGGTTGTAGGCGT (SEQ ID NO:4967), GGAGGTATTGGAGTCGGGTTGTAGGCG (SEQ ID NO:4968), AGGAGGTATTGGAGTCGGGTTGTAGGCG (SEQ ID NO:4969), GAGGTATTGGAGTCGGGTTGTAGGCGT (SEQ ID NO:4970), AGGAGGTATTGGAGTCGGGTTGTAGGCGT (SEQ ID NO:4971) |
| Target523 | chr4:155664153-155664191 | AGGGAGGCGGATAAAGTTTCGGTGGGT (SEQ ID NO:4972), TTTTTGGCGGGCGTTGGGATTTCGTCG (SEQ ID NO:4973), GGCGGGCGTTGGGATTTCGTCGTTTTT (SEQ ID NO:4974), GGGAGGCGGATAAAGTTTCGGTGGGTG (SEQ ID NO:4975), GCGGGCGTTGGGATTTCGTCGTTTTTT (SEQ ID NO:4976), TTTGCGCGTCGGTGATTTGAATTCGAG (SEQ ID NO:4977), CGAGTTTAGTTTTTGCGCGTCGGTGAT (SEQ ID NO:4978), TTTTGCGCGTCGGTGATTTGAATTCGA (SEQ ID NO:4979), TTTTGCGCGTCGGTGATTTGAATTCGAG (SEQ ID NO:4980), GAGGGTGTGTGTAGGGCGGGGG (SEQ ID NO:4981) |
| Target524 | chr4:155664237-155664243 | TTTTTGGCGGGCGTTGGGATTTCGTCG (SEQ ID NO:4982), GGCGGGCGTTGGGATTTCGTCGTTTTT (SEQ ID NO:4983), GCGGGCGTTGGGATTTCGTCGTTTTTT (SEQ ID NO:4984), TTTTTTGGCGGGCGTTGGGATTTCGTC (SEQ ID NO:4985), TGGCGGGCGTTGGGATTTCGTCGTTTT (SEQ ID NO:4986), GAGGGTGTGTGTAGGGCGGGGG (SEQ ID NO:4987), TCGGCGCGAGGGTGTGTGTGTAGG (SEQ ID NO:4988), CGAGGGTGTGTGTGTAGGGCGGGG (SEQ ID NO:4989), CGCGAGGGTGTGTGTGTAGGGCG (SEQ ID NO:4990), CGGCGCGAGGGTGTGTGTGTAGG (SEQ ID NO:4991) |
| Target525 | chr4:155664309-155664315 | AGGTTTCGGGTTTAAATTATCGGCGCG (SEQ ID NO:4992), GGTGTTTAGGAGCGTAGAGAGGTTTCGGG (SEQ ID NO:4993), GGTGTTTAGGAGCGTAGAGAGGTTTCGGGT (SEQ ID NO:4994), TGTTTAGGAGCGTAGAGAGGTTTCGGGT (SEQ ID NO:4995), GTTTAGGAGCGTAGAGAGGTTTCGGGT (SEQ ID NO:4996) |
| Target526 | chr4:158141377-158141450 | TTCGGTTGGGTTAGGTGAGGAGGATGA (SEQ ID NO:4997), TGTTTTCGGTTGGGTTAGGTGAGGAGG (SEQ ID NO:4998), AGTAGGGTTTGGTGAGAGGACGTTTCG (SEQ ID NO:4999), TTTCGGTTGGGTTAGGTGAGGAGGATGA (SEQ ID NO:5000), CGGTTGGGTTAGGTGAGGAGGATGATAGGG (SEQ ID NO:5001), TCGTGCGGTTGTTGTAGTTGTTGCGGA (SEQ ID NO:5002), CGTGCGGTTGTTGTAGTTGTTGCGGAG (SEQ ID NO:5003), CGTGCGGTTGTTGTAGTTGTTGCGGAGA (SEQ ID NO:5004), TCGTGCGGTTGTTGTAGTTGTTGCGGAG (SEQ ID NO:5005), TTCGTGCGGTTGTTGTAGTTGTTGCGG (SEQ ID NO:5006) |

FIGURE 5 CONTINUED

| | | |
|---|---|---|
| Target527 | chr4:158141492-158141575 | AGTAGGGTTTGGTGAGAGGACGTTTCG (SEQ ID NO:5007), TTCGGTGTTGAAAGGTCGAGGCGC (SEQ ID NO:5008), TAGTAGGGTTTGGTGAGAGGACGTTTCG (SEQ ID NO:5009), ATAGTAGGGTTTGGTGAGAGGACGTTTCG (SEQ ID NO:5010), TCGGTGTTGAAAGGTCGAGGCGC (SEQ ID NO:5011), GCGCGGCCGTTGAGAAAGTATAGTTCGGG (SEQ ID NO:5012), GAGATTTCGGGTTTTCGGGGTTGTCGC (SEQ ID NO:5013), CGCGGCGTTGAGAAAGTATAGTTCGGGG (SEQ ID NO:5014), GCGCGGCCGTTGAGAAAGTATAGTTCGG (SEQ ID NO:5015), TGCGCGGCCGTTGAGAAAGTATAGTTCGG (SEQ ID NO:5016) |
| Target528 | chr4:158141581-158141718 | GTTTACGGTGGTGCGGGGTGTCGG (SEQ ID NO:5017), GTTTACGGTGGTGCGGGGTGTCGGG (SEQ ID NO:5018), TTTACGGTGGTGCGGGGTGTCGGG (SEQ ID NO:5019), TTTACGGTGGTGCGGGGTGTCGG (SEQ ID NO:5020), GTTTACGGTGGTGCGGGGTGTCGGGC (SEQ ID NO:5021), TAGAGAGGGGTAGGTAGTTTCGGGCGC (SEQ ID NO:5022), AGAGAGGGGTAGGTAGTTTCGGGCGCG (SEQ ID NO:5023), GCGCGGCCGTTGAGAAAGTATAGTTCGGG (SEQ ID NO:5024), GAGAGGGGTAGGTAGTTTCGGGCGCG (SEQ ID NO:5025), TAGAGAGGGGTAGGTAGTTTCGGGCGCG (SEQ ID NO:5026) |
| Target529 | chr4:170101207-170101387 | TGTTGTTACGTAGATGGTTTGGTTTTGGTTGTT (SEQ ID NO:5027), TTGTTGTTACGTAGATGGTTTGGTTTTGGTTGT (SEQ ID NO:5028), TGTTGTTACGTAGATGGTTTGGTTTTGGTTGTTT (SEQ ID NO:5029), TTGTTGTTACGTAGATGGTTTGGTTTTGGTTGTT (SEQ ID NO:5030), TTTGTTGTTACGTAGATGGTTTGGTTTTGGTTGT (SEQ ID NO:5031) |
| Target530 | chr4:170101458-170101589 | CGGAGAGTTTGAGGATTCGTGTTTTAAGTTTCG (SEQ ID NO:5032), CGGAGAGTTTGAGGATTCGTGTTTTAAGTTTCGT (SEQ ID NO:5033), TCGGAGAGTTTGAGGATTCGTGTTTTAAGTTTCG (SEQ ID NO:5034), TCGGAGAGTTTGAGGATTCGTGTTTTAAGTTTCGT (SEQ ID NO:5035), CGGAGAGTTTGAGGATTCGTGTTTTAAGTTTCGTT (SEQ ID NO:5036) |
| Target531 | chr4:174429587-174429721 | GGTGGAGGTGGAGGTGAAATGTCGAGGT (SEQ ID NO:5037), GGTGGAGGTGGAGGTGAAATGTCGAGG (SEQ ID NO:5038), GGAGGTGGAGGTGGAGGTGAAATGTCG (SEQ ID NO:5039), AGGTGGAGGTGGAGGTGAAATGTCGAGG (SEQ ID NO:5040), AGGAGGTGGAGGTGGAGGTGAAATGTCG (SEQ ID NO:5041), GGGGCGGGGGGTTGTGGTTTGGTTTTAT (SEQ ID NO:5042), TGGGGCGGGGGTTGTGGTTTGGTTTTA (SEQ ID NO:5043), TTTATGTGTTGGCGGTGGTGGGGC (SEQ ID NO:5044), GGGGCGGGGGGTTGTGGTTTGGTTTTATT (SEQ ID NO:5045), GGGGCGGGGGGTTGTGGTTTGGTTTTA (SEQ ID NO:5046) |
| Target532 | chr4:174429886-174429939 | AGGTGAGGGTAGGGGTTTTTTTGAAAGGT (SEQ ID NO:5047), AGGTGAGGGTAGGGGTTTTTTTGAAAGGTATT (SEQ ID NO:5048), AGGTGAGGGTAGGGGTTTTTTTGAAAGGTATTAG (SEQ ID NO:5049), GGTGAGGGTAGGGGTTTTTTTGAAAGGTATTAGA (SEQ ID NO:5050), AGGTGAGGGTAGGGGTTTTTTTGAAAGGTATTAGA (SEQ ID NO:5051), GGATGCGGAGTGGTTTTTTTGGTGGTCGT (SEQ ID NO:5052), GGATGCGGAGTGGTTTTTTTGGTGGTCG (SEQ ID NO:5053), AGGATGCGGAGTGGTTTTTTTGGTGGTCG (SEQ ID NO:5054), GATGCGGAGTGGTTTTTTTGGTGGTCGT (SEQ ID NO:5055), AGGATGCGGAGTGGTTTTTTTGGTGGTC (SEQ ID NO:5056) |
| Target533 | chr4:190861696-190861763 | CGTAGGTTAGCGAGGGTAGTTTGAGTCGT (SEQ ID NO:5057), CGTAGGTTAGCGAGGGTAGTTTGAGTCG (SEQ ID NO:5058), GTTGGGTTGTCGGGTGCGTTGTGGAAT (SEQ ID NO:5059), GGTTGTCGGGTGCGTTGTGGAATCGTT (SEQ ID NO:5060), TTGGGTTGTCGGGTGCGTTGTGGAATC (SEQ ID NO:5061), GTTGGGTTGTCGGGTGCGTTGTGGAA (SEQ ID NO:5062), GGTTGTCGGGTGCGTTGTGGAATCGTTT (SEQ ID NO:5063) |
| Target534 | chr4:190861770-190861807 | CGTAGGTTAGCGAGGGTAGTTTGAGTCGT (SEQ ID NO:5064), CGTAGGTTAGCGAGGGTAGTTTGAGTCG (SEQ ID NO:5065), CGTCGTTAGTTCGTTGTTTTAGTAGGAGGCG (SEQ ID NO:5066), TCGTCGTTAGTTCGTTGTTTTAGTAGGAGGCG (SEQ ID NO:5067), TCGTCGTTAGTTCGTTGTTTTAGTAGGAGGC (SEQ ID NO:5068), GTTGGGTTGTCGGGTGCGTTGTGGAAT (SEQ ID NO:5069), GGTTGTCGGGTGCGTTGTGGAATCGTT (SEQ ID NO:5070), TTGGGTTGTCGGGTGCGTTGTGGAATC (SEQ ID NO:5071), GTTGGGTTGTCGGGTGCGTTGTGGAA (SEQ ID NO:5072), GGTTGTCGGGTGCGTTGTGGAATCGTTT (SEQ ID NO:5073) |
| Target535 | chr4:190861849-190861859 | CGTAGGTTAGCGAGGGTAGTTTGAGTCGT (SEQ ID NO:5074), CGTAGGTTAGCGAGGGTAGTTTGAGTCG (SEQ ID NO:5075), CGTAGGTTAGCGAGGGTAGTTTGAGTCGTT (SEQ ID NO:5076), AGGTTAGCGAGGGTAGTTTGAGTCGTTT (SEQ ID NO:5077), GTAGGTTAGCGAGGGTAGTTTGAGTCGTT (SEQ ID NO:5078), TTTCGGGTTTTTGTCGGGGAGTTACGG (SEQ ID NO:5079), TTCGGGTTTTTGTCGGGGAGTTACGG (SEQ ID NO:5080), GGTATTCGCGCGTAGTTGTTTTTTGGC (SEQ ID NO:5081), CGTAGAGGGTTAAAAGGTATTCGCGCGT (SEQ ID NO:5082), CGTAGAGGGTTAAAAGGTATTCGCGCG (SEQ ID NO:5083) |
| Target536 | chr4:190861931-190861981 | AGGGAGTAGTTGCGCGCGGATGTTTT (SEQ ID NO:5084), CGTTAGGGAGTAGTTGCGCGCGGATGT (SEQ ID NO:5085), GTTAGGGAGTAGTTGCGCGCGGATGTT (SEQ ID NO:5086), TAGGGAGTAGTTGCGCGCGGATGTTTT (SEQ ID NO:5087), TTAGGGAGTAGTTGCGCGCGGATGTTTT (SEQ ID NO:5088), CGGGGTAGTATAGGGGCGCGGAGAAAT (SEQ ID NO:5089), CGGGGTAGTATAGGGGCGCGGAGAAA (SEQ ID NO:5090), CGGGGTAGTATAGGGGCGCGGAGAAATA (SEQ ID NO:5091), TTTCGGGTTTTTGTCGGGGAGTTACGG (SEQ ID NO:5092), CGGGGTAGTATAGGGGCGCGGAGAA (SEQ ID NO:5093) |

FIGURE 5 CONTINUED

| Target537 | chr4:190862105-190862129 | GTTTGGGTGAAGACGGAGGCGGGTTTT (SEQ ID NO:5094), TTTGGGTGAAGACGGAGGCGGGTTTTA (SEQ ID NO:5095), GTTTGGGTGAAGACGGAGGCGGGTTT (SEQ ID NO:5096), TTGGGTGAAGACGGAGGCGGGTTTTAT (SEQ ID NO:5097), GTTTGGGTGAAGACGGAGGCGGGTTTTA (SEQ ID NO:5098), ATTTTTGCGCGGAGAGGTTGAGGTCGG (SEQ ID NO:5099), CGCGGAGAGGTTGAGGTCGGTTTTGGA (SEQ ID NO:5100), TTGCGCGGAGAGGTTGAGGTCGGTTTT (SEQ ID NO:5101), TTTGCGCGGAGAGGTTGAGGTCGGTTT (SEQ ID NO:5102), TTTTGCGCGGAGAGGTTGAGGTCGGTT (SEQ ID NO:5103) |
|---|---|---|
| Target538 | chr4:190940267-190940284 | TGGTAGGGAATGGAGGTTTCGGGCGTT (SEQ ID NO:5104), TTGGTAGGGAATGGAGGTTTCGGGCGT (SEQ ID NO:5105), TGGTAGGGAATGGAGGTTTCGGGCGTTT (SEQ ID NO:5106), TTGGTAGGGAATGGAGGTTTCGGGCGTT (SEQ ID NO:5107), TTTGGTAGGGAATGGAGGTTTCGGGCGT (SEQ ID NO:5108) |
| Target539 | chr4:190940313-190940328 | TGGTAGGGAATGGAGGTTTCGGGCGTT (SEQ ID NO:5109), TTGGTAGGGAATGGAGGTTTCGGGCGT (SEQ ID NO:5110), TGGTAGGGAATGGAGGTTTCGGGCGTTT (SEQ ID NO:5111), TTGGTAGGGAATGGAGGTTTCGGGCGTT (SEQ ID NO:5112), TTTGGTAGGGAATGGAGGTTTCGGGCGT (SEQ ID NO:5113), CGCGAGGTTGGGATTAGGTATTTTCGGA (SEQ ID NO:5114), TCGCGAGGTTGGGATTAGGTATTTTCGG (SEQ ID NO:5115), TCGCGAGGTTGGGATTAGGTATTTTCGGA (SEQ ID NO:5116), CGCGAGGTTGGGATTAGGTATTTTCGGAG (SEQ ID NO:5117), CGCGAGGTTGGGATTAGGTATTTTCGGAGT (SEQ ID NO:5118) |
| Target540 | chr4:190940381-190940432 | TAGAGGGGGAGAGTAGTTCGGTCGCGG (SEQ ID NO:5119), ATAGAGGGGGAGAGTAGTTCGGTCGCGG (SEQ ID NO:5120), ATAGAGGGGGAGAGTAGTTCGGTCGCG (SEQ ID NO:5121), TGGTGTTTGGGCGTATAGAGGGGGAGA (SEQ ID NO:5122), GCGATTGGTGTTTGGGCGTATAGAGGGG (SEQ ID NO:5123), GCGGTGGCGTTTGGTTGGTTTAAGAGT (SEQ ID NO:5124), GCGGTGGCGTTTGGTTGGTTTAAGAGTT (SEQ ID NO:5125), CGGTGGCGTTTGGTTGGTTTAAGAGTTCGG (SEQ ID NO:5126), GCGGTGGCGTTTGGTTGGTTTAAGAGTTC (SEQ ID NO:5127), CGGTGGCGTTTGGTTGGTTTAAGAGTTCG (SEQ ID NO:5128) |
| Target541 | chr5:1130914-1130995 | GTGGTGGGAGGGTGGTAGAAGCGGAAA (SEQ ID NO:5129), GTATAGACGTAGGTGGGCGGGTGGTGG (SEQ ID NO:5130), TGGTGGGAGGGTGGTAGAAGCGGAAAG (SEQ ID NO:5131), GGTGGGAGGGTGGTAGAAGCGGAAAGA (SEQ ID NO:5132), TGGGAGGGTGGTAGAAGCGGAAAGAGG (SEQ ID NO:5133), TGGTCGGAAGGAGATTGTATGGGTTGTGT (SEQ ID NO:5134), GGTCGGAAGGAGATTGTATGGGTTGTGT (SEQ ID NO:5135), TGGTCGGAAGGAGATTGTATGGGTTGTG (SEQ ID NO:5136), TTGGTCGGAAGGAGATTGTATGGGTTGT (SEQ ID NO:5137), TGGTCGGAAGGAGATTGTATGGGTTGTGTT (SEQ ID NO:5138) |
| Target542 | chr5:1131271-1131326 | GGGTGAGGTTTGGGGGAGGGTAGTAAGG (SEQ ID NO:5139), AGGGTGAGGTTTGGGGGAGGGTAGTAA (SEQ ID NO:5140), TTAGGGTGAGGTTTGGGGGAGGGTAGT (SEQ ID NO:5141), AGGGTGAGGTTTGGGGGAGGGTAGTAAGG (SEQ ID NO:5142), GGTGAGGTTTGGGGGAGGGTAGTAAGGT (SEQ ID NO:5143), TGGTAAGGAGTAGGACGGTCGGGAGGG (SEQ ID NO:5144), GGTAAGGAGTAGGACGGTCGGGAGGGA (SEQ ID NO:5145), TTGGTAAGGAGTAGGACGGTCGGGAGGG (SEQ ID NO:5146), TTGGTAAGGAGTAGGACGGTCGGGAGG (SEQ ID NO:5147), TGGTAAGGAGTAGGACGGTCGGGAGGGA (SEQ ID NO:5148) |
| Target543 | chr5:1131364-1131378 | GTTCGGATTTACGGGGATTTGTAGGGGTTTATG (SEQ ID NO:5149), TGGTAAGGAGTAGGACGGTCGGGAGGG (SEQ ID NO:5150), GGTAAGGAGTAGGACGGTCGGGAGGGA (SEQ ID NO:5151), TTGGTAAGGAGTAGGACGGTCGGGAGGG (SEQ ID NO:5152), GGTAAGGAGTAGGACGGTCGGGAGGGAT (SEQ ID NO:5153), TTGGTAAGGAGTAGGACGGTCGGGAGG (SEQ ID NO:5154) |
| Target544 | chr5:1876208-1876216 | AAAAGGTTGCGGCGGGAGTTTTCGGTTT (SEQ ID NO:5155), AAAAGGTTGCGGCGGGAGTTTTCGGTT (SEQ ID NO:5156), AAGGTTGCGGCGGGAGTTTTCGGTTTG (SEQ ID NO:5157), TAAAAGGTTGCGGCGGGAGTTTTCGGT (SEQ ID NO:5158), AAAAGGTTGCGGCGGGAGTTTTCGGTTT (SEQ ID NO:5159) |
| Target545 | chr5:1876286-1876433 | CGTTCGTTAGGTCGGGGGTTTTCGTCG (SEQ ID NO:5160), GTTCGTTAGGTCGGGGGTTTTCGTCGT (SEQ ID NO:5161), TCGTTCGTTAGGTCGGGGGTTTTCGTCG (SEQ ID NO:5162), TCGTTCGTTAGGTCGGGGGTTTTCGTC (SEQ ID NO:5163), CGTTCGTTAGGTCGGGGGTTTTCGTCGT (SEQ ID NO:5164), AAAGGTTGCGGCGGGAGTTTTCGGTTT (SEQ ID NO:5165), AAAAGGTTGCGGCGGGAGTTTTCGGTT (SEQ ID NO:5166), AAGGTTGCGGCGGGAGTTTTCGGTTTG (SEQ ID NO:5167), AGGGTTTGGATCGGGTTTTGAGGGGGA (SEQ ID NO:5168), TAAAAGGTTGCGGCGGGAGTTTTCGGT (SEQ ID NO:5169) |
| Target546 | chr5:1876557-1876571 | CGCGGGGGATTTTGGTGGTTTAGGGGT (SEQ ID NO:5170), ACGCGGGGGATTTTGGTGGTTTAGGGG (SEQ ID NO:5171), CGCGGGGGATTTTGGTGGTTTAGGGG (SEQ ID NO:5172), TACGCGGGGGATTTTGGTGGTTTAGGG (SEQ ID NO:5173), TACGCGGGGGATTTTGGTGGTTTAGGGG (SEQ ID NO:5174), GAGACGTAGGATTGTTTTGCGGGCGGG (SEQ ID NO:5175), GGAGACGTAGGATTGTTTTGCGGGCGG (SEQ ID NO:5176), GGGCGGGCGGTTTTGGAGGGATTTATT (SEQ ID NO:5177), CGGGCGGGCGGTTTTGGAGGGATTTAT (SEQ ID NO:5178), AGACGTAGGATTGTTTTGCGGGCGGGC (SEQ ID NO:5179) |
| Target547 | chr5:1876630-1876660 | GCGGGGGATTTTGGTGGTTTAGGGGTT (SEQ ID NO:5180), CGCGGGGGATTTTGGTGGTTTAGGGGT (SEQ ID NO:5181), ACGCGGGGGATTTTGGTGGTTTAGGGG (SEQ ID NO:5182), CGCGGGGGATTTTGGTGGTTTAGGGG (SEQ ID NO:5183), TACGCGGGGGATTTTGGTGGTTTAGGG (SEQ ID NO:5184), GAGACGTAGGATTGTTTTGCGGGCGGG (SEQ ID NO:5185), |

FIGURE 5 CONTINUED

|  |  |  |
|---|---|---|
|  |  | GGAGACGTAGGATTGTTTTGCGGGCGG (SEQ ID NO:5186), TTAAGGATTACGGGAGCGGTTCGGGGG (SEQ ID NO:5187), AGACGTAGGATTGTTTTGCGGGCGGGT (SEQ ID NO:5188), TTTAAGGATTACGGGAGCGGTTCGGGGG (SEQ ID NO:5189) |
| Target548 | chr5:1877909-1877921 | GGTTTAGGTTTAGGCGGTGGAGGTTTCGG (SEQ ID NO:5190), TTTAGGTTTAGGCGGTGGAGGTTTCGG (SEQ ID NO:5191), CGGTGGAGGTTTCGGCGTGGTAGC (SEQ ID NO:5192), GCGGTGGAGGTTTCGGCGTGGTAG (SEQ ID NO:5193), AGGTTTAGGTTTAGGCGGTGGAGGTTTCGG (SEQ ID NO:5194), CGGAGAGGGGGTTTTTGAATTTGGATTTTTGGG (SEQ ID NO:5195), CGGAGAGGGGGTTTTTGAATTTGGATTTTTGGGA (SEQ ID NO:5196), TCGGAGAGGGGGTTTTTGAATTTGGATTTTTGGG (SEQ ID NO:5197), CGGAGAGGGGGTTTTTGAATTTGGATTTTTGG (SEQ ID NO:5198), GGAGAGGGGGTTTTTGAATTTGGATTTTTGGG (SEQ ID NO:5199) |
| Target549 | chr5:1877967-1878069 | GCGTGGTAGCGTCGGGTTTGTTTATGT (SEQ ID NO:5200), GCGTGGTAGCGTCGGGTTTGTTTATGTT (SEQ ID NO:5201), GGTTTAGGTTTAGGCGGTGGAGGTTTCGG (SEQ ID NO:5202), TTTAGGTTTAGGCGGTGGAGGTTTCGG (SEQ ID NO:5203), GCGGTGGAGGTTTCGGCGTGGTAG (SEQ ID NO:5204), TTTTTTGCGTTTGAGGCGGGCGGGTTT (SEQ ID NO:5205), TTTTTGCGTTTGAGGCGGGCGGGTTTC (SEQ ID NO:5206), TTTTTGCGTTTGAGGCGGGCGGGTTT (SEQ ID NO:5207), TTTTTTGCGTTTGAGGCGGGCGGGTT (SEQ ID NO:5208), TTTTGCGTTTGAGGCGGGCGGGTTTC (SEQ ID NO:5209) |
| Target550 | chr5:1878079-1878210 | TTGTCGTCGGTTTTGGGTAGGGCGAGT (SEQ ID NO:5210), GGTTTGTCGTCGGTTTTGGGTAGGGCG (SEQ ID NO:5211), GCGTTTGTAGTTGGGGCGTTTTGGGGT (SEQ ID NO:5212), GGGTTTGTCGTCGGTTTTGGGTAGGGC (SEQ ID NO:5213), GGAAAGGCGCGGGGTTAGGGGTGTAGTT (SEQ ID NO:5214), TTCGGGTTTTTGGGACGTTCGTTGGGG (SEQ ID NO:5215), TCGGGTTTTTGGGACGTTCGTTGGGG (SEQ ID NO:5216), TTTCGGGTTTTTGGGACGTTCGTTGGGG (SEQ ID NO:5217), CGGGTTTTTGGGACGTTCGTTGGGGG (SEQ ID NO:5218), TCGGGTTTTTGGGACGTTCGTTGGGG (SEQ ID NO:5219) |
| Target551 | chr5:1878215-1878266 | TTGTCGTCGGTTTTGGGTAGGGCGAGT (SEQ ID NO:5220), GGTTTGTCGTCGGTTTTGGGTAGGGCG (SEQ ID NO:5221), GCGTTTGTAGTTGGGGCGTTTTGGGGT (SEQ ID NO:5222), GGGTTTGTCGTCGGTTTTGGGTAGGGC (SEQ ID NO:5223), GGAAAGGCGCGGGGTTAGGGGTGTAGTT (SEQ ID NO:5224), TTCGGGTTTTTGGGACGTTCGTTGGGG (SEQ ID NO:5225), TCGGGTTTTTGGGACGTTCGTTGGGG (SEQ ID NO:5226), TTTCGGGTTTTTGGGACGTTCGTTGGGG (SEQ ID NO:5227), CGGGTTTTTGGGACGTTCGTTGGGGG (SEQ ID NO:5228), CGGGTTTTTGGGACGTTCGTTGGGGGT (SEQ ID NO:5229) |
| Target552 | chr5:2134732-2135132 | TGGGGTATGGAAGTTTGACGGGAAGAGGG (SEQ ID NO:5230), GGGGTATGGAAGTTTGACGGGAAGAGGG (SEQ ID NO:5231), GGGGTATGGAAGTTTGACGGGAAGAGGGA (SEQ ID NO:5232), TGGGGTATGGAAGTTTGACGGGAAGAGGGA (SEQ ID NO:5233), TGGGGTATGGAAGTTTGACGGGAAGAGG (SEQ ID NO:5234), AGTGCGTGCGGTTTTTGGTATTGGGGT (SEQ ID NO:5235), GAGTGCGTGCGGTTTTTGGTATTGGGGT (SEQ ID NO:5236), GAGTGCGTGCGGTTTTTGGTATTGGGG (SEQ ID NO:5237), GGAGTGCGTGCGGTTTTTGGTATTGGG (SEQ ID NO:5238), GTGCGTGCGGTTTTTGGTATTGGGGTT (SEQ ID NO:5239) |
| Target553 | chr5:2149263-2149663 | TTTGTCGGGTGGTTTTTGCGTGGTTGA (SEQ ID NO:5240), GGGTAATGAAGTTGGAGGTAGGCGTGCG (SEQ ID NO:5241), CGGGTAATGAAGTTGGAGGTAGGCGTGC (SEQ ID NO:5242), TGTCGGGTGGTTTTTGCGTGGTTGATT (SEQ ID NO:5243), TTGTCGGGTGGTTTTTGCGTGGTTGAT (SEQ ID NO:5244), GTAGAGCGGTTCGATGAGGGGGTTGTGT (SEQ ID NO:5245), AGTAGAGCGGTTCGATGAGGGGGTTGTGT (SEQ ID NO:5246), AGTAGAGCGGTTCGATGAGGGGGTTGTG (SEQ ID NO:5247), AGAGCGGTTCGATGAGGGGGTTGTGTTA (SEQ ID NO:5248), TAGAGCGGTTCGATGAGGGGGTTGTGTT (SEQ ID NO:5249) |
| Target554 | chr5:3602148-3602161 | TAGATGGGTTAGTCGGGATGCGGTGCG (SEQ ID NO:5250), ATAGATGGGTTAGTCGGGATGCGGTGCG (SEQ ID NO:5251), AGATGGGTTAGTCGGGATGCGGTGCG (SEQ ID NO:5252), ATAGATGGGTTAGTCGGGATGCGGTGC (SEQ ID NO:5253), GATGGGTTAGTCGGGATGCGGTGCG (SEQ ID NO:5254) |
| Target555 | chr5:3602272-3602308 | ACGAGGGGTTGAGGTTGTGGTGGGAAG (SEQ ID NO:5255), GGGTTGAGGTTGTGGTGGGAAGCGAGA (SEQ ID NO:5256), GGTGGGAAGCGAGAAAGAGGAGGTGGT (SEQ ID NO:5257), TGGTGGGAAGCGAGAAAGAGGAGGTGG (SEQ ID NO:5258), TTTTGCGGTGTGAGGTGTGAACGAGGG (SEQ ID NO:5259), GGTGCGCGCGTTTGAGGGTAAAGGAC (SEQ ID NO:5260), GGTGCGCGCGTTTGAGGGTAAAGGA (SEQ ID NO:5261), CGGTGCGCGCGTTTGAGGGTAAAGGAC (SEQ ID NO:5262), CGGTGCGCGCGTTTGAGGGTAAAGGA (SEQ ID NO:5263), CGGTGCGCGCGTTTGAGGGTAAAGG (SEQ ID NO:5264) |
| Target556 | chr5:3602339-3602483 | TATTCGTAGCGGGGTTGGTTTCGGGCG (SEQ ID NO:5265), ATATTCGTAGCGGGGTTGGTTTCGGGC (SEQ ID NO:5266), GCGCGAGTGGGGAAAGGTTTAGGAGTT (SEQ ID NO:5267), ATATTCGTAGCGGGGTTGGTTTCGGGCG (SEQ ID NO:5268), AATATTCGTAGCGGGGTTGGTTTCGGGC (SEQ ID NO:5269), TTTTGAAGGTGTTTGTTGCGGCGCGTG (SEQ ID NO:5270), TTTTTGAAGGTGTTTGTTGCGGCGCGT (SEQ ID NO:5271), TTTGAAGGTGTTTGTTGCGGCGCGTGG (SEQ ID NO:5272), TTTTTGAAGGTGTTTGTTGCGGCGCGTG (SEQ ID NO:5273), TTTGAAGGTGTTTGTTGCGGCGCGTG (SEQ ID NO:5274) |

FIGURE 5 CONTINUED

| Target557 | chr5:3602487-3602497 | TATTCGTAGCGGGGTTGGTTTCGGGCG (SEQ ID NO:5275), ATATTCGTAGCGGGGTTGGTTTCGGGC (SEQ ID NO:5276), GCGCGAGTGGGGAAAGGTTTAGGAGTT (SEQ ID NO:5277), ATATTCGTAGCGGGGTTGGTTTCGGGCG (SEQ ID NO:5278), AATATTCGTAGCGGGGTTGGTTTCGGGC (SEQ ID NO:5279), TTTTTGAAGGTGTTTGTTGCGGCGCGTG (SEQ ID NO:5280), TTTTTGAAGGTGTTTGTTGCGGCGCGT (SEQ ID NO:5281), TTTGAAGGTGTTTGTTGCGGCGCGTGG (SEQ ID NO:5282), TTTTTGAAGGTGTTTGTTGCGGCGCGTG (SEQ ID NO:5283), TTTGAAGGTGTTTGTTGCGGCGCGTG (SEQ ID NO:5284) |
| Target558 | chr5:3602501-3602582 | TATTCGTAGCGGGGTTGGTTTCGGGCG (SEQ ID NO:5285), ATATTCGTAGCGGGGTTGGTTTCGGGC (SEQ ID NO:5286), GCGCGAGTGGGGAAAGGTTTAGGAGTT (SEQ ID NO:5287), ATATTCGTAGCGGGGTTGGTTTCGGGCG (SEQ ID NO:5288), AATATTCGTAGCGGGGTTGGTTTCGGGC (SEQ ID NO:5289), CGTTTTGAAGGTTTCGCGTCGGGTTC (SEQ ID NO:5290), GTTTTTTGAAGGTGTTTGTTGCGGCGT (SEQ ID NO:5291), AGTTTTTTGAAGGTGTTTGTTGCGGCGT (SEQ ID NO:5292), AGTTTTTTGAAGGTGTTTGTTGCGGCG (SEQ ID NO:5293), AAGTTTTTTGAAGGTGTTTGTTGCGGCGT (SEQ ID NO:5294) |
| Target559 | chr5:3602672-3602707 | TGTTAGCGAGGATGTGGGTTGTCGGGA (SEQ ID NO:5295), GCGAGGATGTGGGTTGTCGGGAAAAACG (SEQ ID NO:5296), TTGTTAGCGAGGATGTGGGTTGTCGGG (SEQ ID NO:5297), AGCGAGGATGTGGGTTGTCGGGAAAAA (SEQ ID NO:5298), CGAGGATGTGGGTTGTCGGGAAAAACGG (SEQ ID NO:5299), GTCGGGAAGGGCGGGTTATAGGTTGGG (SEQ ID NO:5300), GGAAGGGCGGGTTATAGGTTGGGGGTG (SEQ ID NO:5301), AGTCGGGAAGGGCGGGTTATAGGTTGG (SEQ ID NO:5302), GTTATAGGTTGGGGGTGCGAGCGGAGG (SEQ ID NO:5303), GGTTATAGGTTGGGGGTGCGAGCGGAG (SEQ ID NO:5304) |
| Target560 | chr5:5140383-5140428 | CGTCGTCGCGGTTGTTATTTCGTTTTTC (SEQ ID NO:5305), GTGCGAGCGGGTAGGGAGGATTCGATT (SEQ ID NO:5306), TGCGAGCGGGTAGGGAGGATTCGATTT (SEQ ID NO:5307), GTGCGAGCGGGTAGGGAGGATTCGAT (SEQ ID NO:5308), GTGCGAGCGGGTAGGGAGGATTCGATTT (SEQ ID NO:5309), TGCGAGCGGGTAGGGAGGATTCGATT (SEQ ID NO:5310) |
| Target561 | chr5:5140434-5140492 | CGGAGTCGTTGTGGGGAATTTTTTCGC (SEQ ID NO:5311), CGTCGTCGCGGTTGTTATTTCGTTTTTC (SEQ ID NO:5312), CGGAGTTTTAGTAATAATTTCGGCGCGGC (SEQ ID NO:5313), GTGCGAGCGGGTAGGGAGGATTCGATT (SEQ ID NO:5314), GGGGTTATCGGAGGGTTTTCGGTCGGT (SEQ ID NO:5315), AGGGGTTATCGGAGGGTTTTCGGTCGG (SEQ ID NO:5316), TCGAGGGGTTAGGGGTTATCGGAGGGT (SEQ ID NO:5317), TGCGAGCGGGTAGGGAGGATTCGATTT (SEQ ID NO:5318) |
| Target562 | chr5:5140520-5140539 | CGGAGTCGTTGTGGGGAATTTTTTCGC (SEQ ID NO:5319), ATTTTTTCGCGTTTTGTTTGGGTCGGG (SEQ ID NO:5320), GGGAATTTTTTCGCGTTTTGTTTGGGTCGGG (SEQ ID NO:5321), AATTTTTTCGCGTTTTGTTTGGGTCGGG (SEQ ID NO:5322), CGCGTTTTGTTTGGGTCGGGTTTTTT (SEQ ID NO:5323), GGGGTTATCGGAGGGTTTTCGGTCGGT (SEQ ID NO:5324), AGGGGTTATCGGAGGGTTTTCGGTCGG (SEQ ID NO:5325), TCGAGGGGTTAGGGGTTATCGGAGGGT (SEQ ID NO:5326), CGAGGGGTTAGGGGTTATCGGAGGGTT (SEQ ID NO:5327), GCGTTTCGAGGGGTTAGGGGTTATCGG (SEQ ID NO:5328) |
| Target563 | chr5:5140549-5140879 | CGTTGTCGGTCGGGGATTTTTCGGTGG (SEQ ID NO:5329), GGCGTTGTGGATGTTGTTGGCGTAGGT (SEQ ID NO:5330), GTTTGGCGGCGTTGTGGATGTTGTTGG (SEQ ID NO:5331), GGTTTGGCGGCGTTGTGGATGTTGTTG (SEQ ID NO:5332), CGGTAGCGTTTGGGAGTTCGAGCGTTT (SEQ ID NO:5333), GGAGAGGAGTCGCGCGGGGGATTCGTTTT (SEQ ID NO:5334), GCGTTGGTGGGAGCGTTCGGGATTTAT (SEQ ID NO:5335), GGAGAGGAGTCGCGCGGGGGATTCGTTT (SEQ ID NO:5336), AGGAGCGTTTCGAGGGGTTAGGGGTTA (SEQ ID NO:5337), TAGGAGCGTTTCGAGGGGTTAGGGGTT (SEQ ID NO:5338) |
| Target564 | chr5:10333225-10333253 | TTTCGCGTGTGATGGGGGTTGTTTGGG (SEQ ID NO:5339), AGGTGGGTGAGGAGTTTTTAGGCGCGT (SEQ ID NO:5340), GTGATGGGGGTTGTTTGGGTGGGGTTG (SEQ ID NO:5341), TGATGGGGGTTGTTTGGGTGGGGTTGT (SEQ ID NO:5342), TGTGATGGGGGTTGTTTGGGTGGGGTT (SEQ ID NO:5343), TGAGTGTTCGGGGTTTGGGTAGTGTTGT (SEQ ID NO:5344), GAGTGTTCGGGGTTTGGGTAGTGTTGT (SEQ ID NO:5345), TGAGTGTTCGGGGTTTGGGTAGTGTTG (SEQ ID NO:5346), TGGTTGGTATTTGGTCGTTTGTAGGCGGT (SEQ ID NO:5347), GGTTGGTATTTGGTCGTTTGTAGGCGGT (SEQ ID NO:5348) |
| Target565 | chr5:10333262-10333318 | TTTCGCGTGTGATGGGGGTTGTTTGGG (SEQ ID NO:5349), AGGTGGGTGAGGAGTTTTTAGGCGCGT (SEQ ID NO:5350), GTGATGGGGGTTGTTTGGGTGGGGTTG (SEQ ID NO:5351), TGATGGGGGTTGTTTGGGTGGGGTTGT (SEQ ID NO:5352), TGTGATGGGGGTTGTTTGGGTGGGGTT (SEQ ID NO:5353), ACGGTTGGGGTGTTTTGGCGTTAAGAGC (SEQ ID NO:5354), CGGTTGGGGTGTTTTGGCGTTAAGAGC (SEQ ID NO:5355), GGACGGTTGGGGTGTTTTGGCGTTAAG (SEQ ID NO:5356), GGACGGTTGGGGTGTTTTGGCGTTAAGA (SEQ ID NO:5357), ACGGTTGGGGTGTTTTGGCGTTAAGAG (SEQ ID NO:5358) |
| Target566 | chr5:10333439-10333565 | GATTTTAGATCGCGGGGGTGTGGGGC (SEQ ID NO:5359), ATTTTAGATCGCGGGGGTGTGGGGC (SEQ ID NO:5360), CGTCGGGGATTTGTTATTTGGGTTCGGT (SEQ ID NO:5361), CGTCGGGGATTTGTTATTTGGGTTCGG (SEQ ID NO:5362), TCGTCGGGGATTTGTTATTTGGGTTCGGT (SEQ ID NO:5363), GCGGTTTTGGGCGGCGTTTGTTTTTT (SEQ ID NO:5364), GCGGTTTTGGGCGGCGTTTGTTTTT (SEQ ID NO:5365), GGTTTAAGGTCGGTAGCGATTTTGGGG (SEQ ID NO:5366), GGTTTAAGGTCGGTAGCGATTTTGGGGA (SEQ ID NO:5367), GCGGTTTTGGGCGGCGTTTGTTTT (SEQ ID NO:5368) |

FIGURE 5 CONTINUED

| Target567 | chr5:10333591-10333637 | GTGGGGCGTCGGGGAAGGAGATAGAAG (SEQ ID NO:5369), TATTTGGGGTTGCGTTTTGGGTGGGCG (SEQ ID NO:5370), TAGGGTCGCGGGGGATATTTGGGGTTGC (SEQ ID NO:5371), TGTGGGGCGTCGGGGAAGGAGATAGAA (SEQ ID NO:5372), GGGGCGTCGGGGAAGGAGATAGAAGGA (SEQ ID NO:5373), GGTTTTCGGTTAGGGGGAGTTAGGGCGT (SEQ ID NO:5374), GGTTTTCGGTTAGGGGGAGTTAGGGCG (SEQ ID NO:5375), GTTTTCGGTTAGGGGGAGTTAGGGCGT (SEQ ID NO:5376), GGTTTTCGGTTAGGGGGAGTTAGGGCGTA (SEQ ID NO:5377), TTTTCGGTTAGGGGGAGTTAGGGCGTA (SEQ ID NO:5378) |
| Target568 | chr5:16180103-16180184 | GGGCGGGTTGGAAGTGGGGGATTTTTT (SEQ ID NO:5379), CGGGCGGGTTGGAAGTGGGGGATTTTT (SEQ ID NO:5380), GGGCGGGTTGGAAGTGGGGGATTTTT (SEQ ID NO:5381), GGGCGGGTTGGAAGTGGGGGATTTTTTA (SEQ ID NO:5382), CGGGCGGGTTGGAAGTGGGGGATTTT (SEQ ID NO:5383), AGCGTTGCGTCGTTTGGAGAGGGGTTA (SEQ ID NO:5384), TAGCGTTGCGTCGTTTGGAGAGGGGTT (SEQ ID NO:5385), GCGTTGCGTCGTTTGGAGAGGGGTTAT (SEQ ID NO:5386), GTAGCGTTGCGTCGTTTGGAGAGGGGT (SEQ ID NO:5387), TAGCGTTGCGTCGTTTGGAGAGGGGT (SEQ ID NO:5388) |
| Target569 | chr5:16180231-16180278 | GGGAAGTAGGGGGGTAGGGGAGAGGTCG (SEQ ID NO:5389), TATTGGATGGGTCGGTGGGATGTGGCG (SEQ ID NO:5390), TGGGAAGTAGGGGGGTAGGGGAGAGGTC (SEQ ID NO:5391), CGTGAGTTGGGAAGTAGGGGGGTAGGGG (SEQ ID NO:5392), TTGGGAAGTAGGGGGGTAGGGGAGAGGT (SEQ ID NO:5393), TGGAAGTGGCGTTATAGTTTCGGGTT (SEQ ID NO:5394), TGTTTAGTTAGTTCGGGCGCGTTTAGGG (SEQ ID NO:5395), GTTTAGTTAGTTCGGGCGCGTTTAGGG (SEQ ID NO:5396), TGGAAGTGGCGGTTATAGTTTCGGGTTT (SEQ ID NO:5397), TTGTTTAGTTAGTTCGGGCGCGTTTAGGG (SEQ ID NO:5398) |
| Target570 | chr5:16180290-16180342 | GGGAAGTAGGGGGGTAGGGGAGAGGTCG (SEQ ID NO:5399), TATTGGATGGGTCGGTGGGATGTGGCG (SEQ ID NO:5400), TGGGAAGTAGGGGGGTAGGGGAGAGGTC (SEQ ID NO:5401), CGTGAGTTGGGAAGTAGGGGGGTAGGGG (SEQ ID NO:5402), TTGGGAAGTAGGGGGGTAGGGGAGAGGT (SEQ ID NO:5403), GGAGCGAGGGTTTGGAAGTGGCGGTTA (SEQ ID NO:5404), GAGCGAGGGTTTGGAAGTGGCGGTTAT (SEQ ID NO:5405), GGAGCGAGGGTTTGGAAGTGGCGGTTAT (SEQ ID NO:5406), AGCGAGGGTTTGGAAGTGGCGGTTATA (SEQ ID NO:5407), GAGCGAGGGTTTGGAAGTGGCGGTTA (SEQ ID NO:5408) |
| Target571 | chr5:16180362-16180394 | TGGTTGAGTAGTGGAGCGGGAAAGGGCG (SEQ ID NO:5409), GGTTGAGTAGTGGAGCGGGAAAGGGCGC (SEQ ID NO:5410), GTTGAGTAGTGGAGCGGGAAAGGGCGC (SEQ ID NO:5411), TTGGTTGAGTAGTGGAGCGGGAAAGGGC (SEQ ID NO:5412), TTGAGTAGTGGAGCGGGAAAGGGCGC (SEQ ID NO:5413), GGAGCGAGGGTTTGGAAGTGGCGGTTA (SEQ ID NO:5414), GAGCGAGGGTTTGGAAGTGGCGGTTAT (SEQ ID NO:5415), GGAGCGAGGGTTTGGAAGTGGCGGTTAT (SEQ ID NO:5416), AGCGAGGGTTTGGAAGTGGCGGTTATA (SEQ ID NO:5417), CGAGGGCGGGATAGATAGGGAGAGGAT (SEQ ID NO:5418) |
| Target572 | chr5:37834738-37834807 | TTAGGTTGGTTTGGGGTACGTGCGGGG (SEQ ID NO:5419), ATTAGGTTGGTTTGGGGTACGTGCGGG (SEQ ID NO:5420), GTTTGGGGTACGTGCGGGGTTGGTTG (SEQ ID NO:5421), GTTGGTTTGGGGTACGTGCGGGGTTG (SEQ ID NO:5422), TAGGTTGGTTTGGGGTACGTGCGGGG (SEQ ID NO:5423), CGTCGGTAAGAGGTTTTTCGAGGCGTT (SEQ ID NO:5424), CGTCGGTAAGAGGTTTTTCGAGGCGTTC (SEQ ID NO:5425), TGGGATGTCGTGGTTGTTTGTTTGGTGT (SEQ ID NO:5426), GGGATGTCGTGGTTGTTTGTTTGGTGT (SEQ ID NO:5427), TGGGATGTCGTGGTTGTTTGTTTGGTG (SEQ ID NO:5428) |
| Target573 | chr5:37834826-37834845 | CGGCGGGCGTTTCGGGAGGTTTTTTAT (SEQ ID NO:5429), TCGGCGGGCGTTTCGGGAGGTTTTTTA (SEQ ID NO:5430), GCGTTTCGGGAGGTTTTTTATCGGCGG (SEQ ID NO:5431), GGCGTTTCGGGAGGTTTTTTATCGGCG (SEQ ID NO:5432), GCGGGCGTTTCGGGAGGTTTTTTATCG (SEQ ID NO:5433), TTTCGTTTGTTCGCGTAGGTGTCGTCG (SEQ ID NO:5434), TTTTCGTTTGTTCGCGTAGGTGTCGTCG (SEQ ID NO:5435), TTCGTTTGTTCGCGTAGGTGTCGTCG (SEQ ID NO:5436), TGGGATGTCGTGGTTGTTTGTTTGGTGT (SEQ ID NO:5437), TTTTCGTTTGTTCGCGTAGGTGTCGTC (SEQ ID NO:5438) |
| Target574 | chr5:37834848-37835000 | CGGCGGGCGTTTCGGGAGGTTTTTTAT (SEQ ID NO:5439), TCGGCGGGCGTTTCGGGAGGTTTTTTA (SEQ ID NO:5440), GGTAGGCGGGAGGTGGGGGAGAGAATC (SEQ ID NO:5441), GCGTTTCGGGAGGTTTTTTATCGGCGG (SEQ ID NO:5442), GGCGTTTCGGGAGGTTTTTTATCGGCG (SEQ ID NO:5443), GGAGAGGGGCGTAGGGATTCGTAGGGA (SEQ ID NO:5444), GAGGTTGGAGAGGGGCGTAGGGATTCG (SEQ ID NO:5445), CGAGGTTGGAGAGGGGCGTAGGGATTC (SEQ ID NO:5446), AGAGGGGCGTAGGGATTCGTAGGGAGT (SEQ ID NO:5447), TGGAGAGGGGCGTAGGGATTCGTAGGG (SEQ ID NO:5448) |
| Target575 | chr5:37835015-37835110 | GGTAGGCGGGAGGTGGGGGAGAGAATC (SEQ ID NO:5449), GTAGGCGGGAGGTGGGGGAGAGAATC (SEQ ID NO:5450), GGTAGGCGGGAGGTGGGGGAGAGAAT (SEQ ID NO:5451), GGGTAGGCGGGAGGTGGGGGAGAGAAT (SEQ ID NO:5452), GTAGGCGGGAGGTGGGGGAGAGAAT (SEQ ID NO:5453), AGTTGTTTTTGGGGCGCGTTGAGGAGG (SEQ ID NO:5454), CGAGTTGTTTTTGGGGCGCGTTGAGGA (SEQ ID NO:5455), GTGGTGGGGGGTGGGGGGTTAATTGGAG (SEQ ID NO:5456), TTTTTGGGGCGCGTTGAGGAGGGGAGAA (SEQ ID NO:5457), GCGTTGAGGAGGGGAGAAGCGAATTGGG (SEQ ID NO:5458) |
| Target576 | chr5:40680972-40680986 | CGCGAGTTTGGAGATTTTGGTGGTCGT (SEQ ID NO:5459), TCGCGAGTTTGGAGATTTTGGTGGTCGT (SEQ ID NO:5460), TCGCGAGTTTGGAGATTTTGGTGGTCG (SEQ ID NO:5461), ATCGCGAGTTTGGAGATTTTGGTGGTCG (SEQ ID NO:5462), ATCGCGAGTTTGGAGATTTTGGTGGTCGT |

FIGURE 5 CONTINUED

|  |  | {SEQ ID NO:5463}, GGTTGGCGGTGCGTAGTTTTGGAGTGT {SEQ ID NO:5464}, GTGGTTGGCGGTGCGTAGTTTTGGAGT {SEQ ID NO:5465}, TGGTTGGCGGTGCGTAGTTTTGGAGTG {SEQ ID NO:5466}, AGTGGTTGGCGGTGCGTAGTTTTGGAG {SEQ ID NO:5467}, GTGGTTGGCGGTGCGTAGTTTTGGAGTG {SEQ ID NO:5468} |
| Target577 | chr5:40681015-40681119 | AGATTTTGGTGGTCGTAGTTGGTAAGTGGT {SEQ ID NO:5469}, CGGGCGCGGGGTTTAATATTTTATAAGTGGT {SEQ ID NO:5470}, TCGGGCGCGGGGTTTAATATTTTATAAGTGGT {SEQ ID NO:5471}, GAGATTTTGGTGGTCGTAGTTGGTAAGTGGT {SEQ ID NO:5472}, AGATTTTGGTGGTCGTAGTTGGTAAGTGGTT {SEQ ID NO:5473}, GGTCGGGGTTTAAGGAGGCGGACGAAT {SEQ ID NO:5474}, GGTTGGCGGTGCGTAGTTTTGGAGTGT {SEQ ID NO:5475}, GTGGTTGGCGGTGCGTAGTTTTGGAGT {SEQ ID NO:5476}, TTAGTCGGTCGGGGTTTAAGGAGGCGG {SEQ ID NO:5477}, TGGTTGGCGGTGCGTAGTTTTGGAGTG {SEQ ID NO:5478} |
| Target578 | chr5:40681137-40681170 | CGATCGGTTGAATAGTTTAGTGATTATTTCGGCG {SEQ ID NO:5479}, TCGATCGGTTGAATAGTTTAGTGATTATTTCGGCG {SEQ ID NO:5480}, TTCGATCGGTTGAATAGTTTAGTGATTATTTCGGCG {SEQ ID NO:5481}, TGTTTTTTGCGCGATTTGTATAGTATTACGATGGT {SEQ ID NO:5482}, TGTTTTTTGCGCGATTTGTATAGTATTACGATGGTT {SEQ ID NO:5483}, TTGTTTTTTGCGCGATTTGTATAGTATTACGATGGT {SEQ ID NO:5484}, TGCGCGATTTGTATAGTATTACGATGGTTATTAGGT {SEQ ID NO:5485} |
| Target579 | chr5:40681212-40681372 | TTCGGGGTGGTGGGTAATTTGGTGGTT {SEQ ID NO:5486}, GGCGGTGATGTTTATTTTCGGGGTGGTGG {SEQ ID NO:5487}, TTTCGGGGTGGTGGGTAATTTGGTGGTT {SEQ ID NO:5488}, GCGGTGATGTTTATTTTCGGGGTGGTGG {SEQ ID NO:5489}, AGGGTTAATGGTTCGGGGGGTTAGTCGT {SEQ ID NO:5490}, AGCGGTTGGTTTTCGGGTTATTGGTTT {SEQ ID NO:5491}, GGCGTAGATGATGTTGAGGTCGGATAGGT {SEQ ID NO:5492}, TGGCGTAGATGATGTTGAGGTCGGATAGG {SEQ ID NO:5493}, TGGCGTAGATGATGTTGAGGTCGGATAGGT {SEQ ID NO:5494}, GGCGTAGATGATGTTGAGGTCGGATAGG {SEQ ID NO:5495} |
| Target580 | chr5:40681410-40681441 | AGGGTTAATGGTTCGGGGGGTTAGTCGT {SEQ ID NO:5496}, TAATGGTTCGGGGGGTTAGTCGTTGTGC {SEQ ID NO:5497}, GGGTTAATGGTTCGGGGGGTTAGTCGTT {SEQ ID NO:5498}, AGGGTTAATGGTTCGGGGGGTTAGTCGTT {SEQ ID NO:5499}, AAGGGTTAATGGTTCGGGGGGTTAGTCGT {SEQ ID NO:5500}, AGGTATGGTTGATGGTTAGGTAGCGTTCG {SEQ ID NO:5501}, GGTATGGTTGATGGTTAGGTAGCGTTCGA {SEQ ID NO:5502}, AGGTATGGTTGATGGTTAGGTAGCGTTCGA {SEQ ID NO:5503}, GGTATGGTTGATGGTTAGGTAGCGTTCGAT {SEQ ID NO:5504}, AGGTATGGTTGATGGTTAGGTAGCGTTCGAT {SEQ ID NO:5505} |
| Target581 | chr5:40681485-40682018 | TCGTTCGTGGTGAGTGATCGGGGTTGG {SEQ ID NO:5506}, TTGTGTGCGGCGCGTTGTTTCGTATGT {SEQ ID NO:5507}, GCGGTCGTTTCGGTTGTTTTTCGGGGT {SEQ ID NO:5508}, TGTGTGCGGCGCGTTGTTTCGTATGTA {SEQ ID NO:5509}, TGTTTGTGTGCGGCGCGTTGTTTCGTA {SEQ ID NO:5510}, CGGTCGCGTGGTGTTGTTCGGTGTTTA {SEQ ID NO:5511}, GGTAGCGGGGTGGTTTCGGGAGGTAAT {SEQ ID NO:5512}, TAGCGGGGTGGTTTCGGGAGGTAATCG {SEQ ID NO:5513}, GGGAAAGTAGGGAGCGGGGAATGGACG {SEQ ID NO:5514}, GGACGGTGGCGAGAATGAGGAAGGAGT {SEQ ID NO:5515} |
| Target582 | chr5:50685400-50685513 | CGGGCGGGTCGGTAAGCGAGTTTTTAG {SEQ ID NO:5516}, GGGCGGGTCGGTAAGCGAGTTTTTAGT {SEQ ID NO:5517}, TGTTTTGAGTATTTCGGGCGGGCGAGT {SEQ ID NO:5518}, GCGGGCGGGTCGGTAAGCGAGTTTTTA {SEQ ID NO:5519}, CGGGCGGGTCGGTAAGCGAGTTTTTAGT {SEQ ID NO:5520}, TGTTTGGCGGAGATGGGTTTCGTTGCG {SEQ ID NO:5521}, GTGGGGTCGTAGGGTTGGTTGTTTGGC {SEQ ID NO:5522}, CGTGAGCGTTGGGTTGGAGGTTCGTTT {SEQ ID NO:5523}, GATGGGTTTCGTTGCGGGGTAAGGAGC {SEQ ID NO:5524}, AGGGTTGGTTGTTTGGCGGAGATGGGT {SEQ ID NO:5525} |
| Target583 | chr5:50685534-50685625 | CGGGCGGGTCGGTAAGCGAGTTTTTAG {SEQ ID NO:5526}, GGGCGGGTCGGTAAGCGAGTTTTTAGT {SEQ ID NO:5527}, GCGGGCGGGTCGGTAAGCGAGTTTTTA {SEQ ID NO:5528}, CGGGCGGGTCGGTAAGCGAGTTTTTAGT {SEQ ID NO:5529}, CGGGCGGGTCGGTAAGCGAGTTTTTA {SEQ ID NO:5530}, GCGGGTTTGCGGCGTAGTAGGTTCGTA {SEQ ID NO:5531}, CGGGTTTGCGGCGTAGTAGGTTCGTAA {SEQ ID NO:5532}, CGGGTTTGCGGCGTAGTAGGTTCGTAAG {SEQ ID NO:5533}, GCGGGTTTGCGGCGTAGTAGGTTCGTAA {SEQ ID NO:5534}, CGGGTTTGCGGCGTAGTAGGTTCGTA {SEQ ID NO:5535} |
| Target584 | chr5:50685654-50685699 | ACGGGTTTTAGTTTTCGTGTGATTCGGGT {SEQ ID NO:5536}, CGGGTTTTAGTTTTCGTGTGATTCGGGT {SEQ ID NO:5537}, ACGGGTTTTAGTTTTCGTGTGATTCGGG {SEQ ID NO:5538}, GACGGGTTTTAGTTTTCGTGTGATTCGGG {SEQ ID NO:5539}, GACGGGTTTTAGTTTTCGTGTGATTCGGGT {SEQ ID NO:5540}, AGTTTTGTTATTGGGTTGTTGTTGTTGGAGTTGT {SEQ ID NO:5541}, AGTTTTGTTATTGGGTTGTTGTTGTTGGAGTTGTT {SEQ ID NO:5542}, TAGTTTTGTTATTGGGTTGTTGTTGTTGGAGTTGT {SEQ ID NO:5543}, TAGTTTTGTTATTGGGTTGTTGTTGTTGGAGTTGTT {SEQ ID NO:5544}, GTTTTGTTATTGGGTTGTTGTTGTTGGAGTTGTTTT {SEQ ID NO:5545} |

FIGURE 5 CONTINUED

| | | |
|---|---|---|
| Target585 | chr5:50685784-50685848 | TGTGAGTGGTTTTGGGGTCGGGTAGGG (SEQ ID NO:5546), GGGAATGCGAGGGGGAAGGAGACGTAG (SEQ ID NO:5547), GTAGGGAATGCGAGGGGGAAGGAGACG (SEQ ID NO:5548), TTTTGGGGTCGGGTAGGGAATGCGAGG (SEQ ID NO:5549), GGAATGCGAGGGGGAAGGAGACGTAGC (SEQ ID NO:5550), CGGCGTCGGGTAGTTTGTTTTTCGGGG (SEQ ID NO:5551), ATGGGTAGGGGGGTAAGGATGAGGGGT (SEQ ID NO:5552), GGCGTCGGGTAGTTTGTTTTTCGGGGT (SEQ ID NO:5553), TTCGGGGTATGGGTAGGGGGGTAAGGA (SEQ ID NO:5554), TCGGGGTATGGGTAGGGGGGTAAGGAT (SEQ ID NO:5555) |
| Target586 | chr5:72594949-72594960 | GGCGAGTAGTTTGGTGGTTTTGGCGGT (SEQ ID NO:5556), TCGGACGAGGCGAGTAGTTTGGTGGTT (SEQ ID NO:5557), TTCGGACGAGGCGAGTAGTTTGGTGGT (SEQ ID NO:5558), AGGCGAGTAGTTTGGTGGTTTTGGCGG (SEQ ID NO:5559), CGAGGCGAGTAGTTTGGTGGTTTTGGCG (SEQ ID NO:5560), GCGGAGTTTAGGGCGTACGGTTGTGTC (SEQ ID NO:5561), CGGAGTTTAGGGCGTACGGTTGTGTCG (SEQ ID NO:5562), TGTGTCGTTCGGGTTTGTTTTCGGAGC (SEQ ID NO:5563), GTTTAGCGGTGGTAGTCGGGAGTTCGT (SEQ ID NO:5564), GCGGAGTTTAGGGCGTACGGTTGTGT (SEQ ID NO:5565) |
| Target587 | chr5:72677125-72677162 | AGGTATAGAGGAGGTCGTTTTGTTTTTGCGA (SEQ ID NO:5566), AAGGTATAGAGGAGGTCGTTTTGTTTTTGCGA (SEQ ID NO:5567), AAAGGTATAGAGGAGGTCGTTTTGTTTTTGCG (SEQ ID NO:5568), AAAGGTATAGAGGAGGTCGTTTTGTTTTTGCGA (SEQ ID NO:5569), TAAAGGTATAGAGGAGGTCGTTTTGTTTTTGCGA (SEQ ID NO:5570), GTGGGGGCGGGAGGTGGTTTTGTTTTTT (SEQ ID NO:5571), GGGGGCGGGAGGTGGTTTGTTTTTTTG (SEQ ID NO:5572), TGGGGGCGGGAGGTGGTTTTGTTTTTTTG (SEQ ID NO:5573), GTGGGGGCGGGAGGTGGTTTTGTTTT (SEQ ID NO:5574), AACGTTTGAATTTCGGCGGTTGGAGGC (SEQ ID NO:5575) |
| Target588 | chr5:72677195-72677368 | CGTCGGGGTTTAGGCGTTTGTGAAAGA (SEQ ID NO:5576), CGTCGGGGGTTTAGGCGTTTGTGAAAGAT (SEQ ID NO:5577), GCGTTAGGTCGGTGTAGGAGGGCG (SEQ ID NO:5578), CGTCGGGGTTTAGGCGTTTGTGAAAG (SEQ ID NO:5579), CGTCGGGGTTTAGGCGTTTGTGAAAGATA (SEQ ID NO:5580), TGTCGGGTAGGGGTGGTAGGTCGAGTT (SEQ ID NO:5581), ATGTCGGGTAGGGGTGGTAGGTCGAGT (SEQ ID NO:5582), TGGCGTTGGAGAGAGCGTTCGTTGGAT (SEQ ID NO:5583), GGTTTGGCGTTGGAGAGAGCGTTCGTT (SEQ ID NO:5584), TTTGGCGTTGGAGAGAGCGTTCGTTGG (SEQ ID NO:5585) |
| Target589 | chr5:72677377-72677662 | AGGAGGGCGTTGGGGGTTCGGTTGTTA (SEQ ID NO:5586), TAGGAGGGCGTTGGGGGTTCGGTTTGTT (SEQ ID NO:5587), GTTAGGTCGGTGTAGGAGGGCGTTGGG (SEQ ID NO:5588), CGTTAGGTCGGTGTAGGAGGGCGTTGG (SEQ ID NO:5589), TGTAGGAGGGCGTTGGGGGTTCGGTTTG (SEQ ID NO:5590), CGCGGGTTTGATTTCGTCGGTTCGGAT (SEQ ID NO:5591), GCGGCGTGCGGTTTTTTCGTTCGAATG (SEQ ID NO:5592), GATTTCGTCGGTTCGGATGGATGGGCG (SEQ ID NO:5593), GTTTGTGGCGCGGGTTTGATTTCGTCG (SEQ ID NO:5594), TTCGAGACGGGTATGCGGGAGGAGGAA (SEQ ID NO:5595) |
| Target590 | chr5:72677710-72677737 | TGTTGGGTTCGGGTTTGGTTTAGAGCGT (SEQ ID NO:5596), GTTGGGTTCGGGTTTGGTTTAGAGCGT (SEQ ID NO:5597), TGTTGGGTTCGGGTTTGGTTTAGAGCG (SEQ ID NO:5598), CGTATTCGGGCGGGGAGGTCGTACG (SEQ ID NO:5599), AGGGTTGTTGGGTTCGGGTTTGGTTTA (SEQ ID NO:5600), TCGGGAGGTATTTGGTTGGTTCGGAGT (SEQ ID NO:5601), AGTCGGGAGGTATTTGGTTGGTTCGGA (SEQ ID NO:5602), CGGGTTCGGAGGAGAGGTTCGGGTG (SEQ ID NO:5603), GGGTTCGGAGGAGAGGTTCGGGTGC (SEQ ID NO:5604), GGTTCGGGGTTTCGTATTAGTCGGGAGG (SEQ ID NO:5605) |
| Target591 | chr5:72677755-72677812 | TGTTGGGTTCGGGTTTGGTTTAGAGCGT (SEQ ID NO:5606), GTTGGGTTCGGGTTTGGTTTAGAGCGT (SEQ ID NO:5607), TGTTGGGTTCGGGTTTGGTTTAGAGCG (SEQ ID NO:5608), CGTATTCGGGCGGGGAGGTCGTACG (SEQ ID NO:5609), AGGGTTGTTGGGTTCGGGTTTGGTTTA (SEQ ID NO:5610), TCGGGAGGTATTTGGTTGGTTCGGAGT (SEQ ID NO:5611), AGTCGGGAGGTATTTGGTTGGTTCGGA (SEQ ID NO:5612), GGTTCGGGGTTTCGTATTAGTCGGGAGG (SEQ ID NO:5613), GGTTCGGGGTTTCGTATTAGTCGGGAGGT (SEQ ID NO:5614), GTCGGGAGGTATTTGGTTGGTTCGGAGT (SEQ ID NO:5615) |
| Target592 | chr5:72715325-72715334 | GGGTAGTGGGGAGGGGGCGTTAAGAGT (SEQ ID NO:5616), ATATTTGGTCGGGTAGTGGGGAGGGGG (SEQ ID NO:5617), TATTTGGTCGGGTAGTGGGGAGGGGGC (SEQ ID NO:5618), GGGTAGTGGGGAGGGGGCGTTAAGAGTA (SEQ ID NO:5619), GGGTAGTGGGGAGGGGGCGTTAAGAG (SEQ ID NO:5620), TCGTGGTTAGTTGCGTTCGGTCGTTT (SEQ ID NO:5621), TTCGTGGTTAGTTGCGTTCGGTCGTTT (SEQ ID NO:5622), ATTCGTGGTTAGTTGCGTTCGGTCGTT (SEQ ID NO:5623), CGTGGTTAGTTGCGTTCGGTCGTTTTC (SEQ ID NO:5624), TCGTGGTTAGTTGCGTTCGGTCGTTTC (SEQ ID NO:5625) |
| Target593 | chr5:72715408-72715469 | TTGGTTTGTTTGGATTGTCGGGTCGGC (SEQ ID NO:5626), GCGGTTTGGTTTGTTTGGATTGTCGGGT (SEQ ID NO:5627), GCGGTTTGGTTTGTTTGGATTGTCGGG (SEQ ID NO:5628), AGCGGTTTGGTTTGTTTGGATTGTCGGG (SEQ ID NO:5629), AGCGGTTTGGTTTGTTTGGATTGTCGGGT (SEQ ID NO:5630), TTTCGGTGGTTTGGTTTTTTCGCGCGG (SEQ ID NO:5631), GTTTCGGTGGTTTGGTTTTTTCGCGCGG (SEQ ID NO:5632), CGTTTCGGTGGTTTGGTTTTTTCGCGCG (SEQ ID NO:5633), GTTTCGGTGGTTTGGTTTTTTCGCGCG (SEQ ID NO:5634), CGTTTCGGTGGTTTGGTTTTTTCGCGC (SEQ ID NO:5635) |

FIGURE 5 CONTINUED

| Target594 | chr5:72715485-72715515 | CGCGGAGGAGTTAGATTATCGGGGCGT (SEQ ID NO:5636), TCGCGCGGAGGAGTTAGATTATCGGGG (SEQ ID NO:5637), GTCGCGCGGAGGAGTTAGATTATCGGGG (SEQ ID NO:5638), GTCGCGCGGAGGAGTTAGATTATCGGG (SEQ ID NO:5639), CGCGGAGGAGTTAGATTATCGGGGCGTA (SEQ ID NO:5640) |
|---|---|---|
| Target595 | chr5:76249401-76249527 | AAGCGGGAGTTGGTTGGGGAGTAGTCG (SEQ ID NO:5641), GGTTGGGGAGTAGTCGTATCGTCGCGT (SEQ ID NO:5642), TGGTTGGGGAGTAGTCGTATCGTCGCG (SEQ ID NO:5643), GCGGGAGTTGGTTGGGGAGTAGTCGTA (SEQ ID NO:5644), TGAAGCGGGAGTTGGTTGGGGAGTAGT (SEQ ID NO:5645), TGGCGTTGAAGAGTAGGAAAGGATCGT (SEQ ID NO:5646), GGTTGGCGTTGAAGAGTAGGAAAGGATCG (SEQ ID NO:5647), GGTTGGCGTTGAAGAGTAGGAAAGGATCGT (SEQ ID NO:5648), TTGGCGTTGAAGAGTAGGAAAGGATCGT (SEQ ID NO:5649), AGGTTGGCGTTGAAGAGTAGGAAAGGATCG (SEQ ID NO:5650) |
| Target596 | chr5:76249541-76249811 | AGGTGGGATTTTGTGCGGGGGGGTAGAG (SEQ ID NO:5651), AGGTTGGAAGTCGGGGCGTTGGGTATT (SEQ ID NO:5652), TTTAGGTTGGAAGTCGGGGCGTTGGGT (SEQ ID NO:5653), AAGCGGGAGTTGGTTGGGGAGTAGTCG (SEQ ID NO:5654), AAGGTGGGATTTTGTGCGGGGGGTAGA (SEQ ID NO:5655), CGGTCGGCGGTGAAGGTGAATTGGTTT (SEQ ID NO:5656), TCGGTCGGCGGTGAAGGTGAATTGGTT (SEQ ID NO:5657), TTGCGTAGTGTAGTTGCGGTCGGTCGG (SEQ ID NO:5658), GTCGGTCGGCGGTGAAGGTGAATTGGT (SEQ ID NO:5659), GTCGGTCGGCGGTGAAGGTGAATTGG (SEQ ID NO:5660) |
| Target597 | chr5:77140543-77140645 | GCGTGGGGAGAATTGGAGCGGTTGTTC (SEQ ID NO:5661), TGGGGAGAATTGGAGCGGTTGTTCGGA (SEQ ID NO:5662), GGTTGTGGGGAGGTGGTGTGGGAGTAC (SEQ ID NO:5663), CGTGGGGAGAATTGGAGCGGTTGTTCG (SEQ ID NO:5664), GAGGTGGTGTGGGAGTACGGTCGTTGT (SEQ ID NO:5665), CGGGGGCGTTCGGGGTAGTCGTTTTAGT (SEQ ID NO:5666), AAAGTATTCGGGATTAGGGCGGGGGCG (SEQ ID NO:5667), GAGGGGGTTGGGGGGGTGAGTGGAAATA (SEQ ID NO:5668), GTATTCGGGATTAGGGCGGGGGCGTTC (SEQ ID NO:5669), AGGGGGGTTGGGGGGGTGAGTGGAAATAA (SEQ ID NO:5670) |
| Target598 | chr5:77140667-77140698 | GCGTGGGGAGAATTGGAGCGGTTGTTC (SEQ ID NO:5671), TGGGGAGAATTGGAGCGGTTGTTCGGA (SEQ ID NO:5672), GGTTGTGGGGAGGTGGTGTGGGAGTAC (SEQ ID NO:5673), CGTGGGGAGAATTGGAGCGGTTGTTCG (SEQ ID NO:5674), GAGGTGGTGTGGGAGTACGGTCGTTGT (SEQ ID NO:5675), GTTTCGGGGAGGGCGCGATGTGTTTTT (SEQ ID NO:5676), TTTCGGGGAGGGCGCGATGTGTTTTTT (SEQ ID NO:5677), GAGGGGGTTGGGGGGGTGAGTGGAAATA (SEQ ID NO:5678), GTTTGGAATTAGGACGGCGGGAGGGGG (SEQ ID NO:5679), GGTTTGGAATTAGGACGGCGGGAGGGG (SEQ ID NO:5680) |
| Target599 | chr5:77140757-77140827 | AGGTTGTCGGGGAGGGGGTATATCGCG (SEQ ID NO:5681), TAGGTTGTCGGGGAGGGGGTATATCGC (SEQ ID NO:5682), GGTTGTCGGGGAGGGGGTATATCGCG (SEQ ID NO:5683), TCGGTTTGGTTGTAGTCGCGTGGATGT (SEQ ID NO:5684), TAGGTTGTCGGGGAGGGGGTATATCGCG (SEQ ID NO:5685), GACGACGGGGTAGTGGAGGGATGTTCG (SEQ ID NO:5686), GAGGAGACGACGGGGTAGTGGAGGGAT (SEQ ID NO:5687), AGAGAGTGGAAGGAGGAGACGACGGGG (SEQ ID NO:5688), GTTTCGGGGAGGGCGCGATGTGTTTTT (SEQ ID NO:5689), TTTCGGGGAGGGCGCGATGTGTTTTT (SEQ ID NO:5690) |
| Target600 | chr5:77140834-77140914 | TCGTGGGGAGCGTTCGAGTAGGTAGGG (SEQ ID NO:5691), GTGGGGAGCGTTCGAGTAGGTAGGGTT (SEQ ID NO:5692), CGTGGGGAGCGTTCGAGTAGGTAGGGT (SEQ ID NO:5693), AGGTTGTCGGGGAGGGGGTATATCGCG (SEQ ID NO:5694), CGTGGGGAGCGTTCGAGTAGGTAGGG (SEQ ID NO:5695), GACGACGGGGTAGTGGAGGGATGTTCG (SEQ ID NO:5696), GAGGAGACGACGGGGTAGTGGAGGGAT (SEQ ID NO:5697), AGAGAGTGGAAGGAGGAGACGACGGGG (SEQ ID NO:5698), GGAAGGAGGAGACGACGGGGTAGTGGA (SEQ ID NO:5699), AAGGAGGAGACGACGGGGTAGTGGAGG (SEQ ID NO:5700) |
| Target601 | chr5:115912075-115912099 | GGGGCGGTGGGTAGGATTGCGTTTTTT (SEQ ID NO:5701), TATAGATTTGGGGTAGTGGGGGGCGCG (SEQ ID NO:5702), TAGTTTCGGGAGGGGGTTGGGGAGTGT (SEQ ID NO:5703), GTTAGTTTCGGGAGGGGGTTGGGGAGT (SEQ ID NO:5704), TTAGTTTCGGGAGGGGGTTGGGGAGTG (SEQ ID NO:5705), CGCGGGATTTTGAGGAGACGTTTTGGA (SEQ ID NO:5706), TCGCGGGATTTTGAGGAGACGTTTTGG (SEQ ID NO:5707), TCGCGGGATTTTGAGGAGACGTTTTGGA (SEQ ID NO:5708), CGCGGGATTTTGAGGAGACGTTTTGGAG (SEQ ID NO:5709), CGCGGGATTTTGAGGAGACGTTTTGGAGT (SEQ ID NO:5710) |
| Target602 | chr5:115912143-115912177 | GGGGCGGTGGGTAGGATTGCGTTTTTT (SEQ ID NO:5711), GCGGGGTTAGGAGAAGGATTTGGCGGT (SEQ ID NO:5712), TAGTTTCGGGAGGGGGTTGGGGAGTGT (SEQ ID NO:5713), GTTAGTTTCGGGAGGGGGTTGGGGAGT (SEQ ID NO:5714), TTAGTTTCGGGAGGGGGTTGGGGAGTG (SEQ ID NO:5715), AAGGGGTTGTAGTATCGCGTTTGGGGC (SEQ ID NO:5716), GAAGGGGTTGTAGTATCGCGTTTGGGC (SEQ ID NO:5717), CGAAGGGGTTGTAGTATCGCGTTTGGGG (SEQ ID NO:5718), TCGAAGGGGTTGTAGTATCGCGTTTGGGG (SEQ ID NO:5719), AGGGGTTGTAGTATCGCGTTTGGGGC (SEQ ID NO:5720) |
| Target603 | chr5:115912257-115912294 | GCGGGGTTAGGAGAAGGATTTGGCGGT (SEQ ID NO:5721), CGCGGGGTTAGGAGAAGGATTTGGCGG (SEQ ID NO:5722), TTCGCGGGGTTAGGAGAAGGATTTGGC (SEQ ID NO:5723), CGGGGTTAGGAGAAGGATTTGGCGGTT (SEQ ID NO:5724), CGCGGGGTTAGGAGAAGGATTTGGCG (SEQ ID NO:5725), CGGTTGGGTGGAGCGCGGGATAAAAAA (SEQ ID NO:5726), AGGGGTTGTAGTATCGCGTTTGGGGC (SEQ ID NO:5727), CGGTTGGGTGGAGCGCGGGATAAAAAAT |

FIGURE 5 CONTINUED

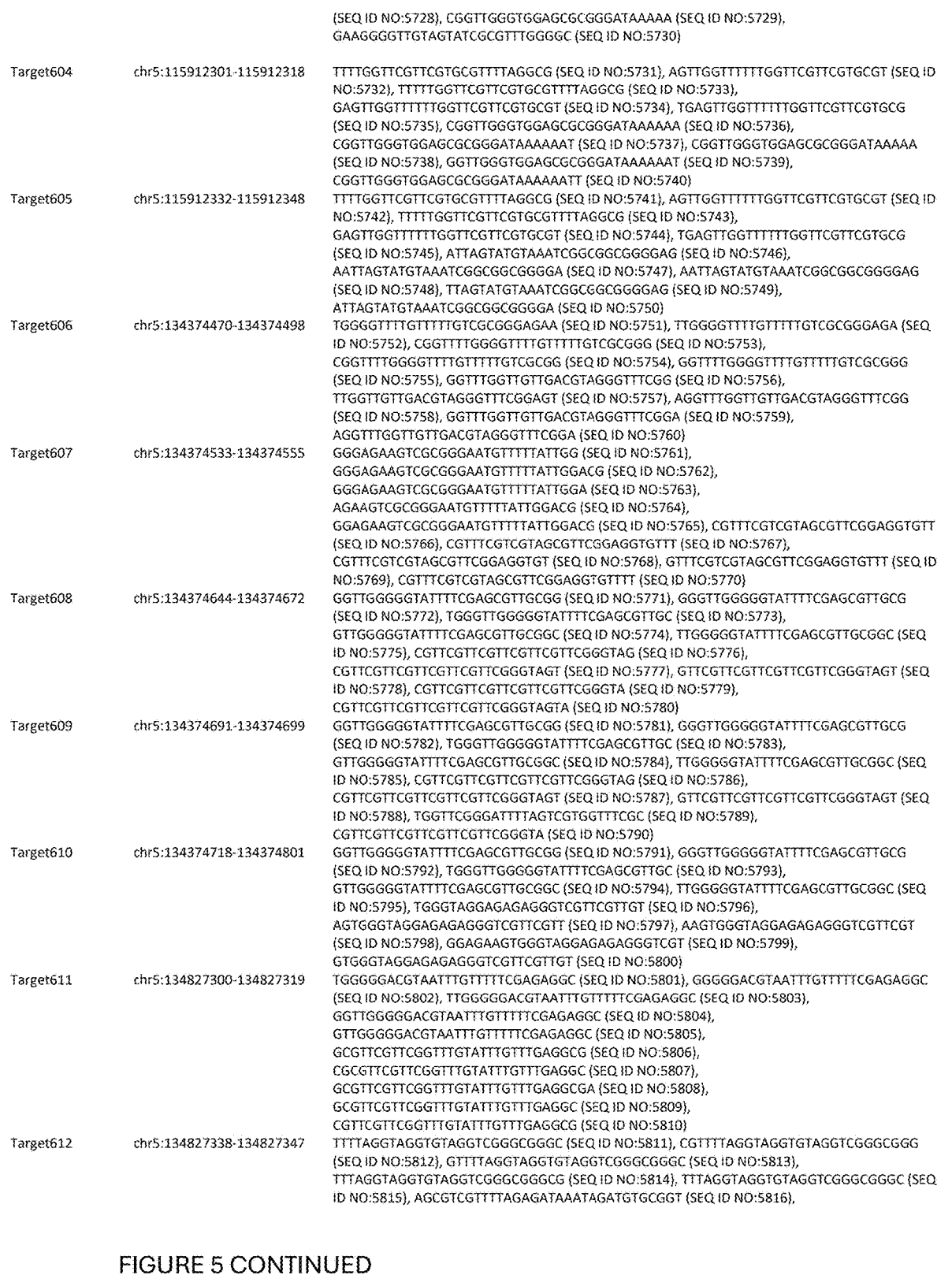

{SEQ ID NO:5728}, CGGTTGGGTGGAGCGCGGGATAAAAA {SEQ ID NO:5729},
GAAGGGGTTGTAGTATCGCGTTTGGGGC {SEQ ID NO:5730}

Target604    chr5:115912301-115912318    TTTTGGTTCGTTCGTGCGTTTAGGCG {SEQ ID NO:5731}, AGTTGGTTTTTTGGTTCGTTCGTGCGT {SEQ ID
NO:5732}, TTTTTGGTTCGTTCGTGCGTTTTAGGCG {SEQ ID NO:5733},
GAGTTGGTTTTTTGGTTCGTTCGTGCGT {SEQ ID NO:5734}, TGAGTTGGTTTTTTGGTTCGTTCGTGCG
{SEQ ID NO:5735}, CGGTTGGGTGGAGCGCGGGATAAAAAA {SEQ ID NO:5736},
CGGTTGGGTGGAGCGCGGGATAAAAAAT {SEQ ID NO:5737}, CGGTTGGGTGGAGCGCGGGATAAAAA
{SEQ ID NO:5738}, GGTTGGGTGGAGCGCGGGATAAAAAAT {SEQ ID NO:5739},
CGGTTGGGTGGAGCGCGGGATAAAAAATT {SEQ ID NO:5740}

Target605    chr5:115912332-115912348    TTTTGGTTCGTTCGTGCGTTTTAGGCG {SEQ ID NO:5741}, AGTTGGTTTTTTGGTTCGTTCGTGCGT {SEQ ID
NO:5742}, TTTTTGGTTCGTTCGTGCGTTTTAGGCG {SEQ ID NO:5743},
GAGTTGGTTTTTTGGTTCGTTCGTGCGT {SEQ ID NO:5744}, TGAGTTGGTTTTTTGGTTCGTTCGTGCG
{SEQ ID NO:5745}, ATTAGTATGTAAATCGGCGGCGGGGAG {SEQ ID NO:5746},
AATTAGTATGTAAATCGGCGGCGGGGA {SEQ ID NO:5747}, AATTAGTATGTAAATCGGCGGCGGGGAG
{SEQ ID NO:5748}, TTAGTATGTAAATCGGCGGCGGGGAG {SEQ ID NO:5749},
ATTAGTATGTAAATCGGCGGCGGGGA {SEQ ID NO:5750}

Target606    chr5:134374470-134374498    TGGGGTTTTGTTTTTGTCGCGGGAGAA {SEQ ID NO:5751}, TTGGGGTTTTGTTTTTGTCGCGGGAGA {SEQ
ID NO:5752}, CGGTTTTGGGGTTTTGTTTTTGTCGCGGG {SEQ ID NO:5753},
CGGTTTTGGGGTTTTGTTTTTGTCGCGG {SEQ ID NO:5754}, GGTTTTGGGGTTTTGTTTTTGTCGCGGG
{SEQ ID NO:5755}, GGTTTGGTTGTTGACGTAGGGTTTCGG {SEQ ID NO:5756},
TTGGTTGTTGACGTAGGGTTTCGGAGT {SEQ ID NO:5757}, AGGTTTGGTTGTTGACGTAGGGTTTCGG
{SEQ ID NO:5758}, GGTTTGGTTGTTGACGTAGGGTTTCGGA {SEQ ID NO:5759},
AGGTTTGGTTGTTGACGTAGGGTTTCGG {SEQ ID NO:5760}

Target607    chr5:134374533-134374555    GGGAGAAGTCGCGGGAATGTTTTTATTGG {SEQ ID NO:5761},
GGGAGAAGTCGCGGGAATGTTTTTATTGGACG {SEQ ID NO:5762},
GGGAGAAGTCGCGGGAATGTTTTTATTGGA {SEQ ID NO:5763},
AGAAGTCGCGGGAATGTTTTTATTGGACG {SEQ ID NO:5764},
GGAGAAGTCGCGGGAATGTTTTTATTGGACG {SEQ ID NO:5765}, CGTTTCGTCGTAGCGTTCGGAGGTGTT
{SEQ ID NO:5766}, CGTTTCGTCGTAGCGTTCGGAGGTGTTT {SEQ ID NO:5767},
CGTTTCGTCGTAGCGTTCGGAGGTGT {SEQ ID NO:5768}, GTTTCGTCGTAGCGTTCGGAGGTGTTT {SEQ ID
NO:5769}, CGTTTCGTCGTAGCGTTCGGAGGTGTTTT {SEQ ID NO:5770}

Target608    chr5:134374644-134374672    GGTTGGGGGTATTTTCGAGCGTTGCGG {SEQ ID NO:5771}, GGGTTGGGGGTATTTTCGAGCGTTGCG
{SEQ ID NO:5772}, TGGGTTGGGGGTATTTTCGAGCGTTGC {SEQ ID NO:5773},
GTTGGGGGTATTTTCGAGCGTTGCGG {SEQ ID NO:5774}, TTGGGGGTATTTTCGAGCGTTGCGGC {SEQ
ID NO:5775}, CGTTCGTTCGTTCGTTCGTTCGGGTAG {SEQ ID NO:5776},
CGTTCGTTCGTTCGTTCGTTCGGGTAGT {SEQ ID NO:5777}, GTTCGTTCGTTCGTTCGTTCGGGTAGT {SEQ
ID NO:5778}, CGTTCGTTCGTTCGTTCGTTCGGGTA {SEQ ID NO:5779},
CGTTCGTTCGTTCGTTCGTTCGGGTAGTA {SEQ ID NO:5780}

Target609    chr5:134374691-134374699    GGTTGGGGGTATTTTCGAGCGTTGCGG {SEQ ID NO:5781}, GGGTTGGGGGTATTTTCGAGCGTTGCG
{SEQ ID NO:5782}, TGGGTTGGGGGTATTTTCGAGCGTTGC {SEQ ID NO:5783},
GTTGGGGGTATTTTCGAGCGTTGCGGC {SEQ ID NO:5784}, TTGGGGGTATTTTCGAGCGTTGCGGC {SEQ
ID NO:5785}, CGTTCGTTCGTTCGTTCGTTCGGGTAG {SEQ ID NO:5786},
CGTTCGTTCGTTCGTTCGTTCGGGTAGT {SEQ ID NO:5787}, GTTCGTTCGTTCGTTCGTTCGGGTAGT {SEQ
ID NO:5788}, TGGTTCGGGATTTTAGTCGTGGTTTCGC {SEQ ID NO:5789},
CGTTCGTTCGTTCGTTCGGGTA {SEQ ID NO:5790}

Target610    chr5:134374718-134374801    GGTTGGGGGTATTTTCGAGCGTTGCGG {SEQ ID NO:5791}, GGGTTGGGGGTATTTTCGAGCGTTGCG
{SEQ ID NO:5792}, TGGGTTGGGGGTATTTTCGAGCGTTGC {SEQ ID NO:5793},
GTTGGGGGTATTTTCGAGCGTTGCGGC {SEQ ID NO:5794}, TTGGGGGTATTTTCGAGCGTTGCGGC {SEQ
ID NO:5795}, TGGGTAGGAGAGAGGGTCGTTCGTTGT {SEQ ID NO:5796},
AGTGGGTAGGAGAGAGGGTCGTTCGTT {SEQ ID NO:5797}, AAGTGGGTAGGAGAGAGGGTCGTTCGT
{SEQ ID NO:5798}, GGAGAAGTGGGTAGGAGAGAGGGTCGT {SEQ ID NO:5799},
GTGGGTAGGAGAGAGGGTCGTTCGTTGT {SEQ ID NO:5800}

Target611    chr5:134827300-134827319    TGGGGGACGTAATTTGTTTTTCGAGAGGC {SEQ ID NO:5801}, GGGGGACGTAATTTGTTTTTCGAGAGGC
{SEQ ID NO:5802}, TTGGGGGACGTAATTTGTTTTTCGAGAGGC {SEQ ID NO:5803},
GGTTGGGGGACGTAATTTGTTTTTCGAGAGGC {SEQ ID NO:5804},
GTTGGGGGACGTAATTTGTTTTTCGAGAGGC {SEQ ID NO:5805},
GCGTTCGTTCGGTTTGTATTTGTTTGAGCG {SEQ ID NO:5806},
CGCGTTCGTTCGGTTTGTATTTGTTTGAGGC {SEQ ID NO:5807},
GCGTTCGTTCGGTTTGTATTTGTTTGAGGCGA {SEQ ID NO:5808},
GCGTTCGTTCGGTTTGTATTTGTTTGAGGC {SEQ ID NO:5809},
CGTTCGTTCGGTTTGTATTTGTTTGAGGCG {SEQ ID NO:5810}

Target612    chr5:134827338-134827347    TTTTAGGTAGGTGTAGGTCGGGCGGGC {SEQ ID NO:5811}, CGTTTTAGGTAGGTGTAGGTCGGGCGGG
{SEQ ID NO:5812}, GTTTTAGGTAGGTGTAGGTCGGGCGGGC {SEQ ID NO:5813},
TTTAGGTAGGTGTAGGTCGGGCGGGCG {SEQ ID NO:5814}, TTTAGGTAGGTGTAGGTCGGGCGGGC {SEQ
ID NO:5815}, AGCGTCGTTTTAGAGATAAATAGATGTGCGGT {SEQ ID NO:5816},

FIGURE 5 CONTINUED

|  |  |  |
|---|---|---|
|  |  | AGCGTCGTTTTAGAGATAAATAGATGTGCGGTT (SEQ ID NO:5817), |
|  |  | TAGCGTCGTTTTAGAGATAAATAGATGTGCGGT (SEQ ID NO:5818), |
|  |  | GCGTCGTTTTAGAGATAAATAGATGTGCGGTTT (SEQ ID NO:5819), |
|  |  | AGCGTCGTTTTAGAGATAAATAGATGTGCGGTTT (SEQ ID NO:5820) |
| Target613 | chr5:134827413-134827494 | GGGGCGGGGTAGGGGCGTTATTTTTTG (SEQ ID NO:5821), TTTTAGGTAGGTGTAGGTCGGGCGGGC (SEQ ID NO:5822), TGGGGCGGGGTAGGGGCGTTATTTTTT (SEQ ID NO:5823), GGGCGGGGTAGGGGCGTTATTTTTTGA (SEQ ID NO:5824), GTGGGGCGGGGTAGGGGCGTTATTTTT (SEQ ID NO:5825), TATTTAGACGGAGGAGGGGCGGGAGGT (SEQ ID NO:5826), AGGAGGGGCGGGAGGTTTTGTTTTCGA (SEQ ID NO:5827), GAGGAGGGGCGGGAGGTTTTGTTTTCG (SEQ ID NO:5828), GCGTTTTAGGATGGGGTGCGTAGTGGG (SEQ ID NO:5829), TGGGGTGCGTAGTGGGTAGTTAAGCGT (SEQ ID NO:5830) |
| Target614 | chr5:134870741-134870766 | AAGGAGAAAATAGGGTCGTCGGGGCGG (SEQ ID NO:5831), AAAATAGGGTCGTCGGGGCGGTAGGTG (SEQ ID NO:5832), GAAAATAGGGTCGTCGGGGCGGTAGGT (SEQ ID NO:5833), AGAAAATAGGGTCGTCGGGGCGGTAGG (SEQ ID NO:5834), GGAGAAAATAGGGTCGTCGGGGCGGTA (SEQ ID NO:5835), GCGACGCGGAGTTTTGGGGTTTAGGTG (SEQ ID NO:5836), AGCGACGCGGAGTTTTGGGGTTTAGGT (SEQ ID NO:5837), CGCGGAGTTTTGGGGTTTAGGTGTCGT (SEQ ID NO:5838), ACGCGGAGTTTTGGGGTTTAGGTGTCG (SEQ ID NO:5839), CGACGCGGAGTTTTGGGGTTTAGGTGT (SEQ ID NO:5840) |
| Target615 | chr5:134870796-134870808 | AAGGAGAAAATAGGGTCGTCGGGGCGG (SEQ ID NO:5841), AAAATAGGGTCGTCGGGGCGGTAGGTG (SEQ ID NO:5842), TCGGGGCGGTAGGTGAAGTTTTCGGAG (SEQ ID NO:5843), TTCGGAGGCGGTTGGGTTATTGGGGTT (SEQ ID NO:5844), TTTCGGAGGCGGTTGGGTTATTGGGGT (SEQ ID NO:5845), GCGACGCGGAGTTTTGGGGTTTAGGTG (SEQ ID NO:5846), AGCGACGCGGAGTTTTGGGGTTTAGGT (SEQ ID NO:5847), CGGATTAAGGGTTGTTCGGAGGCGGTG (SEQ ID NO:5848), CGCGGAGTTTTGGGGTTTAGGTGTCGT (SEQ ID NO:5849), ACGCGGAGTTTTGGGGTTTAGGTGTCG (SEQ ID NO:5850) |
| Target616 | chr5:134870832-134870936 | AAGGAGAAAATAGGGTCGTCGGGGCGG (SEQ ID NO:5851), AAAATAGGGTCGTCGGGGCGGTAGGTG (SEQ ID NO:5852), TTCGGAGGCGGTTGGGTTATTGGGGTT (SEQ ID NO:5853), TTTCGGAGGCGGTTGGGTTATTGGGGT (SEQ ID NO:5854), GAAAATAGGGTCGTCGGGGCGGTAGGT (SEQ ID NO:5855), CGGATTAAGGGTTGTTCGGAGGCGGTG (SEQ ID NO:5856), TTGGCGGATTAAGGGTTGTTCGGAGGC (SEQ ID NO:5857), TGGCGGATTAAGGGTTGTTCGGAGGCG (SEQ ID NO:5858), GCGGATTAAGGGTTGTTCGGAGGCGGT (SEQ ID NO:5859), GGTGTTCGGGAGCGTTTTTTGTCGTCG (SEQ ID NO:5860) |
| Target617 | chr5:134870972-134870983 | TTTGGGGGATCGGGTAGGTAGGGGACG (SEQ ID NO:5861), TGGGGGATCGGGTAGGTAGGGGACGTA (SEQ ID NO:5862), GGGGGATCGGGTAGGTAGGGGACGTA (SEQ ID NO:5863), TTGGGGGATCGGGTAGGTAGGGGACG (SEQ ID NO:5864), TTGGGGGATCGGGTAGGTAGGGGACGT (SEQ ID NO:5865), TCGTATGTATAATTTGAACGCGGTTTTGGACG (SEQ ID NO:5866), ATCGTATGTATAATTTGAACGCGGTTTTGGACG (SEQ ID NO:5867), AATCGTATGTATAATTTGAACGCGGTTTTGGACG (SEQ ID NO:5868), TAATCGTATGTATAATTTGAACGCGGTTTTGGACG (SEQ ID NO:5869), CGTAATCGTATGTATAATTTGAACGCGGTTTTGGA (SEQ ID NO:5870) |
| Target618 | chr5:134871011-134871140 | TTGGTGAGTTTGGTGTCGTCGGGGAAC (SEQ ID NO:5871), TTTGGTGAGTTTGGTGTCGTCGGGGAA (SEQ ID NO:5872), TTTTGGTGAGTTTGGTGTCGTCGGGGA (SEQ ID NO:5873), TTTGGTGAGTTTGGTGTCGTCGGGGAAC (SEQ ID NO:5874), TGGTGAGTTTGGTGTCGTCGGGGAAC (SEQ ID NO:5875), CGTCGGTTCGTAGGGGCGCGTTTAATA (SEQ ID NO:5876), TATAGGACGACGAGTAGGAGAGGCGGC (SEQ ID NO:5877), CGTCGGTTCGTAGGGGCGCGTTTAAT (SEQ ID NO:5878), GTATAGGACGACGAGTAGGAGAGGCGGC (SEQ ID NO:5879), GTTGTATTCGTTGCGTAGGAGTCGGCG (SEQ ID NO:5880) |
| Target619 | chr5:134880147-134880156 | GGGAGGCGGAGGTTGTAGTGAGTCGAG (SEQ ID NO:5881), TTCGGGAGGCGGAGGTTGTAGTGAGTC (SEQ ID NO:5882), CGTTTGAATTCGGGAGGCGGAGGTTGT (SEQ ID NO:5883), TCGTTTGAATTCGGGAGGCGGAGGTTG (SEQ ID NO:5884), ATTCGGGAGGCGGAGGTTGTAGTGAGT (SEQ ID NO:5885), GGGGAGGGGCGGGGGGTTAGAATGTTTT (SEQ ID NO:5886), GGGGAGGGGCGGGGGTTAGAATGTTTT (SEQ ID NO:5887), GGGGAGGGGCGGGGGTTAGAATGTTT (SEQ ID NO:5888), GGGGAGGGGCGGGGGGTTAGAATGTTTTT (SEQ ID NO:5889), CGGGGAGGGGCGGGGGTTAGAATGTTT (SEQ ID NO:5890) |
| Target620 | chr5:140800769-140800814 | TCGGTTTAGAGTTTGTTATGGCGAATCGGT (SEQ ID NO:5891), CGGTTTAGAGTTTGTTATGGCGAATCGGTT (SEQ ID NO:5892), CGCGGAATATCGGTTTAGAGTTTGTTATGGCG (SEQ ID NO:5893), TCGGTTTAGAGTTTGTTATGGCGAATCGGTT (SEQ ID NO:5894), ATCGGTTTAGAGTTTGTTATGGCGAATCGGT (SEQ ID NO:5895), CGCGTTGTAGTCGATTCGTTATGGTAGGT (SEQ ID NO:5896), TCGCGTTGTAGTCGATTCGTTATGGTAGG (SEQ ID NO:5897), TCGCGTTGTAGTCGATTCGTTATGGTAGGT (SEQ ID NO:5898), CGCGTTGTAGTCGATTCGTTATGGTAGGTT (SEQ ID NO:5899), TCGCGTTGTAGTCGATTCGTTATGGTAGGTT (SEQ ID NO:5900) |
| Target621 | chr5:140800815-140800829 | TCGGTTTAGAGTTTGTTATGGCGAATCGGT (SEQ ID NO:5901), CGGTTTAGAGTTTGTTATGGCGAATCGGTT (SEQ ID NO:5902), CGCGGAATATCGGTTTAGAGTTTGTTATGGCG (SEQ ID NO:5903), |

FIGURE 5 CONTINUED

TCGGTTTAGAGTTTGTTATGGCGAATCGGTT (SEQ ID NO:5904),
ATCGGTTTAGAGTTTGTTATGGCGAATCGGT (SEQ ID NO:5905),
CGGATTTGTTTGGTTCGGAATTTTCGTAGCG (SEQ ID NO:5906),
CGGATTTGTTTGGTTCGGAATTTTCGTAGCGT (SEQ ID NO:5907),
TCGGATTTGTTTGGTTCGGAATTTTCGTAGCG (SEQ ID NO:5908),
TCGGATTTGTTTGGTTCGGAATTTTCGTAGCGT (SEQ ID NO:5909),
GGATTTGTTTGGTTCGGAATTTTCGTAGCGT (SEQ ID NO:5910)

Target622    chr5:140800862-140800930    CGTTGCGGGGGTTTCGGGTTAGGTAGA (SEQ ID NO:5911), GACGTTGCGGGGGTTTCGGGTTAGGTA (SEQ ID NO:5912), ACGTTGCGGGGGTTTCGGGTTAGGTAG (SEQ ID NO:5913), TTTTTTGGGGACGTTGCGGGGGTTTCG (SEQ ID NO:5914), ACGTTGCGGGGGTTTCGGGTTAGGTA (SEQ ID NO:5915), CGCGTTTCGTTAGTTTTCGGGGTTTTAGT (SEQ ID NO:5916), CGCGTTTCGTTAGTTTTCGGGGTTTTAGTT (SEQ ID NO:5917), CGCGTTTCGTTAGTTTTCGGGGTTTTAGTTT (SEQ ID NO:5918), CGCGTTTCGTTAGTTTTCGGGGTTTTAGTTTT (SEQ ID NO:5919), CGCGTTTCGTTAGTTTTCGGGGTTTTAGTTTTA (SEQ ID NO:5920)

Target623    chr5:140800981-140800996    CGTTGCGGGGGTTTCGGGTTAGGTAGA (SEQ ID NO:5921), GACGTTGCGGGGGTTTCGGGTTAGGTA (SEQ ID NO:5922), ACGTTGCGGGGGTTTCGGGTTAGGTAG (SEQ ID NO:5923), GGGTTGGAGTTTCGGGAGTTGGCGAAG (SEQ ID NO:5924), TTTGGGGTTGGAGTTTCGGGAGTTGGC (SEQ ID NO:5925), ATTTTGTTTGTCGTGATTAAGTTGTCGTTTCGC (SEQ ID NO:5926), TCGGTTTATTTTGTTTGTCGTGATTAAGTTGTCGT (SEQ ID NO:5927), TCGGTTTATTTTGTTTGTCGTGATTAAGTTGTCGTT (SEQ ID NO:5928), TTCGGTTTATTTTGTTTGTCGTGATTAAGTTGTCGT (SEQ ID NO:5929), TTTATTTTGTTTGTCGTGATTAAGTTGTCGTTTCGC (SEQ ID NO:5930)

Target624    chr5:140801033-140801091    GGGTTGGAGTTTCGGGAGTTGGCGAAG (SEQ ID NO:5931), TTTGGGGTTGGAGTTTCGGGAGTTGGC (SEQ ID NO:5932), GGGGTTGGAGTTTCGGGAGTTGGCGAA (SEQ ID NO:5933), TTGGGGTTGGAGTTTCGGGAGTTGGCG (SEQ ID NO:5934), GGGGTTGGAGTTTCGGGAGTTGGCGA (SEQ ID NO:5935), TCGGTTTATTTTGTTTGTCGTGATTAAGTTGTCGT (SEQ ID NO:5936), TCGGTTTATTTTGTTTGTCGTGATTAAGTTGTCGTT (SEQ ID NO:5937), TTCGGTTTATTTTGTTTGTCGTGATTAAGTTGTCGT (SEQ ID NO:5938)

Target625    chr5:140892549-140892926    AGGTGGGTGTTGGAAGAAGGGCGGAAT (SEQ ID NO:5939), GGTGGGGATTTGAGTGCGGCGTGTTAG (SEQ ID NO:5940), ATCGGTTCGTTGTGGGGGTGGGGATTT (SEQ ID NO:5941), AGGTAGAAGAGGAGATTTCGGCGCGGG (SEQ ID NO:5942), GAGGTGGGTGTTGGAAGAAGGGCGGAA (SEQ ID NO:5943), GGGGGTGCGGGGGGTAAAGGAGAGTTTA (SEQ ID NO:5944), AAGTTTTTCGGGGCGTTTCGGGTAGGT (SEQ ID NO:5945), GGGGGTGCGGGGGGTAAAGGAGAGTTT (SEQ ID NO:5946), TGGGGGTGCGGGGGGTAAAGGAGAGTTT (SEQ ID NO:5947), GGGGGTGCGGGGGGTAAAGGAGAGTTTAT (SEQ ID NO:5948)

Target626    chr5:140892953-140893456    GAGTGGGAGGGAATGCGGGAGGTGATT (SEQ ID NO:5949), AGGTAGAAGAGGAGATTTCGGCGCGGG (SEQ ID NO:5950), AGCGTTTCGGAGGGGTTTTACGGGAGGA (SEQ ID NO:5951), AGTGGGAGGGAATGCGGGAGGTGATTT (SEQ ID NO:5952), GCGTTTCGGAGGGGTTTTACGGGAGGAG (SEQ ID NO:5953), CGGGGAAGTAGGGGAGAGTAGGCGAGTGA (SEQ ID NO:5954), GGGGGTGCGGGGGGTAAAGGAGAGTTTA (SEQ ID NO:5955), ATTTTTAGGTAGCGGGGGGTGGGGGTGC (SEQ ID NO:5956), AGGGAGGGGAGTTGAGTTTGCGATGGA (SEQ ID NO:5957), AAGGAGGGAGGGGAGTTGAGTTTGCGA (SEQ ID NO:5958)

Target627    chr5:149979264-149979770    GATGGAGGGCGAGAGGGGATTTGGGAG (SEQ ID NO:5959), TGTATTGTGAGTTTGGGGGTCGGCGGT (SEQ ID NO:5960), GGAGGGCGAGAGGGGATTTGGGAGTTG (SEQ ID NO:5961), GTATTGTGAGTTTGGGGGTCGGCGGTG (SEQ ID NO:5962), AGATGGAGGGCGAGAGGGGATTTGGGA (SEQ ID NO:5963), GGGTGACGTTAGTAGGGTTGGGAATGGGG (SEQ ID NO:5964), GGGGTGACGTTAGTAGGGTTGGGAATGGG (SEQ ID NO:5965), GGTGACGTTAGTAGGGTTGGGAATGGGGT (SEQ ID NO:5966), GGTGACGTTAGTAGGGTTGGGAATGGGG (SEQ ID NO:5967), GGGTGACGTTAGTAGGGTTGGGAATGGG (SEQ ID NO:5968)

Target628    chr5:153862183-153862194    GGTTTTTGGAAGTTTAGGTCGCGGCGT (SEQ ID NO:5969), AGGTTTTTGGAAGTTTAGGTCGCGGCGT (SEQ ID NO:5970), AGGTTTTTGGAAGTTTAGGTCGCGGCG (SEQ ID NO:5971), GGTTTTTGGAAGTTTAGGTCGCGGCGTT (SEQ ID NO:5972), TGGACGTTTTGTAGTGGTGGGGTTTCGT (SEQ ID NO:5973), GCGGGGATTGTTCGTGGCGTTAAGGTT (SEQ ID NO:5974), GTGCGGGGATTGTTCGTGGCGTTAAGG (SEQ ID NO:5975), GGTGCGGGGATTGTTCGTGGCGTTAAG (SEQ ID NO:5976), TAAGGTTACGGGATTGCGGCGGGAGAA (SEQ ID NO:5977), TTAAGGTTACGGGATTGCGGCGGGAGA (SEQ ID NO:5978)

Target629    chr5:153862230-153862252    GGTTTTTGGAAGTTTAGGTCGCGGCGT (SEQ ID NO:5979), AGGTTTTTGGAAGTTTAGGTCGCGGCGT (SEQ ID NO:5980), AGGTTTTTGGAAGTTTAGGTCGCGGCG (SEQ ID NO:5981), GGTTTTTGGAAGTTTAGGTCGCGGCGTT (SEQ ID NO:5982), AGGTTTTTGGAAGTTTAGGTCGCGGCGTT (SEQ ID NO:5983), AGATAAGGGGTTCGGTGCGGGGATTGT (SEQ ID NO:5984), TAAGGGGTTCGGTGCGGGGATTGTTCG (SEQ ID NO:5985), ATAAGGGGTTCGGTGCGGGGATTGTTC (SEQ ID NO:5986), GATAAGGGGTTCGGTGCGGGGATTGTT (SEQ ID NO:5987), AGATAAGGGGTTCGGTGCGGGGATTGTT (SEQ ID NO:5988)

FIGURE 5 CONTINUED

| | | |
|---|---|---|
| Target630 | chr5:153862357-153862422 | TTTCGTTGTTTTGGGGAATCGCGTCGC (SEQ ID NO:5989), TTTTCGTTGTTTTGGGGAATCGCGTCGC (SEQ ID NO:5990), TTCGTTGTTTTGGGGAATCGCGTCGC (SEQ ID NO:5991), TTTTCGTTGTTTTGGGGAATCGCGTCG (SEQ ID NO:5992), ATTTTCGTTGTTTTGGGGAATCGCGTCGC (SEQ ID NO:5993), GCGTTTAAGTTGCGGGGTAAATGGTTCG (SEQ ID NO:5994), GGGGTAAATGGTTCGCGGGTTGATTTATGGC (SEQ ID NO:5995), GGGTAAATGGTTCGCGGGTTGATTTATGGC (SEQ ID NO:5996), GGGGTAAATGGTTCGCGGGTTGATTT (SEQ ID NO:5997), GGGGTAAATGGTTCGCGGGTTGATTTATGG (SEQ ID NO:5998) |
| Target631 | chr5:168307062-168307160 | AGGGGAATCGGGGATAGGAGGAGGTGG (SEQ ID NO:5999), GGGGAATCGGGGATAGGAGGAGGTGGT (SEQ ID NO:6000), GGAGGTGGTAGAAGGAAAGGTCGGGGT (SEQ ID NO:6001), GGAAGGGGAATCGGGGATAGGAGGAGGT (SEQ ID NO:6002), TGGAAGGGGAATCGGGGATAGGAGGAGG (SEQ ID NO:6003) |
| Target632 | chr5:172672831-172672843 | GGGGTTTTTTCGTTCGGGGTTAGGCGT (SEQ ID NO:6004), TGGGGTTTTTTCGTTCGGGGTTAGGCG (SEQ ID NO:6005), TTGGGGTTTTTTCGTTCGGGGTTAGGCG (SEQ ID NO:6006), TGGGGTTTTTTCGTTCGGGGTTAGGCGT (SEQ ID NO:6007), GGGGTTTTTTCGTTCGGGGTTAGGCGTA (SEQ ID NO:6008), TTTCGGATTTTTAAAGGGGCGGCGGGG (SEQ ID NO:6009), CGGATTTTTAAAGGGGCGGCGGGGTTT (SEQ ID NO:6010), TCGGATTTTTAAAGGGGCGGCGGGGTT (SEQ ID NO:6011), TTCGGATTTTTAAAGGGGCGGCGGGGT (SEQ ID NO:6012), TTTTCGGATTTTTAAAGGGGCGGCGGGG (SEQ ID NO:6013) |
| Target633 | chr5:172672959-172672971 | AGGGTGCGGGGGGTTTAGAATTCGAGG (SEQ ID NO:6014), TAGGGGTTCGGGGAGGGTGGAGAGAAGG (SEQ ID NO:6015), GAAGGGGCGGGAGTTAGGATGAGGGTG (SEQ ID NO:6016), AGAAGGGGCGGGAGTTAGGATGAGGGT (SEQ ID NO:6017), GAGTTAGGATGAGGGTGCGGGGGGTTT (SEQ ID NO:6018) |
| Target634 | chr5:172673096-172673103 | AGAGGATAGAGGTTAGGACGGTGGCGA (SEQ ID NO:6019), GAGGATAGAGGTTAGGACGGTGGCGAA (SEQ ID NO:6020), AGAGGATAGAGGTTAGGACGGTGGCGAA (SEQ ID NO:6021), AGGATAGAGGTTAGGACGGTGGCGAAA (SEQ ID NO:6022), GAGGATAGAGGTTAGGACGGTGGCGAAA (SEQ ID NO:6023) |
| Target635 | chr5:177411494-177411511 | GGTCGGGTTGAGTCGGGTTGGTTTCGA (SEQ ID NO:6024), TCGGTCGGGTTGAGTCGGGTTGGTTTC (SEQ ID NO:6025), GTCGGTCGGGTTGAGTCGGGTTGGTTT (SEQ ID NO:6026), TCGGTCGGGTTGAGTCGGGTTGGTTT (SEQ ID NO:6027), CGGTCGGGTTGAGTCGGGTTGGTTTCG (SEQ ID NO:6028), AGTCGAGGGTAGGGTTTTGTTGTGCGT (SEQ ID NO:6029), GGAGTCGAGGGTAGGGTTTTGTTGTGCG (SEQ ID NO:6030), GGAGTCGAGGGTAGGGTTTTGTTGTGCGT (SEQ ID NO:6031), GAGTCGAGGGTAGGGTTTTGTTGTGCGT (SEQ ID NO:6032), GAGTCGAGGGTAGGGTTTTGTTGTGCG (SEQ ID NO:6033) |
| Target636 | chr5:177411600-177411615 | GGCGCGGAGATGGGTTAGAGTTCGGTT (SEQ ID NO:6034), GGTGAGGGGGTAAAGTCGGTTCGGAGT (SEQ ID NO:6035), AGGTGAGGGGGTAAAGTCGGTTCGGAG (SEQ ID NO:6036), GACGGCGCGGAGATGGGTTAGAGTTCG (SEQ ID NO:6037), CGACGGCGCGGAGATGGGTTAGAGTTC (SEQ ID NO:6038), GTCGAGGGTTTGTTGGAATTCGCGGGG (SEQ ID NO:6039), CGAGGGTTTGTTGGAATTCGCGGGGTT (SEQ ID NO:6040), CGTCGAGGGTTTGTTGGAATTCGCGGG (SEQ ID NO:6041), TCGAGGGTTTGTTGGAATTCGCGGGGT (SEQ ID NO:6042), CGAGGGTTTGTTGGAATTCGCGGGGTTT (SEQ ID NO:6043) |
| Target637 | chr5:177411654-177411797 | AAGTCGGTTCGGAGTTTTCGGGGGTGT (SEQ ID NO:6044), CGGTTCGGAGTTTTCGGGGGTGTAGGA (SEQ ID NO:6045), TCGGTTCGGAGTTTTCGGGGGTGTAGG (SEQ ID NO:6046), TAGAGGGTTTTCGTTCGTAGGGGCGCG (SEQ ID NO:6047), TTTTCGGGGGTGTAGGAGGGGTTTCGC (SEQ ID NO:6048), TGAGTGGTTCGGTCGGGCGTAGAGTTT (SEQ ID NO:6049), TTGAGTGGTTCGGTCGGGCGTAGAGTT (SEQ ID NO:6050), TTTGAGTGGTTCGGTCGGGCGTAGAGT (SEQ ID NO:6051), GGAGTTTTGAGTGGTTCGGTCGGGCGT (SEQ ID NO:6052), TTCGGTCGGGCGTAGAGTTTTAGGGGA (SEQ ID NO:6053) |
| Target638 | chr5:177411807-177411831 | TAGAGGGTTTTCGTTCGTAGGGGCGCG (SEQ ID NO:6054), AGGGTTTTCGTTCGTAGGGGCGCGTTC (SEQ ID NO:6055), GAGGGTTTTCGTTCGTAGGGGCGCGTT (SEQ ID NO:6056), TTAGAGGGTTTTCGTTCGTAGGGGCGC (SEQ ID NO:6057), GGGTTTTCGTTCGTAGGGGCGCGTTC (SEQ ID NO:6058), TGAGTGGTTCGGTCGGGCGTAGAGTTT (SEQ ID NO:6059), TTGAGTGGTTCGGTCGGGCGTAGAGTT (SEQ ID NO:6060), TTTGAGTGGTTCGGTCGGGCGTAGAGT (SEQ ID NO:6061), ATTTGGAGTTCGAAGTGGGTGTGCGGG (SEQ ID NO:6062), GGAGTTTTGAGTGGTTCGGTCGGGCGT (SEQ ID NO:6063) |
| Target639 | chr5:178003699-178003824 | GGGTCGTGGAGGGTTTCGGGTTGTTT (SEQ ID NO:6064), GGGGTCGTGGAGGGTTTCGGGTTGTTT (SEQ ID NO:6065), TCGTCGCGTCGGTTTTTCGGTTTTGTT (SEQ ID NO:6066), GGGTCGTGGAGGGTTTCGGGTTGTTTT (SEQ ID NO:6067), GGGGTCGTGGAGGGTTTCGGGTTGTT (SEQ ID NO:6068), CGTCGGGGGATTCGTTGGGGTTTTTCG (SEQ ID NO:6069), GCGGAGGTTTGGCGTTTCGGAGGATAG (SEQ ID NO:6070), GGCGGAGGTTTGGCGTTTCGGAGGATA (SEQ ID NO:6071), GTCGGGGGATTCGTTGGGGTTTTTCGT (SEQ ID NO:6072), GTCGTCGGGGGATTCGTTGGGGTTTTT (SEQ ID NO:6073) |
| Target640 | chr5:178003825-178004122 | CGGGAGGTCGTTTGGGTTCGGTTTTGG (SEQ ID NO:6074), GGGAGGTCGTTTGGGTTCGGTTTTGGA (SEQ ID NO:6075), CGGGAGGTCGTTTGGGTTCGGTTTTGGA (SEQ ID NO:6076), GGGAGGTCGTTTGGGTTCGGTTTTGGAT (SEQ ID NO:6077), GATCGTCGCGTCGGTTTTTCGGTTTTG (SEQ ID NO:6078), CGATAGGGAGGATTTCGGCGGGGAGTT (SEQ ID NO:6079), GGGTTTTGGGAGTTGGGTTGAGCGAGG (SEQ ID NO:6080), TGGGTTTTGGGAGTTGGGTTGAGCGAG |

FIGURE 5 CONTINUED (SEQ ID NO:6081), GGGGTTTCGGTTTATAGGGCGCGGAGG (SEQ ID NO:6082),
GCGGGGTTGATTCGGTAGAGCGGTTAG (SEQ ID NO:6083)

| Target641 | chr5:179894247-179894340 | AAGGTCGGGGCGGAGTGGGGTTGTTTAA (SEQ ID NO:6084), GAAGTTAGAAGGTCGGGGCGGAGTGGG (SEQ ID NO:6085), CGGGAAGTTTTGGGTAGGCGTTCGTGG (SEQ ID NO:6086), GGTCGGGGCGGAGTGGGTTGTTTAAGA (SEQ ID NO:6087), GAAGGTCGGGGCGGAGTGGGTTGTTTA (SEQ ID NO:6088), ACGGGCGTTTGTTTAGGGTTTTTCGGT (SEQ ID NO:6089), ACGGGCGTTTGTTTAGGGTTTTTCGGTT (SEQ ID NO:6090), CGGGCGTTTGTTTAGGGTTTTTCGGTT (SEQ ID NO:6091), CGGGCGTTTGTTTAGGGTTTTTCGGTG (SEQ ID NO:6092), CGGGCGTTTGTTTAGGGTTTTTCGGTGT (SEQ ID NO:6093) |
| Target642 | chr5:180486301-180486314 | CGGGGTTTAGATCGTTTCGGGCGGGTA (SEQ ID NO:6094), GGAGGTGTCGGAGGATGGTAAGAGCGT (SEQ ID NO:6095), TGGAGGTGTCGGAGGATGGTAAGAGCG (SEQ ID NO:6096), AGGTGTCGGAGGATGGTAAGAGCGTGT (SEQ ID NO:6097), CGGGGTTTAGATCGTTTCGGGCGGGTAT (SEQ ID NO:6098), GAGAATCGTTGCGGGTGGTTAGGCGTC (SEQ ID NO:6099), AGAATCGTTGCGGGTGGTTAGGCGTCG (SEQ ID NO:6100), GAATCGTTGCGGGTGGTTAGGCGTCG (SEQ ID NO:6101), GAATCGTTGCGGGTGGTTAGGCGTCGG (SEQ ID NO:6102), AGAATCGTTGCGGGTGGTTAGGCGTC (SEQ ID NO:6103) |
| Target643 | chr5:180486321-180486452 | GGAGGTGTCGGAGGATGGTAAGAGCGT (SEQ ID NO:6104), TGGAGGTGTCGGAGGATGGTAAGAGCG (SEQ ID NO:6105), AGGTGTCGGAGGATGGTAAGAGCGTGT (SEQ ID NO:6106), GGAGGTGTCGGAGGATGGTAAGAGCGTG (SEQ ID NO:6107), TGGAGGTGTCGGAGGATGGTAAGAGCGT (SEQ ID NO:6108), GTAGTCGGTCGTAGGGTTTAGGCGCGT (SEQ ID NO:6109), GTCGGTCGTAGGGTTTAGGCGCGTAGG (SEQ ID NO:6110), AGTCGGTCGTAGGGTTTAGGCGCGTAG (SEQ ID NO:6111), AGTAGTCGGTCGTAGGGTTTAGGCGCG (SEQ ID NO:6112), GAGAATCGTTGCGGGTGGTTAGGCGTC (SEQ ID NO:6113) |
| Target644 | chr5:180486463-180486489 | CGTTGAGTTTGGAGCGGTTTTTCGTCGG (SEQ ID NO:6114), GCGTTGAGTTTGGAGCGGTTTTTCGTC (SEQ ID NO:6115), GCGTTGAGTTTGGAGCGGTTTTTCGTCGG (SEQ ID NO:6116), GTTGAGTTTGGAGCGGTTTTTCGTCGG (SEQ ID NO:6117), TCGTTGGTTTTTGGGCGTTTGTTTGGT (SEQ ID NO:6118), CGGTCGTAGGGTTTAGGCGCGTAGGTT (SEQ ID NO:6119), GTAGTCGGTCGTAGGGTTTAGGCGCGT (SEQ ID NO:6120), GTCGGTCGTAGGGTTTAGGCGCGTAGG (SEQ ID NO:6121), AGTCGGTCGTAGGGTTTAGGCGCGTAG (SEQ ID NO:6122), AGTAGTCGGTCGTAGGGTTTAGGCGCG (SEQ ID NO:6123) |
| Target645 | chr5:180486501-180486539 | GCGGTCGGTTATTGGGTGTTGGGGTTG (SEQ ID NO:6124), TTTGCGGTCGGTTATTGGGTGTTGGGG (SEQ ID NO:6125), TGCGGTCGGTTATTGGGTGTTGGGGTT (SEQ ID NO:6126), TTGCGGTCGGTTATTGGGTGTTGGGGT (SEQ ID NO:6127), CGGTCGGTTATTGGGTGTTGGGGTTGT (SEQ ID NO:6128), CGTTTAGGCGTCGCGGGGGTAC (SEQ ID NO:6129), GCGGTGCGGGGTTAGGACGAAG (SEQ ID NO:6130), GCGGTGCGGGGTTAGGACGAA (SEQ ID NO:6131), CGTTTAGGCGTCGCGGGGGTA (SEQ ID NO:6132), CGTTTAGGCGTCGCGGGGGT (SEQ ID NO:6133) |
| Target646 | chr5:180486547-180486594 | GCGGTCGGTTATTGGGTGTTGGGGTTG (SEQ ID NO:6134), TTTGCGGTCGGTTATTGGGTGTTGGGG (SEQ ID NO:6135), TGCGGTCGGTTATTGGGTGTTGGGGTT (SEQ ID NO:6136), TTGCGGTCGGTTATTGGGTGTTGGGGT (SEQ ID NO:6137), CGGTCGGTTATTGGGTGTTGGGGTTGT (SEQ ID NO:6138), TGGAAGGTGAAGATGTGGGAGTCGTCGG (SEQ ID NO:6139), GGAAGGTGAAGATGTGGGAGTCGTCGG (SEQ ID NO:6140), GGAAGGTGAAGATGTGGGAGTCGTCGGA (SEQ ID NO:6141), AGGTGTCGTGGAAGGTGAAGATGTGGG (SEQ ID NO:6142), GGTGTCGTGGAAGGTGAAGATGTGGA (SEQ ID NO:6143) |
| Target647 | chr5:180486596-180486620 | GCGGTCGGTTATTGGGTGTTGGGGTTG (SEQ ID NO:6144), TTTGCGGTCGGTTATTGGGTGTTGGGG (SEQ ID NO:6145), TGCGGTCGGTTATTGGGTGTTGGGGTT (SEQ ID NO:6146), TTGCGGTCGGTTATTGGGTGTTGGGGT (SEQ ID NO:6147), CGGTCGGTTATTGGGTGTTGGGGTTGT (SEQ ID NO:6148), TGGAAGGTGAAGATGTGGGAGTCGTCGG (SEQ ID NO:6149), GGAAGGTGAAGATGTGGGAGTCGTCGG (SEQ ID NO:6150), GGAAGGTGAAGATGTGGGAGTCGTCGGA (SEQ ID NO:6151), AGGTGTCGTGGAAGGTGAAGATGTGGG (SEQ ID NO:6152), GGTGTCGTGGAAGGTGAAGATGTGGGA (SEQ ID NO:6153) |
| Target648 | chr5:180486679-180486697 | AGCGGGTAGATGGTTAGGGGATTCGGA (SEQ ID NO:6154), TCGGTAGCGGGTAGATGGTTAGGGGAT (SEQ ID NO:6155), ATCGGTAGCGGGTAGATGGTTAGGGGA (SEQ ID NO:6156), CGTCGTCGTGGGTTTTGGGTTTGAAGT (SEQ ID NO:6157), TGGTTAGGGGATTCGGATGTTCGTCGT (SEQ ID NO:6158) |
| Target649 | chr6:1378623-1378653 | GCGGTTGCGTTGTTTGAGGTTTCG (SEQ ID NO:6159) |
| Target650 | chr6:1378777-1378828 | CGGGGAAGAATTTGGTTAAGGGTCGGA (SEQ ID NO:6160), TCGGGGAAGAATTTGGTTAAGGGTCGG (SEQ ID NO:6161), TCGGGGAAGAATTTGGTTAAGGGTCGGA (SEQ ID NO:6162), TTCGGGGAAGAATTTGGTTAAGGGTCGG (SEQ ID NO:6163), CGGGGAAGAATTTGGTTAAGGGTCGGAT (SEQ ID NO:6164), TCGAATTGTTGGGGGGTGCGGAGTGTTT (SEQ ID NO:6165), TTCGAATTGTTGGGGGGTGCGGAGTGTT (SEQ ID NO:6166), TTTCGAATTGTTGGGGGGTGCGGAGTGT (SEQ ID NO:6167), TGTTTCGAATTGTTGGGGGGTGCGGAGT (SEQ ID NO:6168), AGGGCGGCGTTTAGAAGTTGTAGGTGG (SEQ ID NO:6169) |

FIGURE 5 CONTINUED

Target651    chr6:1378846-1378869    CGGGGAAGAATTTGGTTAAGGGTCGGA (SEQ ID NO:6170), TCGGGGAAGAATTTGGTTAAGGGTCGG (SEQ ID NO:6171), TCGGGGAAGAATTTGGTTAAGGGTCGGA (SEQ ID NO:6172), TTCGGGGAAGAATTTGGTTAAGGGTCGG (SEQ ID NO:6173), CGGGGAAGAATTTGGTTAAGGGTCGGAT (SEQ ID NO:6174), TCGAATTGTTGGGGGTGCGGAGTGTTT (SEQ ID NO:6175), TTCGAATTGTTGGGGGTGCGGAGTGTT (SEQ ID NO:6176), TTTCGAATTGTTGGGGGTGCGGAGTGT (SEQ ID NO:6177), TGTTTCGAATTGTTGGGGGTGCGGAGT (SEQ ID NO:6178), GTTTCGAATTGTTGGGGGTGCGGAGTGT (SEQ ID NO:6179)

Target652    chr6:1378947-1379043    GTAATTCGGGGTATGGAGTCGGCGGGG (SEQ ID NO:6180), AGTAATTCGGGGTATGGAGTCGGCGGG (SEQ ID NO:6181), CGGTCGGGGTTTGGAGAAGTAGCGTTG (SEQ ID NO:6182), GCGGTCGGGGTTTGGAGAAGTAGCGTT (SEQ ID NO:6183), CGGTCGGGGTTTGGAGAAGTAGCGTTGA (SEQ ID NO:6184), CGGAGTCGTCGGTTTAAGTCGGGAGCG (SEQ ID NO:6185), TTTAAGAGGGGTTTGGTGGGCGGTGTC (SEQ ID NO:6186), TTTTAAGAGGGGTTTGGTGGGCGGTGT (SEQ ID NO:6187), TTTTTAAGAGGGGTTTGGTGGGCGGTGTC (SEQ ID NO:6188), GGAGTCGTCGGTTTAAGTCGGGAGCG (SEQ ID NO:6189)

Target653    chr6:1379049-1379078    CGGTCGGGGTTTGGAGAAGTAGCGTTG (SEQ ID NO:6190), GCGGTCGGGGTTTGGAGAAGTAGCGTT (SEQ ID NO:6191), CGGTCGGGGTTTGGAGAAGTAGCGTTGA (SEQ ID NO:6192), GGTCGGGGTTTGGAGAAGTAGCGTTGA (SEQ ID NO:6193), GCGGTCGGGGTTTGGAGAAGTAGCGT (SEQ ID NO:6194), CGGAGTCGTCGGTTTAAGTCGGGAGCG (SEQ ID NO:6195), GGAGTCGTCGGTTTAAGTCGGGAGCG (SEQ ID NO:6196), CGGAGTCGTCGGTTTAAGTCGGGAGC (SEQ ID NO:6197), GTTTAAGTCGGGAGCGCGGCGGAG (SEQ ID NO:6198), GGTTTAAGTCGGGAGCGCGGCGGAG (SEQ ID NO:6199)

Target654    chr6:1379098-1379147    GCGTGTATTTGTTTCGTTTCGTCGCGT (SEQ ID NO:6200), TCGCGTGTATTTGTTTCGTTTCGTCGC (SEQ ID NO:6201), GCGTGTATTTGTTTCGTTTCGTCGCGTT (SEQ ID NO:6202), TTCGCGTGTATTTGTTTCGTTTCGTCGC (SEQ ID NO:6203), GTTCGCGTGTATTTGTTTCGTTTCGTCGC (SEQ ID NO:6204), CGGAGTCGTCGGTTTAAGTCGGGAGCG (SEQ ID NO:6205), GGAGTCGTCGGTTTAAGTCGGGAGCG (SEQ ID NO:6206), CGGAGTCGTCGGTTTAAGTCGGGAGC (SEQ ID NO:6207), TGGGGAGAATTGGGTTTTTGCGTTTGT (SEQ ID NO:6208), AGTTTGGGGAGAATTGGGTTTTTGCGT (SEQ ID NO:6209)

Target655    chr6:1379297-1379312    TTGGTTGGGGTTGGGATAGGCGTAGGG (SEQ ID NO:6210), GAAAGTCGTAGGGGCGCGTCGGTTTAC (SEQ ID NO:6211), GGAAAGTCGTAGGGGCGCGTCGGTTTA (SEQ ID NO:6212), GGTTGGGGTTGGGATAGGCGTAGGGAT (SEQ ID NO:6213), TGGTTGGGGTTGGGATAGGCGTAGGGA (SEQ ID NO:6214), TCGGTTTTGAAATTGACGGTGTAGAGTTTTTTGA (SEQ ID NO:6215), TGAAATTGACGGTGTAGAGTTTTTTGAATTCGGT (SEQ ID NO:6216), GTCGGTTTTGAAATTGACGGTGTAGAGTTTTTTG (SEQ ID NO:6217), GTCGGTTTTGAAATTGACGGTGTAGAGTTTTTTGA (SEQ ID NO:6218), TCGGTTTTGAAATTGACGGTGTAGAGTTTTTTGAA (SEQ ID NO:6219)

Target656    chr6:3247668-3247681    TGTTGTGAATTGGGGACGGTTGATTGTGT (SEQ ID NO:6220), GTTGTGAATTGGGGACGGTTGATTGTGT (SEQ ID NO:6221), TGTTGTGAATTGGGGACGGTTGATTGTG (SEQ ID NO:6222), TTGTGAATTGGGGACGGTTGATTGTGTC (SEQ ID NO:6223), GTTGTGAATTGGGGACGGTTGATTGTGTC (SEQ ID NO:6224), TGTGTGTTAGGTATTGTTTTGAGTGTTGGGAAGA (SEQ ID NO:6225), TTGTGTGTTAGGTATTGTTTTGAGTGTTGGGAAG (SEQ ID NO:6226), TTGTGTGTTAGGTATTGTTTTGAGTGTTGGGAAGA (SEQ ID NO:6227), TGTGTGTTAGGTATTGTTTTGAGTGTTGGGAAGAT (SEQ ID NO:6228), TTTGTGTGTTAGGTATTGTTTTGAGTGTTGGGAAG (SEQ ID NO:6229)

Target657    chr6:3247767-3247867    CGAGGCGGGGGTTATCGTTTTGAAGGG (SEQ ID NO:6230), GAGGCGGGGGTTATCGTTTTGAAGGGT (SEQ ID NO:6231), CGAGGCGGGGGTTATCGTTTTGAAGGGT (SEQ ID NO:6232), CGAGGCGGGGGTTATCGTTTTGAAGGGTA (SEQ ID NO:6233), AGGCGGGGGTTATCGTTTTGAAGGGTA (SEQ ID NO:6234), GGGAATATGGTTGTTCGGGAGGGGCGA (SEQ ID NO:6235), TCGGGAATATGGTTGTTCGGGAGGGGC (SEQ ID NO:6236), TGGTTGTTCGGGAGGGGCGATTTTTGT (SEQ ID NO:6237), CGGGAATATGGTTGTTCGGGAGGGGCG (SEQ ID NO:6238), GGGAATATGGTTGTTCGGGAGGGGCGAT (SEQ ID NO:6239)

Target658    chr6:6003886-6003983    TAAAAGTTGAGCGGCGGGAGGAGGAGG (SEQ ID NO:6240), GCGGGAGGAGGAGGAGGAGGAGGAAAT (SEQ ID NO:6241), AGGGATAAAAGTTGAGCGGCGGGAGGA (SEQ ID NO:6242), GGATAAAAGTTGAGCGGCGGGAGGAGG (SEQ ID NO:6243), GGGATAAAAGTTGAGCGGCGGGAGGAG (SEQ ID NO:6244), CGGGTTCGTCGGTTTTAGGGCGGAAAG (SEQ ID NO:6245), GGCGTTCGGGTTGTTTGGGTCGTTAGG (SEQ ID NO:6246), GGGTTCGTCGGTTTTAGGGCGGAAAGA (SEQ ID NO:6247), GCGTTCGGGTTGTTTTGGGTCGTTAGGT (SEQ ID NO:6248), GCGTTCGGGTTGTTTTGGGTCGTTAGG (SEQ ID NO:6249)

Target659    chr6:6003991-6004033    CGGGCGCGCGGTTGTGGTTATTTTTT (SEQ ID NO:6250), GCGGGCGCGCGGTTGTGGTTATTTTTT (SEQ ID NO:6251), GAGGCGCGGGATTGGAAGGATAGGTAT (SEQ ID NO:6252), AGGCGCGGGATTGGAAGGATAGGTATT (SEQ ID NO:6253), GCGGGCGCGCGGTTGTGGTTATTTTT (SEQ ID NO:6254), GGCGTTCGGGTTGTTTTGGGTCGTTAGG (SEQ ID NO:6255), GCGTTCGGGTTGTTTTGGGTCGTTAGGT (SEQ ID NO:6256), GCGTTCGGGTTGTTTTGGGTCGTTAGG (SEQ ID NO:6257), GGCGTTCGGGTTGTTTTGGGTCGTTAG (SEQ ID NO:6258), CGTTCGGGTTGTTTTGGGTCGTTAGGT (SEQ ID NO:6259)

FIGURE 5 CONTINUED

Target660    chr6:6004059-6004161    GCGTTAGGGCGGGGAAGAAAGGGTGAA (SEQ ID NO:6260), TGGGCGTCGGTTTGGTTTTCGGTAGTT (SEQ ID NO:6261), TTGGGCGTCGGTTTGGTTTTCGGTAGT (SEQ ID NO:6262), CGTTAGGGCGGGGAAGAAAGGGTGAAT (SEQ ID NO:6263), CGGGCGCGCGGTTGTGGTTATTTTTT (SEQ ID NO:6264), GGGTCGGGGGATTGAGGTGTTCGGTTT (SEQ ID NO:6265), GTTGGGGGTCGGGGGATTGAGGTGTTC (SEQ ID NO:6266), GGTCGGGGGATTGAGGTGTTCGGTTTT (SEQ ID NO:6267), TTGGGGGTCGGGGGATTGAGGTGTTC (SEQ ID NO:6268), GGGTCGGGGGATTGAGGTGTTCGGTT (SEQ ID NO:6269)

Target661    chr6:6004181-6004208    GCGTTAGGGCGGGGAAGAAAGGGTGAA (SEQ ID NO:6270), TGGGCGTCGGTTTGGTTTTCGGTAGTT (SEQ ID NO:6271), TTGGGCGTCGGTTTGGTTTTCGGTAGT (SEQ ID NO:6272), CGTTAGGGCGGGGAAGAAAGGGTGAAT (SEQ ID NO:6273), GCGTTAGGGCGGGGAAGAAAGGGTGA (SEQ ID NO:6274), GGGTCGGGGGATTGAGGTGTTCGGTTT (SEQ ID NO:6275), GTTGGGGGTCGGGGGATTGAGGTGTTC (SEQ ID NO:6276), GGTCGGGGGATTGAGGTGTTCGGTTTT (SEQ ID NO:6277), TTGGGGGTCGGGGGATTGAGGTGTTC (SEQ ID NO:6278), GGGTCGGGGGATTGAGGTGTTCGGTT (SEQ ID NO:6279)

Target662    chr6:6004217-6004389    GGAAGAGCGAGGCGGGTTTTGCGTTTT (SEQ ID NO:6280), TAGGAAGAGCGAGGCGGGTTTTGCGTT (SEQ ID NO:6281), TTGTAGGAAGAGCGAGGCGGGTTTTGC (SEQ ID NO:6282), TGTAGGAAGAGCGAGGCGGGTTTTGCG (SEQ ID NO:6283), GTAGGAAGAGCGAGGCGGGTTTTGCGT (SEQ ID NO:6284), TCGTTGTAAGGTGAATTCGGAGGTTTGAGA (SEQ ID NO:6285), GGTGAATTCGGAGGTTTGAGAAGGTTTACG (SEQ ID NO:6286), GGTGAATTCGGAGGTTTGAGAAGGTTTACGT (SEQ ID NO:6287), TGTAAGGTGAATTCGGAGGTTTGAGAAGGT (SEQ ID NO:6288), AGGTGAATTCGGAGGTTTGAGAAGGTTTACG (SEQ ID NO:6289)

Target663    chr6:10417266-10417517    CGGTTGAATCGGGTTGGAGGTTTGGCG (SEQ ID NO:6290), GGTTGAATCGGGTTGGAGGTTTGGCGT (SEQ ID NO:6291), TCGGTTGAATCGGGTTGGAGGTTTGGC (SEQ ID NO:6292), GGTTGAATCGGGTTGGAGGTTTGGCGTC (SEQ ID NO:6293), TTCGGTTGAATCGGGTTGGAGGTTTGGC (SEQ ID NO:6294), GTGGAAACGGGGGTTGAAATGGGGTGG (SEQ ID NO:6295), GGTGGAAACGGGGGTTGAAATGGGGTG (SEQ ID NO:6296), AGGTGGAAACGGGGGTTGAAATGGGGT (SEQ ID NO:6297), GGGTGGTAGAGGATGGAGGGCGGTTTT (SEQ ID NO:6298), ACGGGGGTTGAAATGGGGTGGTAGAGG (SEQ ID NO:6299)

Target664    chr6:10417531-10417544    TGCGGGTTTGGAAAGGTCGTTTTTATTTTTTG (SEQ ID NO:6300), TTGCGGGTTTGGAAAGGTCGTTTTTATTTTTG (SEQ ID NO:6301), TTTGCGGGTTTGGAAAGGTCGTTTTTATTTTTTG (SEQ ID NO:6302), TTTTCGTTGTTTCGCGTTTAATAGATTTTCGGTTTC (SEQ ID NO:6303), CGGGGGCGGTAGTTTAGAGTCGGTAGG (SEQ ID NO:6304), GGGGGCGGTAGTTTAGAGTCGGTAGGT (SEQ ID NO:6305), TCGGGGGCGGTAGTTTAGAGTCGGTAG (SEQ ID NO:6306), TCGGGGGCGGTAGTTTAGAGTCGGTAGG (SEQ ID NO:6307), ATCGGGGGCGGTAGTTTAGAGTCGGTA (SEQ ID NO:6308)

Target665    chr6:10417577-10417689    TGTAGGCGTTGATGAAAGGTTCGGGCG (SEQ ID NO:6309), GTAGGCGTTGATGAAAGGTTCGGGCGA (SEQ ID NO:6310), TAGGCGTTGATGAAAGGTTCGGGCGAG (SEQ ID NO:6311), GTGTAGGCGTTGATGAAAGGTTCGGGCG (SEQ ID NO:6312), CGTTGATGAAAGGTTCGGGCGAGCGT (SEQ ID NO:6313), CGGGGGCGGTAGTTTAGAGTCGGTAGG (SEQ ID NO:6314), GGGGGCGGTAGTTTAGAGTCGGTAGGT (SEQ ID NO:6315), TCGGGGGCGGTAGTTTAGAGTCGGTAG (SEQ ID NO:6316), TCGGGGGCGGTAGTTTAGAGTCGGTAGG (SEQ ID NO:6317), TGGCGTTGTTGTTTCGGGGTTTTGGTT (SEQ ID NO:6318)

Target666    chr6:10417836-10417842    GCGTTAGGTTTGGGGTTGGAGGTCGGA (SEQ ID NO:6319), AGCGTTAGGTTTGGGGTTGGAGGTCGG (SEQ ID NO:6320), ACGTGGGGGGTATAAAAAGGGCGTCGC (SEQ ID NO:6321), GTGGGGGGGTATAAAAAGGGCGTCGCG (SEQ ID NO:6322), CGTGGGGGGGTATAAAAAGGGCGTCGC (SEQ ID NO:6323), GGGTTTGTTGGGGTTTTCGGTTTTTATTGGGT (SEQ ID NO:6324), TGGGTTTGTTGGGGTTTTCGGTTTTTATTGGG (SEQ ID NO:6325), TGGGTTTGTTGGGGTTTTCGGTTTTTATTGGGT (SEQ ID NO:6326), TTGGGTTTGTTGGGGTTTTCGGTTTTTATTGGG (SEQ ID NO:6327), TTGGGTTTGTTGGGGTTTTCGGTTTTTATTGGGT (SEQ ID NO:6328)

Target667    chr6:10421386-10421420    TTTTAGACGGTGGAAATAGGGCGGTGA (SEQ ID NO:6329), AGACGGTGGAAATAGGGCGGTGATTAA (SEQ ID NO:6330), TTAGACGGTGGAAATAGGGCGGTGATT (SEQ ID NO:6331), TTTAGACGGTGGAAATAGGGCGGTGAT (SEQ ID NO:6332), TTTTTAGACGGTGGAAATAGGGCGGTGA (SEQ ID NO:6333), CGAAGCGGTGGTAGGTTGAAATCGTCGT (SEQ ID NO:6334), CGAAGCGGTGGTAGGTTGAAATCGTCG (SEQ ID NO:6335), GAAGCGGTGGTAGGTTGAAATCGTCGT (SEQ ID NO:6336), CGAAGCGGTGGTAGGTTGAAATCGTCGTT (SEQ ID NO:6337), AGCGGTGGTAGGTTGAAATCGTCGTTT (SEQ ID NO:6338)

Target668    chr6:10421442-10421620    ATTTCGGGTTTAGTCGGACGGGTCGGG (SEQ ID NO:6339), GACGTGTTTTAGGGTTAGGGTGGGGCG (SEQ ID NO:6340), AGACGTGTTTTAGGGTTAGGGTGGGGCG (SEQ ID NO:6341), GATTTCGGGTTTAGTCGGACGGGTCGG (SEQ ID NO:6342), TTTCGGGTTTAGTCGGACGGGTCGGG (SEQ ID NO:6343), GTTCGGTTCGGTTCGTTCGGTTGGGTT (SEQ ID NO:6344), TTCGGTTCGGTTCGTTCGGTTGGGTTC (SEQ ID NO:6345), AGGTTCGGTTCGTTCGGTTCGTTCGGTTGGG (SEQ ID NO:6346), CGGTTCGGTTCGTTCGGTTGGGTTCGA (SEQ ID NO:6347), TCGGTTCGGTTCGTTCGGTTGGGTTCG (SEQ ID NO:6348)

FIGURE 5 CONTINUED

| | | |
|---|---|---|
| Target669 | chr6:10421628-10422390 | TTTTTGGGGTGGGGGATTTGAGCGTGC (SEQ ID NO:6349), ACGTGTTTTAGGGTTAGGGTGGGGCGT (SEQ ID NO:6350), ATTTCGGGTTTAGTCGGACGGGTCGGG (SEQ ID NO:6351), GGGAGAGAGGCGGAGGGAGGTGAAATG (SEQ ID NO:6352), GCGGAGGGAGGTGAAATGCGGGAGTTA (SEQ ID NO:6353), GAGGGAGGTCGGGGTGGGGAAAGGTTTT (SEQ ID NO:6354), GGAGGTCGGGGTGGGGAAAGGTTTTGA (SEQ ID NO:6355), GGGCGTAGTTTCGTTGGTGCGGAGTTG (SEQ ID NO:6356), AGGAGGTCGGGGTGGGGAAAGGTTTTG (SEQ ID NO:6357), GGCGTAGTTTCGTTGGTGCGGAGTTGC (SEQ ID NO:6358) |
| Target670 | chr6:11785719-11785770 | TGGTAGTGAGTTTTTTCGGGGTTTAGGTTGT (SEQ ID NO:6359), TGGTAGTGAGTTTTTTCGGGGTTTAGGTTGTT (SEQ ID NO:6360), TTGGTAGTGAGTTTTTTCGGGGTTTAGGTTGT (SEQ ID NO:6361), TGGTAGTGAGTTTTTTCGGGGTTTAGGTTGTTT (SEQ ID NO:6362), TTGGTAGTGAGTTTTTTCGGGGTTTAGGTTGTT (SEQ ID NO:6363) |
| Target671 | chr6:11785994-11786090 | GTTGTTGGGTTGTGGGGAGGAGGTGGA (SEQ ID NO:6364), AGTTGTTGGGTTGTGGGGAGGAGGTGG (SEQ ID NO:6365), TTGTTGGGTTGTGGGGAGGAGGTGGAA (SEQ ID NO:6366), TGTTGGGTTGTGGGGAGGAGGTGGAAT (SEQ ID NO:6367), GTTGTTGGGTTGTGGGGAGGAGGTGGAA (SEQ ID NO:6368) |
| Target672 | chr6:16729533-16729698 | ACGGTTGGATTGAGAGAGTAAAGAGAAAATGAGTT (SEQ ID NO:6369), AACGGTTGGATTGAGAGAGTAAAGAGAAAATGAGT (SEQ ID NO:6370), AACGGTTGGATTGAGAGAGTAAAGAGAAAATGAGTT (SEQ ID NO:6371) |
| Target673 | chr6:19691747-19691781 | GTCGGGGTTTTGGAGTTTTCGGATTTTGT (SEQ ID NO:6372), AGTCGGGGTTTTGGAGTTTTCGGATTTTGT (SEQ ID NO:6373), CGGGGTTTTGGAGTTTTCGGATTTTGTTCG (SEQ ID NO:6374), AGTCGGGGTTTTGGAGTTTTCGGATTTTG (SEQ ID NO:6375), CGGGGTTTTGGAGTTTTCGGATTTTGTTCGT (SEQ ID NO:6376), GCGTTTGTTTATATGATGAAAGGCGGGTAGG (SEQ ID NO:6377), GCGTTTGTTTATATGATGAAAGGCGGGTAGGA (SEQ ID NO:6378), GCGTTTGTTTATATGATGAAAGGCGGGTAGGAT (SEQ ID NO:6379), GCGTTTGTTTATATGATGAAAGGCGGGTAGGATT (SEQ ID NO:6380), GCGTTTGTTTATATGATGAAAGGCGGGTAGGATTT (SEQ ID NO:6381) |
| Target674 | chr6:19691827-19692233 | TTTCGTTATTTGGGTCGCGGGTTGGGC (SEQ ID NO:6382), GCGTTAGGAGCGAGGCGTTTTTGGTGA (SEQ ID NO:6383), TTTTGGTAGAGGCGTCGGAGGAAGGGG (SEQ ID NO:6384), TATATTTAGGGCGGGGGAGGTCGGGGG (SEQ ID NO:6385), AGGAGCGAGGCGTTTTTGGTGATAGCG (SEQ ID NO:6386), GATGGCGGAGTAGTTTCGAGCGGGGAT (SEQ ID NO:6387), TAGATGGCGGAGTAGTTTCGAGCGGGG (SEQ ID NO:6388), TGGCGGAGTAGTTTCGAGCGGGGATAT (SEQ ID NO:6389), ATGGCGGAGTAGTTTCGAGCGGGGATA (SEQ ID NO:6390), AGATGGCGGAGTAGTTTCGAGCGGGGA (SEQ ID NO:6391) |
| Target675 | chr6:27173544-27173557 | CGGTTAATGTTATTGTCGGACGTTCGGGT (SEQ ID NO:6392), CGGTTAATGTTATTGTCGGACGTTCGGG (SEQ ID NO:6393), TCGGTTAATGTTATTGTCGGACGTTCGGG (SEQ ID NO:6394), TCGGTTAATGTTATTGTCGGACGTTCGGGT (SEQ ID NO:6395), TTCGGTTAATGTTATTGTCGGACGTTCGGG (SEQ ID NO:6396), TTTGGAAGAGTGTAAGAGAAAGGAATCGGGTT (SEQ ID NO:6397), TTTTGGAAGAGTGTAAGAGAAAGGAATCGGGT (SEQ ID NO:6398), AGGGGTTTTTGGAAGAGTGTAAGAGAAAGGAA (SEQ ID NO:6399), AAGGGGTTTTTGGAAGAGTGTAAGAGAAAGGA (SEQ ID NO:6400), GGGGTTTTTGGAAGAGTGTAAGAGAAAGGAATCGGG (SEQ ID NO:6401) |
| Target676 | chr6:27173745-27173857 | CGTGGTTGCGAGAGTTTTTTAGGGAGAGT (SEQ ID NO:6402), CGTGGTTGCGAGAGTTTTTTAGGGAGAG (SEQ ID NO:6403), CGTAGAAGTGATAGGGAGAGGGGGAAAGT (SEQ ID NO:6404), TCGTAGAAGTGATAGGGAGAGGGGGAAAGT (SEQ ID NO:6405), TCGTAGAAGTGATAGGGAGAGGGGGAAAG (SEQ ID NO:6406) |
| Target677 | chr6:30131458-30131521 | GGAGTGGACGGGTTGGGGAAGGTATCG (SEQ ID NO:6407), CGGAGTGGACGGGTTGGGGAAGGTATC (SEQ ID NO:6408), GAGATCGGAGTGGACGGGTTGGGGAAG (SEQ ID NO:6409), GTGGGTTGAGGAGATCGGAGTGGACGG (SEQ ID NO:6410), TTCGCGTGGGTTGAGGAGATCGGAGTG (SEQ ID NO:6411), CGCGGGGAGGTAGAGTCGGTAGAAGGT (SEQ ID NO:6412), TGGGTTTTTATTTGGGAGAGCGCGGGG (SEQ ID NO:6413), GAGCGCGGGGAGGTAGAGTCGGTAGAA (SEQ ID NO:6414), AGCGCGGGGAGGTAGAGTCGGTAGAAG (SEQ ID NO:6415), GCGGGGAGGTAGAGTCGGTAGAAGGTG (SEQ ID NO:6416) |
| Target678 | chr6:30131538-30131587 | GGAGTGGACGGGTTGGGGAAGGTATCG (SEQ ID NO:6417), CGGAGTGGACGGGTTGGGGAAGGTATC (SEQ ID NO:6418), GAGATCGGAGTGGACGGGTTGGGGAAG (SEQ ID NO:6419), GTGGGTTGAGGAGATCGGAGTGGACGG (SEQ ID NO:6420), CGTGGGTTGAGGAGATCGGAGTGGACG (SEQ ID NO:6421), CGCGGGGAGGTAGAGTCGGTAGAAGGT (SEQ ID NO:6422), GAGCGCGGGGAGGTAGAGTCGGTAGAA (SEQ ID NO:6423), AGCGCGGGGAGGTAGAGTCGGTAGAAG (SEQ ID NO:6424), GCGGGGAGGTAGAGTCGGTAGAAGGTG (SEQ ID NO:6425), ATTTGGGAGAGCGCGGGGAGGTAGAGT (SEQ ID NO:6426) |
| Target679 | chr6:30131613-30131692 | CGGGGTCGTTGGAGGATGCGGTGATTA (SEQ ID NO:6427), CGGGGTCGTTGGAGGATGCGGTGATTAT (SEQ ID NO:6428), GGGGTCGTTGGAGGATGCGGTGATTAT (SEQ ID NO:6429), CGGGGTCGTTGGAGGATGCGGTGATT (SEQ ID NO:6430), CGGGGTCGTTGGAGGATGCGGTGATTATT (SEQ ID NO:6431), AGGAATTTTACGGTGTGCGTTTGGTGC (SEQ ID NO:6432), |

FIGURE 5 CONTINUED

GCGGGTTTAGGGGGTATAGGGGGTTATGGG (SEQ ID NO:6433),
AGCGGGTTTAGGGGGTATAGGGGGTTATGGG (SEQ ID NO:6434),
GCGGGTTTAGGGGGTATAGGGGGTTATGGGA (SEQ ID NO:6435),
AGCGGGTTTAGGGGGTATAGGGGGTTATGGGA (SEQ ID NO:6436)

| | | |
|---|---|---|
| Target680 | chr6:32157485-32157591 | CGGGGTTTGTTGGGTTTGTGTGGGGTT (SEQ ID NO:6437), AACGGGGTTTGTTGGGTTTGTGTGGGG (SEQ ID NO:6438), TTTGTGTGGGGTTTCGGAGTGGGGGTA (SEQ ID NO:6439), TGTGTGGGGTTTCGGAGTGGGGGTATT (SEQ ID NO:6440), TTGTGTGGGGTTTCGGAGTGGGGGTAT (SEQ ID NO:6441), GGATTGGTGAGTGGGGAGTTTGGGGGT (SEQ ID NO:6442), GGGGTTTGGGATTGGTGAGTGGGGAGT (SEQ ID NO:6443), TGGGATTGGTGAGTGGGGAGTTTGGGG (SEQ ID NO:6444), GTGAGTGGGGAGTTTGGGGGTTTTGGC (SEQ ID NO:6445), GGGGAGTTTGGGGGTTTTGGCGAGTTT (SEQ ID NO:6446) |
| Target681 | chr6:32157605-32157670 | GTTTCGTTTAGGTTTTGGTCGGTGATGGT (SEQ ID NO:6447), ATCGGGAGGTTCGTTAGGGTTTTTAGGTT (SEQ ID NO:6448), CGTTATCGGGAGGTTCGTTAGGGTTTTTAGG (SEQ ID NO:6449), CGTTATCGGGAGGTTCGTTAGGGTTTTTAGGT (SEQ ID NO:6450), GTTATCGGGAGGTTCGTTAGGGTTTTTAGGT (SEQ ID NO:6451), GGATTGGTGAGTGGGGAGTTTGGGGGT (SEQ ID NO:6452), GGGGTTTGGGATTGGTGAGTGGGGAGT (SEQ ID NO:6453), TGGGATTGGTGAGTGGGGAGTTTGGGG (SEQ ID NO:6454), GAGAAGTAATTAGGCGGGGGGAGGGGC (SEQ ID NO:6455), GTTGGGGCGGAGGGAGTAGCGGTTTTA (SEQ ID NO:6456) |
| Target682 | chr6:36253000-36253007 | GGTGATTTATGTAGGGATTTTGAGTATTCGTCGGC (SEQ ID NO:6457), AGGTGATTTATGTAGGGATTTTGAGTATTCGTCGGC (SEQ ID NO:6458), AGGTGATTTATGTAGGGATTTTGAGTATTCGTCGG (SEQ ID NO:6459), TAGGTGATTTATGTAGGGATTTTGAGTATTCGTCGG (SEQ ID NO:6460), AGGGGGCGTAGTAGTTTTTGGGGAGGC (SEQ ID NO:6461), GGGGCGTAGTAGTTTTTGGGGAGGCGT (SEQ ID NO:6462), TTTTTAGAGTAGCGTGCGTGGTGGGCG (SEQ ID NO:6463), GGCGTAGTAGTTTTTGGGGAGGCGTCG (SEQ ID NO:6464), GGGCGTAGTAGTTTTTGGGGAGGCGTC (SEQ ID NO:6465) |
| Target683 | chr6:36253026-36253058 | GGTGATTTATGTAGGGATTTTGAGTATTCGTCGGC (SEQ ID NO:6466), AGGTGATTTATGTAGGGATTTTGAGTATTCGTCGGC (SEQ ID NO:6467), AGGTGATTTATGTAGGGATTTTGAGTATTCGTCGG (SEQ ID NO:6468), TAGGTGATTTATGTAGGGATTTTGAGTATTCGTCGG (SEQ ID NO:6469), TTTTTAGAGTAGCGTGCGTGGTGGGCG (SEQ ID NO:6470), GTTTTTAGAGTAGCGTGCGTGGTGGGCG (SEQ ID NO:6471), GGGATTGCGGGGTTTTAGGTTTAGGGC (SEQ ID NO:6472), TGTTTTTAGAGTAGCGTGCGTGGTGGGC (SEQ ID NO:6473), GTTTTTAGAGTAGCGTGCGTGGTGGGC (SEQ ID NO:6474) |
| Target684 | chr6:36253077-36253113 | ACGTTGTTTTGGGAGTAGGGTCGGCGG (SEQ ID NO:6475), GTTGTTTTGGGAGTAGGGTCGGCGGC (SEQ ID NO:6476), TACGTTGTTTTGGGAGTAGGGTCGGCGG (SEQ ID NO:6477), TACGTTGTTTTGGGAGTAGGGTCGGCG (SEQ ID NO:6478), CGTTGTTTTGGGAGTAGGGTCGGCGG (SEQ ID NO:6479), GGGATTGCGGGGTTTTAGGTTTAGGGCG (SEQ ID NO:6480), GGATTGCGGGGTTTTAGGTTTAGGGCGT (SEQ ID NO:6481), GGATTGCGGGGTTTTAGGTTTAGGGCG (SEQ ID NO:6482), TGGGATTGCGGGGTTTTAGGTTTAGGGC (SEQ ID NO:6483), GGGATTGCGGGGTTTTAGGTTTAGGGC (SEQ ID NO:6484) |
| Target685 | chr6:38682982-38683256 | GGTTGAGTGGTCGGGGTATCGGGGTTT (SEQ ID NO:6485), GGTTGGTGAGTATTTGGTCGGAGCGCG (SEQ ID NO:6486), CGGTTGGTGAGTATTTGGTCGGAGCGC (SEQ ID NO:6487), GCGGTTGGTGAGTATTTGGTCGGAGCG (SEQ ID NO:6488), GTCGGGGTATCGGGGTTTAGAGAGCGG (SEQ ID NO:6489), AGAAGGAAAGTGGGCGGGGAATTCGGT (SEQ ID NO:6490), GCGTTGTTTCGGGGGAGTTGTTTCGGT (SEQ ID NO:6491), TGCGTTGTTTCGGGGGAGTTGTTTCGG (SEQ ID NO:6492), CGGTTGCGTTGTTTCGGGGGAGTTGTT (SEQ ID NO:6493), TAGGGTTTTTCGGATAGGGGTCGGCG (SEQ ID NO:6494) |
| Target686 | chr6:41341524-41341631 | GCGGTAGAGAAGTTTGCGTTCGGGATT (SEQ ID NO:6495), TCGTGGGTTTATAGAGGGTGAAGGGGT (SEQ ID NO:6496), GCGGTAGAGAAGTTTGCGTTCGGGAT (SEQ ID NO:6497), GGGGTAGTTTATGTTGAGTGGGGGTGT (SEQ ID NO:6498), CGGGATTAGTAGAGTGAGTCGATCGGC (SEQ ID NO:6499), CGAAGTGAAGTTTGGACGCGAATGGGG (SEQ ID NO:6500), TCGAAGTGAAGTTTGGACGCGAATGGG (SEQ ID NO:6501), TCGAAGTGAAGTTTGGACGCGAATGGG (SEQ ID NO:6502), CGAAGTGAAGTTTGGACGCGAATGGG (SEQ ID NO:6503), GAAGTGAAGTTTGGACGCGAATGGGG (SEQ ID NO:6504) |
| Target687 | chr6:41341646-41341691 | GCGGTAGAGAAGTTTGCGTTCGGGATT (SEQ ID NO:6505), GCGGTAGAGAAGTTTGCGTTCGGGAT (SEQ ID NO:6506), CGGGATTAGTAGAGTGAGTCGATCGGC (SEQ ID NO:6507), GCGGTAGAGAAGTTTGCGTTCGGGATTA (SEQ ID NO:6508), TCGGGATTAGTAGAGTGAGTCGATCGGC (SEQ ID NO:6509) |
| Target688 | chr6:41341707-41341716 | GCGGTAGAGAAGTTTGCGTTCGGGATT (SEQ ID NO:6510), GCGGTAGAGAAGTTTGCGTTCGGGAT (SEQ ID NO:6511), GGGGTAGTTTATGTTGAGTGGGGGTGT (SEQ ID NO:6512), CGGGATTAGTAGAGTGAGTCGATCGGC (SEQ ID NO:6513), AGGGGTAGTTTATGTTGAGTGGGGGTGT (SEQ ID NO:6514), GGGGTGAGGTTATGGAAAGTTTCGAGGT (SEQ ID NO:6515), AGGGGTGAGGTTATGGAAAGTTTCGAGGT (SEQ ID NO:6516), AGGGGTGAGGTTATGGAAAGTTTCGAGG (SEQ ID NO:6517), |

FIGURE 5 CONTINUED

GAGGGGTGAGGTTATGGAAAGTTTCGAGGT (SEQ ID NO:6518),
GAGGGGTGAGGTTATGGAAAGTTTCGAGG (SEQ ID NO:6519)

Target689    chr6:41341733-41341747    GCGGTAGAGAAGTTTGCGTTCGGGATT (SEQ ID NO:6520), GCGGTAGAGAAGTTTGCGTTCGGGAT (SEQ ID NO:6521), CGGGATTAGTAGAGTGAGTCGATCGGC (SEQ ID NO:6522), GCGGTAGAGAAGTTTGCGTTCGGGATTA (SEQ ID NO:6523), TCGGGATTAGTAGAGTGAGTCGATCGGC (SEQ ID NO:6524), AGTGGTGGTTTGGAGGACGTTGGTTAC (SEQ ID NO:6525), TTAGTGGTGGTTTGGAGGACGTTGGTT (SEQ ID NO:6526), TTTAGTGGTGGTTTGGAGGACGTTGGT (SEQ ID NO:6527), TTTAGTGGTGGTTTGGAGGACGTTGGTT (SEQ ID NO:6528), TTTTAGTGGTGGTTTGGAGGACGTTGGT (SEQ ID NO:6529)

Target690    chr6:41341750-41341762    GAGAGAGTCGCGGTGGTTGTACGT (SEQ ID NO:6530), AGAGAGTCGCGGTGGTTGTACGT (SEQ ID NO:6531), GCGGTGGTTGTACGTGCGTGC (SEQ ID NO:6532)

Target691    chr6:41528224-41528958    ATTTTCGGTTAGGGAGGGGATGGGGCG (SEQ ID NO:6533), AATTGATGAGTTGGTAGGGCGGGCGGT (SEQ ID NO:6534), GCGGCGAGGCGTAGGGTGTTATGGTAA (SEQ ID NO:6535), GGTTAGGGAGGGGATGGGGCGGTTTTC (SEQ ID NO:6536), TTTTCGGTAGGACGCGCGTTTAGGAGC (SEQ ID NO:6537), GTTCGGAGTTTATTCGCGGGGGAGGGA (SEQ ID NO:6538), TGTTCGGAGTTTATTCGCGGGGGAGGG (SEQ ID NO:6539), AGGGGGGGATTTACGGGTTGGGGTGTTT (SEQ ID NO:6540), AAGGGGGGGATTTACGGGTTGGGGTGTT (SEQ ID NO:6541), AAAGGGGGGGATTTACGGGTTGGGGTGT (SEQ ID NO:6542)

Target692    chr6:42071961-42072043    AGGTTAGGAGGGGAGGTTAGGGAAGGCGT (SEQ ID NO:6543), GGAGTTGGTGGGGAAAGAGAAGGGAGGT (SEQ ID NO:6544), GGAGTTGGTGGGGAAAGAGAAGGGAGG (SEQ ID NO:6545), GGAGGTTAGGAGGGGAGGTTAGGAAGGCG (SEQ ID NO:6546), AGGAGTTGGTGGGGAAAGAGAAGGGAGG (SEQ ID NO:6547), GGAGGGGTGGAAAGTTAGGCGAGGGTT (SEQ ID NO:6548), AGGAGGGGTGGAAAGTTAGGCGAGGGT (SEQ ID NO:6549), GGAGGGGTGGAAAGTTAGGCGAGGGT (SEQ ID NO:6550), AGGAGGGGTGGAAAGTTAGGCGAGGG (SEQ ID NO:6551), AGGAGGGGTGGAAAGTTAGGCGAGGGTT (SEQ ID NO:6552)

Target693    chr6:42072072-42072628    GTGGGGTAGTTTTGGGTTTCGGTGCGG (SEQ ID NO:6553), GTTGTTTCGGGGAGGGGAGTTTTGGCG (SEQ ID NO:6554), TAGGTTGCGGTCGGTTATCGTGGGG (SEQ ID NO:6555), GCGTTTGTGTTTGGTTTTCGCGGCGT (SEQ ID NO:6556), TTGGGTTTCGGTGCGGTTTTTCGACGT (SEQ ID NO:6557), TCGGAGGTTTGTACGCGTCGAGGTTGT (SEQ ID NO:6558), GGTGCGGGAAGTTAGGAGGGGGTGGAAA (SEQ ID NO:6559), TTCGGTTGGTGCGGGAAGTTAGGAGGG (SEQ ID NO:6560), GGAGGGGTGGAAAGTTAGGCGAGGGTT (SEQ ID NO:6561), GGGTTCGGTTGGTGCGGGAAGTTAGGA (SEQ ID NO:6562)

Target694    chr6:50818149-50818202    TCGGGTTTATTTTTTCGGTTTGGGTTTCGT (SEQ ID NO:6563), TCGGGTTTATTTTTTCGGTTTGGGTTTCGTT (SEQ ID NO:6564), TTCGGGTTTATTTTTTCGGTTTGGGTTTCGT (SEQ ID NO:6565), TTCGGGTTTATTTTTTCGGTTTGGGTTTCGTT (SEQ ID NO:6566), TTTCGGGTTTATTTTTTCGGTTTGGGTTTCGT (SEQ ID NO:6567), GCGGTTTTTGTGTTCGGAGCGTGTGTT (SEQ ID NO:6568), CGGTTCGTTGGTTCGCGGTTTTTGTGT (SEQ ID NO:6569), TTGGTTCGCGGTTTTTGTGTTCGGAGC (SEQ ID NO:6570), CGTTGGTTCGCGGTTTTTGTGTTCGGA (SEQ ID NO:6571), TCGTTGGTTCGCGGTTTTTGTGTTCGG (SEQ ID NO:6572)

Target695    chr6:50818209-50818238    GTTGGGAGATTGGGTAATAATATACGTTTCGGGT (SEQ ID NO:6573), AGTTGGGAGATTGGGTAATAATATACGTTTCGGG (SEQ ID NO:6574), AGTTGGGAGATTGGGTAATAATATACGTTTCGGGT (SEQ ID NO:6575), GTTGGGAGATTGGGTAATAATATACGTTTCGGGTA (SEQ ID NO:6576), AGTTGGGAGATTGGGTAATAATATACGTTTCGGGTA (SEQ ID NO:6577), CGGTTCGACGTAGGTTGGCGCGG (SEQ ID NO:6578), GGTTCGACGTAGGTTGGCGCGGC (SEQ ID NO:6579), CGGTTCGACGTAGGTTGGCGCGGC (SEQ ID NO:6580), GTTCGACGTAGGTTGGCGCGGC (SEQ ID NO:6581), CGGTTCGACGTAGGTTGGCGCGG (SEQ ID NO:6582)

Target696    chr6:50818245-50818261    GTTGGGAGATTGGGTAATAATATACGTTTCGGGT (SEQ ID NO:6583), AGTTGGGAGATTGGGTAATAATATACGTTTCGGG (SEQ ID NO:6584), AGTTGGGAGATTGGGTAATAATATACGTTTCGGGT (SEQ ID NO:6585), GTTGGGAGATTGGGTAATAATATACGTTTCGGGTA (SEQ ID NO:6586), AGTTGGGAGATTGGGTAATAATATACGTTTCGGGTA (SEQ ID NO:6587), TAGTAGTTGGGGTTACGTTCGGGGGCG (SEQ ID NO:6588), AGTAGTTGGGGTTACGTTCGGGGGCG (SEQ ID NO:6589), ATAGTAGTTGGGGTTACGTTCGGGGGCG (SEQ ID NO:6590), ATAGTAGTTGGGGTTACGTTCGGGGGC (SEQ ID NO:6591), GTAGTTGGGGTTACGTTCGGGGGCG (SEQ ID NO:6592)

Target697    chr6:50818268-50818397    CGGGCGTAATTTTAGTTGTTGTGACGGGT (SEQ ID NO:6593), CGGGCGTAATTTTAGTTGTTGTGACGGG (SEQ ID NO:6594), TCGGGCGTAATTTTAGTTGTTGTGACGGG (SEQ ID NO:6595), TCGGGCGTAATTTTAGTTGTTGTGACGGGT (SEQ ID NO:6596), TCGGGCGTAATTTTAGTTGTTGTGACGG (SEQ ID NO:6597), TAGTAGTTGGGGTTACGTTCGGGGGCG (SEQ ID NO:6598), AGTAGTTGGGGTTACGTTCGGGGGCG (SEQ ID NO:6599), ATAGTAGTTGGGGTTACGTTCGGGGGCG (SEQ ID NO:6600), ATAGTAGTTGGGGTTACGTTCGGGGGC (SEQ ID NO:6601), GTAGTTGGGGTTACGTTCGGGGGCG (SEQ ID NO:6602)

FIGURE 5 CONTINUED

Target698    chr6:50818501-50818554    GGGGTTTGAAGGGGTTGTAGCGTGGGA (SEQ ID NO:6603), TGGGGTTTGAAGGGGGTTGTAGCGTGGG (SEQ ID NO:6604), TTGGGGTTTGAAGGGGTTGTAGCGTGG (SEQ ID NO:6605), GGGTTTGAAGGGGTTGTAGCGTGGGAA (SEQ ID NO:6606), GGGGTTTGAAGGGGTTGTAGCGTGGGAA (SEQ ID NO:6607), GGAGGAAAAGCGAAGAGTAGGGTGGGT (SEQ ID NO:6608), AGGAGGAAAAGCGAAGAGTAGGGTGGGT (SEQ ID NO:6609), AGGAGGAAAAGCGAAGAGTAGGGTGGG (SEQ ID NO:6610), GAGGAGGAAAAGCGAAGAGTAGGGTGGGT (SEQ ID NO:6611), GAGGAGGAAAAGCGAAGAGTAGGGTGGG (SEQ ID NO:6612)

Target699    chr6:56716141-56716204    CGTTATGGTTTTTTAGGAGGTAGATGGGCGA (SEQ ID NO:6613), TCGTTATGGTTTTTTAGGAGGTAGATGGGCG (SEQ ID NO:6614), TCGTTATGGTTTTTTAGGAGGTAGATGGGCGA (SEQ ID NO:6615), CGTTATGGTTTTTTAGGAGGTAGATGGGCGAA (SEQ ID NO:6616), TTCGTTATGGTTTTTTAGGAGGTAGATGGGCG (SEQ ID NO:6617), GGGGATGGAGTGGGGGAAGAGAGTTGC (SEQ ID NO:6618), GGATGGAGTGGGGGAAGAGAGTTGCGG (SEQ ID NO:6619), GGGGATGGAGTGGGGGAAGAGAGTTGCGG (SEQ ID NO:6620), GGGAAGGGGATGGAGTGGGGGAAGAGA (SEQ ID NO:6621), GATGGAGTGGGGGAAGAGAGTTGCGGA (SEQ ID NO:6622)

Target700    chr6:56716301-56716537    AGGTGTTTTTCGGAGTTGGGGATGCGG (SEQ ID NO:6623), GGTGTTTTTCGGAGTTGGGGATGCGGA (SEQ ID NO:6624), AGGTGTTTTTCGGAGTTGGGGATGCGGA (SEQ ID NO:6625), GGTGTTTTTCGGAGTTGGGGATGCGGAG (SEQ ID NO:6626), TGTTTTTCGGAGTTGGGGATGCGGAGT (SEQ ID NO:6627), ATTTAGTTTGGGGGTAGGGAGGGCGGC (SEQ ID NO:6628), GGCGGTGGTTGGTGGGGGAGATGTTTA (SEQ ID NO:6629), GCGGTGGTTGGTGGGGGAGATGTTTAA (SEQ ID NO:6630), TTTAGTTTGGGGGTAGGGAGGGCGGC (SEQ ID NO:6631), GATTTAGTTTGGGGGTAGGGAGGGCGGC (SEQ ID NO:6632)

Target701    chr6:75918081-75918119    TCGGAGTTGAGTAGTTATTTTTCGGGGATTTAAAGA (SEQ ID NO:6633), TGGAGAGGGTAATGTGTACGTTTTTGGGG (SEQ ID NO:6634), TGGAGAGGGTAATGTGTACGTTTTTGGGGA (SEQ ID NO:6635), GGAGAGGGTAATGTGTACGTTTTTGGGGA (SEQ ID NO:6636), TGCGGTTTTTAGTCGTAGGAAAGGGAAGT (SEQ ID NO:6637), AGTCGTAGGAAAGGGAAGTTCGTGATTGT (SEQ ID NO:6638)

Target702    chr6:85475878-85475883    AGGTTTGGTTGGGCGGTTTGTTCGTGT (SEQ ID NO:6639), GGTTTGGTTGGGCGGTTTGTTCGTGTT (SEQ ID NO:6640), AGGTTTGGTTGGGCGGTTTGTTCGTGTT (SEQ ID NO:6641), TAGGTTTGGTTGGGCGGTTTGTTCGTGT (SEQ ID NO:6642), TAGGTTTGGTTGGGCGGTTTGTTCGTG (SEQ ID NO:6643)

Target703    chr6:85475908-85475954    ACGCGCGGTTTTTGGAGGTCGGATATT (SEQ ID NO:6644), ACGCGCGGTTTTTGGAGGTCGGATAT (SEQ ID NO:6645), ACGCGCGGTTTTTGGAGGTCGGATATTA (SEQ ID NO:6646), CGCGCGGTTTTTGGAGGTCGGATATTA (SEQ ID NO:6647), AGCGGGAGTAGGAATTTGGTAGGCGAT (SEQ ID NO:6648), AGGTTTGGTTGGGCGGTTTGTTCGTGT (SEQ ID NO:6649), GGTTTGGTTGGGCGGTTTGTTCGTGTT (SEQ ID NO:6650), AGGTTTGGTTGGGCGGTTTGTTCGTGTT (SEQ ID NO:6651), TAGGTTTGGTTGGGCGGTTTGTTCGTGTT (SEQ ID NO:6652), TAGGTTTGGTTGGGCGGTTTGTTCGTG (SEQ ID NO:6653)

Target704    chr6:85476171-85476211    GGTTTTGCGATCGGTTTAGAGTTGTGTGG (SEQ ID NO:6654), GGTTTTGCGATCGGTTTAGAGTTGTGTGGT (SEQ ID NO:6655), AGGTTTTGCGATCGGTTTAGAGTTGTGTGG (SEQ ID NO:6656), AGGTTTTGCGATCGGTTTAGAGTTGTGTGGT (SEQ ID NO:6657), GTTTTGCGATCGGTTTAGAGTTGTGTGGT (SEQ ID NO:6658), TGGGGCGGGGTATTTTAGTTGAACGGA (SEQ ID NO:6659), TTGGGGCGGGGTATTTTAGTTGAACGG (SEQ ID NO:6660), TGGGGCGGGGTATTTTAGTTGAACGGAA (SEQ ID NO:6661), TTGGGGCGGGGTATTTTAGTTGAACGGA (SEQ ID NO:6662), GGGGCGGGGTATTTTAGTTGAACGGAA (SEQ ID NO:6663)

Target705    chr6:85476373-85476389    GAGTGGGAGTGGGATAAGGCGGGAGTT (SEQ ID NO:6664), GGAGTGGGAGTGGGATAAGGCGGGAGT (SEQ ID NO:6665), GGAGTGGGAGTGGGATAAGGCGGGAG (SEQ ID NO:6666), GGGAGTGGGAGTGGGATAAGGCGGGAG (SEQ ID NO:6667), AGTGGGAGTGGGATAAGGCGGGAGTTA (SEQ ID NO:6668)

Target706    chr6:85476905-85476922    AGGGCGTCGAGGATAGGATAAGGCGTT (SEQ ID NO:6669), TAGGGCGTCGAGGATAGGATAAGGCGT (SEQ ID NO:6670), GGGCGTCGAGGATAGGATAAGGCGTTT (SEQ ID NO:6671), AGGGCGTCGAGGATAGGATAAGGCGTTT (SEQ ID NO:6672), AGTGTGAGTAGGGCGTCGAGGATAGGA (SEQ ID NO:6673), GGAGTCGAGGTTGGAGTGGGTTGTAGT (SEQ ID NO:6674), AGGAGTCGAGGTTGGAGTGGGTTGTAGT (SEQ ID NO:6675), AGGAGTCGAGGTTGGAGTGGGTTGTAG (SEQ ID NO:6676), TTAGGAGTCGAGGTTGGAGTGGGTTGT (SEQ ID NO:6677), GGAGTCGAGGTTGGAGTGGGTTGTAGTT (SEQ ID NO:6678)

Target707    chr6:85477151-85477187    TCGAGTTGGTTGGGCGGAGTGGTAGTT (SEQ ID NO:6679), TTCGAGTTGGTTGGGCGGAGTGGTAGT (SEQ ID NO:6680), CGAGTTGGTTGGGCGGAGTGGTAGTTT (SEQ ID NO:6681), TCGAGTTGGTTGGGCGGAGTGGTAGTTT (SEQ ID NO:6682), TTCGAGTTGGTTGGGCGGAGTGGTAGTT (SEQ ID NO:6683), TGATTTGTAAAGTGCGAGGGTTTGGCGT (SEQ ID NO:6684), GATTTGTAAAGTGCGAGGGTTTGGCGT (SEQ ID NO:6685), TGATTTGTAAAGTGCGAGGGTTTGGCG (SEQ ID NO:6686), TGTAAAGTGCGAGGGTTTGGCGTTTTT (SEQ ID NO:6687), TTGTAAAGTGCGAGGGTTTGGCGTTTT (SEQ ID NO:6688)

FIGURE 5 CONTINUED

| | | |
|---|---|---|
| Target708 | chr6:85477236-85477254 | AGTAAAGAAAGCGGGGATAGGGCGCGT (SEQ ID NO:6689), GAGTAAAGAAAGCGGGGATAGGGCGCG (SEQ ID NO:6690), AAGAAAGCGGGGATAGGGCGCGTAATC (SEQ ID NO:6691), AGAGTAAAGAAAGCGGGGATAGGGCGCG (SEQ ID NO:6692), GAGTAAAGAAAGCGGGGATAGGGCGCGT (SEQ ID NO:6693) |
| Target709 | chr6:99295742-99295866 | GTGGCGTTGCGGTGAAAGTCGGTGTTT (SEQ ID NO:6694), TGGCGTTGCGGTGAAAGTCGGTGTTTA (SEQ ID NO:6695), ATTTTGGAGTCGTCGGGAGTGGCGTTG (SEQ ID NO:6696), TGGCGTTGCGGTGAAAGTCGGTGTTT (SEQ ID NO:6697), GTGGCGTTGCGGTGAAAGTCGGTGTTTA (SEQ ID NO:6698), GCGTCGGTAGAATGGTTTTTGGGGAGGT (SEQ ID NO:6699), TGCGTCGGTAGAATGGTTTTTGGGGAGG (SEQ ID NO:6700), TGCGTCGGTAGAATGGTTTTTGGGGAGGT (SEQ ID NO:6701), GCGTCGGTAGAATGGTTTTTGGGGAGG (SEQ ID NO:6702), TGGTTGGGCGTTTTAGGGGTTTTTCGT (SEQ ID NO:6703) |
| Target710 | chr6:99295933-99296103 | GTTTGGCGTTTGGGGAGTCGGGGTTTT (SEQ ID NO:6704), TTGGCGTTTGGGGAGTCGGGGTTTTTG (SEQ ID NO:6705), GCGTTTGGGGAGTCGGGGTTTTTGTGT (SEQ ID NO:6706), TTGGGTGAGAGCGGAGGGGTTTTTGGGA (SEQ ID NO:6707), GGAGTCGGGGTTTTTGTGTGTGTCGGG (SEQ ID NO:6708), TATGCGGTAAGAGGGGAGGTCGGGAGGG (SEQ ID NO:6709), TTATGCGGTAAGAGGGGAGGTCGGGAGG (SEQ ID NO:6710), GTAAGAGGGGAGGTCGGGAGGGCGGAAG (SEQ ID NO:6711), TTATGCGGTAAGAGGGGAGGTCGGGAGGG (SEQ ID NO:6712), TAAGAGGGGAGGTCGGGAGGGCGGAAG (SEQ ID NO:6713) |
| Target711 | chr6:99296148-99296200 | CGGTTTCGTTGCGGGAGGTTAGAGGGT (SEQ ID NO:6714), GTTGCGGGAGGTTAGAGGGTTGCGTTT (SEQ ID NO:6715), TTCGTTGCGGGAGGTTAGAGGGTTGCG (SEQ ID NO:6716), TGCGGGAGGTTAGAGGGTTGCGTTTC (SEQ ID NO:6717), TTTCGTTGCGGGAGGTTAGAGGGTTGC (SEQ ID NO:6718), TTTGGGTTTTGAAAGGTGGCGGGGTGG (SEQ ID NO:6719), TGGTTTGGGTTTTGAAAGGTGGCGGGG (SEQ ID NO:6720), GGTTTGGGTTTTGAAAGGTGGCGGGGT (SEQ ID NO:6721), GTTTGGGTTTTGAAAGGTGGCGGGGTG (SEQ ID NO:6722), TTGGTTTGGGTTTTGAAAGGTGGCGGGG (SEQ ID NO:6723) |
| Target712 | chr6:99296227-99296254 | GAGTAGTGGGGTTTCGGGGAGTAGCGG (SEQ ID NO:6724), GGAGTAGTGGGGTTTCGGGGAGTAGCG (SEQ ID NO:6725), AGAGGGGAGTAGTGGGGTTTCGGGGAG (SEQ ID NO:6726), AGGGGAGTAGTGGGGTTTCGGGGAGTA (SEQ ID NO:6727), GGGAGTAGTGGGGTTTCGGGGAGTAGC (SEQ ID NO:6728), TTTGGGTTTTGAAAGGTGGCGGGGTGG (SEQ ID NO:6729), TGGTTTGGGTTTTGAAAGGTGGCGGGG (SEQ ID NO:6730), GGTTTGGGTTTTGAAAGGTGGCGGGGT (SEQ ID NO:6731), GGTTTGGGGTCGTTTGGGGAGGGGATTA (SEQ ID NO:6732), GTTTGGGTTTTGAAAGGTGGCGGGGTG (SEQ ID NO:6733) |
| Target713 | chr6:99296263-99296330 | GAGTAGTGGGGTTTCGGGGAGTAGCGG (SEQ ID NO:6734), GGAGTAGTGGGGTTTCGGGGAGTAGCG (SEQ ID NO:6735), AGAGGGGAGTAGTGGGGTTTCGGGGAG (SEQ ID NO:6736), AGGGGAGTAGTGGGGTTTCGGGGAGTA (SEQ ID NO:6737), GGGAGTAGTGGGGTTTCGGGGAGTAGC (SEQ ID NO:6738), TTTGGGTTTTGAAAGGTGGCGGGGTGG (SEQ ID NO:6739), TGGTTTGGGTTTTGAAAGGTGGCGGGG (SEQ ID NO:6740), GGTTTGGGTTTTGAAAGGTGGCGGGGT (SEQ ID NO:6741), GGTTTGGGGTCGTTTGGGGAGGGGATTA (SEQ ID NO:6742), TTGGGTTTTGAAAGGTGGCGGGGTGGT (SEQ ID NO:6743) |
| Target714 | chr6:100050797-100050813 | TGCGGGTTTATTCGGTAGCGGTCGGTA (SEQ ID NO:6744), AGTGCGGGTTTATTCGGTAGCGGTCGG (SEQ ID NO:6745), GAGTGCGGGTTTATTCGGTAGCGGTCG (SEQ ID NO:6746), GTGCGGGTTTATTCGGTAGCGGTCGGT (SEQ ID NO:6747), GCGGGTTTATTCGGTAGCGGTCGGTAG (SEQ ID NO:6748), GCGAGCGTGTTGTTGAATTGTAATGTTTCGGG (SEQ ID NO:6749), GCGTGTTGTTGAATTGTAATGTTTCGGGGT (SEQ ID NO:6750), GCGTGTTGTTGAATTGTAATGTTTCGGGG (SEQ ID NO:6751), AGCGTGTTGTTGAATTGTAATGTTTCGGGG (SEQ ID NO:6752), AGCGTGTTGTTGAATTGTAATGTTTCGGGGT (SEQ ID NO:6753) |
| Target715 | chr6:100051019-100051034 | TGGAGAATTTCGGTTAAAAGGTAATTTGAGAGGGA (SEQ ID NO:6754), TTGGAGAATTTCGGTTAAAAGGTAATTTGAGAGGGA (SEQ ID NO:6755), TGGAGAATTTCGGTTAAAAGGTAATTTGAGAGGGAT (SEQ ID NO:6756), GTTGGAGAATTTCGGTTAAAAGGTAATTTGAGAGGG (SEQ ID NO:6757), GGCGGCGATGGGTTTTGGGAACGTTAT (SEQ ID NO:6758), TAATTGTATGGTCGGTGGATGCGCGGC (SEQ ID NO:6759), GGCGGCGATGGGTTTTGGGAACGTTATT (SEQ ID NO:6760), AATTGTATGGTCGGTGGATGCGCGGC (SEQ ID NO:6761), GGCGGCGATGGGTTTTGGGAACGTTA (SEQ ID NO:6762) |
| Target716 | chr6:100051064-100051132 | GGCGTTCGGGTTGCGTTTTGGTTGTTA (SEQ ID NO:6763), GGCGTTCGGGTTGCGTTTTGGTTGTT (SEQ ID NO:6764), GGCGTTCGGGTTGCGTTTTGGTTGTTAT (SEQ ID NO:6765), GCGTTCGGGTTGCGTTTTGGTTGTTAT (SEQ ID NO:6766), GGCGTTCGGGTTGCGTTTTGGTTGT (SEQ ID NO:6767), GGCGGCGATGGGTTTTGGGAACGTTAT (SEQ ID NO:6768), TAAGGTCGGGTTTGAATAGGGCGCGCGG (SEQ ID NO:6769), TCGGGCGGGCGGGTTTAGTTTGGATTAG (SEQ ID NO:6770), GCGCGGGTGGGATATTAAGGTCGGGTT (SEQ ID NO:6771), GAGGCGCGGGTGGGATATTAAGGTCGG (SEQ ID NO:6772) |
| Target717 | chr6:100051147-100051154 | GGCGTGTTATTTGGTGGCGTTTTTAGAGT (SEQ ID NO:6773), TCGGGTTGCGTTTTGGTTGTTATTTTGGA (SEQ ID NO:6774), CGGGTTGCGTTTTGGTTGTTATTTTGGAGT (SEQ ID NO:6775), CGGGTTGCGTTTTGGTTGTTATTTTGGAG (SEQ ID NO:6776), TCGGGTTGCGTTTTGGTTGTTATTTTGGAG (SEQ ID NO:6777), TAAGGTCGGGTTTGAATAGGGCGCGCGG (SEQ ID NO:6778), |

FIGURE 5 CONTINUED

TCGGGCGGGCGGGTTAGTTTGGATTAG (SEQ ID NO:6779), GCGCGGGTGGGATATTAAGGTCGGGTT
{SEQ ID NO:6780}, GAGGCGCGGGTGGGATATTAAGGTCGG {SEQ ID NO:6781},
GTCGGGCGGGCGGGTTAGTTTGGATTA (SEQ ID NO:6782)

Target718   chr6:100051186-100051194   GGCGTGTTATTTGGTGGCGTTTTTAGAGT (SEQ ID NO:6783), GGCGTGTTATTTGGTGGCGTTTTTAGAGTT
{SEQ ID NO:6784}, TTGGTGGCGTTTTTAGAGTTTATCGTCGTC (SEQ ID NO:6785),
TTTGGTGGCGTTTTTAGAGTTTATCGTCGTC (SEQ ID NO:6786),
GGCGTGTTATTTGGTGGCGTTTTTAGAGTTTA (SEQ ID NO:6787),
TCGGGCGGGCGGGTTAGTTTGGATTAG (SEQ ID NO:6788), GTCGGGCGGGCGGGTTAGTTTGGATTA
{SEQ ID NO:6789}, CGGGCGGGCGGGTTAGTTTGGATTAGT (SEQ ID NO:6790),
GGGCGGGCGGGTTAGTTTGGATTAGTT {SEQ ID NO:6791}, GGCGGGCGGGTTAGTTTGGATTAGTTGC
{SEQ ID NO:6792}

Target719   chr6:106429346-106429563   TCGTTGGGGAAATTCGTAGGGGTGCGG {SEQ ID NO:6793}, CGTTGGGGAAATTCGTAGGGGTGCGGT
{SEQ ID NO:6794}, GTTGGGGAAATTCGTAGGGGTGCGGTT (SEQ ID NO:6795),
TGGGGAAATTCGTAGGGGTGCGGTTTG {SEQ ID NO:6796}, TTCGTTGGGGAAATTCGTAGGGGTGCG
{SEQ ID NO:6797}, GGTTTTCGGAAAGGCGAGGAGGAGCGA (SEQ ID NO:6798),
GTTTTCGGAAAGGCGAGGAGGAGCGAG {SEQ ID NO:6799}, TTTTCGGAAAGGCGAGGAGGAGCGAGC
{SEQ ID NO:6800}, CGTAGGCGTGTCGTGTGAGTTTTTGCG (SEQ ID NO:6801),
CGTAGGCGTGTCGTGTGAGTTTTTGCGT (SEQ ID NO:6802)

Target720   chr6:106429659-106429674   GGTTTGCGGGGTTTTTGGGGGCGTATT (SEQ ID NO:6803), TGGGGAAATTCGTAGGGGTGCGGTTTG
{SEQ ID NO:6804}, GTTTGCGGGGTTTTTGGGGGCGTATTT (SEQ ID NO:6805),
GGTTTGCGGGGTTTTTGGGGGCGTAT (SEQ ID NO:6806), GGTTTGCGGGGTTTTTGGGGGCGTATTT {SEQ
ID NO:6807}, TCGTGTGGTTTTCGTCGTAGTGGAGTT {SEQ ID NO:6808},
TTCGTGTGGTTTTCGTCGTAGTGGAGT (SEQ ID NO:6809), CGTGTGGTTTTCGTCGTAGTGGAGTTGT {SEQ
ID NO:6810}, CGTGTGGTTTTCGTCGTAGTGGAGTTG (SEQ ID NO:6811),
TCGTGTGGTTTTCGTCGTAGTGGAGTTGT (SEQ ID NO:6812)

Target721   chr6:106433873-106434266   TGGACGCGGGGTTTTTAGTTCGGAGGT (SEQ ID NO:6813), TGGGTAGGGCGTCGGGGTTTTCGGATTT {SEQ
ID NO:6814}, TTGGGTAGGGCGTCGGGGTTTTCGGATT (SEQ ID NO:6815),
TTTGGGTAGGGCGTCGGGGTTTTCGGAT (SEQ ID NO:6816), TTGTTTTGGGGTTTGGGTAGGGCGTCG {SEQ
ID NO:6817}, GTTTCGGCGGGGAGAGGAAGCGTTTTGG {SEQ ID NO:6818},
TGGGTAGAAGTCGCGCGTGTGTTCGAG (SEQ ID NO:6819), TTTCGGCGGGGAGAGGAAGCGTTTTGGT
{SEQ ID NO:6820}, GTGGGTAGAAGTCGCGCGTGTGTTCGA (SEQ ID NO:6821),
TTCGGCGGGAGAGGAAGCGTTTTGGTC (SEQ ID NO:6822)

Target722   chr6:106434387-106434393   CGGGGCGAGTAAAAGTAGGATTTCGGT (SEQ ID NO:6823), TCGGGGCGAGTAAAAGTAGGATTTCGGT
{SEQ ID NO:6824}, TCGGGGCGAGTAAAAGTAGGATTTCGG (SEQ ID NO:6825},
CGGGGCGAGTAAAAGTAGGATTTCGGTCG (SEQ ID NO:6826),
CGGGGCGAGTAAAAGTAGGATTTCGGTT (SEQ ID NO:6827)

Target723   chr6:137814512-137814524   CGGGTTCGTTCGTTGTTTATTTGAGTAAGTTTTTGG (SEQ ID NO:6828),
CGGGTTCGTTCGTTGTTTATTTGAGTAAGTTTTTG (SEQ ID NO:6829),
GGGTTCGTTCGTTGTTTATTTGAGTAAGTTTTTGGA (SEQ ID NO:6830),
CGTTGTTTATTTGAGTAAGTTTTTGGATTCGGTCGA (SEQ ID NO:6831),
TCGTTGTTTATTTGAGTAAGTTTTTGGATTCGGTCG (SEQ ID NO:6832),
TGGGTAGCGGTTTTTAGTATTGGGTTGGT (SEQ ID NO:6833),
TGGGTAGCGGTTTTTAGTATTGGGTTGGTT (SEQ ID NO:6834),
TTGGGTAGCGGTTTTTAGTATTGGGTTGGT (SEQ ID NO:6835),
GTTGGGTAGCGGTTTTTAGTATTGGGTTGG (SEQ ID NO:6836),
GTTGGGTAGCGGTTTTTAGTATTGGGTTGGT (SEQ ID NO:6837)

Target724   chr6:137814558-137814568   TTGGTTGTGGAGAGAGCGGATAGGTGC (SEQ ID NO:6838), CGGGTTATGTTGGTTGTGGAGAGAGCGG
{SEQ ID NO:6839}, GTTGGTTGTGGAGAGAGCGGATAGGTGC (SEQ ID NO:6840),
TGTTGGTTGTGGAGAGAGCGGATAGGTGC (SEQ ID NO:6841),
CGGGTTATGTTGGTTGTGGAGAGAGCGGA (SEQ ID NO:6842),
TGGGTAGCGGTTTTTAGTATTGGGTTGGT (SEQ ID NO:6843),
TGGGTAGCGGTTTTTAGTATTGGGTTGGTT (SEQ ID NO:6844),
TTGGGTAGCGGTTTTTAGTATTGGGTTGGT (SEQ ID NO:6845),
GTTGGGTAGCGGTTTTTAGTATTGGGTTGG (SEQ ID NO:6846),
GTTGGGTAGCGGTTTTTAGTATTGGGTTGGT (SEQ ID NO:6847)

Target725   chr6:137814636-137814655   GCGGCGGCGGTATTTGGTAGATGGTGT (SEQ ID NO:6848), GCGGCGGCGGTATTTGGTAGATGGTGT {SEQ
ID NO:6849}, CGGCGGCGGTATTTGGTAGATGGTGTA (SEQ ID NO:6850),
GCGGCGGCGGTATTTGGTAGATGGTGTA (SEQ ID NO:6851), TTGGTTGTGGAGAGAGCGGATAGGTGC
{SEQ ID NO:6852}, CGGGTGTATTTTATTTTGGGCGGCGCGT (SEQ ID NO:6853),
TCGGTGTATTTTATTTTGGGCGGCGCGC (SEQ ID NO:6854), TCGGTGTATTTTATTTTGGGCGGCGCGT (SEQ
ID NO:6855), CGGTGTATTTTATTTTGGGCGGCGCGTT (SEQ ID NO:6856),
TTCGGTGTATTTTATTTTGGGCGGCGCG (SEQ ID NO:6857)

Target726   chr6:137814666-137814690   GAGGGCGTTTTGAGTAGCGAGTGGGGA (SEQ ID NO:6858), AGGGCGTTTTGAGTAGCGAGTGGGGAG
{SEQ ID NO:6859}, TGGAGGGCGTTTTGAGTAGCGAGTGGG (SEQ ID NO:6860),
GGCGTTTTGAGTAGCGAGTGGGGAGGT (SEQ ID NO:6861), CGTGGAGGGCGTTTTGAGTAGCGAGTG
{SEQ ID NO:6862}, CGGTGTATTTTATTTTGGGCGGCGCGT (SEQ ID NO:6863),

FIGURE 5 CONTINUED

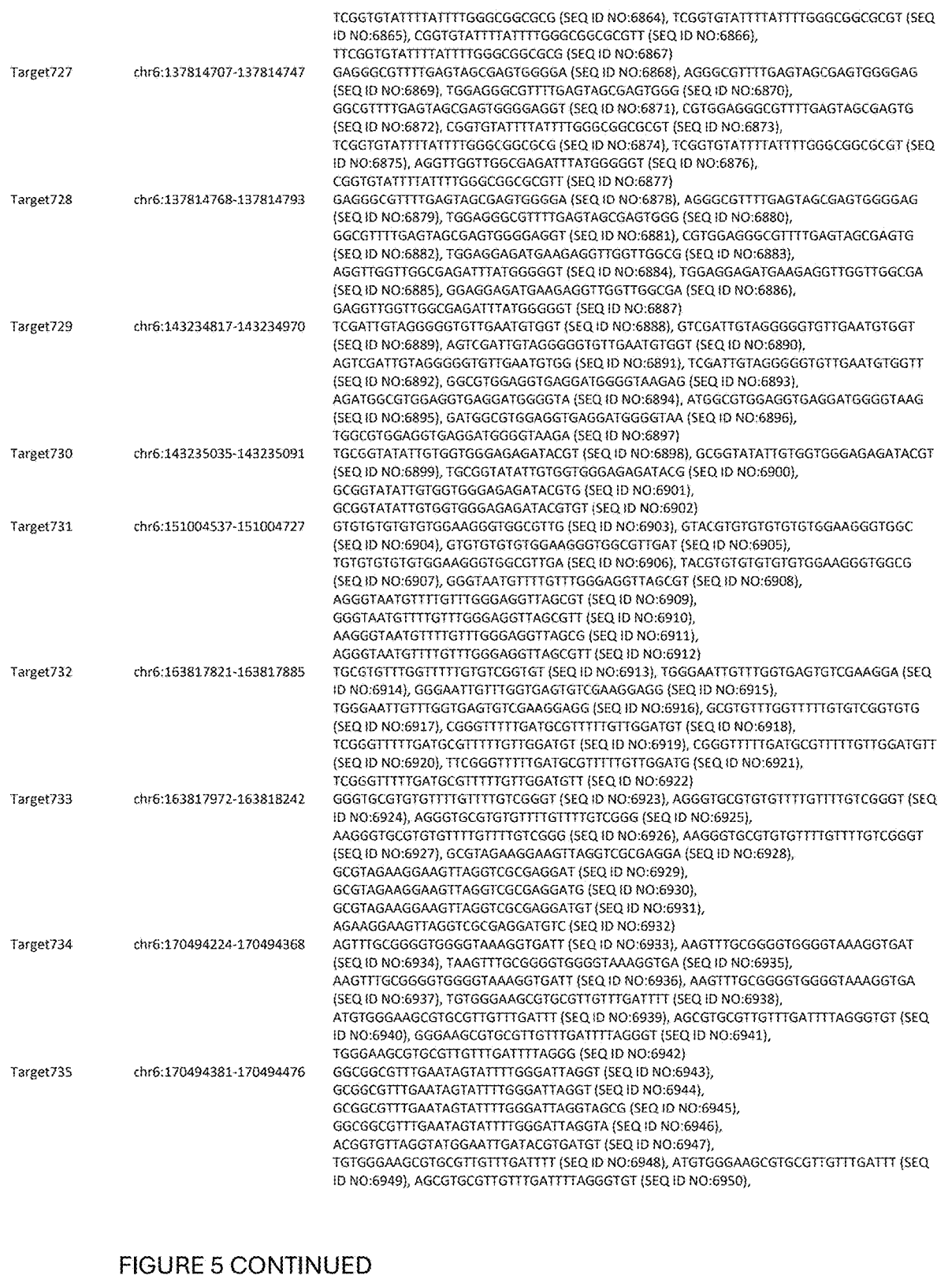

| | | |
|---|---|---|
| | | TCGGTGTATTTTATTTTGGGCGGCGCG (SEQ ID NO:6864), TCGGTGTATTTTATTTTGGGCGGCGCGT (SEQ ID NO:6865), CGGTGTATTTTATTTTGGGCGGCGCGTT (SEQ ID NO:6866), TTCGGTGTATTTTATTTTGGGCGGCGCG (SEQ ID NO:6867) |
| Target727 | chr6:137814707-137814747 | GAGGGCGTTTTGAGTAGCGAGTGGGGA (SEQ ID NO:6868), AGGGCGTTTTGAGTAGCGAGTGGGGAG (SEQ ID NO:6869), TGGAGGGCGTTTTGAGTAGCGAGTGGG (SEQ ID NO:6870), GGCGTTTTGAGTAGCGAGTGGGGAGGT (SEQ ID NO:6871), CGTGGAGGGCGTTTTGAGTAGCGAGTG (SEQ ID NO:6872), CGGTGTATTTTATTTTGGGCGGCGCGT (SEQ ID NO:6873), TCGGTGTATTTTATTTTGGGCGGCGCG (SEQ ID NO:6874), TCGGTGTATTTTATTTTGGGCGGCGCGT (SEQ ID NO:6875), AGGTTGGTTGGCGAGATTTATGGGGGT (SEQ ID NO:6876), CGGTGTATTTTATTTTGGGCGGCGCGTT (SEQ ID NO:6877) |
| Target728 | chr6:137814768-137814793 | GAGGGCGTTTTGAGTAGCGAGTGGGGA (SEQ ID NO:6878), AGGGCGTTTTGAGTAGCGAGTGGGGAG (SEQ ID NO:6879), TGGAGGGCGTTTTGAGTAGCGAGTGGG (SEQ ID NO:6880), GGCGTTTTGAGTAGCGAGTGGGGAGGT (SEQ ID NO:6881), CGTGGAGGGCGTTTTGAGTAGCGAGTG (SEQ ID NO:6882), TGGAGGAGATGAAGAGGTTGGTTGGCG (SEQ ID NO:6883), AGGTTGGTTGGCGAGATTTATGGGGGT (SEQ ID NO:6884), TGGAGGAGATGAAGAGGTTGGTTGGCGA (SEQ ID NO:6885), GGAGGAGATGAAGAGGTTGGTTGGCGA (SEQ ID NO:6886), GAGGTTGGTTGGCGAGATTTATGGGGGT (SEQ ID NO:6887) |
| Target729 | chr6:143234817-143234970 | TCGATTGTAGGGGGTGTTGAATGTGGT (SEQ ID NO:6888), GTCGATTGTAGGGGGTGTTGAATGTGGT (SEQ ID NO:6889), AGTCGATTGTAGGGGGTGTTGAATGTGGT (SEQ ID NO:6890), AGTCGATTGTAGGGGGTGTTGAATGTGG (SEQ ID NO:6891), TCGATTGTAGGGGGTGTTGAATGTGGTT (SEQ ID NO:6892), GGCGTGGAGGTGAGGATGGGGTAAGAG (SEQ ID NO:6893), AGATGGCGTGGAGGTGAGGATGGGGTA (SEQ ID NO:6894), ATGGCGTGGAGGTGAGGATGGGGTAAG (SEQ ID NO:6895), GATGGCGTGGAGGTGAGGATGGGGTAA (SEQ ID NO:6896), TGGCGTGGAGGTGAGGATGGGGTAAGA (SEQ ID NO:6897) |
| Target730 | chr6:143235035-143235091 | TGCGGTATATTGTGGTGGGAGAGATACGT (SEQ ID NO:6898), GCGGTATATTGTGGTGGGAGAGATACGT (SEQ ID NO:6899), TGCGGTATATTGTGGTGGGAGAGATACG (SEQ ID NO:6900), GCGGTATATTGTGGTGGGAGAGATACGTG (SEQ ID NO:6901), GCGGTATATTGTGGTGGGAGAGATACGTGT (SEQ ID NO:6902) |
| Target731 | chr6:151004537-151004727 | GTGTGTGTGTGGAAGGGTGGCGTTG (SEQ ID NO:6903), GTACGTGTGTGTGTGTGGAAGGGTGGC (SEQ ID NO:6904), GTGTGTGTGTGGAAGGGTGGCGTTGAT (SEQ ID NO:6905), TGTGTGTGTGTGGAAGGGTGGCGTTGA (SEQ ID NO:6906), TACGTGTGTGTGTGTGGAAGGGTGGCG (SEQ ID NO:6907), GGGTAATGTTTTGTTTGGGAGGTTAGCGT (SEQ ID NO:6908), AGGGTAATGTTTTGTTTGGGAGGTTAGCGT (SEQ ID NO:6909), GGGTAATGTTTTGTTTGGGAGGTTAGCGTT (SEQ ID NO:6910), AAGGGTAATGTTTTGTTTGGGAGGTTAGCG (SEQ ID NO:6911), AGGGTAATGTTTTGTTTGGGAGGTTAGCGTT (SEQ ID NO:6912) |
| Target732 | chr6:163817821-163817885 | TGCGTGTTTGGTTTTTGTGTCGGTGT (SEQ ID NO:6913), TGGGAATTGTTTGGTGAGTGTCGAAGGA (SEQ ID NO:6914), GGGAATTGTTTGGTGAGTGTCGAAGGAGG (SEQ ID NO:6915), TGGGAATTGTTTGGTGAGTGTCGAAGGAGG (SEQ ID NO:6916), GCGTGTTTGGTTTTTGTGTCGGTGTG (SEQ ID NO:6917), CGGGTTTTTGATGCGTTTTTGTTGGATGT (SEQ ID NO:6918), TCGGGTTTTTGATGCGTTTTTGTTGGATGT (SEQ ID NO:6919), CGGGTTTTTGATGCGTTTTTGTTGGATGTT (SEQ ID NO:6920), TTCGGGTTTTTGATGCGTTTTTGTTGGATG (SEQ ID NO:6921), TCGGGTTTTTGATGCGTTTTTGTTGGATGTT (SEQ ID NO:6922) |
| Target733 | chr6:163817972-163818242 | GGGTGCGTGTGTTTTGTTTTGTCGGGT (SEQ ID NO:6923), AGGGTGCGTGTGTTTTGTTTTGTCGGGT (SEQ ID NO:6924), AGGGTGCGTGTGTTTTGTTTTGTCGGG (SEQ ID NO:6925), AAGGGTGCGTGTGTTTTGTTTTGTCGGG (SEQ ID NO:6926), AAGGGTGCGTGTGTTTTGTTTTGTCGGGT (SEQ ID NO:6927), GCGTAGAAGGAAGTTAGGTCGCGAGGA (SEQ ID NO:6928), GCGTAGAAGGAAGTTAGGTCGCGAGGAT (SEQ ID NO:6929), GCGTAGAAGGAAGTTAGGTCGCGAGGATG (SEQ ID NO:6930), GCGTAGAAGGAAGTTAGGTCGCGAGGATGT (SEQ ID NO:6931), AGAAGGAAGTTAGGTCGCGAGGATGTC (SEQ ID NO:6932) |
| Target734 | chr6:170494224-170494368 | AGTTTGCGGGGTGGGGTAAAGGTGATT (SEQ ID NO:6933), AAGTTTGCGGGGTGGGGTAAAGGTGAT (SEQ ID NO:6934), TAAGTTTGCGGGGTGGGGTAAAGGTGA (SEQ ID NO:6935), AAGTTTGCGGGGTGGGGTAAAGGTGATT (SEQ ID NO:6936), AAGTTTGCGGGGTGGGGTAAAGGTGA (SEQ ID NO:6937), TGTGGGAAGCGTGCGTTGTTTGATTTT (SEQ ID NO:6938), ATGTGGGAAGCGTGCGTTGTTTGATTT (SEQ ID NO:6939), AGCGTGCGTTGTTTGATTTTAGGGTGT (SEQ ID NO:6940), GGGAAGCGTGCGTTGTTTGATTTTAGGGT (SEQ ID NO:6941), TGGGAAGCGTGCGTTGTTTGATTTTAGGG (SEQ ID NO:6942) |
| Target735 | chr6:170494381-170494476 | GGCGGCGTTTGAATAGTATTTTGGGATTAGGT (SEQ ID NO:6943), GCGGCGTTTGAATAGTATTTTGGGATTAGGT (SEQ ID NO:6944), GCGGCGTTTGAATAGTATTTTGGGATTAGGTAGCG (SEQ ID NO:6945), GGCGGCGTTTGAATAGTATTTTGGGATTAGGTA (SEQ ID NO:6946), ACGGTGTTAGGTATGGAATTGATACGTGATGT (SEQ ID NO:6947), TGTGGGAAGCGTGCGTTGTTTGATTTT (SEQ ID NO:6948), ATGTGGGAAGCGTGCGTTGTTTGATTT (SEQ ID NO:6949), AGCGTGCGTTGTTTGATTTTAGGGTGT (SEQ ID NO:6950), |

FIGURE 5 CONTINUED

GGGAAGCGTGCGTTGTTTGATTTTAGGGT (SEQ ID NO:6951), TGGGAAGCGTGCGTTGTTTGATTTTAGGG (SEQ ID NO:6952)

| | | |
|---|---|---|
| Target736 | chr7:391221-391545 | AGAGGAAGTCGGCGGGGGTTAAAGCGTT (SEQ ID NO:6953), TTGGTGGGGGTTGTAGAGGAAGTCGGC (SEQ ID NO:6954), CGGGTTGGTGGGGGGTTGTAGAGGAAGT (SEQ ID NO:6955), GGGTTGTAGAGGAAGTCGGCGGGGGTTA (SEQ ID NO:6956), TCGGGTTGGTGGGGGTTGTAGAGGAAG (SEQ ID NO:6957), TTCGGTTGTTTTTAACGCGCGTGTGAG (SEQ ID NO:6958), TGTTTCGGTTGTTTTTAACGCGCGTGT (SEQ ID NO:6959), TTTCGGTTGTTTTTAACGCGCGTGTGA (SEQ ID NO:6960), TGTTTCGGTTGTTTTTAACGCGCGTGTG (SEQ ID NO:6961), GTTTCGGTTGTTTTTAACGCGCGTGTG (SEQ ID NO:6962) |
| Target737 | chr7:641200-641348 | GTTGATGGAGGTGTTTGGTGTTCGTGT (SEQ ID NO:6963), AGTTGATGGAGGTGTTTGGTGTTCGTGT (SEQ ID NO:6964), AAGTTGATGGAGGTGTTTGGTGTTCGTGT (SEQ ID NO:6965), AAGTTGATGGAGGTGTTTGGTGTTCGTG (SEQ ID NO:6966), TGAAGTTGATGGAGGTGTTTGGTGTTCGT (SEQ ID NO:6967), GGTAGGGGTGGGCGTTAGGGAGTGTTC (SEQ ID NO:6968), CGGGGTCGGGCGTAGGAGTTGTTTGTA (SEQ ID NO:6969), TTAGGGTAGGGGTGGGCGTTAGGGAGT (SEQ ID NO:6970), AGTTAGGGTAGGGGTGGGCGTTAGGGA (SEQ ID NO:6971), GTAGGGGTGGGCGTTAGGGAGTGTTCG (SEQ ID NO:6972) |
| Target738 | chr7:641360-641449 | GTTGATGGAGGTGTTTGGTGTTCGTGT (SEQ ID NO:6973), AGTTGATGGAGGTGTTTGGTGTTCGTGT (SEQ ID NO:6974), AAGTTGATGGAGGTGTTTGGTGTTCGTGT (SEQ ID NO:6975), AAGTTGATGGAGGTGTTTGGTGTTCGTG (SEQ ID NO:6976), TGAAGTTGATGGAGGTGTTTGGTGTTCGT (SEQ ID NO:6977), GTGGGATGGTCGGGTTTTTTGCGGGAA (SEQ ID NO:6978), TACGTGGGATGGTCGGGTTTTTTGCGG (SEQ ID NO:6979), TGGGATGGTCGGGTTTTTTGCGGGAAT (SEQ ID NO:6980), ACGTGGGATGGTCGGGTTTTTTGCGG (SEQ ID NO:6981), GTGGGATGGTCGGGTTTTTTGCGGGAAT (SEQ ID NO:6982) |
| Target739 | chr7:1263851-1263861 | AAGTGTTCGCGGTGGTGGTTCGAGTTC (SEQ ID NO:6983), GAAAGTGTTCGCGGTGGTGGTTCGAGT (SEQ ID NO:6984), AAAGTGTTCGCGGTGGTGGTTCGAGT (SEQ ID NO:6985), AAAGTGTTCGCGGTGGTGGTTCGAGTTC (SEQ ID NO:6986), GAAAGTGTTCGCGGTGGTGGTTCGAGTT (SEQ ID NO:6987) |
| Target740 | chr7:1275046-1275070 | AGATAGGTGTGGAGGGCGGTTGTGGTT (SEQ ID NO:6988), AAGATAGGTGTGGAGGGCGGTTGTGGT (SEQ ID NO:6989), TCGAAGATAGGTGTGGAGGGCGGTTGT (SEQ ID NO:6990), AGGTGTGGAGGGCGGTTGTGGTTTAGC (SEQ ID NO:6991), CGAAGATAGGTGTGGAGGGCGGTTGTG (SEQ ID NO:6992), GACGGAGAGCGTCGGGTTTTTGGTTCG (SEQ ID NO:6993), AGAGCGTCGGGTTTTTGGTTCGGAGGT (SEQ ID NO:6994), GAGAGCGTCGGGTTTTTGGTTCGGAGG (SEQ ID NO:6995), GGAGAGCGTCGGGTTTTTGGTTCGGAG (SEQ ID NO:6996), GAGCGTCGGGTTTTTGGTTCGGAGGTT (SEQ ID NO:6997) |
| Target741 | chr7:1275258-1275268 | AGGGGCGGTTTTTAGGTTTTCGAGGTG (SEQ ID NO:6998), GGGGCGGTTTTTAGGTTTTCGAGGTGA (SEQ ID NO:6999), AGGGGCGGTTTTTAGGTTTTCGAGGTGA (SEQ ID NO:7000), AAGGGGCGGTTTTTAGGTTTTCGAGGT (SEQ ID NO:7001), GGGGCGGTTTTTAGGTTTTCGAGGTGAG (SEQ ID NO:7002), CGTTCGGTCGGGGTAGGAGTGAAGTCG (SEQ ID NO:7003), GTTCGGTCGGGGTAGGAGTGAAGTCGC (SEQ ID NO:7004), CGGTCGAGCGGGTTTTGAGTTGGGTTT (SEQ ID NO:7005), TCGTTCGGTCGGGGTAGGAGTGAAGTC (SEQ ID NO:7006), TTCGTTCGGTCGGGGTAGGAGTGAAGT (SEQ ID NO:7007) |
| Target742 | chr7:1275593-1275598 | GTTTATGGATTCGGAGGAGATCGCGCG (SEQ ID NO:7008), AGTTTATGGATTCGGAGGAGATCGCGCG (SEQ ID NO:7009), GAGTTTATGGATTCGGAGGAGATCGCGCG (SEQ ID NO:7010), CGAGTTTATGGATTCGGAGGAGATCGCGC (SEQ ID NO:7011), TCGTCGGGTTAAGTGGAGGAAGAAGGA (SEQ ID NO:7012), GTTGTCGGAGTTGGGCGCGTTGTGTAG (SEQ ID NO:7013), AGTTGGGCGCGTTGTGTAGGGATAGGT (SEQ ID NO:7014), CGCGTTGTGTAGGGATAGGTCGTCGGG (SEQ ID NO:7015), TTGGGCGCGTTGTGTAGGGATAGGTCG (SEQ ID NO:7016), CGGAGTTGGGCGCGTTGTGTAGGGATA (SEQ ID NO:7017) |
| Target743 | chr7:1275704-1275723 | GGAGTTGGAGAAGATGGAGAAGAAGAAGCG (SEQ ID NO:7018), GGAGTTGGAGAAGATGGAGAAGAAGAAGCGT (SEQ ID NO:7019), AGGAGTTGGAGAAGATGGAGAAGAAGAAGCG (SEQ ID NO:7020), AGGAGTTGGAGAAGATGGAGAAGAAGAAGCGT (SEQ ID NO:7021), GAGTTGGAGAAGATGGAGAAGAAGAAGCGT (SEQ ID NO:7022), CGAGGCGTGCGTTTCGGGGTTTTTGG (SEQ ID NO:7023), CGAGGCGTGCGTTTCGGGGTTTTTG (SEQ ID NO:7024), GAGGCGTGCGTTTCGGGGTTTTTGGC (SEQ ID NO:7025), GAGGCGTGCGTTTCGGGGTTTTTGG (SEQ ID NO:7026), GAGGCGTGCGTTTCGGGGTTTTTGGCG (SEQ ID NO:7027) |
| Target744 | chr7:1275734-1275749 | CGAGAAGAAGTTGTTGAAGAGTTAGGGTCGT (SEQ ID NO:7028), ACGAGAAGAAGTTGTTGAAGAGTTAGGGTCG (SEQ ID NO:7029), ACGAGAAGAAGTTGTTGAAGAGTTAGGGTCGT (SEQ ID NO:7030), GAGTTAGGGTCGTTATTTGTATTCGTTCGGC (SEQ ID NO:7031), AGAGTTAGGGTCGTTATTTGTATTCGTTCGGC (SEQ ID NO:7032), GTAGGTGTCGGGTGTAGGCGGTTCGTC (SEQ ID NO:7033), GTCGTAGGTGTCGGGTGTAGGCGGTTC (SEQ ID NO:7034), GTAGGTGTCGGGTGTAGGCGGTTCGT (SEQ ID NO:7035), GTCGTAGGTGTCGGGTGTAGGCGGTT (SEQ ID NO:7036), TAGGTGTCGGGTGTAGGCGGTTCGTC (SEQ ID NO:7037) |

FIGURE 5 CONTINUED

Target745    chr7:1594934-1595023    CGTTTCGGGTTAGTGCGGAGGTGAGGA (SEQ ID NO:7038), GTGCGGAGGTGAGGAAGAGTTAGGGGG (SEQ ID NO:7039), TGCGGAGGTGAGGAAGAGTTAGGGGGT (SEQ ID NO:7040), GGAGGTTCGGGGGCGGAAGGGTTTATT (SEQ ID NO:7041), ACGTTTCGGGTTAGTGCGGAGGTGAGG (SEQ ID NO:7042), TGTTTTAGGGGATTTTGGAGATAGTCGGCGT (SEQ ID NO:7043), TGTTTTAGGGGATTTTGGAGATAGTCGGCGTT (SEQ ID NO:7044), ATGTTTTAGGGGATTTTGGAGATAGTCGGCGT (SEQ ID NO:7045), TGTTTTAGGGGATTTTGGAGATAGTCGGCGTTT (SEQ ID NO:7046), ATGTTTTAGGGGATTTTGGAGATAGTCGGCGTT (SEQ ID NO:7047)

Target746    chr7:4859441-4859485    GTCGGGAGGTTGACGGGGTTTTGTTTT (SEQ ID NO:7048), TCGGGAGGTTGACGGGGTTTTGTTTTT (SEQ ID NO:7049), GTCGGGAGGTTGACGGGGTTTTGTTTTT (SEQ ID NO:7050), CGGGAGGTTGACGGGGTTTTGTTTTTTCG (SEQ ID NO:7051), CGGGAGGTTGACGGGGTTTTGTTTTTTCGG (SEQ ID NO:7052), TGTTTGGTTCGGCGATGGGAGTTAGGGT (SEQ ID NO:7053), GTTTGGTTCGGCGATGGGAGTTAGGGT (SEQ ID NO:7054), TGTTTGGTTCGGCGATGGGAGTTAGGG (SEQ ID NO:7055), TCGGCGATGGGAGTTAGGGTTTAGGGA (SEQ ID NO:7056), GTGTTTGGTTCGGCGATGGGAGTTAGGG (SEQ ID NO:7057)

Target747    chr7:4859645-4859668    CGGGGATTATATGGGATTTAGTTGTTTGCGG (SEQ ID NO:7058), CGGGGATTATATGGGATTTAGTTGTTTGCGGT (SEQ ID NO:7059), ACGGGGATTATATGGGATTTAGTTGTTTGCGG (SEQ ID NO:7060), ACGGGGATTATATGGGATTTAGTTGTTTGCGGT (SEQ ID NO:7061), CGGGGATTATATGGGATTTAGTTGTTTGCGGTT (SEQ ID NO:7062), TCGTGTGATAGGGGGACGGGGTTAGTT (SEQ ID NO:7063), TTCGTGTGATAGGGGGACGGGGTTAGT (SEQ ID NO:7064), GGTTTTTTCGTGTGATAGGGGGACGGGG (SEQ ID NO:7065), TTTTTCGTGTGATAGGGGGACGGGGTT (SEQ ID NO:7066), TTTTTTCGTGTGATAGGGGGACGGGGT (SEQ ID NO:7067)

Target748    chr7:4859824-4859837    TGTGGGGGTCGGAATAAAAGGGGTTTT (SEQ ID NO:7068), TTGTGGGGGTCGGAATAAAAGGGGTTT (SEQ ID NO:7069), TTTGTGGGGGTCGGAATAAAAGGGGTT (SEQ ID NO:7070), TTTTGTGGGGGTCGGAATAAAAGGGGT (SEQ ID NO:7071), TTGTGGGGGTCGGAATAAAAGGGGTTTT (SEQ ID NO:7072), GTCGGTAGGTGGTTTTGGGATGGAGGT (SEQ ID NO:7073), AGTCGGTAGGTGGTTTTGGGATGGAGGT (SEQ ID NO:7074), AGTCGGTAGGTGGTTTTGGGATGGAGG (SEQ ID NO:7075), GGGATGGAGGTAATTTCGGAGTTGCGGT (SEQ ID NO:7076), TGGGATGGAGGTAATTTCGGAGTTGCGG (SEQ ID NO:7077)

Target749    chr7:4859918-4859926    GTTAGGTTTGTAGGGAGAGGCGACGGG (SEQ ID NO:7078), AGTTAGGTTTGTAGGGAGAGGCGACGGG (SEQ ID NO:7079), AGTTAGGTTTGTAGGGAGAGGCGACGG (SEQ ID NO:7080), GAGTTAGGTTTGTAGGGAGAGGCGACGGG (SEQ ID NO:7081), GAGTTAGGTTTGTAGGGAGAGGCGACGG (SEQ ID NO:7082), GGGGTTTTTGGGTTTTCGGGATTATAGCGT (SEQ ID NO:7083), TGGGGTTTTTGGGTTTTCGGGATTATAGCG (SEQ ID NO:7084), GGGGTTTTTGGGTTTTCGGGATTATAGCG (SEQ ID NO:7085), TGGGGTTTTTGGGTTTTCGGGATTATAGCGT (SEQ ID NO:7086), GGGTTTTTGGGTTTTCGGGATTATAGCGT (SEQ ID NO:7087)

Target750    chr7:27196023-27196321    CGTAGGAGGCGTAGGGTAGGTTGTCGT (SEQ ID NO:7088), TGGTCGTAGGAGGCGTAGGGTAGGTTGT (SEQ ID NO:7089), GGTCGTAGGAGGCGTAGGGTAGGTTGT (SEQ ID NO:7090), TGGTCGTAGGAGGCGTAGGGTAGGTTG (SEQ ID NO:7091), TCGTAGGAGGCGTAGGGTAGGTTGTCGT (SEQ ID NO:7092), CGGAGGCGGTTATGTGGGCGGTTAC (SEQ ID NO:7093), GCGGAGGCGGTTATGTGGGCGGTTAC (SEQ ID NO:7094), TGGGGTTTGGTGTAAATTTGGGGGGTGT (SEQ ID NO:7095), TGTGAGGATTGTTGAGATTGGCGGAGG (SEQ ID NO:7096), GCGGAGGCGGTTATGTGGGCGGTTA (SEQ ID NO:7097)

Target751    chr7:27196351-27196515    GCGGAAAAAGATTTGGAGGTTTCGCGGG (SEQ ID NO:7098), GCGGAAAAAGATTTGGAGGTTTCGCGGGA (SEQ ID NO:7099), GCGGAAAAAGATTTGGAGGTTTCGCGG (SEQ ID NO:7100), CGGAAAAAGATTTGGAGGTTTCGCGGG (SEQ ID NO:7101), CGGAAAAAGATTTGGAGGTTTCGCGGGA (SEQ ID NO:7102), TGGGTAGGCGGATAGGAGAGGGATGGG (SEQ ID NO:7103), GGCGGATAGGAGAGGGATGGGGAGGAT (SEQ ID NO:7104), GGTAGGCGGATAGGAGAGGGATGGGA (SEQ ID NO:7105), TAGGCGGATAGGAGAGGGATGGGGAGG (SEQ ID NO:7106), GGGTTTGGGTAGGCGGATAGGAGAGGG (SEQ ID NO:7107)

Target752    chr7:27196518-27196556    TCGTATTGGGGTTTGCGGACGTTAGGC (SEQ ID NO:7108), TTCGTATTGGGGTTTGCGGACGTTAGGC (SEQ ID NO:7109), GCGGAAAAAGATTTGGAGGTTTCGCGGG (SEQ ID NO:7110), GCGGAAAAAGATTTGGAGGTTTCGCGGGA (SEQ ID NO:7111), GCGGAAAAAGATTTGGAGGTTTCGCGG (SEQ ID NO:7112), CGGGGTAGGTTGTTGCGGGGGGATAGAG (SEQ ID NO:7113), TGGGTAGGCGGATAGGAGAGGGATGGG (SEQ ID NO:7114), GGCGGATAGGAGAGGGATGGGGAGGAT (SEQ ID NO:7115), GGTAGGCGGATAGGAGAGGGATGGGA (SEQ ID NO:7116), TAGGCGGATAGGAGAGGGATGGGGAGG (SEQ ID NO:7117)

Target753    chr7:27196751-27196772    TGTTTCGCGGTGGTTTTGTGGGTAGGA (SEQ ID NO:7118), AGTTTGTTTCGCGGTGGTTTTGTGGGT (SEQ ID NO:7119), TTGTTTCGCGGTGGTTTTGTGGGTAGG (SEQ ID NO:7120), TTGTTTCGCGGTGGTTTTGTGGGTAGGA (SEQ ID NO:7121), TGTTTCGCGGTGGTTTTGTGGGTAGGAT (SEQ ID NO:7122), TCGATTAAGGAAAGGAAGTTGGGAGACGTT (SEQ ID NO:7123), TTCGATTAAGGAAAGGAAGTTGGGAGACGT (SEQ ID NO:7124),

FIGURE 5 CONTINUED

CGATTAAGGAAAGGAAGTTGGGAGACGTTGA (SEQ ID NO:7125),
TCGATTAAGGAAAGGAAGTTGGGAGACGTTG (SEQ ID NO:7126),
TCGATTAAGGAAAGGAAGTTGGGAGACGTTGA (SEQ ID NO:7127)

Target754    chr7:27204751-27204835    GGGTGTACGTAGGGGTGGTGGTGATGG (SEQ ID NO:7128), GGGGTGTACGTAGGGGTGGTGGTGATGG (SEQ ID NO:7129), TCGGGCGTGGGTTTTAGTTAGGAGCGT (SEQ ID NO:7130), GTTTGGGGGTGTACGTAGGGGTGGTGG (SEQ ID NO:7131), AGGTCGGTTGGAGGGTAAGTTCGCGAA (SEQ ID NO:7132), GCGACGGTGTTTGGCGTTTCGTGGAAT (SEQ ID NO:7133), CGACGGTGTTTGGCGTTTCGTGGAATT (SEQ ID NO:7134), GCGACGGTGTTTGGCGTTTCGTGGAATT (SEQ ID NO:7135), GCGACGGTGTTTGGCGTTTCGTGGAA (SEQ ID NO:7136), AAGGCGACGGTGTTTGGCGTTTCGTG (SEQ ID NO:7137)

Target755    chr7:27204848-27204864    GGGTGTACGTAGGGGTGGTGGTGATGG (SEQ ID NO:7138), GGGGTGTACGTAGGGGTGGTGGTGATGG (SEQ ID NO:7139), TCGGGCGTGGGTTTTAGTTAGGAGCGT (SEQ ID NO:7140), GTTTGGGGGTGTACGTAGGGGTGGTGG (SEQ ID NO:7141), GTACGTAGGGGTGGTGGTGATGGTGGT (SEQ ID NO:7142), GCGACGGTGTTTGGCGTTTCGTGGAAT (SEQ ID NO:7143), CGACGGTGTTTGGCGTTTCGTGGAATT (SEQ ID NO:7144), TGGGTTAGTTTTTTCGGTAGGCGGCGA (SEQ ID NO:7145), GCGACGGTGTTTGGCGTTTCGTGGAATT (SEQ ID NO:7146), GCGACGGTGTTTGGCGTTTCGTGGAA (SEQ ID NO:7147)

Target756    chr7:27204879-27205108    GGGTGTACGTAGGGGTGGTGGTGATGG (SEQ ID NO:7148), GGGGTGTACGTAGGGGTGGTGGTGATGG (SEQ ID NO:7149), ACGGGTTGAAGTCGGGGTGTTCGGTTA (SEQ ID NO:7150), TACGGGTTGAAGTCGGGGTGTTCGGTT (SEQ ID NO:7151), TGTACGGGTTGAAGTCGGGGTGTTCGG (SEQ ID NO:7152), TGGGTTAGTTTTTTCGGTAGGCGGCGA (SEQ ID NO:7153), CGTGGATTCGTTTTTGTTGGGCGTCGA (SEQ ID NO:7154), TGGGTTAGTTTTTTCGGTAGGCGGCGAC (SEQ ID NO:7155), GGGTTAGTTTTTTCGGTAGGCGGCGAC (SEQ ID NO:7156), CGTGGATTCGTTTTTGTTGGGCGTCGAC (SEQ ID NO:7157)

Target757    chr7:27205114-27205214    ATCGTGTTTAGCGTTTGGTTCGTTCGG (SEQ ID NO:7158), TCGTGTTTAGCGTTTGGTTCGTTCGG (SEQ ID NO:7159), TATCGTGTTTAGCGTTTGGTTCGTTCGG (SEQ ID NO:7160), TTATCGTGTTTAGCGTTTGGTTCGTTCGG (SEQ ID NO:7161), ATTATCGTGTTTAGCGTTTGGTTCGTTCGG (SEQ ID NO:7162), CGTACGGTTAATGGGGGCGCGGG (SEQ ID NO:7163), CGTACGGTTAATGGGGGCGCGG (SEQ ID NO:7164), GTACGGTTAATGGGGGCGCGGG (SEQ ID NO:7165), GTGATTTACGCGTTATTGTTTTGTTGGACGG (SEQ ID NO:7166), AGTGATTTACGCGTTATTGTTTTGTTGGACGG (SEQ ID NO:7167)

Target758    chr7:27205338-27205351    GGGGGGAGACGGGAGAGTATAGAGATAAGG (SEQ ID NO:7168), GGGGGGAGACGGGAGAGTATAGAGATAAGGT (SEQ ID NO:7169), GGGGGAGACGGGAGAGTATAGAGATAAGGT (SEQ ID NO:7170), GGGGGAGACGGGAGAGTATAGAGATAAGG (SEQ ID NO:7171), GGGGGGAGACGGGAGAGTATAGAGATAAG (SEQ ID NO:7172)

Target759    chr7:27205810-27205823    GGTTAGATTGTTGTGTTTGGTTGGCGAGT (SEQ ID NO:7173), AGGTTAGATTGTTGTGTTTGGTTGGCGAGT (SEQ ID NO:7174), AGGTTAGATTGTTGTGTTTGGTTGGCGAG (SEQ ID NO:7175), GGTTAGATTGTTGTGTTTGGTTGGCGAGTT (SEQ ID NO:7176), AAGGTTAGATTGTTGTGTTTGGTTGGCGAG (SEQ ID NO:7177), TTTGGAGTGTTTTGGTAGGGTCGGCGG (SEQ ID NO:7178), TTGGAGTGTTTTGGTAGGGTCGGCGGC (SEQ ID NO:7179), TGTTTTGGTAGGGTCGGCGGCGGTTTC (SEQ ID NO:7180), GTTTGGAGTGTTTTGGTAGGGTCGGCGG (SEQ ID NO:7181), GTTTTGGTAGGGTCGGCGGCGGTTTC (SEQ ID NO:7182)

Target760    chr7:27205848-27205864    GGTTAGATTGTTGTGTTTGGTTGGCGAGT (SEQ ID NO:7183), AGGTTAGATTGTTGTGTTTGGTTGGCGAGT (SEQ ID NO:7184), AGGTTAGATTGTTGTGTTTGGTTGGCGAG (SEQ ID NO:7185), GGTTAGATTGTTGTGTTTGGTTGGCGAGTT (SEQ ID NO:7186), AAGGTTAGATTGTTGTGTTTGGTTGGCGAG (SEQ ID NO:7187), TTTGGAGTGTTTTGGTAGGGTCGGCGG (SEQ ID NO:7188), TTGGAGTGTTTTGGTAGGGTCGGCGGC (SEQ ID NO:7189), TGTTTTGGTAGGGTCGGCGGCGGTTTC (SEQ ID NO:7190), GTTTGGAGTGTTTTGGTAGGGTCGGCGG (SEQ ID NO:7191), GTTTTGGTAGGGTCGGCGGCGGTTTC (SEQ ID NO:7192)

Target761    chr7:27205943-27205964    AGGTAGGGATCGGTCGTTTAGGGAGT (SEQ ID NO:7193), TTAGGTAGGGATCGGTCGTTTAGGGAGT (SEQ ID NO:7194), AGGTAGGGATCGGTCGTTTAGGGAGTAT (SEQ ID NO:7195), AGGTAGGGATCGGTCGTTTAGGGAGTATC (SEQ ID NO:7196), TTTAGGTAGGGATCGGTCGTTTAGGGAGT (SEQ ID NO:7197), TCGTTTTGGTGGCGGTTGGTCGTTTTT (SEQ ID NO:7198), TTCGTTTTGGTGGCGGTTGGTCGTTTT (SEQ ID NO:7199), TTTCGTTTTGGTGGCGGTTGGTCGTT (SEQ ID NO:7200), TTTTCGTTTTGGTGGCGGTTGGTCGTT (SEQ ID NO:7201), ATTTTCGTTTTGGTGGCGGTTGGTCGT (SEQ ID NO:7202)

Target762    chr7:27206025-27206045    GGAGGAGTTGGTTAGGAGGGAGCGGTT (SEQ ID NO:7203), CGGAGGAGTTGGTTAGGAGGGAGCGGT (SEQ ID NO:7204), ACGGAGGAGTTGGTTAGGAGGGAGCGG (SEQ ID NO:7205), CGGAGGAGTTGGTTAGGAGGGAGCGG (SEQ ID NO:7206), TACGGAGGAGTTGGTTAGGAGGGAGCG (SEQ ID NO:7207), TTAGTTGATGAGAAAGGCGGGTTGGGC (SEQ ID NO:7208), GTTAGTTGATGAGAAAGGCGGGTTGGGC (SEQ ID NO:7209), TGTTAGTTGATGAGAAAGGCGGGTTGGGC (SEQ ID NO:7210), TAGTTGATGAGAAAGGCGGGTTGGGC (SEQ ID NO:7211), TTGTTAGTTGATGAGAAAGGCGGGTTGGGC (SEQ ID NO:7212)

FIGURE 5 CONTINUED

Target763    chr7:27206073-27206083    TTTGAGGGTTTGGTTGGTTGTGCGGCG (SEQ ID NO:7213), GGAGGAGTTGGTTAGGAGGGAGCGGTT
(SEQ ID NO:7214), CGGAGGAGTTGGTTAGGAGGGAGCGGT (SEQ ID NO:7215),
ACGGAGGAGTTGGTTAGGAGGGAGCGG (SEQ ID NO:7216), TTTTGAGGGTTTGGTTGGTTGTGCGGC
(SEQ ID NO:7217), TTAGTTGATGAGAAAGGCGGGTTGGGC (SEQ ID NO:7218),
GTTAGTTGATGAGAAAGGCGGGTTGGGC (SEQ ID NO:7219),
TGTTAGTTGATGAGAAAGGCGGGTTGGGC (SEQ ID NO:7220), TGAGGTTGGAGTATAGGGTTGGGTCGT
(SEQ ID NO:7221), TAGTTGATGAGAAAGGCGGGTTGGGC (SEQ ID NO:7222)

Target764    chr7:27206104-27206166    TTTGAGGGTTTGGTTGGTTGTGCGGCG (SEQ ID NO:7223), GGAGGAGTTGGTTAGGAGGGAGCGGTT
(SEQ ID NO:7224), CGGAGGAGTTGGTTAGGAGGGAGCGGT (SEQ ID NO:7225),
ACGGAGGAGTTGGTTAGGAGGGAGCGG (SEQ ID NO:7226), TTTTGAGGGTTTGGTTGGTTGTGCGGC
(SEQ ID NO:7227), TTAGTTGATGAGAAAGGCGGGTTGGGC (SEQ ID NO:7228),
GTTAGTTGATGAGAAAGGCGGGTTGGGC (SEQ ID NO:7229),
TGTTAGTTGATGAGAAAGGCGGGTTGGGC (SEQ ID NO:7230), TGAGGTTGGAGTATAGGGTTGGGTCGT
(SEQ ID NO:7231), TAGTTGATGAGAAAGGCGGGTTGGGC (SEQ ID NO:7232)

Target765    chr7:27206311-27206378    AGCGTTGTAAGTTTGGTTGCGTTTCGT (SEQ ID NO:7233), TCGTATCGATGTGGTTTGTTTCGGGGT (SEQ
ID NO:7234), GCGTTGTAAGTTTGGTTGCGTTTCGTG (SEQ ID NO:7235),
AGCGTTGTAAGTTTGGTTGCGTTTCGTG (SEQ ID NO:7236), GCGTTGTAAGTTTGGTTGCGTTTCGTGA
(SEQ ID NO:7237), CGGGTTTTTTAGGTTTCGGAGTTGCGGGG (SEQ ID NO:7238),
GCGGGTTTTTTAGGTTTCGGAGTTGCGG (SEQ ID NO:7239), CGGTGCGGGTTTTTTAGGTTTCGGAGT
(SEQ ID NO:7240), TGCGGGTTTTTTAGGTTTCGGAGTTGCGG (SEQ ID NO:7241),
TCGGTGCGGGTTTTTTAGGTTTCGGAGT (SEQ ID NO:7242)

Target766    chr7:27225123-27225128    TATGTTGGTTGGGGGGTTTTTCGGCGC (SEQ ID NO:7243), TTATGTTGGTTGGGGGGGTTTTTCGGCGC
(SEQ ID NO:7244), ATGTTGGTTGGGGGGGTTTTTCGGCGC (SEQ ID NO:7245),
TTATGTTGGTTGGGGGGGTTTTTCGGCG (SEQ ID NO:7246), TTTATGTTGGTTGGGGGGGTTTTTCGGCGC
(SEQ ID NO:7247), ATTCGGGGAGTTGCGGGTGGGAGGTG (SEQ ID NO:7248),
ATTCGGGGAGTTGCGGGTGGGAGG (SEQ ID NO:7249), ATTCGGGGAGTTGCGGGTGGGAGGTGG (SEQ
ID NO:7250), GTTGCGGGTGGGAGGTGGGGACGAGAG (SEQ ID NO:7251),
GAGTTGCGGGTGGGAGGTGGGGACGAG (SEQ ID NO:7252)

Target767    chr7:27225418-27225629    CGTCGTTGTGTGGTTTGTGGTTTCGGA (SEQ ID NO:7253), TCGTCGTTGTGTGGTTTGTGGTTTCGG (SEQ
ID NO:7254), TCGTCGTTGTGTGGTTTGTGGTTTCGGA (SEQ ID NO:7255),
CGTCGTTGTGTGGTTTGTGGTTTCGGAG (SEQ ID NO:7256), CGTCGTTGTGTGGTTTGTGGTTTCGGAGT
(SEQ ID NO:7257), GGTTGTTGGCGGTTTAGGGACGGAAGG (SEQ ID NO:7258),
GTTGTTGGCGGTTTAGGGACGGAAGGT (SEQ ID NO:7259), TGGTTGTTGGCGGTTTAGGGACGGAAG
(SEQ ID NO:7260), TCGCGGGGAGAAGTCGTTTTGGTTGTT (SEQ ID NO:7261),
GGGGAGAAGTCGTTTTGGTTGTTGGCGG (SEQ ID NO:7262)

Target768    chr7:27244531-27244538    TGCGTTAGTTTTGAGGAGTTCGGGCGT (SEQ ID NO:7263), TTGCGTTAGTTTTGAGGAGTTCGGGCGT
(SEQ ID NO:7264), TTGCGTTAGTTTTGAGGAGTTCGGGCG (SEQ ID NO:7265),
TTTGCGTTAGTTTTGAGGAGTTCGGGCG (SEQ ID NO:7266), TTTGCGTTAGTTTTGAGGAGTTCGGGCGT
(SEQ ID NO:7267)

Target769    chr7:27244603-27244632    CGCGTTCGGATTTTTTAGAGTTGGCGT (SEQ ID NO:7268), CGCGTTCGGATTTTTTAGAGTTGGCGTA (SEQ
ID NO:7269), CGCGTTCGGATTTTTTAGAGTTGGCGTAA (SEQ ID NO:7270),
CGCGTTCGGATTTTTTAGAGTTGGCGTAAA (SEQ ID NO:7271),
CGCGTTCGGATTTTTTAGAGTTGGCGTAAAT (SEQ ID NO:7272),
TGAAGAGCGATTAGTGGTATTGTCGGGG (SEQ ID NO:7273), TGAAGAGCGATTAGTGGTATTGTCGGGGA
(SEQ ID NO:7274), GAAGAGCGATTAGTGGTATTGTCGGGGA (SEQ ID NO:7275),
GTGAAGAGCGATTAGTGGTATTGTCGGGG (SEQ ID NO:7276),
AGTGAAGAGCGATTAGTGGTATTGTCGGGG (SEQ ID NO:7277)

Target770    chr7:27244755-27244811    AGGGAGTTTGGTGAAGGGTTCGGTTGG (SEQ ID NO:7278), GGGAGTTTGGTGAAGGGTTCGGTTGGA
(SEQ ID NO:7279), AGGGAGTTTGGTGAAGGGTTCGGTTGGA (SEQ ID NO:7280),
GAGGGAGTTTGGTGAAGGGTTCGGTTGG (SEQ ID NO:7281),
AGAGGGAGTTTGGTGAAGGGTTCGGTTGG (SEQ ID NO:7282), AAGTCGGTGTTTTTCGCGGGTTGGTCG
(SEQ ID NO:7283), AGTCGGTGTTTTTCGCGGGTTGGTCG (SEQ ID NO:7284),
TAAGTCGGTGTTTTTCGCGGGTTGGTCG (SEQ ID NO:7285), GTAAGTCGGTGTTTTTCGCGGGTTGGT
(SEQ ID NO:7286), AGTAAGTCGGTGTTTTTCGCGGGTTGGT (SEQ ID NO:7287)

Target771    chr7:27244856-27244875    AGTTCGCGGGGGATATCGGTTTGTTGG (SEQ ID NO:7288), GTTCGCGGGGGATATCGGTTTGTTGGA (SEQ
ID NO:7289), AGTTCGCGGGGGATATCGGTTTGTTGGA (SEQ ID NO:7290),
AGGGAGTTTGGTGAAGGGTTCGGTTGGA (SEQ ID NO:7291), GGGAGTTTGGTGAAGGGTTCGGTTGGA
(SEQ ID NO:7292), TTTTTTGGGTTAGTGGTAGCGTCGGGT (SEQ ID NO:7293),
TGGGTTAGTGGTAGCGTCGGGTATAGA (SEQ ID NO:7294), TTTTTGGGTTAGTGGTAGCGTCGGGTA (SEQ
ID NO:7295), TTTTGGGTTAGTGGTAGCGTCGGGTAT (SEQ ID NO:7296),
TGGGTTAGTGGTAGCGTCGGGTATAGAG (SEQ ID NO:7297)

Target772    chr7:27244885-27244898    TTGCGGGTTATTTAGTCGGGGCGTTGG (SEQ ID NO:7298), TGCGGGTTATTTAGTCGGGGCGTTGGG (SEQ
ID NO:7299), AGTTCGCGGGGGATATCGGTTTGTTGG (SEQ ID NO:7300),
GTTCGCGGGGGATATCGGTTTGTTGGA (SEQ ID NO:7301), AGTTCGCGGGGGATATCGGTTTGTTGGA
(SEQ ID NO:7302), TTAAGTTAGGGTGGGGTGGGCGTTCGC (SEQ ID NO:7303),
ATTAAGTTAGGGTGGGGTGGGCGTTCG (SEQ ID NO:7304), TAAGTTAGGGTGGGGTGGGCGTTCGC (SEQ

FIGURE 5 CONTINUED

ID NO:7305), ATTAAGTTAGGGTGGGGTGGGCGTTCGC (SEQ ID NO:7306),
TATTAAGTTAGGGTGGGGTGGGCGTTCGC (SEQ ID NO:7307)

| Target773 | chr7:27244907-27244918 | TTGCGGGGTTATTTAGTCGGGGCGTTGG (SEQ ID NO:7308), TGCGGGGTTATTTAGTCGGGGCGTTGGG (SEQ ID NO:7309), AGTTCGCGGGGGGATATCGGTTTGTTGG (SEQ ID NO:7310), GTTCGCGGGGGGATATCGGTTTGTTGGA (SEQ ID NO:7311), AGTTCGCGGGGGGATATCGGTTTGTTGGA (SEQ ID NO:7312), TTAAGTTAGGGTGGGGTGGGCGTTCGC (SEQ ID NO:7313), ATTAAGTTAGGGTGGGGTGGGCGTTCG (SEQ ID NO:7314), TAAGTTAGGGTGGGGTGGGCGTTCGC (SEQ ID NO:7315), ATTAAGTTAGGGTGGGGTGGGCGTTCGC (SEQ ID NO:7316), TATTAAGTTAGGGTGGGGTGGGCGTTCGC (SEQ ID NO:7317) |
| Target774 | chr7:27260168-27260259 | TAGTTTTACGGAGGAGGTCGGGTCGCG (SEQ ID NO:7318), GTTGGCGGGGGATTTTGTAGGTCGGGTC (SEQ ID NO:7319), TTGGCGGGGATTTTGTAGGTCGGGTCG (SEQ ID NO:7320), GGTTGGCGGGGATTTTGTAGGTCGGGT (SEQ ID NO:7321), GGGTTGGCGGGGATTTTGTAGGTCGGG (SEQ ID NO:7322), TTCGTGGGGTTGTGGTTTTTCGCGGTC (SEQ ID NO:7323), TTTCGTGGGGTTGTGGTTTTTCGCGGT (SEQ ID NO:7324), TTTTCGGGTAAGTCGGGTAGGCGGGAG (SEQ ID NO:7325), GGTAAGTCGGGTAGGCGGGAGGTTGTT (SEQ ID NO:7326), ATTTTCGGGTAAGTCGGGTAGGCGGGA (SEQ ID NO:7327) |
| Target775 | chr7:27260274-27260311 | TAGTTTTACGGAGGAGGTCGGGTCGCG (SEQ ID NO:7328), GTTGGCGGGGGATTTTGTAGGTCGGGTC (SEQ ID NO:7329), TTGGCGGGGATTTTGTAGGTCGGGTCG (SEQ ID NO:7330), GGTTGGCGGGGATTTTGTAGGTCGGGT (SEQ ID NO:7331), GGGTTGGCGGGGGATTTTGTAGGTCGGG (SEQ ID NO:7332), AGTCGGGTAGGCGGGAGGTTGTTTTGT (SEQ ID NO:7333), TTTTCGGGTAAGTCGGGTAGGCGGGAG (SEQ ID NO:7334), GGTAAGTCGGGTAGGCGGGAGGTTGTT (SEQ ID NO:7335), ATTTTCGGGTAAGTCGGGTAGGCGGGA (SEQ ID NO:7336), AAGTCGGGTAGGCGGGAGGTTGTTTTGT (SEQ ID NO:7337) |
| Target776 | chr7:27260366-27260397 | TCGGTTTGTTCGGGGATGTGGGTGGAT (SEQ ID NO:7338), TTCGGTTTGTTCGGGGATGTGGGTGGA (SEQ ID NO:7339), GTTCGGTTTGTTCGGGGATGTGGGTGG (SEQ ID NO:7340), TGTTCGGTTTGTTCGGGGATGTGGGTG (SEQ ID NO:7341), CGGTTTGTTCGGGGATGTGGGTGGATT (SEQ ID NO:7342), GCGAGGGGTTACGTTGTTGGTTAGGGGC (SEQ ID NO:7343), CGAGGGGTTACGTTGTTGGTTAGGGGCG (SEQ ID NO:7344), TGCGAGGGGTTACGTTGTTGGTTAGGGG (SEQ ID NO:7345), TGCGAGGGGTTACGTTGTTGGTTAGGGGC (SEQ ID NO:7346), TTGCGAGGGGTTACGTTGTTGGTTAGGGG (SEQ ID NO:7347) |
| Target777 | chr7:27260417-27260467 | TCGGTTTGTTCGGGGATGTGGGTGGAT (SEQ ID NO:7348), TTCGGTTTGTTCGGGGATGTGGGTGGA (SEQ ID NO:7349), TCGTTCGGTGGGAGGAATTCGGGGTTT (SEQ ID NO:7350), TTCGTTCGGTGGGAGGAATTCGGGGTT (SEQ ID NO:7351), TTTCGTTCGGTGGGAGGAATTCGGGGT (SEQ ID NO:7352), GCGAGGGGTTACGTTGTTGGTTAGGGGC (SEQ ID NO:7353), CGAGGGGTTACGTTGTTGGTTAGGGGCG (SEQ ID NO:7354), TGCGAGGGGTTACGTTGTTGGTTAGGGG (SEQ ID NO:7355), TGCGAGGGGTTACGTTGTTGGTTAGGGGC (SEQ ID NO:7356), TTGCGAGGGGTTACGTTGTTGGTTAGGGG (SEQ ID NO:7357) |
| Target778 | chr7:27283367-27283410 | GTGTTTTGAGTGCGGGGTGTTGAGGGG (SEQ ID NO:7358), GGGGTGTTGAGGGGGGCGGATGTAAGTT (SEQ ID NO:7359), AGTGTTTTGAGTGCGGGGTGTTGAGGG (SEQ ID NO:7360), TGTTTTGAGTGCGGGGTGTTGAGGGGG (SEQ ID NO:7361), GTTTTGAGTGCGGGGTGTTGAGGGGG (SEQ ID NO:7362), CGGCGTTTGATTTTGTTTTCGTTTGGGG (SEQ ID NO:7363), TCGGATCGGCGTTTGATTTTGTTTTCGT (SEQ ID NO:7364), CGGCGTTTGATTTTGTTTTCGTTTGGGGA (SEQ ID NO:7365), TCGGCGTTTGATTTTGTTTTCGTTTGGGG (SEQ ID NO:7366), TCGGCGTTTGATTTTGTTTTCGTTTGGGGA (SEQ ID NO:7367) |
| Target779 | chr7:27283425-27283434 | GGCGGATGTAAGTTTTGGATTTGGGGG (SEQ ID NO:7368), GGCGGATGTAAGTTTTGGATTTGGGGGA (SEQ ID NO:7369), GGCGGATGTAAGTTTTGGATTTGGGGGAT (SEQ ID NO:7370), GGCGGATGTAAGTTTTGGATTTGGGGGATT (SEQ ID NO:7371), GGCGGATGTAAGTTTTGGATTTGGGGGATTCG (SEQ ID NO:7372), TGGTCGGAGGGGTTGTAGTATTCGGGGTT (SEQ ID NO:7373), TTGGTCGGAGGGGTTGTAGTATTCGGGGT (SEQ ID NO:7374), TGGTCGGAGGGGTTGTAGTATTCGGGGTGT (SEQ ID NO:7375), GGTCGGAGGGGTTGTAGTATTCGGGGTGT (SEQ ID NO:7376), TGGTCGGAGGGGTTGTAGTATTCGGGGTTG (SEQ ID NO:7377) |
| Target780 | chr7:27283528-27283562 | GGGTGTAAGAGGTATGGAGGCGCGGAA (SEQ ID NO:7378), AGGGTGTAAGAGGTATGGAGGCGCGGA (SEQ ID NO:7379), TAGGGTGTAAGAGGTATGGAGGCGCGG (SEQ ID NO:7380), TAGGGTGTAAGAGGTATGGAGGCGCGGA (SEQ ID NO:7381), AGGTATGGAGGCGCGGAAGTTAGGAGT (SEQ ID NO:7382), ACGTGTAAATTGGTCGGAGGGTTGTAGT (SEQ ID NO:7383), GACGTGTAAATTGGTCGGAGGGTTGTAGT (SEQ ID NO:7384), GACGTGTAAATTGGTCGGAGGGTTGTAGTA (SEQ ID NO:7385), GACGTGTAAATTGGTCGGAGGGTTGTAGTAT (SEQ ID NO:7386), ACGTGTAAATTGGTCGGAGGGTTGTAGTATT (SEQ ID NO:7387) |
| Target781 | chr7:27283600-27283614 | TGCGGTTTATTTGGGTAGTTCGGGTGT (SEQ ID NO:7388), TGCGGTTTATTTGGGTAGTTCGGGTGTT (SEQ ID NO:7389), TTGCGGTTTATTTGGGTAGTTCGGGTGT (SEQ ID NO:7390), GCGGTTTATTTGGGTAGTTCGGGTGTTGT (SEQ ID NO:7391), TGCGGTTTATTTGGGTAGTTCGGGTGTTG (SEQ ID NO:7392), AGGAAGGAAAGGGGAAGGGGGGAGGAT (SEQ ID NO:7393), AGGAAAGGGGAAGGGGGGAGGATTCGA (SEQ ID NO:7394), TAGGAAGGAAAGGGGAAGGGGGGAGGA |

FIGURE 5 CONTINUED (SEQ ID NO:7395), AAGGAAAGGGGAAGGGGGGAGGATTCG (SEQ ID NO:7396), GGAAAGGGGAAGGGGGGAGGATTCGAT (SEQ ID NO:7397)

| | | |
|---|---|---|
| Target782 | chr7:29603009-29603473 | CGCGATGGGGTTAAGGGATAGTTGTTGCG (SEQ ID NO:7398), GCGATGGGGTTAAGGGATAGTTGTTGCGG (SEQ ID NO:7399), GCGATGGGGTTAAGGGATAGTTGTTGCG (SEQ ID NO:7400), CGCGATGGGGTTAAGGGATAGTTGTTGC (SEQ ID NO:7401), AGGGGGGAAAAATAAATCGCGATGGGGT (SEQ ID NO:7402), ACGGCGGAGATTTGAGATTCGGAGGTT (SEQ ID NO:7403), AACGGCGGAGATTTGAGATTCGGAGGT (SEQ ID NO:7404), TGAGGTTGTAGGTGGGTTTCGTTGGGT (SEQ ID NO:7405), CGGAGGTTGAGGTTGTAGGTGGGTTTCG (SEQ ID NO:7406), CGGAGGTTGAGGTTGTAGGTGGGTTTCGT (SEQ ID NO:7407) |
| Target783 | chr7:29605642-29605961 | GTGGTAAGTCGGGGAAGGGGTGGAGTG (SEQ ID NO:7408), GTGTGGTAAGTCGGGGAAGGGGTGGAG (SEQ ID NO:7409), TGGTAAGTCGGGGAAGGGGTGGAGTGA (SEQ ID NO:7410), TGTGGTAAGTCGGGGAAGGGGTGGAGT (SEQ ID NO:7411), TAAGTCGGGGAAGGGGTGGAGTGAACG (SEQ ID NO:7412), ATACGTGGGTTGCGGGGTGGATGTTGA (SEQ ID NO:7413), TGGGTTGCGGGGTGGATGTTGAGGTAG (SEQ ID NO:7414), GTGGGTTGCGGGGTGGATGTTGAGGTA (SEQ ID NO:7415), TACGTGGGTTGCGGGGTGGATGTTGAG (SEQ ID NO:7416), TGGTCGGAGGGTTTAGGGGTTTTCGGT (SEQ ID NO:7417) |
| Target784 | chr7:29605992-29606278 | CGATAGCGGCGATGTTGGTAGTTTCGG (SEQ ID NO:7418), CGATAGCGGCGATGTTGGTAGTTTCGG (SEQ ID NO:7419), CGGAGATTACGTGGAGAAAGGGGTCGT (SEQ ID NO:7420), AGGAAGTCGTAGTGGGGGTGTCGTTTT (SEQ ID NO:7421), AAGGAAGTCGTAGTGGGGGTGTCGTTT (SEQ ID NO:7422), TTGTTGGTTTAGTTCGGGTTGGGCGGC (SEQ ID NO:7423), TTTGTTTGGTTTGGGGGGGTTCGTCGGC (SEQ ID NO:7424), TCGGGTTTGGAATTGGGGGTTTGGGGT (SEQ ID NO:7425), GGGGGTTTGGGGTAGTGTTGGGTAGGT (SEQ ID NO:7426), TGGGGGTTTGGGGTAGTGTTGGGTAGG (SEQ ID NO:7427) |
| Target785 | chr7:29606320-29606352 | TTTCGGAGGCGGGTAGGTTTTCGGAGG (SEQ ID NO:7428), GGCGGGTAGGTTTTCGGAGGAGGTAGG (SEQ ID NO:7429), GCGTTACGTTGTTTTCGGAGGCGGGTA (SEQ ID NO:7430), GCGGGTAGGTTTTCGGAGGAGGTAGGT (SEQ ID NO:7431), TTCGGAGGCGGGTAGGTTTTCGGAGGA (SEQ ID NO:7432), TAAGGGGGCGGGTTTGAAGTTTCGGGT (SEQ ID NO:7433), CGTAAGGGGGCGGGTTTGAAGTTTCGG (SEQ ID NO:7434), GGGCGGGTTTGAAGTTTCGGGTTTGGA (SEQ ID NO:7435), GTAAGGGGGCGGGTTTGAAGTTTCGGG (SEQ ID NO:7436), TCGGGTTTGGAATTGGGGGTTTGGGGT (SEQ ID NO:7437) |
| Target786 | chr7:35293506-35293532 | CGTTTCGGGGCGTTCGGTAGGACG (SEQ ID NO:7438), AGGGTTTATCGAGTATTACGGCGGGTG (SEQ ID NO:7439), GAGGGTTTATCGAGTATTACGGCGGGT (SEQ ID NO:7440), AGAGGGTTTATCGAGTATTACGGCGGGT (SEQ ID NO:7441), AGAGGGTTTATCGAGTATTACGGCGGG (SEQ ID NO:7442), GTTTTAGAGGGAGGAAGGACGCGGAGG (SEQ ID NO:7443), AGTTTTAGAGGGAGGAAGGACGCGGAGG (SEQ ID NO:7444), AGTTTTAGAGGGAGGAAGGACGCGGAG (SEQ ID NO:7445), TAGTTTTAGAGGGAGGAAGGACGCGGA (SEQ ID NO:7446), TTTTAGAGGGAGGAAGGACGCGGAGG (SEQ ID NO:7447) |
| Target787 | chr7:35293652-35293659 | TGGGGTTGGGGATAGTCGGGATGTTTT (SEQ ID NO:7448), TTGGGGTTGGGGATAGTCGGGATGTTT (SEQ ID NO:7449), TTTGGGGTTGGGGATAGTCGGGATGTT (SEQ ID NO:7450), TTTTGGGGTTGGGGATAGTCGGGATGT (SEQ ID NO:7451), TTGGGGTTGGGGATAGTCGGGATGTTTT (SEQ ID NO:7452), GGCGTAGGGTAGCGAGCGTTAGGGTTT (SEQ ID NO:7453), GCGTTGATTGGTTGCGGGTTTTCGGGA (SEQ ID NO:7454), AGGCGTAGGGTAGCGAGCGTTAGGGTT (SEQ ID NO:7455), GGCGTAGGGTAGCGAGCGTTAGGGGTT (SEQ ID NO:7456), GGCGTTGATTGGTTGCGGGTTTTCGGG (SEQ ID NO:7457) |
| Target788 | chr7:35293670-35293797 | GCGGCGCGGAATTACGGATAGTGAGTT (SEQ ID NO:7458), GCGGCGCGGAATTACGGATAGTGAGTTT (SEQ ID NO:7459), GCGGCGCGGAATTACGGATAGTGAGT (SEQ ID NO:7460), TGGGGTTGGGGATAGTCGGGATGTTTT (SEQ ID NO:7461), TTGGGGTTGGGGATAGTCGGGATGTTT (SEQ ID NO:7462), AGACGGCGTTGATTGGTTGCGGGTTTT (SEQ ID NO:7463), GGCGTAGGGTAGCGAGCGTTAGGGTTT (SEQ ID NO:7464), GAGACGGCGTTGATTGGTTGCGGGTTT (SEQ ID NO:7465), GCGTTGATTGGTTGCGGGTTTTCGGGA (SEQ ID NO:7466), GTTTTCGGCGGCGGAATTAGGAAGCGG (SEQ ID NO:7467) |
| Target789 | chr7:35293979-35293999 | CGCGTGGTTTGTCGTTTCGGTTGTTCG (SEQ ID NO:7468), GCGTGGTTTGTCGTTTCGGTTGTTCGG (SEQ ID NO:7469), GTTCGCGTGGTTTGTCGTTTCGGTTGT (SEQ ID NO:7470), TCGCGTGGTTTGTCGTTTCGGTTGTTCG (SEQ ID NO:7471), GCGTGGTTTGTCGTTTCGGTTGTTCGGT (SEQ ID NO:7472) |
| Target790 | chr7:35294157-35294186 | AGGGAAGCGTTTAGTAGAATTCGGCGTT (SEQ ID NO:7473), AGGGAAGCGTTTAGTAGAATTCGGCGTT (SEQ ID NO:7474), TAGGGAAGCGTTTAGTAGAATTCGGCGT (SEQ ID NO:7475), GGGAAGCGTTTAGTAGAATTCGGCGTTT (SEQ ID NO:7476), AGGGAAGCGTTTAGTAGAATTCGGCGTTT (SEQ ID NO:7477), CGAGTATGGATTTGGTTAGTTGGCGTCGG (SEQ ID NO:7478), CGAGTATGGATTTGGTTAGTTGGCGTCGG (SEQ ID NO:7479), AGTATGGATTTGGTTAGTTGGCGTCGGT (SEQ ID NO:7480), TCGAGTATGGATTTGGTTAGTTGGCGTCGG (SEQ ID NO:7481), TCGAGTATGGATTTGGTTAGTTGGCGTCGGT (SEQ ID NO:7482) |
| Target791 | chr7:35297344-35297475 | AGTCGGGAGGGCGGGTTTGAGTTTTGT (SEQ ID NO:7483), GAGTCGGGAGGGCGGGTTTGAGTTTTG (SEQ ID NO:7484), GTCGGGAGGGCGGGTTTGAGTTTTGTT (SEQ ID NO:7485), CGAGTCGGGAGGGCGGGTTTGAGTTTT (SEQ ID NO:7486), TCGGGAGGGCGGGTTTGAGTTTTGTTT (SEQ |

FIGURE 5 CONTINUED

ID NO:7487), TGGTGCGGAGGTTTTTTGGGTCGGTTC (SEQ ID NO:7488), GTGCGGAGGTTTTTTGGGTCGGTTCGA (SEQ ID NO:7489), GGTGCGGAGGTTTTTTGGGTCGGTTCG (SEQ ID NO:7490), TGGTGCGGAGGTTTTTTGGGTCGGTT (SEQ ID NO:7491), TGCGGAGGTTTTTTGGGTCGGTTCGA (SEQ ID NO:7492)

| Target792 | chr7:35297483-35297501 | AGTCGGGAGGGCGGGTTTGAGTTTTGT (SEQ ID NO:7493), GAGTCGGGAGGGCGGGTTTGAGTTTTG (SEQ ID NO:7494), GTCGGGAGGGCGGGTTTGAGTTTTGTT (SEQ ID NO:7495), CGAGTCGGGAGGGCGGGTTTGAGTTTT (SEQ ID NO:7496), TCGGGAGGGCGGGTTTGAGTTTTGTTT (SEQ ID NO:7497), TGGTGCGGAGGTTTTTTGGGTCGGTTC (SEQ ID NO:7498), GTGCGGAGGTTTTTTGGGTCGGTTCGA (SEQ ID NO:7499), GGTGCGGAGGTTTTTTGGGTCGGTTCG (SEQ ID NO:7500), TTGGTGCGGAGGTTTTTTGGGTCGGTT (SEQ ID NO:7501), TTTGGTGCGGAGGTTTTTTGGGTCGGT (SEQ ID NO:7502) |

| Target793 | chr7:35297516-35297533 | AGTCGGGAGGGCGGGTTTGAGTTTTGT (SEQ ID NO:7503), GAGTCGGGAGGGCGGGTTTGAGTTTTG (SEQ ID NO:7504), GTCGGGAGGGCGGGTTTGAGTTTTGTT (SEQ ID NO:7505), CGAGTCGGGAGGGCGGGTTTGAGTTTT (SEQ ID NO:7506), TCGGGAGGGCGGGTTTGAGTTTTGTTT (SEQ ID NO:7507), TGGTGCGGAGGTTTTTTGGGTCGGTTC (SEQ ID NO:7508), GTGCGGAGGTTTTTTGGGTCGGTTCGA (SEQ ID NO:7509), GGTGCGGAGGTTTTTTGGGTCGGTTCG (SEQ ID NO:7510), TTGGTGCGGAGGTTTTTTGGGTCGGTT (SEQ ID NO:7511), TTTGGTGCGGAGGTTTTTTGGGTCGGT (SEQ ID NO:7512) |

| Target794 | chr7:35297556-35297579 | CGGGAGGGCGGGTTTGAGTTTTGTTTT (SEQ ID NO:7513), CGGGAGGGCGGGTTTGAGTTTTGTTTTT (SEQ ID NO:7514), CGGGAGGGCGGGTTTGAGTTTTGTTT (SEQ ID NO:7515), GGGAGGGCGGGTTTGAGTTTTGTTTTT (SEQ ID NO:7516), CGGGAGGGCGGGTTTGAGTTTTGTTTTTT (SEQ ID NO:7517), TGGTGCGGAGGTTTTTTGGGTCGGTTC (SEQ ID NO:7518), GTGCGGAGGTTTTTTGGGTCGGTTCGA (SEQ ID NO:7519), GGTGCGGAGGTTTTTTGGGTCGGTTCG (SEQ ID NO:7520), TTGGTGCGGAGGTTTTTTGGGTCGGTT (SEQ ID NO:7521), TTTGGTGCGGAGGTTTTTTGGGTCGGT (SEQ ID NO:7522) |

| Target795 | chr7:35297699-35297709 | AGTTTTTGGATGGGGTGTGAGTGCGCG (SEQ ID NO:7523), GTTTTTGGATGGGGTGTGAGTGCGCGC (SEQ ID NO:7524), AAGTTTTTGGATGGGGTGTGAGTGCGCG (SEQ ID NO:7525), TTTTTGGATGGGGTGTGAGTGCGCGC (SEQ ID NO:7526), AAGTTTTTGGATGGGGTGTGAGTGCGC (SEQ ID NO:7527), TCGGTTTTGGAGATGGGCGCGAAG (SEQ ID NO:7528), TCGGTTTTATAGTTGGGCGAGATTGAGGT (SEQ ID NO:7529), CGGTTTTGGAGATGGGCGCGAAG (SEQ ID NO:7530), CGGTTTTATAGTTGGGCGAGATTGAGGTTTC (SEQ ID NO:7531), CGGTTTTGGAGATGGGCGCGAA (SEQ ID NO:7532) |

| Target796 | chr7:55242342-55242742 | GTTGTAGGGTTGCGGGGGCGTTATAGT (SEQ ID NO:7533), AGTTGTAGGGTTGCGGGGGCGTTATAGT (SEQ ID NO:7534), AGTTGTAGGGTTGCGGGGGCGTTATAG (SEQ ID NO:7535), TGTAGGGTTGCGGGGGCGTTATAGTTT (SEQ ID NO:7536), TTGTAGGGTTGCGGGGGCGTTATAGTT (SEQ ID NO:7537), GGGAGAGGTTAGTGTTGTTTTTAAGGGGAGGG (SEQ ID NO:7538), TGGGAGAGGTTAGTGTTGTTTTTAAGGGGAGGG (SEQ ID NO:7539), GGGAGAGGTTAGTGTTGTTTTTAAGGGGAGGGA (SEQ ID NO:7540), GGAGAGGTTAGTGTTGTTTTTAAGGGGAGGG (SEQ ID NO:7541), GGGGAGAGGTTAGTGTTGTTTTTAAGGGGAGG (SEQ ID NO:7542) |

| Target797 | chr7:55249057-55249088 | GGAGGTAGTCGAAGGGTATGAGTTGCGT (SEQ ID NO:7543), GGAGGTAGTCGAAGGGTATGAGTTGCG (SEQ ID NO:7544), AGGAGGTAGTCGAAGGGTATGAGTTGCGT (SEQ ID NO:7545), AGGAGGTAGTCGAAGGGTATGAGTTGCG (SEQ ID NO:7546), AGGTAGTCGAAGGGTATGAGTTGCGTG (SEQ ID NO:7547) |

| Target798 | chr7:55259233-55259800 | TGGGTTGGTTAAATTGTTGGGTGCGGA (SEQ ID NO:7548), TTGGGTTGGTTAAATTGTTGGGTGCGG (SEQ ID NO:7549), TGGGTTGGTTAAATTGTTGGGTGCGGAA (SEQ ID NO:7550), TTGGGTTGGTTAAATTGTTGGGTGCGGA (SEQ ID NO:7551), GGGTTGGTTAAATTGTTGGGTGCGGAA (SEQ ID NO:7552), ACGTTTTTGGTTGTTAGGTCGCGGTGT (SEQ ID NO:7553), ACGTTTTTGGTTGTTAGGTCGCGGTGTA (SEQ ID NO:7554), TACGTTTTTGGTTGTTAGGTCGCGGTGT (SEQ ID NO:7555), GTACGTTTTTGGTTGTTAGGTCGCGGT (SEQ ID NO:7556), CGTTTTTGGTTGTTAGGTCGCGGTGTA (SEQ ID NO:7557) |

| Target799 | chr7:67016016-67016255 | TGGGGGTACGGTTGGTTTTGTTATAGTCGT (SEQ ID NO:7558), GGGGGTACGGTTGGTTTTGTTATAGTCGT (SEQ ID NO:7559), TGGGGGTACGGTTGGTTTTGTTATAGTCG (SEQ ID NO:7560), GGTTTATTTGGGGGTACGGTTGGTTTTGT (SEQ ID NO:7561), AGGTTTATTTGGGGGTACGGTTGGTTTTGT (SEQ ID NO:7562), AGATGGAAAGTTGTTCGGGTAGCGTCG (SEQ ID NO:7563), GATGGAAAGTTGTTCGGGTAGCGTCGA (SEQ ID NO:7564), ACGGAAAGTTACGGTTGCGGTTGTAAT (SEQ ID NO:7565), AGATGGAAAGTTGTTCGGGTAGCGTCGA (SEQ ID NO:7566), GAGATGGAAAGTTGTTCGGGTAGCGTCG (SEQ ID NO:7567) |

| Target800 | chr7:70111632-70111709 | TGGGGATGAGTTAGTTCGTTGGAGGGG (SEQ ID NO:7568), TGGGGATGAGTTAGTTCGTTGGAGGGGA (SEQ ID NO:7569), GGGGATGAGTTAGTTCGTTGGAGGGGA (SEQ ID NO:7570), GGGGATGAGTTAGTTCGTTGGAGGGGAGT (SEQ ID NO:7571), TGGGGATGAGTTAGTTCGTTGGAGGGGAG (SEQ ID NO:7572), GCGGGTTTTGAGTAGTCGTTTTGTATGGT (SEQ ID NO:7573), AGCGGGTTTTGAGTAGTCGTTTTGTATGGT (SEQ ID NO:7574), AGGGTTTTCGTATTAGAGCGGGTTTTGAGT (SEQ ID NO:7575), GAGCGGGTTTTGAGTAGTCGTTTTGTATGG (SEQ ID NO:7576), GAGCGGGTTTTGAGTAGTCGTTTTGTATGGT (SEQ ID NO:7577) |

FIGURE 5 CONTINUED

Target801    chr7:70111742-70111820    AGTGCGAGGGTTTTGGTTTAGGGTAGT (SEQ ID NO:7578), GCGAGGGTTTTGGTTTAGGGTAGTAGGGT (SEQ ID NO:7579), TGCGAGGGTTTTGGTTTAGGGTAGTAGGG (SEQ ID NO:7580), TGCGAGGGTTTTGGTTTAGGGTAGTAGGGT (SEQ ID NO:7581), GCGAGGGTTTTGGTTTAGGGTAGTAGGG (SEQ ID NO:7582), AGGGTTTTCGTATTAGAGCGGGTTTTGAGT (SEQ ID NO:7583), AGGGTTTTCGTATTAGAGCGGGTTTTGAGTA (SEQ ID NO:7584), TAGGGTTTTCGTATTAGAGCGGGTTTTGAGT (SEQ ID NO:7585), TGAGTTAGGGTTTTCGTATTAGAGCGGGTTT (SEQ ID NO:7586), TTGAGTTAGGGTTTTCGTATTAGAGCGGGTT (SEQ ID NO:7587)

Target802    chr7:70574860-70575061    GGAGGTATTGTTTTGGGAGTTGTTTTTGGTGT (SEQ ID NO:7588), AGGAGGTATTGTTTTGGGAGTTGTTTTTGGTG (SEQ ID NO:7589), AGGAGGTATTGTTTTGGGAGTTGTTTTTGGTGT (SEQ ID NO:7590), GGAGGTATTGTTTTGGGAGTTGTTTTTGGTGTT (SEQ ID NO:7591), AAGGAGGTATTGTTTTGGGAGTTGTTTTTGGTG (SEQ ID NO:7592), TGAGGTTTTTAGGTATGTTGTTTAAGGGGGTTTAGG (SEQ ID NO:7593), AGGTTTTTAGGTATGTTGTTTAAGGGGGTTTAGGAT (SEQ ID NO:7594), AGTATTGAGGTTTTTAGGTATGTTGTTTAAGGGGGT (SEQ ID NO:7595)

Target803    chr7:71801500-71802283    GTTCGCGGGGTGGGTGTTTTAGTGTCG (SEQ ID NO:7596), AAGGTGGTCGGCGCGGTTTTTAGTTCG (SEQ ID NO:7597), CGAGGGAAGAAGAAAAGAGAGCGCGCG (SEQ ID NO:7598), CGGTTTTTAGTTCGCGGGGTGGGTGTT (SEQ ID NO:7599), GGTAAGTTAGGGAGTCGGCGGCGGTAT (SEQ ID NO:7600), TTGGGGGATTCGTTGGGGAGGAGTTGG (SEQ ID NO:7601), GTGTTGTCGGCGGTAAGGTTTTGGGGG (SEQ ID NO:7602), GGTGTTGTCGGCGGTAAGGTTTTGGGG (SEQ ID NO:7603), TAGAGCGAGGAGTGTGGTGTTGTCGGC (SEQ ID NO:7604), GGATTCGTTGGGGAGGAGTTGGGGAGG (SEQ ID NO:7605)

Target804    chr7:71802362-71802405    TCGGGTTTTTGGGTTCGTTTTGGTCGT (SEQ ID NO:7606), GTCGGGTTTTTGGGTTCGTTTTGGTCGT (SEQ ID NO:7607), GTCGGGTTTTTGGGTTCGTTTTGGTCG (SEQ ID NO:7608), GCGTTTAGGAGTCGGGTTTTTGGGTTCG (SEQ ID NO:7609), GCGTTTAGGAGTCGGGTTTTTGGGTTCGT (SEQ ID NO:7610), CGTGTATGTGTATGCGTGTGTGTGT (SEQ ID NO:7611), TCGTGTATGTGTATGCGTGTGTGTGT (SEQ ID NO:7612), TGTCGTGTATGTGTATGCGTGTGTGTGT (SEQ ID NO:7613), TGTGTCGTGTATGTGTATGCGTGTGTGT (SEQ ID NO:7614), TGTGTGTCGTGTATGTGTATGCGTGTGT (SEQ ID NO:7615)

Target805    chr7:97361421-97361463    CGTGGGGAGAATGTTACGTGGGTTTGG (SEQ ID NO:7616), CGTGGGGAGAATGTTACGTGGGTTTGGA (SEQ ID NO:7617), TGGGGAGAATGTTACGTGGGTTTGGAGGT (SEQ ID NO:7618), GGGGAGAATGTTACGTGGGTTTGGAGGT (SEQ ID NO:7619), TGGGGAGAATGTTACGTGGGTTTGGAGG (SEQ ID NO:7620), CGACGGATAGTTCGCGGGGTGTTGAG (SEQ ID NO:7621), GATAGATGCGGGGCGGGGTGATTCGG (SEQ ID NO:7622), GGATAGATGCGGGGCGGGGTGATTCG (SEQ ID NO:7623), GATAGATGCGGGGCGGGGTGATTCGGG (SEQ ID NO:7624), GGATAGATGCGGGGCGGGGTGATTCGG (SEQ ID NO:7625)

Target806    chr7:97361489-97361578    TCGTCGTAGTAAGTGTTCGCGCGGTGT (SEQ ID NO:7626), CGTAGTAAGTGTTCGCGCGGTGTTGGT (SEQ ID NO:7627), CGTCGTAGTAAGTGTTCGCGCGGTGTT (SEQ ID NO:7628), TAGTAAGTGTTCGCGCGGTGTTGGTCG (SEQ ID NO:7629), TCGTAGTAAGTGTTCGCGCGGTGTTGG (SEQ ID NO:7630), GATAGATGCGGGGCGGGGTGATTCGG (SEQ ID NO:7631), GGATAGATGCGGGGCGGGGTGATTCG (SEQ ID NO:7632), GATAGATGCGGGGCGGGGTGATTCGGG (SEQ ID NO:7633), GGATAGATGCGGGGCGGGGTGATTCGG (SEQ ID NO:7634), GATAGATGCGGGGCGGGGTGATTCG (SEQ ID NO:7635)

Target807    chr7:97361586-97361598    TCGTCGTAGTAAGTGTTCGCGCGGTGT (SEQ ID NO:7636), CGTAGTAAGTGTTCGCGCGGTGTTGGT (SEQ ID NO:7637), CGTCGTAGTAAGTGTTCGCGCGGTGTT (SEQ ID NO:7638), TAGTAAGTGTTCGCGCGGTGTTGGTCG (SEQ ID NO:7639), TCGTAGTAAGTGTTCGCGCGGTGTTGG (SEQ ID NO:7640), TAGGTGGAAGATAAAGAGGGGCGTTGG (SEQ ID NO:7641), TGTAGGTGGAAGATAAAGAGGGGCGTTGG (SEQ ID NO:7642), GTAGGTGGAAGATAAAGAGGGGCGTTGG (SEQ ID NO:7643), AGGTGGAAGATAAAGAGGGGCGTTGG (SEQ ID NO:7644), TGTAGGTGGAAGATAAAGAGGGGCGTTG (SEQ ID NO:7645)

Target808    chr7:98739441-98739878    GCGTTATTAAGTCGTAGGTTCGCGGTAGAGC (SEQ ID NO:7646), TGAGAGTGAGAAAGGGAAGACGAGGATGT (SEQ ID NO:7647), GCGTTATTAAGTCGTAGGTTCGCGGTAGA (SEQ ID NO:7648), GCGGTAGAGCGTTGCGTTTATTTTTGAAGG (SEQ ID NO:7649), TGGTTTAGAATTTTTGGAGTTCGGGGGGA (SEQ ID NO:7650), CGATTTGGTGGCGCGGATGTGATGTTA (SEQ ID NO:7651), CGATTTGGTGGCGCGGATGTGATGTT (SEQ ID NO:7652), CGATTTGGTGGCGCGGATGTGATGTTAA (SEQ ID NO:7653), TGGTGGCGCGGATGTGATGTTAATTTGT (SEQ ID NO:7654), GGTGGCGCGGATGTGATGTTAATTTGT (SEQ ID NO:7655)

Target809    chr7:121950250-121950507    TCGCGTCGATTCGTTGGTTTTGGTCGT (SEQ ID NO:7656), CGCGTCGATTCGTTGGTTTTGGTCGTT (SEQ ID NO:7657), TCGCGTCGATTCGTTGGTTTTGGTCGTT (SEQ ID NO:7658), CGCGTCGATTCGTTGGTTTTGGTCGTTT (SEQ ID NO:7659), TCGCGTCGATTCGTTGGTTTTGGTCGTTT (SEQ ID NO:7660), TTTTTTGGGTAGTCGGGGGTAGGGGGC (SEQ ID NO:7661), TAGTCGGGGGTAGGGGGCGTTAAGGTC (SEQ ID NO:7662), GCGGGGTATTTTCGGGTCGGAGTGGTT

FIGURE 5 CONTINUED

{SEQ ID NO:7663}, GTAGTCGGGGGTAGGGGGCGTTAAGGT {SEQ ID NO:7664},
GCGGGGTATTTTCGGGTCGGAGTGGTTA {SEQ ID NO:7665}

| Target810 | chr7:121950519-121950555 | GGAGTTTCGTTTTATTTAGGATTCGGTGGTTAGC {SEQ ID NO:7666}, AGGAGTTTCGTTTTATTTAGGATTCGGTGGTTAGC {SEQ ID NO:7667}, CGGTTGGGTTTTTATTTTTCGGTTTTTGTTTACGA {SEQ ID NO:7668}, TCGGTTGGGTTTTTATTTTTCGGTTTTTGTTTACG {SEQ ID NO:7669}, GGGAGTTTTAGTTCGGTAGCGGCGTTC {SEQ ID NO:7670}, GGGAGTTTTAGTTCGGTAGCGGCGTT {SEQ ID NO:7671}, GGAGTTTTAGTTCGGTAGCGGCGTTC {SEQ ID NO:7672}, GGGAGTTTTAGTTCGGTAGCGGCGT {SEQ ID NO:7673}, AGTTCGGTGGTTTTCGGTTTTGTTAACGT {SEQ ID NO:7674} |
|---|---|---|
| Target811 | chr7:121950564-121950713 | GGCGGTTGGGAGTTGGGGCGTAATTTT {SEQ ID NO:7675}, TCGAGAAGTTTGGAGGCGGTTGGGAGT {SEQ ID NO:7676}, GAAGTTTGGAGGCGGTTGGGAGTTGGG {SEQ ID NO:7677}, AGGCGGTTGGGAGTTGGGGCGTAATTT {SEQ ID NO:7678}, AAGTTTGGAGGCGGTTGGGAGTTGGGG {SEQ ID NO:7679}, TCGGCGGGATTTGATCGAAGGTAGCGT {SEQ ID NO:7680}, GGCGGTGGTGGTTTAGAGGTTCGAGGT {SEQ ID NO:7681}, TGTAGAGGAGAAGGGGAGGAGCGCGAT {SEQ ID NO:7682}, ATGTAGAGGAGAAGGGGAGGAGCGCGA {SEQ ID NO:7683}, AGTTGGGGCGGTGGTGGTTTAGAGGTT {SEQ ID NO:7684} |
| Target812 | chr7:121950721-121950736 | GGCGGTTGGGAGTTGGGGCGTAATTTT {SEQ ID NO:7685}, TCGAGAAGTTTGGAGGCGGTTGGGAGT {SEQ ID NO:7686}, GAAGTTTGGAGGCGGTTGGGAGTTGGG {SEQ ID NO:7687}, AGGCGGTTGGGAGTTGGGGCGTAATTT {SEQ ID NO:7688}, AAGTTTGGAGGCGGTTGGGAGTTGGGG {SEQ ID NO:7689}, GGCGGTGGTGGTTTAGAGGTTCGAGGT {SEQ ID NO:7690}, TGTAGAGGAGAAGGGGAGGAGCGCGAT {SEQ ID NO:7691}, ATGTAGAGGAGAAGGGGAGGAGCGCGA {SEQ ID NO:7692}, AGTTGGGGCGGTGGTGGTTTAGAGGTT {SEQ ID NO:7693}, TTGGGGCGGTGGTGGTTTAGAGGTTCG {SEQ ID NO:7694} |
| Target813 | chr7:121950760-121950800 | TCGGGTTGGGGTTTTTAAGCGTTCGGT {SEQ ID NO:7695}, GTCGGGTTGGGGTTTTTAAGCGTTCGGT {SEQ ID NO:7696}, TGTCGGGTTGGGGTTTTTAAGCGTTCGG {SEQ ID NO:7697}, GTCGGGTTGGGGTTTTTAAGCGTTCGG {SEQ ID NO:7698}, CGGGTTGGGGTTTTTAAGCGTTCGGTT {SEQ ID NO:7699}, TGTAGAGGAGAAGGGGAGGAGCGCGAT {SEQ ID NO:7700}, ATGTAGAGGAGAAGGGGAGGAGCGCGA {SEQ ID NO:7701}, AATGTAGAGGAGAAGGGGAGGAGCGCG {SEQ ID NO:7702}, GTAGAGGAGAAGGGGAGGAGCGCGATT {SEQ ID NO:7703}, TAGAGGAGAAGGGGAGGAGCGCGATTG {SEQ ID NO:7704} |
| Target814 | chr7:127991924-127991947 | GGTCGGATTGGTCGTCGTAGTTTAGGGC {SEQ ID NO:7705}, AGGTCGGATTGGTCGTCGTAGTTTAGGGC {SEQ ID NO:7706}, GTCGGATTGGTCGTCGTAGTTTAGGGC {SEQ ID NO:7707}, GGTCGGATTGGTCGTCGTAGTTTAGGG {SEQ ID NO:7708}, AGGTCGGATTGGTCGTCGTAGTTTAGGG {SEQ ID NO:7709}, TTGGGAGGGTCGGGTTTTAAGGGCGTT {SEQ ID NO:7710}, TTTGGGAGGGTCGGGTTTTAAGGGCGT {SEQ ID NO:7711}, TGGGAGGGTCGGGTTTTAAGGGCGTTA {SEQ ID NO:7712}, GGGCGTTTTTGGGAGGGTCGGGTTTTA {SEQ ID NO:7713}, TTTTGGGAGGGTCGGGTTTTAAGGGCG {SEQ ID NO:7714} |
| Target815 | chr7:127992031-127992040 | GCGGTAGGGGTGTGGCGTTTTTGAAGT {SEQ ID NO:7715}, TGCGGTAGGGGTGTGGCGTTTTTGAAG {SEQ ID NO:7716}, CGTTTTTGCGGTAGGGGTGTGGCGTTT {SEQ ID NO:7717}, TTGCGGTAGGGGTGTGGCGTTTTTGAA {SEQ ID NO:7718}, TTTGCGGTAGGGGTGTGGCGTTTTTGA {SEQ ID NO:7719}, CGTTTCGCGCGGGTTGTACGTTTTTT {SEQ ID NO:7720}, CGTTTCGCGCGGGTTGTACGTTTTT {SEQ ID NO:7721}, GCGTATCGTTCGTTGCGGTTTTTGC {SEQ ID NO:7722}, CGTTTCGCGCGGGTTGTACGTTTT {SEQ ID NO:7723}, GTTTCGCGCGGGTTGTACGTTTTTT {SEQ ID NO:7724} |
| Target816 | chr7:127992042-127992177 | TTCGGAAAGGAAAGCGGCGAGAAAGGC {SEQ ID NO:7725}, GCGGTAGGGGTGTGGCGTTTTTGAAGT {SEQ ID NO:7726}, TGCGGTAGGGGTGTGGCGTTTTTGAAG {SEQ ID NO:7727}, CGTTTTTGCGGTAGGGGTGTGGCGTTT {SEQ ID NO:7728}, TTGCGGTAGGGGTGTGGCGTTTTTGAA {SEQ ID NO:7729}, TGTTTGTTGTTGGTTCGGTCGCGTTCG {SEQ ID NO:7730}, GGTTTGTTTGTTGTTGGTTCGGTCGCGT {SEQ ID NO:7731}, TGGTTTGTTTGTTGTTGGTTCGGTCGCG {SEQ ID NO:7732}, GGTTTGTTTGTTGGTTCGGTCGCG {SEQ ID NO:7733}, TTGTTTGTTGTTGGTTCGGTCGCGTTCG {SEQ ID NO:7734} |
| Target817 | chr7:127992225-127992241 | GAGTCGTAGGGGTCGTAGCGGGCG {SEQ ID NO:7735}, CGAGTCGTAGGGGTCGTAGCGGGC {SEQ ID NO:7736}, AGTCGTAGGGGTCGTAGCGGGC {SEQ ID NO:7737}, CGAGTCGTAGGGGTCGTAGCGGGCG {SEQ ID NO:7738}, GAGTCGTAGGGGTCGTAGCGGGC {SEQ ID NO:7739}, TGTTTGTTGTTGGTTCGGTCGCGTTCG {SEQ ID NO:7740}, GGTTTGTTTGTTGTTGGTTCGGTCGCGT {SEQ ID NO:7741}, TGGTTTGTTTGTTGTTGGTTCGGTCGCG {SEQ ID NO:7742}, GGTTTGTTTGTTGTTGGTTCGGTCGCG {SEQ ID NO:7743}, TTGTTTGTTGTTGGTTCGGTCGCGTTCG {SEQ ID NO:7744} |
| Target818 | chr7:127992316-127992331 | CGCGGTCGGGTTAGTAGTAGGTAGGTT {SEQ ID NO:7745}, CGCGGTCGGGTTAGTAGTAGGTAGGT {SEQ ID NO:7746}, GCGTAGTTAGGTCGGTGGGGTATCG {SEQ ID NO:7747}, CGCGGTCGGGTTAGTAGTAGGTAGGTTAGTT {SEQ ID NO:7748}, GCGGAAGGTTTTGTAGTAGTAGTTAGGCGAGCG {SEQ ID NO:7749}, TGTTGTTGTTGTCGGTCGGGATTACGC {SEQ ID NO:7750}, TGGATTTGTTGTTGTTGTCGGTCGGGA {SEQ ID NO:7751}, TTGTTGTTGTTGTCGGTCGGGATTACGC {SEQ ID NO:7752}, |

FIGURE 5 CONTINUED

TTGGATTTGTTGTTGTTGTCGGTCGGG (SEQ ID NO:7753), TTGGATTTGTTGTTGTTGTCGGTCGGGA (SEQ ID NO:7754)

Target819    chr7:127992352-127992375    CGCGGTCGGGTTAGTAGTAGGTAGGTT (SEQ ID NO:7755), GAGCGCGGGTAGTCGATTTTTGTGTTT (SEQ ID NO:7756), CGCGGTCGGGTTAGTAGTAGGTAGGT (SEQ ID NO:7757), GAGCGCGGGTAGTCGATTTTTGTGTT (SEQ ID NO:7758), GAGCGCGGGTAGTCGATTTTTGTGTTTA (SEQ ID NO:7759), TGTTGTTGTTGTCGGTCGGGATTACGC (SEQ ID NO:7760), TGGATTTGTTGTTGTTGTCGGTCGGGA (SEQ ID NO:7761), TTGTTGTTGTTGTCGGTCGGGATTACGC (SEQ ID NO:7762), TTGGATTTGTTGTTGTTGTCGGTCGGG (SEQ ID NO:7763), TTGGATTTGTTGTTGTTGTCGGTCGGGA (SEQ ID NO:7764)

Target820    chr7:150329236-150329322    TGTTTGTGAGTTGGTGTAGAGGTAAGTTTGAGT (SEQ ID NO:7765), TTGTTTGTGAGTTGGTGTAGAGGTAAGTTTGAGT (SEQ ID NO:7766), TTTGTTTGTGAGTTGGTGTAGAGGTAAGTTTGAGT (SEQ ID NO:7767), TTGTTTGTGAGTTGGTGTAGAGGTAAGTTTGAGTA (SEQ ID NO:7768), TTTTGTTTGTGAGTTGGTGTAGAGGTAAGTTTGAGT (SEQ ID NO:7769)

Target821    chr7:150329374-150329487    CGTTGGAGATGGAGGAATAGGAAGTGGGT (SEQ ID NO:7770), CGTTGGAGATGGAGGAATAGGAAGTGGG (SEQ ID NO:7771), TCGTTGGAGATGGAGGAATAGGAAGTGGGT (SEQ ID NO:7772), TCGTTGGAGATGGAGGAATAGGAAGTGGG (SEQ ID NO:7773), TGGAGATGGAGGAATAGGAAGTGGGTAGG (SEQ ID NO:7774)

Target822    chr7:150655169-150655189    TAGTAGAAGAAGCGTGGGTTGGGGCGG (SEQ ID NO:7775), TAGAAGAAGCGTGGGTTGGGGCGGAAC (SEQ ID NO:7776), GTAGAAGAAGCGTGGGTTGGGGCGGAA (SEQ ID NO:7777), TTTCGCGGCGTTTTTATCGGTGTTGGC (SEQ ID NO:7778), TAGAAGAAGCGTGGGTTGGGGCGGAA (SEQ ID NO:7779), GAGGTTATGCGCGTCGGGGTGTTGTTT (SEQ ID NO:7780), AGGTTATGCGCGTCGGGGTGTTGTTTT (SEQ ID NO:7781), GAGGTTATGCGCGTCGGGGTGTTGTTTT (SEQ ID NO:7782), GGTTATGCGCGTCGGGGTGTTGTTTTT (SEQ ID NO:7783), GAGGTTATGCGCGTCGGGGTGTTGTT (SEQ ID NO:7784)

Target823    chr7:150655204-150655212    TAGTAGAAGAAGCGTGGGTTGGGGCGG (SEQ ID NO:7785), CGGGGGGTAGTATTTCGGCGCGTATGGT (SEQ ID NO:7786), TAGAAGAAGCGTGGGTTGGGGCGGAAC (SEQ ID NO:7787), GTAGAAGAAGCGTGGGTTGGGGCGGAA (SEQ ID NO:7788), TTTCGCGGCGTTTTTATCGGTGTTGGC (SEQ ID NO:7789), AGTTGTAGTTTGGTTCGGACGCGTTTT (SEQ ID NO:7790), GCGTTCGGTTAGTTTTTATCGTTTCGGGCG (SEQ ID NO:7791), CGCGTTCGGTTAGTTTTTATCGTTTCGGGC (SEQ ID NO:7792), GCGTTCGGTTAGTTTTTATCGTTTCGGGCGT (SEQ ID NO:7793), CGCGTTCGGTTAGTTTTTATCGTTTCGGGCG (SEQ ID NO:7794)

Target824    chr7:150655214-150655222    TAGTAGAAGAAGCGTGGGTTGGGGCGG (SEQ ID NO:7795), CGGGGGGTAGTATTTCGGCGCGTATGGT (SEQ ID NO:7796), TAGAAGAAGCGTGGGTTGGGGCGGAAC (SEQ ID NO:7797), GTAGAAGAAGCGTGGGTTGGGGCGGAA (SEQ ID NO:7798), TTTCGCGGCGTTTTTATCGGTGTTGGC (SEQ ID NO:7799), AGTTGTAGTTTGGTTCGGACGCGTTTT (SEQ ID NO:7800), GCGTTCGGTTAGTTTTTATCGTTTCGGGCG (SEQ ID NO:7801), CGCGTTCGGTTAGTTTTTATCGTTTCGGGC (SEQ ID NO:7802), GCGTTCGGTTAGTTTTTATCGTTTCGGGCGT (SEQ ID NO:7803), CGCGTTCGGTTAGTTTTTATCGTTTCGGGCG (SEQ ID NO:7804)

Target825    chr7:150655234-150655258    CGGGGGGTAGTATTTCGGCGCGTATGGT (SEQ ID NO:7805), TTTCGCGGCGTTTTTATCGGTGTTGGC (SEQ ID NO:7806), GCGGGGGTAGTATTTCGGCGCGTATGG (SEQ ID NO:7807), GGGTTTCGCGGCGTTTTTATCGGTGTT (SEQ ID NO:7808), GCGTTTTTATCGGTGTTGGCGTGGCG (SEQ ID NO:7809), GCGTGCGTTGGTGGGTTTCGGTTTTTC (SEQ ID NO:7810), CGTGCGTTGGTGGGTTTCGGTTTTTCG (SEQ ID NO:7811), GGCGTGCGTTGGTGGGTTTCGGTTTTT (SEQ ID NO:7812), GTGCGTTGGTGGGTTTCGGTTTTTCGT (SEQ ID NO:7813), TGCGTTGGTGGGTTTCGGTTTTTCGTT (SEQ ID NO:7814)

Target826    chr7:150655285-150655344    CGGGGGTAGTATTTCGGCGCGTATGGT (SEQ ID NO:7815), GCGGGGGTAGTATTTCGGCGCGTATGG (SEQ ID NO:7816), CGGGGGGTAGTATTTCGGCGCGTATGGT (SEQ ID NO:7817), GGGGGTAGTATTTCGGCGCGTATGGTT (SEQ ID NO:7818), GCGGGGGGTAGTATTTCGGCGCGTATG (SEQ ID NO:7819), GCGTGCGTTGGTGGGTTTCGGTTTTTC (SEQ ID NO:7820), CGTGCGTTGGTGGGTTTCGGTTTTTCG (SEQ ID NO:7821), GGCGTGCGTTGGTGGGTTTCGGTTTTT (SEQ ID NO:7822), GTGCGTTGGTGGGTTTCGGTTTTTCGT (SEQ ID NO:7823), TGCGTTGGTGGGTTTCGGTTTTTCGTT (SEQ ID NO:7824)

Target827    chr7:150655351-150655380    TTGCGGGGCGGAGAGTCGGGATTTATT (SEQ ID NO:7825), GTTGCGGGGCGGAGAGTCGGGATTTAT (SEQ ID NO:7826), TGCGGGGCGGAGAGTCGGGATTTATTA (SEQ ID NO:7827), TGCGGGGCGGAGAGTCGGGATTTATT (SEQ ID NO:7828), TTGCGGGGCGGAGAGTCGGGATTTAT (SEQ ID NO:7829), GCGGCGTGCGTTGGTGGGTTTT (SEQ ID NO:7830), TGGATAATTACGTGGTAGGGTTCGGGTTC (SEQ ID NO:7831), GCGGCGTGCGTTGGTGGGGTTT (SEQ ID NO:7832), CGTGGTGGTGGACGTGGATTTGAC (SEQ ID NO:7833), ATGGATAATTACGTGGTAGGGTTCGGGTTC (SEQ ID NO:7834)

FIGURE 5 CONTINUED

| | | |
|---|---|---|
| Target828 | chr7:150655454-150655472 | TTGCGGGGCGGAGAGTCGGGATTTATT (SEQ ID NO:7835), GTTGCGGGGCGGAGAGTCGGGATTTAT (SEQ ID NO:7836), TGCGGGGCGGAGAGTCGGGATTTATTA (SEQ ID NO:7837), TGCGGGGCGGAGAGTCGGGATTTATT (SEQ ID NO:7838), TTGCGGGGCGGAGAGTCGGGATTTAT (SEQ ID NO:7839), CGGGAGTCGTCGGTGCGGTCG (SEQ ID NO:7840), GGAGTCGTCGGTGCGGTCGGG (SEQ ID NO:7841), GGGAGTCGTCGGTGCGGTCGG (SEQ ID NO:7842), GAGTCGTCGGTGCGGTCGGGC (SEQ ID NO:7843), GGGAGTCGTCGGTGCGGTCGGG (SEQ ID NO:7844) |
| Target829 | chr7:150655495-150655502 | GGGTTAGCGATTCGTTGTTGGGTGTCG (SEQ ID NO:7845), AGGGTTAGCGATTCGTTGTTGGGTGTCG (SEQ ID NO:7846), AGGGTTAGCGATTCGTTGTTGGGTGTC (SEQ ID NO:7847), CGATTCGTTGTTGGGTGTCGCGGGC (SEQ ID NO:7848), TAGGGTTAGCGATTCGTTGTTGGGTGTCG (SEQ ID NO:7849), CGGGAGTCGTCGGTGCGGTCG (SEQ ID NO:7850), GGAGTCGTCGGTGCGGTCGGG (SEQ ID NO:7851), GGGAGTCGTCGGTGCGGTCGG (SEQ ID NO:7852), GAGTCGTCGGTGCGGTCGGGC (SEQ ID NO:7853), GGGAGTCGTCGGTGCGGTCGGG (SEQ ID NO:7854) |
| Target830 | chr7:150655541-150655557 | GGGTTAGCGATTCGTTGTTGGGTGTCG (SEQ ID NO:7855), AGGGTTAGCGATTCGTTGTTGGGTGTCG (SEQ ID NO:7856), AGGGTTAGCGATTCGTTGTTGGGTGTC (SEQ ID NO:7857), CGATTCGTTGTTGGGTGTCGCGGGC (SEQ ID NO:7858), TAGGGTTAGCGATTCGTTGTTGGGTGTCG (SEQ ID NO:7859), AGCGGTTGGGGGGTTTATTTTTTAGGTTTTGT (SEQ ID NO:7860), GCGGTTGGGGGGTTTATTTTTTAGGTTTTGTTCG (SEQ ID NO:7861), GCGGTTGGGGGGTTTATTTTTTAGGTTTTGTTCGT (SEQ ID NO:7862), AGCGGTTGGGGGGTTTATTTTTTAGGTTTTGTT (SEQ ID NO:7863), AGCGGTTGGGGGGTTTATTTTTTAGGTTTTGTTCG (SEQ ID NO:7864) |
| Target831 | chr7:150655572-150655595 | TTTAGGCGGAAGGTTTTGGCGCGGTT (SEQ ID NO:7865), TTTTAGGCGGAAGGTTTTGGCGCGGTT (SEQ ID NO:7866), AGTTTTAGGCGGAAGGTTTTGGCGCGG (SEQ ID NO:7867), TTAGGCGGAAGGTTTTGGCGCGGTTG (SEQ ID NO:7868), GTTTTAGGCGGAAGGTTTTGGCGCGGT (SEQ ID NO:7869), GGAAGTGGGGATGGGGGGGTGTTCGTT (SEQ ID NO:7870), GAAGTGGGGATGGGGGGGTTGTTCGTTT (SEQ ID NO:7871), AGTGGGGATGGGGGGGTTGTTCGTTTT (SEQ ID NO:7872), AAGTGGGGATGGGGGGGTTGTTCGTTTT (SEQ ID NO:7873), GGAAGTGGGGATGGGGGGGTTGTTCGT (SEQ ID NO:7874) |
| Target832 | chr7:154409589-154409878 | AGGTTATCGGGAGGCGTCGTGTTTTT (SEQ ID NO:7875), TAGGTTATCGGGAGGCGTCGTGTTTTT (SEQ ID NO:7876), TTAGGTTATCGGGAGGCGTCGTGTTTT (SEQ ID NO:7877), TTTAGGTTATCGGGAGGCGTCGTGTTT (SEQ ID NO:7878), TTTTAGGTTATCGGGAGGCGTCGTGTT (SEQ ID NO:7879), GGGGGAAAGTTTGTGTGAGTAGATAGTATTGTGGG (SEQ ID NO:7880), GGGGAAAGTTTGTGTGAGTAGATAGTATTGTGGG (SEQ ID NO:7881), GGGGGAAAGTTTGTGTGAGTAGATAGTATTGTGG (SEQ ID NO:7882), AGGGGGAAAGTTTGTGTGAGTAGATAGTATTGTGGG (SEQ ID NO:7883), GGGGGAAAGTTTGTGTGAGTAGATAGTATTGTGGGA (SEQ ID NO:7884) |
| Target833 | chr7:155302254-155302259 | CGCGTAGTTAAGGGTAGTTTCGGGGAGGG (SEQ ID NO:7885), CGCGTAGTTAAGGGTAGTTTCGGGGAGG (SEQ ID NO:7886), GCGTAGTTAAGGGTAGTTTCGGGGAGGGT (SEQ ID NO:7887), GCGTAGTTAAGGGTAGTTTCGGGGAGGG (SEQ ID NO:7888), AGGGGATTTGAAGTTAGTTGAGCGCGT (SEQ ID NO:7889) |
| Target834 | chr7:155302342-155302375 | CGAGAGAGAGAGCGCGCGTTTAGTTGG (SEQ ID NO:7890), TCGGGGTTGTTTTTTGGTTGCGCGTTTT (SEQ ID NO:7891), TTCGGGGTTGTTTTTTGGTTGCGCGTTTT (SEQ ID NO:7892), TTTCGGGGTTGTTTTTTGGTTGCGCGTT (SEQ ID NO:7893), TTTTCGGGGTTGTTTTTTGGTTGCGCGT (SEQ ID NO:7894), GTTTGGGAGATGGGGCGTTCGTTCGTG (SEQ ID NO:7895), AGGAGTTCGTTTGGGAGATGGGGCGTT (SEQ ID NO:7896), GAGGAGTTCGTTTGGGAGATGGGGCGT (SEQ ID NO:7897), TTTGGGAGATGGGGCGTTCGTTCGTGA (SEQ ID NO:7898), AGTTCGTTTGGGAGATGGGGCGTTCGT (SEQ ID NO:7899) |
| Target835 | chr7:156400350-156400882 | GTTACGGAGGAGAAGTTGGGGGTGGGG (SEQ ID NO:7900), GAGTTAGGTAGAGGAGGCGGCGGTTCG (SEQ ID NO:7901), GGAGTTAGGTAGAGGAGGCGGCGGTTC (SEQ ID NO:7902), TTTTCGAACGAGGCGGGTAGGGAGAGG (SEQ ID NO:7903), TGGGGGTGGGGGATTTAGGAATTGCGG (SEQ ID NO:7904), AGCGGCGTTTGAGTTCGGATGTTTCGG (SEQ ID NO:7905), CGGAGCGGCGTTTGAGTTCGGATGTTT (SEQ ID NO:7906), TTTTCGTTTGTAGTTCGGTGCGCGGGG (SEQ ID NO:7907), CGCGGGGTGTTTTTGTTGTTGGAGGGT (SEQ ID NO:7908), CGTAGTGGGAGGAACGGTTTGGAGGGG (SEQ ID NO:7909) |
| Target836 | chr7:156400926-156401053 | TTTTGTAGTTCGGTGGGTTTCGCGGCG (SEQ ID NO:7910), GTAGTTCGGTGGGTTTCGCGGCGTTTT (SEQ ID NO:7911), AGTTCGGTGGGTTTCGCGCGCGTTTTA (SEQ ID NO:7912), TAGTTCGGTGGGTTTCGCGGCGTTTTT (SEQ ID NO:7913), CGGTGGGTTTCGCGGCGTTTTTATTCG (SEQ ID NO:7914), GAGGGGCGGATGGGTTTAGGTAGGGG (SEQ ID NO:7915), GGGGCGGATGGGTTTAGGTAGGGGTT (SEQ ID NO:7916), CGTAGTGGGAGGAACGGTTTGGAGGGG (SEQ ID NO:7917), AGTGGGAGGAACGGTTTGGAGGGGAAG (SEQ ID NO:7918), GGAAGGAGTTTGGTTGGACGTTGCGGT (SEQ ID NO:7919) |
| Target837 | chr7:156796576-156796588 | CGCGTTTTGAGGTAGAGGAGTGGTTGCG (SEQ ID NO:7920), GCGTTTTGAGGTAGAGGAGTGGTTGCGT (SEQ ID NO:7921), GCGTTTTGAGGTAGAGGAGTGGTTGCG (SEQ ID NO:7922), CGCGTTTTGAGGTAGAGGAGTGGTTGC (SEQ ID NO:7923), TCGCGTTTTGAGGTAGAGGAGTGGTTGC (SEQ ID NO:7924), GCGTTTTATTTGGGTGATTATCGCGGGGC (SEQ ID NO:7925), CGTTTTATTTGGGTGATTATCGCGGGGC (SEQ ID NO:7926), GCGTTTTATTTGGGTGATTATCGCGGGGG |

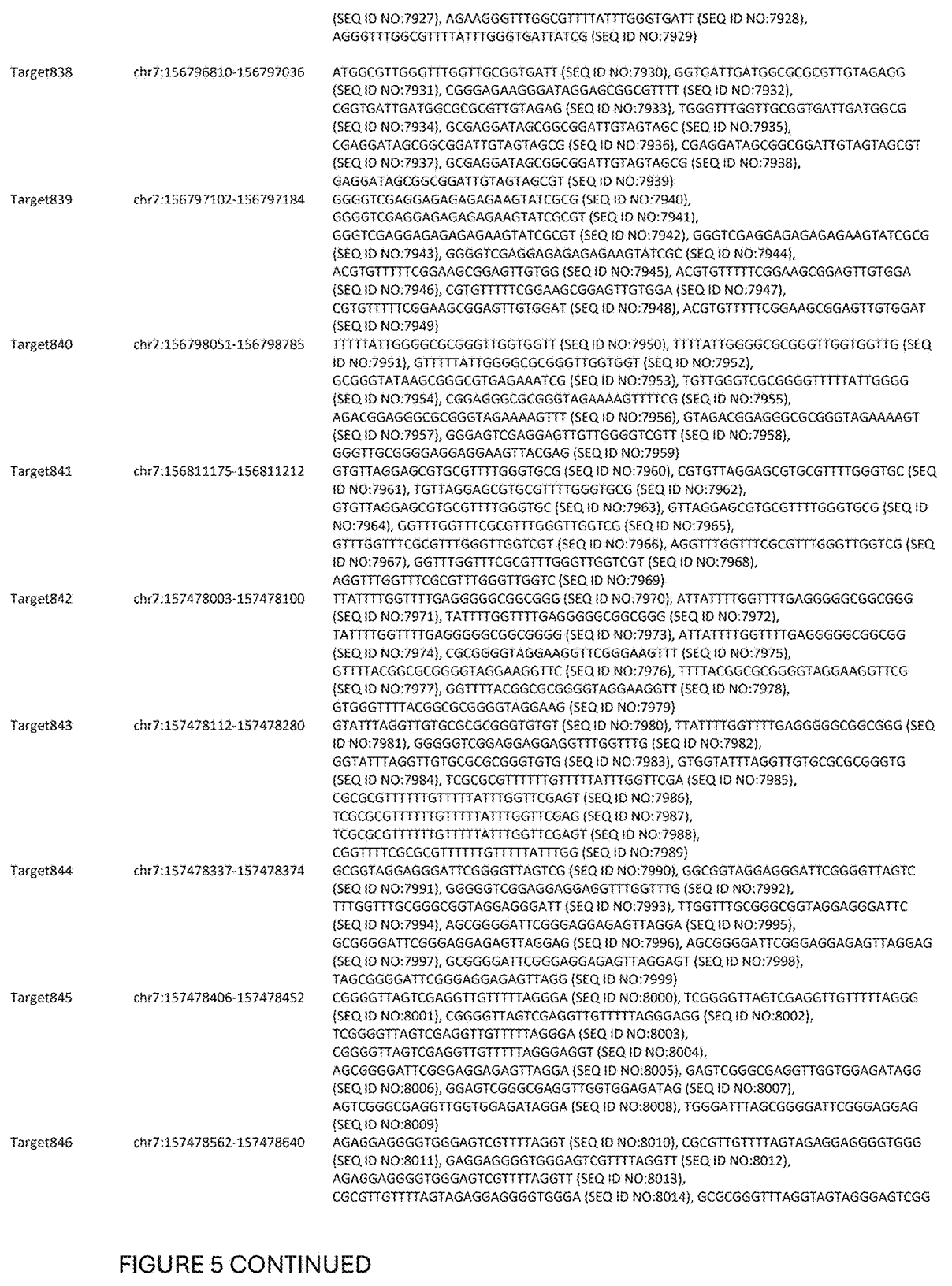

FIGURE 5 CONTINUED (SEQ ID NO:7927), AGAAGGGTTTGGCGTTTTATTTGGGTGATT (SEQ ID NO:7928),
AGGGTTTGGCGTTTTATTTGGGTGATTATCG (SEQ ID NO:7929)

Target838     chr7:156796810-156797036     ATGGCGTTGGGTTTGGTTGCGGTGATT (SEQ ID NO:7930), GGTGATTGATGGCGCGCGTTGTAGAGG
(SEQ ID NO:7931), CGGGAGAAGGGATAGGAGCGGCGTTTT (SEQ ID NO:7932),
CGGTGATTGATGGCGCGCGTTGTAGAG (SEQ ID NO:7933), TGGGTTTGGTTGCGGTGATTGATGGCG
(SEQ ID NO:7934), GCGAGGATAGCGGCGGATTGTAGTAGC (SEQ ID NO:7935),
CGAGGATAGCGGCGGATTGTAGTAGCG (SEQ ID NO:7936), CGAGGATAGCGGCGGATTGTAGTAGCGT
(SEQ ID NO:7937), GCGAGGATAGCGGCGGATTGTAGTAGCGC (SEQ ID NO:7938),
GAGGATAGCGGCGGATTGTAGTAGCGT (SEQ ID NO:7939)

Target839     chr7:156797102-156797184     GGGGTCGAGGAGAGAGAGAAGTATCGCG (SEQ ID NO:7940),
GGGGTCGAGGAGAGAGAGAAGTATCGCGT (SEQ ID NO:7941),
GGGTCGAGGAGAGAGAGAAGTATCGCGT (SEQ ID NO:7942), GGGTCGAGGAGAGAGAGAAGTATCGCGG
(SEQ ID NO:7943), GGGGTCGAGGAGAGAGAGAAGTATCGC (SEQ ID NO:7944),
ACGTGTTTTTCGGAAGCGGAGTTGTGG (SEQ ID NO:7945), ACGTGTTTTTCGGAAGCGGAGTTGTGGA
(SEQ ID NO:7946), CGTGTTTTTCGGAAGCGGAGTTGTGGA (SEQ ID NO:7947),
CGTGTTTTTCGGAAGCGGAGTTGTGGAT (SEQ ID NO:7948), ACGTGTTTTTCGGAAGCGGAGTTGTGGAT
(SEQ ID NO:7949)

Target840     chr7:156798051-156798785     TTTTTATTGGGGCGCGGGTTGGTGGTT (SEQ ID NO:7950), TTTTTATTGGGGCGCGGGTTGGTGGTTG (SEQ
ID NO:7951), GTTTTTATTGGGGCGCGGGTTGGTGGT (SEQ ID NO:7952),
GCGGGTATAAGCGGGCGTGAGAAATCG (SEQ ID NO:7953), TGTTGGGTCGCGGGGTTTTTATTGGGG
(SEQ ID NO:7954), CGGAGGGGCGCGGGTAGAAAAGTTTTCG (SEQ ID NO:7955),
AGACGGAGGGGCGCGGGTAGAAAAGTTT (SEQ ID NO:7956), GTAGACGGAGGGGCGCGGGTAGAAAAGT
(SEQ ID NO:7957), GGGAGTCGAGGAGTTGTTGGGGTCGTT (SEQ ID NO:7958),
GGGTTGCGGGGAGGAGGAAGTTACGAG (SEQ ID NO:7959)

Target841     chr7:156811175-156811212     GTGTTAGGAGCGTGCGTTTTGGGTGCG (SEQ ID NO:7960), CGTGTTAGGAGCGTGCGTTTTGGGTGC (SEQ
ID NO:7961), TGTTAGGAGCGTGCGTTTTGGGTGCG (SEQ ID NO:7962),
GTGTTAGGAGCGTGCGTTTTGGGTGC (SEQ ID NO:7963), GTTAGGAGCGTGCGTTTTGGGTGCG (SEQ ID
NO:7964), GGTTTGGTTTCGCGTTTGGGTTGGTCG (SEQ ID NO:7965),
GTTTGGTTTCGCGTTTGGGTTGGTCGT (SEQ ID NO:7966), AGGTTTGGTTTCGCGTTTGGGTTGGTCG (SEQ
ID NO:7967), GGTTTGGTTTCGCGTTTGGGTTGGTCGT (SEQ ID NO:7968),
AGGTTTGGTTTCGCGTTTGGGTTGGTC (SEQ ID NO:7969)

Target842     chr7:157478003-157478100     TTATTTTGGTTTTGAGGGGGCGGCGGG (SEQ ID NO:7970), ATTATTTTGGTTTTGAGGGGGCGGCGGG
(SEQ ID NO:7971), TATTTTGGTTTTGAGGGGGCGGCGGG (SEQ ID NO:7972),
TATTTTGGTTTTGAGGGGGCGGCGGG (SEQ ID NO:7973), ATTATTTTGGTTTTGAGGGGGCGGCGG
(SEQ ID NO:7974), CGCGGGTAGGAAGGTTCGGGAAGTTT (SEQ ID NO:7975),
GTTTTACGGCGCGGGGTAGGAAGGTTC (SEQ ID NO:7976), TTTTACGGCGCGGGGTAGGAAGGTTCG
(SEQ ID NO:7977), GGTTTTACGGCGCGGGGTAGGAAGGTT (SEQ ID NO:7978),
GTGGGTTTTACGGCGCGGGGTAGGAAG (SEQ ID NO:7979)

Target843     chr7:157478112-157478280     GTATTTAGGTTGTGCGCGCGGGTGTGT (SEQ ID NO:7980), TTATTTTGGTTTTGAGGGGGCGGCGGG (SEQ
ID NO:7981), GGGGGTCGGAGGAGGAGGTTTGGTTTG (SEQ ID NO:7982),
GGTATTTAGGTTGTGCGCGCGGGTGTG (SEQ ID NO:7983), GTGGTATTTAGGTTGTGCGCGCGGGTG
(SEQ ID NO:7984), TCGCGCGTTTTTTGTTTTTATTTGGTTCGA (SEQ ID NO:7985),
CGCGCGTTTTTTGTTTTTATTTGGTTCGAGT (SEQ ID NO:7986),
TCGCGCGTTTTTTGTTTTTATTTGGTTCGAG (SEQ ID NO:7987),
TCGCGCGTTTTTTGTTTTTATTTGGTTCGAGT (SEQ ID NO:7988),
CGGTTTTCGCGCGTTTTTTGTTTTTATTTGG (SEQ ID NO:7989)

Target844     chr7:157478337-157478374     GCGGTAGGAGGGATTCGGGGTTAGTCG (SEQ ID NO:7990), GGCGGTAGGAGGGATTCGGGGTTAGTC
(SEQ ID NO:7991), GGGGGTCGGAGGAGGAGGTTTGGTTTG (SEQ ID NO:7992),
TTTGGTTTGCGGGCGGTAGGAGGGATT (SEQ ID NO:7993), TTGGTTTGCGGGCGGTAGGAGGGATTC
(SEQ ID NO:7994), AGCGGGGATTCGGGAGGAGAGTTAGGA (SEQ ID NO:7995),
GCGGGGATTCGGGAGGAGAGTTAGGAG (SEQ ID NO:7996), AGCGGGGATTCGGGAGGAGAGTTAGGAG
(SEQ ID NO:7997), GCGGGGATTCGGGAGGAGAGTTAGGAGT (SEQ ID NO:7998),
TAGCGGGGATTCGGGAGGAGAGTTAGG (SEQ ID NO:7999)

Target845     chr7:157478406-157478452     CGGGGTTAGTCGAGGTTGTTTTTAGGGA (SEQ ID NO:8000), TCGGGGTTAGTCGAGGTTGTTTTTAGGG
(SEQ ID NO:8001), CGGGGTTAGTCGAGGTTGTTTTTAGGGAGG (SEQ ID NO:8002),
TCGGGGTTAGTCGAGGTTGTTTTTAGGGA (SEQ ID NO:8003),
CGGGGTTAGTCGAGGTTGTTTTTAGGGAGGT (SEQ ID NO:8004),
AGCGGGGATTCGGGAGGAGAGTTAGGA (SEQ ID NO:8005), GAGTCGGGCGAGGTTGGTGGAGATAGG
(SEQ ID NO:8006), GGAGTCGGGCGAGGTTGGTGGAGATAG (SEQ ID NO:8007),
AGTCGGGCGAGGTTGGTGGAGATAGGA (SEQ ID NO:8008), TGGGATTTAGCGGGGATTCGGGAGGAG
(SEQ ID NO:8009)

Target846     chr7:157478562-157478640     AGAGGAGGGGTGGGAGTCGTTTTAGGT (SEQ ID NO:8010), CGCGTTGTTTTAGTAGAGGAGGGGTGGG
(SEQ ID NO:8011), GAGGAGGGGTGGGAGTCGTTTTAGGTT (SEQ ID NO:8012),
AGAGGAGGGGTGGGAGTCGTTTTAGGTT (SEQ ID NO:8013),
CGCGTTGTTTTAGTAGAGGAGGGGTGGGA (SEQ ID NO:8014), GCGCGGGTTTAGGTAGTAGGGAGTCGG

FIGURE 5 CONTINUED

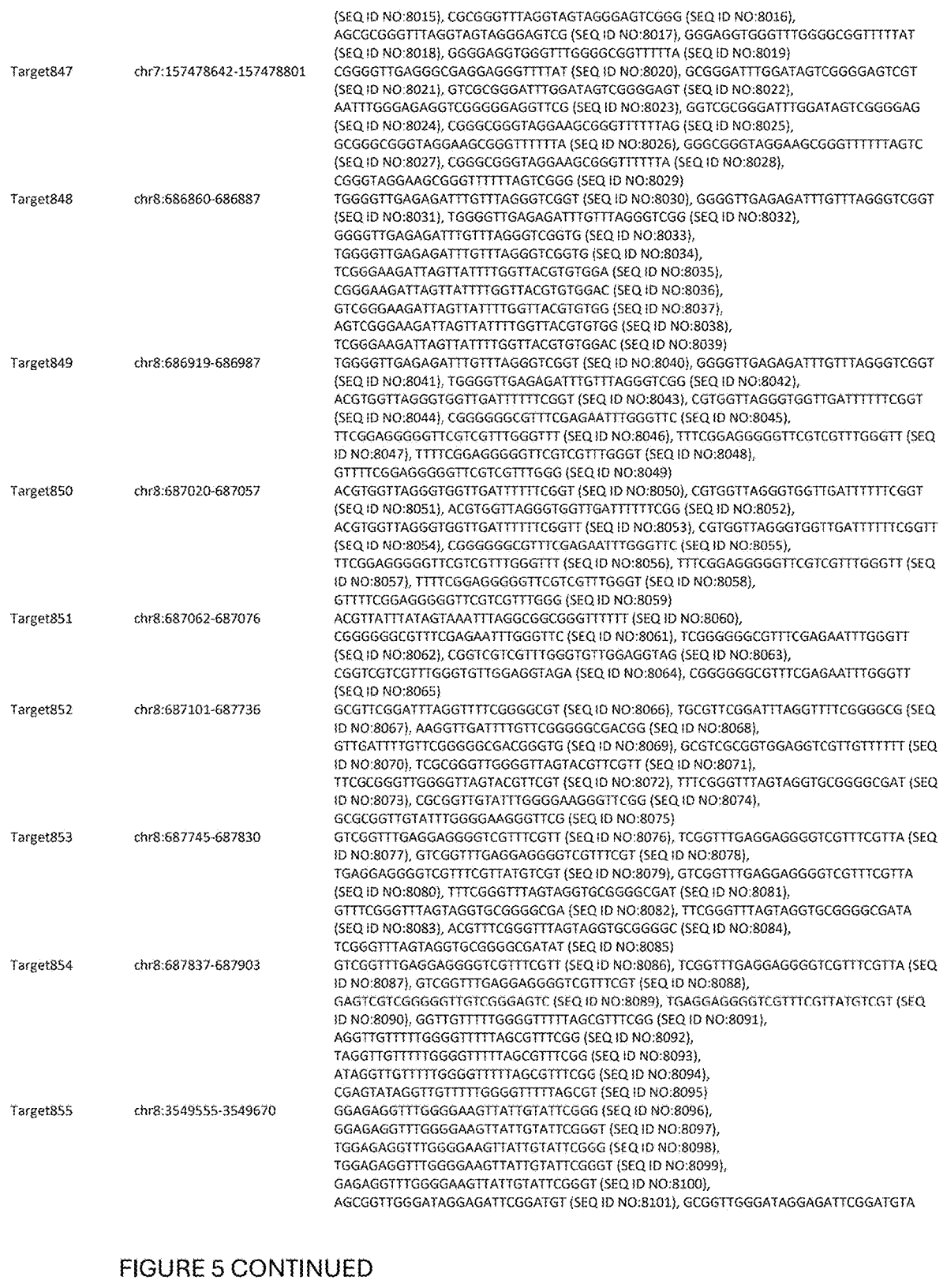

|  |  |  |
|---|---|---|
|  |  | {SEQ ID NO:8015}, CGCGGGTTTAGGTAGTAGGGAGTCGGG {SEQ ID NO:8016}, AGCGCGGGTTTAGGTAGTAGGGAGTCG {SEQ ID NO:8017}, GGGGAGGTGGGTTTGGGGCGGTTTTTAT {SEQ ID NO:8018}, GGGGAGGTGGGTTTGGGGCGGTTTTTA {SEQ ID NO:8019} |
| Target847 | chr7:157478642-157478801 | CGGGGTTGAGGGCGAGGAGGGTTTTAT {SEQ ID NO:8020}, GCGGGATTTGGATAGTCGGGGAGTCGT {SEQ ID NO:8021}, GTCGCGGGATTTGGATAGTCGGGGAGT {SEQ ID NO:8022}, AATTTGGGAGAGGTCGGGGGAGGTTCG {SEQ ID NO:8023}, GGTCGCGGGATTTGGATAGTCGGGGAG {SEQ ID NO:8024}, CGGGCGGGTAGGAAGCGGGTTTTTTAG {SEQ ID NO:8025}, GCGGGCGGGTAGGAAGCGGGTTTTTTA {SEQ ID NO:8026}, GGGCGGGTAGGAAGCGGGTTTTTTAGTC {SEQ ID NO:8027}, CGGGCGGGTAGGAAGCGGGTTTTTTA {SEQ ID NO:8028}, CGGGTAGGAAGCGGGTTTTTTAGTCGGG {SEQ ID NO:8029} |
| Target848 | chr8:686860-686887 | TGGGGTTGAGAGATTTGTTTAGGGTCGGT {SEQ ID NO:8030}, GGGGTTGAGAGATTTGTTTAGGGTCGGT {SEQ ID NO:8031}, TGGGGTTGAGAGATTTGTTTAGGGGTCGG {SEQ ID NO:8032}, GGGGTTGAGAGATTTGTTTAGGGTCGGTG {SEQ ID NO:8033}, TGGGGTTGAGAGATTTGTTTAGGGTCGGTG {SEQ ID NO:8034}, TCGGGAAGATTAGTTATTTTGGTTACGTGTGGA {SEQ ID NO:8035}, CGGGAAGATTAGTTATTTTGGTTACGTGTGGAC {SEQ ID NO:8036}, GTCGGGAAGATTAGTTATTTTGGTTACGTGTGG {SEQ ID NO:8037}, AGTCGGGAAGATTAGTTATTTTGGTTACGTGTGG {SEQ ID NO:8038}, TCGGGAAGATTAGTTATTTTGGTTACGTGTGGAC {SEQ ID NO:8039} |
| Target849 | chr8:686919-686987 | TGGGGTTGAGAGATTTGTTTAGGGTCGGT {SEQ ID NO:8040}, GGGGTTGAGAGATTTGTTTAGGGTCGGT {SEQ ID NO:8041}, TGGGGTTGAGAGATTTGTTTAGGGTCGG {SEQ ID NO:8042}, ACGTGGTTAGGGTGGTTGATTTTTTCGGT {SEQ ID NO:8043}, CGTGGTTAGGGTGGTTGATTTTTTCGGT {SEQ ID NO:8044}, CGGGGGGGCGTTTCGAGAATTTGGGTTC {SEQ ID NO:8045}, TTCGGAGGGGGGTTCGTCGTTTGGGTTT {SEQ ID NO:8046}, TTTCGGAGGGGGGTTCGTCGTTTGGGTT {SEQ ID NO:8047}, TTTTCGGAGGGGGGTTCGTCGTTTGGGT {SEQ ID NO:8048}, GTTTTCGGAGGGGGGTTCGTCGTTTGGG {SEQ ID NO:8049} |
| Target850 | chr8:687020-687057 | ACGTGGTTAGGGTGGTTGATTTTTTCGGT {SEQ ID NO:8050}, CGTGGTTAGGGTGGTTGATTTTTTCGGT {SEQ ID NO:8051}, ACGTGGTTAGGGTGGTTGATTTTTTCGG {SEQ ID NO:8052}, ACGTGGTTAGGGTGGTTGATTTTTTCGGTT {SEQ ID NO:8053}, CGTGGTTAGGGTGGTTGATTTTTTCGGTT {SEQ ID NO:8054}, CGGGGGGCGTTTCGAGAATTTGGGTTC {SEQ ID NO:8055}, TTCGGAGGGGGGTTCGTCGTTTGGGTTT {SEQ ID NO:8056}, TTTCGGAGGGGGGTTCGTCGTTTGGGTT {SEQ ID NO:8057}, TTTTCGGAGGGGGGTTCGTCGTTTGGGT {SEQ ID NO:8058}, GTTTTCGGAGGGGGGTTCGTCGTTTGGG {SEQ ID NO:8059} |
| Target851 | chr8:687062-687076 | ACGTTATTTATAGTAAATTTAGGCGGCGGGTTTTT {SEQ ID NO:8060}, CGGGGGGGCGTTTCGAGAATTTGGGTTC {SEQ ID NO:8061}, TCGGGGGGCGTTTCGAGAATTTGGGTT {SEQ ID NO:8062}, CGGTCGTCGTTTGGGTGTTGGAGGTAG {SEQ ID NO:8063}, CGGTCGTCGTTTGGGTGTTGGAGGTAGA {SEQ ID NO:8064}, CGGGGGGGCGTTTCGAGAATTTGGGTT {SEQ ID NO:8065} |
| Target852 | chr8:687101-687736 | GCGTTCGGATTTAGGTTTTCGGGGCGT {SEQ ID NO:8066}, TGCGTTCGGATTTAGGTTTTCGGGGCG {SEQ ID NO:8067}, AAGGTTGATTTTGTTCGGGGGGCGACGG {SEQ ID NO:8068}, GTTGATTTTGTTCGGGGGCGACGGGTG {SEQ ID NO:8069}, GCGTCGCGGTGGAGGTCGTTGTTTTTT {SEQ ID NO:8070}, TCGCGGGTTGGGGTTAGTACGTTCGTT {SEQ ID NO:8071}, TTCGCGGGTTGGGGTTAGTACGTTCGT {SEQ ID NO:8072}, TTTCGGGTTTAGTAGGTGCGGGGCGAT {SEQ ID NO:8073}, CGCGGTTGTATTTGGGGAAGGGTTCGG {SEQ ID NO:8074}, GCGCGGTTGTATTTGGGGAAGGGTTCG {SEQ ID NO:8075} |
| Target853 | chr8:687745-687830 | GTCGGTTTGAGGAGGGGTCGTTTCGTT {SEQ ID NO:8076}, TCGGTTTGAGGAGGGGTCGTTTCGTTA {SEQ ID NO:8077}, GTCGGTTTGAGGAGGGGTCGTTTCGT {SEQ ID NO:8078}, TGAGGAGGGGTCGTTTCGTTATGTCGT {SEQ ID NO:8079}, GTCGGTTTGAGGAGGGGTCGTTTCGTTA {SEQ ID NO:8080}, TTTCGGGTTTAGTAGGTGCGGGGCGAT {SEQ ID NO:8081}, GTTTCGGGTTTAGTAGGTGCGGGGCGA {SEQ ID NO:8082}, TTCGGGTTTAGTAGGTGCGGGGCGATA {SEQ ID NO:8083}, ACGTTTCGGGTTTAGTAGGTGCGGGGC {SEQ ID NO:8084}, TCGGGTTTAGTAGGTGCGGGGCGATAT {SEQ ID NO:8085} |
| Target854 | chr8:687837-687903 | GTCGGTTTGAGGAGGGGTCGTTTCGTT {SEQ ID NO:8086}, TCGGTTTGAGGAGGGGTCGTTTCGTTA {SEQ ID NO:8087}, GTCGGTTTGAGGAGGGGTCGTTTCGT {SEQ ID NO:8088}, GAGTCGTCGGGGGTTGTCGGGAGTC {SEQ ID NO:8089}, TGAGGAGGGGTCGTTTCGTTATGTCGT {SEQ ID NO:8090}, GGTTGTTTTTGGGGTTTTTAGCGTTTCGG {SEQ ID NO:8091}, AGGTTGTTTTTGGGGTTTTTAGCGTTTCGG {SEQ ID NO:8092}, TAGGTTGTTTTTGGGGTTTTTAGCGTTTCGG {SEQ ID NO:8093}, ATAGGTTGTTTTTGGGGTTTTTAGCGTTTCGG {SEQ ID NO:8094}, CGAGTATAGGTTGTTTTTGGGGTTTTTAGCGT {SEQ ID NO:8095} |
| Target855 | chr8:3549555-3549670 | GGAGAGGTTTGGGGAAGTTATTGTATTCGGG {SEQ ID NO:8096}, GGAGAGGTTTGGGGAAGTTATTGTATTCGGGT {SEQ ID NO:8097}, TGGAGAGGTTTGGGGAAGTTATTGTATTCGGG {SEQ ID NO:8098}, TGGAGAGGTTTGGGGAAGTTATTGTATTCGGGT {SEQ ID NO:8099}, GAGAGGTTTGGGGAAGTTATTGTATTCGGGT {SEQ ID NO:8100}, AGCGGTTGGGATAGGAGATTCGGATGT {SEQ ID NO:8101}, GCGGTTGGGATAGGAGATTCGGATGTA |

FIGURE 5 CONTINUED

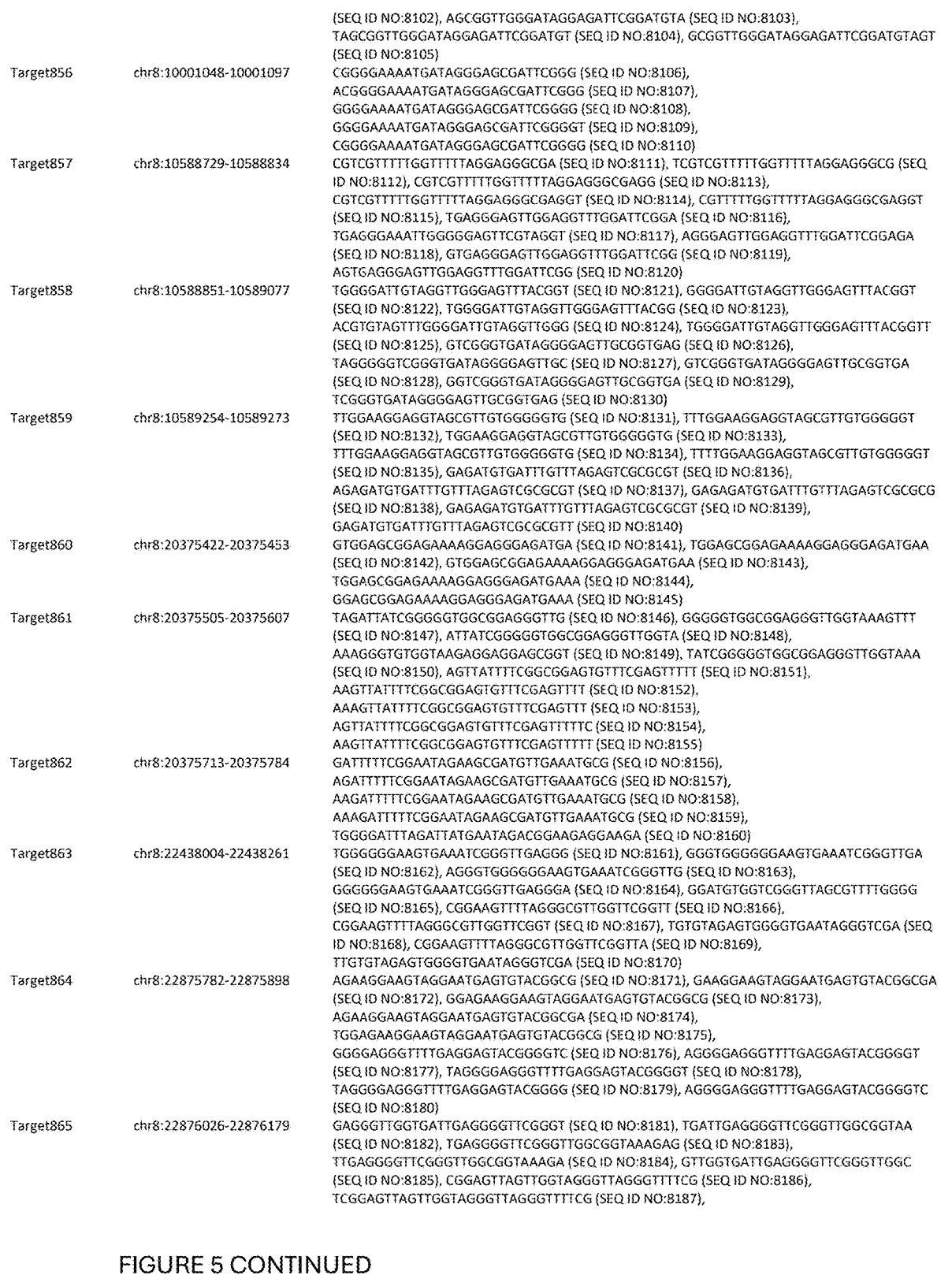

|  |  |  |
|---|---|---|
|  |  | (SEQ ID NO:8102), AGCGGTTGGGATAGGAGATTCGGATGTA (SEQ ID NO:8103), TAGCGGTTGGGATAGGAGATTCGGATGT (SEQ ID NO:8104), GCGGTTGGGATAGGAGATTCGGATGTAGT (SEQ ID NO:8105) |
| Target856 | chr8:10001048-10001097 | CGGGGAAAATGATAGGGAGCGATTCGGG (SEQ ID NO:8106), ACGGGGAAAATGATAGGGAGCGATTCGGG (SEQ ID NO:8107), GGGGAAAATGATAGGGAGCGATTCGGGG (SEQ ID NO:8108), GGGGAAAATGATAGGGAGCGATTCGGGGT (SEQ ID NO:8109), CGGGGAAAATGATAGGGAGCGATTCGGGG (SEQ ID NO:8110) |
| Target857 | chr8:10588729-10588834 | CGTCGTTTTTGGTTTTTAGGAGGGCGA (SEQ ID NO:8111), TCGTCGTTTTTGGTTTTTAGGAGGGCG (SEQ ID NO:8112), CGTCGTTTTTGGTTTTTAGGAGGGCGAGG (SEQ ID NO:8113), CGTCGTTTTTGGTTTTTAGGAGGGCGAGGT (SEQ ID NO:8114), CGTTTTTGGTTTTTAGGAGGGCGAGGT (SEQ ID NO:8115), TGAGGGAGTTGGAGGTTTGGATTCGGA (SEQ ID NO:8116), TGAGGGAAATTGGGGGAGTTCGTAGGT (SEQ ID NO:8117), AGGGAGTTGGAGGTTTGGATTCGGAGA (SEQ ID NO:8118), GTGAGGGAGTTGGAGGTTTGGATTCGG (SEQ ID NO:8119), AGTGAGGGAGTTGGAGGTTTGGATTCGG (SEQ ID NO:8120) |
| Target858 | chr8:10588851-10589077 | TGGGGATTGTAGGTTGGGAGTTTACGGT (SEQ ID NO:8121), GGGGATTGTAGGTTGGGAGTTTACGGT (SEQ ID NO:8122), TGGGGATTGTAGGTTGGGAGTTTACGG (SEQ ID NO:8123), ACGTGTAGTTTGGGGATTGTAGGTTGGG (SEQ ID NO:8124), TGGGGATTGTAGGTTGGGAGTTTACGTT (SEQ ID NO:8125), GTCGGGTGATAGGGGAGTTGCGGTGAG (SEQ ID NO:8126), TAGGGGGTCGGGTGATAGGGGAGTTGC (SEQ ID NO:8127), GTCGGGTGATAGGGGAGTTGCGGTGA (SEQ ID NO:8128), GGTCGGGTGATAGGGGAGTTGCGGTGA (SEQ ID NO:8129), TCGGGTGATAGGGGAGTTGCGGTGAG (SEQ ID NO:8130) |
| Target859 | chr8:10589254-10589273 | TTGGAAGGAGGTAGCGTTGTGGGGGTG (SEQ ID NO:8131), TTTGGAAGGAGGTAGCGTTGTGGGGGT (SEQ ID NO:8132), TGGAAGGAGGTAGCGTTGTGGGGGTG (SEQ ID NO:8133), TTTGGAAGGAGGTAGCGTTGTGGGGGTG (SEQ ID NO:8134), TTTTGGAAGGAGGTAGCGTTGTGGGGGT (SEQ ID NO:8135), GAGATGTGATTTGTTTAGAGTCGCGCGT (SEQ ID NO:8136), AGAGATGTGATTTGTTTAGAGTCGCGCGT (SEQ ID NO:8137), GAGAGATGTGATTTGTTTAGAGTCGCGCG (SEQ ID NO:8138), GAGAGATGTGATTTGTTTAGAGTCGCGCGT (SEQ ID NO:8139), GAGATGTGATTTGTTTAGAGTCGCGCGT (SEQ ID NO:8140) |
| Target860 | chr8:20375422-20375453 | GTGGAGCGGAGAAAAGGAGGGAGATGA (SEQ ID NO:8141), TGGAGCGGAGAAAAGGAGGGAGATGAA (SEQ ID NO:8142), GTGGAGCGGAGAAAAGGAGGGAGATGAA (SEQ ID NO:8143), TGGAGCGGAGAAAAGGAGGGAGATGAAA (SEQ ID NO:8144), GGAGCGGAGAAAAGGAGGGAGATGAAA (SEQ ID NO:8145) |
| Target861 | chr8:20375505-20375607 | TAGATTATCGGGGGTGGCGGAGGGGTTG (SEQ ID NO:8146), GGGGGTGGCGGAGGGGTTGGTAAAGTTT (SEQ ID NO:8147), ATTATCGGGGGTGGCGGAGGGGTTGGTA (SEQ ID NO:8148), AAAGGGGTGTGGTAAGAGGAGGAGCGGT (SEQ ID NO:8149), TATCGGGGGTGGCGGAGGGGTTGGTAAA (SEQ ID NO:8150), AGTTATTTTCGGCGGAGTGTTTCGAGTTTT (SEQ ID NO:8151), AAGTTATTTTCGGCGGAGTGTTTCGAGTTTT (SEQ ID NO:8152), AAAGTTATTTTCGGCGGAGTGTTTCGAGTTT (SEQ ID NO:8153), AGTTATTTTCGGCGGAGTGTTTCGAGTTTTTC (SEQ ID NO:8154), AAGTTATTTTCGGCGGAGTGTTTCGAGTTTTT (SEQ ID NO:8155) |
| Target862 | chr8:20375713-20375784 | GATTTTTCGGAATAGAAGCGATGTTGAAATGCG (SEQ ID NO:8156), AGATTTTTCGGAATAGAAGCGATGTTGAAATGCG (SEQ ID NO:8157), AAGATTTTTCGGAATAGAAGCGATGTTGAAATGCG (SEQ ID NO:8158), AAAGATTTTTCGGAATAGAAGCGATGTTGAAATGCG (SEQ ID NO:8159), TGGGGATTTAGATTATGAATAGACGGAAGAGGAAGA (SEQ ID NO:8160) |
| Target863 | chr8:22438004-22438261 | TGGGGGGGAAGTGAAATCGGGTTGAGGG (SEQ ID NO:8161), GGGTGGGGGGGAAGTGAAATCGGGTTGA (SEQ ID NO:8162), AGGGTGGGGGGGAAGTGAAATCGGGTTG (SEQ ID NO:8163), GGGGGGAAGTGAAATCGGGTTGAGGGA (SEQ ID NO:8164), GGATGTGGTCGGGTTAGCGTTTTGGGG (SEQ ID NO:8165), CGGAAGTTTTAGGGCGTTGGTTCGGTT (SEQ ID NO:8166), CGGAAGTTTTAGGGCGTTGGTTCGGT (SEQ ID NO:8167), TGTGTAGAGTGGGGTGAATAGGGTCGA (SEQ ID NO:8168), CGGAAGTTTTAGGGCGTTGGTTCGGTTA (SEQ ID NO:8169), TTGTGTAGAGTGGGGTGAATAGGGTCGA (SEQ ID NO:8170) |
| Target864 | chr8:22875782-22875898 | AGAAGGAAGTAGGAATGAGTGTACGGCG (SEQ ID NO:8171), GAAGGAAGTAGGAATGAGTGTACGGCGA (SEQ ID NO:8172), GGAGAAGGAAGTAGGAATGAGTGTACGGCG (SEQ ID NO:8173), AGAAGGAAGTAGGAATGAGTGTACGGCGA (SEQ ID NO:8174), TGGAGAAGGAAGTAGGAATGAGTGTACGGCG (SEQ ID NO:8175), GGGGGAGGGTTTTGAGGAGTACGGGGTC (SEQ ID NO:8176), AGGGGAGGGTTTTGAGGAGTACGGGGT (SEQ ID NO:8177), TAGGGGAGGGTTTTGAGGAGTACGGGGT (SEQ ID NO:8178), TAGGGGAGGGTTTTGAGGAGTACGGGG (SEQ ID NO:8179), AGGGGAGGGTTTTGAGGAGTACGGGGTC (SEQ ID NO:8180) |
| Target865 | chr8:22876026-22876179 | GAGGGTTGGTGATTGAGGGGTTCGGGT (SEQ ID NO:8181), TGATTGAGGGGTTCGGGTTGGCGGTAA (SEQ ID NO:8182), TGAGGGGTTCGGGTTGGCGGTAAAGAG (SEQ ID NO:8183), TTGAGGGGTTCGGGTTGGCGGTAAAGA (SEQ ID NO:8184), GTTGGTGATTGAGGGGTTCGGGTTGGC (SEQ ID NO:8185), CGGAGTTAGTTGGTAGGGTTAGGGTTTTCG (SEQ ID NO:8186), TCGGAGTTAGTTGGTAGGGTTAGGGTTTTCG (SEQ ID NO:8187), |

FIGURE 5 CONTINUED

TGTGTTGTTTTCGGAGTTAGTTGGTAGGGT (SEQ ID NO:8188),
TGTTTTCGGAGTTAGTTGGTAGGGTTAGGGT (SEQ ID NO:8189),
GTTTTCGGAGTTAGTTGGTAGGGTTAGGGT (SEQ ID NO:8190)

Target866  chr8:23563902-23563929  GCGGCGGCGGTGATAGAAAGTTGGATG (SEQ ID NO:8191), CGGCGGCGGTGATAGAAAGTTGGATGG (SEQ ID NO:8192), AGAGGTTTATAACGTTGGTGGCGGCGG (SEQ ID NO:8193), GGCGGCGGTGATAGAAAGTTGGATGGT (SEQ ID NO:8194), GCGGCGGCGGTGATAGAAAGTTGGAT (SEQ ID NO:8195)

Target867  chr8:23563960-23564121  GAAGGGGGTGGAGGTGACGGGGTTTAG (SEQ ID NO:8196), AGGGGGTGGAGGTGACGGGGTTTAGTA (SEQ ID NO:8197), GGGGGTGGAGGTGACGGGGTTTAGTAG (SEQ ID NO:8198), AGAAGGGGGTGGAGGTGACGGGGTTTA (SEQ ID NO:8199), TTGATCGAGAAGGGGGTGGAGGTGACG (SEQ ID NO:8200), TGCGGGGTTTGTAGCGATAAGACGGGA (SEQ ID NO:8201), TGGGTTTGTTTGCGGGGTTTGTAGCGA (SEQ ID NO:8202), TTGCGGGGTTTGTAGCGATAAGACGGG (SEQ ID NO:8203), TGCGGGGTTTGTAGCGATAAGACGGGAA (SEQ ID NO:8204), TTGCGGGGTTTGTAGCGATAAGACGGGA (SEQ ID NO:8205)

Target868  chr8:23564145-23564241  GAAGGGGGTGGAGGTGACGGGGTTTAG (SEQ ID NO:8206), AGGGGGTGGAGGTGACGGGGTTTAGTA (SEQ ID NO:8207), GGGGGTGGAGGTGACGGGGTTTAGTAG (SEQ ID NO:8208), AGAAGGGGGTGGAGGTGACGGGGTTTA (SEQ ID NO:8209), TTGATCGAGAAGGGGGTGGAGGTGACG (SEQ ID NO:8210), GGGAAGAAAGCGTTGGGGGAGGAAGGT (SEQ ID NO:8211), TGCGGGGTTTGTAGCGATAAGACGGGA (SEQ ID NO:8212), TGGGTTTGTTTGCGGGGTTTGTAGCGA (SEQ ID NO:8213), GGAAGAAAGCGTTGGGGGAGGAAGGTG (SEQ ID NO:8214), CGGGAAGAAAGCGTTGGGGGAGGAAGG (SEQ ID NO:8215)

Target869  chr8:23564354-23564375  TGGTAGGTTCGGGTTTAGGGTCGGGTG (SEQ ID NO:8216), GGTAGGTTCGGGTTTAGGGTCGGGTGA (SEQ ID NO:8217), TTGGTAGGTTCGGGTTTAGGGTCGGGT (SEQ ID NO:8218), TGGTAGGTTCGGGTTTAGGGTCGGGTGA (SEQ ID NO:8219), GTTGGTAGGTTCGGGTTTAGGGTCGGGT (SEQ ID NO:8220), TTGGGGATTGGAGAGGATTCGACGGGC (SEQ ID NO:8221), ATTGGGGATTGGAGAGGATTCGACGGGC (SEQ ID NO:8222), AGGAAGGCGATTGGGGATTGGAGAGGA (SEQ ID NO:8223), TGGGGATTGGAGAGGATTCGACGGGC (SEQ ID NO:8224), AGGCGATTGGGGATTGGAGAGGATTCG (SEQ ID NO:8225)

Target870  chr8:23564418-23564470  CGTGGAGAGATAGTGTTGCGCGCG (SEQ ID NO:8226), AAGAAAACGTGGAGAGATAGTGTTGCGC (SEQ ID NO:8227), AAAGAAAACGTGGAGAGATAGTGTTGCGC (SEQ ID NO:8228), GTGGAGAGATAGTGTTGCGCGCG (SEQ ID NO:8229), CGTGGAGAGATAGTGTTGCGCGC (SEQ ID NO:8230), ACGGAGATTTAAGTCGCGCGTAGTATTGT (SEQ ID NO:8231), ACGGAGATTTAAGTCGCGCGTAGTATTGTT (SEQ ID NO:8232), ACGGAGATTTAAGTCGCGCGTAGTATTGTTT (SEQ ID NO:8233), CGGAGATTTAAGTCGCGCGTAGTATTGTTT (SEQ ID NO:8234), ACGGAGATTTAAGTCGCGCGTAGTATTGTTT (SEQ ID NO:8235)

Target871  chr8:25907747-25907758  AGTCGGTAGGGGAAAGTTCGAGGGATT (SEQ ID NO:8236), TTAGTCGGTAGGGGAAAGTTCGAGGGA (SEQ ID NO:8237), TAGTCGGTAGGGGAAAGTTCGAGGGAT (SEQ ID NO:8238), GTTAGTCGGTAGGGGAAAGTTCGAGGG (SEQ ID NO:8239), GTCGGTAGGGGAAAGTTCGAGGGATTT (SEQ ID NO:8240), AGTGTACGTGTGAAATGTGGCGGCGT (SEQ ID NO:8241), TAGTGTACGTGTGAAATGTGGCGGCGT (SEQ ID NO:8242), AGTGTACGTGTGAAATGTGGCGGCGT (SEQ ID NO:8243), TAGTGTACGTGTGAAATGTGGCGGCGTC (SEQ ID NO:8244), TTAGTGTACGTGTGAAATGTGGCGGCGT (SEQ ID NO:8245)

Target872  chr8:25907796-25907867  GGCGGAGGTGTGAGCGATGTGTTGATT (SEQ ID NO:8246), TTTTTTCGGATCGCGGCGGAGGTGTGA (SEQ ID NO:8247), CGGCGGAGGTGTGAGCGATGTGTTGAT (SEQ ID NO:8248), TTTTTTCGGATCGCGGCGGAGGTGTG (SEQ ID NO:8249), TTTTTCGGATCGCGGCGGAGGTGTGAG (SEQ ID NO:8250), GAAAAGGTAGTCGGGTTGGGGGTGGGT (SEQ ID NO:8251), GGGGTGGGTAGGTAGTAGTGAGCGGGA (SEQ ID NO:8252), AGGAAAAGGTAGTCGGGTTGGGGGTGG (SEQ ID NO:8253), AGTGTACGTGTGAAATGTGGCGGCGTC (SEQ ID NO:8254), TGGGGGTGGGTAGGTAGTAGTGAGCGG (SEQ ID NO:8255)

Target873  chr8:25907880-25907894  GCGGAGGTGTGAGCGATGTGTTGATTA (SEQ ID NO:8256), GCGGAGGTGTGAGCGATGTGTTGATT (SEQ ID NO:8257), GCGGAGGTGTGAGCGATGTGTTGATTAT (SEQ ID NO:8258), GCGGAGGTGTGAGCGATGTGTTGAT (SEQ ID NO:8259), GCGGAGGTGTGAGCGATGTGTTGATTATT (SEQ ID NO:8260), GAAAAGGTAGTCGGGTTGGGGGTGGGT (SEQ ID NO:8261), GGGGTGGGTAGGTAGTAGTGAGCGGGA (SEQ ID NO:8262), AGGAAAAGGTAGTCGGGTTGGGGGTGG (SEQ ID NO:8263), TGGGGGTGGGTAGGTAGTAGTGAGCGG (SEQ ID NO:8264), GGTAGTCGGGTTGGGGGTGGGTAGGTA (SEQ ID NO:8265)

Target874  chr8:25907900-25907907  GAAAAGGTAGTCGGGTTGGGGGTGGGT (SEQ ID NO:8266), GGGGTGGGTAGGTAGTAGTGAGCGGGA (SEQ ID NO:8267), AGGAAAAGGTAGTCGGGTTGGGGGTGG (SEQ ID NO:8268), TGGGGGTGGGTAGGTAGTAGTGAGCGG (SEQ ID NO:8269), GGTAGTCGGGTTGGGGGTGGGTAGGTA (SEQ ID NO:8270)

Target875  chr8:25908055-25908102  TTTGAGGATGGGGGAGATTTTGGCGGC (SEQ ID NO:8271), TTGAGGATGGGGGAGATTTTGGCGGCG (SEQ ID NO:8272), ATTTGAGGATGGGGGAGATTTTGGCGGC (SEQ ID NO:8273), TTGAGGATGGGGGAGATTTTGGCGGC (SEQ ID NO:8274), TGAGGATGGGGGAGATTTTGGCGGCG (SEQ ID NO:8275), TGCGTGTGTGTGTTGGAGGAGGAGGTT (SEQ ID NO:8276), AGTGCGTGTGTGTGTTGGAGGAGGAGG (SEQ ID NO:8277), AGGTGGAGGTGATCGTGATGGTGTGCG

FIGURE 5 CONTINUED (SEQ ID NO:8278), CGAGTGCGTGTGTGTGTTGGAGGAGGA (SEQ ID NO:8279),
GTGCGTGTGTGTGTTGGAGGAGGAGGT (SEQ ID NO:8280)

| | | |
|---|---|---|
| Target876 | chr8:38757667-38758053 | TGCGGCGTGGATTAAATGAGATAGCGT (SEQ ID NO:8281), GGTTGCGGCGTGGATTAAATGAGATAGCG (SEQ ID NO:8282), TTGCGGCGTGGATTAAATGAGATAGCGT (SEQ ID NO:8283), GGTTGCGGCGTGGATTAAATGAGATAGCG (SEQ ID NO:8284), TTGCGGCGTGGATTAAATGAGATAGCG (SEQ ID NO:8285), AAATGTAGAAGATTCGCGCGGGTTTGC (SEQ ID NO:8286), CGTTGGGATTTTTTCGGTGTGATGCGA (SEQ ID NO:8287), TCGTTGGGATTTTTTCGGTGTGATGCG (SEQ ID NO:8288), GGAATTAAGAGAGTTGTTGTGCGCGGGT (SEQ ID NO:8289), TCGTTGGGATTTTTTCGGTGTGATGCGA (SEQ ID NO:8290) |
| Target877 | chr8:38758076-38758134 | GGGTACGGTGTAGGCGTTTGTGGTTTT (SEQ ID NO:8291), ATTCGGGAGGTTGGGGTAGAAGGATCG (SEQ ID NO:8292), GGGTACGGTGTAGGCGTTTGTGGTTT (SEQ ID NO:8293), TTCGGGAGGTTGGGGTAGAAGGATCG (SEQ ID NO:8294), GGGTACGGTGTAGGCGTTTGTGGTTTTA (SEQ ID NO:8295), TTTGTCGTTTAGGTTGGAGTGCGGTGG (SEQ ID NO:8296), GGTTTTGTCGTTTAGGTTGGAGTGCGGT (SEQ ID NO:8297), TGGTTTTGTCGTTTAGGTTGGAGTGCGG (SEQ ID NO:8298), TTTTGTCGTTTAGGTTGGAGTGCGGTGG (SEQ ID NO:8299), TGGTTTTGTCGTTTAGGTTGGAGTGCGG (SEQ ID NO:8300) |
| Target878 | chr8:55370650-55371091 | GCGGTGATGGTCGGGTTGGGTTTTTGT (SEQ ID NO:8301), GGGAGCGGGGTAGGTTTGGAGCGTTAT (SEQ ID NO:8302), GGGATATGAAGGTGAAGGGCGAGGCGT (SEQ ID NO:8303), GTTGAGGGGAGCGGGGTAGGTTTGGAG (SEQ ID NO:8304), GCGATAGGTTAGAATACGGGCGGCGGT (SEQ ID NO:8305), AGCGCGTTTTGGGTTTGGTTTTGGTCG (SEQ ID NO:8306), AAAGTTGTTTTGGAGGGTCGGAGGGCG (SEQ ID NO:8307), AGGCGGAAAGTTGTTTTGGAGGGTCGG (SEQ ID NO:8308), GGCGGAAAGTTGTTTTGGAGGGTCGGA (SEQ ID NO:8309), AAGTTGTTTTGGAGGGTCGGAGGGCGG (SEQ ID NO:8310) |
| Target879 | chr8:55371122-55371160 | TGACGTTTAAAATTAGGGGTGTGTAGCGGT (SEQ ID NO:8311), TGACGTTTAAAATTAGGGGTGTGTAGCGGTT (SEQ ID NO:8312), TTGACGTTTAAAATTAGGGGTGTGTAGCGGT (SEQ ID NO:8313), GCGAGTTTGACGTTTAAAATTAGGGGTGTGT (SEQ ID NO:8314), TGCGAGTTTGACGTTTAAAATTAGGGGTGTG (SEQ ID NO:8315), GTCGTTCGGAGGTGTCGGGAAGTCGTT (SEQ ID NO:8316), TCGTTCGGAGGTGTCGGGAAGTCGTTT (SEQ ID NO:8317), AAAGTTGTTTTGGAGGGTCGGAGGGCG (SEQ ID NO:8318), AGGCGGAAAGTTGTTTTGGAGGGTCGG (SEQ ID NO:8319), GGCGGAAAGTTGTTTTGGAGGGTCGGA (SEQ ID NO:8320) |
| Target880 | chr8:55371173-55371214 | TGACGTTTAAAATTAGGGGTGTGTAGCGGT (SEQ ID NO:8321), TGACGTTTAAAATTAGGGGTGTGTAGCGGTT (SEQ ID NO:8322), TTGACGTTTAAAATTAGGGGTGTGTAGCGGT (SEQ ID NO:8323), GCGAGTTTGACGTTTAAAATTAGGGGTGTGT (SEQ ID NO:8324), TGCGAGTTTGACGTTTAAAATTAGGGGTGTG (SEQ ID NO:8325), GTCGTTCGGAGGTGTCGGGAAGTCGTT (SEQ ID NO:8326), TCGTTCGGAGGTGTCGGGAAGTCGTTT (SEQ ID NO:8327), CGTTCGGAGGTGTCGGGAAGTCGTTTT (SEQ ID NO:8328), GTCGTTCGGAGGTGTCGGGAAGTCGT (SEQ ID NO:8329), TCGTTCGGAGGTGTCGGGAAGTCGTTTT (SEQ ID NO:8330) |
| Target881 | chr8:55379448-55379488 | CGTTGTCGGGTAGGGATCGGGCGA (SEQ ID NO:8331), CGTTGTCGGGTAGGGATCGGGCG (SEQ ID NO:8332), GCGTTAAGGTTTCGGAAGTTTTTAGCGGG (SEQ ID NO:8333), GCGTTAAGGTTTCGGAAGTTTTTAGCGGGA (SEQ ID NO:8334), AGGGAAGAGGGAGGGGATTTGTGTTTTTGT (SEQ ID NO:8335) |
| Target882 | chr8:55379496-55379518 | TTTTTCGTCGTTGAGGTGGAGTTCGGC (SEQ ID NO:8336), GTTTTTCGTCGTTGAGGTGGAGTTCGGC (SEQ ID NO:8337), AGTTTTTCGTCGTTGAGGTGGAGTTCGGC (SEQ ID NO:8338), TTTTCGTCGTTGAGGTGGAGTTCGGC (SEQ ID NO:8339), CGTTGTCGGGTAGGGATCGGGCGA (SEQ ID NO:8340), TCGGGTTAGTTTTAGTTTACGGCGTGGT (SEQ ID NO:8341), TCGGGTTAGTTTTAGTTTACGGCGTGGTT (SEQ ID NO:8342), TTCGGGTTAGTTTTAGTTTACGGCGTGGT (SEQ ID NO:8343), TTCGGGTTAGTTTTAGTTTACGGCGTGGTT (SEQ ID NO:8344), TTTCGGGTTAGTTTTAGTTTACGGCGTGGT (SEQ ID NO:8345) |
| Target883 | chr8:55379566-55379574 | TGGAGTTCGGCGGCGGGAGTTTAGATT (SEQ ID NO:8346), GTGGAGTTCGGCGGCGGGAGTTTAGAT (SEQ ID NO:8347), GGAGTTCGGCGGCGGGAGTTTAGATTT (SEQ ID NO:8348), TGGAGTTCGGCGGCGGGAGTTTAGATTT (SEQ ID NO:8349), TGGAGTTCGGCGGCGGGAGTTTAGAT (SEQ ID NO:8350), AGATGTTTCGACGGTTGCGCGGGTTTT (SEQ ID NO:8351), GAGATGTTTCGACGGTTGCGCGGGTTT (SEQ ID NO:8352), GATGTTTCGACGGTTGCGCGGGTTTTC (SEQ ID NO:8353), ATGTTTCGACGGTTGCGCGGGTTTTCG (SEQ ID NO:8354), GAGATGTTTCGACGGTTGCGCGGGTT (SEQ ID NO:8355) |
| Target884 | chr8:55379583-55379839 | TGGAGTTCGGCGGCGGGAGTTTAGATT (SEQ ID NO:8356), CGTCGTGGGTTGGGATTGGTTCGGAAC (SEQ ID NO:8357), ACGTCGTGGGTTGGGATTGGTTCGGAA (SEQ ID NO:8358), CGGGGTAGGTTTGGAGCGTCGTGAGTA (SEQ ID NO:8359), TACGTCGTGGGTTGGGATTGGTTCGGA (SEQ ID NO:8360), AGATGTTTCGACGGTTGCGCGGGTTTT (SEQ ID NO:8361), GAGATGTTTCGACGGTTGCGCGGGTTT (SEQ ID NO:8362), GACGCGGAGGAAAAGAAGGTGGTGAGC |

FIGURE 5 CONTINUED (SEQ ID NO:8363), CGGACGCGGAGGAAAAGAAGGTGGTGA (SEQ ID NO:8364), TCGGACGCGGAGGAAAAGAAGGTGGTG (SEQ ID NO:8365)

| Target885 | chr8:55382674-55382690 | GAGGTGGGCGTAGGAGGAGGAGTTGTT (SEQ ID NO:8366), CGAGGTGGGCGTAGGAGGAGGAGTTGT (SEQ ID NO:8367), AGGTGGGCGTAGGAGGAGGAGTTGTTT (SEQ ID NO:8368), CGAGGTGGGCGTAGGAGGAGGAGTTG (SEQ ID NO:8369), GAGGTGGGCGTAGGAGGAGGAGTTGTTT (SEQ ID NO:8370), TTTGCGCGGGGAAGGGTAGGTTTAGGT (SEQ ID NO:8371), CGCGGGGAAGGGTAGGTTTAGGTCGTT (SEQ ID NO:8372), GGAAAGTTTTGCGCGGGGAAGGGTAGG (SEQ ID NO:8373), GGGAAAGTTTTGCGCGGGGAAGGGTAG (SEQ ID NO:8374), TTGCGCGGGGAAGGGTAGGTTTAGGTC (SEQ ID NO:8375) |

| Target886 | chr8:55382691-55382762 | GAGGTGGGCGTAGGAGGAGGAGTTGTT (SEQ ID NO:8376), CGAGGTGGGCGTAGGAGGAGGAGTTGT (SEQ ID NO:8377), AGGTGGGCGTAGGAGGAGGAGTTGTTT (SEQ ID NO:8378), CGAGGTGGGCGTAGGAGGAGGAGTTG (SEQ ID NO:8379), GAGGTGGGCGTAGGAGGAGGAGTTGTTT (SEQ ID NO:8380), TAGGGCGTGGGTAGTGGTGGTAGTGGA (SEQ ID NO:8381), TTTGCGCGGGGAAGGGTAGGTTTAGGT (SEQ ID NO:8382), CGCGGGGAAGGGTAGGTTTAGGTCGTT (SEQ ID NO:8383), GGAAAGTTTTGCGCGGGGAAGGGTAGG (SEQ ID NO:8384), GGGAAAGTTTTGCGCGGGGAAGGGTAG (SEQ ID NO:8385) |

| Target887 | chr8:55382784-55382817 | GCGTAGTTTTGGGCGGTTTGGGTTTGT (SEQ ID NO:8386), GCGTAGTTTTGGGCGGTTTGGGTTTGTT (SEQ ID NO:8387), GCGGGGATTTTGCGGGATTAGGTTAGA (SEQ ID NO:8388), GCGTAGTTTTGGGCGGTTTGGGTTTGTTT (SEQ ID NO:8389), CGTAGTTTTGGGCGGTTTGGGTTTGTT (SEQ ID NO:8390), TAGGGCGTGGGTAGTGGTGGTAGTGGA (SEQ ID NO:8391), GTAGGGCGTGGGTAGTGGTGGTAGTGG (SEQ ID NO:8392), CGGGGTAGCGATCGGTAGGAGGGAAAG (SEQ ID NO:8393), TGGGTAGTGGTGGTAGTGGAGCGGGAG (SEQ ID NO:8394), GGGTAGTGGTGGTAGTGGAGCGGGAGT (SEQ ID NO:8395) |

| Target888 | chr8:55382870-55382887 | GCGTAGTTTTGGGCGGTTTGGGTTTGT (SEQ ID NO:8396), GCGTAGTTTTGGGCGGTTTGGGTTTGTT (SEQ ID NO:8397), GCGTAGTTTTGGGCGGTTTGGGTTTGTTT (SEQ ID NO:8398), CGTAGTTTTGGGCGGTTTGGGTTTGTT (SEQ ID NO:8399), GCGTAGTTTTGGGCGGTTTGGGTTTG (SEQ ID NO:8400), TAGGTTTAGCGATGAGGGGGTTGCGGG (SEQ ID NO:8401), TTGTTGGTGCGGGGTAGGTTTGGGGTA (SEQ ID NO:8402), TGTTGGTGCGGGGTAGGTTTGGGGTAG (SEQ ID NO:8403), TAGCGATGAGGGGGTTGCGGGTTTGTA (SEQ ID NO:8404), TTAGCGATGAGGGGGTTGCGGGTTTGT (SEQ ID NO:8405) |

| Target889 | chr8:55382910-55382918 | GTTTTCGTTTGATCGCGTGGAGTCGGA (SEQ ID NO:8406), TCGTTTGATCGCGTGGAGTCGGATTTC (SEQ ID NO:8407), TTCGTTTGATCGCGTGGAGTCGGATTT (SEQ ID NO:8408), TTTCGTTTGATCGCGTGGAGTCGGATT (SEQ ID NO:8409), TTTTCGTTTGATCGCGTGGAGTCGGAT (SEQ ID NO:8410), TAGGTTTAGCGATGAGGGGGTTGCGGG (SEQ ID NO:8411), TTGTTGGTGCGGGGTAGGTTTGGGGTA (SEQ ID NO:8412), TGTTGGTGCGGGGTAGGTTTGGGGTAG (SEQ ID NO:8413), TAGCGATGAGGGGGTTGCGGGTTTGTA (SEQ ID NO:8414), TTAGCGATGAGGGGGTTGCGGGTTTGT (SEQ ID NO:8415) |

| Target890 | chr8:55382987-55383035 | GTTTTCGTTTGATCGCGTGGAGTCGGA (SEQ ID NO:8416), TCGTTTGATCGCGTGGAGTCGGATTTC (SEQ ID NO:8417), TTCGTTTGATCGCGTGGAGTCGGATTT (SEQ ID NO:8418), TTTCGTTTGATCGCGTGGAGTCGGATT (SEQ ID NO:8419), TTTTCGTTTGATCGCGTGGAGTCGGAT (SEQ ID NO:8420), TTTCGTTGGTTGCGTGGGGTTAGCGTC (SEQ ID NO:8421), GTTGGTTGCGTGGGGTTAGCGTCGTTT (SEQ ID NO:8422), ATTTCGTTGGTTGCGTGGGGTTAGCGT (SEQ ID NO:8423), GGTTGCGTGGGGTTAGCGTCGTTTAGT (SEQ ID NO:8424), TGGTTGCGTGGGGTTAGCGTCGTTTAG (SEQ ID NO:8425) |

| Target891 | chr8:56901515-56901792 | GAGTTTGCGTTTCGGGTGGGAGAGAGT (SEQ ID NO:8426), GCGTTTCGGGTGGGAGAGAGTTTGTTGG (SEQ ID NO:8427), TGCGTTTCGGGTGGGAGAGAGTTTGTT (SEQ ID NO:8428), TTGCGTTTCGGGTGGGAGAGAGTTTGT (SEQ ID NO:8429), AGAGTTTGCGTTTCGGGTGGGAGAGAGT (SEQ ID NO:8430) |

| Target892 | chr8:67873476-67873541 | AGGTCGTTTTTTCGGTCGGTTTTTCGT (SEQ ID NO:8431), GAGGTCGTTTTTTCGGTCGGTTTTTCGT (SEQ ID NO:8432), AGGTCGTTTTTTCGGTCGGTTTTTCGTT (SEQ ID NO:8433), GAGGTCGTTTTTTCGGTCGGTTTTTCGT (SEQ ID NO:8434), AGGTCGTTTTTTCGGTCGGTTTTTCGTTT (SEQ ID NO:8435), TTTTCGGGTGAGGCGGGAAGTCGATCG (SEQ ID NO:8436), CGCGGGGTTGGGGTCGAGATTAGGATA (SEQ ID NO:8437), TCGCGGGGTTGGGGTCGAGATTAGGAT (SEQ ID NO:8438), TTTTTCGGGTGAGGCGGGAAGTCGATC (SEQ ID NO:8439), CGCGGGGTTGGGGTCGAGATTAGGAT (SEQ ID NO:8440) |

| Target893 | chr8:67873588-67873596 | TTGGTTTCGGTTTTAGTTTCGCGGTGC (SEQ ID NO:8441), TTTGGTTTCGGTTTTAGTTTCGCGGTGC (SEQ ID NO:8442), AGGTCGTTTTTTCGGTCGGTTTTTCGT (SEQ ID NO:8443), TGGTTTCGGTTTTAGTTTCGCGGTGC (SEQ ID NO:8444), GAGGTCGTTTTTTCGGTCGGTTTTTCGT (SEQ ID NO:8445), TGCGCGGCGATGGTTATTTGTATTCGGT (SEQ ID NO:8446), GCGCGGCGATGGTTATTTGTATTCGGT (SEQ ID NO:8447), TGCGCGGCGATGGTTATTTGTATTCGG (SEQ ID NO:8448), GCGCGGCGATGGTTATTTGTATTCGGTT (SEQ ID NO:8449), TTGCGCGGCGATGGTTATTTGTATTCGG (SEQ ID NO:8450) |

| Target894 | chr8:67873600-67874082 | GGCGTCGTTTTGTAGGTTGCGGGTGAG (SEQ ID NO:8451), AAAGGATCGAAGGTGCGGTGAGGTCGG (SEQ ID NO:8452), GTTGGCGTTGAGGGGGTTGTTCGTTGG (SEQ ID NO:8453), GGTGAGATGCGCGATGTAGGTGGTGG (SEQ ID NO:8454), GCGTCGTTTTGTAGGTTGCGGGTGAGA |

FIGURE 5 CONTINUED (SEQ ID NO:8455), CGTACGGGGAGAATTAGGGGGGTTGCGT (SEQ ID NO:8456),
TTTCGTTGGGTTGTTGGTGGGCGTACG (SEQ ID NO:8457), TTGGTGGGCGTACGGGGAGAATTAGGG
(SEQ ID NO:8458), GGGCGTACGGGGAGAATTAGGGGGGTTG (SEQ ID NO:8459),
GGTTGTTGGTGGGCGTACGGGGAGAAT (SEQ ID NO:8460)

Target895          chr8:70946939-70946971          AAGCGGTTCGGAGTTGTAGGAAGGGCG (SEQ ID NO:8461), GGTTCGGAGTTGTAGGAAGGGCGTCGG
(SEQ ID NO:8462), CGGTTCGGAGTTGTAGGAAGGGCGTCG (SEQ ID NO:8463),
GAAGCGGTTCGGAGTTGTAGGAAGGGC (SEQ ID NO:8464), GCGGTTCGGAGTTGTAGGAAGGGCGTC
(SEQ ID NO:8465), CGTAGTCGGGTATTTTTGCGGCGCG (SEQ ID NO:8466)

Target896          chr8:70947164-70947176          AGATTTAGAGGCGGGTTGGGGACGTGA (SEQ ID NO:8467), GATTTAGAGGCGGGTTGGGGACGTGAG
(SEQ ID NO:8468), AGATTTAGAGGCGGGTTGGGGACGTGAG (SEQ ID NO:8469),
GGGGCGGGGTTTGCGGTTTTTAGATTT (SEQ ID NO:8470), TAGATTTAGAGGCGGGTTGGGGACGTG
(SEQ ID NO:8471), GAGGGGACGTTTAAGGTTATCGCGGCG (SEQ ID NO:8472),
GGAGGGGACGTTTAAGGTTATCGCGGC (SEQ ID NO:8473), GGGGAGGGGACGTTTAAGGTTATCGCGG
(SEQ ID NO:8474), GGGGAGGGGACGTTTAAGGTTATCGCG (SEQ ID NO:8475),
CGGGGAGGGGACGTTTAAGGTTATCGC (SEQ ID NO:8476)

Target897          chr8:70981730-70981761          TCGTAGGGGGCGGTGGAATTAAAGTGT (SEQ ID NO:8477), CGTAGGGGGCGGTGGAATTAAAGTGTT
(SEQ ID NO:8478), TCGTAGGGGGCGGTGGAATTAAAGTGTT (SEQ ID NO:8479),
TTCGTAGGGGGCGGTGGAATTAAAGTGT (SEQ ID NO:8480), GGGGGCGGTGGAATTAAAGTGTTAGGT
(SEQ ID NO:8481), TGAGTTCGGGTTTGGGTTTATAGAGGGAGT (SEQ ID NO:8482),
TGTTGAGTTCGGGTTTGGGTTTATAGAGGG (SEQ ID NO:8483),
GTTGAGTTCGGGTTTGGGTTTATAGAGGGA (SEQ ID NO:8484),
TGTTGAGTTCGGGTTTGGGTTTATAGAGGGA (SEQ ID NO:8485),
TGAGTTCGGGTTTGGGTTTATAGAGGGAGTT (SEQ ID NO:8486)

Target898          chr8:70981881-70981917          GAAGGGGGGTATGGCGGGGGGTAGTAGA (SEQ ID NO:8487), AAGGGGGGTATGGCGGGGGGTAGTAGAC
(SEQ ID NO:8488), TATTCGGAAGGGGAAGGGGGGTATGGC (SEQ ID NO:8489),
GGAAGGGGGGTATGGCGGGGGGTAGTAG (SEQ ID NO:8490), AAGGGGGGTATGGCGGGGGGTAGTAGA
(SEQ ID NO:8491), TGGAGGTCGTAGCGTTTGTTGTTTTCGT (SEQ ID NO:8492),
GGAGGTCGTAGCGTTTGTTGTTTTCGT (SEQ ID NO:8493), TGGAGGTCGTAGCGTTTGTTGTTTTCG (SEQ
ID NO:8494), GGTAGTTGGAGGTCGTAGCGTTTGTTGT (SEQ ID NO:8495),
TGGAGGTCGTAGCGTTTGTTGTTTTCGTT (SEQ ID NO:8496)

Target899          chr8:70982012-70982028          GGGGTATGGCGGGGGTAGTAGACGTTG (SEQ ID NO:8497), GAAGGGGGGTATGGCGGGGGTAGTAGA
(SEQ ID NO:8498), GGGTATGGCGGGGGTAGTAGACGTTGC (SEQ ID NO:8499),
GTATGGCGGGGGTAGTAGACGTTGCGG (SEQ ID NO:8500), GGTATGGCGGGGGTAGTAGACGTTGCG
(SEQ ID NO:8501), CGGGATGGTTTTATTTCGGTTAAGTGAGGTCG (SEQ ID NO:8502),
CGGGATGGTTTTATTTCGGTTAAGTGAGGTCGT (SEQ ID NO:8503),
TCGGGATGGTTTTATTTCGGTTAAGTGAGGT (SEQ ID NO:8504),
TCGGGATGGTTTTATTTCGGTTAAGTGAGGTCG (SEQ ID NO:8505),
CGGTTTCGGGATGGTTTTATTTCGGTTAAGT (SEQ ID NO:8506)

Target900          chr8:70982082-70982109          TTTGCGGGTTGTTTTTCGGCGGGTAGT (SEQ ID NO:8507), AGGTTTTGCGGGTTGTTTTTCGGCGGG (SEQ
ID NO:8508), TTGCGGGTTGTTTTTCGGCGGGTAGTA (SEQ ID NO:8509),
GGTTTTGCGGGTTGTTTTTCGGCGGGT (SEQ ID NO:8510), GTTTTGCGGGTTGTTTTTCGGCGGGTA (SEQ
ID NO:8511), GGATTTGGGGTTGGTTGGGGTGGAGGA (SEQ ID NO:8512),
ATTTGGGGTTGGTTGGGGTGGAGGAGG (SEQ ID NO:8513), TGGATTTGGGGTTGGTTGGGGTGGAGG
(SEQ ID NO:8514), GTTGGTTGGGGTGGAGGAGGTTGGTGG (SEQ ID NO:8515),
GGTTGGTTGGGGTGGAGGAGGTTGGTG (SEQ ID NO:8516)

Target901          chr8:70982112-70982155          TTTGCGGGTTGTTTTTCGGCGGGTAGT (SEQ ID NO:8517), AGGTTTTGCGGGTTGTTTTTCGGCGGG (SEQ
ID NO:8518), TTGCGGGTTGTTTTTCGGCGGGTAGTA (SEQ ID NO:8519),
GGTTTTGCGGGTTGTTTTTCGGCGGGT (SEQ ID NO:8520), GTTTTGCGGGTTGTTTTTCGGCGGGTA (SEQ
ID NO:8521), GGATTTGGGGTTGGTTGGGGTGGAGGA (SEQ ID NO:8522),
ATTTGGGGTTGGTTGGGGTGGAGGAGG (SEQ ID NO:8523), TGGATTTGGGGTTGGTTGGGGTGGAGG
(SEQ ID NO:8524), GTTGGTTGGGGTGGAGGAGGTTGGTGG (SEQ ID NO:8525),
GGTTGGTTGGGGTGGAGGAGGTTGGTG (SEQ ID NO:8526)

Target902          chr8:70984131-70984156          CGGGTGGTCGTTTTGTTTTTTCGGGGG (SEQ ID NO:8527), CGGGTGGTCGTTTTGTTTTTTCGGGGGT (SEQ
ID NO:8528), TCGGGTGGTCGTTTTGTTTTTTCGGGGG (SEQ ID NO:8529),
GGGTGGTCGTTTTGTTTTTTCGGGGGT (SEQ ID NO:8530), TCGGGTGGTCGTTTTGTTTTTTCGGGG (SEQ
ID NO:8531), ATGCGGTTTTTGGGCGTTCGGTATGGG (SEQ ID NO:8532),
GCGGTTTTTGGGCGTTCGGTATGGGTT (SEQ ID NO:8533), TGCGGTTTTTGGGCGTTCGGTATGGG (SEQ
ID NO:8534), GCGGTTTTTGGGCGTTCGGTATGGGT (SEQ ID NO:8535),
TGCGGTTTTTGGGCGTTCGGTATGGGT (SEQ ID NO:8536)

Target903          chr8:70984158-70984365          AGAAAGAAGCGTCGAGGGTGGGGGAAA (SEQ ID NO:8537), GAAGCGTCGAGGGTGGGGGAAACGTAG
(SEQ ID NO:8538), GAAAGAAGCGTCGAGGGTGGGGGAAAC (SEQ ID NO:8539),
AAAGAAGCGTCGAGGGTGGGGGAAACG (SEQ ID NO:8540), TAGAAAGAAGCGTCGAGGGTGGGGGAA
(SEQ ID NO:8541), ATGCGGTTTTTGGGCGTTCGGTATGGG (SEQ ID NO:8542),
GGTCGGGGGTAGGCGAGGAATTTGTT (SEQ ID NO:8543), GCGGTTTTTGGGCGTTCGGTATGGGTT
(SEQ ID NO:8544), AAGAGGAAGTAGCGGTCGGGGGGTAGG (SEQ ID NO:8545),
TCGTTGTTAGGTCGGGGGGTGAGGTTGT (SEQ ID NO:8546)

FIGURE 5 CONTINUED

| Target904 | chr8:70984378-70984394 | AGAAAGAAGCGTCGAGGGTGGGGGAAA (SEQ ID NO:8547), GAAGCGTCGAGGGTGGGGGAAACGTAG (SEQ ID NO:8548), GAAAGAAGCGTCGAGGGTGGGGGAAAC (SEQ ID NO:8549), AAAGAAGCGTCGAGGGTGGGGGAAACG (SEQ ID NO:8550), TAGAAAGAAGCGTCGAGGGTGGGGGAA (SEQ ID NO:8551), AAGAGGAAGTAGCGGTCGGGGGGTAGG (SEQ ID NO:8552), TCGTTGTTAGGTCGGGGGTGAGGTTGT (SEQ ID NO:8553), GTTAAGAGGAAGTAGCGGTCGGGGGGT (SEQ ID NO:8554), AGTCGTTGTTAGGTCGGGGGTGAGGTT (SEQ ID NO:8555), AAGTCGTTGTTAGGTCGGGGGTGAGGT (SEQ ID NO:8556) |
|---|---|---|
| Target905 | chr8:70984421-70984445 | AGAAAGAAGCGTCGAGGGTGGGGGAAA (SEQ ID NO:8557), GAAGCGTCGAGGGTGGGGGAAACGTAG (SEQ ID NO:8558), GAAAGAAGCGTCGAGGGTGGGGGAAAC (SEQ ID NO:8559), AAAGAAGCGTCGAGGGTGGGGGAAACG (SEQ ID NO:8560), TAGAAAGAAGCGTCGAGGGTGGGGGAA (SEQ ID NO:8561), TCGTTGTTAGGTCGGGGGTGAGGTTGT (SEQ ID NO:8562), AGTCGTTGTTAGGTCGGGGGTGAGGTT (SEQ ID NO:8563), AAGTCGTTGTTAGGTCGGGGGTGAGGT (SEQ ID NO:8564), GTCGTTGTTAGGTCGGGGGTGAGGTTGT (SEQ ID NO:8565), GTCGTTGTTAGGTCGGGGGTGAGGTTG (SEQ ID NO:8566) |
| Target906 | chr8:70984535-70984567 | GCGGTTTGGAAGAGAGAGGGAAAGGAGG (SEQ ID NO:8567), AGCGGTTTGGAAGAGAGAGGGAAAGGA (SEQ ID NO:8568), AGCGGTTTGGAAGAGAGAGGGAAAGGAGG (SEQ ID NO:8569), GCGGTTTGGAAGAGAGAGGGAAAGGAGGA (SEQ ID NO:8570), TGGTAGCGGTTTGGAAGAGAGAGGGAA (SEQ ID NO:8571), GGTTGCGGGCGTTTTGAAGATTCGGGA (SEQ ID NO:8572), TCGGTTGCGGGCGTTTTGAAGATTCGG (SEQ ID NO:8573), GGAGTTTAGAAGTTCGGTTGCGGGCGT (SEQ ID NO:8574), CGGTTGCGGGCGTTTTGAAGATTCGGG (SEQ ID NO:8575), AGGAGTTTAGAAGTTCGGTTGCGGGCG (SEQ ID NO:8576) |
| Target907 | chr8:92606987-92607479 | GCGGTTGGATGTGAGGGCGATTTGGTT (SEQ ID NO:8577), GGTAGGCGGTTGGATGTGAGGGCGATT (SEQ ID NO:8578), ATTGGTAGGCGGTTGGATGTGAGGGCG (SEQ ID NO:8579), AATTGGTAGGCGGTTGGATGTGAGGGC (SEQ ID NO:8580), GTAGGCGGTTGGATGTGAGGGCGATTT (SEQ ID NO:8581), TGGAGTAGTGAGGTAGGAAGGGGATATTCGT (SEQ ID NO:8582), GGAGTAGTGAGGTAGGAAGGGGATATTCGT (SEQ ID NO:8583), TGGAGTAGTGAGGTAGGAAGGGGATATTCG (SEQ ID NO:8584), TGGTTGGTGAGGAAGTTGAAGGTTAAGGAA (SEQ ID NO:8585), ATGGTTGGTGAGGAAGTTGAAGGTTAAGGA (SEQ ID NO:8586) |
| Target908 | chr8:97171868-97171902 | CGTGTTGAGGTTTCGGAGTAGTCGGGA (SEQ ID NO:8587), TCGTGTTGAGGTTTCGGAGTAGTCGGG (SEQ ID NO:8588), TCGTGTTGAGGTTTCGGAGTAGTCGGGA (SEQ ID NO:8589), CGTGTTGAGGTTTCGGAGTAGTCGGGAG (SEQ ID NO:8590), CGTGTTGAGGTTTCGGAGTAGTCGGGAGT (SEQ ID NO:8591), GGGTGGGATGGTTAGTCGGGTTGGAGT (SEQ ID NO:8592), TGGGTGGGATGGTTAGTCGGGTTGGAG (SEQ ID NO:8593), TTGCGTTGGGTGGGATGGTTAGTCGGG (SEQ ID NO:8594), GCGTTGGGTGGGATGGTTAGTCGGGTT (SEQ ID NO:8595), TTGGGTGGGATGGTTAGTCGGGTTGGA (SEQ ID NO:8596) |
| Target909 | chr8:97171960-97172022 | GCGGCGTTAGGATTAGGGGGTTGTTCG (SEQ ID NO:8597), CGCGGCGTTAGGATTAGGGGGTTGTTC (SEQ ID NO:8598), TCGGAGGGCGTAGGGGTTTTAGTTCGGT (SEQ ID NO:8599), GCGCGGCGTTAGGATTAGGGGGTTGTT (SEQ ID NO:8600), GTCGGAGGGCGTAGGGGTTTTAGTTCGGT (SEQ ID NO:8601), TCGCGCGGGGTTTTTCGTTGGTTTTTGT (SEQ ID NO:8602), GTCGCGCGGGGTTTTTCGTTGGTTTTTG (SEQ ID NO:8603), GTCGCGCGGGGTTTTTCGTTGGTTTTTGT (SEQ ID NO:8604), CGGGTAGTTTTTTGGTTTTGGCGTCGCG (SEQ ID NO:8605), GGCGTCGGGTAGTTTTTTGGTTTTGGCG (SEQ ID NO:8606) |
| Target910 | chr8:97172128-97172151 | GTGGGATTTTTTAGTGTCGGTTTTGTTTAGGGT (SEQ ID NO:8607), TGTGGGATTTTTTAGTGTCGGTTTTGTTTAGGG (SEQ ID NO:8608), TGTGGGATTTTTTAGTGTCGGTTTTGTTTAGGGT (SEQ ID NO:8609), GTGGGATTTTTTAGTGTCGGTTTTGTTTAGGGTT (SEQ ID NO:8610), TTGTGGGATTTTTTAGTGTCGGTTTTGTTTAGGG (SEQ ID NO:8611), AGGCGGATGAATTCGGTTGGAGAGGGG (SEQ ID NO:8612), GTTGGAGAGGGGTCGGGATGGGGATTG (SEQ ID NO:8613), GGAGGACGGGAGGTAGTAGGCGGATGA (SEQ ID NO:8614), AATTCGGTTGGAGAGGGGTCGGGATGG (SEQ ID NO:8615), AGAGGGGTCGGGATGGGGATTGATGGA (SEQ ID NO:8616) |
| Target911 | chr8:99960237-99960958 | TAGTCGGGGGTTGGGAGGAGAGTTCGT (SEQ ID NO:8617), AGGTTAGTGCGGGGCGAGGTGAGTTTT (SEQ ID NO:8618), ATTTTCGAGGTTAGTGCGGGGCGAGGT (SEQ ID NO:8619), AGTTCGTGGATAGGAGGAGGGGGCGAT (SEQ ID NO:8620), GGTTGGGTTGGGTTGGGTGTTGTTCGG (SEQ ID NO:8621), TTAGGTTTTTAGGGGGTGGGGTGGGGG (SEQ ID NO:8622), CGGATGGTAAGTCGGCGTGTAAGAGCG (SEQ ID NO:8623), CGTTGTCGTCGCGTTTTGTGGTCGTTT (SEQ ID NO:8624), CGGATGGTAAGTCGGCGTGTAAGAGCGA (SEQ ID NO:8625), TCGGATGGTAAGTCGGCGTGTAAGAGCG (SEQ ID NO:8626) |
| Target912 | chr8:99960991-99961662 | CGGGTGGGGAGGGAGATTTAGGTGTGG (SEQ ID NO:8627), GTTTTCGGGGGGGTTTTGGAGTCGGGTG (SEQ ID NO:8628), GTTTTGGAGTCGGGTGGGGAGGGAGAT (SEQ ID NO:8629), TTTTCGGGGGGGTTTTGGAGTCGGGTGG (SEQ ID NO:8630), GGTTTTCGGGGGGGTTTTGGAGTCGGGT (SEQ ID NO:8631), AAAAGGTAGGGTCGGGAAGGGGAAGCG (SEQ ID NO:8632), TCGTGATGGTGGAGCGGGTGATTTCGT (SEQ ID NO:8633), CGTGATGGTGGAGCGGGTGATTTCGTG (SEQ ID NO:8634), ATTAGAGGTCGGAGGGCGTGGGGTTTC (SEQ ID NO:8635), GAATTAGAGGTCGGAGGGCGTGGGGTT (SEQ ID NO:8636) |

FIGURE 5 CONTINUED

Target913    chr8:99986368-99986430    TCGTTAGTGTTTTTAGGGGAGGTTGCGGA (SEQ ID NO:8637), TCGTTAGTGTTTTTAGGGGAGGTTGCGGAA (SEQ ID NO:8638), ATCGTTAGTGTTTTTAGGGGAGGTTGCGGA (SEQ ID NO:8639), AGGGGAGGTTGCGGAAAAGTAGAGGTAATG (SEQ ID NO:8640), GGGGAGGTTGCGGAAAAGTAGAGGTAATGA (SEQ ID NO:8641), GGGTTTGTGGGGGAGGGTCGAGTTGGAT (SEQ ID NO:8642), TTGGGTTTGTGGGGGAGGGTCGAGTTGG (SEQ ID NO:8643), GGTTTGTGGGGGAGGGTCGAGTTGGATG (SEQ ID NO:8644), GGGTTTGTGGGGGAGGGTCGAGTTGGA (SEQ ID NO:8645), GGTTTGTGGGGGAGGGTCGAGTTGGATGT (SEQ ID NO:8646)

Target914    chr8:99986453-99986707    GCGGGGTTGGGTTCGGTCGGTATAAGT (SEQ ID NO:8647), TCGGTGAGGCGTTCGGTATGGATTGGG (SEQ ID NO:8648), ATTCGAGACGGAGCGGGGGTTATACGG (SEQ ID NO:8649), CGGTGAGGCGTTCGGTATGGATTGGGT (SEQ ID NO:8650), GGAGCGGTTTTGGGCGATGGGTTTGAC (SEQ ID NO:8651), CGGAAGGCGGGAAAATGCGAGTGGTTT (SEQ ID NO:8652), CGGAAGGCGGGAAAATGCGAGTGGTT (SEQ ID NO:8653), CGGAAGGCGGGAAAATGCGAGTGGTTTT (SEQ ID NO:8654), TCGTAGGGTTTTTGGGTTGTTCGCGGA (SEQ ID NO:8655), GGAAGGCGGGAAAATGCGAGTGGTTTT (SEQ ID NO:8656)

Target915    chr8:99986725-99986813    ATTCGAGACGGAGCGGGGGTTATACGG (SEQ ID NO:8657), TTCGGGTGGGGGATAGGTCGTCGAGTT (SEQ ID NO:8658), TTTTCGGGTGGGGGATAGGTCGTCGAGT (SEQ ID NO:8659), TTTTCGGGTGGGGGATAGGTCGTCGAG (SEQ ID NO:8660), TCGGGTGGGGGATAGGTCGTCGAGTTC (SEQ ID NO:8661), CGGAAGGCGGGAAAATGCGAGTGGTTT (SEQ ID NO:8662), GCGTAGGGAAGGGCGGATTTTCGGGAT (SEQ ID NO:8663), CGGAAGGCGGGAAAATGCGAGTGGTT (SEQ ID NO:8664), CGGAAGGCGGGAAAATGCGAGTGGTTTT (SEQ ID NO:8665), TCGTAGGGTTTTTGGGTTGTTCGCGGA (SEQ ID NO:8666)

Target916    chr8:99986839-99987001    TTTTGCGGGAGGAGGAGAGGGTTTCGG (SEQ ID NO:8667), GGGTTTTGCGGGAGGAGGAGAGGGTTT (SEQ ID NO:8668), TTCGGGTGGGGGATAGGTCGTCGAGTT (SEQ ID NO:8669), TTTCGGGTGGGGGATAGGTCGTCGAGT (SEQ ID NO:8670), TTTTCGGGTGGGGGATAGGTCGTCGAG (SEQ ID NO:8671), TAATAGGGGAGGGAGGCGGTGGAGGAG (SEQ ID NO:8672), TTAATAGGGGAGGGAGGCGGTGGAGGA (SEQ ID NO:8673), GGGAGGGAGGCGGTGGAGGAGATTTTA (SEQ ID NO:8674), TTTAATAGGGGAGGGAGGCGGTGGAGG (SEQ ID NO:8675), TTAATAGGGGAGGGAGGCGGTGGAGGAG (SEQ ID NO:8676)

Target917    chr8:102504296-102504696    TCGGAGAAGGGTTTTATTTGAGCGCGT (SEQ ID NO:8677), CGGAGAAGGGGTTTTATTTGAGCGCGTT (SEQ ID NO:8678), TCGGAGAAGGGGTTTTATTTGAGCGCGTT (SEQ ID NO:8679), CGGAGAAGGGGTTTTATTTGAGCGCGT (SEQ ID NO:8680), TCGGAGAAGGGGTTTTATTTGAGCGCG (SEQ ID NO:8681), CGAGTTGCGCGATGATTGGTTGGGGAG (SEQ ID NO:8682), AGGGATTGTGGGTCGAGCGGAAGAGTT (SEQ ID NO:8683), GAGTTGCGCGATGATTGGTTGGGGAGT (SEQ ID NO:8684), AGTTGCGCGATGATTGGTTGGGGAGTT (SEQ ID NO:8685), GAGTAGAAAGTGGCGGATTTGGGCGGT (SEQ ID NO:8686)

Target918    chr8:104384375-104384474    GGTGGGAGGGATAGGGCGGTAGTGAGA (SEQ ID NO:8687), TTTTGGGAAGGGTGGGAGGGATAGGGC (SEQ ID NO:8688), GAAGGGTGGGAGGGATAGGGCGGTAGT (SEQ ID NO:8689), TGGGAGGGATAGGGCGGTAGTGAGAGT (SEQ ID NO:8690), AAGGGTGGGAGGGATAGGGCGGTAGTG (SEQ ID NO:8691), AGAGTTGGACGGATGTTTTGTGGGGGT (SEQ ID NO:8692), GTTGGACGGATGTTTTGTGGGGGTTGT (SEQ ID NO:8693), AGTTGGACGGATGTTTTGTGGGGGTTGT (SEQ ID NO:8694), AGTTGGACGGATGTTTTGTGGGGGTTG (SEQ ID NO:8695), GAGTTGGACGGATGTTTTGTGGGGGTT (SEQ ID NO:8696)

Target919    chr8:104384518-104384585    GGATTTGGGTTTGGGTTAGGGCGGTGT (SEQ ID NO:8697), TGGATTTGGGTTTGGGTTAGGGCGGTG (SEQ ID NO:8698), TGGATTTGGGTTTGGGTTAGGGCGGTGT (SEQ ID NO:8699), ATGGATTTGGGTTTGGGTTAGGGCGGT (SEQ ID NO:8700), TGGGGTTGGTGGTTACGTTTGTTTGCG (SEQ ID NO:8701), AGAGTTGGACGGATGTTTTGTGGGGGT (SEQ ID NO:8702), GTTGGACGGATGTTTTGTGGGGGTTGT (SEQ ID NO:8703), AGTTGGACGGATGTTTTGTGGGGGTTGT (SEQ ID NO:8704), AGTTGGACGGATGTTTTGTGGGGGTTG (SEQ ID NO:8705), GAGTTGGACGGATGTTTTGTGGGGGTT (SEQ ID NO:8706)

Target920    chr8:104384675-104384817    CGGAAAGGGAAATGAAGGGGTTCGGCG (SEQ ID NO:8707), GGAAAGGGAAATGAAGGGGTTCGGCGT (SEQ ID NO:8708), TCGGAAAGGGAAATGAAGGGGGTTCGGC (SEQ ID NO:8709), GTCGGAAAGGGAAATGAAGGGGTTCGGC (SEQ ID NO:8710), TCGGAAAGGGAAATGAAGGGGTTCGGCG (SEQ ID NO:8711), AGGTTTTTAGAGGGTTAGCGTCGGGTT (SEQ ID NO:8712), AGGTTTTTAGAGGGTTAGCGTCGGGTTT (SEQ ID NO:8713), AGGTTTTTAGAGGGTTAGCGTCGGGTTTT (SEQ ID NO:8714), TAGGTTTTTAGAGGGTTAGCGTCGGGTTT (SEQ ID NO:8715), AGGTTTTTAGAGGGTTAGCGTCGGGTTTTT (SEQ ID NO:8716)

Target921    chr8:104384851-104384941    GGAAATGAACGGTTCGAGTGTTTTTTAGGGG (SEQ ID NO:8717), GGAAATGAACGGTTCGAGTGTTTTTTAGGGGT (SEQ ID NO:8718), TGGAAATGAACGGTTCGAGTGTTTTTTAGGGG (SEQ ID NO:8719), TGGAAATGAACGGTTCGAGTGTTTTTTAGGGGT (SEQ ID NO:8720), GAAATGAACGGTTCGAGTGTTTTTTAGGGGT (SEQ ID NO:8721)

Target922    chr8:105478778-105478799    TCGTCGAGAAGGGGCGTTTGAAAGGGA (SEQ ID NO:8722), GTCGTCGAGAAGGGGCGTTTGAAAGGG (SEQ ID NO:8723), GGTTGTCGTCGAGAAGGGGCGTTTGAA (SEQ ID NO:8724), CGGTTGTCGTCGAGAAGGGGCGTTTGA (SEQ ID NO:8725), TGTCGTCGAGAAGGGGCGTTTGAAAGG (SEQ ID NO:8726), TTTCGCGGTATTTACGGAGGTTCGGGT (SEQ ID NO:8727), CGCGGTATTTACGGAGGTTCGGGTAGT (SEQ ID NO:8728), TCGCGGTATTTACGGAGGTTCGGGTAGT

FIGURE 5 CONTINUED

{SEQ ID NO:8729}, TCGCGGTATTTACGGAGGTTCGGGTAG {SEQ ID NO:8730},
GTTTCGCGGTATTTACGGAGGTTCGGG {SEQ ID NO:8731}

| | | |
|---|---|---|
| Target923 | chr8:105478816-105479009 | GCGGGGCGGGTATTTTGGTGTTTTGGT {SEQ ID NO:8732}, GGCGGGGCGGGTATTTTGGTGTTTTGG {SEQ ID NO:8733}, CGGCGGGGCGGGTATTTTGGTGTTTTG {SEQ ID NO:8734}, CGGGGGCGGGTATTTTGGTGTTTTGGTG {SEQ ID NO:8735}, GCGAGGCGGTTTTGTTGAGGATTTCGG {SEQ ID NO:8736}, GAGGTGGTCGCACGTGTTGGTGGAGGAC {SEQ ID NO:8737}, GAGGTGGTCGACGTGTTGGTGGAGGA {SEQ ID NO:8738}, AGGTGGTCGACGTGTTGGTGGAGGAC {SEQ ID NO:8739}, GGAGGTGGTCGACGTGTTGGTGGAGGA {SEQ ID NO:8740}, TCGGAGGTGGTCGACGTGTTGGTGGAG {SEQ ID NO:8741} |
| Target924 | chr8:105479061-105479141 | TGTATGTGCGTGTGTGTCGATGTTTT {SEQ ID NO:8742}, TGTATGTGCGTGTGTGTGTCGATGTTTTC {SEQ ID NO:8743}, AGTTCGGGGGTTGTCGGTGGGGATTTT {SEQ ID NO:8744}, GAGGTGGTCGACGTGTTGGTGGAGGAT {SEQ ID NO:8745}, GTTCGGGGGTTGTCGGTGGGGATTTTG {SEQ ID NO:8746}, TCGGGGGTTGTCGGTGGGGATTTTGTA {SEQ ID NO:8747}, TTCGGGGGTTGTCGGTGGGGATTTTGT {SEQ ID NO:8748} |
| Target925 | chr8:105479283-105479327 | CGGGGTTTTATTCGGTTCGGGTTGCGC {SEQ ID NO:8749}, GCGGGGTTTTATTCGGTTCGGGTTGCG {SEQ ID NO:8750}, CGCGGGGGTTTTATTCGGTTCGGGTTGC {SEQ ID NO:8751}, GCGCGGGGTTTTATTCGGTTCGGGTTG {SEQ ID NO:8752}, GCGCGGGGTTTTATTCGGTTCGGGTT {SEQ ID NO:8753}, TCGGGGGGGAGGAGTCGTATATGCGGTT {SEQ ID NO:8754}, TTCGGGGGGAGGAGTCGTATATGCGGT {SEQ ID NO:8755}, TTTCGGGGGGAGGAGTCGTATATGCGG {SEQ ID NO:8756}, CGGGGGGAGGAGTCGTATATGCGGTTA {SEQ ID NO:8757}, TCGGGGGGAGGAGTCGTATATGCGGTTA {SEQ ID NO:8758} |
| Target926 | chr8:116679514-116680058 | TTGAGGCGGGTGTATTAAGGGATGCGA {SEQ ID NO:8759}, TGAGGCGGGTGTATTAAGGGATGCGAT {SEQ ID NO:8760}, TGTTTTGAGTCGTTTTGAGGCGGGTGT {SEQ ID NO:8761}, TTTGAGGCGGGTGTATTAAGGGATGCG {SEQ ID NO:8762}, TTTGAGGCGGGTGTATTAAGGGATGCGA {SEQ ID NO:8763}, GGGGTTCGTGATAAGCGGGGCGTAGAT {SEQ ID NO:8764}, CGCGGGTTAGGGGATATTGGTCGGTGA {SEQ ID NO:8765}, TCGGGAGGGTCGGGAGGGTTTTAGAGA {SEQ ID NO:8766}, TGTCGCGCGGGTTAGGGGATATTGGTC {SEQ ID NO:8767}, AGGGTCGGGAGGGTTTTAGAGACGGGT {SEQ ID NO:8768} |
| Target927 | chr8:116680083-116680187 | CGAGTTTTTAGAAAATTTGTAGTGGCGGCGG {SEQ ID NO:8769}, ACGAGTTTTTAGAAAATTTGTAGTGGCGGCGG {SEQ ID NO:8770}, ACGAGTTTTTAGAAAATTTGTAGTGGCGGCG {SEQ ID NO:8771}, TACGAGTTTTTAGAAAATTTGTAGTGGCGGCGG {SEQ ID NO:8772}, TACGAGTTTTTAGAAAATTTGTAGTGGCGGCG {SEQ ID NO:8773}, GGGGTTCGTGATAAGCGGGGCGTAGAT {SEQ ID NO:8774}, TTGGAGGTGGTTGGATTCGAGGGGTCG {SEQ ID NO:8775}, GGAGGTGGTTGGATTCGAGGGGTCGTC {SEQ ID NO:8776}, CGTAGCGGAGGAGTTGGAGGTGGTTGG {SEQ ID NO:8777}, TTTTTGGGGGTTCGTGATAAGCGGGGC {SEQ ID NO:8778} |
| Target928 | chr8:142696266-142696666 | ACGGAGGTTCGGGAAGGGGTTTTAGGA {SEQ ID NO:8779}, AACGGAGGTTCGGGAAGGGGTTTTAGG {SEQ ID NO:8780}, AACGGAGGTTCGGGAAGGGGTTTTAGGA {SEQ ID NO:8781}, ACGGAGGTTCGGGAAGGGGTTTTAGGAT {SEQ ID NO:8782}, CGGAGGTTCGGGAAGGGGTTTTAGGAT {SEQ ID NO:8783}, GTAGGTCGGGGGCGGGGGAAAATGTAT {SEQ ID NO:8784}, GTTTATAGTGTAGGTCGGGGGCGGGGG {SEQ ID NO:8785}, TATAGTGTAGGTCGGGGGCGGGGGAAA {SEQ ID NO:8786}, TTATAGTGTAGGTCGGGGGCGGGGGAA {SEQ ID NO:8787}, TTTATAGTGTAGGTCGGGGGCGGGGGA {SEQ ID NO:8788} |
| Target929 | chr8:142850598-142850645 | GGCGAGGTTGGTAGGTATATGCGTGGG {SEQ ID NO:8789}, GGCGAGGTTGGTAGGTATATGCGTGGG {SEQ ID NO:8790}, AGGCGAGGTTGGTAGGTATATGCGTGGG {SEQ ID NO:8791}, GCGAGGTTGGTAGGTATATGCGTGGGT {SEQ ID NO:8792}, AGGCGAGGTTGGTAGGTATATGCGTGG {SEQ ID NO:8793}, GGGAGGTTTGTGTGGGGAGGATAGGGT {SEQ ID NO:8794}, GGGAGGTTTGTGTGGGGAGGATAGGGTT {SEQ ID NO:8795}, GGGAGGTTTGTGTGGGGAGGATAGGGTTG {SEQ ID NO:8796}, GGAGGTTTGTGTGGGGAGGATAGGGTT {SEQ ID NO:8797}, AGGTTTGTGTGGGGAGGATAGGGTTGT {SEQ ID NO:8798} |
| Target930 | chr8:143667621-143667639 | AGAAGTTGGTCGGGTGTAGGTTGCGGG {SEQ ID NO:8799}, GTTGGTCGGGTGTAGGTTGCGGGGTAG {SEQ ID NO:8800}, AGGTTGCGGGGTAGGTATGAGGGGAGG {SEQ ID NO:8801}, GTCGGGTGTAGGTTGCGGGGTAGGTAT {SEQ ID NO:8802}, CGGGTGTAGGTTGCGGGGTAGGTATGA {SEQ ID NO:8803} |
| Target931 | chr8:144105681-144105731 | GCGGGAGGGAGTTCGGGTTGTGTTTTG {SEQ ID NO:8804}, GTAGCGGGAGGGAGTTCGGGTTGTGTT {SEQ ID NO:8805}, GAGTAGCGGGAGGGAGTTCGGGTTGTG {SEQ ID NO:8806}, TAGGAGTAGCGGGAGGGAGTTCGGGTT {SEQ ID NO:8807}, TTAGGAGTAGCGGGAGGGAGTTCGGGT {SEQ ID NO:8808}, GGGGGTTTAGTTTCGGGTCGGTGTGGA {SEQ ID NO:8809}, GGAGGGGGTTTAGTTTCGGGTCGGTGT {SEQ ID NO:8810}, AGGGGGGTTTAGTTTCGGGTCGGTGTGG {SEQ ID NO:8811}, GCGGAGAGGAGGGGGTTTAGTTTCGGG {SEQ ID NO:8812}, GGGTTGCGGAGAGGAGGGGGTTTAGTT {SEQ ID NO:8813} |
| Target932 | chr8:144105767-144105871 | GCGGATGAGTTTTTGGAGGATGGGCGG {SEQ ID NO:8814}, CGCGGATGAGTTTTTGGAGGATGGGCG {SEQ ID NO:8815}, TCGCGGATGAGTTTTTGGAGGATGGGC {SEQ ID NO:8816}, CGGATGAGTTTTTGGAGGATGGGCGGT {SEQ ID NO:8817}, TGGGGGAGGGAGAGGAAGAGAGTTTCGT |

FIGURE 5 CONTINUED (SEQ ID NO:8818), TTTATAGGGGTTGAGCGGTGGGGGGTG (SEQ ID NO:8819), GCGGGGGTGTTAAGGGGGTAGAGGGTTG (SEQ ID NO:8820), GGGTTGCGGAGAGGGAGGGGGTTTAGTT (SEQ ID NO:8821), GAAGTGGGGTTGGATGGGGTTGCGGAGA (SEQ ID NO:8822), ATGGGTTGCGGAGAGGAGGGGGTTTAG (SEQ ID NO:8823)

Target933     chr8:144105875-144105903     GCGGATGAGTTTTTGGAGGATGGGCGG (SEQ ID NO:8824), CGCGGATGAGTTTTTGGAGGATGGGCG (SEQ ID NO:8825), TTTTGGAGGATGGGCGGTTCGTTTCG (SEQ ID NO:8826), TCGCGGATGAGTTTTTGGAGGATGGGC (SEQ ID NO:8827), CGGATGAGTTTTTGGAGGATGGGCGGT (SEQ ID NO:8828), AAGGGGGTAGAGGTTGTGGATGGGGGA (SEQ ID NO:8829), TTTATAGGGGTTGAGCGGTGGGGGGTG (SEQ ID NO:8830), GCGGGGGTGTTAAGGGGGTAGAGGTTG (SEQ ID NO:8831), TAGAGGGCGGGGGTGTTAAGGGGGTAG (SEQ ID NO:8832), GTAGAGGGCGGGGGTGTTAAGGGGGTA (SEQ ID NO:8833)

Target934     chr8:144105994-144106052     AGGAGTCGTTAGTTTGTGGGTTCGGGA (SEQ ID NO:8834), GGAGTCGTTAGTTTGTGGGTTCGGGAT (SEQ ID NO:8835), AGGAGTCGTTAGTTTGTGGGTTCGGGAT (SEQ ID NO:8836), TAGGAGTCGTTAGTTTGTGGGTTCGGG (SEQ ID NO:8837), TAGGAGTCGTTAGTTTGTGGGTTCGGGA (SEQ ID NO:8838), GTTGACGGAGGGGTGGAGGTATCGTGG (SEQ ID NO:8839), GGTTGACGGAGGGGTGGAGGTATCGTG (SEQ ID NO:8840), AGATTTGTTGGGGGTTGACGGAGGGGT (SEQ ID NO:8841), GATTTGTTGGGGGTTGACGGAGGGGTG (SEQ ID NO:8842), ATTTGTTGGGGGTTGACGGAGGGGTG (SEQ ID NO:8843)

Target935     chr8:145104273-145105390     GGGCGGCGTTGTTGTTGTTGTTGTTGG (SEQ ID NO:8844), TTCGTGGTGTTGTAGGCGAGGTTGGGT (SEQ ID NO:8845), AGTCGTTCGTGGTGTTGTAGGCGAGGT (SEQ ID NO:8846), TGGAGTCGTTCGTGGTGTTGTAGGCGA (SEQ ID NO:8847), TAGGCGAGGTTGGGTAGTTTGGACGGG (SEQ ID NO:8848), ATGGTTTCGGTCGGTCGTTGGTTGTGC (SEQ ID NO:8849), GGCGGGGTGTAGGCGAATGTAGGGGATT (SEQ ID NO:8850), GGTCGTTGGTTGTGCGGTAGGTTGTCG (SEQ ID NO:8851), CGGTCGTTGGTTGTGCGGTAGGTTGTC (SEQ ID NO:8852), GTCGGTCGTTGGTTGTGCGGTAGGTTG (SEQ ID NO:8853)

Target936     chr8:145105404-145106067     GGTGGTTGGGTTTGCGGTATTGGGACG (SEQ ID NO:8854), ATCGGAGCGGGAAGTGGATTTGGGGAG (SEQ ID NO:8855), GAGTTTTCGGGTGGTTGGGTTTGCGGT (SEQ ID NO:8856), GGGTGGTTGGGTTTGCGGTATTGGGAC (SEQ ID NO:8857), TTTAGGGGGAGGGTATCGGAGCGGGAA (SEQ ID NO:8858), TTTAGCGCGGTTTTTGGGGGATTCGGG (SEQ ID NO:8859), GGGAAGGTCGGTTAGGTAGAGGTGGCG (SEQ ID NO:8860), CGGGAAGGTCGGTTAGGTAGAGGTGGC (SEQ ID NO:8861), GGAGGTGTTTAGCGCGGTTTTTGGGGG (SEQ ID NO:8862), TGGTGGAGTACGGAGGTGTTTAGCGCG (SEQ ID NO:8863)

Target937     chr8:145106087-145106384     GGTAAGTATAGATGAGGGGCGCGCGGT (SEQ ID NO:8864), GGTGGGGCGGGGTTTTTCGGGTTTTTA (SEQ ID NO:8865), AGGTAAGTATAGATGAGGGGCGCGCGG (SEQ ID NO:8866), AAGTATAGATGAGGGGCGCGCGGTTGG (SEQ ID NO:8867), GGAAAGGTTAGTGTTTGCGGGGGGCGAT (SEQ ID NO:8868), GGCCGGTGGTTATGGGGGATTCGGAGGAT (SEQ ID NO:8869), GGTTTTCGTGGTTTATGGGGGCGGGTG (SEQ ID NO:8870), TTGTTCGGTGGGGAGGGGATTGCGTAG (SEQ ID NO:8871), TTATGGGGGCGGGTGATGGACGTTGTT (SEQ ID NO:8872), TTTATGGGGGCGGGTGATGGACGTTGT (SEQ ID NO:8873)

Target938     chr9:1042442-1042462     GGAAGGGTTTGATACGGAATTTGATTAAGGTTGG (SEQ ID NO:8874), TGGAAGGGTTTGATACGGAATTTGATTAAGGTTGG (SEQ ID NO:8875), GGAAGGGTTTGATACGGAATTTGATTAAGGTTGGA (SEQ ID NO:8876), TGGAAGGGTTTGATACGGAATTTGATTAAGGTTGGA (SEQ ID NO:8877), AGTTGGAAGGGTTTGATACGGAATTTGATTAAGGT (SEQ ID NO:8878), TCGGAGGGTTTTTGCGTTTTTGGGGTT (SEQ ID NO:8879), TTCGGAGGGTTTTTGCGTTTTTGGGGT (SEQ ID NO:8880), GTTCGGAGGGTTTTTGCGTTTTTGGGGT (SEQ ID NO:8881), GTTCGGAGGGTTTTTGCGTTTTTGGGG (SEQ ID NO:8882), AGTTCGGAGGGTTTTTGCGTTTTTGGGG (SEQ ID NO:8883)

Target939     chr9:1042502-1042523     CGGAGTAGTCGTTTGAGGGTTGGAAGG (SEQ ID NO:8884), CGGAGTAGTCGTTTGAGGGTTGGAAGGA (SEQ ID NO:8885), TCGGAGTAGTCGTTTGAGGGTTGGAAGG (SEQ ID NO:8886), TCGGAGTAGTCGTTTGAGGGTTGGAAGGA (SEQ ID NO:8887), TCGGAGTAGTCGTTTGAGGGGTTGGAAG (SEQ ID NO:8888), GGCGGTCGGGGGAGGATAGTGATC (SEQ ID NO:8889), GGCGGTCGGGGGAGGATAGTGAT (SEQ ID NO:8890), GGCGGTCGGGGGAGGATAGTGA (SEQ ID NO:8891), GCGGTCGGGGGAGGATAGTGATC (SEQ ID NO:8892), GGCGGTCGGGGGAGGATAGTG (SEQ ID NO:8893)

Target940     chr9:1042552-1042664     GGGGGCGTTGGGTTTTAGGTTCGGATG (SEQ ID NO:8894), GGAAGTCGGGGGCGTTGGGTTTTAGGT (SEQ ID NO:8895), AGTCGGGGGCGTTGGGTTTTAGGTTCG (SEQ ID NO:8896), GGGGGCGTTGGGTTTTAGGTTCGGATGT (SEQ ID NO:8897), CGGGGGCGTTGGGTTTTAGGTTCGGAT (SEQ ID NO:8898), AAACGTTAGGGTTATTCGCGGCGGGTC (SEQ ID NO:8899), AAACGTTAGGGTTATTCGCGGCGGGTCG (SEQ ID NO:8900), CGTTAGGGTTATTCGCGGCGGGTCGTC (SEQ ID NO:8901), TAAACGTTAGGGTTATTCGCGGCGGGT (SEQ ID NO:8902), GTTAGGGTTATTCGCGGCGGGTCGTC (SEQ ID NO:8903)

Target941     chr9:1042682-1042693     GGGGGCGTTGGGTTTTAGGTTCGGATG (SEQ ID NO:8904), GGAAGTCGGGGGCGTTGGGTTTTAGGT (SEQ ID NO:8905), AGTCGGGGGCGTTGGGTTTTAGGTTCG (SEQ ID NO:8906), GGGGCGTTGGGTTTTAGGTTCGGATGT (SEQ ID NO:8907), CGGGGGCGTTGGGTTTTAGGTTCGGAT (SEQ ID NO:8908), AAACGTTAGGGTTATTCGCGGCGGGTC (SEQ ID NO:8909),

FIGURE 5 CONTINUED

|  |  |  |
|---|---|---|
|  |  | AACGTTAGGGTTATTCGCGGCGGGTCG (SEQ ID NO:8910), CGTTAGGGTTATTCGCGGCGGGTCGTC (SEQ ID NO:8911), TAAACGTTAGGGTTATTCGCGGCGGGT (SEQ ID NO:8912), GTTAGGGTTATTCGCGGCGGGTCGTC (SEQ ID NO:8913) |
| Target942 | chr9:1042703-1042744 | GGGGGCGTTGGGTTTTAGGTTCGGATG (SEQ ID NO:8914), GGAAGTCGGGGGCGTTGGGTTTTAGGT (SEQ ID NO:8915), AGTCGGGGGCGTTGGGTTTTAGGTTCG (SEQ ID NO:8916), GGGGCGTTGGGTTTTAGGTTCGGATGT (SEQ ID NO:8917), CGGGGGCGTTGGGTTTTAGGTTCGGAT (SEQ ID NO:8918), AAACGTTAGGGTTATTCGCGGCGGGTCG (SEQ ID NO:8919), AACGTTAGGGTTATTCGCGGCGGGTCG (SEQ ID NO:8920), CGTTAGGGTTATTCGCGGCGGGTCGTC (SEQ ID NO:8921), TAAACGTTAGGGTTATTCGCGGCGGGT (SEQ ID NO:8922), GTTAGGGTTATTCGCGGCGGGTCGTC (SEQ ID NO:8923) |
| Target943 | chr9:1042753-1042760 | GGGTTTTAGGTTCGGATGTTGAGCGCGG (SEQ ID NO:8924), TGGGTTTTAGGTTCGGATGTTGAGCGCG (SEQ ID NO:8925), GGTTTTAGGTTCGGATGTTGAGCGCGG (SEQ ID NO:8926), GGGTTTTAGGTTCGGATGTTGAGCGCG (SEQ ID NO:8927), GGTTTTAGGTTCGGATGTTGAGCGCGGA (SEQ ID NO:8928), GTCGAAAATTTATTGACGCGGCGAGGT (SEQ ID NO:8929), TCGAAAATTTATTGACGCGGCGAGGTT (SEQ ID NO:8930), GTCGAAAATTTATTGACGCGGCGAGGTT (SEQ ID NO:8931), TCGAAAATTTATTGACGCGGCGAGGT (SEQ ID NO:8932), CGAAAATTTATTGACGCGGCGAGGTTAGG (SEQ ID NO:8933) |
| Target944 | chr9:1042852-1042870 | AGTGTTGTTAGTTTGGTTTCGTCGCGT (SEQ ID NO:8934), AGGATCGTTAGAGTTGGGGGGGAGATTAAAGT (SEQ ID NO:8935), AGTGTTGTTAGTTTGGTTTCGTCGCGTTAAT (SEQ ID NO:8936), GAGGATCGTTAGAGTTGGGGGGGAGATTAAAG (SEQ ID NO:8937), TTTGGTTTCGTCGCGTTAATAAATTTTCGGC (SEQ ID NO:8938) |
| Target945 | chr9:13323162-13323186 | GGTCGTTTTTGTGGTGATTTCGTCGTGG (SEQ ID NO:8939), GGTCGTTTTTGTGGTGATTTCGTCGTGGT (SEQ ID NO:8940), TGGTCGTTTTTGTGGTGATTTCGTCGTGG (SEQ ID NO:8941), TGGTCGTTTTTGTGGTGATTTCGTCGTGGT (SEQ ID NO:8942), TCGTTTTTGTGGTGATTTCGTCGTGGT (SEQ ID NO:8943), TGCGGGGAAGAATGATAATTACGTAGGGAG (SEQ ID NO:8944), TGCGGGGAAGAATGATAATTACGTAGGGAGA (SEQ ID NO:8945), ATGCGGGGAAGAATGATAATTACGTAGGGAG (SEQ ID NO:8946), GCGGGGAAGAATGATAATTACGTAGGGAGAA (SEQ ID NO:8947), TGCGGGGAAGAATGATAATTACGTAGGGAGA (SEQ ID NO:8948) |
| Target946 | chr9:13323204-13323239 | GGTCGTTTTTGTGGTGATTTCGTCGTGG (SEQ ID NO:8949), GGTCGTTTTTGTGGTGATTTCGTCGTGGT (SEQ ID NO:8950), TGGTCGTTTTTGTGGTGATTTCGTCGTGG (SEQ ID NO:8951), TGGTCGTTTTTGTGGTGATTTCGTCGTGGT (SEQ ID NO:8952), TCGTTTTTGTGGTGATTTCGTCGTGGT (SEQ ID NO:8953), CGACGAAGGAGTTGGTGGAGAGTAGGA (SEQ ID NO:8954), ACGAAGGAGTTGGTGGAGAGTAGGATCGG (SEQ ID NO:8955), CGAAGGAGTTGGTGGAGAGTAGGATCGG (SEQ ID NO:8956), CGAAGGAGTTGGTGGAGAGTAGGATCGGA (SEQ ID NO:8957), ACGAAGGAGTTGGTGGAGAGTAGGATCGGA (SEQ ID NO:8958) |
| Target947 | chr9:13323300-13323322 | TGGTTGTTGTTTAAGGAGTTCGGCGAGA (SEQ ID NO:8959), TTGGTTGTTGTTTAAGGAGTTCGGCGAG (SEQ ID NO:8960), TTGGTTGTTGTTTAAGGAGTTCGGCGAGA (SEQ ID NO:8961), TGGTTGTTGTTTAAGGAGTTCGGCGAGAT (SEQ ID NO:8962), TTTGGTTGTTGTTTAAGGAGTTCGGCGAG (SEQ ID NO:8963), TCGGAGTTAGGAGTTGGGCGTTGAGAA (SEQ ID NO:8964), TTCGGAGTTAGGAGTTGGGCGTTGAGA (SEQ ID NO:8965), CGACGAAGGAGTTGGTGGAGAGTAGGA (SEQ ID NO:8966), CGGAGTTAGGAGTTGGGCGTTGAGAAG (SEQ ID NO:8967), CGGAGTTAGGAGTTGGGCGTTGAGAAGA (SEQ ID NO:8968) |
| Target948 | chr9:14346424-14346730 | ACGTGTGATAGGAGTCGTTTGGTTAAGTGG (SEQ ID NO:8969), CGTGTGATAGGAGTCGTTTGGTTAAGTGGA (SEQ ID NO:8970), ACGTGTGATAGGAGTCGTTTGGTTAAGTGGA (SEQ ID NO:8971), CGTGTGATAGGAGTCGTTTGGTTAAGTGGAA (SEQ ID NO:8972), ACGTGTGATAGGAGTCGTTTGGTTAAGTGGAA (SEQ ID NO:8973), GCGTGGATTGTTGGGTTTGGGGACGTT (SEQ ID NO:8974), GACGTGTGGCGTGGATTGTTGGGTTT (SEQ ID NO:8975), ACGTGTGGCGTGGATTGTTGGGTTTG (SEQ ID NO:8976), GTGGCGTGGATTGTTGGGTTTGGGGAC (SEQ ID NO:8977), GGATTGTTGGGTTTGGGGACGTTGGGC (SEQ ID NO:8978) |
| Target949 | chr9:14346914-14347026 | GTTTCGGGTGAGGGTGGGGTAAGAGGT (SEQ ID NO:8979), AGTTTCGGGTGAGGGTGGGGTAAGAGG (SEQ ID NO:8980), AGTTTCGGGTGAGGGTGGGGTAAGAGGT (SEQ ID NO:8981), TTTCGGGTGAGGGTGGGGTAAGAGGTA (SEQ ID NO:8982), TCGGGTGAGGGTGGGGTAAGAGGTATT (SEQ ID NO:8983), GTGGGGGTTAGGGGTTTTTTGGTCGCG (SEQ ID NO:8984), TGGGGGGTTAGGGGTTTTTTGGTCGCGA (SEQ ID NO:8985), GGCGGGTTGTTTTTCGAGTGGGGGTTA (SEQ ID NO:8986), GGGGGTTAGGGGTTTTTTGGTCGCGAT (SEQ ID NO:8987), AGTGGGGGTTAGGGGTTTTTTGGTCGC (SEQ ID NO:8988) |
| Target950 | chr9:14347063-14347101 | GCGAAGGGTGCGTTTTTTGAGTTTTACGT (SEQ ID NO:8989), GCGAAGGGTGCGTTTTTTGAGTTTTACG (SEQ ID NO:8990), GCGAAGGGTGCGTTTTTTGAGTTTTACGTCG (SEQ ID NO:8991), GCGAAGGGTGCGTTTTTTGAGTTTTACGTC (SEQ ID NO:8992), CGAAGGGTGCGTTTTTTGAGTTTTACGTCG (SEQ ID NO:8993), CGGCGGGGAATTGCGGGTTTGTAGTTT (SEQ ID NO:8994), CGGCGGGGAATTGCGGGTTTGTAGTT (SEQ ID NO:8995), |

FIGURE 5 CONTINUED

CGGCGGGGAATTGCGGGTTTGTAGTTTA (SEQ ID NO:8996), CGGCGGGGAATTGCGGGTTTGTAGT (SEQ ID NO:8997), CGGCGGGGAATTGCGGGTTTGTAGTTTAG (SEQ ID NO:8998)

Target951    chr9:14347122-14347127    GGGAGTTGGAAGGTAGGTAGACGCGCG (SEQ ID NO:8999), CGGGAGTTGGAAGGTAGGTAGACGCGC (SEQ ID NO:9000), TCGGGAGTTGGAAGGTAGGTAGACGCG (SEQ ID NO:9001), GTCGGGAGTTGGAAGGTAGGTAGACGCG (SEQ ID NO:9002), GTCGGGAGTTGGAAGGTAGGTAGACGC (SEQ ID NO:9003), CGGCGGGGAATTGCGGGTTTGTAGTTT (SEQ ID NO:9004), CGGCGGGGAATTGCGGGTTTGTAGTT (SEQ ID NO:9005), CGGCGGGGAATTGCGGGTTTGTAGTTTA (SEQ ID NO:9006), CGGCGGGGAATTGCGGGTTTGTAGT (SEQ ID NO:9007), CGGCGGGGAATTGCGGGTTTGTAGTTTAG (SEQ ID NO:9008)

Target952    chr9:14347212-14347232    GGTAGGTAGACGCGCGAGGTTTGGGAA (SEQ ID NO:9009), TAGGTAGACGCGCGAGGTTTGGGAAGG (SEQ ID NO:9010), AAGGTAGGTAGACGCGCGAGGTTTGGG (SEQ ID NO:9011), GTTGGAAGGTAGGTAGACGCGCGAGGT (SEQ ID NO:9012), AGTTGGAAGGTAGGTAGACGCGCGAGG (SEQ ID NO:9013), GCGCGGTGGTGGAGTTTTCGAAGGTAT (SEQ ID NO:9014), CGCGCGGTGGTGGAGTTTTCGAAGGTA (SEQ ID NO:9015), GCGCGGTGGTGGAGTTTTCGAAGGTATT (SEQ ID NO:9016), GCGCGGTGGTGGAGTTTTCGAAGGTA (SEQ ID NO:9017), CGCGCGGTGGTGGAGTTTTCGAAGGTAT (SEQ ID NO:9018)

Target953    chr9:19788625-19788640    TGTAGGTGGTTGGGGAATGGAAGCGTT (SEQ ID NO:9019), TTGTAGGTGGTTGGGGAATGGAAGCGT (SEQ ID NO:9020), CGTTTGTAGGTGGTTGGGGAATGGAAGCG (SEQ ID NO:9021), AGGTGGTTGGGGAATGGAAGCGTTTTT (SEQ ID NO:9022), TGTAGGTGGTTGGGGAATGGAAGCGTTT (SEQ ID NO:9023), TGTTTTTGGTTTGGGATGGGGGGCGTG (SEQ ID NO:9024), TTGTTTTTGGTTTGGGATGGGGGGCGT (SEQ ID NO:9025), GTTTTTGGTTTGGGATGGGGGGCGTGG (SEQ ID NO:9026), TCGGGGCGTGGATTTGGAGTTTTCGTT (SEQ ID NO:9027), TGTGTTTCGGGGCGTGGATTTGGAGTT (SEQ ID NO:9028)

Target954    chr9:19788803-19788819    AAGGGTAGGAGAGGCGGGGGTTTTAAA (SEQ ID NO:9029), AGGGGTAGGAGAGGCGGGGGTTTTAAAT (SEQ ID NO:9030), TGGTTAATTTTTAGCGGGGTTTGGGGCGT (SEQ ID NO:9031), GGTTAATTTTTAGCGGGGTTTGGGGCGT (SEQ ID NO:9032), TGGTTAATTTTTAGCGGGGTTTGGGGCG (SEQ ID NO:9033), TGTCGTTGTAGTCGTTGTGGCGGTCGT (SEQ ID NO:9034), GTCGTTGTAGTCGTTGTGGCGGTCGTT (SEQ ID NO:9035), TTGTCGTTGTAGTCGTTGTGGCGGTCG (SEQ ID NO:9036), TCGTTGTAGTCGTTGTGGCGGTCGTTT (SEQ ID NO:9037), TGTCGTTGTAGTCGTTGTGGCGGTCGTT (SEQ ID NO:9038)

Target955    chr9:19788835-19788913    TGGTTAATTTTTAGCGGGGTTTGGGGCGT (SEQ ID NO:9039), GGTTAATTTTTAGCGGGGTTTGGGGCGT (SEQ ID NO:9040), TGGTTAATTTTTAGCGGGGTTTGGGGCG (SEQ ID NO:9041), GGTTAATTTTTAGCGGGGTTTGGGGCG (SEQ ID NO:9042), GTTAATTTTTAGCGGGGTTTGGGGCGT (SEQ ID NO:9043), AGAGTTCGGGTTTTAGAGCGGGTAGGC (SEQ ID NO:9044), TAGAGTTCGGGTTTTAGAGCGGGTAGGC (SEQ ID NO:9045), GAGTTCGGGTTTTAGAGCGGGTAGGC (SEQ ID NO:9046), GCGTTCGGGGGTTTCGTCGTGTGC (SEQ ID NO:9047), TTAGAGTTCGGGTTTTAGAGCGGGTAGGC (SEQ ID NO:9048)

Target956    chr9:19788925-19788946    GTATACGGCGGGGTTTTCGAGCG (SEQ ID NO:9049), CGTATTTATTAGGATAAGATGGGAGGACGCGT (SEQ ID NO:9050), TCGTATTTATTAGGATAAGATGGGAGGACGCGT (SEQ ID NO:9051), TTCGTATTTATTAGGATAAGATGGGAGGACGCG (SEQ ID NO:9052), CGTTCGTATTTATTAGGATAAGATGGGAGGACGCG (SEQ ID NO:9053), GATTCGGAGCGTCGGGTTTATAGCGGT (SEQ ID NO:9054), TTCGGAGCGTCGGGTTTATAGCGGTTT (SEQ ID NO:9055), AGATTCGGAGCGTCGGGTTTATAGCGGT (SEQ ID NO:9056), AGATTCGGAGCGTCGGGTTTATAGCGG (SEQ ID NO:9057), ATTCGGAGCGTCGGGTTTATAGCGGTT (SEQ ID NO:9058)

Target957    chr9:19788948-19788965    GTATACGGCGGGGTTTTCGAGCG (SEQ ID NO:9059), CGTATTTATTAGGATAAGATGGGAGGACGCGT (SEQ ID NO:9060), TCGTATTTATTAGGATAAGATGGGAGGACGCGT (SEQ ID NO:9061), TTCGTATTTATTAGGATAAGATGGGAGGACGCG (SEQ ID NO:9062), CGTTCGTATTTATTAGGATAAGATGGGAGGACGCG (SEQ ID NO:9063), GGTAGCGTTAGATTCGGAGCGTCGGGT (SEQ ID NO:9064), GGTCGGGTAGCGTTAGATTCGGAGCGT (SEQ ID NO:9065), TCGGGTAGCGTTAGATTCGGAGCGTCG (SEQ ID NO:9066), GGGGGTCGGGTAGCGTTAGATTCGGAG (SEQ ID NO:9067), GGGGTCGGGTAGCGTTAGATTCGGAGC (SEQ ID NO:9068)

Target958    chr9:19789000-19789041    CGGGTTGGGTTCGGGAGGAGATTGAGT (SEQ ID NO:9069), AGTCGGGTTGGGTTCGGGAGGAGATTG (SEQ ID NO:9070), GTCGGGTTGGGTTCGGGAGGAGATTGA (SEQ ID NO:9071), TCGGGTTGGGTTCGGGAGGAGATTGAG (SEQ ID NO:9072), GTTAGTCGGGTTGGGTTCGGGAGGAGA (SEQ ID NO:9073), GGTAGCGTTAGATTCGGAGCGTCGGGT (SEQ ID NO:9074), GGTCGGGTAGCGTTAGATTCGGAGCGT (SEQ ID NO:9075), TCGGGTAGCGTTAGATTCGGAGCGTCG (SEQ ID NO:9076), GGGGGTCGGGTAGCGTTAGATTCGGAG (SEQ ID NO:9077), GGGGTCGGGTAGCGTTAGATTCGGAGC (SEQ ID NO:9078)

Target959    chr9:19789051-19789060    CGGGTTGGGTTCGGGAGGAGATTGAGT (SEQ ID NO:9079), AGTCGGGTTGGGTTCGGGAGGAGATTG (SEQ ID NO:9080), GTCGGGTTGGGTTCGGGAGGAGATTGA (SEQ ID NO:9081), TCGGGTTGGGTTCGGGAGGAGATTGAG (SEQ ID NO:9082), GTTAGTCGGGTTGGGTTCGGGAGGAGA (SEQ ID NO:9083), GGTCGGGTAGCGTTAGATTCGGAGCGT (SEQ ID NO:9084), GGGGGTCGGGTAGCGTTAGATTCGGAG (SEQ ID NO:9085), GGGGTCGGGTAGCGTTAGATTCGGAGC

FIGURE 5 CONTINUED (SEQ ID NO:9086), GGGTCGGGTAGCGTTAGATTCGGAGCG (SEQ ID NO:9087),
ATAGTTTAGAGGGAGGGGTCGGCGGGG (SEQ ID NO:9088)

Target960          chr9:19789107-19789137          CGGGGTTGGGTTCGGGAGGAGATTGAGT (SEQ ID NO:9089), AGTCGGGTTGGGTTCGGGAGGAGATTG (SEQ ID NO:9090), GTCGGGTTGGGTTCGGGAGGAGATTGA (SEQ ID NO:9091), TCGGGTTGGGTTCGGGAGGAGATTGAG (SEQ ID NO:9092), GTTAGTCGGGTTGGGTTCGGGAGGAGA (SEQ ID NO:9093), AGGAGGCGTGGAGTAAAGGATTCGGGA (SEQ ID NO:9094), GGAGGCGTGGAGTAAAGGATTCGGGAGT (SEQ ID NO:9095), GGAGGCGTGGAGTAAAGGATTCGGGAG (SEQ ID NO:9096), AGGAGGCGTGGAGTAAAGGATTCGGGAG (SEQ ID NO:9097), GAGGCGTGGAGTAAAGGATTCGGGAGT (SEQ ID NO:9098)

Target961          chr9:19789174-19789196          GGCGTTTCGAGTTTGGCGTTGTTC (SEQ ID NO:9099), AGCGCGTTTAGTTTTCGAGTTTTTTGTTTTACG (SEQ ID NO:9100), TAGCGCGTTTAGTTTTCGAGTTTTTTGTTTTACG (SEQ ID NO:9101), GTAGCGCGTTTAGTTTTCGAGTTTTTTGTTTTACG (SEQ ID NO:9102), TGCGGAGAAATTTTTTAAGAGACGGTTGTTAGC (SEQ ID NO:9103), TTGCGGAGAAATTTTTTAAGAGACGGTTGTTAGC (SEQ ID NO:9104), ATTGCGGAGAAATTTTTTAAGAGACGGTTGTTAGC (SEQ ID NO:9105), TATTGCGGAGAAATTTTTTAAGAGACGGTTGTTAGC (SEQ ID NO:9106)

Target962          chr9:27690403-27690589          AGGAGTTATCGGGGAGGAGTTAAGATGGT (SEQ ID NO:9107), AGGAGTTATCGGGGAGGAGTTAAGATGGT (SEQ ID NO:9108), AAGGAGTTATCGGGGAGGAGTTAAGATGGT (SEQ ID NO:9109), AAGGAGTTATCGGGGAGGAGTTAAGATGGTT (SEQ ID NO:9110), AAAGGAGTTATCGGGGAGGAGTTAAGATGGT (SEQ ID NO:9111), ACGTTGGGAGTTGTAGATCGGAGTTGTT (SEQ ID NO:9112), ACGTTGGGAGTTGTAGATCGGAGTTGTTT (SEQ ID NO:9113), ACGTTGGGAGTTGTAGATCGGAGTTGTTTT (SEQ ID NO:9114), TACGTTGGGAGTTGTAGATCGGAGTTGTTT (SEQ ID NO:9115), TTACGTTGGGAGTTGTAGATCGGAGTTGTT (SEQ ID NO:9116)

Target963          chr9:36986037-36986057          GGAAGAAAGAGTGGTAGTCGTATTTAGGAGGATTTG (SEQ ID NO:9117), AGAGTGGTAGTCGTATTTAGGAGGATTTGTTTGTTT (SEQ ID NO:9118), AAGAGTGGTAGTCGTATTTAGGAGGATTTGTTTGTT (SEQ ID NO:9119), AAAGAGTGGTAGTCGTATTTAGGAGGATTTGTTTGT (SEQ ID NO:9120), GTTAGTTTTTCGGGGTTTCGGGGGGCG (SEQ ID NO:9121), TGTTAGTTTTTCGGGGTTTCGGGGGGC (SEQ ID NO:9122), GGTAGTCGGGGAGTTGGGTAGCGGAGTA (SEQ ID NO:9123), TTAGTTTTTCGGGGTTTCGGGGGGGCG (SEQ ID NO:9124), TTAGTTTTTCGGGGTTTCGGGGGGGCG (SEQ ID NO:9125)

Target964          chr9:36986101-36986118          TTTTCGTTTCGGCGCGTATTATTTGTTTCG (SEQ ID NO:9126), GTTTTCGTTTCGGCGCGTATTATTTGTTTCG (SEQ ID NO:9127), GTTAGTTTTTCGGGGTTTCGGGGGGCG (SEQ ID NO:9128), TGTTAGTTTTTCGGGGTTTCGGGGGGC (SEQ ID NO:9129), GGTAGTCGGGGAGTTGGGTAGCGGAGTA (SEQ ID NO:9130), TTAGTTTTTCGGGGTTTCGGGGGGCGC (SEQ ID NO:9131), TTAGTTTTTCGGGGTTTCGGGGGGGCG (SEQ ID NO:9132)

Target965          chr9:36986131-36986144          TCGTTTCGGCGCGTATTATTTGTTTCGT (SEQ ID NO:9133), TCGTTTCGGCGCGTATTATTTGTTTCGTT (SEQ ID NO:9134), TTCGTTTCGGCGCGTATTATTTGTTTCGT (SEQ ID NO:9135), CGTTTCGGCGCGTATTATTTGTTTCGTTG (SEQ ID NO:9136), CGTTTCGGCGCGTATTATTTGTTTCGTTGT (SEQ ID NO:9137), GTTAGTTTTTCGGGGTTTCGGGGGGCG (SEQ ID NO:9138), GTTCGCGGCGGTTAGGAGAGGTTCGTA (SEQ ID NO:9139), TGTTAGTTTTTCGGGGTTTCGGGGGGC (SEQ ID NO:9140), TTAGTTTTTCGGGGTTTCGGGGGGGCGC (SEQ ID NO:9141), TTCGCGGCGGTTAGGAGAGGTTCGTA (SEQ ID NO:9142)

Target966          chr9:36986179-36986243          TCGGGGTTTCGGAAAGTTGGTATTCGT (SEQ ID NO:9143), TCGGGGTTTCGGAAAGTTGGTATTCGTT (SEQ ID NO:9144), CGGGGTTTCGGAAAGTTGGTATTCGTTGT (SEQ ID NO:9145), CGGGGTTTCGGAAAGTTGGTATTCGTTG (SEQ ID NO:9146), TCGGGGTTTCGGAAAGTTGGTATTCGTTG (SEQ ID NO:9147), GTTCGCGGCGGTTAGGAGAGGTTCGTA (SEQ ID NO:9148), TTCGGTTCGTTGATTGTCGCGCGGTTC (SEQ ID NO:9149), GTTCGGTTCGTTGATTGTCGCGCGGTT (SEQ ID NO:9150), GTGGTTCGGTTCGTTGATTGTCGCGCG (SEQ ID NO:9151), TTCGGTTCGTTGATTGTCGCGCGGTT (SEQ ID NO:9152)

Target967          chr9:36986257-36986324          TCGGGGTTTCGGAAAGTTGGTATTCGT (SEQ ID NO:9153), TCGGGGTTTCGGAAAGTTGGTATTCGTT (SEQ ID NO:9154), CGTTGGGATTTGTAGGGCGCGTCG (SEQ ID NO:9155), CGGGGTTTCGGAAAGTTGGTATTCGTTGT (SEQ ID NO:9156), CGGGGTTTCGGAAAGTTGGTATTCGTTG (SEQ ID NO:9157), TTCGGTTCGTTGATTGTCGCGCGGTTC (SEQ ID NO:9158), GTTCGGTTCGTTGATTGTCGCGCGGTT (SEQ ID NO:9159), GTGGTTCGGTTCGTTGATTGTCGCGCG (SEQ ID NO:9160), TTCGGTTCGTTGATTGTCGCGCGGTT (SEQ ID NO:9161), TCGGTTCGTTGATTGTCGCGCGGTTC (SEQ ID NO:9162)

Target968          chr9:36986334-36986514          CGTTGGGATTTGTAGGGCGCGTCGTC (SEQ ID NO:9163), CGTTGGGATTTGTAGGGCGCGTCGT (SEQ ID NO:9164), GTTGGGATTTGTAGGGCGCGTCGTC (SEQ ID NO:9165), CGTTGGGATTTGTAGGGCGCGTCG (SEQ ID NO:9166), GTTGGGATTTGTAGGGCGCGTCGT (SEQ ID NO:9167), GTCGGGGGCGGAGGGTAGACGATTTTT (SEQ ID NO:9168), GAGGAGTTTTTAGGGTCGGGGGCGGAG (SEQ ID NO:9169), GTTTTTAGGGTCGGGGGCGGAGGGTAG (SEQ ID NO:9170),

FIGURE 5 CONTINUED

CGTAAAGAGAAGGTTGAGCGCGGCGTT {SEQ ID NO:9171}, TTTTTAGGGTCGGGGGCGGAGGGTAGA {SEQ ID NO:9172}

Target969   chr9:36986536-36986617   CGCGTAGGAAATTTAGGTGATTTTTTGGAAGTCG {SEQ ID NO:9173}, CGCGTAGGAAATTTAGGTGATTTTTTGGAAGTCGT {SEQ ID NO:9174}, TCGCGTAGGAAATTTAGGTGATTTTTTGGAAGTCG {SEQ ID NO:9175}, TCGCGTAGGAAATTTAGGTGATTTTTTGGAAGTCGT {SEQ ID NO:9176}, GCGTAGGAAATTTAGGTGATTTTTTGGAAGTCGT {SEQ ID NO:9177}, GTCGGGGGCGGAGGGTAGACGATTTTT {SEQ ID NO:9178}, GAGGAGTTTTTAGGGTCGGGGGCGGAG {SEQ ID NO:9179}, GTTTTTAGGGTCGGGGGCGGAGGGTAG {SEQ ID NO:9180}, CGGTTCGGGCGTTTCGTGGGTTTAGTT {SEQ ID NO:9181}, GACGGAGGAGTTTTTAGGGTCGGGGGC {SEQ ID NO:9182}

Target970   chr9:36986640-36986658   CGGTTTTGGGGATTTTTTCGTCGGAGT {SEQ ID NO:9183}, TCGGTTTTGGGGATTTTTTCGTCGGAGT {SEQ ID NO:9184}, TCGGTTTTGGGGATTTTTTCGTCGGAG {SEQ ID NO:9185}, CGGTTTTGGGGATTTTTTCGTCGGAGTT {SEQ ID NO:9186}, TCGGTTTTGGGGATTTTTTCGTCGGAGTT {SEQ ID NO:9187}, AGAGAGGTCGAGGTTTTTGCGGGGAGG {SEQ ID NO:9188}, AGAGGTCGAGGTTTTTGCGGGGAGGTC {SEQ ID NO:9189}, GAGAGGTCGAGGTTTTTGCGGGGAGGT {SEQ ID NO:9190}, CGAGGTTTTTGCGGGGAGGTCGGTTTT {SEQ ID NO:9191}, CGGTTCGGGCGTTTCGTGGGTTTAGTT {SEQ ID NO:9192}

Target971   chr9:36986702-36986710   GGATTTTCGGTCGGTGGGCGGGAGTTA {SEQ ID NO:9193}, ATTTTCGGTCGGTGGGCGGGAGTTAGG {SEQ ID NO:9194}, GTCGGTGGGCGGGAGTTAGGTTTACGG {SEQ ID NO:9195}, GGTCGGTGGGCGGGAGTTAGGTTTACG {SEQ ID NO:9196}, CGGTCGGTGGGCGGGAGTTAGGTTTAC {SEQ ID NO:9197}, AGAGAGGTCGAGGTTTTTGCGGGGAGG {SEQ ID NO:9198}, AGAGGTCGAGGTTTTTGCGGGGAGGTC {SEQ ID NO:9199}, GAGAGGTCGAGGTTTTTGCGGGGAGGT {SEQ ID NO:9200}, CGAGGTTTTTGCGGGGAGGTCGGTTTT {SEQ ID NO:9201}, TCGAGGTTTTTGCGGGGAGGTCGGTTT {SEQ ID NO:9202}

Target972   chr9:36986762-36986789   GGATTTTCGGTCGGTGGGCGGGAGTTA {SEQ ID NO:9203}, ATTTTCGGTCGGTGGGCGGGAGTTAGG {SEQ ID NO:9204}, GTCGGTGGGCGGGAGTTAGGTTTACGG {SEQ ID NO:9205}, GGTCGGTGGGCGGGAGTTAGGTTTACG {SEQ ID NO:9206}, CGGTCGGTGGGCGGGAGTTAGGTTTAC {SEQ ID NO:9207}, TGAAGGAGGTTTAGGGATTCGCGGTGT {SEQ ID NO:9208}, TGAAGGAGGTTTAGGGATTCGCGGTGTT {SEQ ID NO:9209}, TTGAAGGAGGTTTAGGGATTCGCGGTGT {SEQ ID NO:9210}, GAAGGAGGTTTAGGGATTCGCGGTGTT {SEQ ID NO:9211}, TTGAAGGAGGTTTAGGGATTCGCGGTG {SEQ ID NO:9212}

Target973   chr9:36986828-36986849   CGAGGAGGAAGGGATCGGTTTTTTCGT {SEQ ID NO:9213}, GGAGGAAGGGATCGGTTTTTTCGTAGGG {SEQ ID NO:9214}, AGGAGGAAGGGATCGGTTTTTTCGTAGGG {SEQ ID NO:9215}, GGAGGAAGGGATCGGTTTTTTCGTAGGGA {SEQ ID NO:9216}, CGAGGAGGAAGGGATCGGTTTTTTCGTAGGG {SEQ ID NO:9217}, TGGGTATGGGTTGGACGGGATTTCGGT {SEQ ID NO:9218}, TGGGTATGGGTTGGACGGGATTTCGTT {SEQ ID NO:9219}, TTGGGTATGGGTTGGACGGGATTTCGGT {SEQ ID NO:9220}, GGGTATGGGTTGGACGGGATTTCGGTT {SEQ ID NO:9221}, TTGGGTATGGGTTGGACGGGATTTCGG {SEQ ID NO:9222}

Target974   chr9:36987001-36987017   GGTTCGAAGGAGATGGTGGTCGGGGTT {SEQ ID NO:9223}, CGAAGGAGATGGTGGTCGGGGTTTCGT {SEQ ID NO:9224}, AGGTTCGAAGGAGATGGTGGTCGGGGT {SEQ ID NO:9225}, TAGGTTCGAAGGAGATGGTGGTCGGGG {SEQ ID NO:9226}, GGTTCGAAGGAGATGGTGGTCGGGGTTT {SEQ ID NO:9227}, TTTGTTTCGGAGGGGTTGTGGGGGAAGA {SEQ ID NO:9228}, TGTTTCGGAGGGGTTGTGGGGGAAGATT {SEQ ID NO:9229}, TTGTTTCGGAGGGGTTGTGGGGGAAGAT {SEQ ID NO:9230}, ATTTGTTTCGGAGGGGTTGTGGGGGAAG {SEQ ID NO:9231}, TTGTTTCGGAGGGGTTGTGGGGGAAGATT {SEQ ID NO:9232}

Target975   chr9:82188645-82188755   GGGTAAGTGTTTGTGTGTATTTGTCGGGG {SEQ ID NO:9233}, AGGGTAAGTGTTTGTGTGTATTTGTCGGGG {SEQ ID NO:9234}, GGGTAAGTGTTTGTGTGTATTTGTCGGGGA {SEQ ID NO:9235}, AGGGTAAGTGTTTGTGTGTATTTGTCGGGGA {SEQ ID NO:9236}, GGAGGGTAAGTGTTTGTGTGTATTTGTCGGGG {SEQ ID NO:9237}

Target976   chr9:82188897-82188984   CGAAATTGGGGAGATTTGGAAAACGTTGAGG {SEQ ID NO:9238}, CGAAATTGGGGAGATTTGGAAAACGTTGAGGT {SEQ ID NO:9239}, GAAATTGGGGAGATTTGGAAAACGTTGAGGT {SEQ ID NO:9240}, AAATTGGGGAGATTTGGAAAACGTTGAGGTT {SEQ ID NO:9241}, CGAAATTGGGGAGATTTGGAAAACGTTGAGGTT {SEQ ID NO:9242}

Target977   chr9:82189045-82189118   CGGGAGAATGAAAGGTTGGGAAGATTTTGGGG {SEQ ID NO:9243}, CGGGAGAATGAAAGGTTGGGAAGATTTTGGGGT {SEQ ID NO:9244}, CGGGAGAATGAAAGGTTGGGAAGATTTTGGG {SEQ ID NO:9245}, GGGAGAATGAAAGGTTGGGAAGATTTTGGGG {SEQ ID NO:9246}, GGGAGAATGAAAGGTTGGGAAGATTTTGGGGT {SEQ ID NO:9247}

Target978   chr9:100616347-100616704   GGTCGGGGTTTTAGGGGAGGTTACGGG {SEQ ID NO:9248}, GGGTCGGGGTTTTAGGGGAGGTTACGG {SEQ ID NO:9249}, GGGGTCGGGGTTTTAGGGGAGGTTACG {SEQ ID NO:9250}, AGTAGGGGTCGGGGTTTTAGGGGAGGT {SEQ ID NO:9251}, CGGGGTTTTAGGGGAGGTTACGGGTCG

FIGURE 5 CONTINUED

|  |  | (SEQ ID NO:9252), CGGTTTCGCGCGGGATTTTGAGGAAGT (SEQ ID NO:9253), AGTCGTTGAGTGTGAGGTTGTGGCGGA (SEQ ID NO:9254), TTGGGGTTGTCGCGGGTAGAAGGGGAAG (SEQ ID NO:9255), TTTGGGGTTGTCGCGGGTAGAAGGGGAA (SEQ ID NO:9256), TTTTGGGGTTGTCGCGGGTAGAAGGGGA (SEQ ID NO:9257) |
| Target979 | chr9:100616709-100616748 | GGTAGTAGATTGGAGGCGGCGCGGTTA (SEQ ID NO:9258), CGACGTCGCGGGGTAGTAGATTGGAGG (SEQ ID NO:9259), GACGTCGCGGGGTAGTAGATTGGAGGC (SEQ ID NO:9260), CGACGGCGGCGCGTAGTTTGTATAGAC (SEQ ID NO:9261), ACGTCGCGGGGTAGTAGATTGGAGGC (SEQ ID NO:9262) |
| Target980 | chr9:100616754-100616762 | GGTAGTAGATTGGAGGCGGCGCGGTTA (SEQ ID NO:9263), CGACGTCGCGGGGTAGTAGATTGGAGG (SEQ ID NO:9264), GACGTCGCGGGGTAGTAGATTGGAGGC (SEQ ID NO:9265), CGACGGCGGCGCGTAGTTTGTATAGAC (SEQ ID NO:9266), ACGTCGCGGGGTAGTAGATTGGAGGC (SEQ ID NO:9267) |
| Target981 | chr9:100616774-100616782 | GGTAGTAGATTGGAGGCGGCGCGGTTA (SEQ ID NO:9268), CGACGTCGCGGGGTAGTAGATTGGAGG (SEQ ID NO:9269), GACGTCGCGGGGTAGTAGATTGGAGGC (SEQ ID NO:9270), CGACGGCGGCGCGTAGTTTGTATAGAC (SEQ ID NO:9271), ACGTCGCGGGGTAGTAGATTGGAGGC (SEQ ID NO:9272) |
| Target982 | chr9:100616796-100616817 | GGTAGTAGATTGGAGGCGGCGCGGTTA (SEQ ID NO:9273), CGACGTCGCGGGGTAGTAGATTGGAGG (SEQ ID NO:9274), GACGTCGCGGGGTAGTAGATTGGAGGC (SEQ ID NO:9275), TCGACGGTGCGGGTTTTAGTTTTGGGT (SEQ ID NO:9276), ACGTCGCGGGGTAGTAGATTGGAGGC (SEQ ID NO:9277) |
| Target983 | chr9:100616838-100616863 | CGTTGGTCGCGTCGTTTTTAGTTTATTATTTCGC (SEQ ID NO:9278), GTTGGTCGCGTCGTTTTTAGTTTATTATTTCGC (SEQ ID NO:9279), TCGACGGTGCGGGTTTTAGTTTTGGGT (SEQ ID NO:9280), TGCGGGTTGGTAGTCGGTGGTGGTAG (SEQ ID NO:9281), TGCGGGTTTTAGTTTTGGGTTGAGCGGT (SEQ ID NO:9282), GCGGGTTTTAGTTTTGGGTTGAGCGGT (SEQ ID NO:9283), TGCGGGTTTTAGTTTTGGGTTGAGCGG (SEQ ID NO:9284) |
| Target984 | chr9:112810205-112810273 | TGGTGGAGGAGGGGATGAGAGATTGAA (SEQ ID NO:9285), ATGGTGGAGGAGGGGATGAGAGATTGA (SEQ ID NO:9286), TGGTGGAGGAGGGGATGAGAGATTGAAA (SEQ ID NO:9287), ATGGTGGAGGAGGGGATGAGAGATTGA (SEQ ID NO:9288), TGGTGGAGGAGGGGATGAGAGATTGA (SEQ ID NO:9289), TCGTGTAGTGGTAGTCGGTGGTTCGGT (SEQ ID NO:9290), CGTGTAGTGGTAGTCGGTGGTTCGGTGT (SEQ ID NO:9291), CGTGTAGTGGTAGTCGGTGGTTCGGTG (SEQ ID NO:9292), TCGTGTAGTGGTAGTCGGTGGTTCGGTG (SEQ ID NO:9293), GCGGAGGGGAAGGAGGTAGTTGATTCGT (SEQ ID NO:9294) |
| Target985 | chr9:112810283-112810306 | CGTTGGTTTTGTTAGTATACGCGTTTTGATATCGG (SEQ ID NO:9295), TCGTTGGTTTTGTTAGTATACGCGTTTTGATATCGG (SEQ ID NO:9296), TCGTTGGTTTTGTTAGTATACGCGTTTTGATATCG (SEQ ID NO:9297), TTCGTTGGTTTTGTTAGTATACGCGTTTTGATATCG (SEQ ID NO:9298), CGATGGGGTTTAGAGGTTGAGGTGTGG (SEQ ID NO:9299), CGATGGGGTTTAGAGGTTGAGGTGTGGA (SEQ ID NO:9300), TCGATGGGGTTTAGAGGTTGAGGTGTGG (SEQ ID NO:9301), TCGATGGGGTTTAGAGGTTGAGGTGTGGA (SEQ ID NO:9302), CGCGTGTTTGAGGATTTTTTCGATGGGGT (SEQ ID NO:9303) |
| Target986 | chr9:112810400-112810743 | CGTGGTGTTAGGTAAGGGACGAGGGGT (SEQ ID NO:9304), TCGTGGTGTTAGGTAAGGGACGAGGGGG (SEQ ID NO:9305), TCGTGGTGTTAGGTAAGGGACGAGGGGT (SEQ ID NO:9306), CGTGGTGTTAGGTAAGGGACGAGGGGTT (SEQ ID NO:9307), ACGGAGGGTAGTAGGAAGGTTTTGGCG (SEQ ID NO:9308), GGGGTGGCGTGTCGTTGTGTGTGTATG (SEQ ID NO:9309), GGAGGGGATGGATGGGCGGGTAAAGTT (SEQ ID NO:9310), GAGGGAAAGACGGAGGGATGGATGGGG (SEQ ID NO:9311), GGGTGGCGTGTCGTTGTGTGTGTATGT (SEQ ID NO:9312), AGGGATGGATGGGGCGGGTAAAGTTGA (SEQ ID NO:9313) |
| Target987 | chr9:120507235-120507278 | GCGGGGTTGTTTAGATTTTGCGGGCGA (SEQ ID NO:9314), CGGGGTTGTTTAGATTTTGCGGGCGAG (SEQ ID NO:9315), GCGGGGTTGTTTAGATTTTGCGGGCG (SEQ ID NO:9316), GCGGGGTTGTTTAGATTTTGCGGGCGAG (SEQ ID NO:9317), CGGGGTTGTTTAGATTTTGCGGGCGA (SEQ ID NO:9318) |
| Target988 | chr9:120507296-120507309 | GGAGACGTCGGGGTTTTCGGTTTTGAGT (SEQ ID NO:9319), GGAGACGTCGGGGTTTTCGGTTTTGAG (SEQ ID NO:9320), GAGACGTCGGGGTTTTCGGTTTTGAGT (SEQ ID NO:9321), AGACGTCGGGGTTTTCGGTTTTGAGTT (SEQ ID NO:9322), TCGGTTTTGAGTTTTTGGAGCGTTCGC (SEQ ID NO:9323), GCGGGGTTGTTTAGATTTTGCGGGCGA (SEQ ID NO:9324), CGGGGTTGTTTAGATTTTGCGGGCG (SEQ ID NO:9325), GCGGGGTTGTTTAGATTTTGCGGGCG (SEQ ID NO:9326), GCGGGGTTGTTTAGATTTTGCGGGCGAG (SEQ ID NO:9327), CGGGGTTGTTTAGATTTTGCGGGCGA (SEQ ID NO:9328) |
| Target989 | chr9:120507342-120507366 | GGAGACGTCGGGGTTTTCGGTTTTGAGT (SEQ ID NO:9329), GGAGACGTCGGGGTTTTCGGTTTTGAG (SEQ ID NO:9330), GAGACGTCGGGGTTTTCGGTTTTGAGT (SEQ ID NO:9331), AGACGTCGGGGTTTTCGGTTTTGAGTT (SEQ ID NO:9332), TCGGTTTTGAGTTTTTGGAGCGTTCGC (SEQ ID NO:9333), GCGGGGTTGTTTAGATTTTGCGGGCGA (SEQ ID NO:9334), CGGGGTTGTTTAGATTTTGCGGGCGAG (SEQ ID NO:9335), GCGGGGTTGTTTAGATTTTGCGGGCG (SEQ ID NO:9336), GCGGGGTTGTTTAGATTTTGCGGGCGAG (SEQ ID NO:9337), CGGGGTTGTTTAGATTTTGCGGGCGA (SEQ ID NO:9338) |

FIGURE 5 CONTINUED

| | | |
|---|---|---|
| *Target990* | chr9:120507384-120507395 | CGCGTTCGTTCGTTCGTAGGATTTGGG (SEQ ID NO:9339), CGCGTTCGTTCGTTCGTAGGATTTGGGT (SEQ ID NO:9340), CGTAGGATTTGGGTAGTTTCGCGGGGA (SEQ ID NO:9341), TCGTAGGATTTGGGTAGTTTCGCGGGG (SEQ ID NO:9342), TCGTAGGATTTGGGTAGTTTCGCGGGGA (SEQ ID NO:9343), TGTATAATGGGTTGCGCGTAGAGTCGG (SEQ ID NO:9344), AGTAGTCGGCGGTTTGAAAGGAGGTTT (SEQ ID NO:9345), AAGTAGTCGGCGGTTTGAAAGGAGGTT (SEQ ID NO:9346), AAAGTAGTCGGCGGTTTGAAAGGAGGT (SEQ ID NO:9347), GCGTTAGTTGTATAATGGGTTGCGCGT (SEQ ID NO:9348) |
| *Target991* | chr9:120507402-120507434 | GGGTAGTTTCGCGGGGATTCGGTTTTGC (SEQ ID NO:9349), TGGGTAGTTTCGCGGGGATTCGGTTTT (SEQ ID NO:9350), TTGGGTAGTTTCGCGGGGATTCGGTTT (SEQ ID NO:9351), TTTGGGTAGTTTCGCGGGGATTCGGTT (SEQ ID NO:9352), GGTAGTTTCGCGGGGATTCGGTTTTGC (SEQ ID NO:9353), AGTAGTCGGCGGTTTGAAAGGAGGTTT (SEQ ID NO:9354), AAGTAGTCGGCGGTTTGAAAGGAGGTT (SEQ ID NO:9355), AAAGTAGTCGGCGGTTTGAAAGGAGGT (SEQ ID NO:9356), AGTCGGCGGTTTGAAAGGAGGTTTAGA (SEQ ID NO:9357), TGAAAGTAGTCGGCGGTTTGAAAGGAGG (SEQ ID NO:9358) |
| *Target992* | chr9:126776105-126776130 | GGAGTTCGGTTTGGGTTCGTGGTTGGC (SEQ ID NO:9359), GTGGGGGGAAGCGCGTCGTATGTTTTG (SEQ ID NO:9360), AATGGGTTTTTTGGGGTGGGGGGAAGC (SEQ ID NO:9361), GAGTTCGGTTTGGGTTCGTGGTTGGCG (SEQ ID NO:9362), TGGCGAGGGGTTGCGTAGGTAGGTTTGG (SEQ ID NO:9363), ACGGTATGGTTTGCGAAGGGAGGGAGG (SEQ ID NO:9364), GGACGGTATGGTTTGCGAAGGGAGGGA (SEQ ID NO:9365), AGGGAGGGAGGCGGAAGATAGTAGCGT (SEQ ID NO:9366), TGGACGGTATGGTTTGCGAAGGGAGGG (SEQ ID NO:9367), TTGCGAAGGGAGGGAGGCGGAAGATAG (SEQ ID NO:9368) |
| *Target993* | chr9:126776169-126776209 | GTGGGGGGAAGCGCGTCGTATGTTTTG (SEQ ID NO:9369), AATGGGTTTTTTGGGGTGGGGGGAAGC (SEQ ID NO:9370), TGGAAATGGGTTTTTTGGGGTGGGGGG (SEQ ID NO:9371), GGAAATGGGTTTTTTGGGGTGGGGGGA (SEQ ID NO:9372), GGGGGAAGCGCGTCGTATGTTTTGGTA (SEQ ID NO:9373), ACGGTATGGTTTGCGAAGGGAGGGAGG (SEQ ID NO:9374), GGACGGTATGGTTTGCGAAGGGAGGGA (SEQ ID NO:9375), AGGGAGGGAGGCGGAAGATAGTAGCGT (SEQ ID NO:9376), TGGACGGTATGGTTTGCGAAGGGAGGG (SEQ ID NO:9377), TTGCGAAGGGAGGGAGGCGGAAGATAG (SEQ ID NO:9378) |
| *Target994* | chr9:126776235-126776288 | AGGGAGTTGTGGGTGTCGGTTTTTCGG (SEQ ID NO:9379), GAGGGAGTTGTGGGTGTCGGTTTTTCG (SEQ ID NO:9380), GAGGGAGTTGTGGGTGTCGGTTTTTCG (SEQ ID NO:9381), AGAGGGAGTTGTGGGTGTCGGTTTTTCGG (SEQ ID NO:9382), AGAGGGAGTTGTGGGTGTCGGTTTTTCG (SEQ ID NO:9383), CGGCGCGGTTATTGTTGATGGACGGTA (SEQ ID NO:9384), CGGCGCGGTTATTGTTGATGGACGGT (SEQ ID NO:9385), CGGCGCGGTTATTGTTGATGGACGGTAT (SEQ ID NO:9386), GCGGCGCGGTTATTGTTGATGGACGGT (SEQ ID NO:9387), GCGGCGCGGTTATTGTTGATGGACGG (SEQ ID NO:9388) |
| *Target995* | chr9:126776345-126776386 | CGGTTGCGGGGGTAAGATTTCGGATCG (SEQ ID NO:9389), CGTCGGTTGCGGGGGTAAGATTTCGGA (SEQ ID NO:9390), GGTTGCGGGGGTAAGATTTCGGATCGT (SEQ ID NO:9391), GTCGGTTGCGGGGGTAAGATTTCGGAT (SEQ ID NO:9392), GCGTCGGTTGCGGGGGTAAGATTTCG (SEQ ID NO:9393), GGGGAGGGGTTTTGAGGGGTAGTTGGG (SEQ ID NO:9394), GGGGGAGGGGTTTTGAGGGGTAGTTGG (SEQ ID NO:9395), GGGGGGAGGGGTTTTGAGGGGTAGTTG (SEQ ID NO:9396), GAGATTGGGGGGGAGGGGTTTTGAGGGG (SEQ ID NO:9397), AGGGGTTTTGAGGGGTAGTTGGGTGGG (SEQ ID NO:9398) |
| *Target996* | chr9:126778240-126778255 | GGGTCGGGGAATTGGGGTAGCGAAGGAA (SEQ ID NO:9399), GTTGAGGGTCGGGAATTGGGGTAGCGA (SEQ ID NO:9400), CGAGGTAGGGCGGCGAGGGTTTTAAGA (SEQ ID NO:9401), AACGAGGTAGGGCGGCGAGGGTTTTAA (SEQ ID NO:9402), GAACGAGGTAGGGCGGCGAGGGTTTTA (SEQ ID NO:9403) |
| *Target997* | chr9:126778345-126778398 | AAGGGCGGTAGGTTTGGGGAATTCGGG (SEQ ID NO:9404), GGGCGGTAGGTTTGGGGAATTCGGGTT (SEQ ID NO:9405), GGCGGTAGGTTTGGGGAATTCGGGTTT (SEQ ID NO:9406), TAAGGGCGGTAGGTTTGGGGAATTCGGG (SEQ ID NO:9407), GCGGTAGGTTTGGGGAATTCGGGTTTGG (SEQ ID NO:9408), CGGCGCGAGGTTAGGTTTGTTTCGGTT (SEQ ID NO:9409), TCGGCGCGAGGTTAGGTTTGTTTCGGT (SEQ ID NO:9410), CGGCGCGAGGTTAGGTTTGTTTCGGTTT (SEQ ID NO:9411), CGGCGCGAGGTTAGGTTTGTTTCGGT (SEQ ID NO:9412), TCGGCGCGAGGTTAGGTTTGTTTCGG (SEQ ID NO:9413) |
| *Target998* | chr9:126778411-126778443 | TTTTTGGCGTTTGTTGGGGTGAGGGTCG (SEQ ID NO:9414), AAGGGCGGTAGGTTTGGGGAATTCGGG (SEQ ID NO:9415), GGGCGGTAGGTTTGGGGAATTCGGGTT (SEQ ID NO:9416), GGCGGTAGGTTTGGGGAATTCGGGTTT (SEQ ID NO:9417), TTTTTGGCGTTTGTTGGGGTGAGGGTCG (SEQ ID NO:9418), CGGCGCGAGGTTAGGTTTGTTTCGGTT (SEQ ID NO:9419), TCGGCGCGAGGTTAGGTTTGTTTCGGT (SEQ ID NO:9420), CGGCGCGAGGTTAGGTTTGTTTCGGTTT (SEQ ID NO:9421), CGGCGCGAGGTTAGGTTTGTTTCGGT (SEQ ID NO:9422), TCGGCGCGAGGTTAGGTTTGTTTCGG (SEQ ID NO:9423) |
| *Target999* | chr9:126778642-126778685 | GGTGGGGGGGTTTGGTTCGGATTTTCGG (SEQ ID NO:9424), GGTGAGGTGGGGGGGTTTGGTTCGGATT (SEQ ID NO:9425), GTGGGGGGGTTTGGTTCGGATTTTCGGT (SEQ ID NO:9426), AGGTGGGGGGGTTTGGTTCGGATTTTCG (SEQ ID NO:9427), GTGAGGTGGGGGGGTTTGGTTCGGATTT (SEQ ID NO:9428), CGGGTTTTGTAGATTTCGGGTAGATGTTGACGG (SEQ ID NO:9429), CGGGTTTTGTAGATTTCGGGTAGATGTTGACGGT (SEQ ID NO:9430), CGGGTTTTGTAGATTTCGGGTAGATGTTGACG (SEQ ID NO:9431), |

FIGURE 5 CONTINUED

TCGGGTTTTGTAGATTTCGGGTAGATGTTGACGG (SEQ ID NO:9432),
GGGTTTTGTAGATTTCGGGTAGATGTTGACGG (SEQ ID NO:9433)

| | | |
|---|---|---|
| Target1000 | chr9:127265555-127265560 | TCGTGCGTTTGAAGAAGTTTTGCGGGA (SEQ ID NO:9434), TGCGGGAGTTGAGAGTTAGCGAGGTTT (SEQ ID NO:9435), TTGCGGGAGTTGAGAGTTAGCGAGGTT (SEQ ID NO:9436), TTTGCGGGAGTTGAGAGTTAGCGAGGT (SEQ ID NO:9437), CGTGCGTTTGAAGAAGTTTTGCGGGAGT (SEQ ID NO:9438), CGTGTGAGAGTTGTAAGGTGAGCGGCG (SEQ ID NO:9439), ACGTGTGAGAGTTGTAAGGTGAGCGGC (SEQ ID NO:9440), CGTGTGCGGGGATAAGGTGTTCGGTTA (SEQ ID NO:9441), CGTGTGAGAGTTGTAAGGTGAGCGGCGA (SEQ ID NO:9442), GTGTGAGAGTTGTAAGGTGAGCGGCGA (SEQ ID NO:9443) |
| Target1001 | chr9:127265656-127265664 | CGGGGTATAGTTCGTTTAGGTTTTCGTCGT (SEQ ID NO:9444), CGGGGTATAGTTCGTTTAGGTTTTCGTCGTA (SEQ ID NO:9445), CGGGGTATAGTTCGTTTAGGTTTTCGTCGTAC (SEQ ID NO:9446), CGTGAGTAGTTCGTAGTGGTAGTCGGATATTTTG (SEQ ID NO:9447), AGTTCGTAGTGGTAGTCGGATATTTTGTTTTCGT (SEQ ID NO:9448), CGGTCGCGGGGATTTTAGGTTGTCGGT (SEQ ID NO:9449), GGTCGCGGGGATTTTAGGTTGTCGGTT (SEQ ID NO:9450), GCGGTCGCGGGGATTTTAGGTTGTCG (SEQ ID NO:9451), CGGTCGCGGGGATTTTAGGTTGTCGG (SEQ ID NO:9452), CGGACGTCGCGGGTATGGATTATTCGT (SEQ ID NO:9453) |
| Target1002 | chr9:127265764-127265817 | GTTTGCGGAGGGATAGCGGGTTAGGGA (SEQ ID NO:9454), TTTGCGGAGGGATAGCGGGTTAGGGAG (SEQ ID NO:9455), ATCGGTAGTTTGGGGTTTTCGCGGTCG (SEQ ID NO:9456), CGTTTGCGGAGGGATAGCGGGTTAGGG (SEQ ID NO:9457), GAGGGATAGCGGGTTAGGGAGGGTCGG (SEQ ID NO:9458), TCGGGCGCGGGGATTGTATCGGATTTA (SEQ ID NO:9459), GAGCGTGGGGTTTGGTAGGGGAAGGTC (SEQ ID NO:9460), GTCGGGCGCGGGGATTGTATCGGATTT (SEQ ID NO:9461), CGGGCGCGGGGATTGTATCGGATTTAT (SEQ ID NO:9462), AGCGTGGGGTTTGGTAGGGGAAGGTC (SEQ ID NO:9463) |
| Target1003 | chr9:127265835-127265843 | ATCGGTAGTTTGGGGTTTTCGCGGTCG (SEQ ID NO:9464), GATCGGTAGTTTGGGGTTTTCGCGGTCG (SEQ ID NO:9465), AGATCGGTAGTTTGGGGTTTTCGCGGT (SEQ ID NO:9466), TCGGTAGTTTGGGGTTTTCGCGGTCG (SEQ ID NO:9467), GGAGATCGGTAGTTTGGGGTTTTCGCGG (SEQ ID NO:9468), TCGGGCGCGGGGATTGTATCGGATTTA (SEQ ID NO:9469), GAGCGTGGGGTTTGGTAGGGGAAGGTC (SEQ ID NO:9470), GTCGGGCGCGGGGATTGTATCGGATTT (SEQ ID NO:9471), CGGGCGCGGGGATTGTATCGGATTTAT (SEQ ID NO:9472), GTTTTAGATCGGGCGCGACGGGGTTC (SEQ ID NO:9473) |
| Target1004 | chr9:127265928-127265933 | TAGCGTTTCGGGGTGGGTTCGGTGTAG (SEQ ID NO:9474), GTAGCGTTTCGGGGTGGGTTCGGTGTA (SEQ ID NO:9475), GGGTGGGTTCGGTGTAGTTTTCGCGTT (SEQ ID NO:9476), TCGGGGTGGGTTCGGTGTAGTTTTCGC (SEQ ID NO:9477), GGGGTGGGTTCGGTGTAGTTTTCGCGT (SEQ ID NO:9478), GTTTTAGATCGGGCGCGACGGGGTTC (SEQ ID NO:9479), GGTTTTAGATCGGGCGCGACGGGGTTC (SEQ ID NO:9480), GGTTTTAGATCGGGCGCGACGGGGTT (SEQ ID NO:9481), CGAGGGTTTTAGATCGGGCGCGACG (SEQ ID NO:9482), GAGGGTTTTAGATCGGGCGCGACGG (SEQ ID NO:9483) |
| Target1005 | chr9:132650532-132651124 | CGTTGGCGGGGGAGTTTATTGTGGAGT (SEQ ID NO:9484), AGTTGTTTCGGAAGGGTGGTGTGTGGT (SEQ ID NO:9485), GCGGGGGAGTTTATTGTGGAGTTGTGGG (SEQ ID NO:9486), GGCGGGGGAGTTTATTGTGGAGTTGTGG (SEQ ID NO:9487), TGGCGGGGGAGTTTATTGTGGAGTTGT (SEQ ID NO:9488), GGGGGGATTGTAAATCGTTTAGGGTTGCGG (SEQ ID NO:9489), GGGGGGATTGTAAATCGTTTAGGGTTGCGG (SEQ ID NO:9490), GGGGGGATTGTAAATCGTTTAGGGTTGCG (SEQ ID NO:9491), GGGGGGATTGTAAATCGTTTAGGGTTGCGGT (SEQ ID NO:9492), GGGGGGATTGTAAATCGTTTAGGGTTGCGGT (SEQ ID NO:9493) |
| Target1006 | chr9:133771616-133771649 | TCGGAGAGGATATGGGGTGGGTGGATA (SEQ ID NO:9494), TCGGAGAGGATATGGGGTGGGTGGAT (SEQ ID NO:9495), CGGAGAGGATATGGGGTGGGTGGATAT (SEQ ID NO:9496), TCGGAGAGGATATGGGGTGGGTGGATAT (SEQ ID NO:9497), TCGGAGAGGATATGGGGTGGGTGGA (SEQ ID NO:9498), TTTAGGGTATGCGGTGGGAGGGGTTGG (SEQ ID NO:9499), CGGTGGGAGGGGTTGGGGGGTTATAGGT (SEQ ID NO:9500), ATGCGGTGGGAGGGGTTGGGGGTTATA (SEQ ID NO:9501), TATGCGGTGGGAGGGGTTGGGGGTTAT (SEQ ID NO:9502), CGGTGGGAGGGGTTGGGGGTTATAGG (SEQ ID NO:9503) |
| Target1007 | chr9:135462376-135462397 | GGTTGGGTTCGGTTTTATCGTCGCGGT (SEQ ID NO:9504), AGGTTGGGTTCGGTTTTATCGTCGCGG (SEQ ID NO:9505), GGTTGGGTTCGGTTTTATCGTCGCGGT (SEQ ID NO:9506), AGGTTGGGTTCGGTTTTATCGTCGCGGTT (SEQ ID NO:9507), GTTGGGTTCGGTTTTATCGTCGCGGTT (SEQ ID NO:9508), CGAGAATTTTAGTTTTTGCGTCGCGTTCG (SEQ ID NO:9509), CGAAGTTGGCGAGAATTTTAGTTTTTGCGTCG (SEQ ID NO:9510), CGTTTTGTTCGCGTTTTTTGGAGGGATAAAC (SEQ ID NO:9511), GAAGTTGGCGAGAATTTTAGTTTTTGCGTCG (SEQ ID NO:9512), CGAAGTTGGCGAGAATTTTAGTTTTTGCGTC (SEQ ID NO:9513) |
| Target1008 | chr9:135462433-135462439 | GGTTGGGTTCGGTTTTATCGTCGCGGT (SEQ ID NO:9514), AGGTTGGGTTCGGTTTTATCGTCGCGG (SEQ ID NO:9515), GTTGGGTTCGGTTTTATCGTCGCGGTT (SEQ ID NO:9516), AGGTTGGGTTCGGTTTTATCGTCGCGGTT (SEQ ID NO:9517), GTTGGGTTCGGTTTTATCGTCGCGGTT (SEQ |

FIGURE 5 CONTINUED

Figure 5:
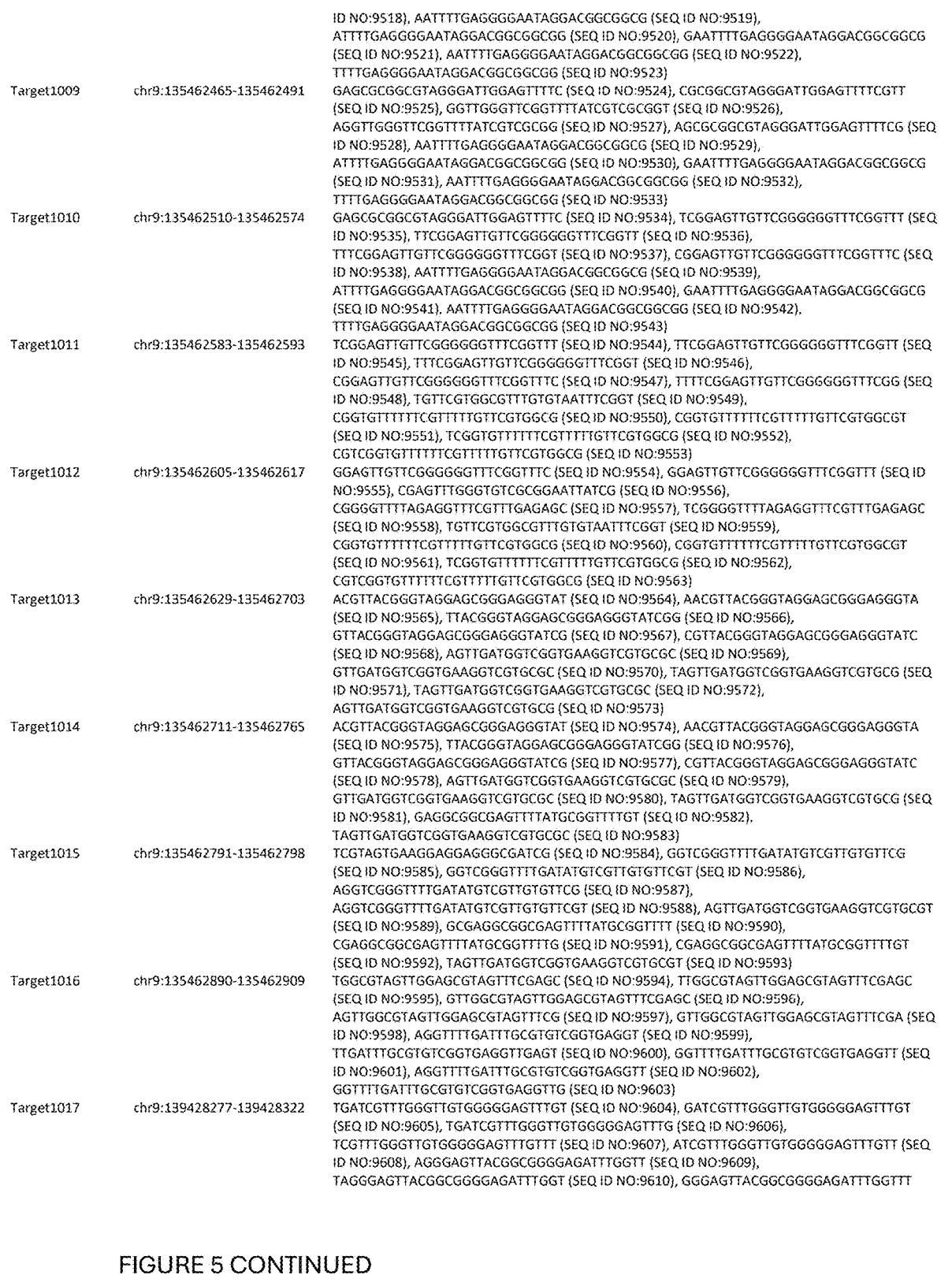

ID NO:9518), AATTTTGAGGGGAATAGGACGGCGGCG (SEQ ID NO:9519), ATTTTGAGGGGAATAGGACGGCGGCGG (SEQ ID NO:9520), GAATTTTGAGGGGAATAGGACGGCGGCG (SEQ ID NO:9521), AATTTTGAGGGGAATAGGACGGCGGCGG (SEQ ID NO:9522), TTTTGAGGGGAATAGGACGGCGGCGG (SEQ ID NO:9523)

Target1009        chr9:135462465-135462491        GAGCGCGGCGTAGGGGATTGGAGTTTTC (SEQ ID NO:9524), CGCGGCGTAGGGGATTGGAGTTTTCGTT (SEQ ID NO:9525), GGTTGGGTTCGGTTTTATCGTCGCGGT (SEQ ID NO:9526), AGGTTGGGTTCGGTTTTATCGTCGCGGT (SEQ ID NO:9527), AGCGCGGCGTAGGGGATTGGAGTTTTCG (SEQ ID NO:9528), AATTTTGAGGGGAATAGGACGGCGGCG (SEQ ID NO:9529), ATTTTGAGGGGAATAGGACGGCGGCGG (SEQ ID NO:9530), GAATTTTGAGGGGAATAGGACGGCGGCG (SEQ ID NO:9531), AATTTTGAGGGGAATAGGACGGCGGCGG (SEQ ID NO:9532), TTTTGAGGGGAATAGGACGGCGGCGG (SEQ ID NO:9533)

Target1010        chr9:135462510-135462574        GAGCGCGGCGTAGGGGATTGGAGTTTTC (SEQ ID NO:9534), TCGGAGTTGTTCGGGGGGGTTTCGGTTT (SEQ ID NO:9535), TTCGGAGTTGTTCGGGGGGGTTTCGGTT (SEQ ID NO:9536), TTTCGGAGTTGTTCGGGGGGGTTTCGGT (SEQ ID NO:9537), CGGAGTTGTTCGGGGGGGTTTCGGTTTC (SEQ ID NO:9538), AATTTTGAGGGGAATAGGACGGCGGCG (SEQ ID NO:9539), ATTTTGAGGGGAATAGGACGGCGGCGG (SEQ ID NO:9540), GAATTTTGAGGGGAATAGGACGGCGGCG (SEQ ID NO:9541), AATTTTGAGGGGAATAGGACGGCGGCGG (SEQ ID NO:9542), TTTTGAGGGGAATAGGACGGCGGCGG (SEQ ID NO:9543)

Target1011        chr9:135462583-135462593        TCGGAGTTGTTCGGGGGGGTTTCGGTTT (SEQ ID NO:9544), TTCGGAGTTGTTCGGGGGGGTTTCGGTT (SEQ ID NO:9545), TTTCGGAGTTGTTCGGGGGGGTTTCGGT (SEQ ID NO:9546), CGGAGTTGTTCGGGGGGGTTTCGGTTTC (SEQ ID NO:9547), TTTTCGGAGTTGTTCGGGGGGGTTTCGG (SEQ ID NO:9548), TGTTCGTGGCGTTTGTGTAATTTCGGT (SEQ ID NO:9549), CGGTGTTTTTTCGTTTTTGTTCGTGGCG (SEQ ID NO:9550), CGGTGTTTTTTCGTTTTTGTTCGTGGCGT (SEQ ID NO:9551), TCGGTGTTTTTTCGTTTTTGTTCGTGGCG (SEQ ID NO:9552), CGTCGGTGTTTTTTCGTTTTTGTTCGTGGCG (SEQ ID NO:9553)

Target1012        chr9:135462605-135462617        GGAGTTGTTCGGGGGGGTTTCGGTTTC (SEQ ID NO:9554), GGAGTTGTTCGGGGGGGTTTCGGTTT (SEQ ID NO:9555), CGAGTTTGGGTGTCGCGGAATTATCG (SEQ ID NO:9556), CGGGGGTTTTAGAGGTTTCGTTTGAGAGC (SEQ ID NO:9557), TCGGGGTTTTAGAGGTTTCGTTTGAGAGC (SEQ ID NO:9558), TGTTCGTGGCGTTTGTGTAATTTCGGT (SEQ ID NO:9559), CGGTGTTTTTTCGTTTTTGTTCGTGGCG (SEQ ID NO:9560), CGGTGTTTTTTCGTTTTTGTTCGTGGCGT (SEQ ID NO:9561), TCGGTGTTTTTTCGTTTTTGTTCGTGGCG (SEQ ID NO:9562), CGTCGGTGTTTTTTCGTTTTTGTTCGTGGCG (SEQ ID NO:9563)

Target1013        chr9:135462629-135462703        ACGTTACGGGTAGGAGCGGGAGGGTAT (SEQ ID NO:9564), AACGTTACGGGTAGGAGCGGGAGGGTA (SEQ ID NO:9565), TTACGGGTAGGAGCGGGAGGGTATCGG (SEQ ID NO:9566), GTTACGGGTAGGAGCGGGAGGGTATCGG (SEQ ID NO:9567), CGTTACGGGTAGGAGCGGGAGGGTATC (SEQ ID NO:9568), AGTTGATGGTCGGTGAAGGTCGTGCGC (SEQ ID NO:9569), GTTGATGGTCGGTGAAGGTCGTGCGC (SEQ ID NO:9570), TAGTTGATGGTCGGTGAAGGTCGTGCG (SEQ ID NO:9571), TAGTTGATGGTCGGTGAAGGTCGTGCGC (SEQ ID NO:9572), AGTTGATGGTCGGTGAAGGTCGTGCG (SEQ ID NO:9573)

Target1014        chr9:135462711-135462765        ACGTTACGGGTAGGAGCGGGAGGGTAT (SEQ ID NO:9574), AACGTTACGGGTAGGAGCGGGAGGGTA (SEQ ID NO:9575), TTACGGGTAGGAGCGGGAGGGTATCGG (SEQ ID NO:9576), GTTACGGGTAGGAGCGGGAGGGTATCG (SEQ ID NO:9577), CGTTACGGGTAGGAGCGGGAGGGTATC (SEQ ID NO:9578), AGTTGATGGTCGGTGAAGGTCGTGCGC (SEQ ID NO:9579), GTTGATGGTCGGTGAAGGTCGTGCGC (SEQ ID NO:9580), TAGTTGATGGTCGGTGAAGGTCGTGCG (SEQ ID NO:9581), GAGGCGGCGAGTTTTATGCGGTTTGT (SEQ ID NO:9582), TAGTTGATGGTCGGTGAAGGTCGTGCG (SEQ ID NO:9583)

Target1015        chr9:135462791-135462798        TCGTAGTGAAGGAGGAGGGCGATCG (SEQ ID NO:9584), GGTCGGGTTTTGATATGTCGTTGTGTTCG (SEQ ID NO:9585), GGTCGGGTTTTGATATGTCGTTGTGTTCGT (SEQ ID NO:9586), AGGTCGGGTTTTGATATGTCGTTGTGTTCG (SEQ ID NO:9587), AGGTCGGGTTTTGATATGTCGTTGTGTTCGT (SEQ ID NO:9588), AGTTGATGGTCGGTGAAGGTCGTGCGT (SEQ ID NO:9589), GCGAGGCGGCGAGTTTTATGCGGTTTT (SEQ ID NO:9590), CGAGGCGGCGAGTTTTATGCGGTTTTG (SEQ ID NO:9591), CGAGGCGGCGAGTTTTATGCGGTTTGT (SEQ ID NO:9592), TAGTTGATGGTCGGTGAAGGTCGTGCGT (SEQ ID NO:9593)

Target1016        chr9:135462890-135462909        TGGCGTAGTTGGAGCGTAGTTTCGAGC (SEQ ID NO:9594), TTGGCGTAGTTGGAGCGTAGTTTCGAGC (SEQ ID NO:9595), GTTGGCGTAGTTGGAGCGTAGTTTCGAGC (SEQ ID NO:9596), AGTTGGCGTAGTTGGAGCGTAGTTTCG (SEQ ID NO:9597), GTTGGCGTAGTTGGAGCGTAGTTTCGA (SEQ ID NO:9598), AGGTTTTGATTTGCGTGTCGGTGAGGT (SEQ ID NO:9599), TTGATTTGCGTGTCGGTGAGGTTGAGT (SEQ ID NO:9600), GGTTTTGATTTGCGTGTCGGTGAGGTT (SEQ ID NO:9601), AGGTTTTGATTTGCGTGTCGGTGAGGTT (SEQ ID NO:9602), GGTTTTGATTTGCGTGTCGGTGAGGTG (SEQ ID NO:9603)

Target1017        chr9:139428277-139428322        TGATCGTTTGGGTTGTGGGGGAGTTTGT (SEQ ID NO:9604), GATCGTTTGGGTTGTGGGGGAGTTTGT (SEQ ID NO:9605), TGATCGTTTGGGTTGTGGGGGAGTTTG (SEQ ID NO:9606), TCGTTTGGGTTGTGGGGGAGTTTGTT (SEQ ID NO:9607), ATCGTTTGGGTTGTGGGGGAGTTTGTT (SEQ ID NO:9608), AGGGAGTTACGGCGGGGAGATTTGGTT (SEQ ID NO:9609), TAGGGAGTTACGGCGGGGAGATTTGGT (SEQ ID NO:9610), GGGAGTTACGGCGGGGAGATTTGGTTT

FIGURE 5 CONTINUED (SEQ ID NO:9611), AGGGAGTTACGGCGGGGAGATTTGGTTT (SEQ ID NO:9612), AGGGAGTTACGGCGGGGAGATTTGGT (SEQ ID NO:9613)

Target1018  chr9:139428353-139428527  GGGCGGGTGTTTGTGGTTCGGGTTATG (SEQ ID NO:9614), TCGTCGTGGTTTTTTGGGCGGGTGTTT (SEQ ID NO:9615), TTCGTCGTGGTTTTTTGGGCGGGTGTT (SEQ ID NO:9616), TTTCGTCGTGGTTTTTTGGGCGGGTGT (SEQ ID NO:9617), TTTTTGGGCGGGTGTTTGTGGTTCGGG (SEQ ID NO:9618), AGGGAGTTACGGCGGGGAGATTTGGTT (SEQ ID NO:9619), TAGGGAGTTACGGCGGGGAGATTTGGT (SEQ ID NO:9620), GGGAGTTACGGCGGGGAGATTTGGTTT (SEQ ID NO:9621), AGGGAGTTACGGCGGGGAGATTTGGTTT (SEQ ID NO:9622), AGGGAGTTACGGCGGGGAGATTTGGT (SEQ ID NO:9623)

Target1019  chr10:555435-555454  TGGGTTGTGTGTGAGTTTTCGTTGCGG (SEQ ID NO:9624), TGGGTTGTGTGTGAGTTTTCGTTGCGGA (SEQ ID NO:9625), GGGTTGTGTGTGAGTTTTCGTTGCGGA (SEQ ID NO:9626), ATGGGTTGTGTGTGAGTTTTCGTTGCGG (SEQ ID NO:9627), GGGTTGTGTGTGAGTTTTCGTTGCGGAA (SEQ ID NO:9628)

Target1020  chr10:3514496-3514575  TGGGGATAGAGAGGGGGAAGGATGGTT (SEQ ID NO:9629), TTGGGGATAGAGAGGGGGAAGGATGGT (SEQ ID NO:9630), TGTTGGGGATAGAGAGGGGGAAGGATGGT (SEQ ID NO:9631), GTTGGGGATAGAGAGGGGGAAGGATGGT (SEQ ID NO:9632), TGTTGGGGATAGAGAGGGGGAAGGATGG (SEQ ID NO:9633)

Target1021  chr10:3514707-3514967  GGTCGGTAGGTTCGGGAAGTTTTTTCGT (SEQ ID NO:9634), GGTCGGTAGGTTCGGGAAGTTTTTTCG (SEQ ID NO:9635), AGGTCGGTAGGTTCGGGAAGTTTTTTCGT (SEQ ID NO:9636), AGGTCGGTAGGTTCGGGAAGTTTTTTCG (SEQ ID NO:9637), AAGGTCGGTAGGTTCGGGAAGTTTTTTCG (SEQ ID NO:9638), TGAATTTTACGTGGGATGGGTTTTGTTAGAGAGA (SEQ ID NO:9639), TTGAATTTTACGTGGGATGGGTTTTGTTAGAGAGA (SEQ ID NO:9640), TGAATTTTACGTGGGATGGGTTTTGTTAGAGAGAT (SEQ ID NO:9641), TTTGAATTTTACGTGGGATGGGTTTTGTTAGAGAGA (SEQ ID NO:9642), TGAATTTTACGTGGGATGGGTTTTGTTAGAGAGATT (SEQ ID NO:9643)

Target1022  chr10:6183284-6183576  CGTCGTATGGATTTGTAGAGGTAGTCGTTTTTGT (SEQ ID NO:9644), TCGTATGGATTTGTAGAGGTAGTCGTTTTTGTCG (SEQ ID NO:9645), TCGTCGTATGGATTTGTAGAGGTAGTCGTTTTTG (SEQ ID NO:9646), TCGTCGTATGGATTTGTAGAGGTAGTCGTTTTTGT (SEQ ID NO:9647), CGTCGTATGGATTTGTAGAGGTAGTCGTTTTTGTCG (SEQ ID NO:9648), AGGGCGGAGGGGGTTGGATTTGTTGAG (SEQ ID NO:9649), TAGGGCGGAGGGGGTTGGATTTGTTGA (SEQ ID NO:9650), GGGCGGAGGGGGTTGGATTTGTTGAGT (SEQ ID NO:9651), GGCGGAGGGGGTTGGATTTGTTGAGTT (SEQ ID NO:9652), TAGGGCGGAGGGGGTTGGATTTGTTGAG (SEQ ID NO:9653)

Target1023  chr10:6183594-6183800  TGGTTGATTTTGGTTGGTGGTGAGAGGA (SEQ ID NO:9654), TGTAGAGGTAGTCGTTTTTGTCGGGTGG (SEQ ID NO:9655), CGTTTTTGTCGGGTGGATTTGTTTTTCGCG (SEQ ID NO:9656), TGTAGAGGTAGTCGTTTTTGTCGGGTGGA (SEQ ID NO:9657), GTAGAGGTAGTCGTTTTTGTCGGGTGGA (SEQ ID NO:9658), TGGAGAGTTGGGAGAATTGGTTTTCGGT (SEQ ID NO:9659), TGGTGTTTGGAGAGTTGGGAGAATTGGT (SEQ ID NO:9660), TGGAGAGTTGGGAGAATTGGTTTTCGGTGT (SEQ ID NO:9661), GGAGAGTTGGGAGAATTGGTTTTCGGTGT (SEQ ID NO:9662), TGGAGAGTTGGGAGAATTGGTTTTCGGTG (SEQ ID NO:9663)

Target1024  chr10:7449679-7449756  GGTTTTTTAGCGTCGTTTCGGGATTTTCGG (SEQ ID NO:9664), CGGGCGGTCGATCGTTAGGGGTTAC (SEQ ID NO:9665), AGGTTTTTTAGCGTCGTTTCGGGATTTTCGG (SEQ ID NO:9666), TTTTTTAGCGTCGTTTCGGGATTTTCGGA (SEQ ID NO:9667), GGTTTTTTAGCGTCGTTTCGGGATTTTCGGA (SEQ ID NO:9668), CGTGGTTGATGGCGTTTGTGGTGTTCG (SEQ ID NO:9669), CGGTGTTCGTGGTTGATGGCGTTTGTG (SEQ ID NO:9670), GGTGTTCGTGGTTGATGGCGTTTGTGG (SEQ ID NO:9671), GGTGTTCGTGGTTGATGGCGTTTGTGGT (SEQ ID NO:9672), CGTGGTTGATGGCGTTTGTGGTGTTCGA (SEQ ID NO:9673)

Target1025  chr10:7449774-7449898  TGCGTTTCGAGTTTTTAGGTGTTAGAGCG (SEQ ID NO:9674), TTTTTTAGCGTCGTTTCGGGATTTTCGGA (SEQ ID NO:9675), GGTTTTTTAGCGTCGTTTCGGGATTTTCGGA (SEQ ID NO:9676), GGTGCGTTTCGAGTTTTTAGGTGTTAGAGCG (SEQ ID NO:9677), TGGTGCGTTTCGAGTTTTTAGGTGTTAGAGCG (SEQ ID NO:9678), TGGGGAGGAGGGAGGAGTCGAGATTGG (SEQ ID NO:9679), GGGAGGAGGGAGGAGTCGAGATTGGGT (SEQ ID NO:9680), GGTGGGGAGGAGGGAGGAGTCGAGATT (SEQ ID NO:9681), TTTTGGTGGGGAGGAGGGAGGAGTCGA (SEQ ID NO:9682), TTTGGTGGGGAGGAGGGAGGAGTCGAG (SEQ ID NO:9683)

Target1026  chr10:7450019-7450043  GGTGGTCGGTCGGGTTTTTGTTTAGTT (SEQ ID NO:9684), GGTCGGTCGGGTTTTTGTTTAGTTTCGGT (SEQ ID NO:9685), TGGTCGGTCGGGTTTTTGTTTAGTTTCGG (SEQ ID NO:9686), GGTCGGTCGGGTTTTTGTTTAGTTTCGG (SEQ ID NO:9687), TGGTCGGTCGGGTTTTTGTTTAGTTTCGGT (SEQ ID NO:9688), CGCGAGGTGGGGAGTAGTTTAAAATGGT (SEQ ID NO:9689), CGCGAGGTGGGGAGTAGTTTAAAATGGTT (SEQ ID NO:9690), CGCGAGGTGGGGAGTAGTTTAAAATGGTTT (SEQ ID NO:9691), TGGTTTTGTGTTGCGAAGTTGTAGTTTTAGTCG (SEQ ID NO:9692), ATGGTTTTGTGTTGCGAAGTTGTAGTTTTAGTCG (SEQ ID NO:9693)

FIGURE 5 CONTINUED

Target1027    chr10:7450049-7450202    GCGACGTTAGGAGGATAAGGGGAGGGG (SEQ ID NO:9694), GGCGACGTTAGGAGGATAAGGGGAGGG (SEQ ID NO:9695), TCGCGGGGTTTATGGGAAAGTCGGTTT (SEQ ID NO:9696), GCGACGTTAGGAGGATAAGGGGAGGGGT (SEQ ID NO:9697), CGACGTTAGGAGGATAAGGGGAGGGGT (SEQ ID NO:9698), TGGGTTTCGCGAGGTGGGGAGTAGTT (SEQ ID NO:9699), ATGGGTTTCGCGAGGTGGGGAGTAGTT (SEQ ID NO:9700), TATGGGTTTCGCGAGGTGGGGAGTAGT (SEQ ID NO:9701), ATGGGTTTCGCGAGGTGGGGAGTAGTT (SEQ ID NO:9702), TGGGTTTCGCGAGGTGGGGAGTAGTT (SEQ ID NO:9703)

Target1028    chr10:7454983-7454990    ATAGCGGGGTTTGTGGAAAGGGAGGGG (SEQ ID NO:9704), GGGTTTGTGGAAAGGGAGGGGTCGAGA (SEQ ID NO:9705), GGGGTTTGTGGAAAGGGAGGGGTCGAG (SEQ ID NO:9706), GGGTTTGTGGAAAGGGAGGGGTCGAGAG (SEQ ID NO:9707), GGGGTTTGTGGAAAGGGAGGGGTCGA (SEQ ID NO:9708), GCGCGGGTTAAGAGTGGGAGGTTTAGG (SEQ ID NO:9709), AGCGCGGGTTAAGAGTGGGAGGTTTAGG (SEQ ID NO:9710), CGCGGGTTAAGAGTGGGAGGTTTAGGGT (SEQ ID NO:9711), CGCGGGTTAAGAGTGGGAGGTTTAGGG (SEQ ID NO:9712), GTAGCGCGGGTTAAGAGTGGGAGGTTT (SEQ ID NO:9713)

Target1029    chr10:7455034-7455064    ATAGCGGGGTTTGTGGAAAGGGAGGGG (SEQ ID NO:9714), GGGTTTGTGGAAAGGGAGGGGTCGAGA (SEQ ID NO:9715), GGGGTTTGTGGAAAGGGAGGGGTCGAG (SEQ ID NO:9716), GGGTTTGTGGAAAGGGAGGGGTCGAGAG (SEQ ID NO:9717), GGGGTTTGTGGAAAGGGAGGGGTCGA (SEQ ID NO:9718), TGCGGGGTTAGGGTTATTGGGTAGGCG (SEQ ID NO:9719), GCGGGGTTAGGGTTATTGGGTAGGCGT (SEQ ID NO:9720), CGCGGGTTTGGGACGTAAATGGGAGGGA (SEQ ID NO:9721), GCGGTTTGGGACGTAAATGGGAGGGAG (SEQ ID NO:9722), GCGCGGGTTAAGAGTGGGAGGTTTAGG (SEQ ID NO:9723)

Target1030    chr10:7455069-7455179    ATAGCGGGGTTTGTGGAAAGGGAGGGG (SEQ ID NO:9724), GGGTTTGTGGAAAGGGAGGGGTCGAGA (SEQ ID NO:9725), GGGGTTTGTGGAAAGGGAGGGGTCGAG (SEQ ID NO:9726), GGGTTTGTGGAAAGGGAGGGGTCGAGAG (SEQ ID NO:9727), GGGGTTTGTGGAAAGGGAGGGGTCGA (SEQ ID NO:9728), TGCGGGGTTAGGGTTATTGGGTAGGCG (SEQ ID NO:9729), GCGGGGTTAGGGTTATTGGGTAGGCGT (SEQ ID NO:9730), CGCGGGTTTGGGACGTAAATGGGAGGGA (SEQ ID NO:9731), GCGGTTTGGGACGTAAATGGGAGGGAG (SEQ ID NO:9732), GCGCGGGTTAAGAGTGGGAGGTTTAGG (SEQ ID NO:9733)

Target1031    chr10:7455186-7455205    GCGTTGCGTTTATTTAGTGGTTTTGGTTTCG (SEQ ID NO:9734), GCGTTGCGTTTATTTAGTGGTTTTGGTTTCGT (SEQ ID NO:9735), GCGTTTATTTAGTGGTTTTGGTTTCGTAGGGC (SEQ ID NO:9736), TGCGTTTATTTAGTGGTTTTGGTTCGTAGGGC (SEQ ID NO:9737), TGCGTTTATTTAGTGGTTTTGGTTCGTAGGG (SEQ ID NO:9738), TCGGGAAGTTTTGCGTTGGTATTAGGGT (SEQ ID NO:9739), TTCGGGAAGTTTTGCGTTGGTATTAGGGT (SEQ ID NO:9740), CGGGAAGTTTTGCGTTGGTATTAGGGTAAGCG (SEQ ID NO:9741), TCGGGAAGTTTTGCGTTGGTATTAGGGTA (SEQ ID NO:9742), TTTCGGGAAGTTTTGCGTTGGTATTAGGGT (SEQ ID NO:9743)

Target1032    chr10:8094268-8094297    GGTGAGGAGGTTTTTCGGTGTAAGGGGC (SEQ ID NO:9744), TGAGGAGGTTTTTCGGTGTAAGGGCGT (SEQ ID NO:9745), GTGAGGAGGTTTTTCGGTGTAAGGGCGT (SEQ ID NO:9746), GTGAGGAGGTTTTTCGGTGTAAGGGCG (SEQ ID NO:9747), TGGTGAGGAGGTTTTTCGGTGTAAGGGCG (SEQ ID NO:9748)

Target1033    chr10:8094328-8094348    GGTGAGGAGGTTTTTCGGTGTAAGGGCG (SEQ ID NO:9749), TGAGGAGGTTTTTCGGTGTAAGGGCGT (SEQ ID NO:9750), GTGAGGAGGTTTTTCGGTGTAAGGGCGT (SEQ ID NO:9751), GTGAGGAGGTTTTTCGGTGTAAGGGCG (SEQ ID NO:9752), TGGTGAGGAGGTTTTTCGGTGTAAGGGCG (SEQ ID NO:9753)

Target1034    chr10:8094431-8094448    GCGGATAGGCGTTTTTGTATCGGAAGGT (SEQ ID NO:9754), GCGGATAGGCGTTTTTGTATCGGAAGG (SEQ ID NO:9755), GCGGATAGGCGTTTTTGTATCGGAAGGTT (SEQ ID NO:9756), GCGGATAGGCGTTTTTGTATCGGAAGGTTT (SEQ ID NO:9757), GCGGATAGGCGTTTTTGTATCGGAAGGTTTT (SEQ ID NO:9758), AGTTGTTATGGGTTTTGCGCGCGGAGA (SEQ ID NO:9759), AAGTTGTTATGGGTTTTGCGCGCGGAG (SEQ ID NO:9760), GTTGTTATGGGTTTTGCGCGCGGAGAT (SEQ ID NO:9761), AAGTTGTTATGGGTTTTGCGCGCGGAGA (SEQ ID NO:9762), AATCGAGGGGTGGATGCGTTACGTAGC (SEQ ID NO:9763)

Target1035    chr10:8094463-8094483    TTTTTTCGGTTTTGAGGTTTTCGCGCG (SEQ ID NO:9764), TTTTTCGGTTTTGAGGTTTTCGCGCG (SEQ ID NO:9765), TTTTCGGTTTTGAGGTTTTCGCGCG (SEQ ID NO:9766), AGTTGTTATGGGTTTTGCGCGCGGAGA (SEQ ID NO:9767), AAGTTGTTATGGGTTTTGCGCGCGGAG (SEQ ID NO:9768), GTTGTTATGGGTTTTGCGCGCGGAGAT (SEQ ID NO:9769), AAGTTGTTATGGGTTTTGCGCGCGGAGA (SEQ ID NO:9770), AATCGAGGGGTGGATGCGTTACGTAGC (SEQ ID NO:9771)

Target1036    chr10:8094513-8094540    ACGCGTGGTTGTGAGTTGGGTTTACGT (SEQ ID NO:9772), ACGCGTGGTTGTGAGTTGGGTTTACGTT (SEQ ID NO:9773), CGCGTGGTTGTGAGTTGGGTTTACGTT (SEQ ID NO:9774), TGGTTTTACGCGTGGTTGTGAGTTGGGT (SEQ ID NO:9775), GGTTTTACGCGTGGTTGTGAGTTGGGT (SEQ ID NO:9776), AATCGAGGGGTGGATGCGTTACGTAGC (SEQ ID NO:9777), ATCGAGGGGTGGATGCGTTACGTAGC (SEQ ID NO:9778), TAATCGAGGGGTGGATGCGTTACGTAGC (SEQ ID NO:9779), GTTAATCGAGGGGTGGATGCGTTACGT (SEQ ID NO:9780), TCGAGGGGTGGATGCGTTACGTAGC (SEQ ID NO:9781)

FIGURE 5 CONTINUED

Target1037    chr10:8529520-8529624    TGATAGTTTTCGGGAGGATTGTTTGGTTTTTGTT (SEQ ID NO:9782),
TTGATAGTTTTCGGGAGGATTGTTTGGTTTTTGT (SEQ ID NO:9783),
TGATAGTTTTCGGGAGGATTGTTTGGTTTTTGTTT (SEQ ID NO:9784),
TTGATAGTTTTCGGGAGGATTGTTTGGTTTTTGTT (SEQ ID NO:9785),
ATTGATAGTTTTCGGGAGGATTGTTTGGTTTTTGT (SEQ ID NO:9786)

Target1038    chr10:23480706-23480716    AGTTTTTAGTAGAATTTAGGTCGGAGTTTCGCGT (SEQ ID NO:9787),
CGTAGTGGGAGTGGGTTCGGATTATTTTTTAATG (SEQ ID NO:9788),
CGTAGTGGGAGTGGGTTCGGATTATTTTTTAATGA (SEQ ID NO:9789),
AAGTTTTTAGTAGAATTTAGGTCGGAGTTTCGCGT (SEQ ID NO:9790),
GAAGTTTTTAGTAGAATTTAGGTCGGAGTTTCGCG (SEQ ID NO:9791),
TCGCGGTAGTTTGGGTAATTTAAGGGTGT (SEQ ID NO:9792), AGGGTGTTGTTTTTAGGGATTAGGTGGGT
(SEQ ID NO:9793), GGGTGTTGTTTTTAGGGATTAGGTGGGTGT (SEQ ID NO:9794),
AGGGTGTTGTTTTTAGGGATTAGGTGGGTG (SEQ ID NO:9795),
AGGGTGTTGTTTTTAGGGATTAGGTGGGTGT (SEQ ID NO:9796)

Target1039    chr10:23480784-23480815    ATTTCGGATAAGGGGGTGGCGGAATGT (SEQ ID NO:9797), TTTCGGATAAGGGGGTGGCGGAATGTA
(SEQ ID NO:9798), TCGGATAAGGGGGTGGCGGAATGTATT (SEQ ID NO:9799),
TTCGGATAAGGGGGTGGCGGAATGTAT (SEQ ID NO:9800), TTTCGGATAAGGGGGTGGCGGAATGT (SEQ
ID NO:9801), TTTAGGGGTGCGCGTCGGTGGTTTAGA (SEQ ID NO:9802),
GTTTTTAGGGGTGCGCGTCGGTGGTTT (SEQ ID NO:9803), GAAGTTTTTAGGGGTGCGCGTCGGTGG (SEQ
ID NO:9804), AGAAGTTTTTAGGGGTGCGCGTCGGTG (SEQ ID NO:9805),
TTAGGGGTGCGCGTCGGTGGTTAGAC (SEQ ID NO:9806)

Target1040    chr10:23480820-23481032    GGCGCGCGGTTGTTTTAGTTTTTAGGGC (SEQ ID NO:9807), CGGCGCGCGGTTGTTTTAGTTTTTAGGG (SEQ
ID NO:9808), ATTTCGGATAAGGGGGTGGCGGAATGT (SEQ ID NO:9809),
CGGCGCGCGGTTGTTTTAGTTTTTAGGGC (SEQ ID NO:9810), TTTCGGATAAGGGGGTGGCGGAATGTA
(SEQ ID NO:9811), TTTAGGGGTGCGCGTCGGTGGTTTAGA (SEQ ID NO:9812),
GTTTTTAGGGGTGCGCGTCGGTGGTTT (SEQ ID NO:9813), GAAGTTTTTAGGGGTGCGCGTCGGTGG (SEQ
ID NO:9814), GAGTTTTTGGGGCGAGGAAAAGGCGGG (SEQ ID NO:9815),
GGAGTTTTTGGGGCGAGGAAAAGGCGG (SEQ ID NO:9816)

Target1041    chr10:23481051-23481062    AGGGAAGAGAGCGGTGCGAGGAGTTTC (SEQ ID NO:9817), GAGGGAAGAGAGCGGTGCGAGGAGTTT
(SEQ ID NO:9818), TAGAGGAGAGGGAAGAGAGCGGTGCGA (SEQ ID NO:9819),
GTAGAGGAGAGGGAAGAGAGCGGTGCG (SEQ ID NO:9820), AGAGGGAAGAGAGCGGTGCGAGGAGTT
(SEQ ID NO:9821), GAGTTTTTGGGGCGAGGAAAAGGCGGG (SEQ ID NO:9822),
GGAGTTTTTGGGGCGAGGAAAAGGCGG (SEQ ID NO:9823), GGGAGTTTTTGGGGCGAGGAAAAGGCG
(SEQ ID NO:9824), TGGGAGTTTTTGGGGCGAGGAAAAGGC (SEQ ID NO:9825),
AGTTTTTGGGGCGAGGAAAAGGCGGG (SEQ ID NO:9826)

Target1042    chr10:23481124-23481143    AGGGAAGAGAGCGGTGCGAGGAGTTTC (SEQ ID NO:9827), GAGGGAAGAGAGCGGTGCGAGGAGTTT
(SEQ ID NO:9828), TAGAGGAGAGGGAAGAGAGCGGTGCGA (SEQ ID NO:9829),
GTAGAGGAGAGGGAAGAGAGCGGTGCG (SEQ ID NO:9830), AGAGGGAAGAGAGCGGTGCGAGGAGTT
(SEQ ID NO:9831), TGGGGAGGGTTGTGGCGGATTTTTTGG (SEQ ID NO:9832),
GGGGAGGGTTGTGGCGGATTTTTTGGA (SEQ ID NO:9833), GGGGAGGGTTGTGGCGGATTTTTTGGAG
(SEQ ID NO:9834), TTGGGGAGGGTTGTGGCGGATTTTTTGG (SEQ ID NO:9835),
TGGGGAGGGTTGTGGCGGATTTTTTGGA (SEQ ID NO:9836)

Target1043    chr10:23481145-23481230    TGGTTGGCGCGATGGGTTTTTGGTACG (SEQ ID NO:9837), CGTTTTGATTGGTTGGCGCGATGGGTT (SEQ
ID NO:9838), TGATTGGTTGGCGCGATGGGTTTTTGGT (SEQ ID NO:9839),
GATTGGTTGGCGCGATGGGTTTTTGGT (SEQ ID NO:9840), TGATTGGTTGGCGCGATGGGTTTTTGG (SEQ
ID NO:9841), CGTTGGGGAGGGTTGTGGCGGATTTTT (SEQ ID NO:9842),
TGGGGAGGGTTGTGGCGGATTTTTTGG (SEQ ID NO:9843), GGGGAGGGTTGTGGCGGATTTTTTGGA
(SEQ ID NO:9844), CGTTGGGGAGGGTTGTGGCGGATTTTT (SEQ ID NO:9845),
GGGGAGGGTTGTGGCGGATTTTTTGGAG (SEQ ID NO:9846)

Target1044    chr10:28034313-28034373    CGTAAGGGGTTCGGGGGCGTGTGAATT (SEQ ID NO:9847), CGTAAGGGGTTCGGGGGCGTGTGAATTA
(SEQ ID NO:9848), GTAAGGGGTTCGGGGGCGTGTGAATTA (SEQ ID NO:9849),
CGTAAGGGGTTCGGGGGCGTGTGAAT (SEQ ID NO:9850), GTAAGGGGTTCGGGGGCGTGTGAATT (SEQ
ID NO:9851), AGTGATTTGAGAAGAGGCGCGGGTGGT (SEQ ID NO:9852),
TCGGCGTTGGGGGAGGGGGATATTTTT (SEQ ID NO:9853), GTCGGCGTTGGGGGAGGGGGATATTTT
(SEQ ID NO:9854), GTGATTTGAGAAGAGGCGCGGGTGGTC (SEQ ID NO:9855),
CGGCGTTGGGGGAGGGGGATATTTTTG (SEQ ID NO:9856)

Target1045    chr10:28034442-28034470    AGTAAAGGAGGCGCGGTTAGGTGGGTT (SEQ ID NO:9857), AAGTAAAGGAGGCGCGGTTAGGTGGGT
(SEQ ID NO:9858), AAAGGAGGCGCGGTTAGGTGGGTTTTT (SEQ ID NO:9859),
GTAAAGGAGGCGCGGTTAGGTGGGTTT (SEQ ID NO:9860), AGTAAAGGAGGCGCGGTTAGGTGGGTTT
(SEQ ID NO:9861), AGGTTTGGTGGAGAGGCGTTCGGGTAG (SEQ ID NO:9862),
AAGGTTTGGTGGAGAGGCGTTCGGGTA (SEQ ID NO:9863), TAAGGTTTGGTGGAGAGGCGTTCGGGT
(SEQ ID NO:9864), GGTTTTTGCGTTTTGGGCGTCGGTGTT (SEQ ID NO:9865),
TTGGTTTTTGCGTTTTGGGCGTCGGTG (SEQ ID NO:9866)

Target1046    chr10:28034494-28034506    AGTAAAGGAGGCGCGGTTAGGTGGGTT (SEQ ID NO:9867), AAGTAAAGGAGGCGCGGTTAGGTGGGT
(SEQ ID NO:9868), AAAGGAGGCGCGGTTAGGTGGGTTTTT (SEQ ID NO:9869),
GTAAAGGAGGCGCGGTTAGGTGGGTTT (SEQ ID NO:9870), AGTAAAGGAGGCGCGGTTAGGTGGGTTT

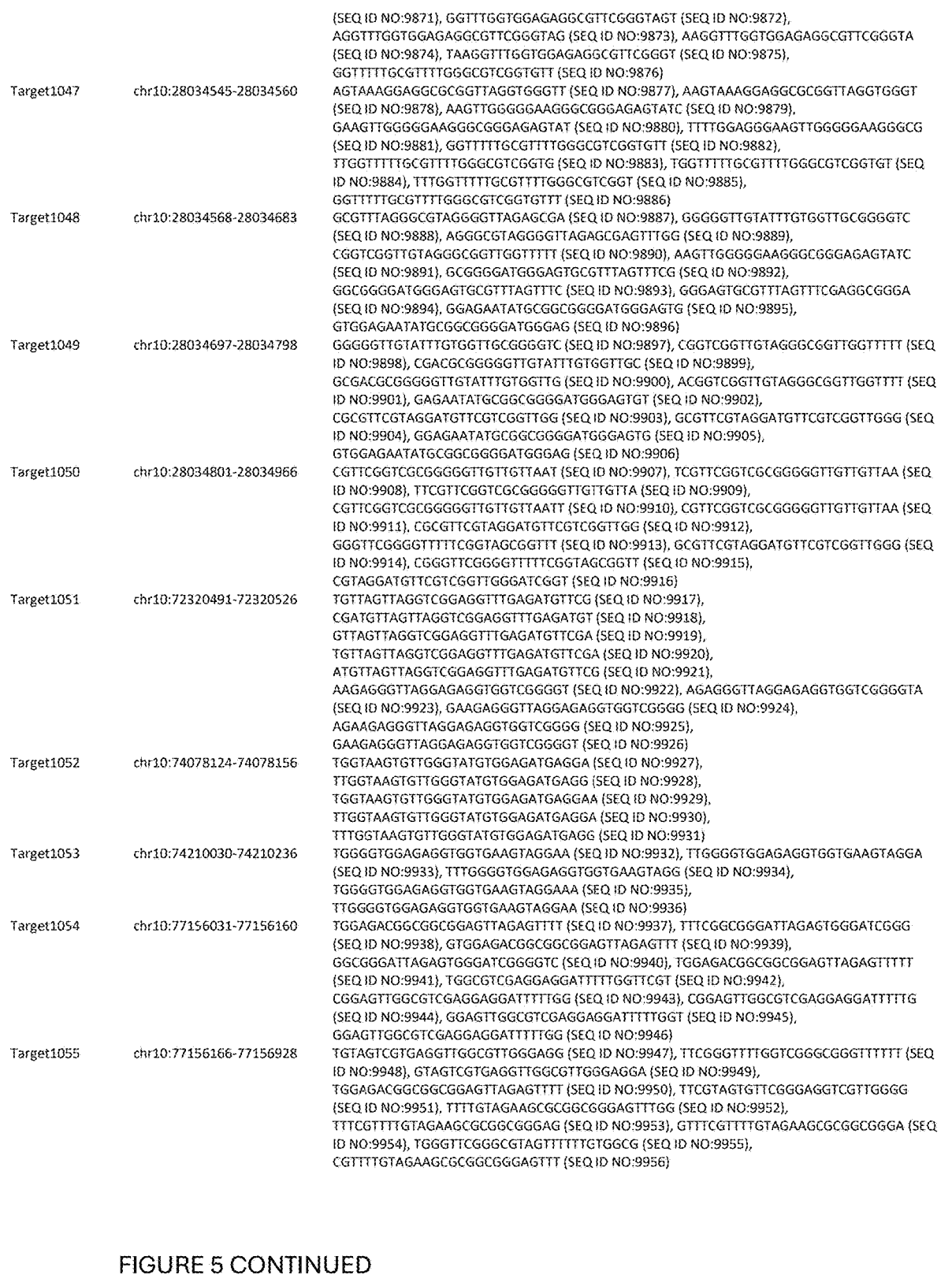

FIGURE 5 CONTINUED (SEQ ID NO:9871), GGTTTGGTGGAGAGGCGTTCGGGTAGT (SEQ ID NO:9872),
AGGTTTGGTGGAGAGGCGTTCGGGTAG (SEQ ID NO:9873), AAGGTTTGGTGGAGAGGCGTTCGGGTA
(SEQ ID NO:9874), TAAGGTTTGGTGGAGAGGCGTTCGGGT (SEQ ID NO:9875),
GGTTTTTGCGTTTTGGGCGTCGGTGTT (SEQ ID NO:9876)

| Target1047 | chr10:28034545-28034560 | AGTAAAGGAGGCGCGGTTAGGTGGGTT (SEQ ID NO:9877), AAGTAAAGGAGGCGCGGTTAGGTGGGT (SEQ ID NO:9878), AAGTTGGGGGAAGGGCGGGAGAGTATC (SEQ ID NO:9879), GAAGTTGGGGGAAGGGCGGGAGAGTAT (SEQ ID NO:9880), TTTTGGAGGGAAGTTGGGGGAAGGGCG (SEQ ID NO:9881), GGTTTTTGCGTTTTGGGCGTCGGTGTT (SEQ ID NO:9882), TTGGTTTTTGCGTTTTGGGCGTCGGTG (SEQ ID NO:9883), TGGTTTTTGCGTTTTGGGCGTCGGTGT (SEQ ID NO:9884), TTTGGTTTTTGCGTTTTGGGCGTCGGT (SEQ ID NO:9885), GGTTTTTGCGTTTTGGGCGTCGGTGTTT (SEQ ID NO:9886) |
|---|---|---|
| Target1048 | chr10:28034568-28034683 | GCGTTTAGGGCGTAGGGGTTAGAGCGA (SEQ ID NO:9887), GGGGGTTGTATTTGTGGTTGCGGGGTC (SEQ ID NO:9888), AGGGCGTAGGGGTTAGAGCGAGTTTGG (SEQ ID NO:9889), CGGTCGGTTGTAGGGCGGTTGGTTTTT (SEQ ID NO:9890), AAGTTGGGGGAAGGGCGGGAGAGTATC (SEQ ID NO:9891), GCGGGGATGGGAGTGCGTTTAGTTTCG (SEQ ID NO:9892), GGCGGGGATGGGAGTGCGTTTAGTTTC (SEQ ID NO:9893), GGGAGTGCGTTTAGTTTCGGAGGCGGGA (SEQ ID NO:9894), GGAGAATATGCGGCGGGGATGGGAGTG (SEQ ID NO:9895), GTGGAGAATATGCGGCGGGGATGGGAG (SEQ ID NO:9896) |
| Target1049 | chr10:28034697-28034798 | GGGGGTTGTATTTGTGGTTGCGGGGTC (SEQ ID NO:9897), CGGTCGGTTGTAGGGCGGTTGGTTTTT (SEQ ID NO:9898), CGACGCGGGGGTTGTATTTGTGGTTGC (SEQ ID NO:9899), GCGACGCGGGGGTTGTATTTGTGGTTG (SEQ ID NO:9900), ACGGTCGGTTGTAGGGCGGTTGGTTTT (SEQ ID NO:9901), GAGAATATGCGGCGGGGATGGGAGTGT (SEQ ID NO:9902), CGCGTTCGTAGGATGTTCGTCGGTTGG (SEQ ID NO:9903), GCGTTCGTAGGATGTTCGTCGGTTGGG (SEQ ID NO:9904), GGAGAATATGCGGCGGGGATGGGAGTG (SEQ ID NO:9905), GTGGAGAATATGCGGCGGGGATGGGAG (SEQ ID NO:9906) |
| Target1050 | chr10:28034801-28034966 | CGTTCGGTCGCGGGGGTTGTTGTTAAT (SEQ ID NO:9907), TCGTTCGGTCGCGGGGGTTGTTGTTAA (SEQ ID NO:9908), TTCGTTCGGTCGCGGGGGTTGTTGTTA (SEQ ID NO:9909), CGTTCGGTCGCGGGGGTTGTTGTTAATT (SEQ ID NO:9910), CGTTCGGTCGCGGGGGTTGTTGTTAA (SEQ ID NO:9911), CGCGTTCGTAGGATGTTCGTCGGTTGG (SEQ ID NO:9912), GGGTTCGGGGTTTTTCGGTAGCGGTTT (SEQ ID NO:9913), GCGTTCGTAGGATGTTCGTCGGTTGGG (SEQ ID NO:9914), CGGGTTCGGGGTTTTTCGGTAGCGGTT (SEQ ID NO:9915), CGTAGGATGTTCGTCGGTTGGGATCGGT (SEQ ID NO:9916) |
| Target1051 | chr10:72320491-72320526 | TGTTAGTTAGGTCGGAGGTTTGAGATGTTCG (SEQ ID NO:9917), CGATGTTAGTTAGGTCGGAGGTTTGAGATGT (SEQ ID NO:9918), GTTAGTTAGGTCGGAGGTTTGAGATGTTCGA (SEQ ID NO:9919), TGTTAGTTAGGTCGGAGGTTTGAGATGTTCGA (SEQ ID NO:9920), ATGTTAGTTAGGTCGGAGGTTTGAGATGTTCG (SEQ ID NO:9921), AAGAGGGTTAGGAGAGGTGGTCGGGGT (SEQ ID NO:9922), AGAGGGTTAGGAGAGGTGGTCGGGGTA (SEQ ID NO:9923), GAAGAGGGTTAGGAGAGGTGGTCGGGG (SEQ ID NO:9924), AGAAGAGGGTTAGGAGAGGTGGTCGGGG (SEQ ID NO:9925), GAAGAGGGTTAGGAGAGGTGGTCGGGGT (SEQ ID NO:9926) |
| Target1052 | chr10:74078124-74078156 | TGGTAAGTGTTGGGTATGTGGAGATGAGGA (SEQ ID NO:9927), TTGGTAAGTGTTGGGTATGTGGAGATGAGG (SEQ ID NO:9928), TGGTAAGTGTTGGGTATGTGGAGATGAGGAA (SEQ ID NO:9929), TTGGTAAGTGTTGGGTATGTGGAGATGAGGA (SEQ ID NO:9930), TTTGGTAAGTGTTGGGTATGTGGAGATGAGG (SEQ ID NO:9931) |
| Target1053 | chr10:74210030-74210236 | TGGGGTGGAGAGGTGGTGAAGTAGGAA (SEQ ID NO:9932), TTGGGGTGGAGAGGTGGTGAAGTAGGA (SEQ ID NO:9933), TTTGGGGTGGAGAGGTGGTGAAGTAGG (SEQ ID NO:9934), TGGGGTGGAGAGGTGGTGAAGTAGGAAA (SEQ ID NO:9935), TTGGGGTGGAGAGGTGGTGAAGTAGGAA (SEQ ID NO:9936) |
| Target1054 | chr10:77156031-77156160 | TGGAGACGGCGGCGGAGTTAGAGTTTT (SEQ ID NO:9937), TTTCGGCGGGATTAGAGTGGGATCGGG (SEQ ID NO:9938), GTGGAGACGGCGGCGGAGTTAGAGTTT (SEQ ID NO:9939), GGCGGGATTAGAGTGGGATCGGGGTC (SEQ ID NO:9940), TGGAGACGGCGGCGGAGTTAGAGTTTTT (SEQ ID NO:9941), TGGCGTCGAGGAGGATTTTTGGTTCGT (SEQ ID NO:9942), CGGAGTTGGCGTCGAGGAGGATTTTTGG (SEQ ID NO:9943), CGGAGTTGGCGTCGAGGAGGATTTTTG (SEQ ID NO:9944), GGAGTTGGCGTCGAGGAGGATTTTTGGT (SEQ ID NO:9945), GGAGTTGGCGTCGAGGAGGATTTTTGG (SEQ ID NO:9946) |
| Target1055 | chr10:77156166-77156928 | TGTAGTCGTGAGGTTGGCGTTGGGAGG (SEQ ID NO:9947), TTCGGGTTTTTGGTCGGGCGGGTTTTTT (SEQ ID NO:9948), GTAGTCGTGAGGTTGGCGTTGGGAGGA (SEQ ID NO:9949), TGGAGACGGCGGCGGAGTTAGAGTTTT (SEQ ID NO:9950), TTCGTAGTGTTCGGGGAGGTCGTTGGGG (SEQ ID NO:9951), TTTTGTAGAAGCGCGGCGGGAGTTTGG (SEQ ID NO:9952), TTTCGTTTTGTAGAAGCGCGGCGGGAG (SEQ ID NO:9953), GTTTCGTTTTGTAGAAGCGCGGCGGGA (SEQ ID NO:9954), TGGGTTCGGGCGTAGTTTTTTTGTGGCG (SEQ ID NO:9955), CGTTTTGTAGAAGCGCGGCGGGAGTTT (SEQ ID NO:9956) |

FIGURE 5 CONTINUED

| | | |
|---|---|---|
| Target1056 | chr10:88516504-88516592 | GAGGAGGTAGGAGCGAGGAGGGAGGAG (SEQ ID NO:9957), TGTCGGGTTTGGCGAAGGAGAAGGGAG (SEQ ID NO:9958), AGGAGGGGTTAAGGGCGGGTAGGAAGGT (SEQ ID NO:9959), AGGAGCGAGGAGGGAGGAGGGTTAAGG (SEQ ID NO:9960), TTGTCGGGTTTGGCGAAGGAGAAGGGA (SEQ ID NO:9961), GGGAACGTATTTTTTAGTTTTCGGCGCGG (SEQ ID NO:9962), AGGGAACGTATTTTTTAGTTTTCGGCGCGG (SEQ ID NO:9963), GGGAACGTATTTTTTAGTTTTCGGCGCGGA (SEQ ID NO:9964), GGAACGTATTTTTTAGTTTTCGGCGCGG (SEQ ID NO:9965), GGGAACGTATTTTTTAGTTTTCGGCGCG (SEQ ID NO:9966) |
| Target1057 | chr10:88516608-88516675 | GGGTAGGAAGGTTTAGGTTCGGCGCGT (SEQ ID NO:9967), CGGGTAGGAAGGTTTAGGTTCGGCGCG (SEQ ID NO:9968), AGGGTTGGAGGATGCGTTTTTTGGGGT (SEQ ID NO:9969), CGAGGGTTGGAGGATGCGTTTTTTGGGG (SEQ ID NO:9970), GGTAGGAAGGTTTAGGTTCGGCGCGTT (SEQ ID NO:9971), TCGGGTCGGGTAGTTTTTGGTTTCGGT (SEQ ID NO:9972), CGGGTCGGGTAGTTTTTGGTTTCGGTT (SEQ ID NO:9973), TCGGGTCGGGTAGTTTTTGGTTTCGGTT (SEQ ID NO:9974), CGGGTCGGGTAGTTTTTGGTTTCGGT (SEQ ID NO:9975), TCGGGTCGGGTAGTTTTTGGTTTCGG (SEQ ID NO:9976) |
| Target1058 | chr10:94451783-94451828 | GAGTTATTTGGGGAAAGAGGGTCGTGGT (SEQ ID NO:9977), CGAGAGTTATTTGGGGAAAGAGGGTCGTGG (SEQ ID NO:9978), CGAGAGTTATTTGGGGAAAGAGGGTCGTGGT (SEQ ID NO:9979), AGAGTTATTTGGGGAAAGAGGGTCGTGGT (SEQ ID NO:9980), CGAGAGTTATTTGGGGAAAGAGGGTCGT (SEQ ID NO:9981) |
| Target1059 | chr10:94451965-94451993 | TGTGTGTCGGTGGGAACGTGTTAGGTT (SEQ ID NO:9982), TTGTGTGTCGGTGGGAACGTGTTAGGT (SEQ ID NO:9983), GGGTATGTTTGTGTGTCGGTGGGAACGT (SEQ ID NO:9984), TGGGTATGTTTGTGTGTCGGTGGGAACG (SEQ ID NO:9985), TGGGTATGTTTGTGTGTCGGTGGGAACGT (SEQ ID NO:9986), GCGGGAAGAGCGGCGTTTATTTATTGT (SEQ ID NO:9987), GCGGGAAGAGCGGCGTTTATTTATTGTT (SEQ ID NO:9988), GCGGCGTTTATTTATTGTTTTGGAGCGGT (SEQ ID NO:9989), GCGGCGTTTATTTATTGTTTTGGAGCGG (SEQ ID NO:9990), AGCGGCGTTTATTTATTGTTTTGGAGCGG (SEQ ID NO:9991) |
| Target1060 | chr10:94452236-94452295 | AGGAAAGGCGGTTAGGTGAGATTTTTTAACGA (SEQ ID NO:9992), AAGGAAAGGCGGTTAGGTGAGATTTTTTAACG (SEQ ID NO:9993), AAGGAAAGGCGGTTAGGTGAGATTTTTTAACGA (SEQ ID NO:9994), AGGAAAGGCGGTTAGGTGAGATTTTTTAACGAT (SEQ ID NO:9995), AAAGGAAAGGCGGTTAGGTGAGATTTTTTAACG (SEQ ID NO:9996), GGGACGTGTTAGAGGGTAGGGTGGTTT (SEQ ID NO:9997), GGGACGTGTTAGAGGGTAGGGTGGTTTT (SEQ ID NO:9998), GGGACGTGTTAGAGGGTAGGGTGGTT (SEQ ID NO:9999), GGACGTGTTAGAGGGTAGGGTGGTTTT (SEQ ID NO:10000), GGGACGTGTTAGAGGGTAGGGTGGTTTTT (SEQ ID NO:10001) |
| Target1061 | chr10:94822093-94822882 | TTTGTAGGGGGCGTTGCGGTATGAGGT (SEQ ID NO:10002), GGTAATTAGCGGGTGGTTTTGGGCGGG (SEQ ID NO:10003), AATTAGCGGGTGGTTTTGGGCGGGTTC (SEQ ID NO:10004), TGGGTTAGGTCGGGGTTTCGGTGTTGG (SEQ ID NO:10005), CGTTTGTAGGGGGCGTTGCGGTATGAG (SEQ ID NO:10006), GAGGGCGTTTCGTTTGGGTTTGGGAGG (SEQ ID NO:10007), GGGCGTTTCGTTTGGGTTTGGGAGGTT (SEQ ID NO:10008), AGGTTTGGAGTCGGGGCGGTCGTATTT (SEQ ID NO:10009), AAGGTTTGGAGTCGGGGCGGTCGTATT (SEQ ID NO:10010), GAAGGTTTGGAGTCGGGGCGGTCGTAT (SEQ ID NO:10011) |
| Target1062 | chr10:94828119-94828197 | ACGGTTGCGGTGTATCGTAGTTTTTTCG (SEQ ID NO:10012), GACGGTTGCGGTGTATCGTAGTTTTTTCG (SEQ ID NO:10013), GGGTTGGAGCGTGATGTATAGTATTCGGG (SEQ ID NO:10014), AGACGGTTGCGGTGTATCGTAGTTTTTTCG (SEQ ID NO:10015), AGGGTTGGAGCGTGATGTATAGTATTCGGG (SEQ ID NO:10016), GAAGCGGTTGGAGGCGTTTCGGGAATT (SEQ ID NO:10017), AGCGGTTGGAGGCGTTTCGGGAATTTT (SEQ ID NO:10018), AAGCGGTTGGAGGCGTTTCGGGAATTT (SEQ ID NO:10019), GGGATGTAATGGAAGCGGTTGGAGGCG (SEQ ID NO:10020), CGGGATGTAATGGAAGCGGTTGGAGGC (SEQ ID NO:10021) |
| Target1063 | chr10:94828206-94828691 | GGTTTGGTCGGTGGTTATGGCGCGTAC (SEQ ID NO:10022), ATACGGTTTGGTCGGTGGTTATGGCGC (SEQ ID NO:10023), GGATTCGAGGAAGGAGGAGGGCGAGTT (SEQ ID NO:10024), CGGTGCGCGTAGTTGTTTCGGTTAGGA (SEQ ID NO:10025), CGGTTTGGTCGGTGGTTATGGCGCGTA (SEQ ID NO:10026), ATAATGGGGAGCGGTAGATGGGTGGCG (SEQ ID NO:10027), AGGCGGGTGTGGTTAGTTTTTAGCGCG (SEQ ID NO:10028), AGGCGTGAGGGGGTGGAAAAAGAGTCG (SEQ ID NO:10029), TGTTGAACGAGTGAAAGAGTGGCGCG (SEQ ID NO:10030), GGGATGTAATGGAAGCGGTTGGAGGCG (SEQ ID NO:10031) |
| Target1064 | chr10:99080800-99080816 | AATGGTGGTGGAAGGGTAGAGAGGCGC (SEQ ID NO:10032), GGGGAAGGTTGTACGATACGGGTGGGG (SEQ ID NO:10033), GGGGGAAGGTTGTACGATACGGGTGGG (SEQ ID NO:10034), GGGCGGGGAGTATTGAATGGTGGTGGA (SEQ ID NO:10035), GAAAGGAGGTGGGGGCGGGGAGTATTG (SEQ ID NO:10036), GTGATTTTGAATCGAGGAGAGGCGGGT (SEQ ID NO:10037), AGTGATTTTGAATCGAGGAGAGGCGGT (SEQ ID NO:10038), AGTGATTTTGAATCGAGGAGAGGCGGG (SEQ ID NO:10039), TGATTTTGAATCGAGGAGAGGCGGGTT (SEQ ID NO:10040), GTGATTTTGAATCGAGGAGAGGCGGGTT (SEQ ID NO:10041) |
| Target1065 | chr10:99080878-99081075 | CGTGTTGGGCGGTTGTGTTTCGGTAGG (SEQ ID NO:10042), ACGTGTTGGGCGGTTGTGTTTCGGTAG (SEQ ID NO:10043), GACGTGTTGGGCGGTTGTGTTTCGGTA (SEQ ID NO:10044), GTGTTGGGCGGTTGTGTTTCGGTAGGC (SEQ ID NO:10045), TGGGCGGTTGTGTTTCGGTAGGCGATT |

FIGURE 5 CONTINUED

|  |  |  |
|---|---|---|
|  |  | {SEQ ID NO:10046), CGTGAAAGTTCGGAGCGCGGTTAGGG (SEQ ID NO:10047), GTGAAAGTTCGGAGCGCGGTTAGGGG (SEQ ID NO:10048), CGTGAAAGTTCGGAGCGCGGTTAGGGG (SEQ ID NO:10049), TGAAAGTTCGGAGCGCGGTTAGGGG (SEQ ID NO:10050), CGTGAAAGTTCGGAGCGCGGTTAGG (SEQ ID NO:10051) |
| Target1066 | chr10:102587099-102587148 | TGGTCGTTCGAAGGTTTTGCGTCGTT (SEQ ID NO:10052), TTGGTCGTTCGAAGGTTTTGCGTCGTT (SEQ ID NO:10053), TTTGGTCGTTCGAAGGTTTTGCGTCGT (SEQ ID NO:10054), TGGTCGTTCGAAGGTTTTGCGTCGTTTT (SEQ ID NO:10055), TTGGTCGTTCGAAGGTTTTGCGTCGTTT (SEQ ID NO:10056), GGGATTCGGATTGGGAGATTTTGGTTGGG (SEQ ID NO:10057), GGGATTCGGATTGGGAGATTTTGGTTGGGT (SEQ ID NO:10058), CGGATTGGGAGATTTTGGTTGGGTAGTGG (SEQ ID NO:10059), GGATTCGGATTGGGAGATTTTGGTTGGGT (SEQ ID NO:10060), CGGATTGGGAGATTTTGGTTGGGTAGTGGA (SEQ ID NO:10061) |
| Target1067 | chr10:102587188-102587330 | CGTAGTCGGGCGTTATTAGATCGGGTT (SEQ ID NO:10062), CGTAGTCGGGCGTTATTAGATCGGGTTT (SEQ ID NO:10063), CGTAGTCGGGCGTTATTAGATCGGGT (SEQ ID NO:10064), TTTCGGATTTTTTGGAGGGTGCGTAGTC (SEQ ID NO:10065), CGTAGTCGGGCGTTATTAGATCGGGTTTT (SEQ ID NO:10066), GGCGGAGTTTCGGGGGGCGGTATTATA (SEQ ID NO:10067), TTTTTCGGGGTGGGGTTAGACGGGGAC (SEQ ID NO:10068), GGCGGAGTTTCGGGGGGCGGTATTATAA (SEQ ID NO:10069), TTTTCGGGGTGGGGTTAGACGGGGAC (SEQ ID NO:10070), TTTTTCGGGGTGGGGTTAGACGGGGA (SEQ ID NO:10071) |
| Target1068 | chr10:102587337-102587435 | CGGGGTTTCGTTTTTGTCGTTGTTGTCG (SEQ ID NO:10072), CGGGGTTTCGTTTTTGTCGTTGTTGTCGT (SEQ ID NO:10073), TCGGGGTTTCGTTTTTGTCGTTGTTGTCG (SEQ ID NO:10074), TCGGGGTTTCGTTTTTGTCGTTGTTGTCGT (SEQ ID NO:10075), TCGGGGTTTCGTTTTTGTCGTTGTTGT (SEQ ID NO:10076), TTTTTCGGGGTGGGGTTAGACGGGGAC (SEQ ID NO:10077), TTTTTTCGGGGTGGGGTTAGACGGGGA (SEQ ID NO:10078), TTCGAGGGGGGTGATGTGAAGGGTTGC (SEQ ID NO:10079), TTTTCGGGGTGGGGTTAGACGGGGAC (SEQ ID NO:10080), TTTTTTCGGGGTGGGGTTAGACGGGGAC (SEQ ID NO:10081) |
| Target1069 | chr10:102587465-102587493 | CGTTTGATTTTATTTCGGAGGGAGGGAGGA (SEQ ID NO:10082), TCGTTTGATTTTATTTCGGAGGGAGGGAGG (SEQ ID NO:10083), TCGTTTGATTTTATTTCGGAGGGAGGGAGGA (SEQ ID NO:10084), TTCGTTTGATTTTATTTCGGAGGGAGGGAGG (SEQ ID NO:10085), CGTTTGATTTTATTTCGGAGGGAGGGAGGAT (SEQ ID NO:10086), TTCGAGGGGGGTGATGTGAAGGGTTGC (SEQ ID NO:10087), TCGAGGGGGGTGATGTGAAGGGTTGC (SEQ ID NO:10088), TTTCGAGGGGGGTGATGTGAAGGGTTGC (SEQ ID NO:10089), TTTCGAGGGGGGTGATGTGAAGGGTTG (SEQ ID NO:10090), TTTTCGAGGGGGGTGATGTGAAGGGTT (SEQ ID NO:10091) |
| Target1070 | chr10:102587602-102587622 | CGTGGGCGGGATTTTTAGGTTCGGGTT (SEQ ID NO:10092), CGTGGGCGGGATTTTTAGGTTCGGGTTC (SEQ ID NO:10093), CGTGGGCGGGATTTTTAGGTTCGGGT (SEQ ID NO:10094), GTGGGCGGGATTTTTAGGTTCGGGTTC (SEQ ID NO:10095), GTGGGCGGGATTTTTAGGTTCGGGTT (SEQ ID NO:10096), GTTTCGGGGTTGGTTTGGTGGAGGTCG (SEQ ID NO:10097), GGTTTCGGGGTTGGTTTGGTGGAGGTC (SEQ ID NO:10098), AGTTCGGTAGGGTGGTTGGCGGGTTTC (SEQ ID NO:10099), GAGTTCGGTAGGGTGGTTGGCGGGTTT (SEQ ID NO:10100), TTTCGGGGTTGGTTTGGTGGAGGTCGG (SEQ ID NO:10101) |
| Target1071 | chr10:102587631-102587906 | TCGGGCGTTAGGAGGTTTCGTTGGAGG (SEQ ID NO:10102), GGCGTTAGGAGGTTTCGTTGGAGGGGT (SEQ ID NO:10103), GGCGTCGTGAGGGGGGATTCGGTTTAGT (SEQ ID NO:10104), CGTTCGGGCGTTAGGAGGTTTCGTTGG (SEQ ID NO:10105), AGGAGGTTTCGTTGGAGGGGTTGGGTT (SEQ ID NO:10106), AGTTCGGTAGGGTGGTTGGCGGGTTTC (SEQ ID NO:10107), GAGTTCGGTAGGGTGGTTGGCGGGTTT (SEQ ID NO:10108), TTTCGGGGTTGGTTTGGTGGAGGTCGG (SEQ ID NO:10109), AGTTCGGTAGGGTGGTTGGCGGGTTT (SEQ ID NO:10110), GTTCGGTAGGGTGGTTGGCGGGTTTC (SEQ ID NO:10111) |
| Target1072 | chr10:102588069-102588175 | GGGGGTGTGGGGGTTCGGTTTTAGGAA (SEQ ID NO:10112), ATGGGGGTGTGGGGGTTCGGTTTTAGG (SEQ ID NO:10113), CGGTTTTAGGAACGGGTTTTGGGGGCG (SEQ ID NO:10114), AAGATGGAATGGGGGTGTGGGGGTTCG (SEQ ID NO:10115), TAGGAACGGGTTTTGGGGGCGTTAGGT (SEQ ID NO:10116), GTTCGATCGGTGCGGGTTGTTGGGTTT (SEQ ID NO:10117), GCGAGTTAGGGAGGAGGATGTAGGGCG (SEQ ID NO:10118), TCGATCGGTGCGGGTTGTTGGGTTTTT (SEQ ID NO:10119), TTCGATCGGTGCGGGTTGTTGGGTTTT (SEQ ID NO:10120), GGGGTTGCGAGTTAGGGAGGAGGATGT (SEQ ID NO:10121) |
| Target1073 | chr10:102821357-102821367 | GTTCGCGTTTTGGTGGGGTAGTTGGGT (SEQ ID NO:10122), TTCGCGTTTTGGTGGGGTAGTTGGGTG (SEQ ID NO:10123), TGTTCGCGTTTTGGTGGGGTAGTTGGG (SEQ ID NO:10124), GGGGTAGTTGGGTGGGTAAGTTTGCGG (SEQ ID NO:10125), TCGCGTTTTGGTGGGGTAGTTGGGTGG (SEQ ID NO:10126), AAGGGGGAGGCGGTAGGAGTTTTGGTG (SEQ ID NO:10127), GGGGGAGGCGGTAGGAGTTTTGGTGTT (SEQ ID NO:10128), AGGGGGAGGCGGTAGGAGTTTTGGTGT (SEQ ID NO:10129), GGGGGAGGCGGTAGGAGTTTTGGTGT (SEQ ID NO:10130), AGGGGGAGGCGGTAGGAGTTTTGGTG (SEQ ID NO:10131) |
| Target1074 | chr10:102821421-102821428 | GGGGAGACGAAGGTGGTTGGTTTTGTT (SEQ ID NO:10132), GGAATTAGTTTTGGGTTGCGGGGAGACG (SEQ ID NO:10133), GGGGAGACGAAGGTGGTTGGTTTTGTTT (SEQ ID NO:10134), GAATTAGTTTTGGGTTGCGGGGAGACG (SEQ ID NO:10135), GGGGAGACGAAGGTGGTTGGTTTTGT |

FIGURE 5 CONTINUED (SEQ ID NO:10136), GGGAGTGGGGGTAGGAGTTTGGTTGGG (SEQ ID NO:10137),
GGGGGAGTGGGGGTAGGAGTTTGGTTGG (SEQ ID NO:10138), CGGGGGAGTGGGGGTAGGAGTTTGGTTG
(SEQ ID NO:10139), GGTTGGGAGAGAGGAAGGGGGTGAGGA (SEQ ID NO:10140),
AGGTTGGGAGAGAGGAAGGGGGTGAGG (SEQ ID NO:10141)

Target1075        chr10:102821552-102821579        GGGATTGTAAAATTAGATGGGATAGGGTTTAGTCGT (SEQ ID NO:10142)

Target1076        chr10:102821630-102821679        GAAATGATTCGGGAGGGTTTTATGCGGTT (SEQ ID NO:10143),
CGTATTGTGATTTTGGGTTAGGTTGGGGG (SEQ ID NO:10144),
CGTATTGTGATTTTGGGTTAGGTTGGGGGA (SEQ ID NO:10145),
TCGTATTGTGATTTTGGGTTAGGTTGGGGG (SEQ ID NO:10146),
TCGTATTGTGATTTTGGGTTAGGTTGGGGGA (SEQ ID NO:10147)

Target1077        chr10:102899883-102899935        TCGCGGAGAGTATATGTAGGTCGGAGT (SEQ ID NO:10148), TCGCGGAGAGTATATGTAGGTCGGAGTT
(SEQ ID NO:10149), ATCGCGGAGAGTATATGTAGGTCGGAGT (SEQ ID NO:10150),
TCGCGGAGAGTATATGTAGGTCGGAGTTT (SEQ ID NO:10151),
ATCGCGGAGAGTATATGTAGGTCGGAGTT (SEQ ID NO:10152), AGTTTCGGGAGTAGGCGAGCGGTATTC
(SEQ ID NO:10153), GAATAGTTTCGGGAGTAGGCGAGCGGT (SEQ ID NO:10154),
TAGTTTCGGGAGTAGGCGAGCGGTATT (SEQ ID NO:10155), AATAGTTTCGGGAGTAGGCGAGCGGTA
(SEQ ID NO:10156), ATAGTTTCGGGAGTAGGCGAGCGGTAT (SEQ ID NO:10157)

Target1078        chr10:102899949-102899961        TTTTAGCGTTGGGGTTTGGGGCGTTCG (SEQ ID NO:10158), TTTAGCGTTGGGGTTTGGGGCGTTCG (SEQ
ID NO:10159), ATTTTAGCGTTGGGGTTTGGGGCGTTCG (SEQ ID NO:10160),
ATTTTAGCGTTGGGGTTTGGGGCGTTC (SEQ ID NO:10161), TTTAGCGTTGGGGTTTGGGGCGTTCGG
(SEQ ID NO:10162), AGTTTCGGGAGTAGGCGAGCGGTATTC (SEQ ID NO:10163),
GAATAGTTTCGGGAGTAGGCGAGCGGT (SEQ ID NO:10164), TAGTTTCGGGAGTAGGCGAGCGGTATT
(SEQ ID NO:10165), AATAGTTTCGGGAGTAGGCGAGCGGTA (SEQ ID NO:10166),
ATAGTTTCGGGAGTAGGCGAGCGGTAT (SEQ ID NO:10167)

Target1079        chr10:102900103-102900169        ATTTTTGGGGACGTTGGGATTCGCGGC (SEQ ID NO:10168), GGTCGTCGGTTGTTCGGGTCGTGTATT
(SEQ ID NO:10169), GATTTTTGGGGACGTTGGGATTCGCGG (SEQ ID NO:10170),
TTTTTGGGGACGTTGGGATTCGCGGC (SEQ ID NO:10171), AGATTTTTGGGGACGTTGGGATTCGCGG
(SEQ ID NO:10172), CGGAGAGGCGGGAGTTTTGCGTGTTTC (SEQ ID NO:10173),
CGGAGAGGCGGGAGTTTTGCGTGTTT (SEQ ID NO:10174), GCGGAGAGGCGGGAGTTTTGCGTGTTT
(SEQ ID NO:10175), CGGAGAGGCGGGAGTTTTGCGTGTT (SEQ ID NO:10176),
GGAGAGGCGGGAGTTTTGCGTGTTTC (SEQ ID NO:10177)

Target1080        chr10:102983415-102983447        CGCGGTTTTAATAGAGTTGTCGGTTGGT (SEQ ID NO:10178), CGCGGTTTTAATAGAGTTGTCGGTTGGG
(SEQ ID NO:10179), TCGCGGTTTTAATAGAGTTGTCGGTTGGG (SEQ ID NO:10180),
TCGCGGTTTTAATAGAGTTGTCGGTTGGGT (SEQ ID NO:10181),
CGCGGTTTTAATAGAGTTGTCGGTTGGGTT (SEQ ID NO:10182), TCGGGTGGGTTTTCGGAGTTTAGTCGA
(SEQ ID NO:10183), TTCGGGTGGGTTTTCGGAGTTTAGTCG (SEQ ID NO:10184),
TTCGGGTGGGTTTTCGGAGTTTAGTCGA (SEQ ID NO:10185), AGGTTTCGGGTGGGTTTTCGGAGTTTA
(SEQ ID NO:10186), TAGGTTTCGGGTGGGTTTTCGGAGTTT (SEQ ID NO:10187)

Target1081        chr10:102983547-102983563        AGAGTTGTCGGTTGGGTTTCGGAAGTT (SEQ ID NO:10188), TAGAGTTGTCGGTTGGGTTTCGGAAGT
(SEQ ID NO:10189), GAGTTGTCGGTTGGGTTTCGGAAGTTT (SEQ ID NO:10190),
AGAGTTGTCGGTTGGGTTTCGGAAGTTT (SEQ ID NO:10191), TCGGTTGGGTTTCGGAAGTTTATTCGGA
(SEQ ID NO:10192), GAAGGATTAGAGTTGCGGCGGGGGGAA (SEQ ID NO:10193),
AAGGATTAGAGTTGCGGCGGGGGGAAG (SEQ ID NO:10194), AAGGAAGGATTAGAGTTGCGGCGGGGG
(SEQ ID NO:10195), GAAGGAAGGATTAGAGTTGCGGCGGGG (SEQ ID NO:10196),
GGAAGGAAGGATTAGAGTTGCGGCGGG (SEQ ID NO:10197)

Target1082        chr10:102983588-102983609        AGAGTAGAGGATATTGCGGAGAGGTTCGA (SEQ ID NO:10198),
AGAGTAGAGGATATTGCGGAGAGGTTCGAA (SEQ ID NO:10199),
AGAGTAGAGGATATTGCGGAGAGGTTCGAAT (SEQ ID NO:10200),
TAGAGTAGAGGATATTGCGGAGAGGTTCGAA (SEQ ID NO:10201),
TTAGAGTAGAGGATATTGCGGAGAGGTTCGA (SEQ ID NO:10202),
GAAGGATTAGAGTTGCGGCGGGGGGAA (SEQ ID NO:10203), AAGGATTAGAGTTGCGGCGGGGGGAAG
(SEQ ID NO:10204), AAGGAAGGATTAGAGTTGCGGCGGGGG (SEQ ID NO:10205),
GAAGGAAGGATTAGAGTTGCGGCGGGG (SEQ ID NO:10206), GGAAGGAAGGATTAGAGTTGCGGCGGG
(SEQ ID NO:10207)

Target1083        chr10:103043997-103044034        GGGGGAGGGGCGTTTGTTTGCGTATAG (SEQ ID NO:10208), CGGGGGAGGGGCGTTTGTTTGCGTATA
(SEQ ID NO:10209), GGGGGAGGGGCGTTTGTTTGCGTATAGT (SEQ ID NO:10210),
GGGGGAGGGGCGTTTGTTTGCGTATAGT (SEQ ID NO:10211), GGGGGAGGGGCGTTTGTTTGCGTATA
(SEQ ID NO:10212), GCGGTTTTTTCGTCGGGTTTTAGTTGCGC (SEQ ID NO:10213),
CGCGGTTTTTTCGTCGGGTTTTAGTTGCG (SEQ ID NO:10214), CGGTTTTTTCGTCGGGTTTTAGTTGCGC
(SEQ ID NO:10215), GCGGTTTTTTCGTCGGGTTTTAGTTGCG (SEQ ID NO:10216),
CGCGGTTTTTTCGTCGGGTTTTAGTTGC (SEQ ID NO:10217)

Target1084        chr10:103044083-103044140        GCGTAGTTGGAGTTCGGCGAGAGGGTC (SEQ ID NO:10218), TGAGGAGTTGGAGTCGAGTCGGGGATC
(SEQ ID NO:10219), GCGTAGTTGGAGTTCGGCGAGAGGGT (SEQ ID NO:10220),
TTGAGGAGTTGGAGTCGAGTCGGGGAT (SEQ ID NO:10221), ATTGAGGAGTTGGAGTCGAGTCGGGGA

FIGURE 5 CONTINUED (SEQ ID NO:10222), GGTTTTTTCGTCGGGTTTTAGTTGCGC (SEQ ID NO:10223), CGCGGTTTTTTCGTCGGGTTTTAGTTG (SEQ ID NO:10224)

| Target1085 | chr10:103044150-103044247 | GAGGGGTATTGCGCGGTTGGGTTTGTT (SEQ ID NO:10225), TATTGCGCGGTTGGGTTTGTTTCGGGG (SEQ ID NO:10226), GCGGTTGGGTTTGTTTCGGGGTTTCGT (SEQ ID NO:10227), AGGGGTATTGCGCGGTTGGGTTTGTTT (SEQ ID NO:10228), GCGTAGTTGGAGTTCGGCGAGAGGGTC (SEQ ID NO:10229), GGGTTGGAGGCGAGGTAGGTACGTTGG (SEQ ID NO:10230), CGGGTTGGAGGCGAGGTAGGTACGTTG (SEQ ID NO:10231), TTTCGGGTTGGAGGCGAGGTAGGTACG (SEQ ID NO:10232), GGTTGGAGGCGAGGTAGGTACGTTGGT (SEQ ID NO:10233), TCGGGTTGGAGGCGAGGTAGGTACGTT (SEQ ID NO:10234) |
| Target1086 | chr10:105344152-105344448 | TTATTCGGGATTGTAACGGTGCGCGCG (SEQ ID NO:10235), TATTCGGGATTGTAACGGTGCGCGCG (SEQ ID NO:10236), GTTATTCGGGATTGTAACGGTGCGCGC (SEQ ID NO:10237), GTTATTCGGGATTGTAACGGTGCGCGCG (SEQ ID NO:10238), GGGATTGTAACGGTGCGCGCGTAGG (SEQ ID NO:10239), TGTTACGTAGGGTTTTCGGGAGGCGGT (SEQ ID NO:10240), TGAGTTTTGCGGGATGGGGTAGTCGGC (SEQ ID NO:10241), GTGAGTTTTGCGGGATGGGGTAGTCGG (SEQ ID NO:10242), GTGTTACGTAGGGTTTTCGGGAGGCGG (SEQ ID NO:10243), AGTGTTACGTAGGGTTTTCGGGAGGCGG (SEQ ID NO:10244) |
| Target1087 | chr10:105344464-105344748 | GAGTAGACGGTGGCGCGCGTGGGAGTAC (SEQ ID NO:10245), GAGTAGACGGTGGCGCGCGTGGGAGTA (SEQ ID NO:10246), AGTAGACGGTGGCGCGCGTGGGAGTAC (SEQ ID NO:10247), GTAGACGGTGGCGCGCGTGGGAGTAC (SEQ ID NO:10248), CGAGTAGACGGTGGCGCGCGTGGGAGTA (SEQ ID NO:10249), ATGTCGTCGTTGTGTAGGGGTTCGGGT (SEQ ID NO:10250), TGTCGTCGTTGTGTAGGGGTTCGGGTA (SEQ ID NO:10251), GATGTCGTCGTTGTGTAGGGGTTCGGGT (SEQ ID NO:10252), GATGTCGTCGTTGTGTAGGGGTTCGGG (SEQ ID NO:10253), GGATGTCGTCGTTGTGTAGGGGTTCGG (SEQ ID NO:10254) |
| Target1088 | chr10:105344798-105344808 | GGTACGTTGCGGTCGGTCGATTTGTTT (SEQ ID NO:10255), GGTACGTTGCGGTCGGTCGATTTGTTTT (SEQ ID NO:10256), GGTACGTTGCGGTCGGTCGATTTGTT (SEQ ID NO:10257), ACGTTGCGGTCGGTCGATTTGTTTTTT (SEQ ID NO:10258), GTACGTTGCGGTCGGTCGATTTGTTTT (SEQ ID NO:10259), GCGGTCGCGTTATTGTGGTTGAGGTGT (SEQ ID NO:10260), ATGTCGTCGTTGTGTAGGGGTTCGGGT (SEQ ID NO:10261), TGTCGTCGTTGTGTAGGGGTTCGGGTA (SEQ ID NO:10262), GATGTCGTCGTTGTGTAGGGGTTCGGGT (SEQ ID NO:10263), GATGTCGTCGTTGTGTAGGGGTTCGGG (SEQ ID NO:10264) |
| Target1089 | chr10:108923824-108923845 | GGTTTGGTTGTGTGTTGAGTTTTTCGTTAGC (SEQ ID NO:10265), TGGTTTGGTTGTGTGTTGAGTTTTTCGTTAGC (SEQ ID NO:10266), ATGGTTTGGTTGTGTGTTGAGTTTTTCGTTAGC (SEQ ID NO:10267), AGTGGATTATGGTTTGGTTGTGTGTTGAGTTTT (SEQ ID NO:10268), GGATTATGGTTTGGTTGTGTGTTGAGTTTTTCGT (SEQ ID NO:10269), AGGAGTTTGGGATTCGGGAGCGGGATT (SEQ ID NO:10270), AGTAGGAGTTTGGGATTCGGGAGCGGG (SEQ ID NO:10271), GTAGGAGTTTGGGATTCGGGAGCGGGA (SEQ ID NO:10272), AGGAGAAGGTAGAACGGGGAGAGGGCG (SEQ ID NO:10273), GGAGTTTGGGATTCGGGAGCGGGATTC (SEQ ID NO:10274) |
| Target1090 | chr10:108923899-108923916 | AGCGGGTGGTTTTGTTCGGGTTTC (SEQ ID NO:10275), GCGGTTGTTGTACGTTTCGGTCGGAGG (SEQ ID NO:10276), GGCGGTTGTTGTACGTTTCGGTCGGAG (SEQ ID NO:10277), ATGGCGGTTGTTGTACGTTTCGGTCGG (SEQ ID NO:10278), AGGAGAAGGTAGAACGGGGAGAGGGCG (SEQ ID NO:10279), TGGCGGTTGTTGTACGTTTCGGTCGGA (SEQ ID NO:10280) |
| Target1091 | chr10:108923926-108923970 | AGCGGGTGGTTTTGTTCGGGTTTC (SEQ ID NO:10281), GCGGTTGTTGTACGTTTCGGTCGGAGG (SEQ ID NO:10282), GGCGGTTGTTGTACGTTTCGGTCGGAG (SEQ ID NO:10283), ATGGCGGTTGTTGTACGTTTCGGTCGG (SEQ ID NO:10284), TGGCGGTTGTTGTACGTTTCGGTCGGA (SEQ ID NO:10285), CGGTTGTTGTACGTTTCGGTCGGAGGA (SEQ ID NO:10286) |
| Target1092 | chr10:108924027-108924039 | GGTCGGAGCGTGTAGTAATCGTTATGGA (SEQ ID NO:10287), GGTCGGAGCGTGTAGTAATCGTTATGGAT (SEQ ID NO:10288), GGTCGGAGCGTGTAGTAATCGTTATGGATG (SEQ ID NO:10289), GGTCGGAGCGTGTAGTAATCGTTATGGATGT (SEQ ID NO:10290), GTCGGAGCGTGTAGTAATCGTTATGGATGT (SEQ ID NO:10291), GGGGCGGTTAGGTAGGGTTTTTGTTACGT (SEQ ID NO:10292), GGGGCGGTTAGGTAGGGTTTTTGTTACG (SEQ ID NO:10293), AGGGGCGGTTAGGTAGGGTTTTTGTTACG (SEQ ID NO:10294), AGGGGCGGTTAGGTAGGGTTTTTGTTACGT (SEQ ID NO:10295), GGGCGGTTAGGTAGGGTTTTTGTTACGT (SEQ ID NO:10296) |
| Target1093 | chr10:108924149-108924166 | GGGGTAGGGGCGTGGTAGGAGTTTTGT (SEQ ID NO:10297), AGGGGTAGGGGCGTGGTAGGAGTTTTG (SEQ ID NO:10298), GAGGGGTAGGGGCGTGGTAGGAGTTTT (SEQ ID NO:10299), CGAGGGGTAGGGGCGTGGTAGGAGTTT (SEQ ID NO:10300), GAGGGGTAGGGGCGTGGTAGGAGTTTTG (SEQ ID NO:10301), CGTCGGCGGCGGTTTTTAAGTTCGGTT (SEQ ID NO:10302), TCGGCGGCGGTTTTTAAGTTCGGTTGA (SEQ ID NO:10303), GCGGCGGTTTTTAAGTTCGGTTGAGCG (SEQ ID NO:10304), GGCGGCGGTTTTTAAGTTCGGTTGAGC (SEQ ID NO:10305), GTCGGCGGCGGTTTTTAAGTTCGGTTG (SEQ ID NO:10306) |

FIGURE 5 CONTINUED

| Target1094 | chr10:108924185-108924347 | GGGGTAGGGGCGTGGTAGGAGTTTTGT (SEQ ID NO:10307), AGGGGTAGGGGCGTGGTAGGAGTTTTG (SEQ ID NO:10308), GCGTTTAGTCGGGTTTGGGAGTCGTCG (SEQ ID NO:10309), GAGGGGTAGGGGCGTGGTAGGAGTTTT (SEQ ID NO:10310), CGAGGGGTAGGGGCGTGGTAGGAGTTT (SEQ ID NO:10311), CGCGGCGTAATTTGGATGGAGTTGGGG (SEQ ID NO:10312), CGTCGGCGGCGGTTTTTAAGTTCGGTT (SEQ ID NO:10313), GGATGGAGTTGGGGTTTTGAGCGTCGG (SEQ ID NO:10314), GCGGCGTAATTTGGATGGAGTTGGGGT (SEQ ID NO:10315), TCGGCGGCGGTTTTTAAGTTCGGTTGA (SEQ ID NO:10316) |
|---|---|---|
| Target1095 | chr10:110671872-110671904 | GTAGGAGTTCGGCGTAGGTGGTGGGGTT (SEQ ID NO:10317), AGGAGTTCGGCGTAGGTGGTGGGTTTA (SEQ ID NO:10318), TAGGAGTTCGGCGTAGGTGGTGGGTTT (SEQ ID NO:10319), GTAGGAGTTCGGCGTAGGTGGTGGGTTT (SEQ ID NO:10320), CGTAGGAGTTCGGCGTAGGTGGTGGG (SEQ ID NO:10321), TGGGAAAGGTTGGTAGATAGCGGCGTT (SEQ ID NO:10322), TTGGGAAAGGTTGGTAGATAGCGGCGT (SEQ ID NO:10323), GTTGGGAAAGGTTGGTAGATAGCGGCGT (SEQ ID NO:10324), GTTGGGAAAGGTTGGTAGATAGCGGCG (SEQ ID NO:10325), AGTTGGGAAAGGTTGGTAGATAGCGGCG (SEQ ID NO:10326) |
| Target1096 | chr10:110672060-110672089 | GCGAAGATAGTTTTAGGGTGGGCGGCG (SEQ ID NO:10327), CGAAGATAGTTTTAGGGTGGGCGGCGG (SEQ ID NO:10328), AGCGAAGATAGTTTTAGGGTGGGCGGC (SEQ ID NO:10329), CGAAGATAGTTTTAGGGTGGGCGGCGGT (SEQ ID NO:10330), AAGATAGTTTTAGGGTGGGCGGCGGTC (SEQ ID NO:10331), CGGTGGTTGTGGTTTTTGTTTTGTTAGCGG (SEQ ID NO:10332), CGGTGGTTGTGGTTTTTGTTTTGTTAGCGGT (SEQ ID NO:10333), TCGGTGGTTGTGGTTTTTGTTTTGTTAGCGG (SEQ ID NO:10334), TCGGTGGTTGTGGTTTTTGTTTTGTTAGCGGT (SEQ ID NO:10335), CGGTGGTTGTGGTTTTTGTTTTGTTAGCG (SEQ ID NO:10336) |
| Target1097 | chr10:110672251-110672267 | GGGGTTGCGGGTTGGTTGTTTGGGTAG (SEQ ID NO:10337), TAGTCGTTGTGGGGATTTCGGTTGCGC (SEQ ID NO:10338), GGGTTGCGGGTTGGTTGTTTGGGTAGT (SEQ ID NO:10339), AGTCGTTGTGGGGATTTCGGTTGCGC (SEQ ID NO:10340), GGGGGTTGCGGGTTGGTTGTTTGGGTA (SEQ ID NO:10341), AATGTGGGGTTGGGTGCGGGATTAGGT (SEQ ID NO:10342), GGCGGGTTAGTGGGGATAGTGGCGTAG (SEQ ID NO:10343), AGAGAAAATGTGGGGTTGGGTGCGGGA (SEQ ID NO:10344), ATGTGGGGTTGGGTGCGGGATTAGGTG (SEQ ID NO:10345), TTGGTAAATTCGGCGGGCGGGTTAGTG (SEQ ID NO:10346) |
| Target1098 | chr10:118892211-118892219 | ATGTGGGTGGTCGTGGTTGTAGGGACG (SEQ ID NO:10347), AGGGTAAGGAAAGAGGGTGTCGCGGTT (SEQ ID NO:10348), CGTAGGGTAAGGAAAGAGGGTGTCGCGG (SEQ ID NO:10349), GGGTAAGGAAAGAGGGTGTCGCGGTTC (SEQ ID NO:10350), TGTGGGTGGTCGTGGTTGTAGGGACG (SEQ ID NO:10351), AGTAGTTTCGGAGTTTAGATAGCGTTTTGTGTGA (SEQ ID NO:10352), AGTTTCGGAGTTTAGATAGCGTTTTGTGTGATTG (SEQ ID NO:10353), GTTTCGGAGTTTAGATAGCGTTTTGTGTGATTGA (SEQ ID NO:10354), AGTTTCGGAGTTTAGATAGCGTTTTGTGTGATTGA (SEQ ID NO:10355), CGGAGTTTAGATAGCGTTTTGTGTGATTGATAGGA (SEQ ID NO:10356) |
| Target1099 | chr10:118892390-118892424 | AGAGGAGGTTCGATTATTTAGCGGCGT (SEQ ID NO:10357), AGAGGAGGTTCGATTATTTAGCGGCGTT (SEQ ID NO:10358), TGCGTGTAGGAAGGGTTTTGTGAATTCG (SEQ ID NO:10359), AGAGGAGGTTCGATTATTTAGCGGCGTTT (SEQ ID NO:10360), TTGCGTGTAGGAAGGGTTTTGTGAATTCG (SEQ ID NO:10361), GGTTGTCGGCGGTAGTTTGCGTAGTC (SEQ ID NO:10362), TACGGTTTTTTAGGCGCGTAGTTTCGG (SEQ ID NO:10363), ACGGTTTTTTAGGCGCGTAGTTTCGG (SEQ ID NO:10364), GGTTGTCGGCGGTAGTTTGCGTAGT (SEQ ID NO:10365), TTACGGTTTTTTAGGCGCGTAGTTTCGG (SEQ ID NO:10366) |
| Target1100 | chr10:118892484-118892495 | TGAATTCGGGTGTTTGGGAGAGGAGGT (SEQ ID NO:10367), TGTGAATTCGGGTGTTTGGGAGAGGAGGT (SEQ ID NO:10368), GTGAATTCGGGTGTTTGGGAGAGGAGGT (SEQ ID NO:10369), TGTGAATTCGGGTGTTTGGGAGAGGAGG (SEQ ID NO:10370), GTGAATTCGGGTGTTTGGGAGAGGAGG (SEQ ID NO:10371), GGTTGTCGGCGGTAGTTTGCGTAGTC (SEQ ID NO:10372), GGTTGTCGGCGGTAGTTTGCGTAGT (SEQ ID NO:10373), GTTGTCGGCGGTAGTTTGCGTAGTC (SEQ ID NO:10374), GGTTGTCGGCGGTAGTTTGCGTAG (SEQ ID NO:10375), GAGTTTGTTCGGGGCGGTGGTC (SEQ ID NO:10376) |
| Target1101 | chr10:118892537-118892548 | TTTGGGAGGTCGTAGGGTGAAGCGTCG (SEQ ID NO:10377), CGTTTGGGAGGTCGTAGGGTGAAGCGT (SEQ ID NO:10378), ACGCGTTTGGGAGGTCGTAGGGTGAAG (SEQ ID NO:10379), GGAGGTCGTAGGGTGAAGCGTCGGTTG (SEQ ID NO:10380), GCGTCGGTTGCGTAGGTTATCGTCGGT (SEQ ID NO:10381), GAGTTTGTTCGGGGCGGTGGTC (SEQ ID NO:10382) |
| Target1102 | chr10:118892581-118892604 | TTTGGGAGGTCGTAGGGTGAAGCGTCG (SEQ ID NO:10383), CGTTTGGGAGGTCGTAGGGTGAAGCGT (SEQ ID NO:10384), ACGCGTTTGGGAGGTCGTAGGGTGAAG (SEQ ID NO:10385), GGAGGTCGTAGGGTGAAGCGTCGGTTG (SEQ ID NO:10386), GCGTCGGTTGCGTAGGTTATCGTCGGT (SEQ ID NO:10387), GAGTTTGTTCGGGGCGGTGGTT (SEQ ID NO:10388) |
| Target1103 | chr10:119292293-119292301 | TTTTTAGTTCGGGGTAGGGACGGGCGG (SEQ ID NO:10389), GCGAGTTGGGGTAGAGGATTTGCGGGA (SEQ ID NO:10390), GCGGTCGCGAGTTGGGGTAGAGGATT (SEQ ID NO:10391), GGTCGCGAGTTGGGGTAGAGGATTTGC (SEQ ID NO:10392), CGGTCGCGAGTTGGGGTAGAGGATTTG (SEQ ID NO:10393), TAGTTTGGGTGTTCGATGCGGAGGGGT (SEQ ID NO:10394), TTCGATGCGGAGGGGTTTGGTAGAGCG (SEQ ID NO:10395), GGGTGTTCGATGCGGAGGGGTTTGGTA (SEQ ID NO:10396), TTTGGGTGTTCGATGCGGAGGGGTTTG (SEQ ID NO:10397), GATGCGGAGGGGTTTGGTAGAGCGGAG (SEQ ID NO:10398) |

FIGURE 5 CONTINUED

Target1104    chr10:119295770-119295809    TTTGAGAGTGTGGTTTTTGGGACGTTAGC (SEQ ID NO:10399),
TTTTGAGAGTGTGGTTTTTGGGACGTTAGC (SEQ ID NO:10400),
AGTTTTTGAGAGTGTGGTTTTTGGGACGTT (SEQ ID NO:10401),
AAGTTTTTGAGAGTGTGGTTTTTGGGACGT (SEQ ID NO:10402),
TTTTTGAGAGTGTGGTTTTTGGGACGTTAGC (SEQ ID NO:10403),
TGTAAGGCGTTATTTGGGTTTGTTAGCGTT (SEQ ID NO:10404),
ATGTAAGGCGTTATTTGGGTTTGTTAGCGTT (SEQ ID NO:10405),
AATGTAAGGCGTTATTTGGGTTTGTTAGCGT (SEQ ID NO:10406),
AGCGTTTTTTGGTTTTTCGTGTTTGAGGT (SEQ ID NO:10407),
TGTAGCGTTTTTTGGTTTTTCGTGTTTGAGGT (SEQ ID NO:10408)

Target1105    chr10:119295840-119295872    AGTAGCGTTTTATATTGTCGGGCGAGGA (SEQ ID NO:10409), AAGTAGCGTTTTATATTGTCGGGCGAGGA
(SEQ ID NO:10410), AGTAGCGTTTTATATTGTCGGGCGAGGAT (SEQ ID NO:10411),
TTTGAGAGTGTGGTTTTTGGGACGTTAGC (SEQ ID NO:10412),
AGTAGCGTTTTATATTGTCGGGCGAGGATT (SEQ ID NO:10413),
AGCGTTTTTTGGTTTTTCGTGTTTGAGGTT (SEQ ID NO:10414),
TGTAGCGTTTTTTGGTTTTTCGTGTTTGAGGT (SEQ ID NO:10415),
AGCGTTTTTTGGTTTTTCGTGTTTGAGGTTT (SEQ ID NO:10416),
AGTTCGGTCGGTTTTTTAATTTGGAGTTTGGT (SEQ ID NO:10417),
GTAGCGTTTTTTGGTTTTTCGTGTTTGAGGTT (SEQ ID NO:10418)

Target1106    chr10:119295925-119295948    GCGTTGTAGAGGCGTGGAAGGTGCG (SEQ ID NO:10419), GCGTTGTAGAGGCGTGGAAGGTGC (SEQ ID
NO:10420), AGTAGCGTTTTATATTGTCGGGCGAGGA (SEQ ID NO:10421),
AGGTCGGTCGGGTTATTAGTGGTAGAGA (SEQ ID NO:10422), CGTTGTAGAGGCGTGGAAGGTGCG (SEQ
ID NO:10423), AGGGTGGGTGGGAGCGTGGTAAGTTTT (SEQ ID NO:10424),
GAGGGTGGGTGGGAGCGTGGTAAGTTT (SEQ ID NO:10425), GGGTGGGTGGGAGCGTGGTAAGTTTTT
(SEQ ID NO:10426), AGGGTGGGTGGGAGCGTGGTAAGTTTTT (SEQ ID NO:10427),
GAGGGTGGGTGGGAGCGTGGTAAGTT (SEQ ID NO:10428)

Target1107    chr10:119295992-119296096    TGTAGAGGCGTGGAAGGTGCGTTTCGT (SEQ ID NO:10429), AGAGGCGTGGAAGGTGCGTTTCGTTTC
(SEQ ID NO:10430), GGCGTGGAAGGTGCGTTTCGTTTCGTT (SEQ ID NO:10431),
CGTTGTAGAGGCGTGGAAGGTGCGTTT (SEQ ID NO:10432), GAGGCGTGGAAGGTGCGTTTCGTTTCG
(SEQ ID NO:10433), TTTTTCGGGATGGAGGGTGGGTGGGAG (SEQ ID NO:10434),
AGGGTGGGTGGGAGCGTGGTAAGTTTT (SEQ ID NO:10435), GAGGGTGGGTGGGAGCGTGGTAAGTTT
(SEQ ID NO:10436), TTTTTTCGGGATGGAGGGTGGGTGGGA (SEQ ID NO:10437),
GGGTGGGTGGGAGCGTGGTAAGTTTTT (SEQ ID NO:10438)

Target1108    chr10:119296118-119296131    TGGGGGCGATGGGAAGGATTTGTTACGT (SEQ ID NO:10439), GGGGGCGATGGGAAGGATTTGTTACGT
(SEQ ID NO:10440), TGGGGGCGATGGGAAGGATTTGTTACG (SEQ ID NO:10441),
GGGGGCGATGGGAAGGATTTGTTACGTT (SEQ ID NO:10442), TTGGGGGCGATGGGAAGGATTTGTTACG
(SEQ ID NO:10443), AGACGGTGGTGTAGGAGTTAGGGAAGA (SEQ ID NO:10444),
ACGGTGGTGTAGGAGTTAGGGAAGAAGT (SEQ ID NO:10445),
AGACGGTGGTGTAGGAGTTAGGGAAGAA (SEQ ID NO:10446),
GACGGTGGTGTAGGAGTTAGGGAAGAAGT (SEQ ID NO:10447),
GACGGTGGTGTAGGAGTTAGGGAAGAAG (SEQ ID NO:10448)

Target1109    chr10:119296170-119296211    CGGGTTGGCGTTCGAATTAGAGAGTGT (SEQ ID NO:10449), TCGGGTTGGCGTTCGAATTAGAGAGTGT
(SEQ ID NO:10450), TCGGGTTGGCGTTCGAATTAGAGAGTG (SEQ ID NO:10451),
CGGGTTGGCGTTCGAATTAGAGAGTGTA (SEQ ID NO:10452),
TCGGGTTGGCGTTCGAATTAGAGAGTGTA (SEQ ID NO:10453),
AGTTTAGGATCGAGTAAGGATTGGGAGGGA (SEQ ID NO:10454),
AAGTTTAGGATCGAGTAAGGATTGGGAGGGA (SEQ ID NO:10455),
CGAGTAAGGATTGGGAGGGATAGATAGACGT (SEQ ID NO:10456),
AGTTTAGGATCGAGTAAGGATTGGGAGGGAT (SEQ ID NO:10457),
TCGAGTAAGGATTGGGAGGGATAGATAGACG (SEQ ID NO:10458)

Target1110    chr10:119296327-119296362    TAGCGTGTGTGTGGTGAGGGAGTGACG (SEQ ID NO:10459), CGTGTGTGTGGTGAGGGAGTGACGAGT
(SEQ ID NO:10460), GCGTGTGTGTGGTGAGGGAGTGACGAG (SEQ ID NO:10461),
CGTGTGTGTGGTGAGGGAGTGACGAGTT (SEQ ID NO:10462), TCGAGATAGCGTGTGTGTGGTGAGGGA
(SEQ ID NO:10463), GCGGGTGGTTGTAGGGGCGTTGTTTTT (SEQ ID NO:10464),
GCGGGTGGTTGTAGGGGCGTTGTTTT (SEQ ID NO:10465), GCGGGTGGTTGTAGGGGCGTTGTTTTTT
(SEQ ID NO:10466), CGGGTGGTTGTAGGGGCGTTGTTTTTT (SEQ ID NO:10467),
GCGGGTGGTTGTAGGGGCGTTGTTT (SEQ ID NO:10468)

Target1111    chr10:119296414-119296468    TAGCGTGTGTGTGGTGAGGGAGTGACG (SEQ ID NO:10469), CGTGTGTGTGGTGAGGGAGTGACGAGT
(SEQ ID NO:10470), GGAGACGTAGAGGTTCGCGCGGATGTT (SEQ ID NO:10471),
AGGTTCGCGCGGATGTTTAGAGGAGGA (SEQ ID NO:10472), GCGTGTGTGTGGTGAGGGAGTGACGAG
(SEQ ID NO:10473), TTGGTTTTTGGGTTTCGCGGGTGGTTGT (SEQ ID NO:10474),
GCGGGTGGTTGTAGGGGCGTTGTTTTT (SEQ ID NO:10475), TTTTTGGGTTTCGCGGGTGGTTGTAGGG
(SEQ ID NO:10476), TGGTTTTTGGGTTTCGCGGGTGGTTGTA (SEQ ID NO:10477),
TTTGGGTTTCGCGGGTGGTTGTAGGGG (SEQ ID NO:10478)

FIGURE 5 CONTINUED

Target1112     chr10:119296552-119296567     AGGTTCGCGCGGATGTTTAGAGGAGGA (SEQ ID NO:10479), GAGGTTCGCGCGGATGTTTAGAGGAGG (SEQ ID NO:10480), GAGACGTAGAGGTTCGCGCGGATGTTT (SEQ ID NO:10481), AGAGGTTCGCGCGGATGTTTAGAGGAGG (SEQ ID NO:10482), GAGGTTCGCGCGGATGTTTAGAGGAGGA (SEQ ID NO:10483), TCGGTGATGTGGGGTCGTGGAATTCGT (SEQ ID NO:10484), CGGTGATGTGGGGTCGTGGAATTCGTT (SEQ ID NO:10485), TCGGTGATGTGGGGTCGTGGAATTCGTT (SEQ ID NO:10486), TTCGGTGATGTGGGGTCGTGGAATTCGT (SEQ ID NO:10487), TTCGGTGATGTGGGGTCGTGGAATTCG (SEQ ID NO:10488)

Target1113     chr10:123922876-123923563     GCGTTGGGGTTGTTCGGCGATGATGAT (SEQ ID NO:10489), GGTCGGGGTAGAGGGAGGGTTTTCGTT (SEQ ID NO:10490), AGGGGTCGGGGTAGAGGGAGGGTTTTC (SEQ ID NO:10491), GAGGGGTCGGGGTAGAGGGAGGGTTTT (SEQ ID NO:10492), TACGTCGGTTATATTCGGGCGCGCGTC (SEQ ID NO:10493), AGGGGAGTAGTTGCGGGTATTCGTGGC (SEQ ID NO:10494), CGGGGCGGTTCGGGCGGAGTATTTATA (SEQ ID NO:10495), GTTTTGTTCGGGGCGTGCGGGTATGAG (SEQ ID NO:10496), GGTTGGGGGTGGGGAGGCGAAGATTTT (SEQ ID NO:10497), GTTGGGGGTGGGGAGGCGAAGATTTTT (SEQ ID NO:10498)

Target1114     chr10:123923578-123923871     TTCGGGGAGGAGGAGAGAGGATGTTCGGG (SEQ ID NO:10499), CGGGGAGGAGGAGAGAGGATGTTCGGGTT (SEQ ID NO:10500), GGGGAGGAGGAGAGAGGATGTTCGGGTTT (SEQ ID NO:10501), TTTCGGGGAGGAGGAGAGAGGATGTTCGG (SEQ ID NO:10502), TCGGGGAGGAGGAGAGAGGATGTTCGGG (SEQ ID NO:10503), CGGGGGTGTAGAGGAAAGATGTTGACGG (SEQ ID NO:10504), CGGGGGTGTAGAGGAAAGATGTTGACGGT (SEQ ID NO:10505), TCGGGGGTGTAGAGGAAAGATGTTGACGG (SEQ ID NO:10506), TGTGTCGGGGGTGTAGAGGAAAGATGT (SEQ ID NO:10507), CGGGGGTGTAGAGGAAAGATGTTGACG (SEQ ID NO:10508)

Target1115     chr10:123923887-123924221     GCGTTTGTGGTTGGGTAGATGGCGTGG (SEQ ID NO:10509), TGCGTTTGTGGTTGGGTAGATGGCGTG (SEQ ID NO:10510), CGTTTGTGGTTGGGTAGATGGCGTGGT (SEQ ID NO:10511), TTGCGTTTGTGGTTGGGTAGATGGCGT (SEQ ID NO:10512), TTCGGGTAGTTGCGTTTGTGGTTGGGT (SEQ ID NO:10513), AGTGGGGGTAGGTGAGGTTGGGAGGTT (SEQ ID NO:10514), AAGTGGGGGTAGGTGAGGTTGGGAGGT (SEQ ID NO:10515), GTGGGGGTAGGTGAGGTTGGGAGGTTT (SEQ ID NO:10516), AAAGTGGGGGTAGGTGAGGTTGGGAGG (SEQ ID NO:10517), AGTGGGGGTAGGTGAGGTTGGGAGGT (SEQ ID NO:10518)

Target1116     chr10:124905635-124905831     GTTGCGACGTGGTTTAGGAGTTTGCGT (SEQ ID NO:10519), AGCGGGGTGGTTGGTATTGTTTTTCGA (SEQ ID NO:10520), GCGGGGTGGTTGGTATTGTTTTTCGAGT (SEQ ID NO:10521), GCGGGGTGGTTGGTATTGTTTTTCGAG (SEQ ID NO:10522), AGCGGGGTGGTTGGTATTGTTTTTCGAGT (SEQ ID NO:10523), TTCGGGAGGTTAGCGAGGGGTAGGTGT (SEQ ID NO:10524), GTTCGGGAGGTTAGCGAGGGGTAGGTG (SEQ ID NO:10525), TCGGGAGGTTAGCGAGGGGTAGGTGTC (SEQ ID NO:10526), TCGGGAGGTTAGCGAGGGGTAGGTGT (SEQ ID NO:10527), CGGGGAGGTTAGCGAGGGGTAGGTGTC (SEQ ID NO:10528)

Target1117     chr10:124905914-124905953     GTCGTTGAGTTTTGAAGAGGTTAATGCGGT (SEQ ID NO:10529), TCGTTGAGTTTTGAAGAGGTTAATGCGGTG (SEQ ID NO:10530), TGTCGTTGAGTTTTGAAGAGGTTAATGCGG (SEQ ID NO:10531), TGTCGTTGAGTTTTGAAGAGGTTAATGCGGT (SEQ ID NO:10532), CGTTGAGTTTTGAAGAGGTTAATGCGGTGAC (SEQ ID NO:10533), TTCGGGAGGTTAGCGAGGGGTAGGTGT (SEQ ID NO:10534), GTTCGGGAGGTTAGCGAGGGGTAGGTG (SEQ ID NO:10535), TCGGGAGGTTAGCGAGGGGTAGGTGTC (SEQ ID NO:10536), GGTTCGGGAGGTTAGCGAGGGGTAGGT (SEQ ID NO:10537), TCGGGAGGTTAGCGAGGGGTAGGTGT (SEQ ID NO:10538)

Target1118     chr10:124905957-124905981     TTTCGTTGGTTTTTCGGGTCGTTGCGC (SEQ ID NO:10539), TTTTCGTTGGTTTTTCGGGTCGTTGCGC (SEQ ID NO:10540), TTCGTTGGTTTTTCGGGTCGTTGCGC (SEQ ID NO:10541), TTTTCGTTGGTTTTTCGGGTCGTTGCG (SEQ ID NO:10542), TTTTTCGTTGGTTTTTCGGGTCGTTGCGC (SEQ ID NO:10543), GTAGTCGGGGTAGGGGTAGGCGAGGG (SEQ ID NO:10544), CGTAGTCGGGGTAGGGGTAGGCGAGG (SEQ ID NO:10545), TAGTCGGGGTAGGGGTAGGCGAGGG (SEQ ID NO:10546), GTAGTCGGGGTAGGGGTAGGCGAGGGG (SEQ ID NO:10547), CGTAGTCGGGGTAGGGGTAGGCGAGGG (SEQ ID NO:10548)

Target1119     chr10:124906003-124906042     CGTTTGTTTTTGTTTCGGTTGCGCGGTC (SEQ ID NO:10549), GTTTGTTTTTGTTTCGGTTGCGCGGT (SEQ ID NO:10550), GTTTGTTTTTGTTTCGGTTGCGCGGT (SEQ ID NO:10551), TTTGTTTTTGTTTCGGTTGCGCGGTC (SEQ ID NO:10552), TTGTTTTTGTTTCGGTTGCGCGGTC (SEQ ID NO:10553), TGGGTTAATTGATTAGGAGTCGGTCGCGT (SEQ ID NO:10554), GGGTTAATTGATTAGGAGTCGGTCGCGT (SEQ ID NO:10555), TGGGTTAATTGATTAGGAGTCGGTCGCG (SEQ ID NO:10556), ATGGGTTAATTGATTAGGAGTCGGTCGCG (SEQ ID NO:10557), ATGGGTTAATTGATTAGGAGTCGGTCGCGT (SEQ ID NO:10558)

Target1120     chr10:124906109-124906152     CGTTTGTTTTTGTTTCGGTTGCGCGGT (SEQ ID NO:10559), TCGTTTGTTTTTGTTTCGGTTGCGCGG (SEQ ID NO:10560), TCGTTTGTTTTTGTTTCGGTTGCGCGGT (SEQ ID NO:10561), CGTTTGTTTTTGTTTCGGTTGCGCGGTC (SEQ ID NO:10562), TCGTTTGTTTTTGTTTCGGTTGCGCGGTC (SEQ ID NO:10563), AGGGTGTTTTTTAAGTGTAGTTAAGGGTGAGTGG (SEQ ID NO:10564), GGGTGTTTTTTAAGTGTAGTTAAGGGTGAGTGGA (SEQ ID NO:10565), AGGGTGTTTTTTAAGTGTAGTTAAGGGTGAGTGGA (SEQ ID NO:10566),

FIGURE 5 CONTINUED

GGGTGTTTTTTAAGTGTAGTTAAGGGTGAGTGGAG (SEQ ID NO:10567),
AGGGTGTTTTTTAAGTGTAGTTAAGGGTGAGTGGAG (SEQ ID NO:10568)

| | | |
|---|---|---|
| Target1121 | chr10:124910456-124910790 | AGGGAATTGGGCGCGGTGAGGTAGTTT (SEQ ID NO:10569), GAGGGAATTGGGCGCGGTGAGGTAGTT (SEQ ID NO:10570), GAGAGGGAATTGGGCGCGGTGAGGTAG (SEQ ID NO:10571), GGGAATTGGGCGCGGTGAGGTAGTTTT (SEQ ID NO:10572), GGGAATTGGGCGCGGTGAGGTAGTTTTG (SEQ ID NO:10573), TTGGAGAGGAAGTGCGCGGTATAGGGT (SEQ ID NO:10574), TGGAGAGGAAGTGCGCGGTATAGGGTA (SEQ ID NO:10575), TTTGTTATCGGTCGGGTAGTTGGGCGT (SEQ ID NO:10576), TTTGGAGAGGAAGTGCGCGGTATAGGGT (SEQ ID NO:10577), TTTGGAGAGGAAGTGCGCGGTATAGGG (SEQ ID NO:10578) |
| Target1122 | chr10:124910846-124910976 | AGGGAATTGGGCGCGGTGAGGTAGTTT (SEQ ID NO:10579), GAGGGAATTGGGCGCGGTGAGGTAGTT (SEQ ID NO:10580), GAGAGGGAATTGGGCGCGGTGAGGTAG (SEQ ID NO:10581), GGGAATTGGGCGCGGTGAGGTAGTTTT (SEQ ID NO:10582), GGGAATTGGGCGCGGTGAGGTAGTTTTG (SEQ ID NO:10583), GCGGTCGTAGGTGTTAGGGCGAGGAAG (SEQ ID NO:10584), CGGTCGTAGGTGTTAGGGCGAGGAAGT (SEQ ID NO:10585), GCGGTCGTAGGTGTTAGGGCGAGGAA (SEQ ID NO:10586), CGGTCGTAGGTGTTAGGGCGAGGAAGTT (SEQ ID NO:10587), GCGGTCGCGTGTTAGTCGGTGATTTAGT (SEQ ID NO:10588) |
| Target1123 | chr10:124910989-124911104 | GGGGTTGGGAGGGCGTTGTATCGAGAG (SEQ ID NO:10589), CGTAGGGGTTGGGAGGGCGTTGTATCG (SEQ ID NO:10590), GTAGGGGTTGGGAGGGCGTTGTATCGA (SEQ ID NO:10591), TAGGGGTTGGGAGGGCGTTGTATCGAG (SEQ ID NO:10592), GCGTAGGGGTTGGGAGGGCGTTGTATC (SEQ ID NO:10593), AGGTCGGAGGAGTTCGTTTTAGGTGGT (SEQ ID NO:10594), GGTCGGAGGAGTTCGTTTTAGGTGGTGT (SEQ ID NO:10595), GGTCGGAGGAGTTCGTTTTAGGTGGTG (SEQ ID NO:10596), AGGTCGGAGGAGTTCGTTTTAGGTGGTGT (SEQ ID NO:10597), AGGTCGGAGGAGTTCGTTTTAGGTGGTG (SEQ ID NO:10598) |
| Target1124 | chr10:126135810-126135833 | TTTTTTATCGGGGGTGTAGGTGCGCGG (SEQ ID NO:10599), TTTTTATCGGGGGTGTAGGTGCGCGGG (SEQ ID NO:10600), TTTTTTATCGGGGGTGTAGGTGCGCGG (SEQ ID NO:10601), TTTTATCGGGGGTGTAGGTGCGCGGG (SEQ ID NO:10602), TTTTATCGGGGGTGTAGGTGCGCGGGT (SEQ ID NO:10603) |
| Target1125 | chr10:126135868-126135881 | AGATTTTTGATTTTTTGGTGGTTCGCGAGGA (SEQ ID NO:10604), CGGTAGATTTTTGATTTTTTGGTGGTTCGCG (SEQ ID NO:10605), ACGGTAGATTTTTGATTTTTTGGTGGTTCGCG (SEQ ID NO:10606), CGGTAGATTTTTGATTTTTTGGTGGTTCGCGA (SEQ ID NO:10607), ACGGTAGATTTTTGATTTTTTGGTGGTTCGCGA (SEQ ID NO:10608), TTTTTTATCGGGGGTGTAGGTGCGCGCG (SEQ ID NO:10609), TTTTTATCGGGGGTGTAGGTGCGCGGG (SEQ ID NO:10610), TTTTTTATCGGGGGTGTAGGTGCGCGG (SEQ ID NO:10611), TTTTATCGGGGGTGTAGGTGCGCGGG (SEQ ID NO:10612), TTTTATCGGGGGTGTAGGTGCGCGGGT (SEQ ID NO:10613) |
| Target1126 | chr10:126135895-126135908 | CGGCGGGTAGGGGTGCGTTGATATTCG (SEQ ID NO:10614), GCGGCGGGTAGGGGTGCGTTGATATTC (SEQ ID NO:10615), GGCGGGTAGGGGTGCGTTGATATTCG (SEQ ID NO:10616), CGGCGGGTAGGGGTGCGTTGATATTC (SEQ ID NO:10617), GCGGCGGGTAGGGGTGCGTTGATATT (SEQ ID NO:10618), TTTTTTATCGGGGGTGTAGGTGCGCGG (SEQ ID NO:10619), TTTTTATCGGGGGTGTAGGTGCGCGGG (SEQ ID NO:10620), TTTTTTATCGGGGGTGTAGGTGCGCGG (SEQ ID NO:10621), TTTTATCGGGGGTGTAGGTGCGCGGG (SEQ ID NO:10622), TTTTATCGGGGGTGTAGGTGCGCGGGT (SEQ ID NO:10623) |
| Target1127 | chr10:126135933-126135947 | CGGCGGGTAGGGGTGCGTTGATATTCG (SEQ ID NO:10624), GCGGCGGGTAGGGGTGCGTTGATATTC (SEQ ID NO:10625), GGCGGGTAGGGGTGCGTTGATATTCG (SEQ ID NO:10626), CGGCGGGTAGGGGTGCGTTGATATTC (SEQ ID NO:10627), GCGGCGGGTAGGGGTGCGTTGATATT (SEQ ID NO:10628), TCGCGGGATTTACGAGGGATTGGTATC (SEQ ID NO:10629), GGGAGTTTTTTCGCGTCGTTTTTTGGGT (SEQ ID NO:10630), GGGAGTTTTTTCGCGTCGTTTTTTGGG (SEQ ID NO:10631), GGGAGTTTTTTCGCGTCGTTTTTTGGGT (SEQ ID NO:10632), GGGAGTTTTTTCGCGTCGTTTTTTGGGTT (SEQ ID NO:10633) |
| Target1128 | chr10:126135960-126135972 | CGGCGGGTAGGGGTGCGTTGATATTCG (SEQ ID NO:10634), GCGGCGGGTAGGGGTGCGTTGATATTC (SEQ ID NO:10635), GGCGGGTAGGGGTGCGTTGATATTCG (SEQ ID NO:10636), CGGCGGGTAGGGGTGCGTTGATATTC (SEQ ID NO:10637), GCGGCGGGTAGGGGTGCGTTGATATT (SEQ ID NO:10638), GGGAGTTTTTTCGCGTCGTTTTTTGGGT (SEQ ID NO:10639), GGGAGTTTTTTCGCGTCGTTTTTTGGG (SEQ ID NO:10640), GGGAGTTTTTTCGCGTCGTTTTTTGGGTT (SEQ ID NO:10641), GGAGTTTTTTCGCGTCGTTTTTTGGGTT (SEQ ID NO:10642), GGGAGTTTTTTCGCGTCGTTTTTTGGGTT (SEQ ID NO:10643) |
| Target1129 | chr10:126135993-126136008 | CGGCGGGTAGGGGTGCGTTGATATTCG (SEQ ID NO:10644), GCGGCGGGTAGGGGTGCGTTGATATTC (SEQ ID NO:10645), TTCGCGAAAGAGGGGTTAGGGGGTTTC (SEQ ID NO:10646), GGCGGGTAGGGGTGCGTTGATATTCG (SEQ ID NO:10647), CGGCGGGTAGGGGTGCGTTGATATTC (SEQ ID NO:10648), GGGAGTTTTTTCGCGTCGTTTTTTGGGT (SEQ ID NO:10649), GGGAGTTTTTTCGCGTCGTTTTTTGGG (SEQ ID NO:10650), GGGAGTTTTTTCGCGTCGTTTTTTGGGTT (SEQ ID NO:10651), GGAGTTTTTTCGCGTCGTTTTTTGGGTT (SEQ ID NO:10652), GGGAGTTTTTTCGCGTCGTTTTTTGGGTTT (SEQ ID NO:10653) |

FIGURE 5 CONTINUED

Target1130     chr10:126136046-126136052     CGGGGCGTAGAAGGGGGTTAGGTAGGA (SEQ ID NO:10654), GGGGTTTCGGATTTATAGACGCGGGGC
(SEQ ID NO:10655), GCGGGGCGTAGAAGGGGGTTAGGTAG (SEQ ID NO:10656),
GGGGGTTTCGGATTTATAGACGCGGGG (SEQ ID NO:10657), AGGGGGTTTCGGATTTATAGACGCGGGG
(SEQ ID NO:10658)

Target1131     chr10:126136069-126136119     CGGGGCGTAGAAGGGGGTTAGGTAGGA (SEQ ID NO:10659), GGGGTTTCGGATTTATAGACGCGGGGC
(SEQ ID NO:10660), GCGGGGCGTAGAAGGGGGTTAGGTAG (SEQ ID NO:10661),
GGGGGTTTCGGATTTATAGACGCGGGG (SEQ ID NO:10662), AGGGGGTTTCGGATTTATAGACGCGGGG
(SEQ ID NO:10663), TAGGTGGGGGGTGGCGCGTTTTAGTTA (SEQ ID NO:10664),
GGCGGTTCGGGGGGGTAGTTTTGGTTTT (SEQ ID NO:10665), AGGTGGGGGGGTGGCGCGTTTTAGTTAG
(SEQ ID NO:10666), GTAGGTGGGGGGGTGGCGCGTTTTAGTT (SEQ ID NO:10667),
TAGGTGGGGGGGTGGCGCGTTTTAGTTAG (SEQ ID NO:10668)

Target1132     chr10:126136120-126136163     CGGGGCGTAGAAGGGGGTTAGGTAGGA (SEQ ID NO:10669), GGCGGACGGGAAGAGGATATTGGTCGC
(SEQ ID NO:10670), TGGTCGCGGAGTAGGAGGGGAAAGTTT (SEQ ID NO:10671),
TTGGTCGCGGAGTAGGAGGGGAAAGTT (SEQ ID NO:10672), ATTGGTCGCGGAGTAGGAGGGGAAAGT
(SEQ ID NO:10673), TAGGTGGGGGGTGGCGCGTTTTAGTTA (SEQ ID NO:10674),
GGCGGTTCGGGGGGGTAGTTTTGGTTTT (SEQ ID NO:10675), AGGTGGGGGGGTGGCGCGTTTTAGTTAG
(SEQ ID NO:10676), GTAGGTGGGGGGGTGGCGCGTTTTAGTT (SEQ ID NO:10677),
TAGGTGGGGGGGTGGCGCGTTTTAGTTAG (SEQ ID NO:10678)

Target1133     chr10:126136184-126136209     GGCGGACGGGAAGAGGATATTGGTCGC (SEQ ID NO:10679), TGGTCGCGGAGTAGGAGGGGAAAGTTT
(SEQ ID NO:10680), TTGGTCGCGGAGTAGGAGGGGAAAGTT (SEQ ID NO:10681),
ATTGGTCGCGGAGTAGGAGGGGAAAGT (SEQ ID NO:10682), TCGCGGAGTAGGAGGGGAAAGTTTGGA
(SEQ ID NO:10683), TAGGTGGGGGGTGGCGCGTTTTAGTTA (SEQ ID NO:10684),
AGGTGGGGGGGTGGCGCGTTTTAGTTAG (SEQ ID NO:10685), GTAGGTGGGGGGGTGGCGCGTTTTAGTT
(SEQ ID NO:10686), TAGGTGGGGGGGTGGCGCGTTTTAGTTAG (SEQ ID NO:10687),
GTAGGTGGGGGGGTGGCGCGTTTTAGTTA (SEQ ID NO:10688)

Target1134     chr10:126136211-126136229     TTTTTCGTCGTTTTTGGTTGGGGCGCG (SEQ ID NO:10689), GGCGGACGGGAAGAGGGATATTGGTCGC
(SEQ ID NO:10690), TGGTCGCGGAGTAGGAGGGGAAAGTTT (SEQ ID NO:10691),
TTGGTCGCGGAGTAGGAGGGGAAAGTT (SEQ ID NO:10692), ATTGGTCGCGGAGTAGGAGGGGAAAGT
(SEQ ID NO:10693), TAGGTGGGGGGTGGCGCGTTTTAGTTA (SEQ ID NO:10694),
AGGTGGGGGGGTGGCGCGTTTTAGTTAG (SEQ ID NO:10695), GTAGGTGGGGGGGTGGCGCGTTTTAGTT
(SEQ ID NO:10696), TAGGTGGGGGGGTGGCGCGTTTTAGTTAG (SEQ ID NO:10697),
GTAGGTGGGGGGGTGGCGCGTTTTAGTTA (SEQ ID NO:10698)

Target1135     chr10:126136244-126136256     TTCGTCGTTTTTGGTTGGGGCGCGTTA (SEQ ID NO:10699), TCGTCGTTTTTGGTTGGGGCGCGTTAT (SEQ
ID NO:10700), TTTTTCGTCGTTTTTGGTTGGGGCGCG (SEQ ID NO:10701),
TTTCGTCGTTTTTGGTTGGGGCGCGTT (SEQ ID NO:10702), TTTTCGTCGTTTTTGGTTGGGGCGCGT (SEQ
ID NO:10703), GCGTTATTTGTTAGTGTGCGAGCGTTTG (SEQ ID NO:10704),
GCGTTATTTGTTAGTGTGCGAGCGTTGA (SEQ ID NO:10705),
GCGTTATTTGTTAGTGTGCGAGCGTTGAA (SEQ ID NO:10706),
GCGTTATTTGTTAGTGTGCGAGCGTTTGAAT (SEQ ID NO:10707),
GCGTTATTTGTTAGTGTGCGAGCGTTGAATT (SEQ ID NO:10708)

Target1136     chr10:126136316-126136358     TTCGTCGTTTTTGGTTGGGGCGCGTTA (SEQ ID NO:10709), TCGTCGTTTTTGGTTGGGGCGCGTTAT (SEQ
ID NO:10710), TTTTTCGTCGTTTTTGGTTGGGGCGCG (SEQ ID NO:10711),
TTTCGTCGTTTTTGGTTGGGGCGCGTT (SEQ ID NO:10712), TTTTCGTCGTTTTTGGTTGGGGCGCGT (SEQ
ID NO:10713), CGTCGGCGTTTGGAGTTTAATTGCGTT (SEQ ID NO:10714),
CGTCGGCGTTTGGAGTTTAATTGCGT (SEQ ID NO:10715), CGTCGGCGTTTGGAGTTTAATTGCGTTA (SEQ
ID NO:10716), GCGTTATTTGTTAGTGTGCGAGCGTTTG (SEQ ID NO:10717),
CGTCGGCGTTTGGAGTTTAATTGCGTTAA (SEQ ID NO:10718)

Target1137     chr10:129534514-129534541     TTATAGCGCGGGGAGTAGGGGAGGTCG (SEQ ID NO:10719), TTTATAGCGCGGGGAGTAGGGGAGGTC
(SEQ ID NO:10720), GCGGGGAGTAGGGGAGGTCGAAAGTC (SEQ ID NO:10721),
TTTTATAGCGCGGGGAGTAGGGGAGGT (SEQ ID NO:10722), TATAGCGCGGGGAGTAGGGGAGGTCGA
(SEQ ID NO:10723), TGTCGTTCGGGGTTGTTGTAGTTCGGGT (SEQ ID NO:10724),
GTCGTTCGGGGTTGTTGTAGTTCGGGT (SEQ ID NO:10725), TGTCGTTCGGGGTTGTTGTAGTTCGGG
(SEQ ID NO:10726), TCGTTCGGGGTTGTTGTAGTTCGGGTT (SEQ ID NO:10727),
GTCGTTCGGGGTTGTTGTAGTTCGGGTT (SEQ ID NO:10728)

Target1138     chr10:129534613-129534710     AGTCGGGTAGTTTGGGGGGTCGGGATA (SEQ ID NO:10729), TTGGGGGGTCGGGATAATTCGGGTTGT
(SEQ ID NO:10730), TTATAGCGCGGGGAGTAGGGGAGGTCG (SEQ ID NO:10731),
AGTTTGGGGGGTCGGGATAATTCGGGT (SEQ ID NO:10732), GTCGGGTAGTTTGGGGGGTCGGGATAA
(SEQ ID NO:10733), GTCGGGGAGTTCGGGGGTTTCGTTAGGT (SEQ ID NO:10734),
AGTCGGGGAGTTCGGGGGTTTCGTTAGG (SEQ ID NO:10735), TCGGGGAGTTCGGGGGTTTCGTTAGGTT
(SEQ ID NO:10736), GTCGGGGAGTTCGGGGGTTTCGTTAGGTT (SEQ ID NO:10737),
AAGTCGGGGAGTTCGGGGGTTTCGTTAGG (SEQ ID NO:10738)

Target1139     chr10:129534807-129534867     TGGCGGGGTTTCGGATTTTTCGGTTTG (SEQ ID NO:10739), TTGGCGGGGTTTCGGATTTTTCGGTTT (SEQ
ID NO:10740), TTTGGCGGGGTTTCGGATTTTTCGGTT (SEQ ID NO:10741),
TTCGTTGTTTTTCGGGTTGAGGGGAGCG (SEQ ID NO:10742), TTGGCGGGGTTTCGGATTTTTCGGTTTG
(SEQ ID NO:10743), GCGGGGTTTGGGTTTGGATAGCGGTTTT (SEQ ID NO:10744),
GGGTTTGGATAGCGGTTTTTGGGGTCGT (SEQ ID NO:10745), TGGGTTTGGATAGCGGTTTTTGGGGTCG

FIGURE 5 CONTINUED (SEQ ID NO:10746), CGGGGTTGGGTTTGGATAGCGGTTTTGG (SEQ ID NO:10747),
GGGTTGGGTTTGGATAGCGGTTTTGGGG (SEQ ID NO:10748)

Target1140    chr10:129534960-129534983    CGTTGTTTTTCGGGTTGAGGGAGCGAGG (SEQ ID NO:10749), TCGTTGTTTTTCGGGTTGAGGGAGCGA
(SEQ ID NO:10750), TTGTTTTTCGGGTTGAGGGAGCGAGGA (SEQ ID NO:10751),
CGTTGTTTTTCGGGTTGAGGGAGCGAG (SEQ ID NO:10752), TGTTTTTCGGGTTGAGGGAGCGAGGAT
(SEQ ID NO:10753), GGGATTCGGGGTTAGGGATAGAGGGCG (SEQ ID NO:10754),
GGGATTCGGGGTTAGGGATAGAGGGCGA (SEQ ID NO:10755),
GGGGATTCGGGGTTAGGGATAGAGGGCGA (SEQ ID NO:10756), TCGTCGGGGTTTTTGGGTTATTCGGGA
(SEQ ID NO:10757), GGATTCGGGGTTAGGGATAGAGGGCGAT (SEQ ID NO:10758)

Target1141    chr10:129535075-129535091    GGGTAATTTAGGGGTTTCGGCGAGGCG (SEQ ID NO:10759), CGGGTAATTTAGGGGTTTCGGCGAGGC
(SEQ ID NO:10760), TAGGGGTTTCGGCGAGGCGAGTTTTTT (SEQ ID NO:10761),
TTAGGGGTTTCGGCGAGGCGAGTTTTT (SEQ ID NO:10762), TTTAGGGGTTTCGGCGAGGCGAGTTTT
(SEQ ID NO:10763), GGTTTGGGAGTTTCGTTTAATGCGCGGT (SEQ ID NO:10764),
TGGTTTGGGAGTTTCGTTTAATGCGCGG (SEQ ID NO:10765), TGGGTTTGGGAGTTTCGTTTAATGCGCGGT
(SEQ ID NO:10766), GGTTTGGGAGTTTCGTTTAATGCGCGG (SEQ ID NO:10767),
GTGGTTTGGGAGTTTCGTTTAATGCGCGG (SEQ ID NO:10768)

Target1142    chr10:130085065-130085094    CGTAGGGTGTAATTCGGACGCGTTTTC (SEQ ID NO:10769), TGTTATTTCGGGGAAGGTTACGTAGGGTGT
(SEQ ID NO:10770), GTTATTTCGGGGAAGGTTACGTAGGGTGT (SEQ ID NO:10771),
TGTTATTTCGGGGAAGGTTACGTAGGGTG (SEQ ID NO:10772),
TTGTTATTTCGGGGAAGGTTACGTAGGGTG (SEQ ID NO:10773),
ATGGGGTGGGCGTTAGTGTAGGTTGGG (SEQ ID NO:10774), GTGTAGGTTGGGGGGTGTGGTTGTTGCG
(SEQ ID NO:10775), TGGGCGTTAGTGTAGGTTGGGGGTGTG (SEQ ID NO:10776),
GGCGTTAGTGTAGGTTGGGGGTGTGGT (SEQ ID NO:10777), GTGGGCGTTAGTGTAGGTTGGGGGTGT
(SEQ ID NO:10778)

Target1143    chr10:130085140-130085149    CGTAGGGTGTAATTCGGACGCGTTTTC (SEQ ID NO:10779), TGTTATTTCGGGGAAGGTTACGTAGGGTGT
(SEQ ID NO:10780), GTTATTTCGGGGAAGGTTACGTAGGGTGT (SEQ ID NO:10781),
TGTTATTTCGGGGAAGGTTACGTAGGGTG (SEQ ID NO:10782),
TTGTTATTTCGGGGAAGGTTACGTAGGGTG (SEQ ID NO:10783), TAGGGAGGGCGTTTTTGGTCGGGTTGT
(SEQ ID NO:10784), GTAGGGAGGGCGTTTTTGGTCGGGTTG (SEQ ID NO:10785),
GGTAGGGAGGGCGTTTTTGGTCGGGTT (SEQ ID NO:10786), CGTTTTTGGTCGGGTTGTGCGTTGGTC
(SEQ ID NO:10787), GCGTTTTTGGTCGGGTTGTGCGTTGGT (SEQ ID NO:10788)

Target1144    chr10:130085154-130085179    CGTAGGGTGTAATTCGGACGCGTTTTC (SEQ ID NO:10789), GGGTAGGGAGCGCGCGTTTTTATCG (SEQ
ID NO:10790), TGTTATTTCGGGGAAGGTTACGTAGGGTGT (SEQ ID NO:10791),
GTTATTTCGGGGAAGGTTACGTAGGGTGT (SEQ ID NO:10792),
TGTTATTTCGGGGAAGGTTACGTAGGGTG (SEQ ID NO:10793), TAGGGAGGGCGTTTTTGGTCGGGTTGT
(SEQ ID NO:10794), GTAGGGAGGGCGTTTTTGGTCGGGTTG (SEQ ID NO:10795),
GATTAAAGGGTCGGCGGCGGTAGGGAG (SEQ ID NO:10796), GGTAGGGAGGGCGTTTTTGGTCGGGTT
(SEQ ID NO:10797), CGTTTTTGGTCGGGTTGTGCGTTGGTC (SEQ ID NO:10798)

Target1145    chr10:130085199-130085219    GGTAGGGAGCGCGCGTTTTTATCGGTT (SEQ ID NO:10799), GGGTAGGGAGCGCGCGTTTTTATCGGT
(SEQ ID NO:10800), GGGTAGGGAGCGCGCGTTTTTATCGG (SEQ ID NO:10801),
TAGGGAGCGCGCGTTTTTATCGGTTGA (SEQ ID NO:10802), GGTAGGGAGCGCGCGTTTTTATCGGTTG
(SEQ ID NO:10803), ATAGCGTTGGTTGTGGTTTGCGGGTCG (SEQ ID NO:10804),
TAGGGAGGGCGTTTTTGGTCGGGTTGT (SEQ ID NO:10805), GTAGGGAGGGCGTTTTTGGTCGGGTTG
(SEQ ID NO:10806), GATTAAAGGGTCGGCGGCGGTAGGGAG (SEQ ID NO:10807),
GGTAGGGAGGGCGTTTTTGGTCGGGTT (SEQ ID NO:10808)

Target1146    chr10:130085262-130085296    GGTAGGGAGCGCGCGTTTTTATCGGTT (SEQ ID NO:10809), GGGTAGGGAGCGCGCGTTTTTATCGGT
(SEQ ID NO:10810), GGGTAGGGAGCGCGCGTTTTTATCGG (SEQ ID NO:10811),
TAGGGAGCGCGCGTTTTTATCGGTTGA (SEQ ID NO:10812), GGTAGGGAGCGCGCGTTTTTATCGGTTG
(SEQ ID NO:10813), ATAGCGTTGGTTGTGGTTTGCGGGTCG (SEQ ID NO:10814),
TAGCGTTGGTTGTGGTTTGCGGGTCG (SEQ ID NO:10815), GTCGGTCGGTCGGGTTTTGATGTGCG (SEQ
ID NO:10816), TATAGCGTTGGTTGTGGTTTGCGGGTCG (SEQ ID NO:10817),
GCGGTTCGGGGATTCGTGCGTTTGAG (SEQ ID NO:10818)

Target1147    chr10:130085311-130085357    GTTAGCGTTGTGTTGGGTAGGTGGCGG (SEQ ID NO:10819), TTAGCGTTGTGTTGGGTAGGTGGCGGT
(SEQ ID NO:10820), TAGCGTTGTGTTGGGTAGGTGGCGGTA (SEQ ID NO:10821),
AGCGTTGTGTTGGGTAGGTGGCGGTAG (SEQ ID NO:10822), TAGCGTTGTGTTGGGTAGGTGGCGGTAG
(SEQ ID NO:10823), GTCGGTCGGTCGGGTTTTGATGTGCG (SEQ ID NO:10824),
GCGGTTCGGGGATTCGTGCGTTTGAG (SEQ ID NO:10825), GTCGGTCGGTCGGGTTTTGATGTGCGG (SEQ
ID NO:10826), GCGGTTCGGGGATTCGTGCGTTTGA (SEQ ID NO:10827),
TCGGTCGGTCGGGTTTTGATGTGCGG (SEQ ID NO:10828)

Target1148    chr10:130085373-130085381    GTTAGCGTTGTGTTGGGTAGGTGGCGG (SEQ ID NO:10829), TTAGCGTTGTGTTGGGTAGGTGGCGGT
(SEQ ID NO:10830), TAGCGTTGTGTTGGGTAGGTGGCGGTA (SEQ ID NO:10831),
AGCGTTGTGTTGGGTAGGTGGCGGTAG (SEQ ID NO:10832), AGTTAGCGTTGTGTTGGGTAGGTGGCG
(SEQ ID NO:10833), GTCGGTCGGTCGGGTTTTGATGTGCG (SEQ ID NO:10834),
GTCGGTCGGTCGGGTTTTGATGTGCGG (SEQ ID NO:10835), TCGGTCGGTCGGGTTTTGATGTGCGG (SEQ

FIGURE 5 CONTINUED

ID NO:10836), TCGGTCGGTCGGGTTTTGATGTGCG (SEQ ID NO:10837),
GTCGGTCGGGTTTTGATGTGCGGCGTG (SEQ ID NO:10838)

| | | |
|---|---|---|
| Target1149 | chr10:130732658-130732844 | GTGTTTTTTGGTTTTTGTTGACGTTGGTTGAGA (SEQ ID NO:10839), TGTGTTTTTTGGTTTTTGTTGACGTTGGTTGAGA (SEQ ID NO:10840), GGATTGTGTTTTTTGGTTTTTGTTGACGTTGGTT (SEQ ID NO:10841), TGGATTGTGTTTTTTGGTTTTTGTTGACGTTGGTT (SEQ ID NO:10842), TGTTTTTTGGTTTTTGTTGACGTTGGTTGAGAAA (SEQ ID NO:10843), GAGTGTATGTGGGTCGTGGAGGGGGAA (SEQ ID NO:10844), GGAGTGTATGTGGGTCGTGGAGGGGGA (SEQ ID NO:10845), AGGAGTGTATGTGGGTCGTGGAGGGGG (SEQ ID NO:10846), AGTGTATGTGGGTCGTGGAGGGGGAAA (SEQ ID NO:10847), GGAGTGTATGTGGGTCGTGGAGGGGG (SEQ ID NO:10848) |
| Target1150 | chr10:131213563-131213642 | AGGTTAACGTCGGGAAAAGTTCGGGGT (SEQ ID NO:10849), GGTTAACGTCGGGAAAAGTTCGGGGTT (SEQ ID NO:10850), AGGTTAACGTCGGGAAAAGTTCGGGGTT (SEQ ID NO:10851), AAGGTTAACGTCGGGAAAAGTTCGGGGT (SEQ ID NO:10852), AAGGTTAACGTCGGGAAAAGTTCGGGG (SEQ ID NO:10853), TTGGAGTGGAATTCGGGAGGTTTCGGA (SEQ ID NO:10854), TGGAGTGGAATTCGGGAGGTTTCGGAT (SEQ ID NO:10855), ATTGGAGTGGAATTCGGGAGGTTTCGG (SEQ ID NO:10856), TTGGAGTGGAATTCGGGAGGTTTCGGAT (SEQ ID NO:10857), ATTGGAGTGGAATTCGGGAGGTTTCGGA (SEQ ID NO:10858) |
| Target1151 | chr10:131223363-131223405 | TGGAAGGGTTGGGTTGTAGGAGGGGTT (SEQ ID NO:10859), TTGGAAGGGTTGGGTTGTAGGAGGGGT (SEQ ID NO:10860), TTGGAAGGGTTGGGTTGTAGGAGGGGTT (SEQ ID NO:10861), TTTGGAAGGGTTGGGTTGTAGGAGGGGT (SEQ ID NO:10862), TTTGGAAGGGTTGGGTTGTAGGAGGGG (SEQ ID NO:10863), CGAGGGCGTTGATAGGTAGAGGAAGTTTCG (SEQ ID NO:10864), AGGGCGTTGATAGGTAGAGGAAGTTTCG (SEQ ID NO:10865), CGAGGGCGTTGATAGGTAGAGGAAGTTT (SEQ ID NO:10866), GGGCGTTGATAGGTAGAGGAAGTTTCGA (SEQ ID NO:10867), AGGGCGTTGATAGGTAGAGGAAGTTTCGA (SEQ ID NO:10868) |
| Target1152 | chr10:131223459-131223546 | TCGAAGAGTTGGCGGAGAGAAGCGGTT (SEQ ID NO:10869), CGAAGAGTTGGCGGAGAGAAGCGGTTT (SEQ ID NO:10870), TCGAAGAGTTGGCGGAGAGAAGCGGTTT (SEQ ID NO:10871), TCGAAGAGTTGGCGGAGAGAAGCGGT (SEQ ID NO:10872), CGAAGAGTTGGCGGAGAGAAGCGGTTTT (SEQ ID NO:10873), TGGAGTGGTTGTTGTGGAGGTTTTCGG (SEQ ID NO:10874), TGGAGTGGTTGTTGTGGAGGTTTTCGGA (SEQ ID NO:10875), GGAGTGGTTGTTGTGGAGGTTTTCGGA (SEQ ID NO:10876), TGGAGTGGTTGTTGTGGAGGTTTTCGGAG (SEQ ID NO:10877), GGAGTGGTTGTTGTGGAGGTTTTCGGAG (SEQ ID NO:10878) |
| Target1153 | chr10:131756715-131756728 | AGCGCGCGTGTATGTGAGAATTGGATT (SEQ ID NO:10879), GCGCGCGTGTATGTGAGAATTGGATTGT (SEQ ID NO:10880), GCGCGCGTGTATGTGAGAATTGGATTG (SEQ ID NO:10881), AGCGCGCGTGTATGTGAGAATTGGATTGT (SEQ ID NO:10882), AGCGCGCGTGTATGTGAGAATTGGATTGT (SEQ ID NO:10883) |
| Target1154 | chr10:131756883-131756961 | AGGATGCGAGCGTTTGAGAAGGAAGTA (SEQ ID NO:10884), TAGGATGCGAGCGTTTGAGAAGGAAGT (SEQ ID NO:10885), GGATGCGAGCGTTTGAGAAGGAAGTAGT (SEQ ID NO:10886), AGGATGCGAGCGTTTGAGAAGGAAGTAGT (SEQ ID NO:10887), AGGATGCGAGCGTTTGAGAAGGAAGTAG (SEQ ID NO:10888), AGCGGATTAATATGTGGGTCGTGTCGT (SEQ ID NO:10889), TGTGGGTCGTGTCGTTGTAGTGTAGTT (SEQ ID NO:10890), GAGCGGATTAATATGTGGGTCGTGTCGT (SEQ ID NO:10891), AGAGCGGATTAATATGTGGGTCGTGTCGT (SEQ ID NO:10892), AGAGCGGATTAATATGTGGGTCGTGTCG (SEQ ID NO:10893) |
| Target1155 | chr10:131756982-131757005 | AGGCGTCGTTATTTCGTTTAGTTTCGGG (SEQ ID NO:10894), GGCGTCGTTATTTCGTTTAGTTTCGGGA (SEQ ID NO:10895), AGGCGTCGTTATTTCGTTTAGTTTCGGGA (SEQ ID NO:10896), CGTCGGGTCGCGGAGGAGTTCG (SEQ ID NO:10897), GGCGTCGTTATTTCGTTTAGTTTCGGGAAGGG (SEQ ID NO:10898) |
| Target1156 | chr10:131757011-131757071 | TTGGGGGGAAGGAGCGCGGGTTTTTTC (SEQ ID NO:10899), GTTGGGGGGAAGGAGCGCGGGTTTTTT (SEQ ID NO:10900), TTGGGGGGAAGGAGCGCGGGTTTTTTT (SEQ ID NO:10901), GGGGGGAAGGAGCGCGGGTTTTTTC (SEQ ID NO:10902), TGGGGGGAAGGAGCGCGGGTTTTTTC (SEQ ID NO:10903), GCGGGTTGTTTCGGCGTTAGTTGCGTT (SEQ ID NO:10904), CGGGTTGTTTCGGCGTTAGTTGCGTTT (SEQ ID NO:10905), GCGGGTTGTTTCGGCGTTAGTTGCGT (SEQ ID NO:10906), GCGGGTTGTTTCGGCGTTAGTTGCGTTT (SEQ ID NO:10907), CGGGTTGTTTCGGCGTTAGTTGCGTT (SEQ ID NO:10908) |
| Target1157 | chr10:131757107-131757192 | TTGGGGGGAAGGAGCGCGGGTTTTTTC (SEQ ID NO:10909), GTTGGGGGGAAGGAGCGCGGGTTTTTT (SEQ ID NO:10910), TTGGGGGGAAGGAGCGCGGGTTTTTT (SEQ ID NO:10911), GGGGGGAAGGAGCGCGGGTTTTTTC (SEQ ID NO:10912), TGGGGGGAAGGAGCGCGGGTTTTTTC (SEQ ID NO:10913), GCGGGTTGTTTCGGCGTTAGTTGCGTT (SEQ ID NO:10914), CGGGTTGTTTCGGCGTTAGTTGCGTTT (SEQ ID NO:10915), ACGAGATTATGTGTAGGTGAGCGGCGGG (SEQ ID NO:10916), CGAGATTATGTGTAGGTGAGCGGCGGG (SEQ ID NO:10917), ACGAGATTATGTGTAGGTGAGCGGCGG (SEQ ID NO:10918) |
| Target1158 | chr10:134977981-134978016 | TCGTGGGGTTTTCGTGGGTGTTGGGTA (SEQ ID NO:10919), GTAGATAGGTGCGTAGGAGGCGGCGTT (SEQ ID NO:10920), TAGATAGGTGCGTAGGAGGCGGCGTTG (SEQ ID NO:10921), TTGTCGTGGGGTTTTCGTGGGTGTTGG (SEQ ID NO:10922), CGTGGGGTTTTCGTGGGTGTTGGGTAG (SEQ ID NO:10923), GTTTAGTCGGGTTGCGGGGTTGTCGAG (SEQ ID NO:10924), |

FIGURE 5 CONTINUED

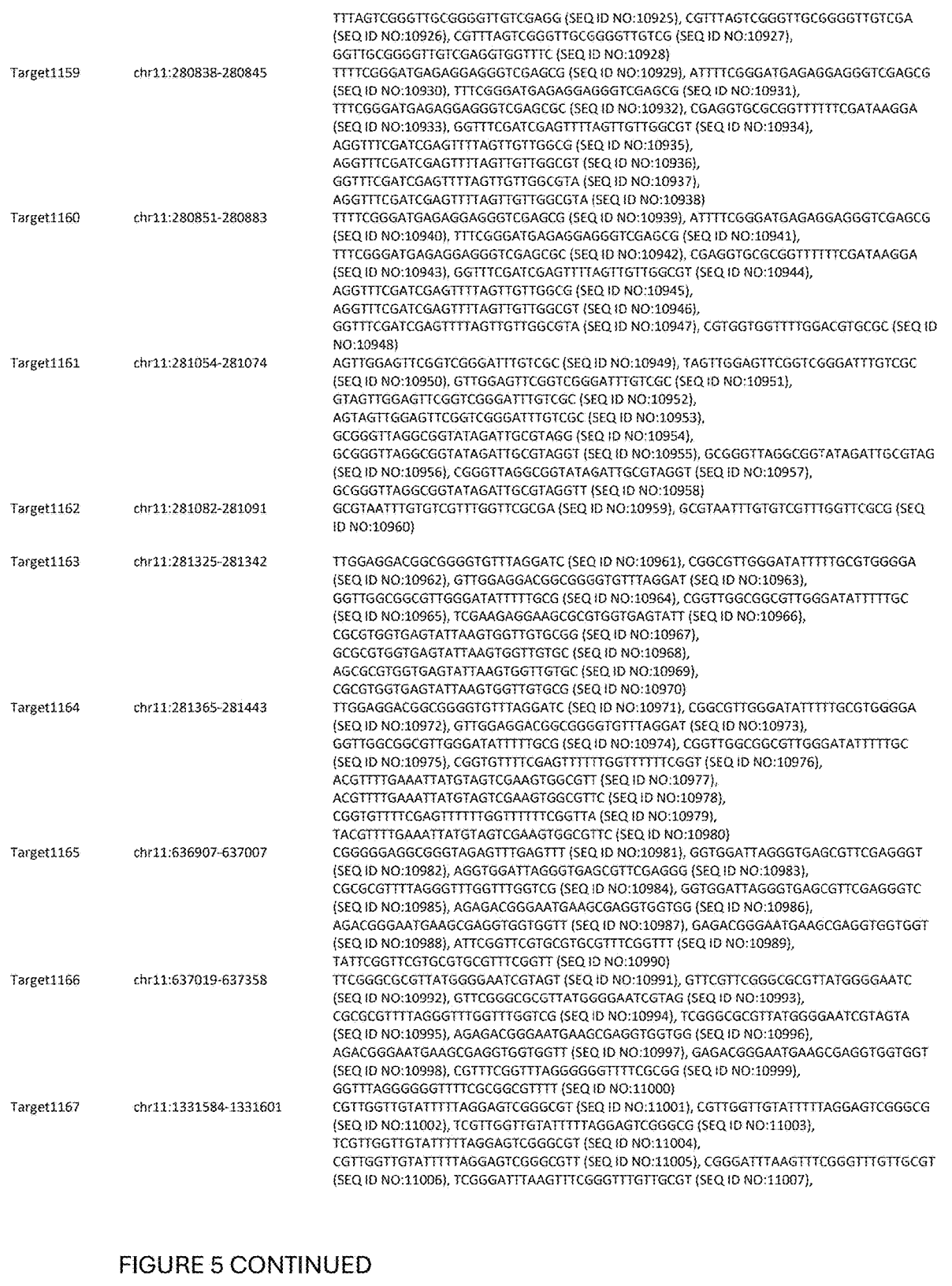

|  |  | TTTAGTCGGGTTGCGGGGTTGTCGAGG (SEQ ID NO:10925), CGTTTAGTCGGGTTGCGGGGTTGTCGA (SEQ ID NO:10926), CGTTTAGTCGGGTTGCGGGGTTGTCG (SEQ ID NO:10927), GGTTGCGGGGTTGTCGAGGTGGTTTC (SEQ ID NO:10928) |
|---|---|---|
| Target1159 | chr11:280838-280845 | TTTTCGGGATGAGAGGAGGGTCGAGCG (SEQ ID NO:10929), ATTTTCGGGATGAGAGGAGGGTCGAGCG (SEQ ID NO:10930), TTTCGGGATGAGAGGAGGGTCGAGCG (SEQ ID NO:10931), TTTCGGGATGAGAGGAGGGTCGAGCGC (SEQ ID NO:10932), CGAGGTGCGCGGTTTTTTCGATAAGGA (SEQ ID NO:10934), GGTTTCGATCGAGTTTTAGTTGTTGGCG (SEQ ID NO:10935), AGGTTTCGATCGAGTTTTAGTTGTTGGCG (SEQ ID NO:10936), AGGTTTCGATCGAGTTTTAGTTGTTGGCGT (SEQ ID NO:10936), GGTTTCGATCGAGTTTTAGTTGTTGGCGTA (SEQ ID NO:10937), AGGTTTCGATCGAGTTTTAGTTGTTGGCGTA (SEQ ID NO:10938) |
| Target1160 | chr11:280851-280883 | TTTTCGGGATGAGAGGAGGGTCGAGCG (SEQ ID NO:10939), ATTTTCGGGATGAGAGGAGGGTCGAGCG (SEQ ID NO:10940), TTTCGGGATGAGAGGAGGGTCGAGCG (SEQ ID NO:10941), TTTCGGGATGAGAGGAGGGTCGAGCGC (SEQ ID NO:10942), CGAGGTGCGCGGTTTTTTCGATAAGGA (SEQ ID NO:10943), GGTTTCGATCGAGTTTTAGTTGTTGGCGT (SEQ ID NO:10944), AGGTTTCGATCGAGTTTTAGTTGTTGGCG (SEQ ID NO:10945), AGGTTTCGATCGAGTTTTAGTTGTTGGCGT (SEQ ID NO:10946), GGTTTCGATCGAGTTTTAGTTGTTGGCGTA (SEQ ID NO:10947), CGTGGTGGTTTTGGACGTGCGC (SEQ ID NO:10948) |
| Target1161 | chr11:281054-281074 | AGTTGGAGTTCGGTCGGGATTTGTCGC (SEQ ID NO:10949), TAGTTGGAGTTCGGTCGGGATTTGTCGC (SEQ ID NO:10950), GTTGGAGTTCGGTCGGGATTTGTCGC (SEQ ID NO:10951), GTAGTTGGAGTTCGGTCGGGATTTGTCGC (SEQ ID NO:10952), AGTAGTTGGAGTTCGGTCGGGATTTGTCGC (SEQ ID NO:10953), GCGGGTTAGGCGGTATAGATTGCGTAGG (SEQ ID NO:10954), GCGGGTTAGGCGGTATAGATTGCGTAGGT (SEQ ID NO:10955), GCGGGTTAGGCGGTATAGATTGCGTAG (SEQ ID NO:10956), CGGGTTAGGCGGTATAGATTGCGTAGGT (SEQ ID NO:10957), GCGGGTTAGGCGGTATAGATTGCGTAGGTT (SEQ ID NO:10958) |
| Target1162 | chr11:281082-281091 | GCGTAATTTGTGTCGTTTGGTTCGCGA (SEQ ID NO:10959), GCGTAATTTGTGTCGTTTGGTTCGCG (SEQ ID NO:10960) |
| Target1163 | chr11:281325-281342 | TTGGAGGACGGCGGGGTGTTTAGGATC (SEQ ID NO:10961), CGGCGTTGGGATATTTTTGCGTGGGGA (SEQ ID NO:10962), GTTGGAGGACGGCGGGGTGTTTAGGAT (SEQ ID NO:10963), GGTTGGCGGCGTTGGGATATTTTTGCG (SEQ ID NO:10964), CGGTTGGCGGCGTTGGGATATTTTTGC (SEQ ID NO:10965), TCGAAGAGGAAGCGCGTGGTGAGTATT (SEQ ID NO:10966), CGCGTGGTGAGTATTAAGTGGTTGTGCGG (SEQ ID NO:10967), GCGCGTGGTGAGTATTAAGTGGTTGTGC (SEQ ID NO:10968), AGCGCGTGGTGAGTATTAAGTGGTTGTGC (SEQ ID NO:10969), CGCGTGGTGAGTATTAAGTGGTTGTGCG (SEQ ID NO:10970) |
| Target1164 | chr11:281365-281443 | TTGGAGGACGGCGGGGTGTTTAGGATC (SEQ ID NO:10971), CGGCGTTGGGATATTTTTGCGTGGGGA (SEQ ID NO:10972), GTTGGAGGACGGCGGGGTGTTTAGGAT (SEQ ID NO:10973), GGTTGGCGGCGTTGGGATATTTTTGCG (SEQ ID NO:10974), CGGTTGGCGGCGTTGGGATATTTTTGC (SEQ ID NO:10975), CGGTGTTTTCGAGTTTTTTGGTTTTTTCGGT (SEQ ID NO:10976), ACGTTTTGAAATTATGTAGTCGAAGTGGCGTT (SEQ ID NO:10977), ACGTTTTGAAATTATGTAGTCGAAGTGGCGTTC (SEQ ID NO:10978), CGGTGTTTTCGAGTTTTTTGGTTTTTTCGGTTA (SEQ ID NO:10979), TACGTTTTGAAATTATGTAGTCGAAGTGGCGTTC (SEQ ID NO:10980) |
| Target1165 | chr11:636907-637007 | CGGGGGGAGGCGGGTAGAGTTTGAGTTT (SEQ ID NO:10981), GGTGGATTAGGGTGAGCGTTCGAGGGT (SEQ ID NO:10982), AGGTGGATTAGGGTGAGCGTTCGAGGG (SEQ ID NO:10983), CGCGCGTTTTAGGGTTTGGTTTGGTCG (SEQ ID NO:10984), GGTGGATTAGGGTGAGCGTTCGAGGGTC (SEQ ID NO:10985), AGAGACGGGAATGAAGCGAGGTGGTGG (SEQ ID NO:10986), AGACGGGAATGAAGCGAGGTGGTGGTT (SEQ ID NO:10987), GAGACGGGAATGAAGCGAGGTGGTGGT (SEQ ID NO:10988), ATTCGGTTCGTGCGTGCGTTTCGGTTT (SEQ ID NO:10989), TATTCGGTTCGTGCGTGCGTTTCGGTT (SEQ ID NO:10990) |
| Target1166 | chr11:637019-637358 | TTCGGGCGCGTTATGGGGAATCGTAGT (SEQ ID NO:10991), GTTCGTTCGGGCGCGTTATGGGGAATC (SEQ ID NO:10992), GTTCGGGCGCGTTATGGGGAATCGTAG (SEQ ID NO:10993), CGCGCGTTTTAGGGTTTGGTTTGGTCG (SEQ ID NO:10994), TCGGGCGCGTTATGGGGAATCGTAGTA (SEQ ID NO:10995), AGAGACGGGAATGAAGCGAGGTGGTGG (SEQ ID NO:10996), AGACGGGAATGAAGCGAGGTGGTGGTT (SEQ ID NO:10997), GAGACGGGAATGAAGCGAGGTGGTGGT (SEQ ID NO:10998), CGTTTCGGTTTAGGGGGGTTTTCGCGG (SEQ ID NO:10999), GGTTTAGGGGGGTTTTCGCGGCGTTTT (SEQ ID NO:11000) |
| Target1167 | chr11:1331584-1331601 | CGTTGGTTGTATTTTTAGGAGTCGGGCGT (SEQ ID NO:11001), CGTTGGTTGTATTTTTAGGAGTCGGGCG (SEQ ID NO:11002), TCGTTGGTTGTATTTTTAGGAGTCGGGCG (SEQ ID NO:11003), TCGTTGGTTGTATTTTTAGGAGTCGGGCG (SEQ ID NO:11004), CGTTGGTTGTATTTTTAGGAGTCGGGCGTT (SEQ ID NO:11005), CGGGATTTAAGTTTCGGGTTTGTTGCGT (SEQ ID NO:11006), TCGGGATTTAAGTTTCGGGTTTGTTGCGT (SEQ ID NO:11007), |

FIGURE 5 CONTINUED

|  |  |  |
|---|---|---|
|  |  | TCGGGATTTAAGTTTCGGGTTTGTTGCG (SEQ ID NO:11008), ATCGGGATTTAAGTTTCGGGTTTGTTGCG (SEQ ID NO:11009), ATCGGGATTTAAGTTTCGGGTTTGTTGCGT (SEQ ID NO:11010) |
| Target1168 | chr11:1331624-1331657 | CGTTGGTTGTATTTTTAGGAGTCGGGCGT (SEQ ID NO:11011), CGTTGGTTGTATTTTTAGGAGTCGGGCG (SEQ ID NO:11012), TCGTTGGTTGTATTTTTAGGAGTCGGGCG (SEQ ID NO:11013), TCGTTGGTTGTATTTTTAGGAGTCGGGCGT (SEQ ID NO:11014), CGTTGGTTGTATTTTTAGGAGTCGGGCGTT (SEQ ID NO:11015) |
| Target1169 | chr11:1331696-1331858 | AGATGTTTGCGGAGGATAGGCGTTATGT (SEQ ID NO:11016), AGATGTTTGCGGAGGATAGGCGTTATGTA (SEQ ID NO:11017), TAGATGTTTGCGGAGGATAGGCGTTATGT (SEQ ID NO:11018), GCGGAGGATAGGCGTTATGTAAAGATTGGT (SEQ ID NO:11019), TGCGGAGGATAGGCGTTATGTAAAGATTGG (SEQ ID NO:11020), CGGGGGAGACGTGTTGTATTATTTGGGT (SEQ ID NO:11021), CGGGGGAGACGTGTTGTATTATTTGGGTT (SEQ ID NO:11022), CGGGGGAGACGTGTTGTATTATTTGGGTTCG (SEQ ID NO:11023), CGGGGGAGACGTGTTGTATTATTTGGGTTCGT (SEQ ID NO:11024), GGGGGAGACGTGTTGTATTATTTGGGTTCG (SEQ ID NO:11025) |
| Target1170 | chr11:1332089-1332115 | TGGTGTTTTGGATGGGGAGTGAAGAAAGT (SEQ ID NO:11026), ATGGTGTTTTGGATGGGGAGTGAAGAAAGT (SEQ ID NO:11027), TGGTGTTTTGGATGGGGAGTGAAGAAAGTA (SEQ ID NO:11028), TGGTGTTTTGGATGGGGAGTGAAGAAAGTAT (SEQ ID NO:11029), ATGGTGTTTTGGATGGGGAGTGAAGAAAGTA (SEQ ID NO:11030) |
| Target1171 | chr11:1682929-1682964 | AGAGGTGGGGATTTTGTTACGGTGGGT (SEQ ID NO:11031), GAGGTGGGGATTTTGTTACGGTGGGTT (SEQ ID NO:11032), AGAGGTGGGGATTTTGTTACGGTGGGTT (SEQ ID NO:11033), AGGTGGGGATTTTGTTACGGTGGGTTT (SEQ ID NO:11034), TAGAGGTGGGGATTTTGTTACGGTGGGT (SEQ ID NO:11035), TCGGGGAGGGGAGGGTTTTTTCGTTGA (SEQ ID NO:11036), TTCGGGGAGGGGAGGGTTTTTTCGTTG (SEQ ID NO:11037), TCGGGTGGGTGTAGGTTATTTCGGGGA (SEQ ID NO:11038), CGGGGAGGGGAGGGTTTTTTCGTTGAT (SEQ ID NO:11039), TTCGGGGAGGGGAGGGTTTTTTCGTTGA (SEQ ID NO:11040) |
| Target1172 | chr11:1683135-1683182 | GGATAGGTAGGGTGTTGCGTTCGTGGT (SEQ ID NO:11041), AGGATAGGTAGGGTGTTGCGTTCGTGGT (SEQ ID NO:11042), AGGATAGGTAGGGTGTTGCGTTCGTGG (SEQ ID NO:11043), GGATAGGTAGGGTGTTGCGTTCGTGGTT (SEQ ID NO:11044), AGGTAGGGTGTTGCGTTCGTGGTTTTT (SEQ ID NO:11045), GGGTTAGGTGTGGGCGAGGTTTGGGAT (SEQ ID NO:11046), ATAGTTCGGGGTTAGGTGTGGGCGAGG (SEQ ID NO:11047), TTCGGGGTTAGGTGTGGGCGAGGTTTG (SEQ ID NO:11048), GTTCGGGGTTAGGTGTGGGCGAGGTTT (SEQ ID NO:11049), TAGTTCGGGGTTAGGTGTGGGCGAGGT (SEQ ID NO:11050) |
| Target1173 | chr11:2114366-2114498 | CGGGGAGGAGGTTGTTTGGTAGGTTGG (SEQ ID NO:11051), TCGGGGAGGAGGTTGTTTGGTAGGTTGG (SEQ ID NO:11052), TTGGGGAGGTTGGGGAGGTTTTTGGTT (SEQ ID NO:11053), TTTGGGGAGGTTGGGGAGGTTTTTGGT (SEQ ID NO:11054), TCGGGGAGGAGGTTGTTTGGTAGGTTG (SEQ ID NO:11055), GGCGGCGGTTTTTATAGGGGAGGTTGGT (SEQ ID NO:11056), AGGCGGCGGTTTTTATAGGGGAGGTTGGT (SEQ ID NO:11057), AGGCGGCGGTTTTTATAGGGGAGGTTGG (SEQ ID NO:11058), AGGAGGGGTTAGGTGGGACGTGTTGTA (SEQ ID NO:11059), TAGGAGGGGTTAGGTGGGACGTGTTGT (SEQ ID NO:11060) |
| Target1174 | chr11:17497522-17497534 | GGGGGGATTTTAGTGGAGAGGTACGTACG (SEQ ID NO:11061), GGGGGGATTTTAGTGGAGAGGTACGTACGA (SEQ ID NO:11062), GGGGGATTTTAGTGGAGAGGTACGTACG (SEQ ID NO:11063), GGGGGATTTTAGTGGAGAGGTACGTACGA (SEQ ID NO:11064), GGGGGGATTTTAGTGGAGAGGTACGTACGAT (SEQ ID NO:11065), GGCGAGGAGAGGCGAGAGTTAGGGATT (SEQ ID NO:11066), GGCGAGGAGAGGCGAGAGTTAGGGATTT (SEQ ID NO:11067), GGCGAGGAGAGGCGAGAGTTAGGGAT (SEQ ID NO:11068), GCGAGGAGAGGCGAGAGTTAGGGATTGG (SEQ ID NO:11069), GGCGAGGAGAGGCGAGAGTTAGGGATTTG (SEQ ID NO:11070) |
| Target1175 | chr11:17497671-17497694 | AGGGCGCGGGTTTGGGATTGTTAGAGA (SEQ ID NO:11071), CGTTTAGGGCGCGGGTTTGGGATTGTT (SEQ ID NO:11072), TTCGTTTAGGGCGCGGGGTTTGGGATTG (SEQ ID NO:11073), AGATATATGTTCGGGTGGGGTGGCGGG (SEQ ID NO:11074), TGGGGTGGCGGGGGAAGGGAATTTAAG (SEQ ID NO:11075), AGTCGTAGTTGGGTTTAGGGAAGAGGGA (SEQ ID NO:11076), TCGTAGTTGGGTTTAGGGAAGAGGGAAGT (SEQ ID NO:11077), AGTCGTAGTTGGGTTTAGGGAAGAGGGAA (SEQ ID NO:11078), AGGGAAGAGGGAAGTTTGTGTTTTGGAGT (SEQ ID NO:11079), GTCGTAGTTGGGTTTAGGGAAGAGGGAAGT (SEQ ID NO:11080) |
| Target1176 | chr11:31819945-31820075 | AGGGGGGTTAGGGAGGGAGGGGGATTTT (SEQ ID NO:11081), AAGGGGGGTTAGGGAGGGAGGGGGATTT (SEQ ID NO:11082), AAAGGGGGGTTAGGGAGGGAGGGGGATT (SEQ ID NO:11083), GAAAGGGGGGTTAGGGAGGGAGGGGGAT (SEQ ID NO:11084), GTTGGGAAAGGGGGGTTAGGGAGGGAGG (SEQ ID NO:11085), TATAGAGTTGTCGGCGTGGGGGTAGCG (SEQ ID NO:11086), GTATAGAGTTGTCGGCGTGGGGGTAGCG (SEQ ID NO:11087), ATAGAGTTGTCGGCGTGGGGGTAGCG (SEQ ID NO:11088), CGAAGTATAGAGTTGTCGGCGTGGGGGT (SEQ ID NO:11089), CGAAGTATAGAGTTGTCGGCGTGGGGG (SEQ ID NO:11090) |

FIGURE 5 CONTINUED

| | | |
|---|---|---|
| Target1177 | chr11:31820087-31820149 | AGGGGGTTAGGGAGGGAGGGGGATTTT (SEQ ID NO:11091), AAGGGGGTTAGGGAGGGAGGGGGATTT (SEQ ID NO:11092), AAAGGGGGTTAGGGAGGGAGGGGGATT (SEQ ID NO:11093), GAAAGGGGGTTAGGGAGGGAGGGGGAT (SEQ ID NO:11094), GTTGGGAAAGGGGGTTAGGGAGGGAGG (SEQ ID NO:11095), TATAGAGTTGTCGGCGTGGGGGTAGCG (SEQ ID NO:11096), GTATAGAGTTGTCGGCGTGGGGGTAGCG (SEQ ID NO:11097), ATAGAGTTGTCGGCGTGGGGGTAGCG (SEQ ID NO:11098), CGAAGTATAGAGTTGTCGGCGTGGGGGT (SEQ ID NO:11099), CGAAGTATAGAGTTGTCGGCGTGGGGG (SEQ ID NO:11100) |
| Target1178 | chr11:31820160-31820485 | AGGGGCGACGGTTTTGTGTTTGAGGTG (SEQ ID NO:11101), GGGGCGACGGTTTTGTGTTTGAGGTGA (SEQ ID NO:11102), GGGGCGACGGTTTTGTGTTTGAGGTGAT (SEQ ID NO:11103), TAGGGGCGACGGTTTTGTGTTTGAGGT (SEQ ID NO:11104), AGGGGCGACGGTTTTGTGTTTGAGGTGA (SEQ ID NO:11105), CGTCGGTAGTTTGAGGGCGGGAAGTGA (SEQ ID NO:11106), TCGTCGGTAGTTTGAGGGCGGGAAGTG (SEQ ID NO:11107), GTCGTCGGTAGTTTGAGGGCGGGAAGT (SEQ ID NO:11108), GTGATGGTTGGGGTCGGAGGTGGAGTT (SEQ ID NO:11109), TTGTGATGGTTGGGGTCGGAGGTGGAG (SEQ ID NO:11110) |
| Target1179 | chr11:31820646-31820666 | TTTAGATTGTTGGGGGCGGAGGGGTGG (SEQ ID NO:11111), TTAGATTGTTGGGGGCGGAGGGGTGGA (SEQ ID NO:11112), TTAGATTGTTGGGGGCGGAGGGGTGG (SEQ ID NO:11113), TTTTAGATTGTTGGGGGCGGAGGGGTG (SEQ ID NO:11114), TTTTAGATTGTTGGGGGCGGAGGGGTGG (SEQ ID NO:11115) |
| Target1180 | chr11:31837359-31837370 | AGGCGGTAGTTAGGGATTAAAAGTCGGG (SEQ ID NO:11116), GGCGGTAGTTAGGGATTAAAAGTCGGGA (SEQ ID NO:11117), AGGCGGTAGTTAGGGATTAAAAGTCGGGA (SEQ ID NO:11118), GAGGCGGTAGTTAGGGATTAAAAGTCGGG (SEQ ID NO:11119), AGAGGCGGTAGTTAGGGATTAAAAGTCGGG (SEQ ID NO:11120), GTGAGATTGGGTTAGGAAGTGACGAAAAGC (SEQ ID NO:11121), TGTGAGATTGGGTTAGGAAGTGACGAAAAGC (SEQ ID NO:11122), TTGTGAGATTGGGTTAGGAAGTGACGAAAAGC (SEQ ID NO:11123), TTTGTGAGATTGGGTTAGGAAGTGACGAAAAGC (SEQ ID NO:11124), TTTTGTGAGATTGGGTTAGGAAGTGACGAAAAGC (SEQ ID NO:11125) |
| Target1181 | chr11:31837419-31837437 | AGAGGGTGATTTTTAAATTTGGTTAGCGGGGA (SEQ ID NO:11126), GAGGGTGATTTTTAAATTTGGTTAGCGGGGA (SEQ ID NO:11127), AGAGGGTGATTTTTAAATTTGGTTAGCGGGGAA (SEQ ID NO:11128), TAGAGGGTGATTTTTAAATTTGGTTAGCGGGGA (SEQ ID NO:11129), GAGGGTGATTTTTAAATTTGGTTAGCGGGGAAA (SEQ ID NO:11130), TGAGGAATTAGAGGTATCGGGTCGCGC (SEQ ID NO:11131), CGTGAGGAATTAGAGGTATCGGGTCGCGC (SEQ ID NO:11132), GTGAGGAATTAGAGGTATCGGGTCGCGC (SEQ ID NO:11133), CGTGAGGAATTAGAGGTATCGGGTCGCG (SEQ ID NO:11134), GGGTCGCGCGCGGGGTTGAGAATTTTTAAA (SEQ ID NO:11135) |
| Target1182 | chr11:31837478-31837489 | AGGGGTTGATAGGAATTGCGGGTTGGT (SEQ ID NO:11136), GAGGGGTTGATAGGAATTGCGGGTTGGT (SEQ ID NO:11137), GAGGGGTTGATAGGAATTGCGGGTTGG (SEQ ID NO:11138), GGGGTTGATAGGAATTGCGGGTTGGTT (SEQ ID NO:11139), AGAGGGGTTGATAGGAATTGCGGGTTGGT (SEQ ID NO:11140), TGAGGAATTAGAGGTATCGGGTCGCGC (SEQ ID NO:11141), CGTGAGGAATTAGAGGTATCGGGTCGCGC (SEQ ID NO:11142), GTGAGGAATTAGAGGTATCGGGTCGCGC (SEQ ID NO:11143), CGTGAGGAATTAGAGGTATCGGGTCGCG (SEQ ID NO:11144), GGGTCGCGCGGGGTTGAGAATTTTTAAA (SEQ ID NO:11145) |
| Target1183 | chr11:31837514-31837524 | AGGGGTTGATAGGAATTGCGGGTTGGT (SEQ ID NO:11146), GAGGGGTTGATAGGAATTGCGGGGTTGGT (SEQ ID NO:11147), GAGGGGTTGATAGGAATTGCGGGGTTGG (SEQ ID NO:11148), GGGGTTGATAGGAATTGCGGGTTGGTT (SEQ ID NO:11149), AGAGGGGTTGATAGGAATTGCGGGTTGGT (SEQ ID NO:11150), TCGGCGTTAGAGTCGGGTTTGAGGAGC (SEQ ID NO:11151), AGAGTCGGGTTTGAGGAGCGGGGTTTG (SEQ ID NO:11152), GTTAGAGTCGGGTTTGAGGAGCGGGGT (SEQ ID NO:11153), CGTTAGAGTCGGGTTTGAGGAGCGGGG (SEQ ID NO:11154), GCGTTAGAGTCGGGTTTGAGGAGCGGG (SEQ ID NO:11155) |
| Target1184 | chr11:31837640-31837651 | TTTAGGTTCGGTTTTGGCGTCGGGTGG (SEQ ID NO:11156), TTAGGTTCGGTTTTGGCGTCGGGTGGC (SEQ ID NO:11157), TTTTAGGTTCGGTTTTGGCGTCGGGTGG (SEQ ID NO:11158), TTAGGTTCGGTTTTGGCGTCGGGTGG (SEQ ID NO:11159), TTTTAGGTTCGGTTTTGGCGTCGGGTG (SEQ ID NO:11160), TTTTTTCGGGGTAGAAGGGGGTAGCGC (SEQ ID NO:11161), GTTTTTTCGGGGTAGAAGGGGGTAGCGC (SEQ ID NO:11162), CGTTTTTTCGGGGTAGAAGGGGGTAGCG (SEQ ID NO:11163), TTTTTCGGGGTAGAAGGGGGTAGCGC (SEQ ID NO:11164), GTTTTTTCGGGGTAGAAGGGGGTAGCG (SEQ ID NO:11165) |
| Target1185 | chr11:31837672-31837682 | TTTAGGTTCGGTTTTGGCGTCGGGTGG (SEQ ID NO:11166), TTAGGTTCGGTTTTGGCGTCGGGTGGC (SEQ ID NO:11167), TTTTAGGTTCGGTTTTGGCGTCGGGTGG (SEQ ID NO:11168), TTAGGTTCGGTTTTGGCGTCGGGTGG (SEQ ID NO:11169), GGCGTCGGGTGGCGTTTAGTTTTTGTA (SEQ ID NO:11170), TTTTTTCGGGGTAGAAGGGGGTAGCGC (SEQ ID NO:11171), GTTTTTTCGGGGTAGAAGGGGGTAGCGC (SEQ ID NO:11172), CGTTTTTTCGGGGTAGAAGGGGGTAGCG (SEQ ID NO:11173), TTTTTCGGGGTAGAAGGGGGTAGCGC (SEQ ID NO:11174), GTTTTTTCGGGGTAGAAGGGGGTAGCG (SEQ ID NO:11175) |

FIGURE 5 CONTINUED

| | | |
|---|---|---|
| Target1186 | chr11:31837723-31837728 | TTTAGGTTCGGTTTTGGCGTCGGGTGG (SEQ ID NO:11176), TTAGGTTCGGTTTTGGCGTCGGGTGGC (SEQ ID NO:11177), TTTTAGGTTCGGTTTTGGCGTCGGGTGG (SEQ ID NO:11178), TTAGGTTCGGTTTTGGCGTCGGGTGG (SEQ ID NO:11179), GGCGTCGGGTGGCGTTTAGTTTTTGTA (SEQ ID NO:11180), TTTTTTCGGGGTAGAAGGGGGTAGCGC (SEQ ID NO:11181), GTTTTTTCGGGGTAGAAGGGGGTAGCGC (SEQ ID NO:11182), CGTTTTTTCGGGGTAGAAGGGGGTAGCG (SEQ ID NO:11183), TTTTTCGGGGTAGAAGGGGGTAGCGC (SEQ ID NO:11184), GTTTTTTCGGGGTAGAAGGGGGTAGCG (SEQ ID NO:11185) |
| Target1187 | chr11:32462725-32462749 | TATTAGCGGTGGAAGACGAGGAAAGCG (SEQ ID NO:11186), ATTAGCGGTGGAAGACGAGGAAAGCG (SEQ ID NO:11187), TTATTAGCGGTGGAAGACGAGGAAAGCG (SEQ ID NO:11188), TTAGCGGTGGAAGACGAGGAAAGCG (SEQ ID NO:11189), TTTATTAGCGGTGGAAGACGAGGAAAGCG (SEQ ID NO:11190) |
| Target1188 | chr11:44326260-44326265 | CGGAGGATTTTGGTTTTTAAGATTAGTTGGGCG (SEQ ID NO:11191), CGGAGGATTTTGGTTTTTAAGATTAGTTGGGCGT (SEQ ID NO:11192), TCGGAGGATTTTGGTTTTTAAGATTAGTTGGGCG (SEQ ID NO:11193), TCGGAGGATTTTGGTTTTTAAGATTAGTTGGGCGT (SEQ ID NO:11194), GGAGGATTTTGGTTTTTAAGATTAGTTGGGCGT (SEQ ID NO:11195) |
| Target1189 | chr11:44326304-44326321 | GCGGTTGAGGGTAGGAAGGCGTTGAGA (SEQ ID NO:11196), TAAAGTTGCGCGCGGTTGAGGGTAGGA (SEQ ID NO:11197), ATAAAGTTGCGCGCGGTTGAGGGTAGG (SEQ ID NO:11198), AAAGTTGCGCGCGGTTGAGGGTAGGAA (SEQ ID NO:11199), GCGGTTGAGGGTAGGAAGGCGTTGAGAT (SEQ ID NO:11200), CGGAGGATTTTGGTTTTTAAGATTAGTTGGGCG (SEQ ID NO:11201), CGGAGGATTTTGGTTTTTAAGATTAGTTGGGCGT (SEQ ID NO:11202), TCGGAGGATTTTGGTTTTTAAGATTAGTTGGGCG (SEQ ID NO:11203), TCGGAGGATTTTGGTTTTTAAGATTAGTTGGGCGT (SEQ ID NO:11204), GGAGGATTTTGGTTTTTAAGATTAGTTGGGCGT (SEQ ID NO:11205) |
| Target1190 | chr11:58672874-58672973 | CGTAGACGCGGGTGTAGTTTGTTTTGC (SEQ ID NO:11206), TGTTGTTGTCGTTGGATTTCGTTTGGATGT (SEQ ID NO:11207), TTGTTGTTGTCGTTGGATTTCGTTTGGATGT (SEQ ID NO:11208), TTTGTTGTTGTCGTTGGATTTCGTTTGGATGT (SEQ ID NO:11209), TGTTGTTGTCGTTGGATTTCGTTTGGATGTAC (SEQ ID NO:11210), CGAGTGGGAGTAGCGCGTTGAGGAGAG (SEQ ID NO:11211), TCGGGTGGGTATGGGAGATGTTTGGCG (SEQ ID NO:11212), GGGTGGGTATGGGAGATGTTTGGCGGT (SEQ ID NO:11213), TGGAAGTTAAGGAGGGGTTGCGCGGTA (SEQ ID NO:11214), GAGTGGGAGTAGCGCGTTGAGGAGAGT (SEQ ID NO:11215) |
| Target1191 | chr11:58672974-58673012 | CGTCGATTTATTAGCGGTAGAAGGGTAGTAATGG (SEQ ID NO:11216), CGTCGATTTATTAGCGGTAGAAGGGTAGTAATGGT (SEQ ID NO:11217), TCGTCGATTTATTAGCGGTAGAAGGGTAGTAATGG (SEQ ID NO:11218), TCGTCGATTTATTAGCGGTAGAAGGGTAGTAATGGT (SEQ ID NO:11219), GTCGTCGATTTATTAGCGGTAGAAGGGTAGTAATGG (SEQ ID NO:11220), TCGGGTGGGTATGGGAGATGTTTGGCG (SEQ ID NO:11221), GGGTGGGTATGGGAGATGTTTGGCGGT (SEQ ID NO:11222), TGGAAGTTAAGGAGGGGTTGCGCGGTA (SEQ ID NO:11223), AGTGGAAGTTAAGGAGGGGTTGCGCGG (SEQ ID NO:11224), GTGGAAGTTAAGGAGGGGTTGCGCGGT (SEQ ID NO:11225) |
| Target1192 | chr11:58673048-58673091 | TGGTTTTTATTGGGAGATAGGGGACGTCG (SEQ ID NO:11226), TTGGTTTTTATTGGGAGATAGGGGACGTCG (SEQ ID NO:11227), TTTGGTTTTTATTGGGAGATAGGGGACGTCG (SEQ ID NO:11228), TTTTGGTTTTTATTGGGAGATAGGGGACGTCG (SEQ ID NO:11229), TTTTTGGTTTTTATTGGGAGATAGGGGACGTCG (SEQ ID NO:11230), TTTAGTGGAAGTTAAGGAGGGGTTGCGT (SEQ ID NO:11231), TTTTAGTGGAAGTTAAGGAGGGGTTGCGT (SEQ ID NO:11232), AGTGGAAGTTAAGGAGGGGTTGCGT (SEQ ID NO:11233), TTTTTAGTGGAAGTTAAGGAGGGGTTGCGT (SEQ ID NO:11234), TTTTTTAGTGGAAGTTAAGGAGGGGTTGCGT (SEQ ID NO:11235) |
| Target1193 | chr11:58673138-58673159 | TGGTACGCGGGAATTGGTTGTGGATCG (SEQ ID NO:11236), TTGGTACGCGGGAATTGGTTGTGGATCG (SEQ ID NO:11237), TTGGTACGCGGGAATTGGTTGTGGATC (SEQ ID NO:11238), TTTTGGTACGCGGGAATTGGTTGTGGA (SEQ ID NO:11239), TTTGGTACGCGGGAATTGGTTGTGGATCG (SEQ ID NO:11240), GGTCGAGGGGATTGCGCGTTTATTCGT (SEQ ID NO:11241), AGGTCGAGGGGATTGCGCGTTTATTCG (SEQ ID NO:11242), CGGTTAGGTCGAGGGGATTGCGCGTTT (SEQ ID NO:11243), GGTTAGGTCGAGGGGATTGCGCGTTTA (SEQ ID NO:11244), AGGTCGAGGGGATTGCGCGTTTATTCGT (SEQ ID NO:11245) |
| Target1194 | chr11:58673273-58673280 | GATAAATAGGGAGGGGTGGGCGGGTGGG (SEQ ID NO:11246), GGATAAATAGGGAGGGTGGGCGGGTGG (SEQ ID NO:11247), TGGATAAATAGGGAGGGTGGGCGGGTG (SEQ ID NO:11248), GGTGGGCGCGTAGTTTTTTCGGTTTG (SEQ ID NO:11249), GGGTGGGCGCGTAGTTTTTTCGGTTTG (SEQ ID NO:11250), GGAAAAGGGATGAGAGTGTACGTTTGGGC (SEQ ID NO:11251), AGGAAAAGGGATGAGAGTGTACGTTTGGGC (SEQ ID NO:11252), GAAAAGGGATGAGAGTGTACGTTTGGGC (SEQ ID NO:11253), GAGGAAAAGGGATGAGAGTGTACGTTTGGGC (SEQ ID NO:11254), AGGAAAAGGGATGAGAGTGTACGTTTGGG (SEQ ID NO:11255) |

FIGURE 5 CONTINUED

| | | |
|---|---|---|
| Target1195 | chr11:61537177-61537202 | GGGGAAGGTCGTGGGTGTAGTTTGGGT (SEQ ID NO:11256), TGGGGAAGGTCGTGGGTGTAGTTTGGG (SEQ ID NO:11257), TAAGTGGGTGGTTGGGGAAGGTCGTGG (SEQ ID NO:11258), GTGGTTGGGGAAGGTCGTGGGTGTAGT (SEQ ID NO:11259), GGTGGTTGGGGAAGGTCGTGGGTGTAG (SEQ ID NO:11260), TTCGGATTGCGGGGAGTTTGTTTTCGT (SEQ ID NO:11261), ATTCGGATTGCGGGGAGTTTGTTTTCGT (SEQ ID NO:11262), ATTCGGATTGCGGGGAGTTTGTTTTCG (SEQ ID NO:11263), TCGGATTGCGGGGAGTTTGTTTTCGT (SEQ ID NO:11264), AATTCGGATTGCGGGGAGTTTGTTTTCGT (SEQ ID NO:11265) |
| Target1196 | chr11:62211752-62211919 | TGGGGGGATTTGTTTTATGGGTTGGGA (SEQ ID NO:11266), TTGGGGGGATTTGTTTTATGGGTTGGGA (SEQ ID NO:11267), TGGGGGGATTTGTTTTATGGGTTGGGAT (SEQ ID NO:11268), TTTGGGGGGATTTGTTTTATGGGTTGGG (SEQ ID NO:11269), TTTGGGGGGATTTGTTTTATGGGTTGGGA (SEQ ID NO:11270), GGTCGGGTATTTATAGGGTCGGTGGTGT (SEQ ID NO:11271), GGTCGGGTATTTATAGGGTCGGTGGTG (SEQ ID NO:11272), AGGTCGGGTATTTATAGGGTCGGTGGTGT (SEQ ID NO:11273), TTTTTACGGCGCGGATATTTTGGAGGG (SEQ ID NO:11274), AGGTCGGGTATTTATAGGGTCGGTGGTG (SEQ ID NO:11275) |
| Target1197 | chr11:62211990-62212002 | AGGAGATTAGGTAGGGTTGGTTGATAGCGT (SEQ ID NO:11276), GGAGATTAGGTAGGGTTGGTTGATAGCGTG (SEQ ID NO:11277), GGAGATTAGGTAGGGTTGGTTGATAGCGTGT (SEQ ID NO:11278), AGGAGATTAGGTAGGGTTGGTTGATAGCGTG (SEQ ID NO:11279), AGGAGATTAGGTAGGGTTGGTTGATAGCGTGT (SEQ ID NO:11280), TTTTTACGGCGCGGATATTTTGGAGGG (SEQ ID NO:11281), GCGGATATTTTGGAGGGCGAGTAGTTGT (SEQ ID NO:11282), TTTTTTACGGCGCGGATATTTTGGAGGG (SEQ ID NO:11283), GCGGATATTTTGGAGGGCGAGTAGTTGTC (SEQ ID NO:11284), TTTTACGGCGCGGATATTTTGGAGGG (SEQ ID NO:11285) |
| Target1198 | chr11:62212028-62212034 | AGGAGATTAGGTAGGGTTGGTTGATAGCGT (SEQ ID NO:11286), GGAGATTAGGTAGGGTTGGTTGATAGCGTG (SEQ ID NO:11287), GGAGATTAGGTAGGGTTGGTTGATAGCGTGT (SEQ ID NO:11288), AGGAGATTAGGTAGGGTTGGTTGATAGCGTG (SEQ ID NO:11289), AGGAGATTAGGTAGGGTTGGTTGATAGCGTGT (SEQ ID NO:11290), TGGGAAAGGGGCGTTAGATGTGATTTTGT (SEQ ID NO:11291), TGGGAAAGGGGCGTTAGATGTGATTTTGTT (SEQ ID NO:11292), GGGAAAGGGGCGTTAGATGTGATTTTGTT (SEQ ID NO:11293), ATGGGAAAGGGGCGTTAGATGTGATTTTGT (SEQ ID NO:11294), GGGAAAGGGGCGTTAGATGTGATTTTGTTT (SEQ ID NO:11295) |
| Target1199 | chr11:62212114-62212196 | GGGGAAGCGGGGGTTTCGTTGGTTTT (SEQ ID NO:11296), TGGGGAAGCGGGGGTTTCGTTGGTTTT (SEQ ID NO:11297), GGGGAAGCGGGGGTTTCGTTGGTTTT (SEQ ID NO:11298), GGGGAAGCGGGGGTTTCGTTGGTTTTTT (SEQ ID NO:11299), GTGGGGAAGCGGGGGTTTCGTTGGTTT (SEQ ID NO:11300), GCGTGTTGTGTTTTATGGGAAAGGGGCG (SEQ ID NO:11301), GCGTGTTGTGTTTTATGGGAAAGGGGCGT (SEQ ID NO:11302), TGCGTGTTGTGTTTTATGGGAAAGGGGCG (SEQ ID NO:11303), TGCGTGTTGTGTTTTATGGGAAAGGGGC (SEQ ID NO:11304), GCGTGTTGTGTTTTATGGGAAAGGGGC (SEQ ID NO:11305) |
| Target1200 | chr11:63686935-63686949 | TTTTTTGTCGTTTCGGGGTTGCGGGGC (SEQ ID NO:11306), TTTTTTGTCGTTTCGGGGTTGCGGGGC (SEQ ID NO:11307), AGGATAAGGGGTTTCGGTCGGTTTGGT (SEQ ID NO:11308), TTTTTTGTCGTTTCGGGGTTGCGGGG (SEQ ID NO:11309), TTTTTGTCGTTTCGGGGTTGCGGGGCG (SEQ ID NO:11310), AGTGGAGTTAGGGAAAGGTGGGTGGGA (SEQ ID NO:11311), AAGTGGAGTTAGGGAAAGGTGGGTGGG (SEQ ID NO:11312), AAGTGGAGTTAGGGAAAGGTGGGTGGGA (SEQ ID NO:11313), GTGGAGTTAGGGAAAGGTGGGTGGGAT (SEQ ID NO:11314), AGTGGAGTTAGGGAAAGGTGGGTGGGAT (SEQ ID NO:11315) |
| Target1201 | chr11:63687154-63687161 | AGGGGAGGGAAGGAGAGGTAGTTCGGG (SEQ ID NO:11316), GGGAGGGAAGGAGAGGTAGTTCGGGGA (SEQ ID NO:11317), GTGTGGGAGGGGAGGGAAGGAGAGGTA (SEQ ID NO:11318), AGGGGTTAAGGAAGTTGGGTAGCGCGG (SEQ ID NO:11319), AATATGGGGGTGTGGGAGGGGAGGGAA (SEQ ID NO:11320), AGGTGAGGGTTTCGGGTTTTCGGTCGT (SEQ ID NO:11321), TGGCGGGGAGGGTATTTTCGGGAGTTT (SEQ ID NO:11322), ATGGCGGGGAGGGTATTTTCGGGAGTT (SEQ ID NO:11323), AATGGCGGGGAGGGTATTTTCGGGAGT (SEQ ID NO:11324), TCGGAGGTAGTTCGGGTAGGTGAGGGT (SEQ ID NO:11325) |
| Target1202 | chr11:63687205-63687213 | AGGGGTTAAGGAAGTTGGGTAGCGCGG (SEQ ID NO:11326), GGGGTTAAGGAAGTTGGGTAGCGCGGT (SEQ ID NO:11327), GGGTTAAGGAAGTTGGGTAGCGCGGTC (SEQ ID NO:11328), AAGGGGTTAAGGAAGTTGGGTAGCGCG (SEQ ID NO:11329), AAGGGGTTAAGGAAGTTGGGTAGCGCGG (SEQ ID NO:11330), TGGCGGGGAGGGTATTTTCGGGAGTTT (SEQ ID NO:11331), ATGGCGGGGAGGGTATTTTCGGGAGTT (SEQ ID NO:11332), AATGGCGGGGAGGGTATTTTCGGGAGT (SEQ ID NO:11333), TGGCGGGGAGGGTATTTTCGGGAGTTTT (SEQ ID NO:11334), GGCGGGGAGGGTATTTTCGGGAGTTTT (SEQ ID NO:11335) |

FIGURE 5 CONTINUED

Target1203    chr11:63687238-63687283    AGGGGTTAAGGAAGTTGGGTAGCGCGG (SEQ ID NO:11336), GGGGTTAAGGAAGTTGGGTAGCGCGGT
(SEQ ID NO:11337), GGGTTAAGGAAGTTGGGTAGCGCGGTC (SEQ ID NO:11338),
GCGAGTCGGAGGGTTTTCGGGAATGTT (SEQ ID NO:11339), AAGGGGTTAAGGAAGTTGGGTAGCGCG
(SEQ ID NO:11340), GCGGTTTGCGTTTTGGTTTGTAGTTTTCG (SEQ ID NO:11341),
GCGGTTTGCGTTTTGGTTTGTAGTTTTCGA (SEQ ID NO:11342),
TGTCGTTTTTAGTGGAAGGGTGAGTTCGA (SEQ ID NO:11343),
TCGTTTTTAGTGGAAGGGTGAGTTCGAGT (SEQ ID NO:11344),
CGTTGTCGTTTTTAGTGGAAGGGTGAGTTCG (SEQ ID NO:11345)

Target1204    chr11:63687288-63687319    GCGAGTCGGAGGGTTTTCGGGAATGTT (SEQ ID NO:11346), GCGAGTCGGAGGGTTTTCGGGAATGTTT
(SEQ ID NO:11347), GCGAGTCGGAGGGTTTTCGGGAATGT (SEQ ID NO:11348),
GCGAGTCGGAGGGTTTTCGGGAATGTTTT (SEQ ID NO:11349), CGAGTCGGAGGGTTTTCGGGAATGTTT
(SEQ ID NO:11350), TGGCGGAGGTTTGTGTAGGGGTTGTGT (SEQ ID NO:11351),
TTGGCGGAGGTTTGTGTAGGGGTTGTG (SEQ ID NO:11352), TTGGCGGAGGTTTGTGTAGGGGTTGTGT
(SEQ ID NO:11353), TTTGGCGGAGGTTTGTGTAGGGGTTGT (SEQ ID NO:11354),
TGGCGGAGGTTTGTGTAGGGGTTGTGTA (SEQ ID NO:11355)

Target1205    chr11:70211242-70211649    TGTTTTGGATGTGGTTGGTGTATTGGGGT (SEQ ID NO:11356),
TGTTTTGGATGTGGTTGGTGTATTGGGGTT (SEQ ID NO:11357),
TTGTTTTGGATGTGGTTGGTGTATTGGGGT (SEQ ID NO:11358),
GTTTTGGATGTGGTTGGTGTATTGGGGTT (SEQ ID NO:11359),
TTGTTTTGGATGTGGTTGGTGTATTGGGG (SEQ ID NO:11360), ACGCGTTGGGAGGAGTGTAGGTTGTGG
(SEQ ID NO:11361), GGAGGAGTGTAGGTTGTGGGGCGTGAT (SEQ ID NO:11362),
GTTGGGAGGAGTGTAGGTTGTGGGGCG (SEQ ID NO:11363), CGTTGGGAGGAGTGTAGGTTGTGGGGC
(SEQ ID NO:11364), GCGTTGGGAGGAGTGTAGGTTGTGGGG (SEQ ID NO:11365)

Target1206    chr11:76032999-76033014    GAGGGTTTGGGGGCGCGGTATTGAC (SEQ ID NO:11366), GAGGGTTTGGGGGCGCGGTATTGACG (SEQ
ID NO:11367), CGAGGGTTTGGGGGCGCGGTATTGAC (SEQ ID NO:11368),
GAGGGTTTGGGGGCGCGGTATTGACGG (SEQ ID NO:11369), CGAGGGTTTGGGGGCGCGGTATTGA
(SEQ ID NO:11370), GAGGTTCGGAGGGGGGTAGAAAACGTTT (SEQ ID NO:11371),
AGGTTCGGAGGGGGGTAGAAAACGTTTT (SEQ ID NO:11372), GAGGTTCGGAGGGGGGTAGAAAACGTTTT
(SEQ ID NO:11373), AGGTTCGGAGGGGGGTAGAAAACGTTTTT (SEQ ID NO:11374),
GAGGTTCGGAGGGGGTAGAAAACGTT (SEQ ID NO:11375)

Target1207    chr11:76033028-76033044    CGCGTAGAAAGGTGGGTCGGGGTTAGA (SEQ ID NO:11376), GCGCGTAGAAAGGTGGGTCGGGGTTAG
(SEQ ID NO:11377), CGCGTAGAAAGGTGGGTCGGGGTTAGAA (SEQ ID NO:11378),
GCGCGTAGAAAGGTGGGTCGGGGTTA (SEQ ID NO:11379), GCGTAGAAAGGTGGGTCGGGGTTAGAA
(SEQ ID NO:11380), CGAGTGCGCGGGGTTTTTCGTTCGTC (SEQ ID NO:11381),
CGAGTGCGCGGGGTTTTTCGTTCGT (SEQ ID NO:11382), GAGTGCGCGGGGTTTTTCGTTCGTC (SEQ ID
NO:11383), GAGGTTCGGAGGGGGGTAGAAAACGTTT (SEQ ID NO:11384),
CGAGTGCGCGGGGTTTTTCGTTCG (SEQ ID NO:11385)

Target1208    chr11:76033147-76033172    CGGGAATATTTGTGGGTTGTCGGCGGG (SEQ ID NO:11386), GGGAATATTTGTGGGTTGTCGGCGGGG
(SEQ ID NO:11387), TATTTGTGGGTTGTCGGCGGGGTAGGC (SEQ ID NO:11388),
GGAATATTTGTGGGTTGTCGGCGGGGT (SEQ ID NO:11389), TCGGGAATATTTGTGGGTTGTCGGCGG
(SEQ ID NO:11390), CGAGGTTGGGGGGTTCGGGTCGTTTTTC (SEQ ID NO:11391),
TTTTTCGGTTGCGGACGGGTCGAGGTT (SEQ ID NO:11392), TTTTTTCGGTTGCGGACGGGTCGAGGT
(SEQ ID NO:11393), TTTTTTTCGGTTGCGGACGGGTCGAGG (SEQ ID NO:11394),
TTTTCGGTTGCGGACGGGTCGAGGTTG (SEQ ID NO:11395)

Target1209    chr11:76033181-76033191    GAGGTTGTTCGGCGGGCGGGAAGTTTC (SEQ ID NO:11396), GGGAATATTTGTGGGTTGTCGGCGGGGTA
(SEQ ID NO:11397), GGAATATTTGTGGGTTGTCGGCGGGGTA (SEQ ID NO:11398),
AGGTTGTTCGGCGGGCGGGAAGTTTC (SEQ ID NO:11399), GAGGTTGTTCGGCGGGCGGGAAGTTT (SEQ
ID NO:11400), CGAGGTTGGGGGGTTCGGGTCGTTTTTC (SEQ ID NO:11401),
TTTTTCGGTTGCGGACGGGTCGAGGTT (SEQ ID NO:11402), TTTTTTCGGTTGCGGACGGGTCGAGGT
(SEQ ID NO:11403), TTTTTTTCGGTTGCGGACGGGTCGAGG (SEQ ID NO:11404),
TTTTCGGTTGCGGACGGGTCGAGGTTG (SEQ ID NO:11405)

Target1210    chr11:76033292-76033340    GGACGGAGAAGGGAGGGAGTTTGGGAG (SEQ ID NO:11406),
GGGACGGAGAAGGGAGGGAGTTTGGGA (SEQ ID NO:11407),
GGGAGTTTGGGAGAGACGTAGGTGTGGC (SEQ ID NO:11408), GGGACGGAGAAGGGAGGGAGTTTGGG
(SEQ ID NO:11409), ACGGAGAAGGGAGGGAGTTTGGGAGAG (SEQ ID NO:11410),
AGATTTCGAGGGTGTTACGTTTCGGTTGT (SEQ ID NO:11411),
GAGATTTCGAGGGTGTTACGTTTCGGTTG (SEQ ID NO:11412),
GAGATTTCGAGGGTGTTACGTTTCGGTTGT (SEQ ID NO:11413),
GATTTCGAGGGTGTTACGTTTCGGTTGTT (SEQ ID NO:11414),
AGATTTCGAGGGTGTTACGTTTCGGTTGTT (SEQ ID NO:11415)

Target1211    chr11:76033355-76033373    TAGGTGTGGCGTTCGTTTGTGTTGGCG (SEQ ID NO:11416), CGTTCGTTTGTGTTGGCGGGGTGGTAG
(SEQ ID NO:11417), GGACGGAGAAGGGAGGGAGTTTGGGAG (SEQ ID NO:11418),
GTTCGTTTGTGTTGGCGGGGTGGTAGT (SEQ ID NO:11419), TTCGTTTGTGTTGGCGGGGTGGTAGTC
(SEQ ID NO:11420), TGAAGGACGTTGTGAGTAGCGGGGGTT (SEQ ID NO:11421),
TTGAAGGACGTTGTGAGTAGCGGGGGT (SEQ ID NO:11422), GTTGAAGGACGTTGTGAGTAGCGGGGG

FIGURE 5 CONTINUED

{SEQ ID NO:11423}, TGTTGAAGGACGTTGTGAGTAGCGGGGG {SEQ ID NO:11424},
GTTGAAGGACGTTGTGAGTAGCGGGGGT {SEQ ID NO:11425}

| | | |
|---|---|---|
| Target1212 | chr11:76750769-76750781 | CGCGGGAGGAGAGGTTTTCGTAGGAGG {SEQ ID NO:11426}, TCGCGGGAGGAGAGGTTTTCGTAGGAG {SEQ ID NO:11427}, GGTTTTCGCGGGAGGAGAGGTTTTCGT {SEQ ID NO:11428}, GCGGGAGGAGAGGTTTTCGTAGGAGGA {SEQ ID NO:11429}, TTCGCGGGAGGAGAGGTTTTCGTAGGA {SEQ ID NO:11430}, GGAAGTTTTGGATGCGCGCGGGTAGTT {SEQ ID NO:11431}, ATCGTAGGAAGTTTTGGATGCGCGCGG {SEQ ID NO:11432}, GATGCGCGCGGGTAGTTGTTCGAAGTC {SEQ ID NO:11433}, AGTTTTGGATGCGCGCGGGTAGTTGTT {SEQ ID NO:11434}, AAGTTTTGGATGCGCGCGGGTAGTTGT {SEQ ID NO:11435} |
| Target1213 | chr11:76750805-76751075 | CGCGGGAGGAGAGGTTTTCGTAGGAGG {SEQ ID NO:11436}, TCGCGGGAGGAGAGGTTTTCGTAGGAG {SEQ ID NO:11437}, GGTTTTCGCGGGAGGAGAGGTTTTCGT {SEQ ID NO:11438}, GCGGGAGGAGAGGTTTTCGTAGGAGGA {SEQ ID NO:11439}, TTCGCGGGAGGAGAGGTTTTCGTAGGA {SEQ ID NO:11440}, GGAAGTTTTGGATGCGCGCGGGTAGTT {SEQ ID NO:11441}, ATCGTAGGAAGTTTTGGATGCGCGCGG {SEQ ID NO:11442}, GATGCGCGCGGGTAGTTGTTCGAAGTC {SEQ ID NO:11443}, AGTTTTGGATGCGCGCGGGTAGTTGTT {SEQ ID NO:11444}, AAGTTTTGGATGCGCGCGGGTAGTTGT {SEQ ID NO:11445} |
| Target1214 | chr11:94600469-94600953 | AGGTTTGGGAGTCGGAGGATTTGTTTGA {SEQ ID NO:11446}, TGGGAGTCGGAGGATTTGTTTGAAGGAA {SEQ ID NO:11447}, TTGGGAGTCGGAGGATTTGTTTGAAGGA {SEQ ID NO:11448}, GGTTTTGGAAGGAGGTGGAGGTGATAGT {SEQ ID NO:11449}, TGATAGGTTTTGGAAGGAGGTGGAGGTG {SEQ ID NO:11450}, TTTAGTTGGGGTGGGAGTTAAATGTTTTTGGG {SEQ ID NO:11451}, TGTAGGATGTTTTCGTAGGGAGTGATAGGTTGA {SEQ ID NO:11452}, TTTTAGTTGGGGTGGGAGTTAAATGTTTTTGGG {SEQ ID NO:11453}, GTTTGTAGGATGTTTTCGTAGGGAGTGATAGGT {SEQ ID NO:11454}, TTGTAGGATGTTTTCGTAGGGAGTGATAGGTTG {SEQ ID NO:11455} |
| Target1215 | chr11:125036180-125036207 | AGGTCGGAGTTGGGGGTTGGAGGAAC {SEQ ID NO:11456}, TGGGGAGGGGTAGTACGAGGGGGTTTTGT {SEQ ID NO:11457}, TTGGAGGAACGGGTGGCGTTTTTAGGA {SEQ ID NO:11458}, TGGAGGAACGGGTGGCGTTTTTAGGAT {SEQ ID NO:11459}, GTTGGAGGAACGGGTGGCGTTTTTAGG {SEQ ID NO:11460} |
| Target1216 | chr11:125036311-125036721 | ATTCGGTTTTTGGTGCGTTCGGGGGGAG {SEQ ID NO:11461}, TTTTTGGTGCGTTCGGGGGAGGAGGAA {SEQ ID NO:11462}, CGTTCGGGGGAGGAGGAAGTTTGGAGT {SEQ ID NO:11463}, AGTGGGTCGAGGAGTTTGGGTTGTGGT {SEQ ID NO:11464}, AATTCGGTTTTTGGTGCGTTCGGGGGA {SEQ ID NO:11465}, TTGTGGGTTTTTTAGTTCGGCGCGGGT {SEQ ID NO:11466}, TGTGGGTTTTTTAGTTCGGCGCGGGTA {SEQ ID NO:11467}, TTTGTGGGTTTTTTAGTTCGGCGCGGGT {SEQ ID NO:11468}, TTTGTGGGTTTTTTAGTTCGGCGCGGG {SEQ ID NO:11469}, TGTGGGTTTTTTAGTTCGGCGCGGGT {SEQ ID NO:11470} |
| Target1217 | chr11:128168780-128169479 | TGATGGGTGGGAAAAGATCGGTGAAGT {SEQ ID NO:11471}, TGGTTATTGGGGAATGGTTGGTTAGCGT {SEQ ID NO:11472}, TGAGAGAAGGGTAGGGAGGTGTTTACGT {SEQ ID NO:11473}, TTGATGGGTGGGAAAAGATCGGTGAAGT {SEQ ID NO:11474}, ATGGTTATTGGGGAATGGTTGGTTAGCGT {SEQ ID NO:11475}, TGGAGGTTGGGTTAAGAAGGTAGAGAAGAGT {SEQ ID NO:11476}, GGGATTGGATTATGATGTTGTTTGGAACGTGG {SEQ ID NO:11477}, ATGGAGGTTGGGTTAAGAAGGTAGAGAAGAGT {SEQ ID NO:11478}, AGGGATTGGATTATGATGTTGTTTGGAACGTGG {SEQ ID NO:11479}, GGGATTGGATTATGATGTTGTTTGGAACGTGGA {SEQ ID NO:11480} |
| Target1218 | chr11:129242486-129242689 | GTGGTCGAGTGGAAGCGGAGAGGAGTG {SEQ ID NO:11481}, GAGTGGAAGCGGAGAGGAGTGAGAGCG {SEQ ID NO:11482}, CGAGTGGAAGCGGAGAGGAGTGAGAGC {SEQ ID NO:11483}, GTGGAAGCGGAGAGGAGTGAGAGCGTT {SEQ ID NO:11484}, TGGAAGCGGAGAGGAGTGAGAGCGTTG {SEQ ID NO:11485}, CGGTTTCGTTTTGGTTGGTCGCGTCGT {SEQ ID NO:11486}, TGGTCGCGGTGTTGTTTTTCGGAAGGT {SEQ ID NO:11487}, GGTTTCGTTTTGGTTGGTCGCGTCGTT {SEQ ID NO:11488}, TGGTCGCGGTGTTGTTTTTCGGAAGGTT {SEQ ID NO:11489}, TTGGTCGCGGTGTTGTTTTTCGGAAGGT {SEQ ID NO:11490} |
| Target1219 | chr11:129242959-129243195 | GGAGTTAGTGGCGGTGGAAGGAAGGGG {SEQ ID NO:11491}, GGCGTTGCGGGTGAGATCGTTCGTAAG {SEQ ID NO:11492}, GGGCGTCGGGTTTTGGTGTTGTCGTTT {SEQ ID NO:11493}, AGTGGCGGTGGAAGGAAGGGGAAGAAT {SEQ ID NO:11494}, AGGAGTTAGTGGCGGTGGAAGGAAGGG {SEQ ID NO:11495}, TAATGTCGGGCGGGGAGTTTTAGGCGT {SEQ ID NO:11496}, GTCGAGTCGGGGTTGGGTTTTAGGGGT {SEQ ID NO:11497}, GTTACGACGGAGGGGGTTTTTTCGGGC {SEQ ID NO:11498}, CGGGGTAATGTCGGGCGGGGAGTTTTA {SEQ ID NO:11499}, ACGAGGCGGGTTTGGAGTTGGGGATTA {SEQ ID NO:11500} |
| Target1220 | chr11:129243209-129243493 | AGTAGGGGGCGCGTTTGGGGTTAGTTT {SEQ ID NO:11501}, AAGTAGGGGGCGCGTTTGGGGTTAGTT {SEQ ID NO:11502}, GGGGGCGCGTTTGGGGTTAGTTTAG {SEQ ID NO:11503}, GTAGGGGGCGCGTTTGGGGTTAGTTTG {SEQ ID NO:11504}, GGCGTTGCGGGTGAGATCGTTCGTAAG {SEQ ID NO:11505}, TTCGCGGCGGGATTTTGAGGTTGGTTC {SEQ ID NO:11506}, CGGGGGTTTTGTCGTCGGATTTTGGGG {SEQ ID NO:11507}, GTCGAGTCGGGGTTGGGTTTTAGGGGT |

FIGURE 5 CONTINUED (SEQ ID NO:11508), GTTACGACGGAGGGGGTTTTTCGGGC (SEQ ID NO:11509), TTTCGCGGCGGGATTTTGAGGTTGGTT (SEQ ID NO:11510)

Target1221    chr11:133994800-133994973    GGGGATCGGGTATTGAAGTTCGGCGGT (SEQ ID NO:11511), GGATCGGGTATTGAAGTTCGGCGGTGG (SEQ ID NO:11512), GGGATCGGGTATTGAAGTTCGGCGGTG (SEQ ID NO:11513), CGGGTATTGAAGTTCGGCGGTGGTAGG (SEQ ID NO:11514), CGGGTATTGAAGTTCGGCGGTGGTAGGA (SEQ ID NO:11515), GGCGGTCGTGTATTTCGGGAGGCGATA (SEQ ID NO:11516), TTCGGGAGCGGTTGGAGTAGTAGTGGC (SEQ ID NO:11517), GGCGGTCGTGTATTTCGGGAGGCGATAT (SEQ ID NO:11518), GTTCGGGAGCGGTTGGAGTAGTAGTGGC (SEQ ID NO:11519), TCGGGAGCGGTTGGAGTAGTAGTGGCG (SEQ ID NO:11520)

Target1222    chr11:133994988-133995005    AGTCGTCGTTGTTTTGTGGTGTCGTTT (SEQ ID NO:11521), TGTAGTCGTCGTTGTTTTGTGGTGTCGT (SEQ ID NO:11522), GTAGTCGTCGTTGTTTTGTGGTGTCGT (SEQ ID NO:11523), TGTAGTCGTCGTTGTTTTGTGGTGTCG (SEQ ID NO:11524), AGTCGTCGTTGTTTTGTGGTGTCGTTTT (SEQ ID NO:11525), AGAGAGAGAAGAGGGGGCGGGAGTTGT (SEQ ID NO:11526), TGAGAGAGAAGAGGGGGCGGGAGTT (SEQ ID NO:11527), TTCGGGAGCGGTTGGAGTAGTAGTGGC (SEQ ID NO:11528), GAGGGGGCGGGAGTTGTTTTTGGTTGT (SEQ ID NO:11529), AGAGGGGGCGGGAGTTGTTTTTGGTTG (SEQ ID NO:11530)

Target1223    chr11:133995029-133995090    TGTTTTTGTAGTCGTCGTTGTTTTGTGGTGT (SEQ ID NO:11531), TGTTTTTGTAGTCGTCGTTGTTTTGTGGTGTC (SEQ ID NO:11532), TTGTTTTTGTAGTCGTCGTTGTTTTGTGGTGT (SEQ ID NO:11533), TGTTGTTTTTGTAGTCGTCGTTGTTTTGTGGT (SEQ ID NO:11534), GATATTCGTTCGGTGGCGGCGG (SEQ ID NO:11535), AGAGAGAGAAGAGGGGGCGGGAGTTGT (SEQ ID NO:11536), TGAGAGAGAAGAGGGGGCGGGAGTT (SEQ ID NO:11537), TTGAGAGAGAGAAGAGGGGGCGGGAGT (SEQ ID NO:11538), AGTTGAGAGAGAGAAGAGGGGGCGGGA (SEQ ID NO:11539), GAGGGGGCGGGAGTTGTTTTTGGTTGT (SEQ ID NO:11540)

Target1224    chr12:2282206-2282237    AGAGTTGGTGAGGAGTTGGGAGGGGGA (SEQ ID NO:11541), GAGTTGGTGAGGAGTTGGGAGGGGGAT (SEQ ID NO:11542), AGAGTTGGTGAGGAGTTGGGAGGGGGAT (SEQ ID NO:11543), AGTTGGTGAGGAGTTGGGAGGGGGATT (SEQ ID NO:11544), TAGAGTTGGTGAGGAGTTGGGAGGGGG (SEQ ID NO:11545), GGGTAGTGAAGTGGATTTGGGTTAGGGT (SEQ ID NO:11546), AGGGTAGTGAAGTGGATTTGGGTTAGGGT (SEQ ID NO:11547), GGGTAGTGAAGTGGATTTGGGTTAGGGTT (SEQ ID NO:11548), AGGGTAGTGAAGTGGATTTGGGTTAGGGTT (SEQ ID NO:11549), TAGGGTAGTGAAGTGGATTTGGGTTAGGGT (SEQ ID NO:11550)

Target1225    chr12:6184230-6184282    TGAGGGAAGTTAGGGGGCGTTAGGGGA (SEQ ID NO:11551), GAGGGAAGTTAGGGGGCGTTAGGGGAG (SEQ ID NO:11552), AGGGAAGTTAGGGGGCGTTAGGGGAGG (SEQ ID NO:11553), TTGAGGGAAGTTAGGGGGCGTTAGGGG (SEQ ID NO:11554), TTGAGGGAAGTTAGGGGGCGTTAGGGGA (SEQ ID NO:11555)

Target1226    chr12:6184402-6184468    TTGGTTGGTTGGGTGTGGTAAAGTCGT (SEQ ID NO:11556), TGGTTGGTTGGGTGTGGTAAAGTCGTA (SEQ ID NO:11557), ATTGGTTGGTTGGGTGTGGTAAAGTCGT (SEQ ID NO:11558), TGGTTGGTTGGGTGTGGTAAAGTCGT (SEQ ID NO:11559), TTGGTTGGTTGGGTGTGGTAAAGTCGTA (SEQ ID NO:11560), AGGAGGGAATGGTGTTGTACGGTTGGA (SEQ ID NO:11561), GGGTGGTGTTTTTTAGGGTGTTTCGGGGT (SEQ ID NO:11562), TGGGTGGTGTTTTTTAGGGTGTTTCGGGG (SEQ ID NO:11563), GGGTGGTGTTTTTTTAGGGTGTTTCGGGG (SEQ ID NO:11564), AGGGAATGGTGTTGTACGGTTGGATCG (SEQ ID NO:11565)

Target1227    chr12:6184505-6184562    TTTCGGTAGGGTAGGACGGGGTAGGGG (SEQ ID NO:11566), GGGTAGGGACGGGGTAGGGGGTCGATTT (SEQ ID NO:11567), TAGGGTAGGACGGGGTAGGGGGTCGAT (SEQ ID NO:11568), TTCGGTAGGGTAGGACGGGGTAGGGG (SEQ ID NO:11569), GGGTAGGGACGGGGTAGGGGGTCGATTTA (SEQ ID NO:11570), GTGTTGGGGGGGTTGGAGTGCGTTTGTT (SEQ ID NO:11571), TGTGTGAGTGTGTTGGGGGGGTTGGAGT (SEQ ID NO:11572), GTGTGTTGGGGGGGTTGGAGTGCGTTTG (SEQ ID NO:11573), TGGGGGGGTTGGAGTGCGTTTGTTTTGT (SEQ ID NO:11574), TGTTGGGGGGTTGGAGTGCGTTTGTT (SEQ ID NO:11575)

Target1228    chr12:6184734-6184753    CGGGGGTTTATTAGAGGGTGGTAGCGGG (SEQ ID NO:11576), CGGGGGTTTATTAGAGGGTGGTAGCGGG (SEQ ID NO:11577), TCGGGGGTTTATTAGAGGGTGGTAGCGGG (SEQ ID NO:11578), TCGGGGGTTTATTAGAGGGTGGTAGCGGGT (SEQ ID NO:11579), GGGGTTTATTAGAGGGTGGTAGCGGGT (SEQ ID NO:11580), TGGTGTTAGTTTGTTTTAGGTGTTGAGGGAGT (SEQ ID NO:11581), TGGTGTTAGTTTGTTTTAGGTGTTGAGGGAGTT (SEQ ID NO:11582), TTGGTGTTAGTTTGTTTTAGGTGTTGAGGGAGT (SEQ ID NO:11583), GTTTGTTTTAGGTGTTGAGGGAGTTGTTTTGGT (SEQ ID NO:11584), AGTTTGTTTTAGGTGTTGAGGGAGTTGTTTTGG (SEQ ID NO:11585)

Target1229    chr12:6664109-6665508    AGATGGTGTCGGGTATGAAGCGGGTCG (SEQ ID NO:11586), GATGGTGTCGGGTATGAAGCGGGTCGA (SEQ ID NO:11587), ATAGCCGGTCGGTCGGGCGTTTAGTTGT (SEQ ID NO:11588), TTGTAGATAGCGGTCGGTCGGCGTT (SEQ ID NO:11589), GGGGCGGGTCGAGGGGAAGTTAATGAT (SEQ ID NO:11590), TGTCGTGGGTGTATTCGGATGGGGTGG (SEQ ID NO:11591), GGTCGCGAGTTGGTGTGGGTTTCGAAG (SEQ ID NO:11592), GGGCGTTCGGTCGGTCGTTGTTTGTAG (SEQ ID NO:11593), TCGGGGGAGGAGATTTGTTTTCGGCGT (SEQ ID NO:11594), GAGGGTAAGTAGGGTCGGCGGGGTTTG (SEQ ID NO:11595)

FIGURE 5 CONTINUED

Target1230    chr12:6665529-6665547    TCGTTTGGATTTTAGTCGGGGTGGCGT (SEQ ID NO:11596), CGTTTGGATTTTAGTCGGGGTGGCGTA (SEQ ID NO:11597), TCGTTTGGATTTTAGTCGGGGTGGCGTA (SEQ ID NO:11598), CGTTTGGATTTTAGTCGGGGTGGCGT (SEQ ID NO:11599), TCGTTTGGATTTTAGTCGGGGTGGCG (SEQ ID NO:11600), CGGGTGTGGTGGCGGGTGTTTGTAATT (SEQ ID NO:11601), ATTAGTCGGGTGTGGTGGCGGGTGTTT (SEQ ID NO:11602), AATTAGTCGGGTGTGGTGGCGGGTGTT (SEQ ID NO:11603), TCGGGTGTGGTGGCGGGTGTTTGTAAT (SEQ ID NO:11604), TTAGTCGGGTGTGGTGGCGGGTGTTTG (SEQ ID NO:11605)

Target1231    chr12:6756182-6756196    TGGGTTGCGGTAGGTGTTAGAGGTAGG (SEQ ID NO:11606), TGGGTTGCGGTAGGTGTTAGAGGTAGGA (SEQ ID NO:11607), GGGTTGCGGTAGGTGTTAGAGGTAGGA (SEQ ID NO:11608), AGTCGAATTTTGGGTTGCGGTAGGTGT (SEQ ID NO:11609), AGAGAGAGGGTTGTTTGGAGTGGAGGT (SEQ ID NO:11610), CGGAGCGGGTTTTGGGGTTCGGTTTTT (SEQ ID NO:11611), TTGGTTTCGGAGCGGGTTTTGGGGTTC (SEQ ID NO:11612), TTTGGTTTCGGAGCGGGTTTTGGGGTT (SEQ ID NO:11613), TTTTGGTTTCGGAGCGGGTTTTGGGGT (SEQ ID NO:11614), GTTTTGGTTTCGGAGCGGGTTTTGGGG (SEQ ID NO:11615)

Target1232    chr12:6756211-6756231    CGGGCGAACGGATGATGGAAGGATCGA (SEQ ID NO:11616), AGCGGGCGAACGGATGATGGAAGGATC (SEQ ID NO:11617), GAGCGGGCGAACGGATGATGGAAGGAT (SEQ ID NO:11618), AGCGGGCGAACGGATGATGGAAGGAT (SEQ ID NO:11619), GCGGGCGAACGGATGATGGAAGGATCG (SEQ ID NO:11620), TTGGTTTCGGAGCGGGTTTTGGGGTTT (SEQ ID NO:11621), TTTGGTTTCGGAGCGGGTTTTGGGGTT (SEQ ID NO:11622), TTTTGGTTTCGGAGCGGGTTTTGGGGT (SEQ ID NO:11623), GTTTTGGTTTCGGAGCGGGTTTTGGGG (SEQ ID NO:11624), TGTTTTGGTTTCGGAGCGGGTTTTGGGG (SEQ ID NO:11625)

Target1233    chr12:6756300-6756378    CGGGCGAACGGATGATGGAAGGATCGA (SEQ ID NO:11626), AGCGGGCGAACGGATGATGGAAGGATC (SEQ ID NO:11627), GAGCGGGCGAACGGATGATGGAAGGAT (SEQ ID NO:11628), CGGGCGGGGGGAGATGGGAGTATTTTA (SEQ ID NO:11629), CGGGCGGGGGGAGATGGGAGTATTTT (SEQ ID NO:11630), ATGGTGGTCGCGTTGGGTCGGTTTTTT (SEQ ID NO:11631), TGGTGGTCGCGTTGGGTCGGTTTTTTA (SEQ ID NO:11632), TATGGTGGTCGCGTTGGGTCGGTTTTT (SEQ ID NO:11633), TTATGGTGGTCGCGTTGGGTCGGTTTT (SEQ ID NO:11634), TTTATGGTGGTCGCGTTGGGTCGGTTT (SEQ ID NO:11635)

Target1234    chr12:6756385-6756679    CGGGCGGGGGGAGATGGGAGTATTTTA (SEQ ID NO:11636), TCGGGAGGGAGAGGATTAGTTCGGGGA (SEQ ID NO:11637), CGGGAGGGAGAGGATTAGTTCGGGGAG (SEQ ID NO:11638), CGGGCGGGGGGAGATGGGAGTATTTT (SEQ ID NO:11639), GATAGAGGTAAAGGTTCGGTCGCGGGC (SEQ ID NO:11640), TGCGGTTTGGTTCGTTAGAGGCGGTTT (SEQ ID NO:11641), TTGCGGTTTGGTTCGTTAGAGGCGGTT (SEQ ID NO:11642), TTTGCGGTTTGGTTCGTTAGAGGCGGT (SEQ ID NO:11643), GCGGTTTGGTTCGTTAGAGGCGGTTTG (SEQ ID NO:11644), GCGGTTTGGTTCGTTAGAGGCGGTTTGT (SEQ ID NO:11645)

Target1235    chr12:7072338-7072466    GCGGAGAAGGAAGGAGGAAGAGCGGAG (SEQ ID NO:11646), AGTTTGCGTTGGTTGTTCGGTAGGCGG (SEQ ID NO:11647), CGGAGGTTAGGGCGGGGTTTTAGGTCGT (SEQ ID NO:11648), GTTTGCGTTGGTTGTTCGGTAGGCGGA (SEQ ID NO:11649), TTGGCGTTGGGAGGGAAGGGGTTAAGG (SEQ ID NO:11650), GAGAGTGGGTGTTGGGGAGACGAAGGG (SEQ ID NO:11651), TGGGTGTTGGGGAGACGAAGGGGTTTT (SEQ ID NO:11652), GTGGGTGTTGGGGAGACGAAGGGGTTT (SEQ ID NO:11653), AGAGAGTGGGTGTTGGGGAGACGAAGG (SEQ ID NO:11654), AGTGGGTGTTGGGGAGACGAAGGGGTT (SEQ ID NO:11655)

Target1236    chr12:7072582-7072643    GGAAAGGTTGTCGGGGGTAGGGGAAGG (SEQ ID NO:11656), GGGAAAGGTTGTCGGGGGTAGGGGAAG (SEQ ID NO:11657), GTTGTCGGGGGTAGGGGAAGGTGGTTT (SEQ ID NO:11658), TGGGGGTAGGTGGGTTCGGTGATAGGT (SEQ ID NO:11659), GGGGGGATGAGGGTGGGTAAATCGGTG (SEQ ID NO:11660), TGGGGATATTTTTTGGTGAGTTTTGTTGTTCGT (SEQ ID NO:11661), TGGGGATATTTTTTGGTGAGTTTTGTTGTTCGTT (SEQ ID NO:11662), TTGGGGATATTTTTTGGTGAGTTTTGTTGTTCGT (SEQ ID NO:11663), TTGGGGATATTTTTTGGTGAGTTTTGTTGTTCGTT (SEQ ID NO:11664), TTTGGGGATATTTTTTGGTGAGTTTTGTTGTTCGT (SEQ ID NO:11665)

Target1237    chr12:7072705-7072848    GGAAAGGTTGTCGGGGGTAGGGGAAGG (SEQ ID NO:11666), GGGAAAGGTTGTCGGGGGTAGGGGAAG (SEQ ID NO:11667), GTTGTCGGGGGTAGGGGAAGGTGGTTT (SEQ ID NO:11668), GTGTGGTTGGTGGCGGGTAGTAGGGTT (SEQ ID NO:11669), GGGTAGGGGAAGGTGGTTTAGAGGCGG (SEQ ID NO:11670), TGGGGATTTGAGGCGATGGATGTTGTT (SEQ ID NO:11671), TTGGGGATTTGAGGCGATGGATGTTGT (SEQ ID NO:11672), TGGGGATTTGAGGCGATGGATGTTGTTG (SEQ ID NO:11673), GGGGATTTGAGGCGATGGATGTTGTTG (SEQ ID NO:11674), TGGGGATTTGAGGCGATGGATGTTGTTGA (SEQ ID NO:11675)

Target1238    chr12:25055421-25055858    AGGGATGCGGGGAAGGGAAGACGTTTC (SEQ ID NO:11676), GTAGGGATGCGGGGAAGGGAAGACGTT (SEQ ID NO:11677), TCGTTGGAGGCGGAATGGAGGGTAAGG (SEQ ID NO:11678), AGATTTCGGGTAGGGATGCGGGGAAGG (SEQ ID NO:11679), GATTTCGGGTAGGGATGCGGGGAAGGG (SEQ ID NO:11680), GGATTCGTTTTGAGGGAGGAGGCGGGA (SEQ ID NO:11681), GTTTCGGTAGTTCGCGGGTTTGGTCGG (SEQ ID NO:11682), GGTTTCGGTAGTTCGCGGGTTTGGTCG (SEQ ID NO:11683), CGTTTTGAGGGAGGAGGCGGGAGTTGA (SEQ ID NO:11684), TCGTTTTGAGGGAGGAGGCGGGAGTTG (SEQ ID NO:11685)

FIGURE 5 CONTINUED

| | | |
|---|---|---|
| Target1239 | chr12:25055863-25055874 | TCGTTGGAGGCGGAATGGAGGGTAAGG (SEQ ID NO:11686), GCGGAATGGAGGGTAAGGCGAAGGAGG (SEQ ID NO:11687), GGCGGAATGGAGGGTAAGGCGAAGGAG (SEQ ID NO:11688), GAGGCGGAATGGAGGGTAAGGCGAAGG (SEQ ID NO:11689), GGAGGCGGAATGGAGGGTAAGGCGAAG (SEQ ID NO:11690), TGGTTAGTTCGTTTCGTTTCGTTGCGGT (SEQ ID NO:11691), GGTTAGTTCGTTTCGTTTCGTTGCGGT (SEQ ID NO:11692), TGGTTAGTTCGTTTCGTTTCGTTGCGG (SEQ ID NO:11693), CGTTTGTTTTCGTTTTTAGTCGCGCGT (SEQ ID NO:11694), TCGTTTGTTTTCGTTTTTAGTCGCGCGT (SEQ ID NO:11695) |
| Target1240 | chr12:25055885-25056352 | ATTTGGCGGGTAAGGGTCGTAGCGGAG (SEQ ID NO:11696), GATTTGGGGTCGCGCGTTAGGGTTAGG (SEQ ID NO:11697), TATTTGGCGGGTAAGGGTCGTAGCGGA (SEQ ID NO:11698), TCGAGGTATTTGGCGGGTAAGGGTCGT (SEQ ID NO:11699), GCGGGGTTGTAGAGAGCGGTAGTGGTA (SEQ ID NO:11700), CGTTTGGTTTTGGCGCGCGGTTTTAGG (SEQ ID NO:11701), AAGGGATGTTGGAGGGGTTGCGTCGTA (SEQ ID NO:11702), TAAGGGATGTTGGAGGGGTTGCGTCGT (SEQ ID NO:11703), AGGGATGTTGGAGGGGTTGCGTCGTAT (SEQ ID NO:11704), GTTTGGTTTTGGCGCGCGGTTTTAGGT (SEQ ID NO:11705) |
| Target1241 | chr12:25056390-25056447 | TTTGTTTTCGAGAGTTTGCGGGCGGGG (SEQ ID NO:11706), TTGCGGGCGGGGATTGATATTTGTGCG (SEQ ID NO:11707), GTTTTCGAGAGTTTGCGGGCGGGGATT (SEQ ID NO:11708), GCGGGCGGGGATTGATATTTGTGCGTT (SEQ ID NO:11709), TTTTCGAGAGTTTGCGGGCGGGGATTG (SEQ ID NO:11710), TCGGTTTGGGTAGGTGGCGTAGGGAAA (SEQ ID NO:11711), TTCGGTTTGGGTAGGTGGCGTAGGGAA (SEQ ID NO:11712), ATTCGGTTTGGGTAGGTGGCGTAGGGA (SEQ ID NO:11713), CGGTTTGGGTAGGTGGCGTAGGGAAAT (SEQ ID NO:11714), AATTCGGTTTGGGTAGGTGGCGTAGGG (SEQ ID NO:11715) |
| Target1242 | chr12:33592228-33592320 | AGGAAGGAGCGAGGTAGGAAAGCGTGG (SEQ ID NO:11716), GGAGTTTGTAGTTTAGCGCGCGGGGTT (SEQ ID NO:11717), TTCGGAGTTTGTAGTTTAGCGCGCGGG (SEQ ID NO:11718), GGAAGGAGCGAGGTAGGAAAGCGTGGC (SEQ ID NO:11719), TCGGAGTTTGTAGTTTAGCGCGCGGGG (SEQ ID NO:11720), CGCGCGTTAGGTTGTAAGTTTCGGGGT (SEQ ID NO:11721), TCGCGCGTTAGGTTGTAAGTTTCGGGG (SEQ ID NO:11722), CGGGATAGGGGTAGTTAGGGCGGAAGT (SEQ ID NO:11723), TCGCGCGTTAGGTTGTAAGTTTCGGGGT (SEQ ID NO:11724), CGCGCGTTAGGTTGTAAGTTTCGGGGTT (SEQ ID NO:11725) |
| Target1243 | chr12:33592379-33592401 | TGTTTTCGTTTTGGTTGTTTTTGTTTCGAGGGA (SEQ ID NO:11726), GTTTTCGTTTTGGTTGTTTTTGTTTCGAGGGA (SEQ ID NO:11727), TGTTTTCGTTTTGGTTGTTTTTGTTTCGAGGGA (SEQ ID NO:11728), GCGGAGTTTTTTCGGTTATTTGTGTTGTTTTCG (SEQ ID NO:11729), GCGGAGTTTTTTCGGTTATTTGTGTTGTTTTCGT (SEQ ID NO:11730), AGAGGTACGGGAAGAGGAAAAGACGGT (SEQ ID NO:11731), GAGGTACGGGAAGAGGAAAAGACGGTT (SEQ ID NO:11732), AGAGGTACGGGAAGAGGAAAAGACGGTT (SEQ ID NO:11733), TAGAGGTACGGGAAGAGGAAAAGACGGT (SEQ ID NO:11734), ACGGGAAGAGGAAAAGACGGTTAATTGGG (SEQ ID NO:11735) |
| Target1244 | chr12:33592516-33592595 | GCGGTGATTTTGGTTGGAGATTGCGTCG (SEQ ID NO:11736), GCGGTGATTTTGGTTGGAGATTGCGTCGT (SEQ ID NO:11737), TGGTTGGAGATTGCGTCGTTGAGAGTCG (SEQ ID NO:11738), GGTTGGAGATTGCGTCGTTGAGAGTCG (SEQ ID NO:11739), GCGGTGATTTTGGTTGGAGATTGCGTC (SEQ ID NO:11740), GCGGGCGGATTATGGTTTAGGGCGTTA (SEQ ID NO:11741), GCGGGCGGATTATGGTTTAGGGCGTT (SEQ ID NO:11742), GCGGGCGGATTATGGTTTAGGGCGTTAG (SEQ ID NO:11743), GCGGGCGGATTATGGTTTAGGGCGTTAGA (SEQ ID NO:11744), CGGGCGGATTATGGTTTAGGGCGTTAG (SEQ ID NO:11745) |
| Target1245 | chr12:33592629-33592675 | GGTTGGAGATTGCGTCGTTGAGAGTCGG (SEQ ID NO:11746), TTGGAGATTGCGTCGTTGAGAGTCGGT (SEQ ID NO:11747), GCGGTGATTTTGGTTGGAGATTGCGTCG (SEQ ID NO:11748), GCGGTGATTTTGGTTGGAGATTGCGTCGT (SEQ ID NO:11749), GTTGGAGATTGCGTCGTTGAGAGTCGGT (SEQ ID NO:11750), CGGTAGTCGTAGTTTTTTCGCGCGTTT (SEQ ID NO:11751), CGGTAGTCGTAGTTTTTTCGCGCGTTTT (SEQ ID NO:11752), CGGTAGTCGTAGTTTTTTCGCGCGTT (SEQ ID NO:11753), CGGTAGTCGTAGTTTTTTCGCGCGTTTTT (SEQ ID NO:11754), GGCGGGAGAGTTGGCGTAAATTTCG (SEQ ID NO:11755) |
| Target1246 | chr12:33592683-33592728 | GGTTGGAGATTGCGTCGTTGAGAGTCGG (SEQ ID NO:11756), TTGGAGATTGCGTCGTTGAGAGTCGGT (SEQ ID NO:11757), GTTGGAGATTGCGTCGTTGAGAGTCGGT (SEQ ID NO:11758), TGGTTGGAGATTGCGTCGTTGAGAGTCG (SEQ ID NO:11759), TGGTTGGAGATTGCGTCGTTGAGAGTCGG (SEQ ID NO:11760), TATTAGTGCGTTGGGGGAGAGGAGGGGG (SEQ ID NO:11761), ATTAGTGCGTTGGGGGAGAGGAGGGGGG (SEQ ID NO:11762), GCGTGTTTGCGAGTCGAGGGTTTGTTT (SEQ ID NO:11763), TATTAGTGCGTTGGGGGAGAGGAGGGGGG (SEQ ID NO:11764), ATTAGTGCGTTGGGGGAGAGGAGGGGGG (SEQ ID NO:11765) |
| Target1247 | chr12:33592774-33592804 | AGTGTTGAGGGGAGGGGGGAGTCGTAA (SEQ ID NO:11766), GAGTGTTGAGGGGAGGGGGGAGTCGTA (SEQ ID NO:11767), TATGGAGTGTTGAGGGGAGGGGGGAGT (SEQ ID NO:11768), GGTATGGAGTGTTGAGGGGAGGGGGGA (SEQ ID NO:11769), TCGGTATGGAGTGTTGAGGGGAGGGGG (SEQ ID NO:11770), TATTAGTGCGTTGGGGAGAGGAGGGGGG (SEQ ID NO:11771), ATTAGTGCGTTGGGGAGAGGAGGGGGG (SEQ ID NO:11772), GCGTGTTTGCGAGTCGAGGGTTTGTTT (SEQ ID NO:11773), TATTAGTGCGTTGGGGAGAGGAGGGGGG (SEQ ID NO:11774), ATTAGTGCGTTGGGGAGAGGAGGGGG (SEQ ID NO:11775) |

FIGURE 5 CONTINUED

Target1248　　chr12:33592831-33592892　　AGTGTTGAGGGGAGGGGGGAGTCGTAA (SEQ ID NO:11776), GAGTGTTGAGGGGAGGGGGGAGTCGTA (SEQ ID NO:11777), TATGGAGTGTTGAGGGGAGGGGGGAGT (SEQ ID NO:11778), GGTATGGAGTGTTGAGGGGAGGGGGGA (SEQ ID NO:11779), ATTGGTGTTTTTGGCGGGTGTTTGGCG (SEQ ID NO:11780), GTAGGGGCGTCGGGTCGTTCGTTTTT (SEQ ID NO:11781), GGTAGGGGCGTCGGGTCGTTCGTTTTT (SEQ ID NO:11782), GTAGGGGCGTCGGGTCGTTCGTTTTTT (SEQ ID NO:11783), GGTAGGGGCGTCGGGTCGTTCGTTTT (SEQ ID NO:11784), GGTAGGGGCGTCGGGTCGTTCGTTTTTT (SEQ ID NO:11785)

Target1249　　chr12:33592905-33592916　　ATTGGTGTTTTTGGCGGGTGTTTGGCG (SEQ ID NO:11786), TTGGTGTTTTTGGCGGGTGTTTGGCGG (SEQ ID NO:11787), TTGGTGTTTTTGGCGGGTGTTTGGCG (SEQ ID NO:11788), AGCGTATTGGTGTTTTTGGCGGGTGTT (SEQ ID NO:11789), ATTGGTGTTTTTGGCGGGTGTTTGGCGG (SEQ ID NO:11790), GTAGGGGCGTCGGGTCGTTCGTTTTTT (SEQ ID NO:11791), GGTAGGGGCGTCGGGTCGTTCGTTTTT (SEQ ID NO:11792), GTAGGGGCGTCGGGTCGTTCGTTTTTT (SEQ ID NO:11793), GGTAGGGGCGTCGGGTCGTTCGTTTT (SEQ ID NO:11794), GGTAGGGGCGTCGGGTCGTTCGTTTTTT (SEQ ID NO:11795)

Target1250　　chr12:43945543-43945566　　CGGTTGATTGGTTCGGGAGTTTCGGGA (SEQ ID NO:11796), TCGGTTGATTGGTTCGGGAGTTTCGGG (SEQ ID NO:11797), TCGGTTGATTGGTTCGGGAGTTTCGGGA (SEQ ID NO:11798), TTTTGGGAGTGCGATGCGTTTTAGGCG (SEQ ID NO:11799), TGTGGTTTTGGGAGTGCGATGCGTTTT (SEQ ID NO:11800), ACGTTTTTAGCGGTTAAGTGGGGGCGC (SEQ ID NO:11801), TCGAGTGGGATATGTAGGTCGCGGGGA (SEQ ID NO:11802), GTTTTTAGCGGTTAAGTGGGGGCGCGG (SEQ ID NO:11803), TTCGAGTGGGATATGTAGGTCGCGGGG (SEQ ID NO:11804), CGTTTTTAGCGGTTAAGTGGGGGCGCG (SEQ ID NO:11805)

Target1251　　chr12:43945592-43945623　　CGGTTGATTGGTTCGGGAGTTTCGGGA (SEQ ID NO:11806), TCGGTTGATTGGTTCGGGAGTTTCGGG (SEQ ID NO:11807), TCGGTTGATTGGTTCGGGAGTTTCGGGA (SEQ ID NO:11808), CGGTTGATTGGTTCGGGAGTTTCGGGAG (SEQ ID NO:11809), TTCGGTTGATTGGTTCGGGAGTTTCGGG (SEQ ID NO:11810), GCGAGACGTTTTTAGCGGTTAAGTGGGGG (SEQ ID NO:11811), GCGAGACGTTTTTAGCGGTTAAGTGGG (SEQ ID NO:11812), CGAGACGTTTTTAGCGGTTAAGTGGGGG (SEQ ID NO:11813), CGAGACGTTTTTAGCGGTTAAGTGGGGGT (SEQ ID NO:11814), GCGAGACGTTTTTAGCGGTTAAGTGGG (SEQ ID NO:11815)

Target1252　　chr12:43945748-43945800　　TCGGGGAGGTTTATTAGAGTCGTCGGT (SEQ ID NO:11816), TTTTGGGGATTTCGATCGGGGAGGTTT (SEQ ID NO:11817), ATTTTGGGGATTTCGATCGGGGAGGTT (SEQ ID NO:11818), TTTGGGGATTTCGATCGGGGAGGTTTA (SEQ ID NO:11819), CGATCGGGGAGGTTTATTAGAGTCGTCGG (SEQ ID NO:11820), GAGCGGAGATAGGCGGTGTGGTTGGAT (SEQ ID NO:11821), TGGTTGTCGGCGGTTTTGGTGGGTTTT (SEQ ID NO:11822), TTGGTTGTCGGCGGTTTTGGTGGGTTT (SEQ ID NO:11823), TTTGGTTGTCGGCGGTTTTGGTGGGTT (SEQ ID NO:11824), AGCGGAGATAGGCGGTGTGGTTGGATT (SEQ ID NO:11825)

Target1253　　chr12:43945818-43945926　　CGCGGGTTTTGGGTCGGTTGGTTTAGT (SEQ ID NO:11826), GGAATAGTAGCGCGGGTTTTGGGTCGG (SEQ ID NO:11827), GGGAATAGTAGCGCGGGTTTTGGGTCG (SEQ ID NO:11828), GCGCGGGTTTTGGGTCGGTTGGTTTAG (SEQ ID NO:11829), TAGTAGCGCGGGTTTTGGGTCGGTTGG (SEQ ID NO:11830), GAGCGGAGATAGGCGGTGTGGTTGGAT (SEQ ID NO:11831), AGCGGAGATAGGCGGTGTGGTTGGATT (SEQ ID NO:11832), GGCGTAGGAAGGGGGGTGAGGTTGTAG (SEQ ID NO:11833), GGAAGGGGGGTGAGGTTGTAGTGCGAT (SEQ ID NO:11834), AGGAAGGGGGGTGAGGTTGTAGTGCGA (SEQ ID NO:11835)

Target1254　　chr12:43945952-43945959　　CGCGGGTTTTGGGTCGGTTGGTTTAGT (SEQ ID NO:11836), GGAATAGTAGCGCGGGTTTTGGGTCGG (SEQ ID NO:11837), GGGAATAGTAGCGCGGGTTTTGGGTCG (SEQ ID NO:11838), GCGCGGGTTTTGGGTCGGTTGGTTTAG (SEQ ID NO:11839), TAGTAGCGCGGGTTTTGGGTCGGTTGG (SEQ ID NO:11840), TCGTCGGTTCGGGGTGGTTATATTGGT (SEQ ID NO:11841), TAGAGAGTTTTTGAGGGTAGCGCGGGT (SEQ ID NO:11842), GTAGAGAGTTTTTGAGGGTAGCGCGGGT (SEQ ID NO:11843), GTAGAGAGTTTTTGAGGGTAGCGCGGG (SEQ ID NO:11844), AGAGAGTTTTTGAGGGTAGCGCGGGT (SEQ ID NO:11845)

Target1255　　chr12:43945993-43945999　　TCGTTTGTTTTCGTTCGTTGAGTCGTTGT (SEQ ID NO:11846), TCGTTTGTTTTCGTTCGTTGAGTCGTTGTT (SEQ ID NO:11847), ATCGTTTGTTTTCGTTCGTTGAGTCGTTGT (SEQ ID NO:11848), CGTTTGTTTTCGTTCGTTGAGTCGTTGTT (SEQ ID NO:11849), TCGTTTGTTTTCGTTCGTTGAGTCGTTGTTT (SEQ ID NO:11850), TGGTCGGGAATAGTTTATAGGGGCGGGT (SEQ ID NO:11851), TCGTCGGTTCGGGGTGGTTATATTGGT (SEQ ID NO:11852), GGTCGGGAATAGTTTATAGGGGCGGGT (SEQ ID NO:11853), TGGTCGGGAATAGTTTATAGGGGCGGG (SEQ ID NO:11854), TTCGTCGGTTCGGGGTGGTTATATTGGT (SEQ ID NO:11855)

Target1256　　chr12:43946045-43946058　　AGTTCGGCGCGGGGAAGTAATTCGATT (SEQ ID NO:11856), TGTTTAGGTTTAGTTCGGCGCGGGGAA (SEQ ID NO:11857), TTGTTTAGGTTTAGTTCGGCGCGGGGA (SEQ ID NO:11858), TTTAGGTTTAGTTCGGCGCGGGGAAGT (SEQ ID NO:11859), TAGTTCGGCGCGGGGAAGTAATTCGAT (SEQ ID NO:11860), TTTGCGGTTGAGTGGAGAAGGGGAGGGG (SEQ ID NO:11861), CGGTTGAGTGGAGAAGGGGAGGGGGTTG (SEQ ID NO:11862), GGTTGAGTGGAGAAGGGAGGGGGTTGC (SEQ ID NO:11863), GTTGAGTGGAGAAGGGGAGGGGGTTGCG (SEQ ID NO:11864), TTGAGTGGAGAAGGGGAGGGGGTTGCG (SEQ ID NO:11865)

FIGURE 5 CONTINUED

Target1257 chr12:43946060-43946134 AGTTCGGCGCGGGGAAGTAATTCGATT (SEQ ID NO:11866), TGTTTAGGTTTAGTTCGGCGCGGGGAA
(SEQ ID NO:11867), TTGTTTAGGTTTAGTTCGGCGCGGGGA (SEQ ID NO:11868),
TTTAGGTTTAGTTCGGCGCGGGGAAGT (SEQ ID NO:11869), GCGTCGCGGAGAGTTCGTTTTTATGGG
(SEQ ID NO:11870), TTTGCGGTTGAGTGGAGAAGGGAGGGG (SEQ ID NO:11871),
CGGTTGAGTGGAGAAGGGAGGGGGTTG (SEQ ID NO:11872), GGTTGAGTGGAGAAGGGAGGGGGTTGC
(SEQ ID NO:11873), GTTGAGTGGAGAAGGGAGGGGGTTGCG (SEQ ID NO:11874),
TTGAGTGGAGAAGGGAGGGGGTTGCG (SEQ ID NO:11875)

Target1258 chr12:54427638-54427666 TTGAAGGGTGAGGAGCGCGGGGTTTTA (SEQ ID NO:11876), GAAGGGTGAGGAGCGCGGGGTTTTAGA
(SEQ ID NO:11877), AAGGGTGAGGAGCGCGGGGTTTTAGAG (SEQ ID NO:11878),
AGAGGGATTTGAAGGGTGAGGAGCGCG (SEQ ID NO:11879), TGAAGGGTGAGGAGCGCGGGGTTTTAG
(SEQ ID NO:11880), GGAGTCGCGGGGGGGATTTTCGTTTTGG (SEQ ID NO:11881),
GGGAGTCGCGGGGGGATTTTCGTTTTG (SEQ ID NO:11882), GTTTCGTAGGGGAGGGAGGGAGGGAGT
(SEQ ID NO:11883), TTTCGTAGGGGAGGGAGGGAGGGAGTC (SEQ ID NO:11884),
AGGGAGTCGCGGGGGGGATTTTCGTTTT (SEQ ID NO:11885)

Target1259 chr12:54427688-54427701 TTGAAGGGTGAGGAGCGCGGGGTTTTA (SEQ ID NO:11886), GAAGGGTGAGGAGCGCGGGGTTTTAGA
(SEQ ID NO:11887), AAGGGTGAGGAGCGCGGGGTTTTAGAG (SEQ ID NO:11888),
AGAGGGATTTGAAGGGTGAGGAGCGCG (SEQ ID NO:11889), TGAAGGGTGAGGAGCGCGGGGTTTTAG
(SEQ ID NO:11890), GGGTTGGGGGGGAAGAGGGAGATTTAGGT (SEQ ID NO:11891),
TGGGGGGGAAGAGGGAGATTTAGGTTCGG (SEQ ID NO:11892),
GGGTTGGGGGGGAAGAGGGAGATTTAGG (SEQ ID NO:11893), GGGGGGAAGAGGGAGATTTAGGTTCGG
(SEQ ID NO:11894), TGGGGGGGAAGAGGGAGATTTAGGTTCGGA (SEQ ID NO:11895)

Target1260 chr12:54427706-54427732 TTGAAGGGTGAGGAGCGCGGGGTTTTA (SEQ ID NO:11896), GAAGGGTGAGGAGCGCGGGGTTTTAGA
(SEQ ID NO:11897), AAGGGTGAGGAGCGCGGGGTTTTAGAG (SEQ ID NO:11898),
AGAGGGATTTGAAGGGTGAGGAGCGCG (SEQ ID NO:11899), TGAAGGGTGAGGAGCGCGGGGTTTTAG
(SEQ ID NO:11900), TTTTGTAGTCGGAGGGGTTGAGGGGGG (SEQ ID NO:11901),
GGGGGGTTGGGGGGGAAGAGGGAGATTTA (SEQ ID NO:11902), GGGGGGGTTGGGGGGGAAGAGGGAGATTT
(SEQ ID NO:11903), GGGGGTTGGGGGGGAAGAGGGAGATTT (SEQ ID NO:11904),
ATTTTGTAGTCGGAGGGGTTGAGGGGGG (SEQ ID NO:11905)

Target1261 chr12:54428065-54428083 TTTTTCGGTCGCGGGTGGGGGTTTGG (SEQ ID NO:11906), TTTTCGGTCGCGGGTGGGGGTTTG (SEQ ID
NO:11907), TTTTTCGGTCGCGGGTGGGGGTTTGGG (SEQ ID NO:11908),
TGTTTTAGAGACGGACGGTAAGCGGTT (SEQ ID NO:11909), TTTTCGGTCGCGGGTGGGGGTTTGG (SEQ
ID NO:11910), CGGCGAGTGAGGTAGCGGTTAAAGTGG (SEQ ID NO:11911),
CGGCGAGTGAGGTAGCGGTTAAAGTGGA (SEQ ID NO:11912), GGCGAGTGAGGTAGCGGTTAAAGTGGA
(SEQ ID NO:11913), CGGCGAGTGAGGTAGCGGTTAAAGTGAA (SEQ ID NO:11914),
GGCGAGTGAGGTAGCGGTTAAAGTGGAA (SEQ ID NO:11915)

Target1262 chr12:54428139-54428224 TGTTTTAGAGACGGACGGTAAGCGGTT (SEQ ID NO:11916), ATGTTTTAGAGACGGACGGTAAGCGGT
(SEQ ID NO:11917), GGGGTGGGGTTTATGTTTTAGAGACGGACGG (SEQ ID NO:11918),
TGTTTTAGAGACGGACGGTAAGCGGTTT (SEQ ID NO:11919),
GGGTGGGGTTTATGTTTTAGAGACGGACGG (SEQ ID NO:11920),
GGAAAGGCGAAAAGGAAAGGCGTAGGG (SEQ ID NO:11921),
GGAAAGGCGAAAAGGAAAGGCGTAGGGA (SEQ ID NO:11922), ATAGGAATCGGTTAGGGGCGCGTTTTG
(SEQ ID NO:11923), GAAAGGCGAAAAGGAAAGGCGTAGGGA (SEQ ID NO:11924),
GGCGAAAAGGAAAGGCGTAGGGATAGG (SEQ ID NO:11925)

Target1263 chr12:54428283-54428342 TTAGAGGTAGCGGGGGAGGTTCGTAGA (SEQ ID NO:11926), TTTTTTAGAGGTAGCGGGGGAGGTTCGT
(SEQ ID NO:11927), AGGTTTTTTAGAGGTAGCGGGGGAGGT (SEQ ID NO:11928),
TTTAGAGGTAGCGGGGGAGGTTCGTAG (SEQ ID NO:11929), TTTAGAGGTAGCGGGGGAGGTTCGTAGA
(SEQ ID NO:11930), TTCGCGGGAATTTTGGGTCGGTAGGGA (SEQ ID NO:11931),
TCGCGGGAATTTTGGGTCGGTAGGGAT (SEQ ID NO:11932), GCGGGAATTTTGGGTCGGTAGGGATGC
(SEQ ID NO:11933), CGGGAATTTTGGGTCGGTAGGGATGCG (SEQ ID NO:11934),
CGCGGGAATTTTGGGTCGGTAGGGATG (SEQ ID NO:11935)

Target1264 chr12:54428361-54428554 TCGGGTCGGGGGTAGGTGTTGGAGTAT (SEQ ID NO:11936), TTCGGGTCGGGGGTAGGTGTTGGAGTA
(SEQ ID NO:11937), ATTTCGGGTCGGGGGTAGGTGTTGGAG (SEQ ID NO:11938),
CGGGTCGGGGGTAGGTGTTGGAGTATT (SEQ ID NO:11939), TTTCGGGTCGGGGGTAGGTGTTGGAGT
(SEQ ID NO:11940), TTCGCGGGAATTTTGGGTCGGTAGGGA (SEQ ID NO:11941),
TCGCGGGAATTTTGGGTCGGTAGGGAT (SEQ ID NO:11942), GAGTTGAGGGGAGATGGGGTAGCGTCG
(SEQ ID NO:11943), CGAGTTGAGGGGAGATGGGGTAGCGTC (SEQ ID NO:11944),
GTCGAGTTGAGGGGAGATGGGGTAGCG (SEQ ID NO:11945)

Target1265 chr12:54428556-54428593 GGAGGGTTGCGGCGTATAGGTTGGC (SEQ ID NO:11946), GCGGGGTTGTCGGCGTTGTTTTATTTT (SEQ
ID NO:11947), GCGGGGTTGTCGGCGTTGTTTTATTT (SEQ ID NO:11948),
GCGGGGTTGTCGGCGTTGTTTTATTT (SEQ ID NO:11949), GCGGGGTTGTCGGCGTTGTTTTATTTTT
(SEQ ID NO:11950), CGAGGTTAGAGGGTTCGGCGAGGGGTTT (SEQ ID NO:11951),
AGGAGAGGGCGAGGTTAGAGGGTTCGG (SEQ ID NO:11952), TAGAGGGTTCGGCGAGGGTTTTGTGGC
(SEQ ID NO:11953), AAGGAGAGGGCGAGGTTAGAGGGTTCG (SEQ ID NO:11954),
CGAGGTTAGAGGGTTCGGCGAGGGTTTT (SEQ ID NO:11955)

FIGURE 5 CONTINUED

Target1266    chr12:54428600-54428619    GGAGGGTTGCGGCGTATAGGTTGGC (SEQ ID NO:11956), GAGGGTTGCGGCGTATAGGTTGGC (SEQ ID
NO:11957), GGAGGGTTGCGGCGTATAGGTTGG (SEQ ID NO:11958),
AGTTTCGTAGGATTTTTTCGGAGGGTTGC (SEQ ID NO:11959), AGGGTTGCGGCGTATAGGTTGGC (SEQ
ID NO:11960), CGAGGGTTAGAGGGTTCGGCGAGGGTTT (SEQ ID NO:11961),
AGGAGAGGGCGAGGTTAGAGGGTTCGG (SEQ ID NO:11962), TAGAGGGTTCGGCGAGGGTTTTGTGGC
(SEQ ID NO:11963), AAGGAGAGGGCGAGGTTAGAGGGTTCG (SEQ ID NO:11964),
CGAGGTTAGAGGGTTCGGCGAGGGTTTT (SEQ ID NO:11965)

Target1267    chr12:54441100-54441186    CGGGGTCGTTGTAGAGTCGGTTTTTCG (SEQ ID NO:11966), CGGGGGAGGAGAAAAGTATAGGATCGCGG
(SEQ ID NO:11967), CGGGGGAGGAGAAAAGTATAGGATCGCG (SEQ ID NO:11968),
GGGGGAGGAGAAAAGTATAGGATCGCGG (SEQ ID NO:11969),
TCGGGGGAGGAGAAAAGTATAGGATCGCG (SEQ ID NO:11970), GCGGCGCGGGATTTTTAGGTTGTGGTT
(SEQ ID NO:11971), CGGCGCGGGATTTTTAGGTTGTGGTTT (SEQ ID NO:11972),
GCGGCGCGGGATTTTTAGGTTGTGGT (SEQ ID NO:11973), GCGGCGCGGGATTTTTAGGTTGTGGTTT
(SEQ ID NO:11974), CGGCGCGGGATTTTTAGGTTGTGGTTTT (SEQ ID NO:11975)

Target1268    chr12:54441200-54441393    TAGTCGGAGGTAGAGGCGTTTCGAGGC (SEQ ID NO:11976), AGTCGGAGGTAGAGGCGTTTCGAGGC
(SEQ ID NO:11977), ATAGTCGGAGGTAGAGGCGTTTCGAGGC (SEQ ID NO:11978),
CGGGGTCGTTGTAGAGTCGGTTTTTCG (SEQ ID NO:11979), GTTCGTTTCGGATTTAGGTCGCGAGGT
(SEQ ID NO:11980), GCGTTTTGGTTTTGGCGGGCGAGTTAC (SEQ ID NO:11981),
GCGTTTTGGTTTTGGCGGGCGAGTTA (SEQ ID NO:11982), GCGTTTTGGTTTTGGCGGGCGAGTT (SEQ ID
NO:11983), CGTTTTGGTTTTGGCGGGCGAGTTAC (SEQ ID NO:11984),
GCGTTTTGGTTTTGGCGGGCGAGT (SEQ ID NO:11985)

Target1269    chr12:54441420-54441497    CGGAGGAGGCGGTTAAGGTGTAGGTCG (SEQ ID NO:11986), GGGTTCGGAGGAGGCGGTTAAGGTGTA
(SEQ ID NO:11987), GGAGGCGGTTAAGGTGTAGGTCGAGGT (SEQ ID NO:11988),
TAGTCGGAGGTAGAGGCGTTTCGAGGC (SEQ ID NO:11989), GCGGTTAAGGTGTAGGTCGAGGTTGGC
(SEQ ID NO:11990), GCGTTTTGGTTTTGGCGGGCGAGTTAC (SEQ ID NO:11991),
GCGTTTTGGTTTTGGCGGGCGAGTTA (SEQ ID NO:11992), GCGTTTTGGTTTTGGCGGGCGAGTT (SEQ ID
NO:11993), AGTTTTTTCGCGCGTTTTGGTTTTGGC (SEQ ID NO:11994),
CGTTTTGGTTTTGGCGGGCGAGTTAC (SEQ ID NO:11995)

Target1270    chr12:54441529-54441644    CGGAGGAGGCGGTTAAGGTGTAGGTCG (SEQ ID NO:11996), GGGTTCGGAGGAGGCGGTTAAGGTGTA
(SEQ ID NO:11997), GGAGGCGGTTAAGGTGTAGGTCGAGGT (SEQ ID NO:11998),
GTTCGTTAGGATTAGAGCGCGCGGAGG (SEQ ID NO:11999), GCGGTTAAGGTGTAGGTCGAGGTTGGC
(SEQ ID NO:12000), CGTGGTATTAGTGGGATTTGGGGAGCGG (SEQ ID NO:12001),
CGTGGTATTAGTGGGATTTGGGGAGCGGT (SEQ ID NO:12002),
TCGTGGTATTAGTGGGATTTGGGGAGCGG (SEQ ID NO:12003), TGGTATTAGTGGGATTTGGGGAGCGGT
(SEQ ID NO:12004), CGTGGTATTAGTGGGATTTGGGGAGCG (SEQ ID NO:12005)

Target1271    chr12:58013414-58013637    GCGTGGCGTTTGTTGTTGGTTCGGTTG (SEQ ID NO:12006), TAGGGGCGTGGCGTTTGTTGTTGGTTC
(SEQ ID NO:12007), GTTTTTCGGGTTGTGGAGGTTGCGGGT (SEQ ID NO:12008),
GATAGGGGCGTGGCGTTTGTTGTTGGT (SEQ ID NO:12009), GGATAGGGGCGTGGCGTTTGTTGTTGG
(SEQ ID NO:12010), GGGGTAGTTAGTGTAGCGCGGGTAGTCG (SEQ ID NO:12011),
GGGTAGTTAGTGTAGCGCGGGTAGTCG (SEQ ID NO:12012), GGGTAGTTAGTGTAGCGCGGGTAGTCGA
(SEQ ID NO:12013), CGCGGGTAGTCGAGGTTAGTAGTAGGCGT (SEQ ID NO:12014),
GGGGTAGTTAGTGTAGCGCGGGTAGTC (SEQ ID NO:12015)

Target1272    chr12:58013651-58013714    GCGTGGCGTTTGTTGTTGGTTCGGTTG (SEQ ID NO:12016), TAGGGGCGTGGCGTTTGTTGTTGGTTC
(SEQ ID NO:12017), GATAGGGGCGTGGCGTTTGTTGTTGGT (SEQ ID NO:12018),
GGATAGGGGCGTGGCGTTTGTTGTTGG (SEQ ID NO:12019), GGGATAGGGGCGTGGCGTTTGTTGTTG
(SEQ ID NO:12020), AGAGTTTGTGTTTTCGATAGGTTGTTGTTAGGGT (SEQ ID NO:12021),
GAGTTTGTGTTTTCGATAGGTTGTTGTTAGGGTT (SEQ ID NO:12022),
AGAGTTTGTGTTTTCGATAGGTTGTTGTTAGGGTT (SEQ ID NO:12023),
TAGAGTTTGTGTTTTCGATAGGTTGTTGTTAGGGT (SEQ ID NO:12024),
GAGTTTGTGTTTTCGATAGGTTGTTGTTAGGGTTT (SEQ ID NO:12025)

Target1273    chr12:58130751-58131225    ATTCGGAGTTGGTGGGAGGGTTAGCGG (SEQ ID NO:12026), GGGTTCGGGAAGGGGTTCGGAGTTAGG
(SEQ ID NO:12027), GGGGTTCGGGAAGGGGTTCGGAGTTAG (SEQ ID NO:12028),
GGTTGGATTCGGAGTTGGTGGGAGGGT (SEQ ID NO:12029), TGGTTGGATTCGGAGTTGGTGGGAGGG
(SEQ ID NO:12030), TAGCGGGTTTAGGGAGTTGTTGGGCGT (SEQ ID NO:12031),
CGGGTTTAGGGAGTTGTTGGGCGTCGA (SEQ ID NO:12032), GTAGCGGGTTTAGGGAGTTGTTGGGCG
(SEQ ID NO:12033), TTCGATTTTTGGTGGGGTCGGGGTTGG (SEQ ID NO:12034),
ATTTTTGGTGGGGTCGGGGTTGGGGTT (SEQ ID NO:12035)

Target1274    chr12:58131312-58132106    GGGGTTTCGGAGGGACGGTTTAGAGGG (SEQ ID NO:12036), GGGGGTTTCGGAGGGACGGTTTAGAGG
(SEQ ID NO:12037), GAGTCGGGGATAGGGTTGGGGGTTTCG (SEQ ID NO:12038),
AGTTCGGGTTGTTGAGTAGGGGGCGTC (SEQ ID NO:12039), GGTGGGGGCGTTTTTAGGTTTGGGGTC
(SEQ ID NO:12040), GGGGAGGGGGCGTTTTATGTGATGGGA (SEQ ID NO:12041),
AGGGGGCGTTTTATGTGATGGGAGGGG (SEQ ID NO:12042), AGGGCGCGGGTAGTCGTTTGTTATGGT
(SEQ ID NO:12043), GCGGAGGAGTCGGGTAAGAAGCGGTAC (SEQ ID NO:12044),
TTTTCGGGTTTTATGAGTCGGGGCGCG (SEQ ID NO:12045)

FIGURE 5 CONTINUED

| | | |
|---|---|---|
| Target1275 | chr12:63544123-63544297 | GGCGCGCGGGTTGTTGTAGAGTTTTGA (SEQ ID NO:12046), CGGCGCGCGGGTTGTTGTAGAGTTTTG (SEQ ID NO:12047), CGCGCGGGTTGTTGTAGAGTTTTGAGC (SEQ ID NO:12048), GCGCGCGGGTTGTTGTAGAGTTTTGAG (SEQ ID NO:12049), GGCGCGCGGGTTGTTGTAGAGTTTTGAG (SEQ ID NO:12050), CGATTGGTTGTGTCGCGTGGTGAAGTA (SEQ ID NO:12051), AGGTGTTCGGTATGTTTGCGTCGGTT (SEQ ID NO:12052), TGTAGGTGTTCGGTATGTTTGCGTCGGT (SEQ ID NO:12053), GTAGGTGTTCGGTATGTTTGCGTCGGT (SEQ ID NO:12054), TGTAGGTGTTCGGTATGTTTGCGTCGG (SEQ ID NO:12055) |
| Target1276 | chr12:63544328-63544500 | AGGTCGGTTAGGTTGAGGTGTCGGATG (SEQ ID NO:12056), GGTCGGTTAGGTTGAGGTGTCGGATGA (SEQ ID NO:12057), CGGTTAGGTCGGTTAGGTTGAGGTGTCGG (SEQ ID NO:12058), AGGTCGGTTAGGTTGAGGTGTCGGATGA (SEQ ID NO:12059), CGGTTAGGTCGGTTAGGTTGAGGTGTCG (SEQ ID NO:12060), TGGAGATCGTCGTGTTGGCGGTGATTT (SEQ ID NO:12061), TTGGAGATCGTCGTGTTGGCGGTGATT (SEQ ID NO:12062), AATTGGAGATCGTCGTGTTGGCGGTGA (SEQ ID NO:12063), ATTGGAGATCGTCGTGTTGGCGGTGAT (SEQ ID NO:12064), AAATTGGAGATCGTCGTGTTGGCGGTG (SEQ ID NO:12065) |
| Target1277 | chr12:63544511-63544529 | CGGCGATTTTTAGTTTGGTTAGTTTTTCGTTGCG (SEQ ID NO:12066), CGGCGATTTTTAGTTTGGTTAGTTTTTCGTTGCGT (SEQ ID NO:12067), ACGGCGATTTTTAGTTTGGTTAGTTTTTCGTTGCG (SEQ ID NO:12068), GGCGATTTTTAGTTTGGTTAGTTTTTCGTTGCG (SEQ ID NO:12069), CGGCGATTTTTAGTTTGGTTAGTTTTTCGTTGC (SEQ ID NO:12070), TGGTGGTTTTTGGTTATCGGCGTTGGT (SEQ ID NO:12071), ATGGTGGTTTTTGGTTATCGGCGTTGGT (SEQ ID NO:12072), ATGGTGGTTTTTGGTTATCGGCGTTGG (SEQ ID NO:12073), CGGCGTTGGTAATATAAGTCGGGAGGTCG (SEQ ID NO:12074), CGGCGTTGGTAATATAAGTCGGGAGGT (SEQ ID NO:12075) |
| Target1278 | chr12:63544544-63544591 | CGGTTTGTGTTGTTAGCGTCGGTGGTT (SEQ ID NO:12076), CGGTTTGTGTTGTTAGCGTCGGTGGT (SEQ ID NO:12077), TGTGTTGTTAGCGTCGGTGGTTAGAGGT (SEQ ID NO:12078), GTGTTGTTAGCGTCGGTGGTTAGAGGT (SEQ ID NO:12079), TGTGTTGTTAGCGTCGGTGGTTAGAGG (SEQ ID NO:12080), TTTTTCGAGACGGGGAGGGAGCGGTTC (SEQ ID NO:12081), AAGTTTTTCGAGACGGGGAGGGAGCGG (SEQ ID NO:12082), GTTTTTCGAGACGGGGAGGGAGCGGTT (SEQ ID NO:12083), TTTTTCGAGACGGGGAGGGAGCGGTT (SEQ ID NO:12084), TAAGTTTTTCGAGACGGGGAGGGAGCGG (SEQ ID NO:12085) |
| Target1279 | chr12:63544648-63544687 | CGGTTTGTGTTGTTAGCGTCGGTGGTT (SEQ ID NO:12086), CGGTTTGTGTTGTTAGCGTCGGTGGT (SEQ ID NO:12087), TGTGTTGTTAGCGTCGGTGGTTAGAGGT (SEQ ID NO:12088), GTGTTGTTAGCGTCGGTGGTTAGAGGT (SEQ ID NO:12089), TGTGTTGTTAGCGTCGGTGGTTAGAGG (SEQ ID NO:12090), TTTTTCGAGACGGGGAGGGAGCGGTTC (SEQ ID NO:12091), AAGTTTTTCGAGACGGGGAGGGAGCGG (SEQ ID NO:12092), GTTTTTCGAGACGGGGAGGGAGCGGTT (SEQ ID NO:12093), TTTTTCGAGACGGGGAGGGAGCGGTT (SEQ ID NO:12094), TAAGTTTTTCGAGACGGGGAGGGAGCGG (SEQ ID NO:12095) |
| Target1280 | chr12:63544708-63544789 | CGCGTTCGTAGTTTGTCGGGTTTTGCG (SEQ ID NO:12096), GCGTTCGTAGTTTGTCGGGTTTTGCGA (SEQ ID NO:12097), GCGTTCGTAGTTTGTCGGGTTTTGCGAT (SEQ ID NO:12098), TTGGGTTTTTCGTTCGAAGCGTAGGGT (SEQ ID NO:12099), GCGTTCGTAGTTTGTCGGGTTTTGCG (SEQ ID NO:12100), TGAGAGTTGTTTAGTGGGTAGGCGGGA (SEQ ID NO:12101), TGAGAGTTGTTTAGTGGGTAGGCGGGAC (SEQ ID NO:12102), GAGAGTTGTTTAGTGGGTAGGCGGGAC (SEQ ID NO:12103), TTGAGAGTTGTTTAGTGGGTAGGCGGG (SEQ ID NO:12104), TTGAGAGTTGTTTAGTGGGTAGGCGGGA (SEQ ID NO:12105) |
| Target1281 | chr12:63544889-63544967 | GAGGTCGGGAAGGTGAGTTTCGAGTTT (SEQ ID NO:12106), AGGTCGGGAAGGTGAGTTTCGAGTTTT (SEQ ID NO:12107), AGGTCGGGAAGGTGAGTTTCGAGTTTC (SEQ ID NO:12108), GAGGTCGGGAAGGTGAGTTTCGAGTTTT (SEQ ID NO:12109), GAGGTCGGGAAGGTGAGTTTCGAGTT (SEQ ID NO:12110), TTTTCGGTAATAGGGCGGGAGGGAGCG (SEQ ID NO:12111), TTTCGGTAATAGGGCGGGAGGGAGCG (SEQ ID NO:12112), TTTTTCGGTAATAGGGCGGGAGGGAGCG (SEQ ID NO:12113), TTTTTCGGTAATAGGGCGGGAGGGAGC (SEQ ID NO:12114), GTTTTTCGGTAATAGGGCGGGAGGGAGC (SEQ ID NO:12115) |
| Target1282 | chr12:66122895-66122975 | CGGTAGGAGGTATTTTCGGGGAGCGGT (SEQ ID NO:12116), TCGGTAGGAGGTATTTTCGGGGAGCGG (SEQ ID NO:12117), CGGTAGGAGGTATTTTCGGGGAGCGGTT (SEQ ID NO:12118), TCGGTAGGAGGTATTTTCGGGGAGCGGT (SEQ ID NO:12119), TTCGGTAGGAGGTATTTTCGGGGAGCGG (SEQ ID NO:12120), ATCGGGGATTGAGGAAGGAGGAGTGCG (SEQ ID NO:12121), CGTTTTTAGGGTAGCGCGGGGAGTTCG (SEQ ID NO:12122), GGGATTGAGGAAGGAGGAGTGCGGGAT (SEQ ID NO:12123), GAGGTCGTTTTGGAGATGGCGTCGGTT (SEQ ID NO:12124), GGGGATTGAGGAAGGAGGAGTGCGGGA (SEQ ID NO:12125) |
| Target1283 | chr12:66123010-66123091 | CGGTAGGAGGTATTTTCGGGGAGCGGT (SEQ ID NO:12126), TCGGTAGGAGGTATTTTCGGGGAGCGG (SEQ ID NO:12127), CGGTAGGAGGTATTTTCGGGGAGCGGTT (SEQ ID NO:12128), TCGGTAGGAGGTATTTTCGGGGAGCGGT (SEQ ID NO:12129), TTCGGTAGGAGGTATTTTCGGGGAGCGG (SEQ ID NO:12130), TTCGTCGTTTGGAGCGGGAAAGTTGCG (SEQ ID NO:12131), GTTTTCGAGGTTTGGGCGCGTAGGAGG (SEQ ID NO:12132), TTTTCGAGGTTTGGGCGCGTAGGAGGT (SEQ ID NO:12133), GTTCGGGGTTTTCGTCGTTTGGAGCGG (SEQ ID NO:12134), GGTTCGGGGTTTTCGTCGTTTGGAGCG (SEQ ID NO:12135) |

FIGURE 5 CONTINUED

Target1284    chr12:66123110-66123128    GTTTTAGGCGGCGGGGGATTTCGAGTCG (SEQ ID NO:12136), CGTTTTAGGCGGCGGGGGATTTCGAGTC (SEQ ID NO:12137), TCGTTTTAGGCGGCGGGGGATTTCGAGT (SEQ ID NO:12138), TTCGTTTTAGGCGGCGGGGGATTTCGAG (SEQ ID NO:12139), TTTCGTTTTAGGCGGCGGGGGATTTCGA (SEQ ID NO:12140), GTTTTCGAGGTTTGGGCGCGTAGGAGG (SEQ ID NO:12141), TTTTCGAGGTTTGGGCGCGTAGGAGGT (SEQ ID NO:12142), TTTCGAGGTTTGGGCGCGTAGGAGGTA (SEQ ID NO:12143), TTCGAGGTTTGGGCGCGTAGGAGGTAT (SEQ ID NO:12144), CGAGGTTTGGGCGCGTAGGAGGTATAGG (SEQ ID NO:12145)

Target1285    chr12:66123168-66123214    GTTTTAGGCGGCGGGGGATTTCGAGTCG (SEQ ID NO:12146), CGTTTTAGGCGGCGGGGGATTTCGAGTC (SEQ ID NO:12147), CGGCGGGGGATTTCGAGTCGGAGTTTTG (SEQ ID NO:12148), TCGTTTTAGGCGGCGGGGGATTTCGAGT (SEQ ID NO:12149), GGCGGGGGATTTCGAGTCGGAGTTTTGG (SEQ ID NO:12150), GTAGAGCGGGGCGTTAAGGGTTGTTCG (SEQ ID NO:12151), CGAGTTTTTATGTCGGCGGGCGTAGAG (SEQ ID NO:12152), TAGAGCGGGGCGTTAAGGGTTGTTCG (SEQ ID NO:12153), GTTTAGGCGGAGGGTCGAAACGTTACG (SEQ ID NO:12154), CGTTAAGGGTTGTTCGCGGGGTGTATT (SEQ ID NO:12155)

Target1286    chr12:66123273-66123286    GCGGGTAGTTTTTGGCGTTTCGTTTTGC (SEQ ID NO:12156), TGGTGGATTAGAGGTGTATTTCGCGGGT (SEQ ID NO:12157), GGTGGATTAGAGGTGTATTTCGCGGGT (SEQ ID NO:12158), TGGTGGATTAGAGGTGTATTTCGCGGG (SEQ ID NO:12159), CGGGTAGTTTTTGGCGTTTCGTTTTGC (SEQ ID NO:12160), CGAGTTTTTATGTCGGCGGGCGTAGAG (SEQ ID NO:12161), GTTTAGGCGGAGGGTCGAAACGTTACG (SEQ ID NO:12162), CGAGTTTTTATGTCGGCGGGCGTAGA (SEQ ID NO:12163), TTTAGGCGGAGGGTCGAAACGTTACG (SEQ ID NO:12164), GAGTTTTTATGTCGGCGGGCGTAGAG (SEQ ID NO:12165)

Target1287    chr12:66123289-66123381    TCGGTATGAGGATTCGTGCGTGGCGTT (SEQ ID NO:12166), CGGTATGAGGATTCGTGCGTGGCGTTT (SEQ ID NO:12167), TGAGGATTCGTGCGTGGCGTTTCGATT (SEQ ID NO:12168), GTCGGTATGAGGATTCGTGCGTGGCGT (SEQ ID NO:12169), ATGAGGATTCGTGCGTGGCGTTTCGAT (SEQ ID NO:12170), TTTGCGGGTGGGTGGAGGTTGTAGGTT (SEQ ID NO:12171), TGTTTGCGGGTGGGTGGAGGTTGTAGG (SEQ ID NO:12172), GTTTGCGGGTGGGTGGAGGTTGTAGGT (SEQ ID NO:12173), TTGCGGGTGGGTGGAGGTTGTAGGTTA (SEQ ID NO:12174), TGCGGGTGGGTGGAGGTTGTAGGTTAT (SEQ ID NO:12175)

Target1288    chr12:66275403-66276260    GGGGAGGGAGGGAGGGAGGGAGAAAGAG (SEQ ID NO:12176), GAGGGAGGGAGGGAGGGAGGGAGAAAG (SEQ ID NO:12177), TCGGGTTGCGTTGTTAGGGTTGCGTTT (SEQ ID NO:12178), TTCGGGTTGCGTTGTTAGGGTTGCGTT (SEQ ID NO:12179), TTTCGGGTTGCGTTGTTAGGGTTGCGT (SEQ ID NO:12180), TTTGCGGTAGTTTTTTAGGGCGGGCGG (SEQ ID NO:12181), CGGTAGTTTTTTAGGGCGGGCGGGTTG (SEQ ID NO:12182), GGTAGTTTTTTAGGGCGGGCGGGTTGT (SEQ ID NO:12183), GTTTGCGGTAGTTTTTTAGGGCGGGCG (SEQ ID NO:12184), TTGCGGTAGTTTTTTAGGGCGGGCGG (SEQ ID NO:12185)

Target1289    chr12:66897000-66897016    TGGTTTTTAATAGGGTTTTAGAAATTGGGCGAGTG (SEQ ID NO:12186), GGTTTTTAATAGGGTTTTAGAAATTGGGCGAGTGA (SEQ ID NO:12187), TGGTTTTTAATAGGGTTTTAGAAATTGGGCGAGTGA (SEQ ID NO:12188), TTGGTTTTTAATAGGGTTTTAGAAATTGGGCGAGTG (SEQ ID NO:12189), GGTTTTTAATAGGGTTTTAGAAATTGGGCGAGTGAA (SEQ ID NO:12190), TGGGAAGTGAGTATGTGTAGTGTGTTTAGGAAGT (SEQ ID NO:12191), TGTTTGGGAAGTGAGTATGTGTAGTGTGTTTAGG (SEQ ID NO:12192), GTTTGGGAAGTGAGTATGTGTAGTGTGTTTAGGA (SEQ ID NO:12193), TGTTTGGGAAGTGAGTATGTGTAGTGTGTTTAGGA (SEQ ID NO:12194), GGGAAGTGAGTATGTGTAGTGTGTTTAGGAAGTT (SEQ ID NO:12195)

Target1290    chr12:70051601-70051609    TTGGTTGAATGTTTTGGGACGGCGTTC (SEQ ID NO:12196), ATTGGTTGAATGTTTTGGGACGGCGTT (SEQ ID NO:12197), AATTGGTTGAATGTTTTGGGACGGCGT (SEQ ID NO:12198), ATTGGTTGAATGTTTTGGGACGGCGTTC (SEQ ID NO:12199), TGGTTGAATGTTTTGGGACGGCGTTC (SEQ ID NO:12200), GTGGAGGGTGGGTTAGAAGGTTATTTGGT (SEQ ID NO:12201), AGTGGAGGGTGGGTTAGAAGGTTATTTGGT (SEQ ID NO:12202), AGTGGAGGGTGGGTTAGAAGGTTATTTGG (SEQ ID NO:12203), TGGAGGGTGGGTTAGAAGGTTATTTGGTAGT (SEQ ID NO:12204), AGTGGAGGGTGGGTTAGAAGGTTATTTGGTA (SEQ ID NO:12205)

Target1291    chr12:81312705-81313105    CGTTAAGGAATGTATGTCGGTAGTTGTTGAGATGT (SEQ ID NO:12206), TCGTTAAGGAATGTATGTCGGTAGTTGTTGAGATG (SEQ ID NO:12207), TCGTTAAGGAATGTATGTCGGTAGTTGTTGAGATGT (SEQ ID NO:12208), ATCGTTAAGGAATGTATGTCGGTAGTTGTTGAGATG (SEQ ID NO:12209), CGTTAAGGAATGTATGTCGGTAGTTGTTGAGATGTA (SEQ ID NO:12210)

Target1292    chr12:104193695-104193807    AGGAGGGGTGGAGGAGTAGGTGTTTT (SEQ ID NO:12211), TAGGAGGGGTGGAGGAGTAGGTGTTTT (SEQ ID NO:12212), GGAGGGGTGGAGGAGTAGGTGTTTTT (SEQ ID NO:12213), AGGAGGGGTGGAGGAGTAGGTGTTTTT (SEQ ID NO:12214), ATAGGAGGGGTGGAGGAGTAGGTGTTT (SEQ ID NO:12215)

Target1293    chr12:104193912-104193975    GGGGATGGAGACGGGAGGAAAGAGGT (SEQ ID NO:12216), TGGGTGATGGAGACGGGAGGAAAGAGG (SEQ ID NO:12217), TGGGTGATGGAGACGGGAGGAAAGAGGT (SEQ ID NO:12218), TGTGGGTGATGGAGACGGGAGGAAAGA (SEQ ID NO:12219), GTGGGTGATGGAGACGGGAGGAAAGAGG (SEQ ID NO:12220)

FIGURE 5 CONTINUED

Figure 5:
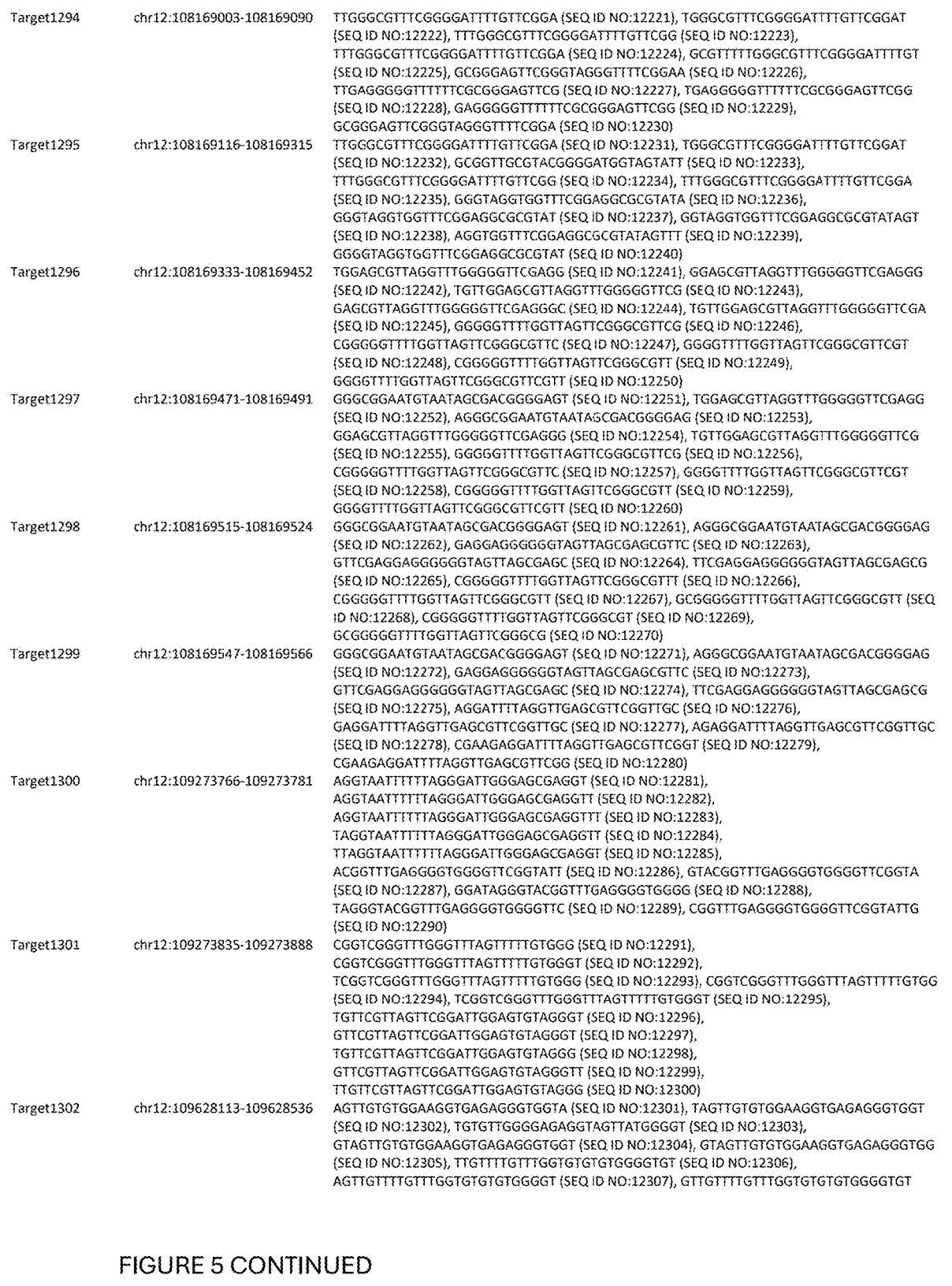

Target1294   chr12:108169003-108169090   TTGGGCGTTCGGGGATTTTGTTCGGA (SEQ ID NO:12221), TGGGCGTTTCGGGGATTTTGTTCGGAT
                                          (SEQ ID NO:12222), TTTGGGCGTTTCGGGGATTTTGTTCGG (SEQ ID NO:12223),
                                          TTTGGGCGTTTCGGGGATTTTGTTCGGA (SEQ ID NO:12224), GCGTTTTTGGGCGTTTCGGGGATTTTGT
                                          (SEQ ID NO:12225), GCGGGGAGTTCGGGTAGGGTTTCGGAA (SEQ ID NO:12226),
                                          TTGAGGGGGTTTTTTCGCGGGAGTTCG (SEQ ID NO:12227), TGAGGGGGTTTTTTCGCGGGAGTTCGG
                                          (SEQ ID NO:12228), GAGGGGGTTTTTTCGCGGGAGTTCGG (SEQ ID NO:12229),
                                          GCGGGAGTTCGGGTAGGGTTTCGGA (SEQ ID NO:12230)
Target1295   chr12:108169116-108169315   TTGGGCGTTCGGGGATTTTGTTCGGA (SEQ ID NO:12231), TGGGCGTTTCGGGGATTTTGTTCGGAT
                                          (SEQ ID NO:12232), GCGGTTGCGTACGGGGATGGTAGTATT (SEQ ID NO:12233),
                                          TTTGGGCGTTTCGGGGATTTTGTTCGG (SEQ ID NO:12234), TTTGGGCGTTTCGGGGATTTTGTTCGGA
                                          (SEQ ID NO:12235), GGGTAGGTGGTTTCGGAGGCGCGTATA (SEQ ID NO:12236),
                                          GGGTAGGTGGTTTCGGAGGCGCGTAT (SEQ ID NO:12237), GGTAGGTGGTTTCGGAGGCGCGTATAGT
                                          (SEQ ID NO:12238), AGGTGGTTTCGGAGGCGCGTATAGTTT (SEQ ID NO:12239),
                                          GGGGTAGGTGGTTTCGGAGGCGCGTAT (SEQ ID NO:12240)
Target1296   chr12:108169333-108169452   TGGAGCGTTAGGTTTGGGGGTTCGAGG (SEQ ID NO:12241), GGAGCGTTAGGTTTGGGGGTTCGAGGG
                                          (SEQ ID NO:12242), TGTTGGAGCGTTAGGTTTGGGGGTTCG (SEQ ID NO:12243),
                                          GAGCGTTAGGTTTGGGGGTTCGAGGGC (SEQ ID NO:12244), TGTTGGAGCGTTAGGTTTGGGGGTTCGA
                                          (SEQ ID NO:12245), GGGGGTTTTGGTTAGTTCGGGCGTTCG (SEQ ID NO:12246),
                                          CGGGGGGTTTTGGTTAGTTCGGGCGTTC (SEQ ID NO:12247), GGGGTTTTGGTTAGTTCGGGCGTTCGT
                                          (SEQ ID NO:12248), CGGGGGGTTTTGGTTAGTTCGGGCGTT (SEQ ID NO:12249),
                                          GGGGTTTTGGTTAGTTCGGGCGTTCGTT (SEQ ID NO:12250)
Target1297   chr12:108169471-108169491   GGGCGGAATGTAATAGCGACGGGGAGT (SEQ ID NO:12251), TGGAGCGTTAGGTTTGGGGGTTCGAGG
                                          (SEQ ID NO:12252), AGGGCGGAATGTAATAGCGACGGGGAG (SEQ ID NO:12253),
                                          GGAGCGTTAGGTTTGGGGGTTCGAGGG (SEQ ID NO:12254), TGTTGGAGCGTTAGGTTTGGGGGTTCG
                                          (SEQ ID NO:12255), GGGGGTTTTGGTTAGTTCGGGCGTTCG (SEQ ID NO:12256),
                                          CGGGGGGTTTTGGTTAGTTCGGGCGTTC (SEQ ID NO:12257), GGGGTTTTGGTTAGTTCGGGCGTTCGT
                                          (SEQ ID NO:12258), CGGGGGGTTTTGGTTAGTTCGGGCGTT (SEQ ID NO:12259),
                                          GGGGTTTTGGTTAGTTCGGGCGTTCGTT (SEQ ID NO:12260)
Target1298   chr12:108169515-108169524   GGGCGGAATGTAATAGCGACGGGGAGT (SEQ ID NO:12261), AGGGCGGAATGTAATAGCGACGGGGAG
                                          (SEQ ID NO:12262), GAGGAGGGGGGTAGTTAGCGAGCGTTC (SEQ ID NO:12263),
                                          GTTCGAGGAGGGGGGTAGTTAGCGAGC (SEQ ID NO:12264), TTCGAGGAGGGGGGTAGTTAGCGAGCG
                                          (SEQ ID NO:12265), CGGGGGGTTTTGGTTAGTTCGGGCGTTT (SEQ ID NO:12266),
                                          CGGGGGGTTTTGGTTAGTTCGGGCGTT (SEQ ID NO:12267), GCGGGGGGTTTTGGTTAGTTCGGGCGTT (SEQ
                                          ID NO:12268), CGGGGGGTTTTGGTTAGTTCGGGCGT (SEQ ID NO:12269),
                                          GCGGGGGTTTTGGTTAGTTCGGGCG (SEQ ID NO:12270)
Target1299   chr12:108169547-108169566   GGGCGGAATGTAATAGCGACGGGGAGT (SEQ ID NO:12271), AGGGCGGAATGTAATAGCGACGGGGAG
                                          (SEQ ID NO:12272), GAGGAGGGGGGTAGTTAGCGAGCGTTC (SEQ ID NO:12273),
                                          GTTCGAGGAGGGGGGTAGTTAGCGAGC (SEQ ID NO:12274), TTCGAGGAGGGGGGTAGTTAGCGAGCG
                                          (SEQ ID NO:12275), AGGATTTTAGGTTGAGCGTTCGGTTGC (SEQ ID NO:12276),
                                          GAGGATTTTAGGTTGAGCGTTCGGTTGC (SEQ ID NO:12277), AGAGGATTTTAGGTTGAGCGTTCGGTTGC
                                          (SEQ ID NO:12278), CGAAGAGGATTTTAGGTTGAGCGTTCGGT (SEQ ID NO:12279),
                                          CGAAGAGGATTTTAGGTTGAGCGTTCGG (SEQ ID NO:12280)
Target1300   chr12:109273766-109273781   AGGTAATTTTTTAGGGATTGGGAGCGAGGT (SEQ ID NO:12281),
                                          AGGTAATTTTTTAGGGATTGGGAGCGAGGTT (SEQ ID NO:12282),
                                          AGGTAATTTTTTAGGGATTGGGAGCGAGGTTT (SEQ ID NO:12283),
                                          TAGGTAATTTTTTAGGGATTGGGAGCGAGGTT (SEQ ID NO:12284),
                                          TTAGGTAATTTTTTAGGGATTGGGAGCGAGGT (SEQ ID NO:12285),
                                          ACGGTTTGAGGGGTGGGGTTCGGTATT (SEQ ID NO:12286), GTACGGTTTGAGGGGTGGGGTTCGGTA
                                          (SEQ ID NO:12287), GGATAGGGTACGGTTTGAGGGGTGGGG (SEQ ID NO:12288),
                                          TAGGGTACGGTTTGAGGGGTGGGGTTC (SEQ ID NO:12289), CGGTTTGAGGGGTGGGGTTCGGTATTG
                                          (SEQ ID NO:12290)
Target1301   chr12:109273835-109273888   CGGTCGGGTTTGGGTTTAGTTTTTTGTGGG (SEQ ID NO:12291),
                                          CGGTCGGGTTTGGGTTTAGTTTTTTGTGGGT (SEQ ID NO:12292),
                                          TCGGTCGGGTTTGGGTTTAGTTTTTTGTGGG (SEQ ID NO:12293), CGGTCGGGTTTGGGTTTAGTTTTTTGTGG
                                          (SEQ ID NO:12294), TCGGTCGGGTTTGGGTTTAGTTTTTTGTGGGT (SEQ ID NO:12295),
                                          TGTTCGTTAGTTCGGATTGGAGTGTAGGGT (SEQ ID NO:12296),
                                          GTTCGTTAGTTCGGATTGGAGTGTAGGG (SEQ ID NO:12297),
                                          TGTTCGTTAGTTCGGATTGGAGTGTAGGG (SEQ ID NO:12298),
                                          GTTCGTTAGTTCGGATTGGAGTGTAGGGTT (SEQ ID NO:12299),
                                          TTGTTCGTTAGTTCGGATTGGAGTGTAGGG (SEQ ID NO:12300)
Target1302   chr12:109628113-109628536   AGTTGTGTGGAAGGTGAGAGGGTGGTA (SEQ ID NO:12301), TAGTTGTGTGGAAGGTGAGAGGGTGGT
                                          (SEQ ID NO:12302), TGTGTTGGGGAGAGGTAGTTATGGGGT (SEQ ID NO:12303),
                                          GTAGTTGTGTGGAAGGTGAGAGGGTGGT (SEQ ID NO:12304), GTAGTTGTGTGGAAGGTGAGAGGGTGG
                                          (SEQ ID NO:12305), TTGTTTTGTTTGGTGTGTGTGGGGTGT (SEQ ID NO:12306),
                                          AGTTGTTTTGTTTGGTGTGTGTGGGGT (SEQ ID NO:12307), GTTGTTTTGTTTGGTGTGTGTGTGGGGTGT

FIGURE 5 CONTINUED (SEQ ID NO:12308), AGTTGTTTTGTTTGGTGTGTGTGGGGTGT (SEQ ID NO:12309), AGTTGTTTTGTTTGGTGTGTGTGGGGTG (SEQ ID NO:12310)

| | | |
|---|---|---|
| Target1303 | chr12:113901279-113901325 | GTTGGAGTCGGTCGGGGATTGCGTTTG (SEQ ID NO:12311), AGGAAGTTGGAGTCGGTCGGGGATTGC (SEQ ID NO:12312), AGTTGGAGTCGGTCGGGGATTGCGTTT (SEQ ID NO:12313), AAGTTGGAGTCGGTCGGGGATTGCGTT (SEQ ID NO:12314), GAAGTTGGAGTCGGTCGGGGATTGCGT (SEQ ID NO:12315) |
| Target1304 | chr12:113901337-113901352 | GTTGGAGTCGGTCGGGGATTGCGTTTG (SEQ ID NO:12316), AGGAAGTTGGAGTCGGTCGGGGATTGC (SEQ ID NO:12317), AGTTGGAGTCGGTCGGGGATTGCGTTT (SEQ ID NO:12318), AAGTTGGAGTCGGTCGGGGATTGCGTT (SEQ ID NO:12319), GAAGTTGGAGTCGGTCGGGGATTGCGT (SEQ ID NO:12320) |
| Target1305 | chr12:113901393-113901409 | GTTGGAGTCGGTCGGGGATTGCGTTTG (SEQ ID NO:12321), GTTTTGGTAGTTTGCGGAGGGGGAGCG (SEQ ID NO:12322), CGTTTTGGTAGTTTGCGGAGGGGGAGC (SEQ ID NO:12323), AGTTGGAGTCGGTCGGGGATTGCGTTT (SEQ ID NO:12324), AAGTTGGAGTCGGTCGGGGATTGCGTT (SEQ ID NO:12325) |
| Target1306 | chr12:113901467-113901478 | GTTTTGGTAGTTTGCGGAGGGGGAGCG (SEQ ID NO:12326), CGTTTTGGTAGTTTGCGGAGGGGGAGC (SEQ ID NO:12327), GGAAGGAGATAGGGCGCGGTGAGAGAA (SEQ ID NO:12328), TTTTGGTAGTTTGCGGAGGGGGAGCGG (SEQ ID NO:12329), AGTCGTTTTGGTAGTTTGCGGAGGGGG (SEQ ID NO:12330) |
| Target1307 | chr12:113901793-113901814 | GGGTCGGTGAGAGATATAGAGATGCGGG (SEQ ID NO:12331), AGGGTCGGTGAGAGATATAGAGATGCGGG (SEQ ID NO:12332), GGGTCGGTGAGAGATATAGAGATGCGGGA (SEQ ID NO:12333), AGGGTCGGTGAGAGATATAGAGATGCGGGA (SEQ ID NO:12334), AGGGTCGGTGAGAGATATAGAGATGCGGG (SEQ ID NO:12335) |
| Target1308 | chr12:113901855-113901867 | CGGTAGAGGGGTAGAGAGAAAGGCGGA (SEQ ID NO:12336), TCGGTAGAGGGGTAGAGAGAAAGGCGG (SEQ ID NO:12337), TCGGTAGAGGGGTAGAGAGAAAGGCGGA (SEQ ID NO:12338), CGGTAGAGGGGTAGAGAGAAAGGCGGAA (SEQ ID NO:12339), ATCGGTAGAGGGGTAGAGAGAAAGGCGG (SEQ ID NO:12340), TGTTTCGGGTTTTCGGGTTTTAGTCGC (SEQ ID NO:12341), ATGTTTCGGGTTTTCGGGTTTTAGTCGC (SEQ ID NO:12342), GATGTTTCGGGTTTTCGGGTTTTAGTCGC (SEQ ID NO:12343) |
| Target1309 | chr12:113901937-113901976 | GATATCGGAGGGTCGCGGAGGAGTCGA (SEQ ID NO:12344), AGATATCGGAGGGTCGCGGAGGAGTCG (SEQ ID NO:12345), CGTAGAGAGAGGAAAGACGGTCGCGGT (SEQ ID NO:12346), GAGATATCGGAGGGTCGCGGAGGAGTC (SEQ ID NO:12347), ATATCGGAGGGTCGCGGAGGAGTCGA (SEQ ID NO:12348) |
| Target1310 | chr12:113902019-113902036 | CGTAGAGAGAGGAAAGACGGTCGCGGT (SEQ ID NO:12349), GCGGTAGCGAGGGAGTTAGGAGTGAGT (SEQ ID NO:12350), CGTAGAGAGAGGAAAGACGGTCGCGGTT (SEQ ID NO:12351), GCGGTAGCGAGGGAGTTAGGAGTGAGTT (SEQ ID NO:12352), GTAGAGAGAGGAAAGACGGTCGCGGTT (SEQ ID NO:12353), TCGCGTTTTGTTTTGTTCGTTGGTTTGTT (SEQ ID NO:12354), TTCGCGTTTTGTTTTGTTCGTTGGTTTGT (SEQ ID NO:12355), TGTTTTGTTCGTTGGTTTGTTTTTTGTCGGTT (SEQ ID NO:12356), TTGTTTTGTTCGTTGGTTTGTTTTTTGTTCGGT (SEQ ID NO:12357), TTGTTTTGTTCGTTGGTTTGTTTTTTGTTCGGTT (SEQ ID NO:12358) |
| Target1311 | chr12:113902128-113902145 | GCGGAGGTTGATAGGTTCGGGGAGAGG (SEQ ID NO:12359), GGTTCGGGGAGAGGAATCGGGTAGGGA (SEQ ID NO:12360), AGGTTCGGGGAGAGGAATCGGGTAGGG (SEQ ID NO:12361), TAGGTTCGGGGAGAGGAATCGGGTAGGG (SEQ ID NO:12362), GTTCGGGGAGAGGAATCGGGTAGGGAT (SEQ ID NO:12363), GGGCGTAGGGATCGAGTTTAGGGCGTT (SEQ ID NO:12364), AGGGCGTAGGGATCGAGTTTAGGGCGT (SEQ ID NO:12365), TAGGGCGTAGGGATCGAGTTTAGGGCG (SEQ ID NO:12366), GGGCGTAGGGATCGAGTTTAGGGCGT (SEQ ID NO:12367), AGGGCGTTAAGGTCGTTTCGTTCGGTT (SEQ ID NO:12368) |
| Target1312 | chr12:113917518-113917544 | CGGTGCGTAGGGTTGGGGGAGTATAGGT (SEQ ID NO:12369), CGGTGCGTAGGGTTGGGGGAGTATAGGTT (SEQ ID NO:12370), GGTGCGTAGGGTTGGGGGAGTATAGGTT (SEQ ID NO:12371), CGGTGCGTAGGGTTGGGGGAGTATAGGTTT (SEQ ID NO:12372), CGGTGCGTAGGGTTGGGGGAGTATAGG (SEQ ID NO:12373) |
| Target1313 | chr12:113917702-113917732 | TGCGGGTTTTGGGGCGAGGTTTAGTTG (SEQ ID NO:12374), GCGGGTTTTGGGGCGAGGTTTAGTTGG (SEQ ID NO:12375), GGCGAGGCGTTGTTTGGGGATAGATCG (SEQ ID NO:12376), TGGGGCGAGGTTTAGTTGGTTTGGGGG (SEQ ID NO:12377), GGGGCGAGGTTTAGTTGGTTTGGGGGT (SEQ ID NO:12378), TGTTTGGGGTGGGTGTTGGAGGGTAGG (SEQ ID NO:12379), GGTGTTTGGGGTGGGTGTTGGAGGGTA (SEQ ID NO:12380), TTGGGGTGGGTGTTGGAGGGTAGGAGA (SEQ ID NO:12381), GTTTGGGGTGGGTGTTGGAGGGTAGGA (SEQ ID NO:12382), TACGGTGTTTGGGGTGGGTGTTGGAGG (SEQ ID NO:12383) |
| Target1314 | chr12:113917733-113917750 | GGCGAGGCGTTGTTTGGGGATAGATCG (SEQ ID NO:12384), AGGCGAGGCGTTGTTTGGGGATAGATCG (SEQ ID NO:12385), AGGCGAGGCGTTGTTTGGGGATAGATC (SEQ ID NO:12386), AGGCGAGGCGTTGTTTGGGGATAGAT (SEQ ID NO:12387), GCGAGGCGTTGTTTGGGGATAGATCG (SEQ ID NO:12388), TGTTTGGGGTGGGTGTTGGAGGGTAGG (SEQ ID NO:12389), GGTGTTTGGGGTGGGTGTTGGAGGGTA (SEQ ID NO:12390), TTGGGGTGGGTGTTGGAGGGTAGGAGA |

FIGURE 5 CONTINUED (SEQ ID NO:12391), GTTTGGGGTGGGTGTTGGAGGGTAGGA (SEQ ID NO:12392),
TACGGTGTTTGGGGTGGGTGTTGGAGG (SEQ ID NO:12393)

Target1315     chr12:114075881-114076058     TCGGTCGTTCGTATTTGGGCGCGTAGA (SEQ ID NO:12394), GTCGGTCGTTCGTATTTGGGCGCGTAG
(SEQ ID NO:12395), CGGTCGTTCGTATTTGGGCGCGTAGAG (SEQ ID NO:12396),
GTCGTTCGTATTGTTCGGGTCGGCGTT (SEQ ID NO:12397), GGTCGTTCGTATTTGGGCGCGTAGAGG
(SEQ ID NO:12398), GTGATAATGGCGGGGTGACGGGGGTTA (SEQ ID NO:12399),
TGATAATGGCGGGGTGACGGGGGTTAA (SEQ ID NO:12400), AATGGCGGGGTGACGGGGGTTAATTCG
(SEQ ID NO:12401), TGAGGGCGGTTATTGTGCGTTGTGTGA (SEQ ID NO:12402),
GCGTTTTTGAGGGCGGTTATTGTGCGT (SEQ ID NO:12403)

Target1316     chr12:114833945-114833953     GATCGAGTGGAGGTAGTTGGGGGAGGC (SEQ ID NO:12404), CGATCGAGTGGAGGTAGTTGGGGGAGG
(SEQ ID NO:12405), AGTGGAGGTAGTTGGGGGAGGCGAGTC (SEQ ID NO:12406),
GAGTGGAGGTAGTTGGGGGAGGCGAGT (SEQ ID NO:12407), ATCGAGTGGAGGTAGTTGGGGGAGGCG
(SEQ ID NO:12408), TTATCGGTCGGGGAGGCGGTCGGGTTA (SEQ ID NO:12409),
TATCGGTCGGGGAGGCGGTCGGGTTAC (SEQ ID NO:12410), TATCGGTCGGGGAGGCGGTCGGGTTA
(SEQ ID NO:12411), GTTATCGGTCGGGGAGGCGGTCGGGTT (SEQ ID NO:12412),
TTATCGGTCGGGGAGGCGGTCGGGTTAC (SEQ ID NO:12413)

Target1317     chr12:114833956-114833974     GATCGAGTGGAGGTAGTTGGGGGAGGC (SEQ ID NO:12414), CGATCGAGTGGAGGTAGTTGGGGGAGG
(SEQ ID NO:12415), AGTGGAGGTAGTTGGGGGAGGCGAGTC (SEQ ID NO:12416),
GAGTGGAGGTAGTTGGGGGAGGCGAGT (SEQ ID NO:12417), ATCGAGTGGAGGTAGTTGGGGGAGGCG
(SEQ ID NO:12418), TTATCGGTCGGGGAGGCGGTCGGGTTA (SEQ ID NO:12419),
TATCGGTCGGGGAGGCGGTCGGGTTAC (SEQ ID NO:12420), TATCGGTCGGGGAGGCGGTCGGGTTA
(SEQ ID NO:12421), GTTATCGGTCGGGGAGGCGGTCGGGTT (SEQ ID NO:12422),
TTATCGGTCGGGGAGGCGGTCGGGTTAC (SEQ ID NO:12423)

Target1318     chr12:114833991-114834066     GATCGAGTGGAGGTAGTTGGGGGAGGC (SEQ ID NO:12424), CGATCGAGTGGAGGTAGTTGGGGGAGG
(SEQ ID NO:12425), AGTGGAGGTAGTTGGGGGAGGCGAGTC (SEQ ID NO:12426),
GAGTGGAGGTAGTTGGGGGAGGCGAGT (SEQ ID NO:12427), ATCGAGTGGAGGTAGTTGGGGGAGGCG
(SEQ ID NO:12428), CGGTTAGCGGGGTTTCGTTGCGTTTTT (SEQ ID NO:12429),
CGGTTAGCGGGGTTTCGTTGCGTTTTT (SEQ ID NO:12430), CGGTTAGCGGGGTTTCGTTGCGTTTT (SEQ
ID NO:12431), TTATCGGTCGGGGAGGCGGTCGGGTTA (SEQ ID NO:12432),
GGTTAGCGGGGTTTCGTTGCGTTTTTT (SEQ ID NO:12433)

Target1319     chr12:114834075-114834139     GGGTCGCGCGTTTTTAATTTTCGGTCG (SEQ ID NO:12434), GGGTCGCGCGTTTTTAATTTTCGGTCGT
(SEQ ID NO:12435), GGTCGCGCGTTTTTAATTTTCGGTCGT (SEQ ID NO:12436),
GGGTCGCGCGTTTTTAATTTTCGGTCGTC (SEQ ID NO:12437), GGTCGCGCGTTTTTAATTTTCGGTCGTC
(SEQ ID NO:12438), CGGTTAGCGGGGTTTCGTTGCGTTTTT (SEQ ID NO:12439),
CGGTTAGCGGGGTTTCGTTGCGTTTTT (SEQ ID NO:12440), CGGTTAGCGGGGTTTCGTTGCGTTTTT (SEQ
ID NO:12441), GGTTAGCGGGGTTTCGTTGCGTTTTTT (SEQ ID NO:12442),
GTCGGTCGGGGATTGTGGCGGTTAG (SEQ ID NO:12443)

Target1320     chr12:114834201-114834210     GTTTTCGGTCGGCGGGGTTATCGGTTC (SEQ ID NO:12444), TCGGCGGGGTTATCGGTTCGGTTTAGT
(SEQ ID NO:12445), TAGTTTTCGGTCGGCGGGGTTATCGGT (SEQ ID NO:12446),
AGTTTTCGGTCGGCGGGGTTATCGGTT (SEQ ID NO:12447), GGTCGGCGGGGTTATCGGTTCGGTTTA
(SEQ ID NO:12448), AGTTGGGGAGAGGGGTTCGGAGTTGTT (SEQ ID NO:12449),
TAGTTGGGGAGAGGGGTTCGGAGTTGT (SEQ ID NO:12450), GTTGGGGAGAGGGGTTCGGAGTTGTTT
(SEQ ID NO:12451), AGTTGGGGAGAGGGGTTCGGAGTTGTTT (SEQ ID NO:12452),
AGTTGGGGAGAGGGGTTCGGAGTTGT (SEQ ID NO:12453)

Target1321     chr12:114840863-114840896     GCGTTTAGTGCGTTTTGGGTTTTGGGCG (SEQ ID NO:12454), GCGTTTAGTGCGTTTTGGGTTTTGGGC
(SEQ ID NO:12455), AGTGCGTTTTGGGTTTTGGGCGTAGAG (SEQ ID NO:12456),
CGTTTAGTGCGTTTTGGGTTTTGGGCGT (SEQ ID NO:12457), CGTTTAGTGCGTTTTGGGTTTTGGGCG
(SEQ ID NO:12458), TGGCGCGTTATTATCGGTCGTTGGGAG (SEQ ID NO:12459),
GGTTGGCGCGTTATTATCGGTCGTTGGG (SEQ ID NO:12460), TTGGCGCGTTATTATCGGTCGTTGGGA
(SEQ ID NO:12461), GTTGGCGCGTTATTATCGGTCGTTGGG (SEQ ID NO:12462),
GGTTGGCGCGTTATTATCGGTCGTTGG (SEQ ID NO:12463)

Target1322     chr12:114840967-114841026     TAGCGGTCGGTGATGGCGCGTTAGTTA (SEQ ID NO:12464), GTTTTTAGCGGTCGGTGATGGCGCGTT
(SEQ ID NO:12465), TTTTAGCGGTCGGTGATGGCGCGTTAG (SEQ ID NO:12466),
TTAGCGGTCGGTGATGGCGCGTTAGTT (SEQ ID NO:12467), TTTAGCGGTCGGTGATGGCGCGTTAGT
(SEQ ID NO:12468), TGTTTTGCGGTCGGGGTTTGGTTGGTT (SEQ ID NO:12469),
TTGTTTTGCGGTCGGGGTTTGGTTGGT (SEQ ID NO:12470), TTTTGCGGTCGGGGTTTGGTTGGTTGG (SEQ
ID NO:12471), CGGGGTTTGGTTGGTTGGCGCGTTATT (SEQ ID NO:12472),
GTTTTGCGGTCGGGGTTTGGTTGGTTG (SEQ ID NO:12473)

Target1323     chr12:114841029-114841071     TAGCGGTCGGTGATGGCGCGTTAGTTA (SEQ ID NO:12474), GTTTTTAGCGGTCGGTGATGGCGCGTT
(SEQ ID NO:12475), TTTTAGCGGTCGGTGATGGCGCGTTAG (SEQ ID NO:12476),
TTAGCGGTCGGTGATGGCGCGTTAGTT (SEQ ID NO:12477), TTTAGCGGTCGGTGATGGCGCGTTAGT
(SEQ ID NO:12478), AAGGGGTTAGGTTAGCGGTCGATTTAGGTC (SEQ ID NO:12479),
AATAAGGGGTTAGGTTAGCGGTCGATTTAGGTC (SEQ ID NO:12480),
TTTAATAAGGGGTTAGGTTAGCGGTCGATTTAGGTC (SEQ ID NO:12481),
TTTTAATAAGGGGTTAGGTTAGCGGTCGATTTAGGTC (SEQ ID NO:12482)

FIGURE 5 CONTINUED

Target1324    chr12:114841155-114841170    GTAGGAGGAGGTAGGAGGAGGCGGGAG (SEQ ID NO:12483),
                                           GAGGTAGGAGGAGGTAGGAGGAGGCGG (SEQ ID NO:12484),
                                           GGAGGTAGGAGGAGGTAGGAGGAGGCG (SEQ ID NO:12485),
                                           GCGGAGGAGGTAGGAGGAGGTAGGAGG (SEQ ID NO:12486),
                                           CGCGGAGGAGGTAGGAGGAGGTAGGAG (SEQ ID NO:12487),
                                           TCGGTCGTTTGGGGTTAGTTAATAATGGTTTAGA (SEQ ID NO:12488),
                                           TTCGGTCGTTTGGGGTTAGTTAATAATGGTTTAGA (SEQ ID NO:12489),
                                           TCGGTCGTTTGGGGTTAGTTAATAATGGTTTAGAT (SEQ ID NO:12490),
                                           TTCGGTCGTTTGGGGTTAGTTAATAATGGTTTAGAT (SEQ ID NO:12491),
                                           ATTCGGTCGTTTGGGGTTAGTTAATAATGGTTTAGA (SEQ ID NO:12492)

Target1325    chr12:114886355-114886374    TGGTTGTGGGTGGATGGATGAAGAAGGT (SEQ ID NO:12493), GGTTGTGGGTGGATGGATGAAGAAGGT
                                           (SEQ ID NO:12494), TGGTTGTGGGTGGATGGATGAAGAAGG (SEQ ID NO:12495),
                                           TGGTTGTGGGTGGATGGATGAAGAAGGTT (SEQ ID NO:12496),
                                           TTGGTTGTGGGTGGATGGATGAAGAAGGT (SEQ ID NO:12497), TTGATGGAGTAGTTCGCGTCGTGGTGC
                                           (SEQ ID NO:12498), TTTGATGGAGTAGTTCGCGTCGTGGTGC (SEQ ID NO:12499),
                                           TGATGGAGTAGTTCGCGTCGTGGTGC (SEQ ID NO:12500), GGAAACGCGGTTGGAGGTTAGTGGATGT
                                           (SEQ ID NO:12501), GGAAACGCGGTTGGAGGTTAGTGGATG (SEQ ID NO:12502)

Target1326    chr12:114886408-114886417    TGGTTGTGGGTGGATGGATGAAGAAGGT (SEQ ID NO:12503), GGTTGTGGGTGGATGGATGAAGAAGGT
                                           (SEQ ID NO:12504), TGGTTGTGGGTGGATGGATGAAGAAGG (SEQ ID NO:12505),
                                           TGGTTGTGGGTGGATGGATGAAGAAGGTT (SEQ ID NO:12506),
                                           TTGGTTGTGGGTGGATGGATGAAGAAGGT (SEQ ID NO:12507), CGGGTTTATTTTGGGGGCGTTTAGTGT
                                           (SEQ ID NO:12508), TCGGGTTTATTTTGGGGGCGTTTAGTGT (SEQ ID NO:12509),
                                           TCGGGTTTATTTTGGGGGCGTTTAGTG (SEQ ID NO:12510), CGGGTTTATTTTGGGGGCGTTTAGTGTT
                                           (SEQ ID NO:12511), TCGGGTTTATTTTGGGGGCGTTTAGTGTT (SEQ ID NO:12512)

Target1327    chr12:114886449-114886466    TTTATTTGGAGTTTAAGTTTTGGCGCGCG (SEQ ID NO:12513),
                                           TTTTATTTGGAGTTTAAGTTTTGGCGCGCG (SEQ ID NO:12514),
                                           CGGTTGTAGTATTGGGCGTTTTTAGAGTGG (SEQ ID NO:12515),
                                           CGGTTGTAGTATTGGGCGTTTTTAGAGTGGA (SEQ ID NO:12516),
                                           TCGGTTGTAGTATTGGGCGTTTTTAGAGTGG (SEQ ID NO:12517),
                                           GCGGTCGTTGGTAGGTAGTCGGATCGG (SEQ ID NO:12518), CGGTCGTTGGTAGGTAGTCGGATCGGG
                                           (SEQ ID NO:12519), AGCGGTCGTTGGTAGGTAGTCGGATCG (SEQ ID NO:12520),
                                           TTGAGCGGTCGTTGGTAGGTAGTCGGA (SEQ ID NO:12521), GGTCGTTGGTAGGTAGTCGGATCGGGA
                                           (SEQ ID NO:12522)

Target1328    chr12:114886504-114886517    GCGGCGAGTTAGGGTATTTCGGATCGG (SEQ ID NO:12523), AGCGGCGAGTTAGGGTATTTCGGATCGG
                                           (SEQ ID NO:12524), GCGGCGAGTTAGGGTATTTCGGATCGGT (SEQ ID NO:12525),
                                           AGCGGCGAGTTAGGGTATTTCGGATCG (SEQ ID NO:12526), TAAGTTATCGGCGCGGTTTAGGAGGGG
                                           (SEQ ID NO:12527), AGGCGGAATGTAGGTCGGTGTGTGAGG (SEQ ID NO:12528),
                                           GGAGGCGGAATGTAGGTCGGTGTGTGA (SEQ ID NO:12529), GGCGGAATGTAGGTCGGTGTGTGAGGT
                                           (SEQ ID NO:12530), GCGGTCGTTGGTAGGTAGTCGGATCGG (SEQ ID NO:12531),
                                           CGGTCGTTGGTAGGTAGTCGGATCGGG (SEQ ID NO:12532)

Target1329    chr12:114886523-114886562    GCGGCGAGTTAGGGTATTTCGGATCGG (SEQ ID NO:12533), AGCGGCGAGTTAGGGTATTTCGGATCGG
                                           (SEQ ID NO:12534), GCGGCGAGTTAGGGTATTTCGGATCGGT (SEQ ID NO:12535),
                                           AGCGGCGAGTTAGGGTATTTCGGATCG (SEQ ID NO:12536), TAAGTTATCGGCGCGGTTTAGGAGGGG
                                           (SEQ ID NO:12537), AGGCGGAATGTAGGTCGGTGTGTGAGG (SEQ ID NO:12538),
                                           GGAGGCGGAATGTAGGTCGGTGTGTGA (SEQ ID NO:12539), GGCGGAATGTAGGTCGGTGTGTGAGGT
                                           (SEQ ID NO:12540), GATGGGGGTTGGGGAGGCGGAATGTAG (SEQ ID NO:12541),
                                           TTCGTGGTAAGGATGGGGGTTGGGGAG (SEQ ID NO:12542)

Target1330    chr12:115103612-115104184    ATAAGAGGGTTGGTCGGGGAGGGGGAT (SEQ ID NO:12543), TCGCGGGAGAGGGAAATTTCGGCGTTA
                                           (SEQ ID NO:12544), CGGATTGCGTTCGGTTTTGGCGTTTGG (SEQ ID NO:12545),
                                           GGTTGGTCGGGGAGGGGGATGTTGAAA (SEQ ID NO:12546), GGACGCGGGGGAGGATTTGAGGTTAGT
                                           (SEQ ID NO:12547), TTCGGGGATTGTAGGTGGAGACGTCGT (SEQ ID NO:12548),
                                           GTTCGGGGATTGTAGGTGGAGACGTCGT (SEQ ID NO:12549), GTTCGGGGATTGTAGGTGGAGACGTCG
                                           (SEQ ID NO:12550), GAGGGAAATCGCGGGGGGAGAGGAAATT (SEQ ID NO:12551),
                                           CGGGGATTGTAGGTGGAGACGTCGTAGG (SEQ ID NO:12552)

Target1331    chr12:122473392-122473522    GGGTTGGGTAGGGTTCGGCGGTTTTTG (SEQ ID NO:12553), AGGGTTGGGTAGGGTTCGGCGGTTTTT
                                           (SEQ ID NO:12554), AGGGGTAGGAGGGTTGGGTAGGGTTCG (SEQ ID NO:12555),
                                           GGTTGGGTAGGGTTCGGCGGTTTTTGT (SEQ ID NO:12556), GAGGGTTGGGTAGGGTTCGGCGGTTTT
                                           (SEQ ID NO:12557), TGCGGGGTTTTTGTTTTTGGGTGAGGA (SEQ ID NO:12558),
                                           TGCGGGGTTTTTGTTTTTGGGTGAGGAG (SEQ ID NO:12559), GCGGGGTTTTTGTTTTTGGGTGAGGAG
                                           (SEQ ID NO:12560), TTGCGGGGTTTTTGTTTTTGGGTGAGG (SEQ ID NO:12561),
                                           TGCGGGGTTTTTGTTTTTGGGTGAGGAGA (SEQ ID NO:12562)

Target1332    chr12:124941570-124941724    ACGTCGTTTGGGTAGCGTTTGGTAATAGA (SEQ ID NO:12563),
                                           ACGTCGTTTGGGTAGCGTTTGGTAATAGAT (SEQ ID NO:12564),
                                           CGTCGTTTGGGTAGCGTTTGGTAATAGATG (SEQ ID NO:12565),
                                           ACGTCGTTTGGGTAGCGTTTGGTAATAGATG (SEQ ID NO:12566),
                                           CGTCGTTTGGGTAGCGTTTGGTAATAGATGA (SEQ ID NO:12567),

FIGURE 5 CONTINUED

|  |  |  |
|---|---|---|
|  |  | TAGGGTTAGGGGTTTAGGGGGAGGGCGG (SEQ ID NO:12568), GGGTGGTTGGAGAGGTGGGTAGGGAGG (SEQ ID NO:12569), GGGGTGGTTGGAGAGGTGGGTAGGGAG (SEQ ID NO:12570), GTGGTTGGAGAGGTGGGTAGGGAGGC (SEQ ID NO:12571), ATAGGGTTAGGGGTTTAGGGGGAGGGCG (SEQ ID NO:12572) |
| Target1333 | chr12:124941781-124941952 | GGGGGAGGGAGGTTCGGGGGTTTTTTGT (SEQ ID NO:12573), TTTAGTACGGGGGAGGGAGGTTCGGGG (SEQ ID NO:12574), TTTTAGTACGGGGGAGGGAGGTTCGGG (SEQ ID NO:12575), TACGGGGGAGGGAGGTTCGGGGTTTTT (SEQ ID NO:12576), CGGGGGAGGGAGGTTCGGGGTTTTTTG (SEQ ID NO:12577), GGGAGGGTTTGTAGGGGGTTTCGGGTT (SEQ ID NO:12578), TGGTTTGTTGGGGTCGTTGTGGGGGTA (SEQ ID NO:12579), GTTGGTTTGTTGGGGTCGTTGTGGGGG (SEQ ID NO:12580), GGTTGGTTTGTTGGGGTCGTTGTGGGG (SEQ ID NO:12581), TTTAGCGTGGGGAGGGTTTGTAGGGGG (SEQ ID NO:12582) |
| Target1334 | chr12:124941977-124942177 | GGAGGGAGGGAGGGTGAGATAGAGGCGT (SEQ ID NO:12583), CGAGGGAAGGAGGAGGAGGAGGAGGAG (SEQ ID NO:12584), AGGAGGAGGGAGGGTGAGATAGAGGCG (SEQ ID NO:12585), GAAGGAGGAGGAGGAGGAGGAGGGAGG (SEQ ID NO:12586), GGAAGGAGGAGGAGGAGGAGGAGGGAG (SEQ ID NO:12587), TTTAGTTGTGAGTGGGGAGGAGGCGGG (SEQ ID NO:12588), TTGGTAGTGTCGGTTGGGTTGGTGGGG (SEQ ID NO:12589), GGTAGTGTCGGTTGGGTTGGTGGGGAG (SEQ ID NO:12590), AGGGTTGGTAGTGTCGGTTGGGTTGGT (SEQ ID NO:12591), AGGCGGGGGAGGTTTCGGGGTAGTTTAG (SEQ ID NO:12592) |
| Target1335 | chr12:132258427-132258452 | CGGTTTCGGGATTTGGGGTTTAGGGCG (SEQ ID NO:12593), GGTTTCGGGATTTGGGGTTTAGGGCG (SEQ ID NO:12594), CGGTTTCGGGATTTGGGGTTTAGGC (SEQ ID NO:12595), GGATAGTATAGTTAGGAGGAGAGTGGCGGT (SEQ ID NO:12596), AGGATAGTATAGTTAGGAGGAGAGTGGCGGT (SEQ ID NO:12597), GGGTTTTTGGTTTTCGTGGGTTTTTATTATTTTGGT (SEQ ID NO:12598), TGGGTTTTTGGTTTTCGTGGGTTTTTATTATTTTGG (SEQ ID NO:12599), TTTTAAGGTTTCGTTTGAGTTTTAGGTTTCGGAGT (SEQ ID NO:12600), TTTTTAAGGTTTCGTTTGAGTTTTAGGTTTCGGAGT (SEQ ID NO:12601) |
| Target1336 | chr12:132258560-132258668 | TGGGGTTTAGGCGAGGTTTTGAGGAGT (SEQ ID NO:12602), TGGGGTTTAGGCGAGGTTTTGAGGAGTT (SEQ ID NO:12603), TTGGGGTTTAGGCGAGGTTTTGAGGAGT (SEQ ID NO:12604), GGGGTTTAGGCGAGGTTTTGAGGAGTT (SEQ ID NO:12605), TTGGGGTTTAGGCGAGGTTTTGAGGAG (SEQ ID NO:12606), GCGGAAATGCGGTTTTTATTTTGTCGGTT (SEQ ID NO:12607), GCGGAAATGCGGTTTTTATTTTGTCGGTTT (SEQ ID NO:12608), GCGGAAATGCGGTTTTTATTTTGTCGGTTTT (SEQ ID NO:12609), GCGGAAATGCGGTTTTTATTTTGTCGGTTTTT (SEQ ID NO:12610), GCGGAAATGCGGTTTTTATTTTGTCGGTTTTTCG (SEQ ID NO:12611) |
| Target1337 | chr12:133481384-133481393 | CGGTTTGGGGATGATTTGAGGTCGCGT (SEQ ID NO:12612), TCGGTTTGGGGATGATTTGAGGTCGCG (SEQ ID NO:12613), TCGGTTTGGGGATGATTTGAGGTCGCGT (SEQ ID NO:12614), CGGTTTGGGGATGATTTGAGGTCGCGTT (SEQ ID NO:12615), TTCGGTTTGGGGATGATTTGAGGTCGCG (SEQ ID NO:12616) |
| Target1338 | chr12:133481463-133481558 | GGGCGCGTTTTGTCGGTTATTAGGGGT (SEQ ID NO:12617), TGGGCGCGTTTTGTCGGTTATTAGGGG (SEQ ID NO:12618), TGGGCGCGTTTTGTCGGTTATTAGGGGT (SEQ ID NO:12619), TTGGGCGCGTTTTGTCGGTTATTAGGGG (SEQ ID NO:12620), GGGTTGGGCGCGTTTTGTCGGTTATTA (SEQ ID NO:12621), TGCGTTGTTTTTGGTGGTCGGTAGGGC (SEQ ID NO:12622), GTTTTTGGTGGTCGGTAGGGCGCGTTT (SEQ ID NO:12623), GTTGTTTTTGGTGGTCGGTAGGGCGCG (SEQ ID NO:12624), CGTTGTTTTTGGTGGTCGGTAGGGCGC (SEQ ID NO:12625), GCGTTGTTTTTGGTGGTCGGTAGGGCG (SEQ ID NO:12626) |
| Target1339 | chr12:133481570-133481590 | GGGCGCGTTTTGTCGGTTATTAGGGGT (SEQ ID NO:12627), TGGGCGCGTTTTGTCGGTTATTAGGGG (SEQ ID NO:12628), TGGGCGCGTTTTGTCGGTTATTAGGGGT (SEQ ID NO:12629), TTGGGCGCGTTTTGTCGGTTATTAGGGG (SEQ ID NO:12630), GGGTTGGGCGCGTTTTGTCGGTTATTA (SEQ ID NO:12631) |
| Target1340 | chr13:21520242-21520564 | GGATGGAGAAACGGTGGAGAGACGGGG (SEQ ID NO:12632), GGGATGGAGAAACGGTGGAGAGACGGG (SEQ ID NO:12633), GGGGATGGAGAAACGGTGGAGAGACGG (SEQ ID NO:12634), GGGGGATGGAGAAACGGTGGAGAGACG (SEQ ID NO:12635), TTTCGGGGGGGATGGAGAAACGGTGGAG (SEQ ID NO:12636), CGGGGGCGTATTAGTTTTTTAGGCGTCGGG (SEQ ID NO:12637), TCGTTAATTGCGGGGGATTTCGTTCGT (SEQ ID NO:12638), ATTAGGAGATTTCGGTGCGGCGAGTTC (SEQ ID NO:12639), CGGGGGCGTATTAGTTTTTTAGGCGTCGG (SEQ ID NO:12640), GGGGCGTATTAGTTTTTTAGGCGTCGGG (SEQ ID NO:12641) |
| Target1341 | chr13:25320032-25320080 | TGTAGCGGGCGGTTTGTAGGGTGAGTT (SEQ ID NO:12642), TTGTAGCGGGCGGTTTGTAGGGTGAGT (SEQ ID NO:12643), AGCGGGCGGTTTGTAGGGTGAGTTACG (SEQ ID NO:12644), GTTGTAGCGGGCGGTTTGTAGGGTGAG (SEQ ID NO:12645), CGTTGTAGCGGGCGGTTTGTAGGGTGA (SEQ ID NO:12646), GTAGTTCGTGGTTGCGCGGGAAAGTCG (SEQ ID NO:12647), GTGGCGGTAGTGTAGTTCGTGGTTGCG (SEQ ID NO:12648), CGTGGCGGTAGTGTAGTTCGTGGTTGC (SEQ ID NO:12649), GCGTGGCGGTAGTGTAGTTCGTGGTTG (SEQ ID NO:12650), GTGTAGTTCGTGGTTGCGCGGGAAAGT (SEQ ID NO:12651) |

FIGURE 5 CONTINUED

| Target1342 | chr13:25320106-25320227 | TGTAGCGGGCGGTTTGTAGGGTGAGTT (SEQ ID NO:12652), TTGTAGCGGGCGGTTTGTAGGGTGAGT (SEQ ID NO:12653), AGCGGGCGGTTTGTAGGGTGAGTTACG (SEQ ID NO:12654), GTTGTAGCGGGCGGTTTGTAGGGTGAG (SEQ ID NO:12655), TGTTCGTGGGTTATTTCGGCGCGTAGG (SEQ ID NO:12656), GTTGGAGTTTTTGTCGGCGTGGCGGTA (SEQ ID NO:12657), GTAGTTCGTGGTTGCGCGGGAAAGTCG (SEQ ID NO:12658), GGAGTTTTTGTCGGCGTGGCGGTAGTG (SEQ ID NO:12659), GGCGTAGGAAGGGGAGGTTTCGGGAAG (SEQ ID NO:12660), GCGTAGGAAGGGGAGGTTTCGGGAAGT (SEQ ID NO:12661) |
| Target1343 | chr13:25320247-25320389 | AGGTTTCGGTTCGTAGTTTCGCGCGTT (SEQ ID NO:12662), TAGGTTTCGGTTCGTAGTTTCGCGCGT (SEQ ID NO:12663), GGTTTCGGTTCGTAGTTTCGCGCGTTT (SEQ ID NO:12664), AGGTTTCGGTTCGTAGTTTCGCGCGTTT (SEQ ID NO:12665), AGGTTTCGGTTCGTAGTTTCGCGCGT (SEQ ID NO:12666), GGCGTAGGAAGGGGAGGTTTCGGGAAG (SEQ ID NO:12667), GCGTAGGAAGGGGAGGTTTCGGGAAGT (SEQ ID NO:12668), GGTGGTGGCGTAGGAAGGGGAGGTTTC (SEQ ID NO:12669), GTGGTGGCGTAGGAAGGGGAGGTTTCG (SEQ ID NO:12670), GCGGGTCGGGGTTTGGTTTCGGTTTTC (SEQ ID NO:12671) |
| Target1344 | chr13:25320541-25320560 | GGGTGCGTAGGGAGAATGGGTTGTGGT (SEQ ID NO:12672), GAGGTGTGGGGGTGCGTAGGGAGAATG (SEQ ID NO:12673), TTAGAGAGGTTTGGCGAGGTGTGGGGG (SEQ ID NO:12674), TGCGTAGGGAGAATGGGTTGTGGTCGT (SEQ ID NO:12675), GGGGTGCGTAGGGAGAATGGGTTGTGG (SEQ ID NO:12676), TCGTCGGTTTTTTAAGGAGAACGCGGT (SEQ ID NO:12677), CGTCGGTTTTTTAAGGAGAACGCGGTG (SEQ ID NO:12678), CGTCGGTTTTTTAAGGAGAACGCGGTGA (SEQ ID NO:12679), TCGTCGGTTTTTTAAGGAGAACGCGGTG (SEQ ID NO:12680), TCGTCGGTTTTTTAAGGAGAACGCGGTGA (SEQ ID NO:12681) |
| Target1345 | chr13:25320608-25320617 | TGGTGCGTGTTGGTTTTGTGGAGATGG (SEQ ID NO:12682), TGGTGCGTGTTGGTTTTGTGGAGATGGA (SEQ ID NO:12683), GGTGCGTGTTGGTTTTGTGGAGATGGA (SEQ ID NO:12684), ATGGTGCGTGTTGGTTTTGTGGAGATGG (SEQ ID NO:12685), TGGTGCGTGTTGGTTTTGTGGAGATGGAT (SEQ ID NO:12686), TCGTCGGTTTTTTAAGGAGAACGCGGT (SEQ ID NO:12687), CGTCGGTTTTTTAAGGAGAACGCGGTG (SEQ ID NO:12688), CGTCGGTTTTTTAAGGAGAACGCGGTGA (SEQ ID NO:12689), TCGTCGGTTTTTTAAGGAGAACGCGGTG (SEQ ID NO:12690), TCGTCGGTTTTTTAAGGAGAACGCGGTGA (SEQ ID NO:12691) |
| Target1346 | chr13:25320665-25320698 | CGAAGGTGGTGGGGATTGTCGTGAGGA (SEQ ID NO:12692), TTGGCGAAGGTGGTGGGGATTGTCGTG (SEQ ID NO:12693), GTTGGCGAAGGTGGTGGGGATTGTCGT (SEQ ID NO:12694), GCGAAGGTGGTGGGGATTGTCGTGAGG (SEQ ID NO:12695), GGCGAAGGTGGTGGGGATTGTCGTGAG (SEQ ID NO:12696), GCGGGTGGAGCGTAGTTTTTTGGGAGA (SEQ ID NO:12697), GCGGGTGGAGCGTAGTTTTTTGGGAGAG (SEQ ID NO:12698), CGGGTGGAGCGTAGTTTTTTGGGAGAGT (SEQ ID NO:12699), CGGGTGGAGCGTAGTTTTTTGGGAGAG (SEQ ID NO:12700), GCGGGTGGAGCGTAGTTTTTTGGGAGAGT (SEQ ID NO:12701) |
| Target1347 | chr13:25320780-25320804 | GCGCGGTAGTGGTTTCGAGTTTTGGGT (SEQ ID NO:12702), CGCGCGGTAGTGGTTTCGAGTTTTGGG (SEQ ID NO:12703), GCGCGCGGTAGTGGTTTCGAGTTTTGG (SEQ ID NO:12704), GGCGCGCGGTAGTGGTTTCGAGTTTTG (SEQ ID NO:12705), GCGCGGTAGTGGTTTCGAGTTTTGGGTT (SEQ ID NO:12706), CGTGGTAGGGGCGTTTAGGGGTTTAGGT (SEQ ID NO:12707), CGTGGTAGGGGCGTTTAGGGGTTTAGG (SEQ ID NO:12708), TGAAGAGGTTTAGTGTTGGGACGGGGG (SEQ ID NO:12709), GTGGTAGGGGCGTTTAGGGGTTTAGGT (SEQ ID NO:12710), TGAAGAGGTTTAGTGTTGGGACGGGGGA (SEQ ID NO:12711) |
| Target1348 | chr13:51417461-51417509 | TGGGTTAGGGTGTAGGGTTCGCGGTTT (SEQ ID NO:12712), TTGGGTTAGGGTGTAGGGTTCGCGGTT (SEQ ID NO:12713), TTTGGGTTAGGGTGTAGGGTTCGCGGT (SEQ ID NO:12714), TCGGGGGAAGGGTAGTAATTCGGCGTT (SEQ ID NO:12715), TTCGGGGGAAGGGTAGTAATTCGGCGT (SEQ ID NO:12716), GAGGAGGAGGTAGTGCGAGGCGTTGAG (SEQ ID NO:12717), AGAGGAGGAGGTAGTGCGAGGCGTTGA (SEQ ID NO:12718), GTTGAGGGGGGCGTCGAGTTGTTGTTT (SEQ ID NO:12719), TAGAGGAGGAGGTAGTGCGAGGCGTTG (SEQ ID NO:12720), TGAGGGGGGCGTCGAGTTGTTGTTTTT (SEQ ID NO:12721) |
| Target1349 | chr13:51417538-51417648 | TGGGTTAGGGTGTAGGGTTCGCGGTTT (SEQ ID NO:12722), TTGGGTTAGGGTGTAGGGTTCGCGGTT (SEQ ID NO:12723), TTTGGGTTAGGGTGTAGGGTTCGCGGT (SEQ ID NO:12724), TCGGGGGAAGGGTAGTAATTCGGCGTT (SEQ ID NO:12725), TTCGGGGGAAGGGTAGTAATTCGGCGT (SEQ ID NO:12726), TAGGAGTGGGGTTGGGGGGACGGTTTA (SEQ ID NO:12727), TGTAGTAGGAGTGGGGTTGGGGGGACG (SEQ ID NO:12728), TGTTGTAGTAGGAGTGGGGTTGGGGGG (SEQ ID NO:12729), GTAGTAGGAGTGGGGTTGGGGGGACGG (SEQ ID NO:12730), TGTTGTAGTAGGAGTGGGGTTGGGGGGA (SEQ ID NO:12731) |
| Target1350 | chr13:51417661-51417687 | CGTGGTTTGGGTTTCGCGGGTTTTCG (SEQ ID NO:12732), GCGGGTTTTCGGGGGCGATTGGATC (SEQ ID NO:12733), GCGGGTTTTCGGGGGCGATTGGAT (SEQ ID NO:12734), GGTTTGAGCGACGGGTTGGAGCGG (SEQ ID NO:12735), GGGTTTGAGCGACGGGTTGGAGCG (SEQ ID NO:12736), TAGGAGTGGGGTTGGGGGGACGGTTTA (SEQ ID NO:12737), TGTAGTAGGAGTGGGGTTGGGGGGACG (SEQ ID NO:12738), TGTTGTAGTAGGAGTGGGGTTGGGGGG (SEQ ID NO:12739), GTAGTAGGAGTGGGGTTGGGGGGACGG (SEQ ID NO:12740), TGTTGTAGTAGGAGTGGGGTTGGGGGGA (SEQ ID NO:12741) |
| Target1351 | chr13:51417768-51417796 | CGTGGTTTGGGTTTCGCGGGTTTTCGG (SEQ ID NO:12742), CGTGGTTTGGGTTTCGCGGGTTTTCG (SEQ ID NO:12743), GTGGTTTGGGTTTCGCGGGTTTTCGG (SEQ ID NO:12744), GCGGGTTTTCGGGGGCGATTGGATC (SEQ ID NO:12745), GCGGGTTTTCGGGGGCGATTGGAT (SEQ ID |

FIGURE 5 CONTINUED

NO:12746), GAGCGCGTCGGGTCGTTAGC (SEQ ID NO:12747),
TCGATTATATACGTTGTGAGATTTAGAGGTCGAGGA (SEQ ID NO:12748),
GTCGATTATATACGTTGTGAGATTTAGAGGTCGAGG (SEQ ID NO:12749),
GGTCGATTATATACGTTGTGAGATTTAGAGGTCGAG (SEQ ID NO:12750)

| Target1352 | chr13:51417803-51417813 | TGGAGGTTATTAAGGGCGTAGGGTTGGT (SEQ ID NO:12751), GGAGGTTATTAAGGGCGTAGGGTTGGT (SEQ ID NO:12752), TGGAGGTTATTAAGGGCGTAGGGTTGG (SEQ ID NO:12753), TGGTGGTTGATGGAGGTTATTAAGGGCGT (SEQ ID NO:12754), GGTGGTTGATGGAGGTTATTAAGGGCGT (SEQ ID NO:12755), TTTAGAGTCGGGGGCGGGGTC (SEQ ID NO:12756), GGGGTCGATTATATACGTTGTGAGATTTAGAGGTCG (SEQ ID NO:12757), GGGTCGATTATATACGTTGTGAGATTTAGAGGTCG (SEQ ID NO:12758), GGGGTCGATTATATACGTTGTGAGATTTAGAGGTC (SEQ ID NO:12759), GGGTCGATTATATACGTTGTGAGATTTAGAGGTCGA (SEQ ID NO:12760) |
| Target1353 | chr13:51417831-51417847 | GCGTGTAGGTGGAGTAGTAGCGAGGGA (SEQ ID NO:12761), TGTAGGTGGAGTAGTAGCGAGGGAGGC (SEQ ID NO:12762), GCGTGTAGGTGGAGTAGTAGCGAGGGAG (SEQ ID NO:12763), GTGTAGGTGGAGTAGTAGCGAGGGAGGC (SEQ ID NO:12764), CGTGTAGGTGGAGTAGTAGCGAGGGAGG (SEQ ID NO:12765), AGGCGAAGGTAGAGGTTAGTACGGGTT (SEQ ID NO:12766), TAGGCGAAGGTAGAGGTTAGTACGGGT (SEQ ID NO:12767), AGGCGAAGGTAGAGGTTAGTACGGGT (SEQ ID NO:12768), AGGCGAAGGTAGAGGTTAGTACGGGTTA (SEQ ID NO:12769), TAGGCGAAGGTAGAGGTTAGTACGGGTT (SEQ ID NO:12770) |
| Target1354 | chr13:51417855-51417881 | CGGGGGCGTTGGGGTCGTTAAGGTTAT (SEQ ID NO:12771), CGGGGGCGTTGGGGTCGTTAAGGTTATA (SEQ ID NO:12772), GCGTGTAGGTGGAGTAGTAGCGAGGGA (SEQ ID NO:12773), CGGGGGCGTTGGGGTCGTTAAGGTTA (SEQ ID NO:12774), TGTAGGTGGAGTAGTAGCGAGGGAGGC (SEQ ID NO:12775), AGGCGAAGGTAGAGGTTAGTACGGGTT (SEQ ID NO:12776), TAGGCGAAGGTAGAGGTTAGTACGGGT (SEQ ID NO:12777), AGGCGAAGGTAGAGGTTAGTACGGGT (SEQ ID NO:12778), AGGCGAAGGTAGAGGTTAGTACGGGTTA (SEQ ID NO:12779), TAGGCGAAGGTAGAGGTTAGTACGGGTT (SEQ ID NO:12780) |
| Target1355 | chr13:53313143-53313336 | TAGTCGCGCGGGGTTGGAGGGTTTTAT (SEQ ID NO:12781), GGGGGAGTTTACGTTGGGTTCGAGGGGT (SEQ ID NO:12782), AGGGGAGTTTACGTTGGGTTCGAGGGG (SEQ ID NO:12783), GTAGTCGCGCGGGGTTGGAGGGTTTTA (SEQ ID NO:12784), TTTTGAGTAGTCGCGCGGGGTTGGAGG (SEQ ID NO:12785), GCGCGGTTGTTTAAGGTGGGAGTCGTG (SEQ ID NO:12786), GTTGGGGGTCGTAGGTGTTGGCGGTAT (SEQ ID NO:12787), CGCGGTTGTTTAAGGTGGGAGTCGTGG (SEQ ID NO:12788), TTTTTGGGGGTTATCGCGTGGGGTTCG (SEQ ID NO:12789), GGGGTATTCGTAGGAGTTCGGGCGAGT (SEQ ID NO:12790) |
| Target1356 | chr13:53313337-53313459 | TAGTCGCGCGGGGTTGGAGGGTTTTAT (SEQ ID NO:12791), AGTTTTTAGGGAGTGGGGAGTCGGGCG (SEQ ID NO:12792), AGTGGGGAGTCGGGCGGGAAATAGTTC (SEQ ID NO:12793), GAGTGGGGAGTCGGGCGGGAAATAGTT (SEQ ID NO:12794), GTAGTCGCGCGGGGTTGGAGGGTTTTA (SEQ ID NO:12795), GTTGGGGGTCGTAGGTGTTGGCGGTAT (SEQ ID NO:12796), CGGTAGAGGGTGTAGGTTTTGGGGCGA (SEQ ID NO:12797), TCGGTAGAGGGTGTAGGTTTTGGGGCG (SEQ ID NO:12798), GGCGAAGGTTTTGTGTTGCGGGGTTTG (SEQ ID NO:12799), TTTTTGGGGGTTATCGCGTGGGGTTCG (SEQ ID NO:12800) |
| Target1357 | chr13:53313529-53313622 | GTAGTCGGGCGTGGAAGTGGGATGAGT (SEQ ID NO:12801), TGTAGTCGGGCGTGGAAGTGGGATGAG (SEQ ID NO:12802), TTGTAGTCGGGCGTGGAAGTGGGATGA (SEQ ID NO:12803), AGTCGGGCGTGGAAGTGGGATGAGTAA (SEQ ID NO:12804), CGAGGGTTTTTTGTAGTCGGGCGTGGA (SEQ ID NO:12805), GTTATCGAATGGGTGTGTTGGCGGGGG (SEQ ID NO:12806), CGAATGGGTGTGTTGGCGGGGGGATAA (SEQ ID NO:12807), TTATCGAATGGGTGTGTTGGCGGGGGG (SEQ ID NO:12808), TGTTATCGAATGGGTGTGTTGGCGGGG (SEQ ID NO:12809), GAATGGGTGTGTTGGCGGGGGGATAAA (SEQ ID NO:12810) |
| Target1358 | chr13:53421357-53421510 | GAAGGGTGAGGTTGTCGGCGCGTTTG (SEQ ID NO:12811), GAAGGGTGAGGTTGTCGGCGCGTTTGG (SEQ ID NO:12812), GAAGGGTGAGGTTGTCGGCGCGTTT (SEQ ID NO:12813), CGAAGGGTGAGGTTGTCGGCGCGTTTG (SEQ ID NO:12814), GTAGCGGCGAAGGGTGAGGTTGTCGG (SEQ ID NO:12815), GTCGTTGTATTCGGGGGAGCGGACGTT (SEQ ID NO:12816), TCGTTGTATTCGGGGGAGCGGACGTTA (SEQ ID NO:12817), GTCGTCGTTGTATTCGGGGGAGCGGAC (SEQ ID NO:12818), CGTTGTATTCGGGGGAGCGGACGTTAG (SEQ ID NO:12819), CGTTGTATTCGGGGGAGCGGACGTTAGT (SEQ ID NO:12820) |
| Target1359 | chr13:53421578-53421587 | TGATTTTGTAGGTGGTAGCGCGGGGTT (SEQ ID NO:12821), GAAGGGTGAGGTTGTCGGCGCGTTTG (SEQ ID NO:12822), CGATGATTTTGTAGGTGGTAGCGCGGGG (SEQ ID NO:12823), ATGATTTTGTAGGTGGTAGCGCGGGGT (SEQ ID NO:12824), GAAGGGTGAGGTTGTCGGCGCGTTTGG (SEQ ID NO:12825) |
| Target1360 | chr13:53421602-53421670 | GGGTTCGGTTAGGGTGAGGCGGTTTGA (SEQ ID NO:12826), CGGGTTCGGTTAGGGTGAGGCGGTTTG (SEQ ID NO:12827), GGTTCGGTTAGGGTGAGGCGGTTTGAT (SEQ ID NO:12828), TTCGGTTAGGGTGAGGCGGTTTGATCG (SEQ ID NO:12829), GGGTTCGGTTAGGGTGAGGCGGTTTGAT (SEQ ID NO:12830), CGTGGTGTTCGTATTTGGCGTTCGTAT (SEQ ID NO:12831), CGTGGTGTTCGTATTTGGCGTTCGTATT (SEQ ID NO:12832), CGTGGTGTTCGTATTTGGCGTTCGTA (SEQ ID NO:12833), CGTGGTGTTCGTATTTGGCGTTCGTATTT (SEQ ID NO:12834), CGTGGTGTTCGTATTTGGCGTTCGT (SEQ ID NO:12835) |

FIGURE 5 CONTINUED

| Target1361 | chr13:53421688-53421694 | GGGTTCGGTTAGGGTGAGGCGGTTTGA (SEQ ID NO:12836), CGGGTTCGGTTAGGGTGAGGCGGTTTG (SEQ ID NO:12837), GGTTCGGTTAGGGTGAGGCGGTTTGAT (SEQ ID NO:12838), TTCGGTTAGGGTGAGGCGGTTTGATCG (SEQ ID NO:12839), GGGTTCGGTTAGGGTGAGGCGGTTTGAT (SEQ ID NO:12840), CGTGGTGTTCGTATTTGGCGTTCGTAT (SEQ ID NO:12841), CGCGTTCGTGGGTTTTTTGTTTTTCGA (SEQ ID NO:12842), CGTGGTGTTCGTATTTGGCGTTCGTATT (SEQ ID NO:12843), CGCGTTCGTGGGTTTTTTGTTTTTCGAT (SEQ ID NO:12844), CGTGGTGTTCGTATTTGGCGTTCGTA (SEQ ID NO:12845) |
| Target1362 | chr13:53421731-53421738 | CGGGGTGCGGGCGTTAAATGCGAATAT (SEQ ID NO:12846), GGGTTCGGTTAGGGTGAGGCGGTTTGA (SEQ ID NO:12847), CGGGGTGCGGGCGTTAAATGCGAATA (SEQ ID NO:12848), CGGGGTGCGGGCGTTAAATGCGAATATT (SEQ ID NO:12849), CGGGTTCGGTTAGGGTGAGGCGGTTTG (SEQ ID NO:12850), GTGGTCGAAGTGGAGTTGGCGGAAGA (SEQ ID NO:12851), CGCGTTCGTGGGTTTTTTGTTTTTCGA (SEQ ID NO:12852), TGGTCGAAGTGGAGTTGGCGGAAGA (SEQ ID NO:12853), GTGGTCGAAGTGGAGTTGGCGGAAG (SEQ ID NO:12854), CGCGTTCGTGGGTTTTTTGTTTTTCGAT (SEQ ID NO:12855) |
| Target1363 | chr13:100608123-100608186 | GTCGGGGTAAGGACGTAGGGGC (SEQ ID NO:12856), GCGTTTTTTATGTTGGAAGGATTTTTAGTTTGGAGC (SEQ ID NO:12857), CGTTTTTTATGTTGGAAGGATTTTTAGTTTGGAGCG (SEQ ID NO:12858), TTTTATGTTGGAAGGATTTTTAGTTTGGAGCGGAAA (SEQ ID NO:12859), TTTTTATGTTGGAAGGATTTTTAGTTTGGAGCGGAA (SEQ ID NO:12860), GCGGTTAGTCGGGTTAGAAACGTGGGC (SEQ ID NO:12861), TGCGGTTAGTCGGGTTAGAAACGTGGG (SEQ ID NO:12862), TGCGGTTAGTCGGGTTAGAAACGTGGGC (SEQ ID NO:12863), TTGCGGTTAGTCGGGTTAGAAACGTGGG (SEQ ID NO:12864), TTGCGGTTAGTCGGGTTAGAAACGTGGGC (SEQ ID NO:12865) |
| Target1364 | chr13:100608216-100608228 | GTCGGGGTAAGGACGTAGGGGC (SEQ ID NO:12866), ACGTTTTTGGTTCGGTTAGTCGTAATTTTTTGGA (SEQ ID NO:12867), ACGTTTTTGGTTCGGTTAGTCGTAATTTTTTGGAT (SEQ ID NO:12868), TGGTTCGGTTAGTCGTAATTTTTTGGATGTAAACG (SEQ ID NO:12869), CGTTTTTGGTTCGGTTAGTCGTAATTTTTTGGATG (SEQ ID NO:12870), AGGAGCGGGGAGTTGTTGAAAGTCGGG (SEQ ID NO:12871), GGAGCGGGGAGTTGTTGAAAGTCGGGT (SEQ ID NO:12872), GAGGAGCGGGGAGTTGTTGAAAGTCGG (SEQ ID NO:12873), GAGCGGGGAGTTGTTGAAAGTCGGGTT (SEQ ID NO:12874), GGAGCGGGGAGTTGTTGAAAGTCGGG (SEQ ID NO:12875) |
| Target1365 | chr13:100608251-100608317 | CGTTGCGGCGTGTGGGGAAAGATGATT (SEQ ID NO:12876), CGTTGCGGCGTGTGGGGAAAGATGAT (SEQ ID NO:12877), CGTTGCGGCGTGTGGGGAAAGATGATTA (SEQ ID NO:12878), GCGTTGCGGCGTGTGGGGAAAGATGAT (SEQ ID NO:12879), CGTTGCGGCGTGTGGGGAAAGATGA (SEQ ID NO:12880), AGGAGCGGGGAGTTGTTGAAAGTCGGG (SEQ ID NO:12881), TGGGGGGGTTGTAGTTTCGGGCGTAGTT (SEQ ID NO:12882), TTGGGGGGTTGTAGTTTCGGGCGTAGT (SEQ ID NO:12883), GGAGCGGGGAGTTGTTGAAAGTCGGGT (SEQ ID NO:12884), GAGGAGCGGGGAGTTGTTGAAAGTCGG (SEQ ID NO:12885) |
| Target1366 | chr13:100608341-100608371 | CGTTGCGGCGTGTGGGGAAAGATGATT (SEQ ID NO:12886), CGTTGCGGCGTGTGGGGAAAGATGAT (SEQ ID NO:12887), CGTTGCGGCGTGTGGGGAAAGATGATTA (SEQ ID NO:12888), GCGTTGCGGCGTGTGGGGAAAGATGAT (SEQ ID NO:12889), CGTTGCGGCGTGTGGGGAAAGATGA (SEQ ID NO:12890), CGTGCGCGGAGGTAGTTTTTTGGGTGT (SEQ ID NO:12891), AGAGGGGAGTGGGAGTAGGAGGTGTCG (SEQ ID NO:12892), CGGAGAGGGGAGTGGGAGTAGGAGGTG (SEQ ID NO:12893), AGTGGGAGTAGGAGGTGTCGGTTTGGC (SEQ ID NO:12894), TGGGGGGGTTGTAGTTTCGGGCGTAGTT (SEQ ID NO:12895) |
| Target1367 | chr13:100608449-100608462 | TCGTAGTGGAGTTGCGTTCGGGGTTGT (SEQ ID NO:12896), TGTGGGTCGTAGTGGAGTTGCGTTCGG (SEQ ID NO:12897), GGTCGTAGTGGAGTTGCGTTCGGGGTT (SEQ ID NO:12898), GTCGTAGTGGAGTTGCGTTCGGGGTTG (SEQ ID NO:12899), GTGGGTCGTAGTGGAGTTGCGTTCGGG (SEQ ID NO:12900), GGAGTAGGAGGTGTCGGTTTGGCGTGT (SEQ ID NO:12901), TTGTTTACGGTTGGGCGAGAGGGGAG (SEQ ID NO:12902), AGAGGGGAGTGGGAGTAGGAGGTGTCG (SEQ ID NO:12903), CGGAGAGGGGAGTGGGAGTAGGAGGTG (SEQ ID NO:12904), GTTGTTTACGGTTGGGCGGAGAGGGGA (SEQ ID NO:12905) |
| Target1368 | chr13:100641337-100641413 | TGCGTTGCGGGTAGTTGTTCGTAGGGA (SEQ ID NO:12906), GCGTTGCGTTGCGGGTAGTTGTTCGTA (SEQ ID NO:12907), GCGTTGCGGGTAGTTGTTCGTAGGGAG (SEQ ID NO:12908), TTGCGTTGCGGGTAGTTGTTCGTAGGG (SEQ ID NO:12909), CGTTGCGTTGCGGGTAGTTGTTCGTAGG (SEQ ID NO:12910), TGGATGGAGGTGAGCGCGAAGGAAGTC (SEQ ID NO:12911), GTGGATGGAGGTGAGCGCGAAGGAAGT (SEQ ID NO:12912), TTTAGGTGGTGGATGGAGGTGAGCGCG (SEQ ID NO:12913), GGTGGATGGAGGTGAGCGCGAAGGAAG (SEQ ID NO:12914), TAGGTGGTGGATGGAGGTGAGCGCGAA (SEQ ID NO:12915) |
| Target1369 | chr13:100641490-100641497 | TGTCGCGGTTGGAGTACGGTTTTTGTT (SEQ ID NO:12916), TTGTCGCGGTTGGAGTACGGTTTTTGT (SEQ ID NO:12917), TTGTCGCGGTTGGAGTACGGTTTTTGTT (SEQ ID NO:12918), TTTGTCGCGGTTGGAGTACGGTTTTTGT (SEQ ID NO:12919), TTTGTCGCGGTTGGAGTACGGTTTTTG (SEQ ID NO:12920), TGACGGGTTTTTCGAGGGGGTTTTAGT (SEQ ID NO:12921), ACGGGTTTTTCGAGGGGGTTTTAGTGT (SEQ ID NO:12922), TGACGGGTTTTTCGAGGGGGTTTTAGTT (SEQ ID NO:12923), ATGACGGGTTTTTCGAGGGGGTTTTAGT (SEQ ID NO:12924), GACGGGTTTTTCGAGGGGGTTTTAGTGT (SEQ ID NO:12925) |

FIGURE 5 CONTINUED

Target1370    chr13:100641499-100641606    TGTCGCGGTTGGAGTACGGTTTTTGTT (SEQ ID NO:12926), TTGTCGCGGTTGGAGTACGGTTTTTGT (SEQ ID NO:12927), TTGTCGCGGTTGGAGTACGGTTTTTGTT (SEQ ID NO:12928), TGTCGCGGTTGGAGTACGGTTTTTGT (SEQ ID NO:12929), CGCGGTTGGAGTACGGTTTTTGTTAGTCG (SEQ ID NO:12930), TGACGGGTTTTTCGAGGGGGTTTTAGT (SEQ ID NO:12931), TCGACGCGGTTTTTGATTTTGGAGTGA (SEQ ID NO:12932), ACGGGTTTTTCGAGGGGGTTTTAGTTGT (SEQ ID NO:12933), TGACGGGTTTTTCGAGGGGGTTTTAGTT (SEQ ID NO:12934), ATGACGGGTTTTTCGAGGGGGTTTTAGT (SEQ ID NO:12935)

Target1371    chr13:100641681-100641743    CGCGTCGGTTTTTGTTTGGGGTATGGGT (SEQ ID NO:12936), TCGCGTCGGTTTTTGTTTGGGGTATGGG (SEQ ID NO:12937), AGAGGTCGCGTCGGTTTTGTTTGGGGT (SEQ ID NO:12938), GAGGTCGCGTCGGTTTTGTTTGGGGTA (SEQ ID NO:12939), TAGAGGTCGCGTCGGTTTTGTTTGGGG (SEQ ID NO:12940), TAGGGGGTGGGGAAGAGGAAGAGCGAA (SEQ ID NO:12941), TTAGGGGGTGGGGAAGAGGAAGAGCGA (SEQ ID NO:12942), GTTAGGTATGGGCGTGCGGGTTTTGGG (SEQ ID NO:12943), TTAGGTATGGGCGTGCGGGTTTTGGGA (SEQ ID NO:12944), GTTAGGGGGTGGGGAAGAGGAAGAGCG (SEQ ID NO:12945)

Target1372    chr13:100649601-100649626    ATTTTCGCGCGGATGGTTTAGGAGGCG (SEQ ID NO:12946), TTTTCGCGCGGATGGTTTAGGAGGGGC (SEQ ID NO:12947), GATTTTCGCGCGGATGGTTTAGGAGGGG (SEQ ID NO:12948), TTTTCGCGCGGATGGTTTAGGAGGGG (SEQ ID NO:12949), AGGGGAGTATTAGAGGGTCGCGCGAGGTT (SEQ ID NO:12950), CGGTGGGGATCGCGTCGGTATAGGATA (SEQ ID NO:12951), CGTCGGTATAGGATAACGCGGTGGAGGG (SEQ ID NO:12952), CGGTGGGGATCGCGTCGGTATAGGAT (SEQ ID NO:12953), GCGGTGGGGATCGCGTCGGTATAGGAT (SEQ ID NO:12954), TCGGTATAGGATAACGCGGTGGAGGGA (SEQ ID NO:12955)

Target1373    chr13:100649671-100649702    GAGTTAAGGTGGGCGGGGGTAGGTGTT (SEQ ID NO:12956), TTGAGTTAAGGTGGGCGGGGGTAGGTG (SEQ ID NO:12957), AGTTAAGGTGGGCGGGGGTAGGTGTTT (SEQ ID NO:12958), TGAGTTAAGGTGGGCGGGGGTAGGTGT (SEQ ID NO:12959), ATTTTCGCGCGGATGGTTTAGGAGGGG (SEQ ID NO:12960), GGATTCGGTGGGAGGAAGGAGTGCGAA (SEQ ID NO:12961), GGGAATCGTGAAGTCGGGTTTGCGGAT (SEQ ID NO:12962), CGGGAATCGTGAAGTCGGGTTTGCGGA (SEQ ID NO:12963), CGGTGGGGATCGCGTCGGTATAGGATA (SEQ ID NO:12964), CGGGAATCGTGAAGTCGGGTTTGCGG (SEQ ID NO:12965)

Target1374    chr13:100649715-100649726    GAGTTAAGGTGGGCGGGGGTAGGTGTT (SEQ ID NO:12966), TTGAGTTAAGGTGGGCGGGGGTAGGTG (SEQ ID NO:12967), AGTTAAGGTGGGCGGGGGTAGGTGTTT (SEQ ID NO:12968), TGAGTTAAGGTGGGCGGGGGTAGGTGT (SEQ ID NO:12969), ATTTTCGCGCGGATGGTTTAGGAGGGG (SEQ ID NO:12970), GGATTCGGTGGGAGGAAGGAGTGCGAA (SEQ ID NO:12971), GGGAATCGTGAAGTCGGGTTTGCGGAT (SEQ ID NO:12972), CGGGAATCGTGAAGTCGGGTTTGCGGA (SEQ ID NO:12973), CGGGAATCGTGAAGTCGGGTTTGCGG (SEQ ID NO:12974), GGATTCGGTGGGAGGAAGGAGTGCGA (SEQ ID NO:12975)

Target1375    chr13:100649777-100649801    TATGTCGGCGCGGTTTTTATCGTTCGA (SEQ ID NO:12976), ATGTCGGCGCGGTTTTTATCGTTCGA (SEQ ID NO:12977), TTATGTCGGCGCGGTTTTTATCGTTCG (SEQ ID NO:12978), TTATGTCGGCGCGGTTTTTATCGTTCGA (SEQ ID NO:12979), TCGGCGCGGTTTTTATCGTTCGATTTA (SEQ ID NO:12980), TGTGGTTTTGCGGGAGTGAGTTGAGGG (SEQ ID NO:12981), TGTGGTTTTGCGGGAGTGAGTTGAGGGA (SEQ ID NO:12982), GTGGTTTTGCGGGAGTGAGTTGAGGGA (SEQ ID NO:12983), TGGTTTTGCGGGAGTGAGTTGAGGGAGT (SEQ ID NO:12984), GGTTTTGCGGGAGTGAGTTGAGGGAGT (SEQ ID NO:12985)

Target1376    chr13:100649912-100649918    TTTTCGGGTTTTCGGGTATGTGAGGGA (SEQ ID NO:12986), TCGGGTTTTCGGGTATGTGAGGGATTT (SEQ ID NO:12987), TTCGGGTTTTCGGGTATGTGAGGGATT (SEQ ID NO:12988), TTTCGGGTTTTCGGGTATGTGAGGGAT (SEQ ID NO:12989), CGGGTTTTCGGGTATGTGAGGGATTTG (SEQ ID NO:12990), GTCGATCGATGTGGGGAAGGGGAAGGG (SEQ ID NO:12991), GGTCGATCGATGTGGGGAAGGGGAAGG (SEQ ID NO:12992), CGGTCGATCGATGTGGGGAAGGGGAAG (SEQ ID NO:12993), ATCGATGTGGGGAAGGGGAAGGGGTTC (SEQ ID NO:12994), GATCGATGTGGGGAAGGGGAAGGGGTT (SEQ ID NO:12995)

Target1377    chr13:100649941-100649966    CGGTCGGTCGAGGGAGTTTAGAGTCG (SEQ ID NO:12996), GGTCGGTCGAGGGAGTTTAGAGTCG (SEQ ID NO:12997), CGGTCGGTCGAGGGAGTTTAGAGTC (SEQ ID NO:12998), GTGGGAAGTCGACGATGTTTGAGGCG (SEQ ID NO:12999), TGGGAAGTCGACGATGTTTGAGGCG (SEQ ID NO:13000), GTGGGAAGTCGACGATGTTTGAGGC (SEQ ID NO:13001), CGATGTTTGAGGCGTTTTGTTTTCGGTTT (SEQ ID NO:13002), TCGTAGGAAAGGATTAGGAGAGGTCGTTGT (SEQ ID NO:13003)

Target1378    chr13:109148125-109148632    TCGGGAGGGTGTTTCGGGTCGGATTTG (SEQ ID NO:13004), GTCGGGAGGGTGTTTCGGGTCGGATTT (SEQ ID NO:13005), GGGCGTGGAGAGGAGGTTTGTCGGTTT (SEQ ID NO:13006), GGGTCGGATTTGCGGCGTTGGGTTTTT (SEQ ID NO:13007), GGCGTGGAGAGGAGGTTTGTCGGTTTT (SEQ ID NO:13008), GCGGGTGAGAGGGGTCGGTAGTTGTTT (SEQ ID NO:13009), GCGTTTGGGAGCGGTTGTGTAGGTGAT (SEQ ID NO:13010), TCGTGCGGGAATTTTGGGTGGGGATTT (SEQ ID NO:13011), ATCGTGCGGGAATTTTGGGTGGGGATT (SEQ ID NO:13012), GCGGGTGAGAGGGGTCGGTAGTTGTT (SEQ ID NO:13013)

Target1379    chr13:111178104-111178204    GGGGGGACGAGTTTTTAGGAAGTAGTTGTGG (SEQ ID NO:13014), AGAGTTTTTAGTAGGGAGGGTCGAGTCGA (SEQ ID NO:13015), AGGTGAGAGTTTTTAGTAGGGAGGGTCGA (SEQ ID NO:13016), GGGGGGACGAGTTTTTAGGAAGTAGTTGTGGG (SEQ ID NO:13017),

FIGURE 5 CONTINUED

| | | |
|---|---|---|
| | | GGGGGGACGAGTTTTTAGGAAGTAGTTGTGG (SEQ ID NO:13018), TCGAGAGGTAGGTGGGGGTTAAGGTGT (SEQ ID NO:13019), TTCGAGAGGTAGGTGGGGGTTAAGGTGT (SEQ ID NO:13020), TTGAGAGGTAGGTGGGGGTTAAGGTG (SEQ ID NO:13021), CGAGAGGTAGGTGGGGGTTAAGGTGTA (SEQ ID NO:13022), TTTCGAGAGGTAGGTGGGGGTTAAGGT (SEQ ID NO:13023) |
| Target1380 | chr13:111178351-111178399 | TGGTAGGAAGGGGTTTTATAGACGTTTTTGGT (SEQ ID NO:13024), TGGTAGGAAGGGGTTTTATAGACGTTTTTGGTG (SEQ ID NO:13025), GGTAGGAAGGGGTTTTATAGACGTTTTTGGTGA (SEQ ID NO:13026), AGGAAGGGGTTTTATAGACGTTTTTGGTGATGT (SEQ ID NO:13027), TGGTAGGAAGGGGTTTTATAGACGTTTTTGGTGA (SEQ ID NO:13028), AGGGAGGAGGGGATGAGTTGGTTTGTA (SEQ ID NO:13029), TAGGGAGGAGGGGATGAGTTGGTTTGT (SEQ ID NO:13030), GGGGAGGAGGGGATGAGTTGGTTTGTAGT (SEQ ID NO:13031), GGGAGGAGGGGATGAGTTGGTTTGTAG (SEQ ID NO:13032), AGGGAGGAGGGGATGAGTTGGTTTGTAGT (SEQ ID NO:13033) |
| Target1381 | chr13:112547564-112547607 | GCGTTTCGTGTGATTTCGTGTCGTTGT (SEQ ID NO:13034), GCGTTTCGTGTGATTTCGTGTCGTTGTT (SEQ ID NO:13035), GCGTTTCGTGTGATTTCGTGTCGTTGTTT (SEQ ID NO:13036), GCGTTTCGTGTGATTTCGTGTCGTTG (SEQ ID NO:13037), TCGCGTTTTTGTTGTTTGGGAGAAAGC (SEQ ID NO:13038), GAGAAACGGATATTTTTGGTTGTTACGAGGGTC (SEQ ID NO:13039) |
| Target1382 | chr13:112547626-112547671 | GCGTTTCGTGTGATTTCGTGTCGTTGT (SEQ ID NO:13040), GCGTTTCGTGTGATTTCGTGTCGTTGTT (SEQ ID NO:13041), CGCGTTCGGGAGGGGATTATATTTTTGCG (SEQ ID NO:13042), CGCGTTCGGGAGGGGATTATATTTTTGCGT (SEQ ID NO:13043), GCGTTCGGGAGGGGATTATATTTTTGCGT (SEQ ID NO:13044), CGATGGGATAGGTTGTGTTGCGTTTCG (SEQ ID NO:13045), TGGGATAGGTTGTGTTGCGTTTCGAGA (SEQ ID NO:13046), CGATGGGATAGGTTGTGTTGCGTTTCGA (SEQ ID NO:13047), TCGATGGGATAGGTTGTGTTGCGTTTCG (SEQ ID NO:13048), TCGATGGGATAGGTTGTGTTGCGTTTCGA (SEQ ID NO:13049) |
| Target1383 | chr13:112547730-112547774 | TGCGTTGTTGGCGGAAGTGATTTGTTT (SEQ ID NO:13050), CGCGTTCGGGAGGGGATTATATTTTTGCG (SEQ ID NO:13051), CGCGTTCGGGAGGGGATTATATTTTTGCGT (SEQ ID NO:13052), TGCGTTGTTGGCGGAAGTGATTTGTTTT (SEQ ID NO:13053), GCGTTGTTGGCGGAAGTGATTTGTTTT (SEQ ID NO:13054), AGGTTTTTGGTTTGTTTGTTTTTCGTTACGGGA (SEQ ID NO:13055), GGTTTTTGGTTTGTTTGTTTTTCGTTACGGGA (SEQ ID NO:13056), AGGTTTTTGGTTTGTTTGTTTTTCGTTACGGGA (SEQ ID NO:13057), GGTTTTTGGTTTGTTTGTTTTTCGTTACGGGAG (SEQ ID NO:13058), GAGGTTTTTGGTTTGTTTGTTTTTCGTTACGGG (SEQ ID NO:13059) |
| Target1384 | chr13:112717140-112717159 | AGTTCGGGTTAGGGCGTAGATGATGGA (SEQ ID NO:13060), GTTCGGGTTAGGGCGTAGATGATGGAT (SEQ ID NO:13061), AGTTCGGGTTAGGGCGTAGATGATGGAT (SEQ ID NO:13062), TAGTTCGGGTTAGGGCGTAGATGATGGA (SEQ ID NO:13063), GTTCGGGTTAGGGCGTAGATGATGGATT (SEQ ID NO:13064), AGGTTTTGTTCGAGGGTTTGGAGCGCG (SEQ ID NO:13065), GGTTTTGTTCGAGGGTTTGGAGCGCGC (SEQ ID NO:13066), GAGGTTTTGTTCGAGGGTTTGGAGCGCG (SEQ ID NO:13067), GAGGTTTTGTTCGAGGGTTTGGAGCGC (SEQ ID NO:13068), GTTTTGTTCGAGGGTTTGGAGCGCGC (SEQ ID NO:13069) |
| Target1385 | chr13:112717207-112717256 | GGAGAGTTTCGGTGTTTTCGCGAGGGC (SEQ ID NO:13070), GCGGAGAGTTTCGGTGTTTTCGCGAGG (SEQ ID NO:13071), TTGGTTGTTAGAGCGAGTGAGGGGCGT (SEQ ID NO:13072), CGGAGAGTTTCGGTGTTTTCGCGAGGG (SEQ ID NO:13073), TGGTTGTTAGAGCGAGTGAGGGGCGTA (SEQ ID NO:13074), CGCGCGGAGTTATGAGGGGTAAAGAGGT (SEQ ID NO:13075), CGCGCGGAGTTATGAGGGGTAAAGAGG (SEQ ID NO:13076), TCGCGCGGAGTTATGAGGGGTAAAGAGG (SEQ ID NO:13078), GCGCGCGGAGTTATGAGGGGTAAAGAGG (SEQ ID NO:13077), TCGCGCGGAGTTATGAGGGGTAAAGAG (SEQ ID NO:13079) |
| Target1386 | chr13:112717281-112717303 | GGAGAGTTTCGGTGTTTTCGCGAGGGC (SEQ ID NO:13080), GCGGAGAGTTTCGGTGTTTTCGCGAGG (SEQ ID NO:13081), TTGGTTGTTAGAGCGAGTGAGGGGCGT (SEQ ID NO:13082), CGGAGAGTTTCGGTGTTTTCGCGAGGG (SEQ ID NO:13083), TGGTTGTTAGAGCGAGTGAGGGGCGTA (SEQ ID NO:13084), GGCGGGGCGGAGAAGGTTCGGTTTTTT (SEQ ID NO:13085), CGCGCGGAGTTATGAGGGGTAAAGAGGT (SEQ ID NO:13086), CGCGCGGAGTTATGAGGGGTAAAGAGG (SEQ ID NO:13087), TCGCGCGGAGTTATGAGGGGTAAAGAGG (SEQ ID NO:13088), GGGCGGGGCGGAGAAGGTTCGGTTTTTT (SEQ ID NO:13089) |
| Target1387 | chr13:112717310-112717324 | GGAGAGTTTCGGTGTTTTCGCGAGGGC (SEQ ID NO:13090), GCGGAGAGTTTCGGTGTTTTCGCGAGG (SEQ ID NO:13091), CGGAGAGTTTCGGTGTTTTCGCGAGGG (SEQ ID NO:13092), TGTTAGAGCGAGTGAGGGGCGTAGAGG (SEQ ID NO:13093), TTGTTAGAGCGAGTGAGGGGCGTAGAGG (SEQ ID NO:13094), GGCGGGGCGGAGAAGGTTCGGTTTTTT (SEQ ID NO:13095), CGCGCGGAGTTATGAGGGGTAAAGAGGT (SEQ ID NO:13096), CGCGCGGAGTTATGAGGGGTAAAGAGG (SEQ ID NO:13097), GGGCGGGGGTGTTGGGGATATCGTAG (SEQ ID NO:13098), TCGCGCGGAGTTATGAGGGGTAAAGAGG (SEQ ID NO:13099) |
| Target1388 | chr13:112717328-112717421 | GGAGAGTTTCGGTGTTTTCGCGAGGGC (SEQ ID NO:13100), GCGGAGAGTTTCGGTGTTTTCGCGAGG (SEQ ID NO:13101), CGGAGAGTTTCGGTGTTTTCGCGAGGG (SEQ ID NO:13102), TGTTTTTTATGGTTTCGCGGGAGGA (SEQ ID NO:13103), GCGGAGAGTTTCGGTGTTTTCGCGAG (SEQ ID NO:13104), GGCGGGGCGGAGAAGGTTCGGTTTTTT (SEQ ID NO:13105), CGCGCGGAGTTATGAGGGGTAAAGAGGT (SEQ ID NO:13106), CGCGCGGAGTTATGAGGGGTAAAGAGG |

FIGURE 5 CONTINUED

{SEQ ID NO:13107), GGGCGGGGGGTGTTGGGGGATATCGTAG {SEQ ID NO:13108},
TCGCGCGGAGTTATGAGGGGTAAAGAGG {SEQ ID NO:13109)

| | | |
|---|---|---|
| Target1389 | chr13:112758613-112758653 | GGGGTTCGGGGATTTTGGGGGTCGAG {SEQ ID NO:13110), GTTCGGGGATTTTGGGGGTCGAGCG {SEQ ID NO:13111), GGGTTCGGGGATTTTGGGGGTCGAGC {SEQ ID NO:13112}, GGTTCGGGGATTTTGGGGGTCGAGC {SEQ ID NO:13113), GGTTCGGGGATTTTGGGGGTCGAGCG {SEQ ID NO:13114}, CGGCGGTGTTTTCGTTCGGGTTGGTTT {SEQ ID NO:13115), GCGGTGTTTTCGTTCGGGTTGGTTTCG {SEQ ID NO:13116}, GGCGGTGTTTTCGTTCGGGTTGGTTTC {SEQ ID NO:13117}, GCGGTGTTTTCGTTCGGGTTGGTTTCGT {SEQ ID NO:13118}, CGGCGGTGTTTTCGTTCGGGTTGGTT {SEQ ID NO:13119) |
| Target1390 | chr13:112758676-112758712 | GGGGATTTTGGGGGTCGAGCGAGGTTA {SEQ ID NO:13120), GTTCGGGGATTTTGGGGGTCGAGCGAG {SEQ ID NO:13121), GGGATTTTGGGGGTCGAGCGAGGTTAGT {SEQ ID NO:13122), GGGATTTTGGGGGTCGAGCGAGGTTAG {SEQ ID NO:13123), GGGGATTTTGGGGGTCGAGCGAGGTTAG {SEQ ID NO:13124}, GCGTTTTGAGTTTCGGTTTGGTCGTAGC {SEQ ID NO:13125), AGCGTTTTGAGTTTCGGTTTGGTCGTAGC {SEQ ID NO:13126}, AGCGTTTTGAGTTTCGGTTTGGTCGTAG {SEQ ID NO:13127), AGCGTTTTGAGTTTCGGTTTGGTCGT {SEQ ID NO:13128}, CGTGTTTTTATTAGGGTTGATATCGGTTCGTCGG {SEQ ID NO:13129} |
| Target1391 | chr13:112758718-112758745 | GGGGATTTTGGGGGTCGAGCGAGGTTA {SEQ ID NO:13130), TCGGCGATAGGGGGGAATTTCGTTGGG {SEQ ID NO:13131), GTCGGCGATAGGGGGGAATTTCGTTGG {SEQ ID NO:13132), GTTCGGGGATTTTGGGGGTCGAGCGAG {SEQ ID NO:13133}, GGGATTTTGGGGGTCGAGCGAGGTTAGT {SEQ ID NO:13134), GCGTTTTGAGTTTCGGTTTGGTCGTAGT {SEQ ID NO:13135), AGCGTTTTGAGTTTCGGTTTGGTCGTAGT {SEQ ID NO:13136), AGCGTTTTGAGTTTCGGTTTGGTCGTAG {SEQ ID NO:13137), AGCGTTTTGAGTTTCGGTTTGGTCGT {SEQ ID NO:13138}, CGTGTTTTTATTAGGGTTGATATCGGTTCGTCGG {SEQ ID NO:13139} |
| Target1392 | chr13:112758756-112758882 | GGGGATTTTGGGGGTCGAGCGAGGTTA {SEQ ID NO:13140), TAGGTCGGGGTTTAGGGCGTTGGGTTG {SEQ ID NO:13141), GTTAGGTCGGGGTTTAGGGCGTTGGGT {SEQ ID NO:13142), GGGTTTAGGGCGTTGGGTTGTGCGTTT {SEQ ID NO:13143}, TCGGCGATAGGGGGGAATTTCGTTGGG {SEQ ID NO:13144), TGGGAAAGGTGGGTTGGGGAGAAAGGG {SEQ ID NO:13145), AAGGTGGGTTGGGGAGAAAGGGCGTAG {SEQ ID NO:13146), GGTGGGTTGGGGAGAAAGGGCGTAGAG {SEQ ID NO:13147), AAAGGTGGGTTGGGGAGAAAGGGCGTA {SEQ ID NO:13148}, GAAAGGTGGGTTGGGGAGAAAGGGCGT {SEQ ID NO:13149) |
| Target1393 | chr13:112758986-112759113 | GTGGAGTGGGGACGGCGGGGTATAG {SEQ ID NO:13150), GAGTGGGGACGGCGGGGTATAGGAC {SEQ ID NO:13151), TGGGAGTGGGGACGGCGGGGTATAGGAC {SEQ ID NO:13152), GTGGAGTGGGGACGGCGGGGTATAGGA {SEQ ID NO:13153), GGAGTGGGGACGGCGGGGTATAGGAC {SEQ ID NO:13154}, CGGGGTCGTTTTTTGCGGGGTC {SEQ ID NO:13155), CGGGGTCGTTTTTTGCGGGGT {SEQ ID NO:13156), GGCGTTCGTAGTATTAAGTTGTTGGTTTTTGAGT {SEQ ID NO:13157), TGGCGTTCGTAGTATTAAGTTGTTGGTTTTTGAG {SEQ ID NO:13158), TGGCGTTCGTAGTATTAAGTTGTTGGTTTTTGAGT {SEQ ID NO:13159) |
| Target1394 | chr13:113436226-113436480 | TGTCGGGTTAAACGTCGTTATATTGTTGGGT {SEQ ID NO:13160), GTGTCGGGTTAAACGTCGTTATATTGTTGGGT {SEQ ID NO:13161), GTGTCGGGTTAAACGTCGTTATATTGTTGGGT {SEQ ID NO:13162), TGTGTCGGGTTAAACGTCGTTATATTGTTGGG {SEQ ID NO:13163), TGTGTCGGGTTAAACGTCGTTATATTGTTGGGT {SEQ ID NO:13164), GTGGGTTTTGTTTGGTAAGTGCGCGGT {SEQ ID NO:13165), AGTGGGTTTTGTTTGGTAAGTGCGCGGT {SEQ ID NO:13166}, AGTGGGTTTTGTTTGGTAAGTGCGCGG {SEQ ID NO:13167), TGGGTTTTGTTTGGTAAGTGCGCGGT {SEQ ID NO:13168}, GTGGGTTTTGTTTGGTAAGTGCGCGGTT {SEQ ID NO:13169} |
| Target1395 | chr13:113436564-113436678 | GTTGTTGGTTGGAAGCGGTCGGGAAGC {SEQ ID NO:13170), TGTTGTTGGTTGGAAGCGGTCGGGAAG {SEQ ID NO:13171), TTGTTGTTGGTTGGAAGCGGTCGGGAA {SEQ ID NO:13172), TTTGTTGTTGGTTGGAAGCGGTCGGGA {SEQ ID NO:13173), TTGTTGGTTGGAAGCGGTCGGGAAGC {SEQ ID NO:13174), TGGAGTCGTGTGGTATTGTTTATGTTATAGCGA {SEQ ID NO:13175), GGAGTCGTGTGGTATTGTTTATGTTATAGCGAGT {SEQ ID NO:13176), TGGAGTCGTGTGGTATTGTTTATGTTATAGCGAG {SEQ ID NO:13177), TGGAGTCGTGTGGTATTGTTTATGTTATAGCGAGT {SEQ ID NO:13178), TTGGAGTCGTGTGGTATTGTTTATGTTATAGCGA {SEQ ID NO:13179} |
| Target1396 | chr14:21093540-21093618 | GTGTGGTCGAGCGGTTTAAGGCGTTGG {SEQ ID NO:13180), TGTGGTCGAGCGGTTTAAGGCGTTGGA {SEQ ID NO:13181), AGTGTGGTCGAGCGGTTTAAGGCGTTG {SEQ ID NO:13182), CGTGTGTGGTAGTGTGGTCGAGTCGAGCGG {SEQ ID NO:13183}, AACGTGTGTGGTAGTGTGGTCGAGCGG {SEQ ID NO:13184), ACGTATTATTGGTAGTGGTGGGATTCGAATTTACG {SEQ ID NO:13185), TGTTGTGTTAAAACGTATTATTGGTAGTGGTGGGA {SEQ ID NO:13186), TGTTAAAACGTATTATTGGTAGTGGTGGGATTCGA {SEQ ID NO:13187), GTGTTAAAACGTATTATTGGTAGTGGTGGGATTCG {SEQ ID NO:13188), TGTGTTAAAACGTATTATTGGTAGTGGTGGGATTCG {SEQ ID NO:13189) |
| Target1397 | chr14:21093736-21093819 | CGGTTAGGTAGGGAGGTTTTTTCGTTCGC {SEQ ID NO:13190), TCGGTTAGGTAGGGAGGTTTTTTCGTTCGC {SEQ ID NO:13191), GGTTAGGTAGGGAGGTTTTTTCGTTCGC {SEQ ID NO:13192), TCGGTTAGGTAGGGAGGTTTTTTCGTTCG |

FIGURE 5 CONTINUED (SEQ ID NO:13193), TTCGGTTAGGTAGGGAGGTTTTTTCGTTCGC (SEQ ID NO:13194), GTTAGTATAACGGATAAAGTAGGAGATCGCGAGC (SEQ ID NO:13195), AGTTAGTATAACGGATAAAGTAGGAGATCGCGAGC (SEQ ID NO:13196), GCGGGAATTTAAATGGTGTAGTGTAAAAATTGGGG (SEQ ID NO:13197), GCGGGAATTTAAATGGTGTAGTGTAAAAATTGGGGT (SEQ ID NO:13198), TGCGGGAATTTAAATGGTGTAGTGTAAAAATTGGGG (SEQ ID NO:13199)

| Target1398 | chr14:21093995-21094036 | CGCGGTCGGTATTGTTTTAGGAGTTGTAGT (SEQ ID NO:13200), CGCGGTCGGTATTGTTTTAGGAGTTGTAGTT (SEQ ID NO:13201), CGCGGTCGGTATTGTTTTAGGAGTTGTAGTTT (SEQ ID NO:13202), CGCGGTCGGTATTGTTTTAGGAGTTGTAGTTTT (SEQ ID NO:13203), CGCGGTCGGTATTGTTTTAGGAGTTGTAGTTTTG (SEQ ID NO:13204), AGGGTTTAGGTAGGATATTTCGCGAGTATAGAGT (SEQ ID NO:13205), AGGGTTTAGGTAGGATATTTCGCGAGTATAGAGTT (SEQ ID NO:13206), GGGTTTAGGTAGGATATTTCGCGAGTATAGAGTTG (SEQ ID NO:13207), GGGTTTAGGTAGGATATTTCGCGAGTATAGAGTTGT (SEQ ID NO:13208), AGGGTTTAGGTAGGATATTTCGCGAGTATAGAGTTG (SEQ ID NO:13209) |
| --- | --- | --- |
| Target1399 | chr14:33401997-33402061 | CGGGAAGGAGGGAGTTAGGATTTCGGT (SEQ ID NO:13210), TCGGGAAGGAGGGAGTTAGGATTTCGGT (SEQ ID NO:13211), TCGGGAAGGAGGGAGTTAGGATTTCGG (SEQ ID NO:13212), CGGGAAGGAGGGAGTTAGGATTTCGGTT (SEQ ID NO:13213), TCGGGAAGGAGGGAGTTAGGATTTCGGTT (SEQ ID NO:13214), CGGTAGTCGTTGGGAAATAGAGGGAGGG (SEQ ID NO:13215), AGTCGTTGGGAAATAGAGGGAGGGAGT (SEQ ID NO:13216), CGGTAGTCGTTGGGAAATAGAGGGAGGGA (SEQ ID NO:13217), CGGTAGTCGTTGGGAAATAGAGGGAGG (SEQ ID NO:13218), CGGTAGTCGTTGGGAAATAGAGGGAGGGAG (SEQ ID NO:13219) |
| Target1400 | chr14:33402106-33402304 | TAGTTGCGTCGTGGGTTCGGTTAGCGA (SEQ ID NO:13220), TCGTGGGTTCGGTTAGCGAGAGTTGGG (SEQ ID NO:13221), GTGGGTTCGGTTAGCGAGAGTTGGGGT (SEQ ID NO:13222), GTAGTTGCGTCGTGGGTTCGGTTAGCG (SEQ ID NO:13223), CGTAGTTGCGTCGTGGGTTCGGTTAGC (SEQ ID NO:13224), GGGATTTAGAGGGGTAGGGCGGATTGGT (SEQ ID NO:13225), GGGATTTAGAGGGGTAGGGCGGATTGG (SEQ ID NO:13226), GGATTTAGAGGGGTAGGGCGGATTGGT (SEQ ID NO:13227), GAGGGGTAGGGCGGATTGGTTAGAAGT (SEQ ID NO:13228), AGAGGGGTAGGGCGGATTGGTTAGAAGT (SEQ ID NO:13229) |
| Target1401 | chr14:33402328-33402369 | CGGGTTTGCGGTAAGGGTAGGCGTTTG (SEQ ID NO:13230), TATTAGGGTGGGAGGGGGACGTTCGGGT (SEQ ID NO:13231), GGGTTTGCGGTAAGGGTAGGCGTTTGG (SEQ ID NO:13232), TCGGGTTTGCGGTAAGGGTAGGCGTTT (SEQ ID NO:13233), TTCGGGTTTGCGGTAAGGGTAGGCGTT (SEQ ID NO:13234), TTCGTCGGGATTTAGAGGGGTAGGGCG (SEQ ID NO:13235), CGTCGGGATTTAGAGGGGTAGGGCGGA (SEQ ID NO:13236), TCGTCGGGATTTAGAGGGGTAGGGCGG (SEQ ID NO:13237), GTCGGGATTTAGAGGGGTAGGGCGGAT (SEQ ID NO:13238), CGTCGGGATTTAGAGGGGTAGGGCGG (SEQ ID NO:13239) |
| Target1402 | chr14:33402429-33402617 | CGGGTTTGCGGTAAGGGTAGGCGTTTG (SEQ ID NO:13240), GGGTTTGCGGTAAGGGTAGGCGTTTGG (SEQ ID NO:13241), CGGCGGGTCGGTTGCGTTTTAGGTTTA (SEQ ID NO:13242), TTCGGGTTTGCGGTAAGGGTAGGCGTT (SEQ ID NO:13243), GGGACGTTAGGTTGGGCGGTTTGTGTT (SEQ ID NO:13244), GCGGTCGCGTCGTTTTAGTTTTCGGTT (SEQ ID NO:13245), GCGGTCGCGTCGTTTTAGTTTTCGGT (SEQ ID NO:13246), TGCGCGTTAAGGTTTGGGTTTCGTAGT (SEQ ID NO:13247), GCGGTCGCGTCGTTTTAGTTTTCGGTTA (SEQ ID NO:13248), TTTTGCGCGTTAAGGTTTGGGTTTCGT (SEQ ID NO:13249) |
| Target1403 | chr14:37126751-37126823 | TCGGGTGATCGGAAATAGGTAGGCGGA (SEQ ID NO:13250), CGGGTGATCGGAAATAGGTAGGCGGAG (SEQ ID NO:13251), CGGGTGATCGGAAATAGGTAGGCGGAGA (SEQ ID NO:13252), TCGGGTGATCGGAAATAGGTAGGCGGAG (SEQ ID NO:13253), TCGGGTGATCGGAAATAGGTAGGCGGAGA (SEQ ID NO:13254), AGAATGGTAGCGGGTTGGGTCGGGTTC (SEQ ID NO:13255), TAGAATGGTAGCGGGTTGGGTCGGGTT (SEQ ID NO:13256), TTAGAATGGTAGCGGGTTGGGTCGGGT (SEQ ID NO:13257), TGCGAGAGTAGGGGAGGGGTTTGTTGT (SEQ ID NO:13258), GTTAGAATGGTAGCGGGTTGGGTCGGGT (SEQ ID NO:13259) |
| Target1404 | chr14:37126862-37126949 | TCGTAGGGTTTCGGTCGTGTCGTTGTC (SEQ ID NO:13260), TTCGTAGGGTTTCGGTCGTGTCGTTGT (SEQ ID NO:13261), TTCGTAGGGTTTCGGTCGTGTCGTTGTC (SEQ ID NO:13262), TTTCGTAGGGTTTCGGTCGTGTCGTTGT (SEQ ID NO:13263), TTTCGTAGGGTTTCGGTCGTGTCGTTG (SEQ ID NO:13264), AGAATGGTAGCGGGTTGGGTCGGGTTC (SEQ ID NO:13265), TAGAATGGTAGCGGGTTGGGTCGGGTT (SEQ ID NO:13266), TTAGAATGGTAGCGGGTTGGGTCGGGT (SEQ ID NO:13267), GTTAGAATGGTAGCGGGTTGGGTCGGGT (SEQ ID NO:13268), AGAATGGTAGCGGGTTGGGTCGGGTT (SEQ ID NO:13269) |
| Target1405 | chr14:37127048-37127102 | TGATGAGAAGGTGGAGAGGTTGTCGGGT (SEQ ID NO:13270), GATGAGAAGGTGGAGAGGTTGTCGGGT (SEQ ID NO:13271), TGATGAGAAGGTGGAGAGGTTGTCGGG (SEQ ID NO:13272), ATGAGAAGGTGGAGAGGTTGTCGGGTT (SEQ ID NO:13273), TGAGAAGGTGGAGAGGTTGTCGGGTTA (SEQ ID NO:13274), CGGGAGGGGATGGCGGTTAAAAGGAGT (SEQ ID NO:13275), GTTGCGGGAGGGGATGGCGGTTAAAAG (SEQ ID NO:13276), TGCGGTTTGGATTTGGAGGGGATTGCGG |

FIGURE 5 CONTINUED (SEQ ID NO:13277), TGGTGGGAGAGGAGGATAGGAGGCGTT (SEQ ID NO:13278),
TTGGTGGGAGAGGAGGATAGGAGGCGT (SEQ ID NO:13279)

| | | |
|---|---|---|
| Target1406 | chr14:37127247-37127271 | TTGTAGGGGTTAGCGGTTTAGGGCGGA (SEQ ID NO:13280), TGTAGGGGTTAGCGGTTTAGGGCGGAT (SEQ ID NO:13281), TTTGTAGGGGTTAGCGGTTTAGGGCGG (SEQ ID NO:13282), TTTGTAGGGGTTAGCGGTTTAGGGCGGA (SEQ ID NO:13283), AGGGGTTAGCGGTTTAGGGCGGATTTT (SEQ ID NO:13284), GCGTTTAGGGCGAGGGAGGGTTT (SEQ ID NO:13285), TCGTTTTGTAGGGTAAGCGGTTAGTTGAGT (SEQ ID NO:13286), TTCGTTTTGTAGGGTAAGCGGTTAGTTGAGT (SEQ ID NO:13287), GCGTTTAGGGCGAGGGAGGGGTT (SEQ ID NO:13288), TCGTTTTGTAGGGTAAGCGGTTAGTTGAGTT (SEQ ID NO:13289) |
| Target1407 | chr14:38724381-38724436 | GCGGGCGTTTGGTGGGTATTTCGGTTT (SEQ ID NO:13290), GGTACGGGGTTGGTTGTAGTGGTCGGC (SEQ ID NO:13291), GTACGGGGTTGGTTGTAGTGGTCGGCG (SEQ ID NO:13292), GCGGGCGTTTGGTGGGTATTTCGGTT (SEQ ID NO:13293), GCGGGCGTTTGGTGGGTATTTCGGTTTT (SEQ ID NO:13294), GGCGTTCGTTGGGATAAATTTTCGGGCG (SEQ ID NO:13295), CGGCGTTCGTTGGGATAAATTTTCGGGC (SEQ ID NO:13296), GGCGTTCGTTGGGATAAATTTTCGGGCGA (SEQ ID NO:13297), GCGTTCGTTGGGATAAATTTTCGGGCG (SEQ ID NO:13298), GCGTTCGTTGGGATAAATTTTCGGGCGA (SEQ ID NO:13299) |
| Target1408 | chr14:38724473-38724766 | TTTCGGGGCGCGGCGTAGGATATAAGA (SEQ ID NO:13300), GGTTTCGGGGCGCGGCGTAGGATATAA (SEQ ID NO:13301), TCGGGGCGCGGCGTAGGATATAAGATT (SEQ ID NO:13302), TTCGGGGCGCGGCGTAGGATATAAGAT (SEQ ID NO:13303), GTTGTGTAGTTGGAAGGGCGCGCGATA (SEQ ID NO:13304), TCGAGGTGAGTGCGTTTTGTCGGGGAT (SEQ ID NO:13305), ATCGAGGTGAGTGCGTTTTGTCGGGGA (SEQ ID NO:13306), GATCGAGGTGAGTGCGTTTTGTCGGGG (SEQ ID NO:13307), GGATCGAGGTGAGTGCGTTTTGTCGGG (SEQ ID NO:13308), GGGATCGAGGTGAGTGCGTTTTGTCGG (SEQ ID NO:13309) |
| Target1409 | chr14:38724780-38724874 | TTTCGGGGCGCGGCGTAGGATATAAGA (SEQ ID NO:13310), GGTTTCGGGGCGCGGCGTAGGATATAA (SEQ ID NO:13311), TCGGGGCGCGGCGTAGGATATAAGATT (SEQ ID NO:13312), TTCGGGGCGCGGCGTAGGATATAAGAT (SEQ ID NO:13313), GTTTCGGGGCGCGGCGTAGGATATAAG (SEQ ID NO:13314), TTGCGGGTAGGTTTAGGGTTCGGAGGG (SEQ ID NO:13315), CGGGTAGGTTTAGGGTTCGGAGGGGGT (SEQ ID NO:13316), GGGTAGGTTTAGGGTTCGGAGGGGGTT (SEQ ID NO:13317), GCGGGTAGGTTTAGGGTTCGGAGGGG (SEQ ID NO:13318), TGCGGGTAGGTTTAGGGTTCGGAGGGG (SEQ ID NO:13319) |
| Target1410 | chr14:38724929-38725127 | GGTTTTGGGTTTGTTCGTAGGAGCGCG (SEQ ID NO:13320), GGGTTTTGGGTTTGTTCGTAGGAGCGCG (SEQ ID NO:13321), CGGGTTTTGGGTTTGTTCGTAGGAGCGC (SEQ ID NO:13322), GGGTTTTGGGTTTGTTCGTAGGAGCGC (SEQ ID NO:13323), CGGGTTTTGGGTTTGTTCGTAGGAGCG (SEQ ID NO:13324), GCGGTAGGCGGTCGAGGAGGTTTGTAT (SEQ ID NO:13325), TTGCGGGTAGGTTTAGGGTTCGGAGGG (SEQ ID NO:13326), TTTGGTAGGCGTTTTGGTTCGGGTCGG (SEQ ID NO:13327), CGAGGTGGGGCGTTTAGTATCGTGCGT (SEQ ID NO:13328), GCGGGGTTTTAGAGAATGAGGTCGGCG (SEQ ID NO:13329) |
| Target1411 | chr14:38725145-38725190 | GTACGGTCGGTAGTGGGGTGTTCGTCG (SEQ ID NO:13330), TACGGTCGGTAGTGGGGTGTTCGTCGTC (SEQ ID NO:13331), ACGGTCGGTAGTGGGGTGTTCGTCGTC (SEQ ID NO:13332), CGGTCGGTAGTGGGGTGTTCGTCGTC (SEQ ID NO:13333), CGGTCGGTAGTGGGGTGTTCGTCGT (SEQ ID NO:13334), GTTGGGGAGTAGTTTTGCGTGCGGGGTT (SEQ ID NO:13335), AAGTTGGGAGTAGTTTTGCGTGCGGGG (SEQ ID NO:13336), TTTGGTAGGCGTTTTGGTTCGGGTCGG (SEQ ID NO:13337), AGTTGGGAGTAGTTTTGCGTGCGGGGT (SEQ ID NO:13338), GCGGGGTTTTAGAGAATGAGGTCGGCG (SEQ ID NO:13339) |
| Target1412 | chr14:51338713-51338816 | GTTTGTTTGATCGCGCGGAGGAGGAGG (SEQ ID NO:13340), TTTGTTTGATCGCGCGGAGGAGGAGGG (SEQ ID NO:13341), AGTTTGTTTGATCGCGCGGAGGAGGAG (SEQ ID NO:13342), AGTTTGTTTGATCGCGCGGAGGAGGAGG (SEQ ID NO:13343), TAGTTTGTTTGATCGCGCGGAGGAGGA (SEQ ID NO:13344), TTAGGTAGGTTGGTACGGCGGGGGAGA (SEQ ID NO:13345), ATGCGGTCGTTTGGTAGTTTTGCGCGT (SEQ ID NO:13346), GTTAGGTAGGTTGGTACGGCGGGGGAG (SEQ ID NO:13347), TGCGGTCGTTTGGTAGTTTTGCGCGTT (SEQ ID NO:13348), TTCGCGCGGAGGTAGGTTGGTACGG (SEQ ID NO:13349) |
| Target1413 | chr14:51338844-51338959 | GTTTGTTTGATCGCGCGGAGGAGGAGG (SEQ ID NO:13350), TTCGGATTGTAGTTTTCGCGGCGGTGG (SEQ ID NO:13351), TTTGTTTGATCGCGCGGAGGAGGAGGG (SEQ ID NO:13352), AGTTTGTTTGATCGCGCGGAGGAGGAG (SEQ ID NO:13353), TTTCGGATTGTAGTTTTCGCGGCGGTGG (SEQ ID NO:13354), CGGTTAGGGGTGGATCGGGCGGTATTT (SEQ ID NO:13355), ATGCGGTCGTTTGGTAGTTTTGCGCGT (SEQ ID NO:13356), TGCGGTCGTTTGGTAGTTTTGCGCGTT (SEQ ID NO:13357), GATGCGGTCGTTTGGTAGTTTTGCGCG (SEQ ID NO:13358), GCGGTCGTTTGGTAGTTTTGCGCGTTT (SEQ ID NO:13359) |
| Target1414 | chr14:51338995-51339010 | CGTGGTCGTTTGGTGGGATATGGTCGA (SEQ ID NO:13360), CGTGGTCGTTTGGTGGGATATGGTCGAT (SEQ ID NO:13361), GCGTAGGATTGTTAGGCGGTCGTATCGT (SEQ ID NO:13362), GGTCGTTTGGTGGGATATGGTCGATCGT (SEQ ID NO:13363), TGGTCGTTTGGTGGGATATGGTCGATCG (SEQ ID NO:13364), CGGTTAGGGGTGGATCGGGCGGTATTT (SEQ ID NO:13365), TCGGTTAGGGGTGGATCGGGCGGTATT (SEQ ID NO:13366), TTCGGTTAGGGGTGGATCGGGCGGTAT (SEQ ID NO:13367), CGGTTAGGGGTGGATCGGGCGGTATT (SEQ ID NO:13368), GGGTTCGGGTTAGTAGAGGGGATTGCGG (SEQ ID NO:13369) |

FIGURE 5 CONTINUED

| | | |
|---|---|---|
| Target1415 | chr14:51339024-51339049 | CGTGGTCGTTTGGTGGGATATGGTCGA (SEQ ID NO:13370), CGTGGTCGTTTGGTGGGATATGGTCGAT (SEQ ID NO:13371), GGTCGTTTGGTGGGATATGGTCGATCGT (SEQ ID NO:13372), TGGTCGTTTGGTGGGATATGGTCGATCG (SEQ ID NO:13373), TGGTCGTTTGGTGGGATATGGTCGATCGT (SEQ ID NO:13374), GGGTTCGGGTTAGTAGAGGGGATTGCGG (SEQ ID NO:13375), TTCGCGTAGTTTGAGTCGTCGGGGGTTT (SEQ ID NO:13376), TTTCGCGTAGTTTGAGTCGTCGGGGGTT (SEQ ID NO:13377), TTTTCGCGTAGTTTGAGTCGTCGGGGT (SEQ ID NO:13378), GGTTCGGGTTAGTAGAGGGGATTGCGGT (SEQ ID NO:13379) |
| Target1416 | chr14:51339072-51339085 | TTTCGACGGTTTAGGTTGCGCGGGGAT (SEQ ID NO:13380), GTTTAGGTTGCGCGGGGATGGGGTAGG (SEQ ID NO:13381), GGTTTAGGTTGCGCGGGGATGGGGTAG (SEQ ID NO:13382), TTCGACGGTTTAGGTTGCGCGGGGATG (SEQ ID NO:13383), GTTTCGACGGTTTAGGTTGCGCGGGGA (SEQ ID NO:13384), GGGTTCGGGTTAGTAGAGGGGATTGCGG (SEQ ID NO:13385), GGTTCGGGTTAGTAGAGGGGATTGCGGT (SEQ ID NO:13386), TGGGTTCGGGTTAGTAGAGGGGATTGCG (SEQ ID NO:13387), GGTTCGGGTTAGTAGAGGGGATTGCGG (SEQ ID NO:13388), GGGTTCGGGTTAGTAGAGGGGATTGCG (SEQ ID NO:13389) |
| Target1417 | chr14:52781541-52781816 | GCGTTTCGGGGGTTTGGTCGTGTTGTT (SEQ ID NO:13390), GCGTTTCGGGGGTTTGGTCGTGTTGT (SEQ ID NO:13391), GCGTTTCGGGGGTTTGGTCGTGTTGTTT (SEQ ID NO:13392), CGTTTCGGGGGTTTGGTCGTGTTGTTT (SEQ ID NO:13393), CGTTTCGGGGGTTTGGTCGTGTTGTTTG (SEQ ID NO:13394), CGCGGCGTTGGTAGAAGTAGGGGTGTT (SEQ ID NO:13395), GCGGCGTTGGTAGAAGTAGGGGTGTTC (SEQ ID NO:13396), AGGGGTGTTCGATCGAGAGGTAGCGTT (SEQ ID NO:13397), CGGCGTTGGTAGAAGTAGGGGTGTTCG (SEQ ID NO:13398), AGGTAAGCGGTTCGTTCGTGTCGGATG (SEQ ID NO:13399) |
| Target1418 | chr14:52781834-52781937 | GCGTTTCGGGGGTTTGGTCGTGTTGT (SEQ ID NO:13400), GCGTTTCGGGGGTTTGGTCGTGTTGTTT (SEQ ID NO:13401), CGTTTCGGGGGTTTGGTCGTGTTGTTT (SEQ ID NO:13402), CGTTTCGGGGGTTTGGTCGTGTTGTTTGT (SEQ ID NO:13403), TTCGGGGGTTTGGTCGTGTTGTTTGTT (SEQ ID NO:13404), GGCGGTGTATGCGGATGAGGTTGAGAA (SEQ ID NO:13405), GGCGGTGTATGCGGATGAGGTTGAGAAT (SEQ ID NO:13406), GGCGGTGTATGCGGATGAGGTTGAGA (SEQ ID NO:13407), AGGGAAGGTTCGTAGCGGTTTTTTCGG (SEQ ID NO:13408), GGCGGTGTATGCGGATGAGGTTGAGAATG (SEQ ID NO:13409) |
| Target1419 | chr14:52781945-52781969 | AGGGAAGGTTCGTAGCGGTTTTTTCGG (SEQ ID NO:13410), TAGGGAAGGTTCGTAGCGGTTTTTTCGG (SEQ ID NO:13411), CGGGGTCGTTTCGGTTATTGTTTAGGG (SEQ ID NO:13412), CGGGGTCGTTTCGGTTATTGTTTAGGGA (SEQ ID NO:13413), GGGAAGGTTCGTAGCGGTTTTTTCGG (SEQ ID NO:13414) |
| Target1420 | chr14:52782008-52782046 | GGGGTTCGTAGGAGAGGGGAAAGGGTG (SEQ ID NO:13415), AGGGGAAAGGGGTGTTTATGGCGGAGGA (SEQ ID NO:13416), TTTTTGGGTAGTGGTCGGGGCGGTTTC (SEQ ID NO:13417), CGGGGTTCGTAGGAGAGGGGAAAGGGT (SEQ ID NO:13418), TTTTTTGGGTAGTGGTCGGGGCGGTTT (SEQ ID NO:13419), AGTCGGGTTGTGGAAACGTAGGGGAGTG (SEQ ID NO:13420), GTCGGGTTGTGGAAACGTAGGGGAGTGA (SEQ ID NO:13421), AGTCGGGTTGTGGAAACGTAGGGGAGTGA (SEQ ID NO:13422), GAGTCGGGTTGTGGAAACGTAGGGGAGT (SEQ ID NO:13423), AGAGTCGGGTTGTGGAAACGTAGGGGAGT (SEQ ID NO:13424) |
| Target1421 | chr14:52782125-52782173 | GGGGTTCGTAGGAGAGGGGAAAGGGTG (SEQ ID NO:13425), AGGGGAAAGGGGTGTTTATGGCGGAGGA (SEQ ID NO:13426), AAGGGTGTTTATGGCGGAGGAGACGGA (SEQ ID NO:13427), CGGGGTTCGTAGGAGAGGGGAAAGGGT (SEQ ID NO:13428), AGGGTGTTTATGGCGGAGGAGACGGAT (SEQ ID NO:13429), TTTGTAGGGCGGTGGAAAGGGTGGAGG (SEQ ID NO:13430), GTGGAAAGGGTGGAGGCGTTAGGGGAG (SEQ ID NO:13431), GGAAAGGGTGGAGGCGTTAGGGGAGAG (SEQ ID NO:13432), AGTTTGTAGGGCGGTGGAAAGGGTGGA (SEQ ID NO:13433), TGGAAAGGGTGGAGGCGTTAGGGGAGA (SEQ ID NO:13434) |
| Target1422 | chr14:55243177-55243271 | TGATGTTTTAGTAGTTAGGTAGGGTTCGGCG (SEQ ID NO:13435), TTGATGTTTTAGTAGTTAGGTAGGGTTCGGCG (SEQ ID NO:13436), GTTGATGTTTTAGTAGTTAGGTAGGGTTCGGCG (SEQ ID NO:13437), TGTTGATGTTTTAGTAGTTAGGTAGGGTTCGGCG (SEQ ID NO:13438), TGTTGGCGGTTTTGTTTTTTATTTTAGTGGGGT (SEQ ID NO:13439), AGTGTGTACGGGTAGCGAGCGGGTTTT (SEQ ID NO:13440), AAGTGTGTACGGGTAGCGAGCGGGTTT (SEQ ID NO:13441), GAAGTGTGTACGGGTAGCGAGCGGGTT (SEQ ID NO:13442), TGTGGGGAAGTGTGTACGGGTAGCGAG (SEQ ID NO:13443), GTGGGGAAGTGTGTACGGGTAGCGAGC (SEQ ID NO:13444) |
| Target1423 | chr14:56705456-56705503 | AGTTAGGTGAGTGGTAGATTTCGGGTTTACG (SEQ ID NO:13445), AAGTTAGGTGAGTGGTAGATTTCGGGTTTACG (SEQ ID NO:13446), AAAGTTAGGTGAGTGGTAGATTTCGGGTTTACG (SEQ ID NO:13447), AAAAGTTAGGTGAGTGGTAGATTTCGGGTTTACG (SEQ ID NO:13448), TAAAAGTTAGGTGAGTGGTAGATTTCGGGTTTACG (SEQ ID NO:13449), TGTTCGTGGGTTCGGAATTTGTTATTTATTTGGT (SEQ ID NO:13450), TGTTCGTGGGTTCGGAATTTGTTATTTATTTGGTT (SEQ ID NO:13451), ATGTTCGTGGGTTCGGAATTTGTTATTTATTTGGT (SEQ ID NO:13452), TGTTCGTGGGTTCGGAATTTGTTATTTATTTGGTTT (SEQ ID NO:13453), ATGTTCGTGGGTTCGGAATTTGTTATTTATTTGGTT (SEQ ID NO:13454) |

FIGURE 5 CONTINUED

Target1424    chr14:57265006-57265030    TTCGGTTTTAGTTTTTTCGGGCGTAGGG (SEQ ID NO:13455), TTTCGGTTTTAGTTTTTTCGGGCGTAGGG (SEQ ID NO:13456), GTTTCGGTTTTAGTTTTTTCGGGCGTAGGG (SEQ ID NO:13457), AGTTTCGGTTTTAGTTTTTTCGGGCGTAGGG (SEQ ID NO:13458), AGTTTCGGTTTTAGTTTTTTCGGGCGTAGG (SEQ ID NO:13459), AGGTTCGGTGGCGAGGTTTGTACGTTC (SEQ ID NO:13460), GAGGTTCGGTGGCGAGGTTTGTACGTT (SEQ ID NO:13461), GAGGTTCGGTGGCGAGGTTTGTACGTTC (SEQ ID NO:13462), GCGGGAGTGGGTCGTTAGTTAGAGTCG (SEQ ID NO:13463), GCGGGAGTGGGTCGTTAGTTAGAGTCGA (SEQ ID NO:13464)

Target1425    chr14:57265126-57265138    AGGTTTGATTGTAGGGTTCGGGCGGGG (SEQ ID NO:13465), GGTTTGATTGTAGGGTTCGGGCGGGGT (SEQ ID NO:13466), GAGGTTTGATTGTAGGGTTCGGGCGGG (SEQ ID NO:13467), GGAGGTTTGATTGTAGGGTTCGGGCGG (SEQ ID NO:13468), GTTTGATTGTAGGGTTCGGGCGGGGTT (SEQ ID NO:13469), GGGCGTAGTTTTTAGGTTTCGGGGGCG (SEQ ID NO:13470), CGGGCGTAGTTTTTAGGTTTCGGGGGC (SEQ ID NO:13471), TAGGTTTCGGGGGCGTCGGTTTTAGGG (SEQ ID NO:13472), GGCGTAGTTTTTAGGTTTCGGGGGCGT (SEQ ID NO:13473), CGTCGGTTTTAGGGCGTTGTGGGTCG (SEQ ID NO:13474)

Target1426    chr14:57265187-57265197    GGTTTATAGCGTTTGGGATCGGCGTT (SEQ ID NO:13475), GGTTTATAGCGTTTGGGATCGGCGTTT (SEQ ID NO:13476), GGTTTATAGCGTTTGGGATCGGCGT (SEQ ID NO:13477), GGTTTATAGCGTTTGGGATCGGCGTTTT (SEQ ID NO:13478), GGTTTATAGCGTTTGGGATCGGCGTTTTC (SEQ ID NO:13479), TTGGCGGGTTAGGTAGGGGCGAGATTG (SEQ ID NO:13480), GTTTGGCGGGTTAGGTAGGGGCGAGAT (SEQ ID NO:13481), GCGGGTTAGGTAGGGGCGAGATTGAGG (SEQ ID NO:13482), GGCGGGTTAGGTAGGGGCGAGATTGAG (SEQ ID NO:13483), TTTGGCGGGTTAGGTAGGGGCGAGATT (SEQ ID NO:13484)

Target1427    chr14:57265461-57265483    GGGGAGTTCGGCGTTTGTTTTAGTTGGGGG (SEQ ID NO:13485), GGGGAGTTCGGCGTTTGTTTTAGTTGGGG (SEQ ID NO:13486), TGGGGGTTTTCGGGGTAGAGATGTGAGT (SEQ ID NO:13487), GGGGGGTTTTCGGGGTAGAGATGTGAGT (SEQ ID NO:13488), TGGGGGTTTTCGGGGTAGAGATGTGAG (SEQ ID NO:13489), TAAGACGTTGGGAGGTTGGGGCGGAAT (SEQ ID NO:13490), GTAAGACGTTGGGAGGTTGGGGCGGAA (SEQ ID NO:13491), AAGACGTTGGGAGGTTGGGGCGGAATT (SEQ ID NO:13492), ACGTTGGGAGGTTGGGGCGGAATTGTT (SEQ ID NO:13493), CGTTGGGAGGTTGGGGCGGAATTGTTA (SEQ ID NO:13494)

Target1428    chr14:57265487-57265500    TGGGGGTTTTCGGGGTAGAGATGTGAGT (SEQ ID NO:13495), GGGGGGTTTTCGGGGTAGAGATGTGAGT (SEQ ID NO:13496), TGGGGGTTTTCGGGGTAGAGATGTGAG (SEQ ID NO:13497), AGTTGGGGGTTTTCGGGGTAGAGATGT (SEQ ID NO:13498), TTGGGGGTTTTCGGGGTAGAGATGTGA (SEQ ID NO:13499), TAAGACGTTGGGAGGTTGGGGCGGAAT (SEQ ID NO:13500), GTAAGACGTTGGGAGGTTGGGGCGGAA (SEQ ID NO:13501), AAGACGTTGGGAGGTTGGGGCGGAATT (SEQ ID NO:13502), ACGTTGGGAGGTTGGGGCGGAATTGTT (SEQ ID NO:13503), CGTTGGGAGGTTGGGGCGGAATTGTTA (SEQ ID NO:13504)

Target1429    chr14:57265549-57265561    TTTTGCGTTTGTGGCGGCGGTAGTACG (SEQ ID NO:13505), GTTTTGCGTTTGTGGCGGCGGTAGTAC (SEQ ID NO:13506), TTTGCGTTTGTGGCGGCGGTAGTACG (SEQ ID NO:13507), GTTTTGCGTTTGTGGCGGCGGTAGTACG (SEQ ID NO:13508), TTGCGTTTGTGGCGGCGGTAGTACG (SEQ ID NO:13509), TTTGTGGGTGATTTTTTAGGTTCGTATTGTCGTT (SEQ ID NO:13510), TTTTGTGGGTGATTTTTTAGGTTCGT (SEQ ID NO:13511), TTTTGTGGGTGATTTTTTAGGTTCGTATTGTCGTT (SEQ ID NO:13512), TTTTTGTGGGTGATTTTTTAGGTTCGTATTGTCGT (SEQ ID NO:13513), TTTTTGTGGGTGATTTTTTAGGTTCGTATTGTCGTT (SEQ ID NO:13514)

Target1430    chr14:57275051-57275073    TGATGGAAAGGAAATAAAATTACGCGGATTGGC (SEQ ID NO:13515), ATGATGGAAAGGAAATAAAATTACGCGGATTGGC (SEQ ID NO:13516), TATGATGGAAAGGAAATAAAATTACGCGGATTGGC (SEQ ID NO:13517), GTATGATGGAAAGGAAATAAAATTACGCGGATTGGC (SEQ ID NO:13518), TGTATGATGGAAAGGAAATAAAATTACGCGGATTGG (SEQ ID NO:13519)

Target1431    chr14:57275116-57275144    GCGATTGGTTTGCGGTTGGGAAGACGA (SEQ ID NO:13520), TGCGGTTGGGAAGACGACGAAGAGGAG (SEQ ID NO:13521), TTGCGGTTGGGAAGACGACGAAGAGGA (SEQ ID NO:13522), GCGGTTGGGAAGACGACGAAGAGGAGG (SEQ ID NO:13523), TGGTTTGCGGTTGGGAAGACGACGAAG (SEQ ID NO:13524), TCGCGGGTGGTAGAGTTATTTGATTTTTCGA (SEQ ID NO:13525), CGCGGGTGGTAGAGTTATTTGATTTTTCGAGG (SEQ ID NO:13526), CGCGGGTGGTAGAGTTATTTGATTTTTCGAGGT (SEQ ID NO:13527), TCGCGGGTGGTAGAGTTATTTGATTTTTCGAGG (SEQ ID NO:13528), CGCGGGTGGTAGAGTTATTTGATTTTTCGAG (SEQ ID NO:13529)

Target1432    chr14:57275599-57275613    TCGGTGGAATTTTGATAGGGGATTTGGGT (SEQ ID NO:13530), TCGGTGGAATTTTGATAGGGGATTTGGGTT (SEQ ID NO:13531), TTCGGTGGAATTTTGATAGGGGATTTGGGT (SEQ ID NO:13532), TCGGTGGAATTTTGATAGGGGATTTGGGTTT (SEQ ID NO:13533), TTCGGTGGAATTTTGATAGGGGATTTGGGTT (SEQ ID NO:13534), GCGTTGTTGCGTTTAAGTGATTTTTGAAATCGA (SEQ ID NO:13535), GCGTTGTTGCGTTTAAGTGATTTTTGAAATCGAT (SEQ ID NO:13536), GCGTTGTTGCGTTTAAGTGATTTTTGAAATCGATG (SEQ ID NO:13537),

FIGURE 5 CONTINUED

GCGTTGTTGCGTTTAAGTGATTTTTGAAATCGATGT (SEQ ID NO:13538),
CGTTGTTGCGTTTAAGTGATTTTTGAAATCGATGT (SEQ ID NO:13539)

Target1433    chr14:57275633-57275644    TCGGTGGAATTTTGATAGGGGGATTTGGGT (SEQ ID NO:13540),
TCGGTGGAATTTTGATAGGGGGATTTGGGTT (SEQ ID NO:13541),
TTCGGTGGAATTTTGATAGGGGGATTTGGGT (SEQ ID NO:13542),
TCGGTGGAATTTTGATAGGGGGATTTGGGTTT (SEQ ID NO:13543),
TTCGGTGGAATTTTGATAGGGGGATTTGGGTT (SEQ ID NO:13544),
AGGGGGTTCGTCGAGGTTTAGTTTGTGT (SEQ ID NO:13545), GAGGGGGTTCGTCGAGGTTTAGTTTGTGT
(SEQ ID NO:13546), AGGGGGTTCGTCGAGGTTTAGTTTGTGTT (SEQ ID NO:13547),
GAGGGGGTTCGTCGAGGTTTAGTTTGTGTT (SEQ ID NO:13548),
AGGGGGTTCGTCGAGGTTTAGTTTGTGTTA (SEQ ID NO:13549)

Target1434    chr14:57275681-57275688    CGCGAAGATTTTTTGGGAGTTTGTAGAGCG (SEQ ID NO:13550),
TTTTTGGGAGTTTGTAGAGCGATTCGTCG (SEQ ID NO:13551),
ACGCGAAGATTTTTTGGGAGTTTGTAGAGC (SEQ ID NO:13552),
GCGAAGATTTTTTGGGAGTTTGTAGAGCGA (SEQ ID NO:13553),
TTTTTGGGAGTTTGTAGAGCGATTCGTCG (SEQ ID NO:13554), AGGGGTTCGTCGAGGTTTAGTTTGTGT
(SEQ ID NO:13555), GAGGGGTTCGTCGAGGTTTAGTTTGTGT (SEQ ID NO:13556),
AGGGGGTTCGTCGAGGTTTAGTTTGTGTT (SEQ ID NO:13557), GAGGGGTTCGTCGAGGTTTAGTTTGTGTT
(SEQ ID NO:13558), AGGGGGTTCGTCGAGGTTTAGTTTGTGTTA (SEQ ID NO:13559)

Target1435    chr14:57275821-57275836    TGTTTTGGAGTTTGGGAAGGGGGTGCG (SEQ ID NO:13560), GTTTTGGAGTTTGGGAAGGGGGTGCGC
(SEQ ID NO:13561), TTTTGGAGTTTGGGAAGGGGGTGCGC (SEQ ID NO:13562),
TTGTTTTGGAGTTTGGGAAGGGGGTGCG (SEQ ID NO:13563), TTTTGGAGTTTGGGAAGGGGGTGCGCG
(SEQ ID NO:13564), TTTGGCGGGGAGAGGTAGGGTTCGTTC (SEQ ID NO:13565),
TTTTGGCGGGGAGAGGTAGGGTTCGTT (SEQ ID NO:13566), TTTTTGGCGGGGAGAGGTAGGGTTCGT
(SEQ ID NO:13567), TTTTTGGCGGGGAGAGGTAGGGTTCGTTC (SEQ ID NO:13568),
TTGGCGGGGAGAGGTAGGGTTCGTTC (SEQ ID NO:13569)

Target1436    chr14:57275967-57276001    GTTTTTGGTTCGGTCGCGGTTTTTGGGC (SEQ ID NO:13570), TTTGTTCGTTTTAGGTGCGCGCGGAGG (SEQ
ID NO:13571), CGGTTTTTGGTTCGGTCGCGCGGTTTTGG (SEQ ID NO:13572),
GGTTTTTGGTTCGGTCGCGCGGTTTTGGG (SEQ ID NO:13573), GGATTTCGGTTTTTGGTTCGGTCGCGGG (SEQ
ID NO:13574)

Target1437    chr14:60207676-60208076    CGGTTTGGTTGGAGGAGGGGGAAGGAA (SEQ ID NO:13575), TGGAGGAGGGGGAAGGAAGGGAAGTGT
(SEQ ID NO:13576), TGGAAGGTCGGTTTGGTTGGAGGAGGG (SEQ ID NO:13577),
AAGTGTAAGAGAGTGGTGGCGGTGGGG (SEQ ID NO:13578), AGGAGGGGGAAGGAAGGGAAGTGTGGT
(SEQ ID NO:13579)

Target1438    chr14:60952060-60952098    TGAAGTTTTGGGGATGGGGTGGGAAGT (SEQ ID NO:13580), TTGAAGTTTTGGGGATGGGGTGGGAAGT
(SEQ ID NO:13581), TTGAAGTTTTGGGGATGGGGTGGGAAG (SEQ ID NO:13582),
ACGATTTGAAGTTTTGGGGATGGGGTGGG (SEQ ID NO:13583),
CGATTTGAAGTTTTGGGGATGGGGTGGG (SEQ ID NO:13584),
AGGGTATATTTTGTGGAGAAATTTGGGTGTTCGT (SEQ ID NO:13585),
GGGTATATTTTGTGGAGAAATTTGGGTGTTCGTG (SEQ ID NO:13586),
AGGGTATATTTTGTGGAGAAATTTGGGTGTTCGTG (SEQ ID NO:13587),
GGGTATATTTTGTGGAGAAATTTGGGTGTTCGTGA (SEQ ID NO:13588),
AAGGGTATATTTTGTGGAGAAATTTGGGTGTTCG (SEQ ID NO:13589)

Target1439    chr14:60952196-60952265    CGTTTTGAATATGTTTTTTGGTGGCGTGTGT (SEQ ID NO:13590),
ACGTTTTGAATATGTTTTTTGGTGGCGTGTG (SEQ ID NO:13591),
ACGTTTTGAATATGTTTTTTGGTGGCGTGTGT (SEQ ID NO:13592),
AACGTTTTGAATATGTTTTTTGGTGGCGTGTG (SEQ ID NO:13593),
AACGTTTTGAATATGTTTTTTGGTGGCGTGTGT (SEQ ID NO:13594),
TTCGGGTGTTGGGGAAGGGTTTTCGTT (SEQ ID NO:13595), ATTCGGGTGTTGGGGAAGGGTTTTCGT
(SEQ ID NO:13596), TCGGGTGTTGGGGAAGGGTTTTCGTTA (SEQ ID NO:13597),
AGGTTTATTCGGGTGTTGGGGAAGGGT (SEQ ID NO:13598), ATTCGGGTGTTGGGGAAGGGTTTTCGTT
(SEQ ID NO:13599)

Target1440    chr14:60952325-60952340    GGAGGCGTACGGGTTGTGGTTTTTGGG (SEQ ID NO:13600), GGGAGGCGTACGGGTTGTGGTTTTTGG
(SEQ ID NO:13601), TAGGAGGTTGTGAGGGTGGGAGTCGGT (SEQ ID NO:13602),
CGGGAGGCGTACGGGTTGTGGTTTTTG (SEQ ID NO:13603), AGGGTGGGAGTCGGTCGGCGAATTTTT
(SEQ ID NO:13604)

Target1441    chr14:60952398-60952465    ACGTTTGAGGCGGGGTTTTTGTTTATCGT (SEQ ID NO:13605), CGTTTGAGGCGGGGTTTTTGTTTATCGT
(SEQ ID NO:13606), ACGTTTGAGGCGGGGTTTTTGTTTATCG (SEQ ID NO:13607),
CGTTTGAGGCGGGGTTTTTGTTTATCGTG (SEQ ID NO:13608),
CGTTTGAGGCGGGGTTTTTGTTTATCGTGT (SEQ ID NO:13609), TAGGAGGTTGTGAGGGTGGGAGTCGGT
(SEQ ID NO:13610), GATGCGGTGTTGTAGTTTCGGGCGAGG (SEQ ID NO:13611),
GGATGCGGTGTTGTAGTTTCGGGCGAG (SEQ ID NO:13612), AGGGTGGGAGTCGGTCGGCGAATTTTT
(SEQ ID NO:13613), CGGTGTTGTAGTTTCGGGCGAGGGGAA (SEQ ID NO:13614)

FIGURE 5 CONTINUED

Target1442     chr14:60976532-60976549     TTGCGTGGAAGATTTTTGGGATTTGTGGA (SEQ ID NO:13615),
TGCGTGGAAGATTTTTGGGATTTGTGGAT (SEQ ID NO:13616),
GGTTGAGAAGTTGCGTGGAAGATTTTTGGG (SEQ ID NO:13617),
GTTGCGTGGAAGATTTTTGGGATTTGTGG (SEQ ID NO:13618),
AGTTGCGTGGAAGATTTTTGGGATTTGTGG (SEQ ID NO:13619), GGGGTTAGTTCGGTTGTTTGGGCGAGT
(SEQ ID NO:13620), AGGGGTTAGTTCGGTTGTTTGGGCGAGT (SEQ ID NO:13621),
AGGGGGTTAGTTCGGTTGTTTGGGCGAG (SEQ ID NO:13622), GCGTAGGGGTTAGTTCGGTTGTTTGGGC
(SEQ ID NO:13623), CGTAGGGGTTAGTTCGGTTGTTTGGGCG (SEQ ID NO:13624)

Target1443     chr14:60976654-60976671     ACGTAGGTGGGTAATTGGTTTAAAAATCGTCGA (SEQ ID NO:13625),
TCGGATTGATTTTTACGTAGGTGGGTAATTGGT (SEQ ID NO:13626),
ACGTAGGTGGGTAATTGGTTTAAAAATCGTCGAT (SEQ ID NO:13627),
TCGGATTGATTTTTACGTAGGTGGGTAATTGGTT (SEQ ID NO:13628),
TACGTAGGTGGGTAATTGGTTTAAAAATCGTCGA (SEQ ID NO:13629),
GGAGTCGTTAGGGATTGGGTAAGGGCGT (SEQ ID NO:13630),
TGGAGTCGTTAGGGATTGGGTAAGGGCG (SEQ ID NO:13631), GGAGTCGTTAGGGATTGGGTAAGGGCG
(SEQ ID NO:13632), GGGATTGGGTAAGGGCGTTAGAGGTGT (SEQ ID NO:13633),
GAGTCGTTAGGGATTGGGTAAGGGCGT (SEQ ID NO:13634)

Target1444     chr14:60976708-60976725     TCGGTATTTAGAGGTTTTCGCGTTTTGAGC (SEQ ID NO:13635),
GGTCGGTATTTAGAGGTTTTCGCGTTTTGAGC (SEQ ID NO:13636),
AGGTCGGTATTTAGAGGTTTTCGCGTTTTG (SEQ ID NO:13637),
GGTCGGTATTTAGAGGTTTTCGCGTTTTGA (SEQ ID NO:13638),
GGGATCGAGCGGTTGTAGTTAAGAATAGGT (SEQ ID NO:13639),
GGAGTCGTTAGGGATTGGGTAAGGGCGT (SEQ ID NO:13640),
TGGAGTCGTTAGGGATTGGGTAAGGGCG (SEQ ID NO:13641), GGAGTCGTTAGGGATTGGGTAAGGGCG
(SEQ ID NO:13642), GGGATTGGGTAAGGGCGTTAGAGGTGT (SEQ ID NO:13643),
GAGTCGTTAGGGATTGGGTAAGGGCGT (SEQ ID NO:13644)

Target1445     chr14:60976829-60976862     AGGAGTTGGGAGCGCGGTTTGTTTTGG (SEQ ID NO:13645), AGTTGGGAGCGCGGTTTGTTTTGGGTT
(SEQ ID NO:13646), GGGGAGGAGGCGGGTGGAGGTATTTTT (SEQ ID NO:13647),
GAGTTGGGAGCGCGGTTTGTTTTGGGT (SEQ ID NO:13648), GAGGCGGGTGGAGGTATTTTTGGCGTT
(SEQ ID NO:13649), TGGGGAGTTAGCGGGTGGGGAAGTAGA (SEQ ID NO:13650),
GTGGGGAGTTAGCGGGTGGGGAAGTAG (SEQ ID NO:13651), GCGGGTGGGGAAGTAGAGTCGGTAAGG
(SEQ ID NO:13652), GGGGAGTTAGCGGGTGGGGAAGTAGAG (SEQ ID NO:13653),
CGGGTGGGGAAGTAGAGTCGGTAAGGG (SEQ ID NO:13654)

Target1446     chr14:60976879-60976899     AGGAGTTGGGAGCGCGGTTTGTTTTGG (SEQ ID NO:13655), AGTTGGGAGCGCGGTTTGTTTTGGGTT
(SEQ ID NO:13656), GAGTTGGGAGCGCGGTTTGTTTTGGGT (SEQ ID NO:13657),
GGAGTTGGGAGCGCGGTTTGTTTTGGG (SEQ ID NO:13658), AGTTGGGAGCGCGGTTTGTTTTGGGT
(SEQ ID NO:13659), TCGGGATTAGTTGTTGTAGTTGTTCGTAGGC (SEQ ID NO:13660),
TGGTTTGGTGATCGGGATTAGTTGTTGTAGT (SEQ ID NO:13661),
CGTTTTAGTGAAGTTTTGGTTTGGTGATCGGG (SEQ ID NO:13662),
GGTGATCGGGATTAGTTGTTGTAGTTGTCGT (SEQ ID NO:13663),
TGGTGATCGGGATTAGTTGTTGTAGTTGTTCG (SEQ ID NO:13664)

Target1447     chr14:61104242-61104720     CGTCGCGGCGGTAGTTGTTTACGTTGT (SEQ ID NO:13665), TCGGAGGGGGGGTTTAGGTTTTACGCGT
(SEQ ID NO:13666), TGGTTTGGAGGTCGCGCGGTTTAAGTT (SEQ ID NO:13667),
ATGGTTTGGAGGTCGCGCGGTTTAAGT (SEQ ID NO:13668), CGCGAGGGAGTTGAGTGAGGTTTTTGCG
(SEQ ID NO:13669), AGTATAGGTTGGGGGGGAGGGTTGGGGT (SEQ ID NO:13670),
GGTTGGGGTCGCGGTTGGAAGGTTTTT (SEQ ID NO:13671), TTTGTTTTAGGGGTTTGGGTCGCGCGG
(SEQ ID NO:13672), GTTTTAGGGGTTTGGGTCGCGCGGTTT (SEQ ID NO:13673),
TTTAGGGGTTTGGGTCGCGCGGTTTTT (SEQ ID NO:13674)

Target1448     chr14:61104754-61104791     TCGGAGGGGGGGTTTAGGTTTTACGCGT (SEQ ID NO:13675), CGGAGGGGGGGTTTAGGTTTTACGCGTT
(SEQ ID NO:13676), TCGGAGGGGGGGTTTAGGTTTTACGCGTT (SEQ ID NO:13677),
TTCGGAGGGGGGGTTTAGGTTTTACGCGT (SEQ ID NO:13678), TTCGGAGGGGGGGTTTAGGTTTTACGCG
(SEQ ID NO:13679), TCGGTTTGGAGTTGATGGAGGGGAAAGT (SEQ ID NO:13680),
TTCGGTTTGGAGTTGATGGAGGGGAAAGT (SEQ ID NO:13681), TGAATTCGGTTTGGAGTTGATGGAGGGA
(SEQ ID NO:13682), ATTCGGTTTGGAGTTGATGGAGGGGAAAGT (SEQ ID NO:13683),
TGAATTCGGTTTGGAGTTGATGGAGGGAA (SEQ ID NO:13684)

Target1449     chr14:61104836-61104851     TTGTTGGGGGAGATGTGGGCGTAGGAG (SEQ ID NO:13685), TTGTGTTTGTTGGGGGGAGATGTGGGCG
(SEQ ID NO:13686), TTTGTTGGGGGAGATGTGGGCGTAGGA (SEQ ID NO:13687),
TGTGTTTGTTGGGGGAGATGTGGGCGT (SEQ ID NO:13688), GTTTGTTGGGGGAGATGTGGGCGTAGG
(SEQ ID NO:13689), CGTTCGGTTTGATGTGGGGATAAAAATTTTGGA (SEQ ID NO:13690),
TCGTTCGGTTTGATGTGGGGATAAAAATTTTGG (SEQ ID NO:13691),
TCGTTCGGTTTGATGTGGGGATAAAAATTTTGGA (SEQ ID NO:13692),
CGTTCGGTTTGATGTGGGGATAAAAATTTTGGAT (SEQ ID NO:13693),
ATCGTTCGGTTTGATGTGGGGATAAAAATTTTGG (SEQ ID NO:13694)

Target1450     chr14:73712422-73713084     TTTGGTCGCGGGTTGTTGGGTTGGTTT (SEQ ID NO:13695), TTTTGGTCGCGGGTTGTTGGGTTGGTT (SEQ
ID NO:13696), TTTTTGGTCGCGGGTTGTTGGGTTGGT (SEQ ID NO:13697),
TCGTTTTTGGTCGCGGGTTGTTGGGTT (SEQ ID NO:13698), TTCGTTTTTGGTCGCGGGTTGTTGGGT (SEQ

FIGURE 5 CONTINUED

|  |  | ID NO:13699), CGGAGTCGTCGGAGGTGGAGTTCGTTT (SEQ ID NO:13700), GGGGAAATCGGTTAGGAGGGGTTGGGG (SEQ ID NO:13701), GGGAAGTCGGGATTTAGGAGGGCGGAG (SEQ ID NO:13702), GAGGGGAAGTCGGGATTTAGGAGGGCG (SEQ ID NO:13703), GCGGAGGGGAAGTCGGGATTTAGGAGG (SEQ ID NO:13704) |
| Target1451 | chr14:77491793-77492862 | TGGAATGGGGTTTTAGAGGTGGGGGGCG (SEQ ID NO:13705), TTCGGTTGAGTTCGGGGGGTTTCGGAGA (SEQ ID NO:13706), TGGGGGGGTTGATTTAGGTGGGGTGGTT (SEQ ID NO:13707), TTGGGGGGGTTGATTTAGGTGGGGTGGT (SEQ ID NO:13708), GGTAGGGTTGGGGTAGTATGTCGGCGT (SEQ ID NO:13709), AGTGGATGGCGAATTAGAGCGAGGCGT (SEQ ID NO:13710), TTCGTGTCGGGGTAGCGTCGTTTGGTA (SEQ ID NO:13711), TCGTGTCGGGGTAGCGTCGTTTGGTAT (SEQ ID NO:13712), TTTCGTGTCGGGGTAGCGTCGTTTGGT (SEQ ID NO:13713), GGTTTTCGTGTCGGGGTAGCGTCGTTT (SEQ ID NO:13714) |
| Target1452 | chr14:93153236-93153428 | GACGGAGGGGAGTGGGTCGGGTTTTTT (SEQ ID NO:13715), TTCGGTTATAAGGGGGTAGTTTCGCGC (SEQ ID NO:13716), GACGGAGGGGAGTGGGTCGGGTTTTT (SEQ ID NO:13717), ACGGAGGGAGTGGGTCGGGTTTTTT (SEQ ID NO:13718), ATTCGGTTATAAGGGGGTAGTTTCGCGC (SEQ ID NO:13719), AGGGTTGTAGGGTAGAGAGGTTGCGCGC (SEQ ID NO:13720), CGGGTTGAGGATTTCGGTTCGGCGGAGA (SEQ ID NO:13721), GAGAGGTTGCGCGCGGGGGTTGTTTTTT (SEQ ID NO:13722), TAGGCGTTGGAAGTTTCGGTTCGGAGC (SEQ ID NO:13723), TAGAGAGGTTGCGCGCGGGGTTGTTTT (SEQ ID NO:13724) |
| Target1453 | chr14:93153466-93153595 | AGTTTTGAGTTTCGGGGAAGGCGAGGT (SEQ ID NO:13725), GGTCGTTTCGGGTCGGAGTTTTTAGCG (SEQ ID NO:13726), AGGTCGTTTCGGGTCGGAGTTTTTAGCG (SEQ ID NO:13727), GTTTTGAGTTTCGGGGAAGGCGAGGTC (SEQ ID NO:13728), AGTTTTGAGTTTCGGGGAAGGCGAGGTC (SEQ ID NO:13729), CGTTTGCGGGTTGGGGTTGGGTATTCG (SEQ ID NO:13730), TGCGGGTTGGGGTTGGGTATTCGTAGT (SEQ ID NO:13731), GTTTGCGGGTTGGGGTTGGGTATTCGT (SEQ ID NO:13732), TAGGCGTTGGAAGTTTCGGTTCGGAGC (SEQ ID NO:13733), GCGAGTAGGCGTTGGAAGTTTCGGTTCG (SEQ ID NO:13734) |
| Target1454 | chr14:93153630-93153691 | TTGGGTTTTTAGGGGTGGAGGACGGCG (SEQ ID NO:13735), GGTGTGGGGTTGGGTTTTTAGGGGTGG (SEQ ID NO:13736), GTTGGGTTTTTAGGGGTGGAGGACGGC (SEQ ID NO:13737), TGGGGTTGGGTTTTTAGGGGTGGAGGA (SEQ ID NO:13738), GTGGGGTTGGGTTTTTAGGGGTGGAGG (SEQ ID NO:13739), ATTGGTAAAGCGGGAGGGGATCGGGTG (SEQ ID NO:13740), GGGTAGGGATTGGTAAAGCGGGAGGGG (SEQ ID NO:13741), GGGGTAGGGATTGGTAAAGCGGGAGGG (SEQ ID NO:13742), GATTGGTAAAGCGGGAGGGGATCGGGT (SEQ ID NO:13743), TGGGGTTTTGAGGAGTTGCGTGGGGTA (SEQ ID NO:13744) |
| Target1455 | chr14:93153713-93153873 | TTGGGTTTTTAGGGGTGGAGGACGGCG (SEQ ID NO:13745), GGTGTGGGGTTGGGTTTTTAGGGGTGG (SEQ ID NO:13746), GTTGGGTTTTTAGGGGTGGAGGACGGC (SEQ ID NO:13747), TGGGGTTGGGTTTTTAGGGGTGGAGGA (SEQ ID NO:13748), GTGGGGTTGGGTTTTTAGGGGTGGAGG (SEQ ID NO:13749), ATTGGTAAAGCGGGAGGGGATCGGGTG (SEQ ID NO:13750), GGGTAGGGATTGGTAAAGCGGGAGGGG (SEQ ID NO:13751), GGGGTAGGGATTGGTAAAGCGGGAGGG (SEQ ID NO:13752), GATTGGTAAAGCGGGAGGGGATCGGGT (SEQ ID NO:13753), TGGGGTTTTGAGGAGTTGCGTGGGGTA (SEQ ID NO:13754) |
| Target1456 | chr14:93154010-93154728 | GGACGGGCGTTGTTTTTTAGTTGGCGGA (SEQ ID NO:13755), CGGGCGGGAGTTCGTTTTGTTTGGTGGT (SEQ ID NO:13756), CGGGCGTTGTTTTTAGTTGGCGGACGA (SEQ ID NO:13757), TGGGAAGTTAGGTAGGGAGGGGGACGG (SEQ ID NO:13758), GGAAGTTAGGTAGGGAGGGGGACGGGT (SEQ ID NO:13759), GGGTTTGTGGTTACGGCGGGGTTTTGT (SEQ ID NO:13760), GAGGGGAGGCGTTTCGGAGGGGTTTTA (SEQ ID NO:13761), AGTGGAAGTCGCGTTTGGGTTCGTTGC (SEQ ID NO:13762), TGGCGGGCGTTAAGTTGTTTGCGAGTT (SEQ ID NO:13763), TAGAGGCGGGGTTAGACGTGCGTTTGG (SEQ ID NO:13764) |
| Target1457 | chr14:93522233-93522387 | TGATGAGGTTGGGGTAGGTGAGGTGTT (SEQ ID NO:13765), TTGATGAGGTTGGGGTAGGTGAGGTGT (SEQ ID NO:13766), TGATGAGGTTGGGGTAGGTGAGGTGTTT (SEQ ID NO:13767), TTGATGAGGTTGGGGTAGGTGAGGTGTT (SEQ ID NO:13768), GATGAGGTTGGGGTAGGTGAGGTGTTT (SEQ ID NO:13769) |
| Target1458 | chr14:97499613-97499723 | CGGGGTCGTAGTAGTTTTAGTTTTTTGGCG (SEQ ID NO:13770), CGGGGTCGTAGTAGTTTTAGTTTTTTGGCGT (SEQ ID NO:13771), CGGGGTCGTAGTAGTTTTAGTTTTTTGGCGTT (SEQ ID NO:13772), GGGGTCGTAGTAGTTTTAGTTTTTTGGCGTT (SEQ ID NO:13773), CGGGGTCGTAGTAGTTTTAGTTTTTTGGCGTTT (SEQ ID NO:13774), GTCGGTTAGGAGTTGGGGCGGGAGTC (SEQ ID NO:13775), CGGGGCGAGGGAAGGTATTTGTTTTGGG (SEQ ID NO:13776), ACGCGTTGGGTCGGTTAGGAGTTGGG (SEQ ID NO:13777), GGTCGGTTAGGAGTTGGGGCGGGAGTC (SEQ ID NO:13778), CGGGGCGAGGGAAGGTATTTGTTTTGG (SEQ ID NO:13779) |
| Target1459 | chr14:97499764-97499857 | GGGCGCGGGATTTTAGTAGGTGAGGGT (SEQ ID NO:13780), CGGGCGCGGGATTTTAGTAGGTGAGGG (SEQ ID NO:13781), GCGGGCGCGGGATTTTAGTAGGTGAGG (SEQ ID NO:13782), GGGCGCGGGATTTTAGTAGGTGAGGGTT (SEQ ID NO:13783), GGCGCGGGATTTTAGTAGGTGAGGGTT (SEQ ID NO:13784), GGTTACGCGTGGGGATAGAGGAGGTCG (SEQ ID NO:13785), GTTACGCGTGGGGATAGAGGAGGTCGA (SEQ ID NO:13786), AGGTTACGCGTGGGGATAGAGGAGGTC (SEQ ID NO:13787), GTCGGTTAGGAGTTGGGGCGGGAGTC (SEQ ID NO:13788), TTACGCGTGGGGATAGAGGAGGTCGAA (SEQ ID NO:13789) |

FIGURE 5 CONTINUED

| | | |
|---|---|---|
| Target1460 | chr14:97499908-97499941 | TATGTTTTCGGGGCGCGGCGTAGTAGT (SEQ ID NO:13790), TGTATGTTTTCGGGGCGCGGCGTAGTA (SEQ ID NO:13791), GTATGTTTTCGGGGCGCGGCGTAGTAG (SEQ ID NO:13792), GTTGTATGTTTTCGGGGCGCGGCGTAG (SEQ ID NO:13793), GGTGTCGCGGTGGGTATTTGTTCGGTT (SEQ ID NO:13794), GGGAGGAGTTGGACGCGCGGTTTTC (SEQ ID NO:13795), CGGCGTAGTTTTGGGTTTGTATCGTGGG (SEQ ID NO:13796), CGGCGTAGTTTTGGGTTTGTATCGTGGGA (SEQ ID NO:13797), TCGGCGTAGTTTTGGGTTTGTATCGTGGG (SEQ ID NO:13798), AATTTAGGTTCGGGAGGAGTTGGACGC (SEQ ID NO:13799) |
| Target1461 | chr14:97499959-97499972 | TATGTTTTCGGGGCGCGGCGTAGTAGT (SEQ ID NO:13800), TGTATGTTTTCGGGGCGCGGCGTAGTA (SEQ ID NO:13801), GTATGTTTTCGGGGCGCGGCGTAGTAG (SEQ ID NO:13802), GGTGTCGCGGTGGGTATTTGTTCGGTT (SEQ ID NO:13803), TTGGTGTCGCGGTGGGTATTTGTTCGG (SEQ ID NO:13804), GGGAGGAGTTGGACGCGCGGTTTTC (SEQ ID NO:13805), AATTTAGGTTCGGGAGGAGTTGGACGC (SEQ ID NO:13806), GGGAGGAGTTGGACGCGCGCGGTTTT (SEQ ID NO:13807), TGCGTTGTTTGAGAAGTTGGGGTTACG (SEQ ID NO:13808), TGCGTTGTTTGAGAAGTTGGGGTTACGA (SEQ ID NO:13809) |
| Target1462 | chr14:100857049-100857175 | TGGGGGTTGTGTAGCGTTTAGTGTTTGA (SEQ ID NO:13810), TTGGGGGTTGTGTAGCGTTTAGTGTTTG (SEQ ID NO:13811), TTCGGTATTTGAGTTGGGGAAGAGGGTT (SEQ ID NO:13812), TTTCGGTATTTGAGTTGGGGAAGAGGGT (SEQ ID NO:13813), TTGGGGGTTGTGTAGCGTTTAGTGTTTGA (SEQ ID NO:13814), TTGTCGTTGTGGAGGGTGAGAAGACGT (SEQ ID NO:13815), TGTCGTTGTGGAGGGTGAGAAGACGTA (SEQ ID NO:13816), TTTGTCGTTGTGGAGGGTGAGAAGACGT (SEQ ID NO:13817), TTTGTCGTTGTGGAGGGTGAGAAGACG (SEQ ID NO:13818), TGTCGTTGTGGAGGGTGAGAAGACGT (SEQ ID NO:13819) |
| Target1463 | chr14:100857249-100857281 | TGGGGGTTGTGTAGCGTTTAGTGTTTGA (SEQ ID NO:13820), TTGGGGGTTGTGTAGCGTTTAGTGTTTG (SEQ ID NO:13821), TTGGGGGTTGTGTAGCGTTTAGTGTTTGA (SEQ ID NO:13822), TGGGGGTTGTGTAGCGTTTAGTGTTTGAT (SEQ ID NO:13823), TTTGGGGGTTGTGTAGCGTTTAGTGTTTG (SEQ ID NO:13824), GGGGGGAAGAGGGTAAAATATGATGAAAGGT (SEQ ID NO:13825), GGGGGGAAGAGGGTAAAATATGATGAAAGGTT (SEQ ID NO:13826), AGGGAAAGGGTTAGAGATTTGATAGCGAAAAATGT (SEQ ID NO:13827), GGGGGGAAGAGGGTAAAATATGATGAAAGGTTAAT (SEQ ID NO:13828), AGGGAAAGGGTTAGAGATTTGATAGCGAAAAATGTT (SEQ ID NO:13829) |
| Target1464 | chr14:104155814-104156033 | AGTGTTGGGGGTTGTTGGTTCGGGGTTA (SEQ ID NO:13830), TAGTGTTGGGGGTTGTTGGTTCGGGGTT (SEQ ID NO:13831), ATAGTGTTGGGGGTTGTTGGTTCGGGGT (SEQ ID NO:13832), AGTGTTGGGGGTTGTTGGTTCGGGGTT (SEQ ID NO:13833), GTGTTGGGGGTTGTTGGTTCGGGGTTAT (SEQ ID NO:13834), GGGATTTAGGAATTGGAAATTTAGGGGTGGGG (SEQ ID NO:13835), GGGATTTAGGAATTGGAAATTTAGGGGTGGGGT (SEQ ID NO:13836), AGGGATTTAGGAATTGGAAATTTAGGGGTGGGG (SEQ ID NO:13837), AGGGATTTAGGAATTGGAAATTTAGGGGTGGGGT (SEQ ID NO:13838), GGATTTAGGAATTGGAAATTTAGGGGTGGGGT (SEQ ID NO:13839) |
| Target1465 | chr14:104156111-104156182 | AGTGTTGGGGGTTGTTGGTTCGGGGTTA (SEQ ID NO:13840), TAGTGTTGGGGGTTGTTGGTTCGGGGTT (SEQ ID NO:13841), ATAGTGTTGGGGGTTGTTGGTTCGGGGT (SEQ ID NO:13842), AGTGTTGGGGGTTGTTGGTTCGGGGTT (SEQ ID NO:13843), GTGTTGGGGGTTGTTGGTTCGGGGTTAT (SEQ ID NO:13844) |
| Target1466 | chr14:105750359-105750500 | GTGGAGAGGAAGAGGGATGTGTTGCGT (SEQ ID NO:13845), AGTGGAGAGGAAGAGGGATGTGTTGCGT (SEQ ID NO:13846), AGTGGAGAGGAAGAGGGATGTGTTGCG (SEQ ID NO:13847), TGGAGAGGAAGAGGGATGTGTTGCGTT (SEQ ID NO:13848), GGAGAGGAAGAGGGATGTGTTGCGTTGT (SEQ ID NO:13849), TGTGGACGTGTATGTGTGTTGGGCGTT (SEQ ID NO:13850), TTGTGGACGTGTATGTGTGTTGGGCGT (SEQ ID NO:13851), TGTGGACGTGTATGTGTGTTGGGCGTTT (SEQ ID NO:13852), TTGTGGACGTGTATGTGTGTTGGGCGTT (SEQ ID NO:13853), TTTGTGGACGTGTATGTGTGTTGGGCGT (SEQ ID NO:13854) |
| Target1467 | chr14:105750529-105750596 | GTGGAGAGGAAGAGGGATGTGTTGCGT (SEQ ID NO:13855), AGTGGAGAGGAAGAGGGATGTGTTGCGT (SEQ ID NO:13856), AGTGGAGAGGAAGAGGGATGTGTTGCG (SEQ ID NO:13857), TGGAGAGGAAGAGGGATGTGTTGCGTT (SEQ ID NO:13858), GGAGAGGAAGAGGGATGTGTTGCGTTGT (SEQ ID NO:13859), GGGTTTGCGATGATTTTTTATAGTAGAGTGGATGGA (SEQ ID NO:13860) |
| Target1468 | chr14:106330434-106330539 | TGAGGAGACGGTGATTAGGGTTTTTTGGT (SEQ ID NO:13861), TGAGGAGACGGTGATTAGGGTTTTTTGGTT (SEQ ID NO:13862), TTGAGGAGACGGTGATTAGGGTTTTTTGGT (SEQ ID NO:13863), TGAGGAGACGGTGATTAGGGTTTTTTGGTTT (SEQ ID NO:13864), TTGAGGAGACGGTGATTAGGGTTTTTTGGTT (SEQ ID NO:13865), GGGTTGGTTGTTACGGTCGGTTCGGGA (SEQ ID NO:13866), ACGGGGTTGGTTGTTACGGTCGGTTCG (SEQ ID NO:13867), GGATACGGGGTTGGTTGTTACGGTCGGT (SEQ ID NO:13868), GGATACGGGGTTGGTTGTTACGGTCGG (SEQ ID NO:13869), GGTTGGTTGTTACGGTCGGTTCGGGAT (SEQ ID NO:13870) |
| Target1469 | chr14:106330669-106330724 | GGAGTTTCGGAGGGGTTTTATATGGTTTAGCGT (SEQ ID NO:13871), AGGAGTTTCGGAGGGGTTTTATATGGTTTAGCG (SEQ ID NO:13872), AGGAGTTTCGGAGGGGTTTTATATGGTTTAGCGT (SEQ ID NO:13873), AAGGAGTTTCGGAGGGGTTTTATATGGTTTAGCG (SEQ ID NO:13874), |

FIGURE 5 CONTINUED

|  |  |  |
|---|---|---|
|  |  | AAGGAGTTTCGGAGGGTTTTATATGGTTTAGCGT (SEQ ID NO:13875),<br>CGGGGGTTTTTTGGTTTGCGTTGGGTT (SEQ ID NO:13876), TCGGGGGTTTTTTGGTTTGCGTTGGGTT<br>(SEQ ID NO:13877), GCGTTGGGTTATGTGGGGTTTTTCGGGG (SEQ ID NO:13878),<br>TGCGTTGGGTTATGTGGGGTTTTTCGGG (SEQ ID NO:13879), GCGTTGGGTTATGTGGGGTTTTTCGGG<br>(SEQ ID NO:13880) |
| Target1470 | chr15:22908326-22908385 | TTGGGTAGGTAGACGGGGTTGGGGTTG (SEQ ID NO:13881), TGGGTAGGTAGACGGGGTTGGGGTTGG<br>(SEQ ID NO:13882), GGGTAGGTAGACGGGGTTGGGGTTGGT (SEQ ID NO:13883),<br>TTTGGGTAGGTAGACGGGGTTGGGGTT (SEQ ID NO:13884), ATTTGGGTAGGTAGACGGGGTTGGGGT<br>(SEQ ID NO:13885), AGTGTAGTCGGCGAAGATGTTACGGGT (SEQ ID NO:13886),<br>AAGTGTAGTCGGCGAAGATGTTACGGGT (SEQ ID NO:13887), AAGTGTAGTCGGCGAAGATGTTACGGG<br>(SEQ ID NO:13888), GTGTAGTCGGCGAAGATGTTACGGGTA (SEQ ID NO:13889),<br>AGTGTAGTCGGCGAAGATGTTACGGGTA (SEQ ID NO:13890) |
| Target1471 | chr15:22908489-22908561 | TTTCGGGGAGTTGTCGGGTAGGGGAAA (SEQ ID NO:13891), TTTTCGGGGAGTTGTCGGGTAGGGGAA<br>(SEQ ID NO:13892), TTTTTCGGGGAGTTGTCGGGTAGGGGA (SEQ ID NO:13893),<br>TCGGGGAGTTGTCGGGTAGGGGAAATT (SEQ ID NO:13894), TTCGGGGAGTTGTCGGGTAGGGGAAAT<br>(SEQ ID NO:13895), TGTTCGGTAGTTTTTCGGGGAGTCGGG (SEQ ID NO:13896),<br>TGTTCGGTAGTTTTTCGGGGAGTCGGGA (SEQ ID NO:13897), GTTCGGTAGTTTTTCGGGGAGTCGGGA<br>(SEQ ID NO:13898), TTCGGTAGTTTTTCGGGGAGTCGGGAA (SEQ ID NO:13899),<br>TCGGTAGTTTTTCGGGGAGTCGGGAAT (SEQ ID NO:13900) |
| Target1472 | chr15:27112861-27113062 | TCGGTTGGGGGTGGGGGATATTCGTTG (SEQ ID NO:13901), CGTTGTTCGCGGGGTGGATTCGGATTT<br>(SEQ ID NO:13902), CGGTTGGGGGTGGGGGATATTCGTTGT (SEQ ID NO:13903),<br>CGGGCGGTTTATTTTTGTCGGACGGGG (SEQ ID NO:13904), GGTGATCGGTTGGGGGTGGGGGATATT<br>(SEQ ID NO:13905), TTTTTTGGGTTGGGAGCGCGCGGTGTA (SEQ ID NO:13906),<br>TTTTTGGGTTGGGAGCGCGCGGTGTAG (SEQ ID NO:13907), TTTGGGTTGGGAGCGCGCGGTGTAGTA<br>(SEQ ID NO:13908), CGCGTTTTAGAGTTTCGGGGTTGACGT (SEQ ID NO:13909),<br>TTGGGTTGGGAGCGCGCGGTGTAGTAG (SEQ ID NO:13910) |
| Target1473 | chr15:27113091-27113120 | CGGGGTAGGAGTAGGGGAAGTTTGCGA (SEQ ID NO:13911), TCGGGGTAGGAGTAGGGGAAGTTTGCG<br>(SEQ ID NO:13912), GCGCGGGTTGTTCGAGGTTAGGGGATT (SEQ ID NO:13913),<br>CGCGGGTTGTTCGAGGTTAGGGGATTT (SEQ ID NO:13914), TCGGGGTAGGAGTAGGGGAAGTTTGCGA<br>(SEQ ID NO:13915), TTTGGGTCGTTTTGGTATTCGCGGTCG (SEQ ID NO:13916),<br>GTTTGGGTCGTTTTGGTATTCGCGGTCG (SEQ ID NO:13917), GGTAGGTGGGCGCGGGGGTTGTATTG<br>(SEQ ID NO:13918), GTAGGTGGGCGCGGGGGTTGTATTG (SEQ ID NO:13919),<br>TAGGGTAGGTGGGCGCGGGGGGTTGTAT (SEQ ID NO:13920) |
| Target1474 | chr15:27113137-27113160 | TCGGGGAGTTGGAGATTTTCGGCGTGT (SEQ ID NO:13921), TTGGAGATTTTCGGCGTGTCGTTGCGG<br>(SEQ ID NO:13922), AGGGTCGGGGAGTTGGAGATTTTCGGC (SEQ ID NO:13923),<br>GGGGAGTTGGAGATTTTCGGCGTGTCG (SEQ ID NO:13924), CGGGGAGTTGGAGATTTTCGGCGTGTC<br>(SEQ ID NO:13925), ATTAGGGTCGGCGCGTTAGGGTAGGTG (SEQ ID NO:13926),<br>TTAGGGTCGGCGCGTTAGGGTAGGTG (SEQ ID NO:13927), TATTAGGGTCGGCGCGTTAGGGTAGGT<br>(SEQ ID NO:13928), TTAGGGTCGGCGCGTTAGGGTAGGTGG (SEQ ID NO:13929),<br>GGTTTATTAGGGTCGGCGCGTTAGGGT (SEQ ID NO:13930) |
| Target1475 | chr15:27113170-27113203 | TCGGGGAGTTGGAGATTTTCGGCGTGT (SEQ ID NO:13931), GCGGGTGTTAGGGCGATTTAGGTTGCG<br>(SEQ ID NO:13932), TTGGAGATTTTCGGCGTGTCGTTGCGG (SEQ ID NO:13933),<br>AGGGTCGGGGAGTTGGAGATTTTCGGC (SEQ ID NO:13934), CGGGTGTTAGGGCGATTTAGGTTGCGG<br>(SEQ ID NO:13935), ATTAGGGTCGGCGCGTTAGGGTAGGTG (SEQ ID NO:13936),<br>TTAGGGTCGGCGCGTTAGGGTAGGTG (SEQ ID NO:13937), TATTAGGGTCGGCGCGTTAGGGTAGGT<br>(SEQ ID NO:13938), TTAGGGTCGGCGCGTTAGGGTAGGTGG (SEQ ID NO:13939),<br>GGTTTATTAGGGTCGGCGCGTTAGGGT (SEQ ID NO:13940) |
| Target1476 | chr15:27113216-27113240 | TCGGGGAGTTGGAGATTTTCGGCGTGT (SEQ ID NO:13941), GCGGGTGTTAGGGCGATTTAGGTTGCG<br>(SEQ ID NO:13942), TTGGAGATTTTCGGCGTGTCGTTGCGG (SEQ ID NO:13943),<br>AGGGTCGGGGAGTTGGAGATTTTCGGC (SEQ ID NO:13944), CGGGTGTTAGGGCGATTTAGGTTGCGG<br>(SEQ ID NO:13945), TATGCGGGAAATTCGGGCGGCGTTTTT (SEQ ID NO:13946),<br>ATTAGGGTCGGCGCGTTAGGGTAGGTG (SEQ ID NO:13947), GTATGCGGGAAATTCGGGCGGCGTTTT<br>(SEQ ID NO:13948), ATGCGGGAAATTCGGGCGGCGTTTTTC (SEQ ID NO:13949),<br>TATGCGGGAAATTCGGGCGGCGTTTT (SEQ ID NO:13950) |
| Target1477 | chr15:27113348-27113363 | AGTTTTTGTGGGGGTTCGGAGGGTCGT (SEQ ID NO:13951), TGTTTTGGCGCGTCGGTTTTGGTGAGT<br>(SEQ ID NO:13952), GTTTTTGTGGGGGTTCGGAGGGTCGTG (SEQ ID NO:13953),<br>GGTGAGTTTTTGTGGGGGTTCGGAGGG (SEQ ID NO:13954), TTGGGGGTTTTTGGTTCGGGGGTTGAGG<br>(SEQ ID NO:13955), GGTTCGGGTTAGAGTTAGGCGGCGAGT (SEQ ID NO:13956),<br>GGGTTCGGGTTAGAGTTAGGCGGCGAG (SEQ ID NO:13957), GGGTTCGGGTTAGAGTTAGGCGGCGA<br>(SEQ ID NO:13958), GGGGTTCGGGTTAGAGTTAGGCGGCGA (SEQ ID NO:13959),<br>GGTTCGGGTTAGAGTTAGGCGGCGAGTA (SEQ ID NO:13960) |
| Target1478 | chr15:27113386-27113412 | TTGGGGGTTTTTGGTTCGGGGTTGAGG (SEQ ID NO:13961), TGGGGGTTTTTGGTTCGGGGTTGAGGG<br>(SEQ ID NO:13962), TCGGGTTTTTCGTATGTAGCGTCGCGT (SEQ ID NO:13963),<br>GGGTTTTTGGTTCGGGGTTGAGGGGC (SEQ ID NO:13964), GGGGTTTTTGGTTCGGGGTTGAGGGG (SEQ<br>ID NO:13965), AGAAGGGTAGGGTGTTATGCGGTGGTC (SEQ ID NO:13966),<br>AAGAAGGGTAGGGTGTTATGCGGTGGT (SEQ ID NO:13967), AAGAAGGGTAGGGTGTTATGCGGTGGTC |

FIGURE 5 CONTINUED (SEQ ID NO:13968), AGAAGGGTAGGGTGTTATGCGGTGGT (SEQ ID NO:13969), TAAGAAGGGTAGGGTGTTATGCGGTGGT (SEQ ID NO:13970)

Target1479    chr15:27113413-27113429    TTGGGGGTTTTTGGTTCGGGGTTGAGG (SEQ ID NO:13971), TGGGGGTTTTTGGTTCGGGGTTGAGGG (SEQ ID NO:13972), TCGGGTTTTTCGTATGTAGCGTCGCGT (SEQ ID NO:13973), GGGTTTTTGGTTCGGGGTTGAGGGGC (SEQ ID NO:13974), GGGGTTTTTGGTTCGGGGTTGAGGGG (SEQ ID NO:13975), AGAAGGGTAGGGTGTTATGCGGTGGTC (SEQ ID NO:13976), AAGAAGGGTAGGGTGTTATGCGGTGGT (SEQ ID NO:13977), AAGAAGGGTAGGGTGTTATGCGGTGGTC (SEQ ID NO:13978), AGAAGGGTAGGGTGTTATGCGGTGGT (SEQ ID NO:13979), TAAGAAGGGTAGGGTGTTATGCGGTGGT (SEQ ID NO:13980)

Target1480    chr15:29395738-29395767    GAGTTGGGGTCGGTAGGGCGATTTTTT (SEQ ID NO:13981), GAGTTGGGGTCGGTAGGGCGATTTTTT (SEQ ID NO:13982), AGTTGGGGTCGGTAGGGCGATTTTTT (SEQ ID NO:13983), CGTTTATAGGTTTGGTTGCGAGTTGGGGT (SEQ ID NO:13984), ACGTTTATAGGTTTGGTTGCGAGTTGGGG (SEQ ID NO:13985), CGGTGTTATTTGGGTCGTTGGTGTGTCG (SEQ ID NO:13986), CGGTGTTATTTGGGTCGTTGGTGTGTCGT (SEQ ID NO:13987), TCGGTGTTATTTGGGTCGTTGGTGTGTCG (SEQ ID NO:13988), TCGGTGTTATTTGGGTCGTTGGTGTGT (SEQ ID NO:13989), TCGGTGTTATTTGGGTCGTTGGTGTGTCGT (SEQ ID NO:13990)

Target1481    chr15:29395777-29395803    GCGGTTTAGATGATATCGGAAGGAGGCG (SEQ ID NO:13991), AGCGGTTTAGATGATATCGGAAGGAGGCG (SEQ ID NO:13992), AGCGGTTTAGATGATATCGGAAGGAGGC (SEQ ID NO:13993), TAGCGGTTTAGATGATATCGGAAGGAGGCG (SEQ ID NO:13994), GTGGAGTGACGGGGAGGCGGCGGTTG (SEQ ID NO:13995), TCGGATTTTATTTGGGTTTTTTCGGGTTATCGTT (SEQ ID NO:13996), TTCGGATTTTATTTGGGTTTTTTCGGGTTATCGT (SEQ ID NO:13997), TTCGGATTTTATTTGGGTTTTTTCGGGTTATCGTT (SEQ ID NO:13998), TTTCGGATTTTATTTGGGTTTTTTCGGGTTATCGT (SEQ ID NO:13999), TTTCGGATTTTATTTGGGTTTTTTCGGGTTATCGTT (SEQ ID NO:14000)

Target1482    chr15:29395810-29395819    GCGGTTTAGATGATATCGGAAGGAGGCGT (SEQ ID NO:14001), GCGGTTTAGATGATATCGGAAGGAGGCG (SEQ ID NO:14002), AGCGGTTTAGATGATATCGGAAGGAGGCG (SEQ ID NO:14003), AGCGGTTTAGATGATATCGGAAGGAGGCGT (SEQ ID NO:14004), AGCGGTTTAGATGATATCGGAAGGAGGC (SEQ ID NO:14005), TCGGATTTTATTTGGGTTTTTTCGGGTTATCGTT (SEQ ID NO:14006), TTCGGATTTTATTTGGGTTTTTTCGGGTTATCGT (SEQ ID NO:14007), TTCGGATTTTATTTGGGTTTTTTCGGGTTATCGTT (SEQ ID NO:14008), TTTCGGATTTTATTTGGGTTTTTTCGGGTTATCGT (SEQ ID NO:14009), TTTCGGATTTTATTTGGGTTTTTTCGGGTTATCGTT (SEQ ID NO:14010)

Target1483    chr15:29395962-29395993    AGGAAGAATGGCGGTGGTTCGAGGGAG (SEQ ID NO:14011), GAGGAAGAATGGCGGTGGTTCGAGGGA (SEQ ID NO:14012), GGAAGAATGGCGGTGGTTCGAGGGAGT (SEQ ID NO:14013), GGGCGGAGGATGTCGTTTAAGGGGAGG (SEQ ID NO:14014), GGGGCGGAGGATGTCGTTTAAGGGGAG (SEQ ID NO:14015), GTTGATGGGGTTCGGTAGGAGGGTCGG (SEQ ID NO:14016), GGTTGGTTTGCGGAGTTGGCGAGTTGA (SEQ ID NO:14017), GCGTAGGAGAGGGTCGGGGTTTTTGGGA (SEQ ID NO:14018), GCGAGTTGATGGGGTTCGGTAGGAGGG (SEQ ID NO:14019), GGCGAGTTGATGGGGTTCGGTAGGAGG (SEQ ID NO:14020)

Target1484    chr15:29396043-29396084    GTGGTGGAGTCGGGGTTTTCGGGGTTTT (SEQ ID NO:14021), GGTGGTGGAGTCGGGGTTTTCGGGGTTT (SEQ ID NO:14022), TGGAGTCGGGGTTTTCGGGGTTTTAGGGT (SEQ ID NO:14023), GGAGTCGGGGTTTTCGGGGTTTTAGGGT (SEQ ID NO:14024), TGGAGTCGGGGTTTTCGGGGTTTTAGGG (SEQ ID NO:14025), GTTGATGGGGTTCGGTAGGAGGGTCGG (SEQ ID NO:14026), GGTTGGTTTGCGGAGTTGGCGAGTTGA (SEQ ID NO:14027), GCGAGTTGATGGGGTTCGGTAGGAGGG (SEQ ID NO:14028), GGCGAGTTGATGGGGTTCGGTAGGAGG (SEQ ID NO:14029), TGGTTTGCGGAGTTGGCGAGTTGATGG (SEQ ID NO:14030)

Target1485    chr15:37180583-37180588    GGGGTCGGGGTTGGGAGAAAGTGTCG (SEQ ID NO:14031), CGGGGTCGGGGTTGGGAGAAAGTGTC (SEQ ID NO:14032), GTCGGGGTTGGGAGAAAGTGTCGCGT (SEQ ID NO:14033), GGGTCGGGGTTGGGAGAAAGTGTCGC (SEQ ID NO:14034), GTCGGGGTTGGGAGAAAGTGTCGCGCG (SEQ ID NO:14035)

Target1486    chr15:37180634-37180639    GGAGGGGGTTCGTTTCGGCGCG (SEQ ID NO:14036), CGGAGGGGGTTCGTTTCGGCGC (SEQ ID NO:14037), GAGGGGGTTCGTTTCGGCGCGC (SEQ ID NO:14038), CGGAGGGGGTTCGTTTCGGCGCG (SEQ ID NO:14039), GGAGGGGGTTCGTTTCGGCGCGC (SEQ ID NO:14040), TGTAAATTATGGGGGTACGGGGGGGTTCG (SEQ ID NO:14041), GTAAATTATGGGGGTACGGGGGGGTTCG (SEQ ID NO:14042), TGTAAATTATGGGGGTACGGGGGGGTTC (SEQ ID NO:14043), TTGTAAATTATGGGGGTACGGGGGGGTTCG (SEQ ID NO:14044), TTGTAAATTATGGGGGTACGGGGGGGTTC (SEQ ID NO:14045)

Target1487    chr15:41787560-41787839    GGGAGAGTTGTGGTCGCGCGTTTGTTT (SEQ ID NO:14046), AGAGTTGTGGTCGCGCGTTTGTTTCGT (SEQ ID NO:14047), TAGGTGTTGGGTGCGTCGGTTCGGTTA (SEQ ID NO:14048), AGGTGTTGGGTGCGTCGGTTCGGTTAT (SEQ ID NO:14049), GTCGTTAGGTGTTGGGTGCGTCGGTTC (SEQ ID NO:14050), AGTATTTGGCGGCGGGGGGGTGTTTTTG (SEQ ID NO:14051),

FIGURE 5 CONTINUED

GCGGTAGGTTAGTGATCGAGTCGGCGT (SEQ ID NO:14052), GCGTATTTAGTATTTGGCGGCGGGGGG
{SEQ ID NO:14053}, AGCGGTAGGTTAGTGATCGAGTCGGCG (SEQ ID NO:14054),
GCGGGAGTAGGCGCGCGGTTATAGTTTT {SEQ ID NO:14055}

Target1488    chr15:41787877-41787949    TAGGTGTTGGGTGCGTCGGTTCGGTTA (SEQ ID NO:14056), AGGTGTTGGGTGCGTCGGTTCGGTTAT
{SEQ ID NO:14057}, GTCGTTAGGTGTTGGGTGCGTCGGTTC (SEQ ID NO:14058),
TTAGGTGTTGGGTGCGTCGGTTCGGTT {SEQ ID NO:14059}, GGTGTTGGGTGCGTCGGTTCGGTTATT
{SEQ ID NO:14060}, CGAGTTTTTGCGGGCGGAAGAGGGAAG {SEQ ID NO:14061},
GAGTTTTTGCGGGCGGAAGAGGGAAGC {SEQ ID NO:14062}, TTCGTCGAGTTTTTGCGGGCGGAAGAG
{SEQ ID NO:14063}, GGCGGGGCGGGGGGGTTTTTTATTGTTT {SEQ ID NO:14064},
TCGAGTTTTTGCGGGCGGAAGAGGGAA {SEQ ID NO:14065}

Target1489    chr15:41787977-41788111    TCGGCGAAGTGTTTGGGAGAGGGAGTG {SEQ ID NO:14066}, TGGGAGAGGGAGTGCGTTAGGAGGAGG
{SEQ ID NO:14067}, GGGAGAGGGAGTGCGTTAGGAGGAGGT {SEQ ID NO:14068},
TTCGGCGAAGTGTTTGGGAGAGGGAGT {SEQ ID NO:14069}, GGGAGTGCGTTAGGAGGAGGTTTTGCG
{SEQ ID NO:14070}, CGAGTTTTTGCGGGCGGAAGAGGGAAG {SEQ ID NO:14071},
GAGTTTTTGCGGGCGGAAGAGGGAAGC {SEQ ID NO:14072}, TTCGTCGAGTTTTTGCGGGCGGAAGAG
{SEQ ID NO:14073}, TCGAGTTTTTGCGGGCGGAAGAGGGAA {SEQ ID NO:14074},
TTTCGTCGAGTTTTTGCGGGCGGAAGA {SEQ ID NO:14075}

Target1490    chr15:41788184-41788200    TCGGCGAAGTGTTTGGGAGAGGGAGTG {SEQ ID NO:14076}, TGGGAGAGGGAGTGCGTTAGGAGGAGG
{SEQ ID NO:14077}, GGGAGAGGGAGTGCGTTAGGAGGAGGT {SEQ ID NO:14078},
TTCGGCGAAGTGTTTGGGAGAGGGAGT {SEQ ID NO:14079}, GGAGTGCGTTAGGAGGAGGTTTTGCGG
{SEQ ID NO:14080}, GATTTCGGGGAGGTTTCGGCGGGGTTTG {SEQ ID NO:14081},
GTTTGATTTCGGGGAGGTTTCGGCGGG {SEQ ID NO:14082}, GGGGGTGGGGAAGGTTTGGAAGTCGTA
{SEQ ID NO:14083}, TTGGGGGTGGGGAAGGTTTGGAAGTCG {SEQ ID NO:14084},
TGTTTGATTTCGGGGAGGTTTCGGCGG {SEQ ID NO:14085}

Target1491    chr15:41788209-41788242    GGAGTGCGTTAGGAGGAGGTTTTGCGG {SEQ ID NO:14086}, GGGAGTGCGTTAGGAGGAGGTTTTGCG
{SEQ ID NO:14087}, GAGTGCGTTAGGAGGAGGTTTTGCGGT {SEQ ID NO:14088},
AGTGCGTTAGGAGGAGGTTTTGCGGTT {SEQ ID NO:14089}, GGAGTGCGTTAGGAGGAGGTTTTGCGGT
{SEQ ID NO:14090}, GATTTCGGGGAGGTTTCGGCGGGGTTTG {SEQ ID NO:14091},
GTTTGATTTCGGGGAGGTTTCGGCGGG {SEQ ID NO:14092}, GGGGGTGGGGAAGGTTTGGAAGTCGTA
{SEQ ID NO:14093}, TTGGGGGTGGGGAAGGTTTGGAAGTCG {SEQ ID NO:14094},
TGTTTGATTTCGGGGAGGTTTCGGCGG {SEQ ID NO:14095}

Target1492    chr15:41793563-41793583    TTTAGTTGTTTTCGGTGGGTCGGGGGC {SEQ ID NO:14096}, TTAGTTGTTTTCGGTGGGTCGGGGGCG
{SEQ ID NO:14097}, TTTTAGTTGTTTTCGGTGGGTCGGGGGC {SEQ ID NO:14098},
TTAGTTGTTTTCGGTGGGTCGGGGGC {SEQ ID NO:14099}, TAGTTGTTTTCGGTGGGTCGGGGGCG {SEQ
ID NO:14100}, GGGTTAAGGTTTGATAATCGGCGTTTCGG {SEQ ID NO:14101},
GGGTTAAGGTTTGATAATCGGCGTTTCGGT {SEQ ID NO:14102},
AGGGTTAAGGTTTGATAATCGGCGTTTCGG {SEQ ID NO:14103},
AGGGTTAAGGTTTGATAATCGGCGTTTCGGT {SEQ ID NO:14104},
GGTTAAGGTTTGATAATCGGCGTTTCGGT {SEQ ID NO:14105}

Target1493    chr15:41793621-41794126    GCGTGTTTTGTTAGGTCGGTTGGGGGG {SEQ ID NO:14106}, TGGGGGGGATTAAGTAGGGGTTCGGGGT
{SEQ ID NO:14107}, GTCGGGGGCGTGGCGAGATTTTGTTTT {SEQ ID NO:14108},
CGGGGTCGGGATAGTTGTTTGAGGGGG {SEQ ID NO:14109}, ATATTGGTGAGTAGTGGGGCGGGTGGG
{SEQ ID NO:14110}, AGGTAGCGGTTAGGGTATGAGGGGGCG {SEQ ID NO:14111},
GGTAGCGGTTAGGGTATGAGGGGGCG {SEQ ID NO:14112}, GTAGCGGTTAGGGTATGAGGGGGCGTA
{SEQ ID NO:14113}, GGTAGCGGTTAGGGTATGAGGGGGCGT {SEQ ID NO:14114},
TAGGTAGCGGTTAGGGTATGAGGGGGCG {SEQ ID NO:14115}

Target1494    chr15:41794130-41795305    GCGTGTTTTGTTAGGTCGGTTGGGGGG {SEQ ID NO:14116}, TAGGGCGGGAATTCGGTAAGGGCGTTT
{SEQ ID NO:14117}, TTAGGGCGGGAATTCGGTAAGGGCGTT {SEQ ID NO:14118},
GGGCGGGAATTCGGTAAGGGCGTTTTT {SEQ ID NO:14119}, TGGGGGGATTAAGTAGGGGTTCGGGGT
{SEQ ID NO:14120}, ATTTGGTTATCGGGGAGGGGCGTGGTT {SEQ ID NO:14121},
AGGGTGGGGTGGGAGAGGAGGGTAAAT {SEQ ID NO:14122}, AGGATTTGGTTATCGGGGAGGGGCGTG
{SEQ ID NO:14123}, TTGGTTATCGGGGAGGGGCGTGGTTTT {SEQ ID NO:14124},
TTTGGTTATCGGGGAGGGGCGTGGTTT {SEQ ID NO:14125}

Target1495    chr15:45427396-45427418    ACGTGTTTTTAGATTTGGTGAGCGTGGAAA {SEQ ID NO:14126},
ACGTGTTTTTAGATTTGGTGAGCGTGGAAAT {SEQ ID NO:14127},
ACGTGTTTTTAGATTTGGTGAGCGTGGAAATT {SEQ ID NO:14128},
TTACGTGTTTTTAGATTTGGTGAGCGTGGAAA {SEQ ID NO:14129},
ACGTGTTTTTAGATTTGGTGAGCGTGGAAATTT {SEQ ID NO:14130},
TCGGGGATTGTTGGGATTTCGTTCGGT {SEQ ID NO:14131}, CGGGGATTGTTGGGATTTCGTTCGGTT
{SEQ ID NO:14132}, TCGGGGATTGTTGGGATTTCGTTCGGTT {SEQ ID NO:14133},
TTCGGGGATTGTTGGGATTTCGTTCGGT {SEQ ID NO:14134}, GGGTTTCGGGGATTGTTGGGATTTCGT
{SEQ ID NO:14135}

Target1496    chr15:45427505-45427520    GGATTCGGTGAGGCGGGGAAGGC {SEQ ID NO:14136}, GGGATTCGGTGAGGCGGGGAAGGC {SEQ ID
NO:14137}, GGGATTCGGTGAGGCGGGGAAGG {SEQ ID NO:14138}, GGAAGGCGGCGGGAAGGGATCG
{SEQ ID NO:14139}, GGGAAGGCGGCGGGAAGGGATC {SEQ ID NO:14140},
CGGCGAGTTAGGGAAGGTCGGGGGTTC {SEQ ID NO:14141}, CGGCGAGTTAGGGAAGGTCGGGGGTT {SEQ

FIGURE 5 CONTINUED

|  |  | ID NO:14142), GCGGCGAGTTAGGGAAGGTCGGGGTTC (SEQ ID NO:14143), CGGCGAGTTAGGGAAGGTCGGGGT (SEQ ID NO:14144), GCGGCGAGTTAGGGAAGGTCGGGGTT (SEQ ID NO:14145) |
| Target1497 | chr15:45427592-45427656 | GGTAGGGTTTGGAGGGGAGAGGCGTTT (SEQ ID NO:14146), TTTGGTAGGGTTTGGAGGGGAGAGGCG (SEQ ID NO:14147), CGGGTTTGGTAGGGTTTGGAGGGGAGA (SEQ ID NO:14148), TCGGGTTTGGTAGGGTTTGGAGGGGAG (SEQ ID NO:14149), GGAAGGCGGCGGGAAGGGATCGTATTT (SEQ ID NO:14150), CGGCGAGTTAGGGAAGGTCGGGGTTC (SEQ ID NO:14151), CGGCGAGTTAGGGAAGGTCGGGGTT (SEQ ID NO:14152), GCGGCGAGTTAGGGAAGGTCGGGGTTC (SEQ ID NO:14153), CGGCGAGTTAGGGAAGGTCGGGGT (SEQ ID NO:14154), GCGGCGAGTTAGGGAAGGTCGGGGTT (SEQ ID NO:14155) |
| Target1498 | chr15:45427660-45427773 | TAGGTGACGGGTTGGTTGGACGGTAGC (SEQ ID NO:14156), TGACGGGTTGGTTGGACGGTAGCGTTA (SEQ ID NO:14157), GGTAGGGTTTGGAGGGGAGAGGCGTTT (SEQ ID NO:14158), TTTGGTAGGGTTTGGAGGGGAGAGGCG (SEQ ID NO:14159), CGGGTTTGGTAGGGTTTGGAGGGGAGA (SEQ ID NO:14160), GGTTCGTTTTGTTCGGTGGCGGGGTC (SEQ ID NO:14161), GGGTTCGTTTTGTTCGGTGGCGGGGTC (SEQ ID NO:14162), GGTTCGTTTTGTTCGGTGGCGGGGT (SEQ ID NO:14163), CGGGCGTCGTTTATATGAGTAGGGGGT (SEQ ID NO:14164), GGGTTCGTTTTGTTCGGTGGCGGGG (SEQ ID NO:14165) |
| Target1499 | chr15:53083258-53083384 | GGAGAGCGGAGGGAGTGTTTTGGAGG (SEQ ID NO:14166), GGGAGAGCGGAGGGAGTGTTTTGGAGG (SEQ ID NO:14167), GAGAGCGGAGGGAGTGTTTTGGAGGGT (SEQ ID NO:14168), CGAGGGAGAGCGGAGGGAGTGTTTTGG (SEQ ID NO:14169), GATGATTCGGTTTGTGGAGGGGGGCGA (SEQ ID NO:14170), AGGAGGGTTTGGGAGTAATCGTAGGGA (SEQ ID NO:14171), CGGGTGTTTTAGTAGGAGGGTTTTGGA (SEQ ID NO:14172), TCGGGTGTTTTAGTAGGAGGGTTTTGGG (SEQ ID NO:14173), GGAGGGTTTTAGGGAGTAATCGTAGGGAC (SEQ ID NO:14174), TCGGGTGTTTTAGTAGGAGGGTTTTGGGA (SEQ ID NO:14175) |
| Target1500 | chr15:53083406-53083519 | GTGGAGGTTCGGGTCGTTTTTGCGGTT (SEQ ID NO:14176), GGTCGTGGAGGTTCGGGTCGTTTTTGC (SEQ ID NO:14177), GGAGAGCGGAGGGAGTGTTTTGGAGGG (SEQ ID NO:14178), GGGAGAGCGGAGGGAGTGTTTTGGAGG (SEQ ID NO:14179), GGGTCGTGGAGGTTCGGGTCGTTTTTG (SEQ ID NO:14180), GATTGGAGCGTGATTGTGGGAAGGGCGA (SEQ ID NO:14181), ATTGGAGCGTGATTGTGGGAAGGGCGA (SEQ ID NO:14182), GGAGCGTGATTGTGGGAAGGGCGAAAT (SEQ ID NO:14183), TGGAGCGTGATTGTGGGAAGGGCGAAA (SEQ ID NO:14184), TTGGAGCGTGATTGTGGGAAGGGCGAA (SEQ ID NO:14185) |
| Target1501 | chr15:53083529-53083576 | GGCGCGCGGGTTTTCGTTTGGTTTTTA (SEQ ID NO:14186), GCGCGCGGGTTTTCGTTTGGTTTTTAGG (SEQ ID NO:14187), GGCGCGCGGGTTTTCGTTTGGTTTTTAG (SEQ ID NO:14188), GGCGCGCGGGTTTTCGTTTGGTTTTTT (SEQ ID NO:14189), CGCGCGGGTTTTCGTTTGGTTTTTAGGG (SEQ ID NO:14190), GATTGGAGCGTGATTGTGGGAAGGGCG (SEQ ID NO:14191), ATTGGAGCGTGATTGTGGGAAGGGCGA (SEQ ID NO:14192), GGAGCGTGATTGTGGGAAGGGCGAAAT (SEQ ID NO:14193), TGGAGCGTGATTGTGGGAAGGGCGAAA (SEQ ID NO:14194), TTGGAGCGTGATTGTGGGAAGGGCGAA (SEQ ID NO:14195) |
| Target1502 | chr15:53087132-53087162 | TGAATTGTTCGGATTTGGGGTGGCGGT (SEQ ID NO:14196), TGAATTGTTCGGATTTGGGGTGGCGGTT (SEQ ID NO:14197), TTGAATTGTTCGGATTTGGGGTGGCGGT (SEQ ID NO:14198), GAATTGTTCGGATTTGGGGTGGCGGTT (SEQ ID NO:14199), GGGCGTTGAATTGTTCGGATTTGGGGT (SEQ ID NO:14200), AGCGCGGGGTTAATGGAATGTAGGGTT (SEQ ID NO:14201), TAGCGCGGGGTTAATGGAATGTAGGGT (SEQ ID NO:14202), GCGCGGGGTTAATGGAATGTAGGGTTT (SEQ ID NO:14203), AGCGCGGGGTTAATGGAATGTAGGGTTT (SEQ ID NO:14204), AGCGCGGGGTTAATGGAATGTAGGGT (SEQ ID NO:14205) |
| Target1503 | chr15:53087229-53087254 | GGGGTTGGAGAGGATAAGGGGAAGGACG (SEQ ID NO:14206), GGGGTTGGAGAGGATAAGGGGAAGGACGA (SEQ ID NO:14207), AGGGGTTGGAGAGGATAAGGGGAAGGACG (SEQ ID NO:14208), AGGGGTTGGAGAGGATAAGGGGAAGGA (SEQ ID NO:14209), GGGTTGGAGAGGATAAGGGGAAGGACG (SEQ ID NO:14210), AGGGCGAGAGAATGGTGCGTTTGAAGA (SEQ ID NO:14211), GGGCGAGAGAATGGTGCGTTTGAAGATC (SEQ ID NO:14212), GGGCGAGAGAATGGTGCGTTTGAAGAT (SEQ ID NO:14213), AGGGCGAGAGAATGGTGCGTTTGAAGAT (SEQ ID NO:14214), TGGTGCGTTTGAAGATCGTTTTGGGTCG (SEQ ID NO:14215) |
| Target1504 | chr15:53087282-53087306 | TAGAAGGGGCGGACGGAGGGTAAAGTC (SEQ ID NO:14216), TTAGAAGGGGCGGACGGAGGGTAAAGT (SEQ ID NO:14217), AGAAGGGGCGGACGGAGGGTAAAGTC (SEQ ID NO:14218), GGGGTTGGAGAGGATAAGGGGAAGGACG (SEQ ID NO:14219), TTAGAAGGGGCGGACGGAGGGTAAAGTC (SEQ ID NO:14220), AGGGCGAGAGAATGGTGCGTTTGAAGA (SEQ ID NO:14221), CGGGTGGGGTGGTTGGTTTAAGTTTCGT (SEQ ID NO:14222), CGGGTGGGGTGGTTGGTTTAAGTTTCG (SEQ ID NO:14223), TCGGGTGGGGTGGTTGGTTTAAGTTTCG (SEQ ID NO:14224), TCGGGTGGGGTGGTTGGTTTAAGTTTCGT (SEQ ID NO:14225) |
| Target1505 | chr15:53087377-53087420 | GCGGAGGGTGGTTGTTTAGTCGGAGT (SEQ ID NO:14226), AGCGGAGGGTGGTTGTTTAGTCGGGAG (SEQ ID NO:14227), CGTTTTGGAGGGATAGGGAAGGGCGGA (SEQ ID NO:14228), TCGTTTTGGAGGGATAGGGAAGGGCGGA (SEQ ID NO:14229), AAGCGGAGGGTGGTTGTTTAGTCGGGA (SEQ ID NO:14230), CGGGTGGGGTGGTTGGTTTAAGTTTCGT (SEQ ID NO:14231), CGGGTGGGGTGGTTGGTTTAAGTTTCG (SEQ ID NO:14232), TCGGGTGGGGTGGTTGGTTTAAGTTTCG |

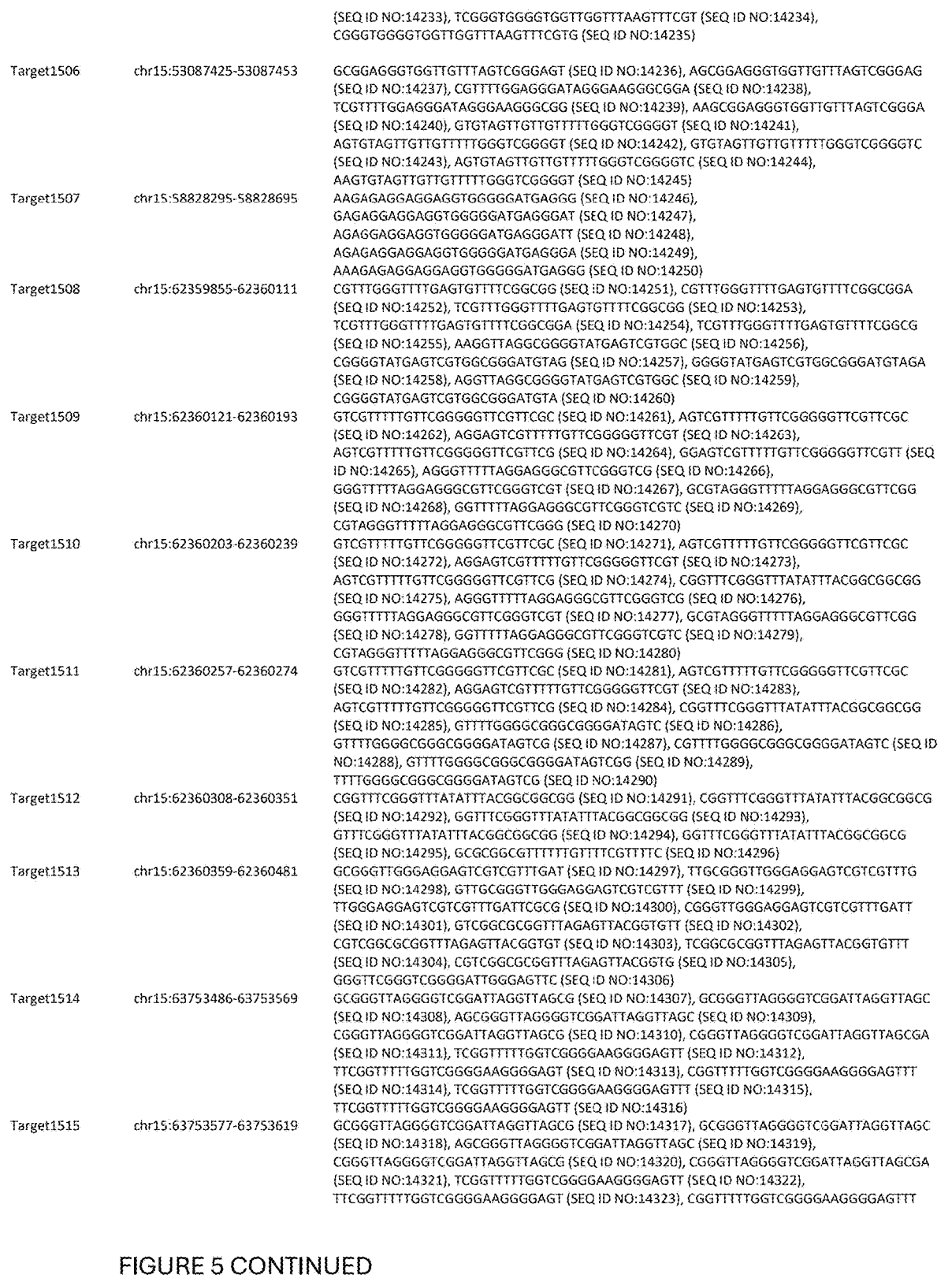

FIGURE 5 CONTINUED (SEQ ID NO:14233), TCGGGTGGGGTGGTTGGTTTAAGTTTCGT (SEQ ID NO:14234),
CGGGTGGGGTGGTTGGTTTAAGTTTCGTG (SEQ ID NO:14235)

Target1506   chr15:53087425-53087453   GCGGAGGGTGGTTGTTTAGTCGGGAGT (SEQ ID NO:14236), AGCGGAGGGTGGTTGTTTAGTCGGGAG
(SEQ ID NO:14237), CGTTTTGGAGGGGATAGGGAAGGGCGGA (SEQ ID NO:14238),
TCGTTTTGGAGGGGATAGGGAAGGGCGG (SEQ ID NO:14239), AAGCGGAGGGTGGTTGTTTAGTCGGGA
(SEQ ID NO:14240), GTGTAGTTGTTGTTTTTGGGTCGGGGT (SEQ ID NO:14241),
AGTGTAGTTGTTGTTTTTGGGTCGGGGT (SEQ ID NO:14242), GTGTAGTTGTTGTTTTTGGGTCGGGGTC
(SEQ ID NO:14243), AGTGTAGTTGTTGTTTTTGGGTCGGGGTC (SEQ ID NO:14244),
AAGTGTAGTTGTTGTTTTTGGGTCGGGGT (SEQ ID NO:14245)

Target1507   chr15:58828295-58828695   AAGAGAGGAGGAGGTGGGGGATGAGGG (SEQ ID NO:14246),
GAGAGGAGGAGGTGGGGGATGAGGGAT (SEQ ID NO:14247),
AGAGGAGGAGGTGGGGGATGAGGGATT (SEQ ID NO:14248),
AGAGAGGAGGAGGTGGGGGATGAGGGA (SEQ ID NO:14249),
AAAGAGAGGAGGAGGTGGGGGATGAGGG (SEQ ID NO:14250)

Target1508   chr15:62359855-62360111   CGTTTGGGTTTTGAGTGTTTTCGGCGG (SEQ ID NO:14251), CGTTTGGGTTTTGAGTGTTTTCGGCGGA
(SEQ ID NO:14252), TCGTTTGGGTTTTGAGTGTTTTCGGCGG (SEQ ID NO:14253),
TCGTTTGGGTTTTGAGTGTTTTCGGCGGA (SEQ ID NO:14254), TCGTTTGGGTTTTGAGTGTTTTCGGCG
(SEQ ID NO:14255), AAGGTTAGGCGGGGTATGAGTCGTGGC (SEQ ID NO:14256),
CGGGGTATGAGTCGTGGCGGGATGTAG (SEQ ID NO:14257), GGGGTATGAGTCGTGGCGGGATGTAGA
(SEQ ID NO:14258), AGGTTAGGCGGGGTATGAGTCGTGGC (SEQ ID NO:14259),
CGGGGTATGAGTCGTGGCGGGATGTA (SEQ ID NO:14260)

Target1509   chr15:62360121-62360193   GTCGTTTTTGTTCGGGGGTTCGTTCGC (SEQ ID NO:14261), AGTCGTTTTTGTTCGGGGGTTCGTTCGC
(SEQ ID NO:14262), AGGAGTCGTTTTTGTTCGGGGGTTCGT (SEQ ID NO:14263),
AGTCGTTTTTGTTCGGGGGTTCGTTCG (SEQ ID NO:14264), GGAGTCGTTTTTGTTCGGGGGTTCGTT (SEQ
ID NO:14265), AGGGTTTTTAGGAGGGCGTTCGGGTCG (SEQ ID NO:14266),
GGGTTTTTAGGAGGGCGTTCGGGTCGT (SEQ ID NO:14267), GCGTAGGGTTTTTAGGAGGGCGTTCGG
(SEQ ID NO:14268), GGTTTTTAGGAGGGCGTTCGGGTCGTC (SEQ ID NO:14269),
CGTAGGGTTTTTAGGAGGGCGTTCGGG (SEQ ID NO:14270)

Target1510   chr15:62360203-62360239   GTCGTTTTTGTTCGGGGGTTCGTTCGC (SEQ ID NO:14271), AGTCGTTTTTGTTCGGGGGTTCGTTCGC
(SEQ ID NO:14272), AGGAGTCGTTTTTGTTCGGGGGTTCGT (SEQ ID NO:14273),
AGTCGTTTTTGTTCGGGGGTTCGTTCG (SEQ ID NO:14274), CGGTTTCGGGTTTATATTTACGGCGGCGG
(SEQ ID NO:14275), AGGGTTTTTAGGAGGGCGTTCGGGTCG (SEQ ID NO:14276),
GGGTTTTTAGGAGGGCGTTCGGGTCGT (SEQ ID NO:14277), GCGTAGGGTTTTTAGGAGGGCGTTCGG
(SEQ ID NO:14278), GGTTTTTAGGAGGGCGTTCGGGTCGTC (SEQ ID NO:14279),
CGTAGGGTTTTTAGGAGGGCGTTCGGG (SEQ ID NO:14280)

Target1511   chr15:62360257-62360274   GTCGTTTTTGTTCGGGGGTTCGTTCGC (SEQ ID NO:14281), AGTCGTTTTTGTTCGGGGGTTCGTTCGC
(SEQ ID NO:14282), AGGAGTCGTTTTTGTTCGGGGGTTCGT (SEQ ID NO:14283),
AGTCGTTTTTGTTCGGGGGTTCGTTCG (SEQ ID NO:14284), CGGTTTCGGGTTTATATTTACGGCGGCGG
(SEQ ID NO:14285), GTTTTGGGGCGGGCGGGGATAGTC (SEQ ID NO:14286),
GTTTTGGGGCGGGCGGGGATAGTCG (SEQ ID NO:14287), CGTTTTGGGGCGGGCGGGGATAGTC (SEQ ID
NO:14288), GTTTTGGGGCGGGCGGGGATAGTCGG (SEQ ID NO:14289),
TTTTGGGGCGGGCGGGGATAGTCG (SEQ ID NO:14290)

Target1512   chr15:62360308-62360351   CGGTTTCGGGTTTATATTTACGGCGGCGG (SEQ ID NO:14291), CGGTTTCGGGTTTATATTTACGGCGGCG
(SEQ ID NO:14292), GGTTTCGGGTTTATATTTACGGCGGCGG (SEQ ID NO:14293),
GTTTCGGGTTTATATTTACGGCGGCGG (SEQ ID NO:14294), GGTTTCGGGTTTATATTTACGGCGGCG
(SEQ ID NO:14295), GCGCGGCGTTTTTTGTTTTCGTTTTC (SEQ ID NO:14296)

Target1513   chr15:62360359-62360481   GCGGGTTGGGAGGAGTCGTCGTTTGAT (SEQ ID NO:14297), TTGCGGGTTGGGAGGAGTCGTCGTTTG
(SEQ ID NO:14298), GTTGCGGGTTGGGAGGAGTCGTCGTTT (SEQ ID NO:14299),
TTGGGAGGAGTCGTCGTTTGATTCGCG (SEQ ID NO:14300), CGGGTTGGGAGGAGTCGTCGTTTGATT
(SEQ ID NO:14301), GTCGGCGCGGTTTAGAGTTACGGTGTT (SEQ ID NO:14302),
CGTCGGCGCGGTTTAGAGTTACGGTGT (SEQ ID NO:14303), TCGGCGCGGTTTAGAGTTACGGTGTTT
(SEQ ID NO:14304), CGTCGGCGCGGTTTAGAGTTACGGTG (SEQ ID NO:14305),
GGGTTCGGGTCGGGGATTGGGAGTTC (SEQ ID NO:14306)

Target1514   chr15:63753486-63753569   GCGGGTTAGGGGTCGGATTAGGTTAGC (SEQ ID NO:14307), GCGGGGTTAGGGGTCGGATTAGGTTAGC
(SEQ ID NO:14308), AGCGGGTTAGGGGTCGGATTAGGTTAGC (SEQ ID NO:14309),
CGGGTTAGGGGTCGGATTAGGTTAGCG (SEQ ID NO:14310), CGGGTTAGGGGTCGGATTAGGTTAGCGA
(SEQ ID NO:14311), TCGGTTTTTGGTCGGGGAAGGGGAGT (SEQ ID NO:14312),
TTCGGTTTTTGGTCGGGGAAGGGGAGT (SEQ ID NO:14313), CGGTTTTTGGTCGGGGAAGGGGAGTTT
(SEQ ID NO:14314), TCGGTTTTTGGTCGGGGAAGGGGAGTTT (SEQ ID NO:14315),
TTCGGTTTTTGGTCGGGGAAGGGGAGTT (SEQ ID NO:14316)

Target1515   chr15:63753577-63753619   GCGGGTTAGGGGTCGGATTAGGTTAGCG (SEQ ID NO:14317), GCGGGTTAGGGGTCGGATTAGGTTAGC
(SEQ ID NO:14318), AGCGGGTTAGGGGTCGGATTAGGTTAGC (SEQ ID NO:14319),
CGGGTTAGGGGTCGGATTAGGTTAGCG (SEQ ID NO:14320), CGGGTTAGGGGTCGGATTAGGTTAGCGA
(SEQ ID NO:14321), TCGGTTTTTGGTCGGGGAAGGGGAGT (SEQ ID NO:14322),
TTCGGTTTTTGGTCGGGGAAGGGGAGT (SEQ ID NO:14323), CGGTTTTTGGTCGGGGAAGGGGAGTTT

FIGURE 5 CONTINUED

{SEQ ID NO:14324), TCGGTTTTTGGTCGGGGAAGGGGAGTTT (SEQ ID NO:14325),
TTCGGTTTTTGGTCGGGGAAGGGGAGTT (SEQ ID NO:14326)

| Target1516 | chr15:63753681-63753700 | CGGGTGTAAGAGGAGTTTGGGGGAGGGA (SEQ ID NO:14327), TCGGGTGTAAGAGGAGTTTGGGGGAGGG {SEQ ID NO:14328), TCGGGTGTAAGAGGAGTTTGGGGGAGGGA (SEQ ID NO:14329), GTCGGGTGTAAGAGGAGTTTGGGGGAGGG (SEQ ID NO:14330), CGGGTGTAAGAGGAGTTTGGGGGAGGGAG (SEQ ID NO:14331), CGGGCGGGTTGTTTTTTATGGTCGTGA {SEQ ID NO:14332), TCGGGCGGGTTGTTTTTTATGGTCGTG (SEQ ID NO:14333), TCGGGCGGGTTGTTTTTTATGGTCGTGA (SEQ ID NO:14334), ATCGGGCGGGTTGTTTTTTATGGTCGT {SEQ ID NO:14335), CGGGCGGGTTGTTTTTTATGGTCGTGAG (SEQ ID NO:14336) |
|---|---|---|
| Target1517 | chr15:65689058-65689153 | TGAGTTCGTTTTTTAGGAGAGCGTTTGAGTGT (SEQ ID NO:14337), GAGTTCGTTTTTTAGGAGAGCGTTTGAGTGTT {SEQ ID NO:14338), TTGAGTTCGTTTTTTAGGAGAGCGTTTGAGTG (SEQ ID NO:14339), TGAGTTCGTTTTTTAGGAGAGCGTTTGAGTGTT (SEQ ID NO:14340), TTGAGTTCGTTTTTTAGGAGAGCGTTTGAGTGT (SEQ ID NO:14341), AGCGGGTTAGTTGGGGTTGGGGTGAAT (SEQ ID NO:14342), ATAGAGTAGGGGGAGGTGGACGGGTGG {SEQ ID NO:14343), GAGCGGGTTAGTTGGGGTTGGGGTGAA (SEQ ID NO:14344), GGACGGGTGGGTGTGTTGGGGGTATTT (SEQ ID NO:14345), TTGAGTTTCGTGTGTTGGGTGAGGCGG {SEQ ID NO:14346) |
| Target1518 | chr15:65689202-65689213 | CGGAGTTTAGCGGTTGTAGTGGCGAAGT (SEQ ID NO:14347), CGGAGTTTAGCGGTTGTAGTGGCGAAG {SEQ ID NO:14348), CGGAGTTTAGCGGTTGTAGTGGCGAAGTC (SEQ ID NO:14349), GGAGTTTAGCGGTTGTAGTGGCGAAGT (SEQ ID NO:14350), GGAGTTTAGCGGTTGTAGTGGCGAAGTC (SEQ ID NO:14351), CGCGTAGTTTTGGTATTTCGGCGTTTATGT (SEQ ID NO:14352), CGCGTAGTTTTGGTATTTCGGCGTTTATGTT (SEQ ID NO:14353), CGCGTAGTTTTGGTATTTCGGCGTTTATGTTT (SEQ ID NO:14354), CGCGTAGTTTTGGTATTTCGGCGTTTATGTTTG (SEQ ID NO:14355), CGCGTAGTTTTGGTATTTCGGCGTTTATGTTGT (SEQ ID NO:14356) |
| Target1519 | chr15:65689216-65689289 | TCGGAGTGTTAGGGTTGCGCGTTGGTA (SEQ ID NO:14357), TGCGGGGTTTGTTGGCGCGGTAGATAT {SEQ ID NO:14358), CGGAGTGTTAGGGTTGCGCGTTGGTAA (SEQ ID NO:14359), GCGGGGTTTGTTGGCGCGGTAGATATA (SEQ ID NO:14360), GTCGGAGTGTTAGGGTTGCGCGTTGGT {SEQ ID NO:14361), GGGTGTAGAGTGTTTTTGAGGTTCGGAGA (SEQ ID NO:14362), CGCGTAGTTTTGGTATTTCGGCGTTTATGT (SEQ ID NO:14363), CGGAGATTGAAGGGAAGGGTAGTTTTTAGCG (SEQ ID NO:14364), CGGAGATTGAAGGGAAGGGTAGTTTTTAGCGT {SEQ ID NO:14365), TCGGAGATTGAAGGGAAGGGTAGTTTTTAGCG (SEQ ID NO:14366) |
| Target1520 | chr15:65689325-65689391 | TCGGAGTGTTAGGGTTGCGCGTTGGTA (SEQ ID NO:14367), TTTGGGGGAAGGAGAGGGGAGACGCGTTG {SEQ ID NO:14368), GTTTGGGGGAAGGAGAGGGGAGACGCGTT (SEQ ID NO:14369), TGCGGGGTTTGTTGGCGCGGTAGATAT (SEQ ID NO:14370), CGGAGTGTTAGGGTTGCGCGTTGGTAA {SEQ ID NO:14371), CGGGTGTAGAGTGTTTTTGAGGTTCGGA (SEQ ID NO:14372), TCGGGTGTAGAGTGTTTTTGAGGTTCGG (SEQ ID NO:14373), TCGGGTGTAGAGTGTTTTTGAGGTTCGGA {SEQ ID NO:14374), GGGACGGTTGTGTTTGTTTTATTCGGGT (SEQ ID NO:14375), CGGGTGTAGAGTGTTTTTGAGGTTCGGAG (SEQ ID NO:14376) |
| Target1521 | chr15:68114430-68114445 | CGAGGGAAAAACGAGGCGAGAGGGGAG (SEQ ID NO:14377), CGAGGCGAGAGGGGAGAAGGCGATTTC {SEQ ID NO:14378), GAGGGAAAAACGAGGCGAGAGGGGAGA (SEQ ID NO:14379), AAAAACGAGGCGAGAGGGGAGAAGGCG (SEQ ID NO:14380), AGGGAAAAACGAGGCGAGAGGGGAGAA (SEQ ID NO:14381), CGGGTCGTTTGGGTAGGGGGCGTAG (SEQ ID NO:14382), CGGGTCGTTTGGGTAGGGGGCGTA (SEQ ID NO:14383), TAGGGATGGTTTGGGGCGCGACGGGTC (SEQ ID NO:14384), AGTTTGTTTTTGGAATTCGGGAGGCGT {SEQ ID NO:14385), TAGGGATGGTTTGGGGCGCGACGG (SEQ ID NO:14386) |
| Target1522 | chr15:68114507-68114529 | CGAGGGAAAAACGAGGCGAGAGGGGAG (SEQ ID NO:14387), CGAGGCGAGAGGGGAGAAGGCGATTTC {SEQ ID NO:14388), GAGGGAAAAACGAGGCGAGAGGGGAGA (SEQ ID NO:14389), AAAAACGAGGCGAGAGGGGAGAAGGCG (SEQ ID NO:14390), AGGGAAAAACGAGGCGAGAGGGGAGAA (SEQ ID NO:14391), TAATGGTAGGGATGGTTTGGGGCGCGA (SEQ ID NO:14392), AATGGTAGGGATGGTTTGGGGCGCGAC (SEQ ID NO:14393), ATAATGGTAGGGATGGTTTGGGGCGCG (SEQ ID NO:14394), ATAATGGTAGGGATGGTTTGGGGCGCGA (SEQ ID NO:14395), TAATGGTAGGGATGGTTTGGGGCGCGAC (SEQ ID NO:14396) |
| Target1523 | chr15:68114543-68114554 | CGTGGTCGTTGCGTTTTTTGTTTAGGCGG (SEQ ID NO:14397), TGGTCGTTGCGTTTTTTGTTTAGGCGGT {SEQ ID NO:14398), GGTCGTTGCGTTTTTTGTTTAGGCGGT (SEQ ID NO:14399), TGGTCGTTGCGTTTTTTGTTTAGGCGG (SEQ ID NO:14400), CGTGGTCGTTGCGTTTTTTGTTTAGGCG (SEQ ID NO:14401), TAATGGTAGGGATGGTTTGGGGCGCGA (SEQ ID NO:14402), AATGGTAGGGATGGTTTGGGGCGCGAC (SEQ ID NO:14403), ATAATGGTAGGGATGGTTTGGGGCGCG (SEQ ID NO:14404), ATAATGGTAGGGATGGTTTGGGGCGCGA (SEQ ID NO:14405), TAATGGTAGGGATGGTTTGGGGCGCGAC (SEQ ID NO:14406) |
| Target1524 | chr15:76632205-76632494 | GGGAGAGATCGTTGCGGGGTAGTTCGG (SEQ ID NO:14407), GGAGAGATCGTTGCGGGGTAGTTCGGT {SEQ ID NO:14408), AGATCGTTGCGGGGTAGTTCGGTTCGG (SEQ ID NO:14409), CGGGAGAGATCGTTGCGGGGTAGTTCG (SEQ ID NO:14410), TCGGGAGAGATCGTTGCGGGGTAGTTC |

FIGURE 5 CONTINUED

|  |  | (SEQ ID NO:14411), TTGCGGGGAGGGAGTGGTTGTTTAGGG (SEQ ID NO:14412), TCGTTGCGGGGAGGGAGTGGTTGTTTA (SEQ ID NO:14413), GCGGGGAGGGAGTGGTTGTTTAGGGAT (SEQ ID NO:14414), CGTTGCGGGGAGGGAGTGGTTGTTTAG (SEQ ID NO:14415), GTTGCGGGGAGGGAGTGGTTGTTTAGG (SEQ ID NO:14416) |
|---|---|---|
| Target1525 | chr15:76639497-76639614 | TCGTTTGGGAGGAGTATTGGGGGCGTT (SEQ ID NO:14417), TTCGTTTGGGAGGAGTATTGGGGGCGT (SEQ ID NO:14418), GGTCGTTCGTTGGGTTCGCGGTAGTTT (SEQ ID NO:14419), GGAGGAGTATTGGGGGCGTTAGGGGTT (SEQ ID NO:14420), TTGGGAGGAGTATTGGGGGCGTTAGGG (SEQ ID NO:14421), GAGTCGTAGGGTCGGGTTGAGTTTCGC (SEQ ID NO:14422), CGGAGTCGTAGGGTCGGGTTGAGTTTCG (SEQ ID NO:14423), GGAGTCGTAGGGTCGGGTTGAGTTTCGC (SEQ ID NO:14424), GGAGTCGTAGGGTCGGGTTGAGTTTCG (SEQ ID NO:14425), CGGAGTCGTAGGGTCGGGTTGAGTTTC (SEQ ID NO:14426) |
| Target1526 | chr15:76639646-76639659 | GTTTCGTTTTTTGGTGTTCGGCGGCGG (SEQ ID NO:14427), GGTTTCGTTTTTTGGTGTTCGGCGGCG (SEQ ID NO:14428), GGGTTTCGTTTTTTGGTGTTCGGCGGC (SEQ ID NO:14429), TTTCGTTTTTTGGTGTTCGGCGGCGGA (SEQ ID NO:14430), TTCGTTTTTTGGTGTTCGGCGGCGGAG (SEQ ID NO:14431), CGAGGGCGGGGATTCGTAGTTTTAAGT (SEQ ID NO:14432), CGAGGGCGGGGATTCGTAGTTTTAAGTT (SEQ ID NO:14433), GGGTGTTTAGCGCGGCGTTTCGG (SEQ ID NO:14434), CGAGGGCGGGGATTCGTAGTTTTAAGTTA (SEQ ID NO:14435), GGGCGGGGATTCGTAGTTTTAAGTTAGAGGG (SEQ ID NO:14436) |
| Target1527 | chr15:76639663-76639693 | GTTTCGTTTTTTGGTGTTCGGCGGCGG (SEQ ID NO:14437), GGTTTCGTTTTTTGGTGTTCGGCGGCG (SEQ ID NO:14438), GGGTTTCGTTTTTTGGTGTTCGGCGGC (SEQ ID NO:14439), TTTCGTTTTTTGGTGTTCGGCGGCGGA (SEQ ID NO:14440), TTCGTTTTTTGGTGTTCGGCGGCGGAG (SEQ ID NO:14441), CGAGGGCGGGGATTCGTAGTTTTAAGT (SEQ ID NO:14442), CGAGGGCGGGGATTCGTAGTTTTAAGTT (SEQ ID NO:14443), GGGTGTTTAGCGCGGCGTTTCGG (SEQ ID NO:14444), CGAGGGCGGGGATTCGTAGTTTTAAGTTA (SEQ ID NO:14445), GGGCGGGGATTCGTAGTTTTAAGTTAGAGGG (SEQ ID NO:14446) |
| Target1528 | chr15:76639721-76639743 | GTTTCGTTTTTTGGTGTTCGGCGGCGG (SEQ ID NO:14447), GGTTTCGTTTTTTGGTGTTCGGCGGCG (SEQ ID NO:14448), GGGTTTCGTTTTTTGGTGTTCGGCGGC (SEQ ID NO:14449), TTTCGTTTTTTGGTGTTCGGCGGCGGA (SEQ ID NO:14450), TTCGTTTTTTGGTGTTCGGCGGCGGAG (SEQ ID NO:14451), GGGTGTTTAGCGCGGCGTTTCGG (SEQ ID NO:14452), GGTGTTTAGCGCGGCGTTTCGG (SEQ ID NO:14453), GGGTGTTTAGCGCGGCGTTTCG (SEQ ID NO:14454), GCGCGGCGTTTCGGTTCGA (SEQ ID NO:14455) |
| Target1529 | chr15:82532826-82532881 | TGAGGTGAGAATAGGTTTTTTGTGGGGTGA (SEQ ID NO:14456), TGAGGTGAGAATAGGTTTTTTGTGGGGTGAA (SEQ ID NO:14457), TTGAGGTGAGAATAGGTTTTTTGTGGGGTGA (SEQ ID NO:14458), TTGAGGTGAGAATAGGTTTTTTGTGGGGTGAA (SEQ ID NO:14459), TTTGAGGTGAGAATAGGTTTTTTGTGGGGTGA (SEQ ID NO:14460) |
| Target1530 | chr15:89952204-89952273 | AGCGTTTGTTAAGTGGGGGAGATTTTATCGA (SEQ ID NO:14461), GCGTTTGTTAAGTGGGGGAGATTTTATCGATCG (SEQ ID NO:14462), AAGCGTTTGTTAAGTGGGGGAGATTTTATCGA (SEQ ID NO:14463), TGTTAAGTGGGGGAGATTTTATCGATCGAACG (SEQ ID NO:14464), AGCGTTTGTTAAGTGGGGGAGATTTTATCGAT (SEQ ID NO:14465), AGTCGAGGTTGGATTTTTAGCGGTCGT (SEQ ID NO:14466), CGAGGTTGGATTTTTAGCGGTCGTTTGC (SEQ ID NO:14467), GAGTCGAGGTTGGATTTTTAGCGGTCGT (SEQ ID NO:14468), TCGAGGTTGGATTTTTAGCGGTCGTTTGC (SEQ ID NO:14469), GAGTCGAGGTTGGATTTTTAGCGGTCG (SEQ ID NO:14470) |
| Target1531 | chr15:89952299-89952387 | TGGCGGTGGTTATACGGGTTTTAGGGA (SEQ ID NO:14471), ATGGCGGTGGTTATACGGGTTTTAGGG (SEQ ID NO:14472), TGGCGGTGGTTATACGGGTTTTAGGGAT (SEQ ID NO:14473), ATGGCGGTGGTTATACGGGTTTTAGGGA (SEQ ID NO:14474), GGCGGTGGTTATACGGGTTTTAGGGAT (SEQ ID NO:14475), AGTCGAGGTTGGATTTTTAGCGGTCGT (SEQ ID NO:14476), CGAGGTTGGATTTTTAGCGGTCGTTTGC (SEQ ID NO:14477), GAGTCGAGGTTGGATTTTTAGCGGTCGT (SEQ ID NO:14478), TCGAGGTTGGATTTTTAGCGGTCGTTTGC (SEQ ID NO:14479), GAGTCGAGGTTGGATTTTTAGCGGTCG (SEQ ID NO:14480) |
| Target1532 | chr15:89952454-89952474 | TTTCGGGGTTTTGCGACGGTGTTGGAG (SEQ ID NO:14481), GGTTTTGCGACGGTGTTGGAGGGTGTT (SEQ ID NO:14482), TTGCGACGGTGTTGGAGGGTGTTTTCG (SEQ ID NO:14483), TTTTCGGGGTTTTGCGACGGTGTTGGA (SEQ ID NO:14484), CGACGGTGTTGGAGGGTGTTTTCGGTT (SEQ ID NO:14485), GGAGTTGGGGAGGTATGGTTATTGGCGT (SEQ ID NO:14486), GGAGTTGGGGAGGTATGGTTATTGGCG (SEQ ID NO:14487), AGGAGTTGGGGAGGTATGGTTATTGGCGT (SEQ ID NO:14488), AGGAGTTGGGGAGGTATGGTTATTGGCG (SEQ ID NO:14489), GAGTTGGGGAGGTATGGTTATTGGCGT (SEQ ID NO:14490) |
| Target1533 | chr15:89952488-89952529 | TTTCGGGGTTTTGCGACGGTGTTGGAG (SEQ ID NO:14491), GGTTTTGCGACGGTGTTGGAGGGTGTT (SEQ ID NO:14492), TTGCGACGGTGTTGGAGGGTGTTTTCG (SEQ ID NO:14493), TTTTCGGGGTTTTGCGACGGTGTTGGA (SEQ ID NO:14494), GGGAGGTTTGCGCGGGGATTAGGTTTT (SEQ ID NO:14495), GATTGGGGTTGGGAGGAGTTGGGGAGG (SEQ ID NO:14496), TGGGGTTGGGAGGAGTTGGGGAGGTAT (SEQ ID NO:14497), TGGGGAGGATTTTCGGGTTAGGCGTCGG (SEQ ID NO:14498), GGGAGGATTTTCGGGTTAGGCGTCGGT (SEQ ID NO:14499), AGTGATTGGGGTTGGGAGGAGTTGGGG (SEQ ID NO:14500) |

FIGURE 5 CONTINUED

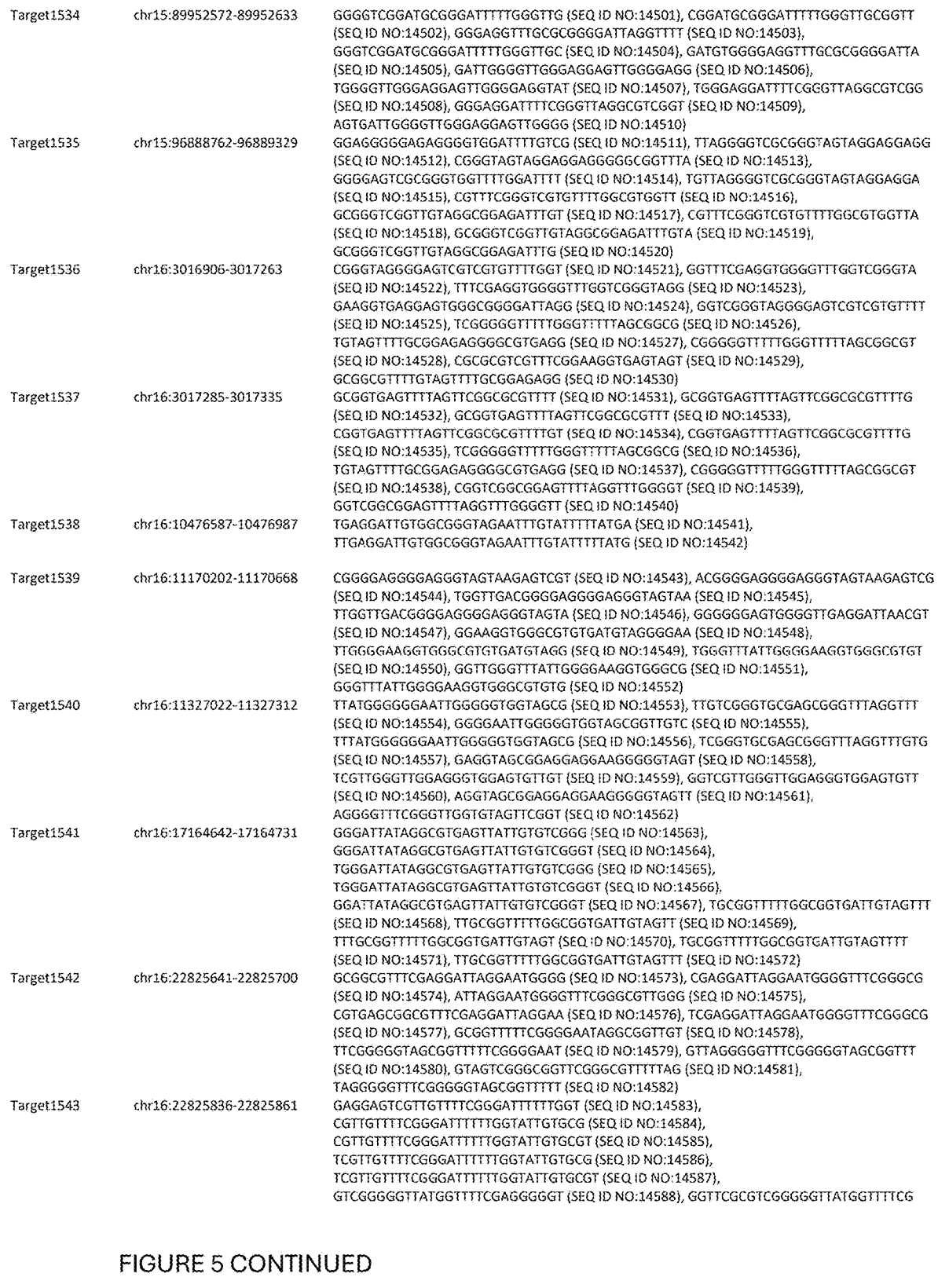

Target1534    chr15:89952572-89952633    GGGGTCGGATGCGGGATTTTTGGGTTG (SEQ ID NO:14501), CGGATGCGGGATTTTTGGGTTGCGGTT (SEQ ID NO:14502), GGGAGGTTTGCGCGGGGATTAGGTTTT (SEQ ID NO:14503), GGGGTCGGATGCGGGATTTTTGGGTTGC (SEQ ID NO:14504), GATGTGGGGAGGTTTGCGCGGGGATTA (SEQ ID NO:14505), GATTGGGGTTGGGAGGAGTTGGGGAGG (SEQ ID NO:14506), TGGGGTTGGGAGGAGTTGGGGAGGTAT (SEQ ID NO:14507), TGGGAGGATTTTCGGGTTAGGCGTCGG (SEQ ID NO:14508), GGGAGGATTTTCGGGTTAGGCGTCGGT (SEQ ID NO:14509), AGTGATTGGGGTTGGGAGGAGTTGGGG (SEQ ID NO:14510)

Target1535    chr15:96888762-96889329    GGAGGGGGGAGAGGGGTGGATTTTGTCG (SEQ ID NO:14511), TTAGGGGTCGCGGGTAGTAGGAGGAGG (SEQ ID NO:14512), CGGGTAGTAGGAGGAGGGGGCGGTTTA (SEQ ID NO:14513), GGGGAGTCGCGGGTGGTTTTGGATTTT (SEQ ID NO:14514), TGTTAGGGGTCGCGGGTAGTAGGAGGA (SEQ ID NO:14515), CGTTTCGGGTCGTGTTTTGGCGTGGTT (SEQ ID NO:14516), GCGGGTCGGTTGTAGGCGGAGATTTGT (SEQ ID NO:14517), CGTTTCGGGTCGTGTTTTGGCGTGGTTA (SEQ ID NO:14518), GCGGGTCGGTTGTAGGCGGAGATTTGTA (SEQ ID NO:14519), GCGGGTCGGTTGTAGGCGGAGATTTG (SEQ ID NO:14520)

Target1536    chr16:3016906-3017263    CGGGTAGGGGAGTCGTCGTGTTTTGGT (SEQ ID NO:14521), GGTTTCGAGGTGGGGTTTGGTCGGGTA (SEQ ID NO:14522), TTTCGAGGTGGGGTTTGGTCGGGTAGG (SEQ ID NO:14523), GAAGGTGAGGAGTGGGCGGGGATTAGG (SEQ ID NO:14524), GGTCGGGTAGGGGAGTCGTCGTGTTTT (SEQ ID NO:14525), TCGGGGGTTTTTGGGTTTTTAGCGGCG (SEQ ID NO:14526), TGTAGTTTTGCGGAGAGGGGCGTGAGG (SEQ ID NO:14527), CGGGGGTTTTTGGGTTTTTAGCGGCGT (SEQ ID NO:14528), CGCGCGTCGTTCGGAAGGTGAGTAGT (SEQ ID NO:14529), GCGGCGTTTTGTAGTTTTGCGGAGAGG (SEQ ID NO:14530)

Target1537    chr16:3017285-3017335    GCGGTGAGTTTTAGTTCGGCGCGTTTT (SEQ ID NO:14531), GCGGTGAGTTTTAGTTCGGCGCGTTTTG (SEQ ID NO:14532), GCGGTGAGTTTTAGTTCGGCGCGTTT (SEQ ID NO:14533), CGGTGAGTTTTAGTTCGGCGCGTTTTGT (SEQ ID NO:14534), CGGTGAGTTTTAGTTCGGCGCGTTTTG (SEQ ID NO:14535), TCGGGGGTTTTTGGGTTTTTAGCGGCG (SEQ ID NO:14536), TGTAGTTTTGCGGAGAGGGGCGTGAGG (SEQ ID NO:14537), CGGGGGTTTTTGGGTTTTTAGCGGCGT (SEQ ID NO:14538), CGGTCGGCGGAGTTTTAGGTTTGGGGT (SEQ ID NO:14539), GGTCGGCGGAGTTTTAGGTTTGGGGTT (SEQ ID NO:14540)

Target1538    chr16:10476587-10476987    TGAGGATTGTGGCGGGTAGAATTTGTATTTTTATGA (SEQ ID NO:14541), TTGAGGATTGTGGCGGGTAGAATTTGTATTTTTATG (SEQ ID NO:14542)

Target1539    chr16:11170202-11170668    CGGGGAGGGGAGGGTAGTAAGAGTCGT (SEQ ID NO:14543), ACGGGGAGGGGAGGGTAGTAAGAGTCG (SEQ ID NO:14544), TGGTTGACGGGGAGGGGAGGGTAGTAA (SEQ ID NO:14545), TTGGTTGACGGGGAGGGGAGGGTAGTA (SEQ ID NO:14546), GGGGGGGAGTGGGGTTGAGGATTAACGT (SEQ ID NO:14547), GGAAGGTGGGCGTGTGATGTAGGGGAA (SEQ ID NO:14548), TTGGGGAAGGTGGGCGTGTGATGTAGG (SEQ ID NO:14549), TGGGTTTATTGGGGAAGGTGGGCGTGT (SEQ ID NO:14550), GGTTGGGTTTATTGGGGAAGGTGGGCG (SEQ ID NO:14551), GGGTTTATTGGGGAAGGTGGGCGTGTG (SEQ ID NO:14552)

Target1540    chr16:11327022-11327312    TTATGGGGGGGAATTGGGGGGTGGTAGCG (SEQ ID NO:14553), TTGTCGGGGTGCGAGCGGGTTTAGGTTT (SEQ ID NO:14554), GGGGAATTGGGGGTGGTAGCGGTTGTC (SEQ ID NO:14555), TTTATGGGGGGGAATTGGGGGTGGTAGCG (SEQ ID NO:14556), TCGGGTGCGAGCGGGTTTAGGTTTGTG (SEQ ID NO:14557), GAGGTAGCGGAGGAGGAAGGGGGTAGT (SEQ ID NO:14558), TCGTTGGGTTGGAGGGTGGAGTGTTGT (SEQ ID NO:14559), GGTCGTTGGGTTGGAGGGTGGAGTGTT (SEQ ID NO:14560), AGGTAGCGGAGGAGGAAGGGGGTAGTT (SEQ ID NO:14561), AGGGGTTTCGGGTTGGTGTAGTTCGGT (SEQ ID NO:14562)

Target1541    chr16:17164642-17164731    GGGATTATAGGCGTGAGTTATTGTGTCGGG (SEQ ID NO:14563), GGGATTATAGGCGTGAGTTATTGTGTCGGGT (SEQ ID NO:14564), TGGGATTATAGGCGTGAGTTATTGTGTCGGG (SEQ ID NO:14565), TGGGATTATAGGCGTGAGTTATTGTGTCGGGT (SEQ ID NO:14566), GGATTATAGGCGTGAGTTATTGTGTCGGGT (SEQ ID NO:14567), TGCGGTTTTTGGCGGTGATTGTAGTTT (SEQ ID NO:14568), TTGCGGTTTTTGGCGGTGATTGTAGTT (SEQ ID NO:14569), TTTGCGGTTTTTGGCGGTGATTGTAGT (SEQ ID NO:14570), TGCGGTTTTTGGCGGTGATTGTAGTTTT (SEQ ID NO:14571), TTGCGGTTTTTGGCGGTGATTGTAGTTTT (SEQ ID NO:14572)

Target1542    chr16:22825641-22825700    GCGGCGTTTCGAGGATTAGGAATGGGG (SEQ ID NO:14573), CGAGGATTAGGAATGGGGTTTCGGGCG (SEQ ID NO:14574), ATTAGGAATGGGGTTTCGGGCGTTGGG (SEQ ID NO:14575), CGTGAGCGGCGTTTCGAGGATTAGGAA (SEQ ID NO:14576), TCGAGGATTAGGAATGGGGTTTCGGGCG (SEQ ID NO:14577), GCGGTTTTTCGGGGAATAGGCGGTTGT (SEQ ID NO:14578), TTCGGGGGTAGCGGTTTTTCGGGGAAT (SEQ ID NO:14579), GTTAGGGGGTTTCGGGGGTAGCGGTTT (SEQ ID NO:14580), GTAGTCGGGCGGTTCGGGCGTTTTTAG (SEQ ID NO:14581), TAGGGGGTTTCGGGGGTAGCGGTTTTT (SEQ ID NO:14582)

Target1543    chr16:22825836-22825861    GAGGAGTCGTTGTTTTCGGGATTTTTTGGT (SEQ ID NO:14583), CGTTGTTTTCGGGATTTTTTGGTATTGTGCG (SEQ ID NO:14584), CGTTGTTTTCGGGATTTTTTGGTATTGTGCGT (SEQ ID NO:14585), TCGTTGTTTTCGGGATTTTTTGGTATTGTGCG (SEQ ID NO:14586), TCGTTGTTTTCGGGATTTTTTGGTATTGTGCGT (SEQ ID NO:14587), GTCGGGGGTTATGGTTTTCGAGGGGGT (SEQ ID NO:14588), GGTTCGCGTCGGGGGGTTATGGTTTTCG

FIGURE 5 CONTINUED

|  |  |  |
|---|---|---|
|  |  | (SEQ ID NO:14589), AGGGGGTATCGGCGGTTGAGTTGTTGT (SEQ ID NO:14590), GGGTTCGCGTCGGGGGGTTATGGTTTTC (SEQ ID NO:14591), GGTTGAGGTGGTTTCGCGCGGTTTAGG (SEQ ID NO:14592) |
| Target1544 | chr16:22825912-22825918 | GGCGATCGTAGGGTTATAGTAGTTTAGTCGTCGG (SEQ ID NO:14593), GCGAGTTTTTTAGGCGATCGTAGGGTTATAGT (SEQ ID NO:14594), GGCGATCGTAGGGTTATAGTAGTTTAGTCGTCGGT (SEQ ID NO:14595), GCGATCGTAGGGTTATAGTAGTTTAGTCGTCGG (SEQ ID NO:14596), GGCGATCGTAGGGTTATAGTAGTTTAGTCGTCG (SEQ ID NO:14597), GGTTGAGGTGGTTTCGCGCGGTTTAGG (SEQ ID NO:14598), CGGTTGAGGTGGTTTCGCGCGGTTTAG (SEQ ID NO:14599), GTTGAGGTGGTTTCGCGCGGTTTAGGA (SEQ ID NO:14600), CGGTTGAGGTGGTTTCGCGCGGTTTA (SEQ ID NO:14601), TGAGGTGGTTTCGCGCGGTTTAGGATT (SEQ ID NO:14602) |
| Target1545 | chr16:22825953-22825973 | GTTTATAGGGGTTTTGGGTCGCGCGGGG (SEQ ID NO:14603), GGTTTATAGGGTTTTGGGTCGCGCGGG (SEQ ID NO:14604), TATAGGGTTTTGGGTCGCGCGGGGTTA (SEQ ID NO:14605), ATAGGGTTTTGGGTCGCGCGGGGTTAT (SEQ ID NO:14606), GGGTTTTGGGTCGCGCGGGGTTATTTT (SEQ ID NO:14607), CGTTTTTCGCGGTTGAGGTGGTTTCG (SEQ ID NO:14608), AGGAAGTTGTAATATAGGTAAGTGTAGGAGAGCGAG (SEQ ID NO:14609), GGAAGTTGTAATATAGGTAAGTGTAGGAGAGCGAGA (SEQ ID NO:14610) |
| Target1546 | chr16:22825974-22825984 | GTTTATAGGGGTTTTGGGTCGCGCGGGG (SEQ ID NO:14611), GGTTTATAGGGTTTTGGGTCGCGCGGG (SEQ ID NO:14612), TATAGGGTTTTGGGTCGCGCGGGGTTA (SEQ ID NO:14613), ATAGGGTTTTGGGTCGCGCGGGGTTAT (SEQ ID NO:14614), GGGTTTTGGGTCGCGCGGGGTTATTTT (SEQ ID NO:14615), AGGAAGTTGTAATATAGGTAAGTGTAGGAGAGCGAG (SEQ ID NO:14616), GGAAGTTGTAATATAGGTAAGTGTAGGAGAGCGAGA (SEQ ID NO:14617) |
| Target1547 | chr16:22825997-22826012 | CGGAGGGCGCGTAGGTTGTTTTTCGTT (SEQ ID NO:14618), GTTTATAGGGGTTTTGGGTCGCGCGGGG (SEQ ID NO:14619), GGTTTATAGGGTTTTGGGTCGCGCGGG (SEQ ID NO:14620), TATAGGGTTTTGGGTCGCGCGGGGTTA (SEQ ID NO:14621), ATAGGGTTTTGGGTCGCGCGGGGGTTAT (SEQ ID NO:14622), CGTTGGGGTCGCGGAGGTAGC (SEQ ID NO:14623), AGGAAGTTGTAATATAGGTAAGTGTAGGAGAGCGAG (SEQ ID NO:14624), GGAAGTTGTAATATAGGTAAGTGTAGGAGAGCGAGA (SEQ ID NO:14625) |
| Target1548 | chr16:22826054-22826118 | CGGAGGGCGCGTAGGTTGTTTTTCGTT (SEQ ID NO:14626), GTTTATAGGGGTTTTGGGTCGCGCGGGG (SEQ ID NO:14627), GGTTTATAGGGTTTTGGGTCGCGCGGG (SEQ ID NO:14628), TATAGGGTTTTGGGTCGCGCGGGGTTA (SEQ ID NO:14629), ATAGGGTTTTGGGTCGCGCGGGGGTTAT (SEQ ID NO:14630), CGTCGGTTCGGAGGGATTATAGGGGCG (SEQ ID NO:14631), GTCGGTTCGGAGGGATTATAGGGGCGG (SEQ ID NO:14632), GGCGTCGGTTCGGAGGGATTATAGGGG (SEQ ID NO:14633), GGGCGTCGGTTCGGAGGGATTATAGGG (SEQ ID NO:14634), GCGTCGGTTCGGAGGGATTATAGGGGC (SEQ ID NO:14635) |
| Target1549 | chr16:24267075-24267088 | GAATGTCGCGTTGGGTGGGTGTTGAGG (SEQ ID NO:14636), GGGTGGGTGTTGAGGGAGCGTTAGAGT (SEQ ID NO:14637), TGGGTGGGTGTTGAGGGAGCGTTAGAG (SEQ ID NO:14638), CGTTGGGTGGGTGTTGAGGGAGCGTTA (SEQ ID NO:14639), TTGGGTGGGTGTTGAGGGAGCGTTAGA (SEQ ID NO:14640), AGGGTTAAGGAAAGGGGAAGGGGAGCG (SEQ ID NO:14641), GGGTTAAGGAAAGGGGAAGGGGAGCGA (SEQ ID NO:14642), AAGGGTTAAGGAAAGGGGAAGGGGAGCG (SEQ ID NO:14643), GGGTTAAGGAAAGGGGAAGGGGAGCGAA (SEQ ID NO:14644), AGGGTTAAGGAAAGGGGAAGGGGAGCGA (SEQ ID NO:14645) |
| Target1550 | chr16:24267162-24267195 | CGGAGGAATCGGGTCGTGTTGTAGCGT (SEQ ID NO:14646), GGGTGGGTGTTGAGGGAGCGTTAGAGT (SEQ ID NO:14647), TGGGTGGGTGTTGAGGGAGCGTTAGAG (SEQ ID NO:14648), AGCGGAGGAATCGGGTCGTGTTGTAGC (SEQ ID NO:14649), CGTTGGGTGGGTGTTGAGGGAGCGTTA (SEQ ID NO:14650), GTCGTTCGGGTTAGAAATTCGGGGTGT (SEQ ID NO:14651), TCGTTCGGGTTAGAAATTCGGGGTGTT (SEQ ID NO:14652), GTCGTTCGGGTTAGAAATTCGGGGTGTT (SEQ ID NO:14653), TCGTTCGGGTTAGAAATTCGGGGTGT (SEQ ID NO:14654), TCGGGTTAGTTAGTCGGTTCGGTTTGT (SEQ ID NO:14655) |
| Target1551 | chr16:27240431-27240445 | TTCGGGTTGTTTTTCGTTTGTTCGTTTCG (SEQ ID NO:14656), TTTCGGGTTGTTTTTCGTTTGTTCGTTTCG (SEQ ID NO:14657), TTTTCGGGTTGTTTTTCGTTTGTTCGTTTCG (SEQ ID NO:14658), GCGTATTTTTCGGGTTGTTTTTCGTTTGTTCG (SEQ ID NO:14659), GCGTATTTTTCGGGTTGTTTTTCGTTTGTTCGT (SEQ ID NO:14660), TGGGAGTTGTTTGGAGTTTGGGGTGGG (SEQ ID NO:14661), TGGGAGTTGTTTGGAGTTTGGGGTGGGA (SEQ ID NO:14662), GGGAGTTGTTTGGAGTTTGGGGTGGGA (SEQ ID NO:14663), GTGGGAGTTGTTTGGAGTTTGGGGTGGG (SEQ ID NO:14664), GGAGTTGTTTGGAGTTTGGGGTGGGAGG (SEQ ID NO:14665) |
| Target1552 | chr16:27240514-27240685 | CGGGTTGTTTTTCGTTTGTTCGTTTCGT (SEQ ID NO:14666), TCGGGTTGTTTTTCGTTTGTTCGTTTCGT (SEQ ID NO:14667), TTCGGGTTGTTTTTCGTTTGTTCGTTTCG (SEQ ID NO:14668), TTCGGGTTGTTTTTCGTTTGTTCGTTTCGT (SEQ ID NO:14669), TCGGGTTGTTTTTCGTTTGTTCGTTTCGTA (SEQ ID NO:14670), TGGGAGTTGTTTGGAGTTTGGGGTGGG (SEQ ID NO:14671), TGGGAGTTGTTTGGAGTTTGGGGTGGGA (SEQ ID NO:14672), GGGAGTTGTTTGGAGTTTGGGGTGGGA (SEQ ID NO:14673), TGGGGTTATGGTTTGGAGGGGGGAGTTCG (SEQ ID NO:14674), GGGGTTATGGTTTGGAGGGGGGAGTTCG (SEQ ID NO:14675) |

FIGURE 5 CONTINUED

| | | |
|---|---|---|
| Target1553 | chr16:51189878-51190020 | GGGCGTCGGGTGTAGCGTCGTGATC (SEQ ID NO:14676), GGCGTCGGGTGTAGCGTCGTGATC (SEQ ID NO:14677), CGAAGTATGGAGTAGGTTTGGGTGGGT (SEQ ID NO:14678), GGGCGTCGGGTGTAGCGTCGTGAT (SEQ ID NO:14679), TCGAAGTATGGAGTAGGTTTGGGTGGGT (SEQ ID NO:14680), TTGGAGATAGTTTTTGGTGGCGGGCGG (SEQ ID NO:14681), TTTGGAGATAGTTTTTGGTGGCGGGCGG (SEQ ID NO:14682), TGGAGATAGTTTTTGGTGGCGGGCGG (SEQ ID NO:14683), TTTTGGAGATAGTTTTTGGTGGCGGGCG (SEQ ID NO:14684), GTTTGGAGATAGTTTTTGGTGGCGGGCGG (SEQ ID NO:14685) |
| Target1554 | chr16:51190029-51190202 | GGTGGTAAGCGGAGGGTGGGTTTGGTA (SEQ ID NO:14686), GGGTGGGTTTGGTAATTATTCGCGCGC (SEQ ID NO:14687), GGTGGTAAGCGGAGGGTGGGTTTGGTAA (SEQ ID NO:14688), AGGGTGGGTTTGGTAATTATTCGCGCGC (SEQ ID NO:14689), GTGGTAAGCGGAGGGTGGGTTTGGTAA (SEQ ID NO:14690), TTGGCGAGGTATTGTTGTATGCGGGGC (SEQ ID NO:14691), GCGAGGTATTGTTGTATGCGGGGCGTA (SEQ ID NO:14692), TGGCGAGGTATTGTTGTATGCGGGGCG (SEQ ID NO:14693), GGCGAGGTATTGTTGTATGCGGGGCG (SEQ ID NO:14694), GGCGAGGTATTGTTGTATGCGGGGCGT (SEQ ID NO:14695) |
| Target1555 | chr16:54968681-54968739 | TGGAGGAAGGAGAAGAGAGATTTAAGTGTGTGT (SEQ ID NO:14696), TGGAGGAAGGAGAAGAGAGATTTAAGTGTGTGTT (SEQ ID NO:14697), TTGGAGGAAGGAGAAGAGAGATTTAAGTGTGTGT (SEQ ID NO:14698), GGAGGAAGGAGAAGAGAGATTTAAGTGTGTGTT (SEQ ID NO:14699), TTTGGAGGAAGGAGAAGAGAGATTTAAGTGTGTG (SEQ ID NO:14700), GGGGTAGAGAAGAAGACGGTGATTTGGG (SEQ ID NO:14701), AGGGGTAGAGAAGAAGACGGTGATTTGGG (SEQ ID NO:14702), GGGGTAGAGAAGAAGACGGTGATTTGGGA (SEQ ID NO:14703), AGGGGTAGAGAAGAAGACGGTGATTTGGGA (SEQ ID NO:14704), AAGGGGTAGAGAAGAAGACGGTGATTTGGG (SEQ ID NO:14705) |
| Target1556 | chr16:54968897-54968917 | AGTGCGGGCGGGAGTATTTAGGGATGT (SEQ ID NO:14706), CGGGTTAGTGCGGGCGGGAGTATTTAG (SEQ ID NO:14707), GGGTTAGTGCGGGCGGGAGTATTTAGGG (SEQ ID NO:14708), GGTTAGTGCGGGCGGGAGTATTTAGGG (SEQ ID NO:14709), GGGTTAGTGCGGGCGGGAGTATTTAGG (SEQ ID NO:14710), CGTAGTTGAGCGGGTATTTTTGGGTCGT (SEQ ID NO:14711), CGTAGTTGAGCGGGTATTTTTGGGTCG (SEQ ID NO:14712), TCGTAGTTGAGCGGGTATTTTTGGGTCGT (SEQ ID NO:14713), TCGTAGTTGAGCGGGTATTTTTGGGTCG (SEQ ID NO:14714), CGTAGTTGAGCGGGTATTTTTGGGTCGTT (SEQ ID NO:14715) |
| Target1557 | chr16:54968927-54969052 | GTTCGTTTAGTTGCGGGGTTGGGGTCG (SEQ ID NO:14716), TTCGTTTAGTTGCGGGGTTGGGGTCGA (SEQ ID NO:14717), GTGTTCGTTTAGTTGCGGGGTTGGGGT (SEQ ID NO:14718), TCGTTTAGTTGCGGGGTTGGGGTCGAG (SEQ ID NO:14719), AGTGTTCGTTTAGTTGCGGGGTTGGGG (SEQ ID NO:14720), AAAGAGGTTCGTTGTGAGAGGGAGGGA (SEQ ID NO:14721), AGAGGTTCGTTGTGAGAGGGAGGGATT (SEQ ID NO:14722), AAGAGGTTCGTTGTGAGAGGGAGGGAT (SEQ ID NO:14723), AAAAGAGGTTCGTTGTGAGAGGGAGGG (SEQ ID NO:14724), AAAAGAGGTTCGTTGTGAGAGGGAGGGA (SEQ ID NO:14725) |
| Target1558 | chr16:57654022-57654470 | GGTTTTGGGAGGAGGTGGAAGGGGAGG (SEQ ID NO:14726), AGGGTAAGAGACGGGTGGGGGATAGGGG (SEQ ID NO:14727), TGTGGTTTTGGGAGGAGGTGGAAGGGG (SEQ ID NO:14728), TTTGGGAGGAGGTGGAAGGGGAGGAGT (SEQ ID NO:14729), GGGAGGAGGTGGAAGGGGAGGAGTAGG (SEQ ID NO:14730), AGGAGGAAGTTGTTTAGGGCGTTGCGG (SEQ ID NO:14731), GGAGGAAGTTGTTTAGGGCGTTGCGGA (SEQ ID NO:14732), AGGGCGTTGCGGAAAGTAGGTAGGAGA (SEQ ID NO:14733), AGGAGGAAGTTGTTTAGGGCGTTGCGGA (SEQ ID NO:14734), GGAGGAAGTTGTTTAGGGCGTTGCGGAA (SEQ ID NO:14735) |
| Target1559 | chr16:57654537-57654590 | TGGAAGGAATAGGGTGTAGGTTTGGGGGG (SEQ ID NO:14736), GGAAGGAATAGGGTGTAGGTTTGGGGG (SEQ ID NO:14737), TGGAAGGAATAGGGTGTAGGTTTGGGGG (SEQ ID NO:14738), GAAGGAATAGGGTGTAGGTTTGGGGGG (SEQ ID NO:14739), GGAAGGAATAGGGTGTAGGTTTGGGGG (SEQ ID NO:14740), GGGAGGGAGGGTTGTGATGTTGGGTGT (SEQ ID NO:14741), GGGGAGGGAGGGGTTGTGATGTTGGGTG (SEQ ID NO:14742), AGGGGAGGGAGGGTTGTGATGTTGGGT (SEQ ID NO:14743), TAGGGGAGGGAGGGTTGTGATGTTGGG (SEQ ID NO:14744), TCGGTGGAGGGAGGGATCGTTTGAAGT (SEQ ID NO:14745) |
| Target1560 | chr16:67428180-67428190 | CGGGGGCGGGGAGGAGGTTTTTGTATA (SEQ ID NO:14746), ATTTTGGTTAGTGGATCGGGGGCGGGG (SEQ ID NO:14747), GATTTTGGTTAGTGGATCGGGGGCGGG (SEQ ID NO:14748), CGGGGGCGGGGAGGAGGTTTTTGTATAG (SEQ ID NO:14749), TCGGGGGCGGGGAGGAGGTTTTTGTAT (SEQ ID NO:14750) |
| Target1561 | chr16:67428315-67428325 | GGGTCGGGTTTTTGGATGGTTCGTGGT (SEQ ID NO:14751), AGGGTCGGGTTTTTGGATGGTTCGTGG (SEQ ID NO:14752), AGGGTCGGGTTTTTGGATGGTTCGTGGT (SEQ ID NO:14753), GGGTCGGGTTTTTGGATGGTTCGTGGTT (SEQ ID NO:14754), GGTCGGGTTTTTGGATGGTTCGTGGTT (SEQ ID NO:14755), TTAGGGGTTTTTACGGTCGGCGGGATC (SEQ ID NO:14756), TTTTAGGGGTTTTTACGGTCGGCGGGA (SEQ ID NO:14757), TTTAGGGGTTTTTACGGTCGGCGGGAT (SEQ ID NO:14758), TTTAGGGGTTTTTACGGTCGGCGGGATC (SEQ ID NO:14759), ATTTTAGGGGTTTTTACGGTCGGCGGG (SEQ ID NO:14760) |

FIGURE 5 CONTINUED

Target1562    chr16:67428400-67428414    AGTCGGTGGGGCGGGTATTGTTGAGTC (SEQ ID NO:14761), CGGGTATTGTTGAGTCGTGGGGGAGGG
(SEQ ID NO:14762), GAGTCGTGGGGGAGGGAGGTCGATTTC (SEQ ID NO:14763),
TGAGTCGTGGGGGAGGGAGGTCGATTT (SEQ ID NO:14764), TTGAGTCGTGGGGGAGGGAGGTCGATT
(SEQ ID NO:14765), GGCGGTCGGGGAGGTTGGTTTGGTTTAG (SEQ ID NO:14766),
GCGGTCGGGGAGGTTGGTTTGGTTTAGT (SEQ ID NO:14767), TTTTAGGGGTTTTTACGGTCGGCGGGA
(SEQ ID NO:14768), GGCGGTCGGGGAGGTTGGTTTGGTTTAGT (SEQ ID NO:14769),
TTAGGGGTTTTTACGGTCGGCGGGATT (SEQ ID NO:14770)

Target1563    chr16:67428489-67428760    CGAGTGGTAGGCGTCGGTAGGGTTAGC (SEQ ID NO:14771), TTCGGTGCGGTAAGGATGGGGTGTTGT
(SEQ ID NO:14772), CGGGTATTGTTGAGTCGTGGGGGAGGG (SEQ ID NO:14773),
GAGTCGTGGGGGAGGGAGGTCGATTTC (SEQ ID NO:14774), AGGGTTAGCGGCGTGTATAGGGTTGGC
(SEQ ID NO:14775), GCGTTTGGGTAGCGTCGTTTTGGTCGT (SEQ ID NO:14776),
GGCGGTCGGGGAGGTTGGTTTGGTTTAG (SEQ ID NO:14777), GGGCGGTCGGGGAGGTTGGTTTGGTTTA
(SEQ ID NO:14778), GCGGTCGGGGAGGTTGGTTTGGTTTAGT (SEQ ID NO:14779),
GCGTTTGGGTAGCGTCGTTTTGGTCGTT (SEQ ID NO:14780)

Target1564    chr16:67428762-67428885    AGCGGCGGTTGGGGGTTTTAGGTTTTG (SEQ ID NO:14781), CGAGTGGTAGGCGTCGGTAGGGTTAGC
(SEQ ID NO:14782), GAGCGGCGGTTGGGGGTTTTAGGTTTT (SEQ ID NO:14783),
GGCGGTTGGGGGTTTTAGGTTTTGCGT (SEQ ID NO:14784), AGGGTTAGCGGCGTGTATAGGGTTGGC
(SEQ ID NO:14785), TGGGAATTCGAGGGAGGGGAAGGTAGA (SEQ ID NO:14786),
TTTTGGGAATTCGAGGGAGGGGAAGGT (SEQ ID NO:14787),
TGGGAATTCGAGGGAGGGGAAGGTAGAGT (SEQ ID NO:14788),
GGGAATTCGAGGGAGGGGAAGGTAGAGT (SEQ ID NO:14789),
TGGGAATTCGAGGGAGGGGAAGGTAGAG (SEQ ID NO:14790)

Target1565    chr16:70771491-70771501    TGTAGAGGGTAGGAGTATGAGGGAGAGTGT (SEQ ID NO:14791),
TGTAGAGGGTAGGAGTATGAGGGAGAGTGTT (SEQ ID NO:14792),
TTGTAGAGGGTAGGAGTATGAGGGAGAGTGT (SEQ ID NO:14793),
TTTGTAGAGGGTAGGAGTATGAGGGAGAGTG (SEQ ID NO:14794),
TTGTAGAGGGTAGGAGTATGAGGGAGAGTGTT (SEQ ID NO:14795),
AGTTTGGGTTTTTGTGTGGAGTGCGTT (SEQ ID NO:14796), TGGGTTTTTGTGTGGAGTGCGTTTTTGT
(SEQ ID NO:14797), AGTTTGGGTTTTTGTGTGGAGTGCGTTT (SEQ ID NO:14798),
GGGTTTTTGTGTGGAGTGCGTTTTTGT (SEQ ID NO:14799), TGGGTTTTTGTGTGGAGTGCGTTTTTGTG
(SEQ ID NO:14800)

Target1566    chr16:70771558-70771860    GGTGGGCGGTCGGGGAGTTAGTTTTGT (SEQ ID NO:14801), GGGTGGGCGGTCGGGGAGTTAGTTTTG
(SEQ ID NO:14802), GGTGGGCGGTCGGGGAGTTAGTTTTGTA (SEQ ID NO:14803),
GGGTGGGCGGTCGGGGAGTTAGTTTT (SEQ ID NO:14804), GTGGGCGGTCGGGGAGTTAGTTTTGTA
(SEQ ID NO:14805), GGAGGGAGGTCGGAGTGGAGTAGGGAT (SEQ ID NO:14806),
TAGGGAGGGAGGTCGGAGTGGAGTAGG (SEQ ID NO:14807),
GGAGGGAGGTCGGAGTGGAGTAGGGATT (SEQ ID NO:14808),
GTAGGGAGGGAGGTCGGAGTGGAGTAGG (SEQ ID NO:14809), AGGGAGGGAGGTCGGAGTGGAGTAGG
(SEQ ID NO:14810)

Target1567    chr16:75098378-75098639    TGTTTGAGTTCGGGGTGTAGAGGTTGT (SEQ ID NO:14811), AGTTCGGGGTGTAGAGGTTGTAGTGAGT
(SEQ ID NO:14812), TGAGTTCGGGGTGTAGAGGTTGTAGTGA (SEQ ID NO:14813),
TTGTTTGAGTTCGGGGTGTAGAGGTTGT (SEQ ID NO:14814),
TGAGTTCGGGGTGTAGAGGTTGTAGTGAGT (SEQ ID NO:14815),
TGGAGTGGGGTAAGTGAGTAGGAGGAA (SEQ ID NO:14816),
TGGAGTGGGGTAAGTGAGTAGGAGGAAG (SEQ ID NO:14817),
TGGAGTGGGGTAAGTGAGTAGGAGGAAGA (SEQ ID NO:14818),
GGAGTGGGGTAAGTGAGTAGGAGGAAGA (SEQ ID NO:14819),
ATGGAGTGGGGTAAGTGAGTAGGAGGAA (SEQ ID NO:14820)

Target1568    chr16:75098750-75098929    GGGTTTAGTAAATTGGTAGGTGTATGGGGTTGT (SEQ ID NO:14821),
AGGGTTTAGTAAATTGGTAGGTGTATGGGGTTG (SEQ ID NO:14822),
AGGGTTTAGTAAATTGGTAGGTGTATGGGGTTGT (SEQ ID NO:14823),
TGGTAGGTGTATGGGGTTGTAAATTTGGTTTTGT (SEQ ID NO:14824),
AGGTGTATGGGGTTGTAAATTTGGTTTTGTAGGA (SEQ ID NO:14825),
TGAGGGAGTAGGAGGGTGAGTTGTGGT (SEQ ID NO:14826), TGGGTTTTGTGAGGGGTAAAGGACGGT
(SEQ ID NO:14827), GGGAGTAGGAGGGTGAGTTGTGGTAGGGT (SEQ ID NO:14828),
GGGAGTAGGAGGGTGAGTTGTGGTAGGG (SEQ ID NO:14829),
AGGGAGTAGGAGGGTGAGTTGTGGTAGGG (SEQ ID NO:14830)

Target1569    chr16:86321612-86321665    TGGACGGTGTTGATGGGATCGGGGATG (SEQ ID NO:14831), GGACGGTGTTGATGGGATCGGGGATGA
(SEQ ID NO:14832), TTTGGACGGTGTTGATGGGATCGGGGA (SEQ ID NO:14833),
TTGGACGGTGTTGATGGGATCGGGGAT (SEQ ID NO:14834), GTTTGGACGGTGTTGATGGGATCGGGG
(SEQ ID NO:14835), ACGGAAGGGGAGGGTGGGTAGATTGGA (SEQ ID NO:14836),
CGGAAGGGGAGGGTGGGTAGATTGGAG (SEQ ID NO:14837), AACGGAAGGGGAGGGTGGGTAGATTGG
(SEQ ID NO:14838), AACGGAAGGGGAGGGTGGGTAGATTGGA (SEQ ID NO:14839),
CGGAAGGGGAGGGTGGGTAGATTGGAGA (SEQ ID NO:14840)

FIGURE 5 CONTINUED

Target1570    chr16:86612256-86612267    GGATAGAGTACGGAGCGGTCGGGGAGA (SEQ ID NO:14841), AAGGGATAGAGTACGGAGCGGTCGGGG (SEQ ID NO:14842), TGGTTTTTCGGGAGGGTTTTTGCGGCG (SEQ ID NO:14843), GAAGGGATAGAGTACGGAGCGGTCGGG (SEQ ID NO:14844), GGGATAGAGTACGGAGCGGTCGGGGAG (SEQ ID NO:14845), GAGGCGGTTAGGGTAGGTAGTCGGGGA (SEQ ID NO:14846), AGGCGGTTAGGGTAGGTAGTCGGGGAT (SEQ ID NO:14847), ATGGGCGAGGCGGTTAGGGTAGGTAGT (SEQ ID NO:14848), AGTATGGGCGAGGCGGTTAGGGTAGGT (SEQ ID NO:14849), TGGGCGAGGCGGTTAGGGTAGGTAGTC (SEQ ID NO:14850)

Target1571    chr16:86612295-86612313    GGGGCGTAGTGTTTAGGTCGTTCGGGT (SEQ ID NO:14851), GGATAGAGTACGGAGCGGTCGGGGAGA (SEQ ID NO:14852), AAGGGATAGAGTACGGAGCGGTCGGGG (SEQ ID NO:14853), TGGTTTTTCGGGAGGGTTTTTGCGGCG (SEQ ID NO:14854), GAAGGGATAGAGTACGGAGCGGTCGGG (SEQ ID NO:14855), GAGGCGGTTAGGGTAGGTAGTCGGGGA (SEQ ID NO:14856), GGCGAAGGTTAGAGGGAGGTCGGGTTT (SEQ ID NO:14857), AGGCGGTTAGGGTAGGTAGTCGGGGAT (SEQ ID NO:14858), ATGGGCGAGGCGGTTAGGGTAGGTAGT (SEQ ID NO:14859), AGTATGGGCGAGGCGGTTAGGGTAGGT (SEQ ID NO:14860)

Target1572    chr16:86612344-86612369    GGGGCGTAGTGTTTAGGTCGTTCGGGT (SEQ ID NO:14861), TGGTTTTTCGGGAGGGTTTTTGCGGCG (SEQ ID NO:14862), CGGGGCGTAGTGTTTAGGTCGTTCGGG (SEQ ID NO:14863), AGGTCGTTCGGGTTTTTTGCGTTGCGG (SEQ ID NO:14864), TTGGTTTTTCGGGAGGGTTTTTGCGGC (SEQ ID NO:14865), GAGGTTTTTGCGGGGTTTCGGTTCGGT (SEQ ID NO:14866), GAGGCGGTTAGGGTAGGTAGTCGGGGA (SEQ ID NO:14867), GGCGAAGGTTAGAGGGAGGTCGGGTTT (SEQ ID NO:14868), AGGCGGTTAGGGTAGGTAGTCGGGGAT (SEQ ID NO:14869), AGGTTTTTGCGGGGTTTCGGTTCGGTT (SEQ ID NO:14870)

Target1573    chr16:86612425-86612434    TCGGTTGTTTGTTTTGGTCGTTTCGTTTATGTT (SEQ ID NO:14871), CGGTTGTTTGTTTTGGTCGTTTCGTTTATGTT (SEQ ID NO:14872), TCGGTTGTTTGTTTTGGTCGTTTCGTTTATGTT (SEQ ID NO:14873), CGGTTGTTTGTTTTGGTCGTTTCGTTTATGTTG (SEQ ID NO:14874), CGGTTGTTTGTTTTGGTCGTTTCGTTTATGTTGT (SEQ ID NO:14875), GAGGTTTTTGCGGGGTTTCGGTTCGGT (SEQ ID NO:14876), TTCGGGCGCGTTTTGGATCGTTATGGC (SEQ ID NO:14877), AGGTTTTTGCGGGGTTTCGGTTCGGTT (SEQ ID NO:14878), TTTTTGCGGGGTTTCGGTTCGGTTCGA (SEQ ID NO:14879), GGAGGTTTTTGCGGGGTTTCGGTTCGG (SEQ ID NO:14880)

Target1574    chr16:86612451-86612462    CGCGGTTGTTTTAGTTGTTTCGGGTCGG (SEQ ID NO:14881), GCGGTTGTTTTAGTTGTTTCGGGTCGGG (SEQ ID NO:14882), CGCGGTTGTTTTAGTTGTTTCGGGTCGGG (SEQ ID NO:14883), GCGGTTGTTTTAGTTGTTTCGGGTCGGGT (SEQ ID NO:14884), TCGCGGTTGTTTTAGTTGTTTCGGGTCGG (SEQ ID NO:14885), GAGGTTTTTGCGGGGTTTCGGTTCGGT (SEQ ID NO:14886), TTCGGGCGCGTTTTGGATCGTTATGGC (SEQ ID NO:14887), AGGTTTTTGCGGGGTTTCGGTTCGGTT (SEQ ID NO:14888), GGAGGTTTTTGCGGGGTTTCGGTTCGG (SEQ ID NO:14889), GGGAGGTTTTTGCGGGGTTTCGGTTCG (SEQ ID NO:14890)

Target1575    chr16:86612494-86612549    CGCGGTTGTTTTAGTTGTTTCGGGTCGG (SEQ ID NO:14891), GCGGTTGTTTTAGTTGTTTCGGGTCGGG (SEQ ID NO:14892), CGCGGTTGTTTTAGTTGTTTCGGGTCGGG (SEQ ID NO:14893), GCGGTTGTTTTAGTTGTTTCGGGTCGGGT (SEQ ID NO:14894), TCGCGGTTGTTTTAGTTGTTTCGGGTCGG (SEQ ID NO:14895), GGTTGTCGTGGTAGAAGGGGAAGCGGT (SEQ ID NO:14896), TTCGGGCGCGTTTTGGATCGTTATGGC (SEQ ID NO:14897), CGGTTGTCGTGGTAGAAGGGGAAGCGG (SEQ ID NO:14898), GTTCGGGCGCGTTTTGGATCGTTATGG (SEQ ID NO:14899), TGTTCGGGCGCGTTTTGGATCGTTATGG (SEQ ID NO:14900)

Target1576    chr16:86612573-86612642    GCGAGAGGTTGTGGCGGATGTTGTTTT (SEQ ID NO:14901), GCGAGAGGTTGTGGCGGATGTTGTTTTG (SEQ ID NO:14902), GCGAGAGGTTGTGGCGGATGTTGTTTTGT (SEQ ID NO:14903), GCGAGAGGTTGTGGCGGATGTTGTTT (SEQ ID NO:14904), CGAGAGGTTGTGGCGGATGTTGTTTTGT (SEQ ID NO:14905)

Target1577    chr16:86612650-86612839    CGAGAAAGGGCGGTCGGGTAAGGGTAG (SEQ ID NO:14906), GAGAAAGGGCGGTCGGGTAAGGGTAGT (SEQ ID NO:14907), AGAAAGGGCGGTCGGGTAAGGGTAGTT (SEQ ID NO:14908), CGAGAAAGGGCGGTCGGGTAAGGGTA (SEQ ID NO:14909), GGGCGGTCGGGTAAGGGTAGTTATTGG (SEQ ID NO:14910), CGTTGTTTGTAGGCGGGAGATTGCGGG (SEQ ID NO:14911), CGGGGCGTTGTTTGTAGGCGGGAGATTG (SEQ ID NO:14912), GTTGTTTGTAGGCGGGAGATTGCGGGG (SEQ ID NO:14913), CGTTTCGGCGCGGGGTTTTTTGGTTTT (SEQ ID NO:14914), GGGCGTTGTTTGTAGGCGGGAGATTGC (SEQ ID NO:14915)

Target1578    chr16:86612844-86613033    GGGGTTTCGGAGGTTAAGAGGTTTCGCG (SEQ ID NO:14916), CGGGGTTTCGGAGGTTAAGAGGTTTCGC (SEQ ID NO:14917), TCGGGGTTTCGGAGGTTAAGAGGTTTCGC (SEQ ID NO:14918), GGGTTTCGGAGGTTAAGAGGTTTCGCGT (SEQ ID NO:14919), GGGTTTCGGAGGTTAAGAGGTTTCGCG (SEQ ID NO:14920), CGTTGTTTGTAGGCGGGAGATTGCGGG (SEQ ID NO:14921), CGGGGCGTTGTTTGTAGGCGGGAGATTG (SEQ ID NO:14922), TGCGCGTTGTTTGGTCGATCGTTACGG (SEQ ID NO:14923), GCGCGTTGTTTGGTCGATCGTTACGGT (SEQ ID NO:14924), GTTGTTTGTAGGCGGGAGATTGCGGGG (SEQ ID NO:14925)

Target1579    chr16:86613062-86613095    CGGTCGTGGCGGTCGGTTAGGTAGC (SEQ ID NO:14926), GCGGTCGTGGCGGTCGGTTAGGTAG (SEQ ID NO:14927), GCGGTCGTGGCGGTCGGTTAGGTA (SEQ ID NO:14928), GGTCGTGGCGGTCGGTTAGGTAGC (SEQ ID NO:14929), GCGGTCGTGGCGGTCGGTTAGGTAGC (SEQ ID NO:14930), GGAGTTCGTTTTTTTGAAGGCGGTTTTTGG (SEQ ID NO:14931),

FIGURE 5 CONTINUED

GGAGTTCGTTTTTTGAAGGCGGTTTTTGGT (SEQ ID NO:14932),
AGGAGTTCGTTTTTTGAAGGCGGTTTTTGG (SEQ ID NO:14933),
AGGAGTTCGTTTTTTGAAGGCGGTTTTTGGT (SEQ ID NO:14934),
GGAGTTCGTTTTTTGAAGGCGGTTTTTGGTT (SEQ ID NO:14935)

Target1580    chr16:86613166-86613217    GGGGTGTTAAGTTTGGGTTCGGCGGTC (SEQ ID NO:14936), AGGGGGTGTTAAGTTTGGGTTCGGCGG
(SEQ ID NO:14937), GGGGGTGTTAAGTTTGGGTTCGGCGGT (SEQ ID NO:14938),
GGGGGTGTTAAGTTTGGGTTCGGCGG (SEQ ID NO:14939), TAGGGGGTGTTAAGTTTGGGTTCGGCGG
(SEQ ID NO:14940), TTGAAAGGCGGACGGAGGTTGGAGGAG (SEQ ID NO:14941),
GTTGAAAGGCGGACGGAGGTTGGAGGA (SEQ ID NO:14942), GACGGAGGTTGGAGGAGGCGGTTAGGA
(SEQ ID NO:14943), ACGGAGGTTGGAGGAGGCGGTTAGGAG (SEQ ID NO:14944),
TGAAAGGCGGACGGAGGTTGGAGGAG (SEQ ID NO:14945)

Target1581    chr16:86613256-86613290    GGGGTGTTAAGTTTGGGTTCGGCGGTC (SEQ ID NO:14946), AGGGGGTGTTAAGTTTGGGTTCGGCGG
(SEQ ID NO:14947), CGGCGGTCGTTTGGGTGTTTCGTTTTT (SEQ ID NO:14948),
GGGGGTGTTAAGTTTGGGTTCGGCGGT (SEQ ID NO:14949), GGGGGTGTTAAGTTTGGGTTCGGCGG
(SEQ ID NO:14950), GCGGAGGTTTAGGTTGGGTCGGGAGA (SEQ ID NO:14951),
GCGGAGGTTTAGGTTGGGTCGGGAG (SEQ ID NO:14952), AAGTCGTTTTGGATATGCGGGTCGAGT (SEQ
ID NO:14953), TCGTGTCGGGAATTTGTAGGGGGGAAAT (SEQ ID NO:14954),
ATCGTGTCGGGAATTTGTAGGGGGGAAA (SEQ ID NO:14955)

Target1582    chr16:88599725-88600068    GCGAGTTGGGTTTGGTCGGGGTTTTGT (SEQ ID NO:14956), GGCGAGTTGGGTTTGGTCGGGGTTTTG
(SEQ ID NO:14957), ATTAAGGTGGAGGCGGTGGAGGAGTCG (SEQ ID NO:14958),
GCGAGTTGGGTTTGGTCGGGGTTTTGTT (SEQ ID NO:14959), TTAAGGTGGAGGCGGTGGAGGAGTCGG
(SEQ ID NO:14960), TTCGGTTTTGATTTTGGTCGGGGCGGG (SEQ ID NO:14961),
GGTTTTGATTTTGGTCGGGGCGGGGTT (SEQ ID NO:14962), TCGGCGTGGGGTTGGATAGTTCGGTTT
(SEQ ID NO:14963), TTCGGCGTGGGGTTGGATAGTTCGGTT (SEQ ID NO:14964),
TGGGGGTTTCGGGGAAGAGTTCGGTTT (SEQ ID NO:14965)

Target1583    chr16:88600094-88600193    TGTATAGTCGGTTGTAGTAGGGCGCGGG (SEQ ID NO:14966), GTATAGTCGGTTGTAGTAGGGCGCGGG
(SEQ ID NO:14967), GTGTATAGTCGGTTGTAGTAGGGCGCGGG (SEQ ID NO:14968),
GGTGTATAGTCGGTTGTAGTAGGGCGCGG (SEQ ID NO:14969), TGTATAGTCGGTTGTAGTAGGGCGCGG
(SEQ ID NO:14970), CGTTTTGGGTTTGCGCGCGGTAGG (SEQ ID NO:14971),
GTCGGGTCGGGGGGCGTTTTGGGTTTG (SEQ ID NO:14972), GGGTCGGGGGGCGTTTTGGGTTTG (SEQ
ID NO:14973), GGGTCGGGGGGCGTTTTGGGTTTT (SEQ ID NO:14974),
GGTCGGGGGGCGTTTTGGGTTTGC (SEQ ID NO:14975)

Target1584    chr16:88769741-88770164    ATTGGTAGGGCGGTTGGGTTCGAGGAG (SEQ ID NO:14976), TAGGGCGGTTGGGTTCGAGGAGTAGGA
(SEQ ID NO:14977), GATTGGTAGGGCGGTTGGGTTCGAGGA (SEQ ID NO:14978),
AAGGAAGTGGTTGAGGGCGATGGGTGT (SEQ ID NO:14979), TTCGATTGGTAGGGCGGTTGGGTTCGA
(SEQ ID NO:14980), GGGTGTTTGTTGGGAGGGTTAGTGCGC (SEQ ID NO:14981),
GGTGTTTGTTGGGAGGGTTAGTGCGCG (SEQ ID NO:14982), CGGGTGTTTGTTGGGAGGGTTAGTGCG
(SEQ ID NO:14983), GTGTTTGTTGGGAGGGTTAGTGCGCGA (SEQ ID NO:14984),
TGTTTGTTGGGAGGGTTAGTGCGCGAT (SEQ ID NO:14985)

Target1585    chr17:4425211-4425222    ACGTGGGTAGTTTGAATTTAGTTAGGGCGG (SEQ ID NO:14986),
CGACGTGGGTAGTTTGAATTTAGTTAGGGCGG (SEQ ID NO:14987),
CGTGGGTAGTTTGAATTTAGTTAGGGCGGA (SEQ ID NO:14988),
ACGTGGGTAGTTTGAATTTAGTTAGGGCGGA (SEQ ID NO:14989),
ACGACGTGGGTAGTTTGAATTTAGTTAGGGCGG (SEQ ID NO:14990),
GTGTTGGGATTATAGGGGTGAGTTATCGTGT (SEQ ID NO:14991),
AGTGTTGGGATTATAGGGGTGAGTTATCGTGT (SEQ ID NO:14992),
GTGTTGGGATTATAGGGGTGAGTTATCGTGTT (SEQ ID NO:14993),
AAGTGTTGGGATTATAGGGGTGAGTTATCGTG (SEQ ID NO:14994),
TGTTGGGATTATAGGGGTGAGTTATCGTGTTC (SEQ ID NO:14995)

Target1586    chr17:8516474-8516531    TGGTCGGGGTGGGAAAAGGAAAATCGA (SEQ ID NO:14996), GTGGTCGGGGTGGGAAAAGGAAAATCG
(SEQ ID NO:14997), AGTGGTCGGGGTGGGAAAAGGAAAATCG (SEQ ID NO:14998),
GTGGTCGGGGTGGGAAAAGGAAAATCGA (SEQ ID NO:14999),
AGTGGTCGGGGTGGGAAAAGGAAAATCGA (SEQ ID NO:15000),
TGGATTTGGAATTTAGAGTCGGCGGTTGT (SEQ ID NO:15001),
TGTTGGATTTGGAATTTAGAGTCGGCGGT (SEQ ID NO:15002),
TGGATTTGGAATTTAGAGTCGGCGGTTGTT (SEQ ID NO:15003),
TTGGATTTGGAATTTAGAGTCGGCGGTTGT (SEQ ID NO:15004),
TGTTGGATTTGGAATTTAGAGTCGGCGGTT (SEQ ID NO:15005)

Target1587    chr17:25867500-25867639    TTAGTGGGAGGTTTGGCGGGGAGGTTG (SEQ ID NO:15006), TTGTTAGTGGGAGGTTTGGCGGGGAGG
(SEQ ID NO:15007), GTTAGTGGGAGGTTTGGCGGGGAGGTT (SEQ ID NO:15008),
TTAGGAGAGTGCGGGTATGGGTCGGGT (SEQ ID NO:15009), GGGAGGTTTGGCGGGGAGGTTGTTTTT
(SEQ ID NO:15010), AGGGAAAGTGGGGTAAGGAGAGGAGAA (SEQ ID NO:15011),
AGGGAAAGTGGGGTAAGGAGAGGAGAAA (SEQ ID NO:15012),
GGGAAAGTGGGGTAAGGAGAGGAGAAGT (SEQ ID NO:15013),
GGGAAAGTGGGGTAAGGAGAGGAGAAAG (SEQ ID NO:15014),
AGGGAAAGTGGGGTAAGGAGAGGAGA (SEQ ID NO:15015)

FIGURE 5 CONTINUED

| | | |
|---|---|---|
| *Target1588* | chr17:25867805-25867830 | CGTGGGCGTTTTTGAGGGGTTGGGTAGT (SEQ ID NO:15016), TCGGAGTTGGGTGTTATGGTCGTTGCG (SEQ ID NO:15017), CGTGGGCGTTTTTGAGGGTTGGGTAGTG (SEQ ID NO:15018), TGGGCGTTTTTGAGGGGTTGGGTAGTGT (SEQ ID NO:15019), TTCGGAGTTGGGTGTTATGGTCGTTGCG (SEQ ID NO:15020), AGGGAGGTTTTTGGAGGTTGTGATGTAGTTGA (SEQ ID NO:15021), AAGGGAGGTTTTTGGAGGTTGTGATGTAGTTGA (SEQ ID NO:15022), AGGGAGGTTTTTGGAGGTTGTGATGTAGTTGAT (SEQ ID NO:15023), TGAGAATGTAAGGAGGTTTTTGGAGGTTGTGA (SEQ ID NO:15024), TGTAAGGAGGTTTTTGGAGGTTGTGATGTAGT (SEQ ID NO:15025) |
| *Target1589* | chr17:28705582-28706059 | CGGGGTTAGCGGCGTTGTTGGAAGATG (SEQ ID NO:15026), GTTTCGGACGGGAGGAGGGTAGGTTCG (SEQ ID NO:15027), GGGGTTAGCGGCGTTGTTGGAAGATGG (SEQ ID NO:15028), TTAGAGGGCGGGATGGGGTTGTTAGGC (SEQ ID NO:15029), CGGTTAGAGGGCGGGATGGGGTTGTTA (SEQ ID NO:15030), CGTTAAGGCGGTCGTTCGTTTCGGTCG (SEQ ID NO:15031), GCGGTCGTTCGTTTCGGTCGTTCGTTA (SEQ ID NO:15032), GTTAAGGCGGTCGTTCGTTTCGGTCGT (SEQ ID NO:15033), GTCGTTAAGGCGGTCGTTCGTTTCGGT (SEQ ID NO:15034), AGTCGTTAAGGCGGTCGTTCGTTTCGG (SEQ ID NO:15035) |
| *Target1590* | chr17:32964522-32964532 | GCGGGTGTATTTTGGGAGGGACGAGGA (SEQ ID NO:15036), TGCGGGTGTATTTTGGGAGGGACGAGG (SEQ ID NO:15037), TGGGTTTGCGGGTGTATTTTGGGAGGG (SEQ ID NO:15038), GGGTTTGCGGGTGTATTTTGGGAGGGA (SEQ ID NO:15039), TGGGTTTGCGGGTGTATTTTGGGAGGGA (SEQ ID NO:15040), TGTTCGGGTTTGGAGTTTTCGGTGCGG (SEQ ID NO:15041), CGGGTAGCGTAGAGTTCGGCGGGTTAG (SEQ ID NO:15042), CGGGTTTGGAGTTTTCGGTGCGGGTAG (SEQ ID NO:15043), TCGGGTTTGGAGTTTTCGGTGCGGGTA (SEQ ID NO:15044), GTTCGGGTTTGGAGTTTTCGGTGCGGG (SEQ ID NO:15045) |
| *Target1591* | chr17:32964537-32964582 | GCGGGTGTATTTTGGGAGGGACGAGGA (SEQ ID NO:15046), GGGAGTTGGTTCGTCGGGTTTTGCGTT (SEQ ID NO:15047), TGCGGGTGTATTTTGGGAGGGACGAGG (SEQ ID NO:15048), GGTTCGGGGAGTTGGTTCGTCGGGTTT (SEQ ID NO:15049), GTTCGGGGAGTTGGTTCGTCGGGTTTT (SEQ ID NO:15050), TGTTCGGGTTTGGAGTTTTCGGTGCGG (SEQ ID NO:15051), CGGGTAGCGTAGAGTTCGGCGGGTTAG (SEQ ID NO:15052), CGGGTTTGGAGTTTTCGGTGCGGGTAG (SEQ ID NO:15053), TCGGGTTTGGAGTTTTCGGTGCGGGTA (SEQ ID NO:15054), GTTCGGGTTTGGAGTTTTCGGTGCGGG (SEQ ID NO:15055) |
| *Target1592* | chr17:32964670-32964727 | GGGAGTTGGTTCGTCGGGTTTTGCGTT (SEQ ID NO:15056), GGGAGTTGGTTCGTCGGGTTTTGCGT (SEQ ID NO:15057), GGGAGTTGGTTCGTCGGGTTTTGCGTTA (SEQ ID NO:15058), GGAGATCGGTATGTACGCGTTGTTGGGC (SEQ ID NO:15059), GGAGTTGGTTCGTCGGGTTTTGCGTTA (SEQ ID NO:15060), CGGGATGCGTTTGTGTCGGTAGCGTAG (SEQ ID NO:15061), GGGATGCGTTTGTGTCGGTAGCGTAGT (SEQ ID NO:15062), GCGGGATGCGTTTGTGTCGGTAGCGTA (SEQ ID NO:15063), TGATGAGGAAGACGAGGATGGCGAGGT (SEQ ID NO:15064), AGACGAGGATGGCGAGGTAGAAGACGT (SEQ ID NO:15065) |
| *Target1593* | chr17:32964769-32964785 | GGAGATCGGTATGTACGCGTTGTTGGGC (SEQ ID NO:15066), GAGATCGGTATGTACGCGTTGTTGGGC (SEQ ID NO:15067), TGGAGATCGGTATGTACGCGTTGTTGGGC (SEQ ID NO:15068), TGGAGATCGGTATGTACGCGTTGTTGGG (SEQ ID NO:15069), GGAGATCGGTATGTACGCGTTGTTGGG (SEQ ID NO:15070), TTTAGCGGGTTGTTTGTTGGCGGCGAT (SEQ ID NO:15071), TTTTAGCGGGTTGTTTGTTGGCGGCGA (SEQ ID NO:15072), TAGCGGGTTGTTTGTTGGCGGCGATAG (SEQ ID NO:15073), TTTTTAGCGGGTTGTTTGTTGGCGGCG (SEQ ID NO:15074), TTAGCGGGTTGTTTGTTGGCGGCGATA (SEQ ID NO:15075) |
| *Target1594* | chr17:32964854-32964913 | TGCGGGTGTAAGGAGAGTTGTCGTCGT (SEQ ID NO:15076), CGTTGCGGGTGTAAGGAGAGTTGTCGT (SEQ ID NO:15077), TGCGGGTGTAAGGAGAGTTGTCGTCGTT (SEQ ID NO:15078), TTGCGGGTGTAAGGAGAGTTGTCGTCGT (SEQ ID NO:15079), GCGGGTGTAAGGAGAGTTGTCGTCGTT (SEQ ID NO:15080), TTTAGCGGGTTGTTTGTTGGCGGCGAT (SEQ ID NO:15081), TTTTAGCGGGTTGTTTGTTGGCGGCGA (SEQ ID NO:15082), GTGGTCGTCGTGGTAGAAGGCGGGTAC (SEQ ID NO:15083), TTGGCGGGGTTTTCGGTTTGGTTTCGG (SEQ ID NO:15084), GCGGGGTTTTCGGTTTGGTTTCGGGTT (SEQ ID NO:15085) |
| *Target1595* | chr17:33640320-33640895 | TGTTTTATGTGAAGGGTGGGGCGGGGA (SEQ ID NO:15086), GTGAAGGGTGGGGCGGGGAGAGTTTTA (SEQ ID NO:15087), TGGGGTAGGGTGGTTGTGTTGTGGGTT (SEQ ID NO:15088), TTTATGTGAAGGGTGGGGCGGGGAGAG (SEQ ID NO:15089), ATGGGGTAGGGTGGTTGTGTTGTGGGT (SEQ ID NO:15090), TGCGTGGGAGGGAAGTGTAAGAGTGTT (SEQ ID NO:15091), TTGCGTGGGAGGGAAGTGTAAGAGTGT (SEQ ID NO:15092), GCGTGGGAGGGAAGTGTAAGAGTGTTTCG (SEQ ID NO:15093), TGCGTGGGAGGGAAGTGTAAGAGTGTTT (SEQ ID NO:15094), TTGCGTGGGAGGGAAGTGTAAGAGTGTT (SEQ ID NO:15095) |
| *Target1596* | chr17:35165510-35165531 | GGGAATCGTCGGGTAGGGGGTTGCG (SEQ ID NO:15096), CGGGAATCGTCGGGTAGGGGGTTTGC (SEQ ID NO:15097), GAATCGTCGGGTAGGGGGTTTGCGC (SEQ ID NO:15098), GCGGTTTGGTTAAGGGTAGCGTTAAGGGC (SEQ ID NO:15099), GGAATCGTCGGGTAGGGGGTTTGCGC (SEQ ID NO:15100), GGGGTTTCGTTCGGGGTAGTTGCGTTT (SEQ ID NO:15101), GGGGTTTCGTTCGGGGTAGTTGCGTT (SEQ ID NO:15102), GGGGTTTCGTTCGGGGTAGTTGCGTTTT (SEQ ID NO:15103), GGGGTTTCGTTCGGGGTAGTTGCGTT (SEQ ID NO:15104), TGTTTTGGAGTATTCGCGCGGTTGTGG (SEQ ID NO:15105) |

FIGURE 5 CONTINUED

Target1597     chr17:35165543-35165563     GCGGTTTGGTTAAGGGTAGCGTTAAGGGC (SEQ ID NO:15106),
CGGTTTGGTTAAGGGTAGCGTTAAGGGC (SEQ ID NO:15107), GCGGTTTGGTTAAGGGTAGCGTTAAGGG
(SEQ ID NO:15108), GCGGTTTGGTTAAGGGTAGCGTTAAGG (SEQ ID NO:15109),
GGTTTGGTTAAGGGTAGCGTTAAGGGC (SEQ ID NO:15110), TGTTTTGGAGTATTCGCGCGGTTGTGG
(SEQ ID NO:15111), TGGATGTTTTGGAGTATTCGCGCGGTT (SEQ ID NO:15112),
TTGGATGTTTTGGAGTATTCGCGCGGT (SEQ ID NO:15113), ATGTTTTGGAGTATTCGCGCGGTTGTGG
(SEQ ID NO:15114), GGATGTTTTGGAGTATTCGCGCGGTTGT (SEQ ID NO:15115)

Target1598     chr17:35165609-35165622     GCGGAGGGCGTAGTTGTTTCGGAC (SEQ ID NO:15116), GCGGAGGGCGTAGTTGTTTCGGA (SEQ ID
NO:15117), CGGAGTTTTCGTTATTTTTATAGTCGCGCGGG (SEQ ID NO:15118),
CGGAGTTTTCGTTATTTTTATAGTCGCGCGGGT (SEQ ID NO:15119),
TCGTTATTTTTATAGTCGCGCGGGTGTTTT (SEQ ID NO:15120), AGGCGAGGCGGATATAAAGGAGAGGCG
(SEQ ID NO:15121), GGCGAGGCGGATATAAAGGAGAGGCGA (SEQ ID NO:15122),
GGCGAGGCGAGGCGGATATAAAGGAGA (SEQ ID NO:15123),
GCGAGGCGGATATAAAGGAGAGGCGAGG (SEQ ID NO:15124),
GGCGAGGCGGATATAAAGGAGAGGCGAG (SEQ ID NO:15125)

Target1599     chr17:35165672-35165692     TTTTATTAGCGGTCGGGGAGTCGGGCG (SEQ ID NO:15126), CGGGCGGGAGATAGGAGGTCGGTTTTG
(SEQ ID NO:15127), GGGCGGGAGATAGGAGGTCGGTTTTGA (SEQ ID NO:15128),
TCGGGCGGGAGATAGGAGGTCGGTTTT (SEQ ID NO:15129), CGGGCGGGAGATAGGAGGTCGGTTTT
(SEQ ID NO:15130), AGGCGAGGCGGATATAAAGGAGAGGCG (SEQ ID NO:15131),
GGCGAGGCGGATATAAAGGAGAGGCGA (SEQ ID NO:15132), GGCGAGGCGAGGCGGATATAAAGGAGA
(SEQ ID NO:15133), GCGAGGCGGATATAAAGGAGAGGCGAGG (SEQ ID NO:15134),
GGCGAGGCGGATATAAAGGAGAGGCGAG (SEQ ID NO:15135)

Target1600     chr17:35165694-35165705     TTTTATTAGCGGTCGGGGAGTCGGGCG (SEQ ID NO:15136), CGGGCGGGAGATAGGAGGTCGGTTTTG
(SEQ ID NO:15137), GGGCGGGAGATAGGAGGTCGGTTTTGA (SEQ ID NO:15138),
TCGGGCGGGAGATAGGAGGTCGGTTTT (SEQ ID NO:15139), CGGGCGGGAGATAGGAGGTCGGTTTT
(SEQ ID NO:15140), AGGCGAGGCGGATATAAAGGAGAGGCG (SEQ ID NO:15141),
GGCGAGGCGGATATAAAGGAGAGGCGA (SEQ ID NO:15142), GGCGAGGCGAGGCGGATATAAAGGAGA
(SEQ ID NO:15143), GCGAGGCGGATATAAAGGAGAGGCGAGG (SEQ ID NO:15144),
GGCGAGGCGGATATAAAGGAGAGGCGAG (SEQ ID NO:15145)

Target1601     chr17:35165739-35165758     CGGGCGGGAGATAGGAGGTCGGTTTTG (SEQ ID NO:15146), GGGCGGGAGATAGGAGGTCGGTTTTGA
(SEQ ID NO:15147), TCGGGCGGGAGATAGGAGGTCGGTTTT (SEQ ID NO:15148),
CGGGCGGGAGATAGGAGGTCGGTTTT (SEQ ID NO:15149), GTCGGGCGGGAGATAGGAGGTCGGTTT
(SEQ ID NO:15150), GGGTTAGCGTCGCGGGAATGGAGC (SEQ ID NO:15151),
AGGAGTAGACGGGTTTTGGAGTTTCGC (SEQ ID NO:15152), GTTTTCGGTTGTTTCGGCGCGTTTAAC (SEQ
ID NO:15153), TAGGAGTAGACGGGTTTTGGAGTTTCGC (SEQ ID NO:15154),
TGGGGGGTATTAGGAGTAGACGGGTTTTGG (SEQ ID NO:15155)

Target1602     chr17:35165762-35165787     CGTTTTATTTTCGCGGCGTTGGTTCG (SEQ ID NO:15156), CGGAGATTGTTCGATACGTTTTGGTTAGGGCG
(SEQ ID NO:15157), TCGGAGATTGTTCGATACGTTTTGGTTAGGGCG (SEQ ID NO:15158),
GGAGATTGTTCGATACGTTTTGGTTAGGGCG (SEQ ID NO:15159),
CGGAGATTGTTCGATACGTTTTGGTTAGGGC (SEQ ID NO:15160),
TCGGTCGGATTTTGAGGAGTTGGGGGT (SEQ ID NO:15161), TTCGGTCGGATTTTGAGGAGTTGGGGGT
(SEQ ID NO:15162), TTCGGTCGGATTTTGAGGAGTTGGGGG (SEQ ID NO:15163),
CGGTCGGATTTTGAGGAGTTGGGGGTA (SEQ ID NO:15164), TCGGTCGGATTTTGAGGAGTTGGGGGTA
(SEQ ID NO:15165)

Target1603     chr17:35165817-35165847     CGTTTTATTTTCGCGGCGTTGGTTCGG (SEQ ID NO:15166), CGTTTTATTTTCGCGGCGTTGGTTCG (SEQ ID
NO:15167), GTTTTATTTTCGCGGCGTTGGTTCGG (SEQ ID NO:15168),
CGGGTCGAGCGAATTGTTTTGTTTTTGGT (SEQ ID NO:15169), CGGGTCGAGCGAATTGTTTTGTTTTTGG
(SEQ ID NO:15170), TTGCGGGGGAGGAGTAGCGAGGTTTTT (SEQ ID NO:15171),
TGCGGGGGAGGAGTAGCGAGGTTTTG (SEQ ID NO:15172), GCGGGGGAGGAGTAGCGAGGTTTTTGT
(SEQ ID NO:15173), GTTGCGGGGGAGGAGTAGCGAGGTTTT (SEQ ID NO:15174),
TCGGTCGGATTTTGAGGAGTTGGGGGT (SEQ ID NO:15175)

Target1604     chr17:35299479-35299683     AGGCGGTGAAGGGGTGTTGGTTAGGTT (SEQ ID NO:15176), GCGGTGAAGGGGTGTTGGTTAGGTTCG
(SEQ ID NO:15177), TTGGTGGATCGTTTGGAGTCGGGCGAG (SEQ ID NO:15178),
GGTGGATCGTTTGGAGTCGGGCGAGTT (SEQ ID NO:15179), GGCGGTGAAGGGGTGTTGGTTAGGTTC
(SEQ ID NO:15180), GGGGATGAGTTCGTTCGGTTTTAGGCGG (SEQ ID NO:15181),
GTCGGGCGTTTAGGGCGTTTAGTTGTT (SEQ ID NO:15182), GGGATGAGTTCGTTCGGTTTTAGGCGGT
(SEQ ID NO:15183), TGGGGATGAGTTCGTTCGGTTTTAGGCG (SEQ ID NO:15184),
GGGATGAGTTCGTTCGGTTTTAGGCGG (SEQ ID NO:15185)

Target1605     chr17:35299710-35299742     TTGGTGGATCGTTTGGAGTCGGGCGAG (SEQ ID NO:15186), GGTGGATCGTTTGGAGTCGGGCGAGTT
(SEQ ID NO:15187), GTCGTTGGTGGATCGTTTGGAGTCGGG (SEQ ID NO:15188),
GGTCGTTGGTGGATCGTTTGGAGTCGG (SEQ ID NO:15189), GTTGGTGGATCGTTTGGAGTCGGGCGA
(SEQ ID NO:15190), AGGGTCGTGAATTGGGTTTTCGGTTTC (SEQ ID NO:15191),
AGTGGTTTATAGAGAGCGAGGCGTGTT (SEQ ID NO:15192), AGTGGTTTATAGAGAGCGAGGCGTGTTT
(SEQ ID NO:15193), AGTGGTTTATAGAGAGCGAGGCGTGTTTT (SEQ ID NO:15194),
AGTGGTTTATAGAGAGCGAGGCGTGTTTTT (SEQ ID NO:15195)

FIGURE 5 CONTINUED

| | | |
|---|---|---|
| Target1606 | chr17:35299913-35300021 | TGGGAGTAAATTAAGGGGAGGCGGCGA (SEQ ID NO:15196),<br>TGGGAGTAAATTAAGGGGAGGCGGCGAG (SEQ ID NO:15197),<br>GGGGAGTAAATTAAGGGGAGGCGGCGAG (SEQ ID NO:15198), TTGGGAGTAAATTAAGGGGAGGCGGCG<br>(SEQ ID NO:15199), GGGAGTAAATTAAGGGGAGGCGGCGAGA (SEQ ID NO:15200),<br>CGGGGGGTTTTGCGGGAAGAAGTCGTA (SEQ ID NO:15201), TAGGACGTTAGGGTTCGGTCGGGGGTC<br>(SEQ ID NO:15202), GGGGGGGTTTTGCGGGAAGAAGTCGTAG (SEQ ID NO:15203),<br>GTAGGACGTTAGGGTTCGGTCGGGGGT (SEQ ID NO:15204), GAGGACGGGGGGGTTTTGCGGGAAGAAG<br>(SEQ ID NO:15205) |
| Target1607 | chr17:35300059-35300075 | CGGGGGGTTTTGCGGGAAGAAGTCGTA (SEQ ID NO:15206), GGGGGGGTTTTGCGGGAAGAAGTCGTAG<br>(SEQ ID NO:15207), GAGGACGGGGGGGTTTTGCGGGAAGAAG (SEQ ID NO:15208),<br>GGACGGGGGGGTTTTGCGGGAAGAAGTC (SEQ ID NO:15209), GGGGGGGTTTTGCGGGAAGAAGTCGTAGT<br>(SEQ ID NO:15210) |
| Target1608 | chr17:35300778-35300801 | GCGGGTGCGTATAGTCGTTGGC (SEQ ID NO:15211), GCGTTTGGTAGGCGGGCGG (SEQ ID NO:15212),<br>TTGGTTGGTTCGGGAGCGTTTTGGGTC (SEQ ID NO:15213), TTTGGTTGGTTCGGGAGCGTTTTGGGT<br>(SEQ ID NO:15214), TTTTGGTTGGTTCGGGAGCGTTTTGGGTC (SEQ ID NO:15215),<br>TGGTTGGTTCGGGAGCGTTTTGGGTC (SEQ ID NO:15216), TTTTTGGTTGGTTCGGGAGCGTTTTGGGT<br>(SEQ ID NO:15217) |
| Target1609 | chr17:37321375-37321792 | GGTTCGGGGGCGTTTCGGGGTTTGTTAA (SEQ ID NO:15218), AAGCGTCGGAGGAAGGGTAGCGTTAGG<br>(SEQ ID NO:15219), GGAAGCGTCGGAGGAAGGGTAGCGTTA (SEQ ID NO:15220),<br>TTTGGAAGCGTCGGAGGAAGGGTAGCG (SEQ ID NO:15221), AGGTTCGGGGCGTTTCGGGGTTTGTTA<br>(SEQ ID NO:15222), GATTTGTGGTCGGACGTACGGGGGGGAT (SEQ ID NO:15223),<br>GGGTAGGTGTCGGAGTTGGGTGGGAAG (SEQ ID NO:15224), CGTTTCGGAGTGGGGTAGGTGTCGGAG<br>(SEQ ID NO:15225), GAGTGGGGTAGGTGTCGGAGTTGGGTG (SEQ ID NO:15226),<br>TTGTGGTCGGACGTACGGGGGGATTTC (SEQ ID NO:15227) |
| Target1610 | chr17:37321886-37321895 | GAGTAGGTAGGGACGGGGGGTAGGGGAG (SEQ ID NO:15228),<br>GAGGAGTAGGTAGGGACGGGGGTAGGG (SEQ ID NO:15229), TAGGTAGGGACGGGGGTAGGGGAGGTC<br>(SEQ ID NO:15230), GGAGTAGGTAGGGACGGGGGTAGGGGA (SEQ ID NO:15231),<br>AGTAGGTAGGGACGGGGGTAGGGGAGG (SEQ ID NO:15232),<br>GGGGCGTATAGGGTATTTAAGCGAGCGT (SEQ ID NO:15233), GGGGCGTATAGGGTATTTAAGCGAGCG<br>(SEQ ID NO:15234), AGGGGCGTATAGGGTATTTAAGCGAGCGT (SEQ ID NO:15235),<br>AGGGGCGTATAGGGTATTTAAGCGAGCG (SEQ ID NO:15236),<br>CGGGAATTAGGGTAAGGGGCGTATAGGGT (SEQ ID NO:15237) |
| Target1611 | chr17:41477218-41477617 | CGTCGGGGGGTAGGAGAAGTTGCGATT (SEQ ID NO:15238), GTGTTTGTGGTGGACGTTGCGGAGGTT<br>(SEQ ID NO:15239), TGTTTGTGGTGGACGTTGCGGAGGTTG (SEQ ID NO:15240),<br>TTAAGTGTGGGACGTCGGGGGGGTAGGA (SEQ ID NO:15241), GTTTGTGGTGGACGTTGCGGAGGTTGA<br>(SEQ ID NO:15242), TCGTTTGTTCGGCGGGTATAAGAGCGT (SEQ ID NO:15243),<br>TATTAGGTGGGAGGAAAGGGAGGGGGG (SEQ ID NO:15244), ATTAGGTGGGAGGAAAGGGAGGGGGG<br>(SEQ ID NO:15245), CGTTTGTTCGGCGGGTATAAGAGCGTT (SEQ ID NO:15246),<br>TCGTTTGTTCGGCGGGTATAAGAGCGTT (SEQ ID NO:15247) |
| Target1612 | chr17:46618870-46618983 | GGAATTAGGTAGGGTGTGGTGGGGGAT (SEQ ID NO:15248), GGTAGGGTGTGGTGGGGGATAGATAGG<br>(SEQ ID NO:15249), AGGTAGGGTGTGGTGGGGGATAGATAGG (SEQ ID NO:15250),<br>GGTAGGGTGTGGTGGGGGATAGATAGGA (SEQ ID NO:15251),<br>AGGTAGGGTGTGGTGGGGGATAGATAGGA (SEQ ID NO:15252),<br>GGAGAGTTCGGGTGGATGTGGGAAGGG (SEQ ID NO:15253), GGGTGGATGTGGGAAGGGAAGGAGAGC<br>(SEQ ID NO:15254), CGGGTGGATGTGGGAAGGGAAGGAGAG (SEQ ID NO:15255),<br>GTGGATGTGGGAAGGGAAGGAGAGCGG (SEQ ID NO:15256),<br>GGTGGATGTGGGAAGGGAAGGAGAGCGG (SEQ ID NO:15257) |
| Target1613 | chr17:46619088-46619146 | TCGGTTGGGTCGGCGTTTTTTGTAGCG (SEQ ID NO:15258), GGTTGGGTCGGCGTTTTTTGTAGCGGT<br>(SEQ ID NO:15259), GTAGGGGCGGGGGTAGATTTCGGTTGG (SEQ ID NO:15260),<br>TGGGTCGGCGTTTTTTGTAGCGGTTGT (SEQ ID NO:15261), CGTAGGGGCGGGGGTAGATTTCGGTTG<br>(SEQ ID NO:15262), CGAGGAGAGCGGGAGGGAGATAGGGAA (SEQ ID NO:15263),<br>ATTTGCGGGGAGAGAAGGAGGAGCGA (SEQ ID NO:15264), GATTTGCGGGGAGAGAAGGAGGAGCGA<br>(SEQ ID NO:15265), TGTTTAAAATGGCGTTGGGGTCGGGCG (SEQ ID NO:15266),<br>GGATTTGCGGGGAGAGAAGGAGGAGCG (SEQ ID NO:15267) |
| Target1614 | chr17:46619180-46619314 | TCGGTTGGGTCGGCGTTTTTTGTAGCG (SEQ ID NO:15268), GGTTGGGTCGGCGTTTTTTGTAGCGGT<br>(SEQ ID NO:15269), GTAGGGGCGGGGGTAGATTTCGGTTGG (SEQ ID NO:15270),<br>TGGGTCGGCGTTTTTTGTAGCGGTTGT (SEQ ID NO:15271), CGTAGGGGCGGGGGTAGATTTCGGTTG<br>(SEQ ID NO:15272), CGAGGAGAGCGGGAGGGAGATAGGGAA (SEQ ID NO:15273),<br>TCGGGCGAGAAGTTTAGGGTGGTTCGG (SEQ ID NO:15274), TGGATTTGCGGGGAGAGAAGGAGGAGC<br>(SEQ ID NO:15275), ATTTGCGGGGAGAGAAGGAGGAGCGAG (SEQ ID NO:15276),<br>GATTTGCGGGGAGAGAAGGAGGAGCGA (SEQ ID NO:15277) |
| Target1615 | chr17:46619368-46619465 | TCGAGTTTATGGGTGTTTCGGTAGCGT (SEQ ID NO:15278), TGGGTGCGGGATTTTGTTTTTCGAGAA (SEQ<br>ID NO:15279), TTGGGTGCGGGATTTTGTTTTTCGAGA (SEQ ID NO:15280),<br>TCGAGTTTATGGGTGTTTCGGTAGCGTT (SEQ ID NO:15281), TTCGAGTTTATGGGTGTTTCGGTAGCGT<br>(SEQ ID NO:15282), GGAGTGGGGTCGGGGATTTTTTCGGGA (SEQ ID NO:15283),<br>TAGGGACGCGAGGTTTGGGGTTTGAGT (SEQ ID NO:15284), TGGAGTGGGGTCGGGGATTTTTTCGGG |

FIGURE 5 CONTINUED (SEQ ID NO:15285), GCGAGGTTTGGGGTTTGAGTCGGGTTT (SEQ ID NO:15286),
AGGGACGCGAGGTTTGGGGTTTGAGTC (SEQ ID NO:15287)

| | | |
|---|---|---|
| Target1616 | chr17:46621872-46622196 | TCGGGTTGGAGGTTGGGGAAGGTTTGT (SEQ ID NO:15288), GCGGTGGCGGCGGTAGAGTAGGTTTAT (SEQ ID NO:15289), GTGGCGGATTGGTTGGGTTTTTTGGCG (SEQ ID NO:15290), CGTGGCGGATTGGTTGGGTTTTTTGGC (SEQ ID NO:15291), CGGAGAAGGAGACGTGGCGGATTGGTT (SEQ ID NO:15292), CGGGGTCGGATCGTTTGTAGGTCGGTA (SEQ ID NO:15293), CGGGGTCGGATCGTTTGTAGGTCGGT (SEQ ID NO:15294), CGGGGTCGGATCGTTTGTAGGTCGGTAA (SEQ ID NO:15295), CGGGGTCGGATCGTTTGTAGGTCGGTAAG (SEQ ID NO:15296), GGGGTCGGATCGTTTGTAGGTCGGTAA (SEQ ID NO:15297) |
| Target1617 | chr17:46622219-46622227 | TCGGGTTGGAGGTTGGGGAAGGTTTGT (SEQ ID NO:15298), CGTCGGGTTGGAGGTTGGGGAAGGTTT (SEQ ID NO:15299), GTCGGGTTGGAGGTTGGGGAAGGTTTG (SEQ ID NO:15300), CGGGTTGGAGGTTGGGGAAGGTTTGTT (SEQ ID NO:15301), TCGGGTTGGAGGTTGGGGAAGGTTTGTT (SEQ ID NO:15302), AGAGGGAGATTGGGTTTATAAATAGTTAGTCGTCGT (SEQ ID NO:15303), GAGAGGGAGATTGGGTTTATAAATAGTTAGTCGTCG (SEQ ID NO:15304) |
| Target1618 | chr17:46832359-46832403 | CGGGTTCGGGTTTTGCGTTGGAGTCG (SEQ ID NO:15305), AGCGAGAGGGAACGGGTTGGTTTAGTT (SEQ ID NO:15306), GCGAGAGGGAACGGGTTGGTTTAGTTT (SEQ ID NO:15307), AGCGAGAGGGAACGGGTTGGTTTAGTTT (SEQ ID NO:15308), AGCGAGAGGGAACGGGTTGGTTTAGT (SEQ ID NO:15309), TCGACGTTGAGTTTTGTAGGCGGGGTT (SEQ ID NO:15310), TTCGACGTTGAGTTTTGTAGGCGGGGT (SEQ ID NO:15311), CGACGTTGAGTTTTGTAGGCGGGGTTT (SEQ ID NO:15312), TCGACGTTGAGTTTTGTAGGCGGGGTTT (SEQ ID NO:15313), TTCGACGTTGAGTTTTGTAGGCGGGGTT (SEQ ID NO:15314) |
| Target1619 | chr17:46832417-46832446 | TGCGTTGGAGTCGGGATGTTTTTCGGC (SEQ ID NO:15315), GTTCGGGTTTTGCGTTGGAGTCGGGAT (SEQ ID NO:15316), TCGGGTTTTGCGTTGGAGTCGGGATGT (SEQ ID NO:15317), GTCGGGATGTTTTTCGGCGGAGGGTG (SEQ ID NO:15318), TTGCGTTGGAGTCGGGATGTTTTTCGGC (SEQ ID NO:15319), TCGACGTTGAGTTTTGTAGGCGGGGTT (SEQ ID NO:15320), TTCGACGTTGAGTTTTGTAGGCGGGGT (SEQ ID NO:15321), CGACGTTGAGTTTTGTAGGCGGGGTTT (SEQ ID NO:15322), TCGACGTTGAGTTTTGTAGGCGGGGTTT (SEQ ID NO:15323), TTCGACGTTGAGTTTTGTAGGCGGGGTT (SEQ ID NO:15324) |
| Target1620 | chr17:46832470-46832494 | TGCGTTGGAGTCGGGATGTTTTTCGGC (SEQ ID NO:15325), GTTCGGGTTTTGCGTTGGAGTCGGGAT (SEQ ID NO:15326), TCGGGTTTTGCGTTGGAGTCGGGATGT (SEQ ID NO:15327), GTCGGGATGTTTTTCGGCGGAGGGTG (SEQ ID NO:15328), TTGCGTTGGAGTCGGGATGTTTTTCGGC (SEQ ID NO:15329), GAGTTTTTGAGTTTCGAGTTTTTTGGCGGAAAA (SEQ ID NO:15330), TGTTTGAAATTGGAGATTAGGACGTTTAGAGAGGAA (SEQ ID NO:15331), TTGTTTGAAATTGGAGATTAGGACGTTTAGAGAGGA (SEQ ID NO:15332) |
| Target1621 | chr17:48042255-48042272 | TCGGAGAGGGGGGACGTAGGTTTTTT (SEQ ID NO:15333), TCGGAGAGGGGGGACGTAGGTTTTTT (SEQ ID NO:15334), CGGAGAGGGGGGACGTAGGTTTTTT (SEQ ID NO:15335), TCGGAGAGGGGGGACGTAGGTTTT (SEQ ID NO:15336), CGGAGAGGGGGGACGTAGGTTTTTT (SEQ ID NO:15337), CGGTTTGGCGGCGGGAAGGAAAGAATT (SEQ ID NO:15338), AATTCGGTTTGGCGGCGGGAAGGAAAG (SEQ ID NO:15339), TCGGTTTGGCGGCGGGAAGGAAAGAAT (SEQ ID NO:15340), ATTCGGTTTGGCGGCGGGAAGGAAAGA (SEQ ID NO:15341), TAATTCGGTTTGGCGGCGGGAAGGAAA (SEQ ID NO:15342) |
| Target1622 | chr17:48042289-48042294 | CGGGTTTCGTTGAATGCGGGGGTTTTA (SEQ ID NO:15343), CGGGTTTCGTTGAATGCGGGGGTTTT (SEQ ID NO:15344), CGGGTTTCGTTGAATGCGGGGGTTTAT (SEQ ID NO:15345), AATGCGGGGGTTTTATTTATAGCGCGC (SEQ ID NO:15346), CGGGTTTCGTTGAATGCGGGGGTTT (SEQ ID NO:15347), CGGTTTGGCGGCGGGAAGGAAAGAATT (SEQ ID NO:15348), AATTCGGTTTGGCGGCGGGAAGGAAAG (SEQ ID NO:15349), TCGGTTTGGCGGCGGGAAGGAAAGAAT (SEQ ID NO:15350), ATTCGGTTTGGCGGCGGGAAGGAAAGA (SEQ ID NO:15351), TAATTCGGTTTGGCGGCGGGAAGGAAA (SEQ ID NO:15352) |
| Target1623 | chr17:48042490-48042509 | GTCGGTGGGTGGGATGGAGGAGAAAGG (SEQ ID NO:15353), GGTCGGTGGGTGGGATGGAGGAGAAAG (SEQ ID NO:15354), GGGTGGGATGGAGGAGAAAGGGTACGG (SEQ ID NO:15355), TTCGTTTTGGGGTCGGTGGGTGGGATG (SEQ ID NO:15356), GTTCGTTTTGGGGTCGGTGGGTGGGAT (SEQ ID NO:15357), GAGTCGTATTTGCGCGGATGTGTTAGC (SEQ ID NO:15358), AGAGTCGTATTTGCGCGGATGTGTTAGC (SEQ ID NO:15359), AGTCGTATTTGCGCGGATGTGTTAGC (SEQ ID NO:15360), TAGAGTCGTATTTGCGCGGATGTGTTAGC (SEQ ID NO:15361), TTAGAGTCGTATTTGCGCGGATGTGTTAGC (SEQ ID NO:15362) |
| Target1624 | chr17:48042531-48042573 | GTCGGTGGGTGGGATGGAGGAGAAAGG (SEQ ID NO:15363), GGTCGGTGGGTGGGATGGAGGAGAAAG (SEQ ID NO:15364), GGGTGGGATGGAGGAGAAAGGGTACGG (SEQ ID NO:15365), CGGAGTGAGGAGGATTATGGTCGCGGT (SEQ ID NO:15366), GCGGAGTGAGGAGGATTATGGTCGCGG (SEQ ID NO:15367), GAGTCGTATTTGCGCGGATGTGTTAGC (SEQ ID NO:15368), AGAGTCGTATTTGCGCGGATGTGTTAGC (SEQ ID NO:15369), AGTCGTATTTGCGCGGATGTGTTAGC (SEQ ID NO:15370), TAGAGTCGTATTTGCGCGGATGTGTTAGC (SEQ ID NO:15371), TTAGAGTCGTATTTGCGCGGATGTGTTAGC (SEQ ID NO:15372) |
| Target1625 | chr17:48042663-48042696 | GTGCGGTTTTGAGTGTTGGTTCGGGGT (SEQ ID NO:15373), AGGTGCGGTTTTGAGTGTTGGTTCGGG (SEQ ID NO:15374), GGTGCGGTTTTGAGTGTTGGTTCGGGG (SEQ ID NO:15375), TGCGGTTTTGAGTGTTGGTTCGGGGTT (SEQ ID NO:15376), GTGCGGTTTTGAGTGTTGGTTCGGGGTT |

FIGURE 5 CONTINUED (SEQ ID NO:15377), TGGTGAGTGCGTAGTGTTTTCGGTAGT (SEQ ID NO:15378), TGGTGAGTGCGTAGTGTTTTCGGTAGTT (SEQ ID NO:15379), TTGGTGAGTGCGTAGTGTTTTCGGTAGT (SEQ ID NO:15380), TGGTGAGTGCGTAGTGTTTTCGGTAGTTT (SEQ ID NO:15381), TTGGTGAGTGCGTAGTGTTTTCGGTAGTT (SEQ ID NO:15382)

Target1626 chr17:48546447-48546852 GTTCGGTCGGGTGTTTTGGATGCGAGG (SEQ ID NO:15383), GTGTTTTGGATGCGAGGCGGGAGGAAG (SEQ ID NO:15384), CGTTCGGTCGGGTGTTTTGGATGCGAG (SEQ ID NO:15385), CGTGTATGAGGGGGTGGGATCGTGGTT (SEQ ID NO:15386), TCGTGTATGAGGGGGTGGGATCGTGGT (SEQ ID NO:15387), TAGGAGAGCGGGGGGGTTATAGTCGGGG (SEQ ID NO:15388), GCGGGGGGGTTATAGTCGGGGTTTAGGG (SEQ ID NO:15389), GGATGGCGCGGCGTGGAGGTTTAAATT (SEQ ID NO:15390), GTAAGCGGGGGTTGGAAGAGAGGGGTGG (SEQ ID NO:15391), TGGCGCGGCGTGGAGGTTTAAATTTGA (SEQ ID NO:15392)

Target1627 chr17:48546884-48546900 GACGCGTCGAAGTTGGTTTTGGGTAGA (SEQ ID NO:15393), ACGCGTCGAAGTTGGTTTTGGGTAGAT (SEQ ID NO:15394), GACGCGTCGAAGTTGGTTTTGGGTAGAT (SEQ ID NO:15395), ACGCGTCGAAGTTGGTTTTGGGTAGATT (SEQ ID NO:15396), CGCGTCGAAGTTGGTTTTGGGTAGATT (SEQ ID NO:15397), GGGGGGATGGTGCGATTGTGTTTGTGG (SEQ ID NO:15398), GGGGGATGGTGCGATTGTGTTTGTGGT (SEQ ID NO:15399), TAGCGGTGGAAAAAGGGGATGAGGGCG (SEQ ID NO:15400), GGTGGAAAAAGGGGATGAGGGCGTCGG (SEQ ID NO:15401), TTAGCGGTGGAAAAAGGGGATGAGGGC (SEQ ID NO:15402)

Target1628 chr17:55520634-55520788 TCGGTTTTGGGTAAAGGGAGTGGGGGG (SEQ ID NO:15403), CGGTTTTGGGTAAAGGGAGTGGGGGGT (SEQ ID NO:15404), TTCGGTTTTGGGTAAAGGGAGTGGGGGG (SEQ ID NO:15405), AGGGAGTGGGGGGTTATGTGTGGAGTT (SEQ ID NO:15406), AAGGGAGTGGGGGGTTATGTGTGGAGT (SEQ ID NO:15407), GTCGAGGAGAGGTAGTTTTTGTCGGTGT (SEQ ID NO:15408), TGGTGGTTGGGGTATAGATTGGGTAGTCG (SEQ ID NO:15409), AGTCGAGGAGAGGTAGTTTTTGTCGGTGT (SEQ ID NO:15410), GGTGGTTGGGGTATAGATTGGGTAGTCG (SEQ ID NO:15411), AGTCGAGGAGAGGTAGTTTTTGTCGGTG (SEQ ID NO:15412)

Target1629 chr17:55951722-55951752 GGTGTTGGGGGAGTTTTTTAGGAGGTCGT (SEQ ID NO:15413), AGGTGTTGGGGGAGTTTTTTAGGAGGTCGT (SEQ ID NO:15414), AGGTGTTGGGGGAGTTTTTTAGGAGGTCG (SEQ ID NO:15415), GGTGTTGGGGGAGTTTTTTAGGAGGTCGTG (SEQ ID NO:15416), GGTGTTGGGGGAGTTTTTTAGGAGGTCGTGT (SEQ ID NO:15417), ACGGGTTTGGAAAGAGCGGTTTTAGAGT (SEQ ID NO:15418), ACGGGTTTGGAAAGAGCGGTTTTAGAGTA (SEQ ID NO:15419), ACGGGTTTGGAAAGAGCGGTTTTAGAGTAT (SEQ ID NO:15420), ACGGGTTTGGAAAGAGCGGTTTTAGAGTATT (SEQ ID NO:15421), ACGGGTTTGGAAAGAGCGGTTTTAGAGTATTT (SEQ ID NO:15422)

Target1630 chr17:55951816-55952168 GTCGGGCGGTGGGGGTTGTTTTAGTTT (SEQ ID NO:15423), TGCGTGGAGATGTGAGTGTGGAAGGGA (SEQ ID NO:15424), CGTGCGTGGAGATGTGAGTGTGGAAGG (SEQ ID NO:15425), GTGCGTGGAGATGTGAGTGTGGAAGGG (SEQ ID NO:15426), TCGGGCGGTGGGGGGTTGTTTTAGTTTT (SEQ ID NO:15427), GGGAGTTTGGGGGGTTAGGGAGGGTGTG (SEQ ID NO:15428), TAGTGAGGGGGCGGGCGGGATTTTTAG (SEQ ID NO:15429), TTAGTGAGGGGGCGGGCGGGATTTTTA (SEQ ID NO:15430), TTTAGTGAGGGGGCGGGCGGGATTTTT (SEQ ID NO:15431), TTTTTTAGTGAGGGGGCGGGCGGGATT (SEQ ID NO:15432)

Target1631 chr17:56405826-56405850 TGTTTGTGTGTGTGTGTGTGGGTGTTT (SEQ ID NO:15433), TGTTTGTGTGTGTGTGTGTGGGGTGTTTG (SEQ ID NO:15434), TTGTTTGTGTGTGTGTGTGTGGGTGTTT (SEQ ID NO:15435), TGTTTGTGTGTGTGTGTGTGGGTGTT (SEQ ID NO:15436), AGTGTCGTGTAGTTGTGTGTATCGGTGTC (SEQ ID NO:15437), AGTTTTTGGTCGGGGTTGAGGGGTTGCG (SEQ ID NO:15438), GTTTTTGGTCGGGTTGAGGGGTTGCGA (SEQ ID NO:15439), TTTTTGGTCGGGGTTGAGGGGTTGCGAT (SEQ ID NO:15440), AAGTTTTTGGTCGGGTTGAGGGGTTGCG (SEQ ID NO:15441), TTTGGTCGGGTTGAGGGGTTGCGATAG (SEQ ID NO:15442)

Target1632 chr17:56405948-56405995 GGGGGTGATTTTTAGTGGTTCGTTGTGGT (SEQ ID NO:15443), TGGGGGTGATTTTTAGTGGTTCGTTGTGG (SEQ ID NO:15444), TGGGGGGTGATTTTTAGTGGTTCGTTGTGGT (SEQ ID NO:15445), GGGGGTGATTTTTAGTGGTTCGTTGTGG (SEQ ID NO:15446), CGGTTAGAGGTTTTAGGAGTTGTTGGGGGT (SEQ ID NO:15447), AGCGAAAGAGTAGTAGTAGAGAGTAGAGTCGGA (SEQ ID NO:15448), GCGAAAGAGTAGTAGTAGAGAGTAGAGTCGGAG (SEQ ID NO:15449), AAGCGAAAGAGTAGTAGTAGAGAGTAGAGTCGG (SEQ ID NO:15450), AGCGAAAGAGTAGTAGTAGAGAGTAGAGTCGGA (SEQ ID NO:15451), GCGAAAGAGTAGTAGTAGAGAGTAGAGTCGGAGA (SEQ ID NO:15452)

Target1633 chr17:59481954-59482071 GGCGGGAGAAAAGGTGAGAGGTCGAGG (SEQ ID NO:15453), AGCGAGTAGGAGGGATGGAGGGATGGG (SEQ ID NO:15454), GAACGGTCGGCGGGAGAAAAGGTGAGA (SEQ ID NO:15455), AACGGTCGGCGGGAGAAAAGGTGAGAG (SEQ ID NO:15456), CGGCGGGAGAAAAGGTGAGAGGTCGAG (SEQ ID NO:15457), TTGCGTTCGGGGAGGTGGGTGGTTTTC (SEQ ID NO:15458), GTTGCGTTCGGGGAGGTGGGTGGTTTT (SEQ ID NO:15459), TTGCGTTCGGGGAGGTGGGTGGTTTTT (SEQ ID NO:15460), GTTCGGGGAGGTGGGTGGTTTTCGC (SEQ ID NO:15461), GCGTTCGGGGAGGTGGGTGGTTTTC (SEQ ID NO:15462)

FIGURE 5 CONTINUED

Target1634　chr17:59482089-59482145　CGATGGCGCGGAGTTAGACGTTTCG (SEQ ID NO:15463), GCGTTTAGTTCGTTGCGTTTGTATCGGG (SEQ ID NO:15464), GCGTTTAGTTCGTTGCGTTTGTATCGGGT (SEQ ID NO:15465), AGCGTTTAGTTCGTTGCGTTTGTATCGGG (SEQ ID NO:15466), AGCGTTTAGTTCGTTGCGTTTGTATCGGGT (SEQ ID NO:15467), AGCGGGTGGTTTAGTAAAAGATTAGTTTAGCGA (SEQ ID NO:15468), AGCGGGTGGTTTAGTAAAAGATTAGTTTAGCGAT (SEQ ID NO:15469), TTTTTTGGTTTTTTAGGTTAGCGGGTGGTTTAGT (SEQ ID NO:15470), TAGCGGGTGGTTTAGTAAAAGATTAGTTTAGCGA (SEQ ID NO:15471), TGGTTTTTTAGGTTAGCGGGTGGTTTAGTAAAAGA (SEQ ID NO:15472)

Target1635　chr17:59482185-59482293　GCGGGGGGTTTTTAGGTCGTTGGGTTG (SEQ ID NO:15473), GGTGAGGGTCGGATCGGAGGAGGGATA (SEQ ID NO:15474), GTCGGATCGGAGGAGGGATAGGGAGGT (SEQ ID NO:15475), TCGGATCGGAGGAGGGATAGGGAGGTG (SEQ ID NO:15476), TGAGGGTCGGATCGGAGGAGGGATAGG (SEQ ID NO:15477), ACGGCGTTTAAGGGGTTAGGTTCGGAGT (SEQ ID NO:15478), CGGCGTTTAAGGGGTTAGGTTCGGAGT (SEQ ID NO:15479), ACGGCGTTTAAGGGGGTTAGGTTCGGAG (SEQ ID NO:15480), CGGCGTTTAAGGGGGTTAGGTTCGGAGTT (SEQ ID NO:15481), ACGGCGTTTAAGGGGGTTAGGTTCGGAGTT (SEQ ID NO:15482)

Target1636　chr17:59482315-59482975　AGGGTTTGGCGTCGTTGGTGGTGTAGA (SEQ ID NO:15483), AGGCGGTCGAGGGTAAGGAGTAGGGTT (SEQ ID NO:15484), GAGGAGTTTGGAGAAGGAGCGCGTCGA (SEQ ID NO:15485), AGGAGGCGGTCGAGGGTAAGGAGTAGG (SEQ ID NO:15486), AGGAGTTTGGAGAAGGAGCGCGTCGAA (SEQ ID NO:15487), GAGTGGGGTTGGCGTTGTTTGGAGTCG (SEQ ID NO:15488), CGAGTGGGGTTGGCGTTGTTTGGAGTC (SEQ ID NO:15489), GGTTAGGTCGGGTAGGTGTTCGGCGTT (SEQ ID NO:15490), TCGGGAAGGGTTGTTTTCGGGGAGGTC (SEQ ID NO:15491), AGGTCGGGTAGGTGTTCGGCGTTAGG (SEQ ID NO:15492)

Target1637　chr17:59528980-59529045　TGTCGCGGAATTTTGGTTTTGGGTCGT (SEQ ID NO:15493), TTGTCGCGGAATTTTGGTTTTGGGTCGT (SEQ ID NO:15494), TTGTCGCGGAATTTTGGTTTTGGGTCG (SEQ ID NO:15495), GTTGTCGCGGAATTTTGGTTTTGGGTCG (SEQ ID NO:15496), GTTGTCGCGGAATTTTGGTTTTGGGTCGT (SEQ ID NO:15497), GCGGAGGTTAGGGGTGAGGATTGGGAG (SEQ ID NO:15498), GTCGCGGAGGTTAGGGGTGAGGATTGG (SEQ ID NO:15499), GGTCGCGGAGGTTAGGGGTGAGGATTG (SEQ ID NO:15500), TTTTGTTTCGGTTTAGGGGGTCGCGGG (SEQ ID NO:15501), GGGGTGAGGATTGGGAGGAAGTTCGGT (SEQ ID NO:15502)

Target1638　chr17:59529083-59529153　GGTTTTTTGGGTCGGGATAAGGAGGGCG (SEQ ID NO:15503), CGGTTTTTTGGGTCGGGATAAGGAGGGC (SEQ ID NO:15504), GCGGTTTTTTGGGTCGGGATAAGGAGGG (SEQ ID NO:15505), GTTTTTTGGGTCGGGATAAGGAGGGCG (SEQ ID NO:15506), GCGGTTTTTTGGGTCGGGATAAGGAGG (SEQ ID NO:15507), TTTTGTTTCGGTTTAGGGGGTCGCGGG (SEQ ID NO:15508), TTTTTGTTTCGGTTTAGGGGGTCGCGGG (SEQ ID NO:15509), TTTGTTTCGGTTTAGGGGGTCGCGGG (SEQ ID NO:15510), TTTTTGTTTCGGTTTAGGGGGTCGCGG (SEQ ID NO:15511), TTTTTTGTTTCGGTTTAGGGGGTCGCGGG (SEQ ID NO:15512)

Target1639　chr17:59529220-59529627　TTAAGAGGAGGGTATTGGGTCGCGCGG (SEQ ID NO:15513), CGTGGTGGGTATGGTAGGGAAGCGGAG (SEQ ID NO:15514), TTGGAAGTGTAAGGTCGCGTGGTGGGT (SEQ ID NO:15515), GGGCGTCGGTAGGGGGTGGTTAGATTC (SEQ ID NO:15516), GGGCGGGTGAGTAGAAGGGTCGTGTTT (SEQ ID NO:15517), TTGCGTTCGTTGTTTTTCGGGGAGGGG (SEQ ID NO:15518), CGAGTCGGGTAGGGGTTGGGAGTTTCG (SEQ ID NO:15519), GCGAGTCGGGTAGGGGTTGGGAGTTTC (SEQ ID NO:15520), GGGAGGGGGGGTTTTAGGGTTTTTCGGC (SEQ ID NO:15521), GAGTCGGGTAGGGGTTGGGAGTTTCGT (SEQ ID NO:15522)

Target1640　chr17:59531878-59531893　CGCGGAGGAGTGGATGTGAAGGACGAG (SEQ ID NO:15523), GCGGAGGAGTGGATGTGAAGGACGAGA (SEQ ID NO:15524), TCGCGGAGGAGTGGATGTGAAGGACGA (SEQ ID NO:15525), CGCGGAGGAGTGGATGTGAAGGACGA (SEQ ID NO:15526), TCGCGGAGGAGTGGATGTGAAGGACG (SEQ ID NO:15527)

Target1641　chr17:59532030-59532059　CGAGGTTTGGATGTGGTTTCGTGGCGG (SEQ ID NO:15528), TCGAGGTTTGGATGTGGTTTCGTGGCG (SEQ ID NO:15529), AGGTTTGGATGTGGTTTCGTGGCGGAG (SEQ ID NO:15530), GGTTTGGATGTGGTTTCGTGGCGGAGA (SEQ ID NO:15531), GAGGTTTGGATGTGGTTTCGTGGCGGA (SEQ ID NO:15532), TGTTTTGTGAGGAGTTGGTTTATCGTTCGC (SEQ ID NO:15533), CGCGTTTAGTTTTGTTTTGTGAGGAGTTGGT (SEQ ID NO:15534), ACGCGTTTAGTTTTGTTTTGTGAGGAGTTGG (SEQ ID NO:15535), ACGCGTTTAGTTTTGTTTTGTGAGGAGTTGGT (SEQ ID NO:15536), TTGTTTTGTGAGGAGTTGGTTTATCGTTCGC (SEQ ID NO:15537)

Target1642　chr17:59532095-59532136　GGGTTGAGCGCGTAGGATTGAGAGC (SEQ ID NO:15538), CGGGAGGGAGAGTATTGAGTAGGTTTCGT (SEQ ID NO:15539), TCGGGAGGGAGAGTATTGAGTAGGTTTCGT (SEQ ID NO:15540), TCGGGAGGGAGAGTATTGAGTAGGTTTCG (SEQ ID NO:15541), TGAGTTCGGGAGGGAGAGTATTGAGTAGGT (SEQ ID NO:15542), CGCGTTTGGTTCGTATGGTTATGGGGT (SEQ ID NO:15543), TCGCGTTTGGTTCGTATGGTTATGGGGT (SEQ ID NO:15544), TCGCGTTTGGTTCGTATGGTTATGGGG (SEQ ID NO:15545), GCGATTCGTTGGTTTTAGATGTGGCGGT (SEQ ID NO:15546), GCGATTCGTTGGTTTTAGATGTGGCGG (SEQ ID NO:15547)

FIGURE 5 CONTINUED

| | | |
|---|---|---|
| Target1643 | chr17:59532148-59532224 | GGGTTGAGCGCGTAGGATTGAGAGC (SEQ ID NO:15548), GGTTGAGCGCGTAGGATTGAGAGC (SEQ ID NO:15549), GCGGGCGGTGAATTAGTTTTTTATAGGGTAGGG (SEQ ID NO:15550), GCGGGCGGTGAATTAGTTTTTTATAGGGTAGGGT (SEQ ID NO:15551), GCGGGCGGTGAATTAGTTTTTTATAGGGTAGG (SEQ ID NO:15552), TGTTCGTTTCGGTTAGCGCGTTGGGTT (SEQ ID NO:15553), TTGTTCGTTTCGGTTAGCGCGTTGGGT (SEQ ID NO:15554), GTTGTTCGTTTCGGTTAGCGCGTTGGG (SEQ ID NO:15555), AGTTGTTCGTTTCGGTTAGCGCGTTGGG (SEQ ID NO:15556), GTTGTTCGTTTCGGTTAGCGCGTTGGGT (SEQ ID NO:15557) |
| Target1644 | chr17:59532248-59532271 | TAGCGGATCGTTTGGTCGTTGGAGTCG (SEQ ID NO:15558), AGCGGATCGTTTGGTCGTTGGAGTCG (SEQ ID NO:15559), TGGGATTAGCGGATCGTTTGGTCGTTGG (SEQ ID NO:15560), GGGATTAGCGGATCGTTTGGTCGTTGG (SEQ ID NO:15561), TTAGCGGATCGTTTGGTCGTTGGAGTCG (SEQ ID NO:15562), TGTTCGTTTCGGTTAGCGCGTTGGGTT (SEQ ID NO:15563), TTGTTCGTTTCGGTTAGCGCGTTGGGT (SEQ ID NO:15564), GTTGTTCGTTTCGGTTAGCGCGTTGGG (SEQ ID NO:15565), AGTTGTTCGTTTCGGTTAGCGCGTTGGG (SEQ ID NO:15566), GTTGTTCGTTTCGGTTAGCGCGTTGGGT (SEQ ID NO:15567) |
| Target1645 | chr17:59532279-59532309 | TAGCGGATCGTTTGGTCGTTGGAGTCG (SEQ ID NO:15568), AGCGGATCGTTTGGTCGTTGGAGTCG (SEQ ID NO:15569), TGGGATTAGCGGATCGTTTGGTCGTTGG (SEQ ID NO:15570), GGGATTAGCGGATCGTTTGGTCGTTGG (SEQ ID NO:15571), TTAGCGGATCGTTTGGTCGTTGGAGTCG (SEQ ID NO:15572), TGTTCGTTTCGGTTAGCGCGTTGGGTT (SEQ ID NO:15573), TTGTTCGTTTCGGTTAGCGCGTTGGGT (SEQ ID NO:15574), GTTGTTCGTTTCGGTTAGCGCGTTGGG (SEQ ID NO:15575), AGTTGTTCGTTTCGGTTAGCGCGTTGGG (SEQ ID NO:15576), GTTGTTCGTTTCGGTTAGCGCGTTGGGT (SEQ ID NO:15577) |
| Target1646 | chr17:59532372-59532387 | GGTCGGAGCGGGTAGTTATTTTATTGGCG (SEQ ID NO:15578), GGTCGGAGCGGGTAGTTATTTTATTGGCGT (SEQ ID NO:15579), TGGTCGGAGCGGGTAGTTATTTTATTGGCG (SEQ ID NO:15580), TCGGAGCGGGTAGTTATTTTATTGGCGT (SEQ ID NO:15581), TGGTCGGAGCGGGTAGTTATTTTATTGGCGT (SEQ ID NO:15582), GGGAGTGAGATTCGTTGGATATGGTTAGCG (SEQ ID NO:15583), GGGAGTGAGATTCGTTGGATATGGTTAGCGT (SEQ ID NO:15584), AGGGAGTGAGATTCGTTGGATATGGTTAGCG (SEQ ID NO:15585), AGGGAGTGAGATTCGTTGGATATGGTTAGCGT (SEQ ID NO:15586), GGAGTGAGATTCGTTGGATATGGTTAGCGT (SEQ ID NO:15587) |
| Target1647 | chr17:62775572-62775676 | GCGGTGGGGAGATTGTGGGTAGTTTTGG (SEQ ID NO:15588), TGCGGTGGGGAGATTGTGGGTAGTTTT (SEQ ID NO:15589), TTGCGGTGGGGAGATTGTGGGTAGTTT (SEQ ID NO:15590), TTTGCGGTGGGGAGATTGTGGGTAGTT (SEQ ID NO:15591), TTTTGCGGTGGGGAGATTGTGGGTAGT (SEQ ID NO:15592), CGTTTAGGCGGGATAGGGTTCGGGGAG (SEQ ID NO:15593), GGTTCGGGGAGCGGTAGGAAATGGGTT (SEQ ID NO:15594), TCGGGGAGCGGTAGGAAATGGGTTGTT (SEQ ID NO:15595), TTCGGGGAGCGGTAGGAAATGGGTTGT (SEQ ID NO:15596), GTTTAGGCGGGATAGGGTTCGGGGAGC (SEQ ID NO:15597) |
| Target1648 | chr17:62775700-62775722 | GGTTGGGATGCGGGTTTTGTAGGCGTT (SEQ ID NO:15598), TGGGATGCGGGTTTTGTAGGCGTTTCG (SEQ ID NO:15599), GGGATGCGGGTTTTGTAGGCGTTTCGG (SEQ ID NO:15600), GGGGTTAGGGTTGGGATGCGGGTTTTG (SEQ ID NO:15601), GGGTTAGGGTTGGGATGCGGGTTTTGT (SEQ ID NO:15602), GGTAGAGTTGTTCGTCGGGGCGTTTGT (SEQ ID NO:15603), AGGTAGAGTTGTTCGTCGGGGCGTTTGT (SEQ ID NO:15604), AGGTAGAGTTGTTCGTCGGGGCGTTTG (SEQ ID NO:15605), CGTTGAAGTCGTTGGGGAAGGGGAGAG (SEQ ID NO:15606), CGTTGAAGTCGTTGGGGAAGGGGAGAGA (SEQ ID NO:15607) |
| Target1649 | chr17:62775797-62775847 | GTGGGGGTTTTCGTTGTTAAGGCGGGG (SEQ ID NO:15608), GGTTGGGATGCGGGTTTTGTAGGCGTT (SEQ ID NO:15609), TGGGATGCGGGTTTTGTAGGCGTTTCG (SEQ ID NO:15610), GGGATGCGGGTTTTGTAGGCGTTTCGG (SEQ ID NO:15611), GGGGTTAGGGTTGGGATGCGGGTTTTG (SEQ ID NO:15612), TTGCGTTGAAGTCGTTGGGGAAGGGGA (SEQ ID NO:15613), GCGTTGAAGTCGTTGGGGAAGGGGAGA (SEQ ID NO:15614), TTTGCGTTGAAGTCGTTGGGGAAGGGG (SEQ ID NO:15615), TGCGTTGAAGTCGTTGGGGAAGGGGAG (SEQ ID NO:15616), GTTTGCGTTGAAGTCGTTGGGGAAGGGG (SEQ ID NO:15617) |
| Target1650 | chr17:62775871-62775904 | GTGGGGGTTTTCGTTGTTAAGGCGGGG (SEQ ID NO:15618), TGTGGGGGTTTTCGTTGTTAAGGCGGG (SEQ ID NO:15619), GGGGTTTTCGTTGTTAAGGCGGGGGAA (SEQ ID NO:15620), GGGGGTTTTCGTTGTTAAGGCGGGGGA (SEQ ID NO:15621), TGGGGGTTTTCGTTGTTAAGGCGGGGG (SEQ ID NO:15622), TTTTTTCGGGGGGCGGCGTGAGAGTC (SEQ ID NO:15623), TTTTTTCGGGGGGCGGCGTGAGAGT (SEQ ID NO:15624), TTTTTTCGGGGGGCGGCGTGAGAGT (SEQ ID NO:15625), TTTTTTCGGGGGGCGGCGTGAGAG (SEQ ID NO:15626), TTTTTCGGGGGGCGGCGTGAGAGTC (SEQ ID NO:15627) |
| Target1651 | chr17:62775998-62776036 | TGTTCGTGCGGAGTTTTAAAGTAGGGGT (SEQ ID NO:15628), TGTTCGTGCGGAGTTTTAAAGTAGGGGTT (SEQ ID NO:15629), TTGTTCGTGCGGAGTTTTAAAGTAGGGGT (SEQ ID NO:15630), TGTTCGTGCGGAGTTTTAAAGTAGGGGTTT (SEQ ID NO:15631), TTGTTCGTGCGGAGTTTTAAAGTAGGGGT (SEQ ID NO:15632), TTATGGTTTTGGTGGAGGGGCGTCGGT (SEQ ID NO:15633), GGTTTTGGTGGAGGGGCGTCGGTAGAT (SEQ ID NO:15634), |

FIGURE 5 CONTINUED

ATGGTTTTGGTGGAGGGGCGTCGGTAG (SEQ ID NO:15635), TATGGTTTTGGTGGAGGGGCGTCGGTA (SEQ ID NO:15636), TTTATGGTTTTGGTGGAGGGGCGTCGG (SEQ ID NO:15637)

Target1652    chr17:70216183-70216505    AAGGTTAGGGTAGGTGGGGTGGGAGGT (SEQ ID NO:15638), GGGGTGGGAGGTGGGGAGAGGGATATGT (SEQ ID NO:15639), AGGTTAGGGTAGGTGGGGTGGGAGGTG (SEQ ID NO:15640), GGGAAGGTTAGGGTAGGTGGGGTGGGA (SEQ ID NO:15641), AGGGAAGGTTAGGGTAGGTGGGGTGGG (SEQ ID NO:15642), TGTTTGGTTCGTGTTGTTCGGGGTTGT (SEQ ID NO:15643), TGTTTGGTTCGTGTTGTTCGGGGTTGTT (SEQ ID NO:15644), TGGTAGTGGGGAGGGATAGTTCGAAGGT (SEQ ID NO:15645), GTTTGGTTCGTGTTGTTCGGGGTTGTT (SEQ ID NO:15646), GGTAGTGGGGAGGGATAGTTCGAAGGT (SEQ ID NO:15647)

Target1653    chr17:73483829-73483938    GGGGTTGGAGTGGTCGGGTAGGGTTTT (SEQ ID NO:15648), TTTTGGGGTTGGAGTGGTCGGGTAGGG (SEQ ID NO:15649), AGAGGTTTTGGGGTTGGAGTGGTCGGG (SEQ ID NO:15650), GGGAAGTGTTGGAACGAGTGGAGGGGT (SEQ ID NO:15651), GAGGTTTTGGGGTTGGAGTGGTCGGGT (SEQ ID NO:15652), AGGGTATTTGAGGGGAATGGAAAGAGGGA (SEQ ID NO:15653), TGAGGGTATTTGAGGGGAATGGAAAGAGGG (SEQ ID NO:15654), GAGGGTATTTGAGGGGAATGGAAAGAGGG (SEQ ID NO:15655), GAGGGTATTTGAGGGGAATGGAAAGAGGGA (SEQ ID NO:15656), TGAGGGTATTTGAGGGGAATGGAAAGAGGGA (SEQ ID NO:15657)

Target1654    chr17:73635995-73636378    CGAGGGTGGAATTTCGGTGTTGCGACG (SEQ ID NO:15658), CGGTGTTGCGACGAGTGTGGGGTTAGT (SEQ ID NO:15659), GGTGTTGCGACGAGTGTGGGGTTAGTC (SEQ ID NO:15660), CGGTGTTGCGACGAGTGTGGGGTTAG (SEQ ID NO:15661), CGGTGTTGCGACGAGTGTGGGGTTAGTC (SEQ ID NO:15662), TTGTTTCGGGGGTTGTCGGTTAAGGCG (SEQ ID NO:15663), TGTTTCGGGGGTTGTCGGTTAAGGCGG (SEQ ID NO:15664), GTTTCGGGGGTTGTCGGTTAAGGCGGT (SEQ ID NO:15665), AAGGGTTTGTTTCGGGGGTTGTCGGTT (SEQ ID NO:15666), GTTTCGGGGGTTGTCGGTTAAGGCGG (SEQ ID NO:15667)

Target1655    chr17:73749587-73749620    TTTCGGGATTTCGGGGTGTGTGTTGGG (SEQ ID NO:15668), TTCGGGATTTCGGGGTGTGTGTTGGGG (SEQ ID NO:15669), TTTTCGGGATTTCGGGGTGTGTGTTGGG (SEQ ID NO:15670), TCGGGATTTCGGGGTGTGTGTTGGGG (SEQ ID NO:15671), TTCGGGATTTCGGGGTGTGTGTTGGG (SEQ ID NO:15672)

Target1656    chr17:73749654-73750226    TTCGGGATTTCGGGAGTTGGAGACGGG (SEQ ID NO:15673), GCGTTACGTGGCGGTTGTTTTCGGAGT (SEQ ID NO:15674), AGGTTCGGGTTTTGGCGGTTGGGAGTA (SEQ ID NO:15675), CGGGATTTCGGGAGTTGGAGACGGGTT (SEQ ID NO:15676), GTCGCGGTTTTTTCGTTTCGGTCGTGC (SEQ ID NO:15677), GGGGGCGGCGGGTGAGTTTGTTATTTT (SEQ ID NO:15678), AGTAGGGTTAGGCGGGGGAAGGTCGTA (SEQ ID NO:15679), GCGGGATGAGTTTCGGGGGTAGTCGTT (SEQ ID NO:15680), TAGGCGGGGGAAGGTCGTAGGTTTTGC (SEQ ID NO:15681), GGTTAGGCGGGGGAAGGTCGTAGGTTT (SEQ ID NO:15682)

Target1657    chr17:75369378-75370663    GGGTTTGCGTGCGGGTAGGGAGAGTAT (SEQ ID NO:15683), TTGAGGGGCGGGTTTGTTTTTTGTCGGG (SEQ ID NO:15684), GGAGAGGATTTTGCGGGTGGGTTTGGC (SEQ ID NO:15685), AAGGTGGGTGTTGGGTTGGTTGTTGCG (SEQ ID NO:15686), CGTGTTGGAGAGGATTTTGCGGGTGGG (SEQ ID NO:15687), AGGGGCGGGGGTTTTAGGTTTCGGTAG (SEQ ID NO:15688), GGGGCGGGGGTTTTAGGTTTCGGTAGA (SEQ ID NO:15689), GAGGGGCGGGGGTTTTAGGTTTCGGTA (SEQ ID NO:15690), TCGTCGGGGAGAGTTAAAGGGAGGGGA (SEQ ID NO:15691), GCGTGGGGGAGGGGAGGGTTGTTTATT (SEQ ID NO:15692)

Target1658    chr17:77386082-77386160    AGGGTTTTAGTTGAGAAGGAGGTTTTGGAGT (SEQ ID NO:15693), GAGGGTTTTAGTTGAGAAGGAGGTTTTGGAGT (SEQ ID NO:15694), AGAGGGTTTTAGTTGAGAAGGAGGTTTTGGAG (SEQ ID NO:15695), AGAGAGGGTTTTAGTTGAGAAGGAGGTTTTGG (SEQ ID NO:15696), GAGAGGGTTTTAGTTGAGAAGGAGGTTTTGGA (SEQ ID NO:15697), TTTCGGTCGGGTGGTTGGTTACGGAGA (SEQ ID NO:15698), TTCGGTCGGGTGGTTGGTTACGGAGAT (SEQ ID NO:15699), CGGTCGGGTGGTTGGTTACGGAGATTC (SEQ ID NO:15700), TTTTCGGTCGGGTGGTTGGTTACGGAG (SEQ ID NO:15701), TCGGTCGGGTGGTTGGTTACGGAGATTC (SEQ ID NO:15702)

Target1659    chr17:77386167-77386185    TTTCGGTCGGGTGGTTGGTTACGGAGA (SEQ ID NO:15703), TCGGTCGGGTGGTTGGTTACGGAGATT (SEQ ID NO:15704), TTCGGTCGGGTGGTTGGTTACGGAGAT (SEQ ID NO:15705), TCGGGTGGTTGGTTACGGAGATTCGGA (SEQ ID NO:15706), GTCGGGTGGTTGGTTACGGAGATTCGG (SEQ ID NO:15707)

Target1660    chr17:77789396-77789413    GCGGTGGGCGGGTAGGTACGTTTTTTC (SEQ ID NO:15708), GCGGGCGGGATAGGAGGGGAATAGTTG (SEQ ID NO:15709), CGGTGGGCGGGTAGGTACGTTTTTTCG (SEQ ID NO:15710), CGGGCGGGATAGGAGGGGAATAGTTGG (SEQ ID NO:15711), GGGCGGGATAGGAGGGGAATAGTTGGT (SEQ ID NO:15712), TGGATAAGGCGGTTGGTTGGACGTGGG (SEQ ID NO:15713), ATGGATAAGGCGGTTGGTTGGACGTGG (SEQ ID NO:15714), GATAAGGCGGTTGGTTGGACGTGGGGG (SEQ ID NO:15715), GGATAAGGCGGTTGGTTGGACGTGGGG (SEQ ID NO:15716), GATAAGGCGGTTGGTTGGACGTGGGG (SEQ ID NO:15717)

Target1661    chr17:77789425-77789530    GCGGTGGGCGGGTAGGTACGTTTTTTC (SEQ ID NO:15718), GCGGGCGGGATAGGAGGGGAATAGTTG (SEQ ID NO:15719), CGGTGGGCGGGTAGGTACGTTTTTTCG (SEQ ID NO:15720), CGGGCGGGATAGGAGGGGAATAGTTGG (SEQ ID NO:15721), GGGCGGGATAGGAGGGGAATAGTTGGT

FIGURE 5 CONTINUED

{SEQ ID NO:15722), CGTGGCGGGTGGTATTCGGGTATTGGA (SEQ ID NO:15723),
ACGTGGCGGGTGGTATTCGGGTATTGG (SEQ ID NO:15724), TGGATAAGGCGGTTGGTTGGACGTGGG
(SEQ ID NO:15725), ATGGATAAGGCGGTTGGTTGGACGTGG (SEQ ID NO:15726),
GATAAGGCGGTTGGTTGGACGTGGGGG (SEQ ID NO:15727)

| Target1662 | chr17:77789575-77789686 | AGTCGAGGGGAGAAAATGGTCGGTGGC (SEQ ID NO:15728), GTGGTCGTCGGGTTGTCGTTTCGGTTT (SEQ ID NO:15729), CGGGTTGTCGTTTCGGTTTTTGTGCGG (SEQ ID NO:15730), GGGTTGTCGTTTCGGTTTTTGTGCGGG (SEQ ID NO:15731), TGGTCGTCGGGTTGTCGTTTCGGTTTT (SEQ ID NO:15732), CGTTTGATCGAGTTTTGAGAGCGGCGT (SEQ ID NO:15733), TCGGGTATTAGGAGTCGTAGGGGTCGT (SEQ ID NO:15734), GTCGGGTATTAGGAGTCGTAGGGGTCGT (SEQ ID NO:15735), GTCGGGTATTAGGAGTCGTAGGGGTCG (SEQ ID NO:15736), CGTTTGATCGAGTTTTGAGAGCGGCGTT (SEQ ID NO:15737) |

| Target1663 | chr17:77789701-77789719 | AGTCGAGGGGAGAAAATGGTCGGTGGC (SEQ ID NO:15738), GTGGTCGTCGGGTTGTCGTTTCGGTTT (SEQ ID NO:15739), CGGGTTGTCGTTTCGGTTTTTGTGCGG (SEQ ID NO:15740), GGGTTGTCGTTTCGGTTTTTGTGCGGG (SEQ ID NO:15741), TGGTCGTCGGGTTGTCGTTTCGGTTTT (SEQ ID NO:15742), CGTTTGATCGAGTTTTGAGAGCGGCGT (SEQ ID NO:15743), TCGGGTATTAGGAGTCGTAGGGGTCGT (SEQ ID NO:15744), GTCGGGTATTAGGAGTCGTAGGGGTCGT (SEQ ID NO:15745), GTCGGGTATTAGGAGTCGTAGGGGTCG (SEQ ID NO:15746), CGTTTGATCGAGTTTTGAGAGCGGCGTT (SEQ ID NO:15747) |

| Target1664 | chr17:77789751-77789785 | TCGTTGGAGGGGCGTCGTTTTTAGGGT (SEQ ID NO:15748), AGTCGAGGGGAGAAAATGGTCGGTGGC (SEQ ID NO:15749), CGGTCGTTGGAGGGGCGTCGTTTTTAG (SEQ ID NO:15750), GTCGTTGGAGGGGCGTCGTTTTTAGGG (SEQ ID NO:15751), GGTCGTTGGAGGGGCGTCGTTTTTAGG (SEQ ID NO:15752), AAAAGCGAGATGGGGTGAGAAGGGGCG (SEQ ID NO:15753), AAAAAGCGAGATGGGGTGAGAAGGGGC (SEQ ID NO:15754), AAAGCGAGATGGGGTGAGAAGGGGCG (SEQ ID NO:15755), AGATGGGGTGAGAAGGGGCGGGGTTTC (SEQ ID NO:15756), GAGATGGGGTGAGAAGGGGCGGGGTTT (SEQ ID NO:15757) |

| Target1665 | chr17:77789814-77789824 | TCGTTGGAGGGGCGTCGTTTTTAGGGT (SEQ ID NO:15758), CGGTCGTTGGAGGGGCGTCGTTTTTAG (SEQ ID NO:15759), GTCGTTGGAGGGGCGTCGTTTTTAGGG (SEQ ID NO:15760), GGTCGTTGGAGGGGCGTCGTTTTTAGG (SEQ ID NO:15761), TGGAGGGGCGTCGTTTTTAGGGTTCGG (SEQ ID NO:15762), AAAAGCGAGATGGGGTGAGAAGGGGC (SEQ ID NO:15763), AAAAAGCGAGATGGGGTGAGAAGGGGC (SEQ ID NO:15764), AAAGCGAGATGGGGTGAGAAGGGGCG (SEQ ID NO:15765), AGATGGGGTGAGAAGGGGCGGGGTTTC (SEQ ID NO:15766), GAGATGGGGTGAGAAGGGGCGGGGTTT (SEQ ID NO:15767) |

| Target1666 | chr17:78999585-78999726 | AGGTTTTGGTAGTAGTTTGCGGCGTTT (SEQ ID NO:15768), AAGGTTTTGGTAGTAGTTTGCGGCGTTT (SEQ ID NO:15769), AAAGGTTTTGGTAGTAGTTTGCGGCGTT (SEQ ID NO:15770), TGGTAGTAGTTTGCGGCGTTTTTTGGAA (SEQ ID NO:15771), TTGGTAGTAGTTTGCGGCGTTTTTTGGA (SEQ ID NO:15772), AGGGTTGGTTAGAGATGGCGGTCGTGG (SEQ ID NO:15773), TCGGGGTTTAGAGGAGGCGTGGTTGTG (SEQ ID NO:15774), GGGTTGGTTAGAGATGGCGGTCGTGGT (SEQ ID NO:15775), CGGGGTTTAGAGGAGGCGTGGTTGTGT (SEQ ID NO:15776), TTAGGAGGCGGGTAGGGTGGGACGTAG (SEQ ID NO:15777) |

| Target1667 | chr17:78999741-78999784 | TGGCGTTAAGTCGGTTGGAGATTGGTT (SEQ ID NO:15778), TTGGCGTTAAGTCGGTTGGAGATTGGT (SEQ ID NO:15779), CGGTAGTTTTGGCGTTAAGTCGGTTGG (SEQ ID NO:15780), CGGTAGTTTTGGCGTTAAGTCGGTTGGA (SEQ ID NO:15781), TCGGTAGTTTTGGCGTTAAGTCGGTTGG (SEQ ID NO:15782), AGGGTTGGTTAGAGATGGCGGTCGTGG (SEQ ID NO:15783), GGGTTGGTTAGAGATGGCGGTCGTGGT (SEQ ID NO:15784), TTAGGAGGCGGGTAGGGTGGGACGTAG (SEQ ID NO:15785), TTAGGGGTTAGGAGGCGGGTAGGGTGG (SEQ ID NO:15786), TGGTTAGGGGTTAGGAGGCGGGTAGGG (SEQ ID NO:15787) |

| Target1668 | chr17:78999895-78999909 | TTGTGTGGTTTCGTGGTTGGGTTGGGG (SEQ ID NO:15788), GTTGTGTGGTTTCGTGGTTGGGTTGGGG (SEQ ID NO:15789), GTTGTGTGGTTTCGTGGTTGGGTTGGG (SEQ ID NO:15790), TGTGTGGTTTCGTGGTTGGGTTGGGG (SEQ ID NO:15791), AGTTGTGTGGTTTCGTGGTTGGGTTGGG (SEQ ID NO:15792), AGGGGTTAGGTTGGATGTGTAGCGGGG (SEQ ID NO:15793), GGGGTTAGGTTGGATGTGTAGCGGGGA (SEQ ID NO:15794), GGGTTAGGTTGGATGTGTAGCGGGGAGG (SEQ ID NO:15795), GGGGTTAGGTTGGATGTGTAGCGGGGAG (SEQ ID NO:15796), GAGGGGTTAGGTTGGATGTGTAGCGGGG (SEQ ID NO:15797) |

| Target1669 | chr17:80535181-80535365 | CGGGCGGTCGGGTTAAGGTTTCGTAGT (SEQ ID NO:15798), TAATTTGTATGTAGGGCGTGGCGGGCG (SEQ ID NO:15799), GCGGGCGGTCGGGTTAAGGTTTCGTAG (SEQ ID NO:15800), AATTTGTATGTAGGGCGTGGCGGGGCG (SEQ ID NO:15801), GGGCGGTCGGGTTAAGGTTTCGTAGTT (SEQ ID NO:15802), GCGGTATGTATAGAGGGTTCGGCGGGG (SEQ ID NO:15803), GGCGGTATGTATAGAGGGTTCGGCGGG (SEQ ID NO:15804), ATAGGCGGGGTAGGAGTTTGTTCGGGG (SEQ ID NO:15805), GCGGGGTAGGAGTTTGTTCGGGGTTGT (SEQ ID NO:15806), TAGGCGGGGTAGGAGTTTGTTCGGGGT (SEQ ID NO:15807) |

| Target1670 | chr17:80535398-80535474 | CGGGCGGTCGGGTTAAGGTTTCGTAGT (SEQ ID NO:15808), TAATTTGTATGTAGGGCGTGGCGGGGCG (SEQ ID NO:15809), AATTTGTATGTAGGGCGTGGCGGGGCG (SEQ ID NO:15810), GGGCGGTCGGGTTAAGGTTTCGTAGTT (SEQ ID NO:15811), AATTTGTATGTAGGGCGTGGCGGGCGG (SEQ ID NO:15812), GCGGTATGTATAGAGGGTTCGGCGGGG (SEQ ID NO:15813), GGCGGTATGTATAGAGGGTTCGGCGGG (SEQ ID NO:15814), CGGTATGTATAGAGGGTTCGGCGGGGT |

FIGURE 5 CONTINUED (SEQ ID NO:15815), CGGTATGTATAGAGGGTTCGGCGGGGTT (SEQ ID NO:15816),
CGAGATTTTGGTTCGTAGTGTCGGCGGT (SEQ ID NO:15817)

| Target1671 | chr17:80535562-80535677 | TTGTTTAGGTTGGAGTGTAGTGGCGCG (SEQ ID NO:15818), GTTGTTTAGGTTGGAGTGTAGTGGCGCG (SEQ ID NO:15819), TGTTGTTTAGGTTGGAGTGTAGTGGCGCG (SEQ ID NO:15820), TGTTGTTTAGGTTGGAGTGTAGTGGCGC (SEQ ID NO:15821), CGTCGATATTGCGGGTTAAGGTTTCGGT (SEQ ID NO:15822), GGAGGTAAAGGTTGTAGTGAGTTGAGATCGC (SEQ ID NO:15823), AGGAGGTAAAGGTTGTAGTGAGTTGAGATCGC (SEQ ID NO:15824), TAGGAGGTAAAGGTTGTAGTGAGTTGAGATCGC (SEQ ID NO:15825), TTAGGAGGTAAAGGTTGTAGTGAGTTGAGATCGC (SEQ ID NO:15826), TTTAGGAGGTAAAGGTTGTAGTGAGTTGAGATCGC (SEQ ID NO:15827) |
|---|---|---|
| Target1672 | chr17:80846604-80846653 | GGTTAGAGGTGGTGGGCGCGTTTGTTT (SEQ ID NO:15828), TGATTGGTTAGAGGTGGTGGGCGCGTT (SEQ ID NO:15829), GTGTGATTGGTTAGAGGTGGTGGGCGC (SEQ ID NO:15830), ATTGGTTAGAGGTGGTGGGCGCGTTTG (SEQ ID NO:15831), GATTGGTTAGAGGTGGTGGGCGCGTTT (SEQ ID NO:15832), GTAAGGGGCGAGGTTAGGGAGGTTGGC (SEQ ID NO:15833), GGCGAGGTTAGGGAGGTTGGCGGTTTT (SEQ ID NO:15834), AGTAAGGGGCGAGGTTAGGGAGGTTGG (SEQ ID NO:15835), GCGAGGTTAGGGAGGTTGGCGGTTTTA (SEQ ID NO:15836), GGCGAGGTTAGGGAGGTTGGCGGTTTTA (SEQ ID NO:15837) |
| Target1673 | chr17:80846860-80847737 | GTTGGTGGTGTGTGTGGTGGTCGTG (SEQ ID NO:15838), TATCGTGTTATGGGTGCGGGTAGGGCG (SEQ ID NO:15839), GTTTTCGCGTGGGTGTTGTTGGGGAGGT (SEQ ID NO:15840), TAAGGGGGGTAGGGTGTTTGGGGAGGA (SEQ ID NO:15841), TTGGTCGGTGCGTTTAAGGGGGGTAGG (SEQ ID NO:15842), CGTGTCGTTTTTTAGGGAGGGCGTTTT (SEQ ID NO:15843), CGTGTCGTTTTTTAGGGAGGGCGTTTTGT (SEQ ID NO:15844), CGTGTCGTTTTTTAGGGAGGGCGTTTTG (SEQ ID NO:15845), CGTTTTTTAGGGAGGGCGTTTTGTTCGT (SEQ ID NO:15846), TCGTTTTTTAGGGAGGGCGTTTTGTTCGT (SEQ ID NO:15847) |
| Target1674 | chr18:909104-909196 | GGGAGAAAGGTTAGGTTTGAAGCGCGCG (SEQ ID NO:15848), GGAGAAAGGTTAGGTTTGAAGCGCGCG (SEQ ID NO:15849), GGAGAAAGGTTAGGTTTGAAGCGCGCGT (SEQ ID NO:15850), TGGGAGAAAGGTTAGGTTTGAAGCGCGC (SEQ ID NO:15851), GGGGAGAAAGGTTAGGTTTGAAGCGCGC (SEQ ID NO:15852), CGGAGGGGGTTCGGGATAAGATTCGGG (SEQ ID NO:15853), TGCGGAGGGGGTTCGGGATAAGATTCG (SEQ ID NO:15854), TGGAAGTAGTCGTGGGGAGGGTCGAGA (SEQ ID NO:15855), GCGGAGGGGGTTCGGGATAAGATTCGG (SEQ ID NO:15856), TCGTGGGGAGGGTCGAGACGGTAGTTT (SEQ ID NO:15857) |
| Target1675 | chr18:909310-909332 | GATTTTGCGTGGGGAGGGGGGTATCGA (SEQ ID NO:15858), ATTTTGCGTGGGGAGGGGGGTATCGAG (SEQ ID NO:15859), AGATTTTGCGTGGGGAGGGGGGTATCG (SEQ ID NO:15860), GGAGATTTTGCGTGGGGAGGGGGGTAT (SEQ ID NO:15861), TTAGGAGATTTTGCGTGGGGAGGGGGG (SEQ ID NO:15862), AAGTAAAGGGGTCGGGAAGAGGGTGGC (SEQ ID NO:15863), GGTGGCGGGGCGGGAGATATAGGTTTA (SEQ ID NO:15864), GGAGTTTTCGGGGAGGGTTCGGGGTTC (SEQ ID NO:15865), GAAGAGGGTGGCGGGGCGGGAGATATA (SEQ ID NO:15866), AAGAGGGTGGCGGGGCGGGAGATATAG (SEQ ID NO:15867) |
| Target1676 | chr18:909349-909389 | GATTTTGCGTGGGGAGGGGGGTATCGA (SEQ ID NO:15868), ATTTTGCGTGGGGAGGGGGGTATCGAG (SEQ ID NO:15869), AGATTTTGCGTGGGGAGGGGGGTATCG (SEQ ID NO:15870), GGAGATTTTGCGTGGGGAGGGGGGTAT (SEQ ID NO:15871), TGGGGTGGGGTTCGTTTGTTTTTCGCG (SEQ ID NO:15872), AAGTAAAGGGGTCGGGAAGAGGGTGGC (SEQ ID NO:15873), GGTGGCGGGGCGGGAGATATAGGTTTA (SEQ ID NO:15874), GAAGAGGGTGGCGGGGCGGGAGATATA (SEQ ID NO:15875), AAGAGGGTGGCGGGGCGGGAGATATAG (SEQ ID NO:15876), GGTGGCGGGGCGGGAGATATAGGTTTT (SEQ ID NO:15877) |
| Target1677 | chr18:5543287-5543382 | TGTTTAGCGGGGATGTTTTGTGCGGAG (SEQ ID NO:15878), TTGTTTAGCGGGGATGTTTTGTGCGGA (SEQ ID NO:15879), CGGGGGTCGTTGTTTTAGTTTGGGGAA (SEQ ID NO:15880), TTGTTTAGCGGGGATGTTTTGTGCGGAG (SEQ ID NO:15881), TTTGTTTAGCGGGGATGTTTTGTGCGG (SEQ ID NO:15882), TTTTTTCGGGGAGGTGCGGGGGATAGG (SEQ ID NO:15883), AGTTGTTTTTCGGGTTGGGGGCGAGC (SEQ ID NO:15884), TTTTTTCGGGGAGGTGCGGGGGATAGG (SEQ ID NO:15885), GAGGTGCGGGGGATAGGGGGCGATATT (SEQ ID NO:15886), AGGTGCGGGGGATAGGGGGCGATATTG (SEQ ID NO:15887) |
| Target1678 | chr18:5543424-5543453 | CGGCGTCGTAGTGTCGTTTTTTGTTTTTCG (SEQ ID NO:15888), GGCGTCGTAGTGTCGTTTTTTTGTTTTCG (SEQ ID NO:15889), CGGCGTCGTAGTGTCGTTTTTTGTTTTTC (SEQ ID NO:15890), AAGTTGTTTTTCGGGTTGGGGGCGAGC (SEQ ID NO:15891), TTTTTTCGGGGAGGTGCGGGGGATAGG (SEQ ID NO:15892), AGTTGTTTTTCGGGTTGGGGGCGAGC (SEQ ID NO:15893), TTTTTCGGGGAGGTGCGGGGGATAGG (SEQ ID NO:15894), GAGGTGCGGGGGATAGGGGGCGATATT (SEQ ID NO:15895) |
| Target1679 | chr18:5543518-5543528 | TCGTATTTTTTCGGGGGAGGGGTCGGT (SEQ ID NO:15896), ATTTTTTCGGGGGAGGGGTCGGTTCGC (SEQ ID NO:15897), CGTATTTTTTCGGGGGAGGGGTCGGTT (SEQ ID NO:15898), TCGTATTTTTTCGGGGGAGGGGTCGGTT (SEQ ID NO:15899), TTCGTATTTTTTTCGGGGGAGGGGTCGGT (SEQ ID NO:15900), TAGTGGTTGGGTCGGCGCGTAGAGTTT (SEQ ID NO:15901), GTAGTGGTTGGGTCGGCGCGTAGAGTT (SEQ ID NO:15902), GGTCGGCGCGTAGAGTTTGAGTTTCGG (SEQ ID NO:15903), GGGTCGGCGCGTAGAGTTTGAGTTTCG (SEQ ID NO:15904), TGGTTGGGTCGGCGCGTAGAGTTTGAG (SEQ ID NO:15905) |

FIGURE 5 CONTINUED

| | | |
|---|---|---|
| Target1680 | chr18:5543548-5543582 | GCGTTTCGGGCGGGGGATTTGTGTAAA (SEQ ID NO:15906), TCGTATTTTTTCGGGGGAGGGGTCGGT (SEQ ID NO:15907), ATTTTTTCGGGGGAGGGGTCGGTTCGC (SEQ ID NO:15908), GCGTTTCGGGCGGGGGATTTGTGTAA (SEQ ID NO:15909), CGTATTTTTTCGGGGGAGGGGTCGGTT (SEQ ID NO:15910), TAGTGGTTGGGTCGGCGCGTAGAGTTT (SEQ ID NO:15911), GTAGTGGTTGGGTCGGCGCGTAGAGTT (SEQ ID NO:15912), GGTCGGCGCGTAGAGTTTGAGTTTCGG (SEQ ID NO:15913), GGGTCGGCGCGTAGAGTTTGAGTTTCG (SEQ ID NO:15914), GTAGTAGTGGTTGGGTCGGCGCGTAGA (SEQ ID NO:15915) |
| Target1681 | chr18:5543634-5543674 | GAGGTCGGGGTTTAGGTTTTGCGCGTC (SEQ ID NO:15916), GCGTTTCGGGCGGGGGATTTGTGTAAA (SEQ ID NO:15917), CGGGGGTTTAGGTTTTGCGCGTCGGTTT (SEQ ID NO:15918), GCGTTTCGGGCGGGGGATTTGTGTAA (SEQ ID NO:15919), TCGGGGGTTTAGGTTTTGCGCGTCGGTT (SEQ ID NO:15920), GTTCGTCGCGGCGTAGTAGTGGTTGGG (SEQ ID NO:15921), CGTTCGTCGCGGCGTAGTAGTGGTTG (SEQ ID NO:15922), CGTTCGTCGCGGCGTAGTAGTGGTTGG (SEQ ID NO:15923), GTTCGTCGCGGCGTAGTAGTGGTTGG (SEQ ID NO:15924), TTCGTCGCGGCGTAGTAGTGGTTGGGT (SEQ ID NO:15925) |
| Target1682 | chr18:5543731-5543758 | GAGGTCGGGGTTTAGGTTTTGCGCGTC (SEQ ID NO:15926), CGGGGGTTTAGGTTTTGCGCGTCGGTTT (SEQ ID NO:15927), GTAGGTTCGGTTCGGTGGGGGTTTCGG (SEQ ID NO:15928), CGTAGGTTCGGTTCGGTGGGGGTTTCG (SEQ ID NO:15929), TCGGGGGTTTAGGTTTTGCGCGTCGGTT (SEQ ID NO:15930), TGCGGAGGAAGAGTTCGAGGTTTGGGG (SEQ ID NO:15931), GGAGGAAGAGTTCGAGGTTTGGGGCGA (SEQ ID NO:15932), CGGAGGAAGAGTTCGAGGTTTGGGGCG (SEQ ID NO:15933), GTGCGGAGGAAGAGTTCGAGGTTTGGG (SEQ ID NO:15934), GGTGCGGAGGAAGAGTTCGAGGTTTGG (SEQ ID NO:15935) |
| Target1683 | chr18:5543766-5543879 | GTAGGTTCGGTTCGGTGGGGGTTTCGG (SEQ ID NO:15936), CGTAGGTTCGGTTCGGTGGGGGTTTCG (SEQ ID NO:15937), GCGTAGGTTCGGTTCGGTGGGGGTTTC (SEQ ID NO:15938), TAGGTTCGGTTCGGTGGGGGTTTCGG (SEQ ID NO:15939), GTAGGTTCGGTTCGGTGGGGGTTTCG (SEQ ID NO:15940), TGCGGAGGAAGAGTTCGAGGTTTGGGG (SEQ ID NO:15941), GGAGGAAGAGTTCGAGGTTTGGGGCGA (SEQ ID NO:15942), CGGAGGAAGAGTTCGAGGTTTGGGGCG (SEQ ID NO:15943), GTGCGGAGGAAGAGTTCGAGGTTTGGG (SEQ ID NO:15944), GGTGCGGAGGAAGAGTTCGAGGTTTGG (SEQ ID NO:15945) |
| Target1684 | chr18:46514295-46514374 | TGGGGAGAGGAAGTTGATTGGTTGGGG (SEQ ID NO:15946), TGGGGAGAGGAAGTTGATTGGTTGGGGA (SEQ ID NO:15947), GGGGAGAGGAAGTTGATTGGTTGGGGA (SEQ ID NO:15948), TGGGGAGAGGAAGTTGATTGGTGGGGAG (SEQ ID NO:15949), GGGGAGAGGAAGTTGATTGGTGGGGAG (SEQ ID NO:15950), CGGTTTTTTGTCGTTTGGAGTTTGGAGGG (SEQ ID NO:15951), CGGTTTTTTGTCGTTTGGAGTTTGGAGGGT (SEQ ID NO:15952), TCGGTTTTTTGTCGTTTGGAGTTTGGAGGG (SEQ ID NO:15953), TCGGTTTTTTGTCGTTTGGAGTTTGGAGGGT (SEQ ID NO:15954), TCGGTTTTTTGTCGTTTGGAGTTTGGAGG (SEQ ID NO:15955) |
| Target1685 | chr18:46514427-46514468 | TGGGGAGAGGAAGTTGATTGGTTGGGG (SEQ ID NO:15956), TGGGGAGAGGAAGTTGATTGGTTGGGGA (SEQ ID NO:15957), GGGGAGAGGAAGTTGATTGGTTGGGGA (SEQ ID NO:15958), TGGGGAGAGGAAGTTGATTGGTGGGGAG (SEQ ID NO:15959), GGGGAGAGGAAGTTGATTGGTGGGGAG (SEQ ID NO:15960), TGTTTGTTGGGGTTTGGGTAAAGTCGTTG (SEQ ID NO:15961), TGTTTGTTGGGGTTTGGGTAAAGTCGTTGA (SEQ ID NO:15962), GTTTGTTGGGGTTTGGGTAAAGTCGTTGA (SEQ ID NO:15963), TTGTTTGTTGGGGTTTGGGTAAAGTCGTT (SEQ ID NO:15964), TTTGTTTGTTGGGGTTTGGGTAAAGTCGT (SEQ ID NO:15965) |
| Target1686 | chr18:47794580-47794978 | GGGTTTCGGTGGGTGATTGTGGTTGGG (SEQ ID NO:15966), GGGCGGTTAGGTTAGGGGTGATGGGTG (SEQ ID NO:15967), GGCGGTTAGGTTAGGGGTGATGGGTGA (SEQ ID NO:15968), GGGTGATGGGTGACGAGCGGTGTTTTT (SEQ ID NO:15969), GTTAGGGGTGATGGGTGACGAGCGGTG (SEQ ID NO:15970), TGGTTTGGTCGTTTTGGGGCGTGGTTT (SEQ ID NO:15971), TTGGTTTGGTCGTTTTGGGGCGTGGTT (SEQ ID NO:15972), TTTGGTTTGGTCGTTTTGGGGCGTGGT (SEQ ID NO:15973), AGTTCGTTTAGGGTGAGGGCGGGGGTTC (SEQ ID NO:15974), GAGTTCGTTTAGGGTGAGGGCGGGGTT (SEQ ID NO:15975) |
| Target1687 | chr18:47794982-47794996 | GGGTTTCGGTGGGTGATTGTGGTTGGG (SEQ ID NO:15976), GGGCGGTTAGGTTAGGGGTGATGGGTG (SEQ ID NO:15977), GGCGGTTAGGTTAGGGGTGATGGGTGA (SEQ ID NO:15978), GGGTGATGGGTGACGAGCGGTGTTTTT (SEQ ID NO:15979), GTTAGGGGTGATGGGTGACGAGCGGTG (SEQ ID NO:15980), TATTTATTTAGGTCGCGGGGGCGGGGG (SEQ ID NO:15981), TTGTTGGTGGGTTCGTTAGGGGGCGT (SEQ ID NO:15982), TTTGTTGGTGGGTTCGTTAGGGGGCGT (SEQ ID NO:15983), ATTTGTTGGTGGGTTCGTTAGGGGGCG (SEQ ID NO:15984), CGGGGGGGTTGGTTGAAGGTTGAGGTTT (SEQ ID NO:15985) |
| Target1688 | chr18:56939637-56939654 | GTCGGTTAGTTTTTCGCGGTTGTATACGT (SEQ ID NO:15986), TGTCGGTTAGTTTTTCGCGGTTGTATACG (SEQ ID NO:15987), TGTCGGTTAGTTTTTCGCGGTTGTATACGT (SEQ ID NO:15988), GGTTGATTTTGTCGGTTAGTTTTTCGCGGT (SEQ ID NO:15989), CGGTTAGTTTTTCGCGGTTGTATACGTTCG (SEQ ID NO:15990), TAGTTGTATGAGTTGGAGCGCGCGTTC (SEQ ID NO:15991), TTAGTTGTATGAGTTGGAGCGCGCGTT (SEQ ID NO:15992), |

FIGURE 5 CONTINUED

|  |  | ATTAGTTGTATGAGTTGGAGCGCGCGT (SEQ ID NO:15993), AGTTGTATGAGTTGGAGCGCGCGTTC (SEQ ID NO:15994), TTAGTTGTATGAGTTGGAGCGCGCGTTC (SEQ ID NO:15995) |
| Target1689 | chr18:56939670-56939788 | CGCGGTTGTATACGTTCGGGTAGTGGG (SEQ ID NO:15996), CGCGGTTGTATACGTTCGGGTAGTGGGA (SEQ ID NO:15997), GCGGTTGTATACGTTCGGGTAGTGGGA (SEQ ID NO:15998), AGTTTCGTTCGTCGGTGGTTGGTTCG (SEQ ID NO:15999), GTTTCGTTCGTCGGTGGTTGGTTCGA (SEQ ID NO:16000), TCGGGGAGGTACGGTCGAGTTTAGGGT (SEQ ID NO:16001), AGGGAGTTCGGGGAGGTACGGTCGAGTT (SEQ ID NO:16002), AAGGAGTTCGGGGAGGTACGGTCGAGT (SEQ ID NO:16003), CGGGGTCGGTTTAAGGGTGTTTTGGGG (SEQ ID NO:16004), GGAGTTCGGGGAGGTACGGTCGAGTTT (SEQ ID NO:16005) |
| Target1690 | chr18:56939939-56939978 | AGATGGTTCGGGGAGGTTCGTGGTGAG (SEQ ID NO:16006), GAGATGGTTCGGGGAGGTTCGTGGTGA (SEQ ID NO:16007), GATGGTTCGGGGAGGTTCGTGGTGAGG (SEQ ID NO:16008), TTGGGGTAGTAGGGTCGAGGGGTTGGG (SEQ ID NO:16009), TTTGGGGTAGTAGGGTCGAGGGGTTGG (SEQ ID NO:16010), GGGTTGGGGATCGTTTATGGCGGGAGT (SEQ ID NO:16011), ATTAAGGTAATTGGGCGCGGGGTTGGG (SEQ ID NO:16012), GGGGTTGGGGATCGTTTATGGCGGGAG (SEQ ID NO:16013), TTAAGGTAATTGGGCGCGGGGTTGGGG (SEQ ID NO:16014), GGTTGGGGATCGTTTATGGCGGGAGTT (SEQ ID NO:16015) |
| Target1691 | chr18:61143902-61144251 | GTAGTGGGCGTGGCGGTGTTGTTTAGG (SEQ ID NO:16016), GGTAGTGGGCGTGGCGGTGTTGTTTAG (SEQ ID NO:16017), TAGTGGGCGTGGCGGTGTTGTTTAGGT (SEQ ID NO:16018), GGCGTGGCGGTGTTGTTTAGGTGAGTT (SEQ ID NO:16019), TGGTAGTGGGCGTGGCGGTGTTGTTTA (SEQ ID NO:16020), TGGATGTGGAGGCGATCGTGTTTGGGT (SEQ ID NO:16021), TTGGATGTGGAGGCGATCGTGTTTGGG (SEQ ID NO:16022), CGTTTCGTTTCGTTTCGTTTCGGCGGT (SEQ ID NO:16023), TTGGATGTGGAGGCGATCGTGTTTGGGT (SEQ ID NO:16024), TGGATGTGGAGGCGATCGTGTTTGGGTA (SEQ ID NO:16025) |
| Target1692 | chr18:76150846-76150881 | CGGAGGATTTAGGGCGGAGTTGTCGGT (SEQ ID NO:16026), TCGGAGGATTTAGGGCGGAGTTGTCGG (SEQ ID NO:16027), CGGAGGATTTAGGGCGGAGTTGTCGGTT (SEQ ID NO:16028), TTCGGAGGATTTAGGGCGGAGTTGTCGG (SEQ ID NO:16029), GGAGGATTTAGGGCGGAGTTGTCGGTT (SEQ ID NO:16030), AACGGGGAAAGTACGGTGAGGTCGGAG (SEQ ID NO:16031), AAACGGGGAAAGTACGGTGAGGTCGGA (SEQ ID NO:16032), GAAACGGGGAAAGTACGGTGAGGTCGG (SEQ ID NO:16033), AAACGGGGAAAGTACGGTGAGGTCGGAG (SEQ ID NO:16034), GAAACGGGGAAAGTACGGTGAGGTCGGA (SEQ ID NO:16035) |
| Target1693 | chr18:76150902-76150929 | CGGTGGTTGTGATCGGAGGTTTTACGCG (SEQ ID NO:16036), ACGGTGGTTGTGATCGGAGGTTTTACGC (SEQ ID NO:16037), GGTGGTTGTGATCGGAGGTTTTACGCG (SEQ ID NO:16038), CGGTGGTTGTGATCGGAGGTTTTACGC (SEQ ID NO:16039), ACGGTGGTTGTGATCGGAGGTTTTACG (SEQ ID NO:16040), GTGGGAGGGAAACGGGGAAAGTACGGT (SEQ ID NO:16041), TGGGAGGGAAACGGGGAAAGTACGGTG (SEQ ID NO:16042), AGTGGGAGGGAAACGGGGAAAGTACGG (SEQ ID NO:16043), CGGTAGTGGGAGGGAAACGGGGAAAGT (SEQ ID NO:16044), GGGAGGGAAACGGGGAAAGTACGGTGA (SEQ ID NO:16045) |
| Target1694 | chr18:76151034-76151043 | CGGAGGTTTTACGCGTTTGTTTGAGGA (SEQ ID NO:16046), TCGGAGGTTTTACGCGTTTGTTTGAGG (SEQ ID NO:16047), TCGGAGGTTTTACGCGTTTGTTTGAGGA (SEQ ID NO:16048), CGGAGGTTTTACGCGTTTGTTTGAGGAA (SEQ ID NO:16049), ATCGGAGGTTTTACGCGTTTGTTTGAGG (SEQ ID NO:16050), TTTTTTAGGGGTTGGCGAGGGGGACG (SEQ ID NO:16051), TTTTTAGGGGTTGGCGAGGGGGACG (SEQ ID NO:16052), TTTTAGGGGTTGGCGAGGGGGACG (SEQ ID NO:16053), TTTTTTAGGGGTTGGCGAGGGGGAC (SEQ ID NO:16054), TTTAGGGGTTGGCGAGGGGGACG (SEQ ID NO:16055) |
| Target1695 | chr18:76709439-76709463 | TGTGGACGGGATTGATGTTTTTAGAAAAGAGG (SEQ ID NO:16056), GTGTGGACGGGATTGATGTTTTTAGAAAAGAGG (SEQ ID NO:16057), GTGTGGACGGGATTGATGTTTTTAGAAAAGAGGT (SEQ ID NO:16058), TGTGGACGGGATTGATGTTTTTAGAAAAGAGGTT (SEQ ID NO:16059), GTGTGGACGGGATTGATGTTTTTAGAAAAGAGGTT (SEQ ID NO:16060), TGGATGTTGGTGTTGGATTTCGGTGAGGT (SEQ ID NO:16061), GGATGTTGGTGTTGGATTTCGGTGAGGT (SEQ ID NO:16062), TGGATGTTGGTGTTGGATTTCGGTGAGG (SEQ ID NO:16063), GGATGTTGGTGTTGGATTTCGGTGAGG (SEQ ID NO:16064), TGGTGTTGGATTTCGGTGAGGTTGTTGT (SEQ ID NO:16065) |
| Target1696 | chr18:77548101-77548126 | TTCGCGGCGTATAAGGGTTGTTCGAGC (SEQ ID NO:16066), TTTCGCGGCGTATAAGGGTTGTTCGAGC (SEQ ID NO:16067), TCGCGGCGTATAAGGGTTGTTCGAGC (SEQ ID NO:16068), CGGTTTTCGCGGCGTATAAGGGTTGTT (SEQ ID NO:16069), CGGTTTTCGCGGCGTATAAGGGTTGTTCG (SEQ ID NO:16070), TTCGTTAGGAGGGATTCGGGAGGTCGC (SEQ ID NO:16071), TTTCGTTAGGAGGGATTCGGGAGGTCGC (SEQ ID NO:16072), CGGTTTCGTTAGGAGGGATTCGGGAGGT (SEQ ID NO:16073), TCGTTAGGAGGGATTCGGGAGGTCGC (SEQ ID NO:16074), GCGGGGATTTTTTGCGTTTCGGGGAC (SEQ ID NO:16075) |
| Target1697 | chr18:77548141-77548153 | GCGGCGTATAAGGGTTGTTCGAGCGTT (SEQ ID NO:16076), TTCGCGGCGTATAAGGGTTGTTCGAGC (SEQ ID NO:16077), GCGGCGTATAAGGGTTGTTCGAGCGTTT (SEQ ID NO:16078), TTTCGCGGCGTATAAGGGTTGTTCGAGC (SEQ ID NO:16079), GCGGCGTATAAGGGTTGTTCGAGCGT (SEQ ID NO:16080), TTCGTTAGGAGGGATTCGGGAGGTCGC (SEQ ID NO:16081), TTTCGTTAGGAGGGATTCGGGAGGTCGC (SEQ ID NO:16082), CGGTTTCGTTAGGAGGGATTCGGGAGGT |

FIGURE 5 CONTINUED

{SEQ ID NO:16083}, TCGTTAGGAGGGATTCGGGAGGTCGC {SEQ ID NO:16084}, GCGGGGATTTTTTGCGTTCGGGGAC {SEQ ID NO:16085}

| Target1698 | chr18:77548166-77548177 | GCGGCGTATAAGGGTTGTTCGAGCGTT {SEQ ID NO:16086}, TTCGCGGCGTATAAGGGTTGTTCGAGC {SEQ ID NO:16087}, GCGGCGTATAAGGGTTGTTCGAGCGTTT {SEQ ID NO:16088}, TTTCGCGGCGTATAAGGGTTGTTCGAGC {SEQ ID NO:16089}, GCGGCGTATAAGGGTTGTTCGAGCGT {SEQ ID NO:16090}, TTTTAAGCGGGTTTATCGGGTCGGCGG {SEQ ID NO:16091}, TTTTAAGCGGGTTTATCGGGTCGGCGGG {SEQ ID NO:16092}, TTCGTTAGGAGGGATTCGGGAGGTCGT {SEQ ID NO:16093}, TTTTTAAGCGGGTTTATCGGGTCGGCGG {SEQ ID NO:16094}, CGGTTTCGTTAGGAGGGATTCGGGAGGT {SEQ ID NO:16095} |
| Target1699 | chr18:77548190-77548312 | GCGGCGTATAAGGGTTGTTCGAGCGTT {SEQ ID NO:16096}, TTCGCGGCGTATAAGGGTTGTTCGAGC {SEQ ID NO:16097}, GCGTAGGTTTCGTCGGTTCGGTGGATT {SEQ ID NO:16098}, CGTCGGTTCGGTGGATTCGTTTGAGGA {SEQ ID NO:16099}, TCGTCGGTTCGGTGGATTCGTTTGAGG {SEQ ID NO:16100}, CGGGGGCGGTAGTTGAGTTTCGTTCGA {SEQ ID NO:16101}, TTTTAAGCGGGTTTATCGGGTCGGCGG {SEQ ID NO:16102}, ACGGGGGCGGTAGTTGAGTTTCGTTCG {SEQ ID NO:16103}, TTTAAGCGGGTTTATCGGGTCGGCGGG {SEQ ID NO:16104}, GGTAACGGGGGCGGTAGTTGAGTTTCG {SEQ ID NO:16105} |
| Target1700 | chr18:77548319-77548340 | GCGTAGGTTTCGTCGGTTCGGTGGATT {SEQ ID NO:16106}, CGTCGGTTCGGTGGATTCGTTTGAGGA {SEQ ID NO:16107}, TCGTCGGTTCGGTGGATTCGTTTGAGG {SEQ ID NO:16108}, TCGTCGGTTCGGTGGATTCGTTTGAGGA {SEQ ID NO:16109}, AGGTTTCGTCGGTTCGGTGGATTCGTT {SEQ ID NO:16110}, CGGGGGCGGTAGTTGAGTTTCGTTCGA {SEQ ID NO:16111}, ACGGGGGCGGTAGTTGAGTTTCGTTCG {SEQ ID NO:16112}, GGTAACGGGGGCGGTAGTTGAGTTTCG {SEQ ID NO:16113}, GGGGGCGGTAGTTGAGTTTCGTTCGAG {SEQ ID NO:16114}, GGGGGCGGTAGTTGAGTTTCGTTCGAGT {SEQ ID NO:16115} |
| Target1701 | chr18:77548341-77548384 | GCGTAGGTTTCGTCGGTTCGGTGGATT {SEQ ID NO:16116}, CGTCGGTTCGGTGGATTCGTTTGAGGA {SEQ ID NO:16117}, TCGTCGGTTCGGTGGATTCGTTTGAGG {SEQ ID NO:16118}, TCGTCGGTTCGGTGGATTCGTTTGAGGA {SEQ ID NO:16119}, AGGTTTCGTCGGTTCGGTGGATTCGTT {SEQ ID NO:16120}, CGGGGGCGGTAGTTGAGTTTCGTTCGA {SEQ ID NO:16121}, ACGGGGGCGGTAGTTGAGTTTCGTTCG {SEQ ID NO:16122}, GGTAACGGGGGCGGTAGTTGAGTTTCG {SEQ ID NO:16123}, GGGGGCGGTAGTTGAGTTTCGTTCGAG {SEQ ID NO:16124}, GGGGGCGGTAGTTGAGTTTCGTTCGAGT {SEQ ID NO:16125} |
| Target1702 | chr18:77548429-77548460 | GGGTGGATGGGATTTTGCGCGTGGAAT {SEQ ID NO:16126}, GGGTGGATGGGATTTTGCGCGTGGAA {SEQ ID NO:16127}, GGGTGGATGGGATTTTGCGCGTGGAATT {SEQ ID NO:16128}, TTTTTCGGGTGGATGGGATTTTGCGCG {SEQ ID NO:16129}, GGTGGATGGGATTTTGCGCGTGGAATT {SEQ ID NO:16130}, TCGTGGAGAAGGAATGGGTTTTGCGGT {SEQ ID NO:16131}, CGTGGAGAAGGAATGGGTTTTGCGGTT {SEQ ID NO:16132}, CGTGGAGAAGGAATGGGTTTTGCGGTTCG {SEQ ID NO:16133}, TCGTGGAGAAGGAATGGGTTTTGCGGTT {SEQ ID NO:16134}, TGGAGAAGGAATGGGTTTTGCGGTTCG {SEQ ID NO:16135} |
| Target1703 | chr18:77548478-77548486 | GGGTGGATGGGATTTTGCGCGTGGAAT {SEQ ID NO:16136}, GGGTGGATGGGATTTTGCGCGTGGAA {SEQ ID NO:16137}, GGGTGGATGGGATTTTGCGCGTGGAATT {SEQ ID NO:16138}, TTTTTCGGGTGGATGGGATTTTGCGCG {SEQ ID NO:16139}, GGTGGATGGGATTTTGCGCGTGGAATT {SEQ ID NO:16140}, TTTTTAAGCGGGGCGGGGTTGTCGTTC {SEQ ID NO:16141}, TTGTTTTTAAGCGGGGCGGGGTTGTCG {SEQ ID NO:16142}, GTTTTTAAGCGGGGCGGGGTTGTCGTT {SEQ ID NO:16143}, CGGGGTTGTCGTTCGGATGTGAGTCGT {SEQ ID NO:16144}, CGGGGTTGTCGTTCGGATGTGAGTCGTA {SEQ ID NO:16145} |
| Target1704 | chr18:77548546-77548582 | GGGTGGATGGGATTTTGCGCGTGGAAT {SEQ ID NO:16146}, TTTTTACGGTGGCGTTGGGGAGGGGTT {SEQ ID NO:16147}, TTTTTTACGGTGGCGTTGGGGAGGGGT {SEQ ID NO:16148}, GGTGGCGTTGGGGAGGGGTTGTTTTTA {SEQ ID NO:16149}, TTTTACGGTGGCGTTGGGGAGGGGTTG {SEQ ID NO:16150}, TTTTTAAGCGGGGCGGGGTTGTCGTTC {SEQ ID NO:16151}, TTGTTTTTAAGCGGGGCGGGGTTGTCG {SEQ ID NO:16152}, GTTTTTAAGCGGGGCGGGGTTGTCGTT {SEQ ID NO:16153}, CGGGGTTGTCGTTCGGATGTGAGTCGT {SEQ ID NO:16154}, CGGGGTTGTCGTTCGGATGTGAGTCGTA {SEQ ID NO:16155} |
| Target1705 | chr19:641826-641902 | GGTCGGGTTGGGAGGTTGTTTCGAGGA {SEQ ID NO:16156}, AGGTCGGGTTGGGAGGTTGTTTCGAGG {SEQ ID NO:16157}, TCGGGTTGGGAGGTTGTTTCGAGGAGT {SEQ ID NO:16158}, GGAAGGTCGGGTTGGGAGGTTGTTTCG {SEQ ID NO:16159}, GTCGGGTTGGGAGGTTGTTTCGAGGAGT {SEQ ID NO:16160}, GGGGTTAGTTGAGGTTTGGGAGTGGTAG {SEQ ID NO:16161}, GGGGTTAGTTGAGGTTTGGGAGTGGT {SEQ ID NO:16162}, GGGGTTAGTTGAGGTTTGGGAGTGGTAGA {SEQ ID NO:16163}, GGGGTTAGTTGAGGTTTGGGAGTGGTAGAG {SEQ ID NO:16164}, GGGGTTAGTTGAGGTTTGGGAGTGGTAGAGT {SEQ ID NO:16165} |
| Target1706 | chr19:1210277-1210342 | TGGGAGTTGGTGTGTTTTGATTGGAGGT {SEQ ID NO:16166}, TTGGGAGTTGGTGTGTGTTTTGATTGGAGGT {SEQ ID NO:16167}, GGGAGTTGGTGTGTGTTTTGATTGGAGGTTGT {SEQ ID NO:16168}, TGGGAGTTGGTGTGTGTTTTGATTGGAGGTTG {SEQ ID NO:16169}, GGGAGTTGGTGTGTGTTTTGATTGGAGGTTG {SEQ ID NO:16170}, CGGACGTTTGAGGTTTGTTTGGAAGGT {SEQ ID NO:16171}, TCGGACGTTTGAGGTTTGTTTGGAAGGT {SEQ ID NO:16172}, TCGGACGTTTGAGGTTTGTTTGGAAGG {SEQ ID NO:16173}, AGGATCGGACGTTTGAGGTTTGTTTGGA {SEQ ID NO:16174}, CGGACGTTTGAGGTTTGTTTGGAAGGTT {SEQ ID NO:16175} |

FIGURE 5 CONTINUED

| Target1707 | chr19:1210346-1210414 | AGGCGTTCGGTTTTTTTAGTTGGTGTGG (SEQ ID NO:16176), GGCGTTCGGTTTTTTTAGTTGGTGTGGA (SEQ ID NO:16177), AGGCGTTCGGTTTTTTTAGTTGGTGTGGA (SEQ ID NO:16178), GGCGTTCGGTTTTTTTAGTTGGTGTGGAA (SEQ ID NO:16179), AGGCGTTCGGTTTTTTTAGTTGGTGTGGAA (SEQ ID NO:16180), TTTTGGGAAGGAAGGGAAGAGACGGGA (SEQ ID NO:16181), TGGGAAGGAAGGGAAGAGACGGGATTT (SEQ ID NO:16182), TTGGGAAGGAAGGGAAGAGACGGGATT (SEQ ID NO:16183), TTTGGGAAGGAAGGGAAGAGACGGGAT (SEQ ID NO:16184), TTTTTGGGAAGGAAGGGAAGAGACGGG (SEQ ID NO:16185) |
|---|---|---|
| Target1708 | chr19:1210449-1210462 | TAAGGGGGGTGGGTTGGGGTAGATGGA (SEQ ID NO:16186), GGTTGGGGTAGATGGAGTCGGCGTGAG (SEQ ID NO:16187), GTTGGGGTAGATGGAGTCGGCGTGAGT (SEQ ID NO:16188), TGGGGTAGATGGAGTCGGCGTGAGTTT (SEQ ID NO:16189), TTGGGGTAGATGGAGTCGGCGTGAGTT (SEQ ID NO:16190), TTTTGGGAAGGAAGGGAAGAGACGGGA (SEQ ID NO:16191), TGGGAAGGAAGGGAAGAGACGGGATTT (SEQ ID NO:16192), TTGGGAAGGAAGGGAAGAGACGGGATT (SEQ ID NO:16193), TTTGGGAAGGAAGGGAAGAGACGGGAT (SEQ ID NO:16194), TTTTTGGGAAGGAAGGGAAGAGACGGG (SEQ ID NO:16195) |
| Target1709 | chr19:1467092-1468062 | GGAGTAGTTTCGGGGCGCGGGTAAGAA (SEQ ID NO:16196), CGGGGCGCGGGTAAGAATAGAGTAGGG (SEQ ID NO:16197), GGGAGTCGTCGTGTTTGTTCGGTTGCG (SEQ ID NO:16198), ATTTTGTAGGGTATCGGCGGCGGGAGG (SEQ ID NO:16199), GAGCGTTCGTAGGGTCGGAAGGAGGTT (SEQ ID NO:16200), GTTCGTTGAGGGAGTTGGCGGAGGAGT (SEQ ID NO:16201), TGAGTCGTTTTTGTTTGCGGGGGCGTT (SEQ ID NO:16202), GGGAGTGCGCGGCGATTTGGTATTAGC (SEQ ID NO:16203), GCGGCGGGGTAGTTGGTGTAGTTTTGG (SEQ ID NO:16204), GGCGGCGGGGTAGTTGGTGTAGTTTTG (SEQ ID NO:16205) |
| Target1710 | chr19:1468067-1468130 | TTGTTTCGTTTAAGGTTGTATTAGTTGTTTCGTCGT (SEQ ID NO:16206), AGGTTAGATACGGGGGGTCGGCGTTTG (SEQ ID NO:16207), GTCGGCGTTTGGGTAGGGTCGAGTTGA (SEQ ID NO:16208), TCGGCGTTTGGGTAGGGTCGAGTTGAT (SEQ ID NO:16209), TAGATACGGGGGGTCGGCGTTTGGGTA (SEQ ID NO:16210), CGGCGTTTGGGTAGGGTCGAGTTGATG (SEQ ID NO:16211) |
| Target1711 | chr19:1468146-1468230 | TAAGGATTCGGGTTTAGGAGGCGGACG (SEQ ID NO:16212), AAGGATTCGGGTTTAGGAGGCGGACG (SEQ ID NO:16213), TTAAGGATTCGGGTTTAGGAGGCGGACG (SEQ ID NO:16214), TTAAGGATTCGGGTTTAGGAGGCGGAC (SEQ ID NO:16215), GGGAGTTCGCGGTTATTAAGGATTCGGGT (SEQ ID NO:16216), AGGTTAGATACGGGGGGTCGGCGTTTG (SEQ ID NO:16217), GTCGGCGTTTGGGTAGGGTCGAGTTGA (SEQ ID NO:16218), TCGGCGTTTGGGTAGGGTCGAGTTGAT (SEQ ID NO:16219), TAGATACGGGGGGTCGGCGTTTGGGTA (SEQ ID NO:16220), CGGCGTTTGGGTAGGGTCGAGTTGATG (SEQ ID NO:16221) |
| Target1712 | chr19:1468242-1468249 | CGGTTTTTCGTGTTTGGTTTGCGGCGT (SEQ ID NO:16222), TCGGTTTTTCGTGTTTGGTTTGCGGCG (SEQ ID NO:16223), CGGTTTTTCGTGTTTGGTTTGCGGCGTC (SEQ ID NO:16224), GTCGGTTTTTCGTGTTTGGTTTGCGGCG (SEQ ID NO:16225), CGTCGGTTTTTCGTGTTTGGTTTGCGGC (SEQ ID NO:16226), ATTTAGTCGGGTGGTTCGGGGTTTGCG (SEQ ID NO:16227), TTTAGTCGGGTGGTTCGGGGTTTGCGG (SEQ ID NO:16228), TTTAGTCGGGTGGTTCGGGGTTTGCG (SEQ ID NO:16229), TGCGGGTCGTTTATTTAGTCGGGTGGT (SEQ ID NO:16230), ATTTAGTCGGGTGGTTCGGGGTTTCG (SEQ ID NO:16231) |
| Target1713 | chr19:3687798-3687839 | TGGTTGGAGGGGAGGGTATATTTGGGGG (SEQ ID NO:16232), GGTTGGAGGGGAGGGTATATTTGGGGG (SEQ ID NO:16233), TGGTTGGAGGGGAGGGTATATTTGGGGGA (SEQ ID NO:16234), GGTTGGAGGGGAGGGTATATTTGGGGGA (SEQ ID NO:16235), GTGGTTGGAGGGGAGGGTATATTTGGGGG (SEQ ID NO:16236), GGGTTTGCGGAGTTTTGGATGTTTCGT (SEQ ID NO:16237), AGGGTTTGCGGAGTTTTGGATGTTTCGT (SEQ ID NO:16238), AGGGTTTGCGGAGTTTTGGATGTTTCG (SEQ ID NO:16239), TGCGGAGTTTTGGATGTTTCGTTCGTT (SEQ ID NO:16240), TTGCGGAGTTTTGGATGTTTCGTTCGT (SEQ ID NO:16241) |
| Target1714 | chr19:3687873-3687901 | TAGGTGGGCGGGTAGGAGTTAGGTCGG (SEQ ID NO:16242), GGTGGGCGGGTAGGAGTTAGGTCGGTA (SEQ ID NO:16243), GTAGGTGGGCGGGTAGGAGTTAGGTCG (SEQ ID NO:16244), GTGGGCGGGTAGGAGTTAGGTCGGTAA (SEQ ID NO:16245), AGTAGGTGGGCGGGTAGGAGTTAGGTCG (SEQ ID NO:16246), TCGGTTCGTTCGGGAGTTTGGTGTTGA (SEQ ID NO:16247), CGGTTCGTTCGGGAGTTTGGTGTTGAG (SEQ ID NO:16248), CGGTTCGTTCGGGAGTTTGGTGTTGAGA (SEQ ID NO:16249), TCGGTTCGTTCGGGAGTTTGGTGTTGAG (SEQ ID NO:16250), TGTTTCGGTTCGTTCGGGAGTTTGGTGT (SEQ ID NO:16251) |
| Target1715 | chr19:3687981-3688011 | TTAAGTTTTCGGGCGGGTCGGGGTAGG (SEQ ID NO:16252), TAAGTTTTCGGGCGGGTCGGGGTAGGA (SEQ ID NO:16253), TAAGTTTTCGGGCGGGTCGGGGTAGG (SEQ ID NO:16254), ATTAAGTTTTCGGGCGGGTCGGGGTAGG (SEQ ID NO:16255), GTATTAAGTTTTCGGGCGGGTCGGGGT (SEQ ID NO:16256), CGGTTTCGTTATTTGCGGGTTGGTTACG (SEQ ID NO:16257), CGGTTTCGTTATTTGCGGGTTGGTTACGT (SEQ ID NO:16258), TTTTAGGGGTTGGCGTGTGTTTTGTGT (SEQ ID NO:16259), AGGGGTTGGCGTGTGTTTTGTGTATTT (SEQ ID NO:16260), GGTTTCGTTATTTGCGGGTTGGTTACGT (SEQ ID NO:16261) |
| Target1716 | chr19:3688088-3688105 | TTTTTGGGGGAAGTTCGGTTCGTGCGG (SEQ ID NO:16262), TGTGGGGCGTGGTTAGTTCGTAGGTGG (SEQ ID NO:16263), TTAAGTTTTCGGGCGGGTCGGGGTAGG (SEQ ID NO:16264), GGGTAGGAGGTTGTGGGGCGTGGTTAG (SEQ ID NO:16265), AGGAGGTTGTGGGGCGTGGTTAGTTCG (SEQ ID NO:16266), TTTTGTTGTGTTGGAGACGGAGCGCGT (SEQ ID NO:16267), TTGTTGTGTTGGAGACGGAGCGCGTAA (SEQ ID NO:16268), TTTGTTGTGTTGGAGACGGAGCGCGTA |

FIGURE 5 CONTINUED (SEQ ID NO:16269), TTTTTGTTGTGTTGGAGACGGAGCGCG (SEQ ID NO:16270), TTTTTGTTGTGTTGGAGACGGAGCGCGT (SEQ ID NO:16271)

Target1717    chr19:3688174-3688206    TTTTTGGGGGAAGTTCGGTTCGTGCGG (SEQ ID NO:16272), GCGGGTTGCGGGAGATTTTGATGGGTT (SEQ ID NO:16273), GTTTTTGGGGGAAGTTCGGTTCGTGCG (SEQ ID NO:16274), GCGGGTTGCGGGAGATTTTGATGGGTT (SEQ ID NO:16275), TTTTGGGGGAAGTTCGGTTCGTGCGG (SEQ ID NO:16276), GCGTTTTTGGAGGATAGGGACGTTGGGG (SEQ ID NO:16277), TGCGTTTTTGGAGGATAGGGACGTTGGG (SEQ ID NO:16278), GCGTTTTTGGAGGATAGGGACGTTGGGGA (SEQ ID NO:16279), GCGTTTTTGGAGGATAGGGACGTTGGG (SEQ ID NO:16280), TGCGTTTTTGGAGGATAGGGACGTTGGGG (SEQ ID NO:16281)

Target1718    chr19:3688313-3688339    TCGTGGTGGGAAATAGAGCGGGGTGTC (SEQ ID NO:16282), GTCGTGGTGGGAAATAGAGCGGGGTGT (SEQ ID NO:16283), GGTCGTGGTGGGAAATAGAGCGGGGTG (SEQ ID NO:16284), TAGGTCGTGGTGGGAAATAGAGCGGGG (SEQ ID NO:16285), CGTGGTGGGAAATAGAGCGGGGTGTCG (SEQ ID NO:16286), AGGTGAGGAATAGGAGTTTTTGCGGGT (SEQ ID NO:16287), AGGTGAGGAATAGGAGTTTTTGCGGGTT (SEQ ID NO:16288), CGTAGGTGAGGAATAGGAGTTTTTGCGGG (SEQ ID NO:16289), CGTAGGTGAGGAATAGGAGTTTTTGCGGGT (SEQ ID NO:16290), TCGTAGGTGAGGAATAGGAGTTTTTGCGGG (SEQ ID NO:16291)

Target1719    chr19:4792019-4792085    GTGGAGTATTTGGTGGATCGGTGCGGC (SEQ ID NO:16292), GGTGGAGTATTTGGTGGATCGGTGCGG (SEQ ID NO:16293), TGGAGTATTTGGTGGATCGGTGCGGCG (SEQ ID NO:16294), GGAGTATTTGGTGGATCGGTGCGGCG (SEQ ID NO:16295), TGGTGGAGTATTTGGTGGATCGGTGCG (SEQ ID NO:16296), GAGGTTTCGCGGCGTAGTAGGTTTCGT (SEQ ID NO:16297), TTACGTTTAGGTGGTCGGTTGCGGAGG (SEQ ID NO:16298), AGGTTTCGCGGCGTAGTAGGTTTCGTA (SEQ ID NO:16299), ATTACGTTTAGGTGGTCGGTTGCGGAGG (SEQ ID NO:16300), TACGTTTAGGTGGTCGGTTGCGGAGG (SEQ ID NO:16301)

Target1720    chr19:4792308-4792366    GAGGTGGTGCGTTATTTGGTCGGCGAG (SEQ ID NO:16302), TTGGAGGTGGTGCGTTATTTGGTCGGC (SEQ ID NO:16303), AGGTGGTGCGTTATTTGGTCGGCGAGT (SEQ ID NO:16304), GGTGGTGCGTTATTTGGTCGGCGAGTA (SEQ ID NO:16305), GGAGGTGGTGCGTTATTTGGTCGGCGA (SEQ ID NO:16306), GGGTCGTGTTGTTTTTGGCGTTGCGTC (SEQ ID NO:16307), AGGGTCGTGTTGTTTTTGGCGTTGCGT (SEQ ID NO:16308), GCGTTGCGTCGGTTTATTTGGGCGTTT (SEQ ID NO:16309), GGCGTTGCGTCGGTTTATTTGGGCGTT (SEQ ID NO:16310), TAGGGTCGTGTTGTTTTTGGCGTTGCG (SEQ ID NO:16311)

Target1721    chr19:5229275-5229659    GCGGTAGGGGAGAGAGGAGGAAGGTGA (SEQ ID NO:16312), AGGTGAGCGGGGGAGGTTAGAGATGGA (SEQ ID NO:16313), TAGGGGAGAGAGGAGGAAGGTGAGCGG (SEQ ID NO:16314), AGGAAGGTGAGCGGGGGAGGTTAGAGA (SEQ ID NO:16315), GAGGCGGTAGGGGAGAGAGGAGGAAGG (SEQ ID NO:16316), GTATTGTTCGGGGTAGGGTCGGGCGTT (SEQ ID NO:16317), TATTGTTCGGGGTAGGGTCGGGCGTTT (SEQ ID NO:16318), ATTGTTCGGGGTAGGGTCGGGCGTTTT (SEQ ID NO:16319), GTGGTATTGTTCGGGGTAGGGTCGGGC (SEQ ID NO:16320), TGTTGGTCGATGTTTAGGTGGGCGGGG (SEQ ID NO:16321)

Target1722    chr19:5229744-5229840    AGGGCGTTCGGTTTTGTTTCGGGTAGT (SEQ ID NO:16322), GGGCGTTCGGTTTTGTTTCGGGTAGTGT (SEQ ID NO:16323), GGGCGTTCGGTTTTGTTTCGGGTAGTG (SEQ ID NO:16324), AGGGCGTTCGGTTTTGTTTCGGGTAGTG (SEQ ID NO:16325), GGCGTTCGGTTTTGTTTCGGGTAGTGT (SEQ ID NO:16326), TAGGGTTGTGGGGGGTGTGTAGGAGGT (SEQ ID NO:16327), GTGGTATTGTTCGGGGTAGGGTCGGGT (SEQ ID NO:16328), AGTGGTATTGTTCGGGGTAGGGTCGGG (SEQ ID NO:16329), AGGGTTGTGGGGGGTGTGTAGGAGGTT (SEQ ID NO:16330), GGGTTGTGGGGGGTGTGTAGGAGGTTA (SEQ ID NO:16331)

Target1723    chr19:11002310-11002590    GGGGGGTGGTTTTTAGTTCGGTTTGTT (SEQ ID NO:16332), GGGGGGTGGTTTTTAGTTCGGTTTGTTT (SEQ ID NO:16333), AGTTAGTAGGGTTTAAAAGGATGTTGGGGGG (SEQ ID NO:16334), TTAGTTAGTAGGGTTTAAAAGGATGTTGGGGGG (SEQ ID NO:16335), TTTAGTTAGTAGGGTTTAAAAGGATGTTGGGGGG (SEQ ID NO:16336), AGATGGGCGGGGAAGGGATAGAGGGAG (SEQ ID NO:16337), AAAAGGTAATGGCGAAGGTTGGGGGCG (SEQ ID NO:16338), TAGATGGGCGGGGAAGGGATAGAGGGA (SEQ ID NO:16339), GGGGAAGGGATAGAGGGAGGAGGGGTA (SEQ ID NO:16340), GATGGGCGGGGAAGGGATAGAGGGAGG (SEQ ID NO:16341)

Target1724    chr19:15292415-15292441    GGGGTTGTAGTCGGGTAGGTTTTGTTCGT (SEQ ID NO:16342), TGGGGTTGTAGTCGGGTAGGTTTTGTTCG (SEQ ID NO:16343), GGGGTTGTAGTCGGGTAGGTTTTGTTCG (SEQ ID NO:16344), TGGGGTTGTAGTCGGGTAGGTTTTGTTCGT (SEQ ID NO:16345), TGGGGTTGTAGTCGGGTAGGTTTTGTT (SEQ ID NO:16346), AGTGTTTGAGTAATTTTTGCGGTTCGGGT (SEQ ID NO:16347), GAGTGTTTGAGTAATTTTTGCGGTTCGGGT (SEQ ID NO:16348), TGAGTGTTTGAGTAATTTTTGCGGTTCGGG (SEQ ID NO:16349), TGAGTGTTTGAGTAATTTTTGCGGTTCGGGT (SEQ ID NO:16350), ATGAGTGTTTGAGTAATTTTTGCGGTTCGGG (SEQ ID NO:16351)

Target1725    chr19:15292472-15292542    TGGCGGGTAGGTGTAGGTGAAGGAGGT (SEQ ID NO:16352), CGTGGTCGGTATAGGTGTTCGGGTCGT (SEQ ID NO:16353), GGCGGGTAGGTGTAGGTGAAGGAGGTT (SEQ ID NO:16354), TTGGCGGGTAGGTGTAGGTGAAGGAGG (SEQ ID NO:16355), CGGTATAGGTGTTCGGGTCGTAGGGGT (SEQ ID NO:16356), AGTGTTTGAGTAATTTTTGCGGTTCGGGT (SEQ ID NO:16357),

FIGURE 5 CONTINUED

GAGTGTTTGAGTAATTTTTGCGGTTCGGGT (SEQ ID NO:16358),
TGAGTGTTTGAGTAATTTTTGCGGTTCGGG (SEQ ID NO:16359),
TGAGTGTTTGAGTAATTTTTGCGGTTCGGGT (SEQ ID NO:16360),
ATGAGTGTTTGAGTAATTTTTGCGGTTCGGG (SEQ ID NO:16361)

Target1726    chr19:15580432-15580647    TCGTCGGGAAGTTGGGGGTTTGGTTGA (SEQ ID NO:16362), AGTCGGTGCGTATTAGTTGGCGGTGGT (SEQ ID NO:16363), TCGGGAAGTTGGGGGTTTGGTTGAGGT (SEQ ID NO:16364), AGGTAGGGGGTAGGGGTTTCGTGGAGT (SEQ ID NO:16365), TCGTGGAGTTTGTGTAGACGGAGGGGC (SEQ ID NO:16366), TCGGGGTTTCGGCGTGGTTATAGTGGG (SEQ ID NO:16367), TGTAGTTTCGTGGTGGGTTCGGACGGT (SEQ ID NO:16368), CGGGGTTTCGGCGTGGTTATAGTGGGT (SEQ ID NO:16369), CGGGGTTTCGGCGTGGTTATAGTGGGTA (SEQ ID NO:16370), TGTAGTTTCGTGGTGGGTTCGGACGGTT (SEQ ID NO:16371)

Target1727    chr19:15580657-15580773    GTTTCGGGAGTTGTGGTCGAGCGTGTG (SEQ ID NO:16372), AGTTTCGGGAGTTGTGGTCGAGCGTGT (SEQ ID NO:16373), AAGTTTCGGGAGTTGTGGTCGAGCGTG (SEQ ID NO:16374), TTTCGGGAGTTGTGGTCGAGCGTGTGG (SEQ ID NO:16375), GAAGTTTCGGGAGTTGTGGTCGAGCGT (SEQ ID NO:16376), CGGGTTTTGGGGTCGGTGGTTTTTGGT (SEQ ID NO:16377), GAGGGGGAGCGGATAAGGGTTCGGGTTT (SEQ ID NO:16378), TGTAGTTTCGTGGTGGGTTCGGACGGT (SEQ ID NO:16379), AGGGGAGCGGATAAGGGTTCGGGTTTT (SEQ ID NO:16380), AATCGGGGAGGGGAGCGGATAAGGGTT (SEQ ID NO:16381)

Target1728    chr19:15580839-15580863    TATTATGCGGCGTGAGGGGGATTCGGG (SEQ ID NO:16382), GTATTATGCGGCGTGAGGGGGATTCGG (SEQ ID NO:16383), CGGCGTGAGGGGGATTCGGGTTTTTAT (SEQ ID NO:16384), AGTATTATGCGGCGTGAGGGGGATTCGG (SEQ ID NO:16385), GCGGCGTGAGGGGGATTCGGGTTTTTA (SEQ ID NO:16386), GGGGAGGAGAAGGGTAGAAAGGGGCGTG (SEQ ID NO:16387), GTGGGGAGGAGAAGGGTAGAAAGGGGC (SEQ ID NO:16388), AGGGGCGTGTTAGTATTGAAGGGCGGA (SEQ ID NO:16389), GGAGGAGAAGGGTAGAAAGGGGCGTGT (SEQ ID NO:16390), TGGGGAGGAGAAGGGTAGAAAGGGGCG (SEQ ID NO:16391)

Target1729    chr19:18043907-18044307    GAAGGTTGGAGGAGGGGTGTTGGGAGG (SEQ ID NO:16392), GGAAGGTTGGAGGAGGGGTGTTGGGAG (SEQ ID NO:16393), TTTCGAGAGGGATAGAGTTGGGCGCGG (SEQ ID NO:16394), AGGTTGGAGGAGGGGTGTTGGGAGGTA (SEQ ID NO:16395), GGCGTTGGGGTAAGAAGGTAGGAGCGT (SEQ ID NO:16396), GGAGTGGTTTAGGTTGGGCGAGGGGTA (SEQ ID NO:16397), TAGGGAGTGGTTTAGGTTGGGCGAGGG (SEQ ID NO:16398), GGAGTGGTTTAGGTTGGGCGAGGGGT (SEQ ID NO:16399), AGGGAGTGGTTTAGGTTGGGCGAGGGG (SEQ ID NO:16400), AGGGAGTGGTTTAGGTTGGGCGAGGGG (SEQ ID NO:16401)

Target1730    chr19:31231293-31231693    AGCGGTATTGTTGACGTTAGGGGTTTGA (SEQ ID NO:16402), AGCGGTATTGTTGACGTTAGGGGTTTGAT (SEQ ID NO:16403), GCGGTATTGTTGACGTTAGGGGTTTGATG (SEQ ID NO:16404), AGCGGTATTGTTGACGTTAGGGGTTTGATG (SEQ ID NO:16405), GCGGTATTGTTGACGTTAGGGGTTTGATGA (SEQ ID NO:16406), TGTGTTTCGGGAATAGCGGGTAGTGTT (SEQ ID NO:16407), TTGTGTTTCGGGAATAGCGGGTAGTGT (SEQ ID NO:16408), TGTGTTTCGGGAATAGCGGGTAGTGTTT (SEQ ID NO:16409), TTGTGTTTCGGGAATAGCGGGTAGTGTT (SEQ ID NO:16410), TTTGTGTTTCGGGAATAGCGGGTAGTGT (SEQ ID NO:16411)

Target1731    chr19:32397371-32397537    AGAGTTAGGAGGCGGAGTTTTTTGTGAGT (SEQ ID NO:16412), AGAGTTAGGAGGCGGAGTTTTTTGTGAGTT (SEQ ID NO:16413), GGAGGCGGAGTTTTTTGTGAGTTTTTAAGGG (SEQ ID NO:16414), AGAGTTAGGAGGCGGAGTTTTTTGTGAGTTT (SEQ ID NO:16415), AGGAGGCGGAGTTTTTTGTGAGTTTTTAAGGG (SEQ ID NO:16416)

Target1732    chr19:39055972-39056314    GTTGGAGACGAGGAGGAGGCGGTGTAC (SEQ ID NO:16417), GCGGTTTGGTGGAGGGCGTTAAGAAGG (SEQ ID NO:16418), GGCGGTTTGGTGGAGGGCGTTAAGAAG (SEQ ID NO:16419), CGTAGTGGCGGCGTTGTTTTGGGTAGT (SEQ ID NO:16420), TCGTAGTGGCGGCGTTGTTTTGGGTAG (SEQ ID NO:16421), TCGTCGTTGGTGGGGTCGGGTATGTTT (SEQ ID NO:16422), TTCGTCGTTGGTGGGGTCGGGTATGTT (SEQ ID NO:16423), TTTCGTCGTTGGTGGGGTCGGGTATGT (SEQ ID NO:16424), TGTATTTCGTCGTTGGTGGGGTCGGGT (SEQ ID NO:16425), AGGATGGGAGAGTTTTCGGGTGTGGGC (SEQ ID NO:16426)

Target1733    chr19:39056318-39056354    GTTGGAGACGAGGAGGAGGCGGTGTAC (SEQ ID NO:16427), TTGGAGACGAGGAGGAGGCGGTGTAC (SEQ ID NO:16428), GTTGGAGACGAGGAGGAGGCGGTGTA (SEQ ID NO:16429), GTTGGAGACGAGGAGGAGGCGGTGT (SEQ ID NO:16430), TGGAGACGAGGAGGAGGCGGTGTAC (SEQ ID NO:16431), AGGATGGGAGAGTTTTCGGGTGTGGGC (SEQ ID NO:16432), GGAGAGTTTTCGGGTGTGGGCGGTTTC (SEQ ID NO:16433), GGGAGAGTTTTCGGGTGTGGGCGGTTT (SEQ ID NO:16434), GATGGGAGAGTTTTCGGGTGTGGGCGG (SEQ ID NO:16435), GGATGGGAGAGTTTTCGGGTGTGGGCG (SEQ ID NO:16436)

Target1734    chr19:39754800-39754842    CGGACGTTTTTTAGGGGATAGTGGTCGGT (SEQ ID NO:16437), CGGACGTTTTTTAGGGGATAGTGGTCGG (SEQ ID NO:16438), TCGGACGTTTTTTAGGGGATAGTGGTCGG (SEQ ID NO:16439), TCGGACGTTTTTTAGGGGATAGTGGTCGGT (SEQ ID NO:16440), TCGGACGTTTTTTAGGGGATAGTGGTCG (SEQ ID NO:16441), TGGGTTAGGTTTATAGGGGAGGCGTAGT (SEQ ID NO:16442), GGTGTTGTCGGTTATTGTTTTTTGGGGGG (SEQ ID NO:16443), GGTGTTGTCGGTTATTGTTTTTTGGGGGGT (SEQ ID NO:16444), AGGTGTTGTCGGTTATTGTTTTTTGGGGGG (SEQ ID NO:16445), AGGTGTTGTCGGTTATTGTTTTTTGGGGGGT (SEQ ID NO:16446)

FIGURE 5 CONTINUED

Target1735    chr19:39755042-39755067    AGGTAGGGGATTGGACGCGTGGGATTT (SEQ ID NO:16447), AAGGTAGGGGATTGGACGCGTGGGATT (SEQ ID NO:16448), TTAAGGTAGGGGATTGGACGCGTGGGA (SEQ ID NO:16449), TAAGGTAGGGGATTGGACGCGTGGGAT (SEQ ID NO:16450), GGTAGGGGATTGGACGCGTGGGATTTT (SEQ ID NO:16451), GTTCGGGGTTTTAGCGAGCGGTAGTGC (SEQ ID NO:16452), TTCGGGGTTTTAGCGAGCGGTAGTGC (SEQ ID NO:16453), CGTTAGCGTTCGGGGTTTTAGCGAGC (SEQ ID NO:16454), TCGGGGTTTTAGCGAGCGGTAGTGC (SEQ ID NO:16455), GTTCGGGGTTTTAGCGAGCGGTAGTG (SEQ ID NO:16456)

Target1736    chr19:39755074-39755167    AGGTAGGGGATTGGACGCGTGGGATTT (SEQ ID NO:16457), AAGGTAGGGGATTGGACGCGTGGGATT (SEQ ID NO:16458), TTAAGGTAGGGGATTGGACGCGTGGGA (SEQ ID NO:16459), TAAGGTAGGGGATTGGACGCGTGGGAT (SEQ ID NO:16460), GGTAGGGGATTGGACGCGTGGGATTTT (SEQ ID NO:16461), AATTCGGCGGGGGTTAGTGTATCGGGGG (SEQ ID NO:16462), TGTGTGGGAATTCGGCGGGGGTTAGTGT (SEQ ID NO:16463), GTTCGGGGTTTTAGCGAGCGGTAGTGC (SEQ ID NO:16464), GTGTGTGGGAATTCGGCGGGGGTTAGTG (SEQ ID NO:16465), GTTAGCGACGGGTGTGTGGGAATTCGG (SEQ ID NO:16466)

Target1737    chr19:39889822-39889941    GATTATCGGGTCGGGGGCGGTGGTTTA (SEQ ID NO:16467), ATTATCGGGTCGGGGGCGGTGGTTTAC (SEQ ID NO:16468), AATTGATTATCGGGTCGGGGGCGGTGG (SEQ ID NO:16469), GGTCGGGGGCGGTGGTTTACGTTTGTA (SEQ ID NO:16470), AAATTGATTATCGGGTCGGGGGCGGTG (SEQ ID NO:16471), CGGGGTTTTATCGTGTTGGTTAGGTTGGT (SEQ ID NO:16472), CGGGGTTTTATCGTGTTGGTTAGGTTGG (SEQ ID NO:16473), AGTCGGGGTTTTATCGTGTTGGTTAGGT (SEQ ID NO:16474), TCGGGGTTTTATCGTGTTGGTTAGGTTGG (SEQ ID NO:16475), TCGGGGTTTTATCGTGTTGGTTAGGTTGGT (SEQ ID NO:16476)

Target1738    chr19:39889945-39889971    TTTGGGAGTTCGAGGCGGGCGGATTAT (SEQ ID NO:16477), TATTTTGGGAGTTCGAGGCGGGCGGAT (SEQ ID NO:16478), ATATTTTGGGAGTTCGAGGCGGGCGGA (SEQ ID NO:16479), GATTATCGGGTCGGGGGCGGTGGTTTA (SEQ ID NO:16480), TTTTGGGAGTTCGAGGCGGGCGGATTA (SEQ ID NO:16481), CGGGGTTTTATCGTGTTGGTTAGGTTGGT (SEQ ID NO:16482), CGGGGTTTTATCGTGTTGGTTAGGTTGG (SEQ ID NO:16483), AGTCGGGGTTTTATCGTGTTGGTTAGGT (SEQ ID NO:16484), TCGGGGTTTTATCGTGTTGGTTAGGTTGG (SEQ ID NO:16485), TCGGGGTTTTATCGTGTTGGTTAGGTTGGT (SEQ ID NO:16486)

Target1739    chr19:40939079-40939095    GAGATGGTAGTGGTATCGTTTCGGTTTATCGT (SEQ ID NO:16487), TGAGATGGTAGTGGTATCGTTTCGGTTTATCG (SEQ ID NO:16488), TGAGATGGTAGTGGTATCGTTTCGGTTTATCGT (SEQ ID NO:16489), TGTTTTTTGAGATGGTAGTGGTATCGTTTCGGT (SEQ ID NO:16490), TTGAGATGGTAGTGGTATCGTTTCGGTTTATCG (SEQ ID NO:16491)

Target1740    chr19:40939114-40939316    CGGAGGTTGCGGTGAGTCGAGAC (SEQ ID NO:16492), CGGAGGTTGCGGTGAGTCGAGA (SEQ ID NO:16493), CGTTTAGGTTGGAGTATAGTGGGGCGA (SEQ ID NO:16494), TCGTTTAGGTTGGAGTATAGTGGGGCG (SEQ ID NO:16495), TCGTTTAGGTTGGAGTATAGTGGGGCGA (SEQ ID NO:16496), TGTCGTTTAGGTTGGAGTATAGTGGGGCG (SEQ ID NO:16497), GTCGTTTAGGTTGGAGTATAGTGGGGCG (SEQ ID NO:16498)

Target1741    chr19:42005037-42005631    GCGTGGGTATAGGGAGAGGGAGGGGAT (SEQ ID NO:16499), GCGTGGGGGAAGGAAGAGGGTATGAGG (SEQ ID NO:16500), AGGAGCGTGGGTATAGGGAGAGGGAGG (SEQ ID NO:16501), GAGCGTGGGTATAGGGAGAGGGAGGGG (SEQ ID NO:16502), GGAGCGTGGGTATAGGGAGAGGGAGGG (SEQ ID NO:16503), TGTTTTGGGGTATTAGGTTGGGGGAAGG (SEQ ID NO:16504), ATGTTTTGGGGTATTAGGTTGGGGGAAGG (SEQ ID NO:16505), AATGTTTTGGGGTATTAGGTTGGGGGAAGG (SEQ ID NO:16506), GAATGTTTTGGGGTATTAGGTTGGGGGAAGG (SEQ ID NO:16507), AGAATGTTTTGGGGTATTAGGTTGGGGGAA (SEQ ID NO:16508)

Target1742    chr19:46996862-46996888    TTGCGGGGTTTGTTCGTAGTTTGGGCG (SEQ ID NO:16509), CGGGGTTTGTTCGTAGTTTGGGCGGTT (SEQ ID NO:16510), GCGGGTGTTTTGCGGGGTTTGTTCGTA (SEQ ID NO:16511), TCGTAGTTTGGGCGGTTTTTTGGGGGG (SEQ ID NO:16512), GGGCGGTTTTTTGGGGGGGTTATTAGCGG (SEQ ID NO:16513), AAGTAGGAAGAAGAAGGGGAGCGCGGG (SEQ ID NO:16514), GGGTAGGCGAGGTTAAGGGTTAGGCGT (SEQ ID NO:16515), AGGGTAGGCGAGGTTAAGGGTTAGGCG (SEQ ID NO:16516), GCGTCGGGGGTTTATGTTAGGGTAGGCG (SEQ ID NO:16517), GAAGTAGGAAGAAGAAGGGGAGCGCGGG (SEQ ID NO:16518)

Target1743    chr19:46996932-46996965    GCGGTTTTGGATTTAGTGGGCGTTTGGT (SEQ ID NO:16519), GCGGTTTTGGATTTAGTGGGCGTTTGG (SEQ ID NO:16520), CGTTTGTTTTGGTATGGGTTTCGGCGT (SEQ ID NO:16521), AGTGGGCGTTTGGTTTTTGGTTTCGTT (SEQ ID NO:16522), TCGTTTGTTTTGGTATGGGTTTCGGCGT (SEQ ID NO:16523), TCGGTCGGCGCGTTTTTTATCGTTTTC (SEQ ID NO:16524), TGATTTCGGTCGGCGCGTTTTTTATCGT (SEQ ID NO:16525), GATTTCGGTCGGCGCGTTTTTTATCGT (SEQ ID NO:16526), TTCGGTCGGCGCGTTTTTTATCGTTTT (SEQ ID NO:16527), TTTCGGTCGGCGCGTTTTTTATCGTTT (SEQ ID NO:16528)

Target1744    chr19:46997057-46997083    GGTTTCGGAAGCGGTGGGAGGCG (SEQ ID NO:16529), GTTTCGGAAGCGGTGGGAGGCGC (SEQ ID NO:16530), TTTCGGAAGCGGTGGGAGGCGC (SEQ ID NO:16531), GGTTTCGGAAGCGGTGGGAGGCGC (SEQ ID NO:16532), GTTTCGGAAGCGGTGGGAGGCGCGT (SEQ ID NO:16533), TTTAGGGGTTTGATTTCGGTCGGCGCG (SEQ ID NO:16534), GGGGTTTGATTTCGGTCGGCGCGTTTT (SEQ ID NO:16535), TAGGGGTTTGATTTCGGTCGGCGCGTT (SEQ ID NO:16536),

FIGURE 5 CONTINUED

TTAGGGGTTTGATTTCGGTCGGCGCGT (SEQ ID NO:16537), GGGTTTGATTTCGGTCGGCGCGTTTTT (SEQ ID NO:16538)

Target1745    chr19:46997103-46997110    GGAGTTAGGTTTTTGGGGGTCGTGCGC (SEQ ID NO:16539), CGGAGTTAGGTTTTTGGGGGTCGTGCG (SEQ ID NO:16540), CGGTCGGAGTTAGGTTTTTGGGGGTCG (SEQ ID NO:16541), TCGGTCGGAGTTAGGTTTTTGGGGGTC (SEQ ID NO:16542), TCGGAGTTAGGTTTTTGGGGGTCGTGC (SEQ ID NO:16543), TTAGGAAGTTTCGGGTTAAGAGGGCGC (SEQ ID NO:16544), CGAGGGGTCGGAGGAGGTTTCGGA (SEQ ID NO:16545), TTTAGGAAGTTTCGGGTTAAGAGGGCGC (SEQ ID NO:16546), TAGGAAGTTTCGGGTTAAGAGGGCGC (SEQ ID NO:16547), AGGAAGTTTCGGGTTAAGAGGGCGC (SEQ ID NO:16548)

Target1746    chr19:46997148-46997179    GGAGTTAGGTTTTTGGGGGTCGTGCGC (SEQ ID NO:16549), CGGAGTTAGGTTTTTGGGGGTCGTGCG (SEQ ID NO:16550), CGGTCGGAGTTAGGTTTTTGGGGGTCG (SEQ ID NO:16551), TCGGTCGGAGTTAGGTTTTTGGGGGTCG (SEQ ID NO:16552), TCGGAGTTAGGTTTTTGGGGGTCGTGC (SEQ ID NO:16553), GGGGGAGGTATTGGCGTTTTTGGTCGT (SEQ ID NO:16554), TGGGGGAGGTATTGGCGTTTTTGGTCG (SEQ ID NO:16555), TGGGGGAGGTATTGGCGTTTTTGGTCGT (SEQ ID NO:16556), GGGGGAGGTATTGGCGTTTTTGGTCGTT (SEQ ID NO:16557), TTGGGGGAGGTATTGGCGTTTTTGGTCG (SEQ ID NO:16558)

Target1747    chr19:46997189-46997203    GGAGTTAGGTTTTTGGGGGTCGTGCGC (SEQ ID NO:16559), CGGAGTTAGGTTTTTGGGGGTCGTGCG (SEQ ID NO:16560), CGGTCGGAGTTAGGTTTTTGGGGGTCG (SEQ ID NO:16561), TCGGTCGGAGTTAGGTTTTTGGGGGTCG (SEQ ID NO:16562), TCGGAGTTAGGTTTTTGGGGGTCGTGC (SEQ ID NO:16563), GGGGGAGGTATTGGCGTTTTTGGTCGT (SEQ ID NO:16564), TGGGGGAGGTATTGGCGTTTTTGGTCG (SEQ ID NO:16565), TGGGGGAGGTATTGGCGTTTTTGGTCGT (SEQ ID NO:16566), GGGGGAGGTATTGGCGTTTTTGGTCGTT (SEQ ID NO:16567), TTGGGGGAGGTATTGGCGTTTTTGGTCG (SEQ ID NO:16568)

Target1748    chr19:46997364-46997529    TCGTTTGGGGAGGGAGATTCGGTTGCG (SEQ ID NO:16569), CGTTTGGGGAGGGAGATTCGGTTGCGT (SEQ ID NO:16570), GTTTGGGGAGGGAGATTCGGTTGCGTT (SEQ ID NO:16571), TTCGTTTGGGGAGGGAGATTCGGTTGC (SEQ ID NO:16572), GGGGAGGGAGATTCGGTTGCGTTAAGGT (SEQ ID NO:16573), GGGGATGACGGGGATTTTCGGGAGTGT (SEQ ID NO:16574), CGTGGTTTTTCGGGGGTTGGAGCGAG (SEQ ID NO:16575), AGAAGGTTGGGCGTGGTTTTTTCGGGG (SEQ ID NO:16576), GAAGGTTGGGCGTGGTTTTTTCGGGGG (SEQ ID NO:16577), GTGGTTTTTTCGGGGGTTGGAGCGAGT (SEQ ID NO:16578)

Target1749    chr19:49238331-49238365    ACGTTTTATTTAGAGTATTTGAGGTTAGCGCGTTTC (SEQ ID NO:16579), GGATTACGTTTTATTAGAGTATTTGAGGTTAGCGCG (SEQ ID NO:16580), AAGGTTCGGGGCGCGTTAGTTTTTAAGT (SEQ ID NO:16581), AGAAGGTTCGGGGCGCGTTAGTTTTAA (SEQ ID NO:16582), TTAGAAGGTTCGGGGCGCGTTAGTTTT (SEQ ID NO:16583), TTTAGAAGGTTCGGGGCGCGTTAGTTT (SEQ ID NO:16584), TTTTAGAAGGTTCGGGGCGCGTTAGTT (SEQ ID NO:16585)

Target1750    chr19:49238428-49238459    GTATAGGGTTTTGGGCGTGCGGGGTTG (SEQ ID NO:16586), GATGGGGTATAGGGTTTTGGGCGTGCG (SEQ ID NO:16587), ATGGGGTATAGGGTTTTGGGCGTGCGG (SEQ ID NO:16588), TATAGGGTTTTGGGCGTGCGGGGTTGG (SEQ ID NO:16589), GGTATAGGGTTTTGGGCGTGCGGGGTT (SEQ ID NO:16590)

Target1751    chr19:49238493-49238813    GTATAGGGTTTTGGGCGTGCGGGGTTG (SEQ ID NO:16591), GTAGGAAGTAGGGGCGGTTGTTGGGGG (SEQ ID NO:16592), GAAGTAGGGGCGGTTGTTGGGGGTTTG (SEQ ID NO:16593), GATGGGGTATAGGGTTTTGGGCGTGCG (SEQ ID NO:16594), AGTAGGAAGTAGGGGCGGTTGTTGGGG (SEQ ID NO:16595), CGTCGGGTGGGGTAGCGTTGGTTAGTT (SEQ ID NO:16596), TCGGAGTTTAGTTTTTAGGGGCGGCGG (SEQ ID NO:16597), CGTCGGGTGGGGTAGCGTTGGTTAGT (SEQ ID NO:16598), GTCGGGTGGGGTAGCGTTGGTTAGTTT (SEQ ID NO:16599), CGTCGGGTGGGGTAGCGTTGGTTAGTT (SEQ ID NO:16600)

Target1752    chr19:49842341-49843187    ATCGGAGGGTGGGGGCGGTTTAGTTTT (SEQ ID NO:16601), ACGGTAGGAGGGGCGGGGTTTTTTGAA (SEQ ID NO:16602), TAGCGGTAGTTTGTGGGGTGGTTGGGG (SEQ ID NO:16603), TTTGCGGGAGGGGGAGGGTTGTTAGTG (SEQ ID NO:16604), GTTTGCGGGAGGGGGAGGGTTGTTAGT (SEQ ID NO:16605), AGGTTTTGCGCGTAGTTTTGGGGGGTG (SEQ ID NO:16606), GGTTTTGCGCGTAGTTTTGGGGGGTGT (SEQ ID NO:16607), TATTTTTCGGTGTTGGGTGGAGCGGCG (SEQ ID NO:16608), GAGGTTTTGCGCGTAGTTTTGGGGGGT (SEQ ID NO:16609), TGGAGGTTTTGCGCGTAGTTTTGGGGG (SEQ ID NO:16610)

Target1753    chr19:52839445-52839743    TGGAGGCGTGGTTTAGGGAAGTTTCGT (SEQ ID NO:16611), TTCGGTTCGTTTTTTATGTTGCGCGCG (SEQ ID NO:16612), TGGAGGCGTGGTTTAGGGAAGTTTCGTT (SEQ ID NO:16613), TTGGAGGCGTGGTTTAGGGAAGTTTCGT (SEQ ID NO:16614), GGAGGCGTGGTTTAGGGAAGTTTCGTT (SEQ ID NO:16615), ATTTATACGGGGTGGAGGGAGCGGTGC (SEQ ID NO:16616), AAGCGCGGGGGAGTTGGGAAGTTTAGA (SEQ ID NO:16617), AGAAGCGCGGGGGAGTTGGGAAGTTTA (SEQ ID NO:16618), TAGAAGCGCGGGGGAGTTGGGAAGTTT (SEQ ID NO:16619), GCGCGGGGTAGGACGTTGGGTTAGTAA (SEQ ID NO:16620)

Target1754    chr19:52839823-52839845    CGGGTTTTGTTTTCGTTCGTTTTGTTTTGGG (SEQ ID NO:16621), CGGGTTTTGTTTTCGTTCGTTTTGTTTTGGGT (SEQ ID NO:16622), ACGGGTTTTGTTTTCGTTCGTTTTGTTTTGGG (SEQ ID NO:16623), ACGGGTTTTGTTTTCGTTCGTTTTGTTTTGGGT (SEQ ID NO:16624),

FIGURE 5 CONTINUED

|  |  | ACGGGTTTTGTTTTCGTTCGTTTTGTTTTGG (SEQ ID NO:16625), GGTTGGGAGGTTTTTCGGGCGGGAATT (SEQ ID NO:16626), AGGTTGGGAGGTTTTTCGGGCGGGAAT (SEQ ID NO:16627), TTTTTTCGTCGGGATTGGGGTTGCGGC (SEQ ID NO:16628), GAGGTTGGGAGGTTTTTCGGGCGGGAA (SEQ ID NO:16629), GTCGGGGGCGAGGTTGGGAGGTTTTTC (SEQ ID NO:16630) |
| Target1755 | chr19:52839863-52840013 | CGTAGTTTTAGTTTCGGCGGGGGAGGT (SEQ ID NO:16631), TCGTAGTTTTAGTTTCGGCGGGGGAGGT (SEQ ID NO:16632), TAGTTTTAGTTTCGGCGGGGGAGGTCG (SEQ ID NO:16633), TCGTAGTTTTAGTTTCGGCGGGGGAGG (SEQ ID NO:16634), GTAGTTTTAGTTTCGGCGGGGGAGGTCG (SEQ ID NO:16635), GGTTGCGAAGGGGAGGTTTGGGGAGTA (SEQ ID NO:16636), TTGCGAAGGGGAGGTTTGGGGAGTAGG (SEQ ID NO:16637), GATGGTTGCGAAGGGGAGGTTTGGGGA (SEQ ID NO:16638), ATGGTTGCGAAGGGGAGGTTTGGGGAG (SEQ ID NO:16639), TTTTTTCGTCGGGATTGGGGTTGCGGC (SEQ ID NO:16640) |
| Target1756 | chr19:54800281-54800681 | AGTCGGGCGCGGTGGTTTACGTTTATA (SEQ ID NO:16641), TAGTCGGGCGCGGTGGTTTACGTTTAT (SEQ ID NO:16642), ATAGTCGGGCGCGGTGGTTTACGTTTA (SEQ ID NO:16643), TATAGTCGGGCGCGGTGGTTACGTTT (SEQ ID NO:16644), ATATAGTCGGGCGCGGTGGTTTACGTT (SEQ ID NO:16645), TCGGGGGAGGTTAGCGGGGGTTATAGT (SEQ ID NO:16646), ATGGGAAATTCGGGGGAGGTTAGCGGG (SEQ ID NO:16647), GAAATTCGGGGGAGGTTAGCGGGGGTT (SEQ ID NO:16648), CGGGGGAGGTTAGCGGGGGTTATAGTG (SEQ ID NO:16649), AAATTCGGGGGAGGTTAGCGGGGGTTA (SEQ ID NO:16650) |
| Target1757 | chr19:54858790-54858970 | AGGATTAGGAGGAGGTTGATGTGGTGGT (SEQ ID NO:16651), GAGGATTAGGAGGAGGTTGATGTGGTGGT (SEQ ID NO:16652), AGTTTGGAGTGAGGGTTTGGAGAAGAGG (SEQ ID NO:16653), GTTTGGAGTGAGGGTTTGGAGAAGAGGA (SEQ ID NO:16654), GAGGATTAGGAGGAGGTTGATGTGGTGGT (SEQ ID NO:16655) |
| Target1758 | chr19:55593556-55593969 | AGGTTCGGTTGCGCGGTAATATCGTCG (SEQ ID NO:16656), CGTTGGGGGGATTCGTGGATTCGTTTCG (SEQ ID NO:16657), TCGTTGGGGGGATTCGTGGATTCGTTTCG (SEQ ID NO:16658), TTTACGTTTTAGGTTCGGTTGCGCGGT (SEQ ID NO:16659), GGGTTCGATTTGTAGAAGGTGTGGCGGT (SEQ ID NO:16660), TCGTTGTAGGGGGGGTTCGAGGGGTTTGG (SEQ ID NO:16661), GTTGTAGGGGGGGTTCGAGGGGTTTGGGG (SEQ ID NO:16662), CGTTGTAGGGGGGGTTCGAGGGTTTGGG (SEQ ID NO:16663), GGTTCGAGGGGTTTGGGGCGGGTTTTAT (SEQ ID NO:16664), GGGTTCGAGGGGTTTGGGGCGGGTTTTA (SEQ ID NO:16665) |
| Target1759 | chr19:57587592-57587717 | GGCGTGGAAATTATAGGTTTTTGTTTCGTGGT (SEQ ID NO:16666), AGGCGTGGAAATTATAGGTTTTTGTTTCGTGG (SEQ ID NO:16667), AGGCGTGGAAATTATAGGTTTTTGTTTCGTGGT (SEQ ID NO:16668), GGCGTGGAAATTATAGGTTTTTGTTTCGTGGTA (SEQ ID NO:16669), TAGGCGTGGAAATTATAGGTTTTTGTTTCGTGG (SEQ ID NO:16670), GGTTGTTTGTATTATCGGTGTTGGCGGT (SEQ ID NO:16671), AGGTTGTTTGTATTATCGGTGTTGGCGGT (SEQ ID NO:16672), AGGTTGTTTGTATTATCGGTGTTGGCGG (SEQ ID NO:16673), GGTTGTTTGTATTATCGGTGTTGGCGTT (SEQ ID NO:16674), AGGTTGTTTGTATTATCGGTGTTGGCGGTT (SEQ ID NO:16675) |
| Target1760 | chr19:57587880-57587906 | AGGAATGTGAGGGTTTTTAAATGATCGGGGT (SEQ ID NO:16676), GGAATGTGAGGGTTTTTAAATGATCGGGGTC (SEQ ID NO:16677), GAGGAATGTGAGGGTTTTTAAATGATCGGGG (SEQ ID NO:16678), AGGAATGTGAGGGTTTTTAAATGATCGGGGTC (SEQ ID NO:16679), GAGGAATGTGAGGGTTTTTAAATGATCGGGGT (SEQ ID NO:16680), GTTGGGAGTAGGGTGTGATTGTTGCGT (SEQ ID NO:16681), AGTTGGGAGTAGGGTGTGATTGTTGCGT (SEQ ID NO:16682), AGTTGGGAGTAGGGTGTGATTGTTGCG (SEQ ID NO:16683), TTGGGAGTAGGGTGTGATTGTTGCGTT (SEQ ID NO:16684), GTTGGGAGTAGGGTGTGATTGTTGCGTT (SEQ ID NO:16685) |
| Target1761 | chr20:19667703-19668103 | TGCGGTTGTGTAGGTTTTTGATGGTTGT (SEQ ID NO:16686), AGGTATCGGTTTATTGCGGTTGTGTAGGT (SEQ ID NO:16687), TGCGGTTGTGTAGGTTTTTGATGGTTGTT (SEQ ID NO:16688), TTGCGGTTGTGTAGGTTTTTGATGGTTGT (SEQ ID NO:16689), AGGTATCGGTTTATTGCGGTTGTGTAGGTT (SEQ ID NO:16690), AGGTGAAGGTGGAGGGGTTTTGTGGTT (SEQ ID NO:16691), TAGGTGAAGGTGGAGGGGTTTTGTGGT (SEQ ID NO:16692), GGTGAAGGTGGAGGGGTTTTGTGGTTT (SEQ ID NO:16693), AGGTGAAGGTGGAGGGGTTTTGTGGTTT (SEQ ID NO:16694), AGGTGAAGGTGGAGGGGTTTTGTGGT (SEQ ID NO:16695) |
| Target1762 | chr20:22562559-22562585 | AGGAGGTATTTGCGGTTAGGGGCGAGG (SEQ ID NO:16696), GTATTTGCGGTTAGGGGCGAGGCGTTT (SEQ ID NO:16697), ATTTGCGGTTAGGGGCGAGGCGTTTAG (SEQ ID NO:16698), GGAGGTATTTGCGGTTAGGGGCGAGGC (SEQ ID NO:16699), CGGTTAGGGGCGAGGCGTTTAGGTTCG (SEQ ID NO:16700), TTTTTTATGTTTGGTAGTTTGGTTATGGGTTCGGTT (SEQ ID NO:16701) |
| Target1763 | chr20:22562737-22562786 | GTGGTGGTGGTGGTTGTGGTGGTGTTG (SEQ ID NO:16702), ACGGGTGGTTGAAGGCGTAGTGGTGTT (SEQ ID NO:16703), GGTGGTGGTGGTTGTGGTGGTGTTGTT (SEQ ID NO:16704), ATTTTGTGGGGTTGGTGGTGGTGGTGG (SEQ ID NO:16705), TGGTGGTGGTGGTTGTGGTGGTGTTGT (SEQ ID NO:16706), CGTCGGTTGCGGCGTTGAGTTTTTTAG (SEQ ID NO:16707), AGGTCGCGGTTTATTTGTTGGGTTCGT (SEQ ID NO:16708), CGTCGGTTGCGGCGTTGAGTTTTTTAGA (SEQ ID NO:16709), GGGTTTGGGAGAGTTGAAGGGGACGT (SEQ ID NO:16710), CGGTTGCGGCGTTGAGTTTTTTAGAGTCG (SEQ ID NO:16711) |

FIGURE 5 CONTINUED

Target1764    chr20:22562824-22562858    AGGTGGGTTTTAGGCGGTAGGTTCGGG (SEQ ID NO:16712), TTTTAGGCGGTAGGTTCGGGTGGTGGG (SEQ ID NO:16713), TGGGTTTTAGGCGGTAGGTTCGGGTGG (SEQ ID NO:16714), GGGTTTTAGGCGGTAGGTTCGGGTGGT (SEQ ID NO:16715), GGTGGGTTTTAGGCGGTAGGTTCGGGT (SEQ ID NO:16716), AGCGAGGGGGTTTGGGAGAGTTGAAGG (SEQ ID NO:16717), GGGGTTTGGGAGAGTTGAAGGGGACGT (SEQ ID NO:16718), CGAGGGGGTTTGGGAGAGTTGAAGGGG (SEQ ID NO:16719), GGGGGTTTGGGAGAGTTGAAGGGGACG (SEQ ID NO:16720), AGGGGGTTTGGGAGAGTTGAAGGGGAC (SEQ ID NO:16721)

Target1765    chr20:22562884-22563031    AGGTGGGTTTTAGGCGGTAGGTTCGGG (SEQ ID NO:16722), TTTGGTACGGGGGAGGCGTTCGAGTGAG (SEQ ID NO:16723), TTTTAGGCGGTAGGTTCGGGTGGTGGG (SEQ ID NO:16724), TGGGTTTTAGGCGGTAGGTTCGGGTGG (SEQ ID NO:16725), GGGTTTTAGGCGGTAGGTTCGGGTGGT (SEQ ID NO:16726), AGCGAGGGGGTTTGGGAGAGTTGAAGG (SEQ ID NO:16727), TTTAATTCGGGGAGGTCGTCGGGTCGG (SEQ ID NO:16728), GGGGTTTGGGAGAGTTGAAGGGGACGT (SEQ ID NO:16729), CGAGGGGGTTTGGGAGAGTTGAAGGGG (SEQ ID NO:16730), GGGGGTTTGGGAGAGTTGAAGGGGACG (SEQ ID NO:16731)

Target1766    chr20:25062056-25062103    GTTTGGCGTTGGGGGGGAAAAATGGTTT (SEQ ID NO:16732), GGTGGTGGCGGTTTTATATCGTTGAGGG (SEQ ID NO:16733), AGGTGGTGGCGGTTTTATATCGTTGAGGG (SEQ ID NO:16734), GGTGGTGGCGGTTTTATATCGTTGAGGGA (SEQ ID NO:16735), TGGTGGCGGTTTTATATCGTTGAGGGA (SEQ ID NO:16736), TAGGCGGGGAGTTTAGAGCGAGGTTC (SEQ ID NO:16737), TTAGGCGGGGAGTTTAGAGCGAGGTTT (SEQ ID NO:16738), TTTAGGCGGGGAGTTTAGAGCGAGGTT (SEQ ID NO:16739), ATTTAGGCGGGGAGTTTAGAGCGAGGT (SEQ ID NO:16740), AGGCGGGGAGTTTAGAGCGAGGTTTC (SEQ ID NO:16741)

Target1767    chr20:25062153-25062196    AGGATGTAGTAAGGGGTAGGCGGCGTA (SEQ ID NO:16742), TAGGATGTAGTAAGGGGTAGGCGGCGT (SEQ ID NO:16743), GGATGTAGTAAGGGGTAGGCGGCGTAGT (SEQ ID NO:16744), GGATGTAGTAAGGGGTAGGCGGCGTAG (SEQ ID NO:16745), AGGATGTAGTAAGGGGTAGGCGGCGT (SEQ ID NO:16746), TAGGCGGGGAGTTTAGAGCGAGGTTC (SEQ ID NO:16747), TTAGGCGGGGAGTTTAGAGCGAGGTTT (SEQ ID NO:16748), TTTAGGCGGGGAGTTTAGAGCGAGGTT (SEQ ID NO:16749), ATTTAGGCGGGGAGTTTAGAGCGAGGT (SEQ ID NO:16750), AGGCGGGGAGTTTAGAGCGAGGTTTC (SEQ ID NO:16751)

Target1768    chr20:25062210-25062257    GATTTGGGTCGTTGGGGTTAGGGGTGC (SEQ ID NO:16752), ATTTGGGTCGTTGGGGTTAGGGGTGCG (SEQ ID NO:16753), GCGGTGGGGCGATGGTTTGTGATTTTT (SEQ ID NO:16754), AGATTTGGGTCGTTGGGGTTAGGGGTGC (SEQ ID NO:16755), GGTGGGGCGATGGTTTGTGATTTTTGCG (SEQ ID NO:16756), CGTTTTTGTTTTTGTTTTTTAGGTTTTGAGTCGCG (SEQ ID NO:16757), CGTTTTTGTTTTTGTTTTTTAGGTTTTGAGTCGCGT (SEQ ID NO:16758), TCGTTTTTGTTTTTGTTTTTTAGGTTTTGAGTCGCG (SEQ ID NO:16759), TTTTGTTTTTGTTTTTTAGGTTTTGAGTCGCTAGG (SEQ ID NO:16760)

Target1769    chr20:25062287-25062356    GCGCGGGTTTGATTATCGGACGTGGAG (SEQ ID NO:16761), AGCGCGGGTTTGATTATCGGACGTGGA (SEQ ID NO:16762), AAGCGCGGGTTTGATTATCGGACGTGG (SEQ ID NO:16763), GATTTGGGTCGTTGGGGTTAGGGGTGC (SEQ ID NO:16764), CGTTGTCGTTGCGTTTTGGCGGTCGA (SEQ ID NO:16765), CGGCGGTCGTTCGAGTATTTTGTTTGT (SEQ ID NO:16766), CGGCGGTCGTTCGAGTATTTTGTTTGTT (SEQ ID NO:16767), CGTGTCGTTTTTGTCGTTTAGGGGTTTCG (SEQ ID NO:16768), CGGCGGTCGTTCGAGTATTTTGTTTGTTT (SEQ ID NO:16769), CGTGTCGTTTTTGTCGTTTAGGGGTTTCGA (SEQ ID NO:16770)

Target1770    chr20:25062362-25062385    GCGCGGGTTTGATTATCGGACGTGGAG (SEQ ID NO:16771), AGCGCGGGTTTGATTATCGGACGTGGA (SEQ ID NO:16772), AAGCGCGGGTTTGATTATCGGACGTGG (SEQ ID NO:16773), CGTTGTCGTTGCGTTTTGGCGGTCGA (SEQ ID NO:16774), CGTTGTCGTTGCGTTTTGGCGGTCG (SEQ ID NO:16775), CGGCGGTCGTTCGAGTATTTTGTTTGT (SEQ ID NO:16776), CGGCGGTCGTTCGAGTATTTTGTTTGTT (SEQ ID NO:16777), CGTGTCGTTTTTGTCGTTTAGGGGTTTCG (SEQ ID NO:16778), CGGCGGTCGTTCGAGTATTTTGTTTGTTT (SEQ ID NO:16779), CGTGTCGTTTTTGTCGTTTAGGGGTTTCGA (SEQ ID NO:16780)

Target1771    chr20:25062403-25062422    GTTCGGGGTTTTTGGGCGGTAGGAACG (SEQ ID NO:16781), GCGCGGGTTTGATTATCGGACGTGGAG (SEQ ID NO:16782), GGTTCGGGGTTTTTGGGCGGTAGGAAC (SEQ ID NO:16783), AGCGCGGGTTTGATTATCGGACGTGGA (SEQ ID NO:16784), AAGCGCGGGTTTGATTATCGGACGTGG (SEQ ID NO:16785), ACGGTTTTAGTTTGGCGCGTGGGGTTT (SEQ ID NO:16786), TTGACGGTTTTAGTTTGGCGCGTGGGG (SEQ ID NO:16787), GACGGTTTTAGTTTGGCGCGTGGGGTT (SEQ ID NO:16788), TTTGGCGCGTGGGGTTTTATCGTTGGG (SEQ ID NO:16789), GTTTGGCGCGTGGGGTTTTATCGTTGG (SEQ ID NO:16790)

Target1772    chr20:25062443-25062464    GTTCGGGGTTTTTGGGCGGTAGGAACG (SEQ ID NO:16791), GGTTCGGGGTTTTTGGGCGGTAGGAAC (SEQ ID NO:16792), CGGGGTTTTTGGGCGGTAGGAACGGTA (SEQ ID NO:16793), GGGGTTTTTGGGCGGTAGGAACGGTAC (SEQ ID NO:16794), GGGTTCGGGGTTTTTGGGCGGTAGGAA (SEQ ID NO:16795), ACGGTTTTAGTTTGGCGCGTGGGGTTT (SEQ ID NO:16796), TTGACGGTTTTAGTTTGGCGCGTGGGG (SEQ ID NO:16797), GACGGTTTTAGTTTGGCGCGTGGGGTT (SEQ ID NO:16798), TTTGGCGCGTGGGGTTTTATCGTTGGG (SEQ ID NO:16799), GTTTGGCGCGTGGGGTTTTATCGTTGG (SEQ ID NO:16800)

Target1773    chr20:25062496-25062512    GTTCGGGGTTTTTGGGCGGTAGGAACG (SEQ ID NO:16801), GGTTCGGGGTTTTTGGGCGGTAGGAAC (SEQ ID NO:16802), CGGGGTTTTTGGGCGGTAGGAACGGTA (SEQ ID NO:16803), GGGGTTTTTGGGCGGTAGGAACGGTAC (SEQ ID NO:16804), GGGTTCGGGGTTTTTGGGCGGTAGGAA

FIGURE 5 CONTINUED

|  |  | {SEQ ID NO:16805}, ACGGTTTTAGTTTGGCGCGTGGGGTTT {SEQ ID NO:16806}, TTTGACGGTTTTAGTTTGGCGCGTGGGG {SEQ ID NO:16807}, GACGGTTTTAGTTTGGCGCGTGGGGTT {SEQ ID NO:16808}, GGGGTTTGACGGTTTTAGTTTGGCGCG {SEQ ID NO:16809}, CGGGGGTTTGACGGTTTTAGTTTGGCGC {SEQ ID NO:16810} |
| Target1774 | chr20:33759725-33759855 | AATGAAGGGCGGGGTAGAGGGAGGGTA {SEQ ID NO:16811}, TAATGAAGGGCGGGGTAGAGGGAGGGT {SEQ ID NO:16812}, GAGGGAGGGTAGGAGGGAGGTCGGTTT {SEQ ID NO:16813}, AGGGGAGGGTAGGAGGGGAGGTCGGTTTT {SEQ ID NO:16814}, ATGAAGGGCGGGGTAGAGGGAGGGTAG {SEQ ID NO:16815}, GTTTGGGAGGGGCGGAGTTTGGGTAGA {SEQ ID NO:16816}, TTTTTGGTTCGGGTCGGTTGCGGGTTT {SEQ ID NO:16817}, TTTTTGGTTCGGGTCGGTTGCGGGTTTC {SEQ ID NO:16818}, GGGCGGAGTTTGGGTAGAGGAGGATGG {SEQ ID NO:16819}, GGGGCGGAGTTTGGGTAGAGGAGGATG {SEQ ID NO:16820} |
| Target1775 | chr20:39597880-39597893 | GGAAGAGGGTTAGGCGTGGTTGTGTGT {SEQ ID NO:16821}, AGGGTTAGGCGTGGTTGTGTGTTTCGA {SEQ ID NO:16822}, AGGAAGAGGGTTAGGCGTGGTTGTGTGT {SEQ ID NO:16823}, AGGAAGAGGGTTAGGCGTGGTTGTGTG {SEQ ID NO:16824}, TGAGGAAGAGGGTTAGGCGTGGTTGTGT {SEQ ID NO:16825} |
| Target1776 | chr20:39597926-39597993 | GGAAGAGGGTTAGGCGTGGTTGTGTGT {SEQ ID NO:16826}, AGGGTTAGGCGTGGTTGTGTGTTTCGA {SEQ ID NO:16827}, AGGAAGAGGGTTAGGCGTGGTTGTGTGT {SEQ ID NO:16828}, AGGAAGAGGGTTAGGCGTGGTTGTGTG {SEQ ID NO:16829}, TGAGGAAGAGGGTTAGGCGTGGTTGTGT {SEQ ID NO:16830} |
| Target1777 | chr20:48626370-48626406 | GCGTAGGTTGGTTGCGATGTTTGTTTTTT {SEQ ID NO:16831}, GCGTAGGTTGGTTGCGATGTTTGTTTTTTG {SEQ ID NO:16832}, GCGTAGGTTGGTTGCGATGTTTGTTTTTTGT {SEQ ID NO:16833}, AGGTCGATTAGGAGGGTGTTATGGGTTTTG {SEQ ID NO:16834}, GGTTCGATTAGGAGGGTGTTATGGGTTTTGA {SEQ ID NO:16835}, GGCGTTCGGGTTGCGAGGGGTTTTC {SEQ ID NO:16836}, GTTTGGAGGGGCGTTCGGGTTGCGAG {SEQ ID NO:16837}, GGGCGTTCGGGTTGCGAGGGGTTTTC {SEQ ID NO:16838}, GTTTGGAGGGGCGTTCGGGTTGCGAGG {SEQ ID NO:16839}, GGTTTGGAGGGGCGTTCGGGTTGCGAG {SEQ ID NO:16840} |
| Target1778 | chr20:48626473-48626498 | GCGTAGGTTGGTTGCGATGTTTGTTTTTT {SEQ ID NO:16841}, GCGTAGGTTGGTTGCGATGTTTGTTTTTTG {SEQ ID NO:16842}, GCGTAGGTTGGTTGCGATGTTTGTTTTTTGT {SEQ ID NO:16843}, TGAATTTGGAGTTTTGGAGGTTGCGTTTGT {SEQ ID NO:16844}, TGAATTTGGAGTTTTGGAGGTTGCGTTTGTC {SEQ ID NO:16845}, GGGTTAGTTTGGCGACGCGTTGTTTGC {SEQ ID NO:16846}, CGTAGGGTTAGTTTGGCGACGCGTTGT {SEQ ID NO:16847}, ACGTAGGGTTAGTTTGGCGACGCGTTG {SEQ ID NO:16848}, AGGGTTAGTTTGGCGACGCGTTGTTTGC {SEQ ID NO:16849}, CGTAGGGTTAGTTTGGCGACGCGTTGTT {SEQ ID NO:16850} |
| Target1779 | chr20:48626514-48626622 | GAAAAATTCGGAGGTGGAAGGCGAGGCG {SEQ ID NO:16851}, GCGTGGAAAAATTCGGAGGTGGAAGGCG {SEQ ID NO:16852}, GGAAAAATTCGGAGGTGGAAGGCGAGGC {SEQ ID NO:16853}, TGCGTGGAAAAATTCGGAGGTGGAAGGC {SEQ ID NO:16854}, CGTGGAAAAATTCGGAGGTGGAAGGCGA {SEQ ID NO:16855}, GCGGGGGGTGGTCGTCGTTTTTAGTTCG {SEQ ID NO:16856}, CGCGGGGGGTGGTCGTCGTTTTTAGTTC {SEQ ID NO:16857}, GGGTTAGTTTGGCGACGCGTTGTTTGC {SEQ ID NO:16858}, CGGGGGGTGGTCGTCGTTTTTAGTTCGG {SEQ ID NO:16859}, CGTAGGGTTAGTTTGGCGACGCGTTGT {SEQ ID NO:16860} |
| Target1780 | chr20:48626638-48626648 | GAAAAATTCGGAGGTGGAAGGCGAGGCG {SEQ ID NO:16861}, GCGTGGAAAAATTCGGAGGTGGAAGGCG {SEQ ID NO:16862}, GGAAAAATTCGGAGGTGGAAGGCGAGGC {SEQ ID NO:16863}, TGCGTGGAAAAATTCGGAGGTGGAAGGC {SEQ ID NO:16864}, GTTTTATTGAGGGGGGTCGGTAGCGGCG {SEQ ID NO:16865}, GCGGGGGGTGGTCGTCGTTTTTAGTTCG {SEQ ID NO:16866}, CGCGGGGGGTGGTCGTCGTTTTTAGTTC {SEQ ID NO:16867}, CGGGGGGTGGTCGTCGTTTTTAGTTCGG {SEQ ID NO:16868}, AATGCGCGGGGGGTGGTCGTCGTTTTTA {SEQ ID NO:16869}, GGGGGTGGTCGTCGTTTTTAGTTCGGT {SEQ ID NO:16870} |
| Target1781 | chr20:48626653-48626682 | GAAAAATTCGGAGGTGGAAGGCGAGGCG {SEQ ID NO:16871}, GCGTGGAAAAATTCGGAGGTGGAAGGCG {SEQ ID NO:16872}, GGAAAAATTCGGAGGTGGAAGGCGAGGC {SEQ ID NO:16873}, TGCGTGGAAAAATTCGGAGGTGGAAGGC {SEQ ID NO:16874}, TTTTATTGAGGGGGGTCGGTAGCGGCGG {SEQ ID NO:16875}, GCGGGGGGTGGTCGTCGTTTTTAGTTCG {SEQ ID NO:16876}, CGCGGGGGGTGGTCGTCGTTTTTAGTTC {SEQ ID NO:16877}, CGGGGGGTGGTCGTCGTTTTTAGTTCGG {SEQ ID NO:16878}, AATGCGCGGGGGGTGGTCGTCGTTTTTA {SEQ ID NO:16879}, GGGGGTGGTCGTCGTTTTTAGTTCGGT {SEQ ID NO:16880} |
| Target1782 | chr20:48626757-48626767 | GTCGGGTTGGGGGCGGCGATTATTTTC {SEQ ID NO:16881}, AGTCGGGTTGGGGGCGGCGATTATTTT {SEQ ID NO:16882}, GAGTCGGGTTGGGGGCGGCGATTATTT {SEQ ID NO:16883}, GTCGGGTTGGGGGCGGCGATTATTTTT {SEQ ID NO:16884}, TCGGGTTGGGGGCGGCGATTATTTTC {SEQ ID NO:16885}, GGGGACGGTGAGGGCGTTTTTTGTTTT {SEQ ID NO:16886}, GGGGACGGTGAGGGCGTTTTTTGTTTTT {SEQ ID NO:16887}, GGGGACGGTGAGGGCGTTTTTTGTTT {SEQ ID NO:16888}, TTTTTTATTTGTCGGTCGGGGCGCGT {SEQ ID NO:16889}, GGGACGGTGAGGGCGTTTTTTGTTTTT {SEQ ID NO:16890} |

FIGURE 5 CONTINUED

| | | |
|---|---|---|
| Target1783 | chr20:55202029-55202049 | GGGGACGTTGGAGGGAGGTTGTTTTGG (SEQ ID NO:16891), GGGGACGTTGGAGGGAGGTTGTTTTGGA (SEQ ID NO:16892), GGGACGTTGGAGGGAGGTTGTTTTGGA (SEQ ID NO:16893), GGGGACGTTGGAGGGGAGGTTGTTTTGGAT (SEQ ID NO:16894), GGGACGTTGGAGGGAGGTTGTTTTGGAT (SEQ ID NO:16895), TTTTGGGTCGGTATTTAGGTACGCGCG (SEQ ID NO:16896), TTTTTGGGTCGGTATTTAGGTACGCGCG (SEQ ID NO:16897), GGTTTTTGGGTCGGTATTTAGGTACGCGCG (SEQ ID NO:16898), CGGTTTTTGGGTCGGTATTTAGGTACGCGC (SEQ ID NO:16899), TTTGGGTCGGTATTTAGGTACGCGCG (SEQ ID NO:16900) |
| Target1784 | chr20:55202128-55202302 | CGCGCGTGTTTGGGTGTCGGTTTAGAA (SEQ ID NO:16901), GAGGGTAGCGTCGGGGTTTAGGGAAGT (SEQ ID NO:16902), AGAGGGTAGCGTCGGGGTTTAGGGAAG (SEQ ID NO:16903), AGGGTAGCGTCGGGGTTTAGGGAAGTT (SEQ ID NO:16904), TTTTCGTATAGAGGGCGCGGAGGTTGC (SEQ ID NO:16905), GGAGTCGATGGGTATTGAGGGGTTCGCGT (SEQ ID NO:16906), GGAGTCGATGGGTATTGAGGGTTCGCG (SEQ ID NO:16907), GGGGAGTCGATGGGTATTGAGGGTTCGCG (SEQ ID NO:16908), GGGGAGTCGATGGGTATTGAGGGTTCGC (SEQ ID NO:16909), AGGGGAGTCGATGGGTATTGAGGGTTCGC (SEQ ID NO:16910) |
| Target1785 | chr20:55202320-55202359 | GGTACGGTGTTGCGCGAGTTTTTAGTGT (SEQ ID NO:16911), GGTACGGTGTTGCGCGAGTTTTTAGTG (SEQ ID NO:16912), ACGGTGTTGCGCGAGTTTTTAGTGTTT (SEQ ID NO:16913), GTACGGTGTTGCGCGAGTTTTTAGTGT (SEQ ID NO:16914), ACGTTTTTAGGCGGGGAGGTATATCGGT (SEQ ID NO:16915), TGGGGTTCGGAATGGGTAAGAAGGTGT (SEQ ID NO:16916), ACGTTGGGGTTCGGAATGGGTAAGAAGGT (SEQ ID NO:16917), CGTTGGGGTTCGGAATGGGTAAGAAGGT (SEQ ID NO:16918), ACGTTGGGGTTCGGAATGGGTAAGAAGG (SEQ ID NO:16919), CGTTGGGGTTCGGAATGGGTAAGAAGG (SEQ ID NO:16920) |
| Target1786 | chr20:55964847-55964886 | TAGTAGGGGAGGGGTTTTAGGTAGGCG (SEQ ID NO:16921), AGTAGGGGAGGGGTTTTAGGTAGGCG (SEQ ID NO:16922), ATAGTAGGGGAGGGGTTTTAGGTAGGCG (SEQ ID NO:16923), AATAGTAGGGGAGGGGTTTTAGGTAGGCG (SEQ ID NO:16924), TCGTAGCGTTTAAATAGTAGGGGAGGGGT (SEQ ID NO:16925), TCGGTTTTGTGTGTTCGTTTGTTTGGAGT (SEQ ID NO:16926), TCGGTTTTGTGTGTTCGTTTGTTTGGAGTT (SEQ ID NO:16927), TTCGGTTTTGTGTGTTCGTTTGTTTGGAGT (SEQ ID NO:16928), CGGTTTTGTGTGTTCGTTTGTTTGGAGTT (SEQ ID NO:16929) |
| Target1787 | chr20:55964964-55964999 | GCGAAGGAAGGAGAGGAAATTACGCGGG (SEQ ID NO:16930), AGTAGGGGAGGGGTTTTAGGTAGGCGA (SEQ ID NO:16931), ATAGGGTCGGGGAGGTGGGAAATTTCG (SEQ ID NO:16932), GCGAAGGAAGGAGAGGAAATTACGCGGGA (SEQ ID NO:16933), GCGAAGGAAGGAGAGGAAATTACGCGG (SEQ ID NO:16934), AGTTTTTTGTATAGTGGGGATGGGATTTTCGAGT (SEQ ID NO:16935), AGTTTTTTGTATAGTGGGGATGGGATTTTCGAGTT (SEQ ID NO:16936), TAGTTTTTTGTATAGTGGGGATGGGATTTTCGAGT (SEQ ID NO:16937), GTTTTTTGTATAGTGGGGATGGGATTTTCGAGTT (SEQ ID NO:16938), AGTTTTTTGTATAGTGGGGATGGGATTTTCGAGTTT (SEQ ID NO:16939) |
| Target1788 | chr20:55965199-55965345 | GTGGGGGAGGGGGCGGGTAGATTTTTT (SEQ ID NO:16940), TGAGAGGAGGTCGTAGGGTTGGGGTCG (SEQ ID NO:16941), GTTGAGAGGAGGTCGTAGGGTTGGGGT (SEQ ID NO:16942), TGTTGAGAGGAGGTCGTAGGGTTGGGG (SEQ ID NO:16943), TGTTGAGAGGAGGTCGTAGGGTTGGGGT (SEQ ID NO:16944), CGTAGGTGGGGTTTGTGGGGATTGGGA (SEQ ID NO:16945), ACGTAGGTGGGGTTTGTGGGGATTGGG (SEQ ID NO:16946), AGGTGGGGTTTGTGGGGATTGGGAGTG (SEQ ID NO:16947), GTGGGGTTTGTGGGGATTGGGAGTGGT (SEQ ID NO:16948), GCGACGTAGGTGGGGTTTGTGGGGATT (SEQ ID NO:16949) |
| Target1789 | chr20:55965436-55965498 | GGGTTGGAGATGAGGCGGGTTTGAGGT (SEQ ID NO:16950), TGAGAGGAGGTCGTAGGGTTGGGGTCG (SEQ ID NO:16951), GTCGTAGGGTTGGGGTCGGGAGTGATT (SEQ ID NO:16952), GGGGTTGGAGATGAGGCGGGTTTGAGG (SEQ ID NO:16953), GGGGGTTGGAGATGAGGCGGGTTTGAG (SEQ ID NO:16954), AGATTTCGGGATTTCGGATTTGCGGGT (SEQ ID NO:16955), GATTTCGGGATTTCGGATTTGCGGGT (SEQ ID NO:16956), AGATTTCGGGATTTCGGATTTGCGGGTT (SEQ ID NO:16957), TAGATTTCGGGATTTCGGATTTGCGGGT (SEQ ID NO:16958), GATTTCGGGATTTCGGATTTGCGGGT (SEQ ID NO:16959) |
| Target1790 | chr20:57638469-57638543 | TTGAGGTTGTGTATATGATTTTGGTAGTGTCGGA (SEQ ID NO:16960), TGAGGTTGTGTATATGATTTTGGTAGTGTCGGATT (SEQ ID NO:16961), TTGAGGTTGTGTATATGATTTTGGTAGTGTCGGAT (SEQ ID NO:16962), ATTGAGGTTGTGTATATGATTTTGGTAGTGTCGGA (SEQ ID NO:16963), AGGTTGTGTATATGATTTTGGTAGTGTCGGATTTGT (SEQ ID NO:16964) |
| Target1791 | chr20:61200973-61201023 | TCGGTGGTGGGTAGTTTGGTCGGATGG (SEQ ID NO:16965), AGAGTCGGTGGTGGGTAGTTTGGTCGG (SEQ ID NO:16966), GAGTCGGTGGTGGGTAGTTTGGTCGGA (SEQ ID NO:16967), AGTCGGTGGTGGGTAGTTTGGTCGGAT (SEQ ID NO:16968), GGTGGTGGGTAGTTTGGTCGGATGGC (SEQ ID NO:16969), GCGGGGTGGGGGGAGTTTTTTCGTTTT (SEQ ID NO:16970), TAGCGGGGTGGGGGGAGTTTTTTCGTT (SEQ ID NO:16971), GGTAGTAGTAGCGGGGTGGGGGGAGTT (SEQ ID NO:16972), AGTAGCGGGGTGGGGGGAGTTTTTTCG (SEQ ID NO:16973), GTAGCGGGGTGGGGGGAGTTTTTTCGT (SEQ ID NO:16974) |

FIGURE 5 CONTINUED

Target1792    chr20:61201058-61201077    TCGGTGGTGGGTAGTTTGGTCGGATGG (SEQ ID NO:16975), TGGGTAGTTTGGTCGGATGGCGGTGAT (SEQ ID NO:16976), GTGGGTAGTTTGGTCGGATGGCGGTGA (SEQ ID NO:16977), AGAGTCGGTGGTGGGTAGTTTGGTCGG (SEQ ID NO:16978), GAGTCGGTGGTGGGTAGTTTGGTCGGA (SEQ ID NO:16979), GGGGGACGCGGGGGGGTAGTAGTAGT (SEQ ID NO:16980), GGGGGACGCGGGGGGGTAGTAGTAG (SEQ ID NO:16981), GGGGACGCGGGGGGGTAGTAGTAGT (SEQ ID NO:16982), GGGGGACGCGGGGGGGTAGTAGTA (SEQ ID NO:16983), GGGGGACGCGGGGGGGTAGTAGT (SEQ ID NO:16984)

Target1793    chr20:61201085-61201167    CGGGAGGCGGATGGGTCGTGATAGTTT (SEQ ID NO:16985), TCGGTGGTGGGTAGTTTGGTCGGATGG (SEQ ID NO:16986), TGGGTAGTTTGGTCGGATGGCGGTGAT (SEQ ID NO:16987), GTGGGTAGTTTGGTCGGATGGCGGTGA (SEQ ID NO:16988), AGAGTCGGTGGTGGGTAGTTTGGTCGG (SEQ ID NO:16989), CGGTAGGAGGTGTTTTTGATCGCGTGGT (SEQ ID NO:16990), CGGTAGGAGGTGTTTTTGATCGCGTGG (SEQ ID NO:16991), GGTAGGAGGTGTTTTTGATCGCGTGGT (SEQ ID NO:16992), TGATCGCGTGGTTGTTGGAAAGGAGT (SEQ ID NO:16993), CGGTAGGAGGTGTTTTTGATCGCGTGGTT (SEQ ID NO:16994)

Target1794    chr20:61201174-61201292    CGGGAGGCGGATGGGTCGTGATAGTTT (SEQ ID NO:16995), GGCGTTGGGAGAGGTTTTGAGTTCGGG (SEQ ID NO:16996), GCGTTGGGAGAGGTTTTGAGTTCGGGT (SEQ ID NO:16997), TGGCGTTGGGAGAGGTTTTGAGTTCGG (SEQ ID NO:16998), CGGGAGGCGGATGGGTCGTGATAGTT (SEQ ID NO:16999), GGGTTGGGTAGGTGTTGCGGTAGGAGG (SEQ ID NO:17000), GGTTGGGTAGGTGTTGCGGTAGGAGGT (SEQ ID NO:17001), AGGGTTGGGTAGGTGTTGCGGTAGGAG (SEQ ID NO:17002), AGAGGGTTGGGTAGGTGTTGCGGTAGG (SEQ ID NO:17003), GAGGGTTGGGTAGGTGTTGCGGTAGGA (SEQ ID NO:17004)

Target1795    chr20:62690139-62690172    TAGTAGCGAGTGTGGGGGTGCGAGGTA (SEQ ID NO:17005), GCGAGTGTGGGGGTGCGAGGTAGTTTT (SEQ ID NO:17006), TAGCGAGTGTGGGGGTGCGAGGTAGTT (SEQ ID NO:17007), TAGTAGTAGCGAGTGTGGGGGTGCGAG (SEQ ID NO:17008), AGTAGCGAGTGTGGGGGTGCGAGGTAG (SEQ ID NO:17009), TGGTTAGTTGGGTTCGTGGTTGATTCGGT (SEQ ID NO:17010), GGTTAGTTGGGTTCGTGGTTGATTCGGT (SEQ ID NO:17011), TGGTTAGTTGGGTTCGTGGTTGATTCGG (SEQ ID NO:17012), GGTTAGTTGGGTTCGTGGTTGATTCGG (SEQ ID NO:17013), TTGGTTAGTTGGGTTCGTGGTTGATTCGG (SEQ ID NO:17014)

Target1796    chr21:36041376-36041404    GCGGGTCGGGTATTTTTAAAGGCGTAGG (SEQ ID NO:17015), AGCGGGTCGGGTATTTTTAAAGGCGTA (SEQ ID NO:17016), TAGCGGGTCGGGTATTTTTAAAGGCGT (SEQ ID NO:17017), AGCGGGTCGGGTATTTTTAAAGGCGTAGG (SEQ ID NO:17018), GCGGGTCGGGTATTTTTAAAGGCGTAGGA (SEQ ID NO:17019), GCGTAGGATTCGTAGGGTAAATTTCGTTTGG (SEQ ID NO:17020), GCGTAGGATTCGTAGGGTAAATTTCGTTTGGT (SEQ ID NO:17021), GCGTAGGATTCGTAGGGTAAATTTCGTTTGTT (SEQ ID NO:17022), GCGTAGGATTCGTAGGGTAAATTTCGTTTGGTTT (SEQ ID NO:17023), GCGTAGGATTCGTAGGGTAAATTTCGTTTGGTTTT (SEQ ID NO:17024)

Target1797    chr21:36041417-36041426    GCGGGTCGGGTATTTTTAAAGGCGTAGG (SEQ ID NO:17025), AGCGGGTCGGGTATTTTTAAAGGCGTA (SEQ ID NO:17026), TAGCGGGTCGGGTATTTTTAAAGGCGT (SEQ ID NO:17027), AGCGGGTCGGGTATTTTTAAAGGCGTAGG (SEQ ID NO:17028), GCGGGTCGGGTATTTTTAAAGGCGTAGGA (SEQ ID NO:17029), AGTCGGGGTATTGGGGTTTTGCGTAGG (SEQ ID NO:17030), GTCGGGGTATTGGGGTTTTGCGTAGGA (SEQ ID NO:17031), AGTCGGGGTATTGGGGTTTTGCGTAGGA (SEQ ID NO:17032), TCGGGGTATTGGGGTTTTGCGTAGGAT (SEQ ID NO:17033), TGGGGTTTTGCGTAGGATTCGTAGGGT (SEQ ID NO:17034)

Target1798    chr21:36041518-36041546    GGGCGTAGAGGTTTGGGGTTAAGCGGA (SEQ ID NO:17035), AGGGGCGTAGAGGTTTGGGGTTAAGCG (SEQ ID NO:17036), GGGTAGAAGGGGCGTAGAGGTTTGGGG (SEQ ID NO:17037), GGTAGAAGGGGCGTAGAGGTTTGGGGT (SEQ ID NO:17038), TGGGTAGAAGGGGCGTAGAGGTTTGGG (SEQ ID NO:17039), TTAAGGGTCGGTGGCGTTGGGTAAGGG (SEQ ID NO:17040), CGTTGTTTAAGGGTCGGTGGCGTTGGG (SEQ ID NO:17041), ACGTTGTTTAAGGGTCGGTGGCGTTGG (SEQ ID NO:17042), GTTGTTTAAGGGTCGGTGGCGTTGGGT (SEQ ID NO:17043), TGACGTTGTTTAAGGGTCGGTGGCGTT (SEQ ID NO:17044)

Target1799    chr21:36041605-36041627    GGGCGTAGAGGTTTGGGGTTAAGCGGA (SEQ ID NO:17045), GGCGTAGAGGTTTGGGGTTAAGCGGAG (SEQ ID NO:17046), GGCGTAGAGGTTTGGGGTTAAGCGGAGT (SEQ ID NO:17047), GCGTAGAGGTTTGGGGTTAAGCGGAGT (SEQ ID NO:17048), GGGCGTAGAGGTTTGGGGTTAAGCGGAG (SEQ ID NO:17049), TTTTCGGCGGTTTTTGGGGATTCGGGG (SEQ ID NO:17050), CGGGGATTTTCGGCGGTTTTTGGGGAT (SEQ ID NO:17051), TTAAGGGTCGGTGGCGTTGGGTAAGGG (SEQ ID NO:17052), CGTTGTTTAAGGGTCGGTGGCGTTGGG (SEQ ID NO:17053), ACGTTGTTTAAGGGTCGGTGGCGTTGG (SEQ ID NO:17054)

Target1800    chr21:36041632-36041810    TAGGGGTCGTCGGAGGTTTTCGCGTTT (SEQ ID NO:17055), TTAGGGGTCGTCGGAGGTTTTCGCGTT (SEQ ID NO:17056), TTTAGGGGTCGTCGGAGGTTTTCGCGT (SEQ ID NO:17057), GGAGTCGGAGGGGGTTGTTTCGGGTTT (SEQ ID NO:17058), TCGGGTTTTTAGGGGTCGTCGGAGGTT (SEQ ID NO:17059), TCGGCGGTTTTTGGGGATTCGGGGTAA (SEQ ID NO:17060), CGGGTTTTTTAGTTAGAGGCGCGGGGA (SEQ ID NO:17061), TCGGGTTTTTTAGTTAGAGGCGCGGGG (SEQ ID NO:17062), CGGGGATTTTCGGCGGTTTTTGGGGA (SEQ ID NO:17063), TCGGGTTTTTTAGTTAGAGGCGCGGGGA (SEQ ID NO:17064)

FIGURE 5 CONTINUED

Target1801   chr21:36041819-36041924   TAGGGGTCGTCGGAGGTTTTCGCGTTT (SEQ ID NO:17065), TTAGGGGTCGTCGGAGGTTTTCGCGTT (SEQ ID NO:17066), TTTAGGGGTCGTCGGAGGTTTTCGCGT (SEQ ID NO:17067), TAGGAGGCGGCGGGTTAGATAGGGGTT (SEQ ID NO:17068), AGGAGGTAGGAGGCGGCGGGTTAGATA (SEQ ID NO:17069), TTTTTGGGGTATTTCGGTATTTTTCGGGGTTT (SEQ ID NO:17070), TTTTTTGGGGTATTTCGGTATTTTTCGGGGTTT (SEQ ID NO:17071), TTTTTTGGGGTATTTCGGTATTTTTCGGGGTTT (SEQ ID NO:17072)

Target1802   chr21:38068859-38068902   TTGGAGGGGGAGTTTCGGGTTTTCGGA (SEQ ID NO:17073), GTTGGAGGGGGAGTTTCGGGTTTTCGG (SEQ ID NO:17074), GTTGGAGGGGGAGTTTCGGGTTTTCGGA (SEQ ID NO:17075), TGTTGGAGGGGGAGTTTCGGGTTTTCGG (SEQ ID NO:17076), TGGAGGGGGAGTTTCGGGTTTTCGGA (SEQ ID NO:17077)

Target1803   chr21:38068930-38069012   CGTAGTTGTGGTTTTGGGGTTTTTGATGGT (SEQ ID NO:17078), CGTAGTTGTGGTTTTGGGGTTTTTGATGGTA (SEQ ID NO:17079), CGTAGTTGTGGTTTTGGGGTTTTTGATGGTAT (SEQ ID NO:17080), TTGTGGTTTTGGGGTTTTTGATGGTATTACGT (SEQ ID NO:17081), GTTGTGGTTTTGGGGTTTTTGATGGTATTACGT (SEQ ID NO:17082)

Target1804   chr21:38069018-38069046   CGTAGTTGTGGTTTTGGGGTTTTTGATGGT (SEQ ID NO:17083), CGTAGTTGTGGTTTTGGGGTTTTTGATGGTA (SEQ ID NO:17084), CGTAGTTGTGGTTTTGGGGTTTTTGATGGTAT (SEQ ID NO:17085), TTGTGGTTTTGGGGTTTTTGATGGTATTACGT (SEQ ID NO:17086), GTTGTGGTTTTGGGGTTTTTGATGGTATTACGT (SEQ ID NO:17087)

Target1805   chr21:38069497-38070022   CGTAGTTAGGAGCGGGATTTTGGGCGC (SEQ ID NO:17088), GCGTAGTTAGGAGCGGGATTTTGGGCG (SEQ ID NO:17089), CGCGGAGGTGGGTTCGATTCGTTAGGT (SEQ ID NO:17090), GGTAGGGGGAGAGTTCGGGTTTGCGTA (SEQ ID NO:17091), GGAAGTTGCGGTAGGGGTTGGGTTCGT (SEQ ID NO:17092), AGTAGAGGGTTATGGGTTAGCGGCGCG (SEQ ID NO:17093), GGTTATGGGTTAGCGGCGCGGGTTTTT (SEQ ID NO:17094), TGGGTTAGCGGCGCGGGTTTTTAATGT (SEQ ID NO:17095), GTAGAGGGTTATGGGTTAGCGGCGCGG (SEQ ID NO:17096), GGTTATGGGTTAGCGGCGCGGGTTTT (SEQ ID NO:17097)

Target1806   chr21:38076700-38077017   GAAAGGGGAGTTTCGGGCGGTTGTGGG (SEQ ID NO:17098), TCGGAGTTAGTAGTTGTTGGGGCGGCG (SEQ ID NO:17099), CGCGGGGGTTAGAGGAGGGGATTTGGAT (SEQ ID NO:17100), TAGCGCGGGGTTAGAGGAGGGGATTTG (SEQ ID NO:17101), CGGAGTTAGTAGTTGTTGGGGCGGCGT (SEQ ID NO:17102), CGATGGGGAGGGGTAGGGAAGGAGGTT (SEQ ID NO:17103), GTCGATGGGGAGGGGTAGGGAAGGAGG (SEQ ID NO:17104), GGTCGATGGGGAGGGGTAGGGAAGGAG (SEQ ID NO:17105), TCGATGGGGAGGGGTAGGGAAGGAGG (SEQ ID NO:17106), TCGATGGGGAGGGGTAGGGAAGGAGGT (SEQ ID NO:17107)

Target1807   chr21:38077042-38077158   TCGGAGTTAGTAGTTGTTGGGGCGGCG (SEQ ID NO:17108), CGGAGTTAGTAGTTGTTGGGGCGGCGT (SEQ ID NO:17109), GGAGTTAGTAGTTGTTGGGGCGGCGTT (SEQ ID NO:17110), GGAGTTTCGGGCGGTTGTGGGTGTC (SEQ ID NO:17111), GAGTTTCGGGCGGTTGTGGGTGTCG (SEQ ID NO:17112), AATTGGGGATCGGGTGAGAAGGGGGTG (SEQ ID NO:17113), CGATGGGGAGGGGTAGGGAAGGAGGTT (SEQ ID NO:17114), AAATTGGGGATCGGGTGAGAAGGGGGT (SEQ ID NO:17115), GTCGATGGGGAGGGGTAGGGAAGGAGG (SEQ ID NO:17116), GGTCGATGGGGAGGGGTAGGGAAGGAG (SEQ ID NO:17117)

Target1808   chr21:38119951-38120471   GATTCGGTTTTTCGGGGTTGCGCGCGTT (SEQ ID NO:17118), GTCGTGCGTAGGTTCGGCGAGGATATC (SEQ ID NO:17119), CGCGTTGGGTTCGGTTAAAGTCGTTCG (SEQ ID NO:17120), CGCGTTGGGTTCGGTTAAAGTCGTTCGT (SEQ ID NO:17121), ATTCGGTTTTTCGGGGTTGCGGCGTT (SEQ ID NO:17122), GGGAGGTCGGGTTTAGGTTTTTGGCGC (SEQ ID NO:17123), CGAGGCGTTTAGGTAGTGCGGTAGGGG (SEQ ID NO:17124), CGGGAGGTCGGGTTTAGGTTTTTGGCG (SEQ ID NO:17125), GAGGTCGGGTTTAGGTTTTTGGCGCGG (SEQ ID NO:17126), GGAGGTCGGGTTTAGGTTTTTGGCGCG (SEQ ID NO:17127)

Target1809   chr21:38120515-38120542   TCGGTTTTTCGGGGTTGCGGCGTTATC (SEQ ID NO:17128), TTCGGTTTTTCGGGGTTGCGGCGTTAT (SEQ ID NO:17129), ATTCGGTTTTTCGGGGTTGCGGCGTTA (SEQ ID NO:17130), TTGGATTCGGTTTTTCGGGGTTGCGGC (SEQ ID NO:17131), GATTCGGTTTTTCGGGGTTGCGGCGTT (SEQ ID NO:17132), GGTTTTCGTAGGATAGAGGCGGGCGGT (SEQ ID NO:17133), CGGTTTTCGTAGGATAGAGGCGGGCGG (SEQ ID NO:17134), GGTTTTCGTAGGATAGAGGCGGGCGGTT (SEQ ID NO:17135), AGAGGCGGGCGGTTATTTGTTCGGATT (SEQ ID NO:17136), GTTTTCGTAGGATAGAGGCGGGCGGTT (SEQ ID NO:17137)

Target1810   chr21:38120552-38120571   GGTTTTCGTAGGATAGAGGCGGGCGGT (SEQ ID NO:17138), CGGTTTTCGTAGGATAGAGGCGGGCGG (SEQ ID NO:17139), GGTTTTCGTAGGATAGAGGCGGGCGGTT (SEQ ID NO:17140), AGAGGCGGGCGGTTATTTGTTCGGATT (SEQ ID NO:17141), GTTTTCGTAGGATAGAGGCGGGCGGTT (SEQ ID NO:17142)

Target1811   chr21:38120577-38120588   GGTTTTCGTAGGATAGAGGCGGGCGGT (SEQ ID NO:17143), CGGTTTTCGTAGGATAGAGGCGGGCGG (SEQ ID NO:17144), GGTTTTCGTAGGATAGAGGCGGGCGGTT (SEQ ID NO:17145), AGAGGCGGGCGGTTATTTGTTCGGATT (SEQ ID NO:17146), GTTTTCGTAGGATAGAGGCGGGCGGTT (SEQ ID NO:17147)

Target1812   chr21:45604990-45605084   AGCGAAGTTACGGGGTTGGGTTAGGTT (SEQ ID NO:17148), TAGCGAAGTTACGGGGTTGGGTTAGGT (SEQ ID NO:17149), GCGAAGTTACGGGGTTGGGTTAGGTTT (SEQ ID NO:17150), AGCGAAGTTACGGGGTTGGGTTAGGTTT (SEQ ID NO:17151), GTTGTTTGGGGGTATTGGGGTGGAAGT

FIGURE 5 CONTINUED

|  |  |  |
|---|---|---|
|  |  | {SEQ ID NO:17152}, GGGTAGGGGTTGGAAGTTTGGGTAGGGG {SEQ ID NO:17153}, TGGGTAGGGGTTAGGATGAAGTGGGGT {SEQ ID NO:17154}, GGTAGGGGTTGGAAGTTTGGGTAGGGGT {SEQ ID NO:17155}, TGGGTAGGGGTTGGAAGTTTGGGTAGGG {SEQ ID NO:17156}, GGGGTAGTTGTGGGTAGGGGTTGGAAGT {SEQ ID NO:17157} |
| Target1813 | chr21:46372625-46372666 | GGGTGTTCGTGTTATGTGTTTCGGGCG {SEQ ID NO:17158}, GGGTGTTCGTGTTATGTGTTTCGGGCGT {SEQ ID NO:17159}, TGGGTGTTCGTGTTATGTGTTTCGGGCG {SEQ ID NO:17160}, GGTGTTCGTGTTATGTGTTTCGGGC {SEQ ID NO:17161}, TGGGTGTTCGTGTTATGTGTTTCGGGC {SEQ ID NO:17162}, CGTTTTTTAGGTAGGGGGGCGTTCGGA {SEQ ID NO:17163}, TCGTTTTTTAGGTAGGGGGGCGTTCGG {SEQ ID NO:17164}, TCGTTTTTTAGGTAGGGGGGCGTTCGGA {SEQ ID NO:17165}, CGTCGTTTTTTAGGTAGGGGGGCGTTCG {SEQ ID NO:17166}, GTCGTTTTTTAGGTAGGGGGGCGTTCGG {SEQ ID NO:17167} |
| Target1814 | chr22:17082736-17083133 | GCGGCGGCGGGAGTTTTTTAAGAGGAG {SEQ ID NO:17168}, CGGCGGCGGGAGTTTTTTAAGAGGAGG {SEQ ID NO:17169}, GGCGGCGGGAGTTTTTTAAGAGGAGGA {SEQ ID NO:17170}, GCGGCGGCGGGAGTTTTTTAAGAGGA {SEQ ID NO:17171}, CGGCGGCGGGAGTTTTTTAAGAGGAGGA {SEQ ID NO:17172}, GGGGTGGTGGTTGCGGTTGTTTTACGT {SEQ ID NO:17173}, GGGGGGTGGTGGTTGCGGTTGTTTTAC {SEQ ID NO:17174}, GTTCGGTGGTAGTTTCGGTTCGGCGTC {SEQ ID NO:17175}, CGGGGTTTTAGGTTTTTCGGGGGGGTGG {SEQ ID NO:17176}, CGGGGTCGGGGTTTTAGGTTTTTCGGG {SEQ ID NO:17177} |
| Target1815 | chr22:17083251-17083588 | CGTGGGCGTTCGGGAAATTCGGAGTTG {SEQ ID NO:17178}, TCGGGTCGGAGTTGTTATCGGGCGTTC {SEQ ID NO:17179}, GTGGGCGTTCGGGAAATTCGGAGTTGT {SEQ ID NO:17180}, GGGTCGGAGTTGTTATCGGGCGTTCGT {SEQ ID NO:17181}, GTCGGGTCGGAGTTGTTATCGGGCGTT {SEQ ID NO:17182}, CGGAGTTCGTTCGGGGATTATTTGCGC {SEQ ID NO:17183}, CGGTTCGGCGGTTCGTTCGGAGTTC {SEQ ID NO:17184}, ACGGTTCGGCGGTTCGTTCGGAGTTC {SEQ ID NO:17185}, ACGGTTCGGCGGTTCGTTCGGAGTT {SEQ ID NO:17186}, CGGTTCGGCGGTTCGTTCGGAGTT {SEQ ID NO:17187} |
| Target1816 | chr22:19753253-19753377 | GAGGTCGGGTGGTTTAGGTTGTAGGGT {SEQ ID NO:17188}, CGTAGAGGAGGGGTAGACGTGGATTGGT {SEQ ID NO:17189}, CGTAGAGGAGGGGTAGACGTGGATTGG {SEQ ID NO:17190}, TCGTAGAGGAGGGGTAGACGTGGATTGGT {SEQ ID NO:17191}, TCGTAGAGGAGGGGTAGACGTGGATTGG {SEQ ID NO:17192}, TGCGTGATTTGTAGGGAGGTGGGTGTG {SEQ ID NO:17193}, TGCGTGATTTGTAGGGAGGTGGGTGTGA {SEQ ID NO:17194}, GCGTGATTTGTAGGGAGGTGGGTGTGA {SEQ ID NO:17195}, TTGCGTGATTTGTAGGGAGGTGGGTGT {SEQ ID NO:17196}, AGTTGCGTGATTTGTAGGGAGGTGGG {SEQ ID NO:17197} |
| Target1817 | chr22:19753383-19753518 | CGTAGGTTTCGGAATTATCGGTTCGGCG {SEQ ID NO:17198}, CGTAGGTTTCGGAATTATCGGTTCGGCGT {SEQ ID NO:17199}, TCGTAGGTTTCGGAATTATCGGTTCGGCG {SEQ ID NO:17200}, TCGTAGGTTTCGGAATTATCGGTTCGGCGT {SEQ ID NO:17201}, AGGTTTCGGAATTATCGGTTCGGCGTA {SEQ ID NO:17202}, TGTCGTTGGGTTGCGTCGGGGAAGTTA {SEQ ID NO:17203}, TTTTTCGTGTCGTTGGGTTGCGTCGGG {SEQ ID NO:17204}, GTCGTTGGGTTGCGTCGGGGAAGTTAC {SEQ ID NO:17205}, AAAGTTTGGAGCGTTTCGGGGGCGTAG {SEQ ID NO:17206}, GAAAGTTTGGAGCGTTTCGGGGGCGTA {SEQ ID NO:17207} |
| Target1818 | chr22:19754574-19754610 | TTCGATCGGGCGTTTTGGTATTGGCGG {SEQ ID NO:17208}, CGTTTTGGTATTGGCGGGCGGGGATTT {SEQ ID NO:17209}, TTTCGATCGGGCGTTTTGGTATTGGCGG {SEQ ID NO:17210}, CGTTTTGGTATTGGCGGGCGGGGATT {SEQ ID NO:17211}, CGTTTTGGTATTGGCGGGCGGGGATTTT {SEQ ID NO:17212} |
| Target1819 | chr22:19754646-19754757 | TCGAGGGTTAAGGGGGTTTTCGTTCGT {SEQ ID NO:17213}, CGTTAGTGTTAAAGCGTTCGGTCGGAGGC {SEQ ID NO:17214}, TTAGTGTTAAAGCGTTCGGTCGGAGGC {SEQ ID NO:17215}, CGAGGGTTAAGGGGGTTTTCGTTCGTT {SEQ ID NO:17216}, TTCGAGGGTTAAGGGGGTTTTCGTTCG {SEQ ID NO:17217}, TTCGATCGGGCGTTTTGGTATTGGCGG {SEQ ID NO:17218}, CGTTTGTAGGCGGGGTTTTCGGGTTGT {SEQ ID NO:17219}, TCGTTTGTAGGCGGGGTTTTCGGGTTG {SEQ ID NO:17220}, TTTCGATCGGGCGTTTTGGTATTGGCGG {SEQ ID NO:17221}, ATCGTTTGTAGGCGGGGTTTTCGGGTT {SEQ ID NO:17222} |
| Target1820 | chr22:19754775-19754845 | TTAGTGTTAAAGCGTTCGGTCGGAGGC {SEQ ID NO:17223}, GTTAGTGTTAAAGCGTTCGGTCGGAGGC {SEQ ID NO:17224}, GCGGTTCGGTCGGTAGTTGTAGTGTAG {SEQ ID NO:17225}, GCGGTTCGGTCGGTAGTTGTAGTGTAGA {SEQ ID NO:17226}, GGTCGGAGGCGGAAGGAAGTGATATTT {SEQ ID NO:17227}, GGATTGGGGTTGGGGAGGTTTTGAGGG {SEQ ID NO:17228}, GGGATTGGGGTTGGGGAGGTTTTGAGG {SEQ ID NO:17229}, AGGGATTGGGGTTGGGGAGGTTTTGAGG {SEQ ID NO:17230}, GGATTGGGGTTGGGGAGGTTTTGAGGGT {SEQ ID NO:17231}, GATTGGGGTTGGGGAGGTTTTGAGGGT {SEQ ID NO:17232} |
| Target1821 | chr22:19754860-19754896 | GAGAGTTTCGTTTGTAGGCGGTGTAGATATATGT {SEQ ID NO:17233}, GAGAGTTTCGTTTGTAGGCGGTGTAGATATATGTAG {SEQ ID NO:17234}, CGGTAGGGATTGGGGTTGGGGAGGTTT {SEQ ID NO:17235}, TCGGTAGGGATTGGGGTTGGGGAGGTT {SEQ ID NO:17236}, AGTCGGTAGGGATTGGGGTTGGGGAGG {SEQ ID NO:17237}, GGATTGGGGTTGGGGAGGTTTTGAGGG {SEQ ID NO:17238}, GGGATTGGGGTTGGGGAGGTTTTGAGG {SEQ ID NO:17239} |
| Target1822 | chr22:19754970-19754999 | GCGTTGGGAATTTTCGGGATAGCGAGT {SEQ ID NO:17240}, GCGTTGGGAATTTTCGGGATAGCGAGTT {SEQ ID NO:17241}, GCGTTGGGAATTTTCGGGATAGCGAGTTC {SEQ ID NO:17242}, GCGTTGGGAATTTTCGGGATAGCGAG {SEQ ID NO:17243}, CGTTGGGAATTTTCGGGATAGCGAGTTC |

FIGURE 5 CONTINUED

|  |  |  |
|---|---|---|
|  |  | (SEQ ID NO:17244), ACGGTGGGAAGGTGGGGGGAGTGTATA (SEQ ID NO:17245), CGGAGAGGGGAGGGGTAGTGGGAGTTT (SEQ ID NO:17246), GGTAGAGGGTAGGAGGCGTGGCGGATA (SEQ ID NO:17247), TTATGGGGCGGGTAGAGGGTAGGAGGC (SEQ ID NO:17248), CGGTGGGAAGGTGGGGGGAGTGTATAG (SEQ ID NO:17249) |
| Target1823 | chr22:20267833-20267867 | TGGTATTTTGTTGGACGGAGAGAGGAGGT (SEQ ID NO:17250), GGTATTTTGTTGGACGGAGAGAGGAGGT (SEQ ID NO:17251), TGGTATTTTGTTGGACGGAGAGAGGAGG (SEQ ID NO:17252), TTGGTATTTTGTTGGACGGAGAGAGGAGGT (SEQ ID NO:17253), TTGGTATTTTGTTGGACGGAGAGAGGAGG (SEQ ID NO:17254), GGCGGGGGGTAGTCGGGATGGTTGTTT (SEQ ID NO:17255), GGGCGGGGGGTAGTCGGGATGGTTGTTT (SEQ ID NO:17256), GGCGGGGGGTAGTCGGGATGGTTGTT (SEQ ID NO:17257), CGTCGGTTCGGTTTTTTGTGTTTACGCG (SEQ ID NO:17258), GGGCGGGGGGTAGTCGGGATGGTTGTT (SEQ ID NO:17259) |
| Target1824 | chr22:20267909-20267971 | CGCGTGGGTATAAAGGGTCGGGTCGG (SEQ ID NO:17260), GCGTGGGTATAAAGGGTCGGGTCGGC (SEQ ID NO:17261), CGTTTCGGTTCGTTAGGAGAGGAGGGA (SEQ ID NO:17262), TCGTTTCGGTTCGTTAGGAGAGGAGGG (SEQ ID NO:17263), TCGTTTCGGTTCGTTAGGAGAGGAGGGA (SEQ ID NO:17264), CGTCGGTTCGGTTTTTTGTGTTTACGCG (SEQ ID NO:17265), CGTCGGTTCGGTTTTTTGTGTTTACGCGT (SEQ ID NO:17266), TCGTCGGTTCGGTTTTTTGTGTTTACGCG (SEQ ID NO:17267), TCGGTTCGGTTTTTTGTGTTTACGCGT (SEQ ID NO:17268), TCGTCGGTTCGGTTTTTTGTGTTTACGCGT (SEQ ID NO:17269) |
| Target1825 | chr22:20792505-20792517 | GGACGGGAAGGCGGATCGGGGATAC (SEQ ID NO:17270), GGGACGGGAAGGCGGATCGGGGATAC (SEQ ID NO:17271), GGACGGGAAGGCGGATCGGGGATA (SEQ ID NO:17272), GGGACGGGAAGGCGGATCGGGGATA (SEQ ID NO:17273), GCGTTATTGCGTAGGTTAGGTTCGGG (SEQ ID NO:17274), GCGGTGGGGTGTTGTGGAGTTGGTTTT (SEQ ID NO:17275), ATTTCGCGGTGGGGTGTTGTGGAGTTG (SEQ ID NO:17276), GATTTCGCGGTGGGGTGTTGTGGAGTT (SEQ ID NO:17277), AAGGATTTCGCGGTGGGGTGTTGTGGA (SEQ ID NO:17278), AGGATTTCGCGGTGGGGTGTTGTGGAG (SEQ ID NO:17279) |
| Target1826 | chr22:20792557-20792586 | CGGAATCGGTTAAGGGAGTGGGGTTCGT (SEQ ID NO:17280), CGGAATCGGTTAAGGGAGTGGGGTTCG (SEQ ID NO:17281), GGAATCGGTTAAGGGAGTGGGGTTCGT (SEQ ID NO:17282), GGACGGGAAGGCGGATCGGGGATAC (SEQ ID NO:17283), CGGAATCGGTTAAGGGAGTGGGGTTCGTA (SEQ ID NO:17284), GCGGTGGGGTGTTGTGGAGTTGGTTTT (SEQ ID NO:17285), ATTTCGCGGTGGGGTGTTGTGGAGTTG (SEQ ID NO:17286), GATTTCGCGGTGGGGTGTTGTGGAGTT (SEQ ID NO:17287), AAGGATTTCGCGGTGGGGTGTTGTGGA (SEQ ID NO:17288), AGGATTTCGCGGTGGGGTGTTGTGGAG (SEQ ID NO:17289) |
| Target1827 | chr22:20792611-20792651 | CGGAATCGGTTAAGGGAGTGGGGTTCGT (SEQ ID NO:17290), CGGAATCGGTTAAGGGAGTGGGGTTCG (SEQ ID NO:17291), GGAATCGGTTAAGGGAGTGGGGTTCGT (SEQ ID NO:17292), AGTTTTTGTAGTGTTGGGGTGTGCGGT (SEQ ID NO:17293), CGGAATCGGTTAAGGGAGTGGGGTTCGTA (SEQ ID NO:17294), TTGCGAGTTTTGAGTGCGTAGGAGTGC (SEQ ID NO:17295), CGTAGGAGTGCGTAGGGGGAGTTGATT (SEQ ID NO:17296), TTTGCGAGTTTTGAGTGCGTAGGAGTGC (SEQ ID NO:17297), TGCGAGTTTTGAGTGCGTAGGAGTGC (SEQ ID NO:17298), CGTAGGAGTGCGTAGGGGGAGTTGAT (SEQ ID NO:17299) |
| Target1828 | chr22:22006370-22006414 | AGCGTTGCGTTTATTGGTCGGCGTTGG (SEQ ID NO:17300), TCGTTGATAGTCGGAGGGGTCGGGTTT (SEQ ID NO:17301), TTCGTTGATAGTCGGAGGGGTCGGGTT (SEQ ID NO:17302), TAGCGTTGCGTTTATTGGTCGGCGTTGG (SEQ ID NO:17303), ATTCGTTGATAGTCGGAGGGGTCGGGT (SEQ ID NO:17304) |
| Target1829 | chr22:22006416-22006433 | TCGTTGATAGTCGGAGGGGTCGGGTTT (SEQ ID NO:17305), TTCGTTGATAGTCGGAGGGGTCGGGTT (SEQ ID NO:17306), ATTCGTTGATAGTCGGAGGGGTCGGGT (SEQ ID NO:17307), CGTTGATAGTCGGAGGGGTCGGGTTTT (SEQ ID NO:17308), TCGTTGATAGTCGGAGGGGTCGGGTTTT (SEQ ID NO:17309) |
| Target1830 | chr22:22006558-22006586 | GTTTGGACGGGGATTCGGGGGTAGACG (SEQ ID NO:17310), AAAGATGGAGTCGGTAGGCGAGGGGTC (SEQ ID NO:17311), AAGATGGAGTCGGTAGGCGAGGGGTCG (SEQ ID NO:17312), GCGGGTTAAAGATGGAGTCGGTAGGCG (SEQ ID NO:17313), TTTGGACGGGGATTCGGGGGTAGACG (SEQ ID NO:17314), TCGTTTAGGGTTCGGTTAGGACGCGGA (SEQ ID NO:17315), CGTTTAGGGTTCGGTTAGGACGCGGAG (SEQ ID NO:17316), GTTTAGGGTTCGGTTAGGACGCGGAGG (SEQ ID NO:17317), TCGTTTAGGGTTCGGTTAGGACGCGGAG (SEQ ID NO:17318), TTCGTTTAGGGTTCGGTTAGGACGCGG (SEQ ID NO:17319) |
| Target1831 | chr22:22006620-22006679 | GGGATTTTGGGTTGGGTTGGGCGGTTT (SEQ ID NO:17320), TGATCGGGTTTTTGGGCGGAAGGGATGT (SEQ ID NO:17321), TGGGTTGGGTTGGGCGGTTTTATTCGG (SEQ ID NO:17322), TCGGGTTTTTGGGCGGAAGGGATGTTTG (SEQ ID NO:17323), GTTTGGACGGGGATTCGGGGGTAGACG (SEQ ID NO:17324), AAAGAGGGTTTTCGGGATTTCGGTCGC (SEQ ID NO:17325), CGGTCGCGTTTTTTCGTTTGATTCGTCG (SEQ ID NO:17326), CGGTCGCGTTTTTTCGTTTGATTCGTCGA (SEQ ID NO:17327), TCGGTCGCGTTTTTTCGTTTGATTCGTCG (SEQ ID NO:17328), TCGGTCGCGTTTTTTCGTTTGATTCGT (SEQ ID NO:17329) |
| Target1832 | chr22:26446381-26446571 | TGGTGTTGGGTGGAGGGTTGTTAGGGA (SEQ ID NO:17330), TTGGTGTTGGGTGGAGGGTTGTTAGGG (SEQ ID NO:17331), TGGTGTTGGGTGGAGGGTTGTTAGGGAA (SEQ ID NO:17332), TTGGTGTTGGGTGGAGGGTTGTTAGGGA (SEQ ID NO:17333), GGTGTTGGGTGGAGGGTTGTTAGGGAA (SEQ ID NO:17334) |

FIGURE 5 CONTINUED

| | | |
|---|---|---|
| Target1833 | chr22:26716017-26716542 | AGGGTTAAGTGTCGTGGGGTTTGGGGA (SEQ ID NO:17335), GGGTTAAGTGTCGTGGGGTTTGGGGAGT (SEQ ID NO:17336), GGGTTAAGTGTCGTGGGGTTTGGGGAG (SEQ ID NO:17337), AGGGTTAAGTGTCGTGGGGTTTGGGGAG (SEQ ID NO:17338), AAGTGTCGTGGGGTTTGGGGAGTTTGT (SEQ ID NO:17339), TGGTTTTTCGGGGGCGGGGTTGTATTT (SEQ ID NO:17340), TCGGGGGCGGGGTTGTATTTGTTTTGT (SEQ ID NO:17341), ATGGTTTTTCGGGGGCGGGGTTGTATT (SEQ ID NO:17342), AATATGGTTTTTCGGGGGCGGGGTTGT (SEQ ID NO:17343), GGTTTTTCGGGGGCGGGGTTGTATTTGT (SEQ ID NO:17344) |
| Target1834 | chr22:28195692-28196145 | AGGAGGCGGTTCGGTTAGGGTTTTGGT (SEQ ID NO:17345), GTGGAAGGAGGCGGTTCGGTTAGGGTT (SEQ ID NO:17346), AGTTCGGGGAGGTTTTTCGGTCGTTGCG (SEQ ID NO:17347), TGGAAGGAGGCGGTTCGGTTAGGGTTT (SEQ ID NO:17348), GTTCGGGGAGGTTTTTCGGTCGTTGCGG (SEQ ID NO:17349), CGGGTCGTTAGGTTTTTGGGGGCGTTT (SEQ ID NO:17350), GTTTTTGGGGGCGTTTTTTCGGGCGTT (SEQ ID NO:17351), GTAGCGGGTCGTTAGGTTTTTGGGGGC (SEQ ID NO:17352), GGGGCGTTTTTTCGGGCGTTTCGGTTA (SEQ ID NO:17353), TTTTGGGGGCGTTTTTTCGGGCGTTTC (SEQ ID NO:17354) |
| Target1835 | chr22:30662647-30662734 | CGTGGGTAGATTTAGTAGGCGGGTTTTGGC (SEQ ID NO:17355), TGGGTAGATTTAGTAGGCGGGTTTTGGC (SEQ ID NO:17356), TCGTGGGTAGATTTAGTAGGCGGGTTTTGGC (SEQ ID NO:17357), GTGGGTAGATTTAGTAGGCGGGTTTTGGC (SEQ ID NO:17358), CGTGGGTAGATTTAGTAGGCGGGTTTTGG (SEQ ID NO:17359), GGGTGTCGGTGGGGAGTAGAGGTATTT (SEQ ID NO:17360), GGGTGTCGGTGGGGAGTAGAGGTATTTT (SEQ ID NO:17361), GTCGAGAGGTGTTATTTTTAGCGGGCG (SEQ ID NO:17362), AGTCGAGAGGTGTTATTTTTAGCGGGCG (SEQ ID NO:17363), GGGTGTCGGTGGGGAGTAGAGGTATT (SEQ ID NO:17364) |
| Target1836 | chr22:30662972-30663077 | GGGAGGGGGGGAGGGTAGGTTTTTTGGG (SEQ ID NO:17365), TGGGGAGGGGGGAGGGTAGGTTTTTTG (SEQ ID NO:17366), TGGGGAGGGGGGAGGGTAGGTTTTTTG (SEQ ID NO:17367), GGAGGGGGGGAGGGTAGGTTTTTTGGA (SEQ ID NO:17368), GGATGGGGAGGGGGGAGGGTAGGTTTT (SEQ ID NO:17369), TCGAAGAAAATAGGAGGAGGAGCGGGT (SEQ ID NO:17370), TCGAAGAAAATAGGAGGAGGAGCGGGTA (SEQ ID NO:17371), CGAAGAAAATAGGAGGAGGAGCGGGT (SEQ ID NO:17372), TCGAAGAAAATAGGAGGAGGAGCGGGTAT (SEQ ID NO:17373), TCGAAGAAAATAGGAGGAGGAGCGGGTATA (SEQ ID NO:17374) |
| Target1837 | chr22:46403726-46403769 | AGGTTGAGGTTTGTATTATTTCGGTCGGGA (SEQ ID NO:17375), AGGTTGAGGTTTGTATTATTTCGGTCGGGAG (SEQ ID NO:17376), GGTTGAGGTTTGTATTATTTCGGTCGGGAGA (SEQ ID NO:17377), AGGTTGAGGTTTGTATTATTTCGGTCGGGAGA (SEQ ID NO:17378), TAGGTTGAGGTTTGTATTATTTCGGTCGGGAG (SEQ ID NO:17379), GTTTTTCGGGAAGATGGTTGTCGTGGT (SEQ ID NO:17380), AGTTTTTCGGGAAGATGGTTGTCGTGGT (SEQ ID NO:17381), GTTTTTCGGGAAGATGGTTGTCGTGGTT (SEQ ID NO:17382), AGTTTTTCGGGAAGATGGTTGTCGTGGTT (SEQ ID NO:17383), GGAGGAGGTTATTGGGAAACGTTGTTGGT (SEQ ID NO:17384) |
| Target1838 | chr22:46403792-46404057 | TTTGGGAGTGGGAGTGGGGAGAGTTGC (SEQ ID NO:17385), CGGAGTTTTTGGGAGTGGGAGTGGGGA (SEQ ID NO:17386), GCGTCGGGTAGGTAGGGTAGGGAGGTT (SEQ ID NO:17387), GGAGTGGGAGTGGGGAGAGTTGCGTTA (SEQ ID NO:17388), TGCGGAGTTTTTGGGAGTGGGAGTGGG (SEQ ID NO:17389), TGGTAGTTGGTCGGTTATGGGTCGTGT (SEQ ID NO:17390), TGGTATCGAGGTTGTTAGGAGGGCGTT (SEQ ID NO:17391), TTGGTATCGAGGTTGTTAGGAGGGCGT (SEQ ID NO:17392), TGGTATCGAGGTTGTTAGGAGGGCGTTG (SEQ ID NO:17393), GGTATCGAGGTTGTTAGGAGGGCGTTG (SEQ ID NO:17394) |
| Target1839 | chr22:46404082-46404141 | GTTAGCGTTTCGGGGTGATCGGGTTGG (SEQ ID NO:17395), TTCGGGGGTGATCGGGTTGGGTTGTAGT (SEQ ID NO:17396), TTAGCGTTTCGGGGTGATCGGGTTGGG (SEQ ID NO:17397), TGTTAGCGTTTCGGGGTGATCGGGTTG (SEQ ID NO:17398), CGTTTCGGGGTGATCGGGTTGGGTTGT (SEQ ID NO:17399), TGTTGGGAGGAGGGTTGGTTTGAGGGG (SEQ ID NO:17400), TGAGGTTTGGGATTGCGGGGTTAGGGT (SEQ ID NO:17401), GTTGGGAGGAGGGTTGGTTTGAGGGGA (SEQ ID NO:17402), TGGGAGGAGGGTTGGTTTGAGGGGAAA (SEQ ID NO:17403), TTGGGAGGAGGGTTGGTTTGAGGGGAA (SEQ ID NO:17404) |
| Target1840 | chr22:46849338-46849888 | GTGTTGATCGGAAGCGGGTGAGAGAGT (SEQ ID NO:17405), AGTGTTGATCGGAAGCGGGTGAGAGAGT (SEQ ID NO:17406), AGTGTTGATCGGAAGCGGGTGAGAGAG (SEQ ID NO:17407), AAGTGTTGATCGGAAGCGGGTGAGAGA (SEQ ID NO:17408), TGAAAGTGTTGATCGGAAGCGGGTGAG (SEQ ID NO:17409), TATCGGCGTTGTGGTGGGGGTTTGGTA (SEQ ID NO:17410), GGCGTTGTGGTGGGGGTTTGGTAGTTT (SEQ ID NO:17411), ATTATCGGCGTTGTGGTGGGGGTTTGG (SEQ ID NO:17412), TTATCGGCGTTGTGGTGGGGGTTTGGT (SEQ ID NO:17413), GGTTTGTTAGGGTTGGGTGTGGTGGGG (SEQ ID NO:17414) |
| Target1841 | chr22:46921700-46922017 | TTCGGGTAGTTGGTGTTGAGGTGGGCG (SEQ ID NO:17415), CGGGTAGTTGGTGTTGAGGTGGGCGTT (SEQ ID NO:17416), GGGTAGTTGGTGTTGAGGTGGGCGTTT (SEQ ID NO:17417), TTTCGGGTAGTTGGTGTTGAGGTGGGC (SEQ ID NO:17418), TCGGGTAGTTGGTGTTGAGGTGGGCG (SEQ ID NO:17419), GGTAGGAGGGGCGGTGTTGGTTACGTT (SEQ ID NO:17420), GTAGGAGGCGGACGGGAAAAAGGGGTT (SEQ ID NO:17421), GGAGGGAATGGAGGAGTAGGAGGCGGA (SEQ ID NO:17422), GGAGCGGGTTTATGTTGTTGGGCGTGT (SEQ ID NO:17423), TGGAGCGGGTTTATGTTGTTGGGCGTG (SEQ ID NO:17424) |

FIGURE 5 CONTINUED

| Target1842 | chr22:49578179-49578201 | AGACGAGGTGAATGTTATTTTTGTTTTGGGGTT (SEQ ID NO:17425), ACGAGGTGAATGTTATTTTTGTTTTGGGGTTAGG (SEQ ID NO:17426), CGAGGTGAATGTTATTTTTGTTTTGGGGTTAGGA (SEQ ID NO:17427), ACGAGGTGAATGTTATTTTTGTTTTGGGGTTAGGA (SEQ ID NO:17428), GACGAGGTGAATGTTATTTTTGTTTTGGGGTTAGG (SEQ ID NO:17429), TGGTTTGCGTGGGGTTTGTGAGTTCGT (SEQ ID NO:17430), TGGTTTGCGTGGGGTTTGTGAGTTCGTT (SEQ ID NO:17431), GGTTTGCGTGGGGTTTGTGAGTTCGTT (SEQ ID NO:17432), ATGGTTTGCGTGGGGTTTGTGAGTTCGT (SEQ ID NO:17433), ATGGTTTGCGTGGGGTTTGTGAGTTCG (SEQ ID NO:17434) |
|---|---|---|
| Target1843 | chr22:50987093-50987454 | TTTTGTAGAGGTTCGGGGGTTGGGGGG (SEQ ID NO:17435), GGATTTTTAAGGGGGAGGCGTCGGGGGA (SEQ ID NO:17436), ATTTTTAAGGGGGAGGCGTCGGGGGAGG (SEQ ID NO:17437), GGCGGCGGTTGGATTTGGGTAGTTGTT (SEQ ID NO:17438), TCGGGGGATTTTTAAGGGGGAGGCGTCG (SEQ ID NO:17439), TAGGGTTCGGGAGTTGGGTTTTCGGGG (SEQ ID NO:17440), TCGGTCGGTTCGTAGGTTGAGGATGCG (SEQ ID NO:17441), CGGTTCGTAGGTTGAGGATGCGTTCGC (SEQ ID NO:17442), CGGTCGGTTCGTAGGTTGAGGATGCGT (SEQ ID NO:17443), GTGGCGGGTTTTAGGGTTCGGGAGTTG (SEQ ID NO:17444) |
| Target1844 | chr22:50987623-50987637 | GCGAGGAGTTTTTTGCGGCGGTTTTTG (SEQ ID NO:17445), GCGAGGAGTTTTTTGCGGCGGTTTTTGT (SEQ ID NO:17446), GCGAGGAGTTTTTTGCGGCGGTTTTTGTG (SEQ ID NO:17447), CGAGGAGTTTTTTGCGGCGGTTTTTGT (SEQ ID NO:17448), CGAGGAGTTTTTTGCGGCGGTTTTTGTG (SEQ ID NO:17449), GTTGGAGTAGACGGTTTTGGTATCGGAGT (SEQ ID NO:17450), AGTAGACGGTTTTGGTATCGGAGTTACGG (SEQ ID NO:17451), GTAGACGGTTTTGGTATCGGAGTTACGGA (SEQ ID NO:17452), GGAGTAGACGGTTTTGGTATCGGAGTTACGG (SEQ ID NO:17453), AGTAGACGGTTTTGGTATCGGAGTTACGGA (SEQ ID NO:17454) |
| Target1845 | chr22:51016271-51016307 | TTGTTTACGTTTTGGGAGAAGTATTTGTGCGT (SEQ ID NO:17455), AGGTAGACGTGTTTTAGGGTTTTTCGATTGAGT (SEQ ID NO:17456), TTTGTTTACGTTTTGGGAGAAGTATTTGTGCGT (SEQ ID NO:17457), GGTAGACGTGTTTTAGGGTTTTTCGATTGAGTC (SEQ ID NO:17458), ACGTTTTGGGAGAAGTATTTGTGCGTATTTTGA (SEQ ID NO:17459), GGATGGCGGAAGTTTATTAGGTCGTGGT (SEQ ID NO:17460), AGGATGGCGGAAGTTTATTAGGTCGTGGT (SEQ ID NO:17461), AGGATGGCGGAAGTTTATTAGGTCGTGG (SEQ ID NO:17462), GGATGGCGGAAGTTTATTAGGTCGTGGTT (SEQ ID NO:17463), AGGATGGCGGAAGTTTATTAGGTCGTGGTT (SEQ ID NO:17464) |
| Target1846 | chr22:51016392-51016493 | GGGGTTGGTCGGTATTTAGGACGGGGG (SEQ ID NO:17465), GGGGGTTGGTCGGTATTTAGGACGGGG (SEQ ID NO:17466), ATTTAGGACGGGGGTAGATGGGTGCGC (SEQ ID NO:17467), GGGTTGGTCGGTATTTAGGACGGGGGT (SEQ ID NO:17468), TGGGGGTTGGTCGGTATTTAGGACGGG (SEQ ID NO:17469), ATTCGGAAGGTTGGCGCGAGGATTTGG (SEQ ID NO:17470), TGTTTATTCGGAAGGTTGGCGCGAGGA (SEQ ID NO:17471), TTCGGAAGGTTGGCGCGAGGATTTGG (SEQ ID NO:17472), TGTGTTTATTCGGAAGGTTGGCGCGAGG (SEQ ID NO:17473), GTGTTTATTCGGAAGGTTGGCGCGAGG (SEQ ID NO:17474) |
| Target1847 | chr22:51016494-51016605 | GCGGGCGCGTTTAGGTCGGTTTC (SEQ ID NO:17475), CGGGTGGGTATAGTTATTGTGGTGTAGGGG (SEQ ID NO:17476), CGGGTGGGTATAGTTATTGTGGTGTAGGGGA (SEQ ID NO:17477), TCGGGTGGGTATAGTTATTGTGGTGTAGGGG (SEQ ID NO:17478), CGGGTGGGTATAGTTATTGTGGTGTAGGG (SEQ ID NO:17479), ATTCGGAAGGTTGGCGCGAGGATTTGG (SEQ ID NO:17480), GGTGGGGAAGGGCGGGTTTTCGAATTT (SEQ ID NO:17481), GGGTGGGGAAGGGCGGGTTTTCGAATT (SEQ ID NO:17482), GGTGGGGAAGGGCGGGTTTTCGAATTTT (SEQ ID NO:17483), TGTTTATTCGGAAGGTTGGCGCGAGGA (SEQ ID NO:17484) |
| Target1848 | chr22:51016632-51016682 | AAGGGTAGTTTGGAGTTGGGGGGCGTT (SEQ ID NO:17485), GAAGGGTAGTTTGGAGTTGGGGGGCGT (SEQ ID NO:17486), CGGGTAGGGGAGAGAGGCGTTTTTGGA (SEQ ID NO:17487), ACGGCGAAGGGTAGTTTGGAGTTGGGG (SEQ ID NO:17488), GGCGAAGGGTAGTTTGGAGTTGGGGGG (SEQ ID NO:17489), CGGTTCGCGGGGGTTTGGGTTTTTAGT (SEQ ID NO:17490), GGTGGGGAAGGGCGGGTTTTCGAATTT (SEQ ID NO:17491), GGGTGGGGAAGGGCGGGTTTTCGAATT (SEQ ID NO:17492), CGGTTCGCGGGGGTTTGGGTTTTTAGTT (SEQ ID NO:17493), GGTGGGGAAGGGCGGGTTTTCGAATTTT (SEQ ID NO:17494) |
| Target1849 | chr22:51016703-51016753 | AAGGGTAGTTTGGAGTTGGGGGGCGTT (SEQ ID NO:17495), GAAGGGTAGTTTGGAGTTGGGGGGCGT (SEQ ID NO:17496), CGGGTAGGGGAGAGAGGCGTTTTTGGA (SEQ ID NO:17497), ACGGCGAAGGGTAGTTTGGAGTTGGGG (SEQ ID NO:17498), GGCGAAGGGTAGTTTGGAGTTGGGGGG (SEQ ID NO:17499), TGTGAGTAGGGGTCGGTATAGGGCGGT (SEQ ID NO:17500), CGGTTCGCGGGGGTTTGGGTTTTTAGT (SEQ ID NO:17501), GAGTAGGGGTCGGTATAGGGCGGTTCG (SEQ ID NO:17502), TGTGAGTAGGGGTCGGTATAGGGCGGTT (SEQ ID NO:17503), TTGTGAGTAGGGGTCGGTATAGGGCGGT (SEQ ID NO:17504) |

FIGURE 5 CONTINUED

COMPOSITIONS AND METHODS FOR CANCER AND NEOPLASIA ASSESSMENT

RELATED APPLICATIONS

This application is a U.S. national phase filing of International Patent Application No. PCT/US2019/026395, entitled "COMPOSITIONS AND METHODS FOR CANCER OR NEOPLASIA ASSESSMENT." filed on Apr. 8, 2019, which PCT application claims priority to U.S. provisional patent application No. 62/656,820, filed on Apr. 12, 2018. In some aspects, the present disclosure relates to U.S. provisional application Ser. No. 62/487,422, filed on Apr. 19, 2017 and U.S. provisional application Ser. No. 62/487,423, filed on Apr. 19, 2017. The contents of all of the above-described applications are incorporated by reference in their entireties for all purposes.

SEQUENCE LISTING ON ASCII TEXT

This patent or application file contains a Sequence Listing submitted in computer readable ASCII text format (file name: 4552-2000430_SeqList_ST25.txt, date recorded: Oct. 8, 2020, size: 3,287,136 bytes). The content of the Sequence Listing file is incorporated herein by reference in its entirety.

TECHNICAL FIELD

The present disclosure relates to certain compositions, kits, devices, systems and methods, e.g., compositions, kits, devices, systems and methods for assessing cancer or neoplasia in a subject. In particular aspects, provided herein are compositions, kits, devices, systems and methods for assessing cancer or neoplasia in a subject based on assessing methylation status of selected target polynucleotide sequences, e.g., target genomic DNA sequences, from the subject.

BACKGROUND

Various reagents, kits and methods for assessing cancer or neoplasia in a subject are known. However, there is a need for improved compositions, kits, devices, systems and methods for assessing cancer or neoplasia in a subject, e.g., tests with better sensitivity, specificity and/or providing more information. The present disclosure addresses this and other related needs.

BRIEF SUMMARY

The summary is not intended to be used to limit the scope of the claimed subject matter. Other features, details, utilities, and advantages of the claimed subject matter will be apparent from the detailed description including those aspects disclosed in the accompanying drawings and in the appended claims.

In one aspect, provided herein is a panel of isolated polynucleotides comprising, consisting of, or consisting essentially of at least two isolated polynucleotides, each of said isolated polynucleotides having a polynucleotide sequence of any of Target 1 to Target 1849 listed in Table 1, or a complementary sequence thereof. A kit, device, system or an article of manufacture that comprises any of the above panels is also provided.

In another aspect, a kit, device, system or an article of manufacture that is configured for assessing methylation status of at least two of Target 1 to Target 1849 listed in Table 1 is provided. In some embodiments, the present kit, device, system or an article of manufacture is configured for assessing cancer or neoplasia in a subject.

In still another aspect, provided herein is a method for assessing cancer or neoplasia in a subject, which method comprises: a) providing a sample from a subject containing at least two target polynucleotides of said subject, said at least two target polynucleotides having polynucleotide sequences of at least two of Target 1 to Target 1849 listed in Table 1, or a complementary sequence thereof; b) assessing methylation status of said at least two target polynucleotides; and c) assessing cancer or neoplasia in said subject based on assessment of methylation status of said at least two target polynucleotides. In some embodiments, the present methods are used for diagnosis, prognosis, stratification, risk assessment, or treatment monitoring of cancer or neoplasia in a subject.

BRIEF DESCRIPTION OF THE DRAWINGS

FIG. 2 illustrates detection of cancer in colon tissue as described in Example 1.

FIGS. 3a and 3b illustrate detection of lung cancer in plasma as described in Example 2.

FIG. 4 illustrates detection of pan-cancer in plasma as described in Example 3.

FIG. 5 (Table 1) shows exemplary target regions and primers.

DETAILED DESCRIPTION

Figure 1:
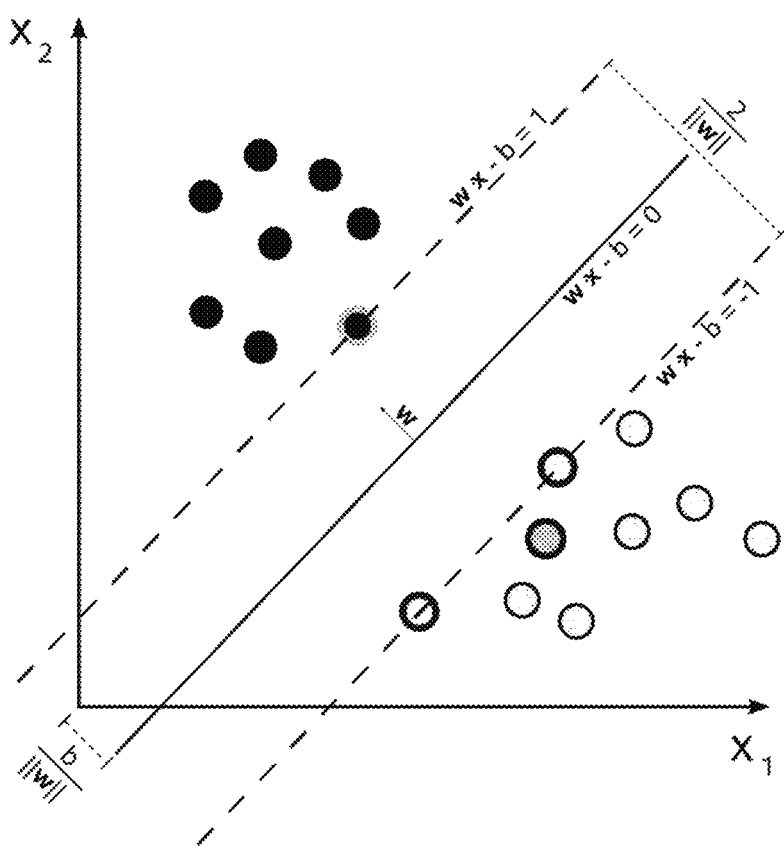
FIG. 1 illustrates an exemplary support vector machines analysis. Image of FIG. 1 is taken from Wikipedia: https://en.wikipedia.org/wiki/Support_vector_machine), and does not represent any DNA methylation status analysis or cancer assessment.

Numerous specific details are set forth in the following description in order to provide a thorough understanding of the present disclosure. These details are provided for the purpose of example and the claimed subject matter may be practiced according to the claims without some or all of these specific details. It is to be understood that other embodiments can be used and structural changes can be made without departing from the scope of the claimed subject matter. It should be understood that the various features and functionality described in one or more of the individual embodiments are not limited in their applicability to the particular embodiment with which they are described. They instead can, be applied, alone or in some combination, to one or more of the other embodiments of the disclosure, whether or not such embodiments are described, and whether or not such features are presented as being a part of a described embodiment. For the purpose of clarity, technical material that is known in the technical fields related to the claimed subject matter has not been described in detail so that the claimed subject matter is not unnecessarily obscured.

All publications, including patent documents, scientific articles and databases, referred to in this application are incorporated by reference in their entireties for all purposes to the same extent as if each individual publication were individually incorporated by reference. Citation of the publications or documents is not intended as an admission that any of them is pertinent prior art, nor does it constitute any admission as to the contents or date of these publications or documents.

All headings are for the convenience of the reader and should not be used to limit the meaning of the text that follows the heading, unless so specified.

The practice of the provided embodiments will employ, unless otherwise indicated, conventional techniques and descriptions of organic chemistry, polymer technology, molecular biology (including recombinant techniques), cell biology, biochemistry, and sequencing technology, which are within the skill of those who practice in the art. Such conventional techniques include polypeptide and protein synthesis and modification, polynucleotide synthesis and modification, polymer array synthesis, hybridization and ligation of polynucleotides, detection of hybridization, and nucleotide sequencing. Specific illustrations of suitable techniques can be had by reference to the examples herein. However, other equivalent conventional procedures can, of course, also be used. Such conventional techniques and descriptions can be found in standard laboratory manuals such as Green, et al., Eds., *Genome Analysis: A Laboratory Manual Series* (Vols. I-IV) (1999); Weiner, Gabriel, Stephens, Eds., *Genetic Variation: A Laboratory Manual* (2007); Dieffenbach, Dveksler, Eds., *PCR Primer: A Laboratory Manual* (2003); Bowtell and Sambrook, *DNA Microarrays: A Molecular Cloning Manual* (2003); Mount, *Bioinformatics: Sequence and Genome Analysis* (2004); Sambrook and Russell, *Condensed Protocols from Molecular Cloning: A Laboratory Manual* (2006); and Sambrook and Russell, *Molecular Cloning: A Laboratory Manual* (2002) (all from Cold Spring Harbor Laboratory Press); Ausubel et al. eds., *Current Protocols in Molecular Biology* (1987); T. Brown ed., *Essential Molecular Biology* (1991), IRL Press; Goeddel ed., *Gene Expression Technology* (1991), Academic Press; A. Bothwell et al. eds., *Methods for Cloning and Analysis of Eukaryotic Genes* (1990), Bartlett Publ.; M. Kriegler, *Gene Transfer and Expression* (1990), Stockton Press; R. Wu et al. eds., *Recombinant DNA Methodology* (1989), Academic Press; M. McPherson et al., *PCR: A Practical Approach* (1991), IRL Press at Oxford University Press; Stryer, *Biochemistry* (4th Ed.) (1995), W. H. Freeman, New York N.Y.; Gait, *Oligonucleotide Synthesis: A Practical Approach* (2002), IRL Press, London; Nelson and Cox, *Lehninger, Principles of Biochemistry* (2000) 3rd Ed., W. H. Freeman Pub., New York, N.Y.; Berg, et al., *Biochemistry* (2002) 5th Ed., W. H. Freeman Pub., New York, N.Y., all of which are herein incorporated in their entireties by reference for all purposes.

A. Definitions

Unless defined otherwise, all technical and scientific terms used herein have the same meaning as is commonly understood by one of ordinary skill in the art to which the present disclosure belongs. If a definition set forth in this section is contrary to or otherwise inconsistent with a definition set forth in the patents, applications, published applications and other publications that are herein incorporated by reference, the definition set forth in this section prevails over the definition that is incorporated herein by reference.

As used herein, "a" or "an" means "at least one" or "one or more." As used herein, the singular forms "a," "an," and "the" include the plural reference unless the context clearly dictates otherwise.

Throughout this disclosure, various aspects of the claimed subject matter are presented in a range format. It should be understood that the description in range format is merely for convenience and brevity and should not be construed as an inflexible limitation on the scope of the claimed subject matter. Accordingly, the description of a range should be considered to have specifically disclosed all the possible sub-ranges as well as individual numerical values within that range. For example, where a range of values is provided, it is understood that each intervening value, between the upper and lower limit of that range and any other stated or intervening value in that stated range is encompassed within the claimed subject matter. The upper and lower limits of these smaller ranges may independently be included in the smaller ranges, and are also encompassed within the claimed subject matter, subject to any specifically excluded limit in the stated range. Where the stated range includes one or both of the limits, ranges excluding either or both of those included limits are also included in the claimed subject matter. This applies regardless of the breadth of the range.

Reference to "about" a value or parameter herein includes (and describes) variations that are directed to that value or parameter per se. For example, description referring to "about X" includes description of "X". Additionally, use of "about" preceding any series of numbers includes "about" each of the recited numbers in that series. For example, description referring to "about X, Y, or Z" is intended to describe "about X, about Y, or about Z."

The term "average" as used herein refers to either a mean or a median, or any value used to approximate the mean or the median, unless the context clearly indicates otherwise.

A "subject" as used herein refers to an organism, or a part or component of the organism, to which the provided compositions, methods, kits, devices, and systems can be administered or applied. For example, the subject can be a mammal or a cell, a tissue, an organ, or a part of the mammal. As used herein, "mammal" refers to any of the mammalian class of species, preferably human (including humans, human subjects, or human patients). Subjects and mammals include, but are not limited to, farm animals, sport animals, pets, primates, horses, dogs, cats, and rodents such as mice and rats.

As used herein the term "sample" refers to anything which may contain a target molecule for which analysis is desired, including a biological sample. As used herein, a "biological sample" can refer to any sample obtained from a living or viral (or prion) source or other source of macromolecules and biomolecules, and includes any cell type or tissue of a subject from which nucleic acid, protein and/or other macromolecule can be obtained. The biological sample can be a sample obtained directly from a biological source or a sample that is processed. For example, isolated nucleic acids that are amplified constitute a biological sample. Biological samples include, but are not limited to, body fluids, such as blood, plasma, serum, cerebrospinal fluid, synovial fluid, urine, sweat, semen, stool, sputum, tears, mucus, amniotic fluid or the like, an effusion, a bone marrow sample, ascitic fluid, pelvic wash fluid, pleural fluid, spinal fluid, lymph, ocular fluid, extract of nasal, throat or genital swab, cell suspension from digested tissue, or extract of fecal material, and tissue and organ samples from humans, animals, e.g., non-human mammals, and plants and processed samples derived therefrom.

The terms "polynucleotide," "oligonucleotide," "nucleic acid" and "nucleic acid molecule" are used interchangeably herein to refer to a polymeric form of nucleotides of any length, and comprise ribonucleotides, deoxyribonucleotides, and analogs or mixtures thereof. The terms include triple-, double- and single-stranded deoxyribonucleic acid ("DNA"), as well as triple-, double- and single-stranded ribonucleic acid ("RNA"). It also includes modified, for example by alkylation, and/or by capping, and unmodified forms of the polynucleotide. More particularly, the terms "polynucleotide," "oligonucleotide," "nucleic acid," and "nucleic acid molecule" include polydeoxyribonucleotides (containing 2-deoxy-D-ribose), polyribonucleotides (containing D-ribose), including tRNA, rRNA, hRNA, and mRNA, whether spliced or unspliced, any other type of polynucleotide which is an N- or C-glycoside of a purine or pyrimidine base, and other polymers containing nonnucleotidic backbones, for example, polyamide (e.g., peptide nucleic acids ("PNAs")) and polymorpholino (commercially available from the Anti-Virals, Inc., Corvallis, OR, as Neugene) polymers, and other synthetic sequence-specific nucleic acid polymers providing that the polymers contain nucleobases in a configuration which allows for base pairing and base stacking, such as is found in DNA and RNA. Thus, these terms include, for example, 3'-deoxy-2',5'-DNA, oligodeoxyribonucleotide N3' to P5' phosphoramidates, 2'-O-alkyl-substituted RNA, hybrids between DNA and RNA or between PNAs and DNA or RNA, and also include known types of modifications, for example, labels, alkylation, "caps," substitution of one or more of the nucleotides with an analog, inter-nucleotide modifications such as, for example, those with uncharged linkages (e.g., methyl phosphonates, phosphotriesters, phosphoramidates, carbamates, etc.), with negatively charged linkages (e.g., phosphorothioates, phosphorodithioates, etc.), and with positively charged linkages (e.g., aminoalkylphosphoramidates, aminoalkylphosphotriesters), those containing pendant moieties, such as, for example, proteins (including enzymes (e.g. nucleases), toxins, antibodies, signal peptides, poly-L-lysine, etc.), those with intercalators (e.g., acridine, psoralen, etc.), those containing chelates (of, e.g., metals, radioactive metals, boron, oxidative metals, etc.), those containing alkylators, those with modified linkages (e.g., alpha anomeric nucleic acids, etc.), as well as unmodified forms of the polynucleotide or oligonucleotide. A nucleic acid generally will contain phosphodiester bonds, although in some cases nucleic acid analogs may be included that have alternative backbones such as phosphoramidite, phosphorodithioate, or methylphophoroamidite linkages; or peptide nucleic acid backbones and linkages. Other analog nucleic acids include those with bicyclic structures including locked nucleic acids, positive backbones, non-ionic backbones and non-ribose backbones. Modifications of the ribose-phosphate backbone may be done to increase the stability of the molecules; for example, PNA:DNA hybrids can exhibit higher stability in some environments. The terms "polynucleotide," "oligonucleotide," "nucleic acid" and "nucleic acid molecule" can comprise any suitable length, such as at least 5, 6, 7, 8, 9, 10, 20, 30, 40, 50, 100, 200, 300, 400, 500, 1,000, 2,000, 3,000, 4,000, 5,000, 6,000, 7,000, 8,000, 9,000, 10,000, or more nucleotides.

It will be appreciated that, as used herein, the terms "nucleoside" and "nucleotide" include those moieties which contain not only the known purine and pyrimidine bases, but also other heterocyclic bases which have been modified. Such modifications include methylated purines or pyrimidines, acylated purines or pyrimidines, or other heterocycles. Modified nucleosides or nucleotides can also include modifications on the sugar moiety, e.g., wherein one or more of the hydroxyl groups are replaced with halogen, aliphatic groups, or are functionalized as ethers, amines, or the like. The term "nucleotidic unit" is intended to encompass nucleosides and nucleotides.

The terms "complementary" and "substantially complementary" include the hybridization or base pairing or the formation of a duplex between nucleotides or nucleic acids, for instance, between the two strands of a double-stranded DNA molecule or between an oligonucleotide primer and a primer binding site on a single-stranded nucleic acid. Complementary nucleotides are, generally, A and T (or A and U), or C and G. Two single-stranded RNA or DNA molecules are said to be substantially complementary when the nucleotides of one strand, optimally aligned and compared and with appropriate nucleotide insertions or deletions, pair with at least about 80% of the other strand, usually at least about 90% to about 95%, and even about 98% to about 100%. In one aspect, two complementary sequences of nucleotides are capable of hybridizing, preferably with less than 25%, more preferably with less than 15%, even more preferably with less than 5%, most preferably with no mismatches between opposed nucleotides. Preferably the two molecules will hybridize under conditions of high stringency.

As used herein, for a reference sequence, the reverse complementary sequence is the complementary sequence of the reference sequence in the reverse order. For example, for 5'-ATCG-3', the complementary sequence is 3'-TAGC-5', and the reverse-complementary sequence is 5'-CGAT-3'.

"Hybridization" as used herein may refer to the process in which two single-stranded polynucleotides bind non-covalently to form a stable double-stranded polynucleotide. In one aspect, the resulting double-stranded polynucleotide can be a "hybrid" or "duplex." "Hybridization conditions" typically include salt concentrations of approximately less than 1 M, often less than about 500 mM and may be less than about 200 mM. A "hybridization buffer" includes a buffered salt solution such as 5% SSPE, or other such buffers known in the art. Hybridization temperatures can be as low as 5° C., but are typically greater than 22° C., and more typically greater than about 30° C., and typically in excess of 37° C. Hybridizations are often performed under stringent conditions, i.e., conditions under which a sequence will hybridize to its target sequence but will not hybridize to other, non-complementary sequences. Stringent conditions are sequence-dependent and are different in different circumstances. For example, longer fragments may require higher hybridization temperatures for specific hybridization than short fragments. As other factors may affect the stringency of hybridization, including base composition and length of the complementary strands, presence of organic solvents, and the extent of base mismatching, the combination of parameters is more important than the absolute measure of any one parameter alone. Generally stringent conditions are selected to be about 5° C. lower than the $T_m$ for the specific sequence at a defined ionic strength and pH. The melting temperature $T_m$ can be the temperature at which a population of double-stranded nucleic acid molecules becomes half dissociated into single strands. Several equations for calculating the $T_m$ of nucleic acids are well known in the art. As indicated by standard references, a simple estimate of the $T_m$ value may be calculated by the equation, $T_m = 81.5 + 0.41$ (% G+C), when a nucleic acid is in aqueous solution at 1 M NaCl (see e.g., Anderson, M. L. M. and Young, B. D. 1985, Quantitative filter hybridization. In: Nucleic acid hybridization: a practical approach, 73-111. B. D. Hames and S. J. Higgins (eds.). IRL Press Limited, Oxford.). Other references (e.g., Allawi and SantaLucia, Jr., *Biochemistry*, 36:10581-94 (1997)) include alternative methods of computation which take structural and environmental, as well as sequence characteristics into account for the calculation of $T_m$.

In general, the stability of a hybrid is a function of the ion concentration and temperature. Typically, a hybridization reaction is performed under conditions of lower stringency, followed by washes of varying, but higher, stringency. Exemplary stringent conditions include a salt concentration of at least 0.01 M to no more than 1 M sodium ion concentration (or other salt) at a pH of about 7.0 to about 8.3 and a temperature of at least 25° C. For example, conditions of 5×SSPE (750 mM NaCl, 50 mM sodium phosphate, 5 mM EDTA at pH 7.4) and a temperature of approximately 30° C. are suitable for allele-specific hybridizations, though a suitable temperature depends on the length and/or GC content of the region hybridized. In one aspect, "stringency of hybridization" in determining percentage mismatch can be as follows: 1) high stringency: 0.1×SSPE, 0.1% SDS, 65° C.; 2) medium stringency: 0.2×SSPE, 0.1% SDS, 50° C. (also referred to as moderate stringency); and 3) low stringency: 1.0×SSPE, 0.1% SDS, 50° C. It is understood that equivalent stringencies may be achieved using alternative buffers, salts and temperatures. For example, moderately stringent hybridization can refer to conditions that permit a nucleic acid molecule such as a probe to bind a complementary nucleic acid molecule. The hybridized nucleic acid molecules generally have at least 60% identity, including for example at least any of 70%, 75%, 80%, 85%, 90%, or 95% identity. Moderately stringent conditions can be conditions equivalent to hybridization in 50% formamide, 5×Denhardt's solution, 5×SSPE, 0.2% SDS at 42° C., followed by washing in 0.2×SSPE, 0.2% SDS, at 42° C. High stringency conditions can be provided, for example, by hybridization in 50% formamide, 5×Denhardt's solution, 5×SSPE, 0.2% SDS at 42° C., followed by washing in 0.1×SSPE, and 0.1% SDS at 65° C. Low stringency hybridization can refer to conditions equivalent to hybridization in 10% formamide, 5×Denhardt's solution, 6×SSPE, 0.2% SDS at 22° C., followed by washing in 1×SSPE, 0.2% SDS, at 37° C. Denhardt's solution contains 1% Ficoll, 1% polyvinylpyrolidone, and 1% bovine serum albumin (BSA). 20×SSPE (sodium chloride, sodium phosphate, EDTA) contains 3 M sodium chloride, 0.2 M sodium phosphate, and 0.025 M EDTA. Other suitable moderate stringency and high stringency hybridization buffers and conditions are well known to those of skill in the art and are described, for example, in Sambrook et al., Molecular Cloning: A Laboratory Manual, 2nd ed., Cold Spring Harbor Press, Plainview, N.Y. (1989); and Ausubel et al., Short Protocols in Molecular Biology, 4th ed., John Wiley & Sons (1999).

Alternatively, substantial complementarity exists when an RNA or DNA strand will hybridize under selective hybridization conditions to its complement. Typically, selective hybridization will occur when there is at least about 65% complementary over a stretch of at least 14 to 25 nucleotides, preferably at least about 75%, more preferably at least about 90% complementary. See M. Kanehisa, *Nucleic Acids Res.* 12:203 (1984).

A "primer" used herein can be an oligonucleotide, either natural or synthetic, that is capable, upon forming a duplex with a polynucleotide template, of acting as a point of initiation of nucleic acid synthesis and being extended from its 3' end along the template so that an extended duplex is formed. The sequence of nucleotides added during the extension process is determined by the sequence of the template polynucleotide. Primers usually are extended by a polymerase, for example, a DNA polymerase.

"Ligation" may refer to the formation of a covalent bond or linkage between the termini of two or more nucleic acids, e.g., oligonucleotides and/or polynucleotides, in a template-driven reaction. The nature of the bond or linkage may vary widely and the ligation may be carried out enzymatically. As used herein, ligations are usually carried out enzymatically to form a phosphodiester linkage between a 5' carbon terminal nucleotide of one oligonucleotide with a 3' carbon of another nucleotide.

"Amplification," as used herein, generally refers to the process of producing multiple copies of a desired sequence. "Multiple copies" means at least 2 copies. A "copy" does not necessarily mean perfect sequence complementarity or identity to the template sequence. For example, copies can include nucleotide analogs such as deoxyinosine, intentional sequence alterations (such as sequence alterations introduced through a primer comprising a sequence that is hybridizable, but not complementary, to the template), and/or sequence errors that occur during amplification.

"Sequence determination" and the like include determination of information relating to the nucleotide base sequence of a nucleic acid. Such information may include the identification or determination of partial as well as full sequence information of the nucleic acid. Sequence information may be determined with varying degrees of statistical reliability or confidence. In one aspect, the term includes the determination of the identity and ordering of a plurality of contiguous nucleotides in a nucleic acid.

The term "Sequencing," "High throughput sequencing," or "next generation sequencing" includes sequence determination using methods that determine many (typically thousands to billions) of nucleic acid sequences in an intrinsically parallel manner, i.e. where DNA templates are prepared for sequencing not one at a time, but in a bulk process, and where many sequences are read out preferably in parallel, or alternatively using an ultra-high throughput serial process that itself may be parallelized. Such methods include but are not limited to pyrosequencing (for example, as commercialized by 454 Life Sciences, Inc., Branford, CT); sequencing by ligation (for example, as commercialized in the SOLiD™ technology, Life Technologies, Inc., Carlsbad, CA); sequencing by synthesis using modified nucleotides (such as commercialized in TruSeq™ and HiSeq™ technology by Illumina, Inc., San Diego, CA; HeliScope™ by Helicos Biosciences Corporation, Cambridge, MA; and PacBio RS by Pacific Biosciences of California, Inc., Menlo Park, CA), sequencing by ion detection technologies (such as Ion Torrent™ technology, Life Technologies, Carlsbad, CA); sequencing of DNA nanoballs (Complete Genomics, Inc., Mountain View, CA); nanopore-based sequencing technologies (for example, as developed by Oxford Nanopore Technologies, LTD, Oxford, UK), and like highly parallelized sequencing methods.

"SNP" or "single nucleotide polymorphism" may include a genetic variation between individuals; e.g., a single nitrogenous base position in the DNA of organisms that is variable. SNPs are found across the genome; much of the genetic variation between individuals is due to variation at SNP loci, and often this genetic variation results in phenotypic variation between individuals. SNPs for use in the present disclosure and their respective alleles may be derived from any number of sources, such as public databases (U.C. Santa Cruz Human Genome Browser Gateway (genome.ucsc.edu/ cgi-bin/hgGateway) or the NCBI dbSNP website (ncbi.nlm-.nih gov/SNP/), or may be experimentally determined as described in U.S. Pat. No. 6,969,589; and US Pub. No. 2006/0188875 entitled "Human Genomic Polymorphisms." Although the use of SNPs is described in some of the embodiments presented herein, it will be understood that other biallelic or multi-allelic genetic markers may also be used. A biallelic genetic marker is one that has two polymorphic forms, or alleles. As mentioned above, for a biallelic genetic marker that is associated with a trait, the allele that is more abundant in the genetic composition of a case group as compared to a control group is termed the "associated allele," and the other allele may be referred to as the "unassociated allele." Thus, for each biallelic polymorphism that is associated with a given trait (e.g., a disease or drug response), there is a corresponding associated allele. Other biallelic polymorphisms that may be used with the methods presented herein include, but are not limited to multinucleotide changes, insertions, deletions, and translocations.

It will be further appreciated that references to DNA herein may include genomic DNA, mitochondrial DNA, episomal DNA, and/or derivatives of DNA such as amplicons, RNA transcripts, cDNA, DNA analogs, etc. The polymorphic loci that are screened in an association study may be in a diploid or a haploid state and, ideally, would be from sites across the genome. Sequencing technologies are available for SNP sequencing, such as the BeadArray platform (GOLDENGATE™ assay) (Illumina, Inc., San Diego, CA) (see Fan, et al., *Cold Spring Symp. Quant. Biol.,* 68:69-78 (2003)), may be employed.

In some embodiments, the term "methylation state" or "methylation status" refers to the presence or absence of 5-methylcytosine ("5-mC" or "5-mCyt") at one or a plurality of CpG dinucleotides within a DNA sequence. Methylation states at one or more particular CpG methylation sites (each having two CpG dinucleotide sequences) within a DNA sequence include "unmethylated," "fully-methylated," and "hemi-methylated." The term "hemi-methylation" or "hemimethylation" refers to the methylation state of a double stranded DNA wherein only one strand thereof is methylated. The term "hypermethylation" refers to the average methylation state corresponding to an increased presence of 5-mCyt at one or a plurality of CpG dinucleotides within a DNA sequence of a test DNA sample, relative to the amount of 5-mCyt found at corresponding CpG dinucleotides within a normal control DNA sample. The term "hypomethylation" refers to the average methylation state corresponding to a decreased presence of 5-mCyt at one or a plurality of CpG dinucleotides within a DNA sequence of a test DNA sample, relative to the amount of 5-mCyt found at corresponding CpG dinucleotides within a normal control DNA sample.

"Multiplexing" or "multiplex assay" herein may refer to an assay or other analytical method in which the presence, amount and/or methylation state (or methylation status) of multiple targets, e.g., multiple nucleic acid sequences, can be assayed simultaneously by using more than one markers, each of which has at least one different detection characteristic, e.g., fluorescence characteristic (for example excitation wavelength, emission wavelength, emission intensity, FWHM (full width at half maximum peak height), or fluorescence lifetime) or a unique nucleic acid or protein sequence characteristic.

As used herein, "disease or disorder" refers to a pathological condition in an organism resulting from, e.g., infection or genetic defect, and characterized by identifiable symptoms.

B. Panels of Isolated Polynucleotides and Related Compositions

In one aspect, provided herein is a panel of isolated polynucleotides comprising, consisting of, or consisting essentially of at least two isolated polynucleotides, each of said isolated polynucleotides having a polynucleotide sequence of any of Target 1 to Target 1849 listed in Table 1 (shown in FIG. 5), or a complementary or substantially complementary sequence thereof.

The present panel can comprise, consist of, or consist essentially of any suitable number of the above isolated polynucleotides. For example, the present panel can comprise, consist of, or consist essentially of at least 2, 3, 4, 5, 6, 7, 8, 9, 10, 20, 30, 40, 50, 60, 70, 80, 90, 100, 200, 300, 400, 500, 600, 700, 800, 900, 1,000, 1,100, 1,200, 1,300, 1,400, 1,500, 1,600, 1,700, 1,800, more of the isolated polynucleotides, or the isolated polynucleotides corresponding to all of Target 1 to Target 1849 listed in Table 1, or a numerical range or subrange thereof.

In one embodiment, the present panel can comprise at least 2, 3, 4, 5, 6, 7, 8, 9, 10, 20, 30, 40, 50, 60, 70, 80, 90, 100, 200, 300, 400, 500, 600, 700, 800, 900, 1,000, 1,100, 1,200, 1,300, 1,400, 1,500, 1,600, 1,700, 1,800, more of the isolated polynucleotides, or the isolated polynucleotides corresponding to all of Target 1 to Target 1849 listed in Table 1, or a numerical range or subrange thereof. In another embodiment, the present panel can consist of at least 2, 3, 4, 5, 6, 7, 8, 9, 10, 20, 30, 40, 50, 60, 70, 80, 90, 100, 200, 300, 400, 500, 600, 700, 800, 900, 1,000, 1,100, 1,200, 1,300, 1,400, 1,500, 1,600, 1,700, 1,800, more of the isolated polynucleotides, or the isolated polynucleotides corresponding to all of Target 1 to Target 1849 listed in Table 1, or a numerical range or subrange thereof. In still another embodiment, the present panel can consist essentially of at least 2, 3, 4, 5, 6, 7, 8, 9, 10, 20, 30, 40, 50, 60, 70, 80, 90, 100, 200, 300, 400, 500, 600, 700, 800, 900, 1,000, 1,100, 1,200, 1,300, 1,400, 1,500, 1,600, 1,700, 1,800, more of the isolated polynucleotides, or the isolated polynucleotides corresponding to all of Target 1 to Target 1849 listed in Table 1, or a numerical range or subrange thereof.

The isolated polynucleotides in the present panel can be any suitable type(s) of polynucleotides. For example, the isolated polynucleotides can be DNA molecules, RNA molecules, or a combination thereof. In some embodiments, the DNA molecules can be genomic DNA molecules or fragments thereof.

The isolated polynucleotides can be immobilized on a substrate. The isolated polynucleotides can be immobilized on any suitable substrate. For example, the substrate can comprise a solid surface, a porous surface, or a combination thereof. In some embodiments, the substrate can be a part of a bead, a tube, a microtiter plate, a membrane, a gel, or a glass slide. In other embodiments, the isolated polynucleotide molecules can be immobilized spatially apart from each other on a substrate so that each of the isolated polynucleotide molecules can be assessed or analyzed individually.

Kits, devices, systems or articles of manufacture that comprise any of the above panel(s) are also provided.

The present kits, devices, systems or articles of manufacture can be configured for any suitable use or purpose. For example, the present kits, devices, systems or articles of manufacture can be configured for assessing methylation status of at least two of Target 1 to Target 1849 listed in Table 1. In some embodiments, the present kits, devices, systems or articles of manufacture can be configured for assessing methylation status of at least 2, 3, 4, 5, 6, 7, 8, 9, 10, 20, 30, 40, 50, 60, 70, 80, 90, 100, 200, 300, 400, 500, 600, 700, 800, 900, 1,000, 1,100, 1,200, 1,300, 1,400, 1,500, 1,600, 1,700, 1,800, more of the isolated polynucleotides, or the isolated polynucleotides corresponding to all of Target 1 to Target 1849 listed in Table 1, or a numerical range or subrange thereof. In other embodiments, the isolated polynucleotides in the present kits, devices, systems or articles of manufacture can be configured as control polynucleotides.

The isolated polynucleotides in the present kits, devices, systems or articles of manufacture can have any suitable level of concentration. For example, the isolated polynucleotides can have a level of concentration from about 1 femtomolar to about 100 millimolar, e.g., at about 1 femtomolar (fM), 10 fM, 100 fM, 1 picomolar (pM), 10 pM, 100 pM, 1 nanomolar (nM), 10 nM, 100 nM, 1 micromolar (µM), 10 µM, 100 µM, 1 millimolar (mM), 10 mM, 100 mM, or a subrange thereof.

The present kits, devices, systems or articles of manufacture can be configured for any suitable use or purpose. For example, the kits, devices, systems or articles of manufacture can be configured for assessing cancer or neoplasia in a subject, e.g., for assessing lung cancer or colorectal cancer in a subject, or for pan-cancer analysis or profiling in a subject.

C. Kits, Systems and Related Compositions for Assessing Methylation

In another aspect, a kit, device, system or an article of manufacture that is configured for assessing methylation status of at least two of Target 1 to Target 1849 listed in Table 1 is provided.

The present kits, devices, systems or articles of manufacture can comprise reagents for assessing methylation status of any suitable number of the Targets listed in Table 1. For example, the present kits, devices, systems or articles of manufacture can comprise reagents for assessing methylation status of at least 2, 3, 4, 5, 6, 7, 8, 9, 10, 20, 30, 40, 50, 60, 70, 80, 90, 100, 200, 300, 400, 500, 600, 700, 800, 900, 1,000, 1,100, 1,200, 1,300, 1,400, 1,500, 1,600, 1,700, 1,800, more of the isolated polynucleotides, or the isolated polynucleotides corresponding to all of Target 1 to Target 1849 listed in Table 1, or a numerical range or subrange thereof.

In some embodiments, the present kits, devices, systems or articles of manufacture can comprise reagents for assessing methylation status of any subgroup of the Targets listed in Table 1. For example, the present kits, devices, systems or articles of manufacture can comprise reagents for assessing methylation status of Targets 1-100 listed in Table 1. In other embodiments, the present kits, devices, systems or articles of manufacture can comprise reagents for assessing methylation status of all of the Targets listed in Table 1, excluding one or more Targets listed in Table 1. For example, the present kits, devices, systems or articles of manufacture can comprise reagents for assessing methylation status of Targets 1-1848 listed in Table 1, but do not comprise reagent(s) for assessing methylation status of Target 1849 listed in Table 1, etc.

The present kits, devices, systems or articles of manufacture can comprise any suitable reagents for assessing methylation status of the target polynucleotides. For example, the reagents can comprise, consist essentially of, or consist of a probe or primer configured for hybridizing with each of the targets whose methylation status is to be assessed. In some embodiments, the reagents comprise, consist essentially of, or consist of a single probe or primer configured for hybridizing with each of the targets whose methylation status is to be assessed. In other embodiments, the reagents comprise, consist essentially of, or consist of multiple probes or primers configured for hybridizing with each of the targets whose methylation status is to be assessed.

In some embodiments, the one or more primers in the present kits, devices, systems or articles of manufacture comprise, consist essentially of, or consist of a sequence set forth in SEQ ID NOs: 1-17504 listed in Table 1, a complementary or substantially complementary sequence thereof, or any combination thereof. For each Target listed in Table 1, the present kits, devices, systems or articles of manufacture can comprise, consist essentially of, or consist of one ore more corresponding primers for that Target. For example, for Target 1 listed in Table 1, the present kits, devices, systems or articles of manufacture can comprise, consist essentially of, or consist of any of a sequence set forth in SEQ ID NOs: 1-10 listed in Table 1, e.g., 1, 2, 3, 4, 5, 6, 7, 8, 9 or 10 primers comprising, consisting essentially of, or consisting of sequence(s) set forth in SEQ ID NOs: 1-10, a complementary or substantially complementary sequence thereof, or any combination thereof. Similarly, for Target 2 listed in Table 1, the present kits, devices, systems or articles of manufacture can comprise, consist essentially of, or consist of any of a sequence set forth in SEQ ID NOs: 11-20 listed in Table 1, e.g., 1, 2, 3, 4, 5, 6, 7, 8, 9 or 10 primers comprising, consisting essentially of, or consisting of sequence(s) set forth in SEQ ID NOs: 11-20, a complementary or substantially complementary sequence thereof, or any combination thereof. For any of Targets 3-1849 listed in Table 1, the present kits, devices, systems or articles of manufacture can comprise, consist essentially of, or consist of any of the corresponding sequence(s) listed in Table 1, a complementary or substantially complementary sequence thereof, or any combination thereof, as illustrated for Target 1 or 2 listed in Table 1 above.

In some embodiments, the present kits, devices, systems or articles of manufacture can comprise a common primer, e.g., a common primer for amplifying each of the targets whose methylation status is to be assessed. An exemplary common primer can comprise, consist essentially of, or consist of a sequence set forth in SEQ ID NO:17505 CACTCTTTCCCTACACGACGC), or a complementary or substantially complementary sequence thereof.

The present kits, devices, systems or articles of manufacture can further comprise any other suitable reagents. In some embodiments, the present kits, devices, systems or articles of manufacture can further comprise any other suitable reagents disclosed and/or claimed in U.S. provisional application Ser. No. 62/487,422, filed on Apr. 19, 2017 and U.S. provisional application Ser. No. 62/487,423, filed on Apr. 19, 2017.

For example, the present kits, devices, systems or articles of manufacture can further comprise an agent for isolating the targets from a sample.

In another example, the present kits, devices, systems or articles of manufacture can further comprise a reagent for preparing a library of the targets. Any suitable reagents for preparing a library of the targets can be included. In some embodiments, the reagent for preparing a library of the targets can comprise an enzyme, e.g., a ligase or a single-stranded DNA (ssDNA) ligase. Any suitable ssDNA ligase can be included, e.g., a *Thermus* bacteriophage RNA ligase such as a bacteriophage TS2126 RNA ligase (e.g., CircLigase™ and CircLigase II™), or an archaebacterium RNA ligase such as *Methanobacterium* thermoautotrophicum RNA ligase 1.

In still another example, the present kits, devices, systems or articles of manufacture can further comprise a reagent for amplifying the targets or a library of the targets. Any suitable reagents for amplifying the targets or a library of the targets can be included. In some embodiments, the reagent for amplifying the targets or a library of the targets can comprise an enzyme, e.g., an enzyme to be used in a polynucleotide amplification reaction. Exemplary polynucleotide amplification reactions include polymerase chain reaction (PCR), strand displacement amplification (SDA), transcription mediated amplification (TMA), ligase chain reaction (LCR), nucleic acid sequence based amplification (NASBA), primer extension, rolling circle amplification (RCA), self sustained sequence replication (3SR), and loop-mediated isothermal amplification (LAMP).

In yet another example, the present kits, devices, systems or articles of manufacture can further comprise an agent for purifying the targets, a library of the targets, amplified targets or a library of amplified targets.

In yet another example, the present kits, devices, systems or articles of manufacture can further comprise a reagent for assessing methylation status of the targets. Any suitable reagents for assessing methylation status of the targets can be included. In some embodiments, the reagent for assessing methylation status of the targets can be a reagent to be used in a polynucleotide methylation, e.g., DNA methylation, detecting method. Exemplary polynucleotide methylation or DNA methylation detecting methods include mass spectrometry, methylation-specific PCR (MSP), bisulphite sequencing, the HpaII tiny fragment Enrichment by ligation-mediated PCR assay (HELP Assay), GlaI hydrolysis and ligation adapter dependent PCR assay (GLAD-PCR assay), restriction landmark genomic scanning (RLGS), methylated DNA immunoprecipitation (MeDIP or mDIP), pyrosequencing, molecular break light assay for DNA adenine methyltransferase activity, methyl sensitive Southern blotting and high resolution Melt (HRM) analysis.

The reagent for assessing methylation status of the targets can be a chemical agent, e.g., bisulfite or sodium bisulfite. The reagent for assessing methylation status of the targets can also be a biological agent, e.g., a polypeptide or an enzyme.

Any suitable enzyme can be included. In some embodiments, the enzyme can be a methylation-sensitive restriction enzyme (MSRE). The MSRE can selectively cleave at a residue when it is unmethylated. The MSRE can also selectively cleave at the residue when it is methylated. Exemplary MSRE can be selected from the group consisting of HpaII, SalI, SalI-HF®, ScrFI, BbeI, NotI, SmaI, XmaI, MboI, BstBI, ClaI, MluI, NaeI, NarI, PvuI, SacII, HhaI, and a combination thereof.

In some embodiments, the enzyme can be a polynucleotide polymerase. The polynucleotide polymerase is configured to be used in polynucleotide amplification reaction, e.g., PCR. Any suitable polynucleotide polymerase can be included. For example, the polynucleotide polymerase can be a DNA polymerase, e.g., a DNA polymerase without a 3' to 5' exonuclease activity.

In yet another example, the present kits, devices, systems or articles of manufacture can further comprise a denaturing reagent for denaturing a double-stranded polynucleotide from a sample to obtain the single-stranded polynucleotide.

In yet another example, the present kits, devices, systems or articles of manufacture can further comprise a crowding agent for the ligation reaction. In one aspect, the crowding agent comprises a polyethylene glycol (PEG), such as PEG 4000 or PEG 6000, Dextran, and/or Ficoll.

In yet another example, the present kits, devices, systems or articles of manufacture can further comprise a set of primers each comprising a sequence that is reverse-complement to the adaptor and/or hybridizable to the adaptor, for converting the single-stranded polynucleotide to a double-stranded polynucleotide.

In yet another example, the present kits, devices, systems or articles of manufacture can further comprise a reagent for removing primer dimer and/or primer-adaptor duplex.

In yet another example, the present kits, devices, systems or articles of manufacture can further comprise a primer comprising a sequence specific for a target sequence (e.g., an EGFR gene sequence), for obtaining an amplified linear, double-stranded ligation product comprising sequence information of the target sequence. In a further aspect, the kit can further comprise a sequencing adapter and/or a sample-specific barcode, for sequencing the amplified linear, double-stranded ligation product.

In yet another example, the present kits, devices, systems or articles of manufacture can further comprise a panel of isolated polynucleotides described in the above Section B.

In yet another example, the present kits, devices, systems or articles of manufacture can further comprise a reference sample and/or information of a control locus.

In yet another example, the present kits, devices, systems or articles of manufacture can further comprise separate containers, e.g., vials, for one or more components and/or instructions for using the kits, devices, systems or articles of manufacture.

In yet another example, the present kits, devices, systems or articles of manufacture can further comprise a computer readable medium containing executable instructions for obtaining a methylation metric of a sample based on the methylation status assessment. The computer readable medium can be configured for obtaining a methylation metric in any suitable form, e.g., in the form of average methylation frequency, methylation haplotype load, unmethylation haplotype load, percent discordant reads, or a combination thereof.

In yet another example, the present kits, devices, systems or articles of manufacture can further comprise a computer readable medium containing executable instructions for classification using the methylation metric(s). Exemplary classification algorithm can be linear discriminant analysis, logistic regression, naïve bayes classification, perceptron classification, quadratic classification, k-nearest neighbors, boosting, decision tree, random forest, neural network, learning vector quantization, or support vector machines, or a combination thereof.

The present kits, devices, systems or articles of manufacture can be configured for any suitable use or purpose. For example, the present kits, devices, systems or articles of manufacture can be configured for assessing cancer or neoplasia in a subject, e.g., for assessing lung cancer or colorectal cancer in a subject, or for pan-cancer analysis or profiling in a subject.

In some embodiments, the kit may additionally comprise reagents for detecting presence of polypeptides. Such reagents may be antibodies or other binding molecules that specifically bind to a polypeptide. In some embodiments, such antibodies or binding molecules may be capable of distinguishing a structural variation to the polypeptide as a result of polymorphism, and thus may be used for genotyping. The antibodies or binding molecules may be labeled with a detectable marker, such as, for example, a radioisotope, fluorescent compound, bioluminescent compound, a chemiluminescent compound, metal chelator or enzyme. Other reagents for performing binding assays, such as ELISA, may be included in the kit.

In some embodiments, the kits comprise reagents for genotyping at least two, at least three, at least five, at least ten, or more markers. The markers may be a polynucleotide marker (such as a cancer-associated mutation or SNP) or a polypeptide marker (such as overexpression or a post-translational modification, including hyper- or hypo-phosphorylation, of a protein) or any combination thereof. In some embodiments, the kits may further comprise a surface or substrate (such as a microarray) for capture probes for detecting of amplified nucleic acids.

The kits may further comprise a carrier means being compartmentalized to receive in close confinement one or more container means such as vials, tubes, and the like, each of the container means comprising one of the separate elements to be used in the method. For example, one of the container means may comprise a probe that is or can be detectably labeled. Such probe may be a polynucleotide specific for a biomarker. The kit may also have containers containing nucleotide(s) for amplification of the target nucleic acid sequence and/or a container comprising a reporter-means bound to a reporter molecule, such as an enzymatic, florescent, or radioisotope label.

The kit typically comprises the container(s) described above and one or more other containers comprising materials desirable from a commercial and user standpoint, including buffers, diluents, filters, needles, syringes, and package inserts with instructions for use. A label may be present on the container to indicate that the composition is used for a specific therapy or non-therapeutic application, and may also indicate directions for either in vivo or in vitro use, such as those described above.

The kit can further comprise a set of instructions and materials for preparing a tissue or cell or body fluid sample and preparing nucleic acids (such as ctDNA) from the sample.

D. Methods for Assessing Cancer or Neoplasia in a Subject

In still another aspect, provided herein is a method for assessing cancer or neoplasia in a subject, which method comprises: a) providing a sample from a subject containing at least two target polynucleotides of said subject, said at least two target polynucleotides having polynucleotide sequences of at least two of Target 1 to Target 1849 listed in Table 1, or a complementary or substantially complementary sequence thereof; b) assessing methylation status of said at least two target polynucleotides; and c) assessing cancer or neoplasia in said subject based on assessment of methylation status of said at least two target polynucleotides.

The present methods can be used on any suitable sample, e.g., any suitable sample obtained or derived from a subject whose cancer or neoplasia status is to be assessed. For example, the sample can comprise circulating cell-free or tumor DNA (ctDNA). In another example, the sample can be a blood, serum, plasma, or body fluid sample, or any combination thereof.

The target or template polynucleotides can be target DNA molecules, RNA molecules, or a complex or a combination thereof. DNA can include be regular genomic DNA, chromosomal DNA, extrachromosomal DNA (such as mitochondrial DNA), or a fragment thereof. In other embodiments, the target or template DNA is a processed DNA, for example, one that has undergone enzyme digestion, cross-linking, chemical or physical shearing, bisulfite conversion, and/or degradation.

In some embodiments, the target nucleic acid molecule of interest disclosed herein is a cell-free DNA, such as cell-free fetal DNA (also referred to as "cfDNA") or ctDNA. cfDNA circulates in the body, such as in the blood, of a pregnant mother, and represents the fetal genome, while ctDNA circulates in the body, such as in the blood, of a cancer patient, and is generally pre-fragmented. In other embodiments, the target nucleic acid molecule of interest disclosed herein is an ancient and/or damaged DNA, for example, due to storage under damaging conditions such as in formalin-fixed samples, or partially digested samples.

As cancer cells die, they release DNA into the bloodstream. This DNA, known as circulating tumor DNA (ctDNA), is highly fragmented, with an average length of approximately 150 base pairs. Once the white blood cells are removed, ctDNA generally comprises a very small fraction of the remaining plasma DNA, for example, ctDNA may constitute less than about 10% of the plasma DNA. Generally, this percentage is less than about 1%, for example, less than about 0.5% or less than about 0.01%. Additionally, the total amount of plasma DNA is generally very low, for example, at about 10 ng/mL of plasma.

The variants in the ctDNA can be interrogated using various methods, including next generation sequencing. Due to the low ratio of ctDNA to plasma DNA, it is difficult to call a variant with high confidence due to PCR and sequencing errors. Unique molecular identifiers (UMIs) can be used to tag original molecules such that any variant seen can be compared to a consensus sequence. This is an effective manner to separate true from false positives. If the variant is matched to a consensus, it is a true positive. Otherwise, it is removed from analysis. Furthermore, it is essential that a high percentage of original molecules are turned into sequencing libraries so that the sensitivity remains high, i.e., variants are not missed due to dropout. Thus, ligation efficiency can be important during library construction.

In one aspect, a technique to improve ligation efficiency while still targeting selected regions of the genome, as disclosed and/or claimed in U.S. provisional application Ser. No. 62/487,423, filed on Apr. 19, 2017, can be used to prepare target polynucleotides to be analyzed in the present methods. In one embodiment, polynucleotides to be detected by sequencing, such as ctDNA, are first dephosphorylated to remove 5' phosphates to prevent ligation of ctDNA to itself. The ctDNA is then denatured such that all DNA is single stranded. Circligase™, a single stranded DNA ligase, is used to ligate an adapter to the 3' end of the ctDNA. In one aspect, the adapter contains 2 specific bases on the 5' end to optimize ligation efficiency, followed by a UMI. In one aspect, the 3' end of the adapter contains a carbon spacer to prevent self-ligation of the adapters. In another aspect, the ligation reaction is further optimized using a crowding agent, such as PEG 4000. In one aspect, following ligation, molecules are double-stranded using a primer that is reverse complement to the adapter. This allows efficient removal of excess unligated adapters without removed usable DNA by a standard purification.

In one aspect, the DNA is then amplified using a semi-targeted PCR. One primer is reverse complement to the adapter, while the other (e.g., as one primer in a primer pool) anneals to specific, targeted regions of the genome. The specific primers were designed to minimize primer-dimer interactions and off-target annealing. In one aspect, the target-specific primers are further optimized to land in close proximity to specific variants due to the small DNA size. Following another cleanup, a PCR adds the full-length sequencing adapters and barcodes. The final library is then sequenced, for example, on an Illumina machine.

In one aspect, the semi-targeted PCR results in enrichments of >about 40,000 fold of the original molecule set despite having a relatively small target region of ~30,000 bp. In one aspect, the overall conversion rates of the present method are at least 60%, implying that at least ~3 times more of the original molecules are converted into sequenceable material when compared to standard library construction and hybridization capture. In other embodiments, the overall conversion rates are between about 60% and about 70%, between about 70% and about 80%, between about 80% and about 90%, or over 90%. In one aspect, the present method thus is able to accurately call genetic or genomic variants, such as SNVs, indels, CNVs, and fusions at extremely low mutant allele fractions, for example, as low as 0.01%. In other aspects, the allele fraction of the genetic or genomic variant is about 0.05%, about 0.1%, about 0.5%, about 1%, or about 2%.

The present methods can be used for assessing cancer or neoplasia in any suitable subject. For example, the present methods can be used for assessing cancer or neoplasia in a mammal. The mammal can be a non-human mammal, e.g., a pet, a farm animal, a companion animal or an experimental animal. Preferably, the mammal is a human. For example, a subject can be a human that needs to be screened for cancer or neoplasia risks, a human in a high-risk group, a human that has been diagnosed as having cancer or neoplasia but needs further stratification, a human that has been diagnosed as having cancer or neoplasia and under active treatment, or a human having cancer or neoplasia and is in remission.

The present methods can comprise assessing methylation status of any suitable number of the Targets listed in Table 1. For example, the methods can comprise assessing methylation status of at least 2, 3, 4, 5, 6, 7, 8, 9, 10, 20, 30, 40, 50, 60, 70, 80, 90, 100, 200, 300, 400, 500, 600, 700, 800, 900, 1,000, 1,100, 1,200, 1,300, 1,400, 1,500, 1,600, 1,700, 1,800, more of the isolated polynucleotides, or the isolated polynucleotides corresponding to all of Target 1 to Target 1849 listed in Table 1, or a numerical range or subrange thereof.

The methylation status of target polynucleotides can be assessed using any suitable methods or reagents. For example, the methylation status of target polynucleotides can be assessed using a probe or primer configured for hybridizing with each of the target polynucleotides. In some embodiments, the methylation status of a target polynucleotide can be assessed using a single probe or primer configured for hybridizing with the target polynucleotide. In other embodiments, the methylation status of a target polynucleotide can be assessed using multiple probes or primers configured for hybridizing with the target polynucleotide.

In some embodiments, the one or more primers used in the present methods can comprise, consist essentially of, or consist of a sequence set forth in any of SEQ ID NOs: 1-17504 listed in Table 1, a complementary or substantially complementary sequence thereof, or any combination thereof. For each Target listed in Table 1, the one or more primers used in the present methods can comprise, consist essentially of, or consist of one or more corresponding primers for that Target. For example, for Target 1 listed in Table 1, the one or more primers used in the present methods can comprise, consist essentially of, or consist of any of a sequence set forth in SEQ ID NOs: 1-10 listed in Table 1, e.g., 1, 2, 3, 4, 5, 6, 7, 8, 9 or 10 primers comprising, consisting essentially of, or consisting of sequence(s) set forth in SEQ ID NOs: 1-10, a complementary or substantially complementary sequence thereof, or any combination thereof. Similarly, for Target 2 listed in Table 1, the one or more primers used in the present methods can comprise, consist essentially of, or consist of any of a sequence set forth in SEQ ID NOs: 11-20 listed in Table 1, e.g., 1, 2, 3, 4, 5, 6, 7, 8, 9 or 10 primers comprising, consisting essentially of, or consisting of sequence(s) set forth in SEQ ID NOs: 11-20, a complementary or substantially complementary sequence thereof, or any combination thereof. For any of Targets 3-1849 listed in Table 1, the one or more primers used in the present methods can comprise, consist essentially of, or consist of any of the corresponding sequence(s) listed in Table 1, a complementary or substantially complementary sequence thereof, or any combination thereof, as illustrated for Target 1 or 2 listed in Table 1 above.

The present methods can further comprise using a common primer for amplifying each of the target polynucleotide whose methylation status is to be assessed. An exemplary common primer can comprise, consist essentially of, or consist of a sequence set forth in SEQ ID NO:17505 CACTCTTTCCCTACACGACGC), or a complementary or substantially complementary sequence thereof.

The present methods can further comprise any other suitable steps. In some embodiments, the present methods can further comprise any other suitable steps disclosed and/or claimed in U.S. provisional application Ser. No. 62/487,422, filed on Apr. 19, 2017 and U.S. provisional application Ser. No. 62/487,423, filed on Apr. 19, 2017. For example, techniques and steps for constructing single-stranded polynucleotide, conversion of single-stranded polynucleotide library to double-stranded polynucleotide library, semi-targeted amplification of double-stranded polynucleotide library, and construction of sequence library and analysis of sequencing reads disclosed and/or claimed in U.S. provisional application Ser. No. 62/487,423, filed on Apr. 19, 2017 can be used to obtain and/or prepare target polynucleotides to be analyzed.

For example, the present methods can further comprise isolating the target polynucleotides from a sample.

In another example, the present methods can further comprise preparing a library of the target polynucleotides. Any suitable reagents for preparing a library of the targets can be used. In some embodiments, the reagent for preparing a library of the targets can comprise an enzyme, e.g., a ligase or a single-stranded DNA (ssDNA) ligase. Any suitable ssDNA ligase can be included, e.g., a *Thermus* bacteriophage RNA ligase such as a bacteriophage TS2126 RNA ligase (e.g., CircLigase™ and CircLigase II™), or an archaebacterium RNA ligase such as *Methanobacterium thermoautotrophicum* RNA ligase 1.

In still another example, the present methods can further comprise amplifying the target polynucleotides. Any suitable reagents for amplifying the targets or a library of the targets can be used. In some embodiments, the reagent for amplifying the targets or a library of the targets can comprise an enzyme, e.g., an enzyme to be used in a polynucleotide amplification reaction. Exemplary polynucleotide amplification reactions include polymerase chain reaction (PCR), strand displacement amplification (SDA), transcription mediated amplification (TMA), ligase chain reaction (LCR), nucleic acid sequence based amplification (NASBA), primer extension, rolling circle amplification (RCA), self-sustained sequence replication (3SR), and loop-mediated isothermal amplification (LAMP).

In yet another example, the present methods can further comprise purifying the target polynucleotides, a library of the target polynucleotides, amplified target polynucleotides or a library of amplified target polynucleotides.

The methylation status of target polynucleotides can be assessed using any suitable methods and/or regents. In some embodiments, the methylation status of target polynucleotides can be assessed using mass spectrometry, methylation-specific PCR (MSP), methylation-sensitive sequencing, e.g., bisulphite sequencing, the HpaII tiny fragment Enrichment by ligation-mediated PCR assay (HELP Assay), Glal hydrolysis and ligation adapter dependent PCR assay (GLAD-PCR assay), restriction landmark genomic scanning (RLGS), methylated DNA immunoprecipitation (MeDIP or mDIP), pyrosequencing, molecular break light assay for DNA adenine methyltransferase activity, methyl sensitive Southern blotting or high resolution Melt (HRM) analysis.

In other embodiments, the methylation status of target polynucleotides can be assessed using a chemical agent, e.g., bisulfite or sodium bisulfite. In still other embodiments, the methylation status of target polynucleotides can be assessed using a biological agent, e.g., a polypeptide or an enzyme.

Any suitable enzyme can be used. In some embodiments, the enzyme can be a methylation-sensitive restriction enzyme (MSRE). The MSRE can selectively cleave at a residue when it is unmethylated. The MSRE can also selectively cleave at the residue when it is methylated. Exemplary MSRE can be selected from the group consisting of HpaII, SalI, SalI-HF®, ScrFI, BbeI, NotI, SmaI, XmaI, MboI, BstBI, ClaI, MluI, NaeI, NarI, PvuI, SacII, HhaI, and a combination thereof.

In some embodiments, the enzyme can be a polynucleotide polymerase. The polynucleotide polymerase can be used in polynucleotide amplification reaction, e.g., PCR. Any suitable polynucleotide polymerase can be used. For example, the polynucleotide polymerase can be a DNA polymerase, e.g., a DNA polymerase without a 3' to 5' exonuclease activity.

In some embodiments, the methylation status of target polynucleotides can be assessed using methylation-sensitive sequencing, e.g., bisulphite sequencing. Bisulfite conversion is a method that uses bisulfite to determine the methylation pattern of DNA. DNA methylation is a biochemical process involving the addition of a methyl group to the cytosine or adenine DNA nucleotides. DNA methylation stably alters the expression of genes in cells as cells divide and differentiate from embryonic stem cells into specific tissues. In bisulfite conversion, target nucleic acids are first treated with bisulfite reagents that specifically convert un-methylated cytosines to uracils while having no impact of methylated cytosine. One consequence of bisulfite conversion is that the double-stranded conformation of the original target is disrupted due to loss of sequence complementarity. The target sequences exist as two separate single-stranded DNAs during sample preparation and analytical or diagnostic testing. Target nucleic acid sequences frequently also exist at very low concentrations. This is an especially important consideration for circulating tumor DNA (also referred to as "cell-free tumor DNA," or "ctDNA") due to its often low concentration in circulation and the very low variant allele fraction.

Any suitable format of methylation-sensitive sequencing can be used. For example, the methylation-sensitive sequencing can be conducted with a format selected from the group consisting of Maxam-Gilbert sequencing, a chain-termination method, shotgun sequencing, bridge PCR, single-molecule real-time sequencing, ion semiconductor (ion torrent sequencing), sequencing by synthesis, sequencing by ligation (SOLiD sequencing), chain termination (Sanger sequencing), massively parallel signature sequencing (MPSS), polony sequencing, 454 pyrosequencing, Illumina (Solexa) sequencing, DNA nanoball sequencing, heliscope single molecule sequencing, single molecule real time (SMRT) sequencing, nanopore DNA sequencing, tunnelling currents DNA sequencing, sequencing by hybridization, sequencing with mass spectrometry, microfluidic Sanger sequencing, a microscopy-based technique, RNAP sequencing, and in vitro virus high-throughput sequencing.

In some embodiments, the present methods can further comprise, prior to the methylation-sensitive sequencing, e.g., bisulphite sequencing, obtaining a library of linear, single-stranded ligation products, each of the linear, single-stranded ligation products comprises of a linear, single-stranded target polynucleotide linked to an adaptor comprising a unique molecular identifier (UMI) sequence that earmarks the single-stranded target polynucleotide to which the adaptor is ligated. The sequencing reads from the target polynucleotides can be first adapter trimmed to remove any adapter sequence originating from the library construction process to obtain trimmed sequencing reads. The trimmed sequencing reads can be mapped to a reference genome, e.g., a human reference genome, using an alignment program to obtain an aligned read file. The aligned read file can be grouped into sets corresponding to each target region from Target 1 to Target 1849 listed in Table 1, or a complementary or substantially complementary sequence thereof, that can be used for methylation status assessment.

Methylation status of one, more or each of the target polynucleotides can be assessed. In some embodiments, the methylation status of each of the target polynucleotides can be assessed to obtain a methylation metric, e.g., in the form of average methylation frequency, methylation haplotype load, unmethylation haplotype load, percent discordant reads, or a combination thereof.

Methylation status of a sample can be assessed using the methylation metrics from each of the target polynucleotides. The methylation metrics can be analyzed or used in any suitable manner. For example, the methylation metric for each of the target polynucleotides can be compared to a threshold or reference value to assess methylation status of a sample.

In another example, a numerical methylation matrix can be computed using the methylation metrics from each of the target polynucleotides to assess methylation status of a sample. The numerical methylation matrix can be in any suitable format. In some embodiments, the numerical methylation matrix from a sample can comprise a single numerical number or value. In other embodiments, the numerical methylation matrix from a sample can comprise multiple numerical numbers or values. The numerical methylation matrix can be obtained or computed using any suitable formulae or algorithm. In some embodiments, the numerical methylation matrix can be computed using a classification algorithm, e.g., linear discriminant analysis, logistic regression, naïve bayes classification, perceptron classification, quadratic classification, k-nearest neighbors, boosting, decision tree, random forest, neural network, learning vector quantization, or support vector machines, or a combination thereof.

The methylation matrix can be used in any suitable manner in assess methylation status of a sample. For example, the methylation matrix can be compared to a threshold or reference value to assess methylation status of a sample.

The methylation status of at least two target polynucleotides from multiple samples, e.g., multiple samples from multiple subjects, can be assessed sequentially or simultaneously. In some embodiments, the methylation status of at least two target polynucleotides from multiple samples, e.g., multiple samples from multiple subjects, can be assessed sequentially. For example, methylation status of at least 2, 3, 4, 5, 6, 7, 8, 9, 10, 20, 30, 40, 50, 60, 70, 80, 90, 100, 200, 300, 400, 500, 600, 700, 800, 900, 1,000, 1,100, 1,200, 1,300, 1,400, 1,500, 1,600, 1,700, 1,800, more of the iso-lated polynucleotides, or the isolated polynucleotides corresponding to all of Target 1 to Target 1849 listed in Table 1, or a numerical range or subrange thereof, can be assessed sequentially. In other embodiments, the methylation status of at least two target polynucleotides from multiple samples, e.g., multiple samples from multiple subjects, can be assessed simultaneously. For example, methylation status of at least 2, 3, 4, 5, 6, 7, 8, 9, 10, 20, 30, 40, 50, 60, 70, 80, 90, 100, 200, 300, 400, 500, 600, 700, 800, 900, 1,000, 1,100, 1,200, 1,300, 1,400, 1,500, 1,600, 1,700, 1,800, more of the isolated polynucleotides, or the isolated polynucleotides corresponding to all of Target 1 to Target 1849 listed in Table 1, or a numerical range or subrange thereof, can be assessed simultaneously.

In some embodiments, the methylation metric for each of the target polynucleotides is obtained using a computer. In other embodiments, the methylation matrix of a sample is obtained using a computer based on the methylation metrics from each of the target polynucleotides.

The present methods can be used for any suitable purpose. For example, the present methods can be used for diagnosis, prognosis, stratification, risk assessment, or treatment monitoring of cancer or neoplasia in a subject.

The present methods can be used for assessing any suitable type of cancer or neoplasia in a subject. For example, the present methods can be used for assessing a lymphoma, a leukemia, a brain cancer, a multiple myeloma, a pancreatic cancer, a liver cancer, a stomach cancer, a breast cancer, a kidney cancer, a lung cancer, a colorectal cancer, a colon cancer, a prostate cancer, an ovarian cancer, a cervical cancer, a skin cancer, an esophagus cancer, or a head and neck cancer in a subject.

In some embodiments, the present methods can be used for diagnosis, prognosis, stratification, risk assessment, or treatment monitoring of lung cancer in a subject. The lung cancer can be non-small-cell lung carcinoma or small-cell lung carcinoma. Exemplary non-small-cell lung carcinoma can be adenocarcinoma of the lung (also known as pulmonary adenocarcinoma), squamous-cell carcinoma (SCC) of the lung or large-cell carcinoma (LCC).

In other embodiments, the present methods can be used for diagnosis, prognosis, stratification, risk assessment, or treatment monitoring of colorectal cancer in a subject. In still other embodiments, the present methods can be used for diagnosis, prognosis, stratification, risk assessment, or treatment monitoring of pan-cancer analysis or profiling in a subject.

The cancer or neoplasia in multiple subjects can be assessed sequentially or simultaneously. In some embodiments, the cancer or neoplasia in multiple subjects can be assessed sequentially. For example, the cancer or neoplasia in at least 2, 3, 4, 5, 6, 7, 8, 9, 10, 20, 30, 40, 50, 60, 70, 80, 90, 100, 200, 300, 400, 500, 600, 700, 800, 900, 1,000, 1,100, 1,200, 1,300, 1,400, 1,500, 1,600, 1,700, 1,800, 1,900, 2,000, 3,000, 4,000, 5,000, 6,000, 7,000, 8,000, 9,000, 10,000 or more subjects can be assessed sequentially. In other embodiments, the cancer or neoplasia in multiple subjects can be assessed simultaneously. For example, the cancer or neoplasia in at least 2, 3, 4, 5, 6, 7, 8, 9, 10, 20, 30, 40, 50, 60, 70, 80, 90, 100, 200, 300, 400, 500, 600, 700, 800, 900, 1,000, 1,100, 1,200, 1,300, 1,400, 1,500, 1,600, 1,700, 1,800, 1,900, 2,000, 3,000, 4,000, 5,000, 6,000, 7,000, 8,000, 9,000, 10,000 or more subjects can be assessed simultaneously.

The present tests can have any suitable sensitivity. For example, the present tests can have a sensitivity of at least 10%, 20%, 30%, 40%, 50%, 60%, 70%, 80%, 90%, 91%, 92%, 93%, 94%, 95%, 96%, 97%, 98%, 99%, 99.9%, 99.999%, 99.9999%, or 100%.

The present tests can have any suitable specificity. For example, the present tests can have a specificity of at least 10%, 20%, 30%, 40%, 50%, 60%, 70%, 80%, 90%, 91%, 92%, 93%, 94%, 95%, 96%, 97%, 98%, 99%, 99.9%, 99.999%, 99.9999%, or 100%.

The present methods can further comprise treating a subject or altering treatment of a subject based on the assessment of cancer or neoplasia in the subject. For example, the present methods can further comprise treating a human patient or altering treatment of a human patient based on the assessment of cancer or neoplasia in the human patient. Exemplary treatment can be chemotherapy, radiotherapy, immunotherapy, cell therapy, surgery, treatment with a drug, e.g., a small molecule drug or a large molecule drug such an antibody drug.

The present methods can further comprise subjecting a subject to further tests, e.g., gold-standard diagnostic or prognostic test(s), based on the assessment of cancer or neoplasia in the subject. For example, the present methods can further comprise subjecting a human patient to further tests, e.g., gold-standard diagnostic or prognostic test(s), based on the assessment of cancer or neoplasia in the human patient. Exemplary test can be any suitable type of tests, e.g., in vivo test, in vitro test, tests on molecules such as DNA, RNA, protein, peptide, a complex or combination thereof, immunotest, molecular test, cellular test, tissue test, organ test or whole-body test, etc.

E. Exemplary Data Analysis Methods

Preprocessing

In some embodiments, sequencing reads are first adapter trimmed (to remove any synthetic adapter sequence originating from the sequencing library construction process) using a trimming program such as Cutadapt (http://journal-.embnet.org/index.php/embnetjournal/article/view/200/479) or Trimmomatic (https://www.ncbi.nlm.nih.gov/pubmed/24695404). Trimmed reads are then mapped to the human reference genome using an alignment program such as Bowtie (http://bowtie-bio.sourceforge.net/index.shtml), Bowtie2 (http://bowtie-bio.sourceforge.net/bowtie2/index.shtml), or BWA (http://bio-bwa.sourceforge.net). The resultant aligned read file is then sorted and indexed using a suitable tool, e.g., Samtools (https://github.com/samtools/samtools). Reads are then grouped into sets corresponding to each target region that can be used for methylation metric computation.

Methylation Metric Computation

In some embodiments, for each target, a "methylation metric" representing that individual region's methylation state is computed using the aligned reads. Four metrics that can be used are Average Methylation Frequency (AMF), Methylation Haplotype Load (MHL), UnMethylation Haplotype Load (UMHL), and Percent Discordant Reads (PDR).

Average Methylation Frequency is computed by summing the number of cytosine bases observed at CpG sites within the target region and dividing by the number of cytosine and thymine bases observed at CpG sites within the target region:

$$AMF = \frac{\sum_{i=1}^{N} C_i}{\sum_{i=1}^{N} C_i + T_i}$$

Where N is the number of reads within the target region, i is the ith read in the target region, $C_i$ is the number of cytosines observed in the ith read, and $T_i$ is the number of thymines observed in the ith read.

Methylation Haplotype Load is computed by taking all possible substrings of adjacent CpG sites within a target region and calculating a weighted sum of the fraction of reads showing full methylation within each substring:

$$MHL = \frac{\sum_{L_i=1}^{n} L_i \frac{C_i}{N_i}}{\sum_{L_i=1}^{n} L_i}$$

Where n is the number of CpG sites within the target region, $L_i$ is the length of the current substring, $C_i$ is the number of reads containing all cytosines at CpG sites within substrings of length $L_i$, and $N_i$ is the number of reads containing a substring of length $L_i$.

Unmethylation Haplotype Load is computed by taking all possible substrings of adjacent CpG sites within a target region and calculating a weighted sum of the fraction of reads showing no methylation within each substring:

$$UMHL = \frac{\sum_{L_i=1}^{n} L_i \frac{T_i}{L_i}}{\sum_{L_i=1}^{n} L_i}$$

Where n is the number of CpG sites within the target region, $L_i$ is the length of the current substring, $T_i$ is the number of reads containing all thymines at CpG sites within substrings of length $L_i$, and $N_i$ is the number of reads containing a substring of length $L_i$.

Percent Discordant Reads is computed by taking one hundred minus the percent of reads within each region showing all cytosines or all thymines at CpG sites within the target region:

$$PDR = 100\left(1 - \frac{C_i + T_i}{N_i}\right)$$

Where $N_i$ is the number of reads within the target region, $C_i$ is the number of reads containing cytosines at all covered CpG sites, and $T_i$ is the number of reads containing thymines at all covered CpG sites.

Classification

In some embodiments, using the methylation metrics for each target region, a numerical matrix is computed (with one row for each target region, one column for each sample, and values representing the methylation metric for that region and sample). Samples are then classified using a classification algorithm such as linear discriminant analysis, logistic regression, naïve bayes classification, perceptron classification, quadratic classification, k-nearest neighbors, boosting, decision tree, random forest, neural network, learning vector quantization, or support vector machines, or a combination thereof.

logistic regression, k-nearest neighbors, random forest, or support vector machines.

Logistic Regression classification involves curve-fitting an equation for the probability of a sample being cancerous to the weighted sum of methylation metric values using a set of known samples. Using a least-squares regression on data from samples with known categories, the parameters for the below equation are estimated:

$$\log\left(\frac{p}{1-p}\right) = \beta_0 + \sum_{i}^{n} \beta_i M_i$$

Where n is the set of target regions, i is the current target region, $M_i$ is the methylation metric value for the ith target region, $\beta_i$ is the least-square parameter for the ith target region, and p is the probability that the sample is a cancer sample. Once the parameters for this equation are derived using known samples, an unknown sample can be classified as cancer or healthy by computing the weighted sum of methylation metric values, computing the probability using the derived equation, and comparing to a threshold.

K-nearest neighbor algorithm classifies an unknown sample using the distance of methylation metric values between the unknown sample and its k closest neighbors with known categories. First, the distances (in this case Euclidean distances) between the methylation metric values of the current sample and all other samples are computed:

$$E_1 = \sqrt{\sum_{i}^{N} \sum_{j}^{n} (M_j - m_{ij})^2}$$

Where N is the set of known samples, i is the current known sample, n is the set of target regions, j is the current target region, $M_j$ is the methylation metric value of the unknown sample in the jth target region, $m_{ij}$ is the methylation metric value of the ith known sample in the jth target region, and $E_i$ is the Euclidean distance between the current sample and the ith known sample. The categories of the k known samples with the lowest Euclidean distance are used to determine the category of the unknown sample; the category with the highest occurrence is assigned to the unknown sample.

In K-Nearest Neighbors, an unknown sample is classified as either normal or cancer by identifying the k known samples that it is most similar to (where k is any number of our choice). If an unknown sample is more similar to known normal samples, we classify it as normal; if it is more similar to cancer samples, we classify it as cancer. The following is a hypothetical example that illustrates how K-Nearest Neighbors analysis may be conducted.

Suppose we are looking at 2 target regions and using the MHL methylation metric for our assay, and we want to use a K nearest neighbors approach with k=3. We would first run some samples that we know are healthy and some samples that we know are cancer, and compute the MHL values for each target in each sample. Suppose we ran 4 known samples of each type, and obtained the matrix shown in Table 2 below.

TABLE 2

|  | Normal 1 | Normal 2 | Normal 3 | Normal 4 | Cancer 1 | Cancer 2 | Cancer 3 | Cancer 4 |
|---|---|---|---|---|---|---|---|---|
| Target 1 | 1 | 0.9 | 0.93 | 0.85 | 0.1 | 0 | 0.05 | 0.08 |
| Target 2 | 0.05 | 0 | 0.1 | 0.2 | 0.98 | 0.7 | 1.0 | 0.6 |

We could then process an unknown sample. Suppose we ran an unknown sample, and obtained the values shown in Table 3 below.

TABLE 3

|  | UNKNOWN |
|---|---|
| Target 1 | 0.2 |
| Target 2 | 0.8 |

Based on the values we observed, we identify the k=3 samples that are most similar to our unknown sample shown in Table 4 below.

TABLE 4

|  | UNKNOWN | Cancer 1 | Cancer 2 | Cancer 4 |
|---|---|---|---|---|
| Target 1 | 0.2 | 0.1 | 0 | 0.08 |
| Target 2 | 0.8 | 0.98 | 0.7 | 0.6 |

Because a majority of these 3 Nearest Neighbors are CANCER, we classify the UNKNOWN sample as CANCER.

Random Forest classification involves creating multiple decision trees using a randomly chosen subset of samples with known categories and a subset of target regions; the methylation metric values of an unknown sample are then subjected to each individual decision tree, and the majority vote is used for classification. For example, using known data, the following three decision trees might be constructed:

$$MHL_1 \begin{cases} \geq 0.5\text{:Cancer} \\ < 0.5\text{:Healthy} \end{cases}$$

$$MHL_2 \begin{cases} \geq 0.1\text{:Cancer} \\ < 0.1\text{:Healthy} \end{cases}$$

$$MHL_3 \begin{cases} \geq 0.2\text{:Cancer} \\ < 0.2\text{:Healthy} \end{cases}$$

An unknown sample containing the MHL values ($MHL_1$: 0.6, $MHL_2$: 0.2, $MHL_3$: 0.6) would then be classified as Cancer, as it would have two votes for cancer and one vote for healthy.

Support Vector Machines construct a hyperplane between known samples of different categories that maximizes the distance between each known sample and the hyperplane.

This plane is then used as a "divider" to classify unknown samples, with samples falling on different sides of the plane being categorized differently. To illustrate an example using 2 target regions, the methylation metric values of known samples are plotted in space, and a hyperplane is drawn between the different groups (see FIG. 1), where $X_1$ is the methylation metric value of the first target region, $X_2$ is the methylation metric value of the second target region, known cancer samples are drawn in black, known healthy samples are drawn in white, and the black line represents the hyperplane. To classify an unknown sample (shown in orange), the methylation metric values are compared to the hyperplane; if the sample falls on the same side as the healthy known samples (as it does here), the sample is classified as healthy. Image of FIG. 1 is taken from Wikipedia: https://en.wikipedia.org/wiki/Support vector machine) for illustration purpose only, and does not represent any DNA methylation status analysis or cancer assessment.

F. Exemplary Polynucleotide Fragment Analysis by Library Construction and Polynucleotide Sequencing In one aspect, the target (or template) polynucleotide of the present method is a fragmented polynucleotide, for example, ranging from about 100 residues to about 1000 residues, and in some embodiments, ranging from about 150 residues to about 400 residues.

The target or template DNA can include be regular genomic DNA, chromosomal DNA, extrachromosomal DNA (such as mitochondrial DNA), or a fragment thereof. In other embodiments, the target or template DNA is a processed DNA, for example, one that has undergone enzyme digestion, cross-linking, chemical or physical shearing, bisulfite conversion, and/or degradation.

Bisulfite conversion is a method that uses bisulfite to determine the methylation pattern of DNA. DNA methylation is a biochemical process involving the addition of a methyl group to the cytosine or adenine DNA nucleotides. DNA methylation stably alters the expression of genes in cells as cells divide and differentiate from embryonic stem cells into specific tissues. In bisulfite conversion, target nucleic acids are first treated with bisulfite reagents that specifically convert un-methylated cytosines to uracils while having no impact of methylated cytosine. One consequence of bisulfite conversion is that the double-stranded conformation of the original target is disrupted due to loss of sequence complementarity. The target sequences exist as two separate single-stranded DNAs during sample preparation and analytical or diagnostic testing. Target nucleic acid sequences frequently also exist at very low concentrations. This is an especially important consideration for circulating tumor DNA (also referred to as "cell-free tumor DNA," or "ctDNA") due to its often low concentration in circulation and the very low variant allele fraction.

In some embodiments, the nucleic acid molecule of interest disclosed herein is a cell-free DNA, such as cell-free fetal DNA (also referred to as "cfDNA") or ctDNA. cfDNA circulates in the body, such as in the blood, of a pregnant mother, and represents the fetal genome, while ctDNA circulates in the body, such as in the blood, of a cancer patient, and is generally pre-fragmented. In other embodiments, the nucleic acid molecule of interest disclosed herein is an ancient and/or damaged DNA, for example, due to storage under damaging conditions such as in formalin-fixed samples, or partially digested samples.

As cancer cells die, they release DNA into the bloodstream. This DNA, known as circulating tumor DNA (ctDNA), is highly fragmented, with an average length of approximately 150 base pairs. Once the white blood cells are removed, ctDNA generally comprises a very small fraction of the remaining plasma DNA, for example, ctDNA may constitute less than about 10% of the plasma DNA. Generally, this percentage is less than about 1%, for example, less than about 0.5% or less than about 0.01%. Additionally, the total amount of plasma DNA is generally very low, for example, at about 10 ng/mL of plasma.

The variants in the ctDNA can be interrogated using various methods, including next generation sequencing. Due to the low ratio of ctDNA to plasma DNA, it is difficult to call a variant with high confidence due to PCR and sequencing errors. Unique molecular identifiers (UMIs) are generally used to tag original molecules such that any variant seen can be compared to a consensus sequence. This is an effective manner to separate true from false positives. If the variant is matched to a consensus, it is a true positive. Otherwise, it is removed from analysis. Furthermore, it is essential that a high percentage of original molecules are turned into sequencing libraries so that the sensitivity remains high, i.e., variants are not missed due to dropout. Thus, ligation efficiency is extremely important during library construction.

In one aspect, provided herein is a technique to vastly improve ligation efficiency while still targeting selected regions of the genome. In one embodiment, polynucleotides to be detected by sequencing, such as ctDNA, are first dephosphorylated to remove 5' phosphates to prevent ligation of ctDNA to itself. The ctDNA is then denatured such that all DNA is single stranded. Circligase™, a single stranded DNA ligase, is used to ligate an adapter to the 3' end of the ctDNA. In one aspect, the adapter contains 2 specific bases on the 5' end to optimize ligation efficiency, followed by a UMI. In one aspect, the 3' end of the adapter contains a carbon spacer to prevent self-ligation of the adapters. In another aspect, the ligation reaction is further optimized using a crowding agent, such as PEG 4000. In one aspect, following ligation, molecules are double-stranded using a primer that is reverse complement to the adapter. This allows efficient removal of excess unligated adapters without removed usable DNA by a standard purification.

In one aspect, the DNA is then amplified using a semi-targeted PCR. One primer is reverse complement to the adapter, while the other (e.g., as one primer in a primer pool) anneals to specific, targeted regions of the genome. The specific primers were designed to minimize primer-dimer interactions and off-target annealing. In one aspect, the target-specific primers are further optimized to land in close proximity to specific variants due to the small DNA size. Following another cleanup, a PCR adds the full-length sequencing adapters and barcodes. The final library is then sequenced, for example, on an Illumina machine.

In one aspect, the semi-targeted PCR results in enrichments of >about 40,000 fold of the original molecule set despite having a relatively small target region of ~30,000 bp. In one aspect, the overall conversion rates of the present method are at least 60%, implying that at least ~3 times more of the original molecules are converted into sequenceable material when compared to standard library construction and hybridization capture. In other embodiments, the overall conversion rates are between about 60% and about 70%, between about 70% and about 80%, between about 80% and about 90%, or over 90%. In one aspect, the present method thus is able to accurately call genetic or genomic variants, such as SNVs, indels, CNVs, and fusions at extremely low mutant allele fractions, for example, as low as 0.01%. In other aspects, the allele fraction of the genetic or genomic variant is about 0.05%, about 0.1%, about 0.5%, about 1%, or about 2%.

The following sections describe certain steps of the present method in greater detail.

Single-Stranded Polynucleotide Libraries and Method of Constructing the Same

Library construction for next generation sequencing, for example, for ctDNA, generally consists of several steps, including end repair, A-tailing, and a double stranded ligation of an adapter molecule. These ligated molecules can then be enriched 1000-2000 times at certain genomic regions using hybridization capture. Despite several improvements in library construction over the last several years, the process remains inefficient, resulting in many original molecules lost during the various steps. Double stranded ligation efficiency remains low, with ~20-30% of the molecules being properly ligated. Additionally, many molecules are lost during the purification and hybridization capture steps, so that the final conversion rate approximates 10-20%. Sensitivity remains low when interrogating low allele fraction variants found in ctDNA. This limits the accuracy when calling low allele fraction mutants, since the low efficiency will result in sensitivity loss when looking at libraries with low allele fractions.

In addition, the small size of certain polynucleotides, such as ctDNA, prevents the use of tagmentation-based library construction. For example, the polynucleotides are first tagged (e.g., with biotin) to generate a targeted library, and then enriched by capturing the tags (e.g., by streptavidin). This way, the library for the regions of interest can be enriched by about 1000-2000 fold. Finally, a PCR is performed to amplify and index the molecules for sequencing. However, PCR based methods prove difficult to add UMIs to original molecules and result in high error rates.

In one aspect, the compositions, kits, and methods described herein addressed the above problems. In some embodiments, the compositions, kits, and methods are useful in sequencing nucleic acid molecules, including but not limited to construction of various libraries, various amplification reactions (such as by PCR and/or primer extension), purification of the constructed libraries, and analysis of sequencing reads.

In certain aspects, a sequencing library can be prepared, for example, from a sample containing fragmented polynucleotides, such as fragment DNA. In one aspect, the sample is obtained a naturally occurring sample, for example, directly from a subject, such as tissue fluid or body fluid, including but not limited to blood, plasma, serum, cerebrospinal fluid, synovial fluid, urine, sweat, semen, sputum, tear, mucus, or amniotic fluid. In other aspects, a sequencing library can be prepared by forming fragments of DNA (for example, by shearing the DNA), and attaching the adapters herein to the DNA fragments. In particular embodiments, the fragmented polynucleotides and the adapters are single-stranded.

The fragments (for example, the ctDNA or fragments formed by fragmenting longer DNA strands) are sometimes referred to as "inserts," as they can be "inserted" or ligated adjacent to an adapter such as a single-stranded adaptor disclosed herein. RNA molecules can also be sequenced, for example by reverse transcribing the RNA molecules to form DNA molecules, which are attached to the adapters.

In one aspect, a method comprising ligating a set of adaptors to a library of single-stranded polynucleotides is provided, and in the method, the ligation is catalyzed by a single-stranded DNA (ssDNA) ligase. As used herein, a ssDNA ligase is capable of ligating ends of ssDNA in the absence of a complementary sequence. For example, CircLigase™ ssDNA Ligase and CircLigase™ II ssDNA Ligase are both thermostable ligases that are typically used to catalyze intramolecular ligation (i.e., circularization) of ssDNA templates having a 5'-phosphate and a 3'-hydroxyl group. In contrast to T4 DNA Ligase and Ampligase® DNA Ligase, which ligate DNA ends that are annealed adjacent to each other on a complementary DNA sequence, a ssDNA ligase ligates ends of ssDNA in the absence of a complementary sequence. The enzyme is therefore useful for making circular ssDNA molecules from linear ssDNA. Circular ssDNA molecules can be used as substrates for rolling-circle replication or rolling-circle transcription. In addition to its activity on ssDNA, a CircLigase enzyme also has activity in ligating a single-stranded nucleic acid having a 3'-hydroxyl ribonucleotide and a 5'-phosphorylated ribonucleotide or deoxyribonucleotide.

Either CircLigase™ ssDNA Ligase or CircLigase™ II ssDNA Ligase can be used in the present disclosure. The two enzymes are different in that CircLigase I is far less adenylated than CircLigase II and requires ATP for best activity. CircLigase I recircularizes ssDNA in the presence of ATP. CircLigase II is nearly 100% adenylated, therefore it is not necessary to add ATP to the reaction buffer. CircLigase II works as a stoichiometric reaction, where the enzyme bonds the 5'-end of an oligo that is adenylated in the enzyme active site, and then ligates the oligo and stops. Since the reaction doesn't contain ATP, CircLigase II works in a 1:1 enzyme:oligo configuration. Once the circularization is complete, the circular ssDNA is released from the active site and the reaction stops.

In one aspect, each single-stranded polynucleotide is blocked at the 5' end to prevent ligation at the 5' end, each adaptor comprises a unique molecular identifier (UMI) sequence that earmarks the single-stranded polynucleotide to which the adaptor is ligated, each adaptor is blocked at the 3' end to prevent ligation at the 3' end, and the 5' end of the adaptor is ligated to the 3' end of the single-stranded polynucleotide by the ssDNA ligase to form a linear ligation product, thereby obtaining a library of linear, single-stranded ligation products. Template-independent circularization of single-stranded DNA is described in WO2010/094040 A1, the disclosure of which is incorporated herein in its entirety. WO2010/094040 A1, however, only discloses intramolecular ligation (e.g., circularization) of single-stranded polynucleotides.

Figure 6:
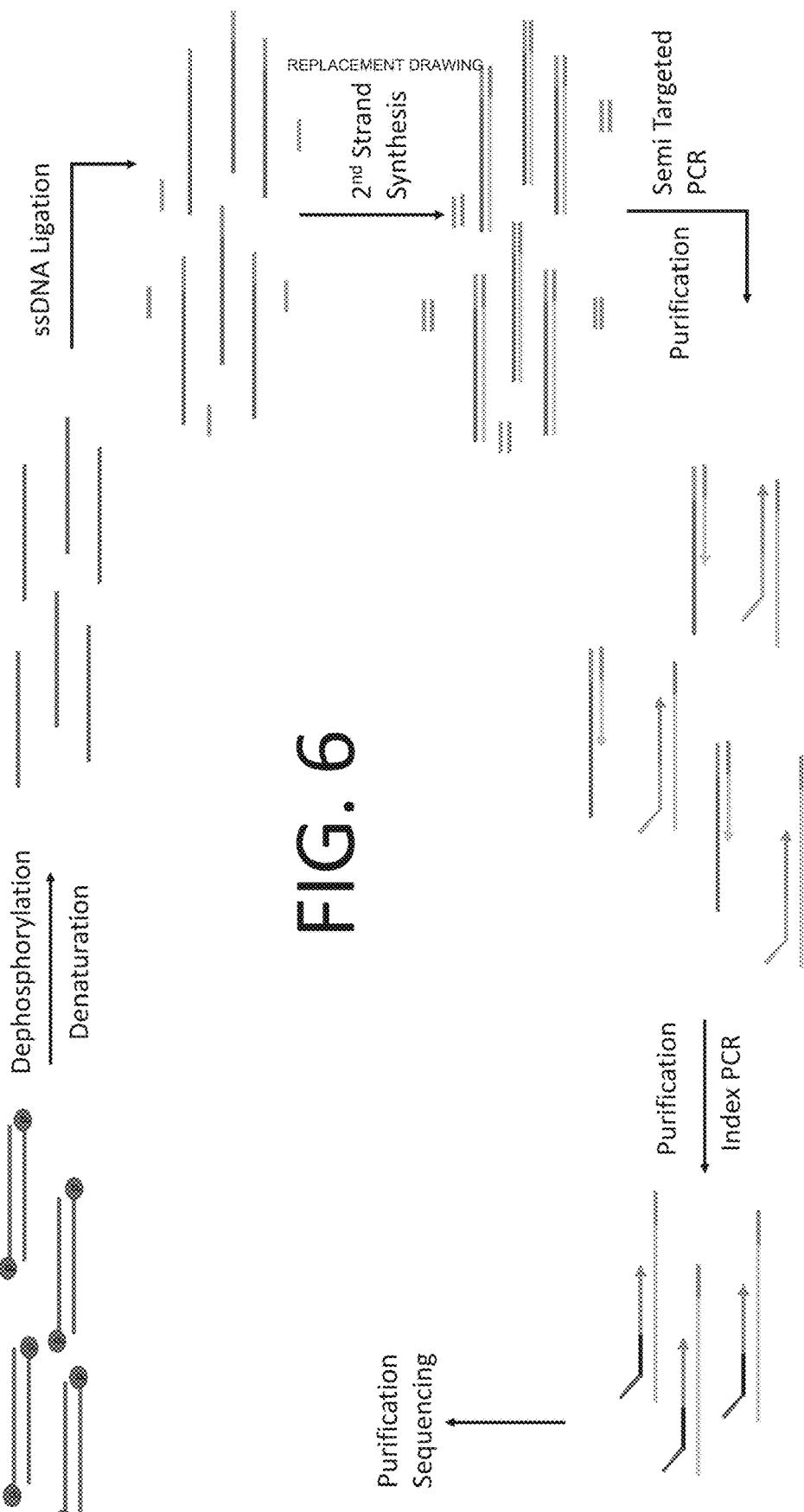
FIG. 6 illustrates steps for constructing a single-stranded polynucleotide library and performing sequencing analysis using the library, according to one aspect of the present disclosure.

Thus, the present method uses a ssDNA ligase, such as CircLigase or CircLigase II, in an unconventional manner. Instead of circularization, the present ligation method aims to generate a linear ligation product between the single-stranded target polynucleotide and an adaptor molecule. In one aspect, the present disclosure uses a ssDNA ligase to carry out intramolecular ligate, e.g., for ligating an adaptor to single-stranded polynucleotides. In order to do, in one aspect, the single-stranded polynucleotide is blocked at the 5' end to prevent circularization. This way, intramolecular ligation of the 3' end of an ssDNA to its own 5' end, as well as intermolecular ligation of the 3' end of one ssDNA to the 5' end of another ssDNA within the same library, is prevented. Thus, in one aspect, both circularization of the single-stranded polynucleotide and formation of linear concatemers (containing the single-stranded polynucleotides and/or the adaptors) are prevented during the ligation reaction. As shown in FIG. 6, the blocking of each single-stranded polynucleotide can comprise dephosphorylation at its 5' end to prevent ligation at that end.

In another aspect, each adaptor is blocked at the 3' end to prevent ligation at the 3' end. This way, intramolecular ligation of the 3' end of an adaptor to its own 5' end, as well as intermolecular ligation of the 3' end of one adaptor molecule to the 5' end of another adaptor molecule, is prevented. The blocking of each adaptor can comprise a carbon spacer, ddCTP, ddATP, ddTTP, ddGTP, hexanediol, triethylene glycol (TEG), and/or hexaethylene glycol, to prevent ligation at its 3' end. Thus, in one aspect, both circularization of the single-stranded adaptor and formation of linear concatemers (containing the single-stranded polynucleotides and/or the adaptors) are prevented during the ligation reaction.

The adaptor may comprise one or more copies of one or more spacers, in any suitable combination. For example, Gansauge and Meyer disclosed an adaptor that comprises ten copies of a C3Spacer and a biotinylated TEG spacer. Gansauge and Meyer (2013), "Single-stranded DNA library preparation for the sequencing of ancient or damaged DNA," *Nature Protocols,* 8(4): 737-48, which is incorporated herein by reference in its entirety. This reference, however, requires capturing the ligated ssDNA, via biotin-streptavidin interaction, immediately after ligation. This step may cause a significant loss of the ssDNA molecules in the library. The reference then converts the captured ssDNA to dsDNA while the ssDNA remains captured on a bead.

As shown in FIG. 6, the present disclosure does not require capturing the ligated ssDNA immediately after ligation. Instead, the ligated ssDNA remains in the ligation reaction volume when it is converted into dsDNA.

In one aspect, the ligation efficiency of the ssDNA in the library is high, for example, at least about 40%, at least about 50%, at least about 60%, at least about 70%, at least about 80%, at least about 85%, at least about 90%, at least about 95%, or at least about 99% of the single-stranded polynucleotides in the sample are ligated to an adaptor. In particular embodiments, the ligation efficiency is about 80%. With this vastly improved ligation efficiency, the presently claimed method is still capable of targeting selected regions of the genome, as explained below.

In one aspect, the adaptor has the following structure: /5'Phos/$N_1N_2 \ldots N_i$-UMI-$M_1M_2 \ldots M_j$-Blocker, wherein "5'Phos" represents a 5' phosphate group, "$N_1 N_2 \ldots N_i$" represents the sequence 5' to the UMI sequence, "$M_1M_2 \ldots M_j$" represents the sequence 3' to the UMI sequence, and "Blocker" indicates that the 3' end of the adaptor is blocked to prevent ligation thereto. Both i and j are integers, wherein i can be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or greater than 30; and j can be 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or greater than 50. In specific embodiments, i can be 2. In some embodiments, the dinucleotide sequence $N_1N_2$ at the 5' end of $N_1N_2 \ldots N_i$ can be GA (5' to 3'), GG (5' to 3'), AA (5' to 3'), or AG (5' to 3'), in order to enhance the ligation efficiency.

In one aspect, a portion or all of the $M_1M_2 \ldots M_j$ sequence is used in later steps for designing a reverse-complement sequence that is used as a primer to convert the ligated single-stranded polynucleotide into a double-stranded polynucleotide, and/or for the semi-targeted PCR to amplify a selected target sequence (the other primer of the primer pair being the target-specific primer). In one aspect, the $M_1M_2 \ldots M_j$ sequence comprises AGATCG-GAAGAGCGTCGTGTAGGGAAAGAGTG (SEQ ID NO:17506) or a portion thereof that comprises between about 18 and 22 nucleotide residues.

In another aspect, the "Blocker" comprises a carbon spacer, ddCTP, ddATP, ddTTP, ddGTP, hexanediol, triethylene glycol (TEG), and/or hexaethylene glycol, in one or more copies of one or more blocker groups in any suitable combination and order in the 5' to 3' direction.

In one aspect, use of the UMI facilitates the determination, selection, and/or isolation of error-free sequencing reads of a target sequence, and the sequencing reads can be selected with high accuracy and high throughput. Such validated, error-free sequencing reads are useful in any technique that requires sequence fidelity, including the construction of larger molecules of known sequence, polymorphism and/or mutation screening, massively parallel sequencing, and quantification methods to preclude bias in the methodologies.

In one aspect, the Unique Molecular Identifier is associated with and uniquely identifies a ligated construct comprising a single-stranded target polynucleotide and an adaptor. In other words, two single-stranded target polynucleotides having the same sequence may be ligated to two different adaptors which differ from each other at their UMI sequences; the resultant ligation products are different, and each ligation product (rather than the target polynucleotides having the same sequence) is uniquely identified by the UMI. In another aspect, when the single-stranded ligation products are converted into double-stranded polynucleotides and amplified, amplification errors may be introduced during repeated copying even though very high fidelity polymerases are available. As a result, even a low error rate can have a significant impact, particularly in the construction of large libraries. Although massively parallel sequencing has advantages in cost and throughput, the accuracy of the reads can be comprised by the limitations of the amplification and/or detection technologies.

By using the UMI, the present method is capable of identifying error-free amplification products and/or sequencing reads, and excluding those with technical errors from analysis. The amplification products and/or sequencing reads having the same UMI can be confirmed as related (identical by descent), and thus sequence differences between molecules with the same UMI can be identified as technical errors rather than real differences in the sequence (e.g., sequence differences between a wild-type sequence and a cancer-related mutant sequence). In other words, since each single-stranded ligation product is unique identifiable by its UMI, all of its descendants (due to amplification and/or sequencing) should have the same target sequence if no technical error is introduced. If, however, an error such as a single-nucleotide insertion is introduced into the target sequence during amplification and/or sequencing, some amplification products and/or sequencing reads identical by descent (e.g., sharing the same UMI) will have the insertion while the others will not. The exact ratio between the products having the insertion and those that do not have the insert will vary, depending on when the error occurs during the amplification and/or sequencing process. In general, when very high fidelity polymerases are used, the products without errors will be in the majority. In another aspect, because amplification products and/or sequencing reads that are identical by descent can be identified, a consensus sequence can be determined using data from multiple molecules, thereby achieving a high accuracy for high throughput sequencing.

In one aspect, the UMI is a degenerate nucleic acid sequence, and the number of nucleotides in the UMI is designed such that the number of potential and actual sequences represented by the UMI sequences is greater than the total number of target single-stranded target polynucleotide in the initial library. In one aspect, UMI sequence diversity (or "uniqueness" with regard to each single UMI sequence) can be provided by using a degenerate collection of sequences randomly generated by synthesizing with a mixture of all four bases at each position. Alternatively, a diverse but pre-defined set of sequences can be synthesized and ligated to the initial single-stranded polynucleotide library. The diversity of the UMI set needs to be sufficient so that molecules that are not related by descent won't be mistaken as such. In one aspect, a "unique" molecular identifier need not be absolutely unique, and may be used on different target single-stranded polynucleotides provided it is clear that they are different and not mistaken for a molecule that is identical by descent. The large number of UMI sequences that can be generated from the random assembly of nucleotides provides a high probability that each individual ligation product can be uniquely identified. For example, if the UMI comprises a 12-mer synthesized with a mixture of A, C, G and T at each position, there are $4^{12}$ possible sequences. If the UMI comprises a 20-mer synthesized with a mixture of A, C, G and T at each position, there are $4^{20}$ (about $10^{12}$) possible sequences. The use of such random identifiers allows a large library with single-stranded target polynucleotides that can be individually distinguished from each other.

In particular aspects, the UMI is a 5-mer, 6-mer, 7-mer, 8-mer, 9-mer, 10-mer, 11-mer, 12-mer, 13-mer, 14-mer, 15-mer, 16-mer, 17-mer, 18-mer, 19-mer, 20-mer, 21-mer, 22-mer, 23-mer, 24-mer, 25-mer, or even longer degenerate sequence. In one aspect, the adaptor has the following structure: /5'Phos/GANNNNNNNNNNNNNAGATCG-GAAGAGCGTCGTGTAGGGAAAGAGTG/3SpC3/, wherein "NNNNNNNNNNNN" represents a 12-mer UMI sequence, and "3SpC3" represents a 3' carbon spacer. The sequence of GANNNNNNNNNNNNNAGATCG-GAAGAGCGTCGTGTAGGGAAAGAGTG is SEQ ID NO:17507.

The concentration of DNA can be artificially increased by adding condensing agents such as cobalt hexamine and biogenic polyamines such as spermidine, or by using crowding agents such as polyethylene glycol (PEG) which also increase the effective concentration of enzymes. In one aspect, additives such as cobalt hexamine can produce exclusively intermolecular reaction, resulting in linear ligation products rather than circular products. Thus, in case the 5' ends of the single-stranded target polynucleotides and the 3' ends of the single-stranded adaptor may not be completely blocked to prevent ligation, additives such as cobalt hexamine may be used to enhance intermolecular reaction and further prevent circularization of the single-stranded target polynucleotide and/or the adaptor.

In some embodiments, more than one configurations of the adaptor can be used in the same ligation reaction. For example, two configurations of the adaptor may be used:

Configuration No. 1: /5'Phos/$N_1N_2$ . . . $N_i$-$UMI_1$-$M_1M_2$ . . . $M_j$-$Blocker_1$, and Configuration No. 2: /5'Phos/$P_1P_2$ . . . $P_k$-$UMI_2$-$Q_1Q_2$ . . . $Q_l$-$Blocker_2$.

$N_1N_2$ . . . $N_i$ and $P_1P_2$ . . . $P_k$ can be the same or different, $UMI_1$ and $UMI_2$ can be the same or different, $M_1M_2$ . . . $M_j$ and $Q_1Q_2$ . . . $Q_l$, can be the same or different, and $Blocker_1$ and $Blocker_2$ can be the same or different. In one embodiment, $UMI_1$ is different from $UMI_2$ (for example, $UMI_1$ is a 12-mer degenerate sequence while $UMI_2$ is a 13-mer degenerate sequence), while the other features of the adaptors are the same. In another embodiment, $N_1N_2$ . . . $N_i$ is different from $P_1P_2$ . . . $P_k$ (for example, one is AG while the other is GA), while the other features of the adaptors are the same. In yet another embodiment, $M_1M_2$ . . . $M_j$ is different from $Q_1Q_2$ . . . $Q_l$, while the other features of the adaptors are the same. In still another embodiment, $Blocker_1$ and $Blocker_2$ are different, while the other features of the adaptors are the same.

After the ligation reaction, the single-stranded ligation products, without any need for purification (e.g., separation of the ligation products from the excess, unligated adaptor molecules), can be immediately subject to conversion into double-stranded ligation products. In addition, neither the single-stranded target polynucleotide nor the adaptor needs to be captured on a solid support (e.g., by biotin-streptavidin mediated binding to a bead) in order for the subsequent conversion of the ligation product into a double-stranded polynucleotide and/or amplification step. Thus, the present method avoids and/or reduces loss of the already small allele fraction of the mutant in a DNA sample, such as ctDNA, due to the purification or isolation of the single-stranded ligation products. Instead, in one aspect, the single-stranded ligation products remain in the solution which is directed subject to primer extension.

Conversion of Single-Stranded Polynucleotide Library to Double-Stranded Polynucleotide Library In one aspect as shown in FIG. 6, following construction of the library containing the single-stranded ligation products, the method can further comprise converting the library of linear, single-stranded ligation products into a library of linear, double-stranded ligation products. In one aspect, the conversion uses a primer or a set of primers each comprising a sequence that is reverse-complement to the adaptor and/or hybridizable to the adaptor.

For an adaptor having the following structure: /5'Phos/$N_1N_2$ . . . $N_i$-UMI-$M_1M_2$ . . . $M_j$-Blocker, the primer can comprise a sequence that is reverse-complement and/or hybridizable to $M_1M_2$ . . . $M_j$. In this example, when the primer hybridizes to the ligated product having the structure ssDNA-$N_1N_2$ . . . $N_i$-UMI-$M_1M_2$ . . . $M_j$-Blocker, the primer extension reaction can convert the ssDNA-$N_1N_2$ . . . $N_i$-UMI sequence (and optionally, all or a portion of the $M_1M_2$ . . . $M_j$ sequence) into double-stranded polynucleotides. In one specific example, a reverse-complement primer comprises the sequence set forth in SEQ ID NO:17505:

CACTCTTTCCCTACACGACGC (5' to 3').

In some embodiments, the primer may not be a perfect reverse-complement of $M_1M_2$ . . . $M_j$ or a portion therefore; nonetheless, the primer is hybridizable to $M_1M_2$ . . . $M_j$ (and thus the ssDNA ligated to the adaptor) under stringent conditions.

In any of the preceding embodiments, the method can further comprise amplifying and/or purifying the library of linear, double-stranded ligation products. In one aspect, the double-stranded ligation products are purified and size selected to remove unbound adaptor molecules and/or unbound primers, and/or complexes formed between an adaptor and its reverse-complement primer. Any suitable methods can be used to remove these fragments which are generally shorter than the desired double-stranded ligation products. For example, using PCR purification column from Qiagen could help to eliminate the smaller fragments from the samples and running the column-purified samples on 2% certified low range ultra agarose gel can help to select the desired fragment size. The beads-based DNA purification including AMPure method is also helpful to remove the smaller fragments. In some embodiments, the desired double-stranded ligation products size is from about 100 bps to about 600 bps, such as from about 100 bps to about 400 bps, from about 150 bps to about 200 bps, from about 200 bps to about 250 bps, and from about 250 bps to about 300 bps. In one embodiment, dsDNA (>150 bps and <400 bps) is purified and collected, for example, by eluting beads suspended in a Tri-EDTA buffer.

In one aspect, the purification is bead-based. In another aspect, the purification is based on size selection, for example, the purification step selectively purifies polynucleotides between about 50 nucleotides and about 1000 nucleotides in lengths, for example, adaptors of about 40 nucleotides in length (and primer dimers and/or primer-adaptor duplexes of about 40 bp) are removed. In one aspect, the purification is column-based, for example, by using a dsDNA or ssDNA purification column, such as those from Zymo or Qiagen.

In another aspect, the purification does not comprise using a specific binding pair (such as biotin/streptavidin), one of which is attached to the linear, double-stranded ligation product and the other is attached to a solid support (such as a bead).

In any of the preceding embodiments, the method herein can further comprise amplifying the library of linear, double-stranded ligation products, e.g., by a polymerase chain reaction (PCR), to obtain an amplified library of linear, double-stranded ligation products comprising sequence information of a target sequence. This amplification can be an unbiased amplification, for example, by ligating a universal adaptor pair to the ends of the double-stranded ligation products, and amplifying all the tagged double-stranded ligation products with a universal primer pair. In other embodiments, a semi-targeted amplification is conducted in lieu of or in addition to the unbiased amplification. The semi-targeted amplification can be performed before or after the unbiased amplification.

Semi-Targeted Amplification of Double-Stranded Polynucleotide Library

In one aspect, as shown in FIG. 6, a semi-targeted amplification of the double-stranded ligation product library comprises using a primer comprising a sequence that is reverse-complement and/or hybridizable to the adaptor, and a primer hybridizable to a target sequence (e.g., an EGFR gene sequence) or primers hybridizable to the same target sequence or multiple target sequences.

For an adaptor having the following structure: /5'Phos/$N_1N_2$ . . . $N_i$-UMI-$M_1M_2$ . . . $M_j$-Blocker, the primer can comprise a sequence that is reverse-complement and/or hybridizable to $M_1M_2$ . . . $M_j$. This way, when the primer hybridizes to one strand of the dsDNA and the target-specific primer hybridizes to the other strand of the dsDNA, the PCR product will contain a target sequence as well as the $N_1N_2$ . . . $N_i$-UMI sequence (and optionally, all or a portion of the $M_1M_2 \ldots M_j$ sequence). In one specific example, a reverse-complement primer comprises the sequence set forth in SEQ ID NO:17505: CACTCTTTCCCTA-CACGACGC (5' to 3').

In one aspect, a plurality of target-specific primers can be used, each comprising a sequence specific for the same or a different target sequence. In other words, the primers can have the same or different target sequences. In some embodiments, the pool of target-specific primers comprises about 5, about 10, about 25, about 50, about 100, about 150, about 200, about 250, about 300, about 400, about 500, about 600, about 700, about 800, about 900, about 1000, or more than about 1000 different primers, such as about $10^4$, about 105, about $10^6$, or more primers. In other embodiments, the pool comprises between about 20 and about 60, between about 60 and about 100, between about 100 and about 140, between about 140 and about 180, between about 180 and about 220, between about 220 and about 260, between about 260 and about 300, between about 300 and about 350, or between about 350 and about 400 different primers. In one aspect, the pool of target-specific primers are used together with one common reverse-complement primer, wherein the common reverse-complement primer forms a primer pair with each individual target-specific primer in the pool to amplify the target sequence in and/or between the primers in a semi-targeted fashion. Thus, in this aspect, the semi-targeted amplification is not a whole genome amplification.

Since ctDNA fragments randomly, in one aspect, the primer position of the target-specific primer may be important. For example, if the primer landing spans a break point, it may result in lower conversion rates. A larger target-specific primer pool and/or using multiple partially overlapping primers for the same target sequence may solve the problem.

In one aspect, the sequence information of the target sequence can comprise a mutation, a single nucleotide polymorphism (SNP), a copy number variation (CNV), or an epigenetic change. In one aspect, the mutation comprises a point mutation, an insertion, a deletion, an inversion, a truncation, a fusion, an amplification, or any combination thereof.

In some embodiments, the amplified library of linear, double-stranded ligation products can be a library other than a whole genome library, for example, a semi-targeted genome library.

In some embodiments, the method can further comprise purifying the amplified library of linear, double-stranded ligation products. Any suitable methods can be used to remove smaller fragments including primer dimers. For example, using PCR purification column from Qiagen could help to eliminate the smaller fragments from the samples and running the column-purified samples on 2% certified low range ultra agarose gel can help to select the desired fragment size. The beads-based DNA purification including AMPure method is also helpful to remove the smaller fragments. In some embodiments, the amplification product size is from about 100 bps to about 600 bps, such as from about 100 bps to about 400 bps, from about 150 bps to about 200 bps, from about 200 bps to about 250 bps, and from about 250 bps to about 300 bps. In one embodiment, dsDNA (>150 bps and <400 bps) is purified and collected, for example, by eluting beads suspended in a Tri-EDTA buffer.

In one aspect, the purification is bead-based. In another aspect, the purification is based on size selection, for example, the purification step selectively purifies polynucleotides greater about 150 nucleotides in lengths. In another aspect, the purification does not comprise using a specific binding pair (such as biotin/streptavidin), one of which is attached to the linear, double-stranded ligation product and the other is attached to a solid support (such as a bead). In one aspect, the purification is column-based, for example, by using a dsDNA or ssDNA purification column, such as those from Zymo or Qiagen.

Construction of Sequence Library and Analysis of Sequencing Reads

In one aspect, the method further comprises sequencing the purified amplified library of linear, double-stranded ligation products. In one aspect, the sequencing step comprises attaching a sequencing adapter and/or a sample-specific barcode to each linear, double-stranded ligation product. In one particular aspect, the attaching step is performed using a polymerase chain reaction (PCR).

Figure 7:
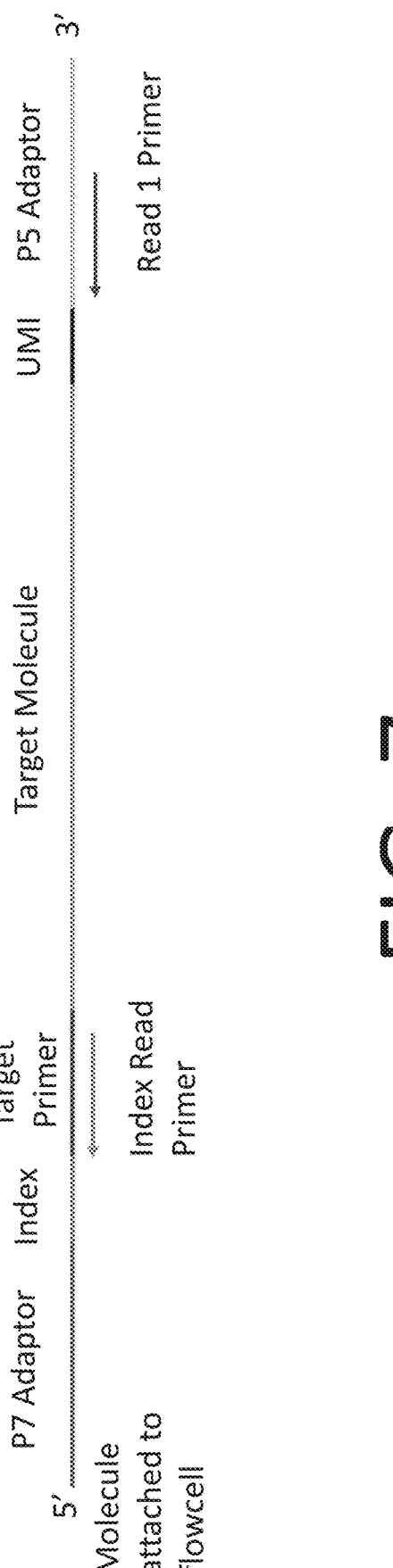
FIG. 7 illustrates a construct comprising a target molecule for sequencing, according to one aspect of the present disclosure.

FIG. 7 shows an exemplary configuration of a construct comprising a target molecule for sequencing. For Illumina sequencing, on each end, these constructs have flow cell binding sites, P5 and P7, which allow the library fragment to attach to the flow cell surface. The P5 and P7 regions of single-stranded library fragments anneal to their complementary oligos on the flowcell surface. The flow cell oligos act as primers and a strand complementary to the library fragment is synthesized. Then, the original strand is washed away, leaving behind fragment copies that are covalently bonded to the flowcell surface in a mixture of orientations. Copies of each fragment are then generated by bridge amplification, creating clusters. Then, the P5 region is cleaved, resulting in clusters containing only fragments which are attached by the P7 region. This ensures that all copies are sequenced in the same direction. The sequencing primer anneals to the P5 end of the fragment, and begins the sequencing by synthesis process. Index reads are performed when a sample is barcoded. When Read 1 is finished, everything from Read 1 is removed and an index primer is added, which anneals at the P7 end of the fragment and sequences the barcode. Then, everything is stripped from the template, which forms clusters by bridge amplification as in Read 1. This leaves behind fragment copies that are covalently bonded to the flowcell surface in a mixture of orientations. This time, P7 is cut instead of P5, resulting in clusters containing only fragments which are attached by the P5 region. This ensures that all copies are sequenced in the same direction (opposite Read 1). The sequencing primer anneals to the P7 region and sequences the other end of the template.

Next-generation sequencing platforms, such as MiSeq (Illumina Inc., San Diego, CA), can be used for highly multiplexed assay readout. A variety of statistical tools, such as the Proportion test, multiple comparison corrections based on False Discovery Rates (see Benjamini and Hochberg, 1995, *Journal of the Royal Statistical Society* Series B (Methodological) 57, 289-300), and Bonferroni corrections for multiple testing, can be used to analyze assay results. In addition, approaches developed for the analysis of differential expression from RNA-Seq data can be used to reduce variance for each target sequence and increase overall power in the analysis. See Smyth, 2004, Stat. Appl. Genet. Mol. Biol. 3, Article 3.

Overall, in some embodiments, the conversion rate of the present method is at least about 40%, at least about 50%, at least about 60%, at least about 70%, at least about 80%, at least about 90%, or at least about 95%. In one aspect, the conversion rate is the percentage of targeted single-stranded polynucleotides in the initial library that give rise to sequencing reads.

In any of the preceding embodiments, the method can be used for the diagnosis and/or prognosis of a disease or condition in a subject, predicting the responsiveness of a subject to a treatment, identifying a pharmacogenetics marker for the disease/condition or treatment, and/or screening a population for a genetic information. In one aspect, the disease or condition is a cancer or neoplasia, and the treatment is a cancer or neoplasia treatment.

Mutant DNA molecules offer unique advantages over cancer-associated biomarkers because they are so specific. Though mutations occur in individual normal cells at a low rate (about $10^{-9}$ to $10^{-10}$ mutations/bp/generation), such mutations represent such a tiny fraction of the total normal DNA that they are orders of magnitude below the detection limit of certain art methods. Several studies have shown that mutant DNA can be detected in stool, urine, and blood of CRC patients (Osborn and Ahlquist, Stool screening for colorectal cancer: molecular approaches, *Gastroenterology* 2005; 128:192-206).

Based on the sequencing results herein, detection of circulating tumor DNA in the patient can be made, and diagnosis of cancer and predictions regarding tumor recurrence can be made. Based on the predictions, treatment and surveillance decisions can be made. For example, circulating tumor DNA which indicates a future recurrence, can lead to additional or more aggressive therapies as well as additional or more sophisticated imaging and monitoring. Circulating DNA refers to DNA that is ectopic to a tumor.

Samples which can be monitored for ctDNA include blood and stool. Blood samples may be for example a fraction of blood, such as serum or plasma. Similarly stool can be fractionated to purify DNA from other components. Tumor samples are used to identify a somatically mutated gene in the tumor that can be used as a marker of tumor in other locations in the body. Thus, as an example, a particular somatic mutation in a tumor can be identified by any standard means known in the art. Typical means include direct sequencing of tumor DNA, using allele-specific probes, allele-specific amplification, primer extension, etc. Once the somatic mutation is identified, it can be used in other compartments of the body to distinguish tumor derived DNA from DNA derived from other cells of the body. Somatic mutations are confirmed by determining that they do not occur in normal tissues of the body of the same patient. Types of tumors which can be diagnosed and/or monitored in this fashion are virtually unlimited. Any tumor which sheds cells and/or DNA into the blood or stool or other bodily fluid can be used. Such tumors include, in addition to colorectal tumors, tumors of the breast, lung, kidney, liver, pancreas, stomach, brain, head and neck, lymphatics, ovaries, uterus, bone, blood, etc.

In one aspect, the method disclosed herein can be used to construct a library for use in sequencing and/or in determining an epigenetic status/state of one or more regions of the target sequence. DNA methylation was first the discovered epigenetic mark. Epigenetics is the study of changes in gene expression or cellular phenotype caused by mechanisms other than changes in the underlying DNA sequence. Methylation predominately involves the addition of a methyl group to the carbon-5 position of cytosine residues of the dinucleotide CpG and is associated with repression or inhibition of transcriptional activity.

Bisulfite conversion is the use of bisulfite reagents to treat DNA to determine its pattern of methylation. The treatment of DNA with bisulfite converts cytosine residues to uracil but leaves 5-methylcytosine residues unaffected. Thus, bisulfite treatment introduces specific changes in the DNA sequence that depend on the methylation status of the individual cytosine residues. Various analyses can be performed on the altered sequence to retrieve this information, for example, in order to differentiate between single nucleotide polymorphisms (SNP) resulting from the bisulfite conversion. U.S. Pat. Nos. 7,620,386, 9,365,902, and U.S. Patent Application Publication 2006/0134643, all of which are incorporated herein by reference, exemplify methods known to one of ordinary skill in the art with regard to detecting sequences altered due to bisulfite conversion.

As discussed above, one consequence of bisulfite conversion is that the double-stranded conformation of the original target is disrupted due to loss of sequence complementarity. While this may cause problem for traditional methods for constructing double-stranded libraries, in one aspect the present method is uniquely suited to construct single-stranded libraries from bisulfite conversion sample for sequencing analysis.

In another aspect, the present method can be used in combination with a method for determining a methylation state/status, for example, as described in U.S. Provisional application Ser. No. 62/487,422, entitled "Compositions and Methods for Detection of Genomic Variance and DNA Methylation Status," filed Apr. 19, 2017, which is incorporated herein by reference in its entirety for all purposes. In one embodiment, a sample is contacted with a methylation-sensitive restriction enzyme (MSRE) before the dephosphorylation and/or the denaturing step, and methylation profiles are then be analyzed by constructing a single-stranded library by ligation as disclosed herein.

Further Exemplary Embodiments

In any of the preceding embodiments, the ssDNA ligase can be a *Thermus* bacteriophage RNA ligase such as a bacteriophage TS2126 RNA ligase (e.g., CircLigase™ and CircLigase II™), or an archaebacterium RNA ligase such as *Methanobacterium* thermoautotrophicum RNA ligase 1. In other aspects, the ssDNA ligase is an RNA ligase, such as a T4 RNA ligase, e.g., T4 RNA ligase I, e.g., New England Biosciences, M0204S, T4 RNA ligase 2, e.g., New England Biosciences, M0239S, T4 RNA ligase 2 truncated, e.g., New England Biosciences, M0242S, T4 RNA ligase 2 truncated KQ, e.g., M0373S, or T4 RNA ligase 2 truncated K227Q, e.g., New England Biosciences, M0351S. In any of the preceding embodiments, the kit can also comprise a thermostable 5' App DNA/RNA ligase, e.g., New England Biosciences, M0319S, or T4 DNA ligase, e.g., New England Biosciences, M0202S.

In some embodiments, the present methods comprise ligating a set of adaptors to a library of single-stranded polynucleotides using a single-stranded DNA (ssDNA) ligase. Any suitable ssDNA ligase, including the ones disclosed herein, can be used. The adaptors can be used at any suitable level or concentration, e.g., from about 1 μM to about 100 μM such as about 1 μM, 10 μM, 20 μM, 30 μM, 40 μM, 50 μM, 60 μM, 70 μM, 80 μM, 90 μM, or 100 μM, or any subrange thereof. The adapter can comprise or begin with any suitable sequences or bases. For example, the adapter sequence can begin with all 2 bp combinations of bases.

In some embodiments, the ligation reaction can be conducted in the presence of a crowding agent. In one aspect, the crowding agent comprises a polyethylene glycol (PEG), such as PEG 4000, PEG 6000, or PEG 8000, Dextran, and/or Ficoll. The crowding agent, e.g., PEG, can be used at any suitable level or concentration. For example, the crowding agent, e.g., PEG, can be used at a level or concentration from about 0% (w/v) to about 25% (w/v), e.g., at about 0% (w/v), 1% (w/v), 2% (w/v), 3% (w/v), 4% (w/v), 5% (w/v), 6% (w/v), 7% (w/v), 8% (w/v), 9% (w/v), 10% (w/v), 11% (w/v), 12% (w/v), 13% (w/v), 14% (w/v), 15% (w/v), 16% (w/v), 17% (w/v), 18% (w/v), 19% (w/v), 20% (w/v), 21% (w/v), 22% (w/v), 23% (w/v), 24% (w/v), or 25% (w/v), or any subrange thereof.

In some embodiments, the ligation reaction can be conducted for any suitable length of time. For example, the ligation reaction can be conducted for a time from about 2 to about 16 hours, %, e.g., for about 2 hours, 3 hours, 4 hours, 5 hours, 6 hours, 7 hours, 8 hours, 9 hours, 10 hours, 11 hours, 12 hours, 13 hours, 14 hours, 15 hours, or 16 hours, or any subrange thereof.

In some embodiments, the ssDNA ligase in the ligation reaction can be used in any suitable volume. For example, the ssDNA ligase in the ligation reaction can be used at a volume from about 0.5 μl to about 2 μl, %, e.g., at about 0.5 μl, 0.6 μl, 0.7 μl, 0.8 μl, 0.9 μl 1 μl, 1.1 μl, 1.2 μl, 1.3 μl, 1.4 μl, 1.5 μl, 1.6 μl, 1.7 μl, 1.8 μl, 1.9 μl, or 2 μl, or any subrange thereof.

In some embodiments, the ligation reaction can be conducted in the presence of a ligation enhancer, e.g., betaine. The ligation enhancer, e.g., betaine, can be used at any suitable volume, e.g., from about 0 ul to about 1 μl, e.g., at about 0 μl, 0.1 μl, 0.2 μl, 0.3 μl, 0.4 μl, 0.5 μl, 0.6 μl, 0.7 μl, 0.8 μl, 0.9 μl, 1 μl, or any subrange thereof.

In some embodiments, the ligation reaction can be conducted using a T4 RNA ligase I, e.g., the T4 RNA ligase I from New England Biosciences, M0204S, in the following exemplary reaction mix (20 μl): 1× Reaction Buffer (50 mM Tris-HCl, pH 7.5, 10 mM MgCl2, 1 mM DTT), 25% (wt/vol) PEG 8000, 1 mM hexamine cobalt chloride (optional), 1 μl (10 units) T4 RNA Ligase, and 1 mM ATP. The reaction can be incubated at 25° C. for 16 hours. The reaction can be stopped by adding 40 μl of 10 mM Tris-HCl pH 8.0, 2.5 mM EDTA.

In some embodiments, the ligation reaction can be conducted using a Thermostable 5' App DNA/RNA ligase, e.g., the Thermostable 5' App DNA/RNA ligase from New England Biosciences, M0319S, in the following exemplary reaction mix (20 μl): ssDNA/RNA Substrate 20 μmol (1 μmol/ul), 5' App DNA Oligonucleotide 40 μmol (2 μmol/μl), 10×NEBuffer 1 (2 μl), 50 mM MnCl2 (for ssDNA ligation only) (2 μl), Thermostable 5' App DNA/RNA Ligase (2 μl (40 μmol)), and Nuclease-free Water (to 20 μl). The reaction can be incubated at 65° C. for 1 hour. The reaction can be stopped by heating at 90° C. for 3 minutes.

In some embodiments, the ligation reaction can be conducted using a T4 RNA ligase 2, e.g., the T4 RNA ligase 2 from New England Biosciences, M0239S, in the following exemplary reaction mix (20 μl): T4 RNA ligase buffer (2 μl), enzyme (1 μl), PEG (10 μl), DNA (1 μl), Adapter (2 μl), and water (4 μl). The reaction can be incubated at 25° C. for 16 hours. The reaction can be stopped by heating at 65° C. for 20 minutes.

In some embodiments, the ligation reaction can be conducted using a T4 RNA ligase 2 Truncated, e.g., the T4 RNA ligase 2 Truncated from New England Biosciences, M0242S, in the following exemplary reaction mix (20 μl): T4 RNA ligase buffer (2 μl), enzyme (1 μl), PEG (10 μl), DNA (1 μl), Adapter (2 μl), and water (4 μl). The reaction can be incubated at 25° C. for 16 hours. The reaction can be stopped by heating at 65° C. for 20 minutes.

In some embodiments, the ligation reaction can be conducted using a T4 RNA ligase 2 Truncated K227Q, e.g., the T4 RNA ligase 2 Truncated K227Q from New England Biosciences, M0351S, in the following exemplary reaction mix (20 μl): T4 RNA ligase buffer (2 μl), enzyme (1 μl), PEG (10 μl), DNA (1 μl), Adenylated Adapter (0.72 μl), and water (5.28 μl). The reaction can be incubated at 25° C. for 16 hours. The reaction can be stopped by heating at 65° C. for 20 minutes.

In some embodiments, the ligation reaction can be conducted using a T4 RNA ligase 2 Truncated KQ, e.g., the T4 RNA ligase 2 Truncated KQ from New England Biosciences, M0373S, in the following exemplary reaction mix (20 μl): T4 RNA ligase buffer (2 μl), enzyme (1 μl), PEG (10 μl), DNA (1 μl), Adenylated Adapter (0.72 μl), and water (5.28 μl). The reaction can be incubated at 25° C. for 16 hours. The reaction can be stopped by heating at 65° C. for 20 minutes.

In some embodiments, the ligation reaction can be conducted using a T4 DNA ligase, e.g., the T4 DNA ligase from New England Biosciences, M0202S, in the following exemplary reaction mix (20 μl): T4 RNA ligase buffer (2 μl), enzyme (1 μl), PEG (10 μl), DNA (1 μl), Adenylated Adapter (0.72 μl), and water (5.28 μl). The reaction can be incubated at 16° C. for 16 hours. The reaction can be stopped by heating at 65° C. for 10 minutes.

The second strand synthesis step can be conducted using any suitable enzyme. For example, the second strand synthesis step can be conducted using Bst polymerase, e.g., New England Biosciences, M0275S or Klenow fragment (3'->5' exo-), e.g., New England Biosciences, M0212S.

In some embodiments, the second strand synthesis step can be conducted using Bst polymerase, e.g., New England Biosciences, M0275S, in the following exemplary reaction mix (10 μl): water (1.5 μl), primer (0.5 μl), dNTP (1 μl), ThermoPol Reaction buffer (5 μl), and Bst (2 μl). The reaction can be incubated at 62° C. for 2 minutes and at 65° C. for 30 minutes. After the reaction, the double stranded DNA molecules are further purified.

In some embodiments, the second strand synthesis step can be conducted using Klenow fragment (3'->5' exo-), e.g., New England Biosciences, M0212S, in the following exemplary reaction mix (10 μl): water (0.5 μl), primer (0.5 μl), dNTP (1 μl), NEB buffer (2 μl), and exo- (3 μl). The reaction can be incubated at 37° C. for 5 minutes and at 75° C. for 20 minutes. After the reaction, the double stranded DNA molecules are further purified.

After the second strand synthesis, but before the first or semi-targeted PCR, the double stranded DNA can be purified. The double stranded DNA can be purified using any suitable technique or procedure. For example, the double stranded DNA can be purified using any of the following kits: Zymo clean and concentrator, Zymo research, D4103; Qiaquick, Qiagen, 28104; Zymo ssDNA purification kit, Zymo Research, D7010; Zymo Oligo purification kit, Zymo Research, D4060; and AmpureXP beads, Beckman Coulter, A63882: 1.2×-4× bead ratio.

The first or semi-targeted PCR can be conducted using any suitable enzyme or reaction conditions. For example, the polynucleotides or DNA strands can be annealed at a temperature ranging from about 52° C. to about 72° C., e.g., at about 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., 70° C., 71° C., or 72° C., or any subrange thereof. The first or semi-targeted PCR can be conducted for any suitable rounds of cycles. For example, the first or semi-targeted PCR can be conducted for 10-40 cycles, e.g., for 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 cycles. The primer pool can be used at any suitable concentration. For example, the primer pool can be used at a concentration ranging from about 5 nm to about 200 nM, e.g., at about 5 nm, 6 nm, 7 nm, 8 nm, 9 nm, 10 nm, 20 nm, 30 nm, 40 nm, 50 nm, 60 nm, 70 nm, 80 nm, 90 nm, 100 nm, 110 nm, 120 nm, 130 nm, 140 nm, 150 nm, 160 nm, 170 nm, 180 nm, 190 nm, or 200 nm, or any subrange thereof.

The first or semi-targeted PCR can be conducted using any suitable temperature cycle conditions. For example, the first or semi-targeted PCR can be conducted using any of the following cycle conditions: 95° C. 3 minutes, (95° C. 15 seconds, 62° C. 30 seconds, 72° C. 90 seconds)×3 or ×5; or (95° C. 15 seconds, 72° C. 90 seconds)×23 or ×21, 72 C 1 minute, 4° C. forever.

In some embodiments, the first or semi-targeted PCR can be conducted using KAPA SYBR FAST, e.g., KAPA biosciences, KK4600, in the following exemplary reaction mix (50 µl): DNA (2 µl), KAPASYBR (25 µl), Primer Pool (26 nM each) (10 µl), Aprimer (100 uM) (0.4 µl), and water (12.6 µl). The first or semi-targeted PCR can be conducted using any of the following cycle conditions: 95° C. 30 seconds, (95° C. 10 seconds, 50-56° C. 45 seconds, 72° C. 35 seconds)×40.

In some embodiments, the first or semi-targeted PCR can be conducted using KAPA HiFi, e.g., KAPA Biosciences, KK2601, in the following exemplary reaction mix (50 µl): DNA (15 µl), KAPAHiFi (25 µl), Primer Pool (26 nM each) (10 µl), and Aprimer (100 uM) (0.4 µl). The first or semi-targeted PCR can be conducted using any of the following cycle conditions: 95° C. 3 min, (98° C. 20 seconds, 53-54° C. 15 seconds, 72° C. 35 seconds)×15, 72° C. 2 minutes, 4° C. forever.

Bisulfite conversion can be conducted using any suitable techniques, procedures or reagents. In some embodiments, bisulfite conversion can be conducted using any of the following kits and procedures provided in the kit: EpiMark Bisulfite Conversion Kit, New England Biosciences, E3318S; EZ DNA Methylation Kit, Zymo Research, D5001; MethylCode Bisulfite Conversion Kit, Thermo Fisher Scientific, MECOV50; EZ DNA Methylation Gold Kit, Zymo Research, D5005; EZ DNA Methylation Direct Kit, Zymo Research, D5020; EZ DNA Methylation Lightning Kit, Zymo Research, D5030T; EpiJET Bisulfite Conversion Kit, Thermo Fisher Scientific, K1461; or EpiTect Bisulfite Kit, Qiagen, 59104.

In some embodiments, DNA molecules can be prepared using the procedures illustrated in Example 4, including the steps for constructing single-stranded polynucleotide, conversion of single-stranded polynucleotide library to double-stranded polynucleotide library, semi-targeted amplification of double-stranded polynucleotide library, and construction of sequence library. Such DNA molecules can further be analyzed for methylation status using any suitable methods or procedures.

G. Examples

Example 1. Detection of Cancer in Colon Tissue

In this example, methylation status of 10 Target Regions listed in Table 1: Target30, Target369, Target677, Target1558, Target1628, Target1691, Target1725, Target1795, Target1823, Target1841 was analyzed. Methylation metric is computed as unmethylation haplotype load (uMHL). The classification method used in the analysis is support vector machines.

An experimental panel interrogating the 10 target regions listed above was developed. Eight (8) healthy colon and 40 colon cancer tissue samples were processed using the experimental panel, and the uMHL metric was computed for each target region to create a data matrix. In order to develop a SVM-based classifier, a subset of 4 healthy colon and 20 colon cancer tissue samples were selected as the "training" set. The training set samples were used to fit an SVM-based classifier in Python (using the scikit-learn library) (FIG. 2). The SVM-based classifier was then used to predict the categories for the remaining 24 "test" set samples. The classifier was able to achieve 100% accuracy in the test set and correctly identify if a colon tissue sample was cancerous.

Example 2. Detection of Lung Cancer in Plasma

In this example, methylation status of 95 Target Regions listed in Table 1: Target35, Target36, Target102, Target115, Target117, Target118, Target120, Target136, Target141, Target154, Target155, Target166, Target207, Target226, Target241, Target243, Target252, Target253, Target267, Target284, Target338, Target397, Target398, Target422, Target423, Target432, Target439, Target440, Target445, Target460, Target461, Target504, Target514, Target574, Target575, Target589, Target596, Target625, Target626, Target637, Target640, Target650, Target674, Target691, Target693, Target710, Target736, Target840, Target852, Target867, Target868, Target884, Target903, Target911, Target916, Target926, Target936, Target940, Target941, Target1005, Target1041, Target1048, Target1085, Target1093, Target1113, Target1139, Target1181, Target1182, Target1183, Target1216, Target1229, Target1240, Target1311, Target1324, Target1333, Target1340, Target1342, Target1356, Target1357, Target1385, Target1392, Target1403, Target1408, Target1489, Target1521, Target1566, Target1584, Target1609, Target1616, Target1626, Target1630, Target1635, Target1655, and Target1656 was analyzed. Methylation metric is computed as percent discordant reads (PDR). The classification method used in the analysis is K-Nearest Neighbors.

An experimental panel interrogating the 95 target regions listed above was developed. Forty (40) lung cancer tissue samples, 10 healthy plasma samples, and 4 lung cancer plasma samples were processed using the experimental panel, and the PDR metric was computed for each target region to create a data matrix. In order to develop a K-Nearest Neighbor-based classifier, a subset of 10 healthy plasma and 40 lung cancer tissue samples were selected as the "training" set. For the remaining test set samples, the Euclidean distance to all training set samples was computed in Python (using the seaborn.clustermap function) (FIG. 3a). Each sample was assigned to the category of its nearest training set neighbor; this led to a sensitivity of 75.00% and a specificity of 100.00% in the plasma samples.

The test or analytic results are shown in FIG. 3b. Each vertical line represents a single sample. Purple samples are KNOWN CANCER SAMPLES. Green samples are KNOWN NORMAL SAMPLES. Red samples are UNKNOWN SAMPLES (for which the truth is that they are CANCER samples). Blue samples are UNKNOWN SAMPLES (for which the truth is that they are NORMAL samples). In this analysis, all five blue samples were most similar to green samples, so they were all called normal (for a specificity of 100%). Three out of four red samples were most similar to purple samples, so three out of four were called cancer (for a sensitivity of 75%). One red sample was most similar to the green samples, so it was miscalled as normal.

Example 3. Pan-Cancer Detection in Plasma

In this example, methylation status of 86 Target Regions listed in Table 1: Target11, Target35, Target36, Target102, Target115, Target141, Target154, Target155, Target168, Target184, Target209, Target210, Target211, Target226, Target241, Target284, Target323, Target333, Target338, Target397, Target432, Target439, Target440, Target460, Target472, Target482, Target485, Target570, Target574, Target589, Target596, Target616, Target637, Target660, Target661, Target674, Target692, Target693, Target710, Target728, Target840, Target852, Target867, Target868, Target903, Target911, Target916, Target940, Target941, Target942, Target1048, Target1055, Target1061, Target1085, Target1093, Target1116, Target1122, Target1129, Target1139, Target1142, Target1190, Target1191, Target1212, Target1213, Target1216, Target1229, Target1247, Target1248, Target1296, Target1297, Target1311, Target1322, Target1324, Target1340, Target1342, Target1343, Target1356, Target1378, Target1392, Target1403, Target1447, Target1522, Target1535, Target1543, Target1566, Target1616 was analyzed. Methylation metric is computed as average methylation frequency (AMF). The classification method used in the analysis is logistic regression.

An experimental panel interrogating the 86 target regions listed above was developed. Twenty (20) healthy plasma samples, 5 lung cancer plasma samples, 4 liver cancer plasma samples, 1 breast cancer plasma sample, 1 ovarian cancer plasma sample, and 2 esophageal cancer plasma samples were processed using the experimental panel, and the AMF metric was computed for each target region to create a data matrix. In order to develop a Logistic Regression-based classifier, a subset of 10 healthy plasma and 6 cancer plasma samples were selected as the "training" set. A Logistic Regression model was fit to the sum of the average methylation values across all target regions in Python (using the sklearn module) (FIG. 4). The cancer status of the remaining test set samples was then predicted; this led to a sensitivity of 85.71% and a specificity of 80.00% in the plasma samples.

Example 4

In this example, the templates (e.g., polynucleotides to be sequenced) are short DNA fragments less than about 200 bp long. These DNA fragments can include extracted DNA from plasma, enzyme-treated (e.g., by a fragmentase) genomic DNA, or physically sheared DNA. The physically sheared DNA may be end repaired. In particular aspects, the template has a 3' hydroxyl group for ligation.

Typically, 10-30 ng of the properly prepared template DNA was dephosphorylated, for example, using 1 U FastAP Thermosensitive Alkaline Phosphatase (Thermo Scientific) in 100 mM MOPS (pH 7.5), 20 mM KCl, 10 mM MgCl$_2$, 2 mM DTT, and 5 mM MnCl$_2$ at 37° C. for 10 minutes. The DNA was then denatured, for example, at 95° C. for 2 minutes and put on ice for 1 minute.

A single-stranded adapter was synthesized from IDT with a 5' phosphate group and a 3' carbon spacer. The 5' end contains GA following by a 12-mer unique molecular identifier (UMI) sequence. A typical single-stranded adapter has the following sequence:

/5Phos/GANNNNNNNNNNNNNAGATCGGAAGAGCGTCGTGTAGGGAAAGA GTG/3SpC3/

("5Phos" represents a 5' phosphate group, "NNNNNNNNNNNN" represents a 12-mer UMI sequence, and "3SpC3" represents a 3' carbon spacer.

A ligation reaction was then performed using the dephosphorylated, single-stranded DNA as template. The following final concentrations were used in the ligation reaction: 50 mM MOPS (pH 7.5), 10 mM KCl, 5 mM MgCl$_2$, 1 mM DTT, and 2.5 mM MnCl$_2$, 50% PEG 4000, 0.5 μM adapter, 125 μM ATP, and 200 U Epicentre Circligase™. The reaction was incubated at 60° C. for 2 hours, 80° C. for 10 minutes, 85° C. for 2 minutes, and held at 4° C.

The DNA was then double-stranded by adding the previous reaction volume to the following: 10 mM Tris-HCl (pH 8.3), 50 mM KCl, 1.5 mM MgCl$_2$, 1.25 U Taq DNA Polymerase (NEB), 1 μM reverse-complement primer (a primer that is reverse-complement to the adpator), and 200 μM dNTP mix. The reaction was incubated at 95° C. for 30 seconds, 62° C. for 2 minutes, 68° C. for 10 minutes, and held at 4° C. A typical reverse-complement primer comprises the sequence set forth in SEQ ID NO:17505: CACTCTTTCCCTACACGACGC (5' to 3'). The following is an alignment between the adaptor and the reverse-complement primer:

```
Adaptor
/5Phos/GANNNNNNNNNNNNNAGATCGGAAGA

GCGTCGTGTAGGGAAAGAGTG/3SpC3/
::::::::::::::::::::::
CGCAGCACATCCCTTTCTCAC
Primer
```

The reaction was then purified using 1.6 (bead ratio)× AmPure® XP beads. The beads were added and incubated for 10 minutes. The mixtures were then transferred to a magnet for 5 minutes. The supernatant was then removed. The beads were washed 2× with 150 μL 80% ethanol for 30 seconds each. All residual ethanol was then removed and the beads were dried for 3 minutes at room temperature off of the magnet. 15 μl of Low TE buffer (Thermo Fisher) was added to the beads and incubated for 2 minutes. The beads were then returned to the magnet for 1 minute. The supernatant was removed and stored for the next reaction. In one aspect, the bead ratio causes size selectivity in the purification process, and a bead ratio (such as 1.6×) can be selected that removes molecules shorter than about 100 bp.

A set of PCR primers were designed to minimize primer-primer interactions and off-target annealing. The primers were further optimized to land within close proximity to specific variants. Once designed, the primers were synthesized by IDT. The primers were mixed in equal volume ratios into a primer pool. A semi-targeted PCR reaction was performed with the following reagents: all purified DNA from previous reaction, 1×KAPA 2G multiplex master mix, 66 nM of each primer from pool, and 800 nM reverse-complement primer. The reaction underwent the following thermo-cycling program: 95° C. 3 minutes, (95° C. 15 seconds, 72° C. 90 seconds)×20, 72° C. 1 minute, and held at 4° C.

The reaction was then purified using 1.6 (bead ratio)× AmPure® XP beads. The beads were added and incubated for 10 minutes. The mixtures were then transferred to a magnet for 5 minutes. The supernatant was then removed. The beads were washed 2× with 150 µL 80% ethanol for 30 seconds each. All residual ethanol was then removed and the beads were dried for 3 minutes at room temperature off of the magnet. 20 µl of Low TE buffer (Thermo Fisher) was added to the beads and incubated for 2 minutes. The beads were then returned to the magnet for 1 minute. The supernatant is removed and stored for the next reaction. A bead ratio (such as 1.6×) can be selected that removes molecules shorter than about 100 bp, including free adaptor molecules, free primer molecules, and/or adaptor/primer dimers.

Another PCR reaction was then completed to add full length sequencing adapters and sample specific barcodes. The PCR reaction contained the following: 2 µL purified DNA from previous reaction, 1×NEB ultra Q5 II master mix, 400 nM universal primer, and 400 nM barcode specific primer. The reaction underwent the following thermo-cycling program: 95° C. 3 minutes, (98° C. 10 seconds, 65° C. 75 seconds)×10, 65° C. 2 minute, and held at 4° C.

The reaction was then purified using 0.8 (bead ratio)× AmPure® XP beads. The beads were added and incubated for 10 minutes. The mixtures were then transferred to a magnet for 5 minutes. The supernatant was then removed. The beads were washed 2× with 150 µL 80% ethanol for 30 seconds each. All residual ethanol was then removed and the beads were dried for 3 minutes at room temperature off of the magnet. 25 µl of Low TE buffer (Thermo Fisher) is added to the beads and incubated for 2 minutes. The beads were then returned to the magnet for 1 minute. The supernatant is removed and is ready for sequencing. A bead ratio (such as 0.8×) can be selected that removes a majority of molecules shorter than about 200 bp said polynucleotide sequence of said Target 192 comprises at least 10 consecutive nucleotides in a polynucleotide sequence that is set forth in, that is complementary with or that hybridizes under stringent conditions to, one or more of polynucleotide sequence(s) set forth in SEQ ID NOs: 1824-1833, said polynucleotide sequence of said Target 248 comprises at least 10 consecutive nucleotides in a polynucleotide sequence that is set forth in, that is complementary with or that hybridizes under stringent conditions to, one or more of polynucleotide sequence(s) set forth in SEQ ID NOs: 2353-2362, said polynucleotide sequence of said Target 916 comprises at least 10 consecutive nucleotides in a polynucleotide sequence that is set forth in, that is complementary with or that hybridizes under stringent conditions to, one or more of polynucleotide sequence(s) forth set in SEQ ID NOs: 8667-8676, said polynucleotide sequence of said Target 936 comprises at least 10 consecutive nucleotides in a polynucleotide sequence that is set forth in, that is complementary with or that hybridizes under stringent conditions to, one or more of polynucleotide sequence(s) set forth in SEQ ID NOs: 8854-8863, said polynucleotide sequence of said Target 1349 comprises at least 10 consecutive nucleotides in a polynucleotide sequence that is set forth in, that is complementary with or that hybridizes under stringent conditions to, one or more of polynucleotide sequence(s) set forth in SEQ ID NOs: 12722-12731, said polynucleotide sequence of said Target 1374 comprises at least 10 consecutive nucleotides in a polynucleotide sequence that is set forth in, that is complementary with or that hybridizes under stringent conditions to, one or more of polynucleotide sequence(s) set forth in SEQ ID NOs: 12966-12975, said polynucleotide sequence of said Target 1392 comprises at least 10 consecutive nucleotides in a poly-

---

SEQUENCE LISTING

The patent contains a lengthy sequence listing. A copy of the sequence listing is available in electronic form from the USPTO web site (https://seqdata.uspto.gov/docdetail?docId=US12686889B2). An electronic copy of the sequence listing will also be available from the USPTO upon request and payment of the fee set forth in 37 CFR 1.19(b)(3).

---

The invention claimed is:

1. A panel of isolated polynucleotides comprising, consisting of, or consisting essentially of at least 10 isolated polynucleotides, said 10 isolated polynucleotides having polynucleotide sequences of at least Targets 60, 192, 248, 916, 936, 1349, 1374, 1392, 1435 and 1447, or a complementary sequence thereof, wherein said isolated polynucleotides have a level or concentration from about 1 femtomolar to about 1 millimolar, and wherein said polynucleotide sequence of said Target 60 comprises at least 10 consecutive nucleotides in a polynucleotide sequence that is set forth in, that is complementary with or that hybridizes under stringent conditions to, one or more of polynucleotide sequence(s) set forth in SEQ ID NOs: 562-571, nucleotide sequence that is set forth in, that is complementary with or that hybridizes under stringent conditions to, one or more of polynucleotide sequence(s) set forth in SEQ ID NO: 13140-13149, said polynucleotide sequence of said Target 1435 comprises at least 10 consecutive nucleotides in a polynucleotide sequence that is set forth in, that is complementary with or that hybridizes under stringent conditions to, one or more of polynucleotide sequence(s) set forth in SEQ ID NOs: 13560-13569, and said polynucleotide sequence of said Target 1447 comprises at least 10 consecutive nucleotides in a polynucleotide sequence that is set forth in, that is complementary with or that hybridizes under stringent conditions to, one or more of polynucleotide sequence(s) set forth in SEQ ID NO: 13665-13674.

2. A kit or system, which comprises a panel of claim 1.

3. The kit or system of claim 2, which is configured for assessing methylation status of at least said Targets 60, 192, 248, 916, 936, 1349, 1374, 1392, 1435 and 1447.

4. A kit or system, which comprises reagents for assessing methylation status of at least Targets 60, 192, 248, 916, 936, 1349, 1374, 1392, 1435 and 1447, wherein said reagents comprise, consist essentially of, or consist of probes or primers configured for hybridizing with each of said at least Targets 60, 192, 248, 916, 936, 1349, 1374, 1392, 1435 and 1447, and said probes or primers have a level of concentration from about 1 femtomolar to about 1 millimolar, and wherein said polynucleotide sequence of said Target 60 comprises at least 10 consecutive nucleotides in a polynucleotide sequence that is set forth in, that is complementary with or that hybridizes under stringent conditions to, one or more of polynucleotide sequence(s) set forth in SEQ ID NOs: 562-571, said polynucleotide sequence of said Target 192 comprises at least 10 consecutive nucleotides in a polynucleotide sequence that is set forth in, that is complementary with or that hybridizes under stringent conditions to, one or more of polynucleotide sequence(s) set forth in SEQ ID NOs: 1824-1833, said polynucleotide sequence of said Target 248 comprises at least 10 consecutive nucleotides in a polynucleotide sequence that is set forth in, that is complementary with or that hybridizes under stringent conditions to, one or more of polynucleotide sequence(s) set forth in SEQ ID NOs: 2353-2362, said polynucleotide sequence of said Target 916 comprises at least 10 consecutive nucleotides in a polynucleotide sequence that is set forth in, that is complementary with or that hybridizes under stringent conditions to, one or more of polynucleotide sequence(s) forth set in SEQ ID NOs: 8667-8676, said polynucleotide sequence of said Target 936 comprises at least 10 consecutive nucleotides in a polynucleotide sequence that is set forth in, that is complementary with or that hybridizes under stringent conditions to, one or more of polynucleotide sequence(s) set forth in SEQ ID NOs: 8854-8863, said polynucleotide sequence of said Target 1349 comprises at least 10 consecutive nucleotides in a polynucleotide sequence that is set forth in, that is complementary with or that hybridizes under stringent conditions to, one or more of polynucleotide sequence(s) set forth in SEQ ID NOs: 12722-12731, said polynucleotide sequence of said Target 1374 comprises at least 10 consecutive nucleotides in a polynucleotide sequence that is set forth in, that is complementary with or that hybridizes under stringent conditions to, one or more of polynucleotide sequence(s) set forth in SEQ ID NOs: 12966-12975, said polynucleotide sequence of said Target 1392 comprises at least 10 consecutive nucleotides in a polynucleotide sequence that is set forth in, that is complementary with or that hybridizes under stringent conditions to, one or more of polynucleotide sequence(s) set forth in SEQ ID NO: 13140-13149, said polynucleotide sequence of said Target 1435 comprises at least 10 consecutive nucleotides in a polynucleotide sequence that is set forth in, that is complementary with or that hybridizes under stringent conditions to, one or more of polynucleotide sequence(s) set forth in SEQ ID NOs: 13560-13569, and said polynucleotide sequence of said Target 1447 comprises at least 10 consecutive nucleotides in a polynucleotide sequence that is set forth in, that is complementary with or that hybridizes under stringent conditions to, one or more of polynucleotide sequence(s) set forth in SEQ ID NO: 13665-13674.

5. The kit or system of claim 4, which further comprises a computer readable medium that is configured for obtaining a methylation metric in the form of average methylation frequency, methylation haplotype load, unmethylation haplotype load, percent discordant reads, or a combination thereof.

6. The kit or system of claim 4, which is configured for assessing cancer or neoplasia in a subject.

7. A method for obtaining methylation status of target polynucleotides in a sample of a subject, which method comprises:

a) providing a sample from a subject containing at least 10 target polynucleotides of said subject, said at least 10 target polynucleotides having polynucleotide sequences of at least Targets 60, 192, 248, 916, 936, 1349, 1374, 1392, 1435 and 1447, or a complementary sequence thereof; and b) assessing methylation status of said at least 10 target polynucleotides; and wherein said step b) is conducted using a panel of isolated polynucleotides comprising, consisting of, or consisting essentially of at least 10 isolated polynucleotides, said 10 isolated polynucleotides having polynucleotide sequences of at least Targets 60, 192, 248, 916, 936, 1349, 1374, 1392, 1435 and 1447, or a complementary sequence thereof, and said isolated polynucleotides have a level or concentration from about 1 femtomolar to about 1 millimolar, and wherein said polynucleotide sequence of said Target 60 comprises at least 10 consecutive nucleotides in a polynucleotide sequence that is set forth in, that is complementary with or that hybridizes under stringent conditions to, one or more of polynucleotide sequence(s) set forth in SEQ ID NOs: 562-571, said polynucleotide sequence of said Target 192 comprises at least 10 consecutive nucleotides in a polynucleotide sequence that is set forth in, that is complementary with or that hybridizes under stringent conditions to, one or more of polynucleotide sequence(s) set forth in SEQ ID NOs: 1824-1833, said polynucleotide sequence of said Target 248 comprises at least 10 consecutive nucleotides in a polynucleotide sequence that is set forth in, that is complementary with or that hybridizes under stringent conditions to, one or more of polynucleotide sequence(s) set forth in SEQ ID NOs: 2353-2362, said polynucleotide sequence of said Target 916 comprises at least 10 consecutive nucleotides in a polynucleotide sequence that is set forth in, that is complementary with or that hybridizes under stringent conditions to, one or more of polynucleotide sequence(s) forth set in SEQ ID NOs: 8667-8676, said polynucleotide sequence of said Target 936 comprises at least 10 consecutive nucleotides in a polynucleotide sequence that is set forth in, that is complementary with or that hybridizes under stringent conditions to, one or more of polynucleotide sequence(s) set forth in SEQ ID NOs: 8854-8863,

said polynucleotide sequence of said Target 1349 com-
prises at least 10 consecutive nucleotides in a poly-
nucleotide sequence that is set forth in, that is comple-
mentary with or that hybridizes under stringent
conditions to, one or more of polynucleotide
sequence(s) set forth in SEQ ID NOs: 12722-12731,
said polynucleotide sequence of said Target 1374 com-
prises at least 10 consecutive nucleotides in a poly-
nucleotide sequence that is set forth in, that is comple-
mentary with or that hybridizes under stringent
conditions to, one or more of polynucleotide
sequence(s) set forth in SEQ ID NOs: 12966-12975,
said polynucleotide sequence of said Target 1392 com-
prises at least 10 consecutive nucleotides in a poly-
nucleotide sequence that is set forth in, that is comple-
mentary with or that hybridizes under stringent
conditions to, one or more of polynucleotide
sequence(s) set forth in SEQ ID NO: 13140-13149,
said polynucleotide sequence of said Target 1435 com-
prises at least 10 consecutive nucleotides in a poly-
nucleotide sequence that is set forth in, that is comple-
mentary with or that hybridizes under stringent
conditions to, one or more of polynucleotide
sequence(s) set forth in SEQ ID NOs: 13560-13569,
and
said polynucleotide sequence of said Target 1447 com-
prises at least 10 consecutive nucleotides in a poly-
nucleotide sequence that is set forth in, that is comple-
mentary with or that hybridizes under stringent
conditions to, one or more of polynucleotide
sequence(s) set forth in SEQ ID NO: 13665-13674.

8. The method of claim 7, which further comprises
isolating the target polynucleotides from a sample.

9. The method of claim 7, which further comprises
preparing a library of the target polynucleotides.

10. The method of claim 7, which further comprises
amplifying the target polynucleotides.

11. The method of claim 7, which further comprises
purifying the target polynucleotides, a library of the target
polynucleotides, amplified target polynucleotides or a
library of amplified target polynucleotides.

12. The method of claim 7, wherein the methylation status
of target polynucleotides is assessed using mass spectrom-
etry, methylation-specific PCR (MSP), methylation-sensi-
tive sequencing, e.g., bisulphite sequencing, the HpaII tiny
fragment Enrichment by ligation-mediated PCR assay
(HELP Assay), GlaI hydrolysis and ligation adapter depen-
dent PCR assay (GLAD-PCR assay), restriction landmark
genomic scanning (RLGS), methylated DNA immunopre-
cipitation (MeDIP or mDIP), pyrosequencing, molecular
break light assay for DNA adenine methyltransferase activ-
ity, methyl sensitive Southern blotting or high resolution
Melt (HRM) analysis.

13. The method of claim 7, wherein the methylation status
of target polynucleotides is assessed using methylation-
sensitive sequencing, e.g., bisulphite sequencing.

14. The method of claim 13, which further comprises,
prior to the methylation-sensitive sequencing, e.g., bisul-
phite sequencing, obtaining a library of linear, single-
stranded ligation products, each of the linear, single-
stranded ligation products comprises of a linear, single-
stranded target polynucleotide linked to an adaptor
comprising a unique molecular identifier (UMI) sequence
that earmarks the single-stranded target polynucleotide to
which the adaptor is ligated.

15. The method of claim 7, wherein the methylation status
of each of the target polynucleotides is assessed to obtain a
methylation metric, e.g., in the form of average methylation
frequency, methylation haplotype load, unmethylation hap-
lotype load, percent discordant reads, or a combination
thereof.

16. The method of claim 15, wherein a numerical meth-
ylation matrix is computed using a classification algorithm
from the methylation metrics from each of the target poly-
nucleotides to assess methylation status of a sample.

17. The method of claim 7, which is used for treatment of
cancer or neoplasia in a subject.

18. The method of claim 17, wherein cancer or neoplasia
in multiple subjects are treated.

* * * * *